US012662479B2

(12) United States Patent
Netherton et al.

(10) Patent No.: US 12,662,479 B2
(45) Date of Patent: Jun. 23, 2026

(54) COMPOUNDS AND USES THEREOF

(71) Applicant: Foghorn Therapeutics Inc., Indianapolis, IN (US)

(72) Inventors: Matthew Netherton, Cambridge, MA (US); Shawn E.R. Schiller, Haverhill, MA (US); Jing Deng, Cambridge, MA (US); Neville John Anthony, Northborough, MA (US); Francois Brucelle, Belmont, MA (US); Sabine K Ruppel, Cambridge, MA (US); Johannes H. Voigt, Cambridge, MA (US)

(73) Assignee: Foghorn Therapeutics Inc., Cambridge, MA (US)

( * ) Notice: Subject to any disclaimer, the term of this patent is extended or adjusted under 35 U.S.C. 154(b) by 892 days.

(21) Appl. No.: 17/795,615

(22) PCT Filed: Jan. 29, 2021

(86) PCT No.: PCT/US2021/015944
§ 371 (c)(1),
(2) Date: Jul. 27, 2022

(87) PCT Pub. No.: WO2021/155321
PCT Pub. Date: Aug. 5, 2021

(65) Prior Publication Data

US 2023/0348452 A1 Nov. 2, 2023

Related U.S. Application Data

(60) Provisional application No. 62/967,565, filed on Jan. 29, 2020.

(51) Int. Cl.
*C07D 417/14* (2006.01)
*A61K 31/4545* (2006.01)
*C07D 471/10* (2006.01)

(52) U.S. Cl.
CPC ......... *C07D 417/14* (2013.01); *C07D 471/10* (2013.01)

(58) Field of Classification Search
CPC .......................... C07D 417/14; C07D 471/14; A61K 31/4545; A61K 31/4535; A61P 35/00; A61P 31/12
USPC .......................... 546/194, 201; 514/318, 323
See application file for complete search history.

(56) References Cited

FOREIGN PATENT DOCUMENTS

| | | | | |
|---|---|---|---|---|
| CN | 102119047 A | 7/2011 | | |
| WO | 2019152437 A1 | 8/2019 | | |
| WO | 2019195201 A | 10/2019 | | |
| WO | WO 2020/160100 A1 * | 8/2020 | ........... | C07D 405/14 |

OTHER PUBLICATIONS

PCT International Search Report and the Written Opinion of the International Searching Authority pertaining to international Application No. PCT/2021/015944; Date of Mailing: Jul. 21, 2021; 11 pages.
Scheepstra, Marcel, Koen FW Hekking, Luc van Hijfte, and Rutger HA Folmer. "Bivalent ligands for protein degradation in drug discovery." *Computational and structural biotechnology journal* 17 (2019): 160-176.
National Center for Biotechnology Information. "PubChem Substance Record for SID 213932275, AKOS018933007, Source: AKos Consulting & Solutions" PubChem, https://pubchem.ncbi.nlm.nih.gov/substance/213932275. Accessed Jun. 24, 2022.
National Center for Biotechnology Information. "PubChem Substance Record for SID 213931336, AKOS018932068, Source: AKos Consulting & Solutions" PubChem, https://pubchem.ncbi.nlm.nih.gov/substance/213931336. Accessed Jun. 24, 2022.
Office Action, CA Application No. 3,166,404, dated Oct. 6, 2025, 12 pages.
Office Action, CN Application No. 202180025865.1, dated Apr. 3, 2024, 9 pages.
Office Action, CN Application No. 202180025865.1, dated Aug. 10, 2024, 6 pages.
Office Action, CN Application No. 202180025865.1, dated Dec. 18, 2024, 4 pages.
Office Action, CN Application No. 202180025865.1, dated Sep. 27, 2023, 10 pages.
Decision of Rejection, JP Application No. 2022-546433, dated Dec. 10, 2024, 3 pages.
Office Action, JP Application No. 2022-546433, dated May 14, 2024, 3 pages.
Request for Appeal Filed, JP Application No. 2022-546433, dated Apr. 9, 2025, 5 pages.
Decision to Grant a Patent, JP Application No. 2022-546433, dated May 27, 2025, 6 pages.
Office Action, JP Application No. 2022-546433, dated Sep. 26, 2023, 5 pages.
Office Action, CA Application No. 3,166,404, dated Aug. 9, 2024, 8 pages.
Communication pursuant to Article 94(3) EPC, EP Application No. 21747487.3, dated Sep. 29, 2025, 3 pages.

* cited by examiner

*Primary Examiner* — Charanjit Aulakh
(74) *Attorney, Agent, or Firm* — Nielsen IP Law LLC

(57) ABSTRACT

The present disclosure features compounds and methods useful for the treatment of BAF complex-related disorders.

5 Claims, No Drawings

COMPOUNDS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In an aspect, the invention features a compound having the structure of Formula I:

A-L-B    Formula I, where

L is a linker;

B is a degradation moiety; and

A has the structure of Formula II:

Formula II

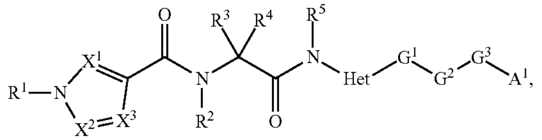

where $X^1$ is N or CH;

$X^2$, and $X^3$ are, independently, N, CH, or $C(CH_3)$;

$R^1$ is H, optionally substituted $C_1$-$C_6$ acyl, optionally substituted $C_1$-$C_6$ alkyl, optionally substituted $C_1$-$C_6$ heteroalkyl, optionally substituted $C_2$-$C_9$ heterocyclyl, or —$SO_2R^6$;

each of $R^2$ and $R^5$ is, independently, H or optionally substituted $C_1$-$C_6$ alkyl;

$R^3$ is H, optionally substituted $C_1$-$C_6$ alkyl, or a bond between A and the linker;

$R^4$ is H, optionally substituted $C_1$-$C_6$ alkyl, or optionally substituted $C_1$-$C_6$ heteroalkyl;

$R^6$ is optionally substituted $C_1$-$C_6$ alkyl or —$NR^7R^8$;

each of $R^7$ and $R^8$ is, independently, optionally substituted $C_1$-$C_6$ alkyl;

Het is a 5-membered or 6-membered heteroarylene;

$G^1$ is optionally substituted $C_6$-$C_{10}$ arylene, optionally substituted $C_2$-$C_9$ heterocyclylene, or optionally substituted $C_2$-$C_9$ heteroarylene;

$G^2$ is absent, —O—, optionally substituted $C_1$-$C_6$ alkylene, optionally substituted $C_1$-$C_6$ alkenylene, optionally substituted $C_1$-$C_6$ heteroalkylene, optionally substituted $C_2$-$C_9$ heterocyclyl $C_1$-$C_6$ alkylene, or optionally substituted $C_2$-$C_9$ heteroaryl $C_1$-$C_6$ alkylene;

$G^3$ is absent, optionally substituted $C_6$-$C_{10}$ arylene, optionally substituted $C_6$-$C_{10}$ cycloalkylene, optionally substituted $C_2$-$C_9$ heterocyclylene, or optionally substituted $C_2$-$C_9$ heteroarylene; and $A^1$ is H or a bond between A and the linker, provided that Formula II includes one and only one bond between A and the linker, or a pharmaceutically acceptable salt thereof.

In some embodiments, $R^3$ is H or optionally substituted $C_1$-$C_6$ alkyl, and $A^1$ is a bond between A and the linker. In some embodiments, $R^3$ is a bond between A and the linker, and $A^1$ is H.

In some embodiments, $R^2$ is hydrogen.

In some embodiments, $R^5$ is hydrogen. In other embodiments, $R^5$ is optionally substituted $C_1$-$C_6$ alkyl, e.g., methyl.

In some embodiments, $X^1$, $X^2$, and $X^3$ are CH. In some embodiments, $X^1$ is N and $X^2$ and $X^3$ are CH. In some embodiments, $X^3$ is N and $X^1$ and $X^2$ are CH. In some embodiments, $X^2$ is N and $X^1$ and $X^3$ are CH. In some embodiments, $X^1$ is CH and $X^2$ and $X^3$ are $C(CH_3)$. In some embodiments, $X^1$ and $X^3$ are CH and $X^2$ is $C(CH_3)$.

In some embodiments, $R^3$ is hydrogen. In some embodiments, $R^3$ is optionally substituted $C_1$-$C_6$ alkyl, e.g., $R^3$ is methyl.

In further embodiments, $R^4$ is hydrogen. In other embodiments, $R^4$ is optionally substituted $C_1$-$C_6$ alkyl, e.g., methyl, tert-butyl, iso-propyl, iso-butyl, or tert-pentyl. In further embodiments, $R^4$ is optionally substituted $C_1$-$C_6$ heteroalkyl, e.g.,

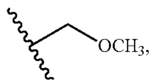 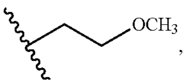 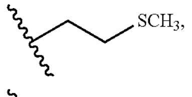 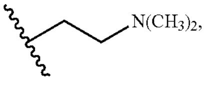 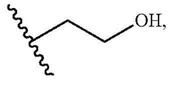 or 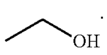

The some embodiments, Het is

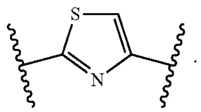 [SMILES: *c1csc(*)n1]

In other embodiments, Het is

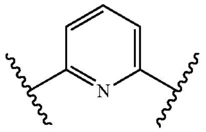

In further embodiments, Het is

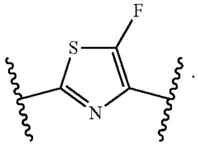 [SMILES: *c1nc(*)c(F)s1]

In some embodiments, $G^2$ is absent. In some embodiments, $G^2$ is optionally substituted $C_1$-$C_6$ alkylene, e.g., $G^2$ is

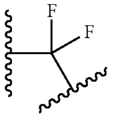,
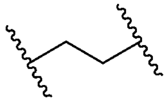
or
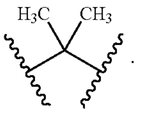

In further embodiments, $G^2$ is optionally substituted $C_1$-$C_6$ heteroalkylene, optionally substituted $C_2$-$C_9$ heterocyclene, or optionally substituted $C_2$-$C_9$ heterocyclyl $C_1$-$C_6$ alkylene, e.g.,

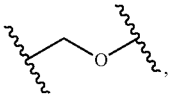,
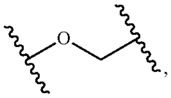,
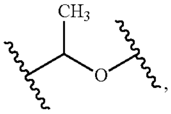,
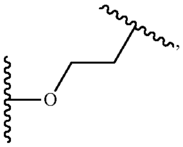,
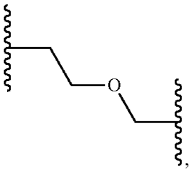,
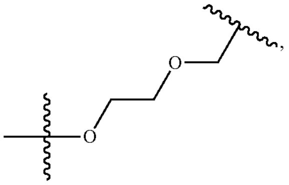,
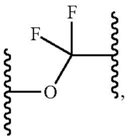,
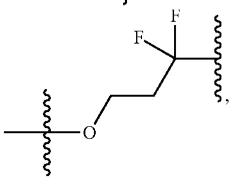, -continued

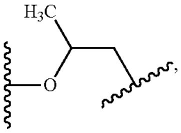,
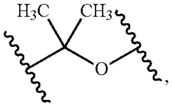,
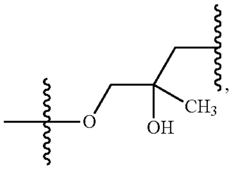,
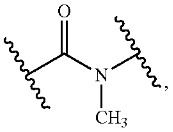,
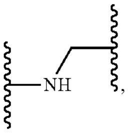,
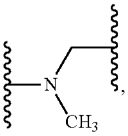,
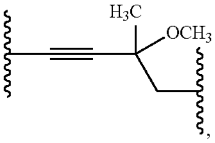,
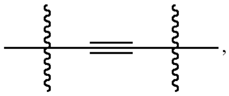,
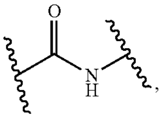,
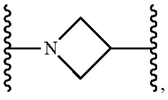,
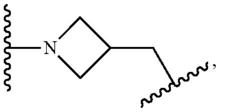,
or
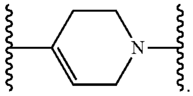

In particular embodiments, $G^2$ is optionally substituted $C_1$-$C_6$ alkenylene, e.g.,

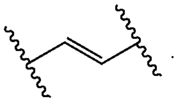 [SMILES: */C=C/*]

In some embodiments, $G^1$ is optionally substituted $C_6$-$C_{10}$ arylene, e.g.,

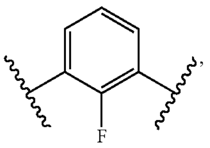,
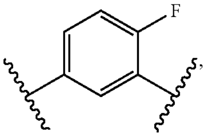,
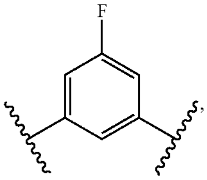,
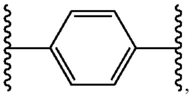,

-continued
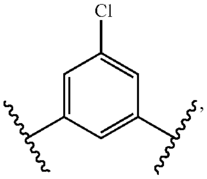, 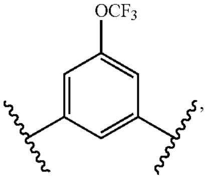,
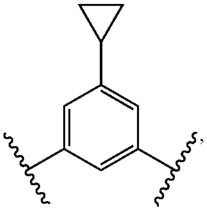, 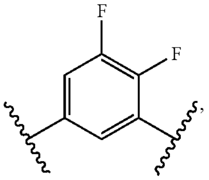,
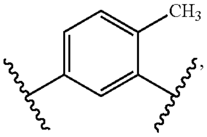, 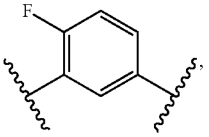, or
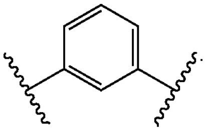.
In other embodiments, $G^1$ is optionally substituted $C_2$-$C_9$ heteroarylene, e.g.,
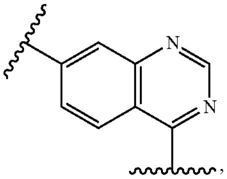, 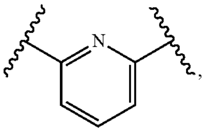,
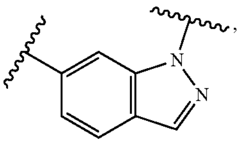, 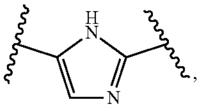,
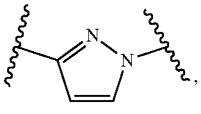, 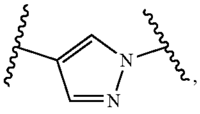,
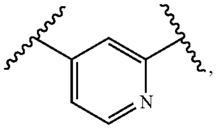, 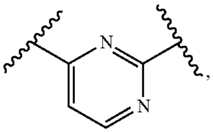,
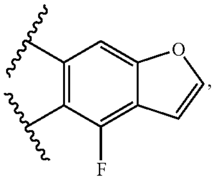, 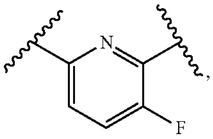, or
-continued
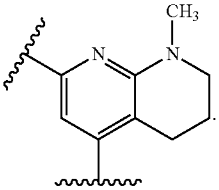.
In further embodiments, $G^1$ is optionally substituted $C_2$-$C_9$ heterocyclylene, e.g.,
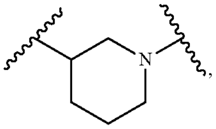, 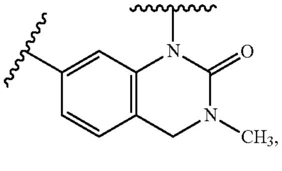,
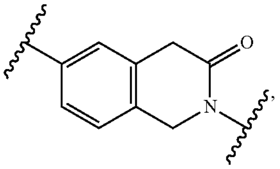, 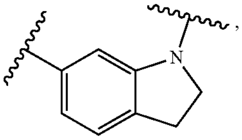,
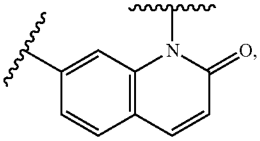, 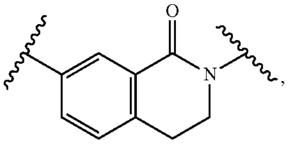,
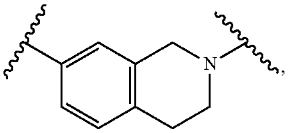,
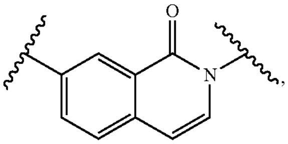,
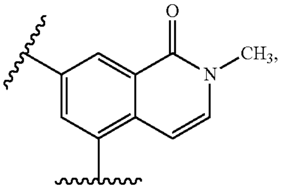,
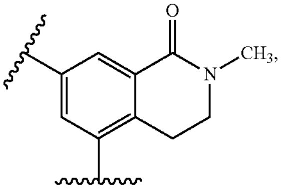

-continued
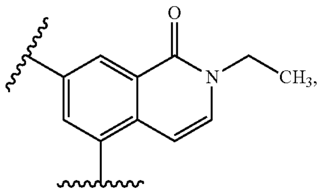
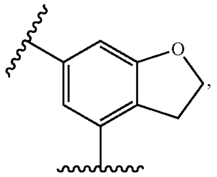
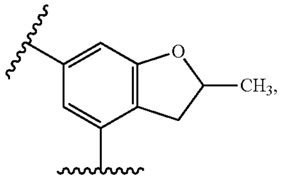
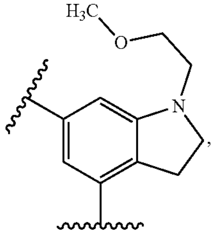
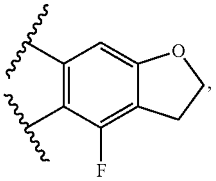
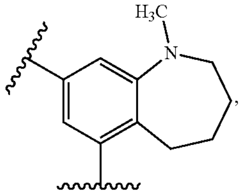
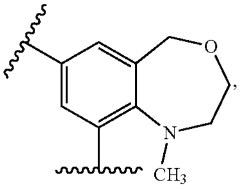
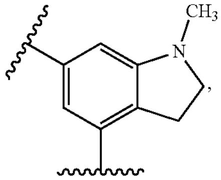
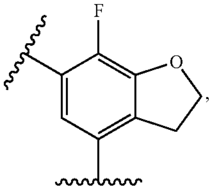
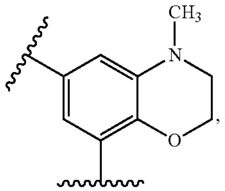
or
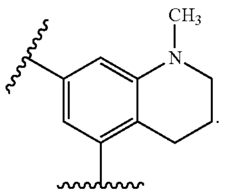
In some embodiments, $G^3$ is absent.
In further embodiments, $G^3$ is optionally substituted $C_6$-$C_{10}$ arylene, e.g.,
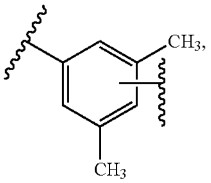
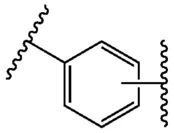
, or
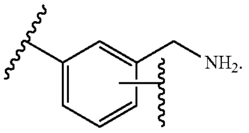
In still further embodiments, $G^3$ is optionally substituted $C_2$-$C_9$ heterocyclylene, e.g.,
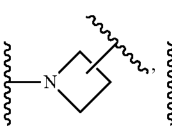
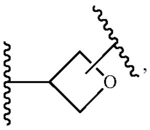
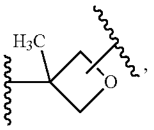
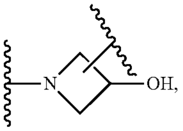
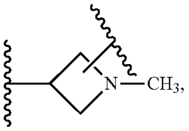
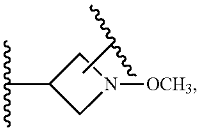
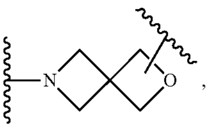
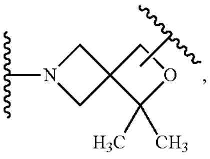
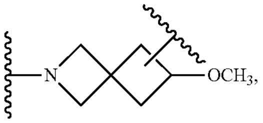
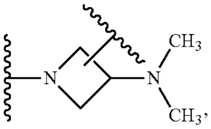
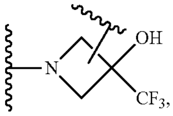
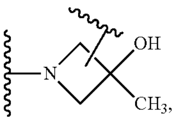
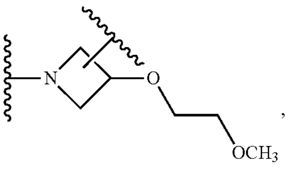
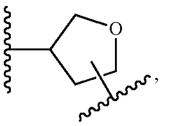
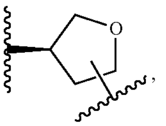
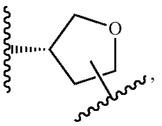
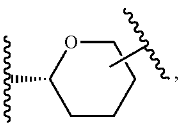
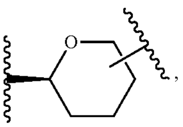
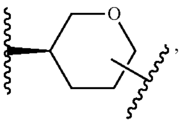
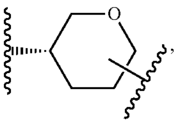

-continued
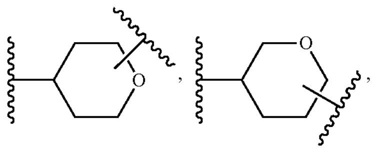
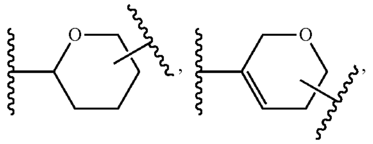
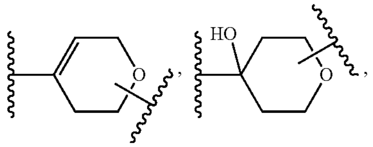
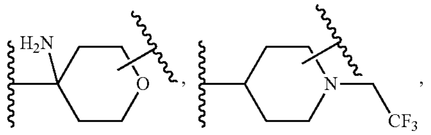
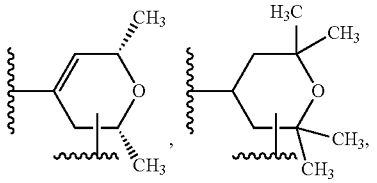
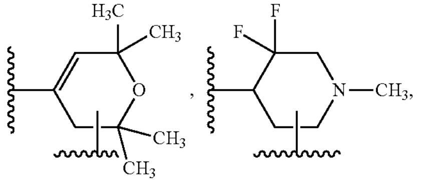
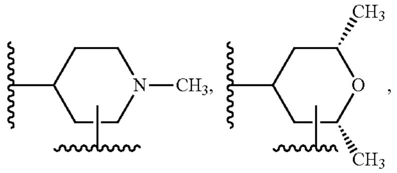
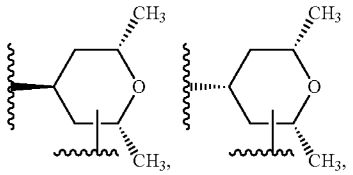
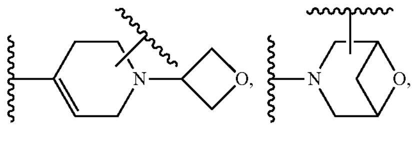
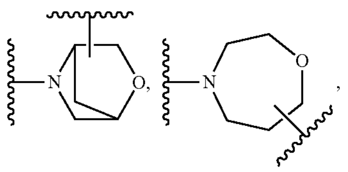
-continued
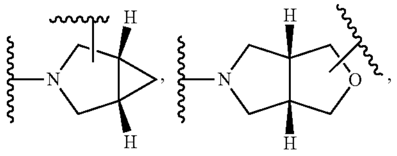
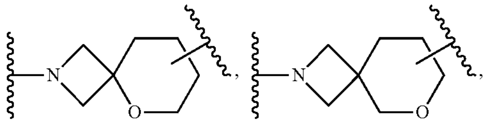
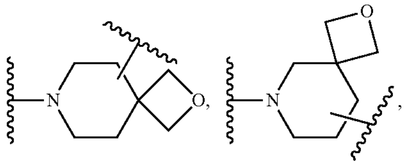
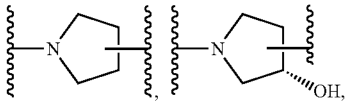
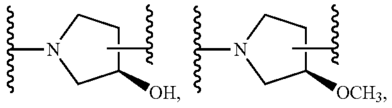
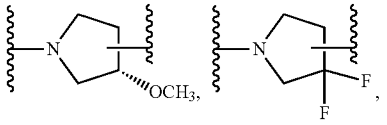
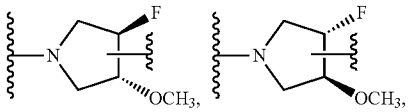
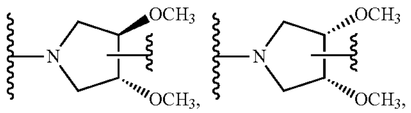
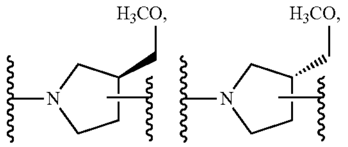
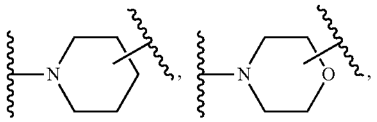
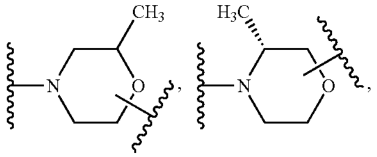
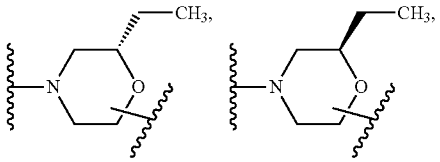

-continued
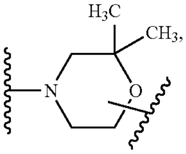
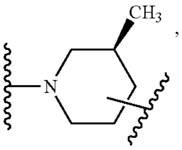
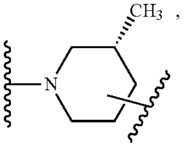
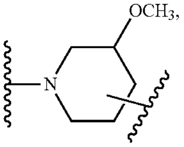
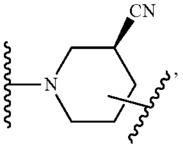
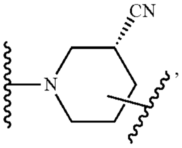
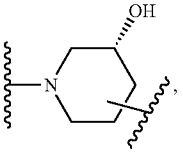
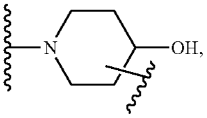
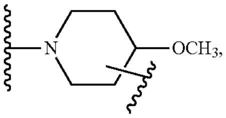
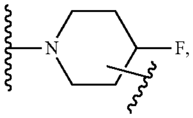
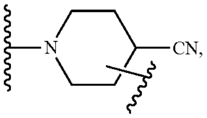
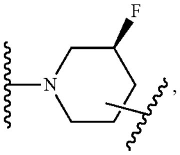
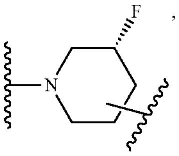
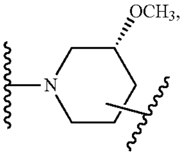
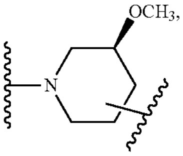
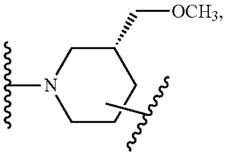
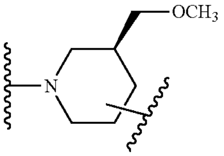
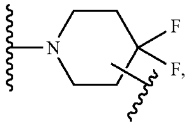
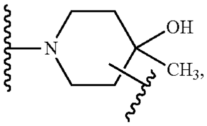
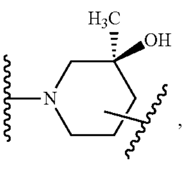
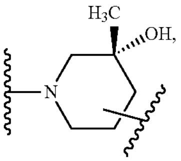
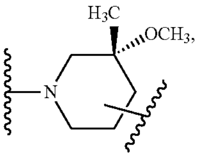
-continued
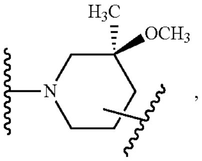
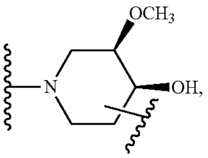
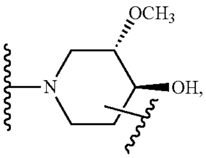
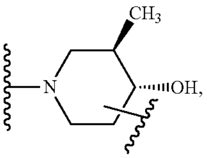
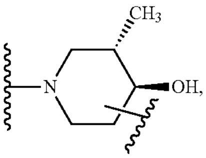
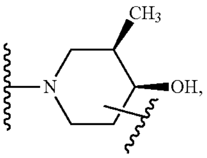
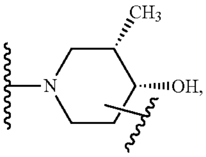
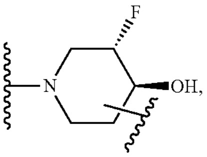
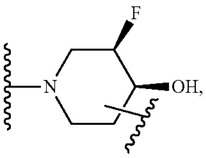
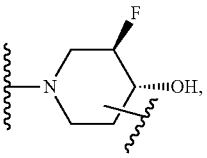
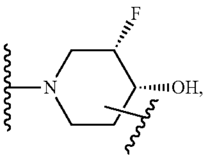
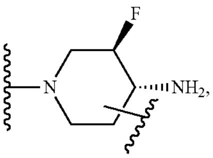
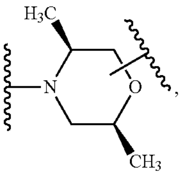
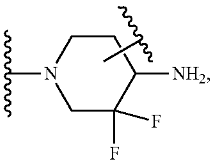
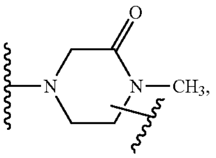
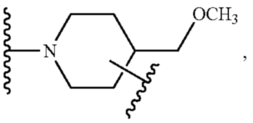
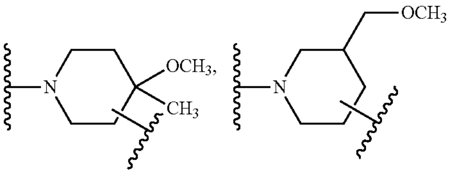
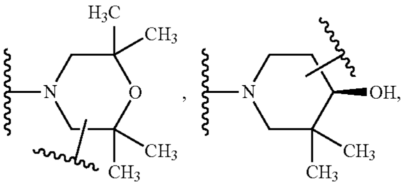

-continued

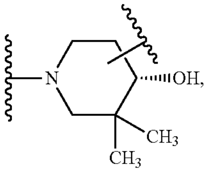 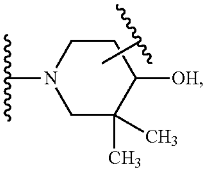

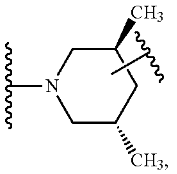 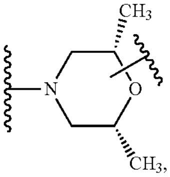 or

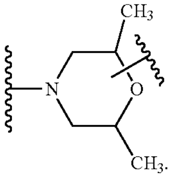

In some embodiments, $G^3$ is

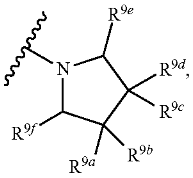

where of $R^{9a}$, $R^{9b}$, $R^{9c}$, and $R^{9d}$ is, independently, $A^1$, H, halogen, hydroxyl, optionally substituted $C_{1-6}$ alkyl, or optionally substituted $C_{1-6}$ heteroalkyl; and each of $R^{9e}$ and $R^{9f}$ is, independently, H or $A^1$. In still other embodiments, $G^3$ is

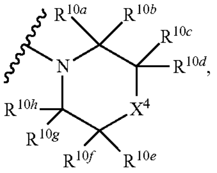

where $X^4$ is O or $CR^{10i}R^{10j}$; and each of $R^{10a}$, $R^{10b}$, $R^{10c}$, $R^{10d}$, $R^{10e}$, $R^{10f}$, $R^{10g}$, $R^{10h}$, $R^{10i}$, and $R^{10j}$ is, independently, H, halogen, cyano, amino, hydroxyl, allyl, heteroallyl, optionally substituted $C_{1-6}$ alkyl, optionally substituted $C_{1-6}$ heteroalkyl, or two combine with the carbon to which they are attached to form C═O.

In yet other embodiments, $G^3$ is optionally substituted $C_2$-$C_9$ heteroarylene, e.g.,

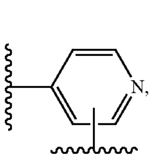 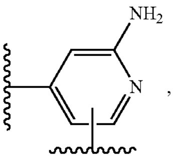 , 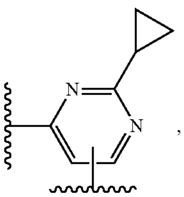 ,

-continued

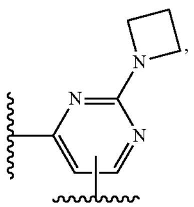 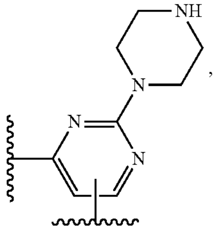

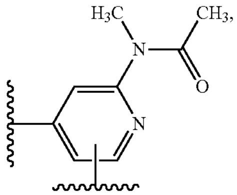

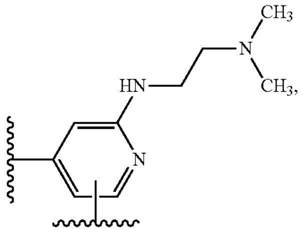

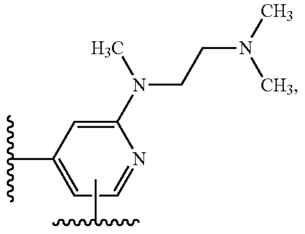

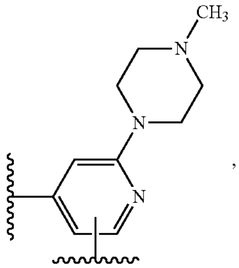 , 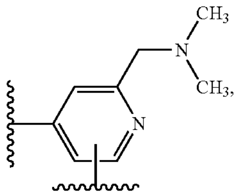

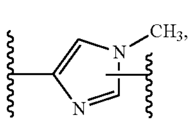 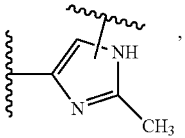 ,

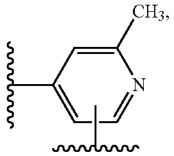 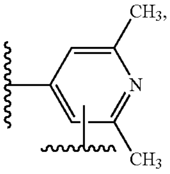

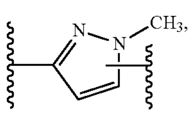 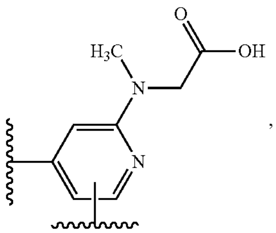 ,

-continued
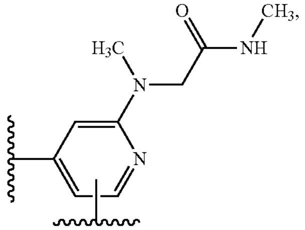
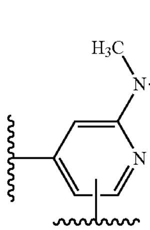
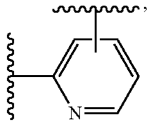
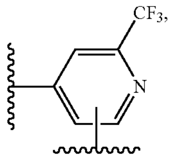
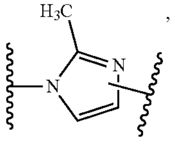
,
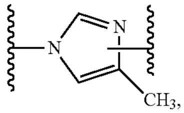
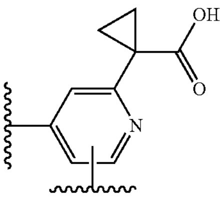
,
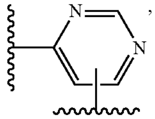
,
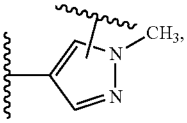
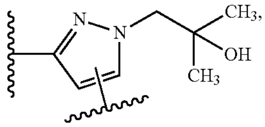
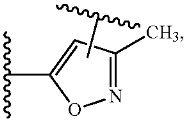
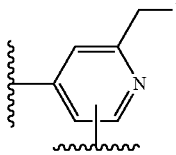
,
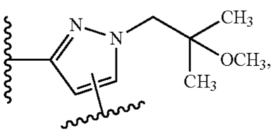
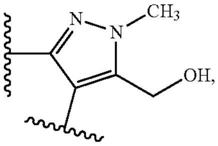
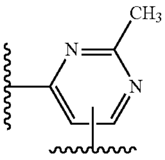
,
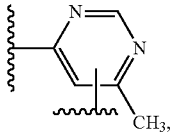
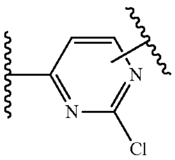
,
-continued
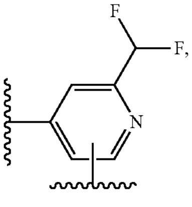
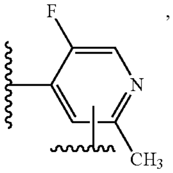
,
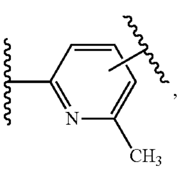
,
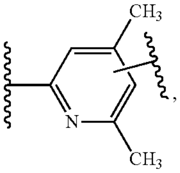
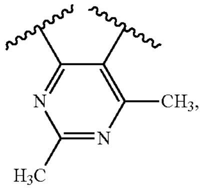
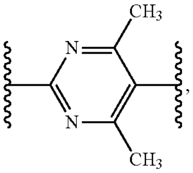
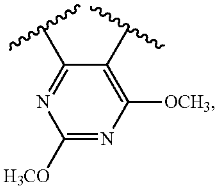
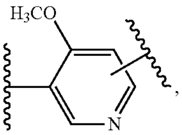
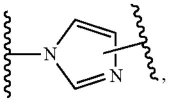
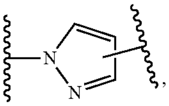
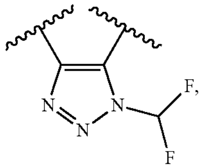
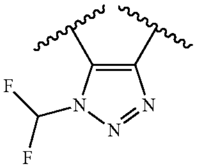
,
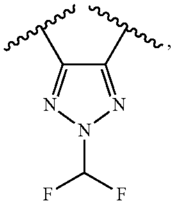
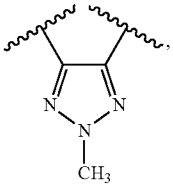
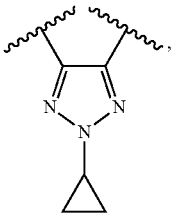
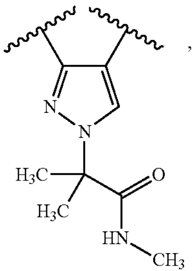
, -continued
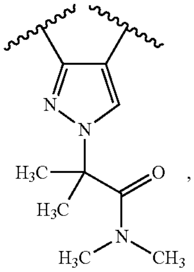 , 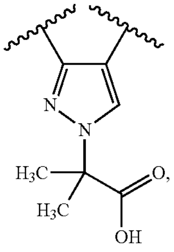
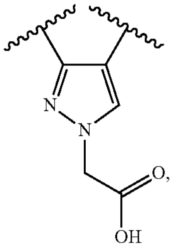 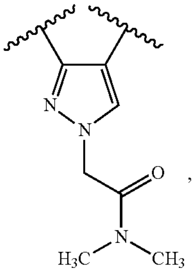 ,
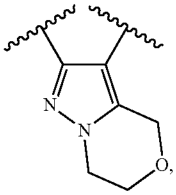 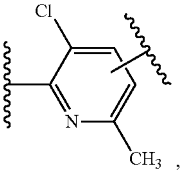 ,
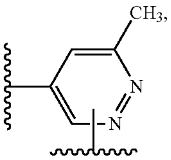 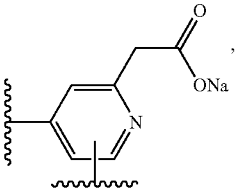 , or
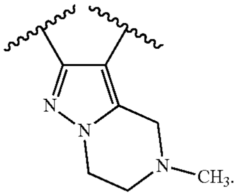
In further embodiments, $G^3$ is optionally substituted $C_6$-$C_{10}$ cycloalkylene, e.g.,
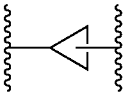, 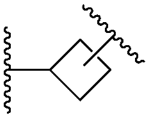, 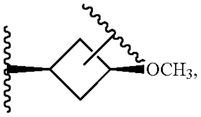
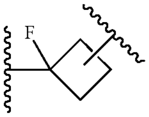, 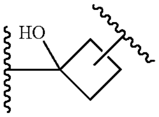,
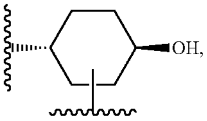 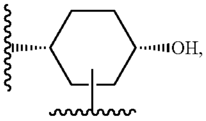 or
-continued
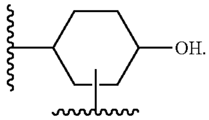
In some embodiments, $A^1$, $G^1$, $G^2$, and $G^3$ combine to form optionally substituted $C_6$-$C_{10}$ aryl, e.g.,
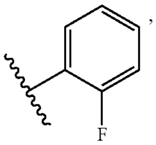, 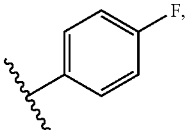 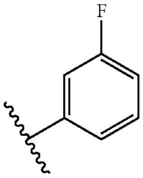,
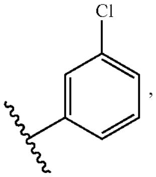, 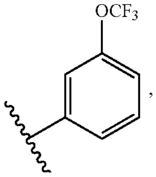, 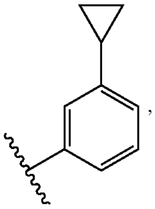,
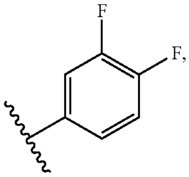 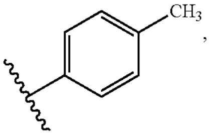, or
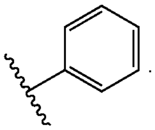.
In other embodiments, $A^1$, $G^1$, $G^2$, and $G^3$ combine to form optionally substituted $C_2$-$C_9$ heteroaryl, e.g.,
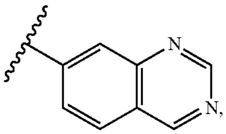 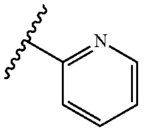,
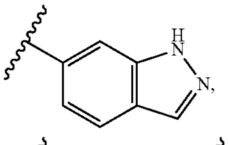 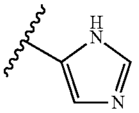,
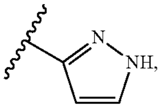 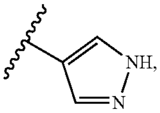 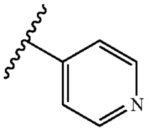,
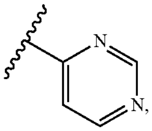 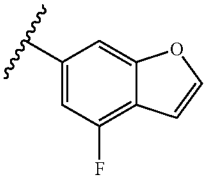, -continued

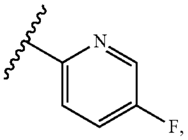, or 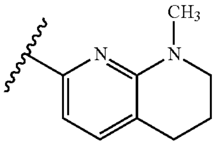,

In further embodiments, $A^1$, $G^1$, $G^2$, and $G^3$ combine to form optionally substituted $C_2$-$C_9$ heterocyclyl, e.g.,

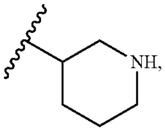, 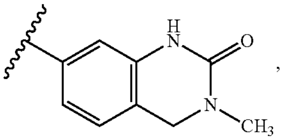,

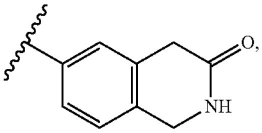, 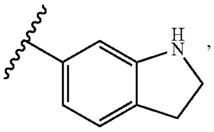,

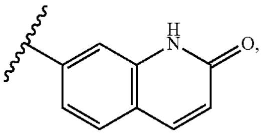, 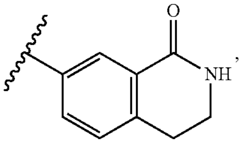,

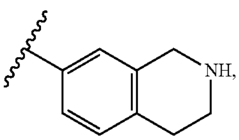, 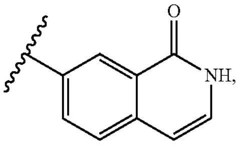,

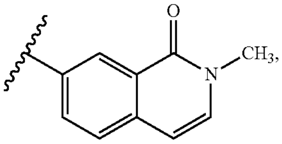,

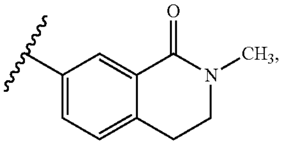,

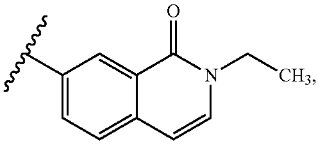,

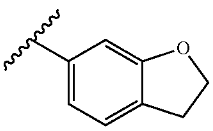, 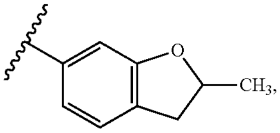,

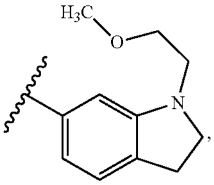, 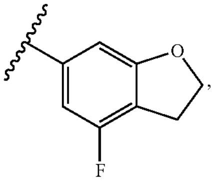,

-continued

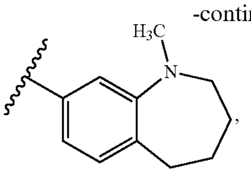, 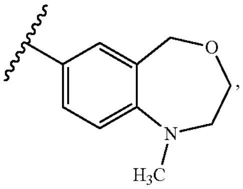,

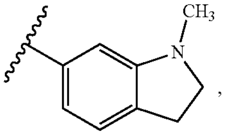, 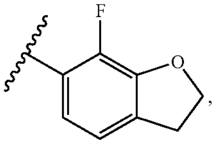,

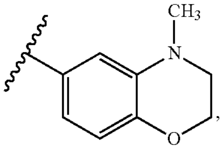, or 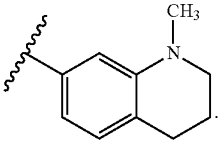.

In certain embodiments, $R^1$ is hydrogen. In other embodiments, $R^1$ is optionally substituted $C_1$-$C_6$ acyl, e.g., acetyl. In further embodiments, $R^1$ is optionally substituted $C_1$-$C_6$ alkyl, e.g., methyl, tert-butyl, iso-propyl, or

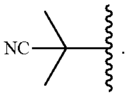.

In yet other embodiments, $R^1$ is optionally substituted $C_1$-$C_6$ heteroalkyl, e.g.,

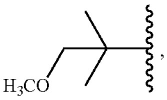, 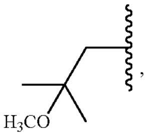, 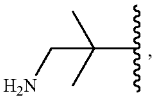,

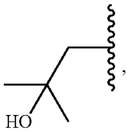, or 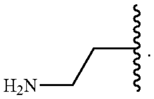.

In some embodiments, $R^1$ is optionally substituted $C_2$-$C_9$ heterocyclyl, e.g.,

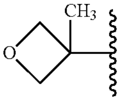, or 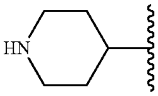.

In further embodiments, $R^1$ is —$SO_2R^6$. In some embodiments, $R^6$ is optionally substituted $C_1$-$C_6$ alkyl, e.g., methyl, iso-propyl, or

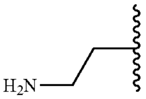.

In some embodiments, $R^1$ is

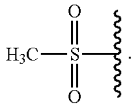 [SMILES: *S(C)(=O)=O]

In some embodiments, the degradation moiety is a ubiquitin ligase binding moiety.

In some embodiments, the ubiquitin ligase binding moiety comprises a Cereblon ligand, an IAP (Inhibitors of Apoptosis) ligand, a mouse double minute 2 homolog (MDM2), or a von Hippel-Lindau (VHL) ligand, or a derivative or analog thereof.

In some embodiments, the degradation moiety is a ubiquitin ligase binding moiety.

In some embodiments, the ubiquitin ligase binding moiety comprises a Cereblon ligand, an IAP (Inhibitors of Apoptosis) ligand, a mouse double minute 2 homolog (MDM2), or a von Hippel-Lindau (VHL) ligand, or a derivative or analog thereof.

In some embodiments, the degradation moiety includes the structure of Formula Y:

Formula Y

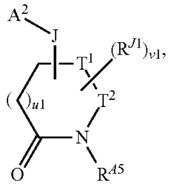

where $A^2$ is a bond between the degradation moiety and the linker;

v1 is 0, 1, 2, 3, 4, or 5;

u1 is 1, 2, or 3;

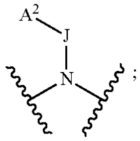

$T^1$ is a bond or N $T^2$ is

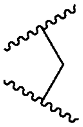 , 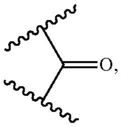 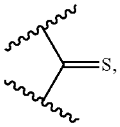 or

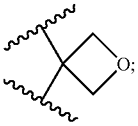

$R^{5A}$ is H, optionally substituted $C_1$-$C_6$ alkyl, or optionally substituted $C_1$-$C_6$ heteroalkyl;

each $R^{J1}$ is, independently, halogen, optionally substituted $C_1$-$C_6$ alkyl, or optionally substituted $C_1$-$C_6$ heteroalkyl; and J is absent, optionally substituted $C_3$-$C_{10}$ carbocyclylene, optionally substituted $C_6$-$C_{10}$ arylene, optionally substituted $C_2$-$C_9$ heterocyclylene, or optionally substituted $C_2$-$C_9$ heteroarylene, or a pharmaceutically acceptable salt thereof.

In some embodiments, $T^1$ is a bond. In some embodiments, $T^1$ is

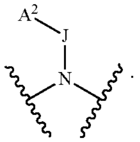

In some embodiments, $T^2$ is

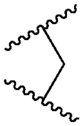 , 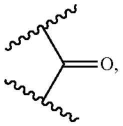 or 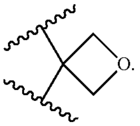

In some embodiments, $T^2$ is

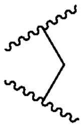 or 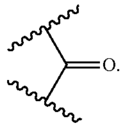

In some embodiments, $T^2$ is

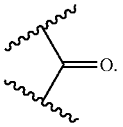 [SMILES: *C(*)=O]

In some embodiments, the structure of Formula Y has the structure of Formula Y1:

Formula Y1

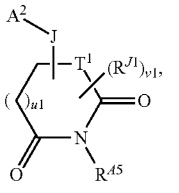

or a pharmaceutically acceptable salt thereof.

In some embodiments, the structure of Formula Y has the structure of Formula Y2:

Formula Y2

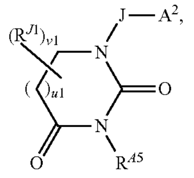

or a pharmaceutically acceptable salt thereof.

In some embodiments, the structure of Formula Y has the structure of Formula Z:

Formula Z

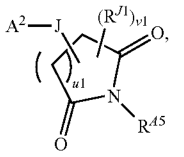

or a pharmaceutically acceptable salt thereof.

In some embodiments, u1 is 1. In some embodiments, u1 is 2. In some embodiments u1 is 3.

In some embodiments, the structure of Formula Z has the structure of Formula AA:

Formula AA

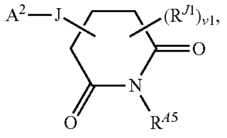

or a pharmaceutically acceptable salt thereof.

Formula AB

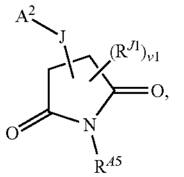

In some embodiments, the structure of Formula Z has the structure of Formula AC:

Formula AC

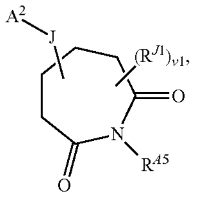

or a pharmaceutically acceptable salt thereof.

In some embodiments, v1 is 0, 1, 2, or 3. In some embodiments, v1 is 0. In some embodiments, v1 is 1. In some embodiments, v1 is 2. In some embodiments, v1 is 3.

In some embodiments, the structure of Formula AA has the structure of Formula AA1:

Formula AA1

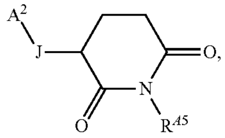

or a pharmaceutically acceptable salt thereof.

In some embodiments, the structure of Formula AB has the structure of Formula AB1:

Formula AB1

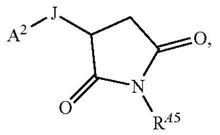

or a pharmaceutically acceptable salt thereof.

In some embodiments, the structure of Formula AC has the structure of Formula AC1:

Formula AC1

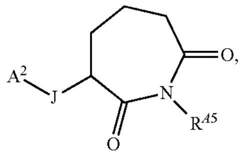

or a pharmaceutically acceptable salt thereof.

In some embodiments, J is absent. In some embodiments, J is optionally substituted $C_3$-$C_{10}$ carbocyclylene or optionally substituted $C_6$-$C_{10}$ arylene. In some embodiments, J is optionally substituted $C_2$-$C_9$ heterocyclylene or optionally substituted $C_2$-$C_9$ heteroarylene.

In some embodiments, J is optionally substituted heterocyclylene. In some embodiments, J is optionally substituted $C_6$-$C_{10}$ arylene.

In some embodiments, the structure of Formula AA has the structure of Formula AA2:

Formula AA1

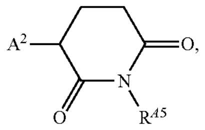

or a pharmaceutically acceptable salt thereof.

In some embodiments, the structure of Formula AA has the structure of Formula AA3:

Formula AA3

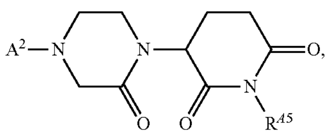

or a pharmaceutically acceptable salt thereof.

In some embodiments, the structure of Formula AA has the structure of Formula AA4:

Formula AA4

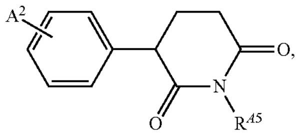

or a pharmaceutically acceptable salt thereof.

In some embodiments, $R^{A5}$ is H or optionally substituted $C_1$-$C_6$ alkyl. In some embodiments, $R^{A5}$ is H or methyl. In some embodiments, $R^{A5}$ is H. In some embodiments, $R^{A5}$ is methyl.

In some embodiments, the structure of Formula AA has the structure of Formula A:

Formula A

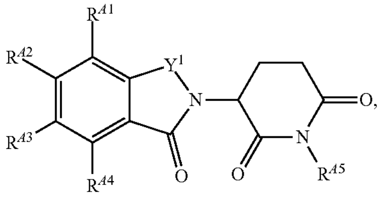

where $Y^1$ is

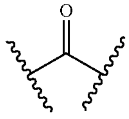 , 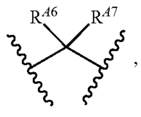 , or 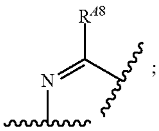 ;

$R^{A5}$ is H, optionally substituted $C_1$-$C_6$ alkyl, or optionally substituted $C_1$-$C_6$ heteroalkyl;

$R^{A6}$ is H or optionally substituted $C_1$-$C_6$ alkyl; and $R^{A7}$ is H or optionally substituted $C_1$-$C_6$ alkyl; or $R^{A6}$ and $R^{A7}$, together with the carbon atom to which each is bound, combine to form optionally substituted $C_3$-$C_6$ carbocyclyl or optionally substituted $C_2$-$C_5$ heterocyclyl; or $R^{A6}$ and $R^{A7}$, together with the carbon atom to which each is bound, combine to form optionally substituted $C_3$-$C_6$ carbocyclyl or optionally substituted $C_2$-$C_5$ heterocyclyl;

$R^{A8}$ is H, optionally substituted $C_1$-$C_6$ alkyl, or optionally substituted $C_1$-$C_6$ heteroalkyl;

each of $R^{A1}$, $R^{A2}$, $R^{A3}$ and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

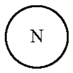 ; and 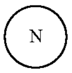

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$, and $R^{A4}$ is $A^2$, or

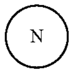

is substituted with $A^2$, or a pharmaceutically acceptable salt thereof.

In some embodiments, each of $R^{A1}$, $R^{A2}$, $R^{A3}$, and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

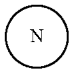 ; and 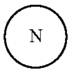

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$ and $R^{A4}$ is $A^2$, or

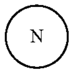

is substituted with $A^2$, or a pharmaceutically acceptable salt thereof.

In some embodiments, each of $R^{A1}$, $R^{A2}$, $R^{A3}$, and $R^{A4}$ is, H, $A^2$, halogen, optionally substituted $C_1$-$C_6$ alkyl, optionally substituted $C_1$-$C_6$ heteroalkyl, optionally substituted —O—$C_3$-$C_6$ carbocyclyl, hydroxyl, optionally substituted amino; or $R^{A1}$ and $R^{A2}$, $R^{A2}$ and $R^{A3}$, or $R^{A3}$ and $R^{A4}$, together with the carbon atoms to which each is attached, combine, to form

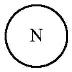 ; and 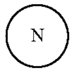

is optionally substituted $C_2$-$C_6$ heterocyclyl, which is optionally substituted with $A^2$, where one of $R^{A1}$, $R^{A2}$, $R^{A3}$, and $R^{A4}$ is $A^2$, or

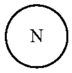

is substituted with $A^2$.

In some embodiments, each of $R^{A1}$, $R^{A2}$, $R^{A3}$, and $R^{A4}$ is, independently, H, $A^2$, F,

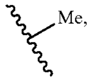 , 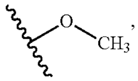 , 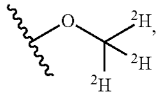 , or 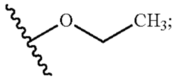 ;

or $R^{A1}$ and $R^{A2}$, $R^{A2}$ and $R^{A3}$, or $R^{A3}$ and $R^{A4}$, together with the carbon atoms to which each is attached, combine to form

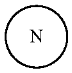 ; and 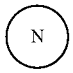

is optionally substituted $C_2$-$C_9$ heterocyclyl, which is optionally substituted with $A^2$, where one of $R^{A1}$, $R^{A2}$, $R^{A3}$, and $R^{A4}$ is $A^2$, or

is substituted with $A^2$.

In some embodiments, $R^{A1}$ is $A^2$. In some embodiments, $R^{A2}$ is $A^2$. In some embodiments, $R^{A3}$ is $A^2$. In some embodiments, $R^{A4}$ is $A^2$. In some embodiments, $R^{A5}$ is $A^2$.

In some embodiments, $R^{A5}$ is H or optionally substituted $C_1$-$C_6$ alkyl.

In some embodiments, $R^{A5}$ is H or

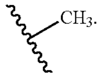

In some embodiments, $R^{A5}$ is H. In some embodiments, $R^{A5}$ is

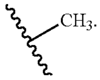

In some embodiments, $Y^1$ is or

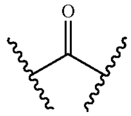 or 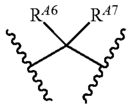 .

In some embodiments, $Y^1$ is

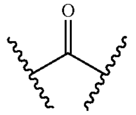 .

In some embodiments, $Y^1$ is

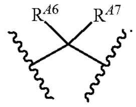

In some embodiments, each of $R^{A6}$ and $R^{A7}$ is, independently, H, F,

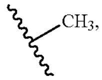 , 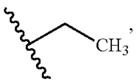 , or 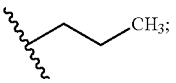 ;

or $R^{A6}$ and $R^{A7}$, together with the carbon atom to which each is bound, combine to form

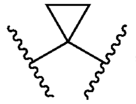 , 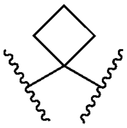 , 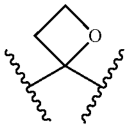 , or 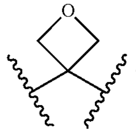 .

In some embodiments, $Y^1$ is

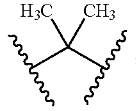 , 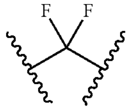 , 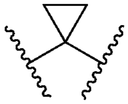 , 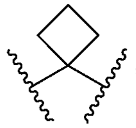 , 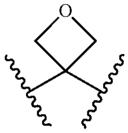 , or 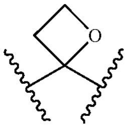 .

In some embodiments, the structure of Formula A has the structure of Formula A1:

Formula A1

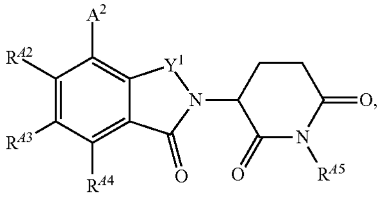

or a pharmaceutically acceptable salt thereof.

In some embodiments, the structure of Formula A has the structure of Formula A2:

Formula A2

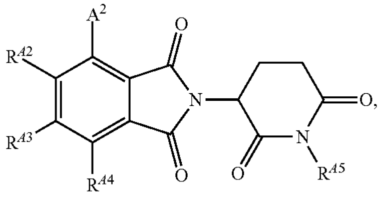

or a pharmaceutically acceptable salt thereof.

In some embodiments, the structure of Formula A has the structure of Formula A3:

Formula A3

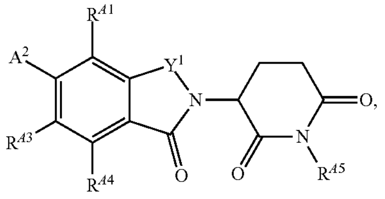

or a pharmaceutically acceptable salt thereof.

In some embodiments, the structure of Formula A has the structure of Formula A4:

Formula A4

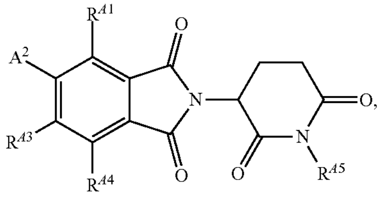

or a pharmaceutically acceptable salt thereof.

In some embodiments, the structure of Formula A has the structure of Formula A5:

Formula A5

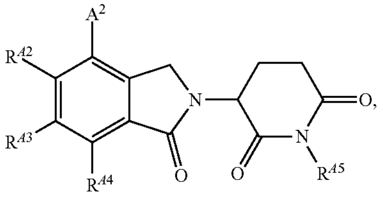

or a pharmaceutically acceptable salt thereof.

In some embodiments, the structure of Formula A has the structure of Formula A6:

Formula A6

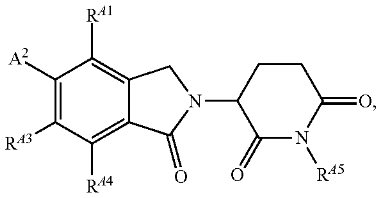

or a pharmaceutically acceptable salt thereof.

In some embodiments, the structure of Formula A has the structure of Formula A7:

Formula A7

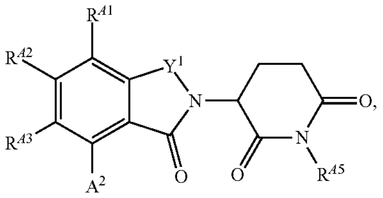

or a pharmaceutically acceptable salt thereof.

In some embodiments, the structure of Formula A has the structure of Formula A8:

Formula A8

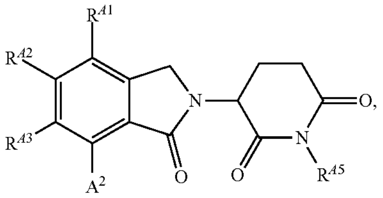

or a pharmaceutically acceptable salt thereof.

In some embodiments, the structure of Formula A has the structure of Formula A9:

Formula A9

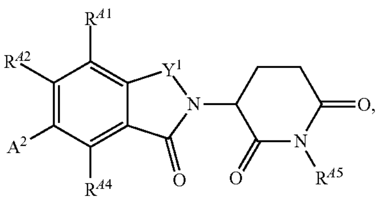

or a pharmaceutically acceptable salt thereof.

In some embodiments, the structure of Formula A has the structure of Formula A10:

Formula A10

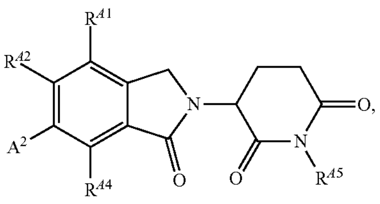

or a pharmaceutically acceptable salt thereof.

In some embodiments, wherein the structure of Formula A is

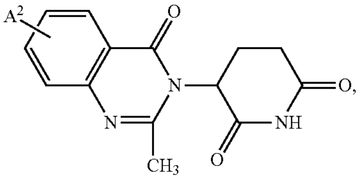

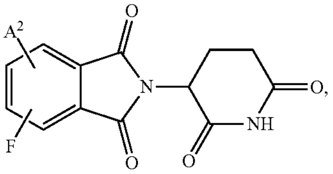

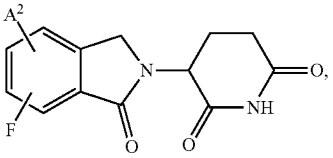

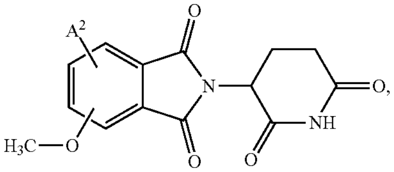

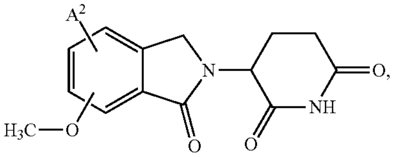

-continued

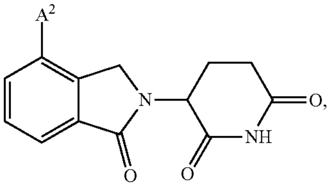

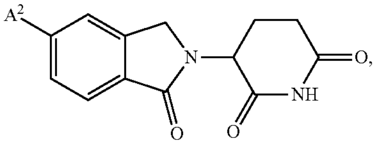

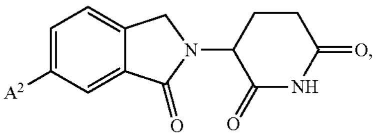

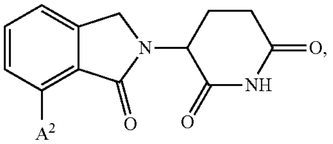

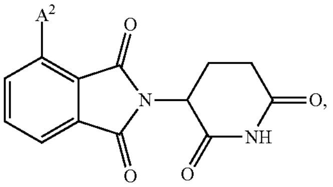

or

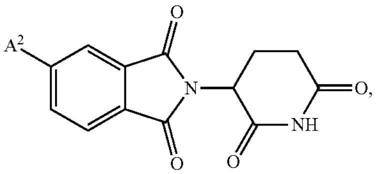

or derivative or analog thereof.

In some embodiments, the structure of Formula A is

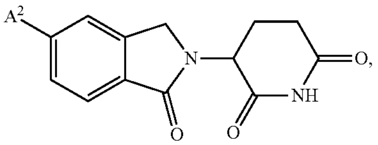

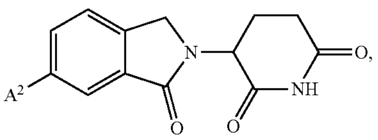

or

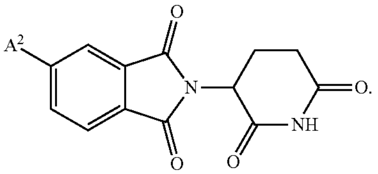

In some embodiments, the structure of Formula A is

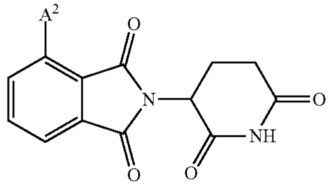

or

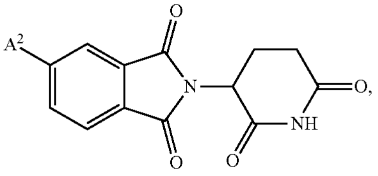

or derivative or analog thereof.

In some embodiments, is

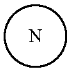 is 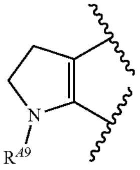 or 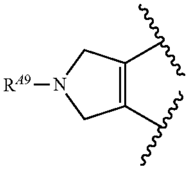, where $R^{A9}$ is H, $A^2$, optionally substituted $C_1$-$C_6$ alkyl, or optionally substituted $C_1$-$C_6$ heteroalkyl.

In some embodiments, the structure of Formula A is

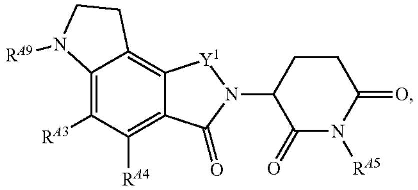

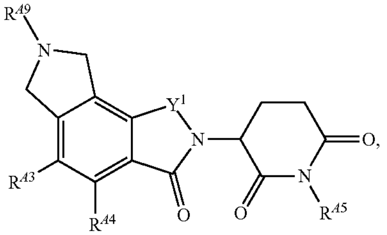

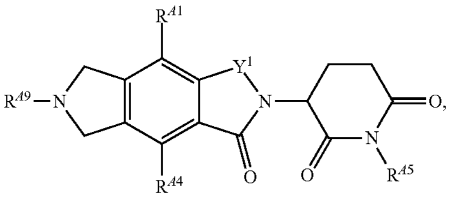

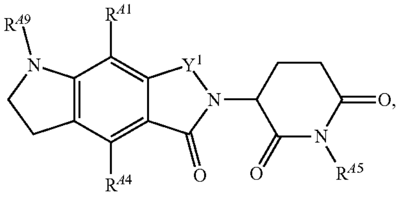

-continued

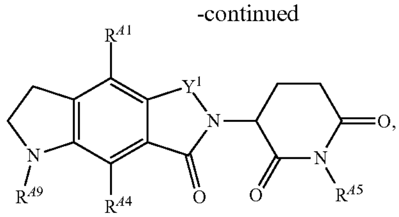

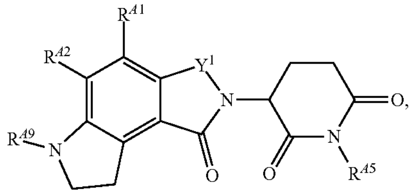

or

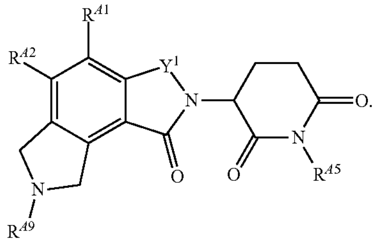

In some embodiments, $R^{A9}$ is H, $A^2$, or optionally substituted $C_1$-$C_6$ alkyl. In some embodiments, $R^{A9}$ is H, $A^2$, or methyl. In some embodiments, $R^{9A}$ is H. In some embodiments, $R^{9A}$ is methyl. In some embodiments, $R^{A9}$ is $A^2$.

In some embodiments, the structure of Formula A is

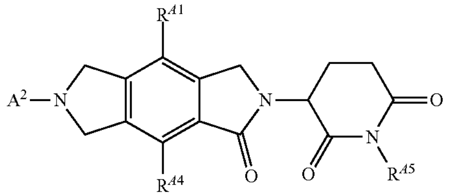

or

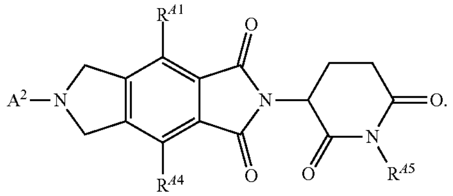

In some embodiments, the structure of Formula AA has the structure of Formula B:

Formula B

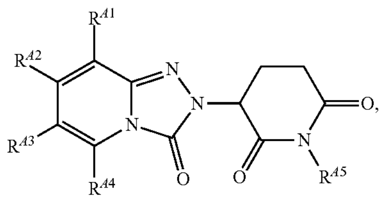

where $R^{A5}$ is H, optionally substituted $C_1$-$C_6$ alkyl, or optionally substituted $C_1$-$C_6$ heteroalkyl; each of $R^{A1}$, $R^{A2}$, $R^{A3}$ and $R^{A4}$ is, independently, H, $A^2$, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted —O—$C_3$-$C_6$ carbocyclyl, hydroxyl, thiol, or optionally substituted amino; or $R^{A1}$ and $R^{A2}$, $R^{A2}$ and $R^{A3}$, and/or $R^{A3}$ and $R^{A4}$, together with the carbon atoms to which each is attached, combine to form

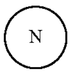 ; and 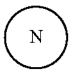

is optionally substituted $C_6$-$C_{10}$ aryl, optionally substituted $C_3$-$C_{10}$ carbocyclyl, optionally substituted $C_2$-$C_9$ heteroaryl, or $C_2$-$C_9$ heterocyclyl, any of which is optionally substituted with $A^2$, where one of $R^{A1}$, $R^{A2}$, $R^{A3}$, and $R^{A4}$ is $A^2$, or

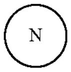

is substituted with $A^2$, or a pharmaceutically acceptable salt thereof.

In some embodiments, each of $R^{A1}$, $R^{A2}$, $R^{A3}$, and $R^{A4}$ is, H, $A^2$, halogen, optionally substituted $C_1$-$C_6$ alkyl, optionally substituted $C_1$-$C_6$ heteroalkyl, optionally substituted —O—$C_3$-$C_6$ carbocyclyl, hydroxyl, optionally substituted amino; or $R^{A1}$ and $R^{A2}$, $R^{A2}$ and $R^{A3}$, or $R^{A3}$ and $R^{A4}$, together with the carbon atoms to which each is attached, combine to form

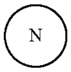 ; and 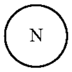

is optionally substituted $C_2$-$C_9$ heterocyclyl, which is optionally substituted with $A^2$, where one of $R^{A1}$, $R^{A2}$, $R^{A3}$, and $R^{A4}$ is $A^2$, or

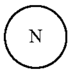

is substituted with $A^2$.

In some embodiments, each of $R^{A1}$, $R^{A2}$, $R^{A3}$, and $R^{A4}$ is, independently, H, $A^2$, F,

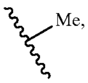 , 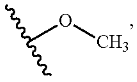 , 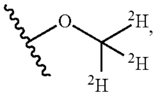 or

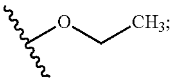 ;

or $R^{A1}$ and $R^{A2}$, $R^{A2}$ and $R^{A3}$, or $R^{A3}$ and $R^{A4}$ together with the carbon atoms to which each is attached, combine to form

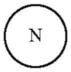 ; and 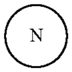

is optionally substituted $C_2$-$C_9$ heterocyclyl, which is optionally substituted with $A^2$, where one of $R^{A1}$, $R^{A2}$, $R^{A3}$, and $R^{A4}$ is $A^2$, or

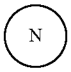

is substituted with $A^2$.

In some embodiments, $R^{A1}$ is $A^2$. In some embodiments, $R^{A2}$ is $A^2$. In some embodiments, $R^{A3}$ is $A^2$. In some embodiments, $R^{A4}$ is $A^2$. In some embodiments, $R^{A5}$ is $A^2$.

In some embodiments, $R^{A5}$ is H or optionally substituted $C_1$-$C_6$ alkyl.

In some embodiments, $R^{A5}$ is H or

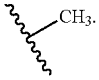 .

In some embodiments, $R^{A5}$ is H. In some embodiments, $R^{A5}$ is

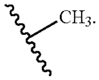 .

In some embodiments, the structure of Formula B has the structure of Formula B1:

Formula B1

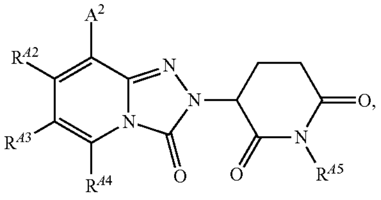

or a pharmaceutically acceptable salt thereof.

In some embodiments, the structure of Formula B has the structure of Formula B2:

Formula B2

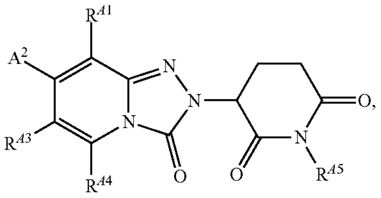

or a pharmaceutically acceptable salt thereof.

In some embodiments, the structure of Formula B has the structure of Formula B3:

Formula B3

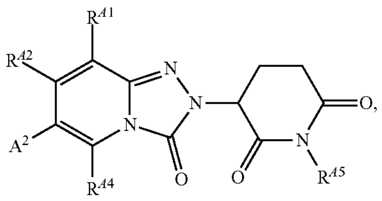

or a pharmaceutically acceptable salt thereof.

In some embodiments, the structure of Formula B has the structure of Formula B4:

Formula B4

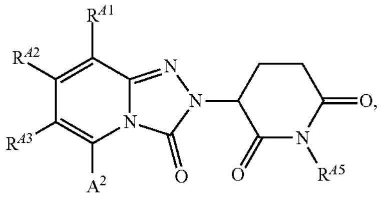

or a pharmaceutically acceptable salt thereof.

In some embodiments, the structure of Formula B is

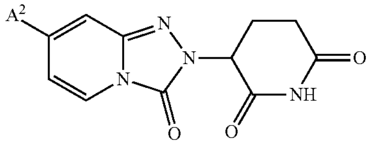

or

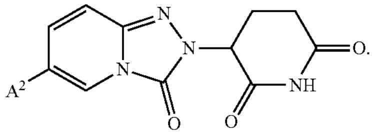

In some embodiments, the structure of Formula B is

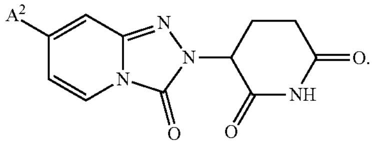

In some embodiments, the structure of Formula B is

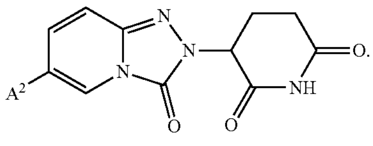

In some embodiments, the ubiquitin ligase binding moiety comprises a von Hippel-Lindau ligand.

In some embodiments, the von Hippel-Lindau ligand has the structure of

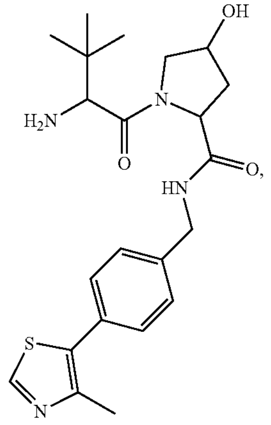 [SMILES: Cc1ncsc1-c1ccc(CNC(=O)C2CC(O)CN2C(=O)C(N)C(C)(C)C)cc1]

or derivative or analog thereof.

In some embodiments, the degradation moiety includes the structure of Formula C:

Formula C

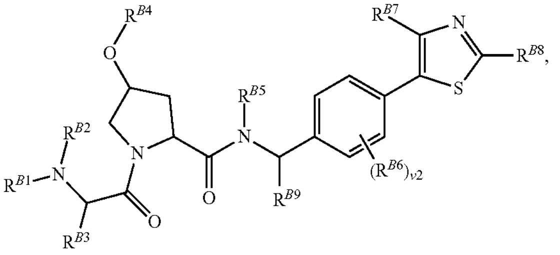

where $R^{B1}$ and $R^{B9}$ are, independently, H, $A^2$, optionally substituted $C_1$-$C_6$ alkyl, or optionally substituted $C_1$-$C_6$ heteroalkyl;

$R^{B2}$ is H, optionally substituted $C_1$-$C_6$ alkyl, or optionally substituted $C_1$-$C_6$ heteroalkyl;

$R^{B3}$ is $A^2$, optionally substituted $C_1$-$C_6$ alkyl, optionally substituted $C_1$-$C_6$ heteroalkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{B4}$ is H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{B5}$ is H, optionally substituted $C_1$-$C_6$ alkyl, or optionally substituted $C_1$-$C_6$ heteroalkyl;

v2 is 0, 1, 2, 3, or 4;

each $R^{B6}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino; and each of $R^{B7}$ and $R^{B8}$ is, independently, H, halogen, optionally substituted $C_1$-$C_6$ alkyl, or optionally substituted $C_6$-$C_{10}$ aryl, where one of $R^{B1}$, $R^{B3}$, $R^{B6}$, and $R^{B9}$ is $A^2$, or a pharmaceutically acceptable salt thereof.
In some embodiments, the structure of Formula C is
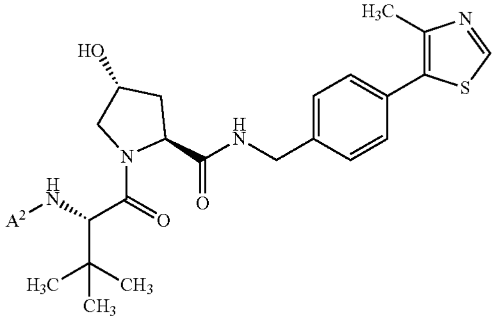
or
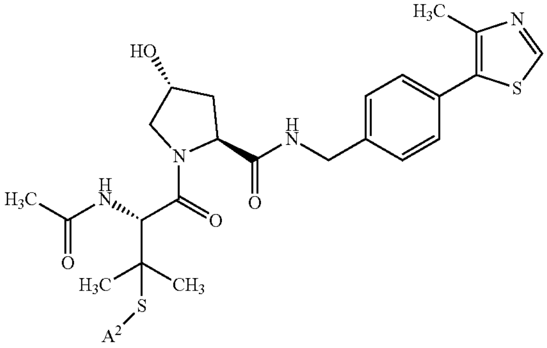
,
or derivative or analog thereof. In some embodiments, the structure of Formula C is
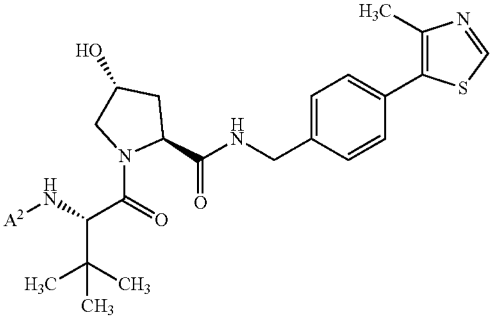
.
In some embodiments, the structure of Formula C is
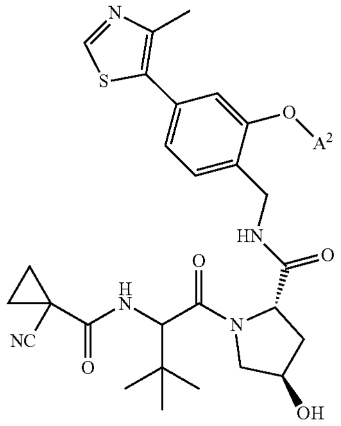
or
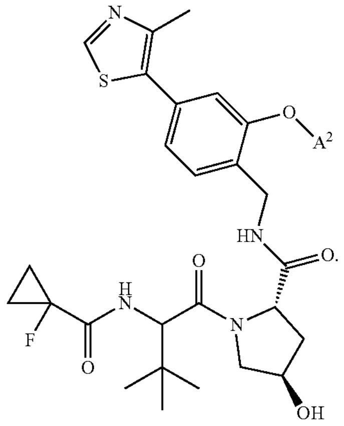
In some embodiments, the structure of Formula C is
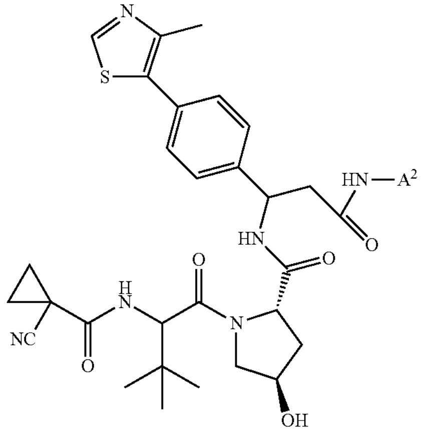
or -continued

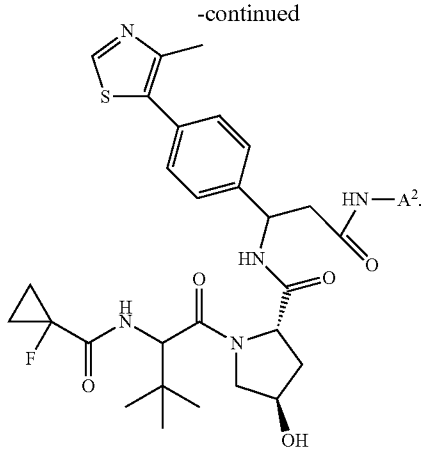

In some embodiments, the degrader moiety is a degrader moiety described in International Patent Publication No. WO2019/195201, the degrader moieties of which are herein incorporated by reference.

In some embodiments, the degrader moiety includes the structure of Formula D:

Formula D

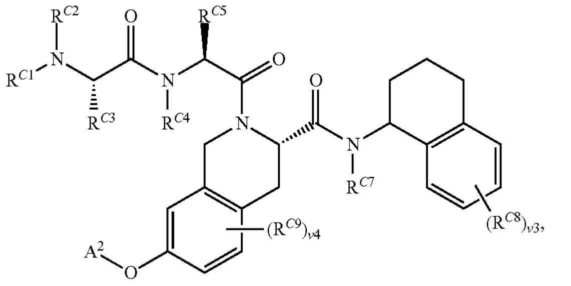

where $A^2$ is a bond between B and the linker;

each of $R^{C1}$, $R^{C2}$, and $R^{C7}$ is, independently, H, optionally substituted $C_1$-$C_6$ alkyl, or optionally substituted $C_1$-$C_6$ heteroalkyl;

$R^{C3}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

$R^{C5}$ is optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

v3 is 0, 1, 2, 3, or 4;

each $R^{C8}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

v4 is 0, 1, 2, 3, or 4; and each $R^{C9}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the structure of Formula D is

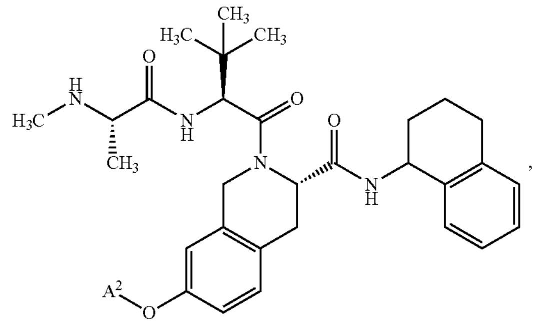

or derivative or analog thereof.

In some embodiments, the degrader moiety includes the structure of Formula E:

Formula E

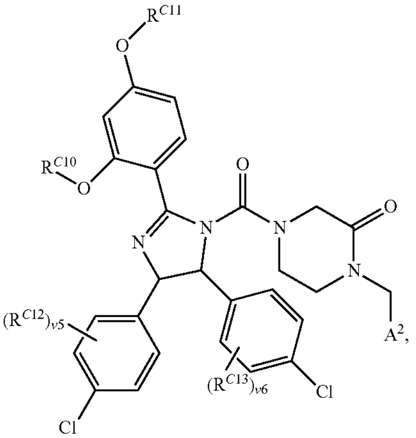

where $A^2$ is a bond between B and the linker;

each of $R^{C10}$ and $R^{C11}$ is, independently, H, optionally substituted $C_1$-$C_6$ alkyl, optionally substituted $C_3$-$C_{10}$ carbocyclyl, optionally substituted $C_6$-$C_{10}$ aryl, optionally substituted $C_1$-$C_6$ alkyl $C_3$-$C_{10}$ carbocyclyl, or optionally substituted $C_1$-$C_6$ alkyl $C_6$-$C_{10}$ aryl;

v5 is 0, 1, 2, 3, or 4;

each $R^{C12}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

v6 is 0, 1, 2, 3, or 4; and each $R^{21}$ is, independently, halogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, hydroxy, thiol, or optionally substituted amino, or a pharmaceutically acceptable salt thereof.

In some embodiments, the structure of Formula E is

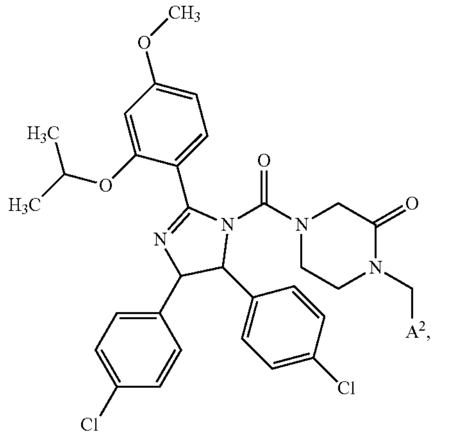

or derivative or analog thereof.

In some embodiments, the degradation moiety includes the structure of Formula FA:

Formula FA

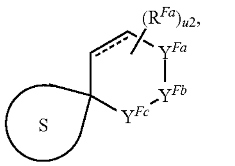

where

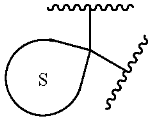 is 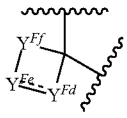, or a bicyclic moiety which is substituted with $A^2$ and substituted with one or more groups independently selected from H, $R^{FF1}$, and oxo;

– – – is a single bond or a double bond;

u2 is 0, 1, 2, or 3;

$A^2$ is a bond between the degrader and the linker;

$Y^{Fa}$ is $CR^{Fb}R^{Fc}$, C═O, C═S, C═$CH_2$, $SO_2$, S(O), P(O)Oalkyl, P(O)NHalkyl, $P(O)N(alkyl)_2$, P(O)alkyl, P(O)OH, $P(O)NH_2$;

$Y^{Fb}$ is NH, $NR^{FF1}$, $CH_2$, $CHR^{FF1}$, $C(R^{FF1})_2$, O, or S;

$Y^{Fc}$ is $CR^{Fd}R^{Fe}$, C═O, C═S, C═$CH_2$, $SO_2$, S(O), P(O)Oalkyl, P(O)NHalkyl, $P(O)N(alkyl)_2$, P(O)alkyl, P(O)OH, $P(O)NH_2$;

each of $R^{Fb}R^{Fc}R^{Fd}$, and $R^{Fe}$ is, independently, H, alkyl, aliphatic, heteroaliphatic, aryl, heteroaryl, carbocyclyl, hydroxyl, alkoxy, amino, —NHalkyl, or —$Nalkyl_2$;

or $R^{Fb}$ and $R^{Fc}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O;

or $R^{Fd}$ and $R^{Fe}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and O; and or $R^{Fd}$ and $R^{Fb}$, together with the carbon atoms to which each is attached, combine to form a 1, 2, 3, or 4 carbon bridged ring;

each of $Y^{Fd}$ and $Y^{Ff}$ is, independently, $CH_2$, $CHR^{FF2}$, $C(R^{FF2})_2$, C(O), N, NH, $NR^{FF3}$, O, S or S(O);

$Y^{Fe}$ is a bond or a divalent moiety attached to $Y^{Fd}$ and $Y^{Ff}$ that contains 1 to 5 contiguous carbon atoms that form a 3 to 8-membered ring, wherein 1, 2, or 3 carbon atoms can be replaced with a nitrogen, oxygen, or sulfur atom;

wherein one of the ring atoms is substituted with $A^2$ and the others are substituted with one or more groups independently selected from H and $R^{FF1}$; and wherein the contiguous atoms of $Y^{Fe}$ can be attached through a single or double bond;

each $R^{FF1}$ is, independently, H, alkyl, alkenyl, alkynyl, aliphatic, heteroaliphatic, carbocyclyl, halogen, hydroxyl, amino, cyano, alkoxy, aryl, heteroaryl, heterocyclyl, alkylamino, alkylhydroxyl, or haloalkyl;

each $R^{FF2}$ is, independently, alkyl, alkene, alkyne, halogen, hydroxyl, alkoxy, azide, amino, —C(O)H, —C(O)OH, —C(O)(aliphatic, including alkyl), —C(O)O(aliphatic, including alkyl), —NH(aliphatic, including alkyl), —N(aliphatic including alkyl)(aliphatic including alkyl), —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, aliphatic, heteroaliphatic, aryl, heteroaryl, hetercyclic, carbocyclic, cyano, nitro, nitroso, —SH, —Salkyl, or haloalkyl; and $R^{FF3}$ is alkyl, alkenyl, alkynyl, —C(O)H, —C(O)OH, —C(O)alkyl, or —C(O)Oalkyl, wherein if $Y^{Fe}$ or $Y^{Ff}$ is substituted with $A^2$, then $Y^{Fe}$ is a bond, or a pharmaceutically acceptable salt thereof.

In some embodiments, the compound of Formula FA has the structure of Formula FA1:

Formula FA1

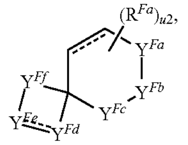

or a pharmaceutically acceptable salt thereof.

In some embodiments, the degradation moiety includes the structure of Formula FB:

Formula FB

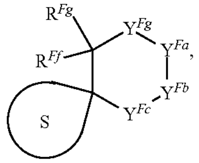

-continued where 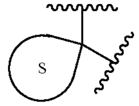 is 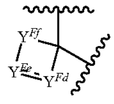 , or a bicyclic moiety which is substituted with $A^2$ and substituted with one or more groups independently selected from H, $R^{FF1}$, and oxo;

$A^2$ is a bond between the degrader and the linker;

$Y^{Fa}$ is $CR^{Fb}R^{Fc}$, C═O, C═S, C═$CH_2$, $SO_2$, S(O), P(O)Oalkyl, P(O)NHalkyl, P(O)N(alkyl)$_2$, P(O)alkyl, P(O)OH, P(O)$NH_2$;

each of $Y^{Fb}$ and $Y^{Fg}$ is, independently, NH, $NR^{FF1}$, $CH_2$, $CHR^{FF1}$, C($R^{FF1}$)$_2$, O, or S;

$Y^{Fc}$ is $CR^{Fd}R^{Fe}$, C═O, C═S, C═$CH_2$, $SO_2$, S(O), P(O)Oalkyl, P(O)NHalkyl, P(O)N(alkyl)$_2$, P(O)alkyl, P(O)OH, P(O)$NH_2$;

each of $R^{Fb}$, $R^{Fc}$, $R^{Fd}$, $R^{Fe}$, $R^{Ff}$, and $R^{Fg}$ is, independently, H, alkyl, aliphatic, heteroaliphatic, aryl, heteroaryl, carbocyclyl, hydroxyl, alkoxy, amino, —NHalkyl, or —Nalkyl$_2$;

or $R^{Fb}$ and $R^{Fc}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and 0;

or $R^{Fd}$ and $R^{Fe}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and 0;

or $R^{Ff}$ and $R^{Fg}$, together with the carbon atom to which each is attached, combine to form a 3-, 4-, 5-, or 6-membered spirocarbocyclylene, or a 4-, 5-, or 6-membered spiroheterocyclylene comprising 1 or 2 heteroatoms selected from N and 0;

or $R^{Fd}$ and $R^{Fb}$, together with the carbon atoms to which each is attached, combine to form a 1, 2, 3, or 4 carbon bridged ring;

or $R^{Fd}$ and $R^{Ff}$, together with the carbon atoms to which each is attached, combine to form a 1, 2, 3, or 4 carbon bridged ring;

or $R^{Fb}$ and $R^{Fg}$, together with the carbon atoms to which each is attached, combine to form a 1, 2, 3, or 4 carbon bridged ring;

each of $Y^{Fd}$ and $Y^{Ff}$ is, independently, $CH_2$, $CHRFF_2$, C($RFF^2$)$_2$, C(O), N, NH $NRFF_3$, O, S or S(O);

$Y^{Fe}$ is a bond or a divalent moiety attached to $Y^{Fd}$ and $Y^{Ff}$ that contains 1 to 5 contiguous carbon atoms that form a 3 to 8-membered ring, wherein 1, 2, or 3 carbon atoms can be replaced with a nitrogen, oxygen, or sulfur atom wherein one of the ring atoms is substituted with $A^2$ and the others are substituted with one or more groups independently selected from H and $R^{FF1}$; and wherein the contiguous atoms of $Y^{Fe}$ can be attached through a single or double bond;

each $R^{FF1}$ is, independently, H, alkyl, alkenyl, alkynyl, aliphatic, heteroaliphatic, carbocyclyl, halogen, hydroxyl, amino, cyano, alkoxy, aryl, heteroaryl, heterocyclyl, alkylamino, alkylhydroxyl, or haloalkyl;

each $R^{FF2}$ is, independently, alkyl, alkene, alkyne, halogen, hydroxyl, alkoxy, azide, amino, —C(O)H, —C(O)OH, —C(O)(aliphatic, including alkyl), —C(O)O(aliphatic, including alkyl), —NH(aliphatic, including alkyl), —N(aliphatic including alkyl)(aliphatic including alkyl), —$NHSO_2$alkyl, —N(alkyl)$SO_2$alkyl, —$NHSO_2$aryl, —N(alkyl)$SO_2$aryl, —$NHSO_2$alkenyl, —N(alkyl)$SO_2$alkenyl, —$NHSO_2$alkynyl, —N(alkyl)$SO_2$alkynyl, aliphatic, heteroaliphatic, aryl, heteroaryl, hetercyclic, carbocyclic, cyano, nitro, nitroso, —SH, —Salkyl, or haloalkyl; and $R^{FF3}$ is alkyl, alkenyl, alkynyl, —C(O)H, —C(O)OH, —C(O)alkyl, or —C(O)Oalkyl, wherein if $Y^{Fd}$ or $Y^{Ff}$ is substituted with $A^2$, then $Y^{Fe}$ is a bond, or a pharmaceutically acceptable salt thereof.

In some embodiments, the compound of Formula FB has the structure of Formula FB1:

Formula FB1

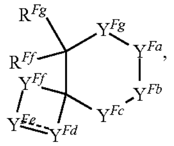

or a pharmaceutically acceptable salt thereof.

In some embodiments, the degradation moiety includes the structure of Formula F1:

Formula F1

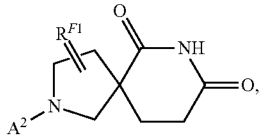

where $A^2$ is a bond between the degrader and the linker; and $R^{F1}$ is absent or O, or a pharmaceutically acceptable salt thereof.

In some embodiments, $R^{F1}$ is absent. In some embodiments, $R^{F1}$ is O.

In some embodiments, the structure of Formula F1 is

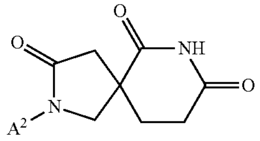

or

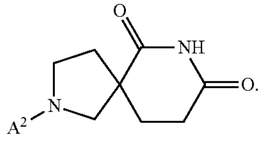

In some embodiments, the degradation moiety includes the structure Formula F2:

Formula F2

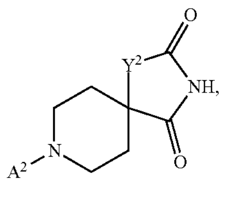

where $A^2$ is a bond between the degrader and the linker; and $Y^2$ is $CH_2$ or NH, or a pharmaceutically acceptable salt thereof.

In some embodiments, $Y^2$ is NH. In some embodiments, $Y^2$ is $CH_2$.

In some embodiments, structure of Formula F2 is

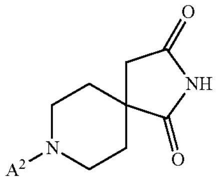 or 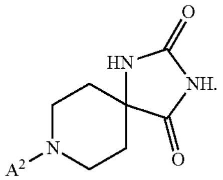

In some embodiments, the degradation moiety includes the structure Formula G:

Formula G

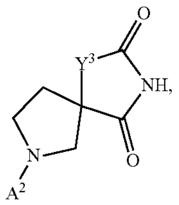

where $A^2$ is a bond between the degrader and the linker; and $Y^3$ is $CH_2$ or NH, or a pharmaceutically acceptable salt thereof.

In some embodiments, $Y^3$ is NH. In some embodiments, $Y^3$ is $CH_2$.

In some embodiments, structure of Formula G is

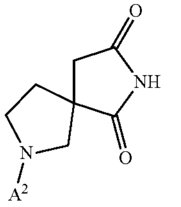 or 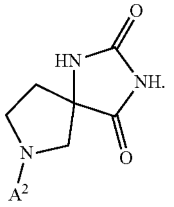

The degradation moiety may also include structures found in, e.g., WO2017/197036; WO2019/204354, WO2019/236483, WO2020/010177; and WO2020/010227, each of which is incorporated by reference in its entirety.

In some embodiments, the linker has the structure of Formula III:

$$A^1\text{-}(B^1)_f\text{—}(C^1)_g\text{—}(B^2)_h\text{-}(D)\text{-}(B^3)_i\text{—}(C^2)_j\text{—}(B^4)_k\text{-}A^2 \quad \text{Formula III}$$

where $A^1$ is a bond between A and the linker; $A^2$ is a bond between the linker and B; each of $B^1$, $B^2$, $B^3$, and $B^4$ is, independently, optionally substituted $C_1$-$C_2$ alkyl, optionally substituted $C_1$-$C_2$ heteroalkyl, O, S, $S(O)_2$, or $NR^N$; each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; each of $C^1$ and $C^2$ is, independently, carbonyl, thiocarbonyl, sulphonyl, or phosphoryl; each of f, g, h, i, j, and k is, independently, 0 or 1; and D is optionally substituted $C_{1-12}$ alkyl, optionally substituted $C_{2-12}$ alkenyl, optionally substituted $C_{2-12}$ alkynyl, optionally substituted $C_2$-$C_{12}$ polyethylene glycol, or optionally substituted $C_{1-12}$ heteroalkyl, or a chemical bond linking $A^1\text{-}(B^1)_f\text{—}(C^1)_g\text{—}(B^2)_h\text{—}$ to $\text{—}(B^3)_i\text{—}(C^2)_j\text{—}(B^4)_k\text{-}A^2$.

In some embodiments, each of $B^1$, $B^2$, $B^3$, and $B^4$ is, independently, optionally substituted $C_1$-$C_4$ alkyl, optionally substituted $C_1$-$C_4$ heteroalkyl, or $NR^N$.

In some embodiments, each $R^N$ is, independently, H or optionally substituted $C_1$-$C_4$ alkyl.

In some embodiments, each $R^N$ is, independently, H or methyl.

In some embodiments, each of $B^1$ and $B^4$ is, independently,

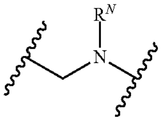, 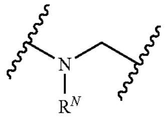,

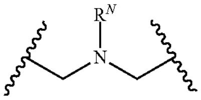, 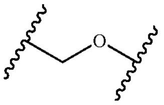,

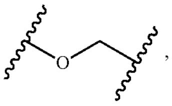, or 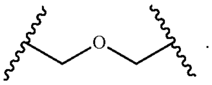.

In some embodiments, $B^1$ is

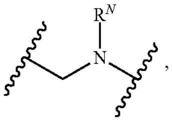, 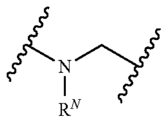,

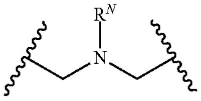, or 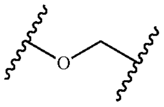.

In some embodiments, each of $C^1$ and $C^2$ is, independently,

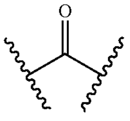 or 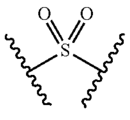.

In some embodiments, $C^1$ is

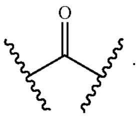 [SMILES: *C(*)=O].

In some embodiments, $B^2$ is $NR^N$. In some embodiments, $B^2$ is optionally substituted $C_1$-$C_4$ alkyl.

In some embodiments, f is 0. In some embodiments, f is 1. In some embodiments, g is 1. In some embodiments, h is 0. In some embodiments, h is 1. In some embodiments, i is 0. In some embodiments, j is 0. In some embodiments, k is 0.

In some embodiments, D is optionally substituted $C_{1-12}$ alkyl, optionally substituted $C_2$-$C_{12}$ polyethylene glycol, or optionally substituted $C_{1-12}$ heteroalkyl. In some embodiments, D is a chemical bond linking $A^1$-$(B^1)_f$—$(C^1)_g$—$(B^2)_h$— to —$(B^3)_i$—$(C^2)_j$—$(B^4)_k$-$A^2$.

In some embodiments, the linker has the structure of

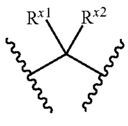,
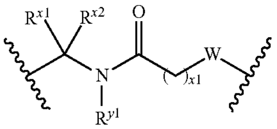,
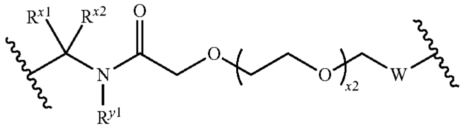,
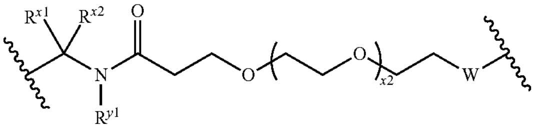,
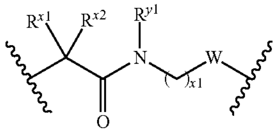,
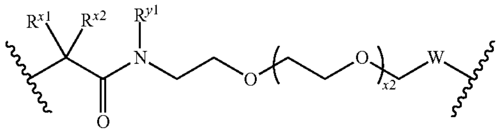,
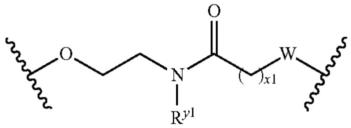,
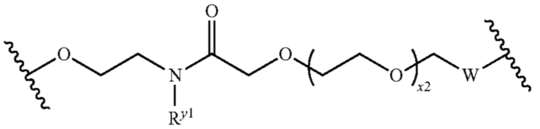,
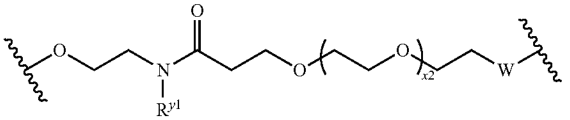,
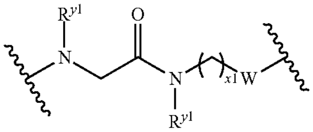,
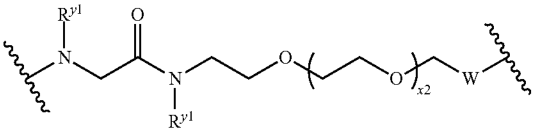,
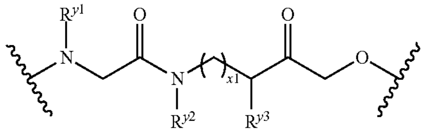, -continued

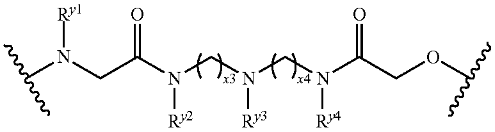,
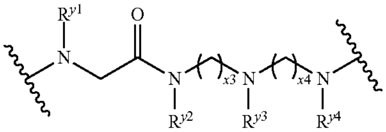,
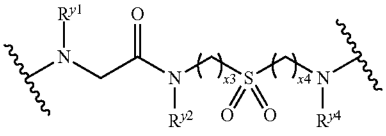,
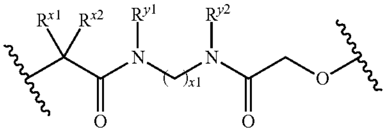,
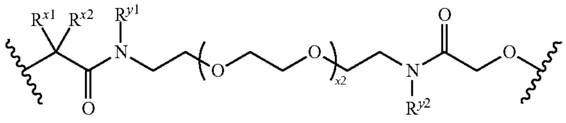,
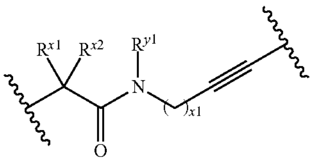,
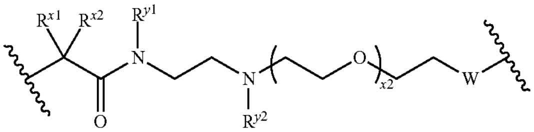,
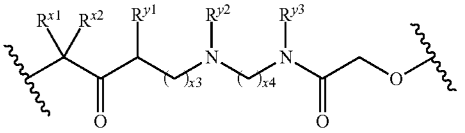,
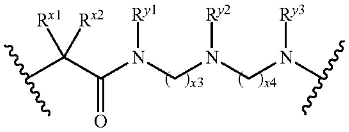,
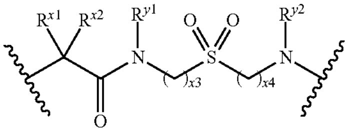,
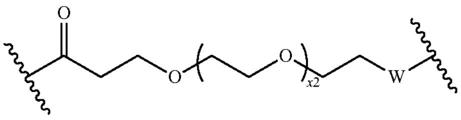, or
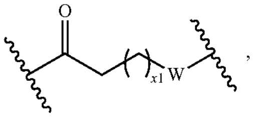, where x1 is 0, 1, 2, 3, 4, 5, 6, 7, 8, 9, 10, 11, 12, 13, or 14; x2 is 0, 1, 2, 3, 4, 5, or 6; x3 is 1 or 2; x4 is 1 or 2; W is

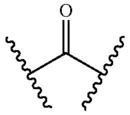, 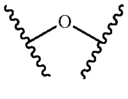, or 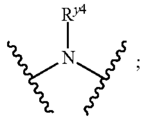;

each of $R^{x1}$ and $R^{x2}$ is, independently, H, halogen, optionally substituted $C_1$-$C_6$ alkyl, optionally substituted $C_1$-$C_6$ heteroalkyl, or optionally substituted $C_3$-$C_6$ carbocyclyl, or $R^{x1}$ and $R^{x2}$, together with the carbon atom to which each is attached, combine to form optionally substituted $C_3$-$C_6$ carbocyclyl or optionally substituted $C_2$-$C_5$ heterocyclyl; and each of $R^{y1}$, $R^{y2}$, $R^{y3}$, and $R^{y4}$ is, independently, H, optionally substituted $C_1$-$C_6$ alkyl, optionally substituted $C_1$-$C_6$ heteroalkyl, or optionally substituted $C_3$-$C_6$ carbocyclyl.

In some embodiments, W is

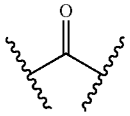.

In some embodiments, W is

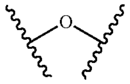.

In some embodiments, W is

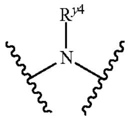.

In some embodiments, each of $R^{x1}$ and $R^{x2}$ is, independently, H, halogen, optionally substituted $C_1$-$C_6$ alkyl, optionally substituted $C_1$-$C_6$ heteroalkyl, or optionally substituted $C_3$-$C_6$ carbocyclyl.

In some embodiments, each of $R^{x1}$ and $R^{x2}$ is, independently, H or optionally substituted $C_1$-$C_6$ alkyl.

In some embodiments, each of $R^{x1}$ and $R^{x2}$ is, independently, H or methyl.

In some embodiments, $R^{x1}$ and $R^{x2}$, together with the carbon atom to which each is attached, combine to form optionally substituted $C_3$-$C_6$ carbocyclyl or optionally substituted $C_2$-$C_5$ heterocyclyl.

In some embodiments, $R^{x1}$ and $R^{x2}$, together with the carbon atom to which each is attached, combine to form optionally substituted $C_3$-$C_6$ carbocyclyl.

In some embodiments, $R^{x1}$ and $R^{x2}$, together with the carbon atom to which each is attached, combine to form cyclopropyl.

In some embodiments, each of $R^{y1}$, $R^{y2}$, $R^{y3}$, and $R^{y4}$ is, independently, H or optionally substituted $C_1$-$C_6$ alkyl.

In some embodiments, each of $R^{y1}$, $R^{y2}$, $R^{y3}$, and $R^{y4}$ is, independently, H or methyl.

In some embodiments, the linker has the structure of

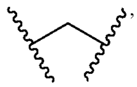, 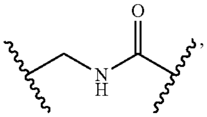,

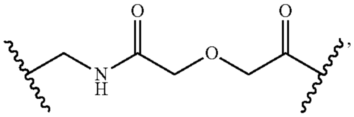,

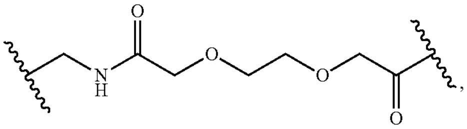,

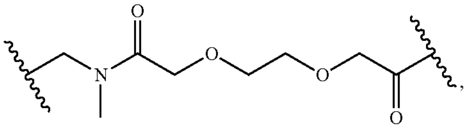,

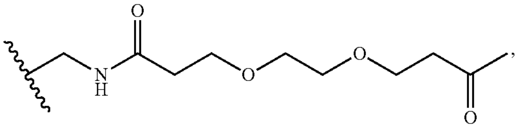,

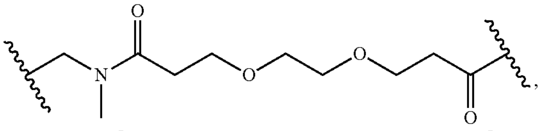,

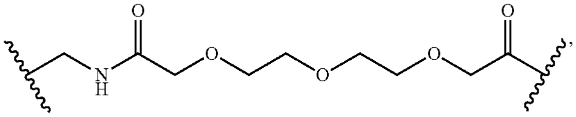,

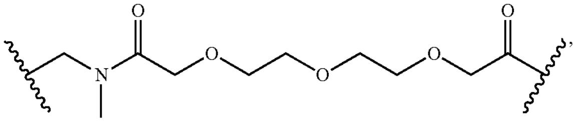,

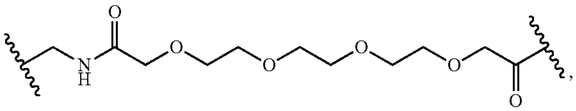,

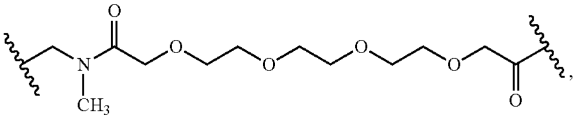,

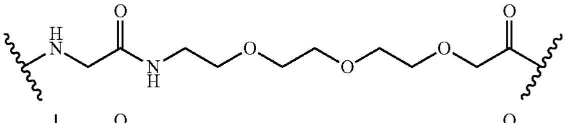,

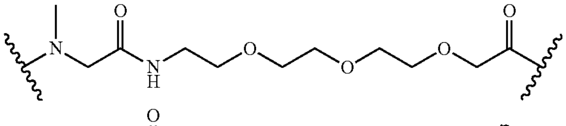,

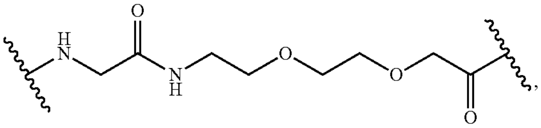,

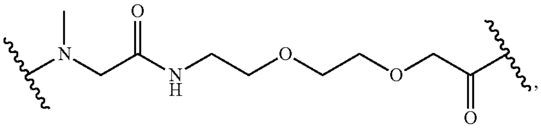,

-continued
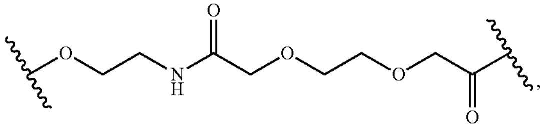,
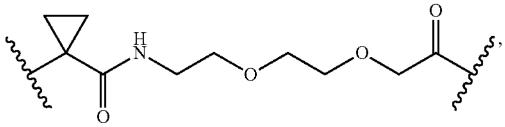,
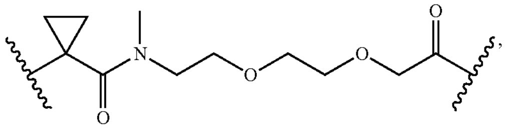,
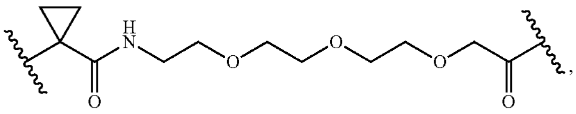,
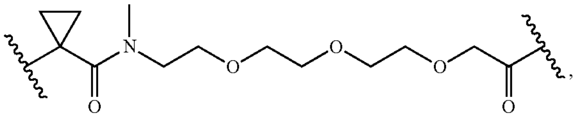,
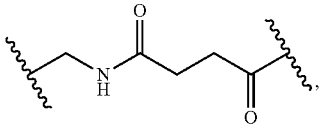,
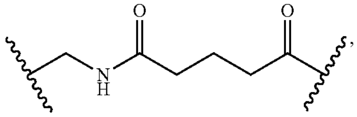,
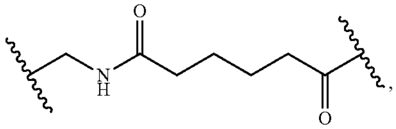,
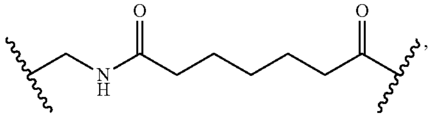,
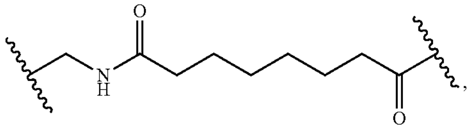,
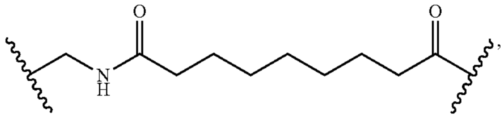,
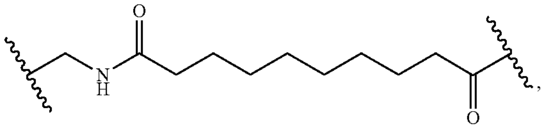,
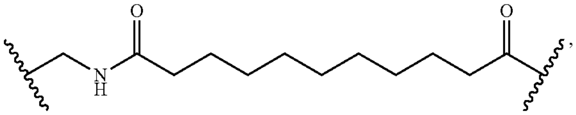,
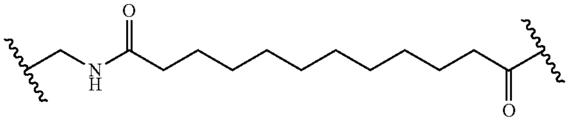,
-continued
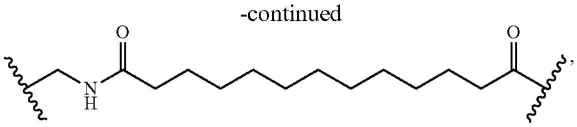,
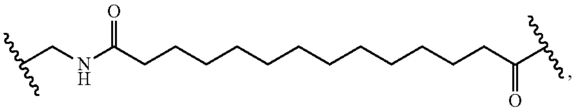,
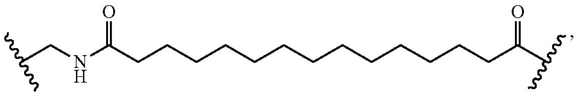,
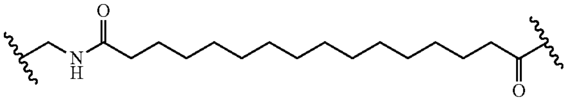,
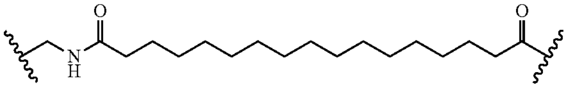,
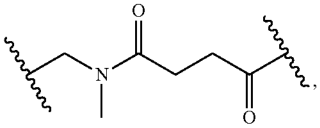,
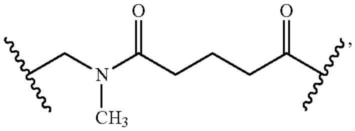,
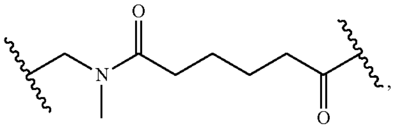,
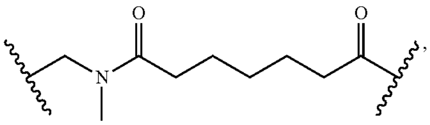,
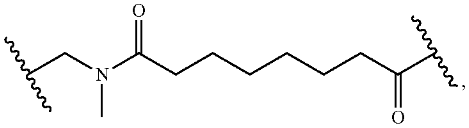,
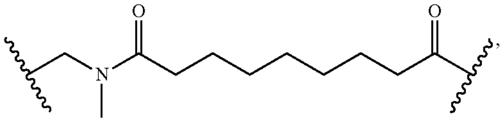,
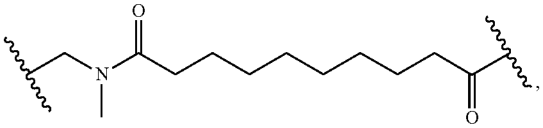,
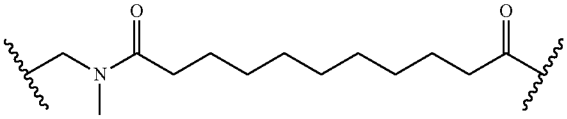,
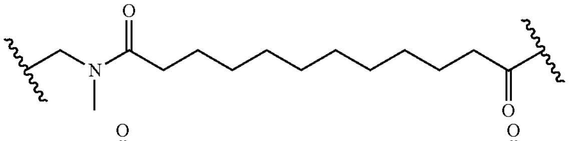,
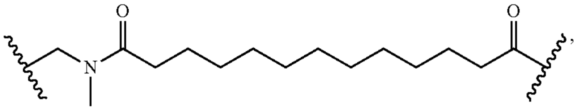, -continued
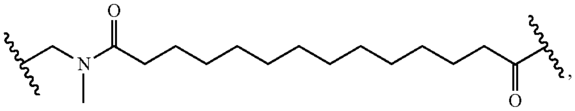,
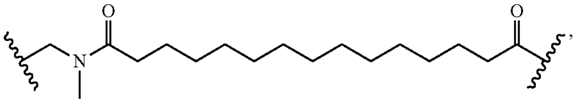,
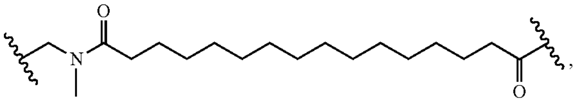,
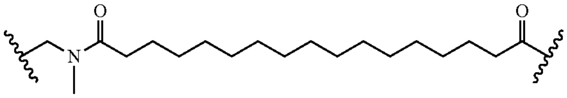,
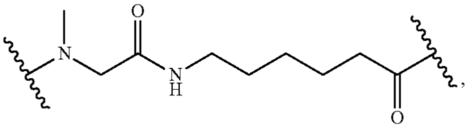,
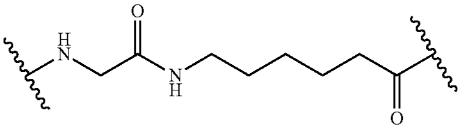,
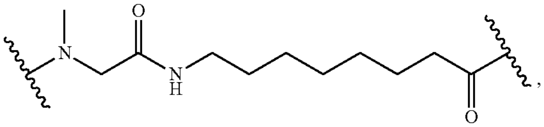,
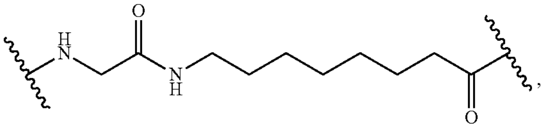,
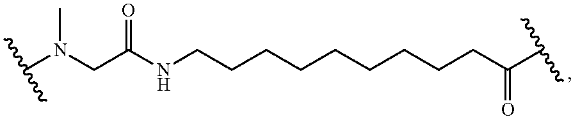,
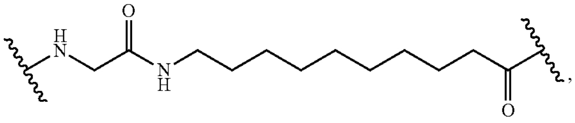,
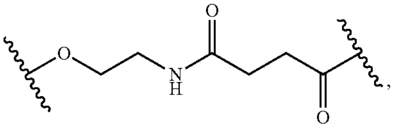,
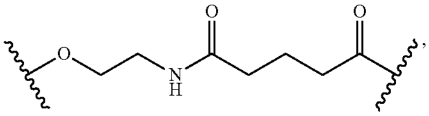,
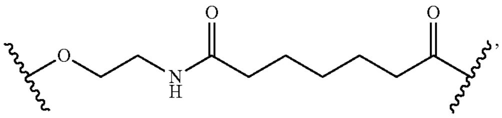,
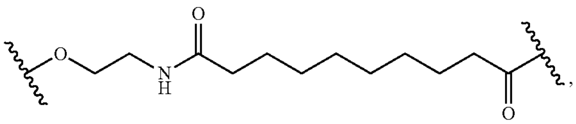,
-continued
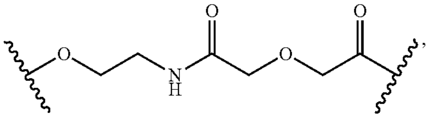,
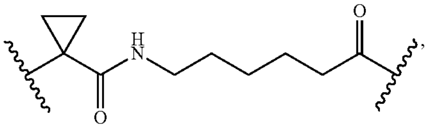,
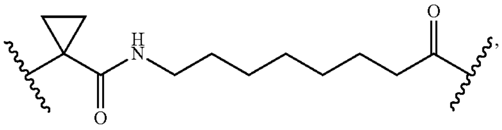,
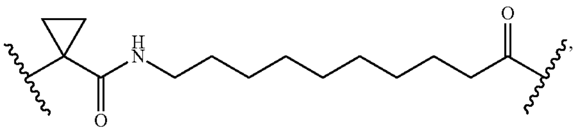,
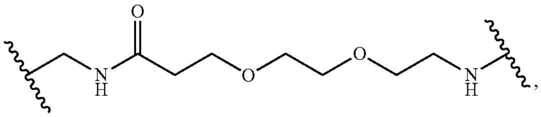,
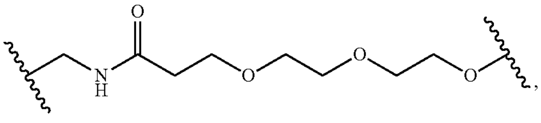,
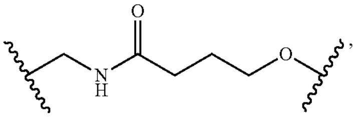,
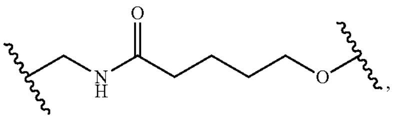,
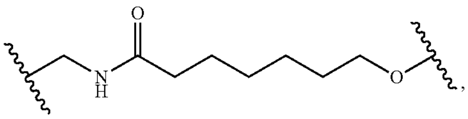,
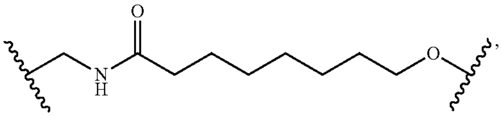,
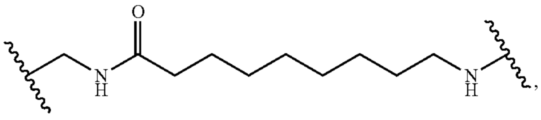,
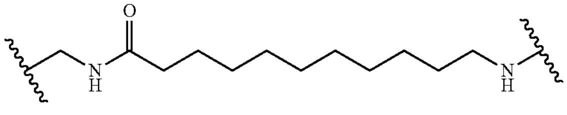,
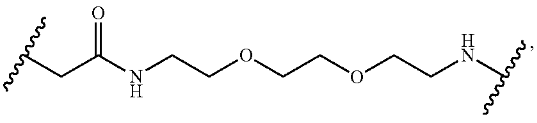,
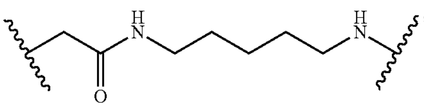, -continued
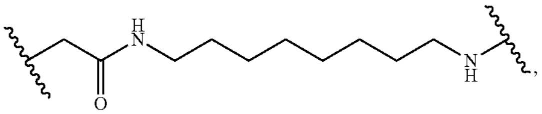,
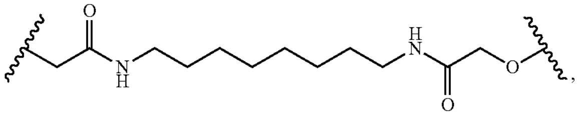,
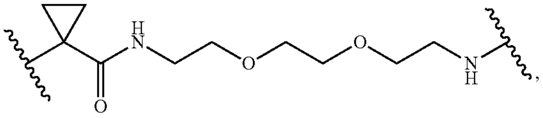,
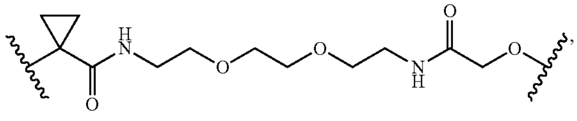,
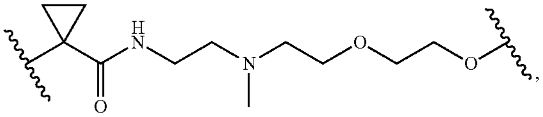,
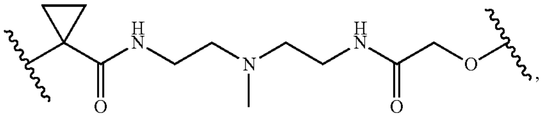,
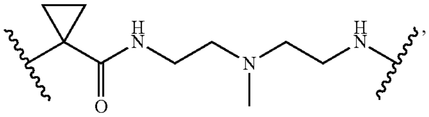,
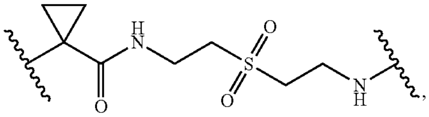,
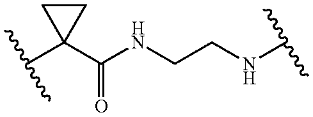
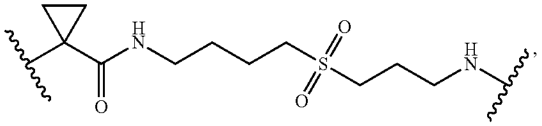,
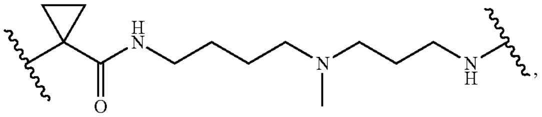,
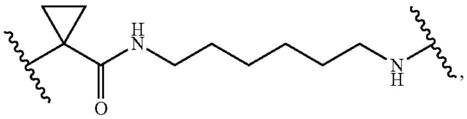,
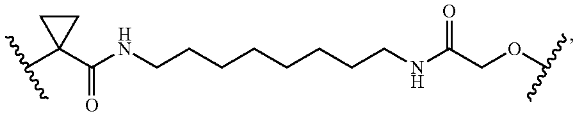,
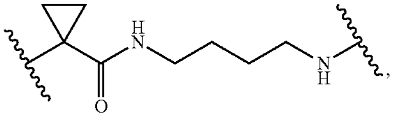,
-continued
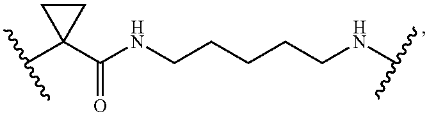,
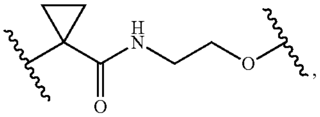,
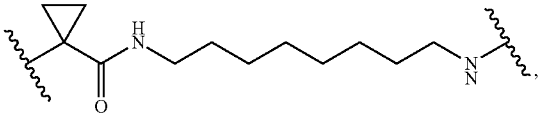,
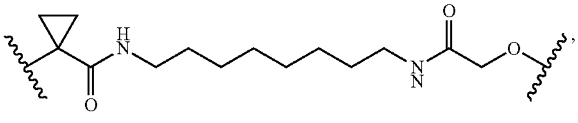,
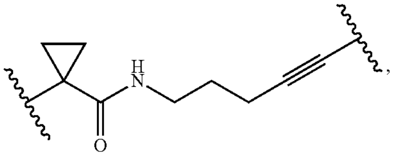,
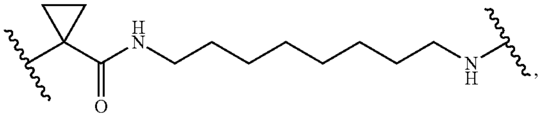,
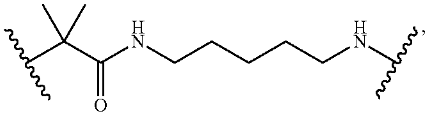,
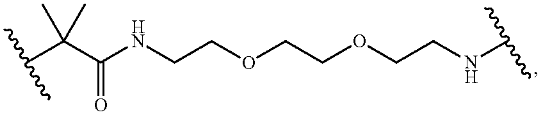,
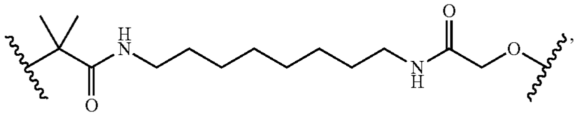,
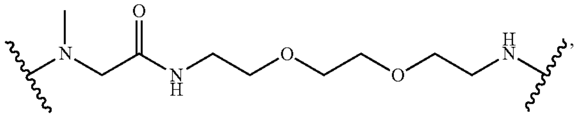,
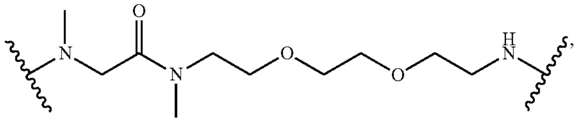,
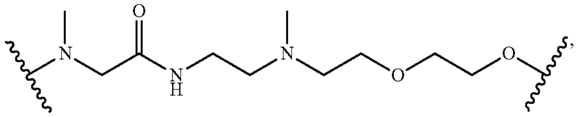,
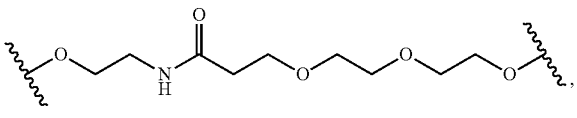,
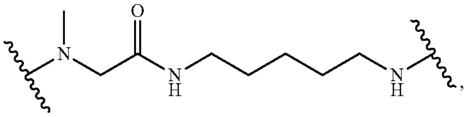, -continued

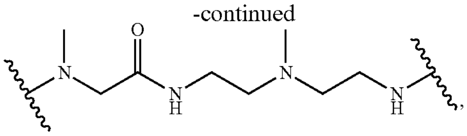
,
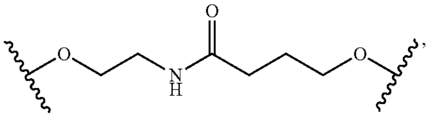
,
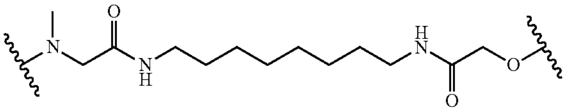
,
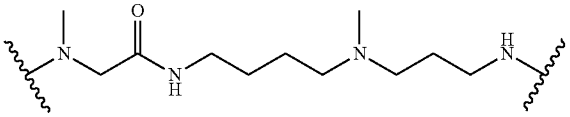
,
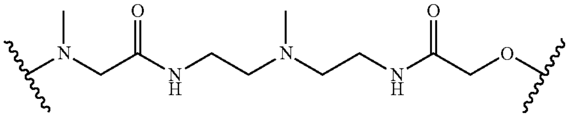
,
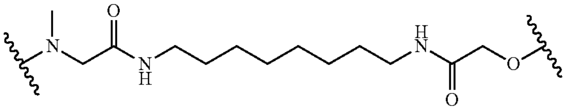
,
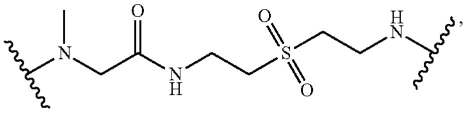
,
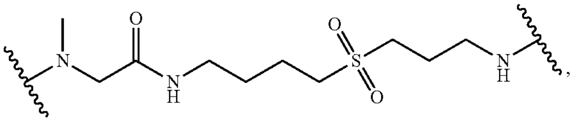
,
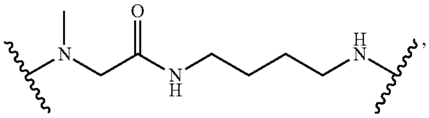
,
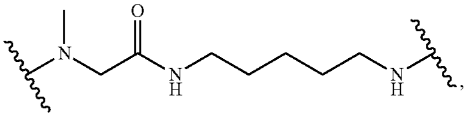
,
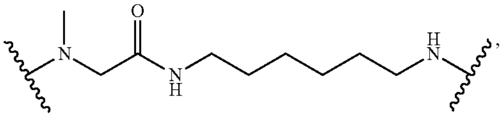
,
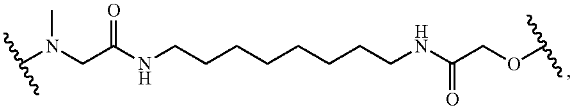
,
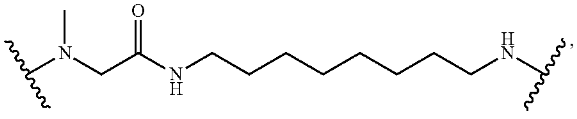
,
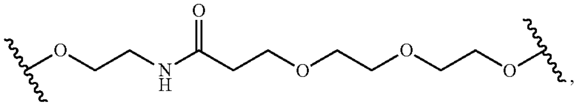
,
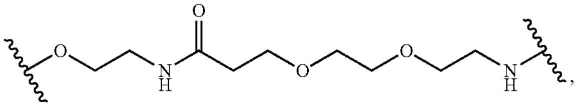
, -continued

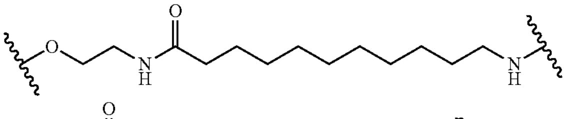
,
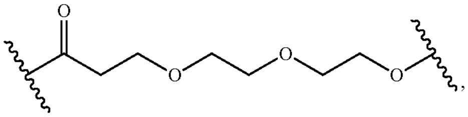
,
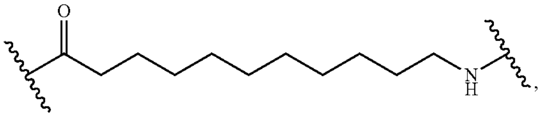
,
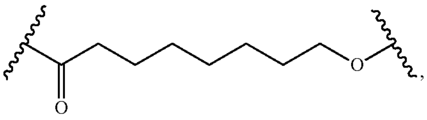
, or
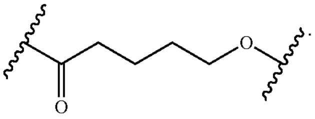
.

In some embodiments, the linker has the structure of Formula IV:

$A^1$-$(E^1)_{p1}$-$(F^1)$—$(C^3)_{m1}$-$(E^3)_{n1}$-$(C^4)_{m2}$—$(F^2)_{o1}$-$(E^3)_{n2}$-$(F^3)_{o2}$-$(E^2)_{p2}$-$A^2$, Formula IV where $A^1$ is a bond between the linker and A; $A^2$ is a bond between B and the linker; each of m1, m2, n1, n2, o1, o2, p1, and p2 is, independently, 0 or 1; each of $E^1$ and $E^2$ is, independently, O, S, $NR^N$, optionally substituted $C_{1-10}$ alkyl, optionally substituted $C_{2-10}$ alkenyl, optionally substituted $C_{2-10}$ alkynyl, optionally substituted $C_2$-$C_{10}$ polyethylene glycol, or optionally substituted $C_{1-10}$ heteroalkyl; each $E^3$ is, independently, optionally substituted $C_{1-10}$ alkyl, optionally substituted $C_{1-10}$ heteroalkyl, O, S, or $NR^N$; each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; each of $C^3$ and $C^4$ is, independently, carbonyl, thiocarbonyl, sulphonyl, or phosphoryl; and each of $F^1$, $F^2$, and $F^3$ is, independently, optionally substituted $C_3$-$C_{10}$ carbocyclyl, optionally substituted $C_{2-10}$ heterocyclyl, optionally substituted $C_6$-$C_{10}$ aryl, or optionally substituted $C_2$-$C_9$ heteroaryl.

In some embodiments, the linker has the structure of Formula IVa:

$A^1$-$(F^1)$—$(C^3)_{m1}$-$(E^2)_{p2}$-$A^2$. Formula IVa

In some embodiments, the linker has the structure of Formula IVb:

$A^1$-$(E^1)$-$(F^1)$-$(E^2)_{p2}$-$A^2$. Formula IVb

In some embodiments, the linker has the structure of Formula IVc:

$A^1$-$(E^1)_{p1}$-$(F^1)$—$(F^2)$-$(E^2)$-$A^2$. Formula IVc

In some embodiments, the linker has the structure of Formula IVd:

$A^1$-$(E^1)_{p1}$-$(F^1)$—$(C^3)_{m1}$-$(E^3)_n$-$(C^4)_{m2}$—$(F^2)$-$(E^2)_{p2}$-$A^2$. Formula IVd In some embodiments, the linker has the structure of Formula IVe:

$A^1$-($F^1$)-$A^2$. Formula IVe

In some embodiments, the linker has the structure of Formula IVf:

$A^1$-$(E^1)_{p1}$-$(F^1)$—$(C^3)_{m1}$-$(E^3)_{n1}$-$(C^4)_{m2}$—$(F^2)_{o1}$-$(F^3)_{o2}$-$(E^2)_{p2}$-$A^2$, Formula IVf where $A^1$ is a bond between the linker and A; $A^2$ is a bond between B and the linker; each of m1, m2, n1, o1, o2, p1, and p2 is, independently, 0 or 1; each of $E^1$ and $E^2$ is, independently, O, S, $NR^N$, optionally substituted $C_{1-10}$ alkyl, optionally substituted $C_{2-10}$ alkenyl, optionally substituted $C_{2-10}$ alkynyl, optionally substituted $C_2$-$C_{10}$ polyethylene glycol, or optionally substituted $C_{1-10}$ heteroalkyl; $E^3$ is, independently, optionally substituted $C_{1-2}$ alkyl, optionally substituted $C_{1-2}$ heteroalkyl, O, S, or $NR^N$; each $R^N$ is, independently, H, optionally substituted $C_{1-4}$ alkyl, optionally substituted $C_{2-4}$ alkenyl, optionally substituted $C_{2-4}$ alkynyl, optionally substituted $C_{2-6}$ heterocyclyl, optionally substituted $C_{6-12}$ aryl, or optionally substituted $C_{1-7}$ heteroalkyl; each of $C^3$ and $C^4$ is, independently, carbonyl, thiocarbonyl, sulphonyl, or phosphoryl; and each of $F^1$, $F^2$, and $F^3$ is, independently, optionally substituted $C_3$-$C_{10}$ carbocyclyl, optionally substituted $C_{2-10}$ heterocyclyl, optionally substituted $C_6$-$C_{10}$ aryl, or optionally substituted $C_2$-$C_9$ heteroaryl.

In some embodiments, each $R^N$ is, independently, H or optionally substituted $C_{1-4}$ alkyl.

In some embodiments, each $R^N$ is, independently, H or methyl.

In some embodiments, each of $E^1$ and $E^2$ is, independently, $NR^N$, optionally substituted $C_{1-10}$ alkyl, optionally substituted $C_2$-$C_{10}$ polyethylene glycol, or optionally substituted $C_{1-10}$ heteroalkyl.

In some embodiments, each of $E^1$ and $E^2$ is, independently, optionally substituted $C_{1-10}$ alkyl or optionally substituted $C_{1-10}$ heteroalkyl.

In some embodiments, $E^1$ is

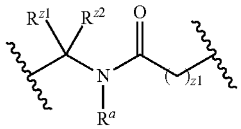 ,
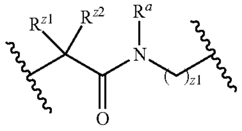 ,
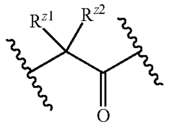 ,
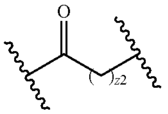 ,
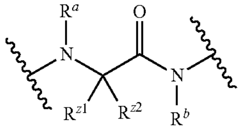 ,
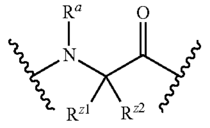 ,
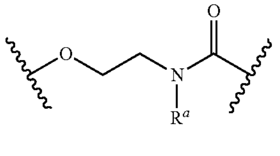 , where z1 is 0, 1, or 2; z2 is 0, 1, 2, 3, 4, 5, or 6; each of $R^{z1}$ and $R^{z2}$ is, independently, H, halogen, optionally substituted $C_1$-$C_6$ alkyl, optionally substituted $C_1$-$C_6$ heteroalkyl, or optionally substituted $C_3$-$C_6$ carbocyclyl, or $R^{x1}$ and $R^{x2}$, together with the carbon atom to which each is attached, combine to form optionally substituted $C_3$-$C_6$ carbocyclyl or optionally substituted $C_2$-$C_5$ heterocyclyl; and each of Ra and $R^b$ is, independently, H, optionally substituted $C_1$-$C_6$ alkyl, optionally substituted $C_1$-$C_6$ heteroalkyl, or optionally substituted $C_3$-$C_6$ carbocyclyl.

In some embodiments, z1 is 0. In some embodiments, z1 is 1.

In some embodiments, each of $R^{z1}$ and $R^{z2}$ is, independently, H, halogen, optionally substituted $C_1$-$C_6$ alkyl, optionally substituted $C_1$-$C_6$ heteroalkyl, or optionally substituted $C_3$-$C_6$ carbocyclyl.

In some embodiments, each of $R^{z1}$ and $R^{z2}$ is, independently, H or optionally substituted $C_1$-$C_6$ alkyl.

In some embodiments, each of $R^{z1}$ and $R^{z2}$ is, independently, H or methyl.

In some embodiments, $R^{z1}$ and $R^{z2}$, together with the carbon atom to which each is attached, combine to form optionally substituted $C_3$-$C_6$ carbocyclyl or optionally substituted $C_2$-$C_5$ heterocyclyl.

In some embodiments, $R^{z1}$ and $R^{z2}$, together with the carbon atom to which each is attached, combine to form optionally substituted $C_3$-$C_6$ carbocyclyl.

In some embodiments, $R^{z1}$ and $R^{z2}$, together with the carbon atom to which each is attached, combine to form cyclopropyl.

In some embodiments, each of Ra and $R^b$ is, independently, H or optionally substituted $C_1$-$C_6$ alkyl.

In some embodiments, each of Ra and $R^b$ is, independently, H or methyl.

In some embodiments, $E^2$ is

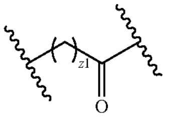 ,
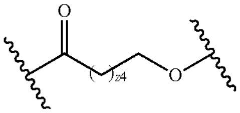 ,
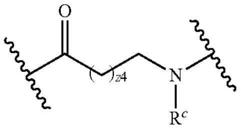 ,
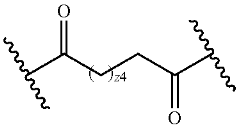 ,
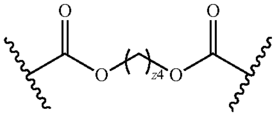 ,
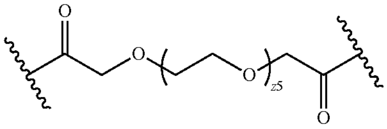 ,
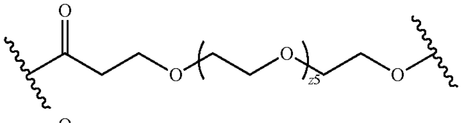 ,
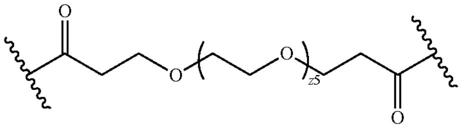 ,
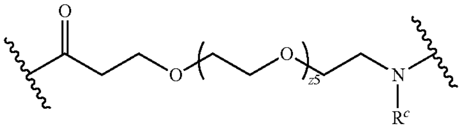 , -continued

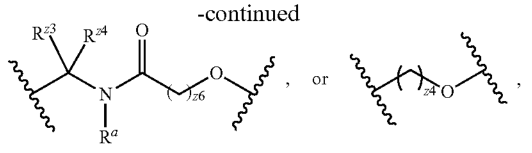

where z3 is 0, 1, 2, 3, 4, 5, or 6; z4 is 0, 1, 2, 3, 4, 5, 6, 7, 8, 9, 10, 11, or 12; z5 is 0, 1, 2, 3, or 4; z6 is 1, 2, 3, or 4; each of $R^{z3}$ and $R^{z4}$ is, independently, H, halogen, optionally substituted $C_1$-$C_6$ alkyl, optionally substituted $C_1$-$C_6$ heteroalkyl, or optionally substituted $C_3$-$C_6$ carbocyclyl, or $R^{x1}$ and $R^{x2}$together with the carbon atom to which each is attached, combine to form optionally substituted $C_3$-$C_6$ carbocyclyl or optionally substituted $C_2$-$C_5$ heterocyclyl; and RC is H, optionally substituted $C_1$-$C_6$ alkyl, optionally substituted $C_1$-$C_6$ heteroalkyl, or optionally substituted $C_3$-$C_6$ carbocyclyl.

In some embodiments, z3 is 0, 1, 2, or 3.

In some embodiments, z4 is 0, 1, 2, 3, 4, 5, or 6.

In some embodiments, z5 is 0, 1, or 2.

In some embodiments, z6 is 1 or 2.

In some embodiments, each of $R^{z3}$ and $R^{z4}$ is, independently, H, halogen, optionally substituted $C_1$-$C_6$ alkyl, optionally substituted $C_1$-$C_6$ heteroalkyl, or optionally substituted $C_3$-$C_6$ carbocyclyl.

In some embodiments, each of $R^{z3}$ and $R^{z4}$ is, independently, H or optionally substituted $C_1$-$C_6$ alkyl.

In some embodiments, each of $R^{z3}$ and $R^{z4}$ is, independently, H or methyl.

In some embodiments, $R^{z3}$ and $R^{z4}$, together with the carbon atom to which each is attached, combine to form optionally substituted $C_3$-$C_6$ carbocyclyl or optionally substituted $C_2$-$C_5$ heterocyclyl.

In some embodiments, $R^{z3}$ and $R^{z4}$, together with the carbon atom to which each is attached, combine to form optionally substituted $C_3$-$C_6$ carbocyclyl.

In some embodiments, $R^{z3}$ and $R^{z4}$, together with the carbon atom to which each is attached, combine to form cyclopropyl.

In some embodiments, $R^c$ is H or optionally substituted $C_1$-$C_6$ alkyl.

In some embodiments, $R^c$ is H or methyl.

In some embodiments, $E^3$ is optionally substituted $C_{1-2}$ alkyl, optionally substituted $C_{1-2}$ heteroalkyl. In some embodiments, $E^3$ is O, S, or $NR^N$.

In some embodiments, $E^3$ is optionally substituted $C_{1-2}$ alkyl.

In some embodiments, $E^3$ is

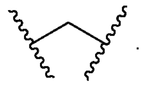 [SMILES: *C*]

In some embodiments, each of $F^1$, $F^2$, or $F^3$ is, independently, optionally substituted $C_3$-$C_{10}$ carbocyclyl. In some embodiments, the $C_3$-$C_{10}$ carbocyclyl is monocyclic. In some embodiments, the $C_3$-$C_{10}$ carbocyclyl is polycyclic. In some embodiments, the $C_3$-$C_{10}$ carbocyclyl is bicyclic. In some embodiments, the $C_3$-$C_{10}$ carbocyclyl is bridged. In some embodiments, the $C_3$-$C_{10}$ carbocyclyl is fused. In some embodiments, the $C_3$-$C_{10}$ carbocyclyl is spirocyclic.

In some embodiments, the $C_3$-$C_{10}$ carbocyclyl is

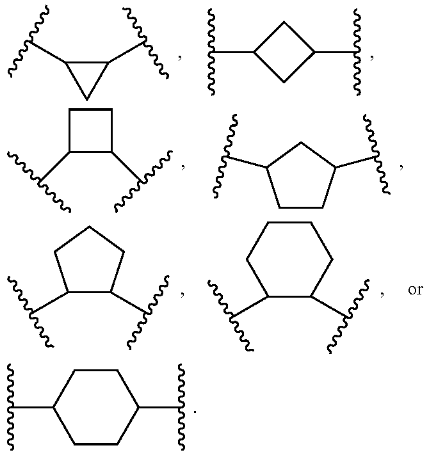

In some embodiments, the $C_3$-$C_{10}$ carbocyclyl is

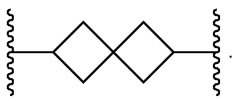 [SMILES: *C1CC2(C1)CC(*)C2]

In some embodiments, each of $F^1$, $F^2$, or $F^3$ is, independently, optionally substituted $C_2$-$C_6$ heterocyclyl. In some embodiments, the $C_2$-$C_9$ heterocyclyl is monocyclic. In some embodiments, the $C_2$-$C_9$ heterocyclyl is polycyclic. In some embodiments, the $C_2$-$C_9$ heterocyclyl is bicyclic. In some embodiments, the $C_2$-$C_9$ heterocyclyl is bridged. In some embodiments, the $C_2$-$C_9$ heterocyclyl is fused. In some embodiments, the $C_2$-$C_9$ heterocyclyl is spirocyclic.

In some embodiments, the $C_2$-$C_6$ heterocyclyl is

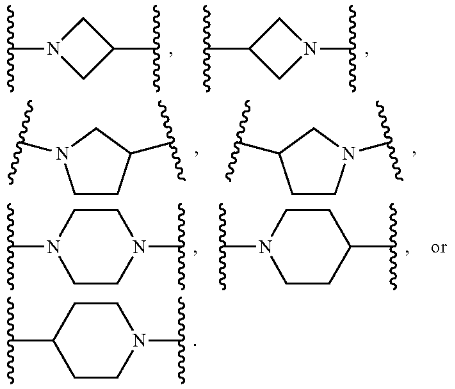

In some embodiments, the $C_2$-$C_6$ heterocyclyl is

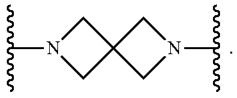 [SMILES: *N1CC2(C1)CN(*)C2]

In some embodiments, each of $F^1$, $F^2$, or $F^3$ is, independently, optionally substituted $C_6$-$C_{10}$ aryl. In some embodiments, each of $F^1$, $F^2$, or $F^3$ is, independently, optionally substituted $C_2$-$C_9$ heteroaryl.

In some embodiments, each of $C^3$ and $C^4$ is, independently, or
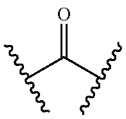 or 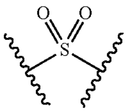.
In some embodiments, $C^3$ is
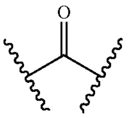.
In some embodiments, the linker has the structure of:
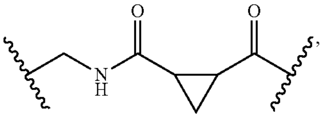,
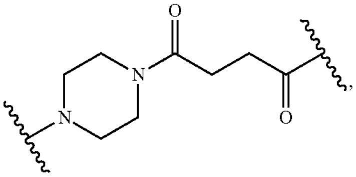,
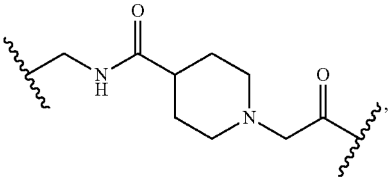,
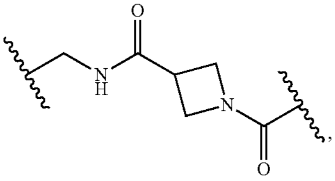,
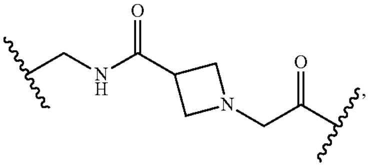,
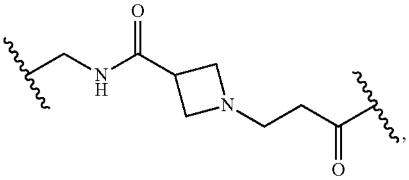,
-continued
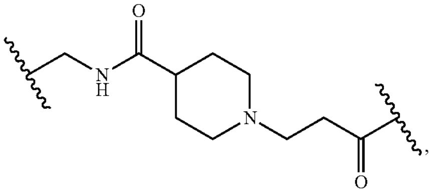,
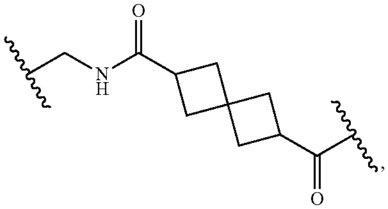,
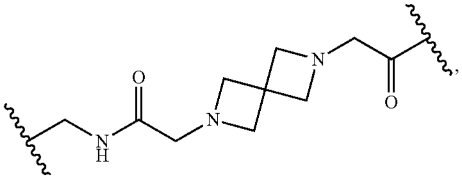,
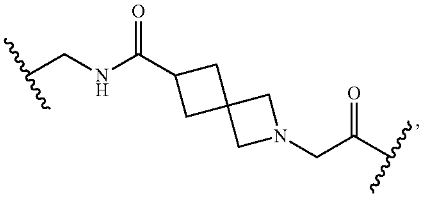,
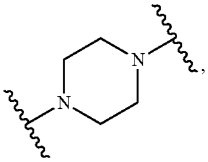,
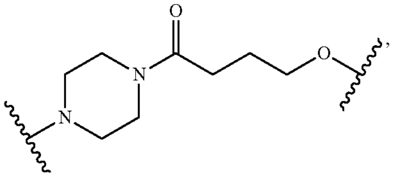,
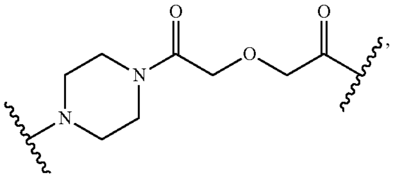,
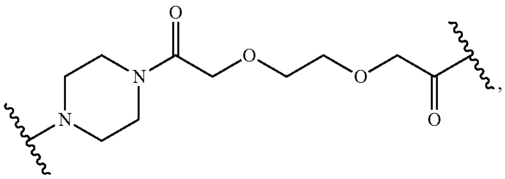,
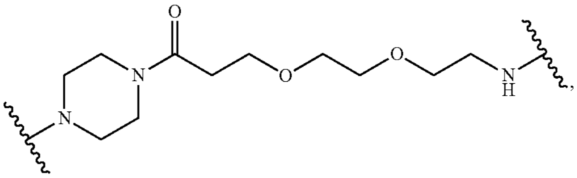, -continued
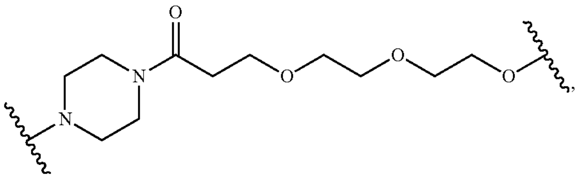,
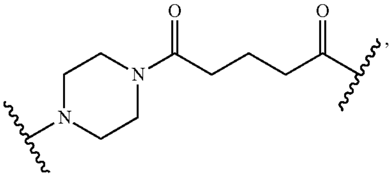,
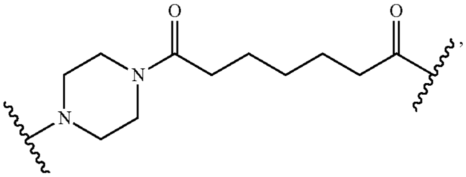,
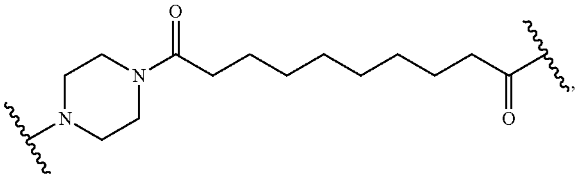,
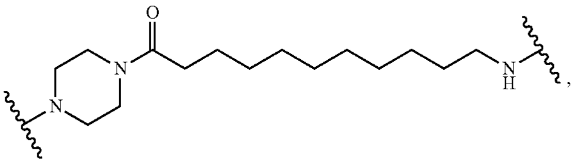,
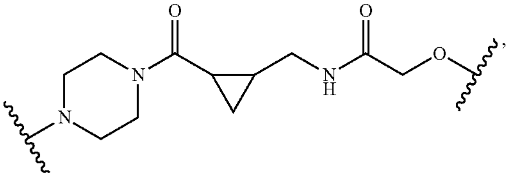,
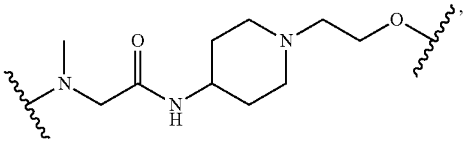,
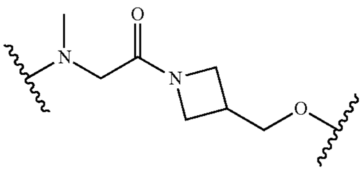,
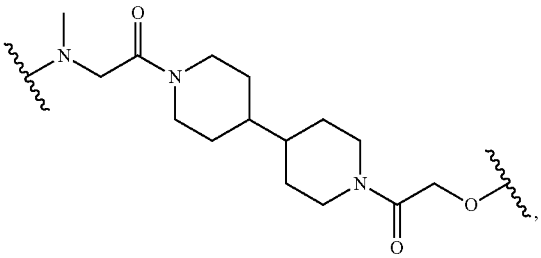,
-continued
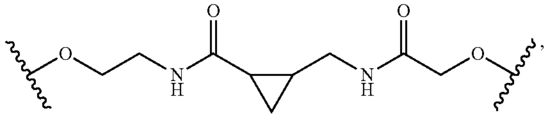,
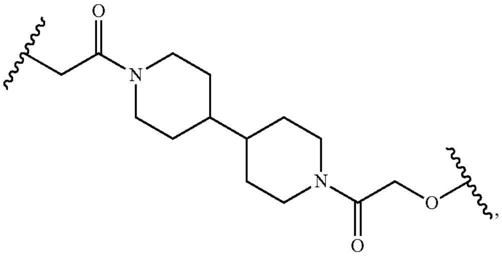,
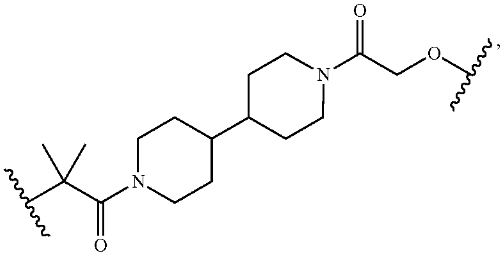,
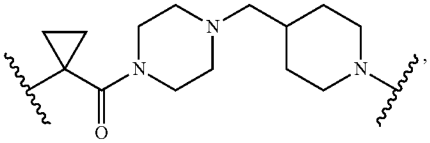,
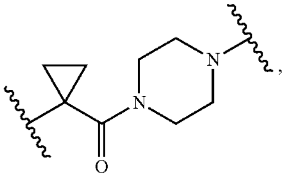,
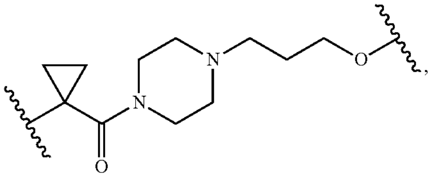,
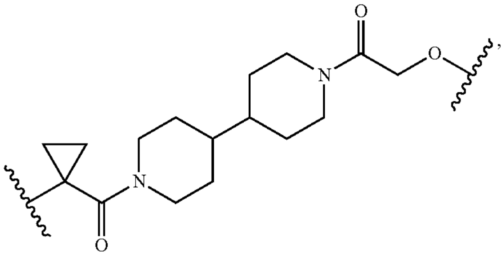,
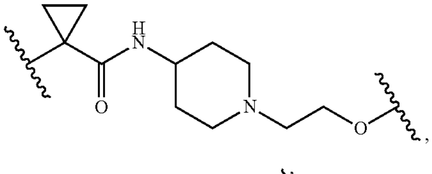,
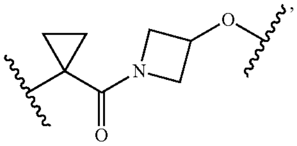, -continued
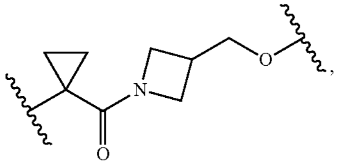
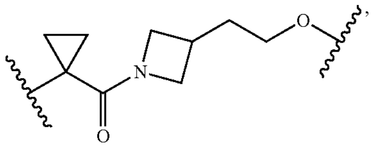
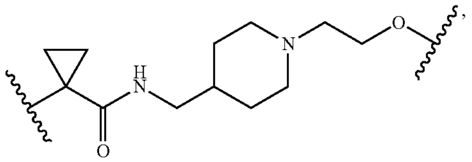
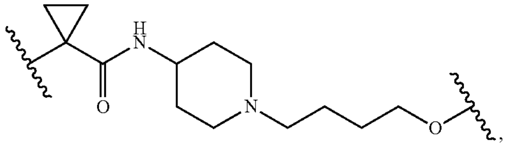
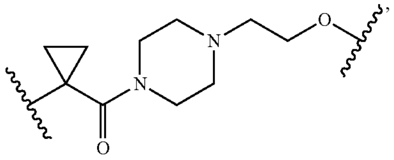
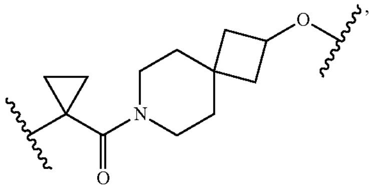
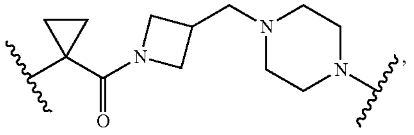
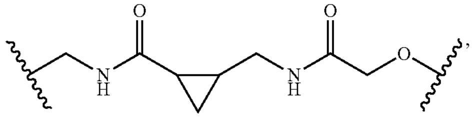
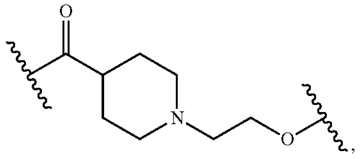
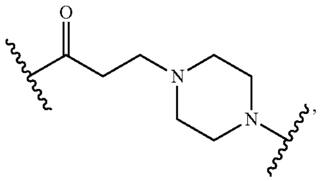
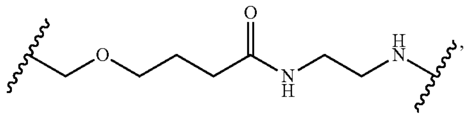
-continued
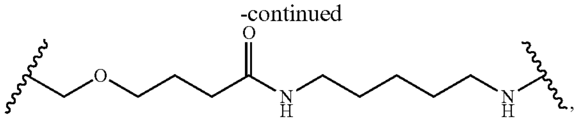
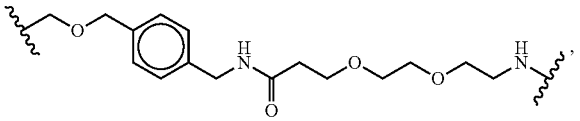
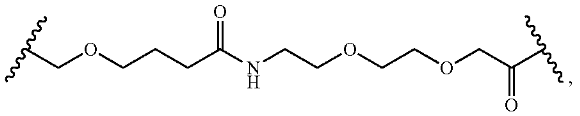
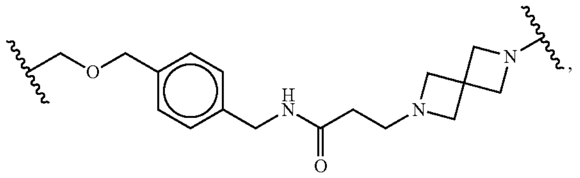
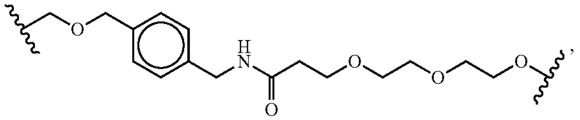
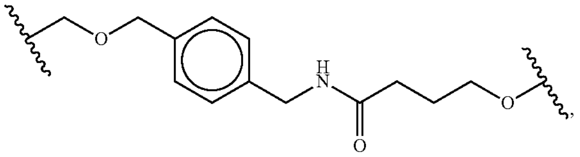
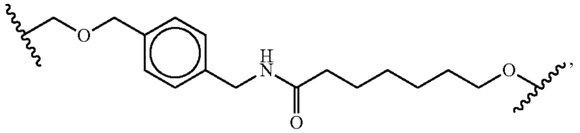
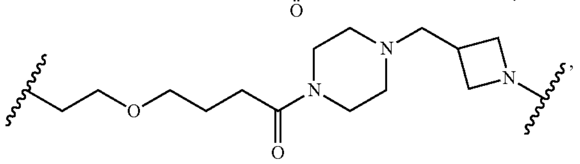
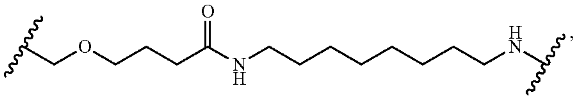
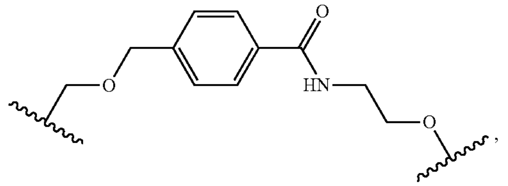
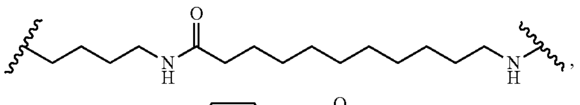
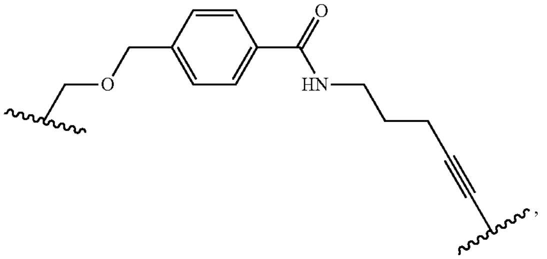

-continued
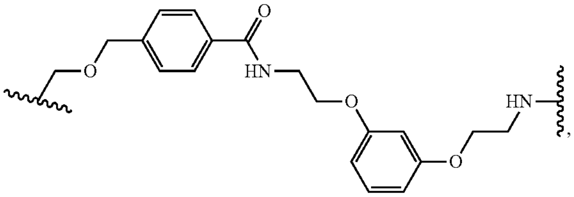
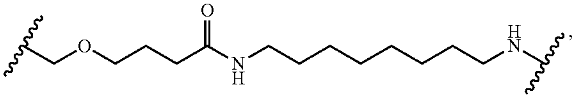
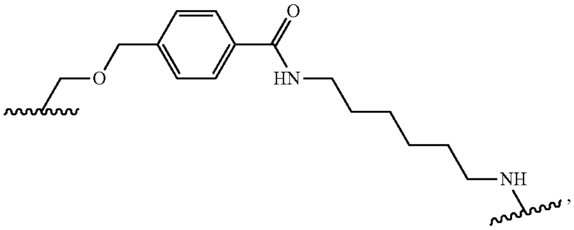
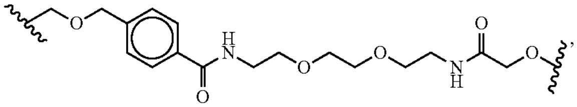
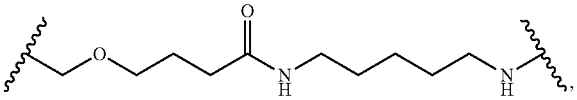
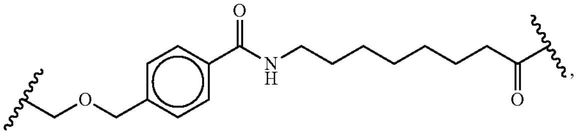
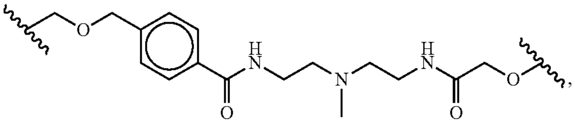
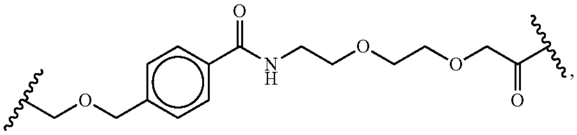
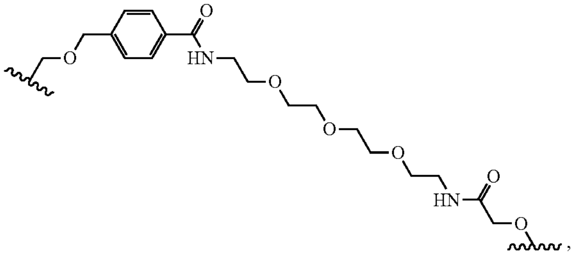
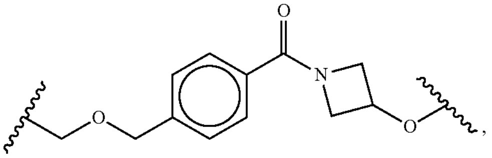
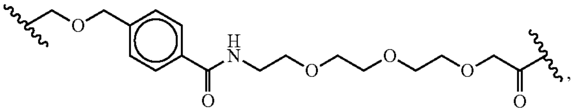
-continued
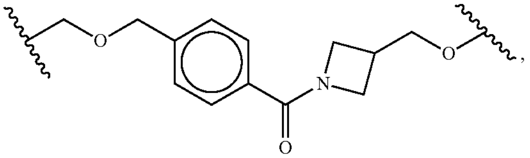
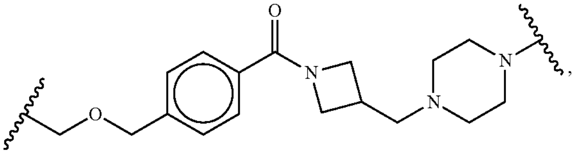
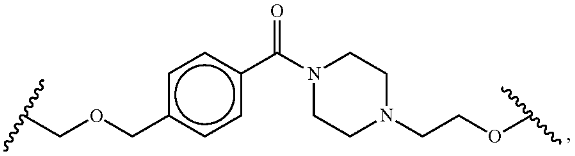
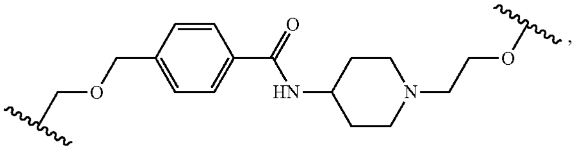
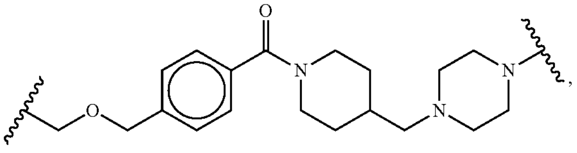
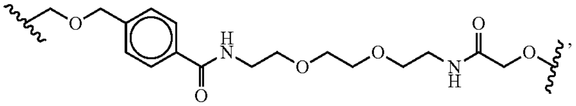
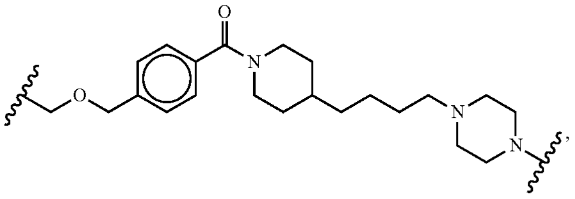
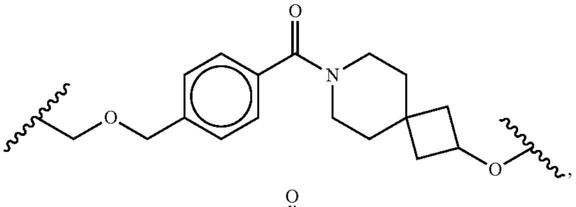
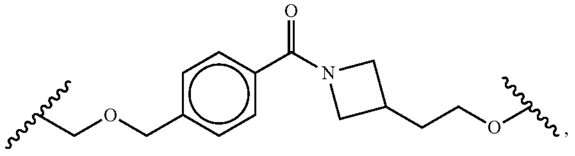
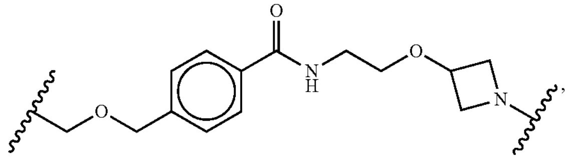
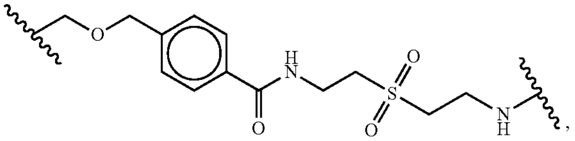

-continued
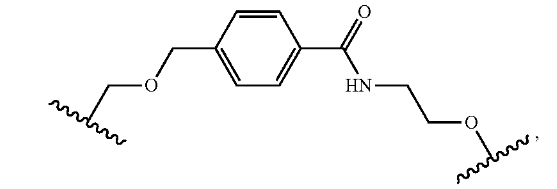
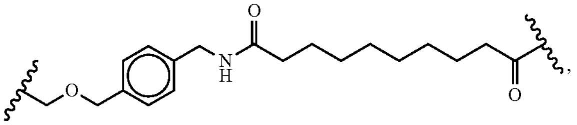
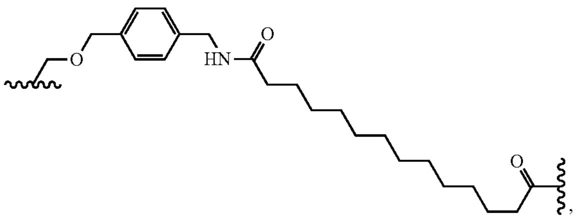
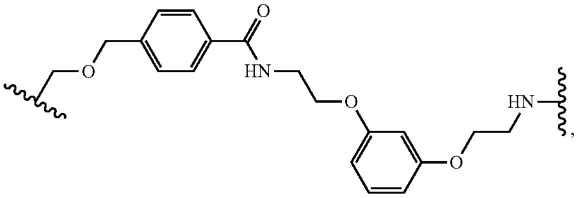
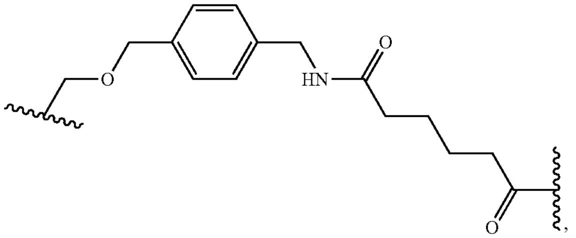
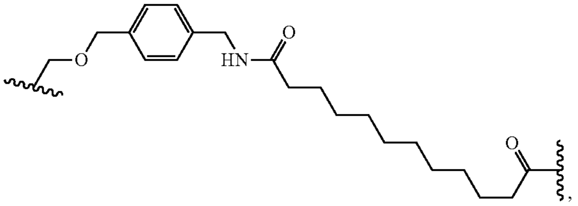
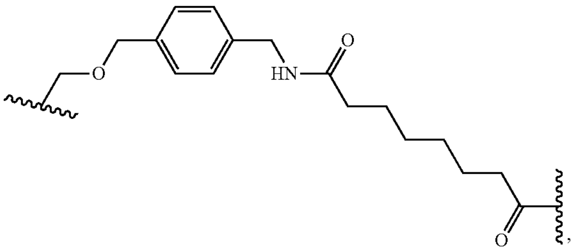
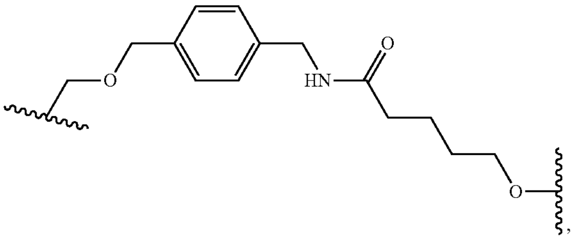
-continued
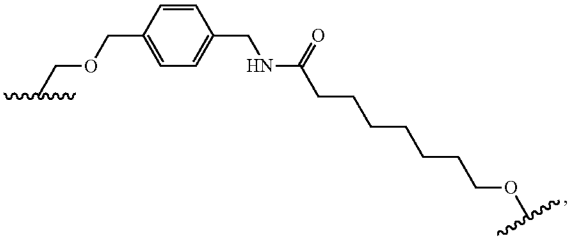
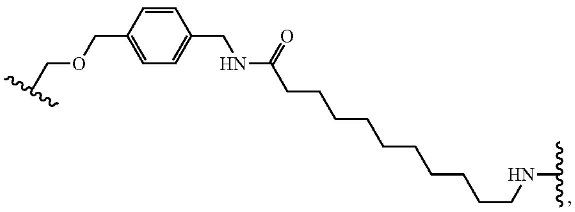
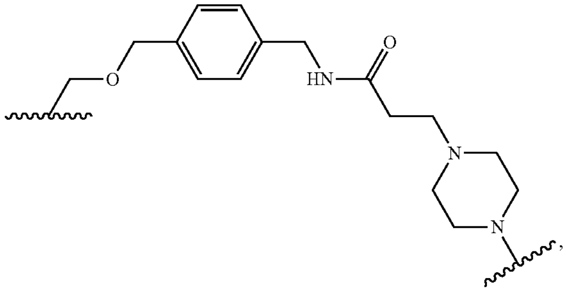
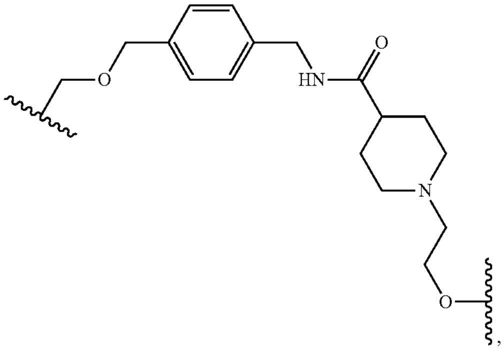
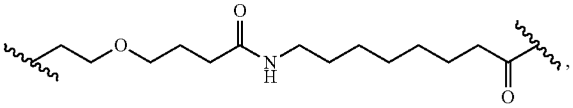
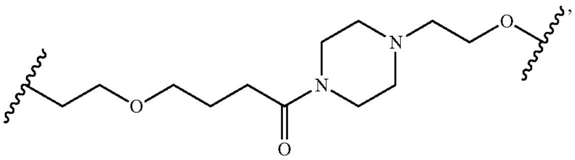
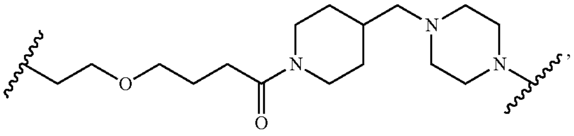
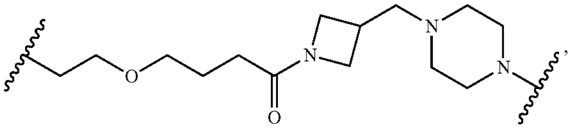

-continued
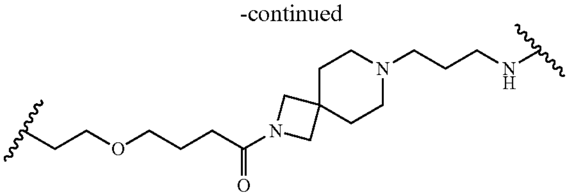,
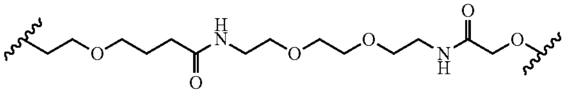,
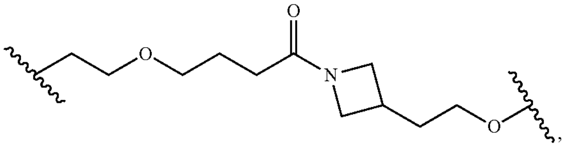,
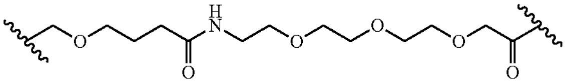,
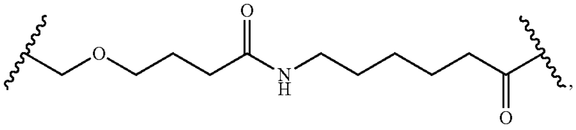,
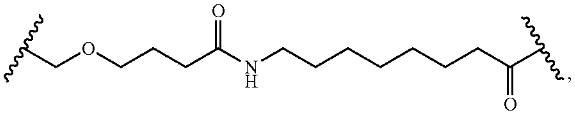,
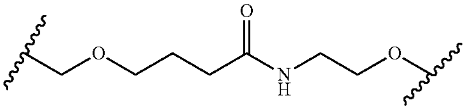,
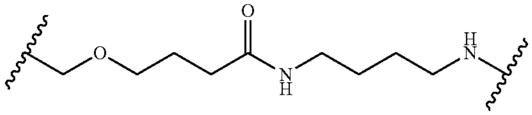,
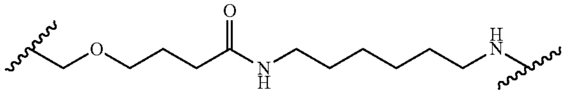,
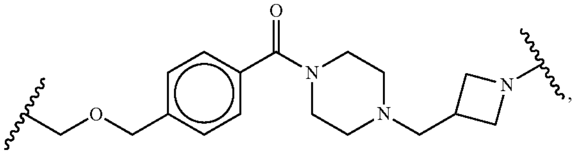,
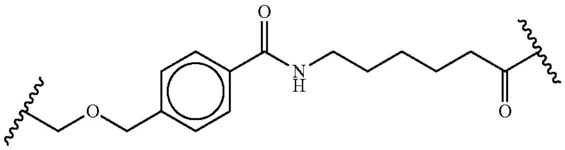,
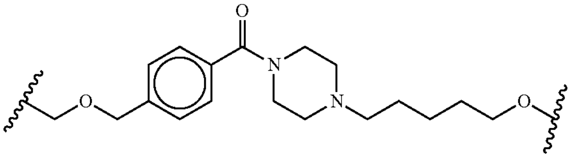,
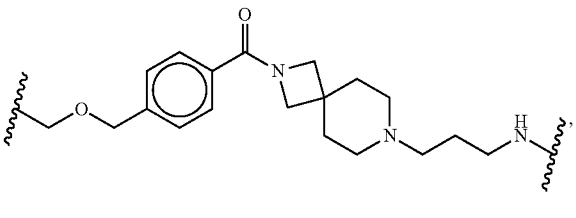,
-continued
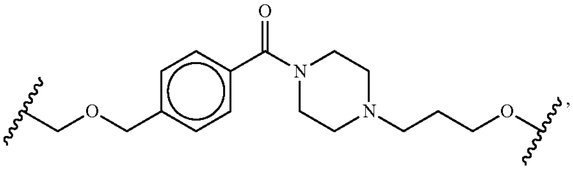,
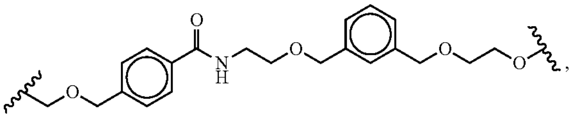,
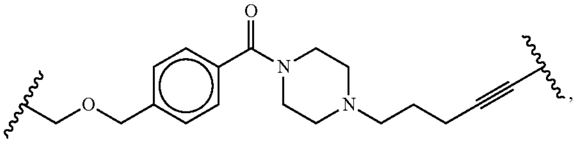,
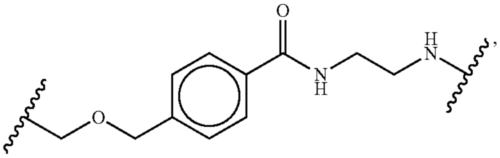,
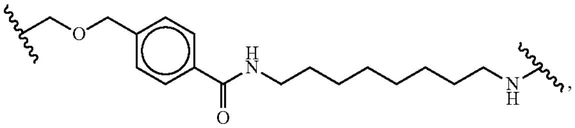,
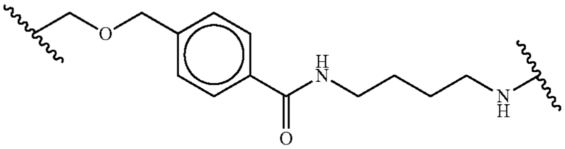,
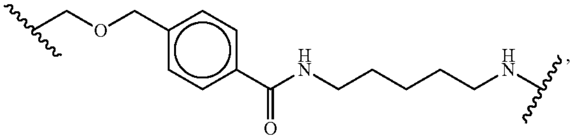,
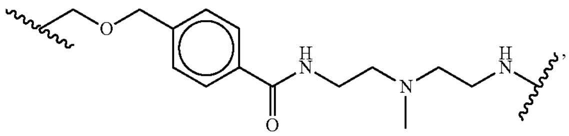,
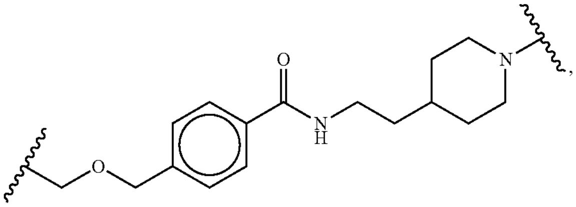,
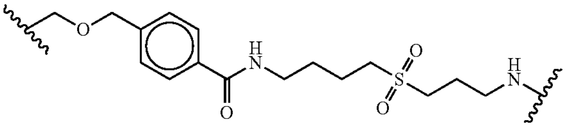,
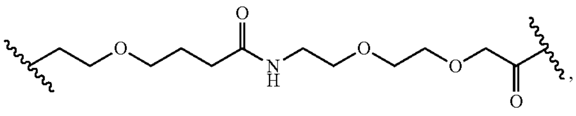,
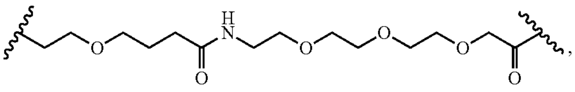, -continued
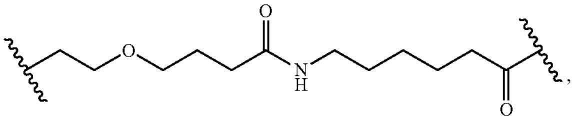,
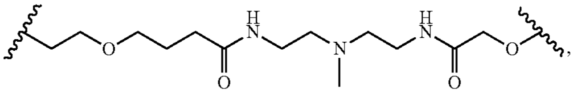,
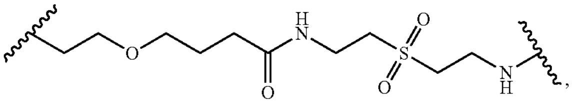,
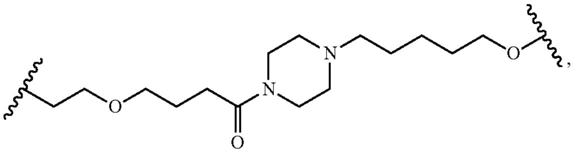,
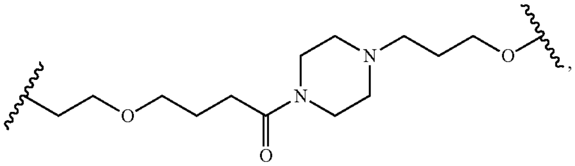,
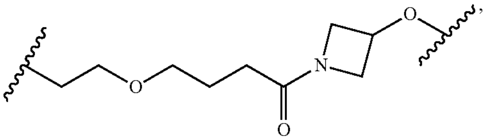,
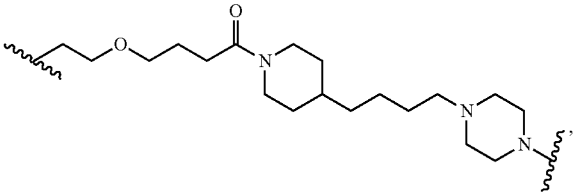,
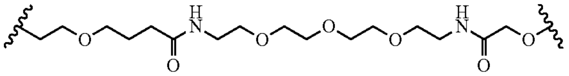,
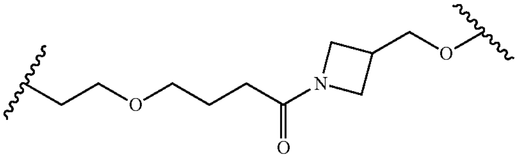,
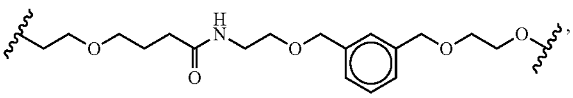,
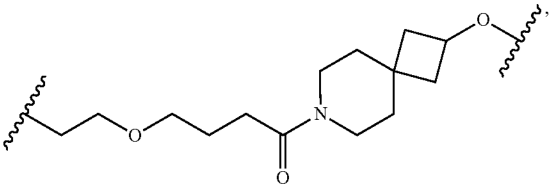,
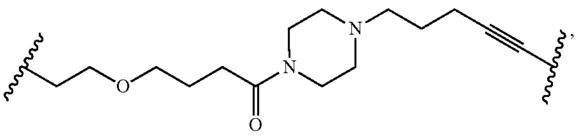,
-continued
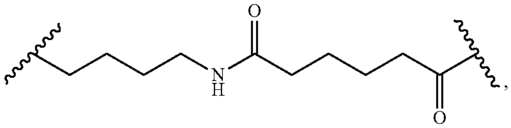,
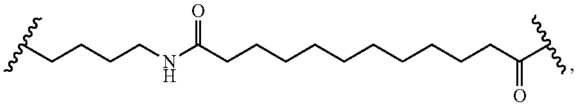,
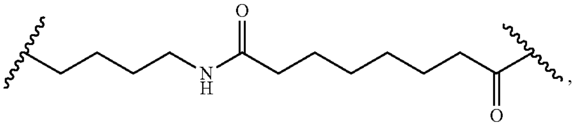,
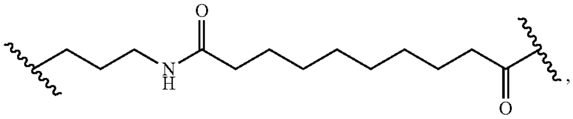,
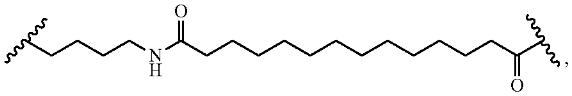,
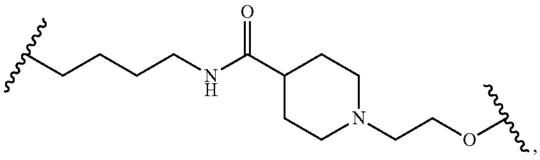,
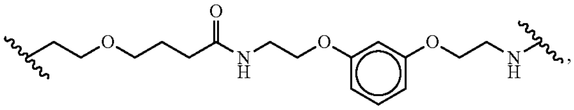,
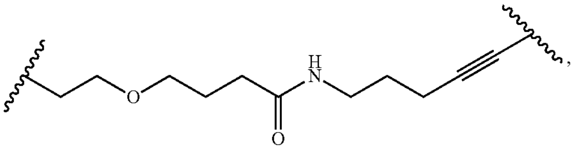,
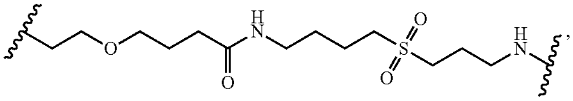,
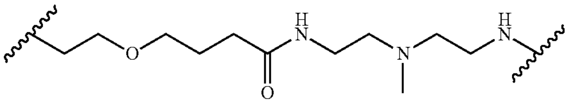,
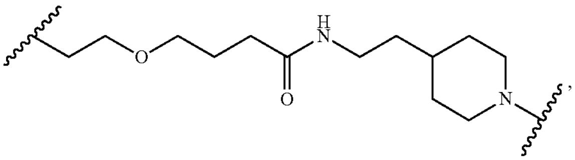,
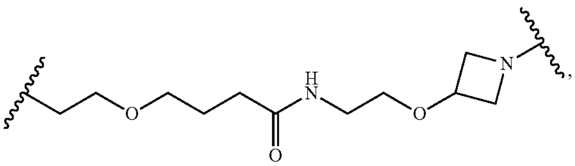,
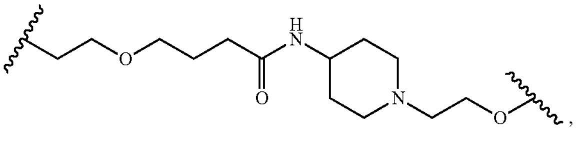, -continued

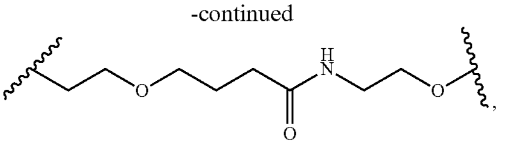,

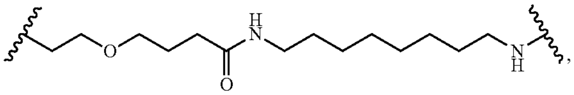,

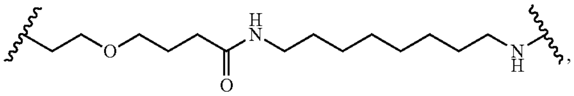,

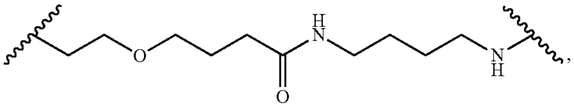,

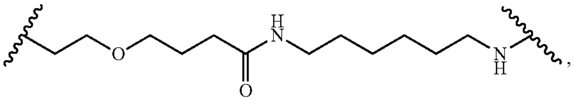,

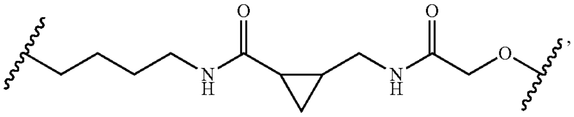,

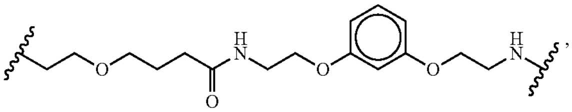,

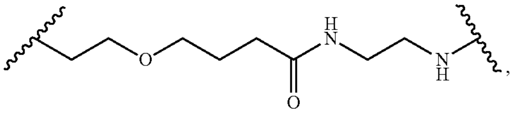,

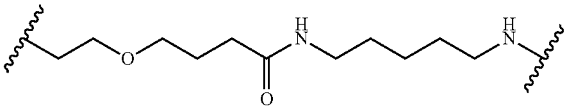,

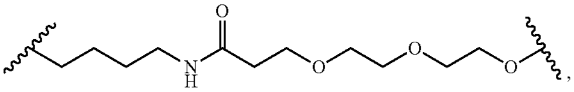,

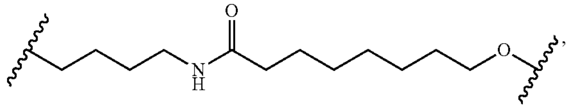,

-continued

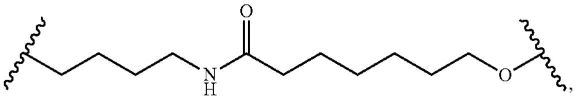,

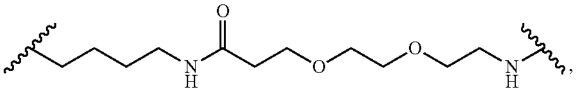,

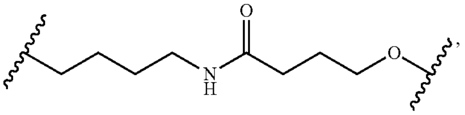,

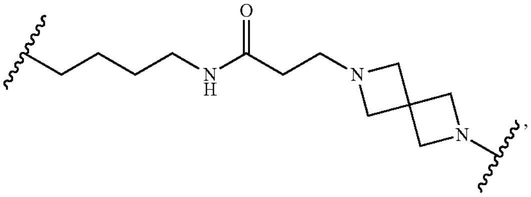,

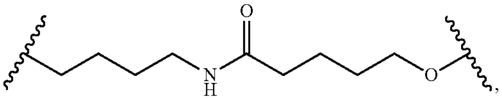,

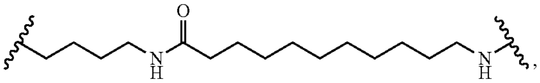, or

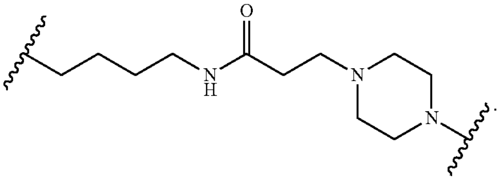.

In some embodiments, the compound is any one of compounds 1-169 in Table 1, or a pharmaceutically acceptable salt thereof. In some embodiments, the compound is any one of compounds 170-297 in Table 1, or a pharmaceutically acceptable salt thereof.

In an aspect, the compound is any one of compounds 1-297 in Table 1, or a pharmaceutically acceptable salt thereof. In some embodiments, the compound is any one of compounds I-169 in Table 1, or a pharmaceutically acceptable salt thereof.

TABLE 1
Compounds of the Invention
| # | Structure |
| --- | --- |
| 1 | 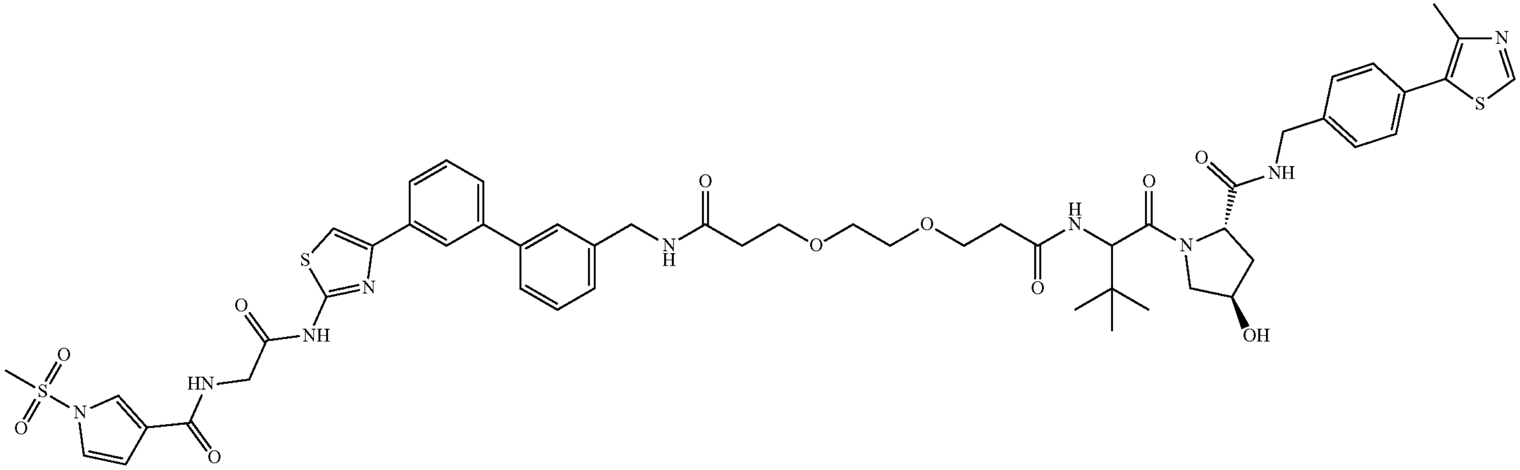 [SMILES: Cc1ncsc1-c1ccc(CNC(=O)[C@@H]2C[C@@H](O)CN2C(=O)C(NC(=O)CCOCCOCCC(=O)NCc2cccc(-c3cccc(-c4csc(NC(=O)CNC(=O)c5ccn(S(C)(=O)=O)c5)n4)c3)c2)C(C)(C)C)cc1] |
| 2 | 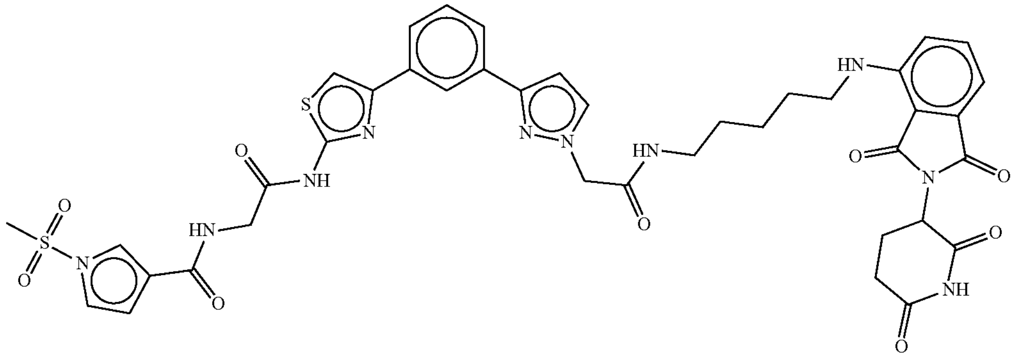 |

TABLE 1-continued
| Compounds of the Invention | |
|---|---|
| # | Structure |
| 3 | 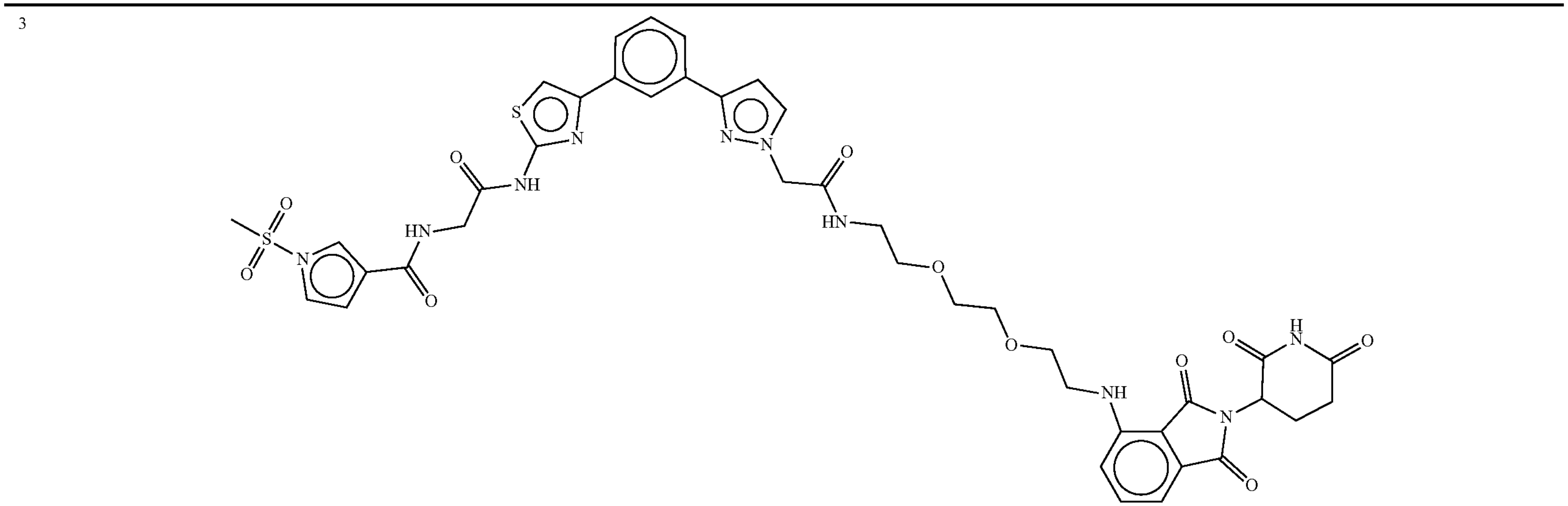 |
| 4 | 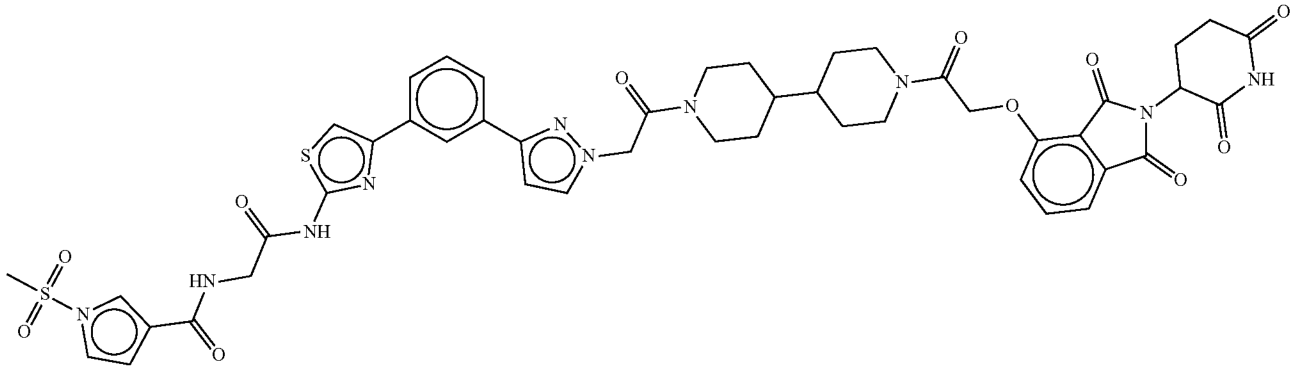 |

TABLE 1-continued
| Compounds of the Invention | |
|---|---|
| # | Structure |
| 5 | 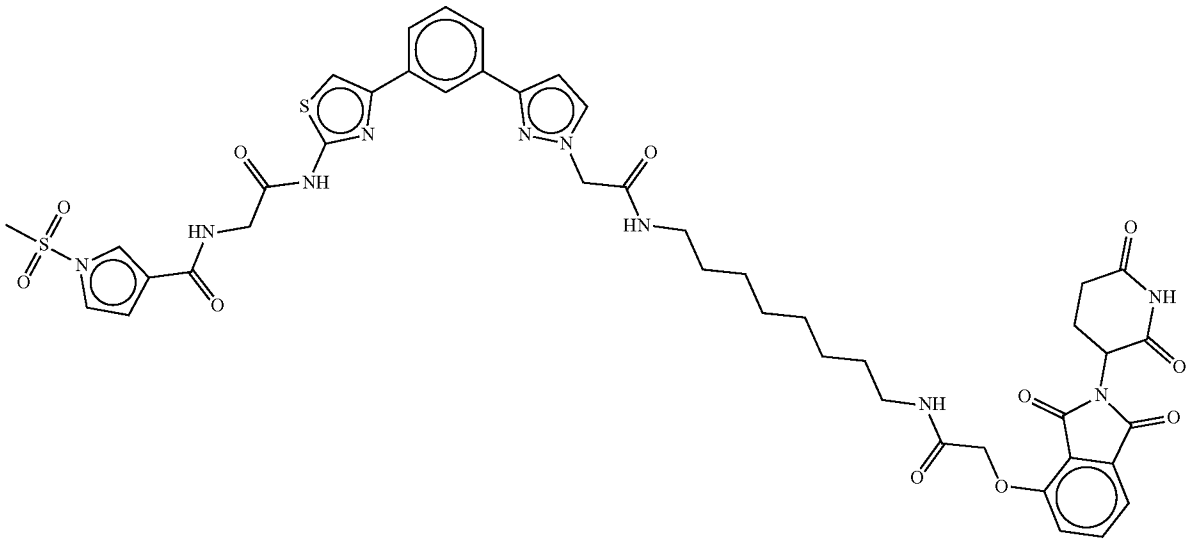 |
| 6 | 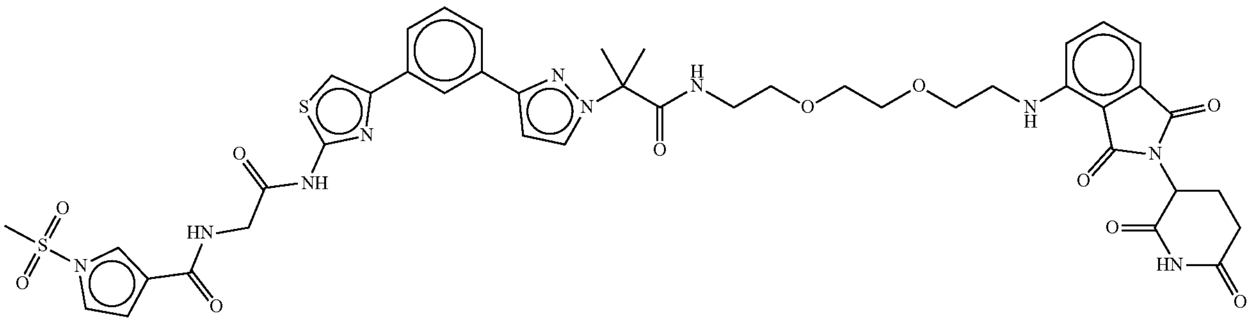 |

TABLE 1-continued
| Compounds of the Invention | |
|---|---|
| # | Structure |
| 7 | 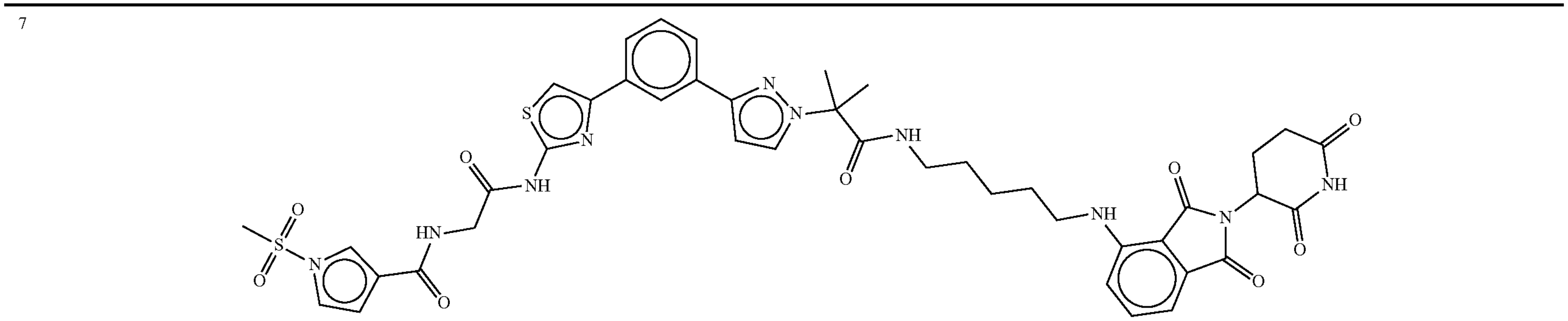 |
| 8 | 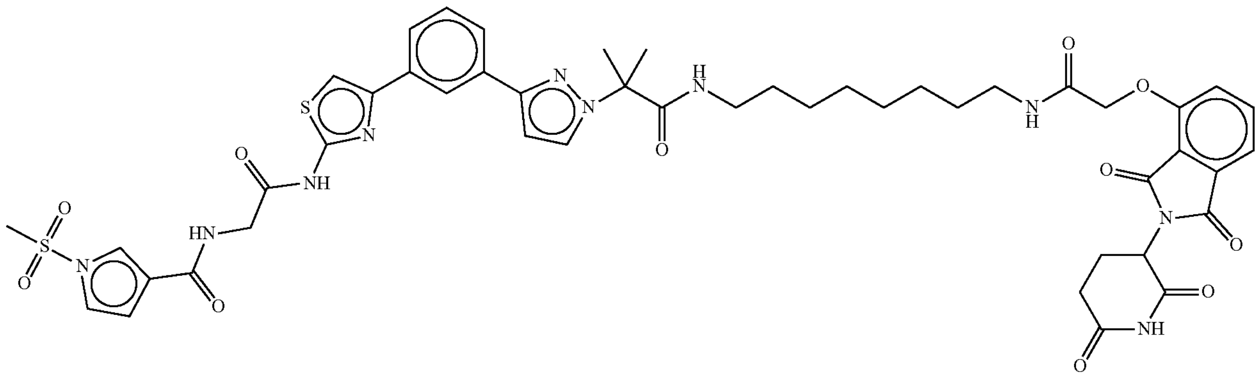 |

TABLE 1-continued
| Compounds of the Invention | |
| --- | --- |
| # | Structure |
| 9 | 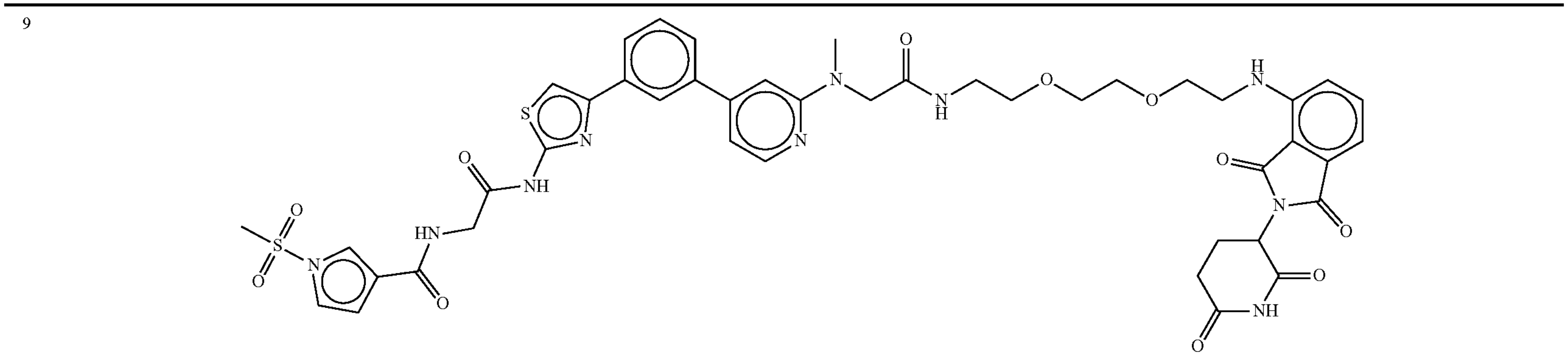 |
| 10 | 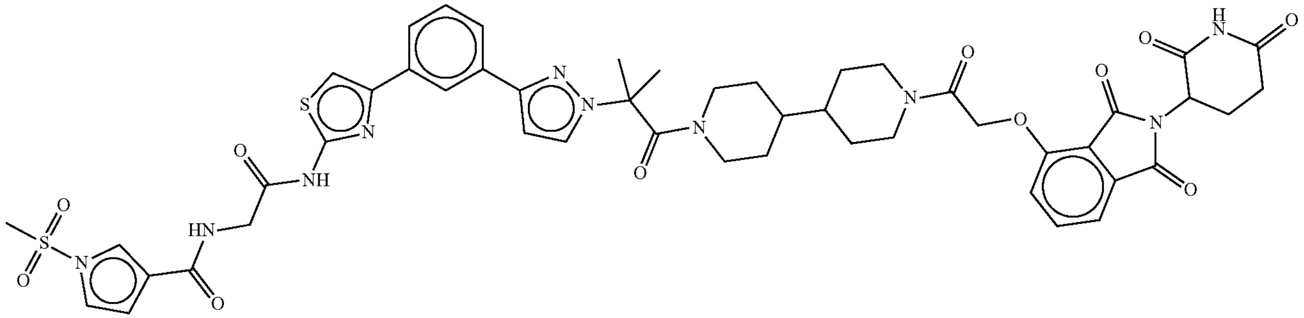 |
| 11 | 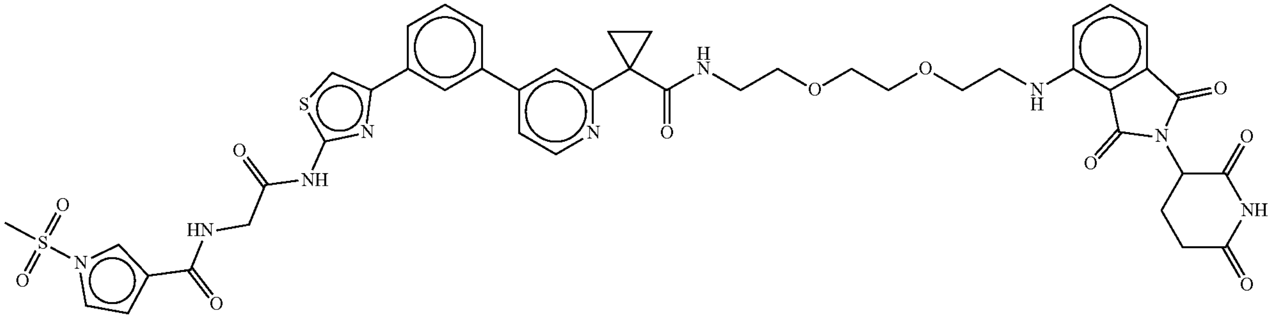 |

TABLE 1-continued
| Compounds of the Invention | |
|---|---|
| # | Structure |
| 12 | 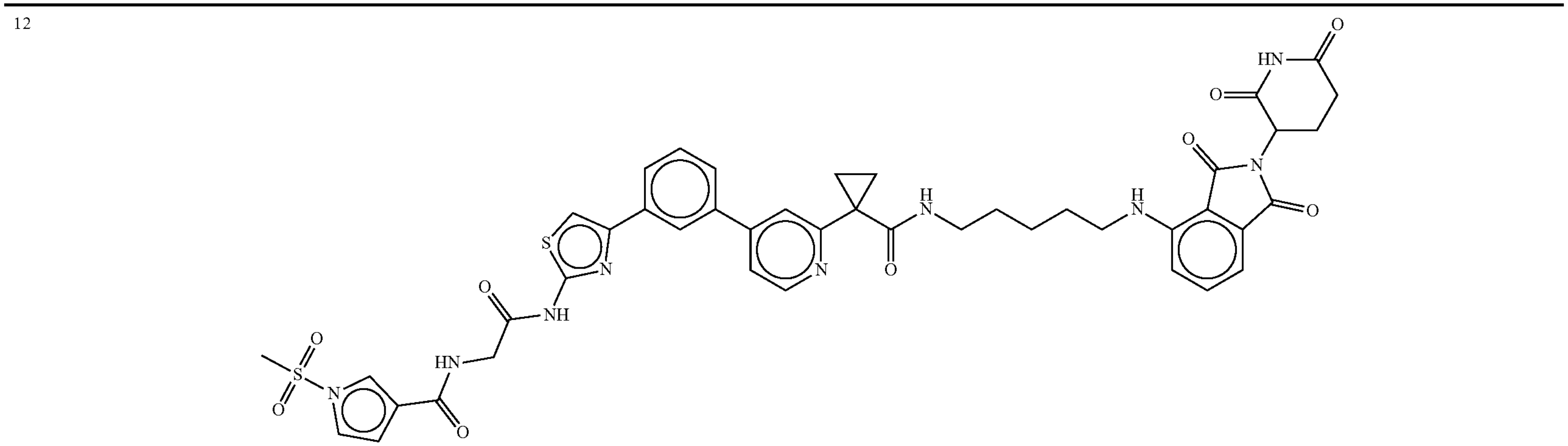 |
| 13 | 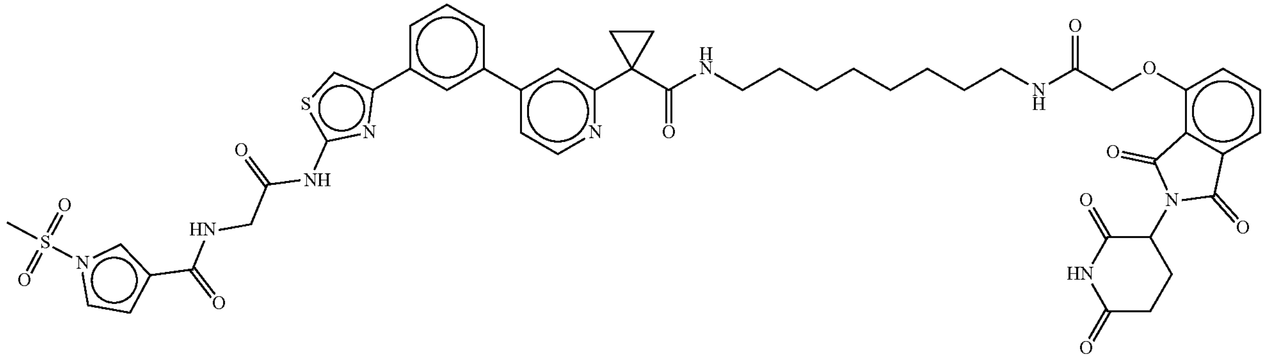 |

TABLE 1-continued
| Compounds of the Invention | |
|---|---|
| # | Structure |
| 14 | 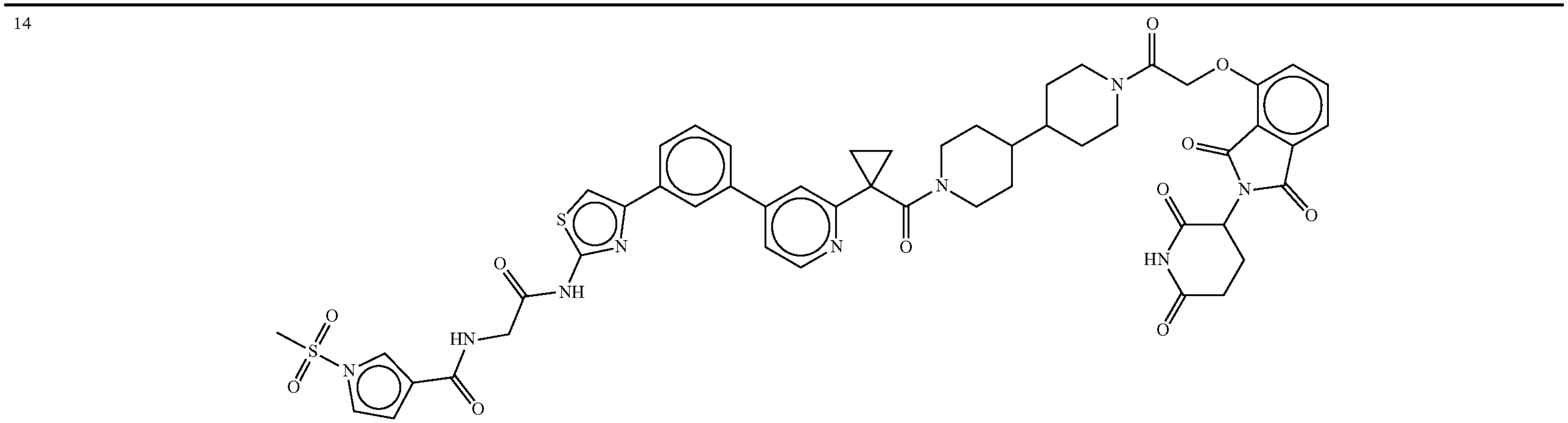 |
| 15 | 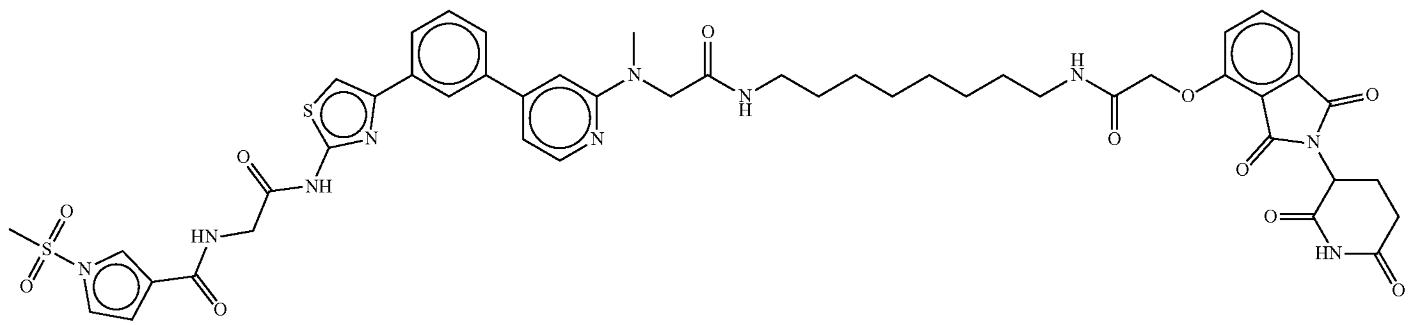 |

TABLE 1-continued
| Compounds of the Invention | |
|---|---|
| # | Structure |
| 16 | 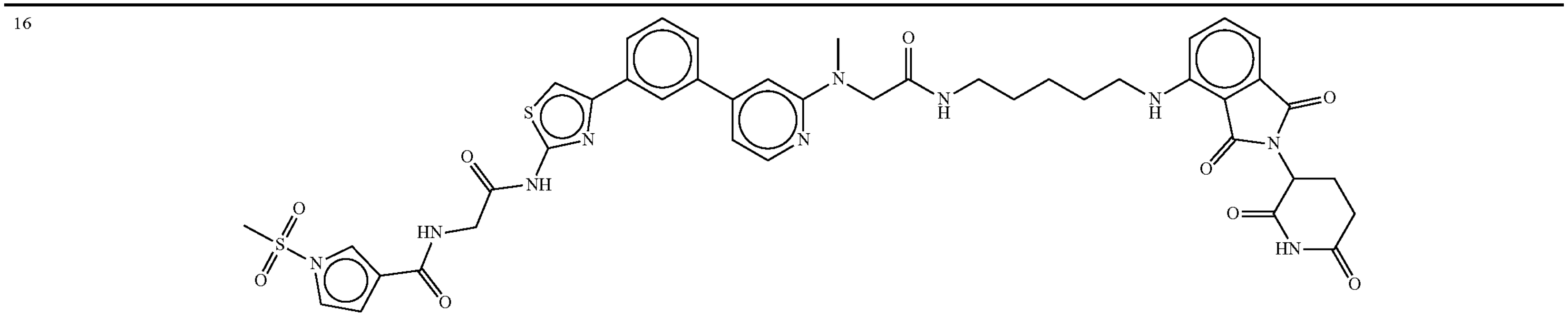 |
| 17 | 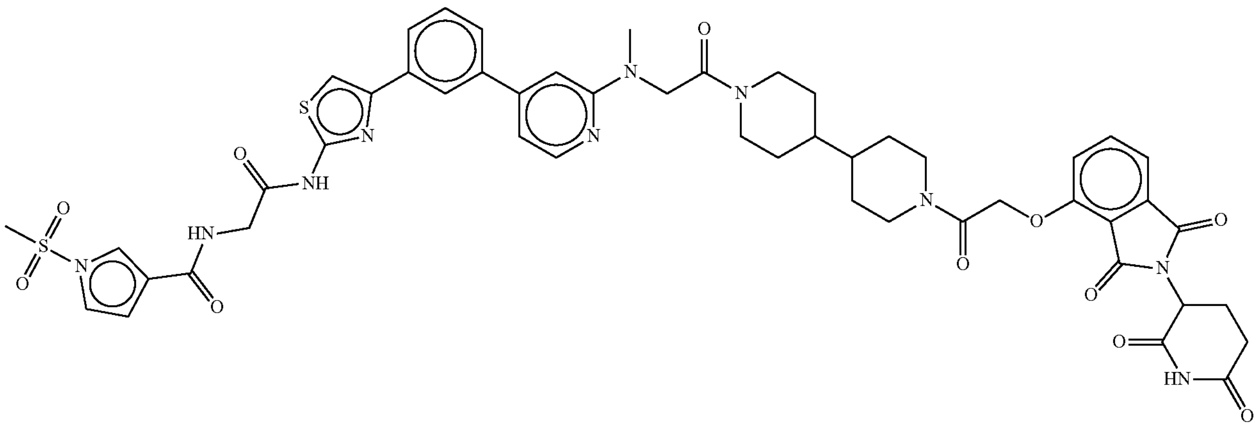 |

TABLE 1-continued
| Compounds of the Invention | |
|---|---|
| # | Structure |
| 18 | 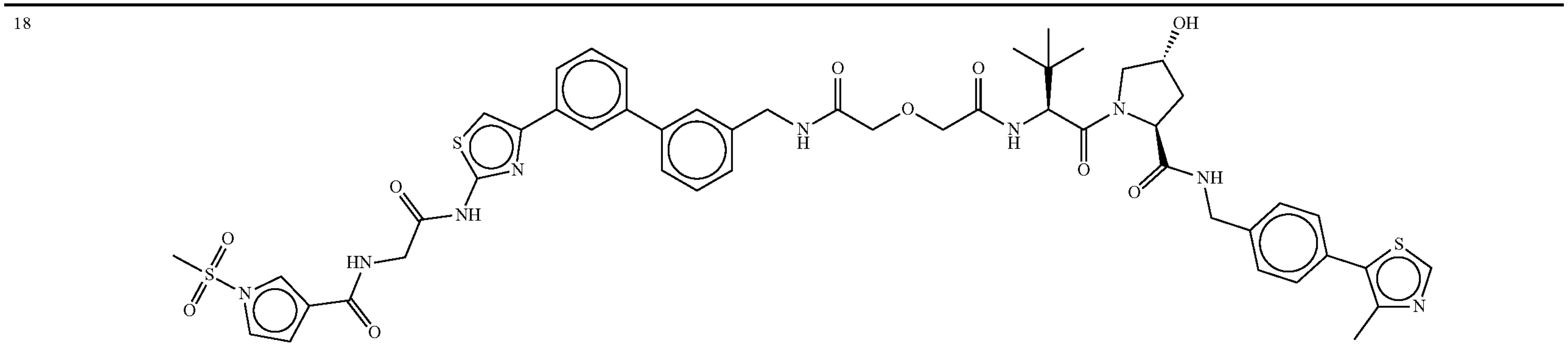 |
| 19 | 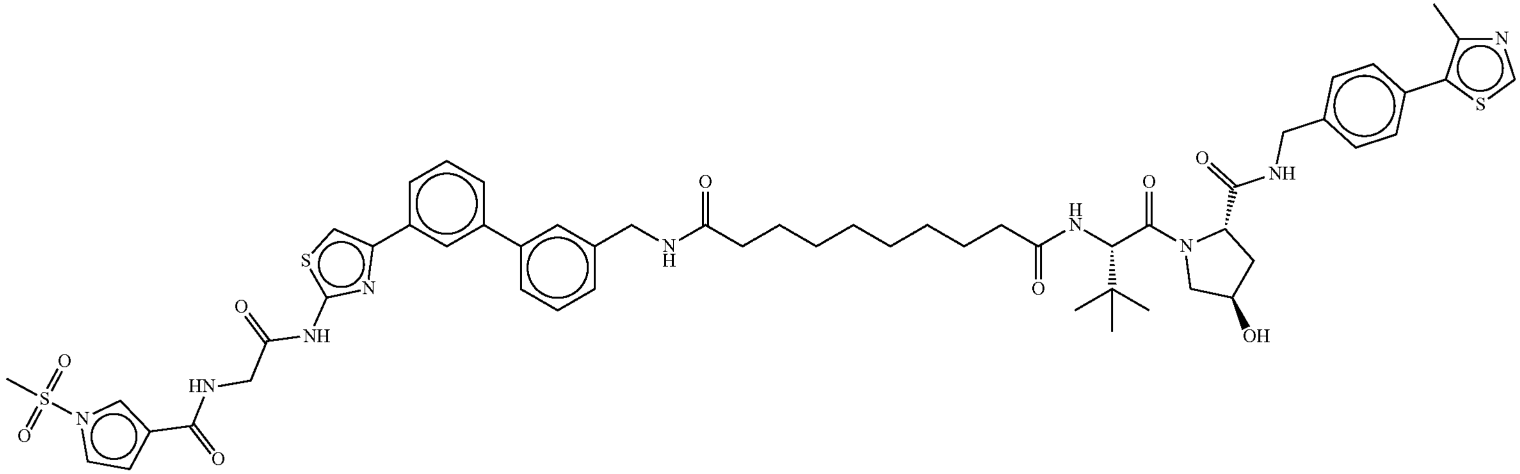 |

TABLE 1-continued
| Compounds of the Invention | |
|---|---|
| # | Structure |
| 20 | 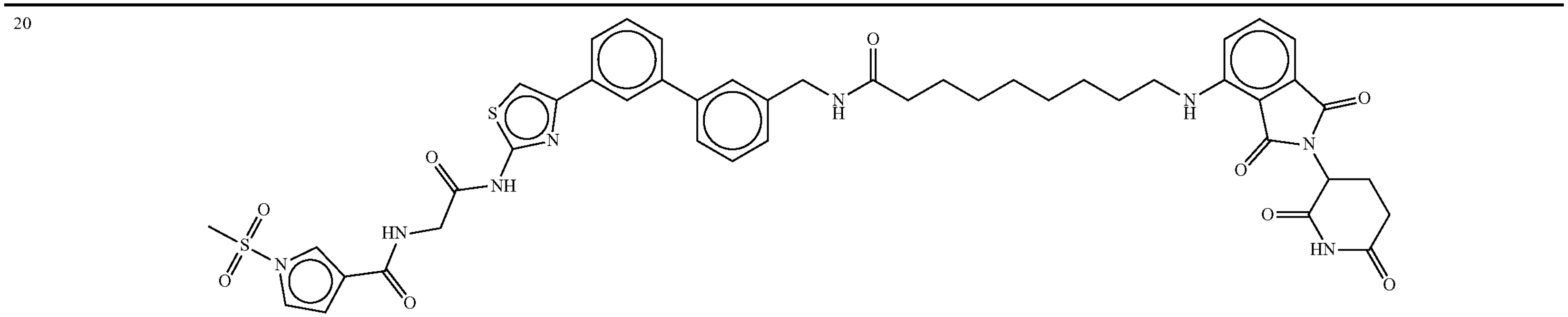 |
| 21 | 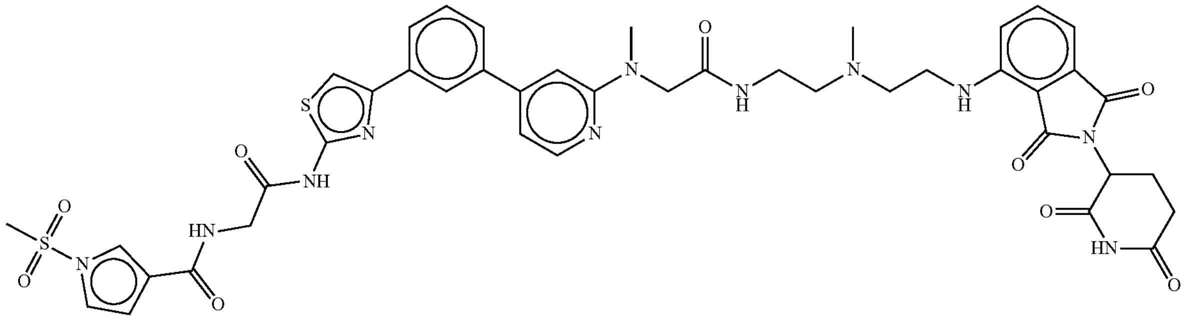 |
| 22 | 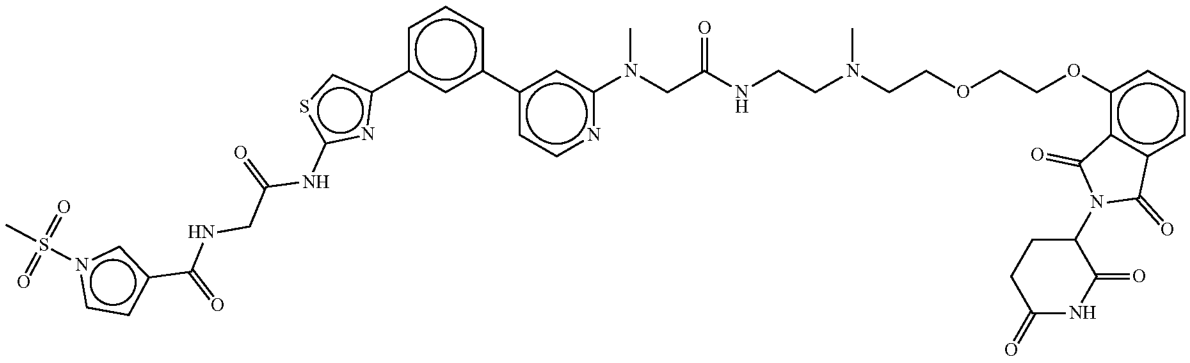 |

TABLE 1-continued
| Compounds of the Invention | |
|---|---|
| # | Structure |
| 23 | 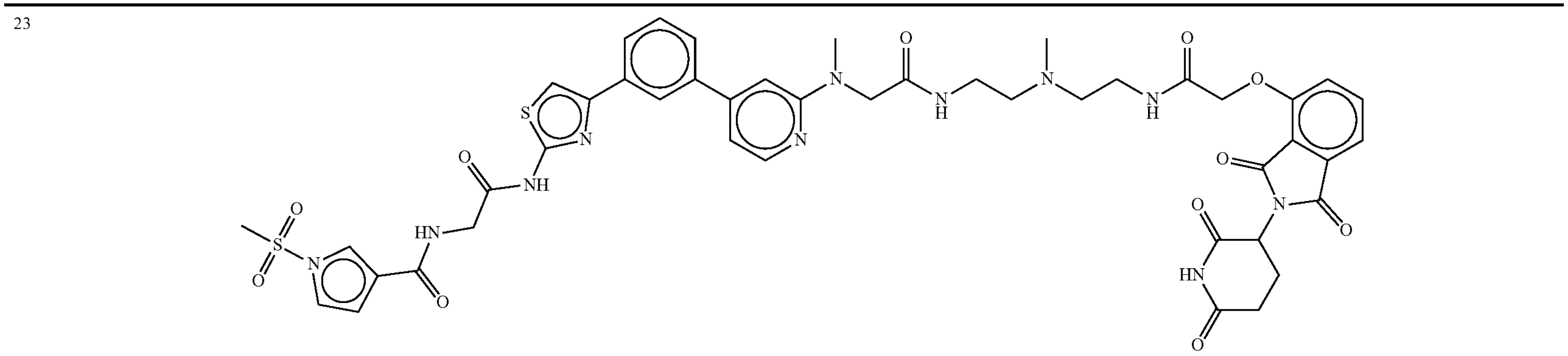 |
| 24 | 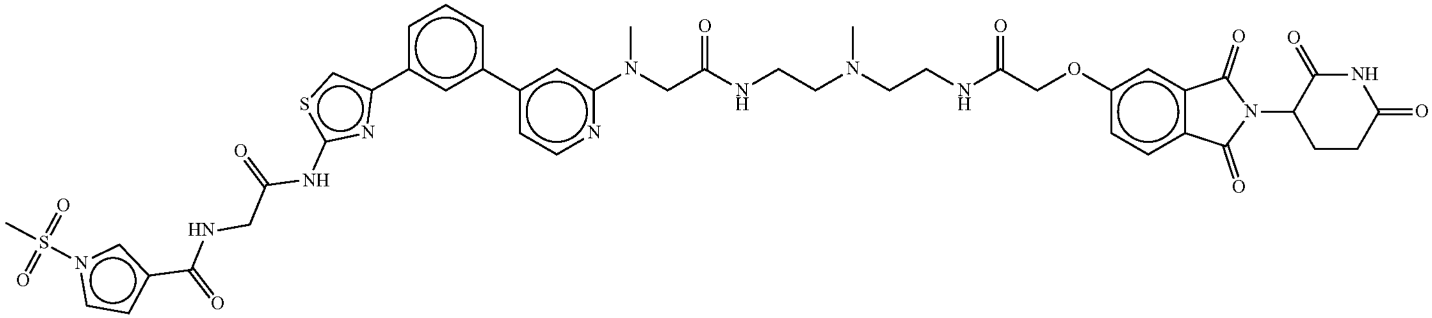 |
| 25 | 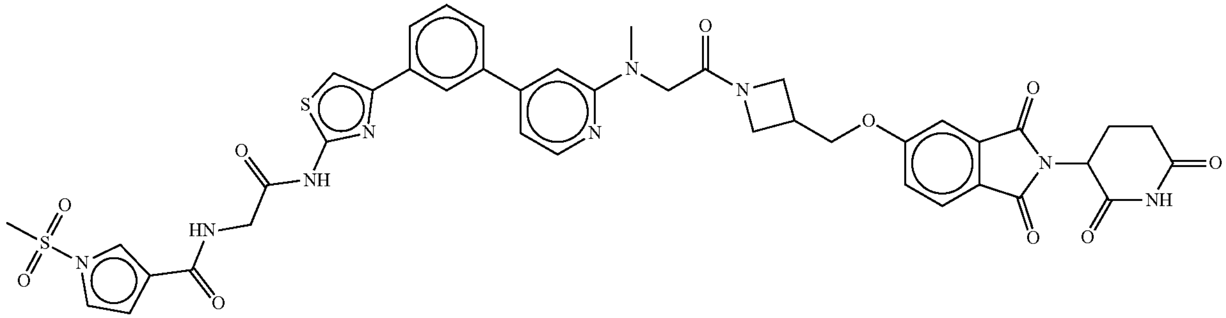 |

TABLE 1-continued
| Compounds of the Invention | |
|---|---|
| # | Structure |
| 26 | 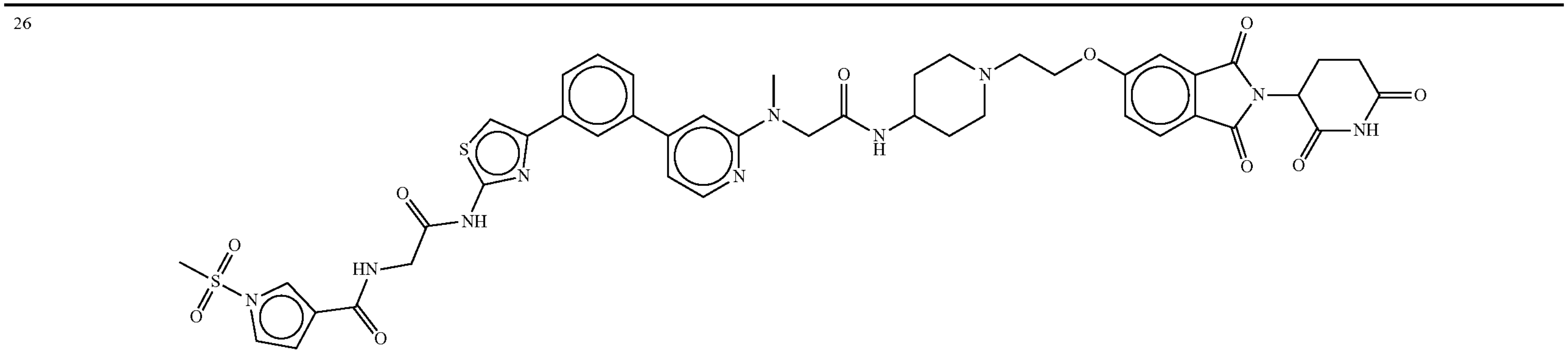 |
| 27 | 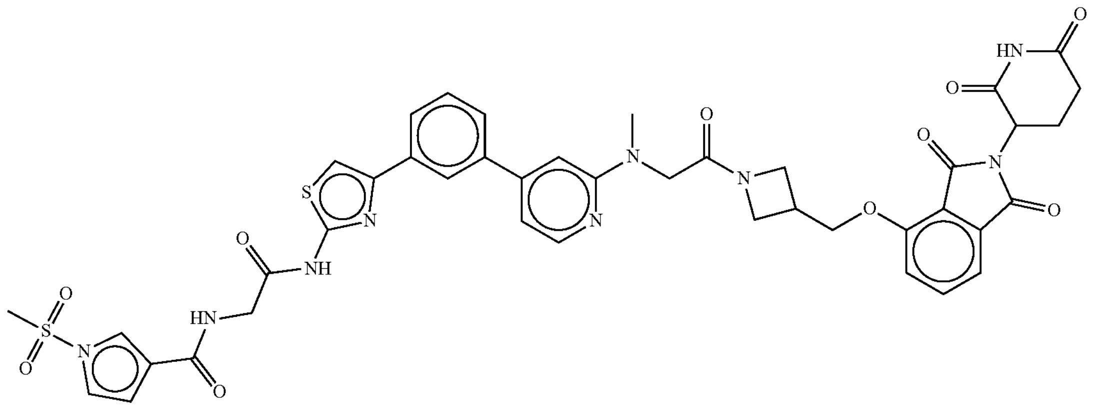 |

TABLE 1-continued
| Compounds of the Invention | |
|---|---|
| # | Structure |
| 28 | 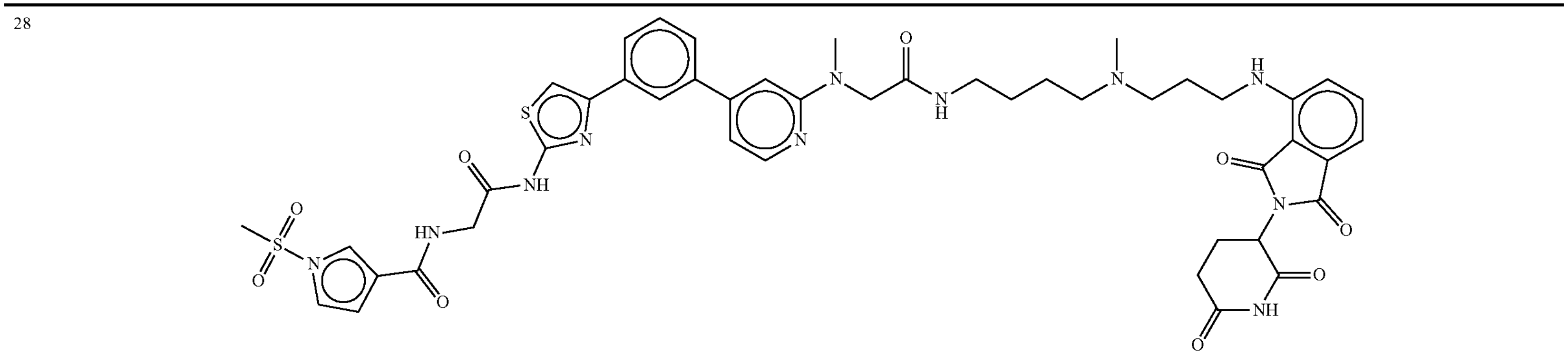 |
| 29 | 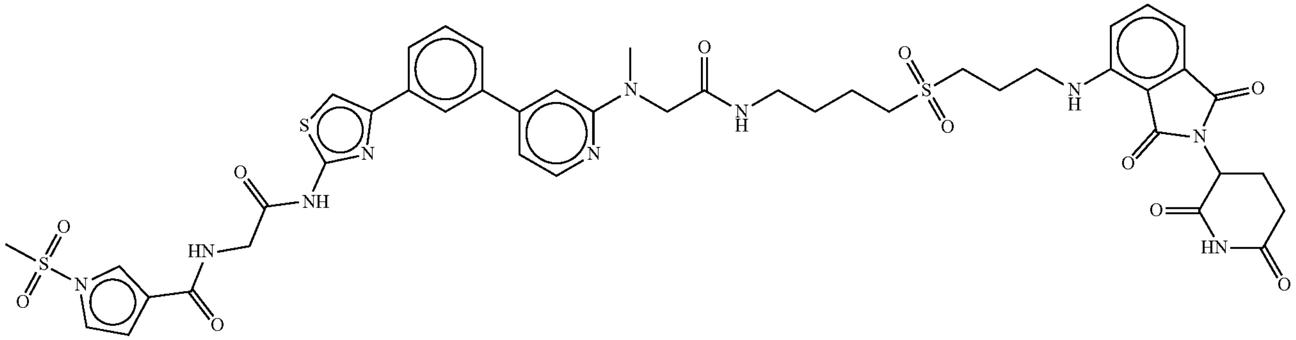 |

TABLE 1-continued
| Compounds of the Invention | |
|---|---|
| # | Structure |
| 30 | 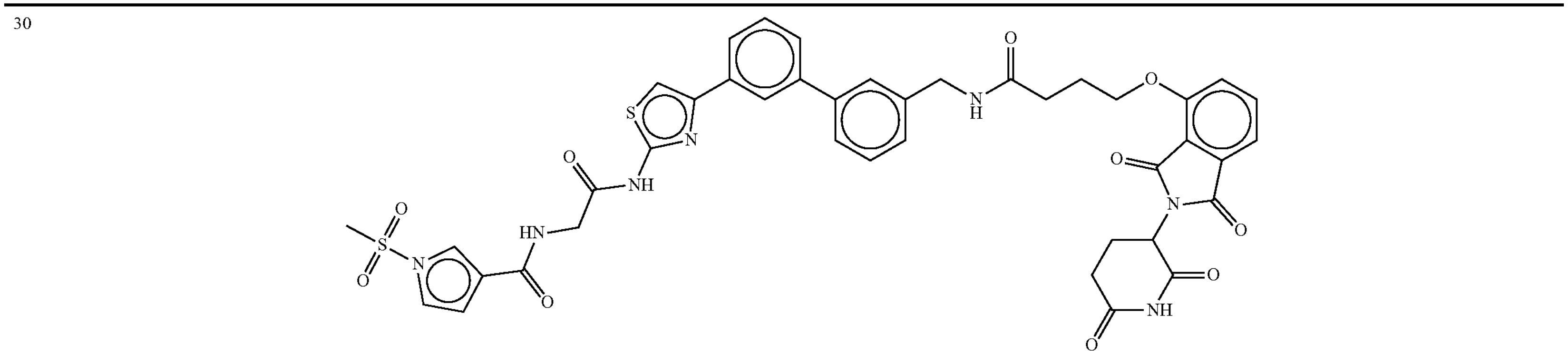 |
| 31 | 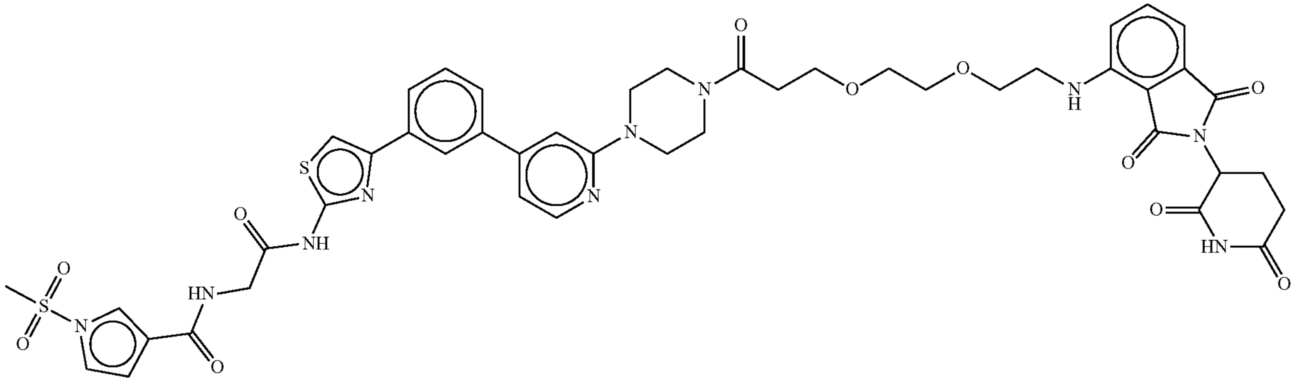 |

TABLE 1-continued
| Compounds of the Invention | |
|---|---|
| # | Structure |
| 32 | 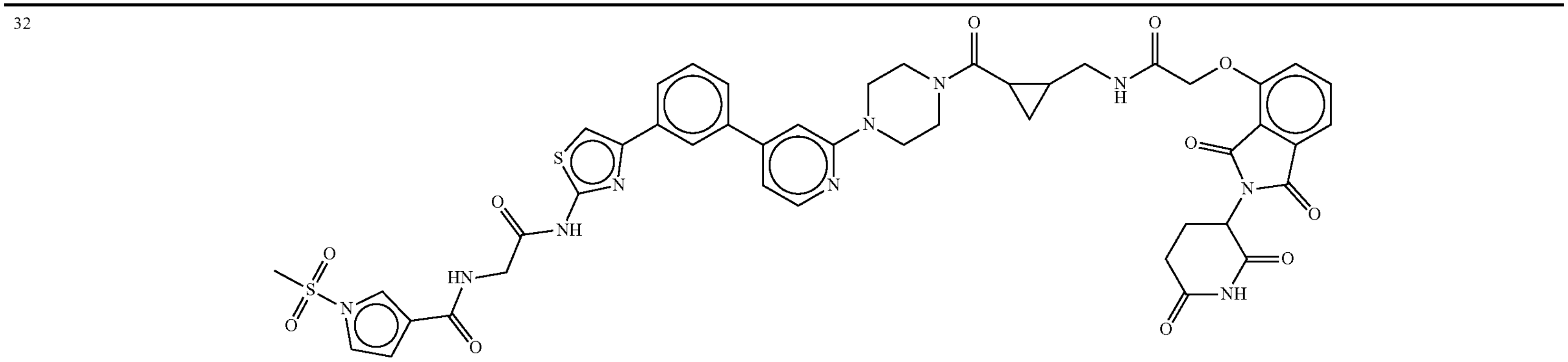 |
| 33 | 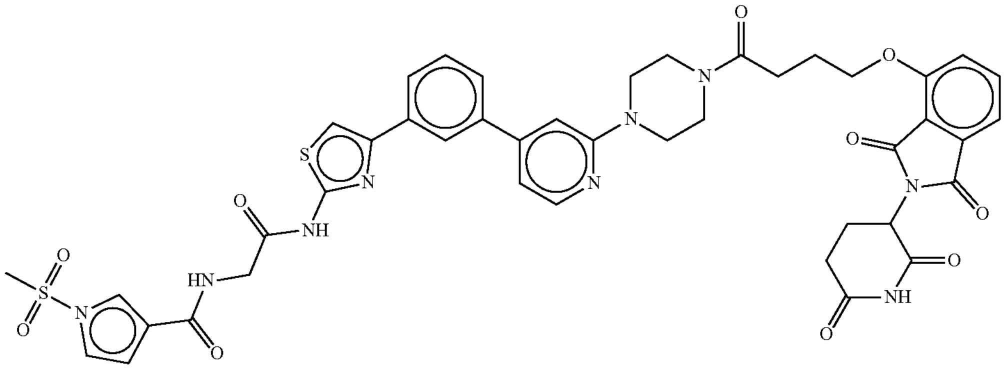 |

TABLE 1-continued
| Compounds of the Invention | |
|---|---|
| # | Structure |
| 34 | 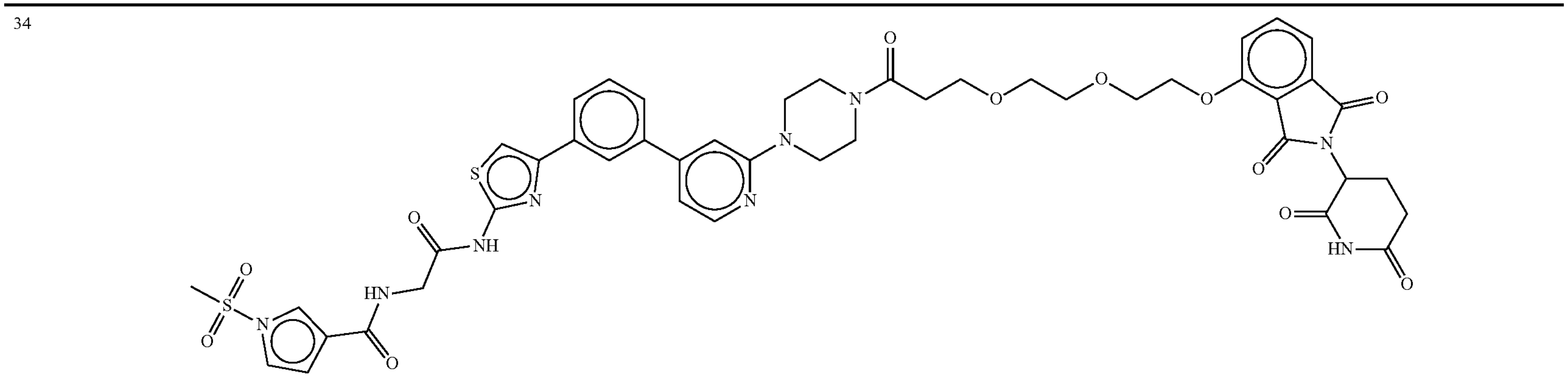 |
| 35 | 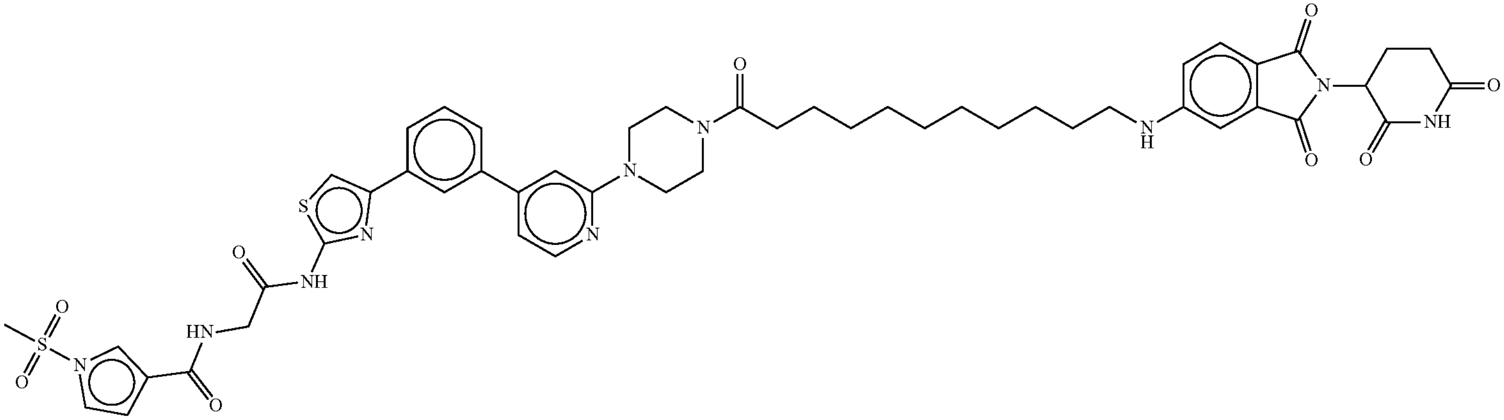 |

TABLE 1-continued
| Compounds of the Invention | |
|---|---|
| # | Structure |
| 36 | 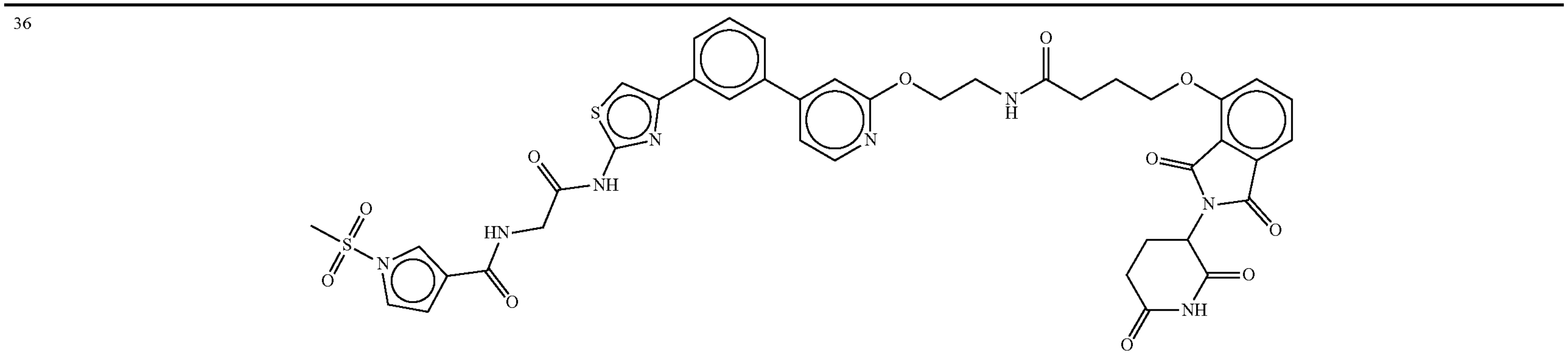 |
| 37 | 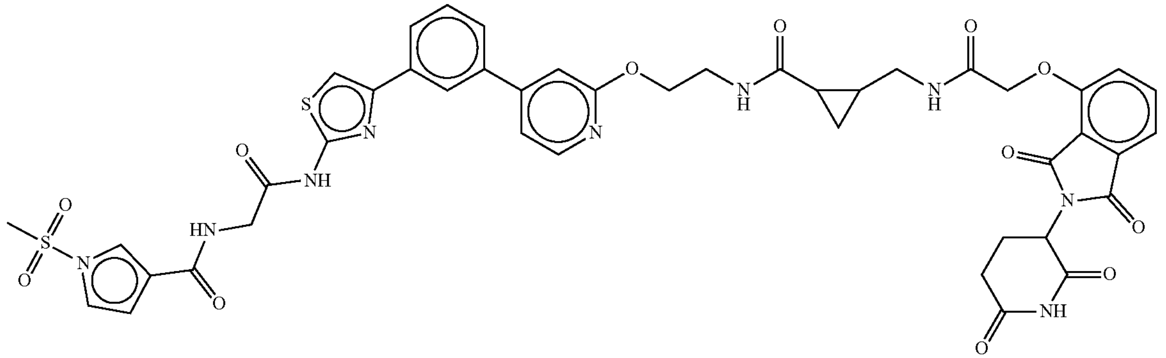 |

TABLE 1-continued
| Compounds of the Invention | |
|---|---|
| # | Structure |
| 38 | 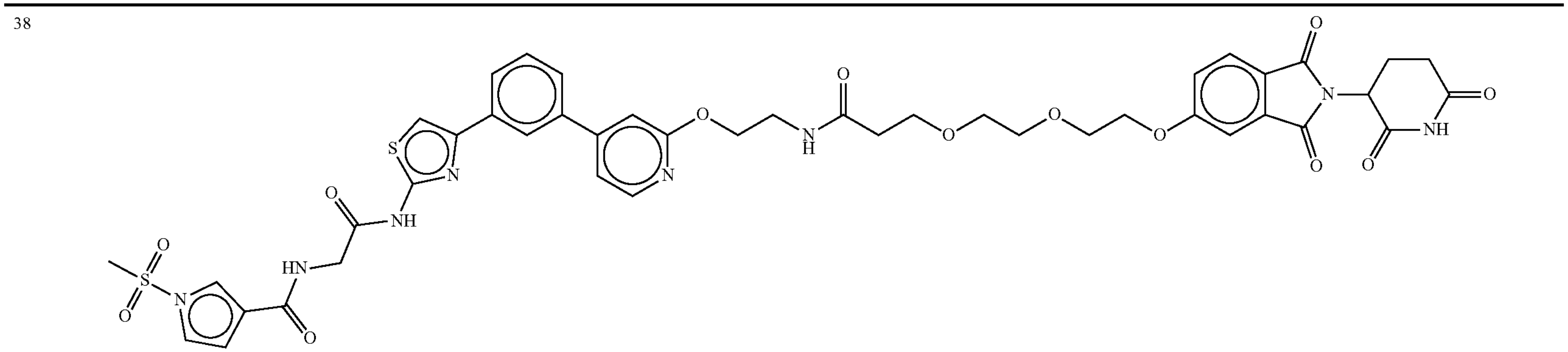 |
| 39 | 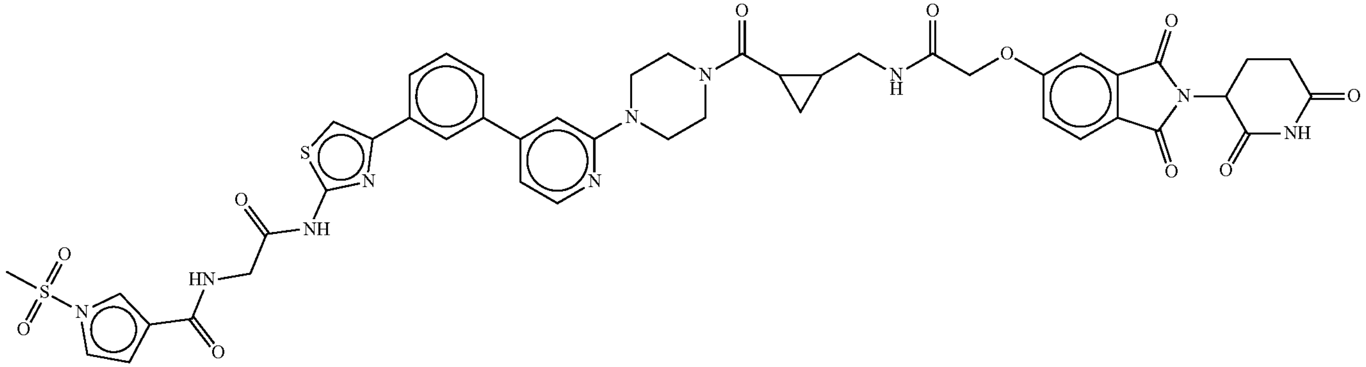 |

TABLE 1-continued
| Compounds of the Invention | |
|---|---|
| # | Structure |
| 40 | 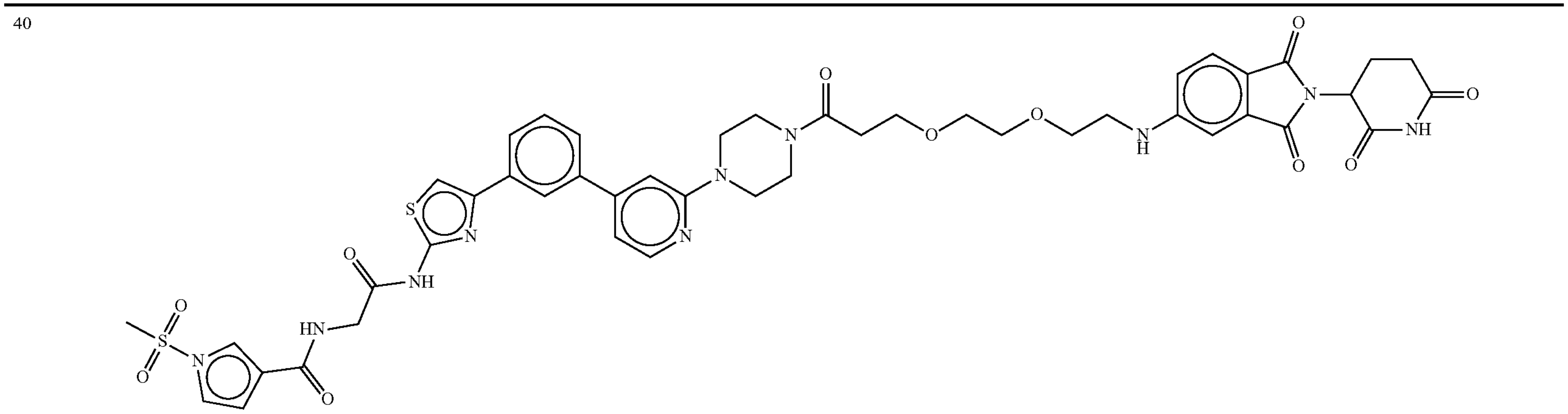 |
| 41 | 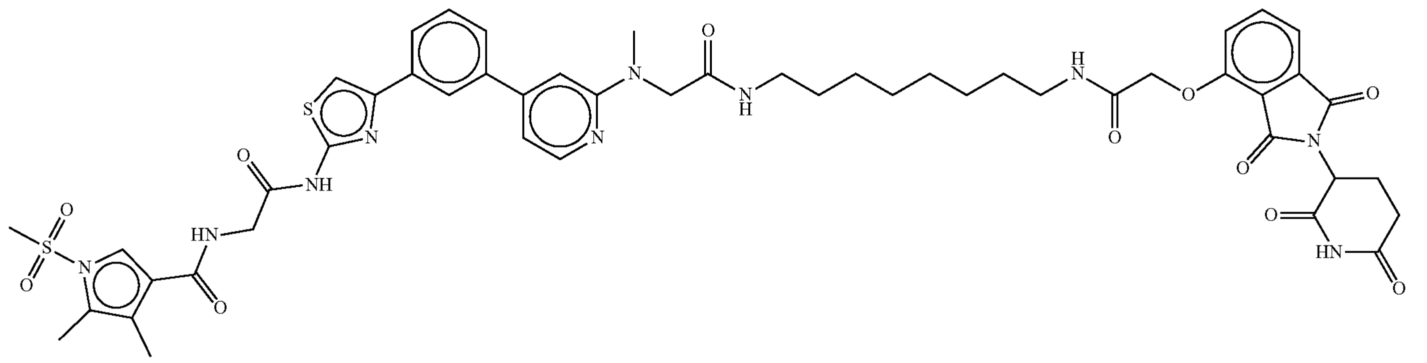 |

TABLE 1-continued
| Compounds of the Invention | |
|---|---|
| # | Structure |
| 42 | 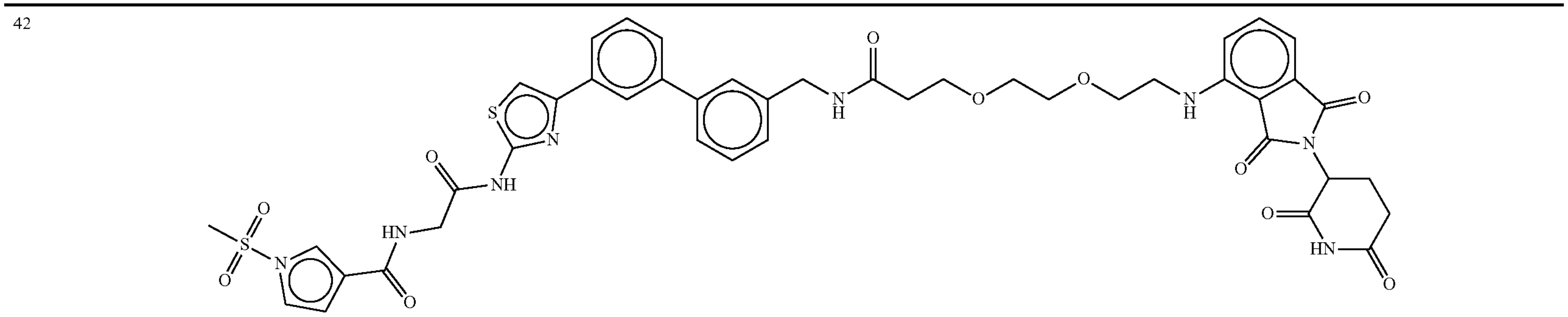 |
| 43 | 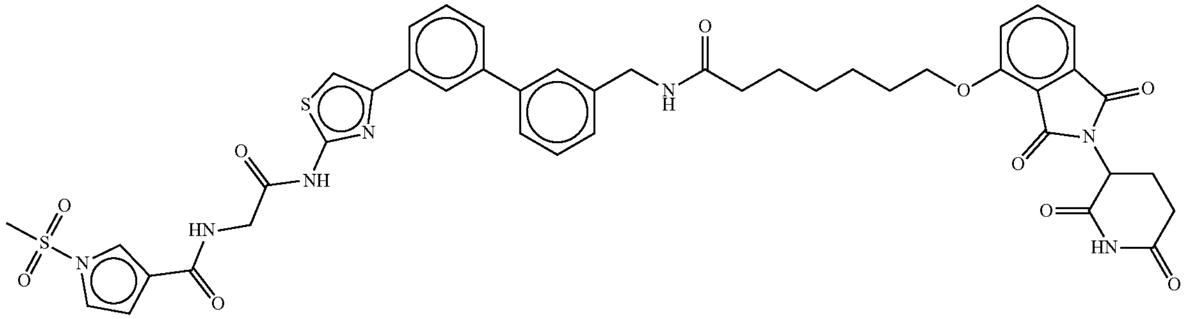 |

TABLE 1-continued
| Compounds of the Invention | |
|---|---|
| # | Structure |
| 44 | 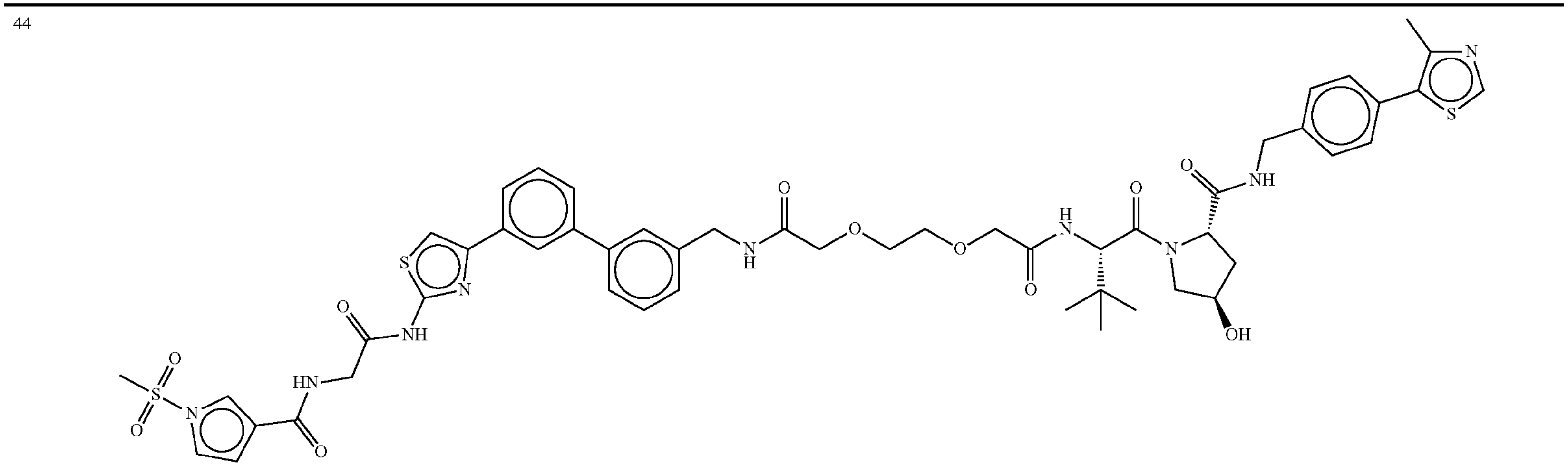 |
| 45 | 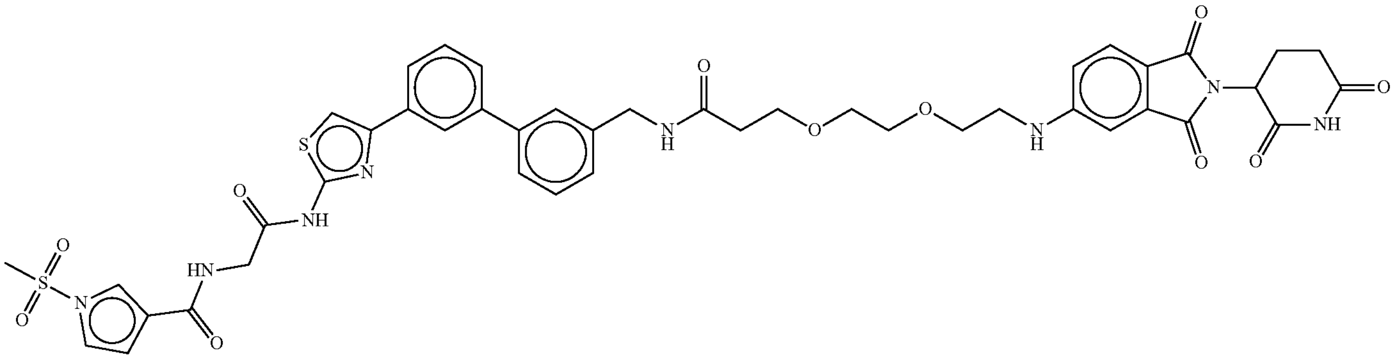 |

TABLE 1-continued
| Compounds of the Invention | |
|---|---|
| # | Structure |
| 46 | 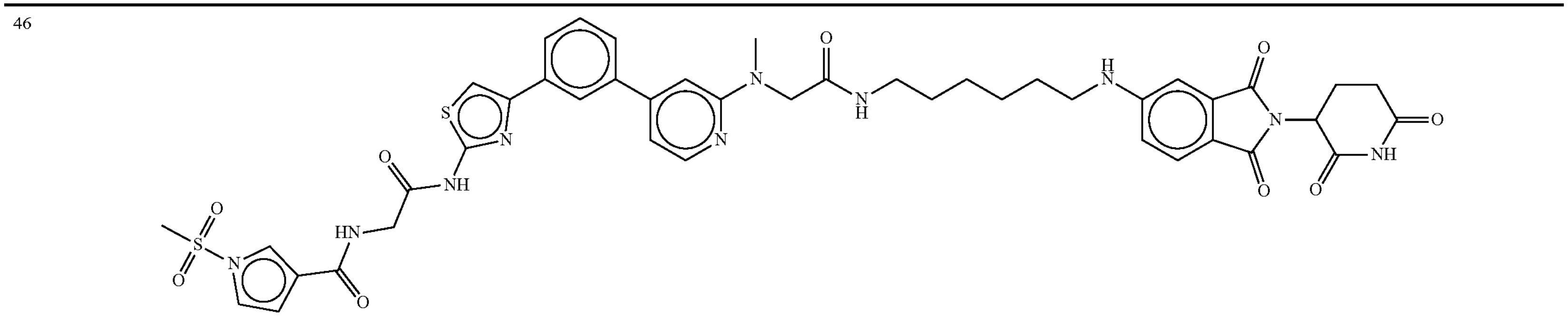 |
| 47 | 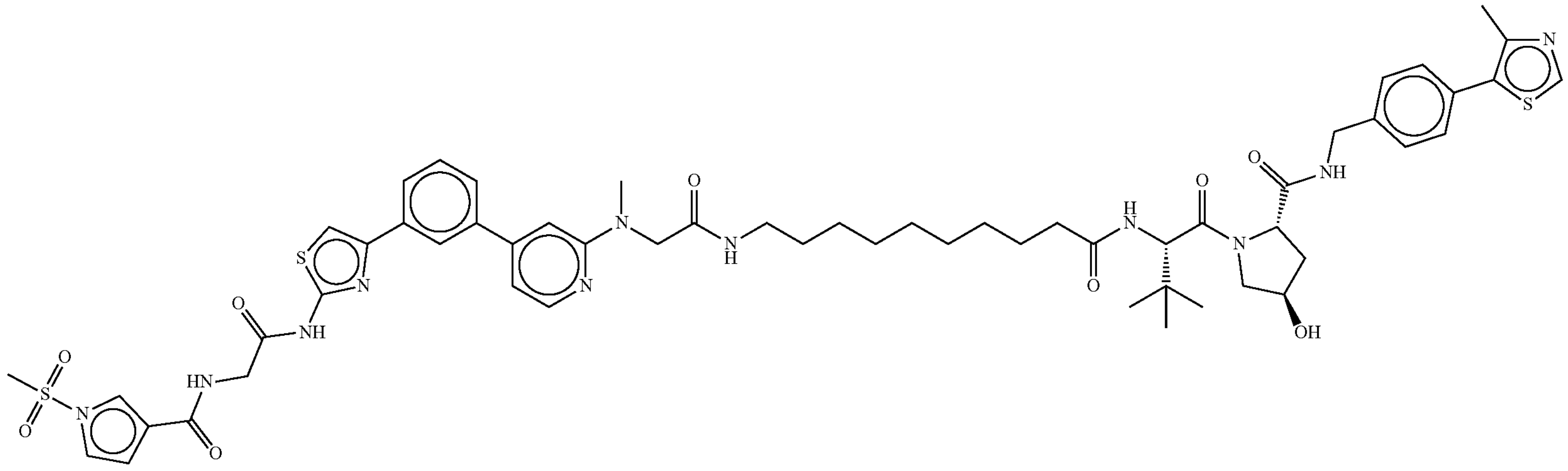 |

TABLE 1-continued
| Compounds of the Invention | |
|---|---|
| # | Structure |
| 48 | 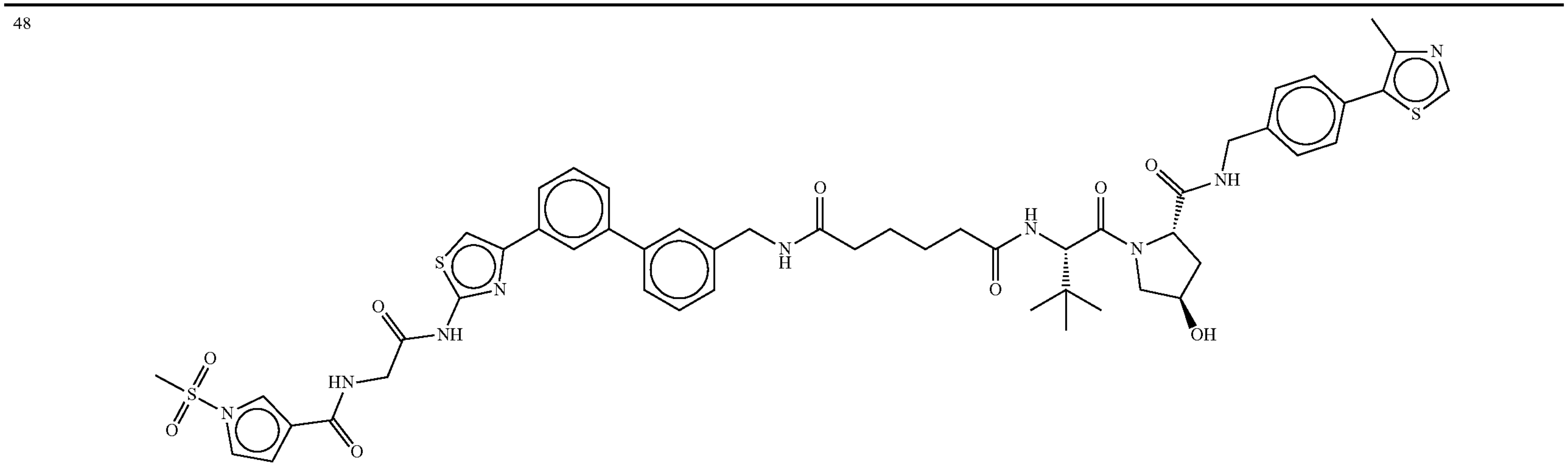 |
| 49 | 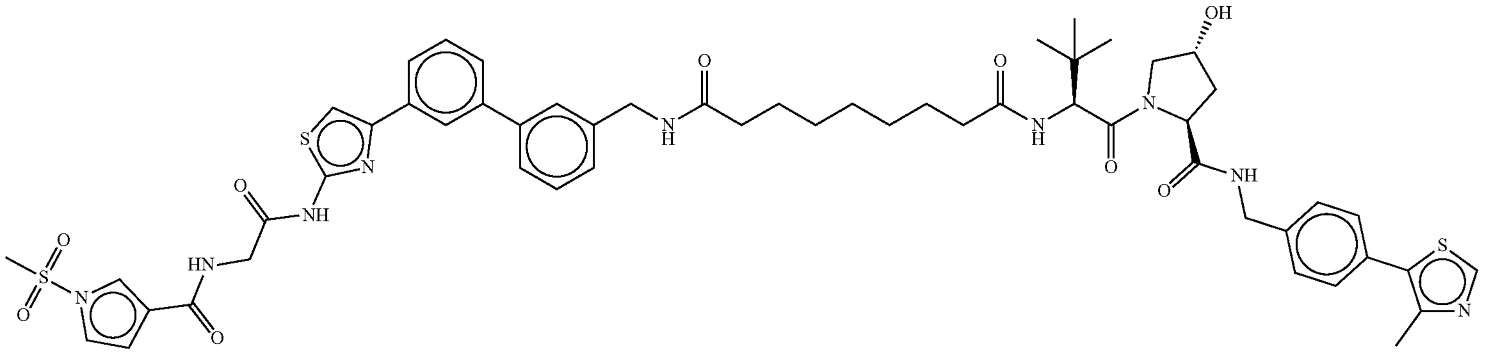 |

TABLE 1-continued
| Compounds of the Invention | |
|---|---|
| # | Structure |
| 50 | 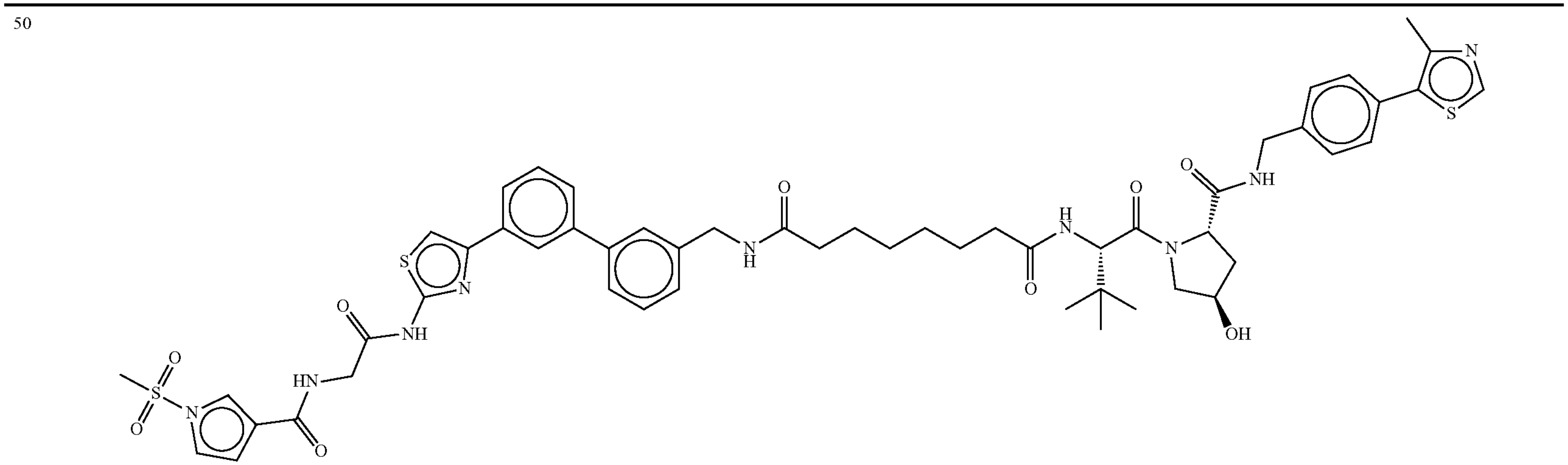 |
| 51 | 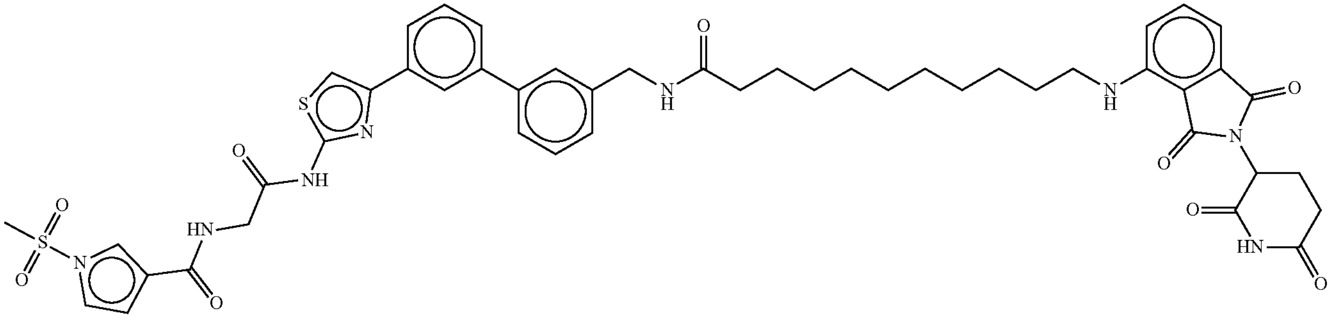 |

TABLE 1-continued
| Compounds of the Invention | |
|---|---|
| # | Structure |
| 52 | 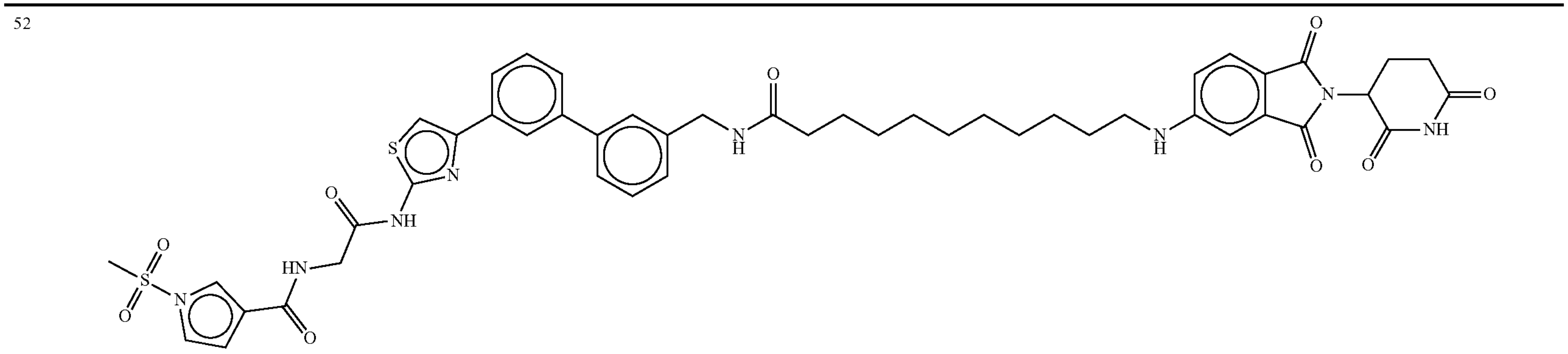 |
| 53 | 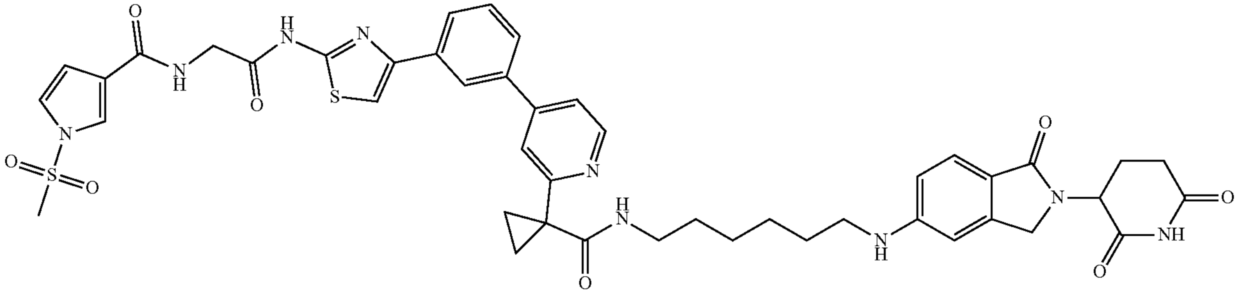 [SMILES: CS(=O)(=O)n1ccc(C(=O)NCC(=O)Nc2nc(-c3cccc(-c4ccnc(C5(C(=O)NCCCCCCNc6ccc7c(c6)CN(C6CCC(=O)NC6=O)C7=O)CC5)c4)c3)cs2)c1] |
| 54 | 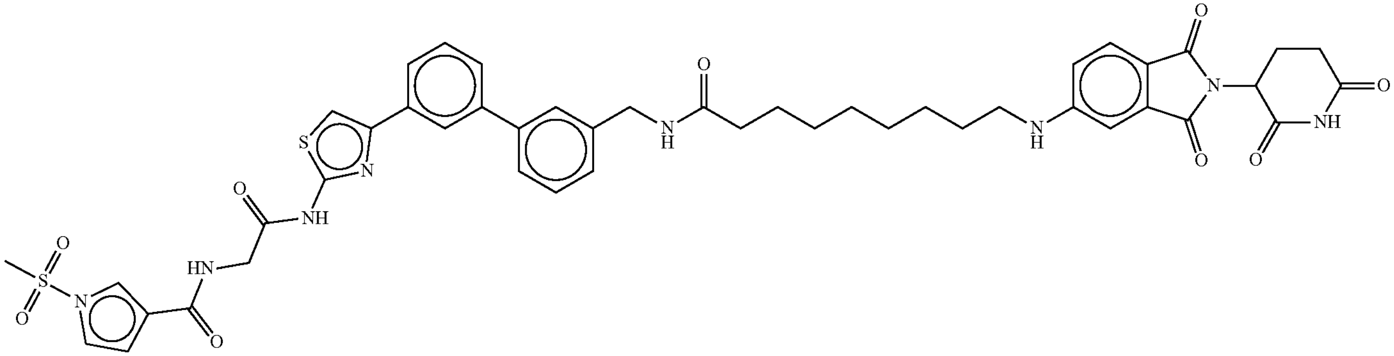 |

TABLE 1-continued
| Compounds of the Invention | |
|---|---|
| # | Structure |
| 55 | 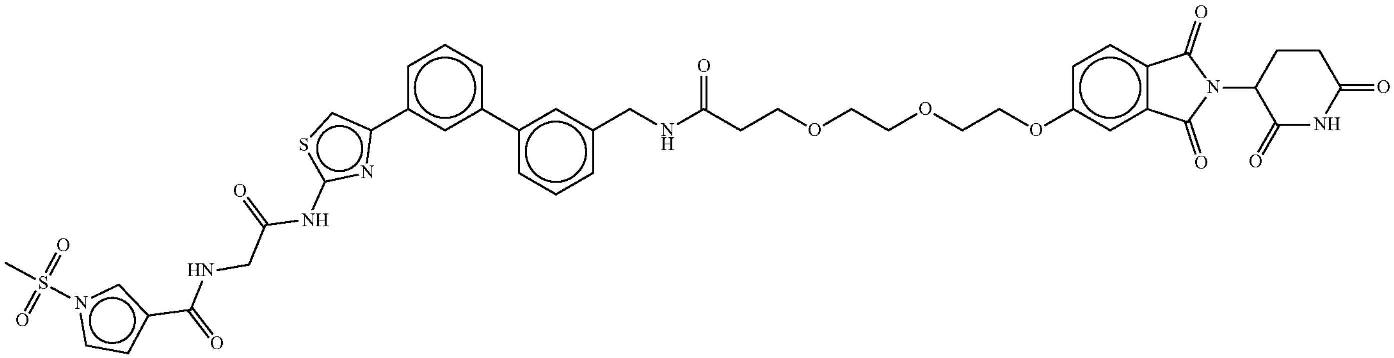 |
| 56 | 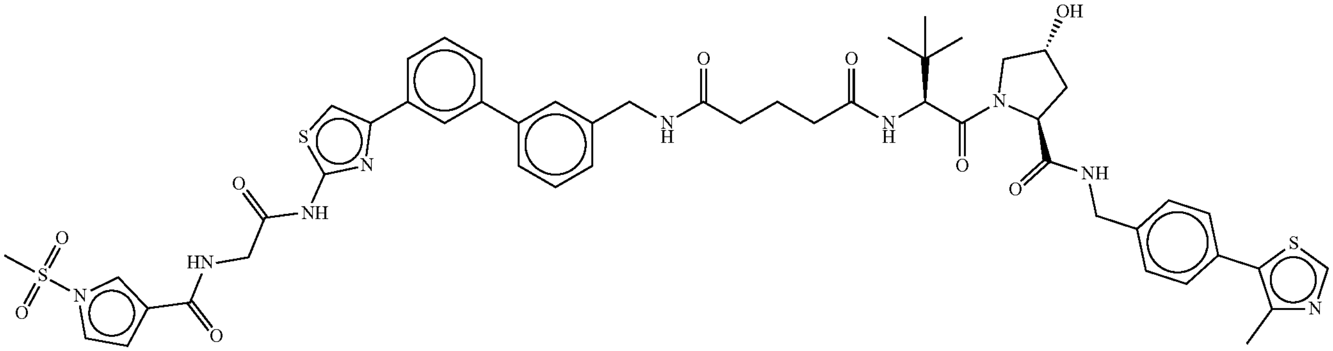 |

TABLE 1-continued
| Compounds of the Invention | |
|---|---|
| # | Structure |
| 57 | 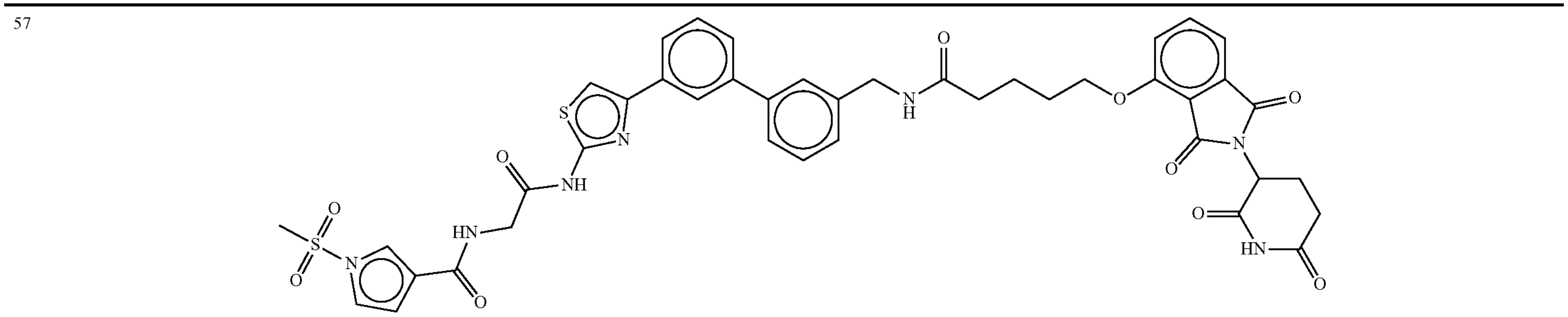 |
| 58 | 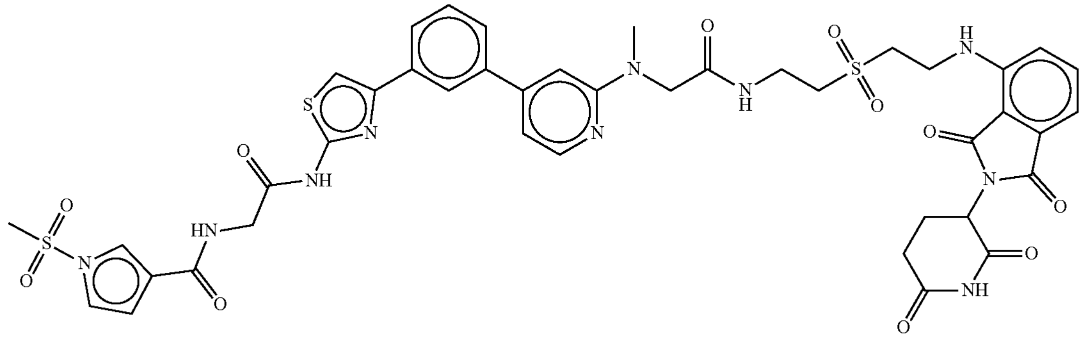 |
| 59 | 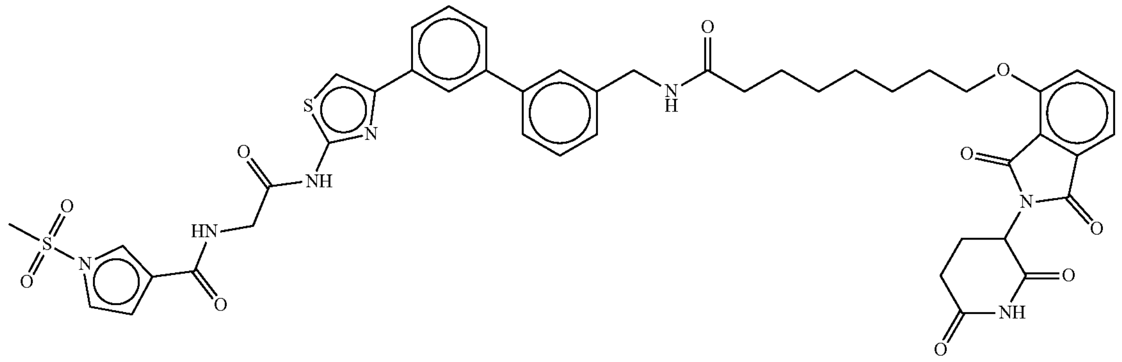 |

TABLE 1-continued
| Compounds of the Invention | |
|---|---|
| # | Structure |
| 60 | 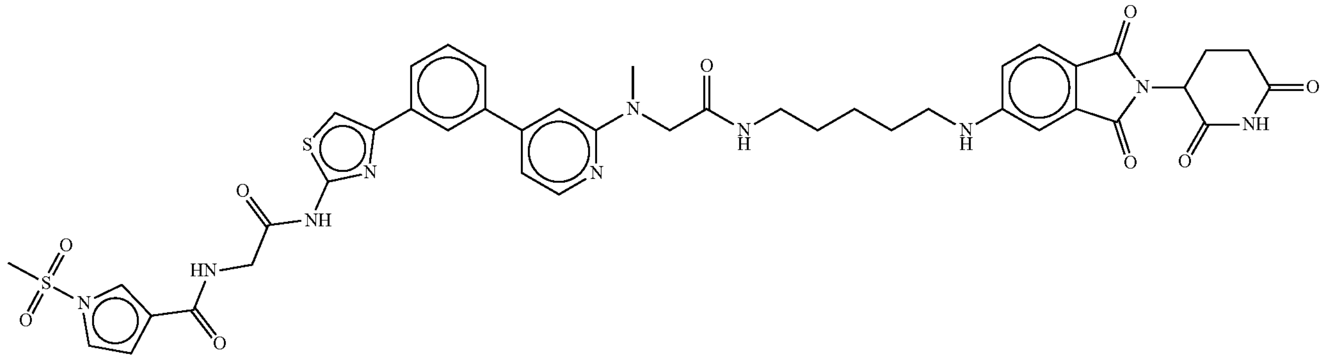 |
| 61 | 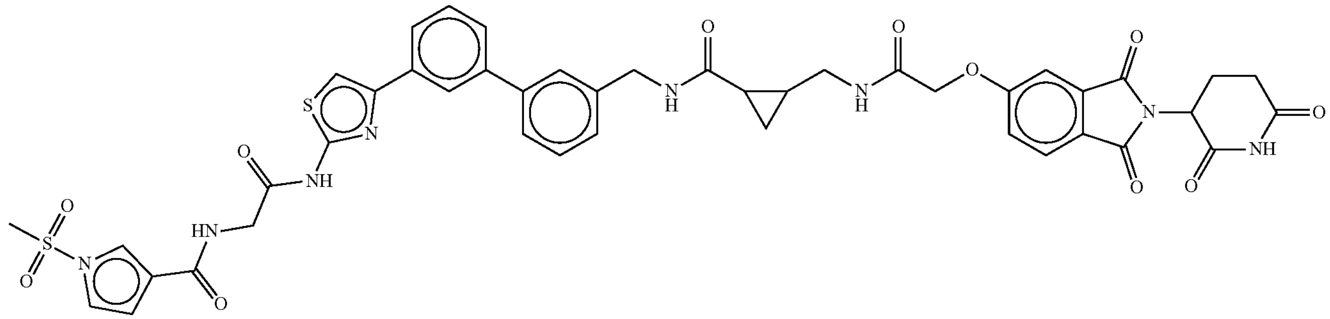 |

TABLE 1-continued
| Compounds of the Invention | |
|---|---|
| # | Structure |
| 62 | 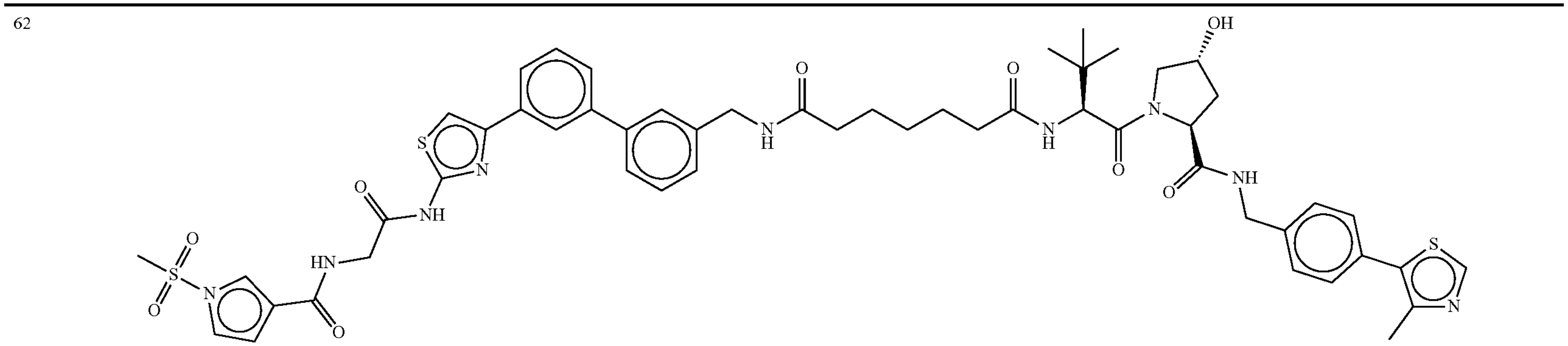 |
| 63 | 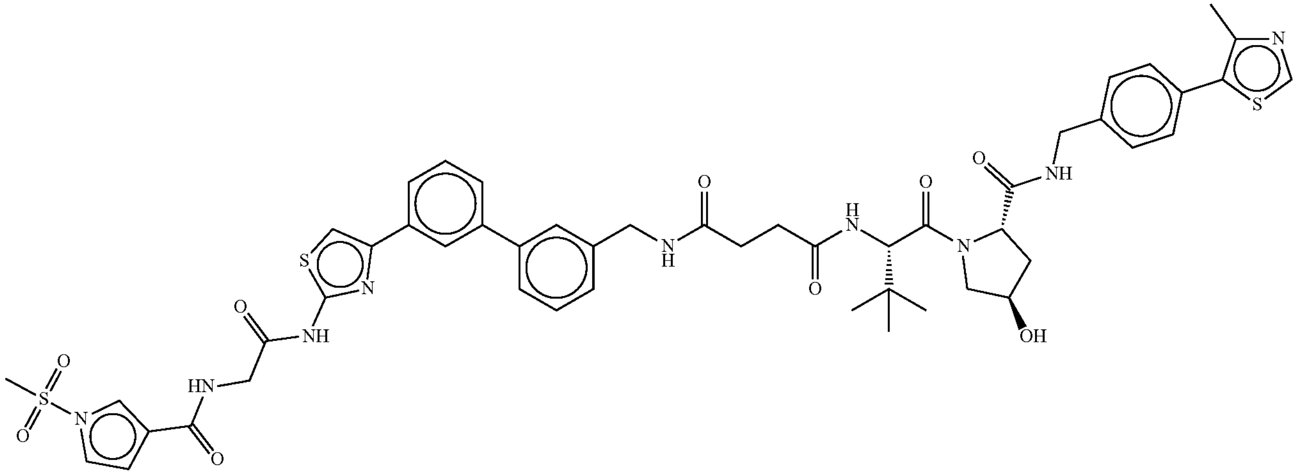 |

TABLE 1-continued
| Compounds of the Invention | |
|---|---|
| # | Structure |
| 64 | 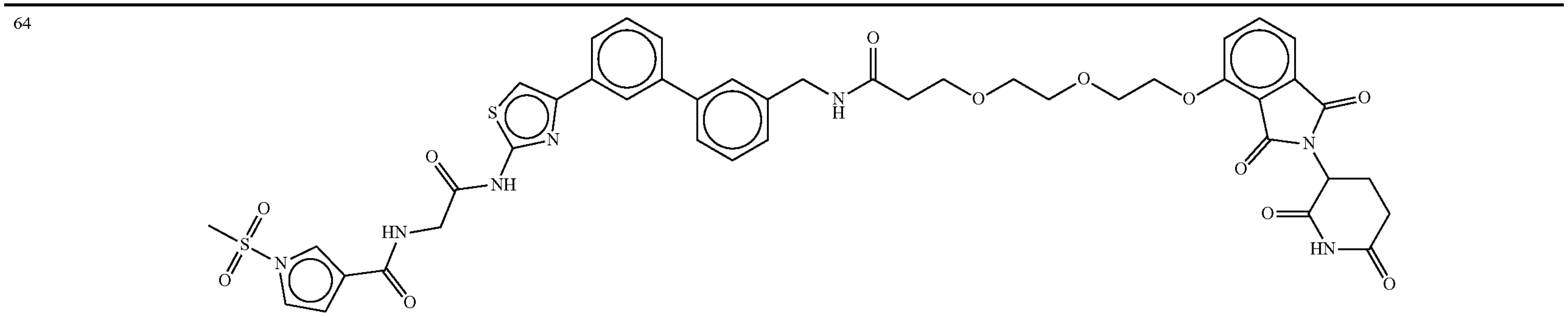 |
| 65 | 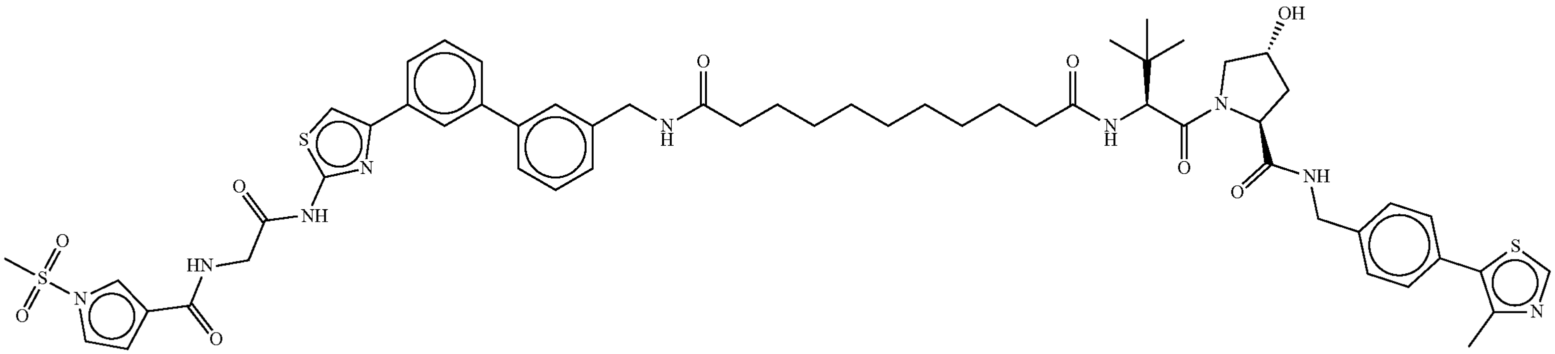 |

TABLE 1-continued
| Compounds of the Invention | |
|---|---|
| # | Structure |
| 66 | 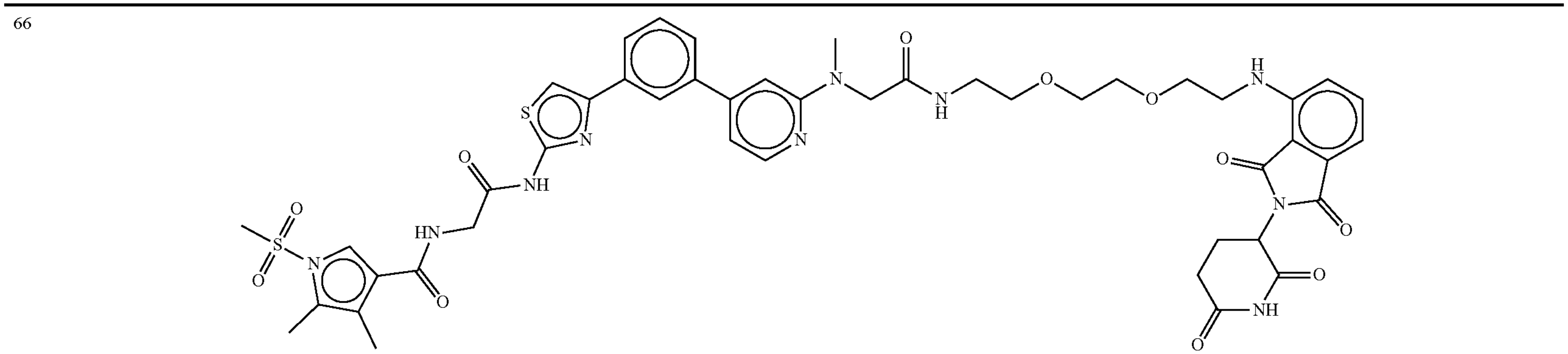 |
| 67 | 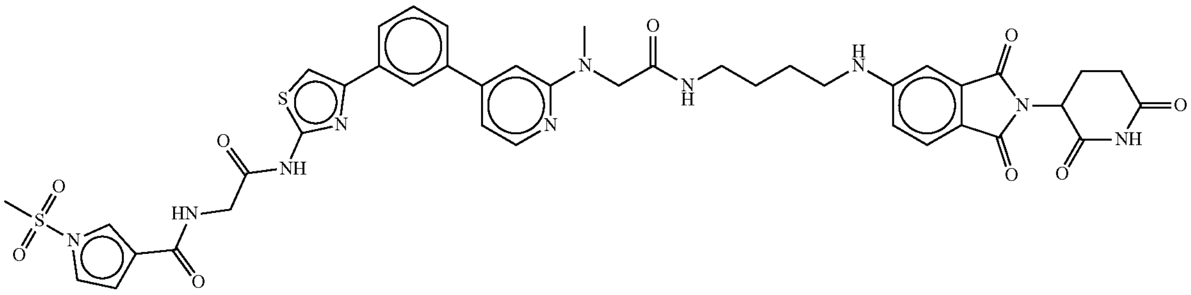 |
| 68 | 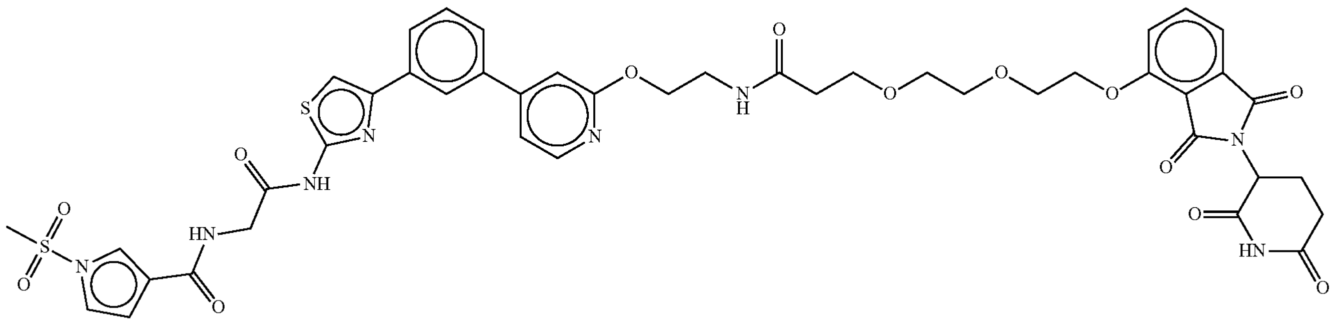 |

TABLE 1-continued
| Compounds of the Invention | |
|---|---|
| # | Structure |
| 69 | 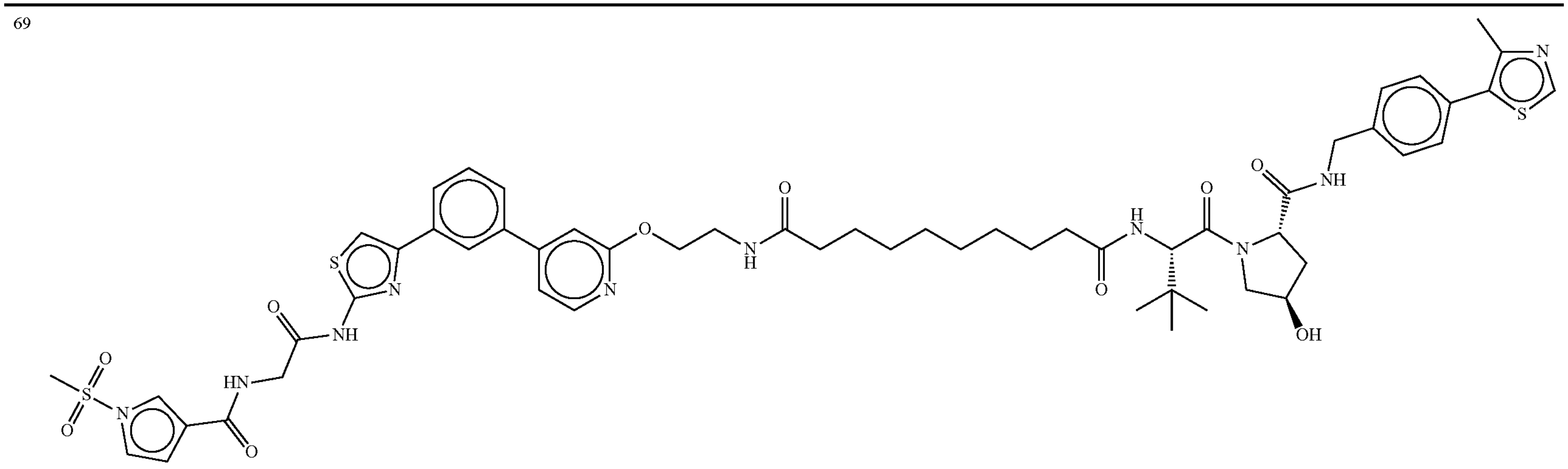 |
| 70 | 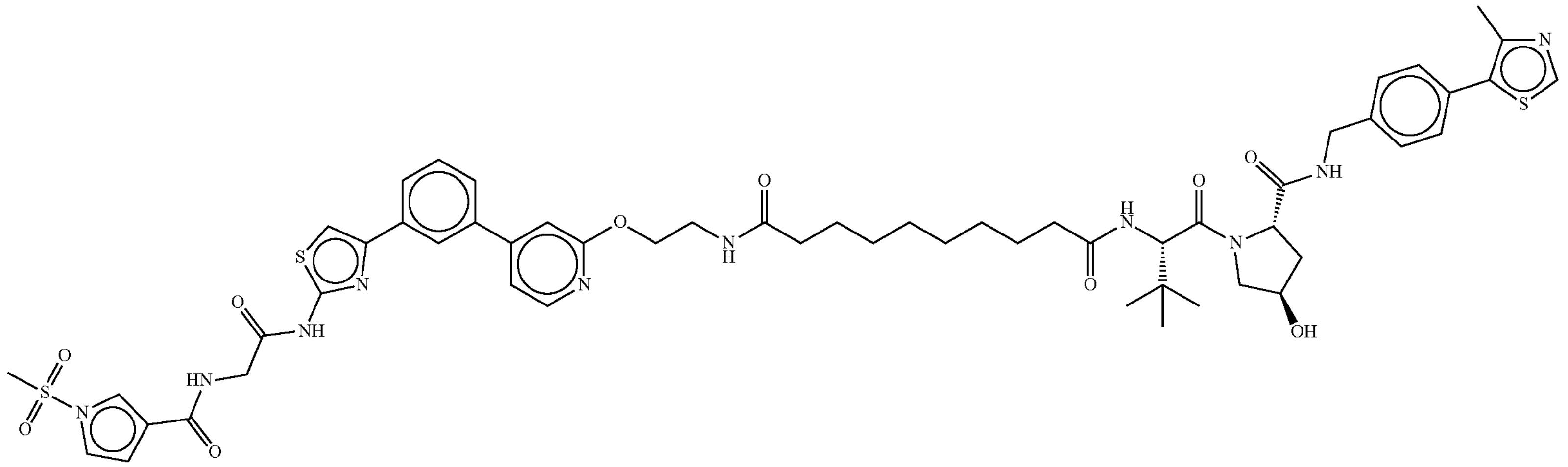 |

TABLE 1-continued
| Compounds of the Invention | |
|---|---|
| # | Structure |
| 71 | 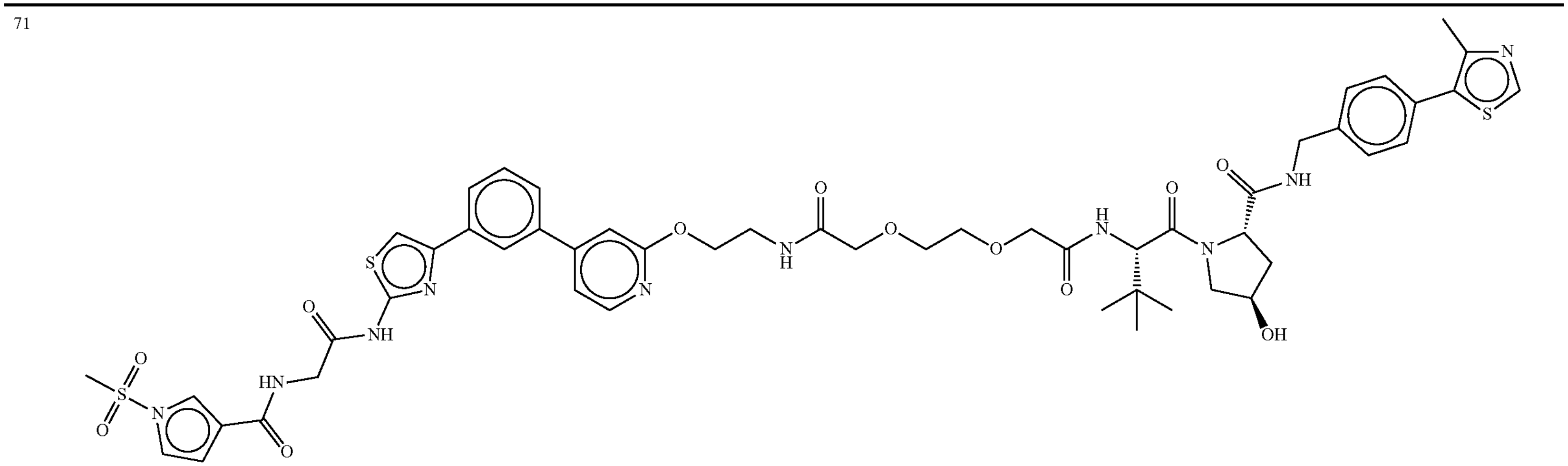 |
| 72 | 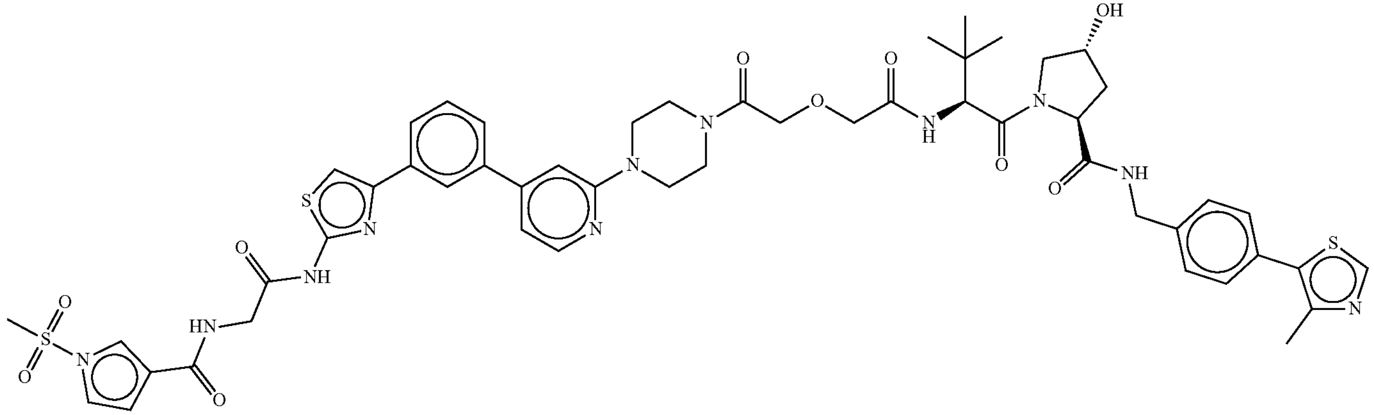 |

TABLE 1-continued
| Compounds of the Invention | |
|---|---|
| # | Structure |
| 73 | 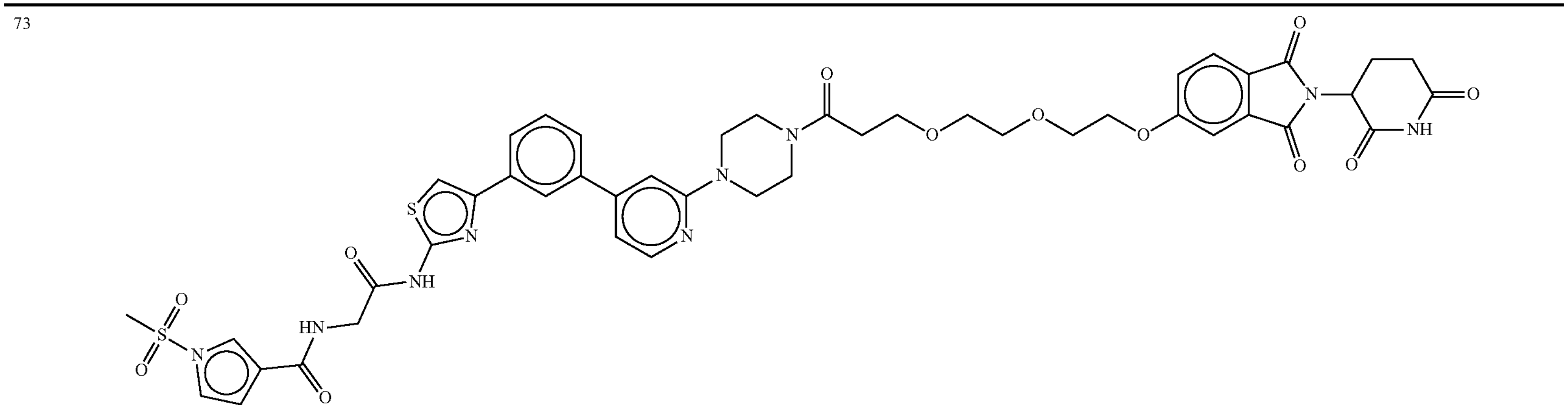 |
| 74 | 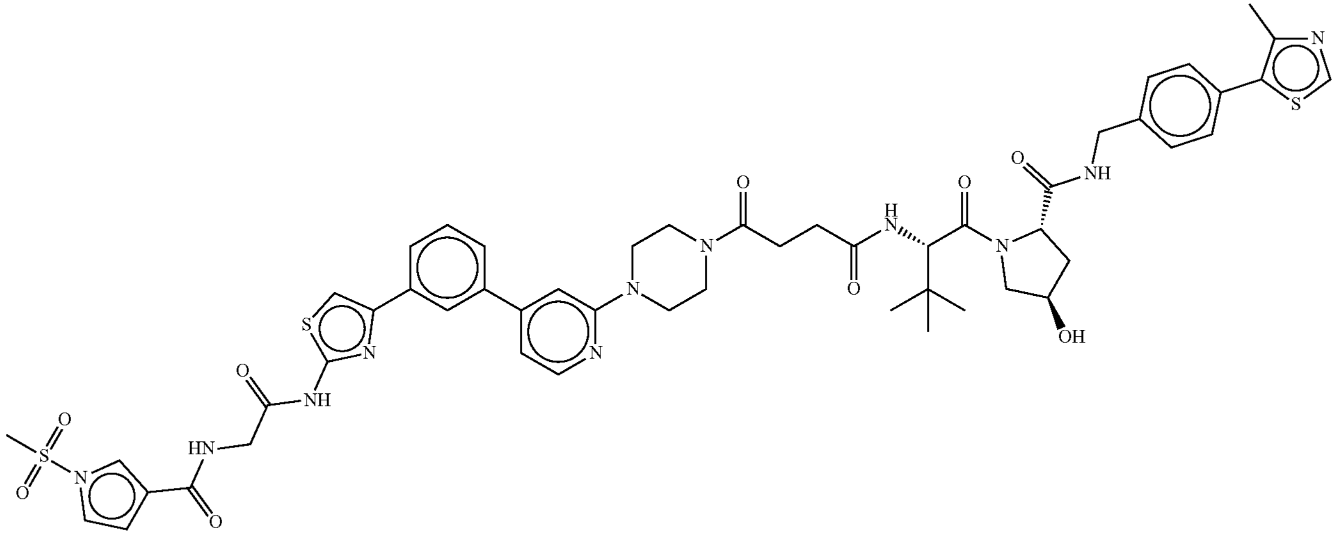 |

TABLE 1-continued
| Compounds of the Invention | |
|---|---|
| # | Structure |
| 75 | 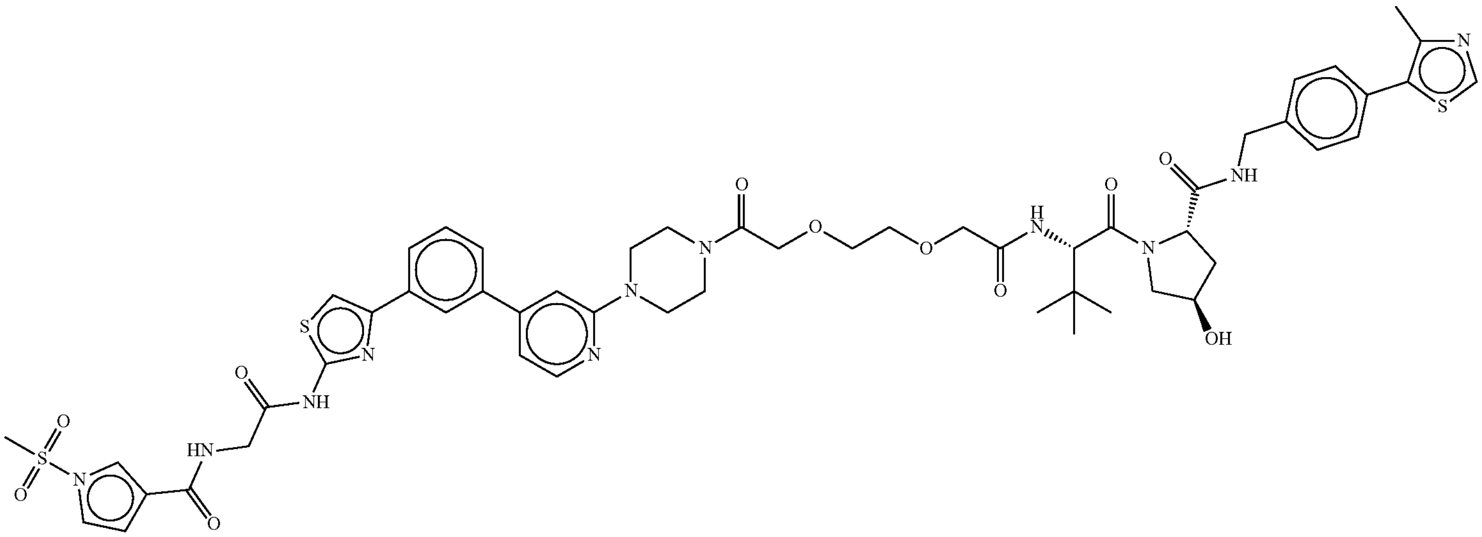 |
| 76 | 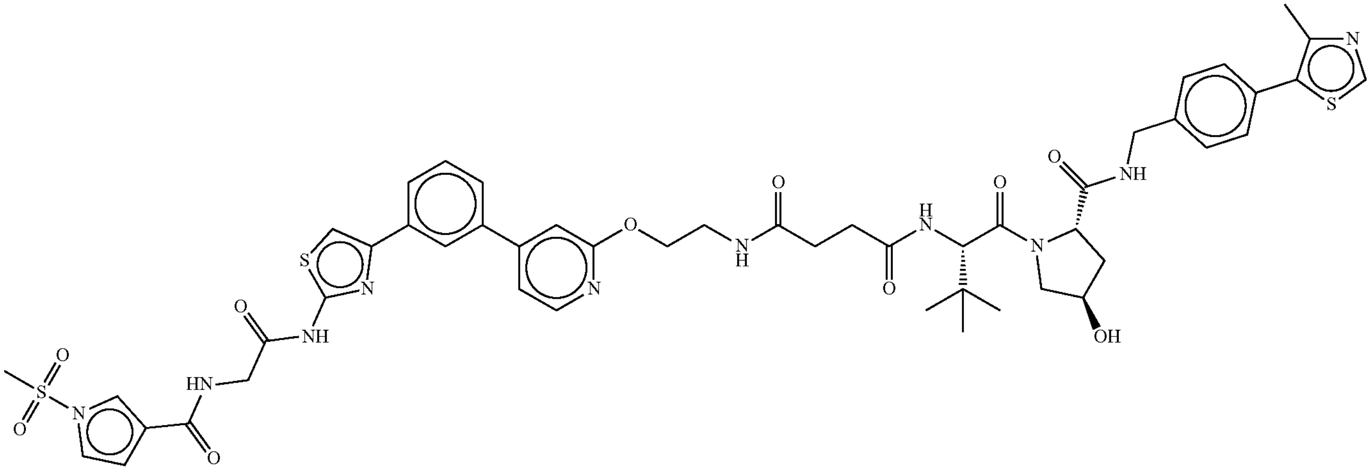 |

TABLE 1-continued
| Compounds of the Invention | |
|---|---|
| # | Structure |
| 77 | 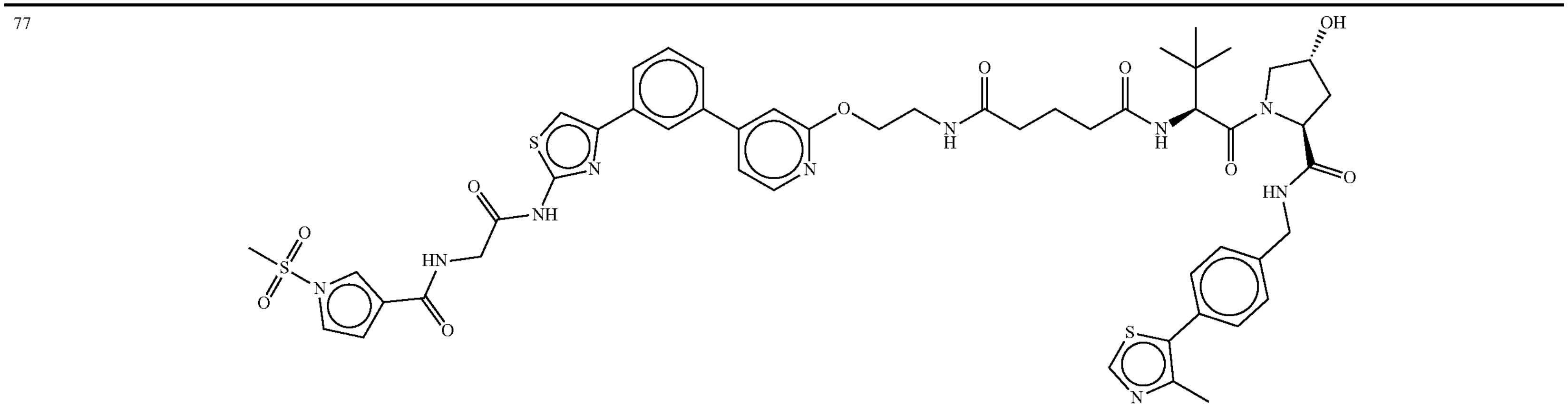 |
| 78 | 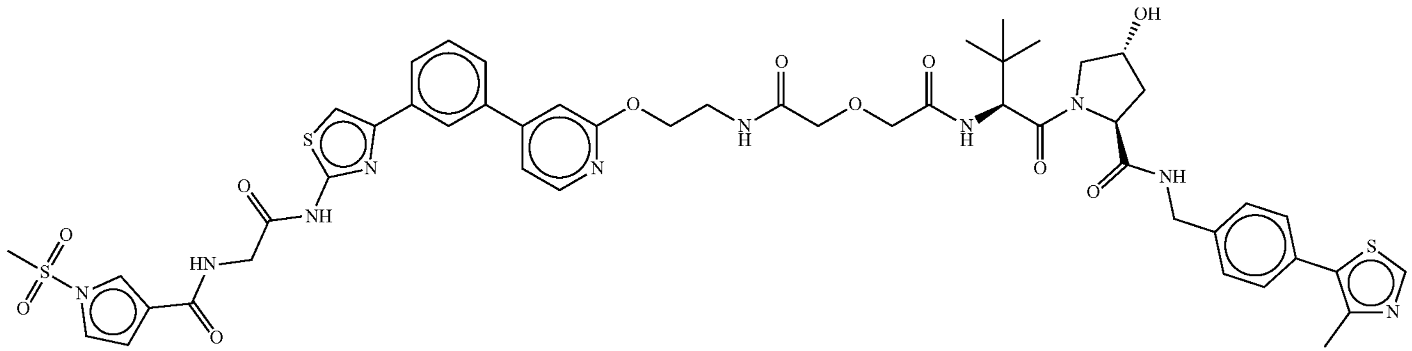 |

TABLE 1-continued
| Compounds of the Invention | |
|---|---|
| # | Structure |
| 79 | 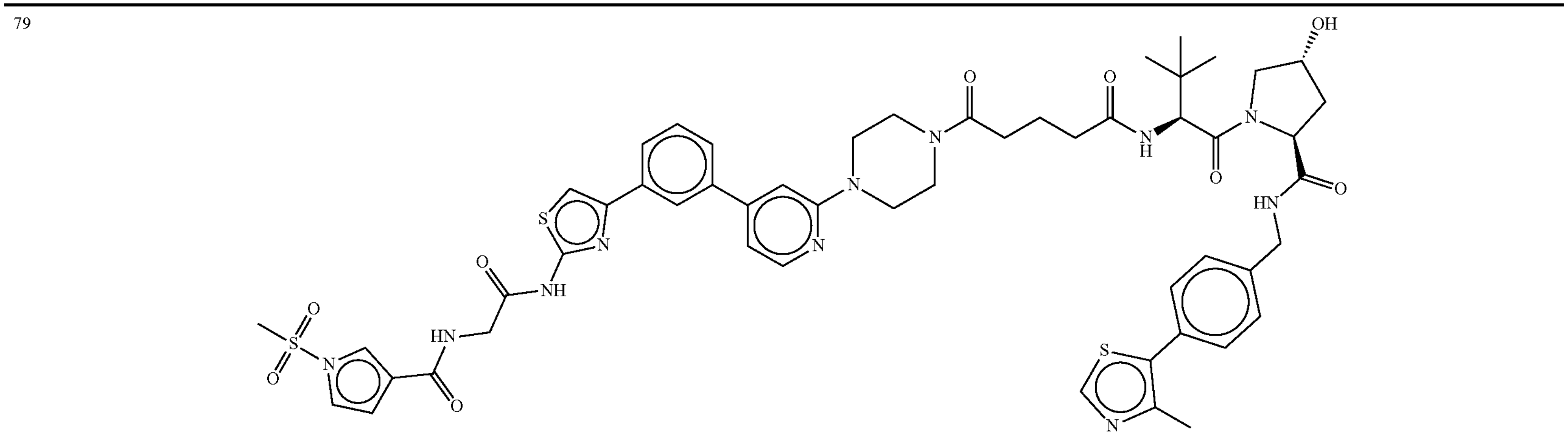 |
| 80 | 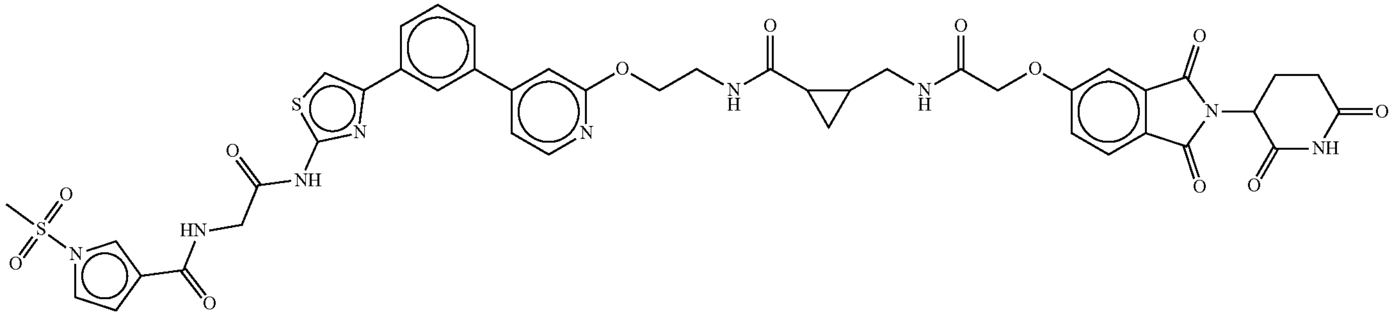 |

TABLE 1-continued
| Compounds of the Invention | |
|---|---|
| # | Structure |
| 81 | 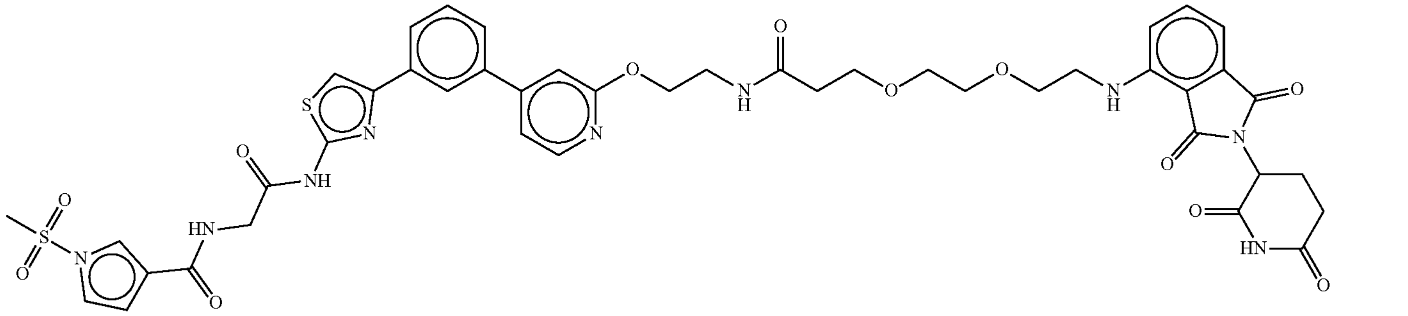 |
| 82 | 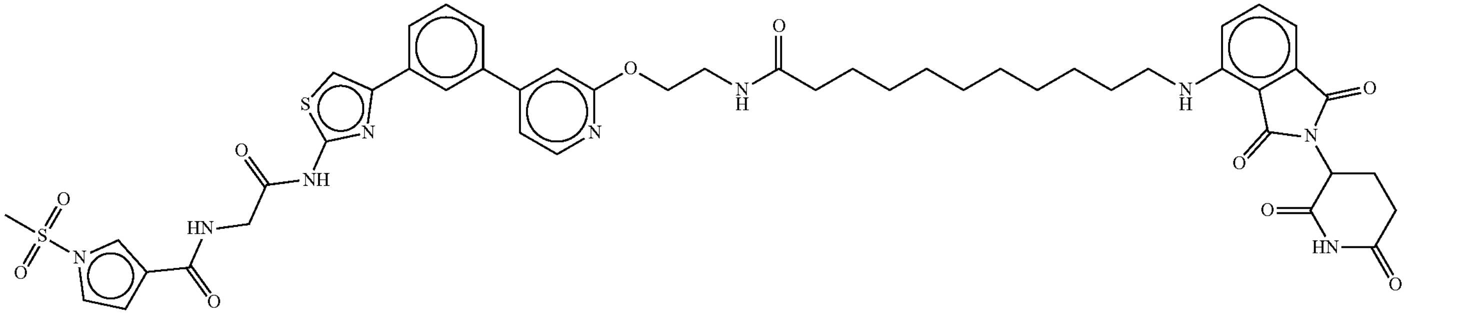 |
| 83 | 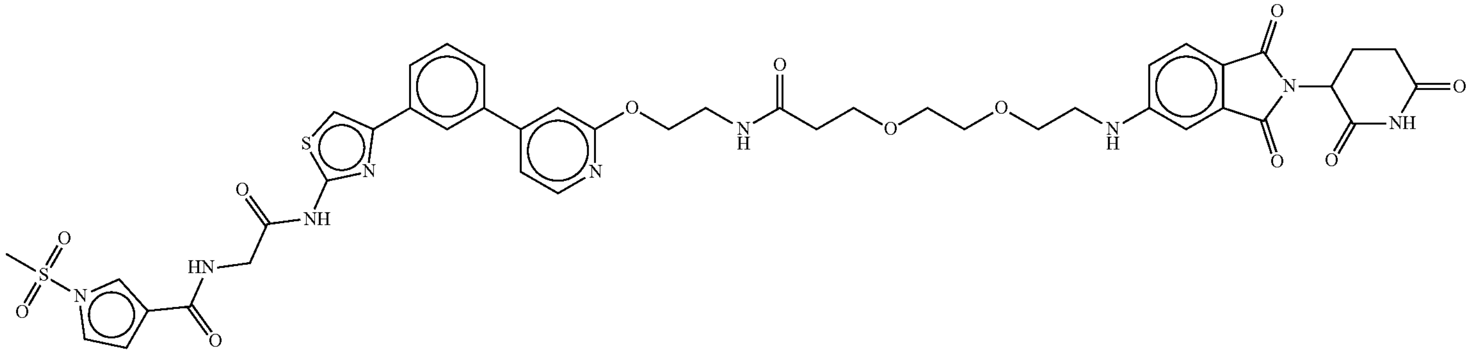 |

TABLE 1-continued
| Compounds of the Invention | |
|---|---|
| # | Structure |
| 84 | 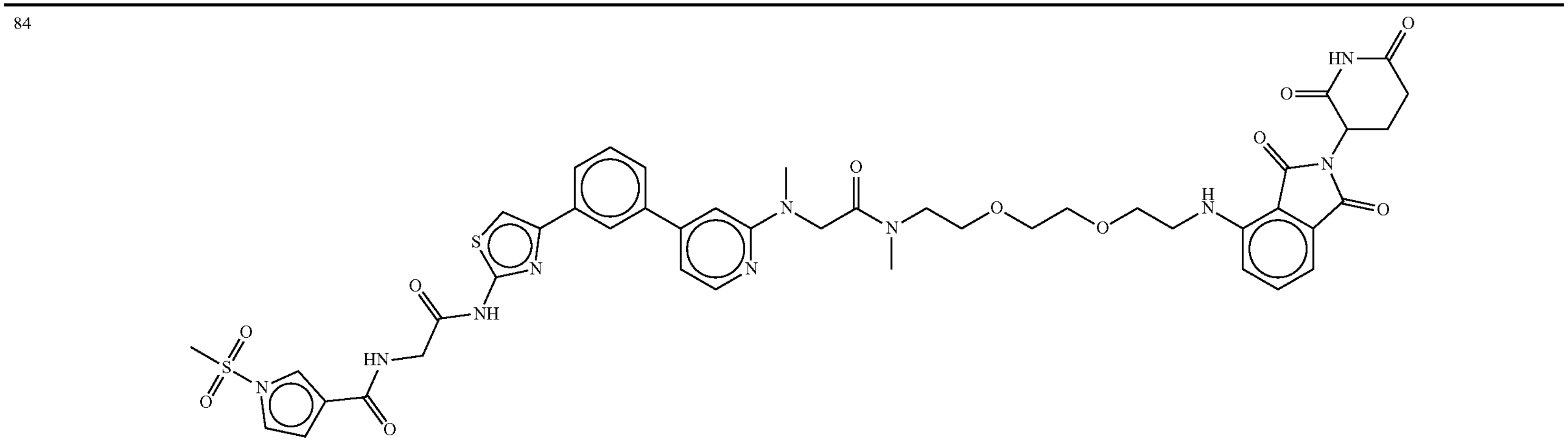 |
| 85 | 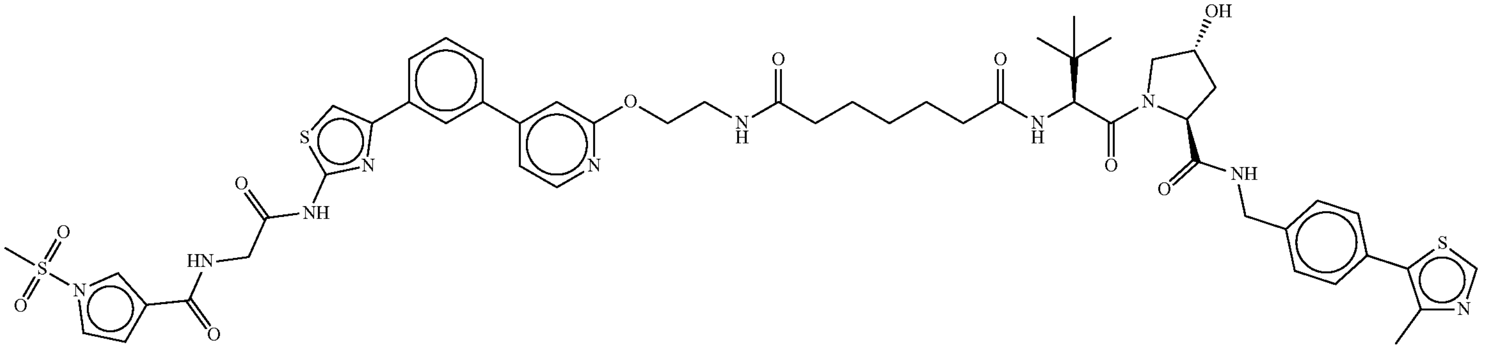 |

TABLE 1-continued
| Compounds of the Invention | |
|---|---|
| # | Structure |
| 86 | 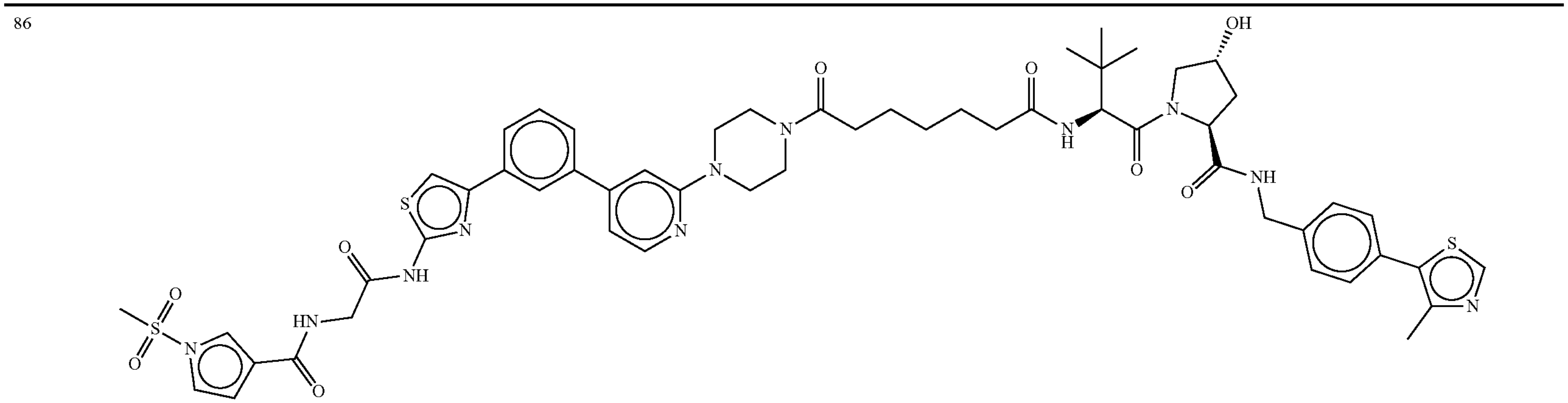 |
| 87 | 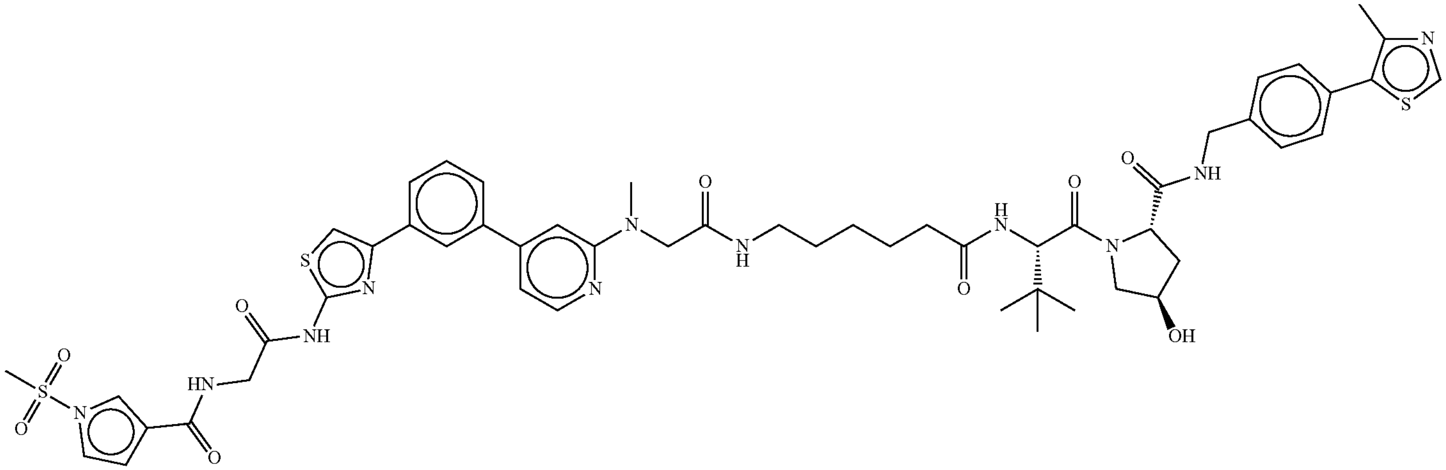 |

TABLE 1-continued
| Compounds of the Invention | |
|---|---|
| # | Structure |
| 88 | 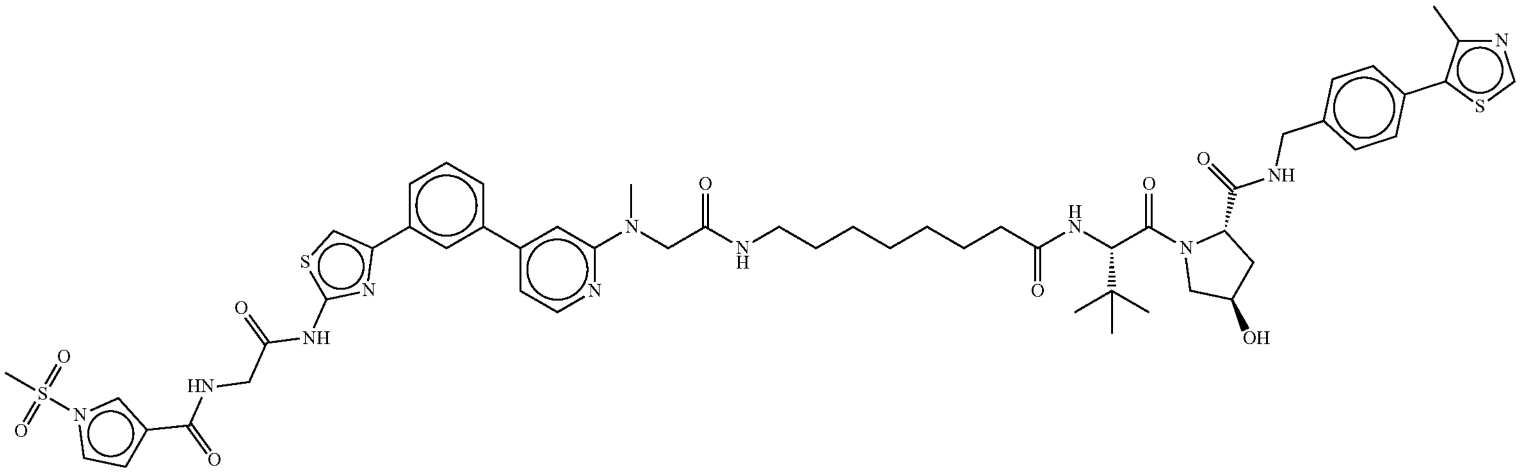 |
| 89 | 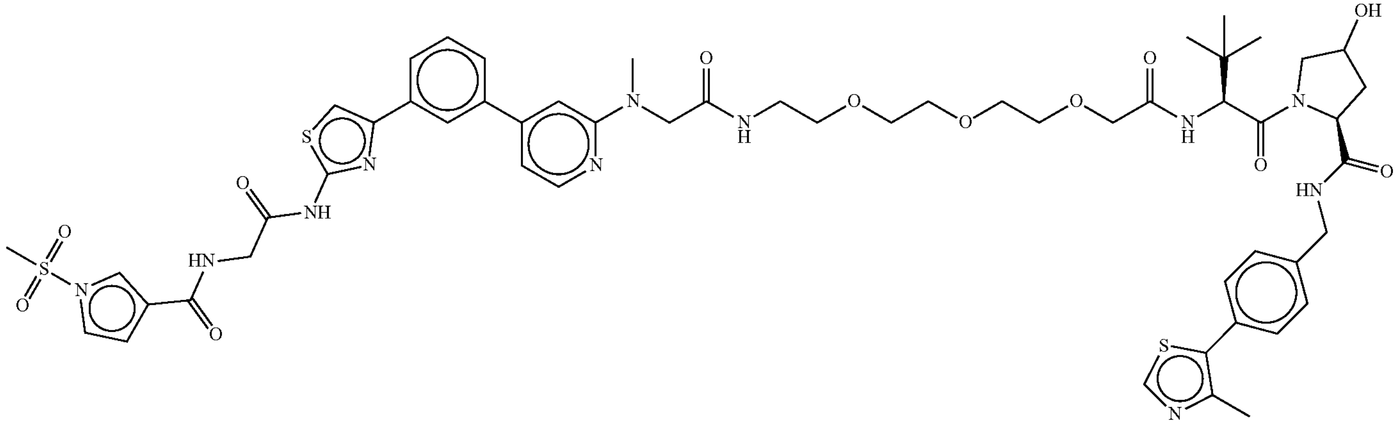 |

TABLE 1-continued
| Compounds of the Invention | |
|---|---|
| # | Structure |
| 90 | 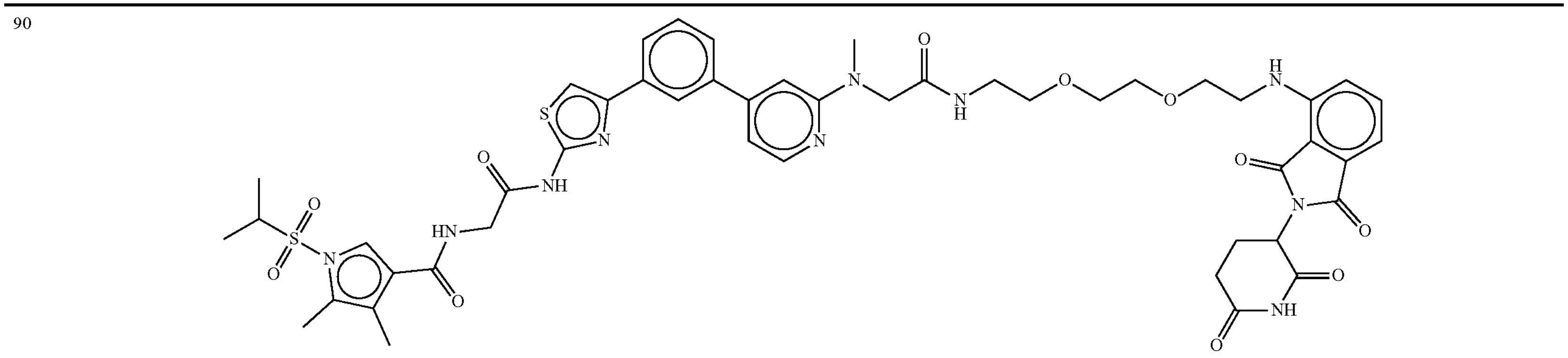 |
| 91 | 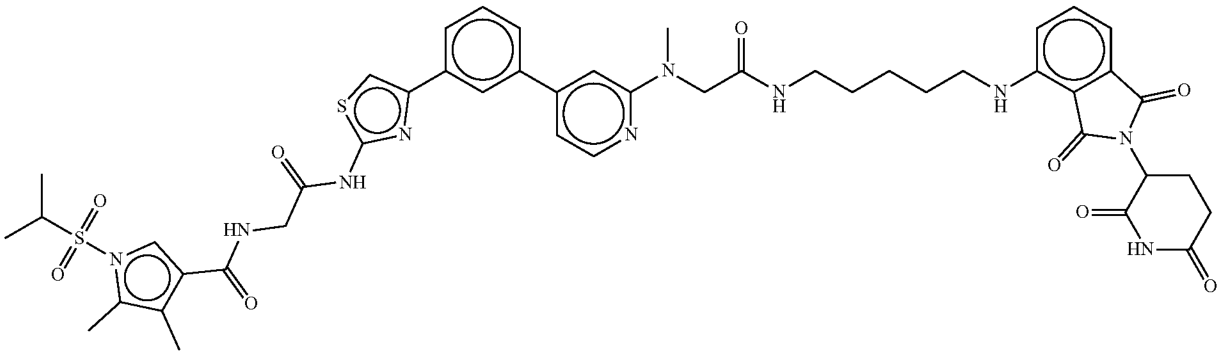 |

TABLE 1-continued
| Compounds of the Invention | |
|---|---|
| # | Structure |
| 92 | 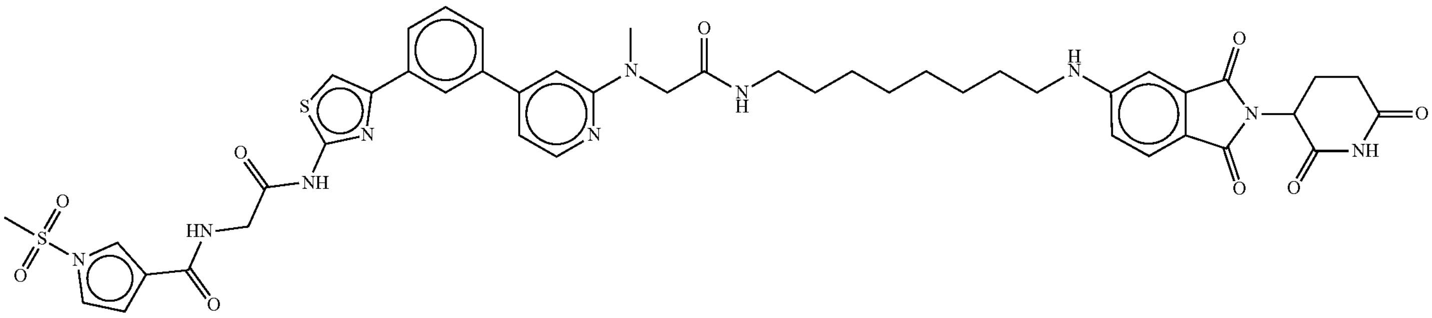 |
| 93 | 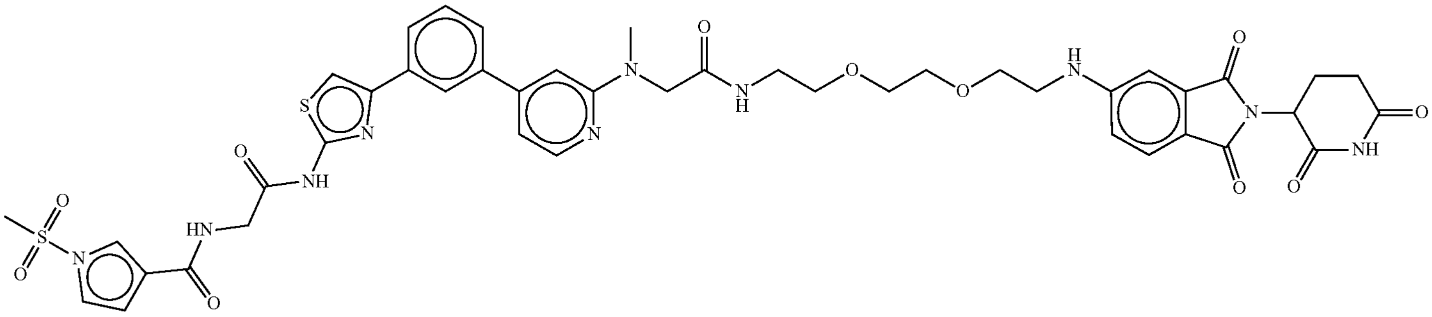 |

TABLE 1-continued
| Compounds of the Invention | |
|---|---|
| # | Structure |
| 94 | 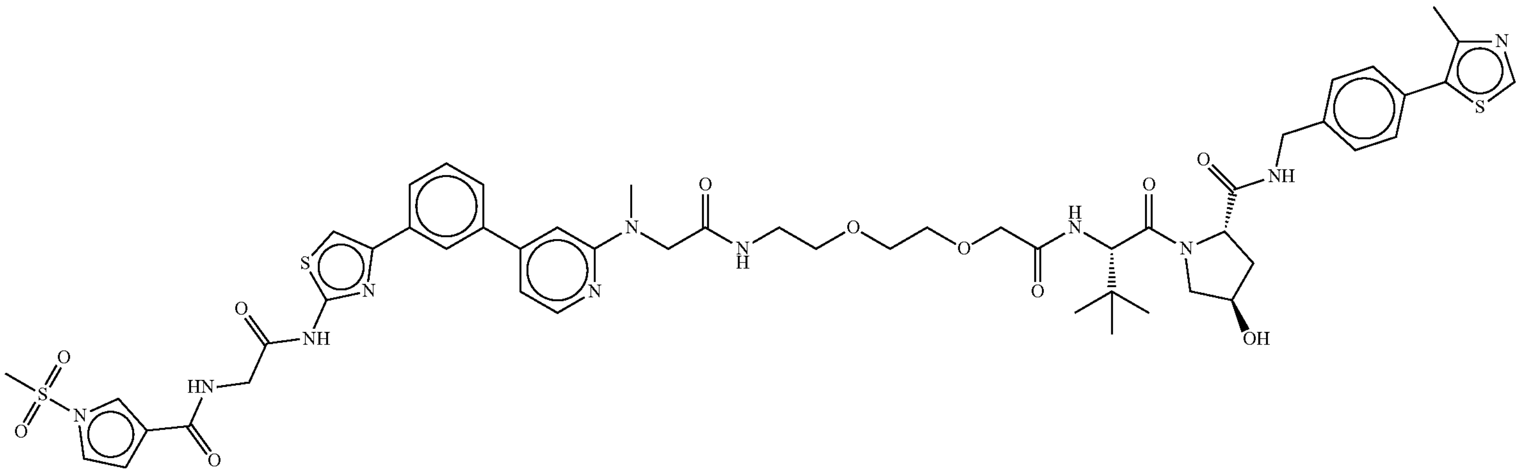 |
| 95 | 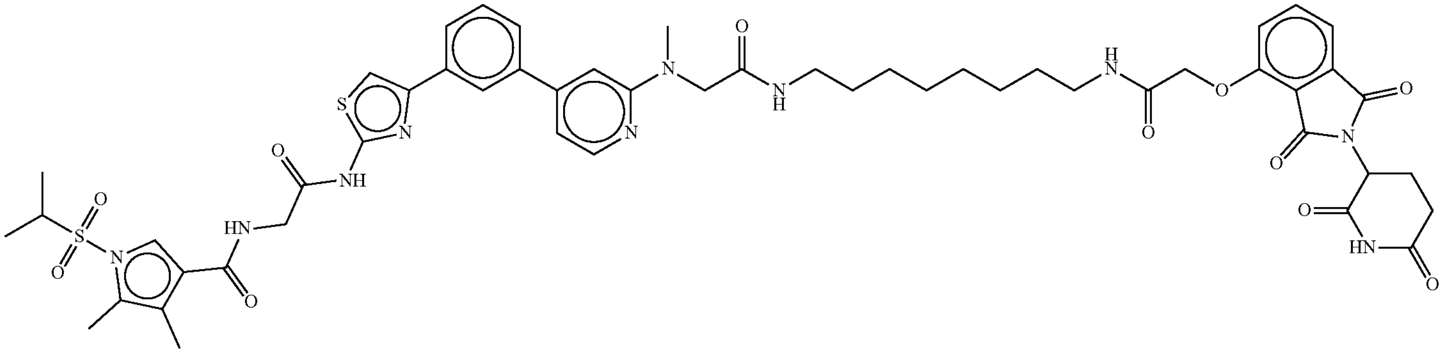 |

TABLE 1-continued
| Compounds of the Invention | |
| --- | --- |
| # | Structure |
| 96 | 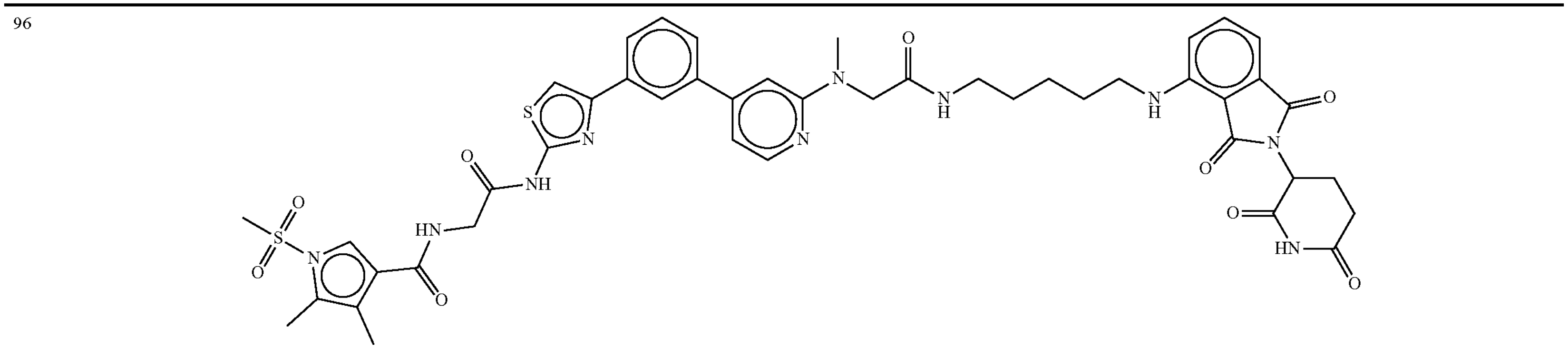 |
| 97 | 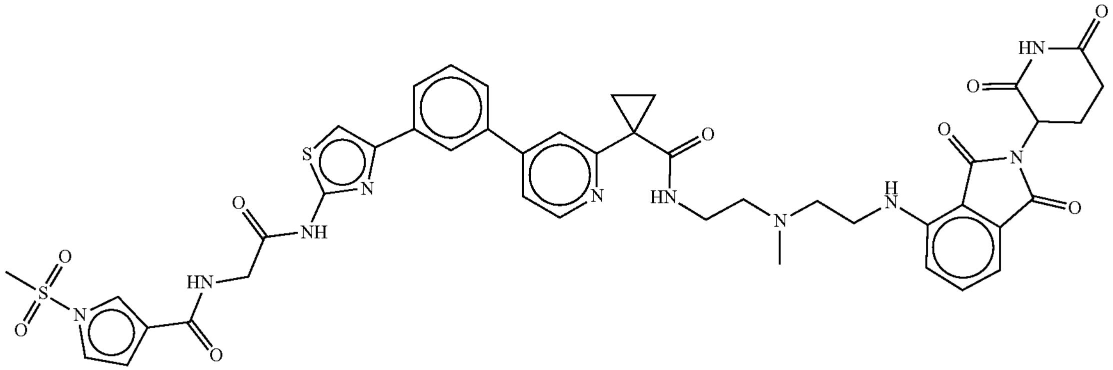 |

TABLE 1-continued
| Compounds of the Invention | |
|---|---|
| # | Structure |
| 98 | 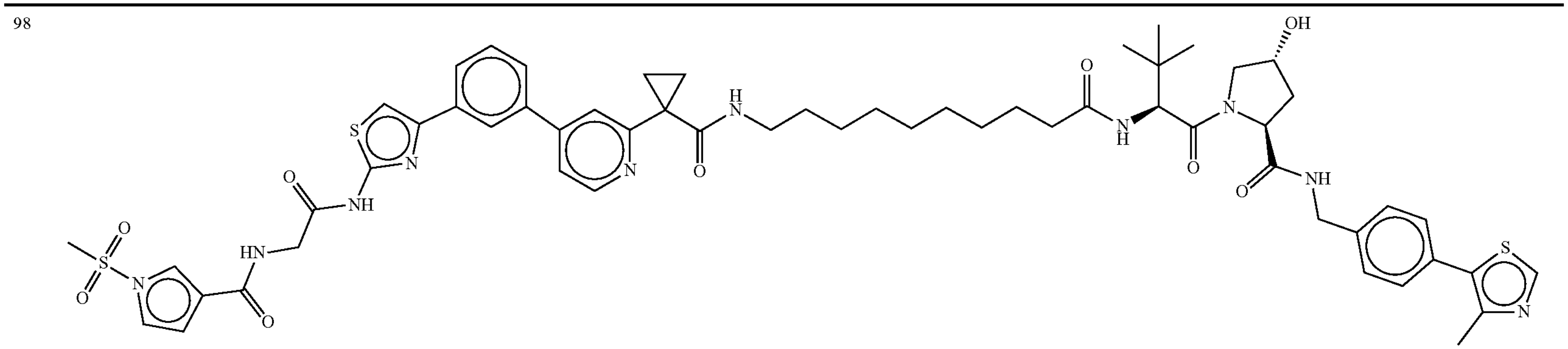 |
| 99 | 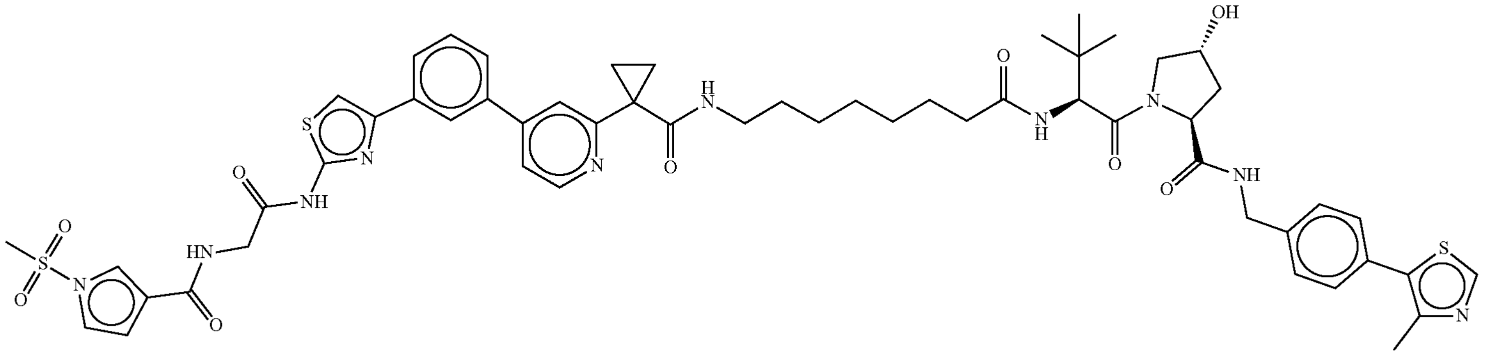 |

TABLE 1-continued
| Compounds of the Invention | |
| --- | --- |
| # | Structure |
| 100 | 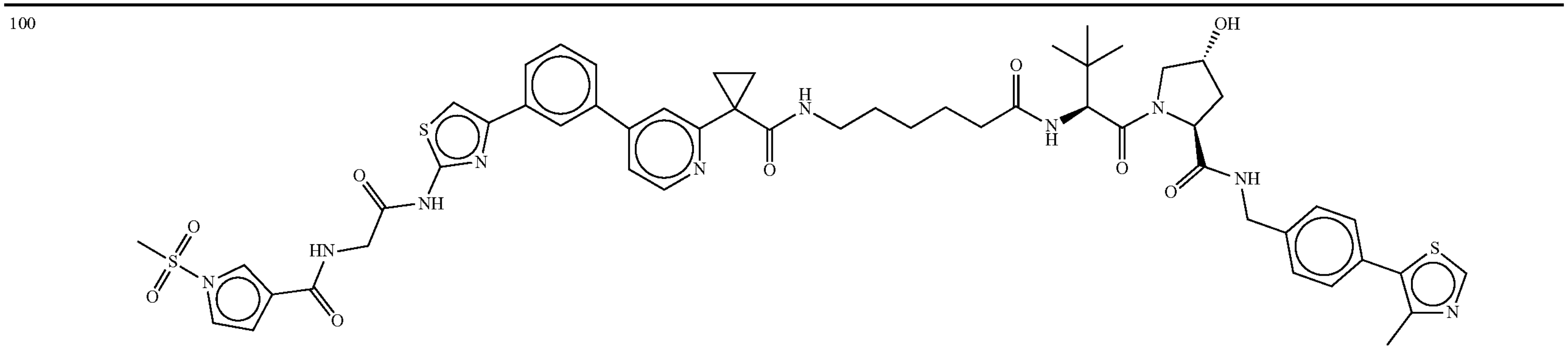 |
| 101 | 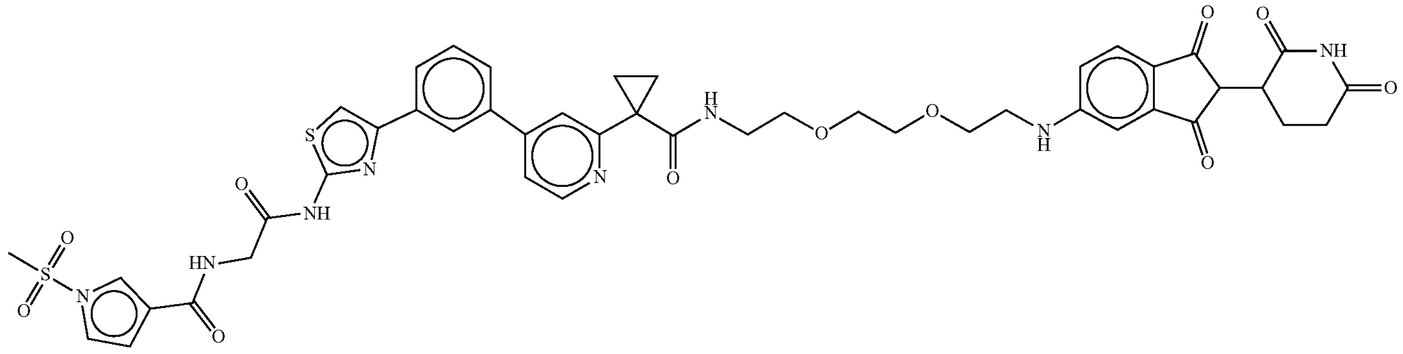 |

TABLE 1-continued
| Compounds of the Invention | |
|---|---|
| # | Structure |
| 102 | 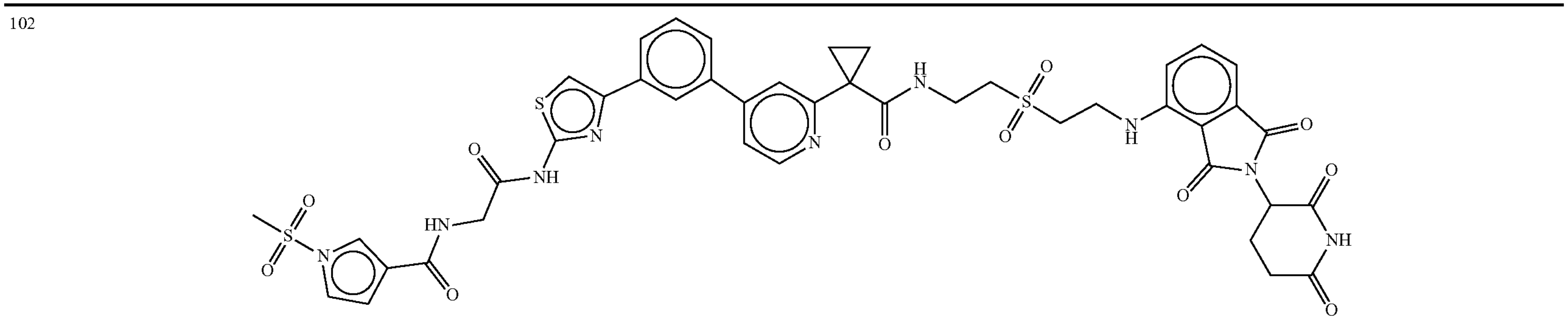 |
| 103 | 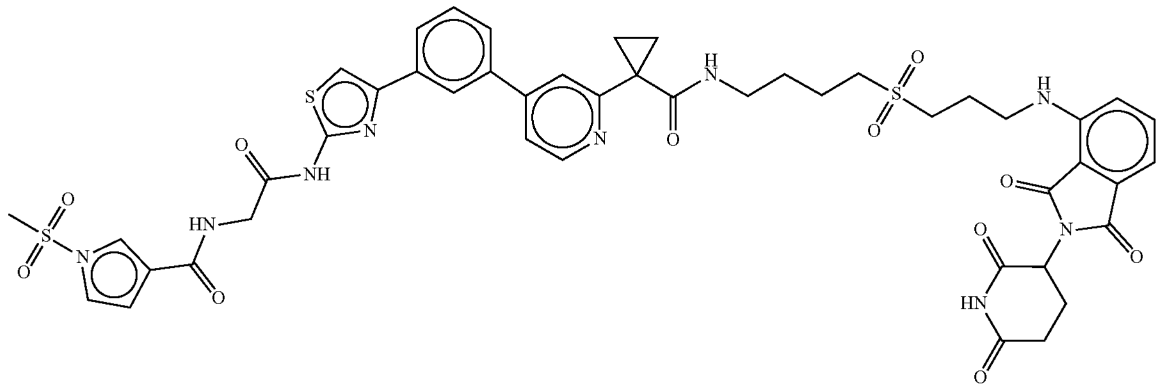 |

TABLE 1-continued
| Compounds of the Invention | |
|---|---|
| # | Structure |
| 104 | 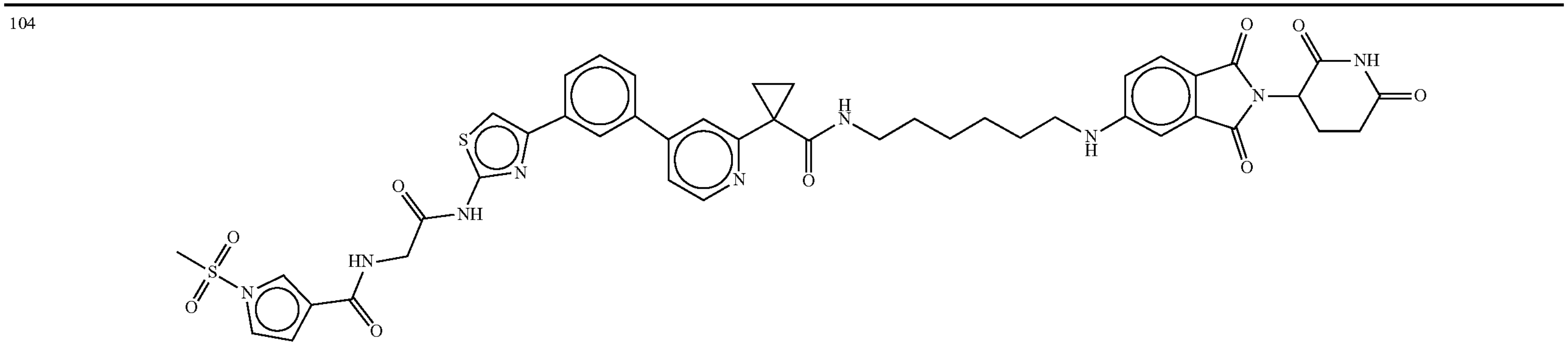 |
| 105 | 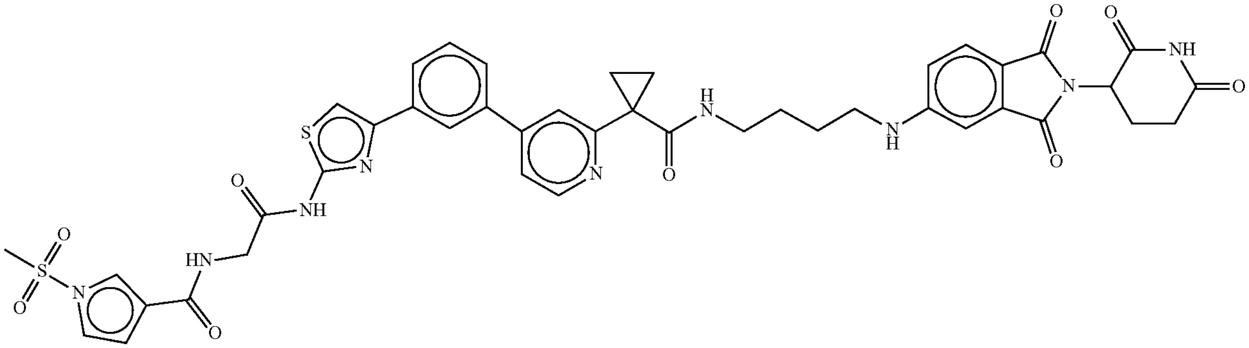 |
| 106 | 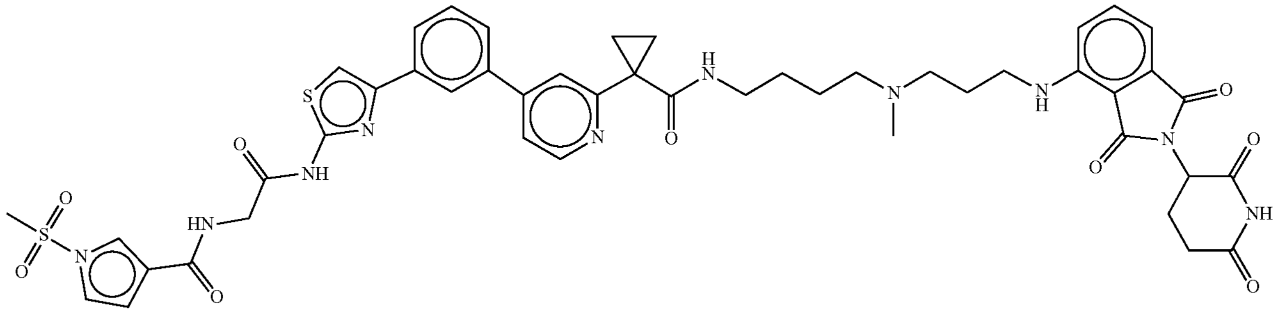 |

TABLE 1-continued
| Compounds of the Invention | |
|---|---|
| # | Structure |
| 107 | 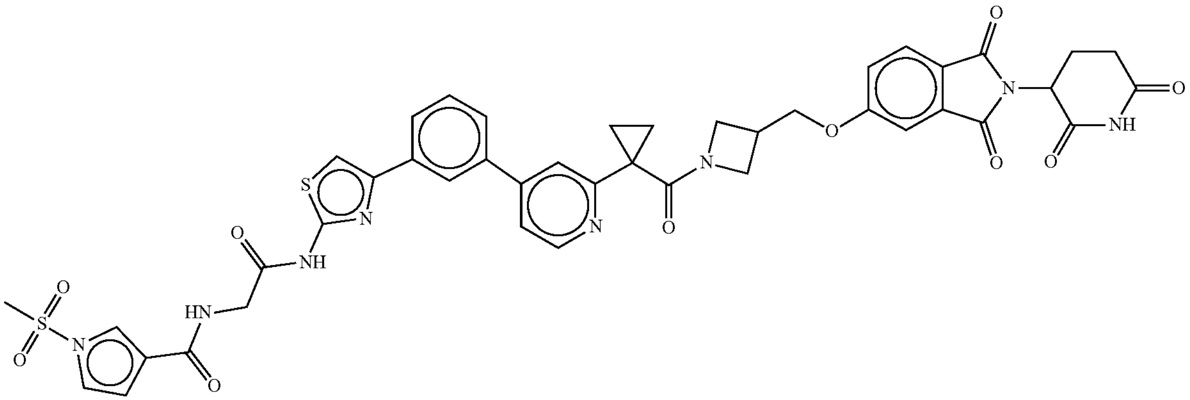 |
| 108 | 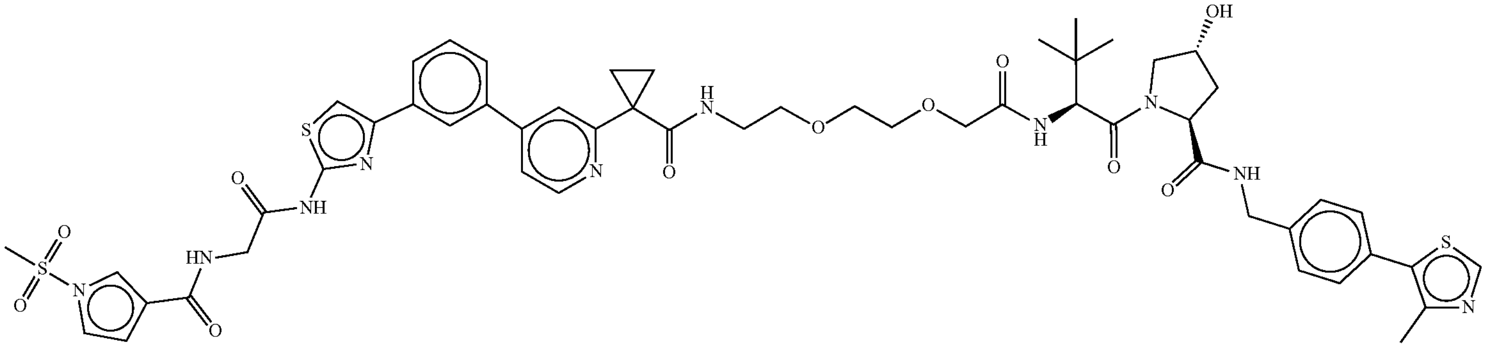 |

TABLE 1-continued
| Compounds of the Invention | |
|---|---|
| # | Structure |
| 109 | 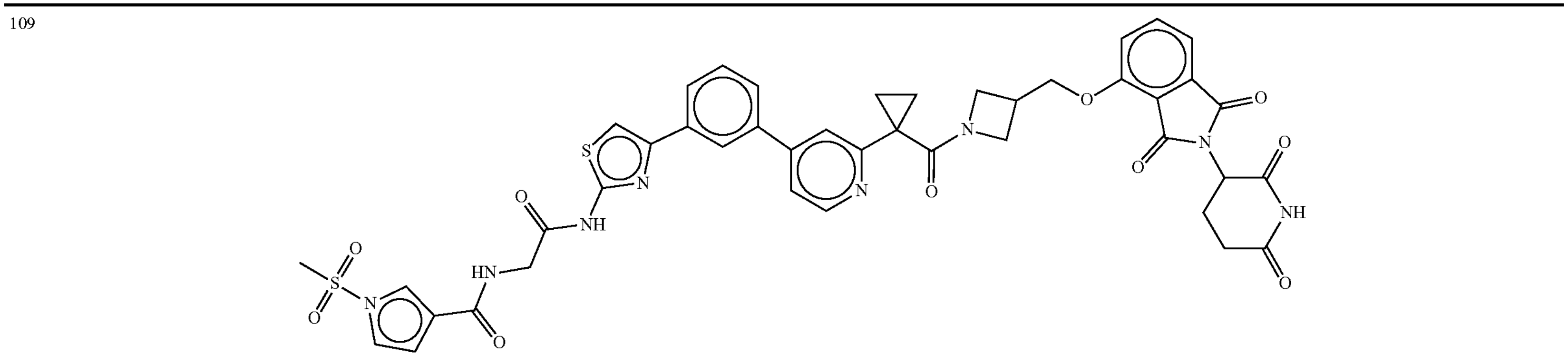 |
| 110 | 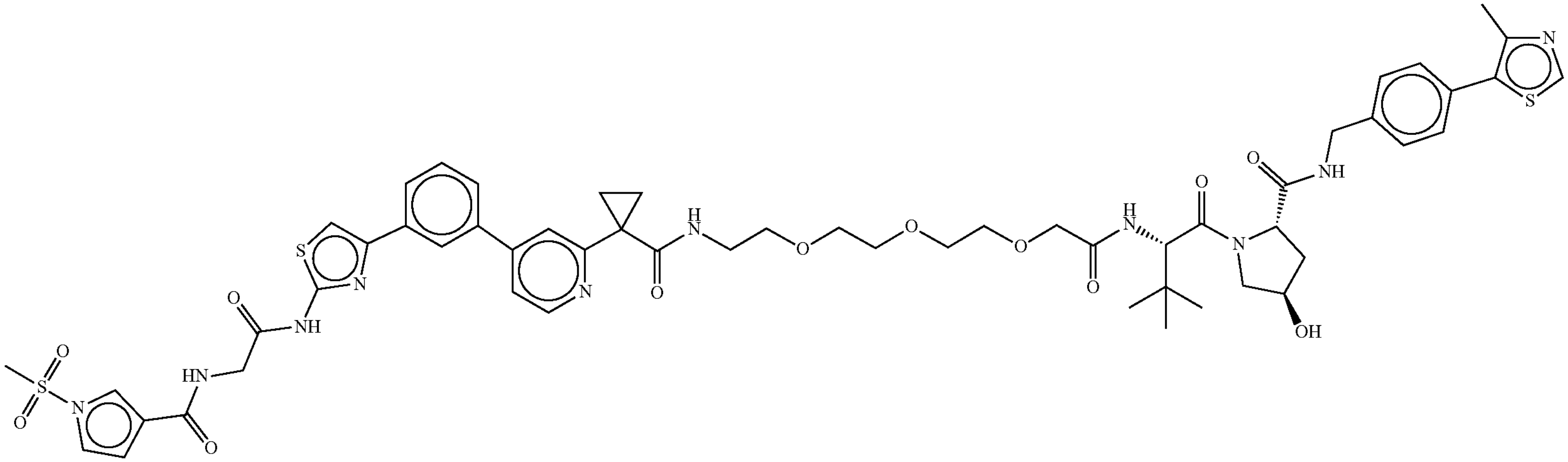 |

TABLE 1-continued
| Compounds of the Invention | |
|---|---|
| # | Structure |
| 111 | 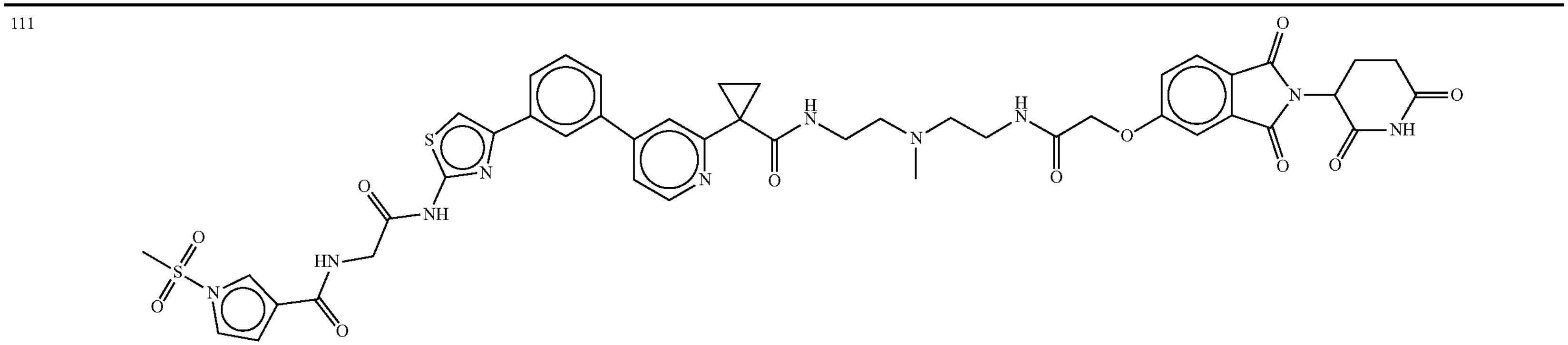 |
| 112 | 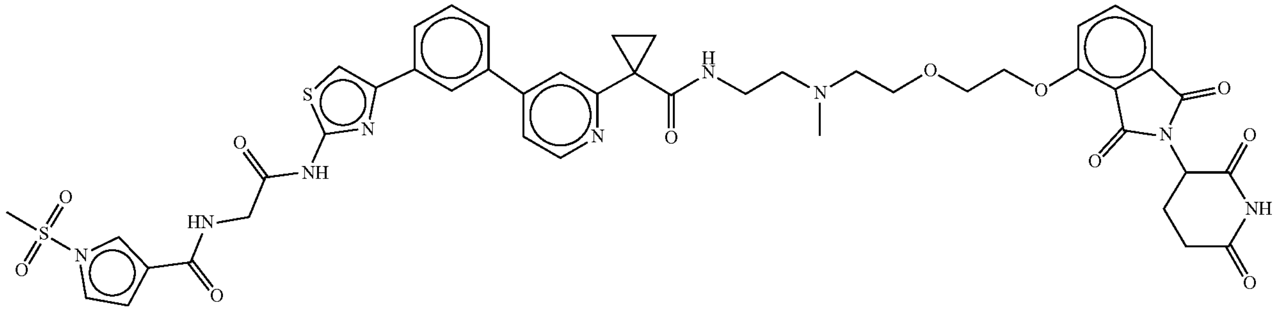 |
| 113 | 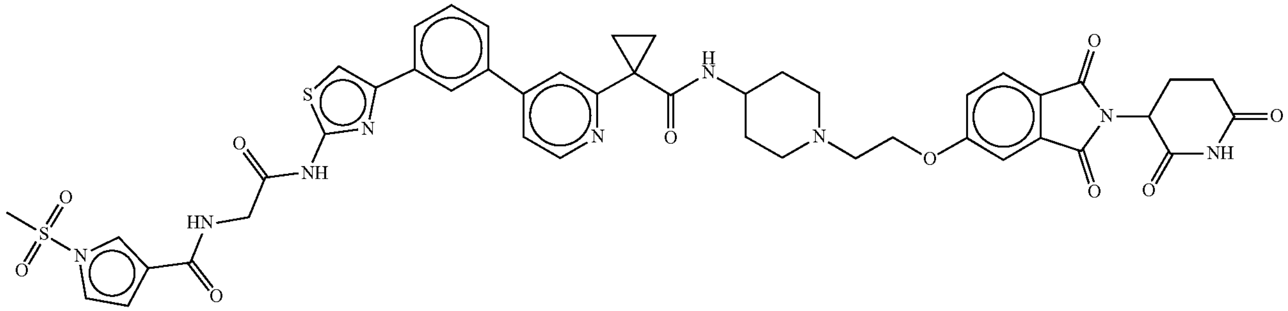 |

TABLE 1-continued
| Compounds of the Invention | |
|---|---|
| # | Structure |
| 114 | 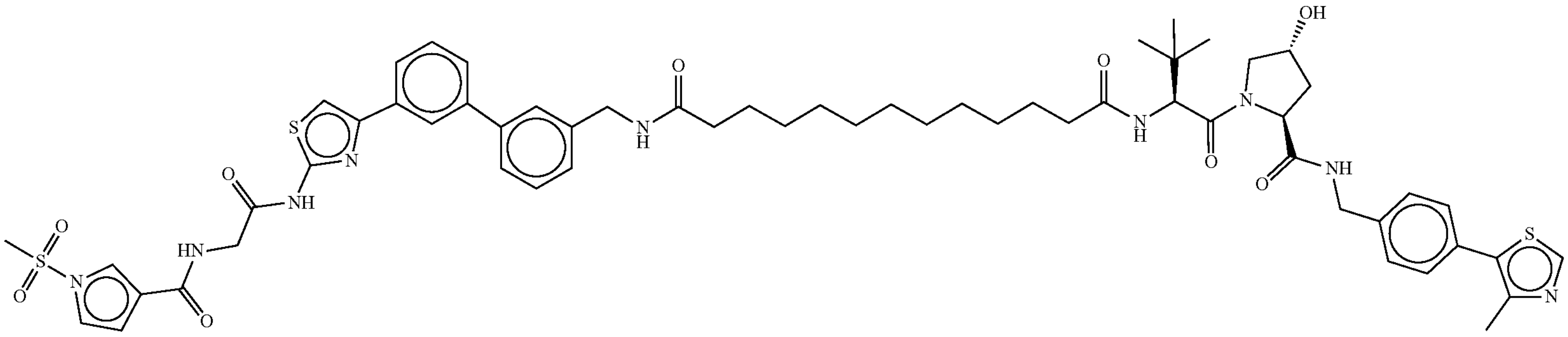 |
| 115 | 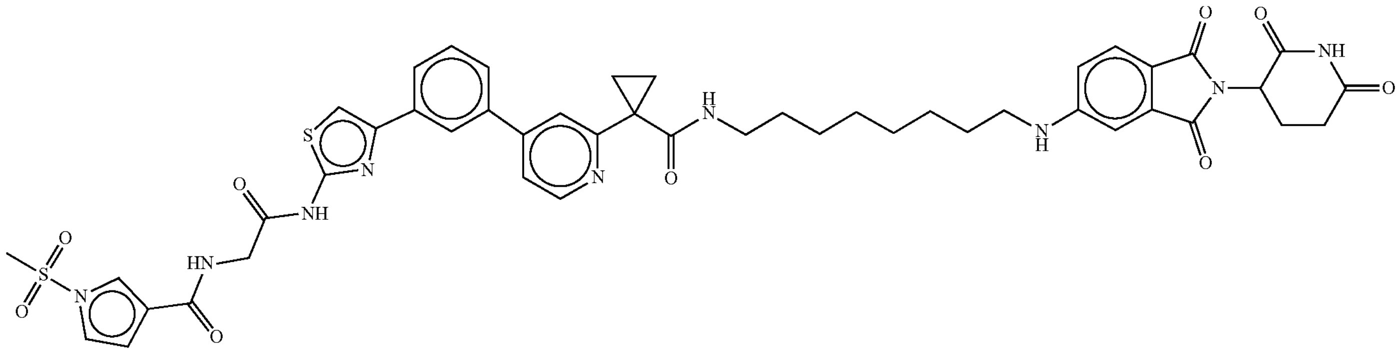 |

TABLE 1-continued
| Compounds of the Invention | |
|---|---|
| # | Structure |
| 116 | 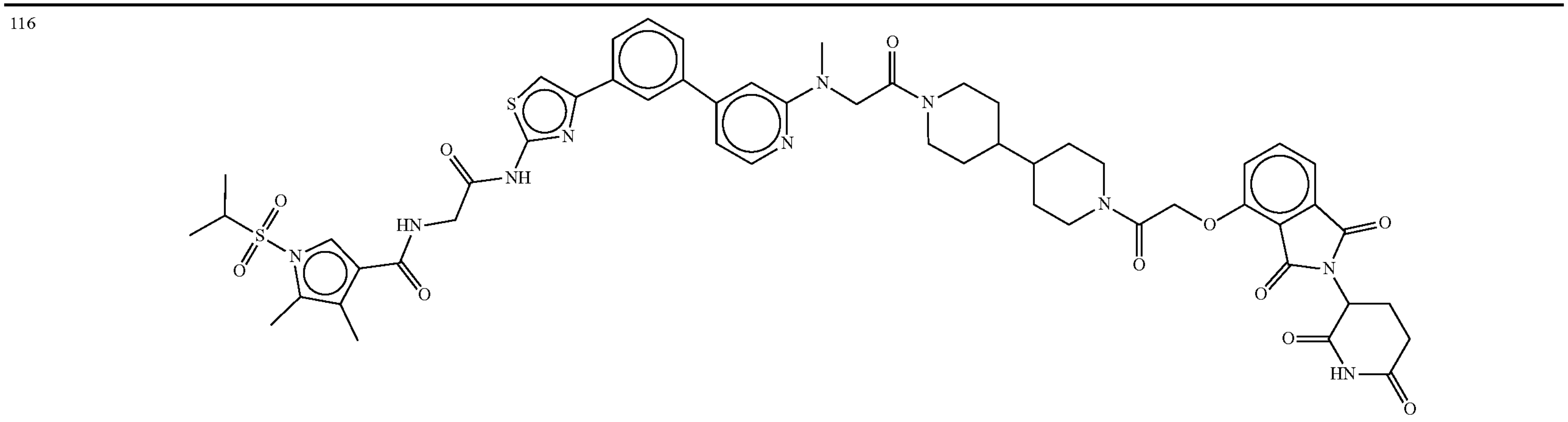 |
| 117 | 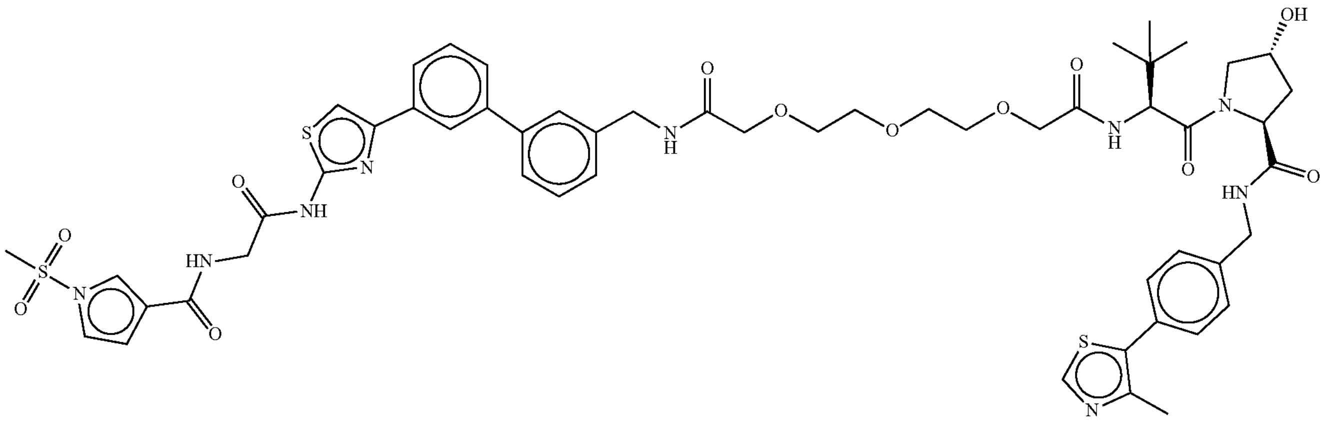 |

TABLE 1-continued
| Compounds of the Invention | |
|---|---|
| # | Structure |
| 118 | 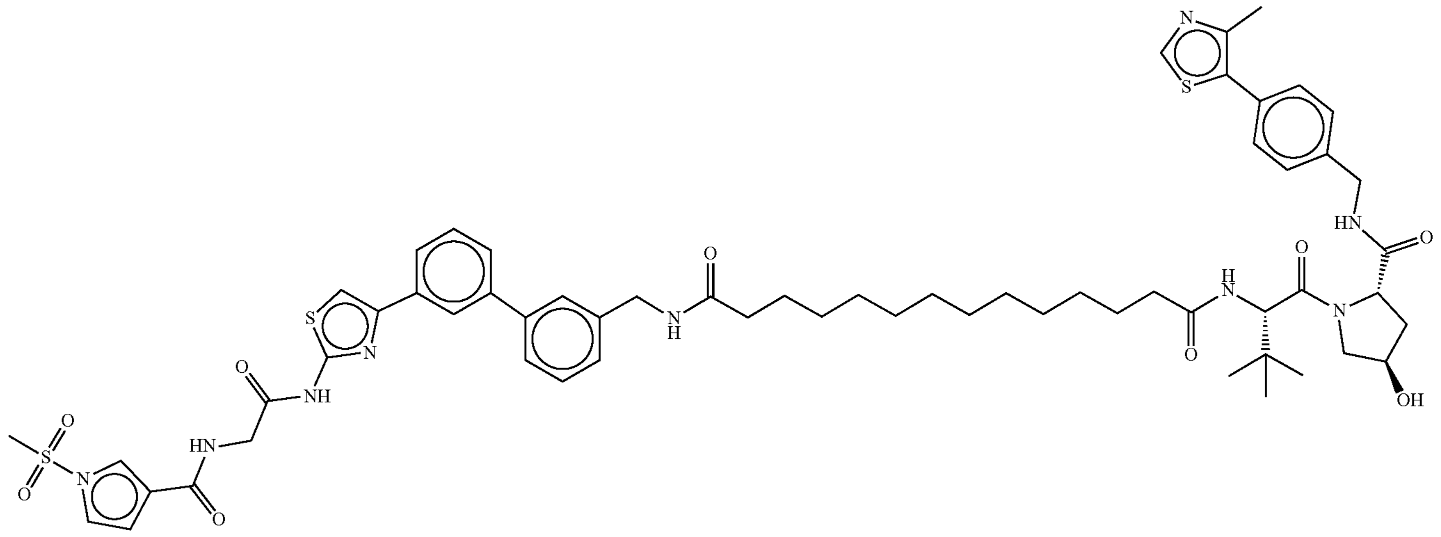 |

TABLE 1-continued
| Compounds of the Invention | |
|---|---|
| # | Structure |
| 119 | 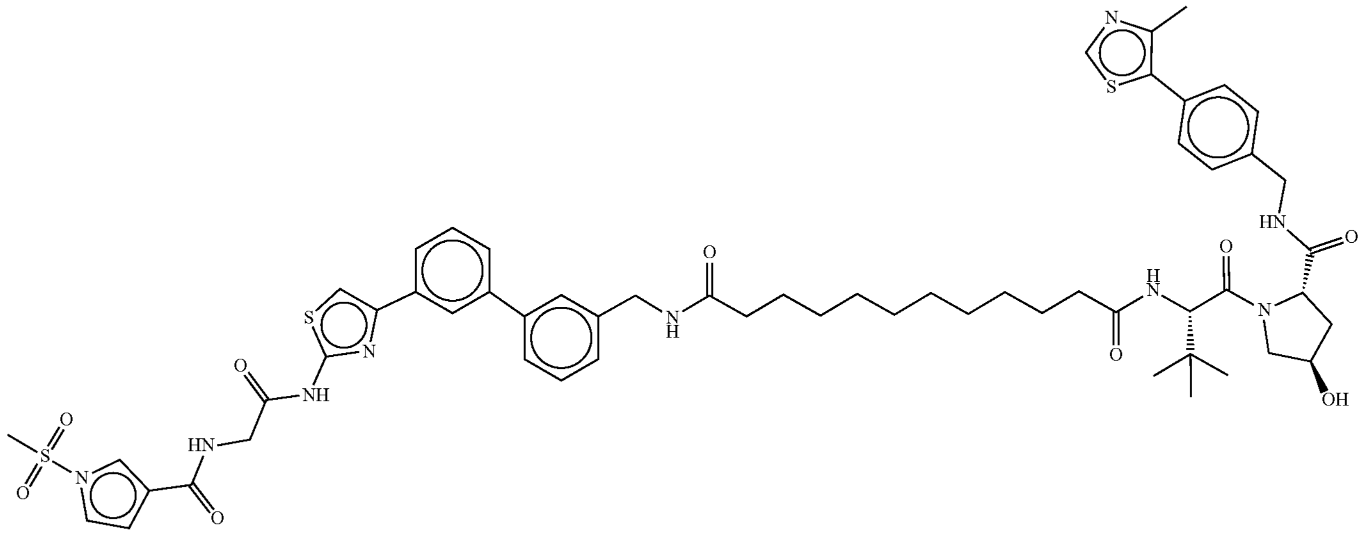 |

TABLE 1-continued
| Compounds of the Invention | |
|---|---|
| # | Structure |
| 120 | 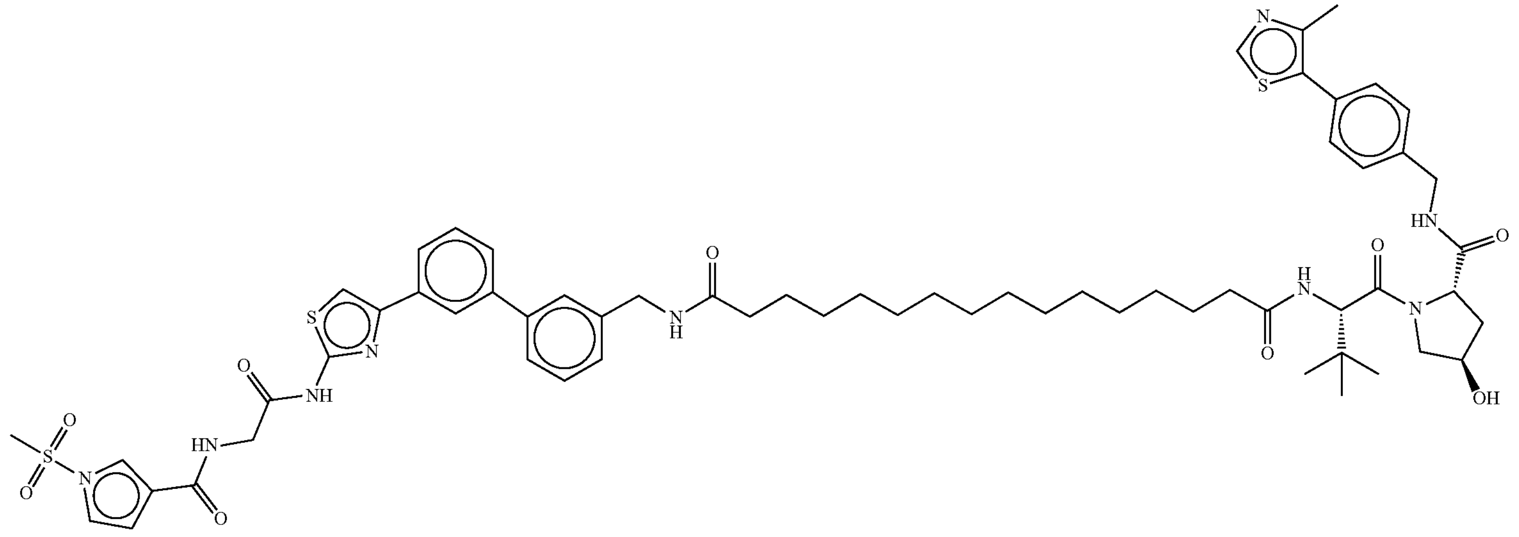 |

TABLE 1-continued
| Compounds of the Invention | |
|---|---|
| # | Structure |
| 121 | 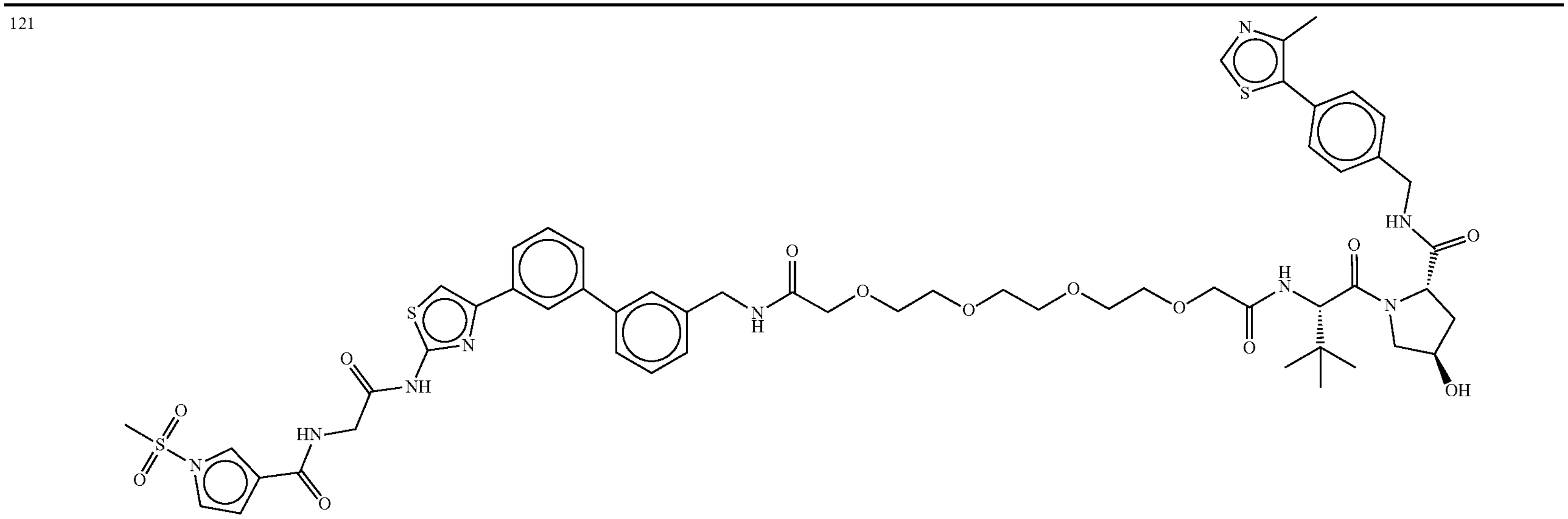 |
| 122 | 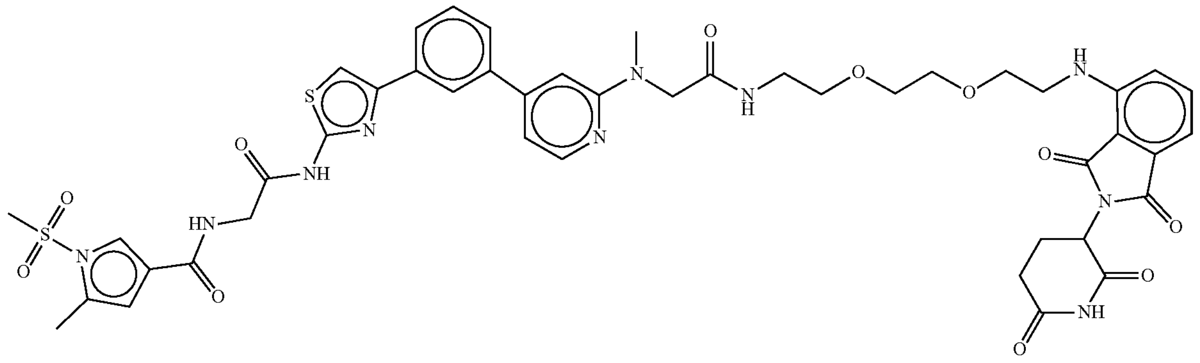 |

TABLE 1-continued
| Compounds of the Invention | |
|---|---|
| # | Structure |
| 123 | 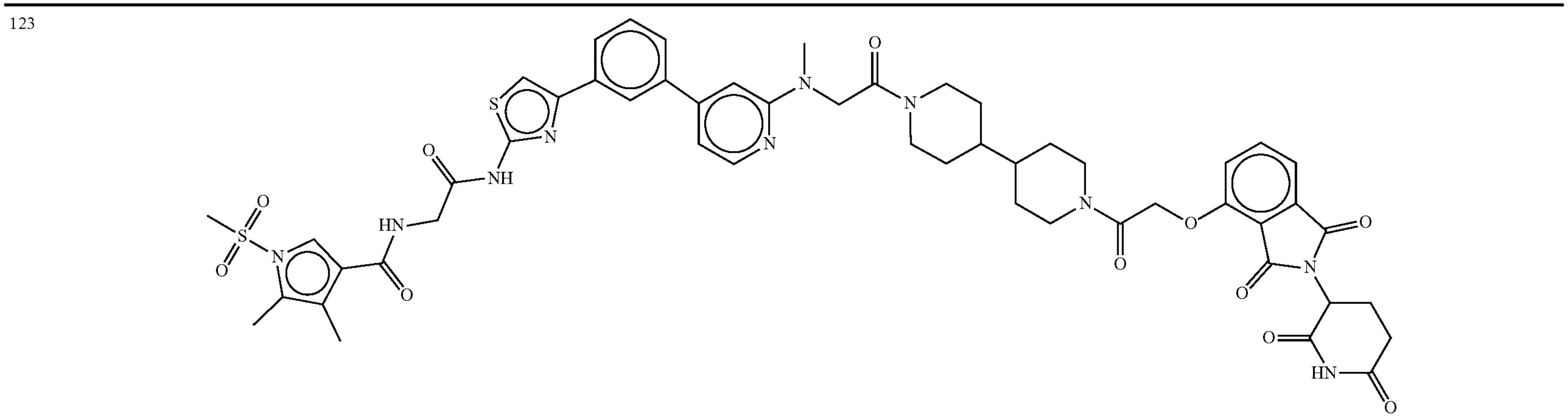 |
| 124 | 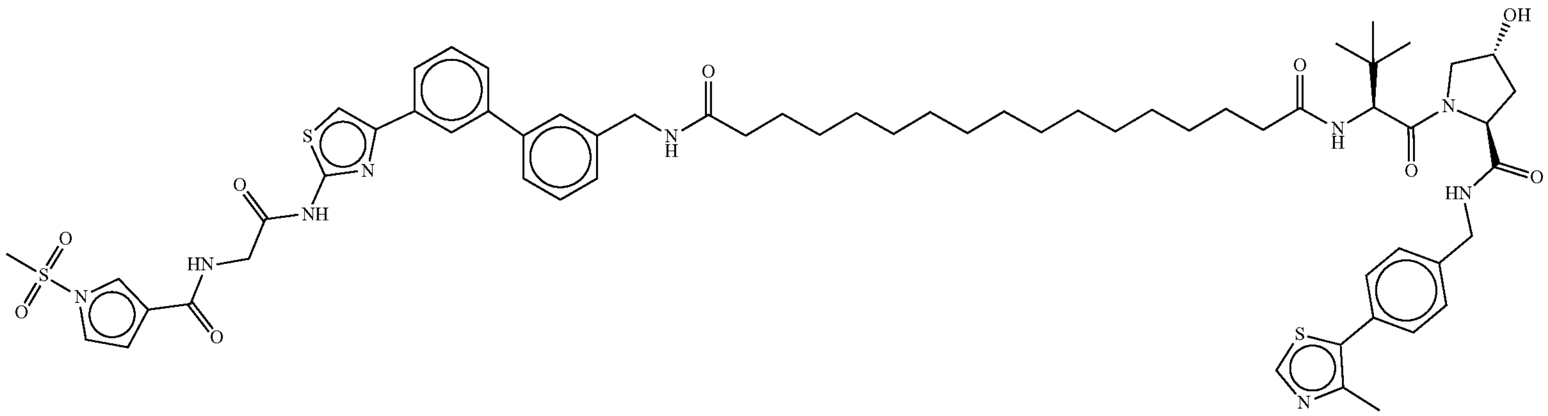 |

TABLE 1-continued
| Compounds of the Invention | |
|---|---|
| # | Structure |
| 125 | 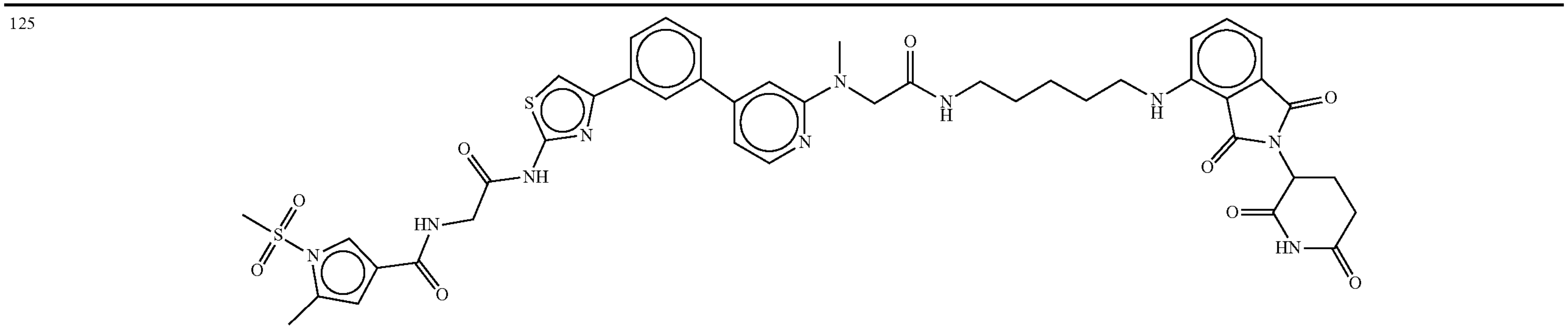 |
| 126 | 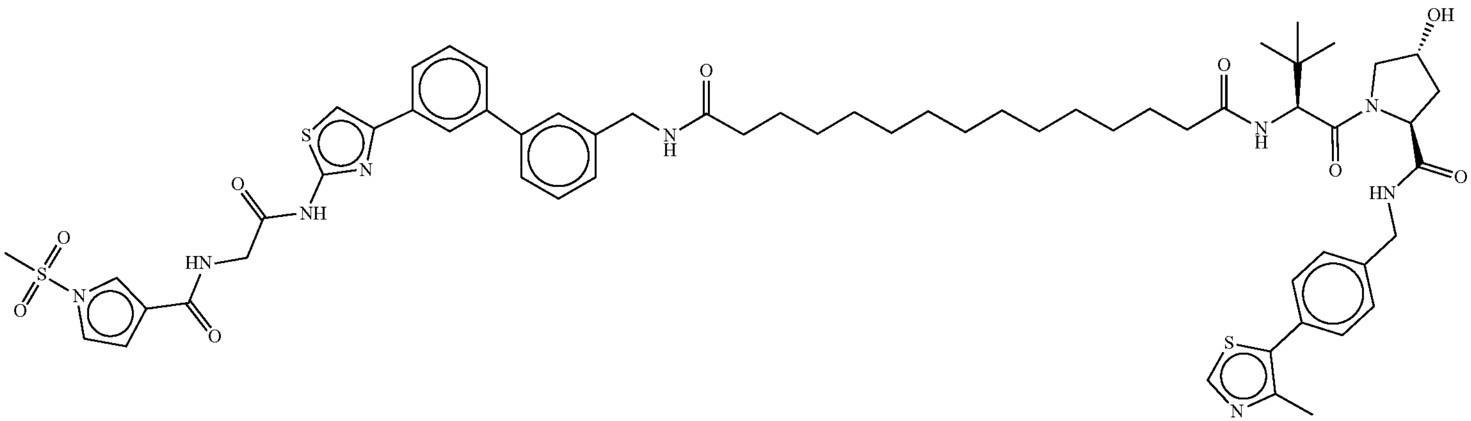 |

TABLE 1-continued
| Compounds of the Invention | |
|---|---|
| # | Structure |
| 127 | 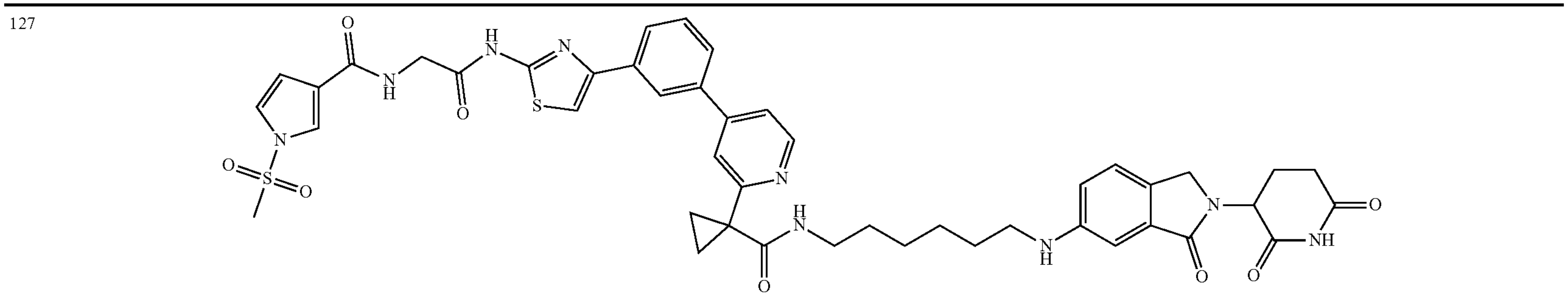 |
| 128 | 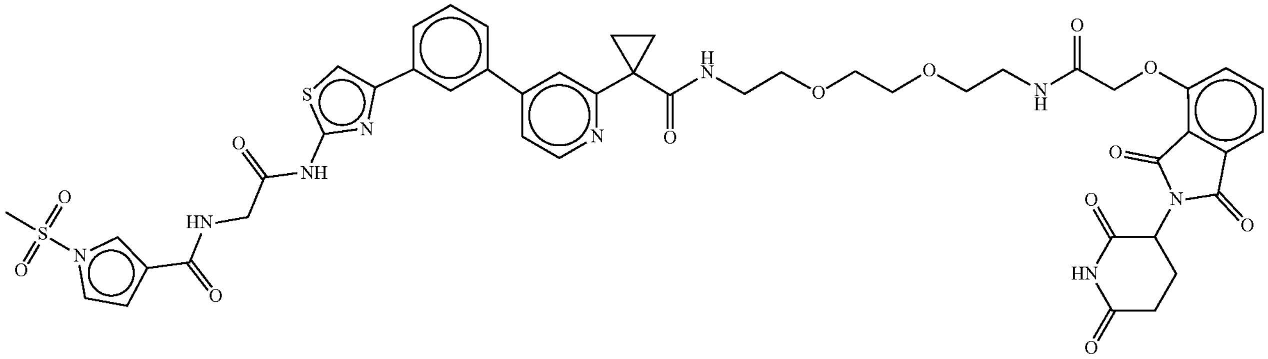 |
| 129 | 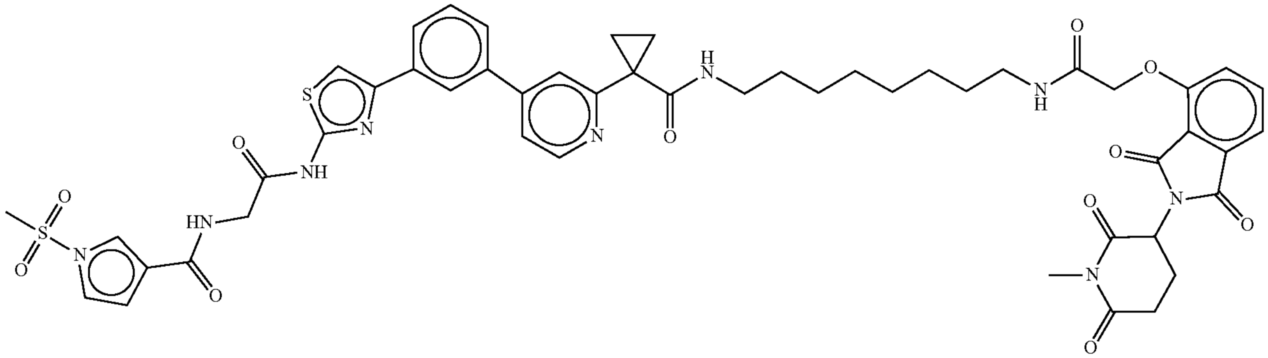 |

TABLE 1-continued
| Compounds of the Invention | |
|---|---|
| # | Structure |
| 130 | 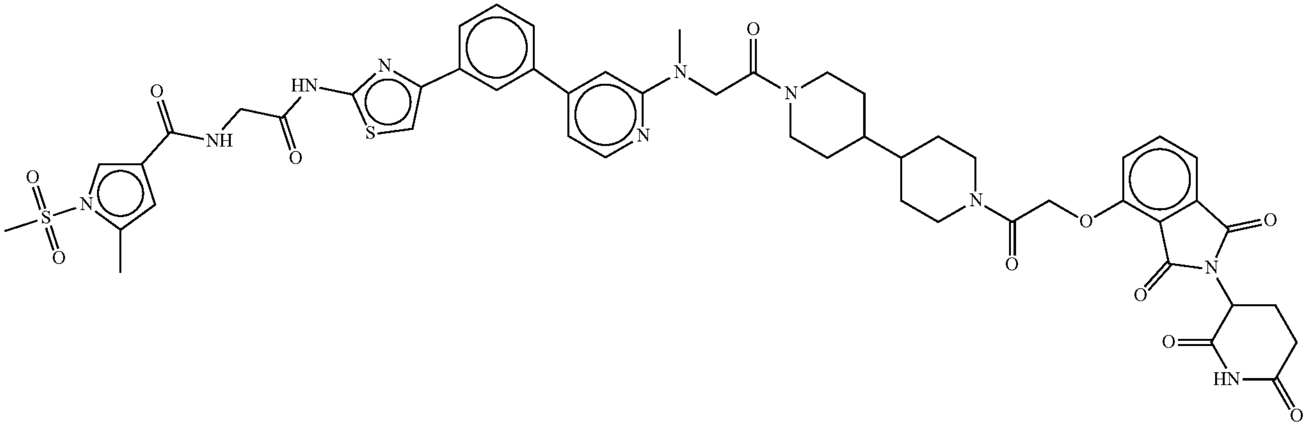 |
| 131 | 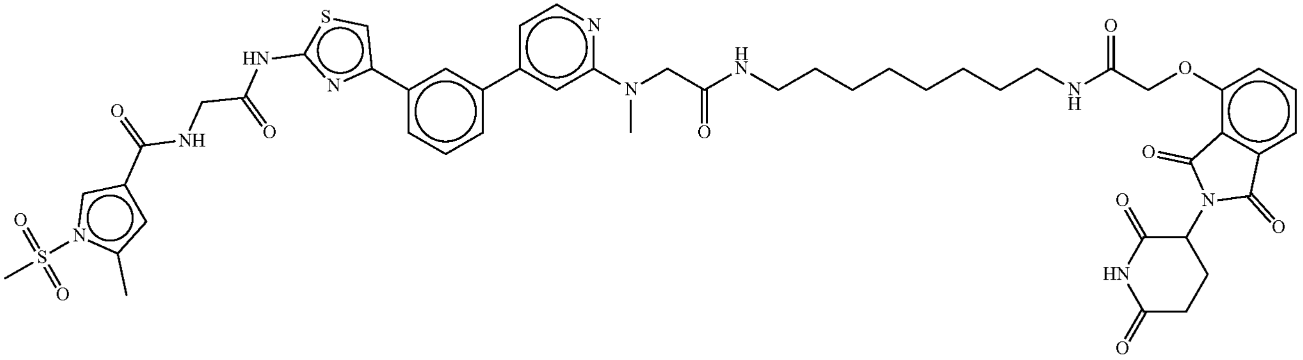 |

TABLE 1-continued
| Compounds of the Invention | |
|---|---|
| # | Structure |
| 132 | 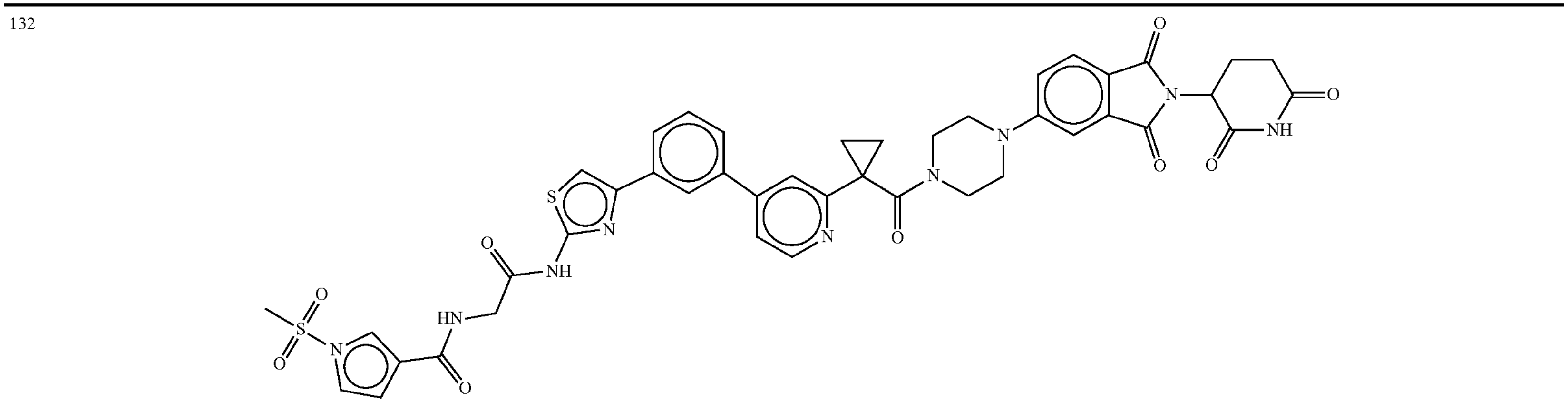 |
| 133 | 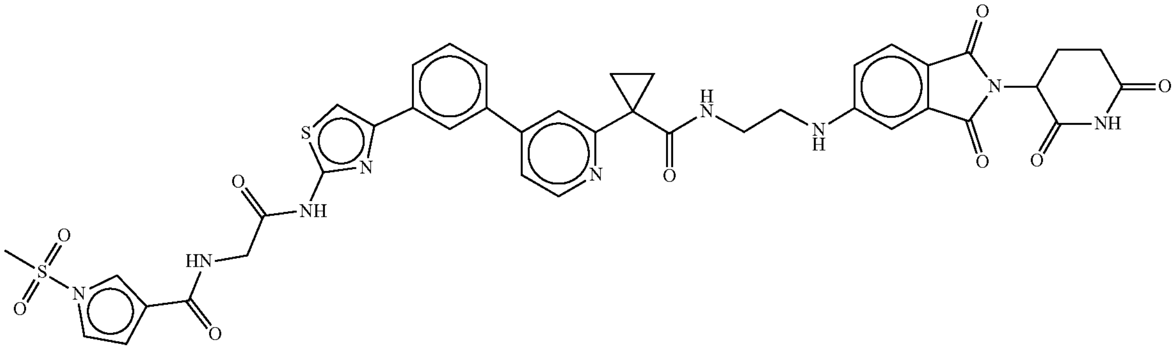 |

TABLE 1-continued
| Compounds of the Invention | |
|---|---|
| # | Structure |
| 134 | 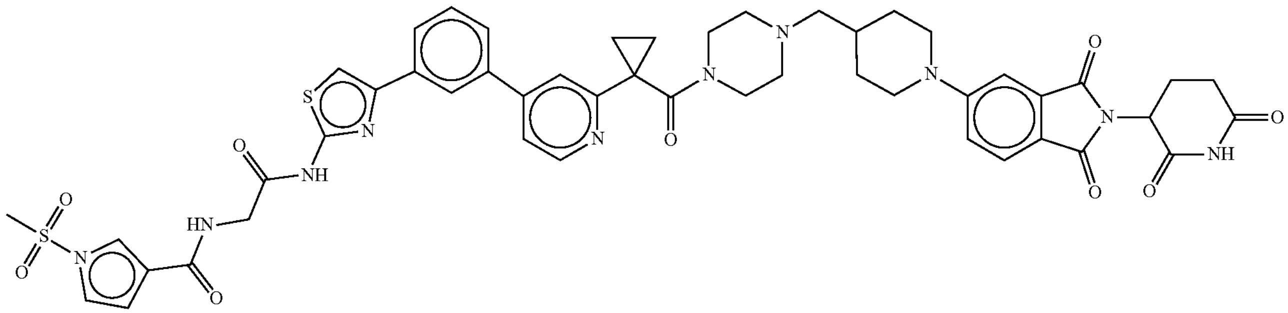 |
| 135 | 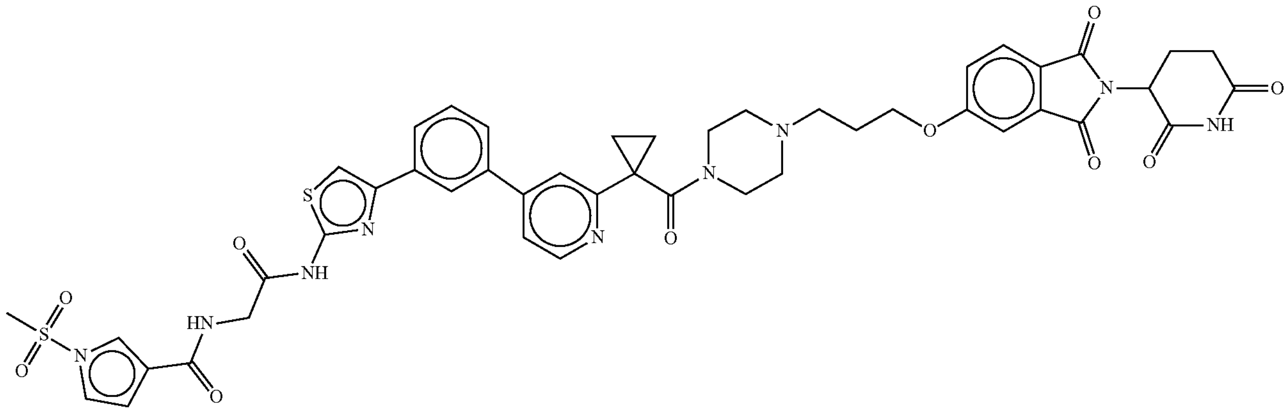 |

TABLE 1-continued
| Compounds of the Invention | |
|---|---|
| # | Structure |
| 136 | 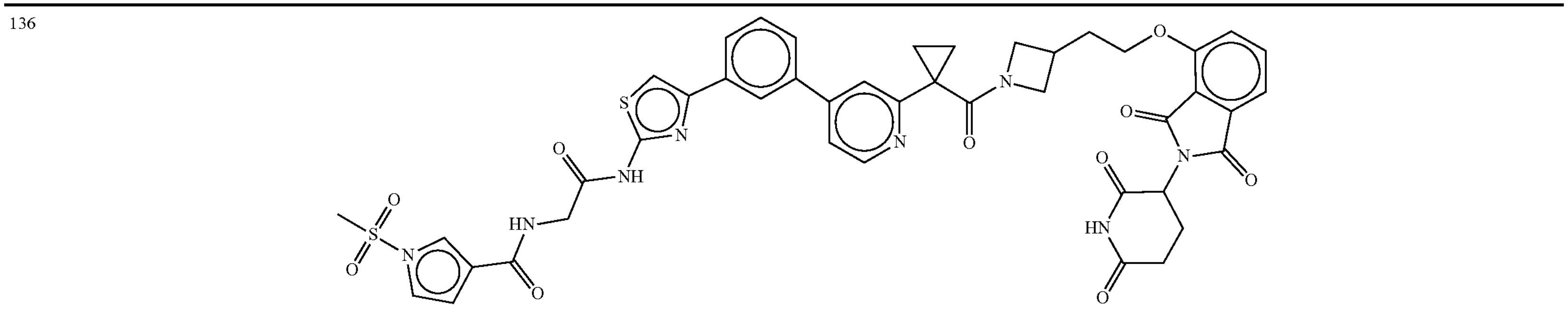 |
| 137 | 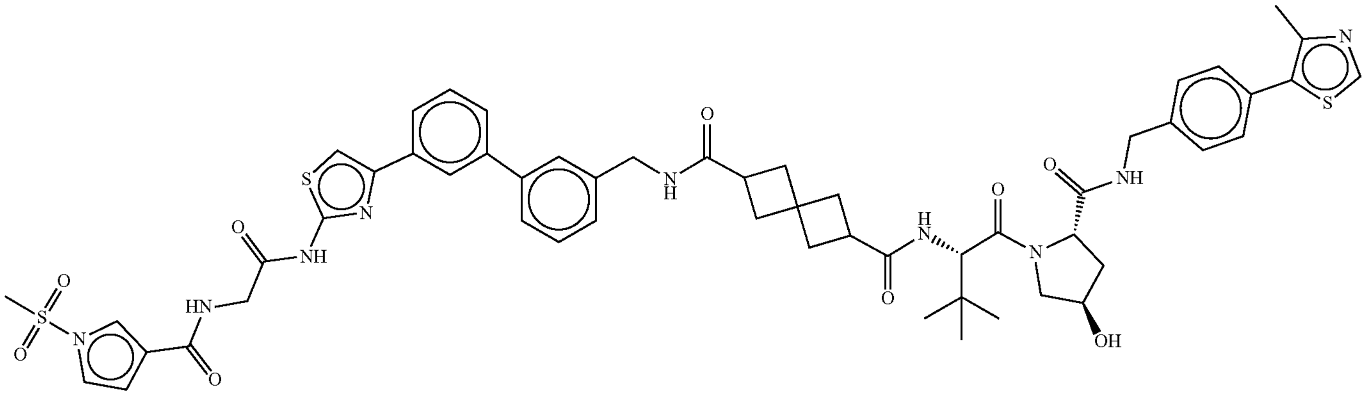 |

TABLE 1-continued
| Compounds of the Invention | |
|---|---|
| # | Structure |
| 138 | 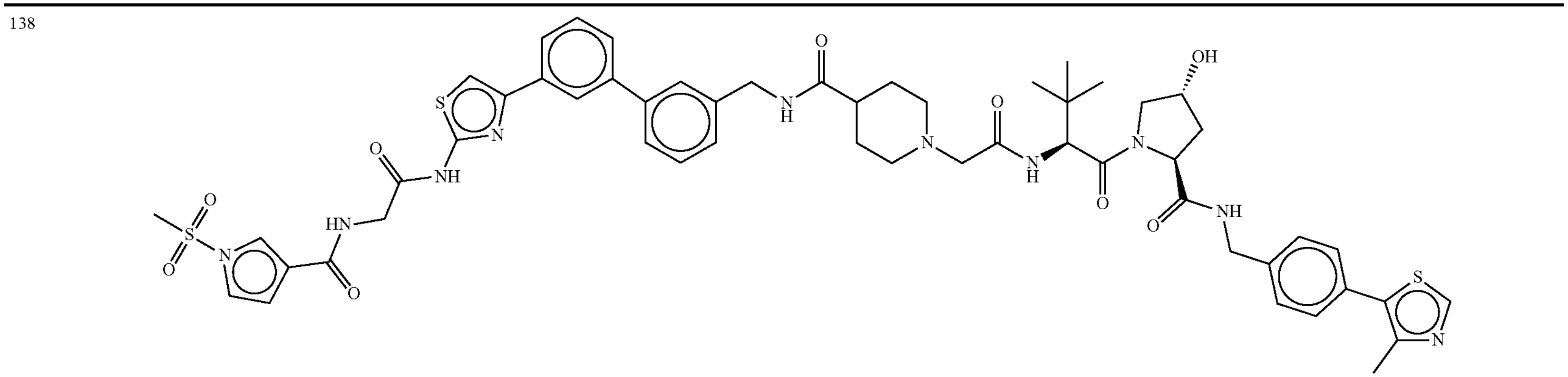 |
| 139 | 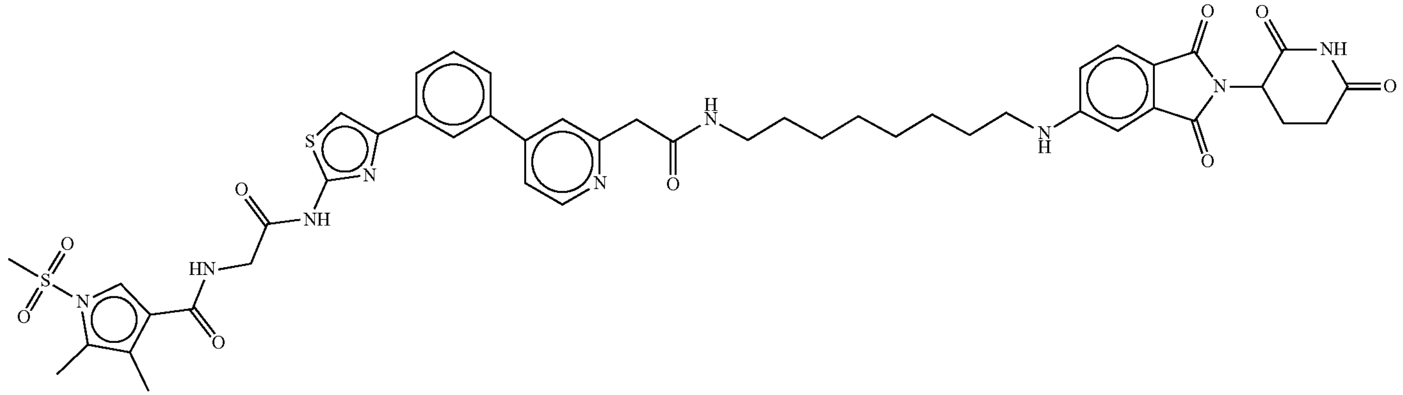 |

TABLE 1-continued
| Compounds of the Invention | |
|---|---|
| # | Structure |
| 140 | 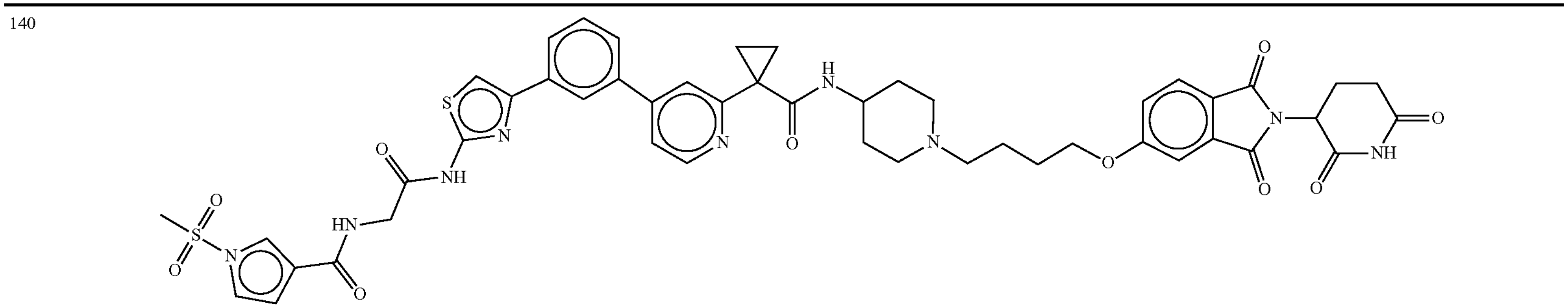 |
| 141 | 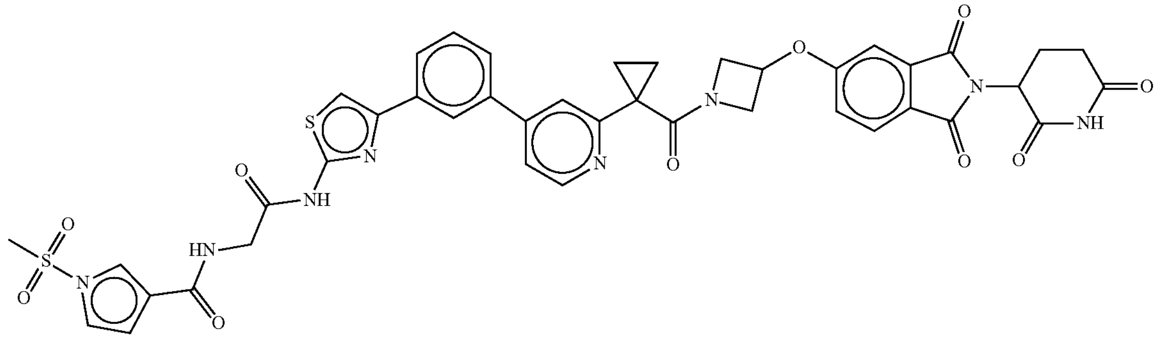 |

TABLE 1-continued
| Compounds of the Invention | |
|---|---|
| # | Structure |
| 142 | 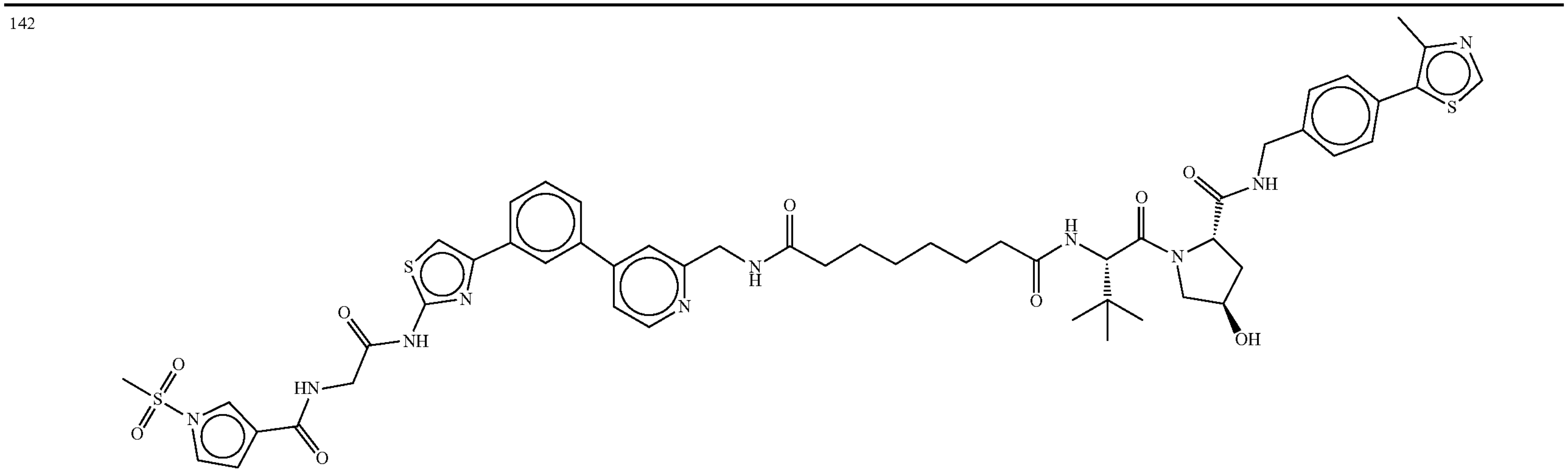 |
| 143 | 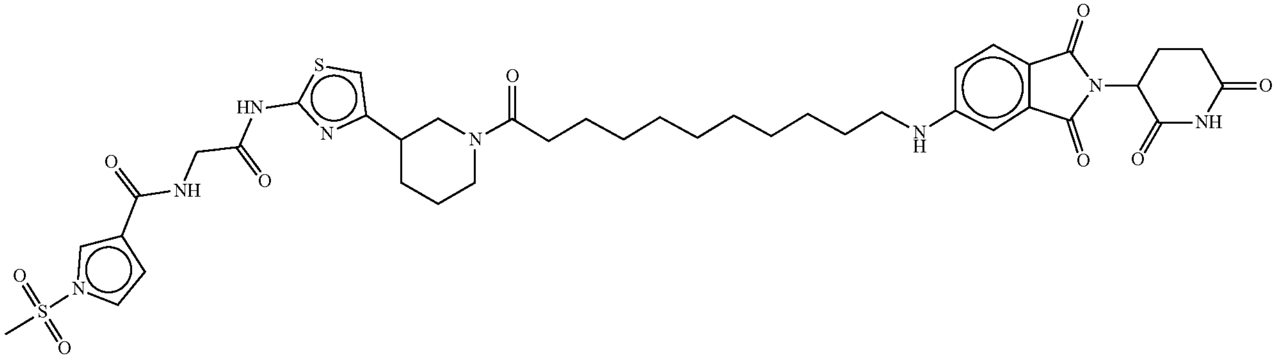 |

TABLE 1-continued
| Compounds of the Invention | |
| --- | --- |
| # | Structure |
| 144 | 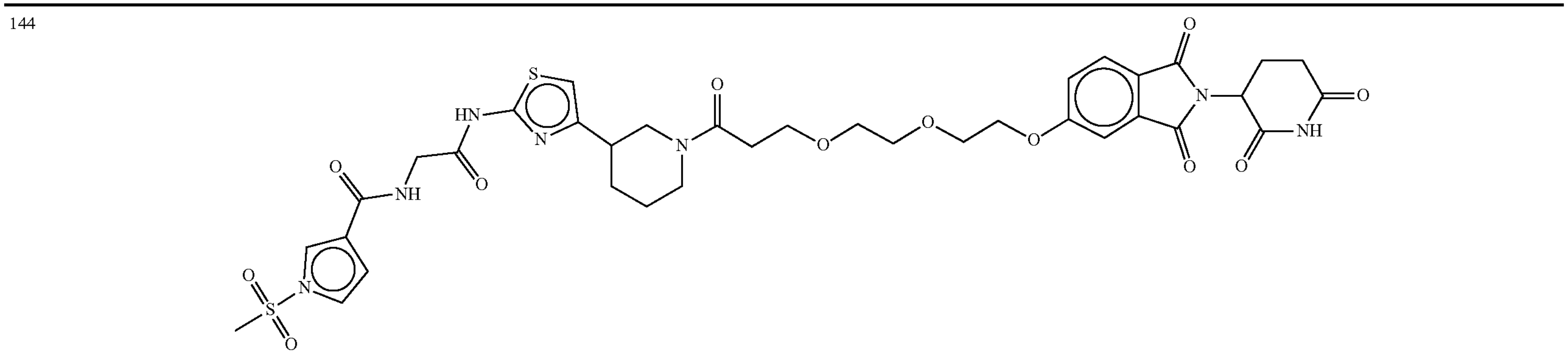 |
| 145 | 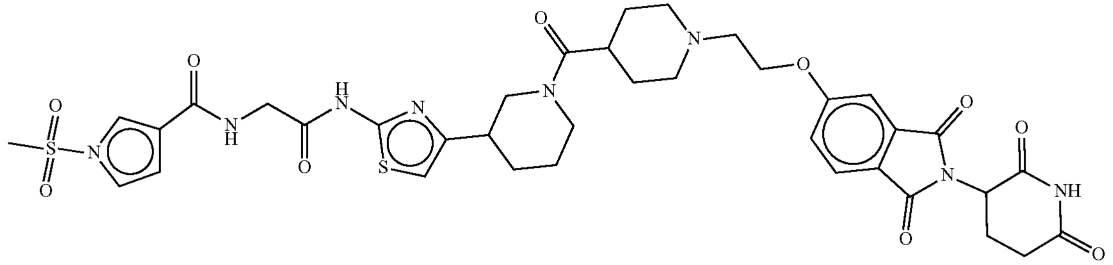 |
| 146 | 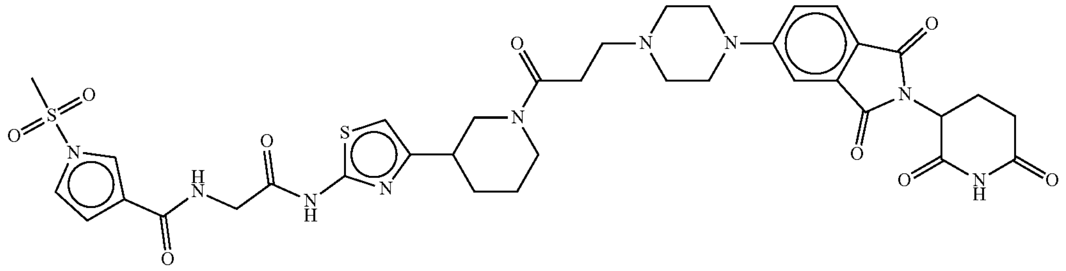 |

TABLE 1-continued
| Compounds of the Invention | |
|---|---|
| # | Structure |
| 147 | 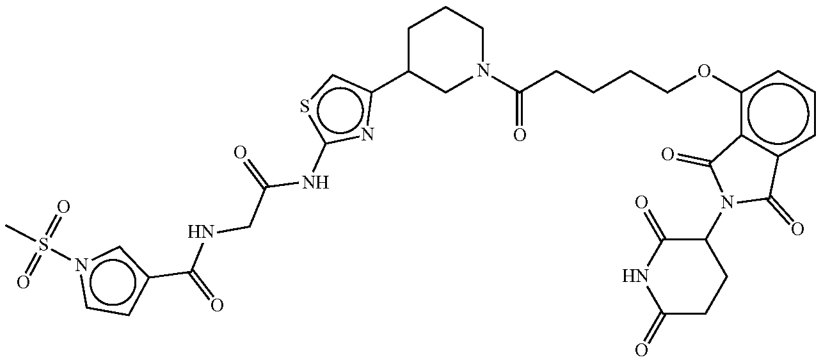 |
| 148 | 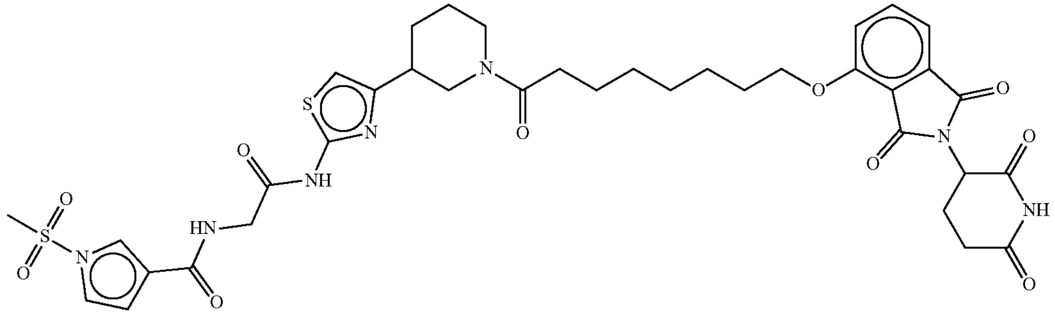 |
| 149 | 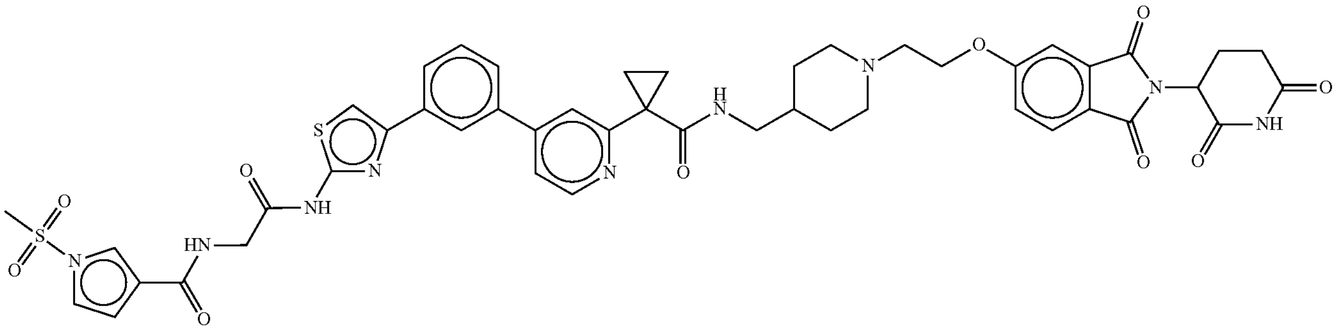 |

TABLE 1-continued
| Compounds of the Invention | |
|---|---|
| # | Structure |
| 150 | 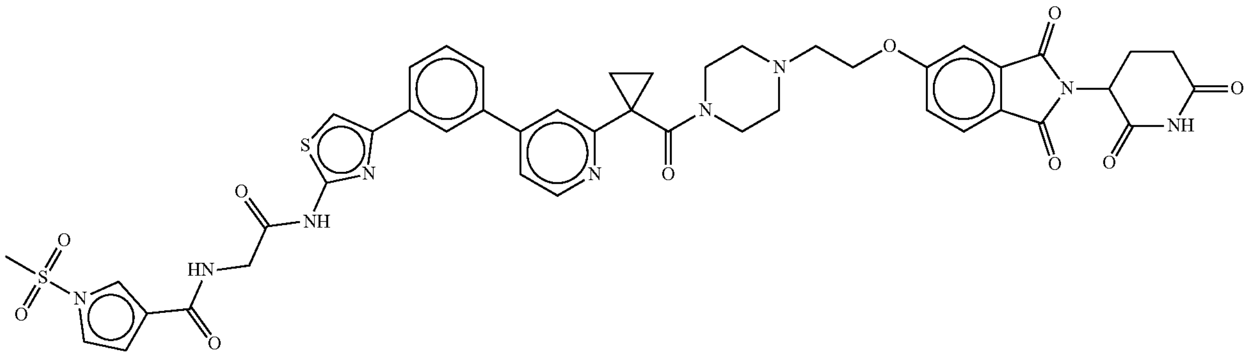 |
| 151 | 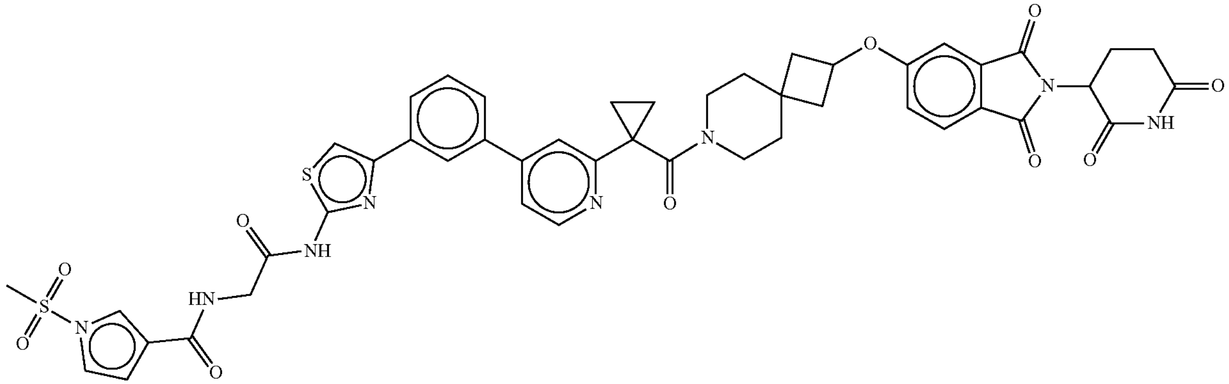 |

TABLE 1-continued
| Compounds of the Invention | |
|---|---|
| # | Structure |
| 152 | 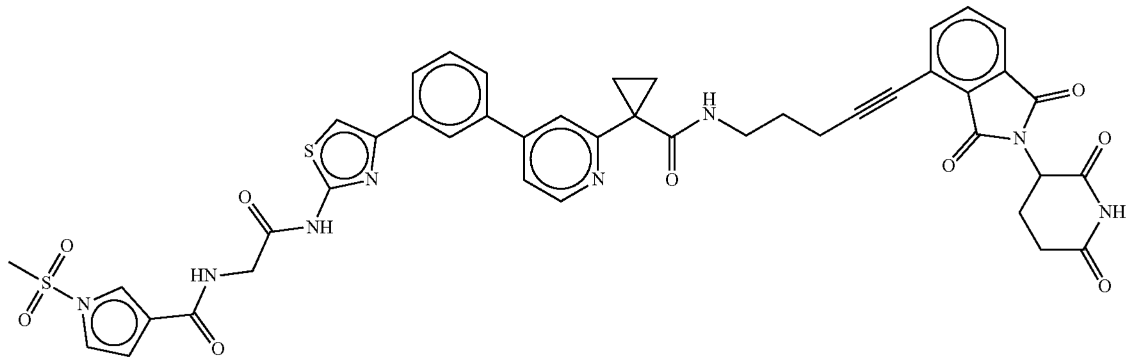 |
| 153 | 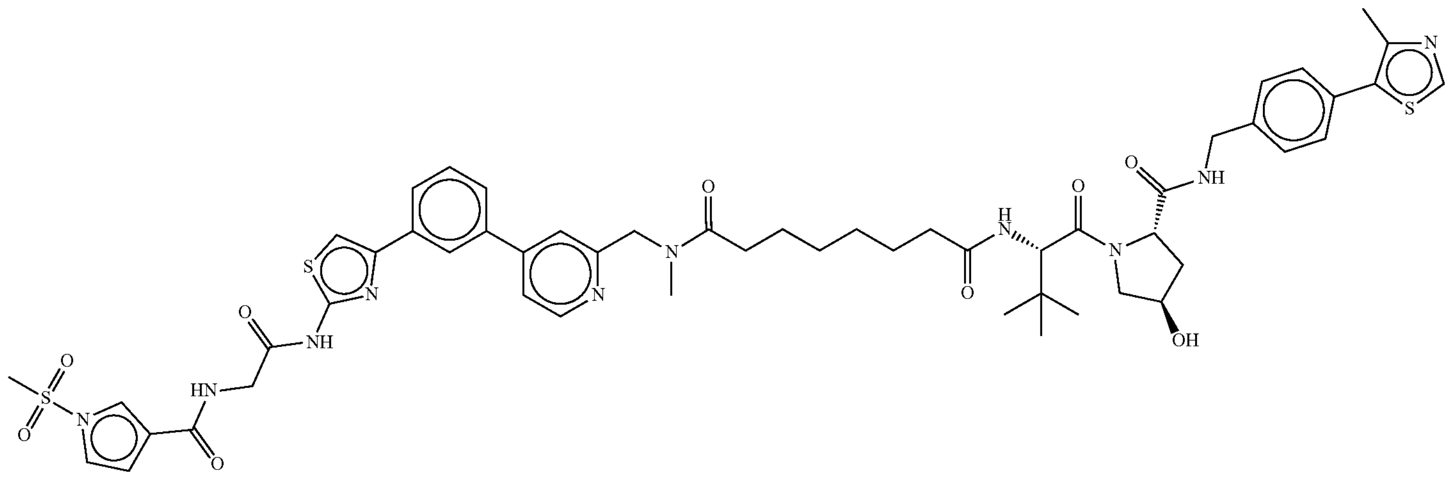 |

TABLE 1-continued
| Compounds of the Invention | |
|---|---|
| # | Structure |
| 154 | 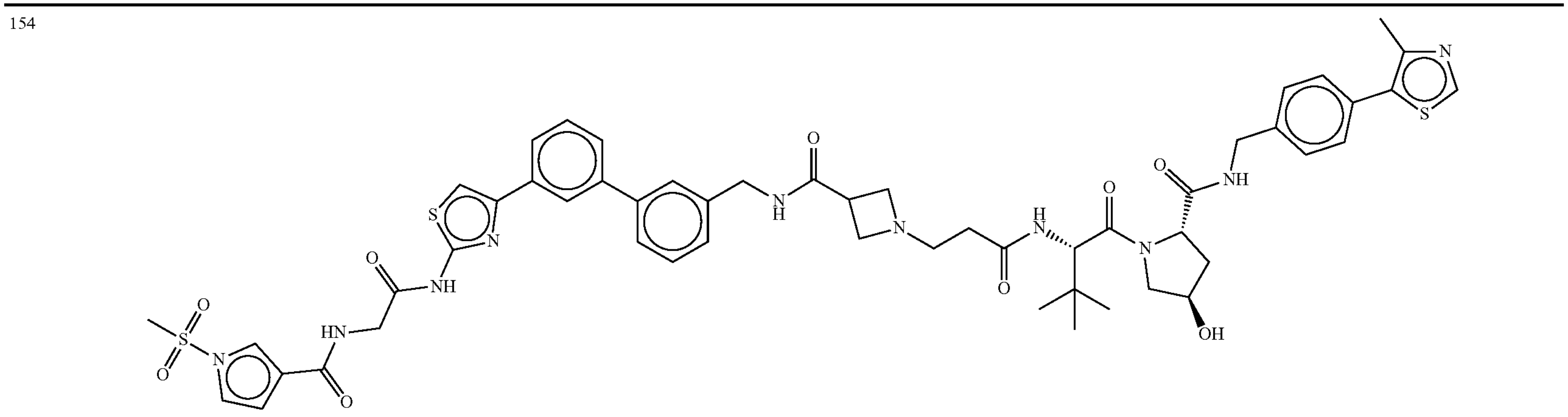 |
| 155 | 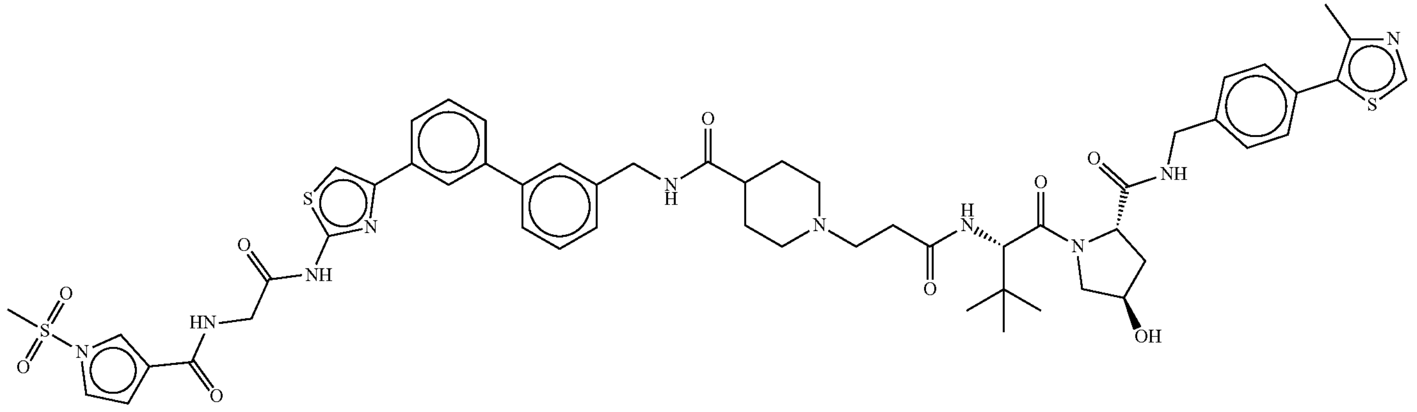 |

TABLE 1-continued
| Compounds of the Invention | |
| --- | --- |
| # | Structure |
| 156 | 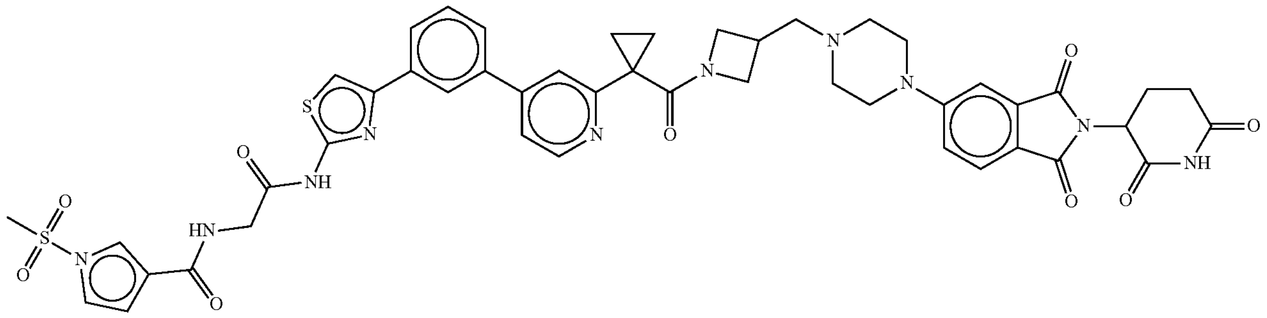 |
| 157 | 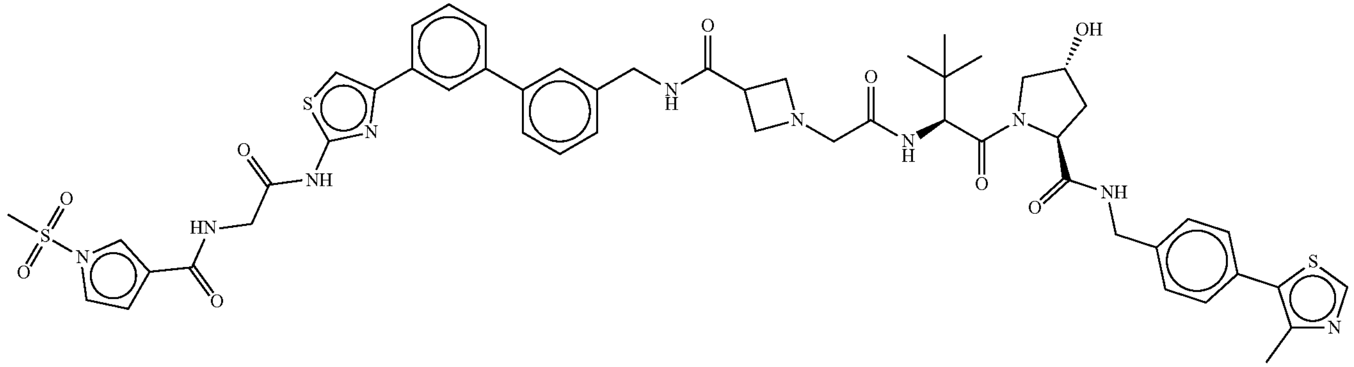 |

TABLE 1-continued
| Compounds of the Invention | |
|---|---|
| # | Structure |
| 158 | 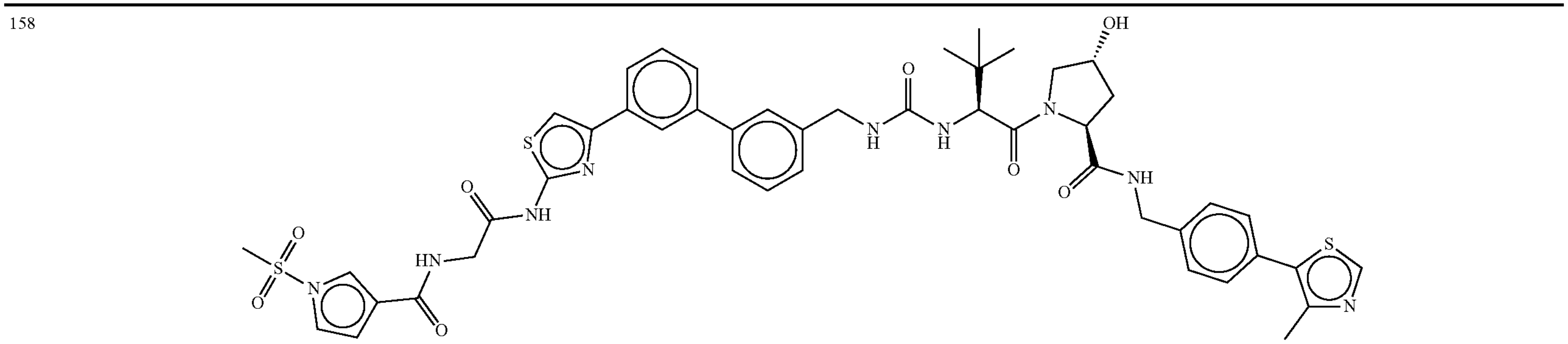 |
| 159 | 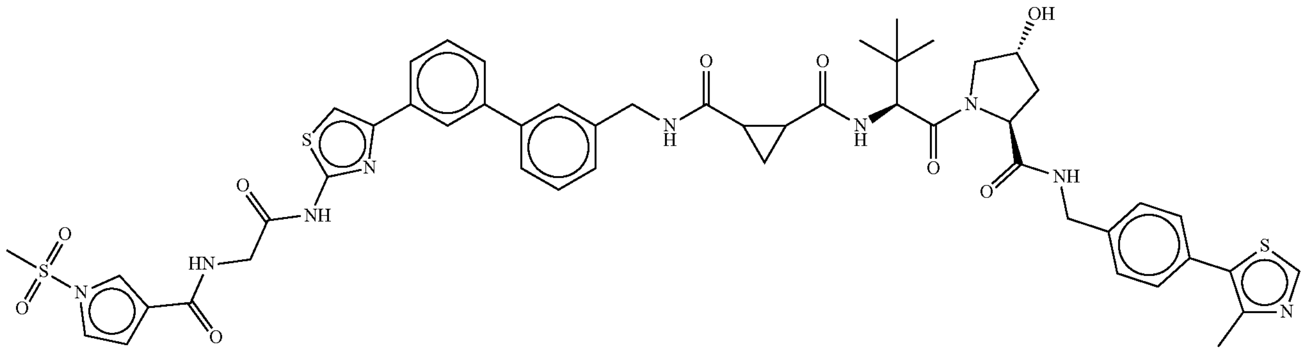 |

TABLE 1-continued
| Compounds of the Invention | |
| --- | --- |
| # | Structure |
| 160 | 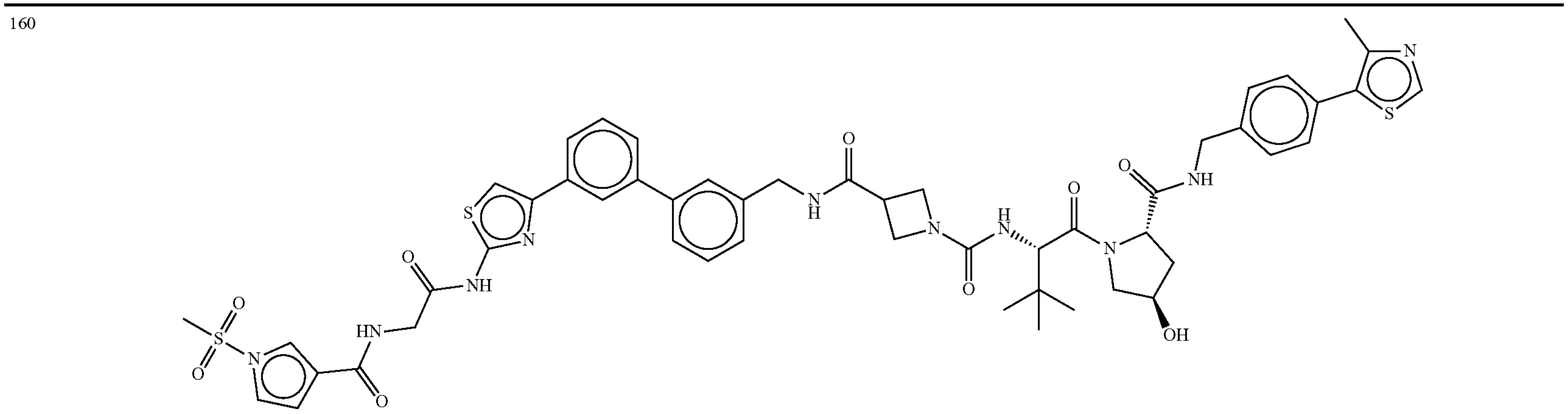 |
| 161 | 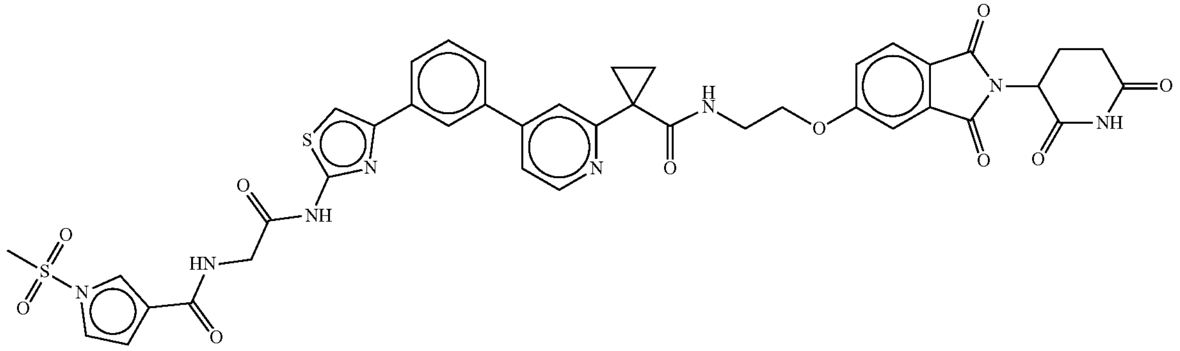 |

TABLE 1-continued
| Compounds of the Invention | |
|---|---|
| # | Structure |
| 162 | 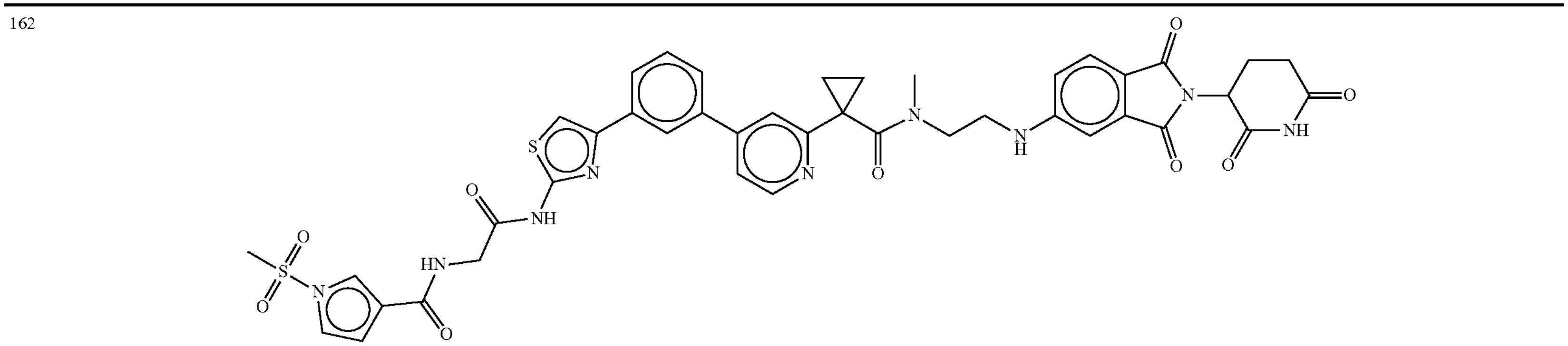 |
| 163 | 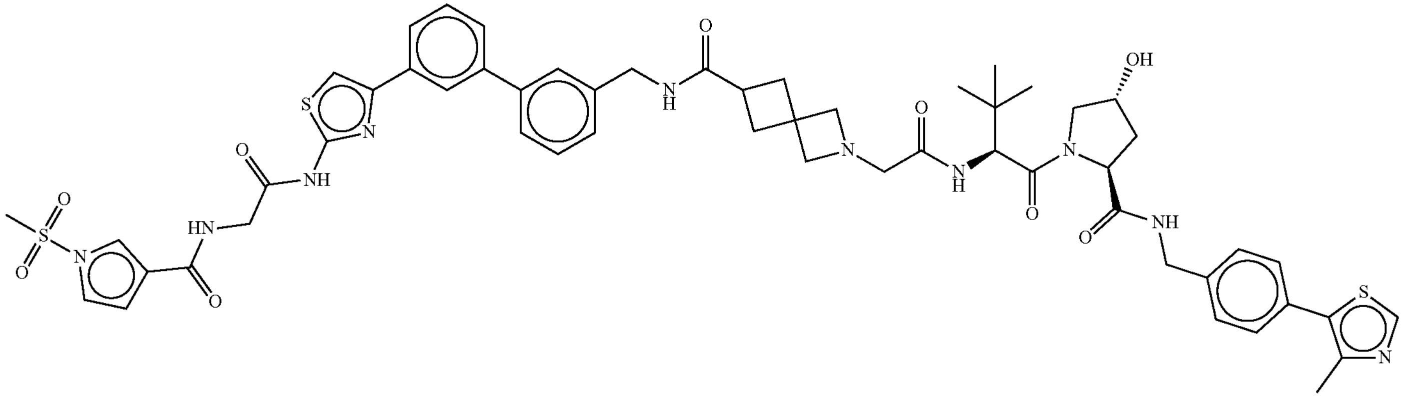 |

TABLE 1-continued
| Compounds of the Invention | |
| --- | --- |
| # | Structure |
| 164 | 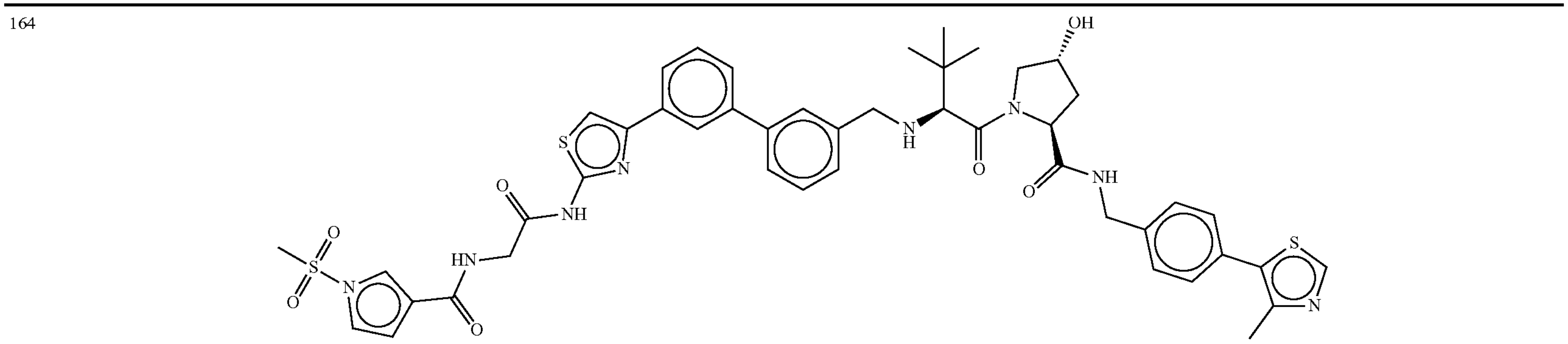 |
| 165 | 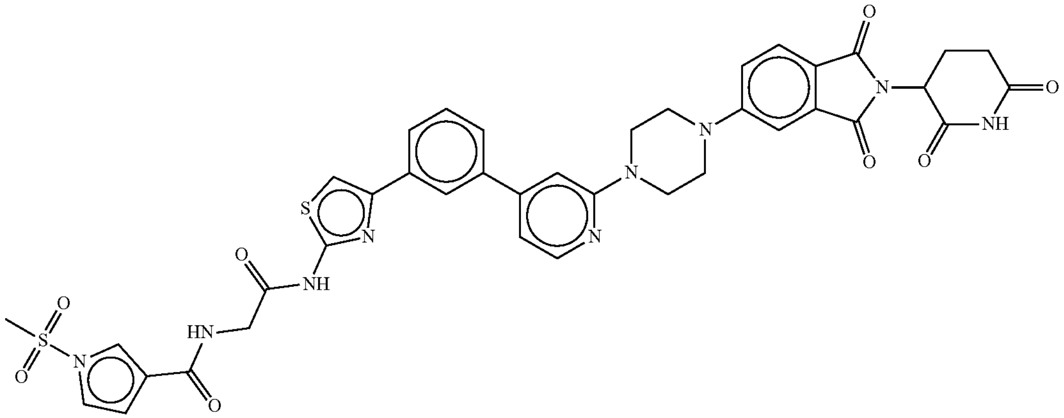 |

TABLE 1-continued
| Compounds of the Invention | |
|---|---|
| # | Structure |
| 166 | 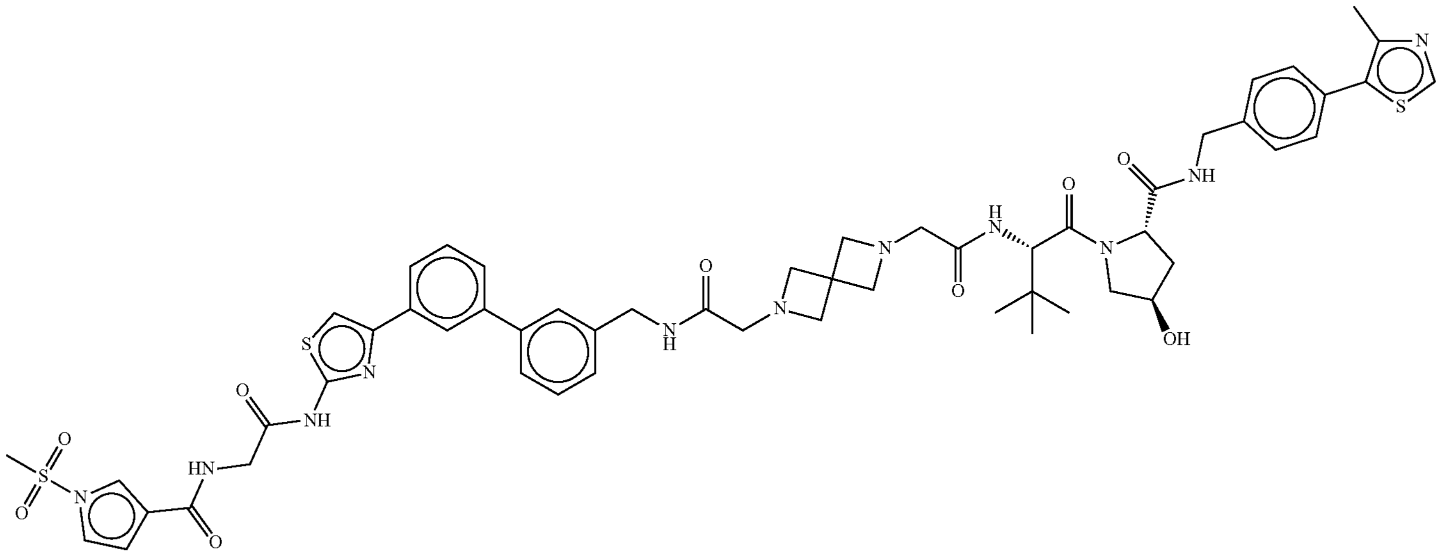 |
| 167 | 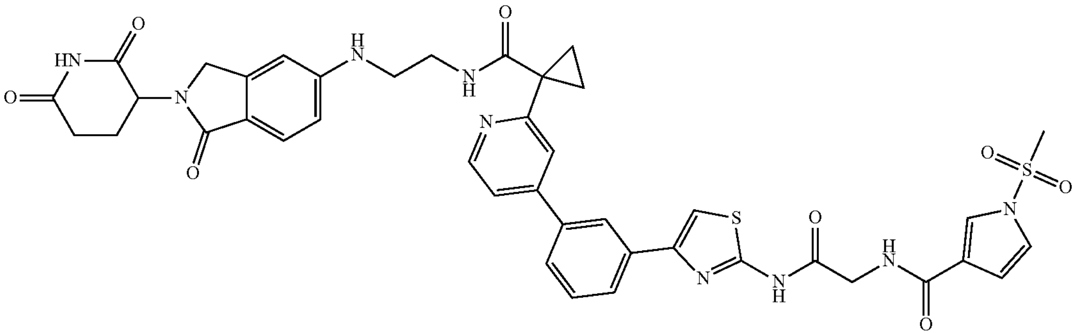 [SMILES: CS(=O)(=O)n1ccc(C(=O)NCC(=O)Nc2nc(-c3cccc(-c4ccnc(C5(C(=O)NCCNc6ccc7c(c6)CN(C6CCC(=O)NC6=O)C7=O)CC5)c4)c3)cs2)c1] |

TABLE 1-continued
| Compounds of the Invention | |
|---|---|
| # | Structure |
| 168 | 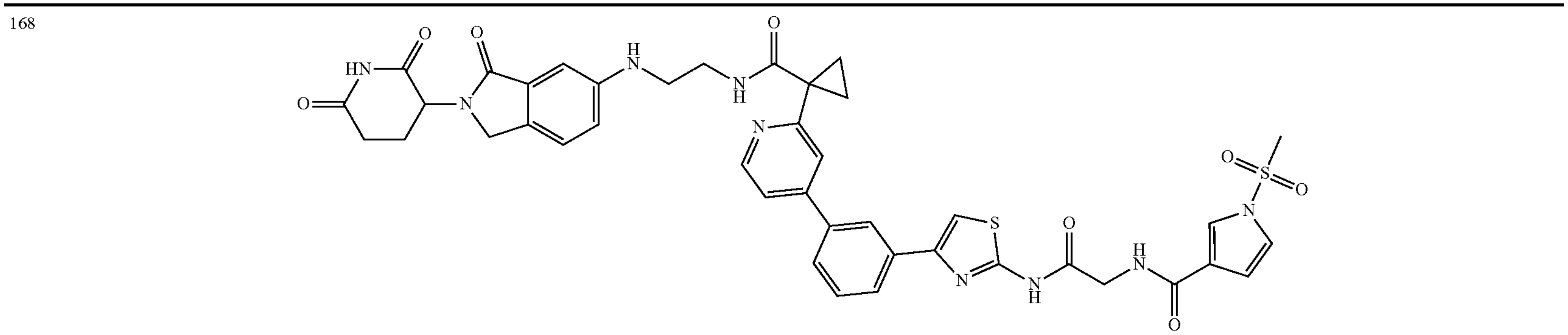 |
| 169 | 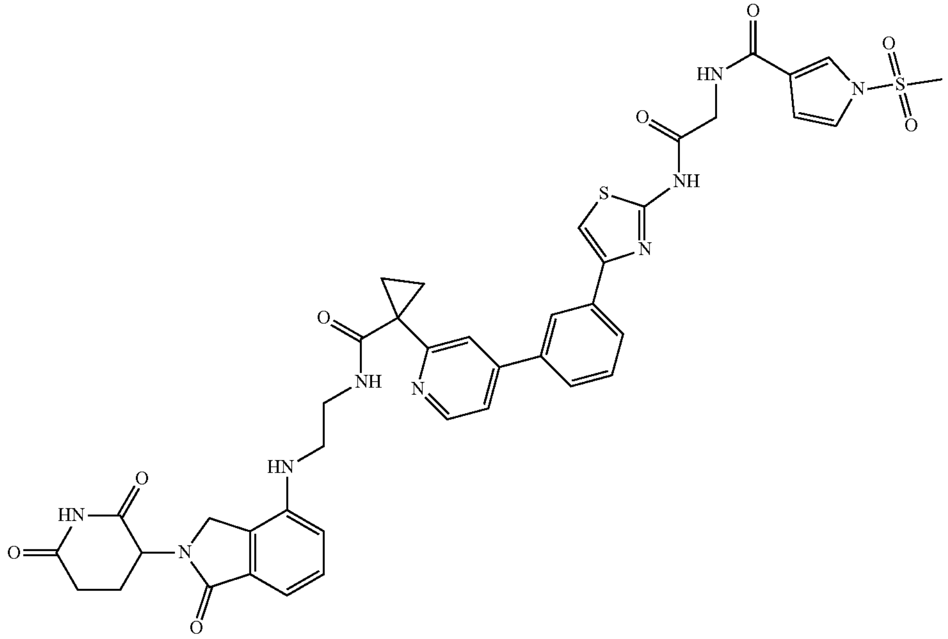 [SMILES: CS(=O)(=O)n1ccc(C(=O)NCC(=O)Nc2nc(-c3cccc(-c4ccnc(C5(C(=O)NCCNc6cccc7c6CN(C6CCC(=O)NC6=O)C7=O)CC5)c4)c3)cs2)c1] |

TABLE 1-continued
| Compounds of the Invention | |
|---|---|
| # | Structure |
| 170 | 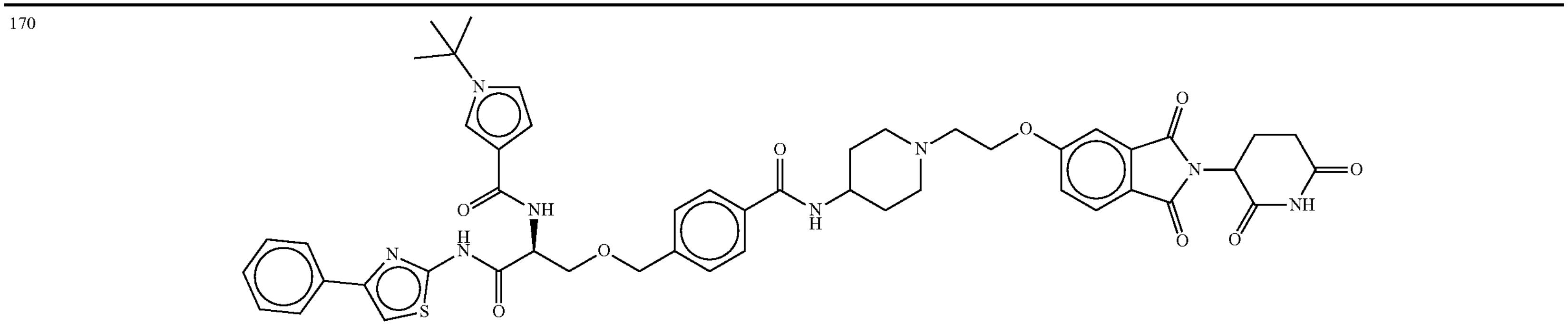 |
| 171 | 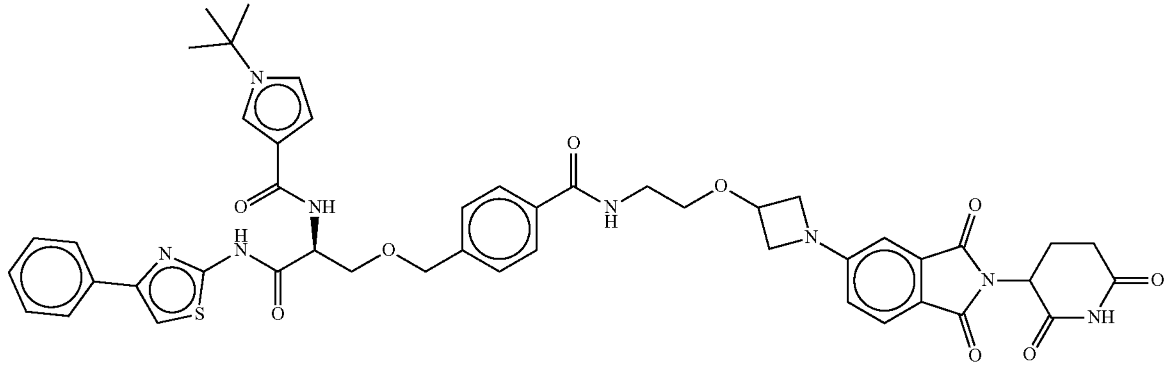 |

TABLE 1-continued
| Compounds of the Invention | |
|---|---|
| # | Structure |
| 172 | 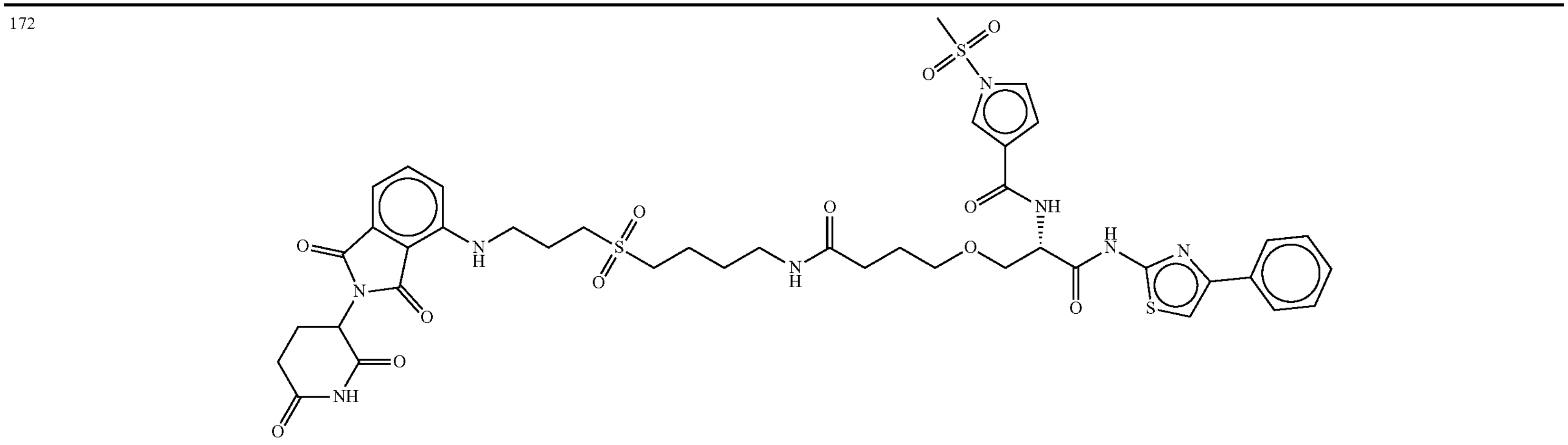 |
| 173 | 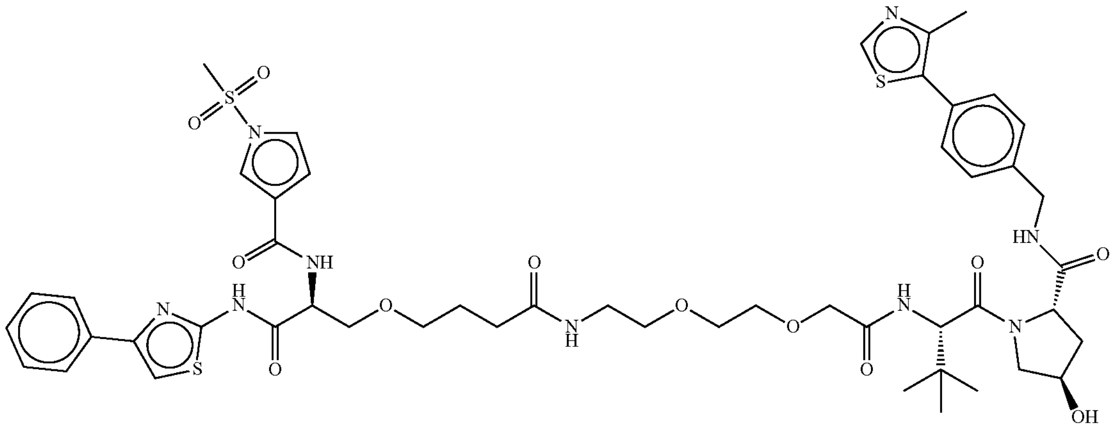 |

TABLE 1-continued
| Compounds of the Invention | |
|---|---|
| # | Structure |
| 174 | 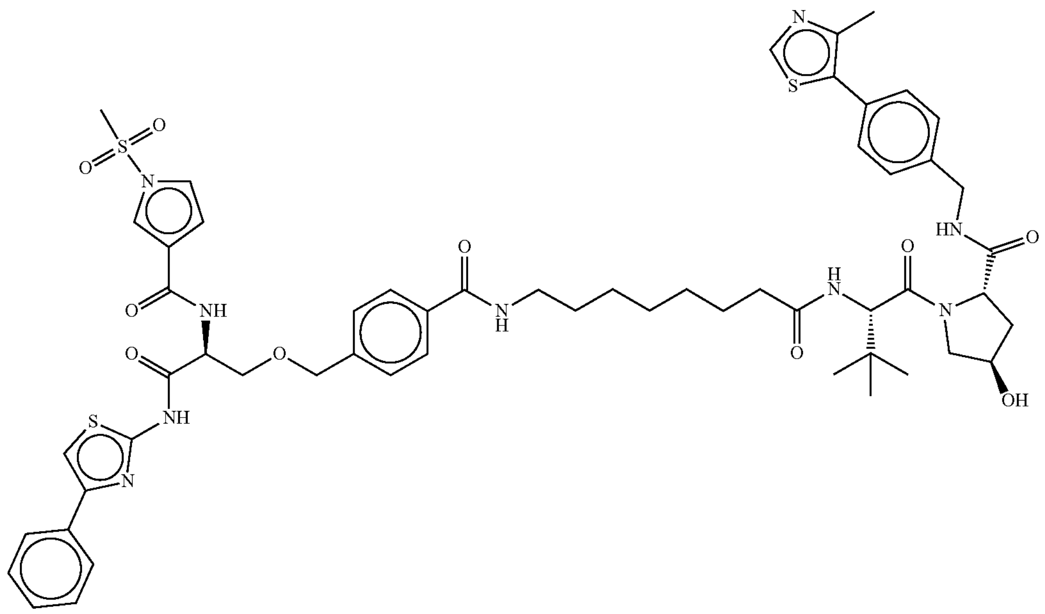 |

TABLE 1-continued
| Compounds of the Invention | |
|---|---|
| # | Structure |
| 175 | 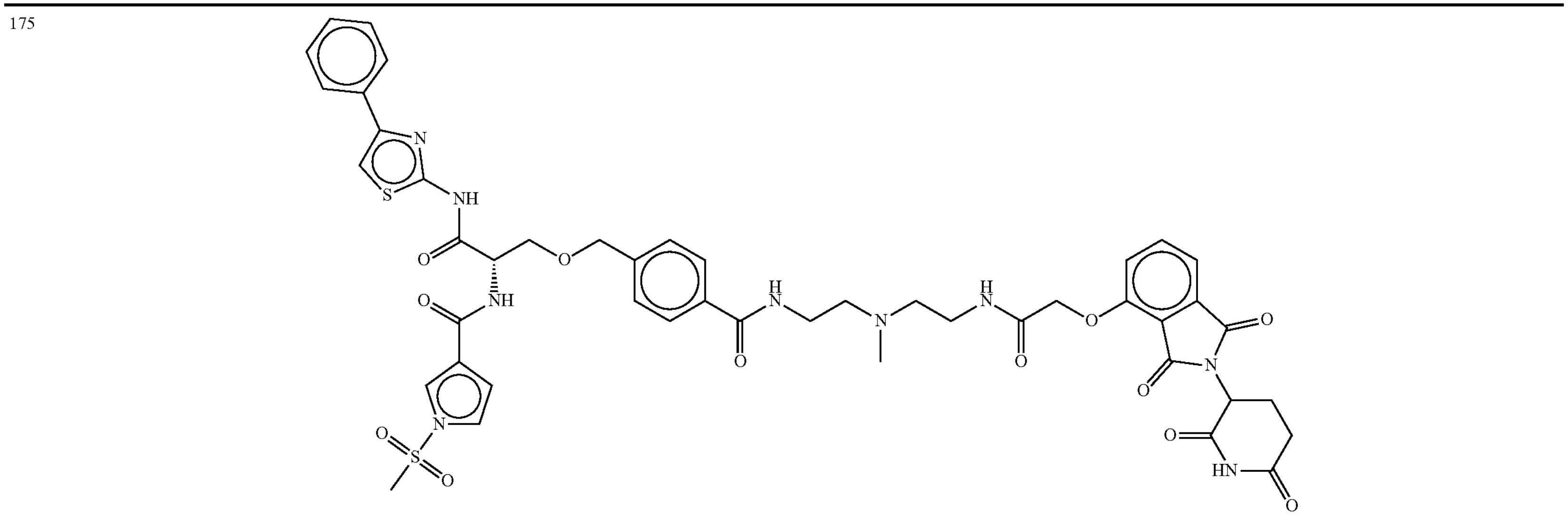 |
| 176 | 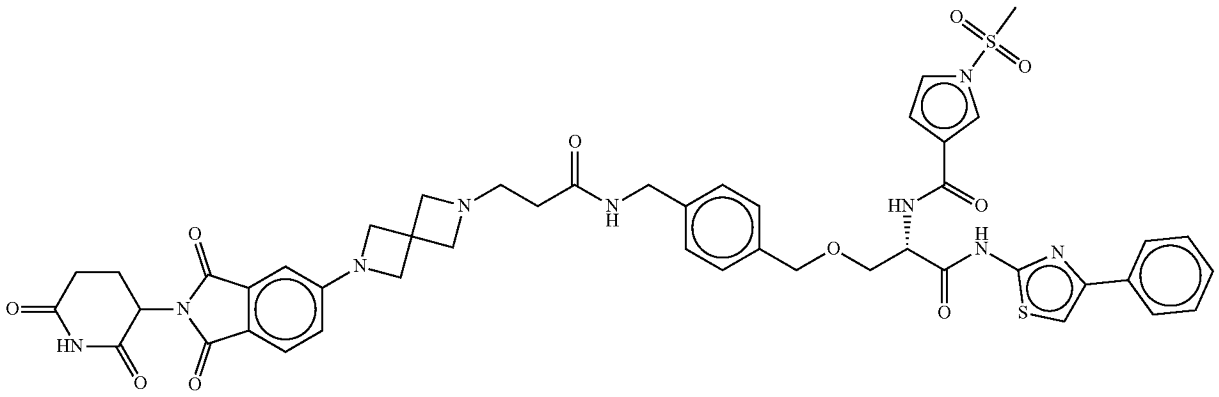 |

TABLE 1-continued
| Compounds of the Invention | |
|---|---|
| # | Structure |
| 177 | 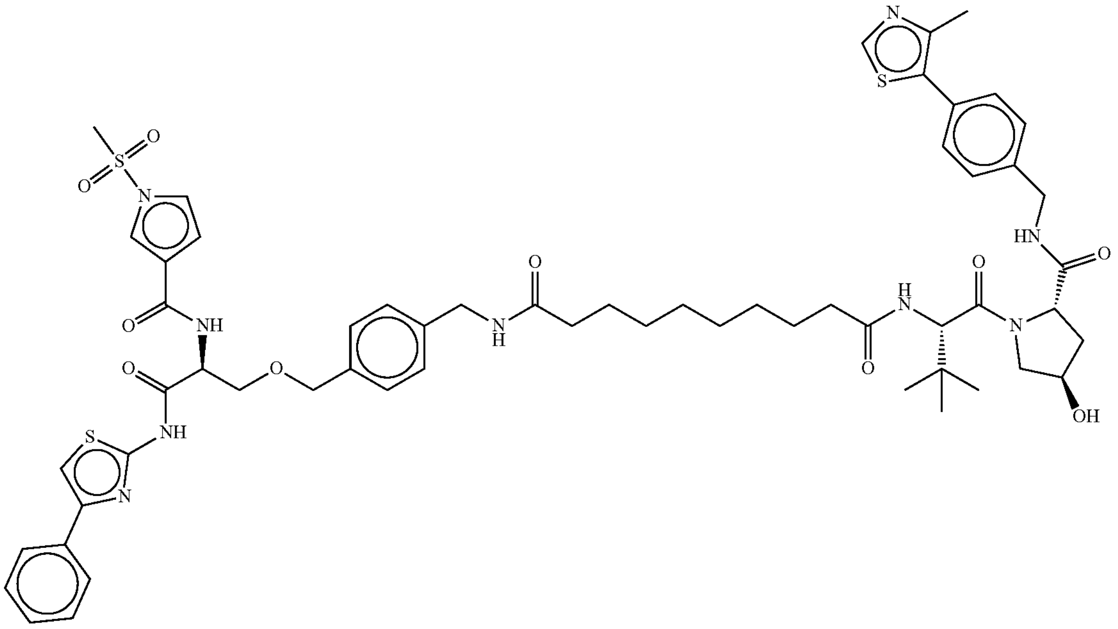 |

TABLE 1-continued
| Compounds of the Invention | |
|---|---|
| # | Structure |
| 178 | 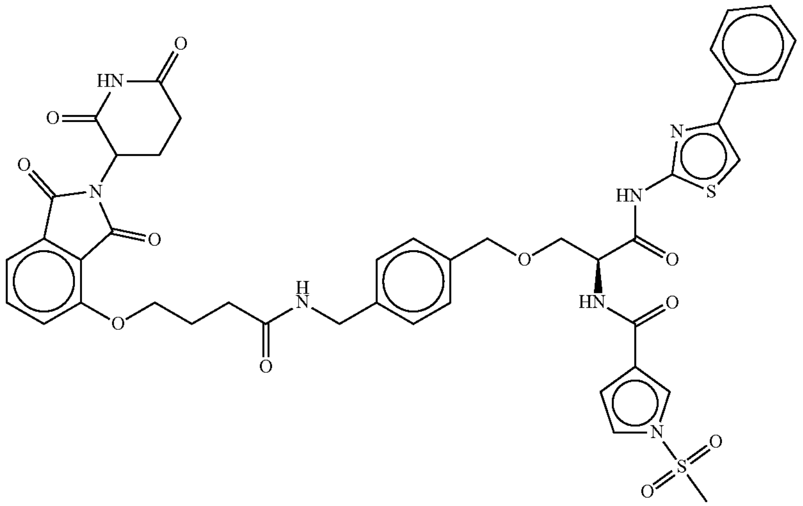 |
| 179 | 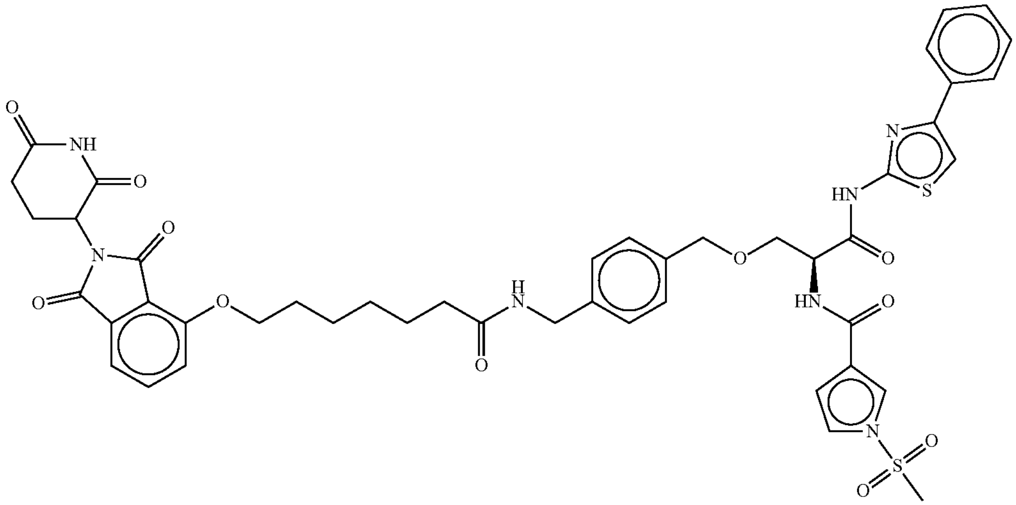 |

TABLE 1-continued
| Compounds of the Invention | |
|---|---|
| # | Structure |
| 180 | 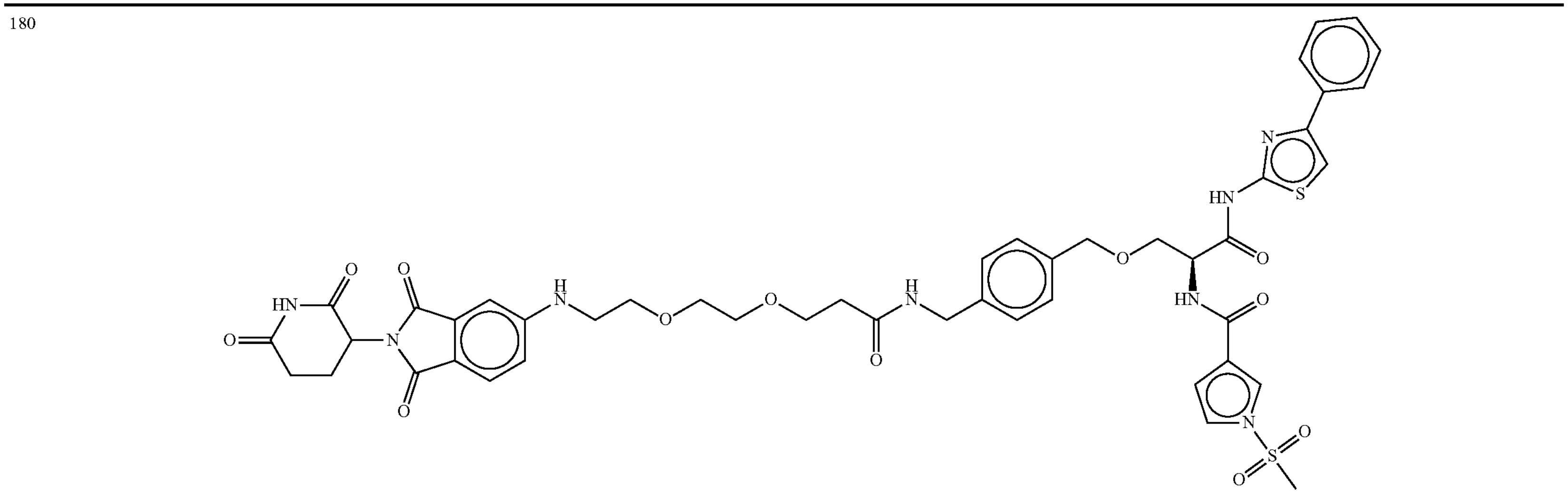 |
| 181 | 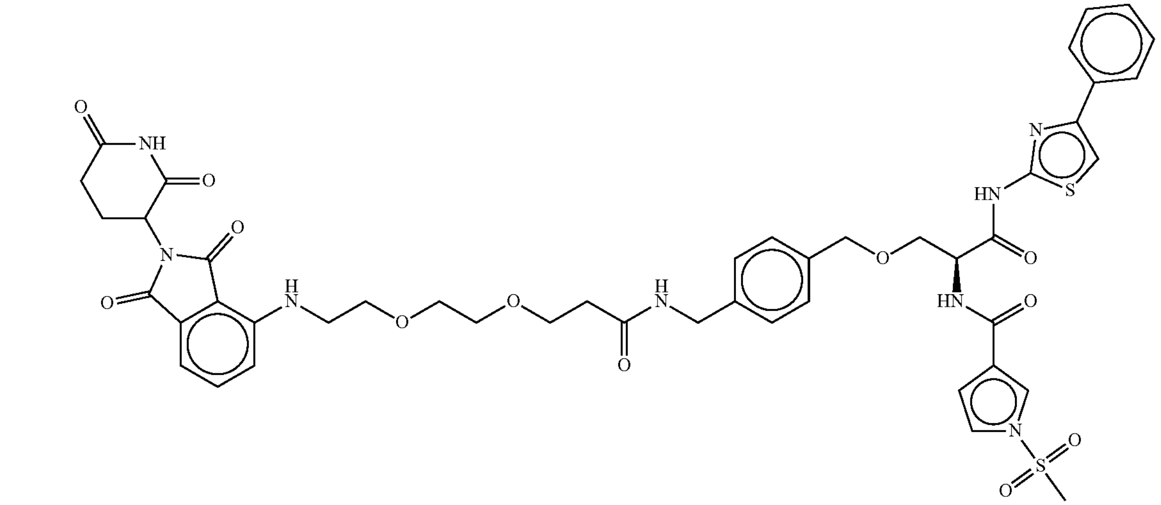 |

TABLE 1-continued
| Compounds of the Invention | |
|---|---|
| # | Structure |
| 182 | 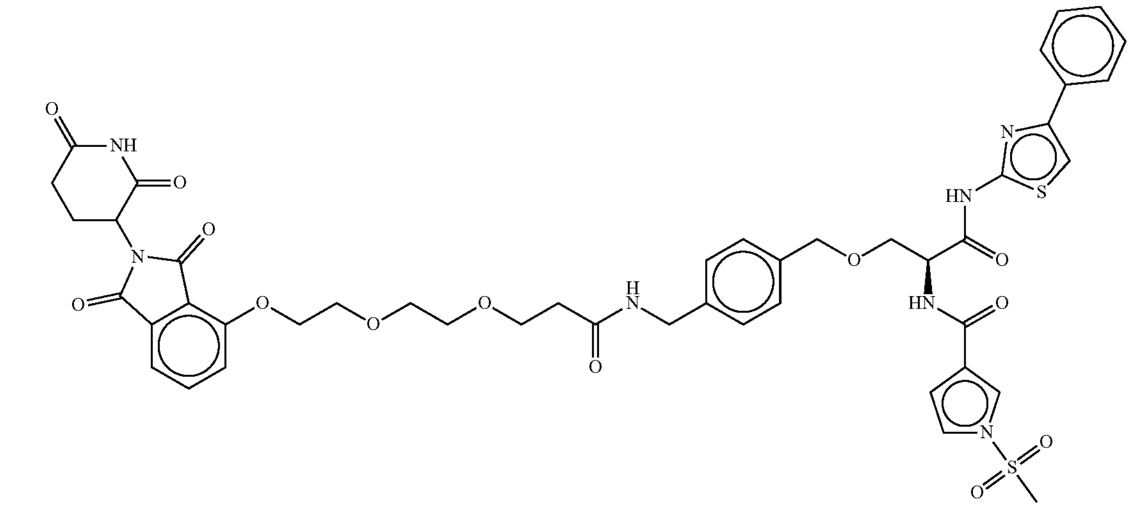 |
| 183 | 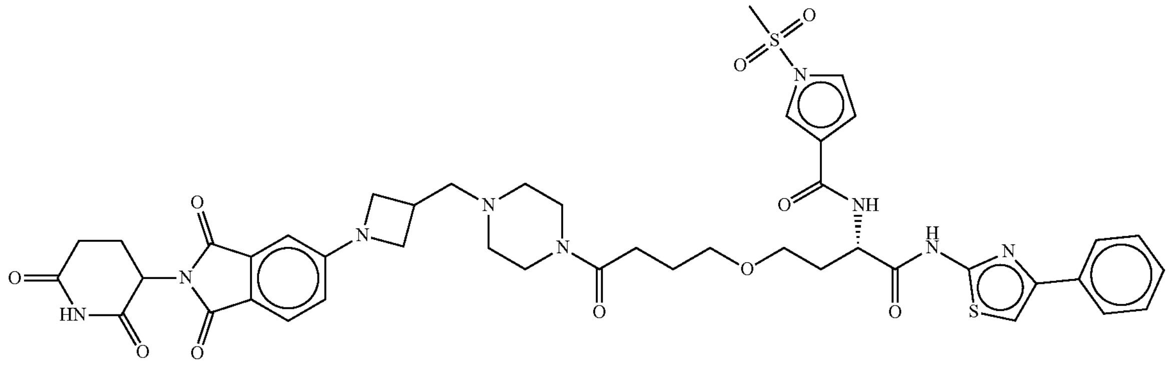 |

TABLE 1-continued
| Compounds of the Invention | |
| --- | --- |
| # | Structure |
| 184 | 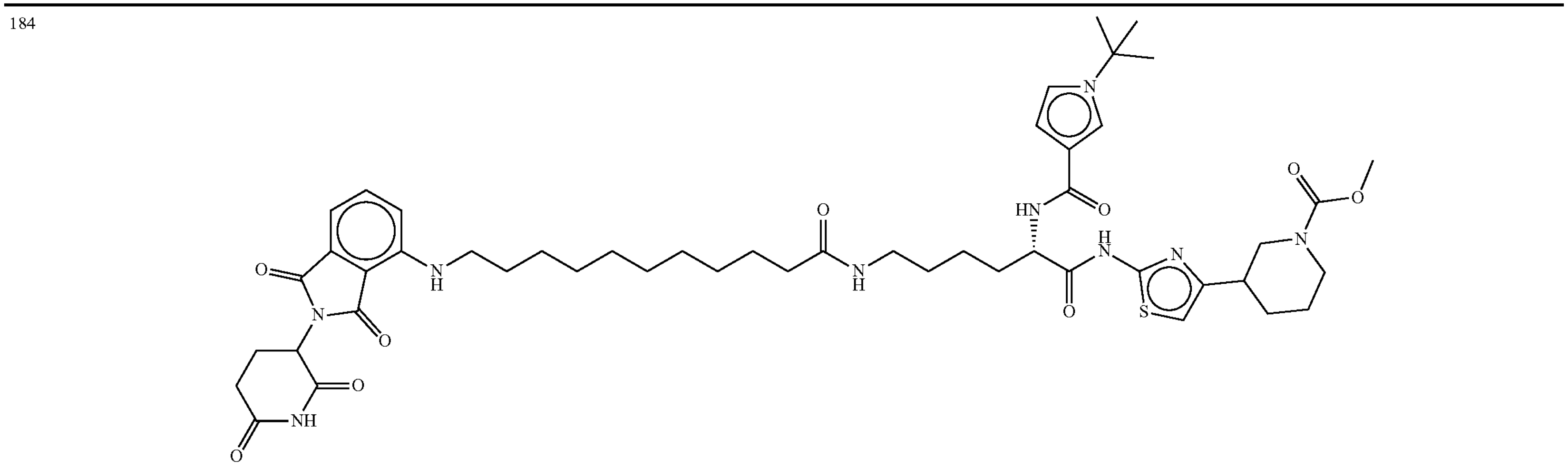 |
| 185 | 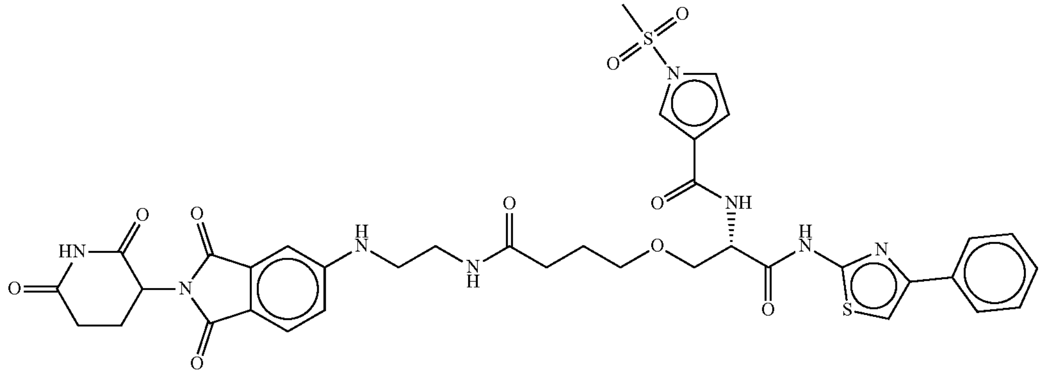 |

TABLE 1-continued
| Compounds of the Invention | |
|---|---|
| # | Structure |
| 186 | 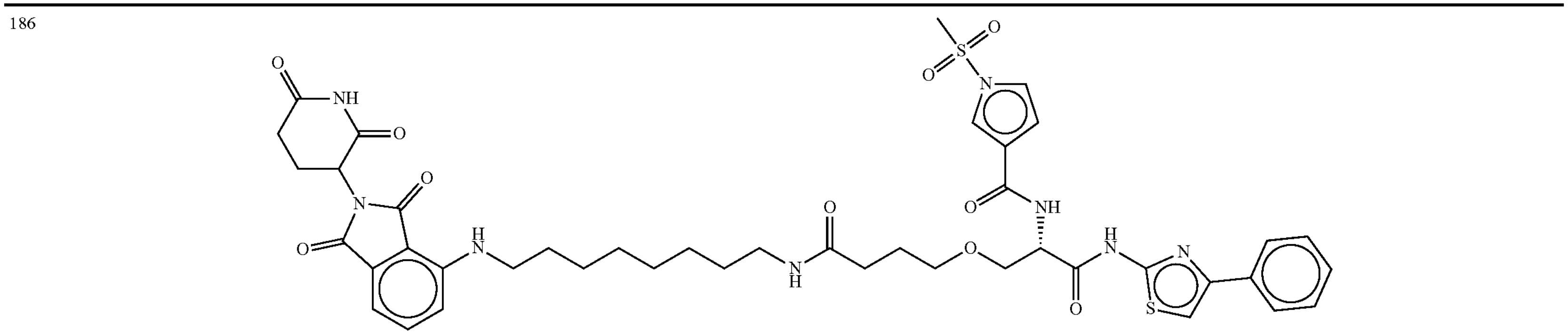 |
| 187 | 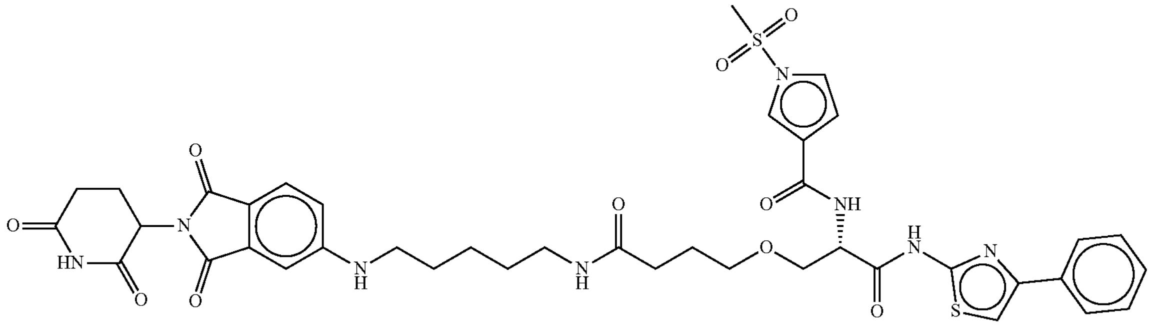 |

TABLE 1-continued
| Compounds of the Invention | |
|---|---|
| # | Structure |
| 188 | 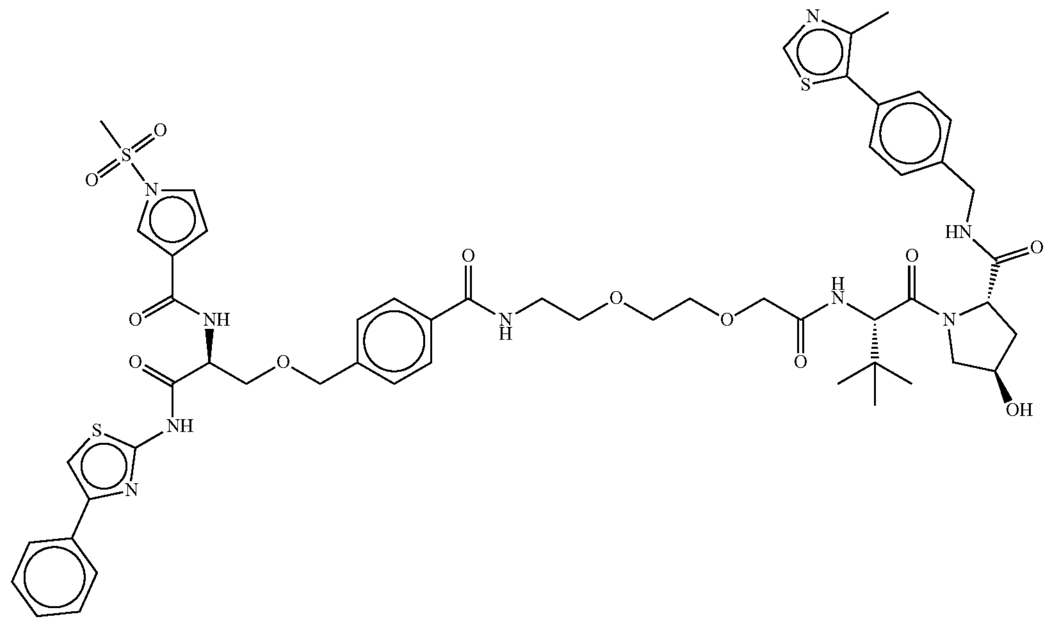 |

TABLE 1-continued
| Compounds of the Invention | |
|---|---|
| # | Structure |
| 189 | 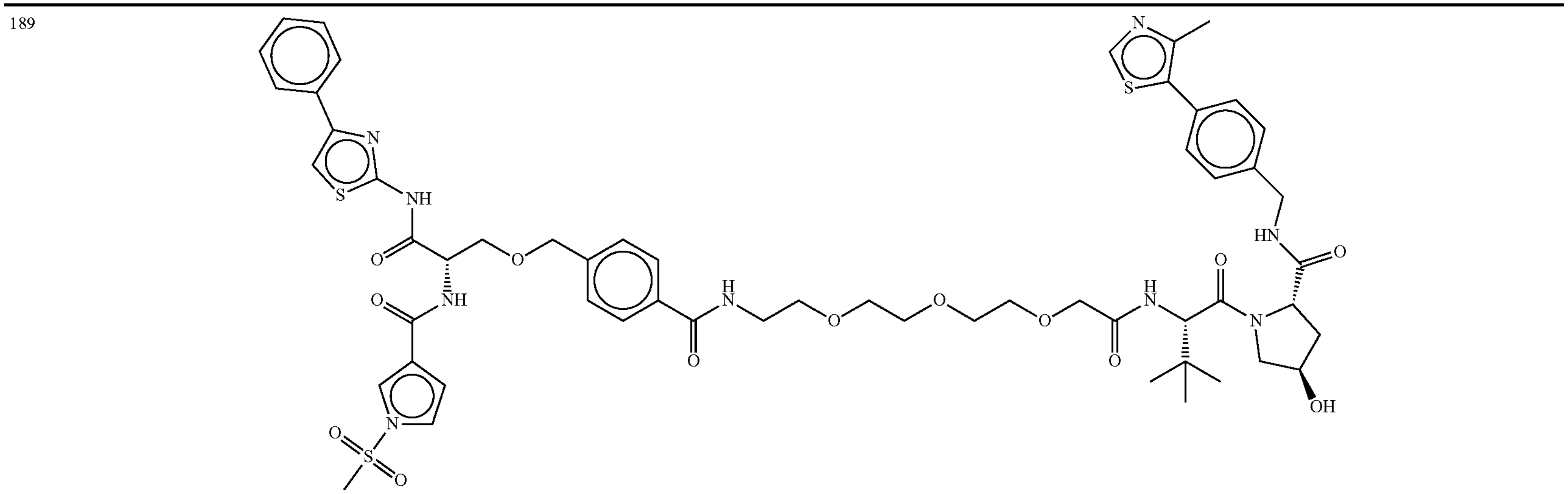 |
| 190 | 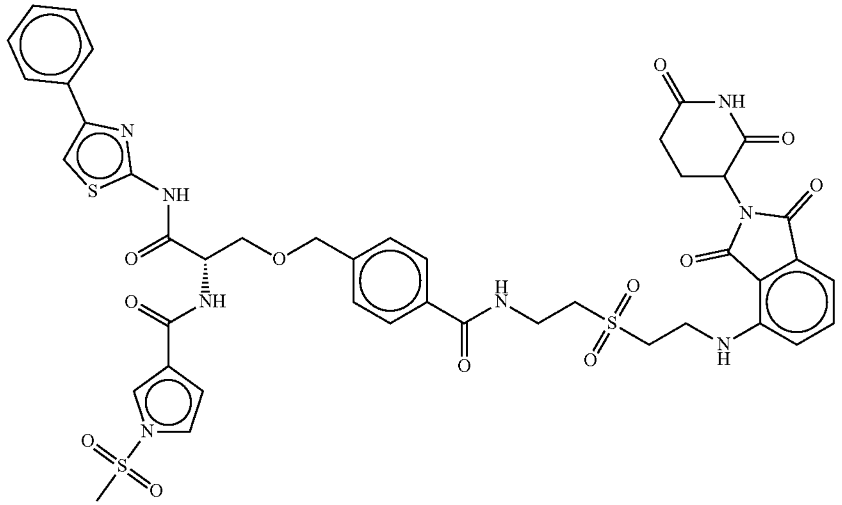 |

TABLE 1-continued
| Compounds of the Invention | |
|---|---|
| # | Structure |
| 191 | 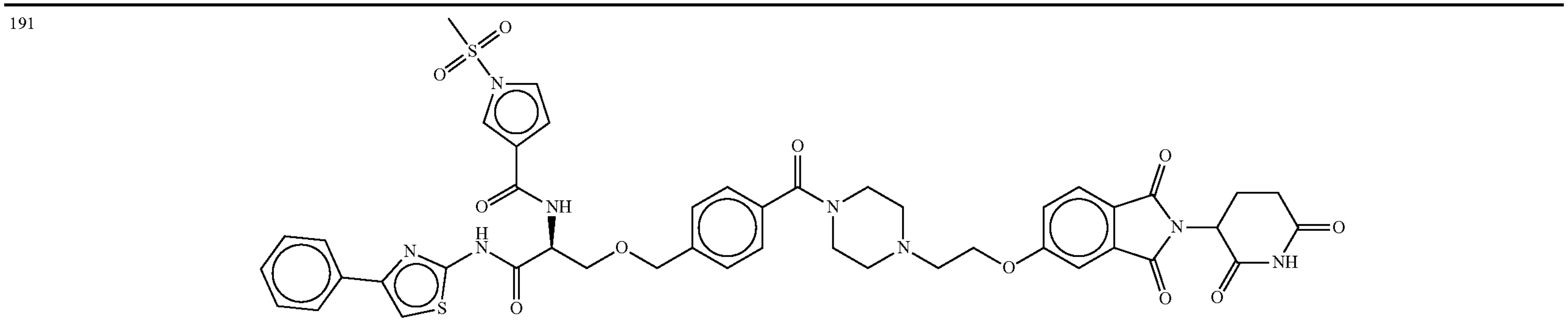 |
| 192 | 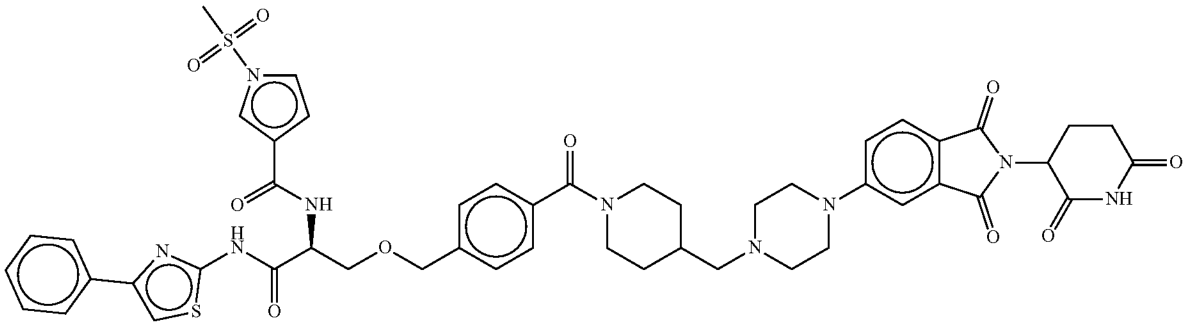 |
| 193 | 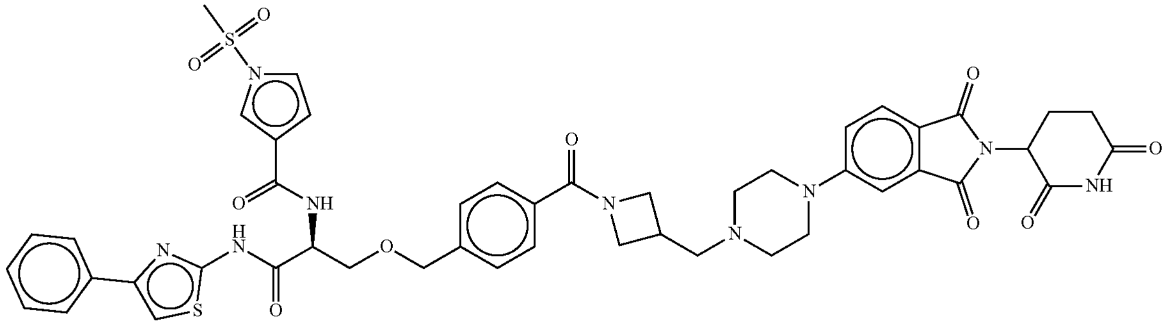 |

TABLE 1-continued
| Compounds of the Invention | |
|---|---|
| # | Structure |
| 194 | 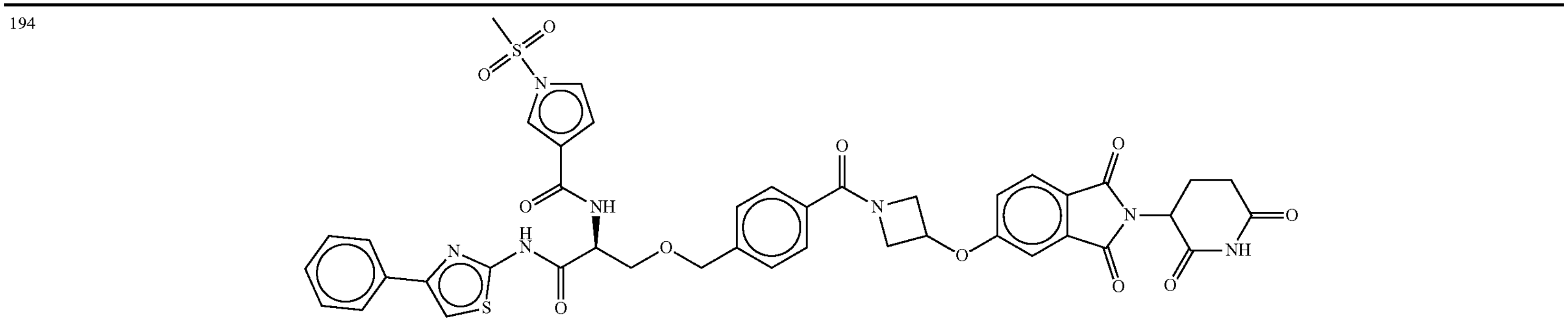 |
| 195 | 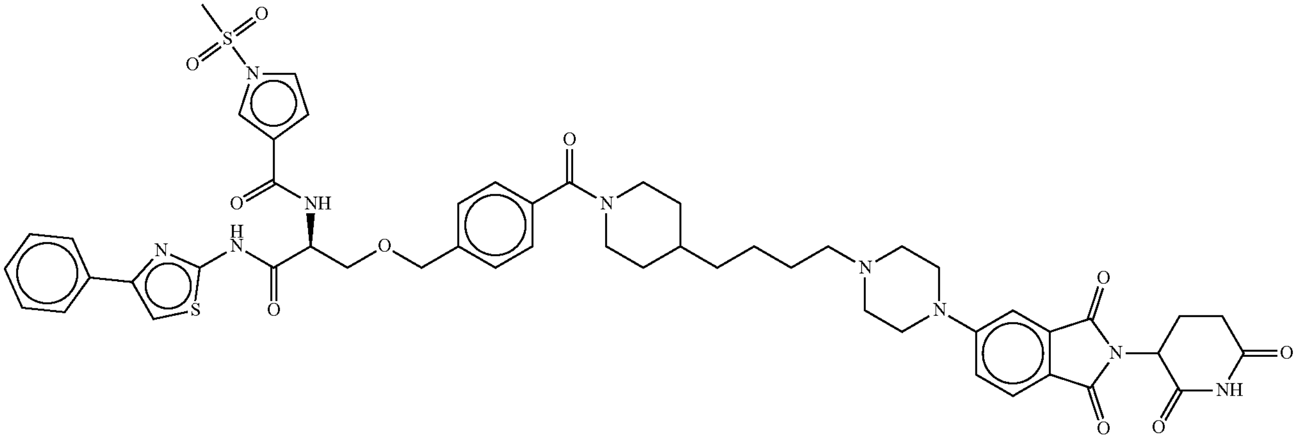 |

TABLE 1-continued
| Compounds of the Invention | |
|---|---|
| # | Structure |
| 196 | 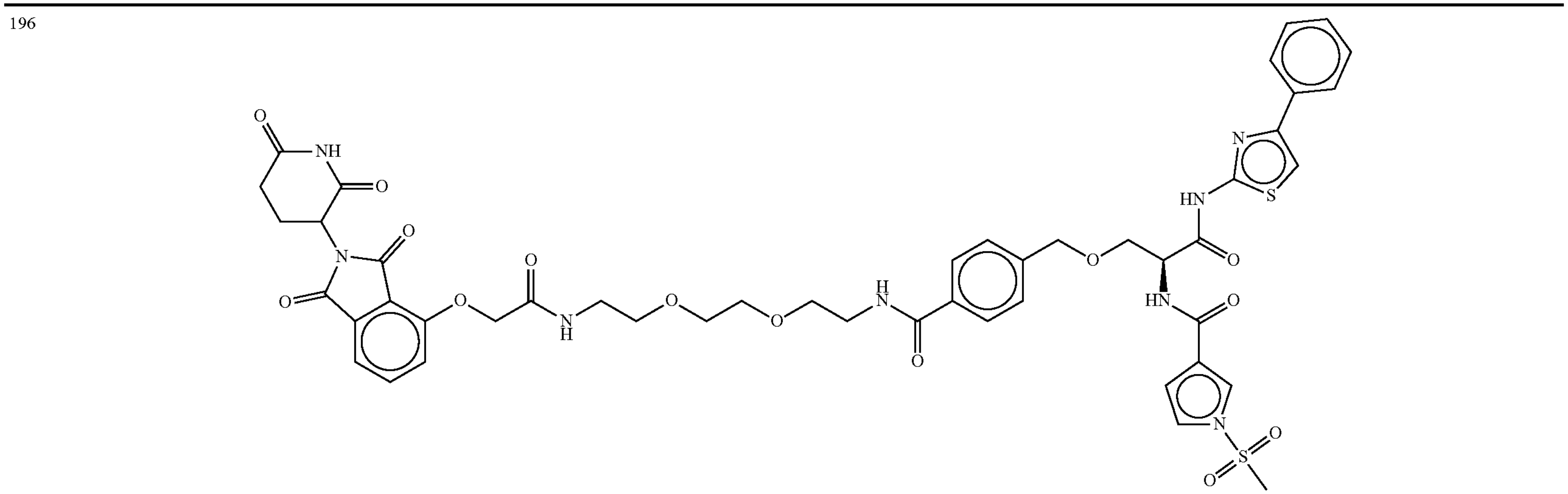 |
| 197 | 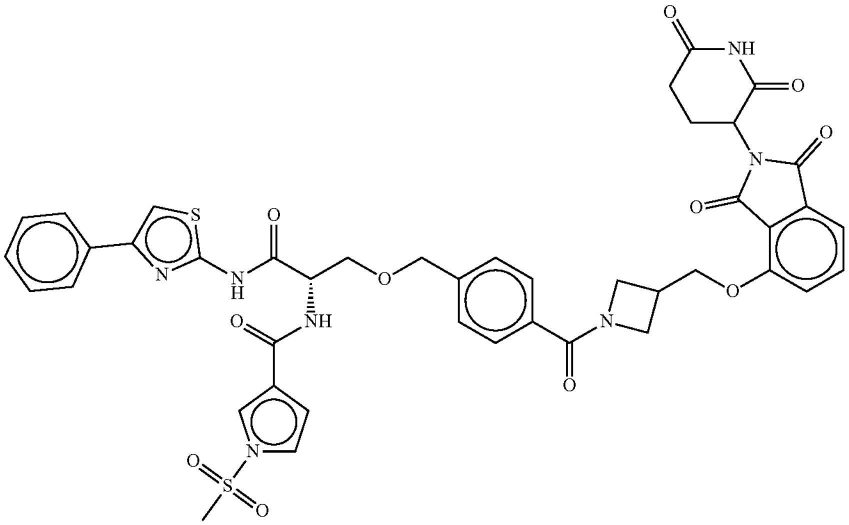 |

TABLE 1-continued
| Compounds of the Invention | |
|---|---|
| # | Structure |
| 198 | 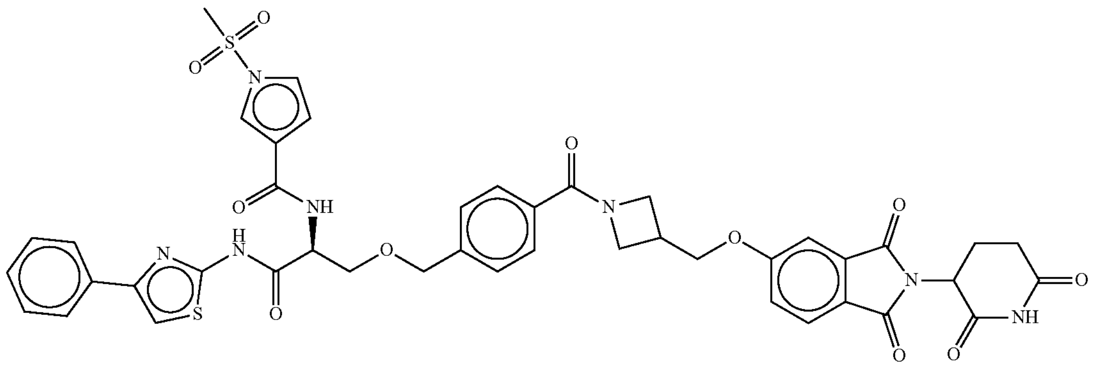 |
| 199 | 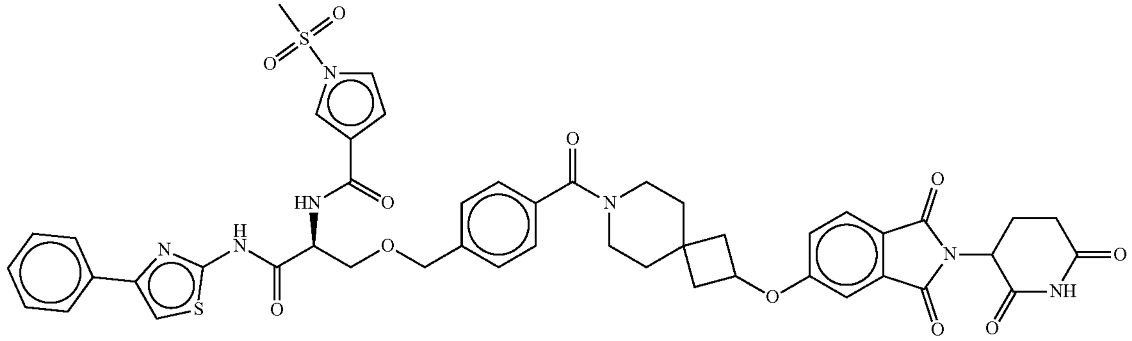 |

TABLE 1-continued
| Compounds of the Invention | |
|---|---|
| # | Structure |
| 200 | 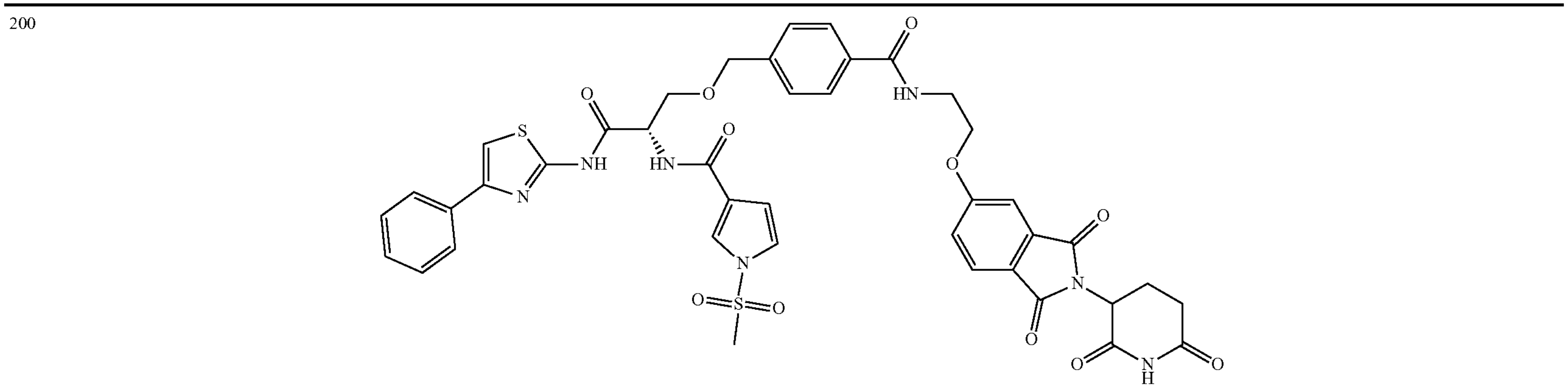 |
| 201 | 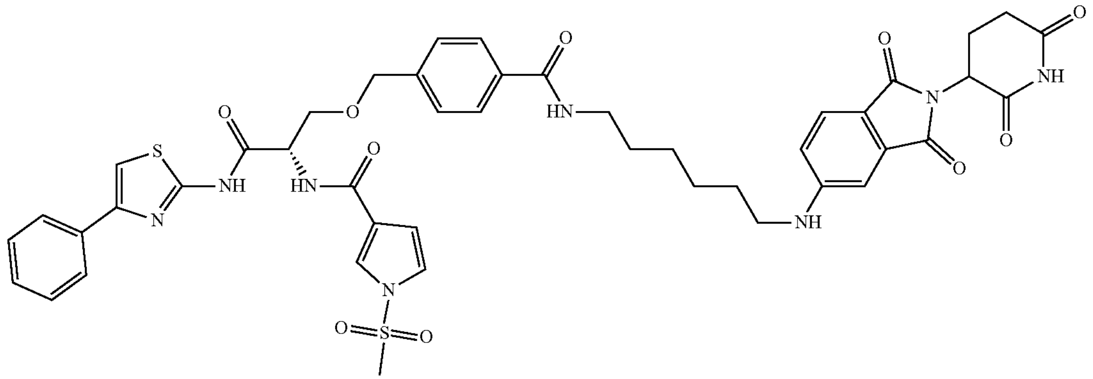 [SMILES: CS(=O)(=O)n1ccc(C(=O)N[C@@H](COCc2ccc(C(=O)NCCCCCCNc3ccc4c(c3)C(=O)N(C3CCC(=O)NC3=O)C4=O)cc2)C(=O)Nc2nc(-c3ccccc3)cs2)c1] |

TABLE 1-continued
| Compounds of the Invention | |
|---|---|
| # | Structure |
| 202 | 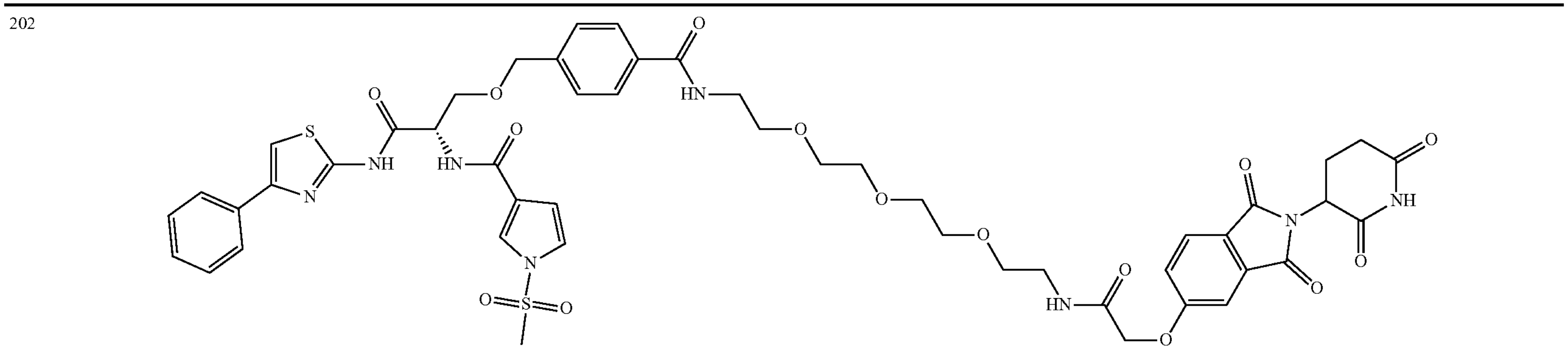 |
| 203 | 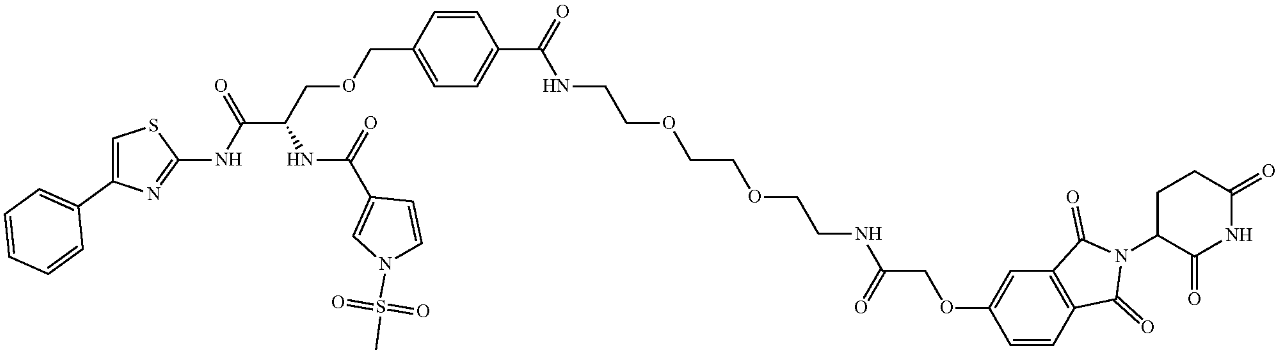 [SMILES: CS(=O)(=O)n1ccc(C(=O)N[C@@H](COCc2ccc(C(=O)NCCOCCOCCNC(=O)COc3ccc4c(c3)C(=O)N(C3CCC(=O)NC3=O)C4=O)cc2)C(=O)Nc2nc(-c3ccccc3)cs2)c1] |

TABLE 1-continued
| Compounds of the Invention | |
|---|---|
| # | Structure |
| 204 | 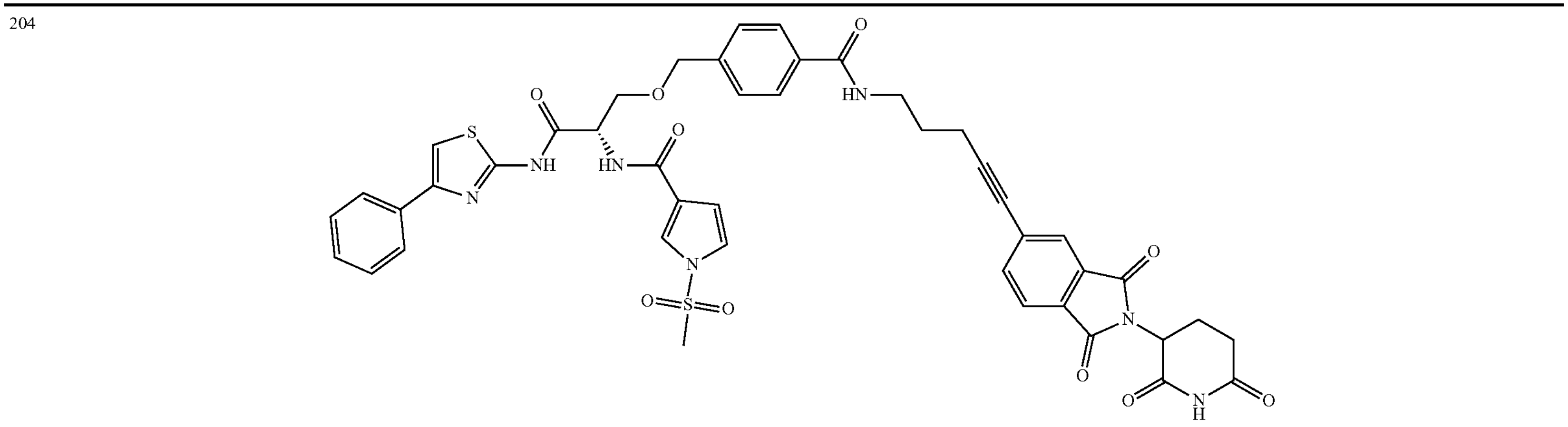 |
| 205 | 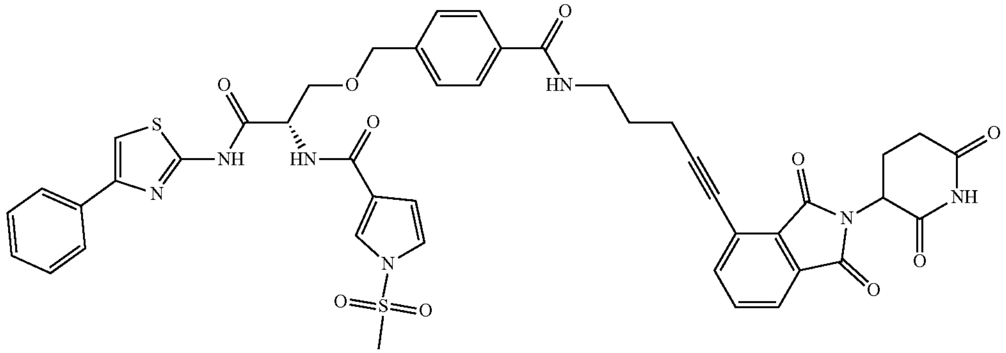 [SMILES: CS(=O)(=O)n1ccc(C(=O)N[C@@H](COCc2ccc(C(=O)NCCCC#Cc3cccc4c3C(=O)N(C3CCC(=O)NC3=O)C4=O)cc2)C(=O)Nc2nc(-c3ccccc3)cs2)c1] |

TABLE 1-continued
| Compounds of the Invention | |
|---|---|
| # | Structure |
| 206 | 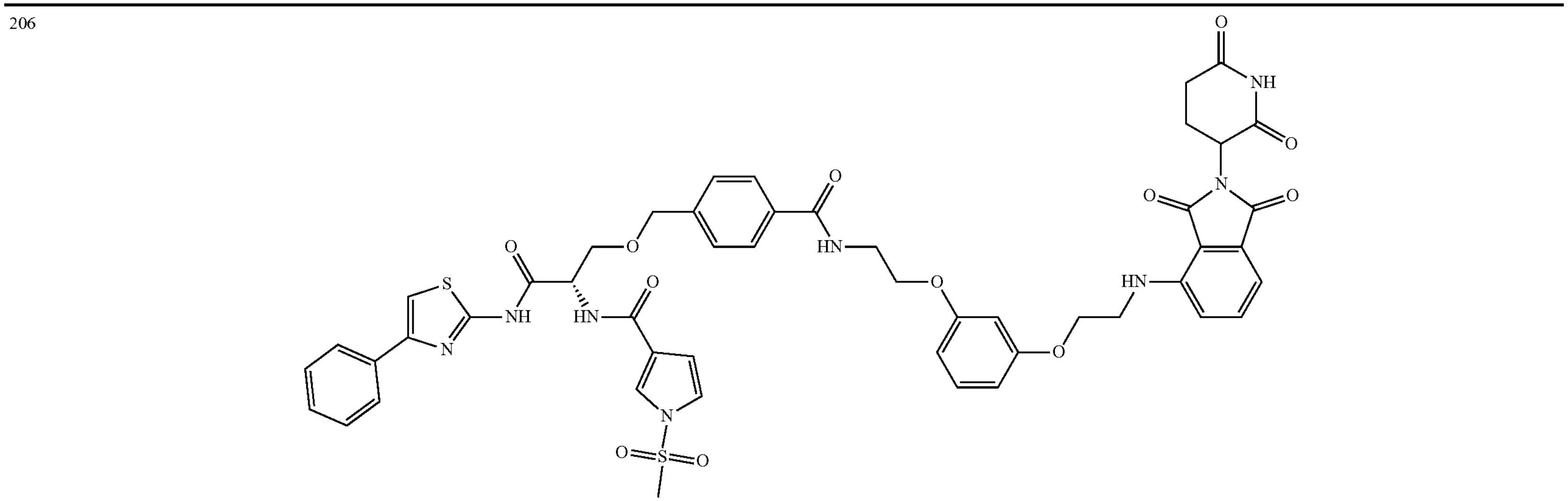 |
| 207 | 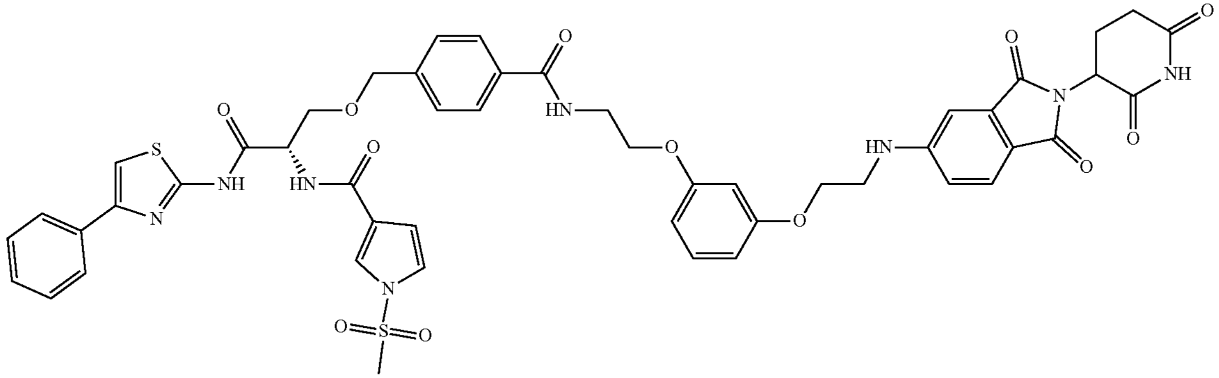 [SMILES: CS(=O)(=O)n1ccc(C(=O)N[C@@H](COCc2ccc(C(=O)NCCOc3cccc(OCCNc4ccc5c(c4)C(=O)N(C4CCC(=O)NC4=O)C5=O)c3)cc2)C(=O)Nc2nc(-c3ccccc3)cs2)c1] |

TABLE 1-continued
Compounds of the Invention
| # | Structure |
| --- | --- |
| 208 | 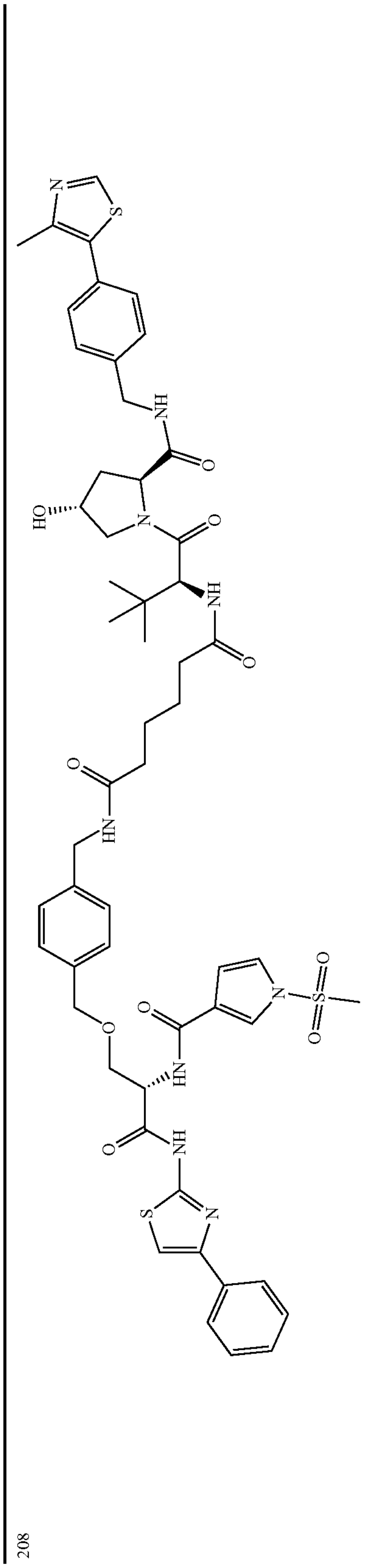 |
| 209 | 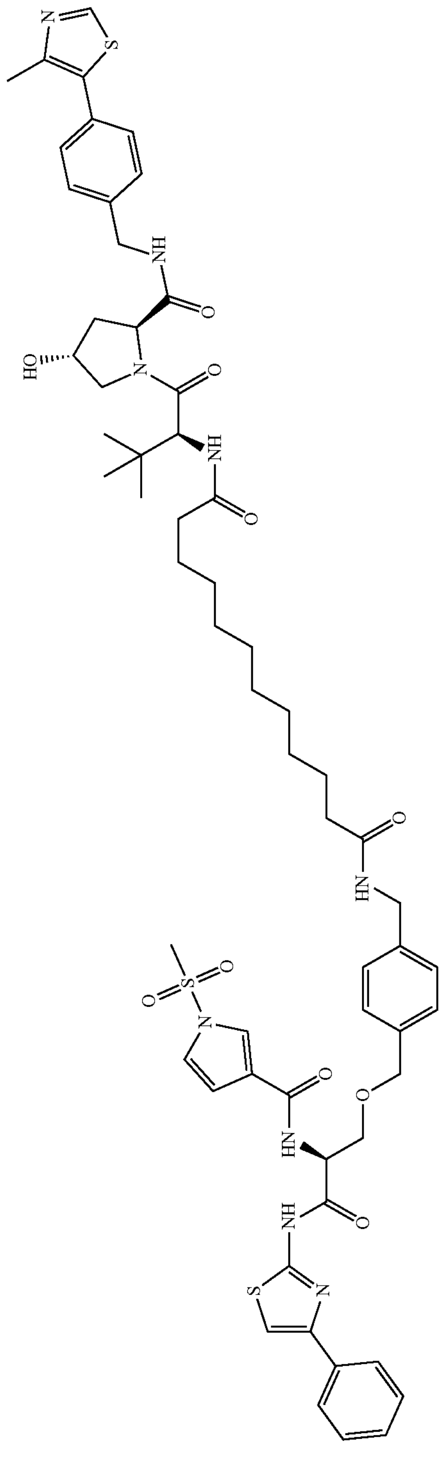 |

TABLE 1-continued
Compounds of the Invention
| # | Structure |
| --- | --- |
| 210 | 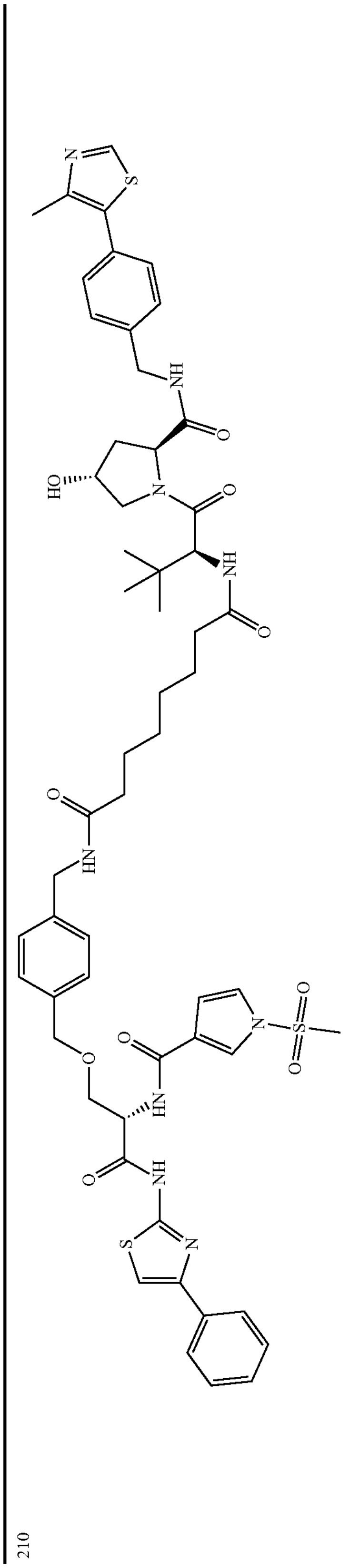 |
| 211 | 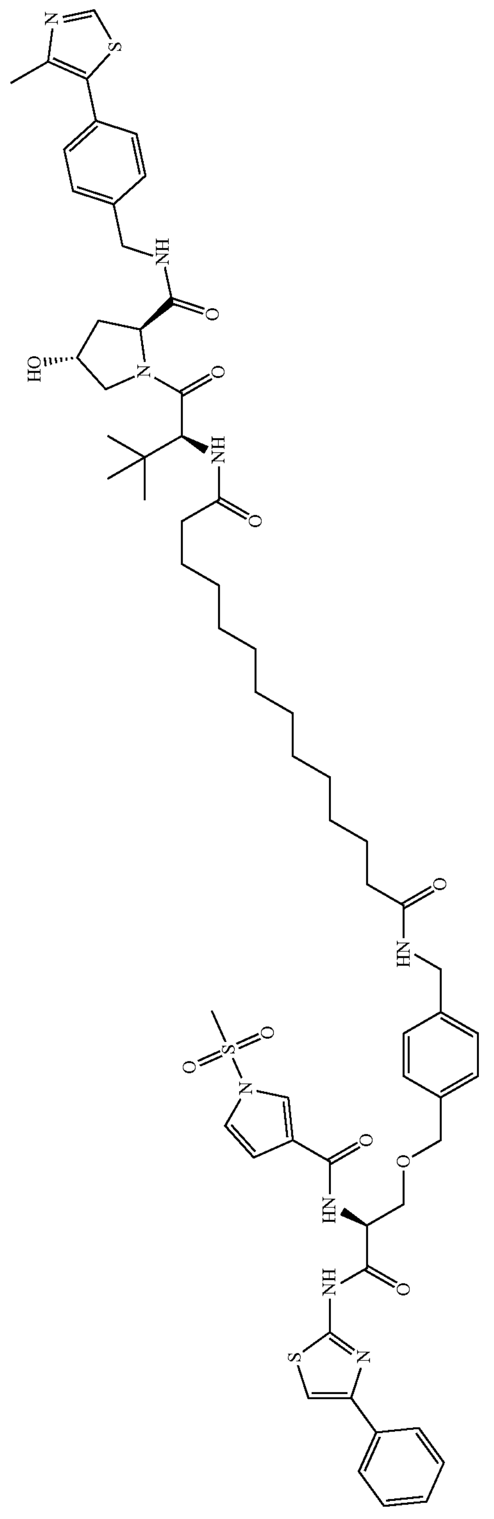 |

TABLE 1-continued
| Compounds of the Invention | |
|---|---|
| # | Structure |
| 212 | 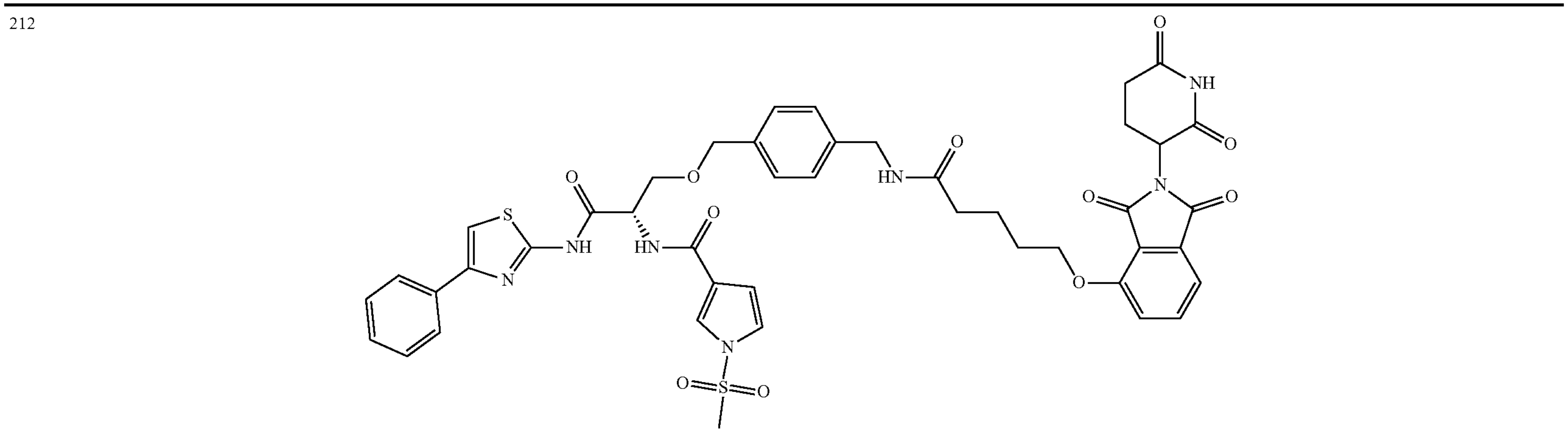 |
| 213 | 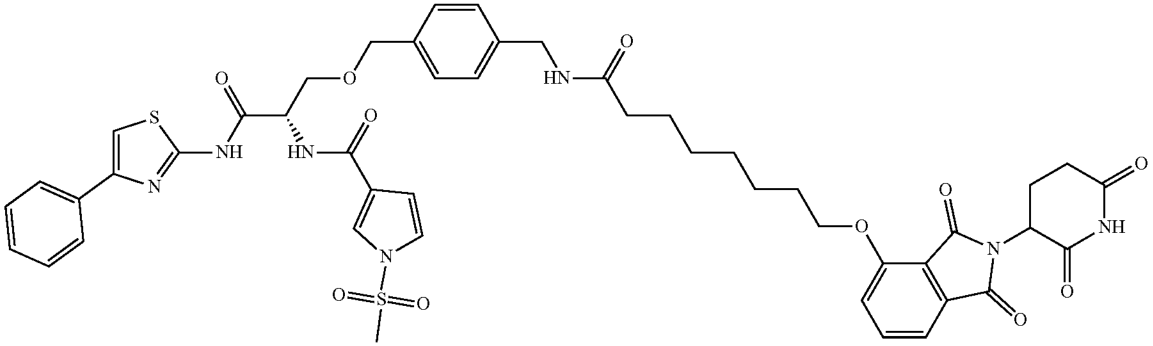 [SMILES: CS(=O)(=O)n1ccc(C(=O)N[C@@H](COCc2ccc(CNC(=O)CCCCCCCOc3cccc4c3C(=O)N(C3CCC(=O)NC3=O)C4=O)cc2)C(=O)Nc2nc(-c3ccccc3)cs2)c1] |

TABLE 1-continued
| Compounds of the Invention | |
|---|---|
| # | Structure |
| 214 | 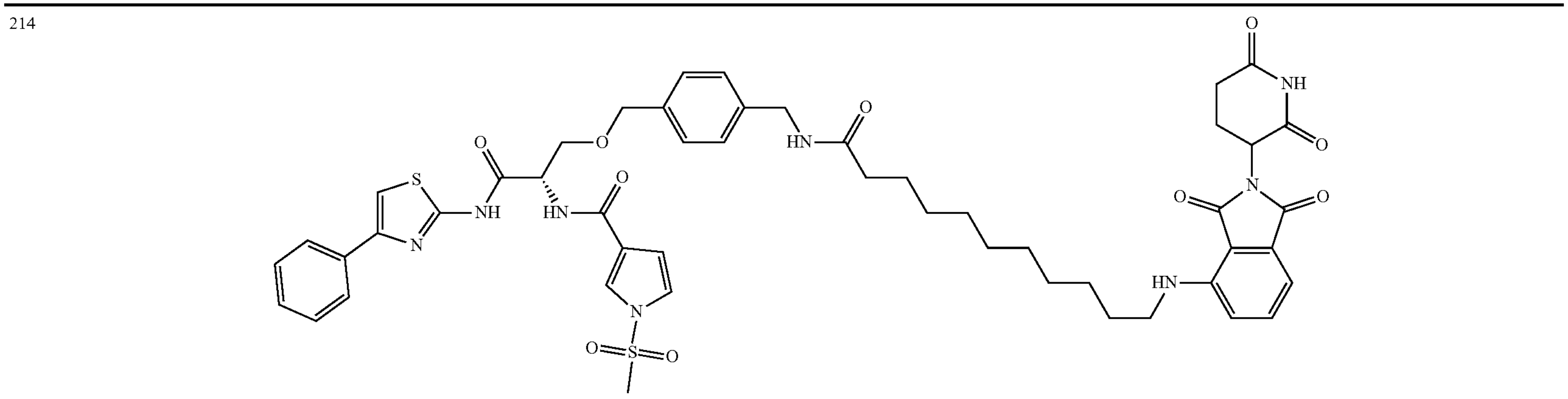 |
| 215 | 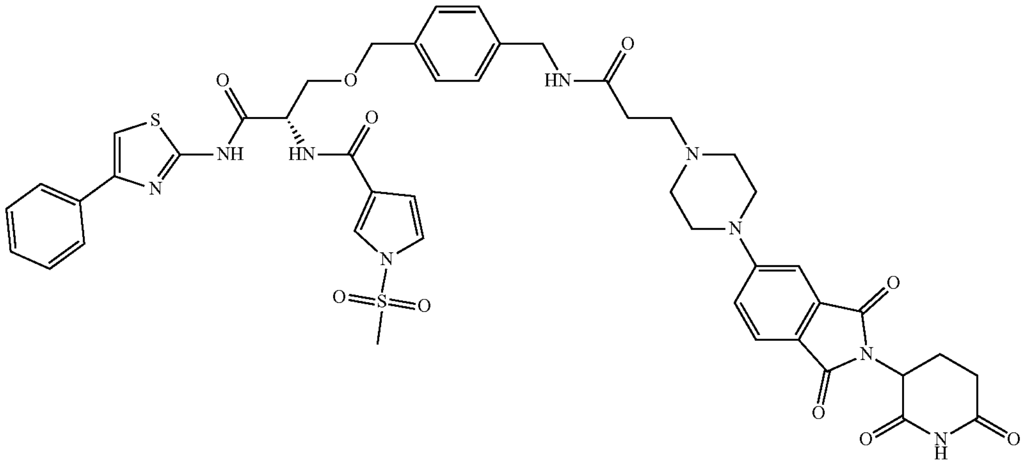 [SMILES: CS(=O)(=O)n1ccc(C(=O)N[C@@H](COCc2ccc(CNC(=O)CCN3CCN(c4ccc5c(c4)C(=O)N(C4CCC(=O)NC4=O)C5=O)CC3)cc2)C(=O)Nc2nc(-c3ccccc3)cs2)c1] |

TABLE 1-continued
| Compounds of the Invention | |
|---|---|
| # | Structure |
| 216 | 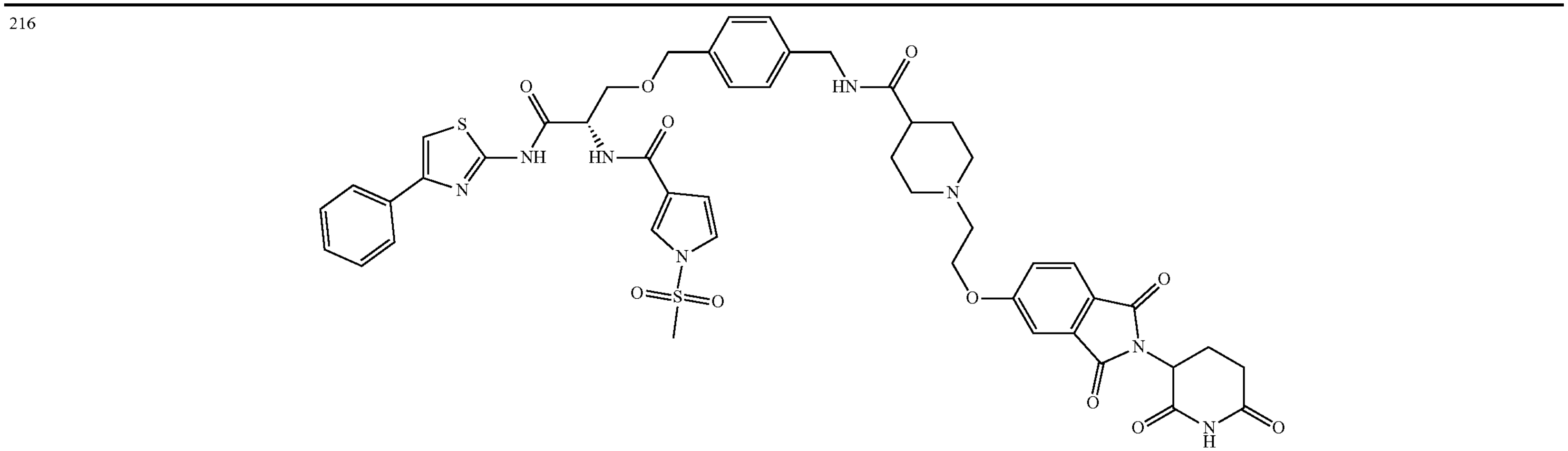 |
| 217 | 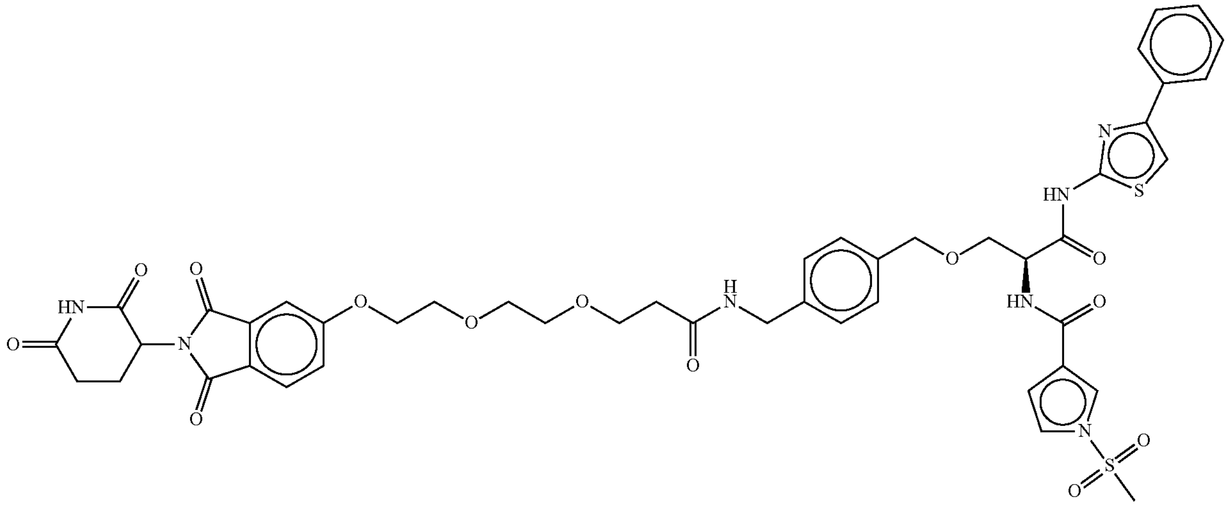 |

TABLE 1-continued
| Compounds of the Invention | |
|---|---|
| # | Structure |
| 218 | 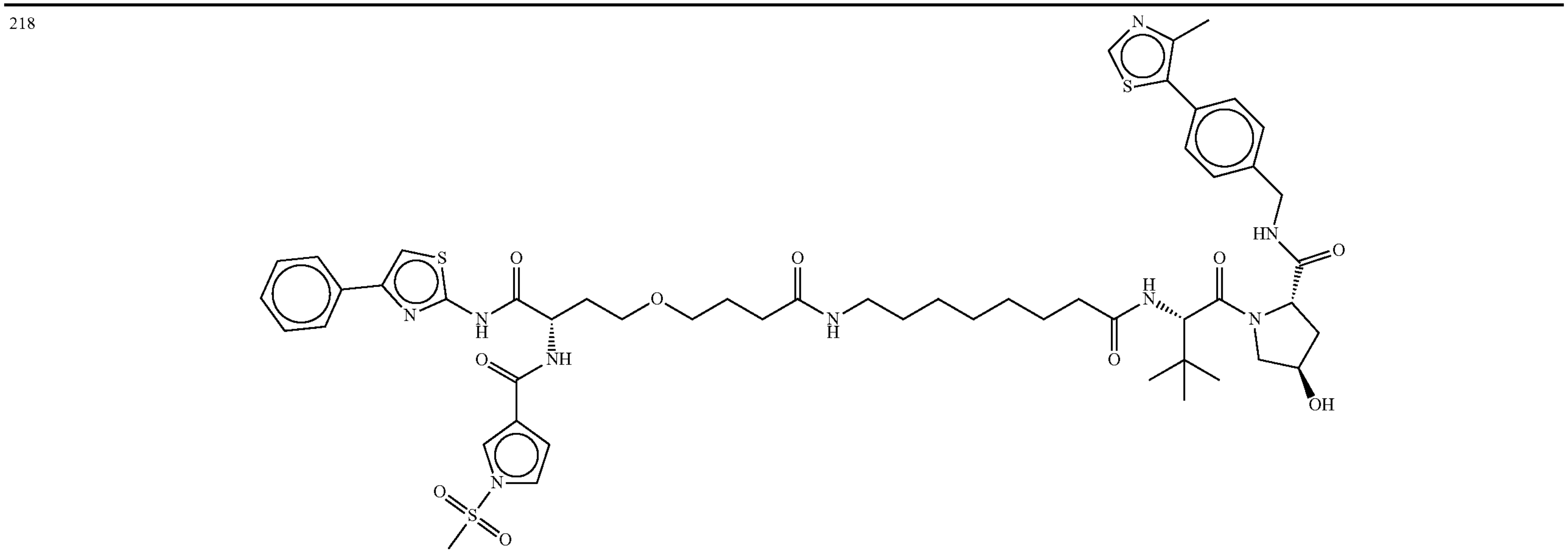 |
| 219 | 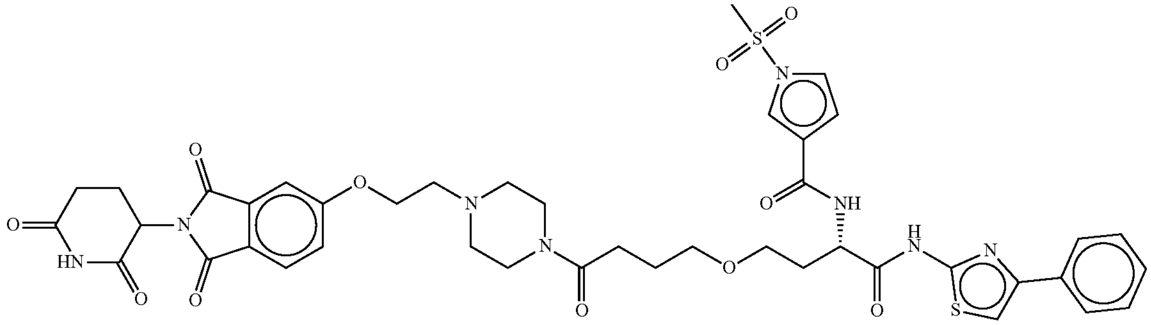 |

TABLE 1-continued
| Compounds of the Invention | |
|---|---|
| # | Structure |
| 220 | 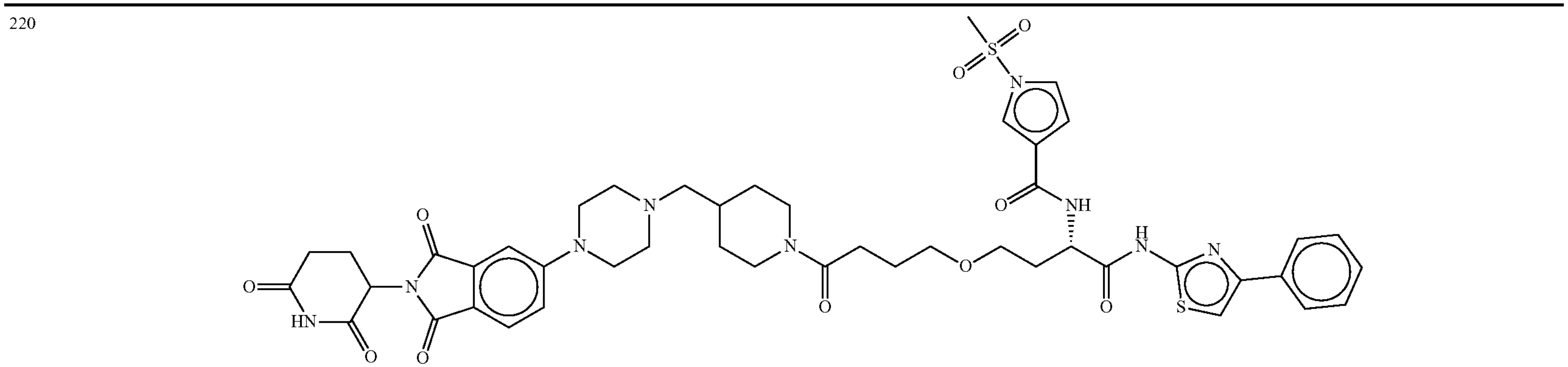 |
| 221 | 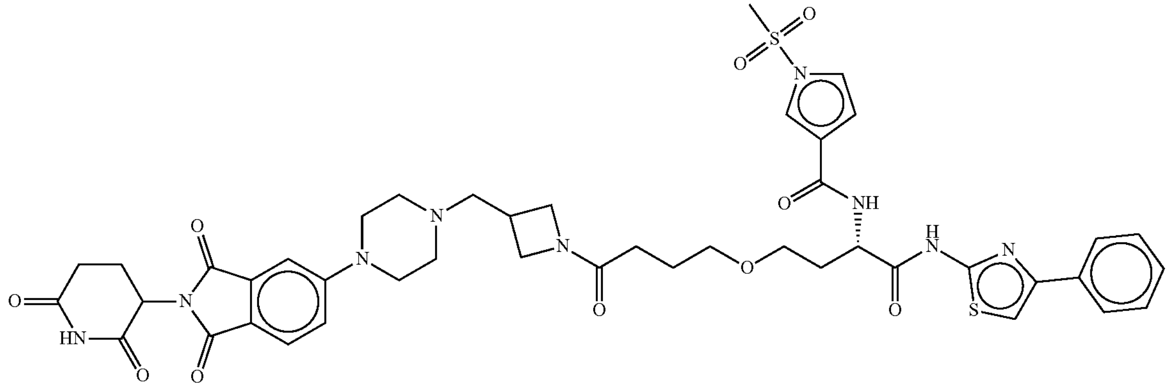 |

TABLE 1-continued
| Compounds of the Invention | |
|---|---|
| # | Structure |
| 222 | 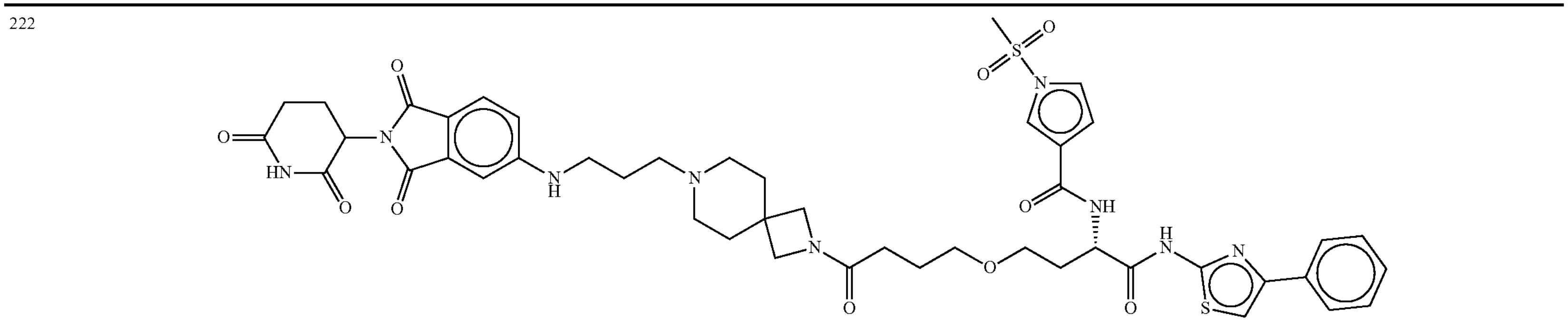 |
| 223 | 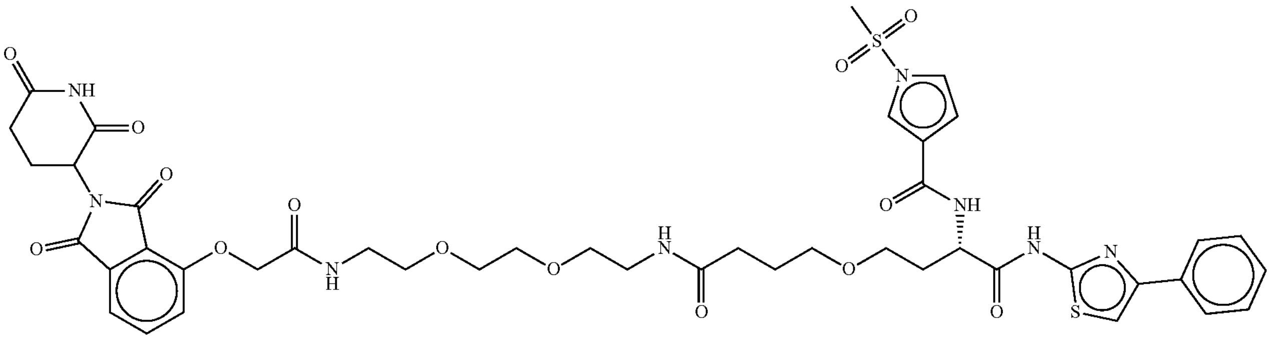 |

TABLE 1-continued
| Compounds of the Invention | |
|---|---|
| # | Structure |
| 224 | 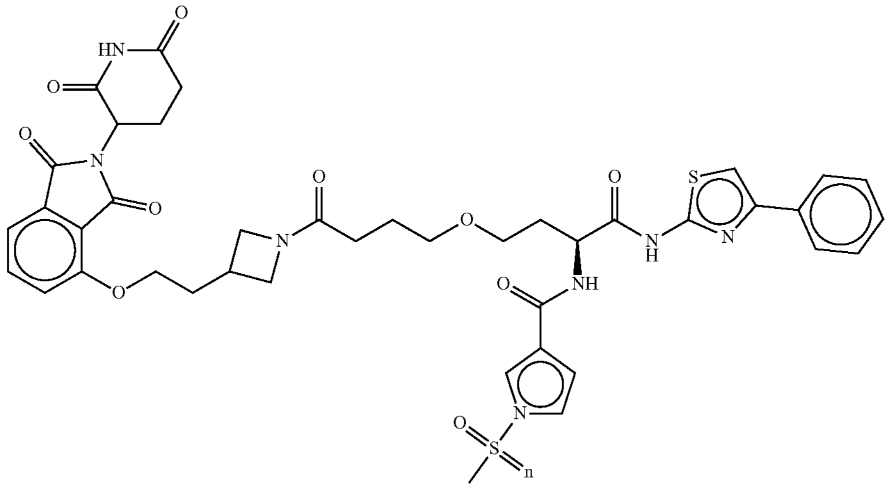 |

TABLE 1-continued
| Compounds of the Invention | |
|---|---|
| # | Structure |
| 225 | 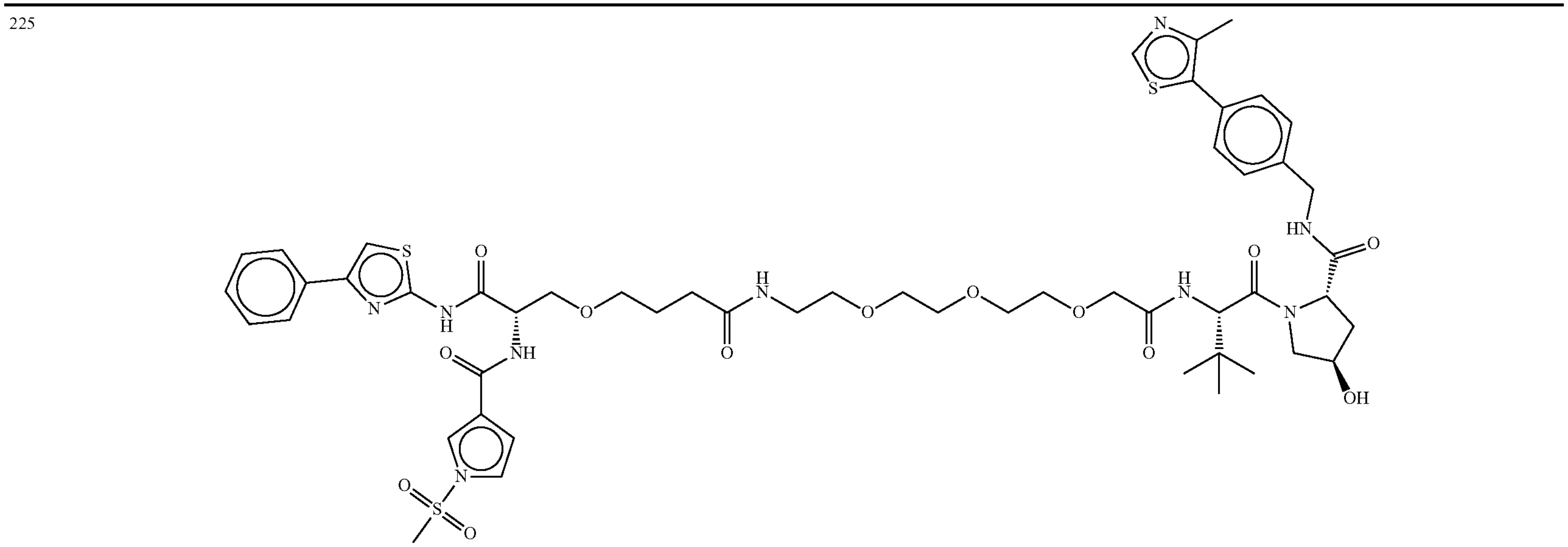 |
| 226 | 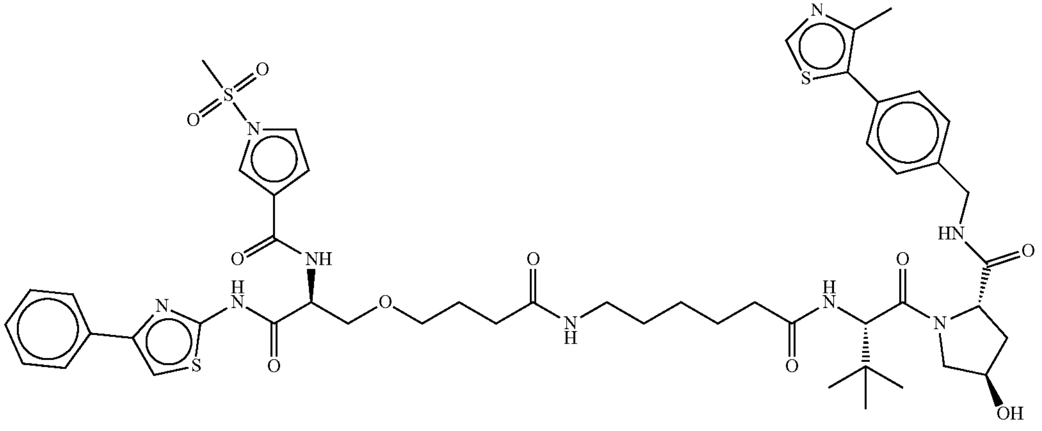 |

TABLE 1-continued
| Compounds of the Invention | |
|---|---|
| # | Structure |
| 227 | 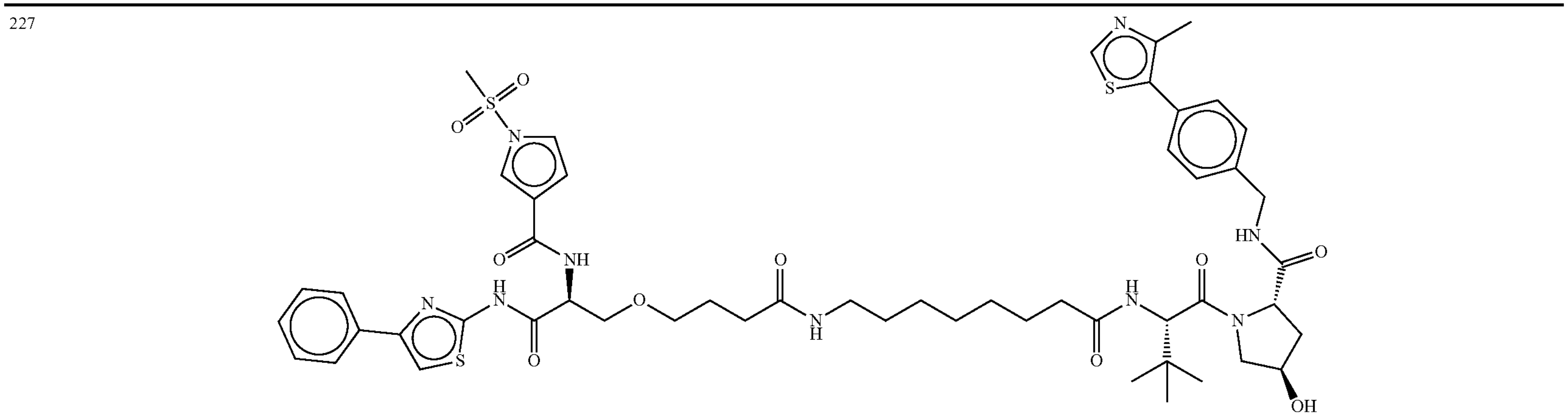 |
| 228 | 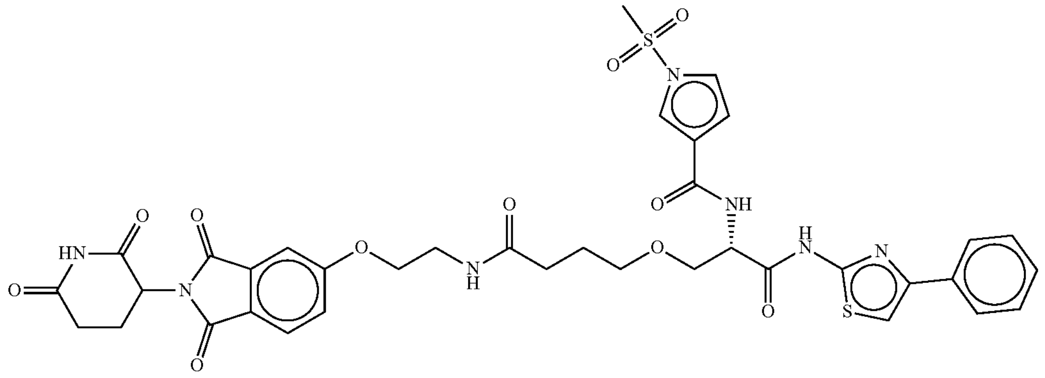 |

TABLE 1-continued
| Compounds of the Invention | |
|---|---|
| # | Structure |
| 229 | 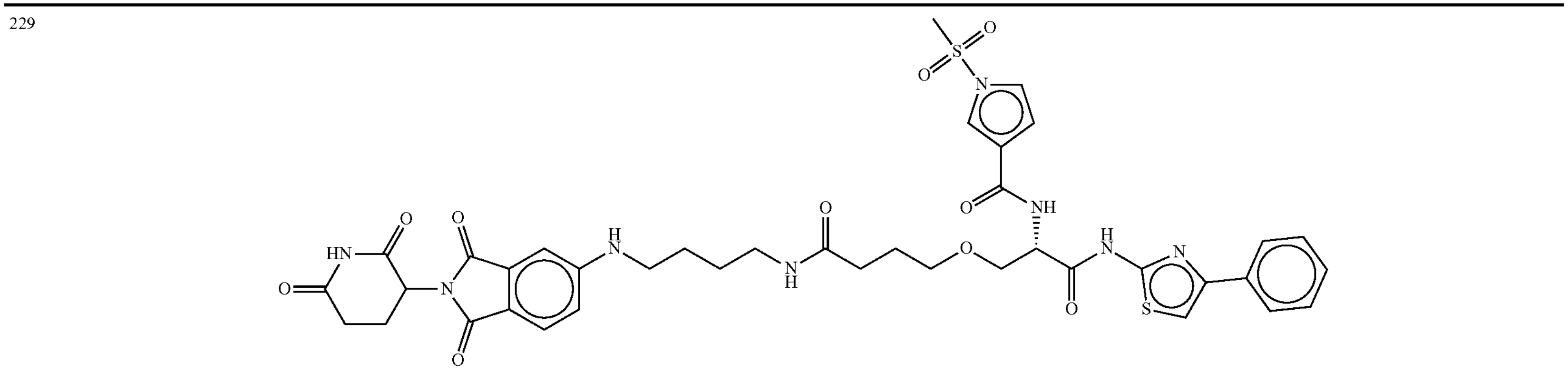 |
| 230 | 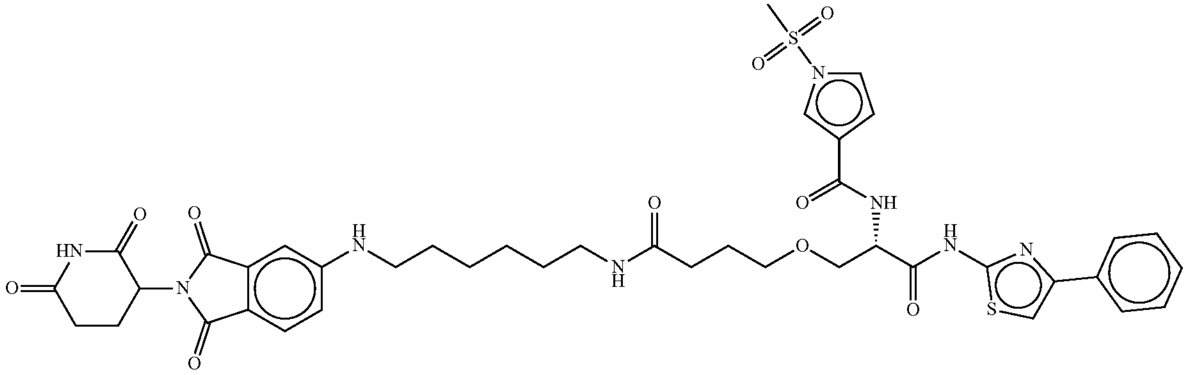 |

TABLE 1-continued
| Compounds of the Invention | |
|---|---|
| # | Structure |
| 231 | 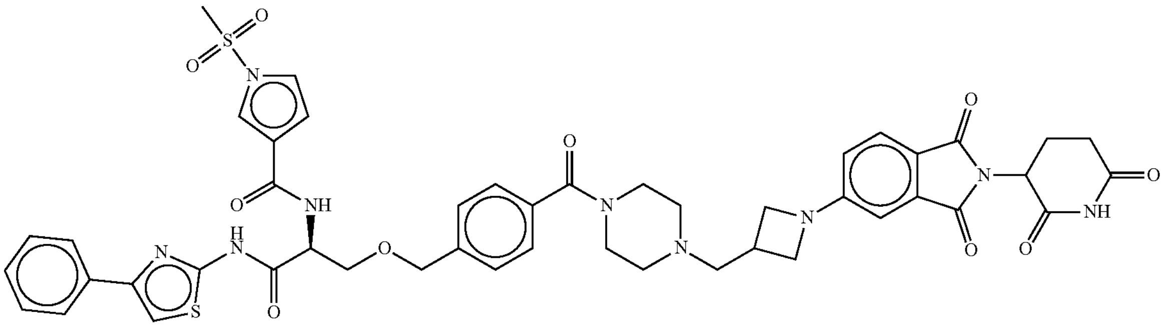 |
| 232 | 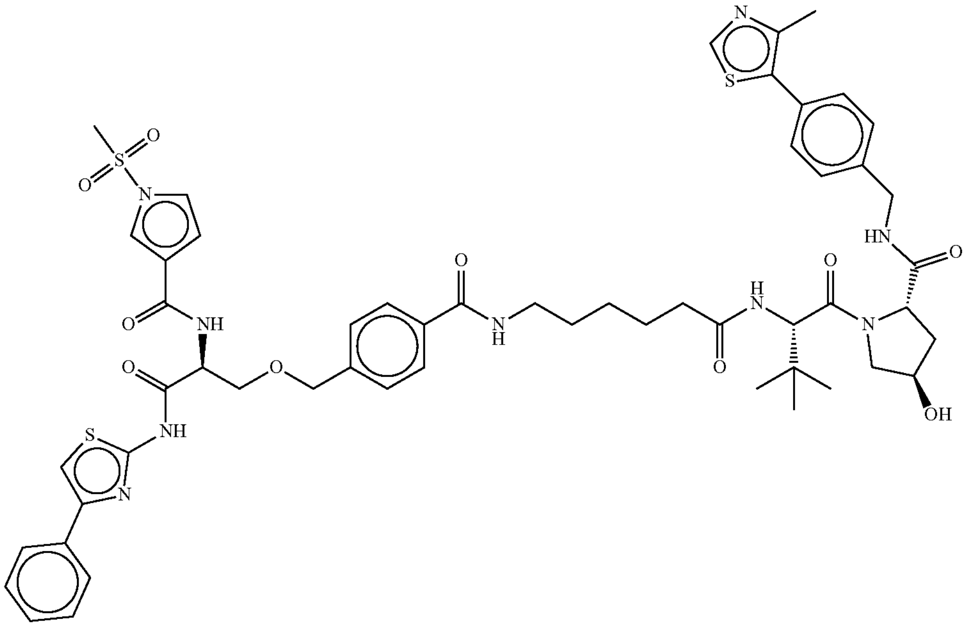 |

TABLE 1-continued
| Compounds of the Invention | |
|---|---|
| # | Structure |
| 233 | 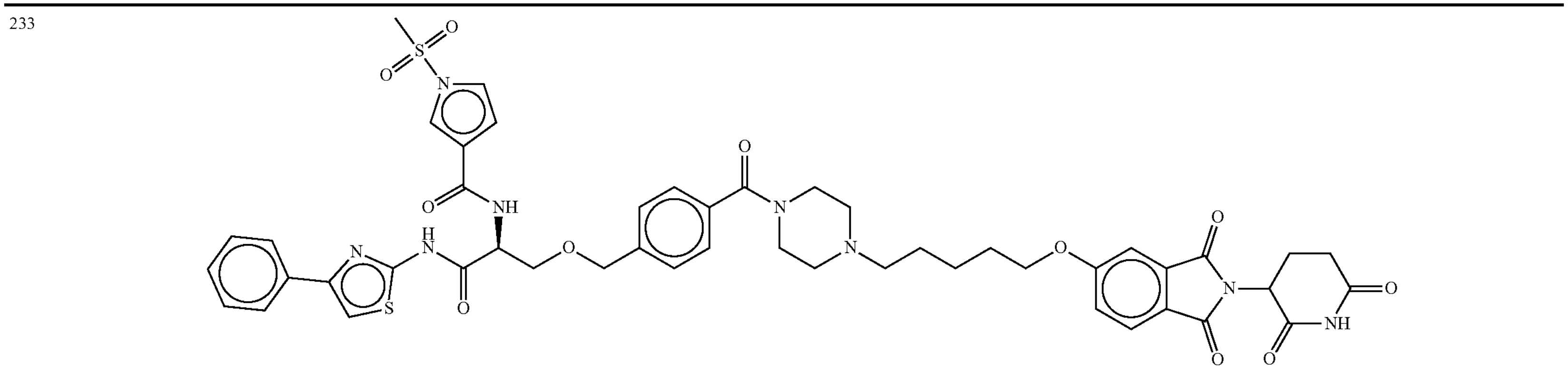 |
| 234 | 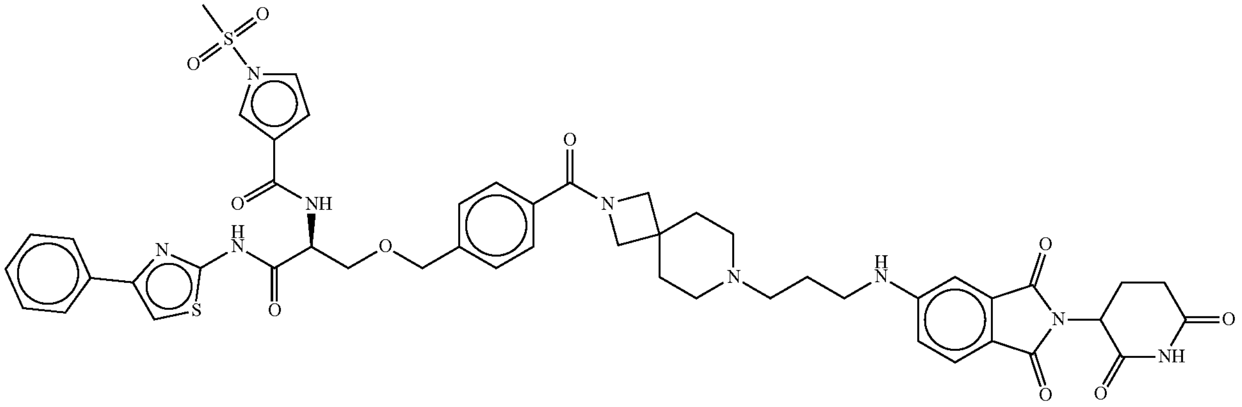 |

TABLE 1-continued
| Compounds of the Invention | |
| --- | --- |
| # | Structure |
| 235 | 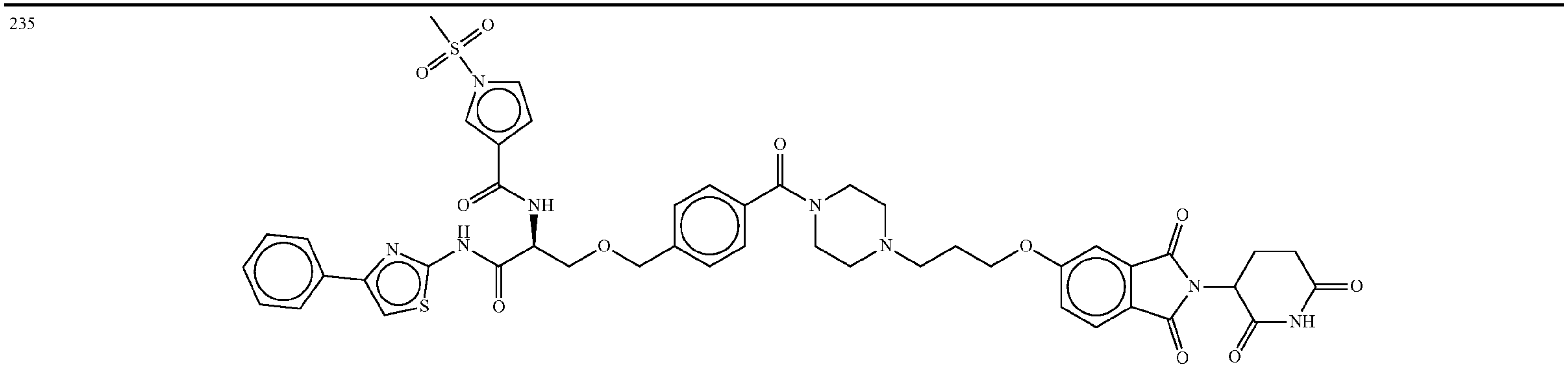 |
| 236 | 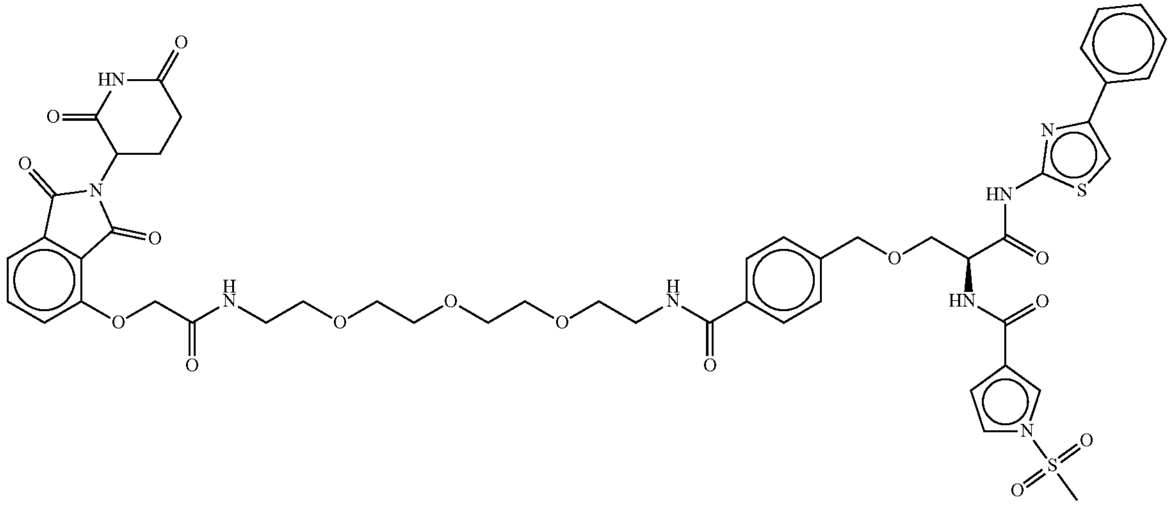 |

TABLE 1-continued
| Compounds of the Invention | |
| --- | --- |
| # | Structure |
| 237 | 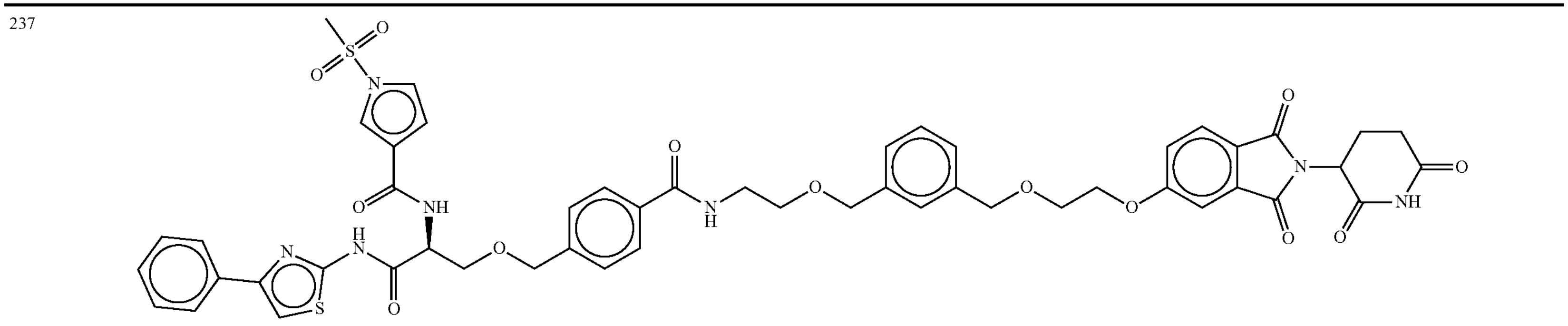 |
| 238 | 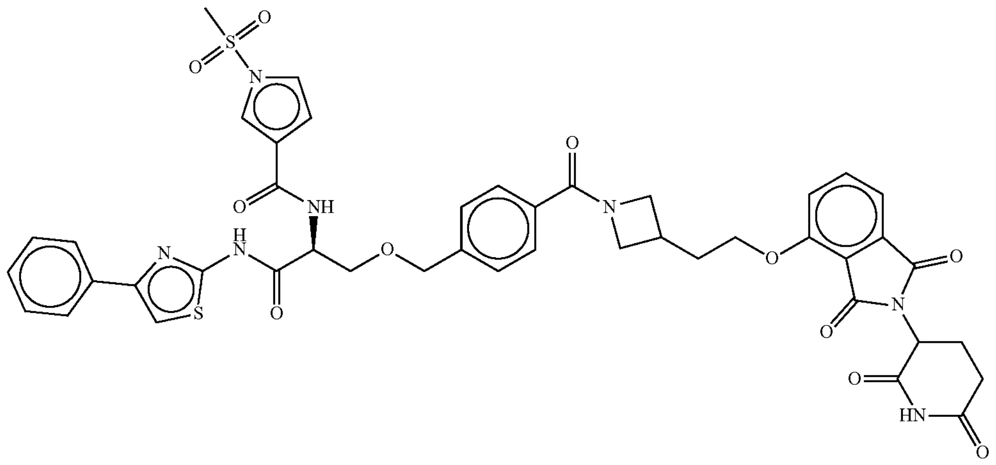 |

TABLE 1-continued
| Compounds of the Invention | |
|---|---|
| # | Structure |
| 239 | 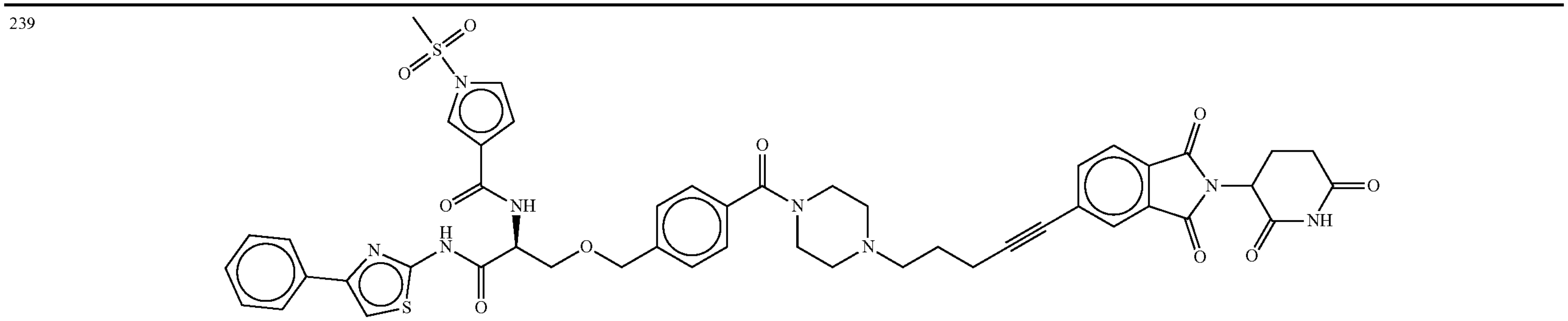 |
| 240 | 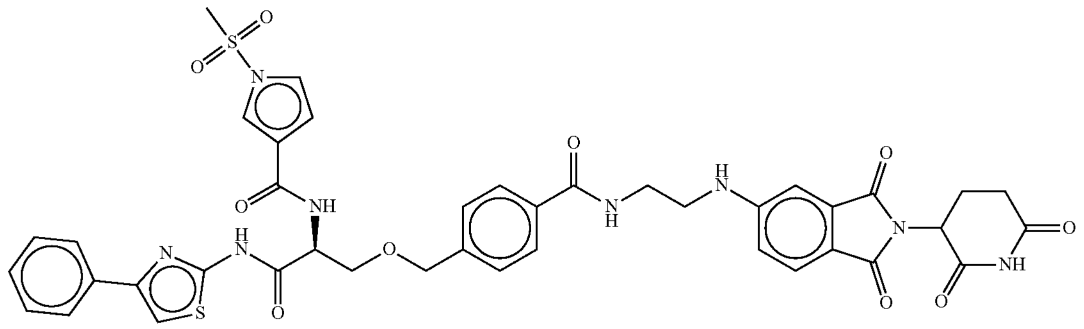 |

TABLE 1-continued
| Compounds of the Invention | |
| --- | --- |
| # | Structure |
| 241 | 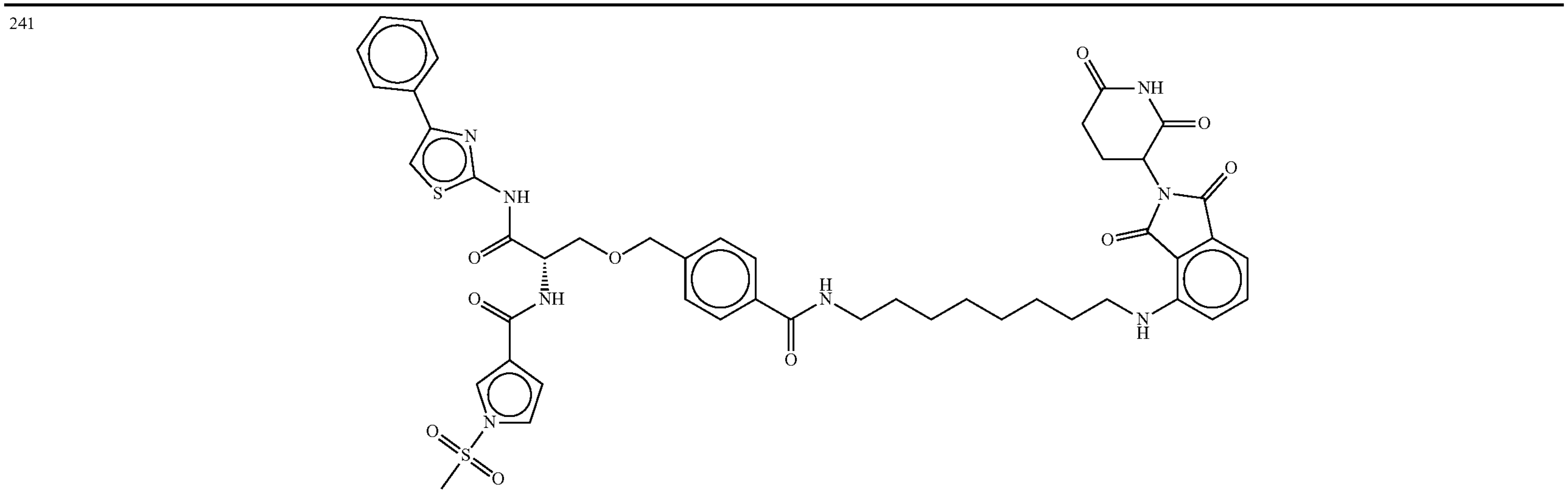 |
| 242 | 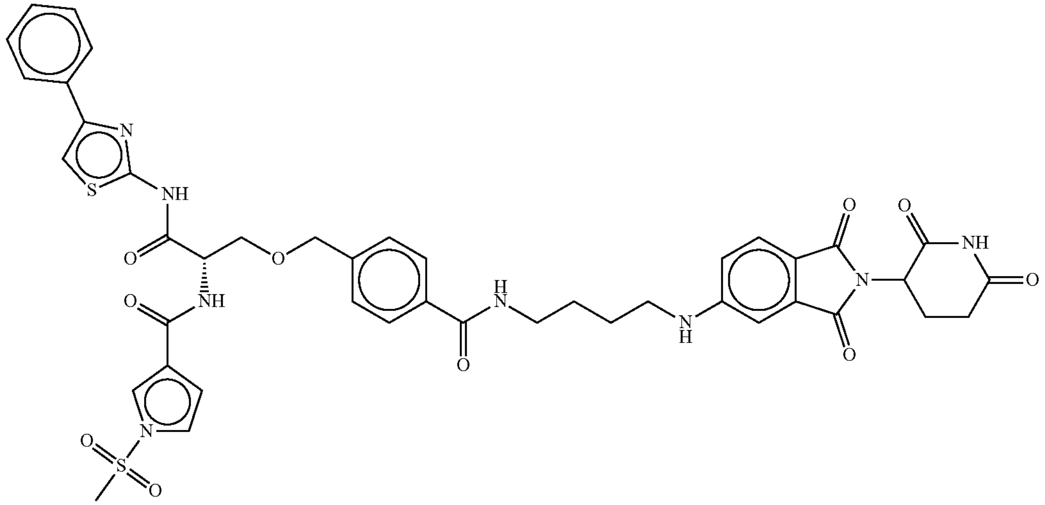 |

TABLE 1-continued
| Compounds of the Invention | |
|---|---|
| # | Structure |
| 243 | 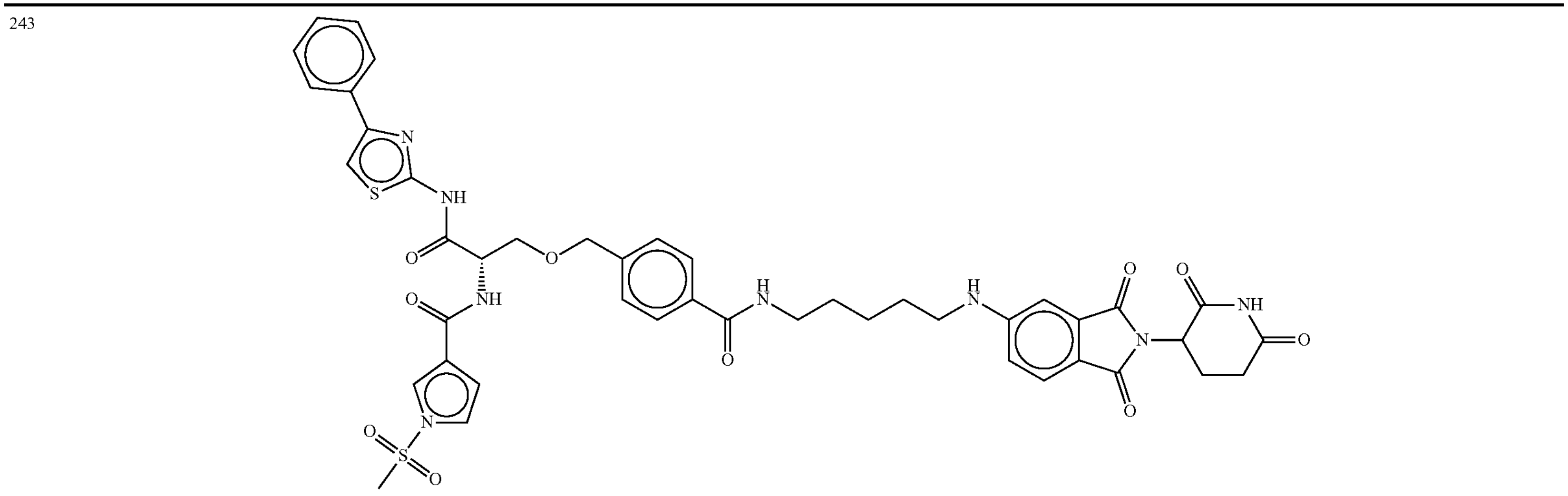 |
| 244 | 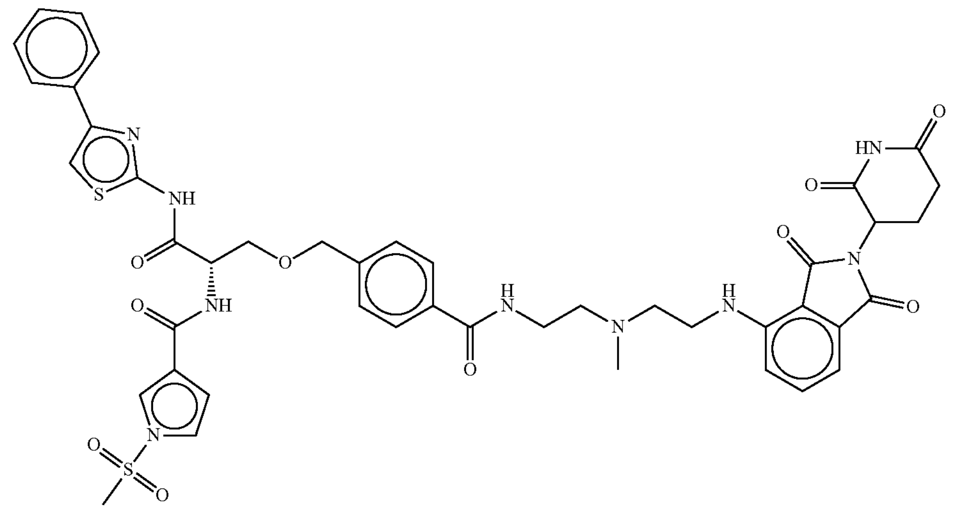 |

TABLE 1-continued
| Compounds of the Invention | |
| --- | --- |
| # | Structure |
| 245 | 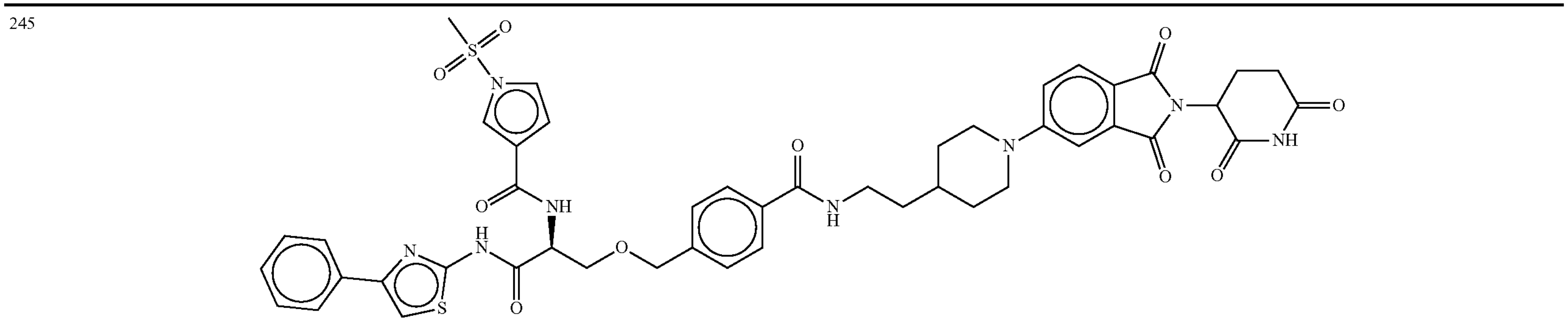 |
| 246 | 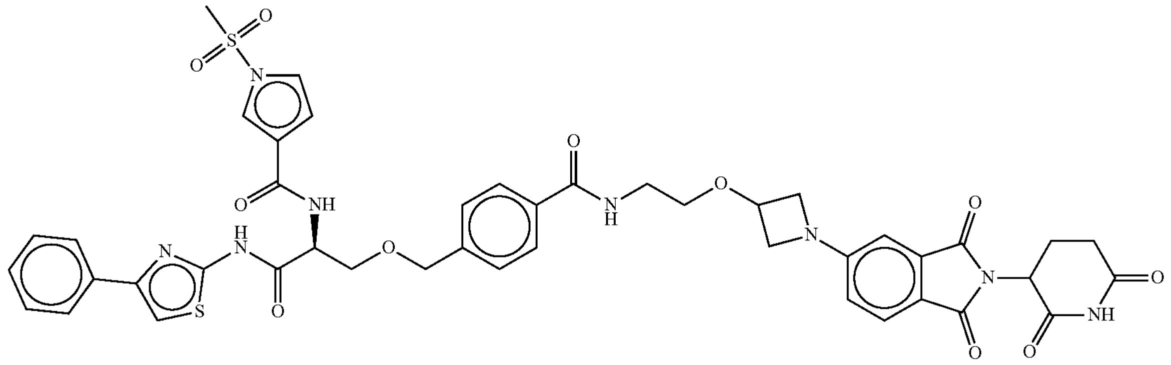 |
| 247 | 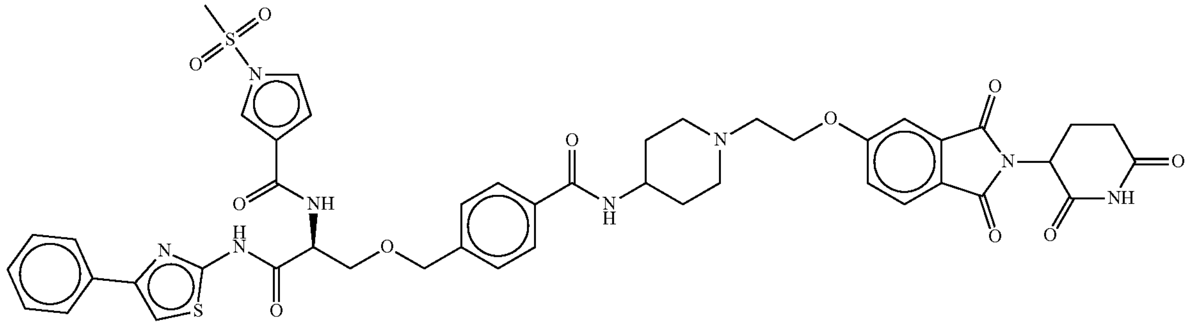 |

TABLE 1-continued
| Compounds of the Invention | |
|---|---|
| # | Structure |
| 248 | 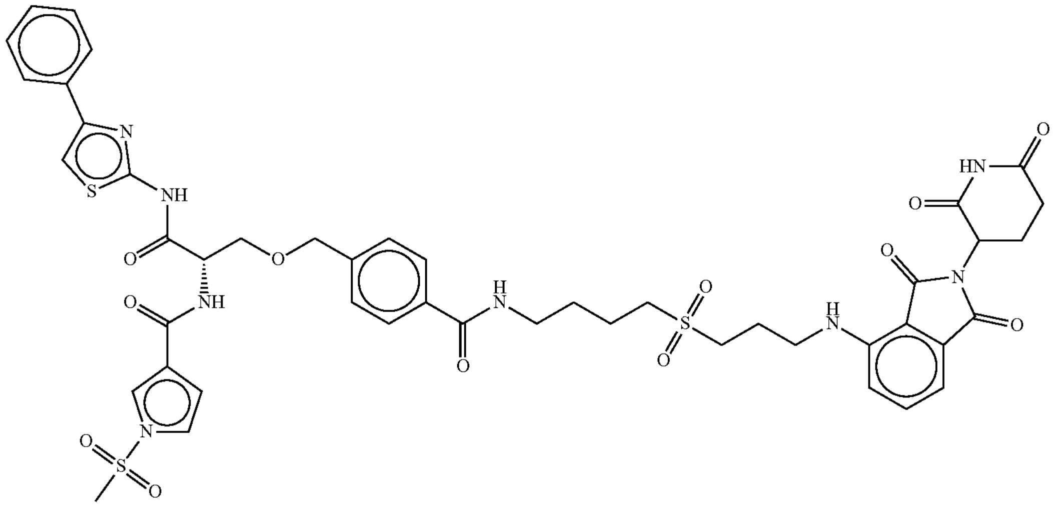 |

TABLE 1-continued
| Compounds of the Invention | |
|---|---|
| # | Structure |
| 249 | 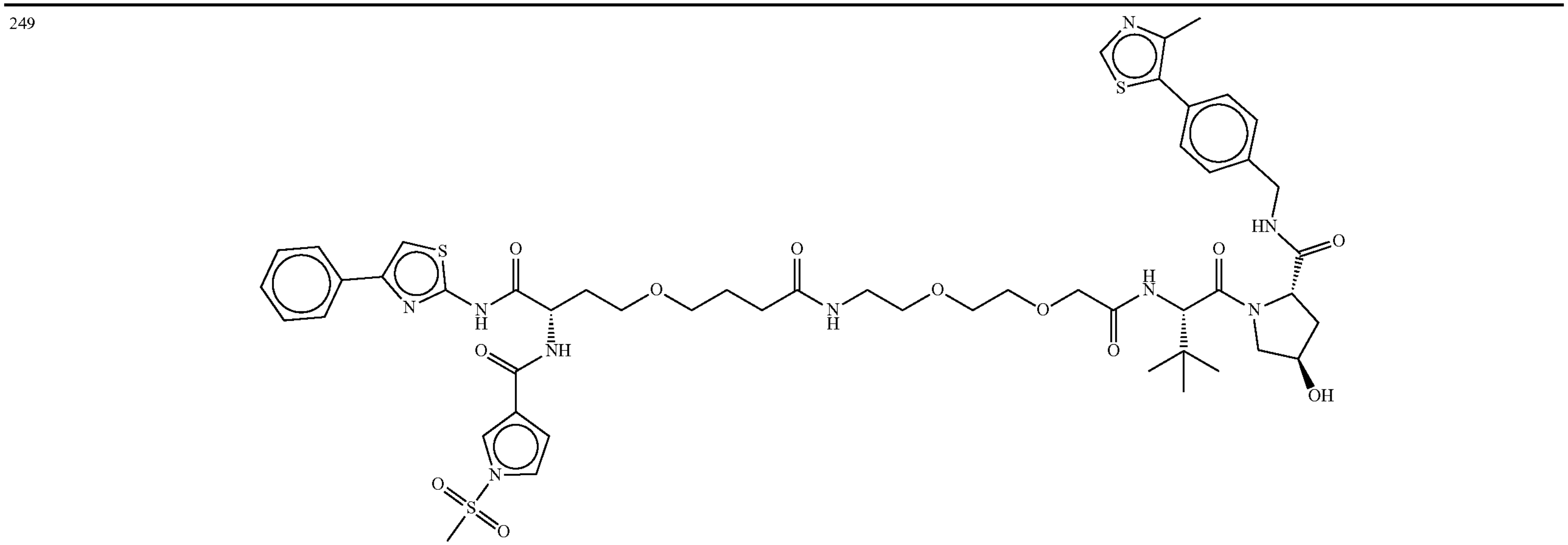 |
| 250 | 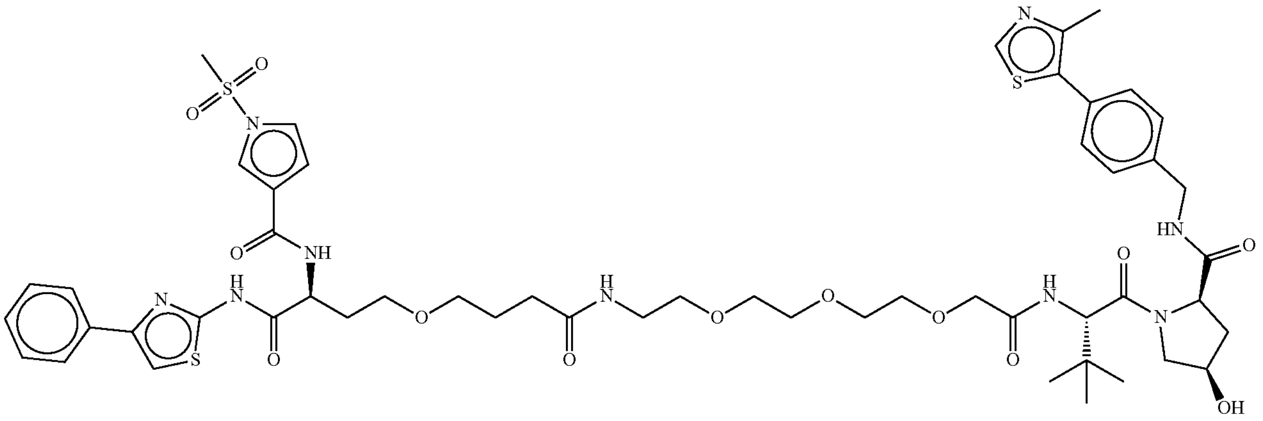 |

TABLE 1-continued
| Compounds of the Invention | |
|---|---|
| # | Structure |
| 251 | 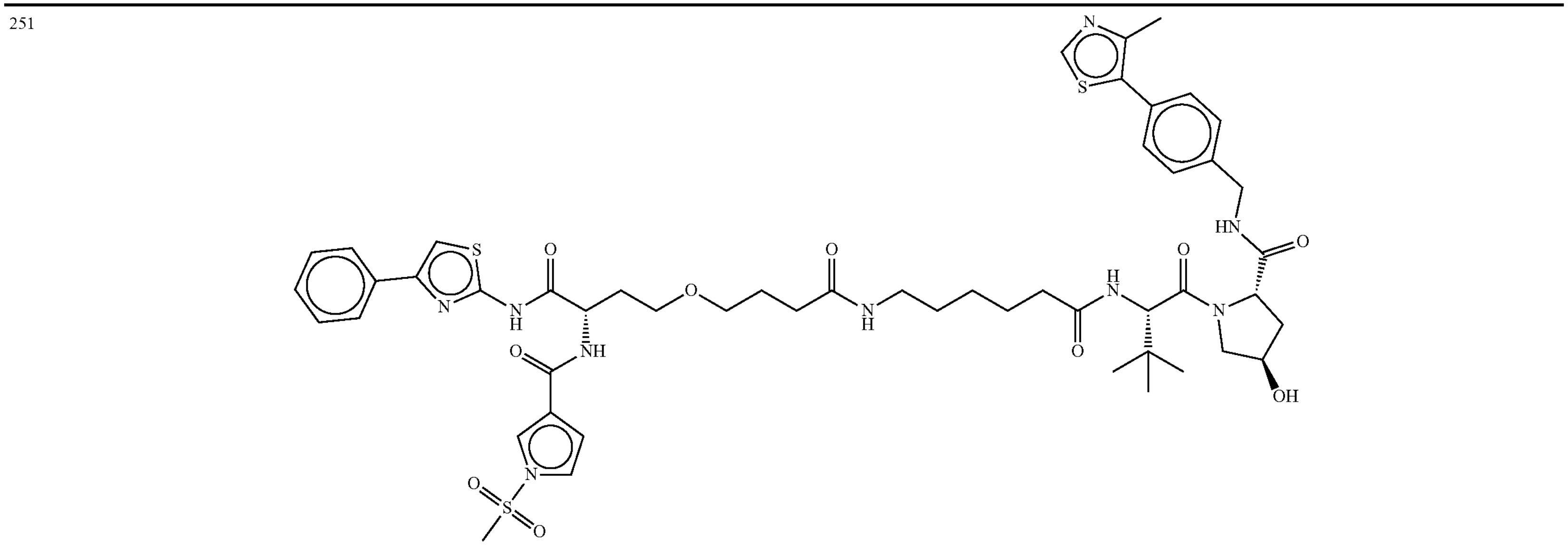 |
| 252 | 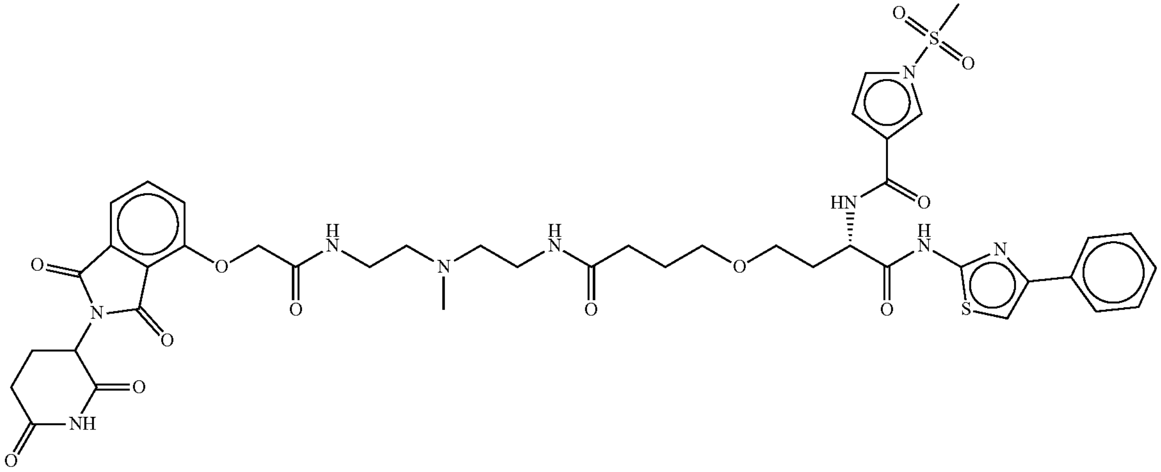 |

TABLE 1-continued
| Compounds of the Invention | |
|---|---|
| # | Structure |
| 253 | 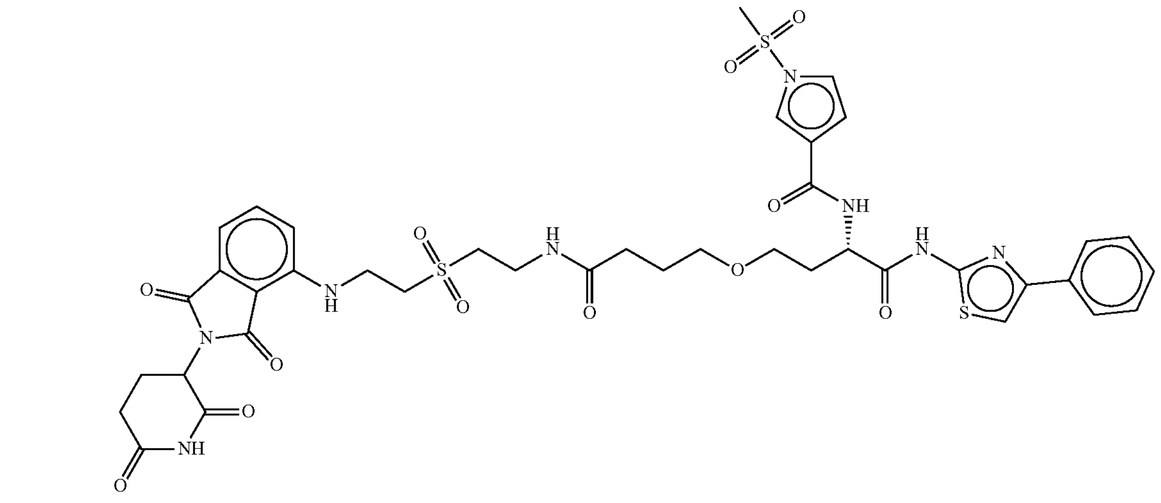 |
| 254 | 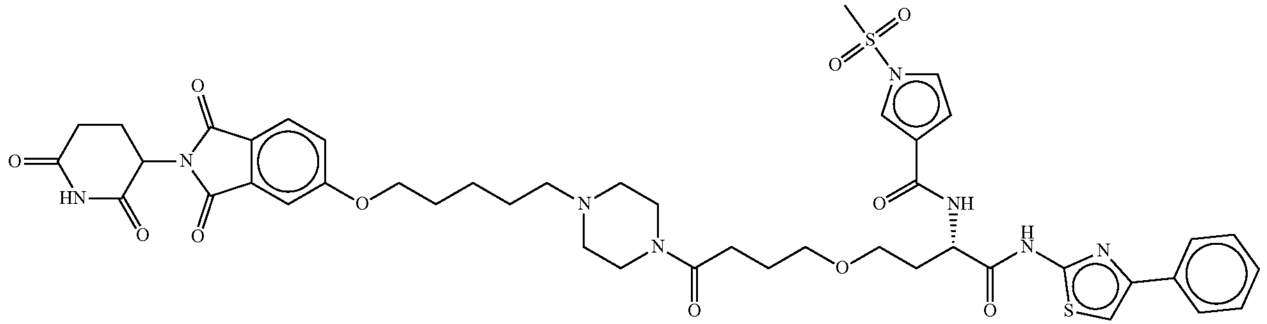 |

TABLE 1-continued
| Compounds of the Invention | |
|---|---|
| # | Structure |
| 255 | 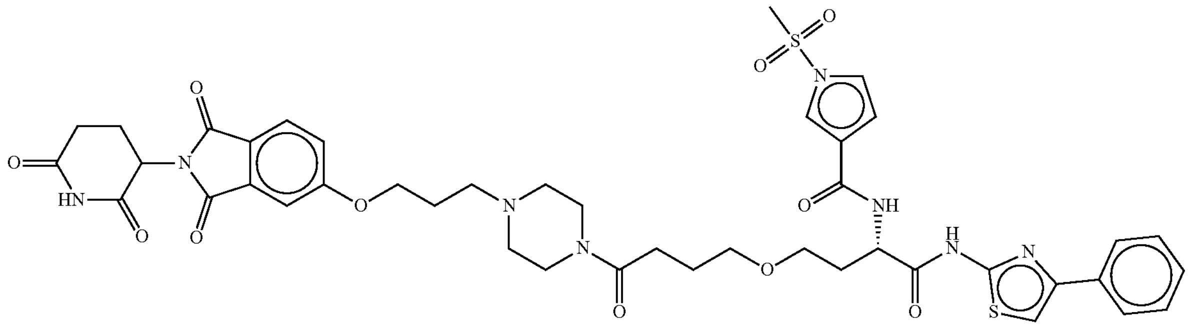 |
| 256 | 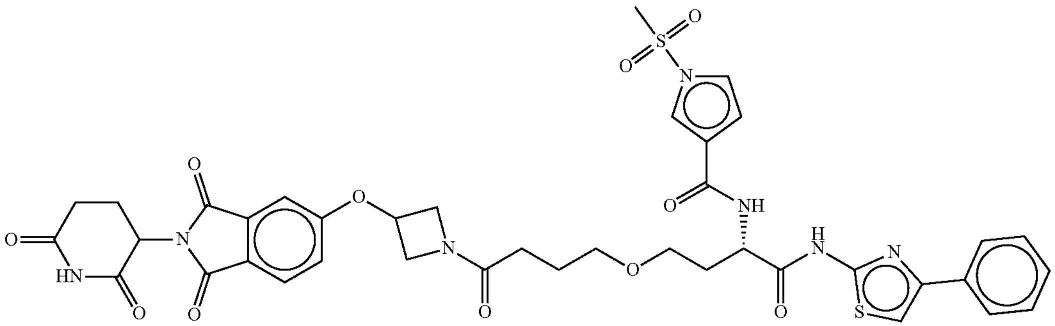 |
| 257 | 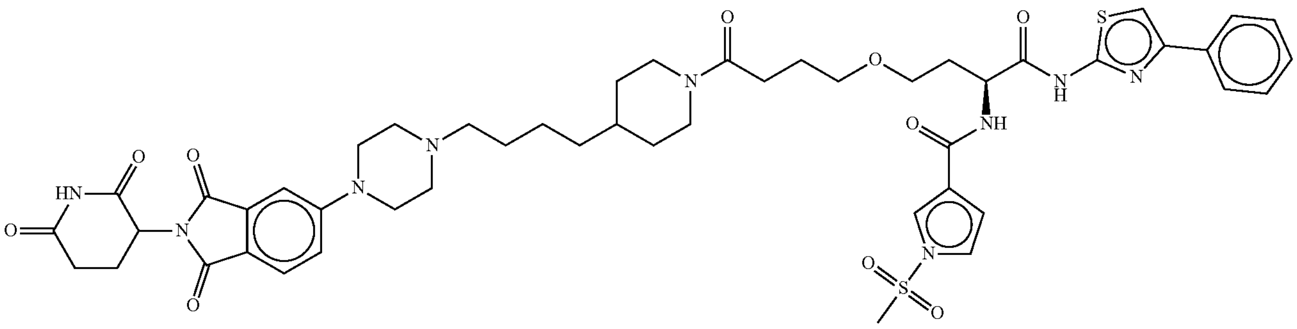 |

TABLE 1-continued
| Compounds of the Invention | |
|---|---|
| # | Structure |
| 258 | 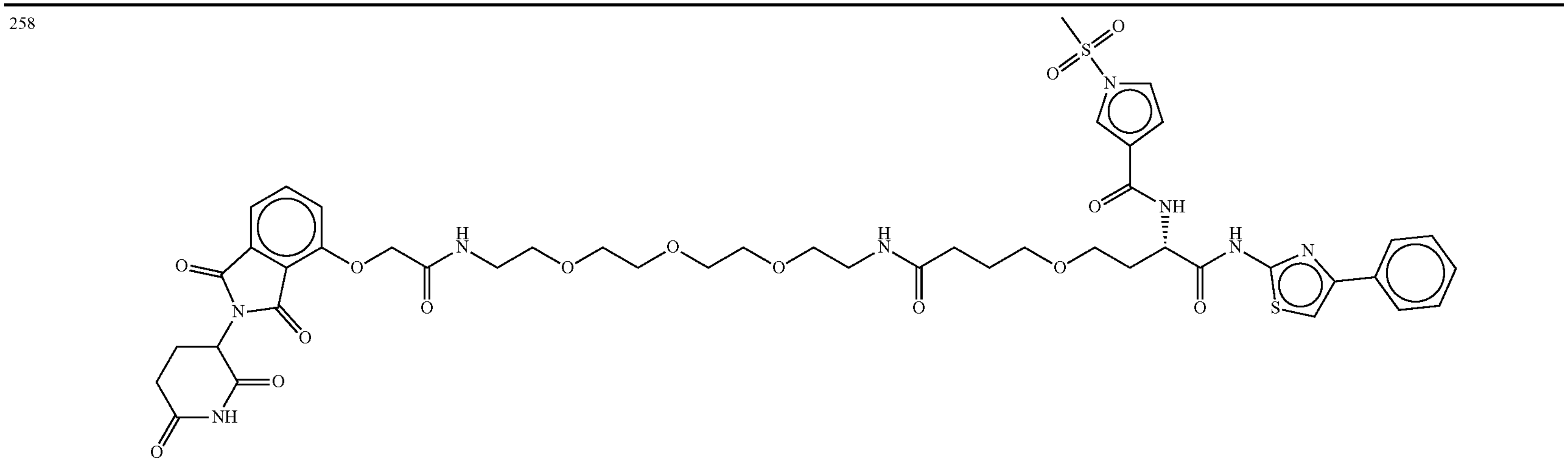 |
| 259 | 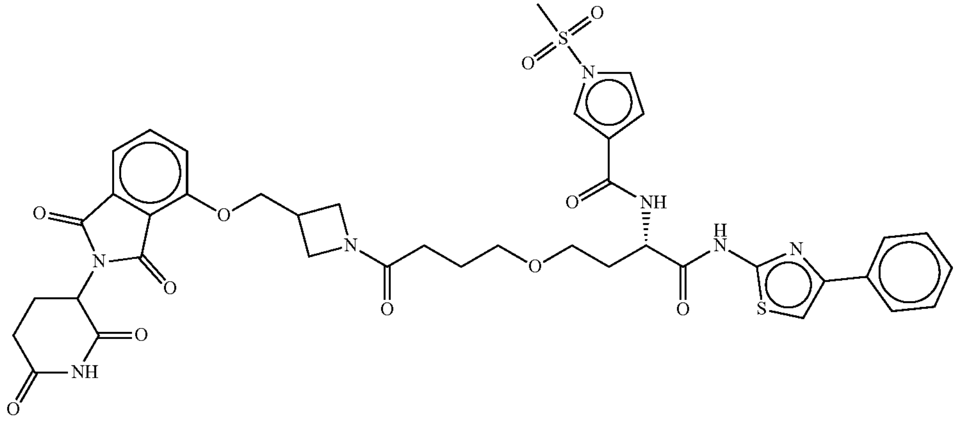 |

TABLE 1-continued
| Compounds of the Invention | |
| --- | --- |
| # | Structure |
| 260 | 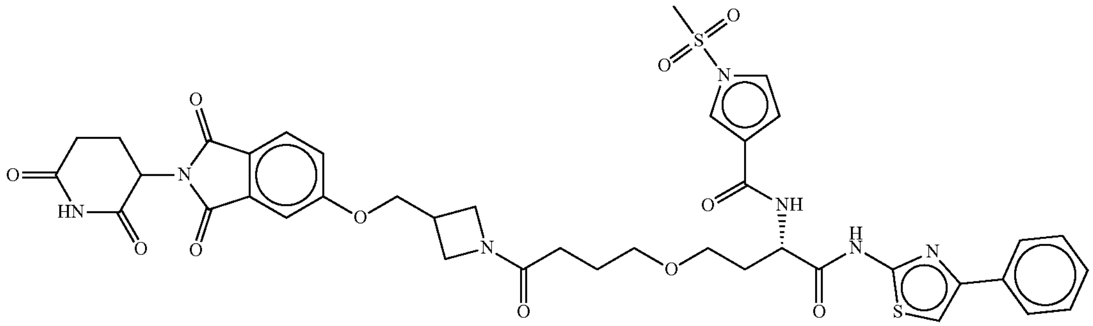 |
| 261 | 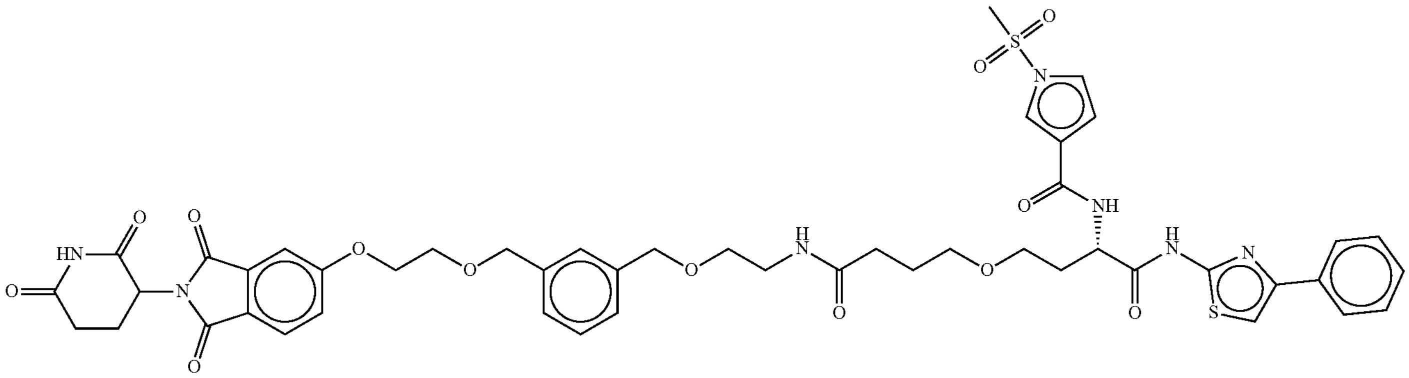 |

TABLE 1-continued
| Compounds of the Invention | |
|---|---|
| # | Structure |
| 262 | 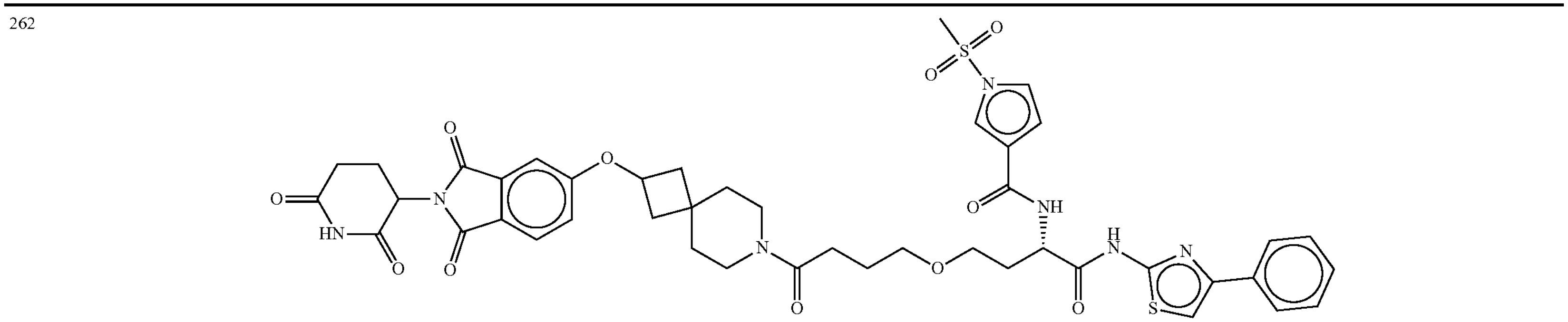 |
| 263 | 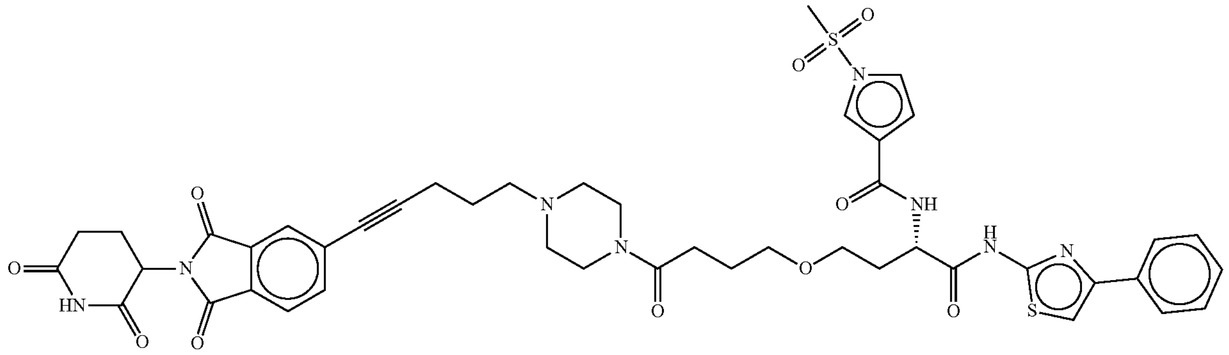 |

TABLE 1-continued
| Compounds of the Invention | |
|---|---|
| # | Structure |
| 264 | 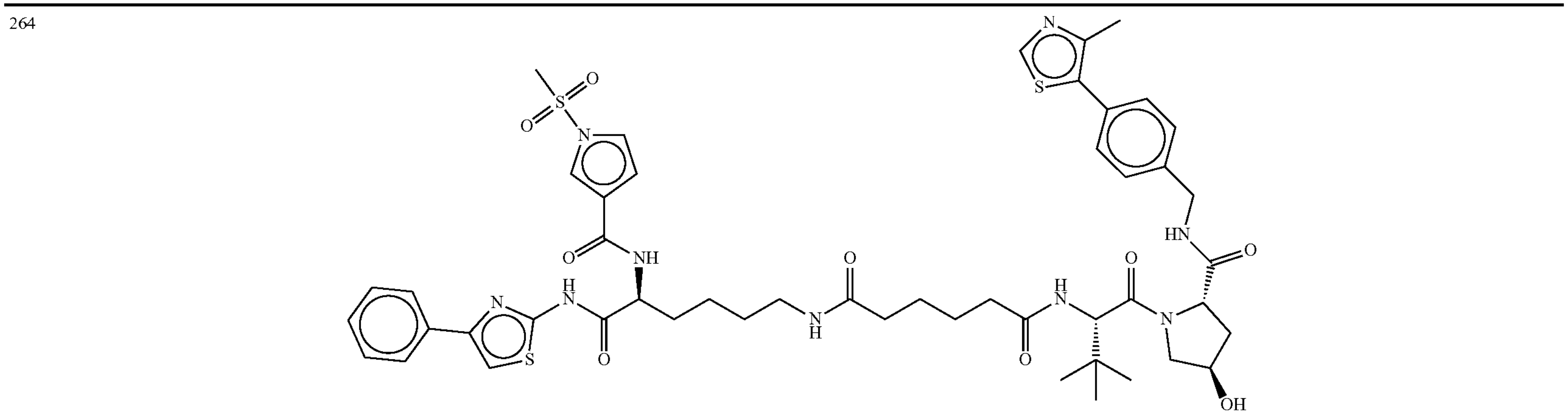 |
| 265 | 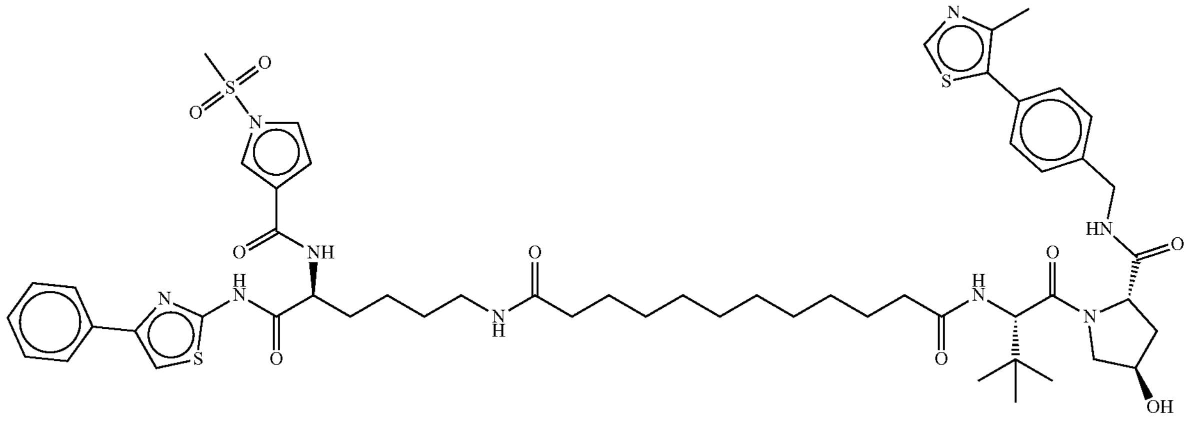 |

TABLE 1-continued
| Compounds of the Invention | |
|---|---|
| # | Structure |
| 266 | 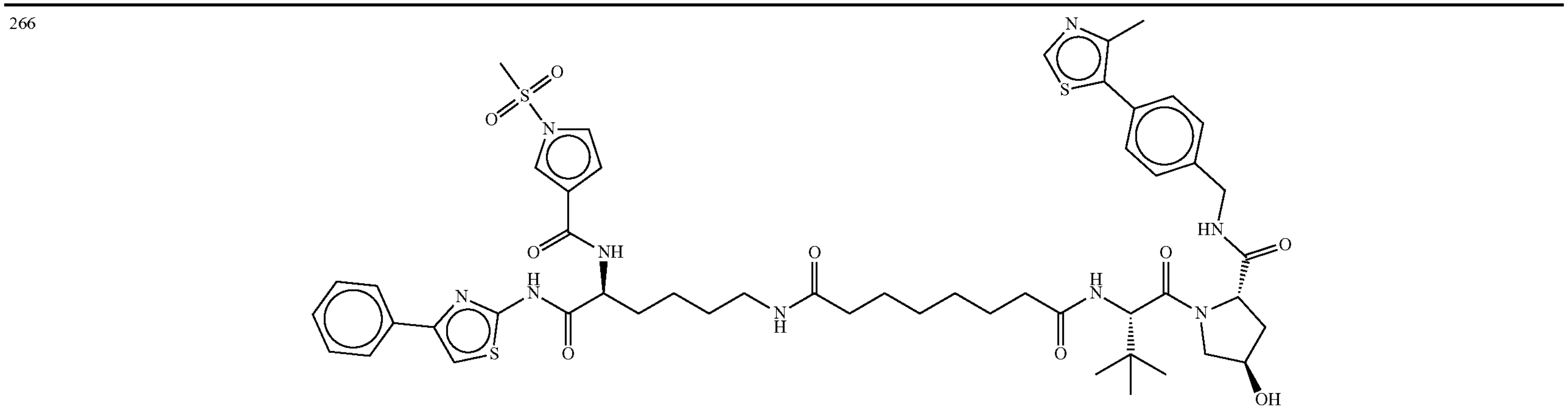 |
| 267 | 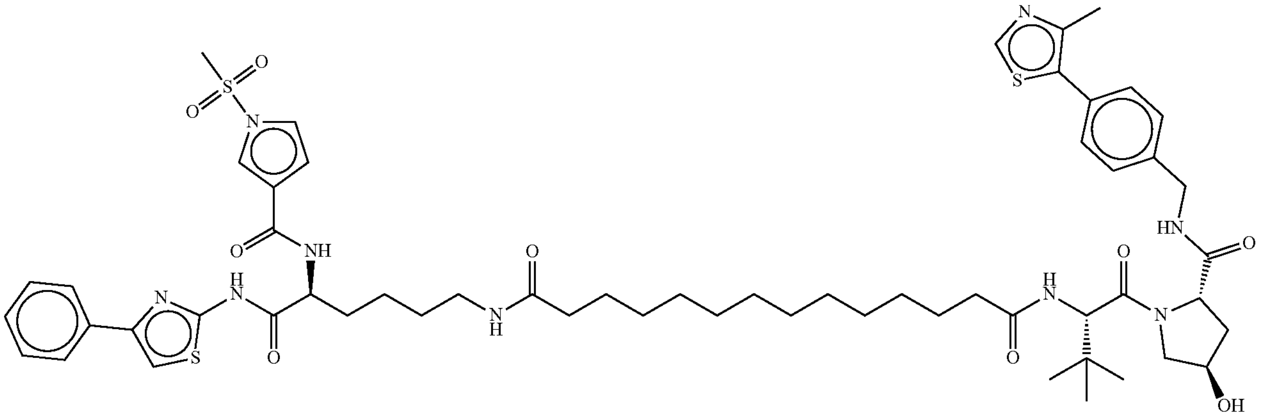 |

TABLE 1-continued
| Compounds of the Invention | |
|---|---|
| # | Structure |
| 268 | 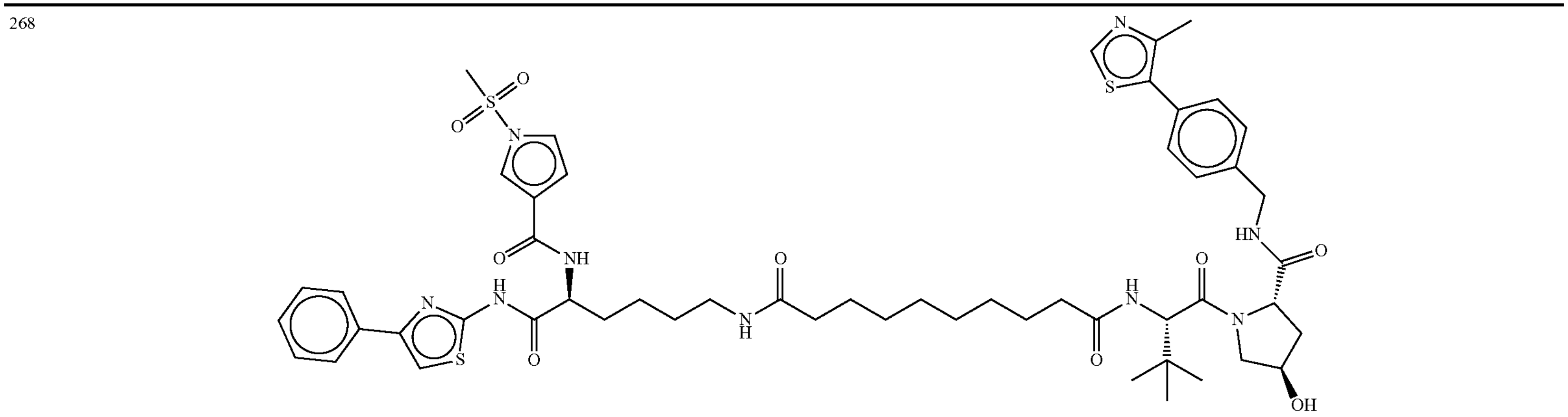 |
| 269 | 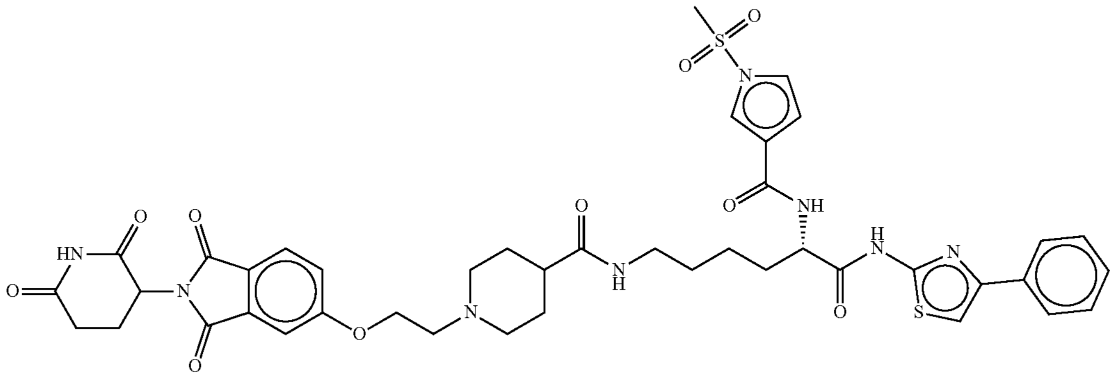 |

TABLE 1-continued
| Compounds of the Invention | |
|---|---|
| # | Structure |
| 270 | 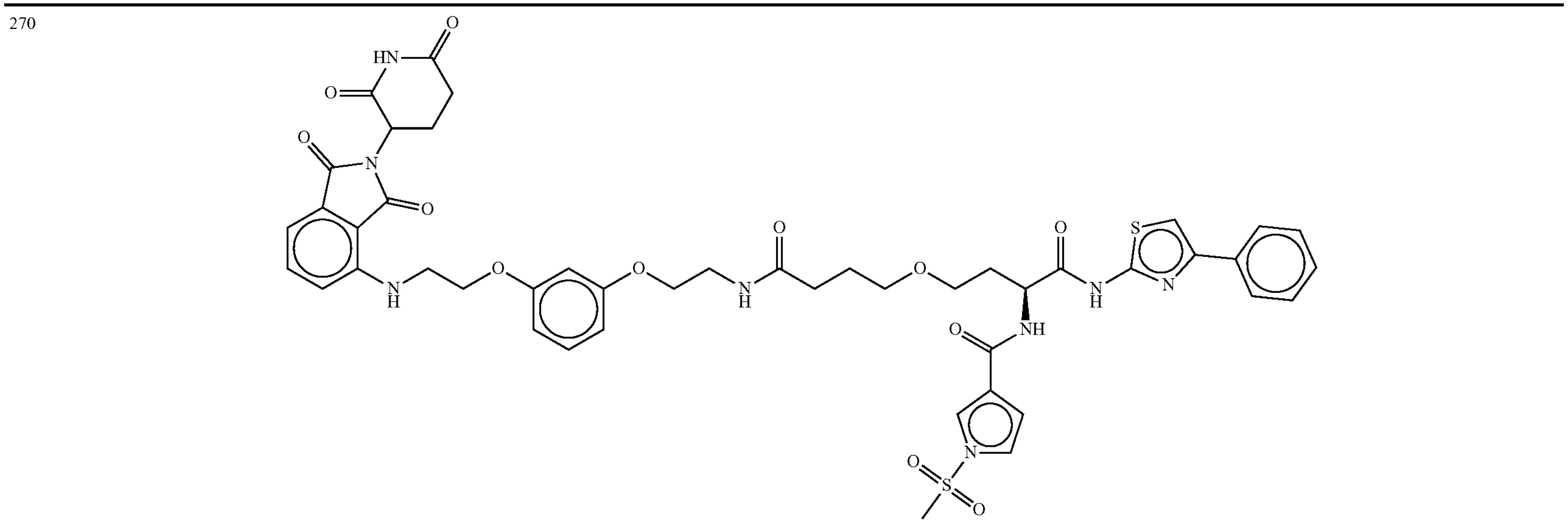 |
| 271 | 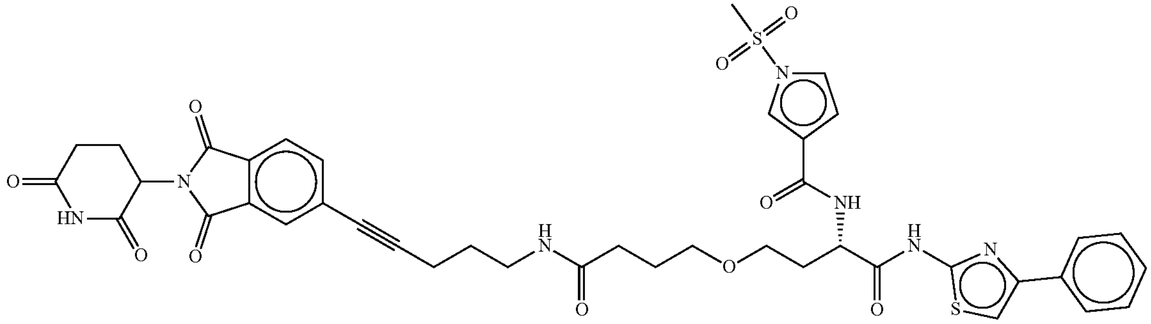 |

TABLE 1-continued
| Compounds of the Invention | |
|---|---|
| # | Structure |
| 272 | 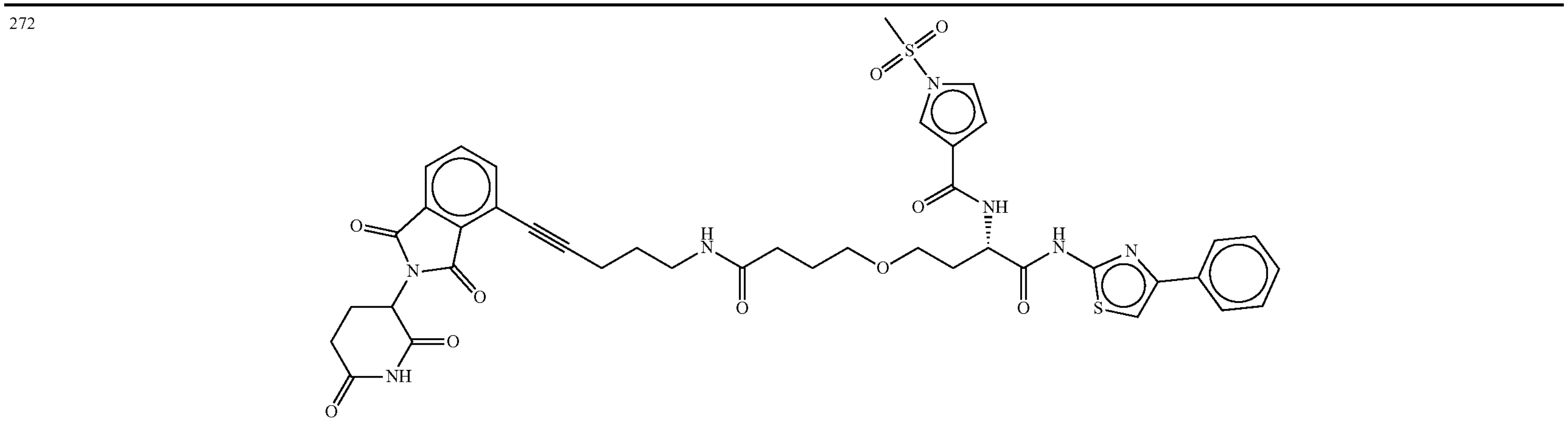 |
| 273 | 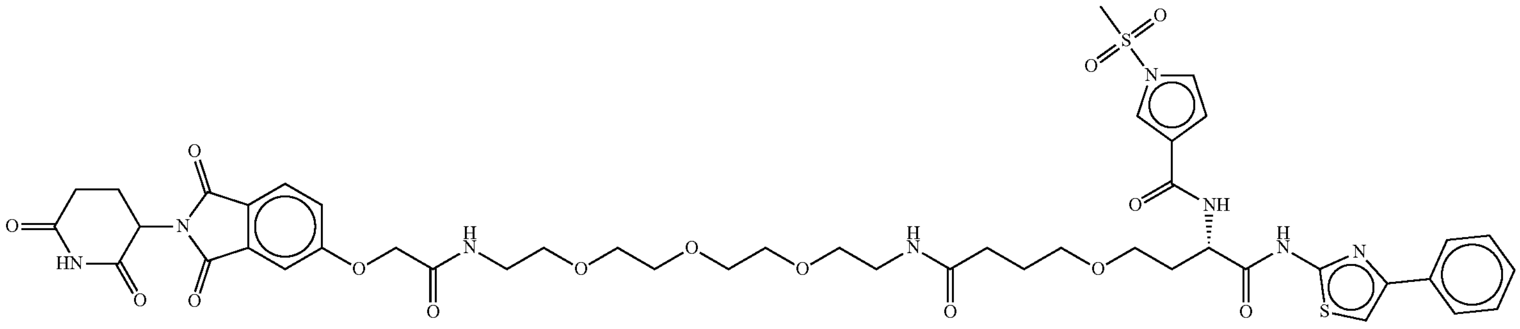 |

TABLE 1-continued
| Compounds of the Invention | |
|---|---|
| # | Structure |
| 274 | 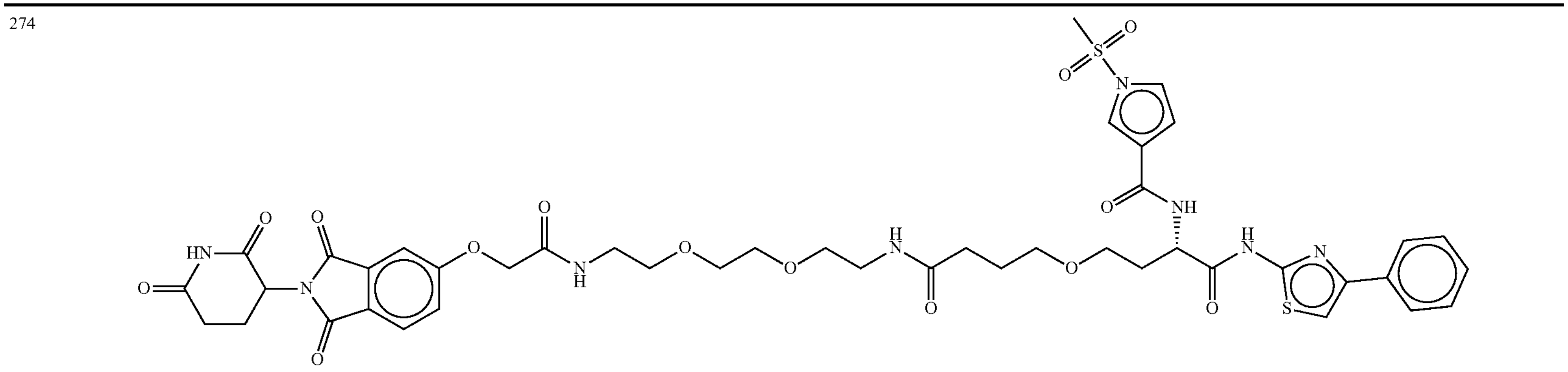 |
| 275 | 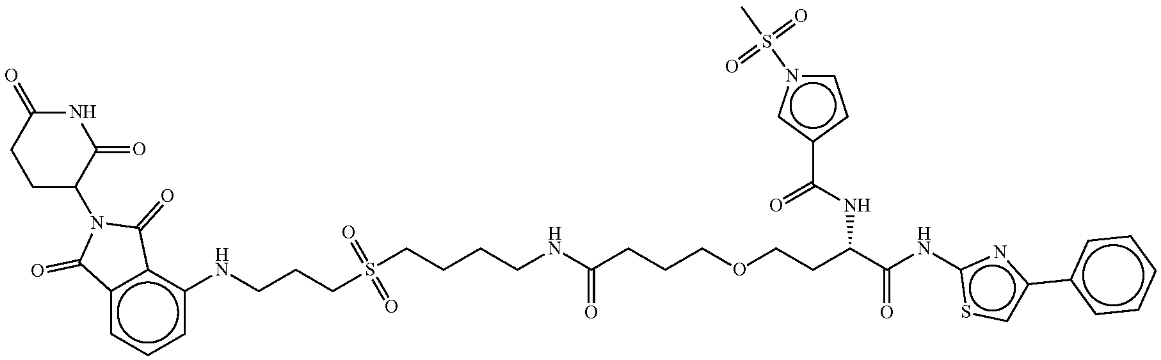 |

TABLE 1-continued
| Compounds of the Invention | |
|---|---|
| # | Structure |
| 276 | 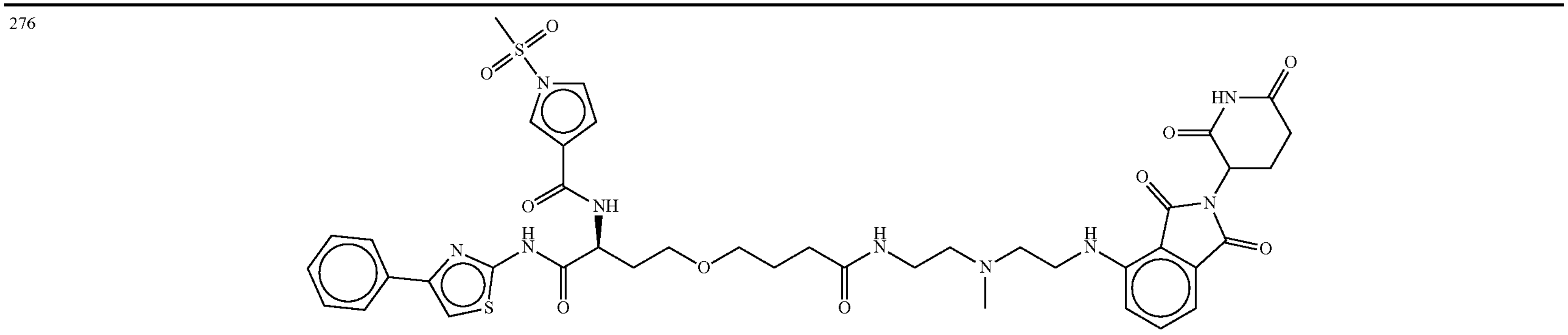 |
| 277 | 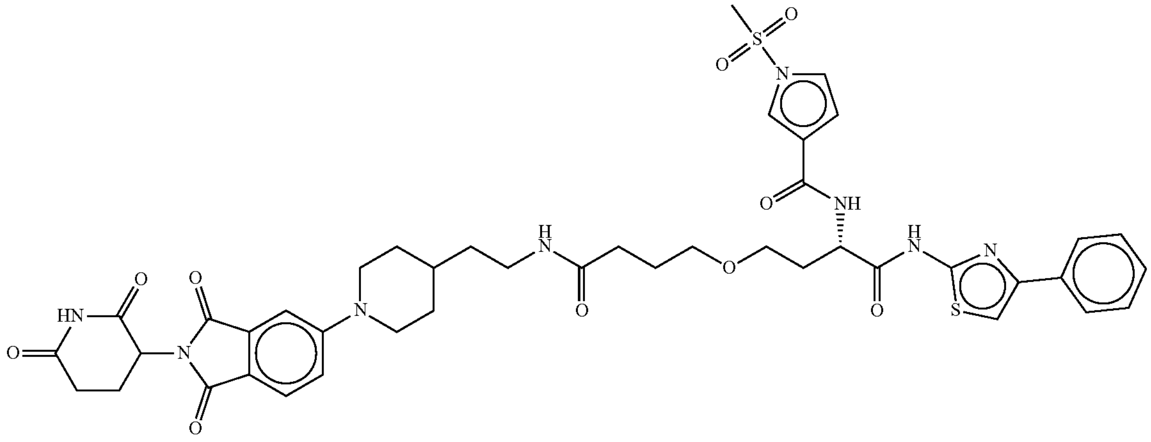 |

TABLE 1-continued
| Compounds of the Invention | |
|---|---|
| # | Structure |
| 278 | 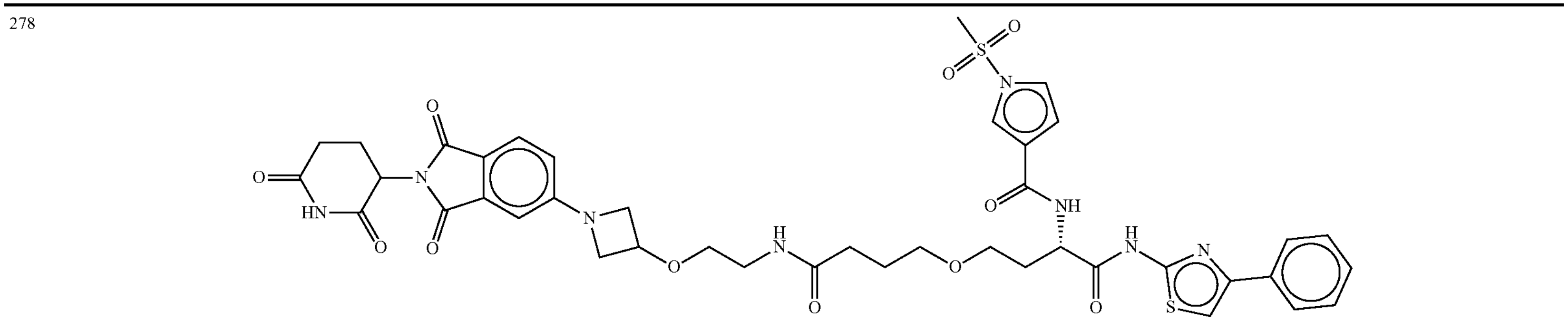 |
| 279 | 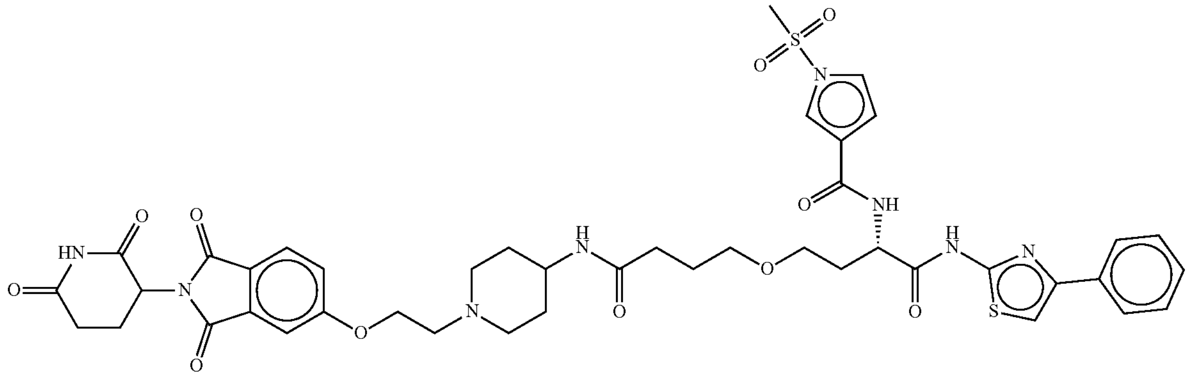 |

TABLE 1-continued
| Compounds of the Invention | |
|---|---|
| # | Structure |
| 280 | 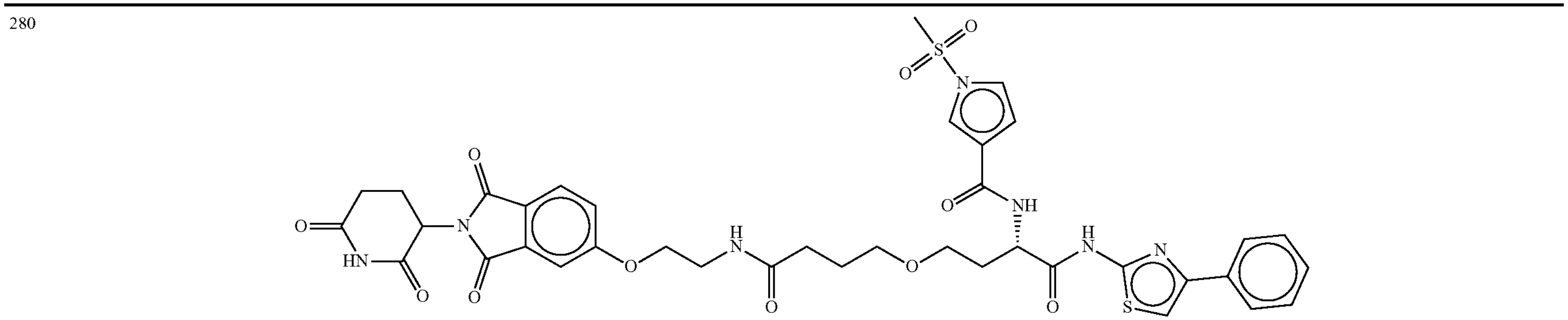 |
| 281 | 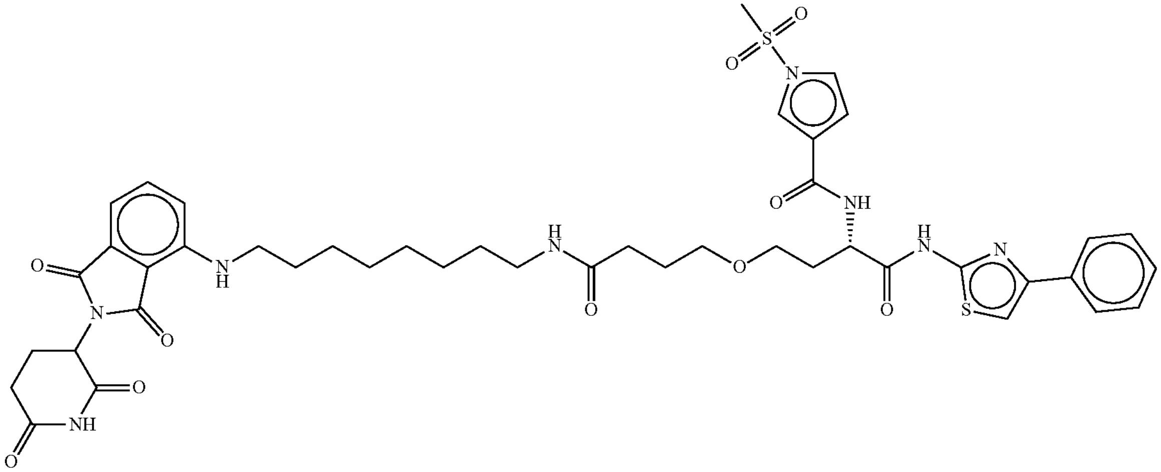 |

TABLE 1-continued
| Compounds of the Invention | |
|---|---|
| # | Structure |
| 282 | 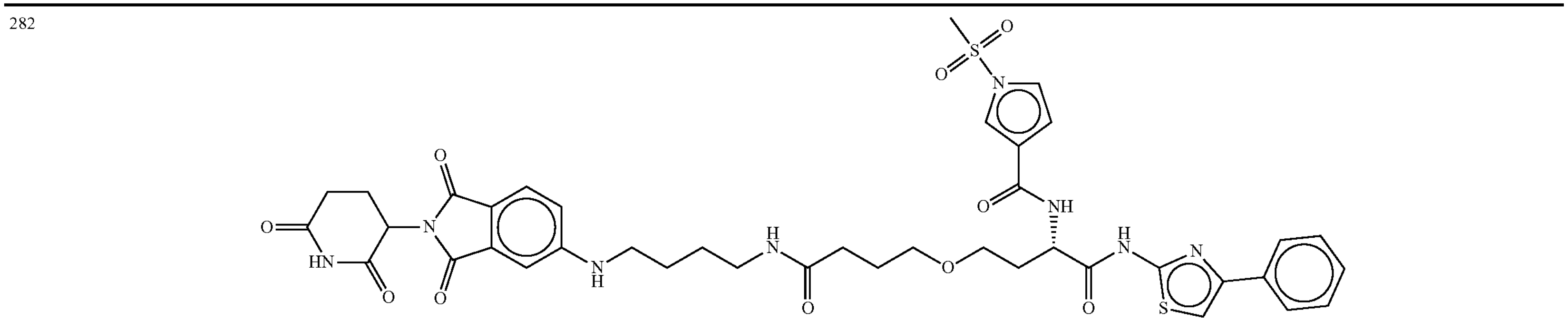 |
| 283 | 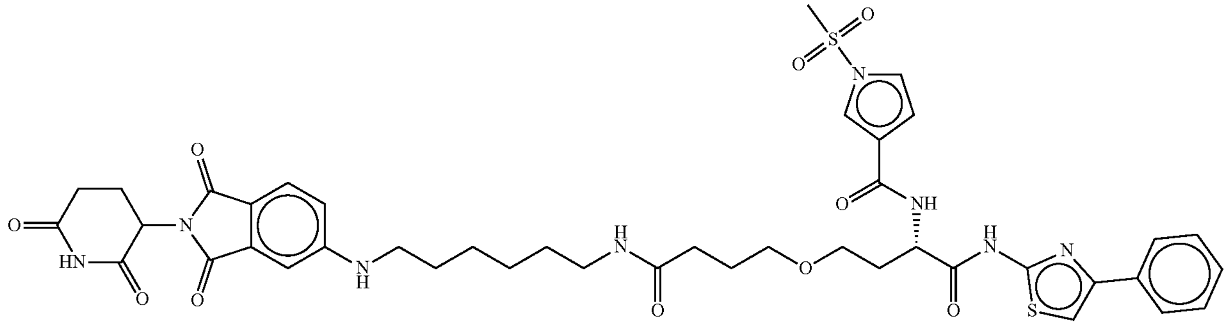 |
| 284 | 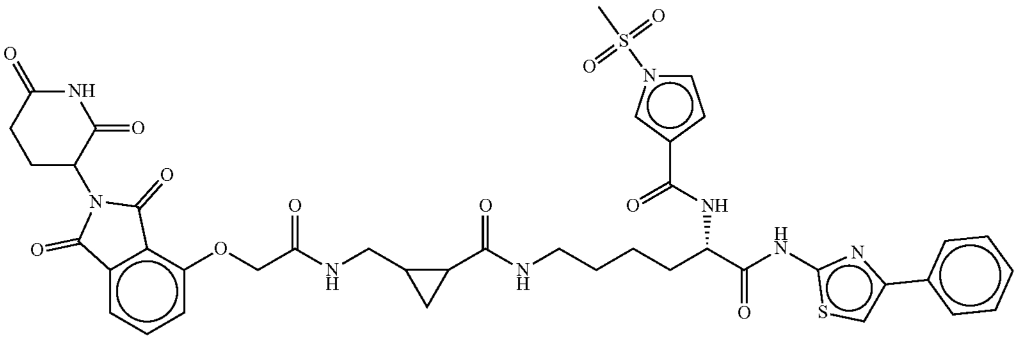 |

TABLE 1-continued
| Compounds of the Invention | |
|---|---|
| # | Structure |
| 285 | 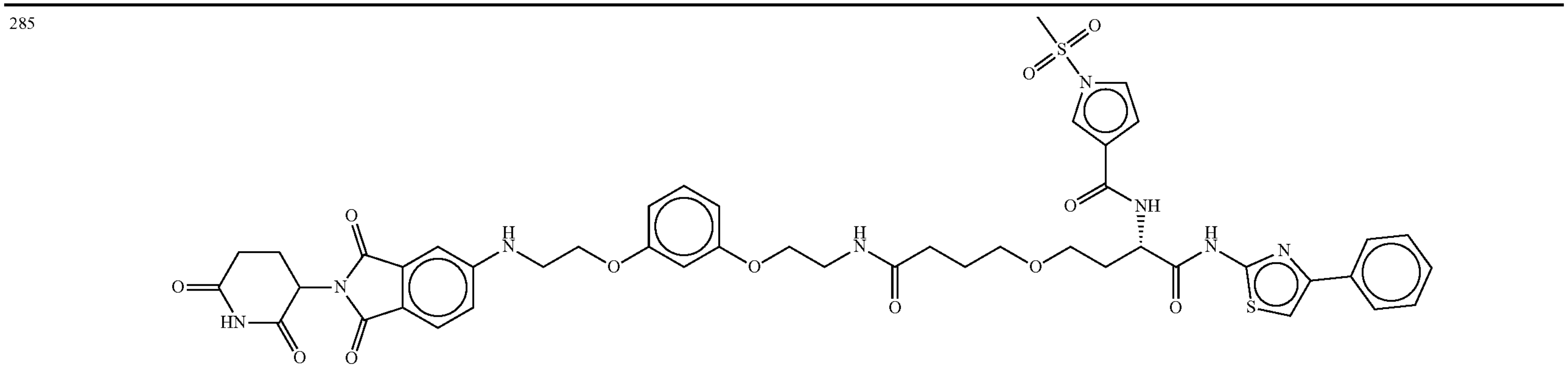 |
| 286 | 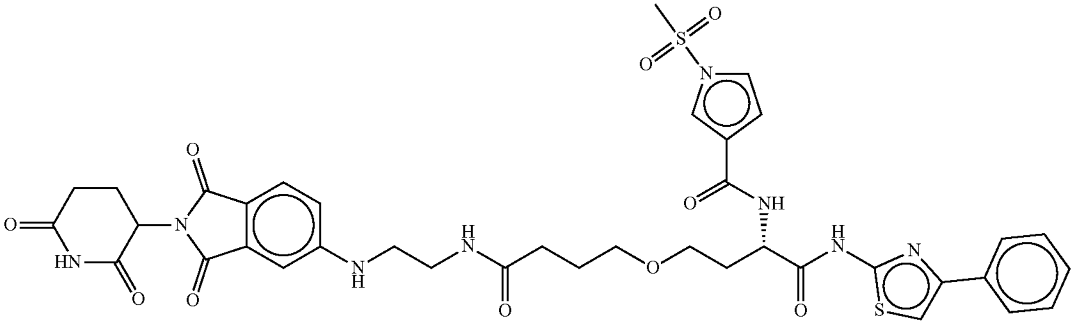 |

TABLE 1-continued
| Compounds of the Invention | |
|---|---|
| # | Structure |
| 287 | 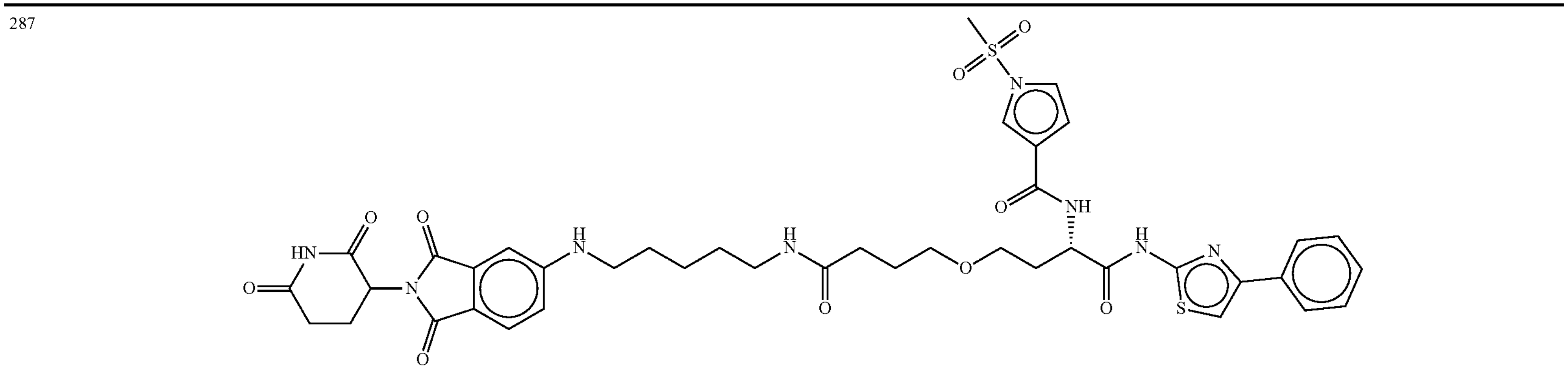 |
| 288 | 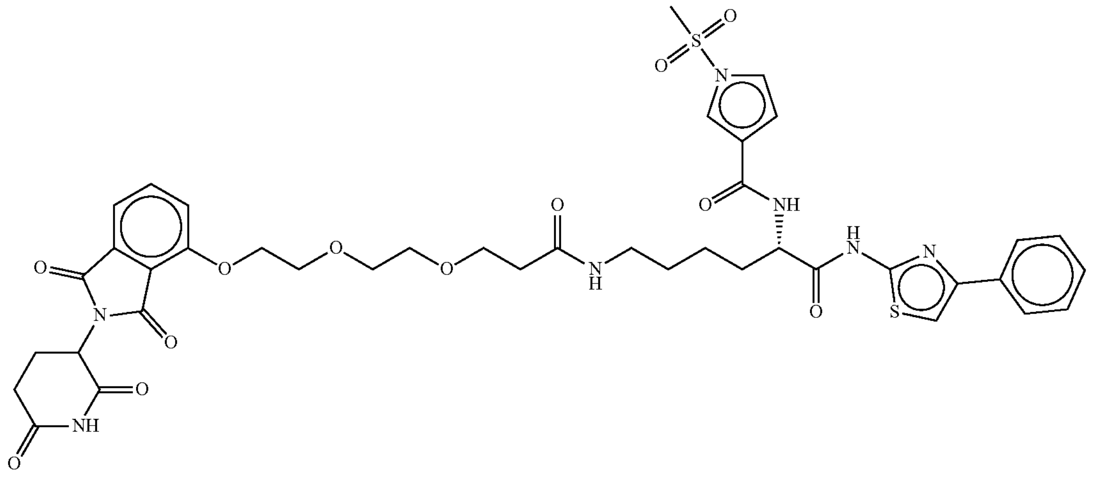 |

TABLE 1-continued
| Compounds of the Invention | |
|---|---|
| # | Structure |
| 289 | 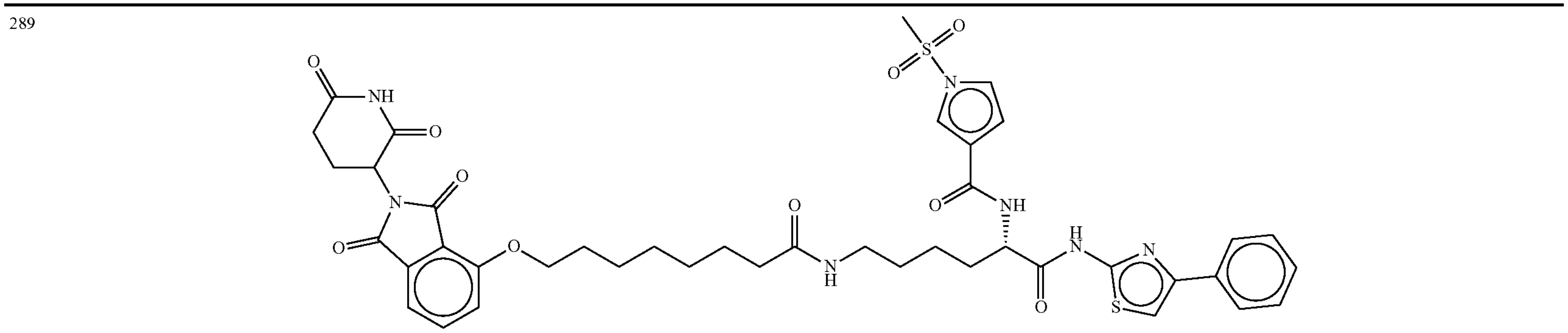 |
| 290 | 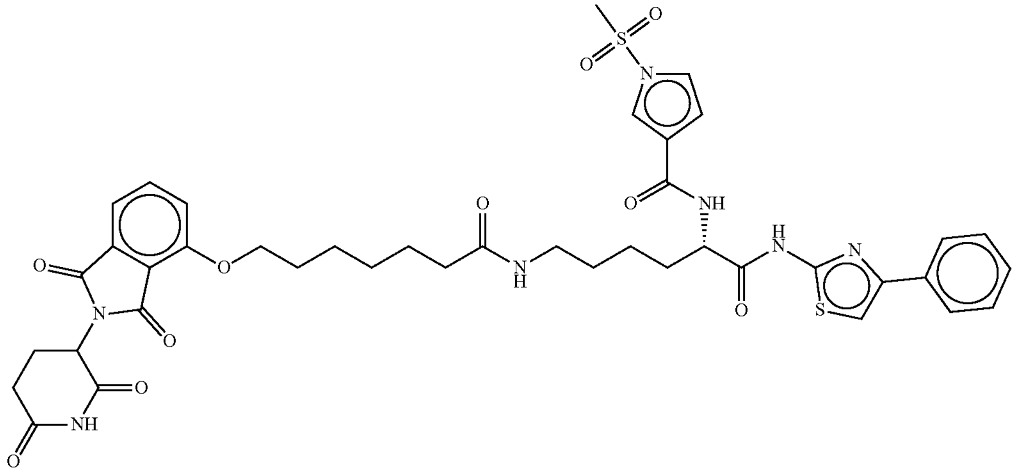 |

TABLE 1-continued
| Compounds of the Invention | |
|---|---|
| # | Structure |
| 291 | 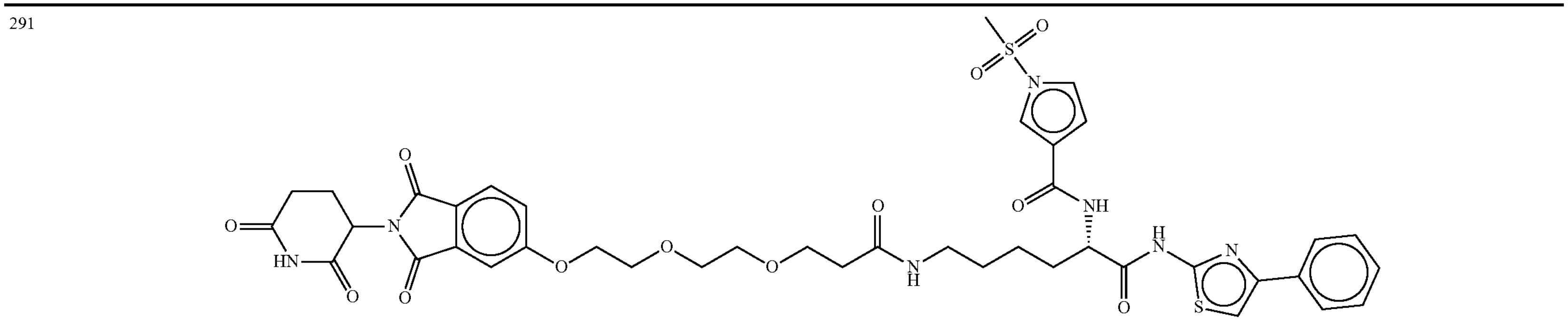 |
| 292 | 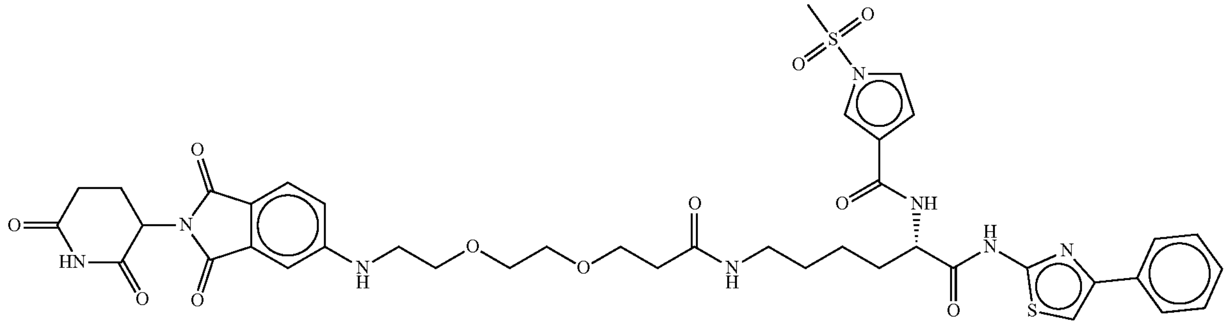 |
| 293 | 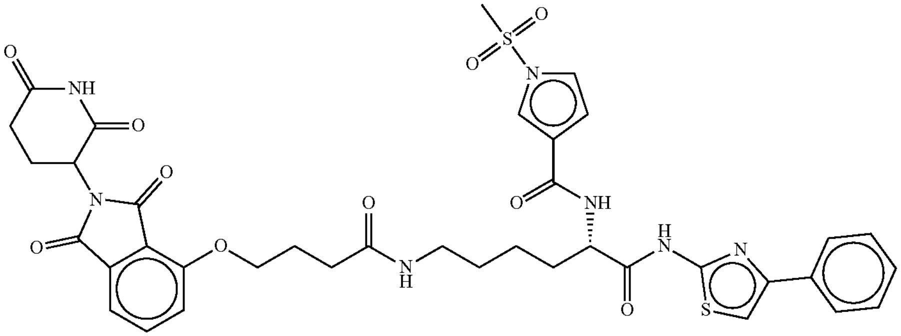 |

TABLE 1-continued
| Compounds of the Invention | |
|---|---|
| # | Structure |
| 294 | 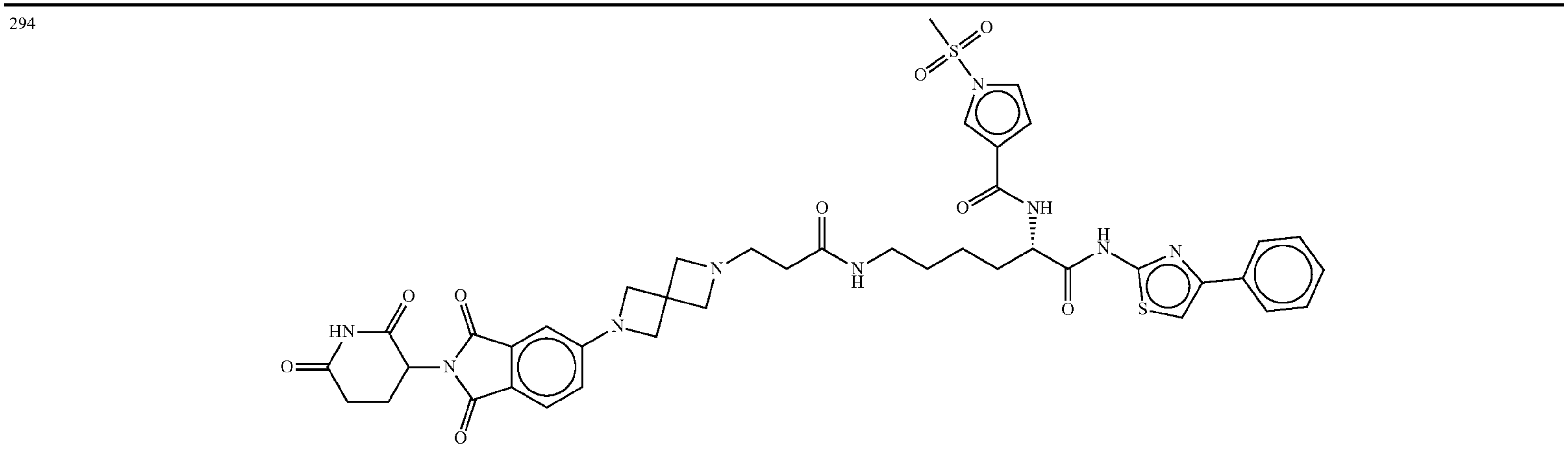 |
| 295 | 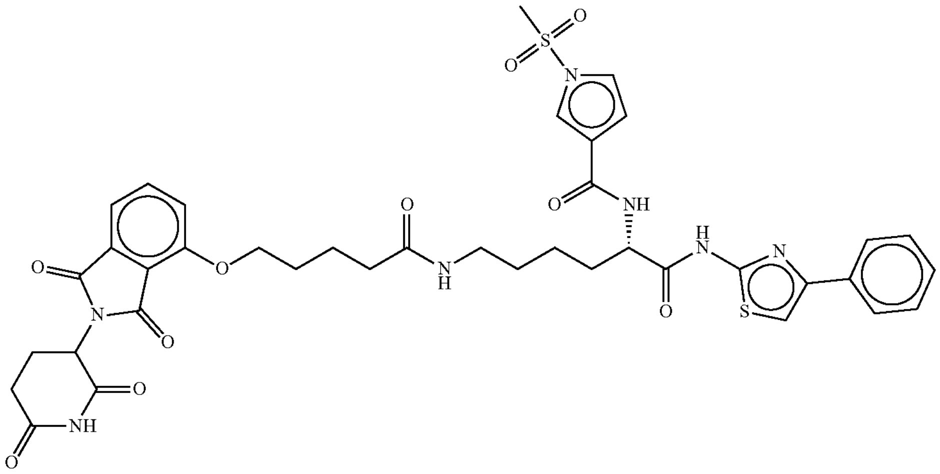 |

TABLE 1-continued
| Compounds of the Invention | |
|---|---|
| # | Structure |
| 296 | 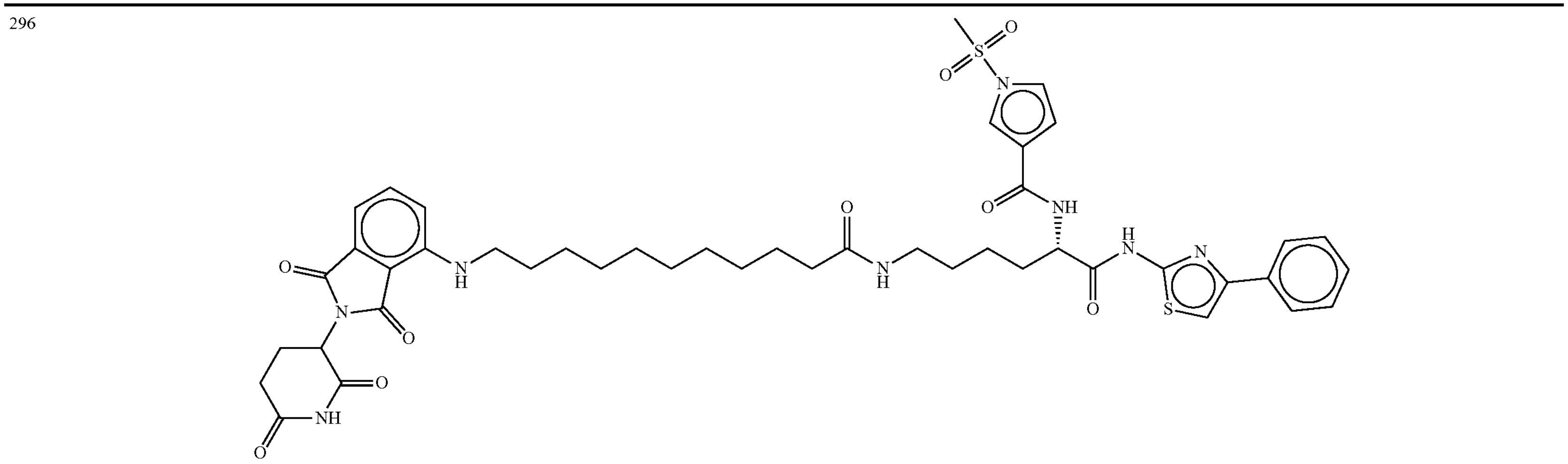 |
| 297 | 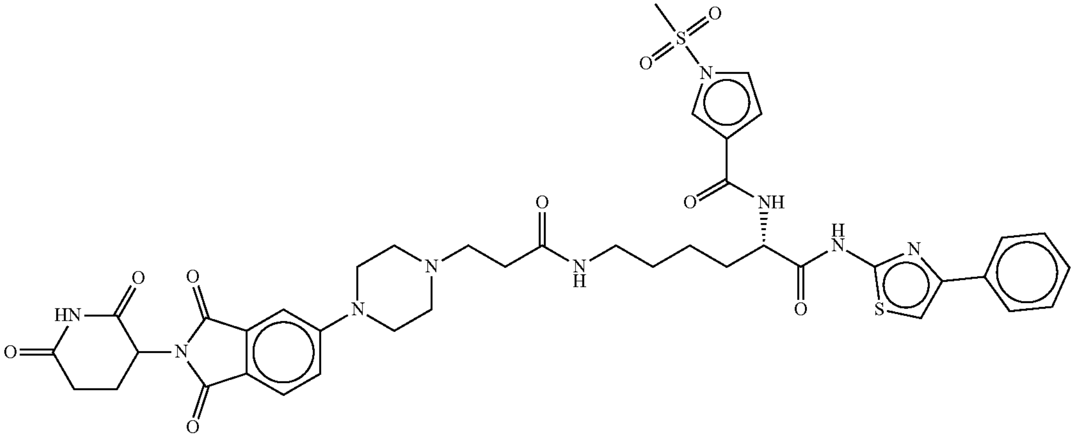 |

In an aspect, the invention features a pharmaceutical composition comprising any of the foregoing compounds and a pharmaceutically acceptable excipient.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds or a pharmaceutical composition thereof.

In some embodiments, the BAF complex-related disorder is cancer.

In a further aspect, the invention features a method of inhibiting BRM, the method involving contacting a cell with an effective amount of any of the foregoing compounds or a pharmaceutical composition thereof.

In some embodiments, the cell is a cancer cell.

In another aspect, the invention features a method of inhibiting BRG1, the method involving contacting the cell with an effective amount of any of the foregoing compounds or a pharmaceutical composition thereof.

In some embodiments, the cell is a cancer cell.

In a further aspect, the invention features a method of inhibiting BRM and BRG1, the method involving contacting the cell with an effective amount of any of the foregoing compounds or a pharmaceutical composition thereof.

In some embodiments, the cell is a cancer cell.

In another aspect, the invention features a method of treating a disorder related to a BRG1 loss of function mutation in a subject in need thereof, the method involving administering to the subject an effective amount of any of the foregoing compounds or a pharmaceutical composition thereof.

In some embodiments, the disorder related to a BRG1 loss of function mutation is cancer. In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds (e.g., a BRM/BRG1 dual inhibitor compound or a BRM-selective compound) or a pharmaceutical composition thereof.

In some embodiments, the cell is a cancer cell.

In a further aspect, the invention features a method of treating cancer in a subject in need thereof, the method including administering to the subject an effective amount of any of the foregoing compounds or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolomide, irinotecan, a CAR-T therapy, trastuzumab, pertuzumab, tamoxifen, capecitabine, docetaxol, platinum agents such as carboplatin, taxanes such as paclitaxel and docetaxel, ALK inhibitors, MET inhibitors, pemetrexed, protein bound paclitaxel, doxorubicin, gemcitabine, bevacizumab, eribulin, neratinib, a PARP inhibitor, brilanestrant, an mTOR inhibitor, topotecan, gemcitabine, a VEGFR2 inhibitor, a folate receptor antagonist, demcizumab, fosbretabulin, or a PD-L1 inhibitor).

In some embodiments of any of the foregoing methods, the cancer has or has been determined to have one or more BRG1 mutations. In some embodiments of any of the foregoing methods, the one or more BRG1 mutations are homozygous. In some embodiments of any of the foregoing methods, the one or more BRG1 mutations are in the ATPase catalytic domain of the protein. In some embodiments of any of the foregoing methods, the one or more BRG1 mutations are a deletion at the C-terminus of BRG1. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation.

In another aspect, the disclosure provides a method treating a disorder related to BAF (e.g., cancer or viral infections) in a subject in need thereof. This method includes contacting a cell with an effective amount of any of the foregoing compounds, or pharmaceutically acceptable salts thereof, or any of the foregoing pharmaceutical compositions. In some embodiments, the disorder is a viral infection. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In some embodiments of any of the foregoing aspects, the compound is a BRM-selective compound. In some embodiments, the BRM-selective compound inhibits the level and/or activity of BRM at least 10-fold greater than the compound inhibits the level and/or activity of BRG1 and/or the compound binds to BRM at least 10-fold greater than the compound binds to BRG1. For example, in some embodiments, a BRM-selective compound has an $IC_{50}$ or $IP_{50}$ that is at least 10-fold lower than the $IC_{50}$ or $IP_{50}$ against BRG1. In some embodiments of any of the foregoing aspects, the compound is a BRM/BRG1 dual inhibitor compound. In some embodiments, the BRM/BRG1 dual inhibitor compound has similar activity against both BRM and BRG1 (e.g., the activity of the compound against BRM and BRG1 with within 10-fold (e.g., less than 5-fold, less than 2-fold). In some embodiments, the activity of the BRM/BRG1 dual inhibitor compound is greater against BRM. In some embodiments, the activity of the BRM/BRG1 dual inhibitor compound is greater against BRG1. For example, in some embodiments, a BRM/BRG1 dual inhibitor compound has an $IC_{50}$ or $IP_{50}$ against BRM that is within 10-fold of the $IC_{50}$ or $IP_{50}$ against BRG1.

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization (e.g., metastatic colonization to the liver and/or brain) of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference. In some embodiments, the effective amount of the compound that reduces the level and/or activity of BRM by at least 90% (e.g., 91%, 92%, 93%, 94%, 95%, 96%, 97%, 98%, or 99%).

In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of an agent that reduces the level and/or activity of BRG1 and/or BRM is an amount effective to inhibit metastatic colonization of the cancer to the liver and/or brain.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a MITF translocation. In some embodiments the cancer harbors an EZH2 mutation. In some embodiments the cancer harbors a SUZ12 mutation. In some embodiments the cancer harbors an EED mutation.

In some embodiments, the method further includes administering to the subject or contacting the cell with an anticancer therapy, e.g., a chemotherapeutic or cytotoxic agent, immunotherapy, surgery, radiotherapy, thermotherapy, or photocoagulation. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor.

In some embodiments, the compound of the invention is used in combination with another anti-cancer therapy used for the treatment of uveal melanoma such as surgery, a MEK inhibitor, and/or a PKC inhibitor. For example, in some embodiments, the method further comprises performing surgery prior to, subsequent to, or at the same time as administration of the compound of the invention. In some embodiments, the method further comprises administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula $—CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms). An "alkylene" is a divalent alkyl group.

The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms). An "alkylenylene" is a divalent alkenyl group.

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms). An "alkynylene" is a divalent alkynyl group.

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl. An "arylene" is a divalent aryl group.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "bridged polycycloalkyl," as used herein, refers to a bridged polycyclic group of 5 to 20 carbons, containing from 1 to 3 bridges.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, and monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl. A "cycloalkylene" is a divalent cycloalkyl group.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A "heteroalkylene" is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A "heteroalkenylene" is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A "heteroalkynylene" is a divalent heteroalkynyl group.

The term "heteroallyl," as used herein, represents the structure

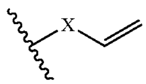
, where X is O or NR, where R is H or optionally substituted alkyl.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. A "heteroarylene" is a divalent heteroaryl group.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a mono- or polycyclic radical having 3 to 12 atoms having at least one ring containing 1, 2, 3, or 4 ring atoms selected from N, O or S and no aromatic ring containing any N, O, or S atoms. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl. A "heterocyclylene" is a divalent heterocyclyl group.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $—NO_2$ group.

The term "oxo," as used herein, represents an =O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, oxo, orthiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on ester opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as $^{15}O$, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HRBM-associated factors complex in a human cell.

As used herein, the term "BAF complex-related disorder" refers to a disorder that is caused or affected by the level and/or activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, "cmpd" refers to compound.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "degrader" refers to a small molecule compound including a degradation moiety, wherein the compound interacts with a protein (e.g., BRG1 and/or BRM) in a way which results in degradation of the protein, e.g., binding of the compound results in at least 5% reduction of the level of the protein, e.g., in a cell or subject.

As used herein, the term "degradation moiety" refers to a moiety whose binding results in degradation of a protein, e.g., BRG1 and/or BRM. In one example, the moiety binds to a protease or a ubiquitin ligase that metabolizes the protein, e.g., BRG1 and/or BRM.

By "modulating the activity of a BAF complex," is meant altering the level of an activity related to a BAF complex (e.g., GBAF), or a related downstream effect. The activity level of a BAF complex may be measured using any method known in the art, e.g., the methods described in Kadoch et al, Cell 153:71-85 (2013), the methods of which are herein incorporated by reference.

By "reducing the activity of BRG1 and/or BRM," is meant decreasing the level of an activity related to an BRG1 and/or BRM, or a related downstream effect. A non-limiting example of inhibition of an activity of BRG1 and/or BRM is decreasing the level of a BAF complex in a cell. The activity level of BRG1 and/or BRM may be measured using any method known in the art. In some embodiments, an agent which reduces the activity of BRG1 and/or BRM is a small molecule BRG1 and/or BRM degrader.

By "reducing the level of BRG1 and/or BRM," is meant decreasing the level of BRG1 and/or BRM in a cell or subject. The level of BRG1 and/or BRM may be measured using any method known in the art.

By "level" is meant a level of a protein, or mRNA encoding the protein, as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein or mRNA in a sample.

As used herein, the term "inhibiting BRM and/or BRG1" refers to blocking or reducing the level or activity of the ATPase catalytic binding domain or the bromodomain of the protein. BRM and/or BRG1 inhibition may be determined using methods known in the art, e.g., a BRM ATPase assay, a Nano DSF assay, or a BRM Luciferase cell assay.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient.

Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

As used herein, the term "pharmaceutically acceptable salt" means any pharmaceutically acceptable salt of a compound, for example, any compound of Formula I or II. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

The present disclosure features compounds useful for reducing the level and/or activity of BRG1 and/or BRM.

These compounds may be used to modulate the activity of a BAF complex, for example, for the treatment of a BAF-related disorder, such as cancer. Exemplary compounds described herein include compounds having a structure according to Formula I:

A-L-B Formula I, where

L is a linker;

B is a degradation moiety; and

A has the structure of Formula II:

Formula II

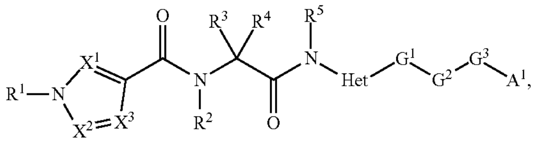

where $X^1$ is N or CH;

$X^2$, and $X^3$ are, independently, N, CH, or $C(CH_3)$;

$R^1$ is H, optionally substituted $C_1$-$C_6$ acyl, optionally substituted $C_1$-$C_6$ alkyl, optionally substituted $C_1$-$C_6$ heteroalkyl, optionally substituted $C_2$-$C_9$ heterocyclyl, or —$SO_2R^6$;

each of $R^2$ and $R^5$ is, independently, H or optionally substituted $C_1$-$C_6$ alkyl;

$R^3$ is H, optionally substituted $C_1$-$C_6$ alkyl, or a bond between A and the linker;

$R^4$ is H, optionally substituted $C_1$-$C_6$ alkyl, or optionally substituted $C_1$-$C_6$ heteroalkyl;

$R^6$ is optionally substituted $C_1$-$C_6$ alkyl or —$NR^7R^8$;

each of $R^7$ and $R^8$ is, independently, optionally substituted $C_1$-$C_6$ alkyl;

Het is a 5-membered or 6-membered heteroarylene;

$G^1$ is optionally substituted $C_6$-$C_{10}$ arylene, optionally substituted $C_2$-$C_9$ heterocyclylene, or optionally substituted $C_2$-$C_9$ heteroarylene;

$G^2$ is absent, —O—, optionally substituted $C_1$-$C_6$ alkylene, optionally substituted $C_1$-$C_6$ alkenylene, optionally substituted $C_1$-$C_6$ heteroalkylene, optionally substituted $C_2$-$C_9$ heterocyclyl $C_1$-$C_6$ alkylene, or optionally substituted $C_2$-$C_9$ heteroaryl $C_1$-$C_6$ alkylene;

$G^3$ is absent, optionally substituted $C_6$-$C_{10}$ arylene, optionally substituted $C_6$-$C_{10}$ cycloalkylene, optionally substituted $C_2$-$C_9$ heterocyclylene, or optionally substituted $C_2$-$C_9$ heteroarylene; and $A^1$ is H or a bond between A and the linker, provided that Formula II includes one and only one bond between A and the linker, or a pharmaceutically acceptable salt thereof.

In some embodiments, $R^3$ is H or optionally substituted $C_1$-$C_6$ alkyl, and $A^1$ is a bond between A and the linker. In some embodiments, $R^3$ is a bond between A and the linker, and $A^1$ is H.

In some embodiments, the compound is any one of compounds I-297 in Table 1, or a pharmaceutically acceptable salt thereof. In some embodiments, the compound is any one of compounds I-169 in Table 1, or a pharmaceutically acceptable salt thereof.

Other embodiments, as well as exemplary methods for the synthesis of production of these compounds, are described herein.

Pharmaceutical Uses The compounds described herein are useful in the methods of the invention and, while not bound by theory, are believed to exert their ability to modulate the level, status, and/or activity of a BAF complex, i.e., by reducing the level and/or activity of the BRG1 and/or BRM proteins within a cell in a mammal. BAF complex-related disorders include, but are not limited to, BRG1 and/or BRM loss of function mutation-related disorders.

An aspect of the present invention relates to methods of treating disorders related to BRG1 and/or BRM loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, and (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel, and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate;

irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response or antagonizes an antigen important for cancer. Such agents include rituximab; daclizumab; basiliximab; palivizumab; infliximab; trastuzumab; gemtuzumab ozogamicin; alemtuzumab; ibritumomab tiuxetan; adalimumab; omalizumab; tositumomab-I-131; efalizumab; cetuximab; bevacizumab; natalizumab; tocilizumab; panitumumab; ranibizumab; eculizumab; certolizumab pegol; golimumab; canakinumab; ustekinumab; ofatumumab; denosumab; motavizumab; raxibacumab; belimumab; ipilimumab; brentuximab vedotin; pertuzumab; ado-trastuzumab emtansine; and obinutuzumab. Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab or tremelimumab). In some embodiments, the inhibitor of checkpoint is an inhibitor (e.g., an inhibitory antibody or small molecule inhibitor) of PD-1 (e.g., nivolumab; pembrolizumab; pidilizumab). In some embodiments, the inhibitor of checkpoint is an inhibitor (e.g., an inhibitory antibody or small molecule inhibitor) of PDL1 (e.g., atezolizumab; durvalumab; avelumab; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., enoblituzumab), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1 to 7, 1 to 14, 1 to 21, or 1 to 30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers. A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-100 mg/kg.

EXAMPLES

Example 1. Synthesis of Compounds of the Invention

Preparation of tert-Butyl N-[2-[2-(2-[[2-(2,6-dioxopiperidin-3-yl)-1,3-dioxo-2,3-dihydro-1H-isoindol-5-yl]amino]ethoxy)ethoxy]ethyl]carbamate trifluoroacetate (I-1)

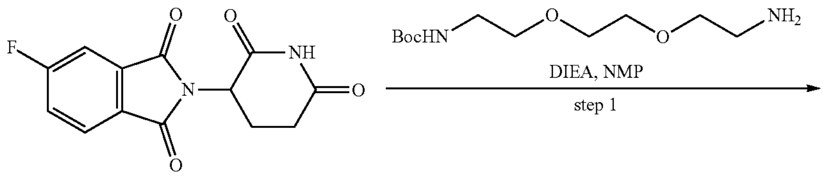

A

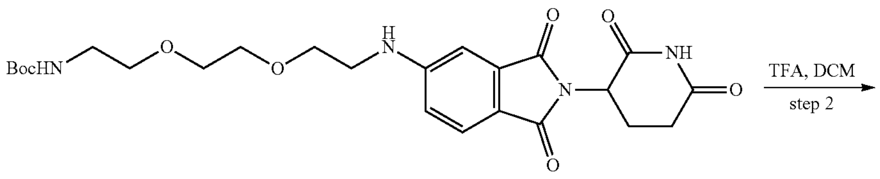

B

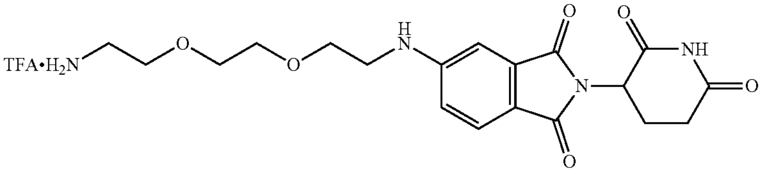

I-1

Step 1: Preparation of tert-butyl N-[2-[2-(2-[[2-(2,6-dioxopiperidin-3-yl)-1,3-dioxo-2,3-dihydro-1H-isoindol-5-yl]amino]ethoxy)ethoxy]ethyl]carbamate (B)

B

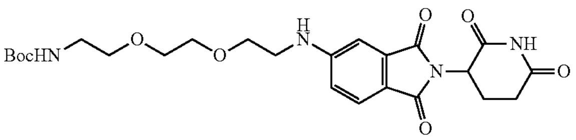

To a stirred mixture of 2-(2,6-dioxopiperidin-3-yl)-5-fluoro-2,3-dihydro-1H-isoindole-1,3-dione (A, 3.00 g, 10.861 mmol, 1.00 equiv) and tert-butyl N-[2-[2-(2-amino-ethoxy)ethoxy]ethyl]carbamate (4.05 g, 16.291 mmol, 1.50 equiv) in NMP (30 mL) was added DIEA (4.21 g, 32.58 mmol, 3.00 equiv) at 90° C. After 3 h, water was added to the mixture (100 mL) followed by extraction with EtOAc (3×200 mL). The residue was purified by reverse phase flash chromatography under the following conditions: column, C18 silica gel; mobile phase, ACN in water, 0% to 50% gradient; detector, UV 254 nm. This resulted in B (1.18 g, 19.94%) as a yellow solid. LCMS (ESI) m/z: $[M+H]^+$=505.

Step 2: Preparation of 5-([2-[2-(2-aminoethoxy)ethoxy]ethyl]amino)-2-(2,6-dioxopiperidin-3-yl)-2,3-dihydro-1H-isoindole-1,3-dione trifluoroacetate (I-1)

I-1

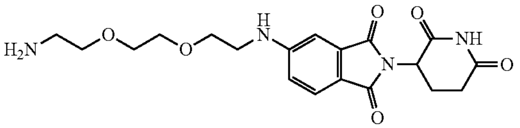 •TFA

To a stirred mixture of B (1.18 g, 0.002 mmol, 1.00 equiv) in DCM (6.00 mL) was added TEA (2.00 mL) at room temperature. The resulting mixture was stirred for 1 h at room temperature. The resulting mixture was concentrated under reduced pressure. This provided I-1 (1.08 g, 89%) as a yellow solid. $^1$H NMR (400 MHz, DMSO-d6) δ 8.38 (d, 1H, formic acid), 7.57 (d, 1H), 7.24 (s, 1H), 7.02 (d, 1H), 6.91 (dd, 1H), 5.04 (dd, 1H), 3.58 (tt, 8H), 3.37 (q, 2H), 2.95-2.81 (m, 3H), 2.63-2.51 (m, 2H), 2.00 (ddq, 1H). LCMS (ESI) m/z: $[M+H]^+$=405.17.

TABLE 2

The following intermediates were prepared in a similar manner as described in the preparation of intermediate I-1.

| Structure | # | Name | LCMS (ESI) m/z: $[M + H]^+$ |
|---|---|---|---|
| 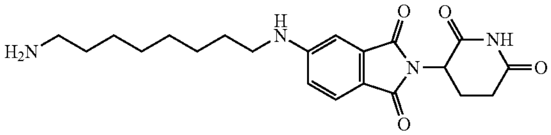 [SMILES: NCCCCCCCCNc1ccc2c(c1)C(=O)N(C1CCC(=O)NC1=O)C2=O] | I-2 | 5-((8-aminooctyl)amino)-2-(2,6-dioxopiperidin-3-yl)isoindoline-1,3-dione | 401.15 |
| 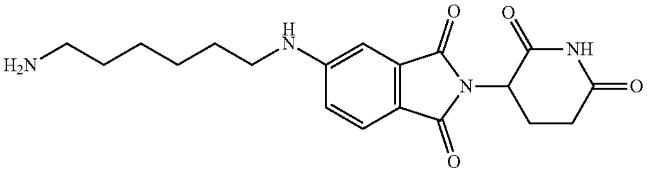 [SMILES: NCCCCCCNc1ccc2c(c1)C(=O)N(C1CCC(=O)NC1=O)C2=O] | I-3 | 5-((6-aminohexyl)amino)-2-(2,6-dioxopiperidin-3-yl)isoindoline-1,3-dione | 373.3 |
| 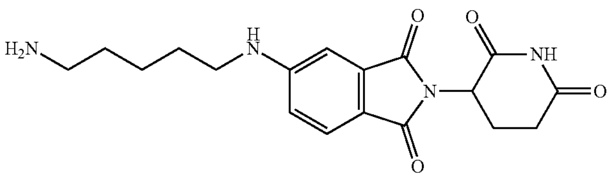 [SMILES: NCCCCCNc1ccc2c(c1)C(=O)N(C1CCC(=O)NC1=O)C2=O] | I-4 | 5-((5-aminopentyl)amino)-2-(2,6-dioxopiperidin-3-yl)isoindoline-1,3-dione | 359.15 |
| 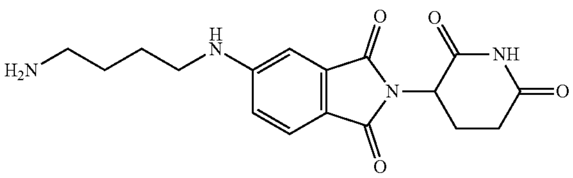 [SMILES: NCCCCNc1ccc2c(c1)C(=O)N(C1CCC(=O)NC1=O)C2=O] | I-5 | 5-((4-aminobutyl)amino)-2-(2,6-dioxopiperidin-3-yl)isoindoline-1,3-dione | 345.15 |

TABLE 2-continued

The following intermediates were prepared in a similar manner as described in the preparation of intermediate I-1.

| Structure | # | Name | LCMS (ESI) m/z: [M + H]$^+$ |
|---|---|---|---|
| 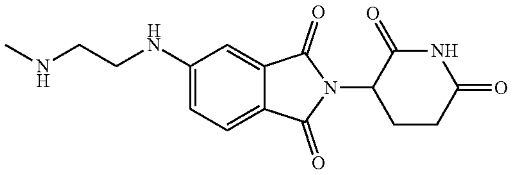 [SMILES: CNCCNc1ccc2c(c1)C(=O)N(C1CCC(=O)NC1=O)C2=O] | I-6 | 2-(2,6-dioxopiperidin-3-yl)-5-[[2-(methylamino)ethyl]amino]isoindole-1,3-dione | 331 |
| 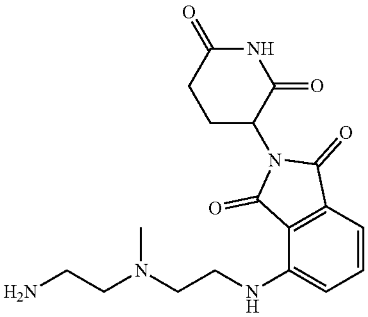 [SMILES: CN(CCN)CCNc1cccc2c1C(=O)N(C1CCC(=O)NC1=O)C2=O] | I-7 | 4-([2-[(2-aminoethyl)(methyl)amino]ethyl] amino)-2-(2,6-dioxopiperidin-3-yl)isoindole-1,3-dione | 374.15 |
| 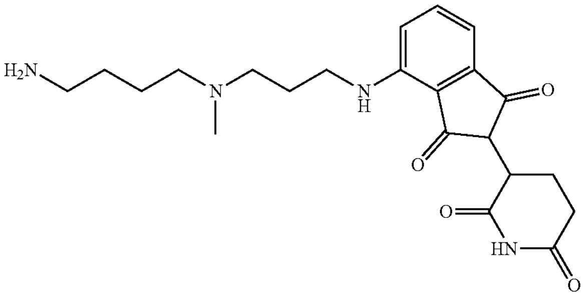 [SMILES: CN(CCCCN)CCCNc1cccc2c1C(=O)C(C1CCC(=O)NC1=O)C2=O] | I-8 | 4-((3-((4-aminobutyl)(methyl)amino)propyl) amino)-2-(2,6-dioxopiperidin-3-yl)isoindoline-1,3-dione | 416.25 |
| 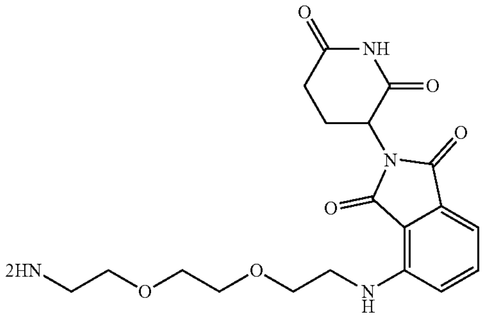 | I-9 | 4-((2-(2-(2-aminoethoxy)ethoxy)ethyl)amino)-2-(2,6-dioxopiperidin-3-yl)isoindoline-1,3-dione | 405.4 |
| 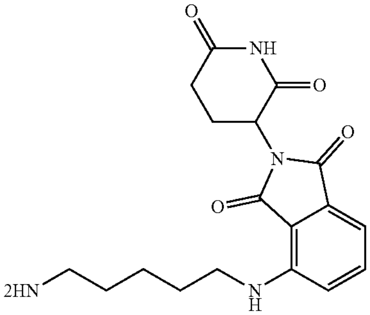 | I-10 | 4-((5-aminopentyl)amino)-2-(2,6-dioxopiperidin-3-yl)isoindoline-1,3-dione | 359.4 |

Preparation of 4-[[2-(2,6-Dioxopiperidin-3-yl)-1,3-dioxo-2,3-dihydro-1H-isoindol-4-yl]oxy]butanoic acid (I-11)

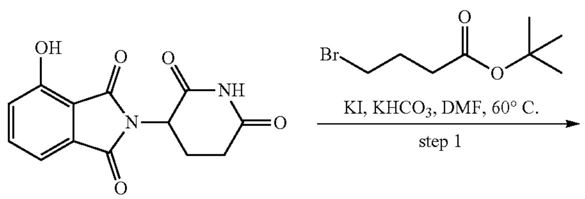

A

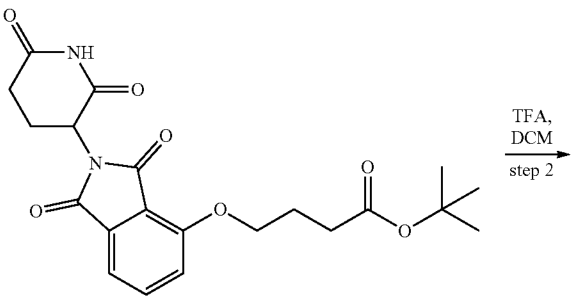

B

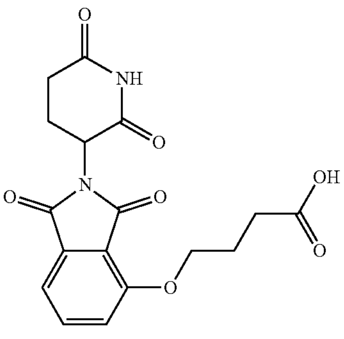

I-11

Step 1: Preparation of tert-butyl 4-[[2-(2,6-dioxopiperidin-3-yl)-1,3-dioxoisoindol-4-yl]oxy] butanoate (B)

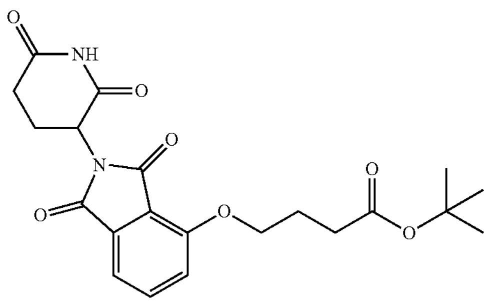

B

To a solution of 2-(2,6-dioxopiperidin-3-yl)-4-hydroxyisoindole-1,3-dione (A, 2.00 g, 7.293 mmol, 1.00 equiv) and tert-butyl 4-bromobutanoate (1.95 g, 8.752 mmol, 1.2 equiv) in DMF (10.00 mL) was added KI (0.12 g, 0.729 mmol, 0.1 equiv) and $KHCO_3$ (1.10 g, 10.940 mmol, 1.5 equiv), and the resulting solution was stirred at 60° C. for 5 h. The mixture was diluted with EtOAc (50 mL) and washed with water (50 mL×3). The organic layer was dried over anhydrous sodium sulfate, filtered and concentrated to give a crude product. The crude product was purified by flash C18 chromatography, elution gradient 0 to 32% ACN in water to give B (1.5 g, 49.39%) as an off-white solid. LCMS (ESI) m/z $[M+H]^+$=417.

Step 2: Preparation of 4-[[2-(2,6-dioxopiperidin-3-yl)-1,3-dioxo-2,3-dihydro-1H-isoindol-4-yl]oxy] butanoic acid (I-11)

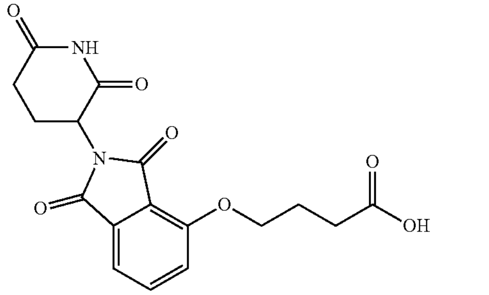

I-11

To a stirred solution of B (450 mg, 1.081 mmol, 1 equiv) in DCM (5 mL) was added TFA (1 mL). The resulting solution was stirred for 2 h at 25° C. then concentrated. This resulted in 360 mg (92.46%) of I-11 as a white solid. $^1H$ NMR (400 MHz, Methanol-d4) δ 7.79 (t, J=8.4, 7.4 Hz, 1H), 7.47 (d, J=7.8 Hz, 2H), 5.12 (dd, J=12.6, 5.5 Hz, 1H), 4.30 (t, J=6.2 Hz, 2H), 2.95-2.66 (m, 3H), 2.60 (t, J=7.3 Hz, 2H), 2.25-2.18 (m, 3H). LCMS (ESI) m/z: $[M+H]^+$=361.10.

TABLE 3
| The following intermediates were prepared in a similar manner as described in the preparation of intermediate I-11. | | | |
|---|---|---|---|
| Structures | # | Name | LCMS (ESI) m/z: $[M + H]^+$ |
| 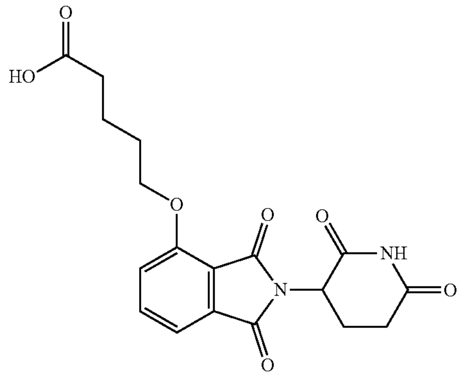 [SMILES: O=C(O)CCCCOc1cccc2c1C(=O)N(C1CCC(=O)NC1=O)C2=O] | I-12 | 5-((2-(2,6-dioxopiperidin-3-yl)-1,3-dioxoisoindolin-4-yl)oxy)pentanoic acid | 375.1 |
| 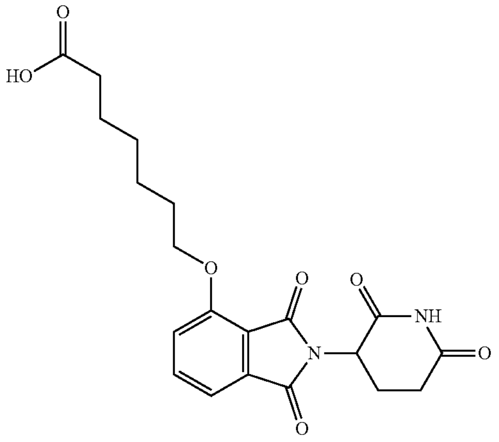 [SMILES: O=C(O)CCCCCCOc1cccc2c1C(=O)N(C1CCC(=O)NC1=O)C2=O] | I-13 | 7-((2-(2,6-dioxopiperidin-3-yl)-1,3-dioxoisoindolin-4-yl)oxy)heptanoic acid | 403.1 |
| 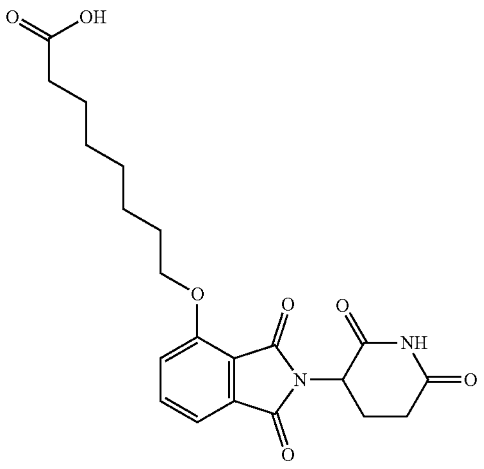 [SMILES: O=C(O)CCCCCCCOc1cccc2c1C(=O)N(C1CCC(=O)NC1=O)C2=O] | I-14 | 8-((2-(2,6-dioxopiperidin-3-yl)-1,3-dioxoisoindolin-4-yl)oxy)octanoic acid | 417.15 |

TABLE 3-continued

| The following intermediates were prepared in a similar manner as described in the preparation of intermediate I-11. | | | |
|---|---|---|---|
| Structures | # | Name | LCMS (ESI) m/z: $[M + H]^+$ |
| 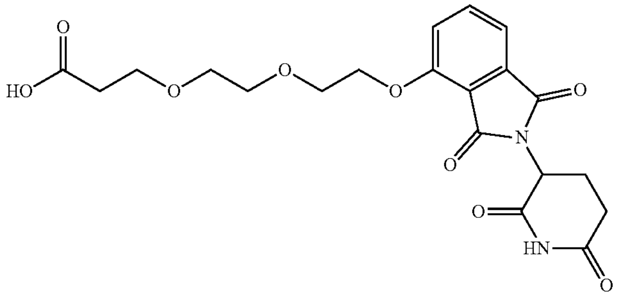 [SMILES: O=C(O)CCOCCOCCOc1cccc2c1C(=O)N(C1CCC(=O)NC1=O)C2=O] | I-15 | 3-(2-(2-((2-(2,6-dioxopiperidin-3-yl)-1,3-dioxoisoindolin-4-yl)oxy)ethoxy)ethoxy)propanoic acid | 435.25 |
| 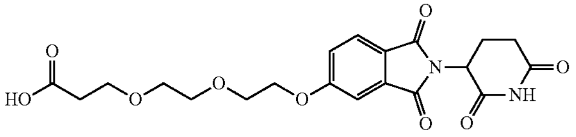 [SMILES: O=C(O)CCOCCOCCOc1ccc2c(c1)C(=O)N(C1CCC(=O)NC1=O)C2=O] | I-16 | 3-(2-(2-((2-(2,6-dioxopiperidin-3-yl)-1,3-dioxoisoindolin-5-yl)oxy)ethoxy)ethoxy)propanoic acid | 435.2 |

Preparation of 3-(2-(2-((2-(2,6-dioxopiperidin-3-yl)-1,3-dioxoisoindolin-4-yl)amino)ethoxy)ethoxy)propanoic acid (I-17)

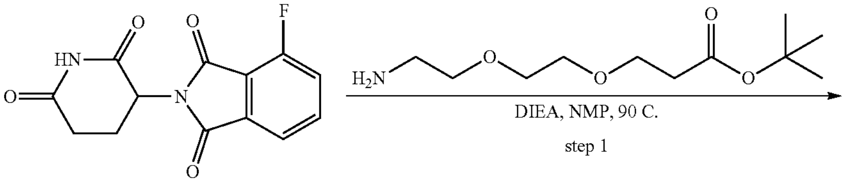

A

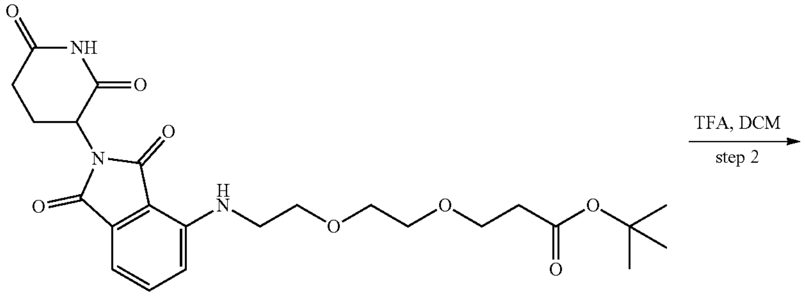

B

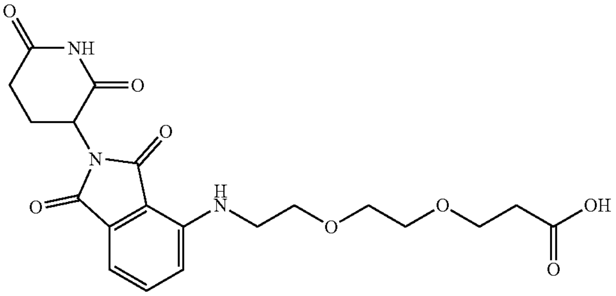

I-17

Step 1: Preparation of tert-butyl 3-(2-(2-((2-(2,6-dioxopiperidin-3-yl)-1,3-dioxoisoindolin-4-yl)amino)ethoxy)ethoxy)propanoate (B)

B

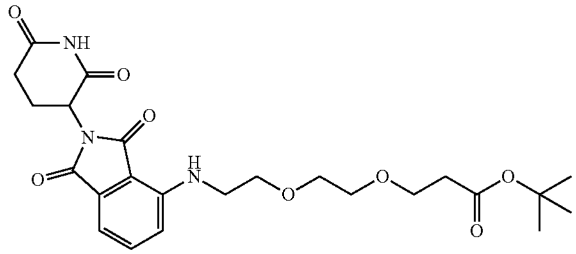

To a solution of 2-(2,6-dioxopiperidin-3-yl)-4-fluoro-2,3-dihydro-1H-isoindole-1,3-dione (A, 1.00 g, 3.620 mmol, 1.00 equiv) in NMP (10.00 mL) was added tert-butyl 3-[2-(2-aminoethoxy)ethoxy]propanoate (929.10 mg, 3.982 mmol, 1.10 equiv). The resulting mixture was stirred overnight at 90° C. The mixture was allowed to cool down to room temperature, then diluted with EtOAc (30 mL). The solution was washed with water (10 mL×5), and then brine (20 mL). The resulting mixture was concentrated under reduced pressure, and the residue was purified by silica gel column chromatography, eluting with Petroleum ether/EtOAc (from 5:1 to 1:1) to afford B (1.14 g, 64.33%) as a yellow solid. LCMS (ESI) m/z: $[M+H]^+$=490.

Step 2: Preparation of 3-(2-(2-((2-(2,6-dioxopiperidin-3-yl)-1,3-dioxoisoindolin-4-yl)amino)ethoxy)ethoxy)propanoic acid (I-17)

I-17

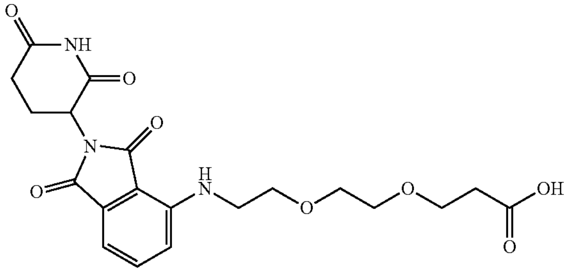

To a stirred solution of B (1.14 g, 2.329 mmol, 1.00 equiv) in DCM (10.00 mL) was added TFA (0.52 mL, 4.551 mmol, 3.00 equiv) dropwise at room temperature. The resulting mixture was stirred for 2 h at room temperature then concentrated under vacuum. The residue was purified by reverse phase flash chromatography under the following conditions: column, C18 spherical column; mobile phase, ACN in water, 0% to 100% gradient over 50 min; 70 ml/min; detector, UV 254 nm to provide I-17 (896 mg, 70.28%) as a yellow solid. $^1$H NMR (400 MHz, DMSO-d6) δ 12.15 (s, 1H), 11.09 (s, 1H), 7.63-7.55 (m, 1H), 7.15 (d, 1H), 7.05 (d, 1H), 6.61 (t, 1H), 5.06 (dd, 1H), 3.65-3.44 (m, 8H), 2.87 (d, 1H), 2.59 (d, 2H), 2.43 (t, 2H), 2.04 (m, 1H); LCMS (ESI) m/z: $[M+H]^+$=434.15.

TABLE 4

The following intermediates were prepared in a similar manner as described in the preparation of intermediate I-17.

| Structures | # | Name | LCMS (ESI) m/z: [M + H]$^+$ |
|---|---|---|---|
| 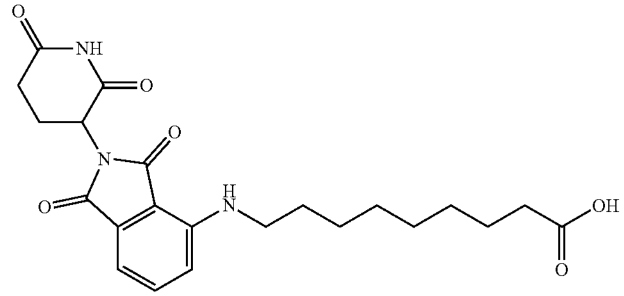 [SMILES: O=C(O)CCCCCCCCNc1cccc2c1C(=O)N(C1CCC(=O)NC1=O)C2=O] | I-18 | 9-[[2-(2,6-dioxopiperidin-3-yl)-1,3-dioxo-2,3-dihydro-1H-isoindol-4-yl]amino]nonanoic acid | 430.19 |
| 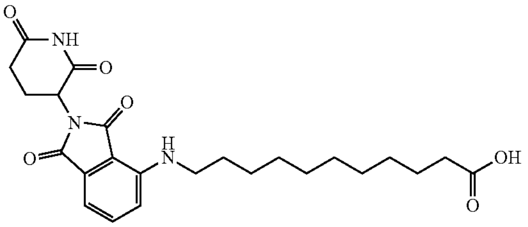 [SMILES: O=C(O)CCCCCCCCCCNc1cccc2c1C(=O)N(C1CCC(=O)NC1=O)C2=O] | I-19 | 11-((2-(2,6-dioxopiperidin-3-yl)-1,3-dioxoisoindolin-4-yl)amino)undecanoic acid | 458.3 |
| 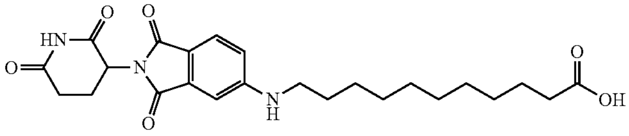 [SMILES: O=C(O)CCCCCCCCCCNc1ccc2c(c1)C(=O)N(C1CCC(=O)NC1=O)C2=O] | I-20 | 11-((2-(2,6-dioxopiperidin-3-yl)-1,3-dioxoisoindolin-5-yl)amino)undecanoic acid | 458.4 |

TABLE 4-continued

| The following intermediates were prepared in a similar manner as described in the preparation of intermediate I-17. | | | |
|---|---|---|---|
| Structures | # | Name | LCMS (ESI) m/z: [M + H]$^+$ |
| 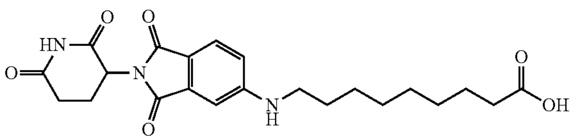 [SMILES: O=C(O)CCCCCCCCNc1ccc2c(c1)C(=O)N(C1CCC(=O)NC1=O)C2=O] | I-21 | 9-((2-(2,6-dioxopiperidin-3-yl)-1,3-dioxoisoindolin-5-yl)amino)nonanoic acid | 430.2 |
| 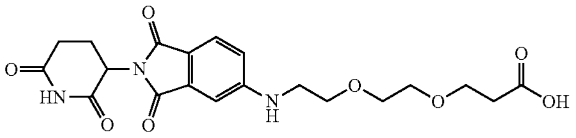 [SMILES: O=C(O)CCOCCOCCNc1ccc2c(c1)C(=O)N(C1CCC(=O)NC1=O)C2=O] | I-22 | 3-(2-(2-((2-(2,6-dioxopiperidin-3-yl)-1,3-dioxoisoindolin-5-yl)amino)ethoxy)ethoxy)propanoic acid | 434.2 |

Preparation of 2-[(2-[[2-(2,6-dioxopiperidin-3-yl)-1,3-dioxoisoindol-5-yl]oxy]acetamido)methyl]cyclopropane-1-carboxylic acid (I-23)

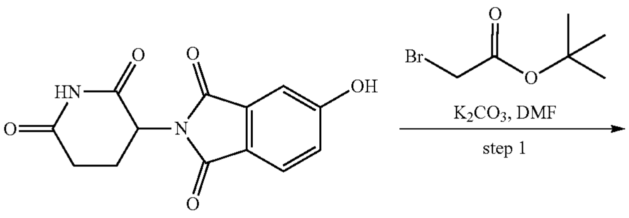

A

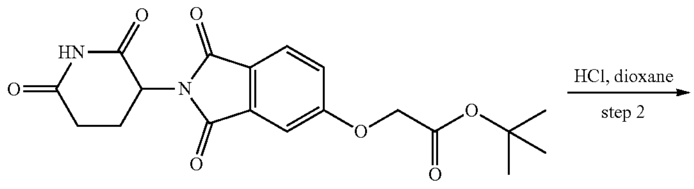

B

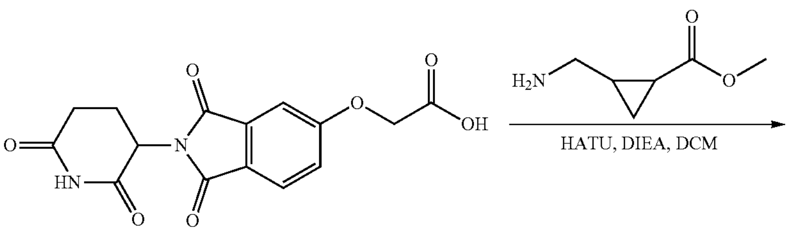

I-100

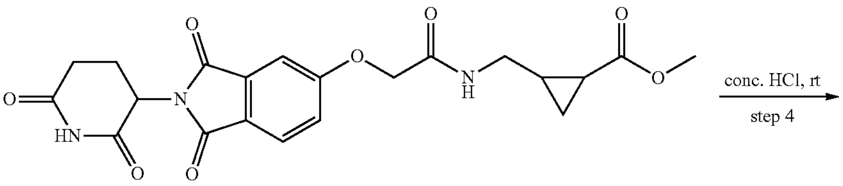

C

-continued

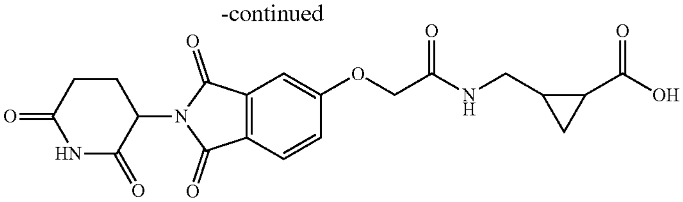

I-23

Step 1: Preparation of tert-butyl 2-[[2-(2,6-dioxopiperidin-3-yl)-1,3-dioxoisoindol-5-yl]oxy] acetate (B)

B

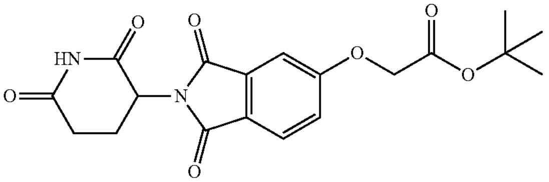

To a stirred solution of 2-(2,6-dioxopiperidin-3-yl)-5-hydroxyisoindole-1,3-dione (A, 5.50 g, 20.056 mmol, 1.00 equiv) and tert-butyl 2-bromoacetate (3.91 g, 20.056 mmol, 1.00 equiv) in DMF (15.00 mL) was added K2CO3 (8.32 g, 60.168 mmol, 3 equiv) dropwise at room temperature. The resulting mixture was washed with 3×200 mL EtOAc. The residue was purified by reverse phase flash chromatography under the following conditions: column, 018 silica gel; mobile phase, ACN in water, 10% to 50% gradient over 10 min; detector, UV 254 nm. This resulted in B (3.2 g, 45.19%) as an off-white solid. LCMS (ESI) m/z: $[M+H]^+$=389.

Step 2: Preparation of [[2-(2,6-dioxopiperidin-3-yl)-1,3-dioxoisoindol-5-yl]oxy]acetic acid (I-100)

I-100

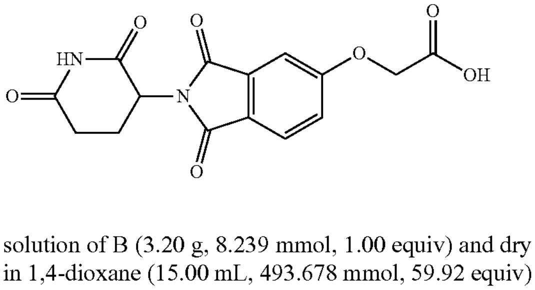

A solution of B (3.20 g, 8.239 mmol, 1.00 equiv) and dry HCl in 1,4-dioxane (15.00 mL, 493.678 mmol, 59.92 equiv) was stirred for 2 h at room temperature. The resulting mixture was concentrated under reduced pressure. This resulted in I-100 (1.12 g) as a yellow solid. LCMS (ESI) m/z: $[M+H]^+$=289.

Step 3: Preparation of methyl 2-[(2-[[2-(2,6-dioxopiperidin-3-yl)-1,3-dioxoisoindol-5-yl]oxy]acetamido) methyl]cyclopropane-1-carboxylate (C)

C

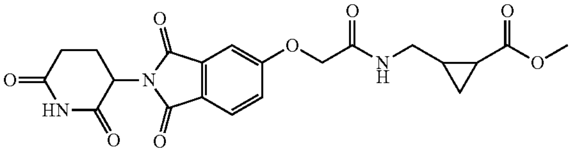

To a stirred solution of I-100 (670.00 mg, 2.016 mmol, 1.00 equiv) and methyl 2-(aminomethyl)cyclopropane-1-carboxylate (260.44 mg, 2.016 mmol, 1.00 equiv) in DMF (15.00 mL) was added HATU (1150.07 mg, 3.025 mmol, 1.50 equiv) and then DIEA (781.84 mg, 6.049 mmol, 3.00 equiv) dropwise over 2 h at room temperature. The resulting mixture was concentrated under reduced pressure and the residue purified by reverse phase flash chromatography under the following conditions: column, C18 silica gel; mobile phase, ACN in water, 10% to 50% gradient over 10 min; detector, UV 254 nm. This resulted in C (778.6 mg, 78.37%) as a yellow oil. LCMS (ESI) m/z: $[M+H]^+$=444.

Step 4: Preparation of 2-[(2-[[2-(2,6-dioxopiperidin-3-yl)-1,3-dioxoisoindol-5-yl]oxy]acetamido)methyl] cyclopropane-1-carboxylic acid (I-23)

I-23

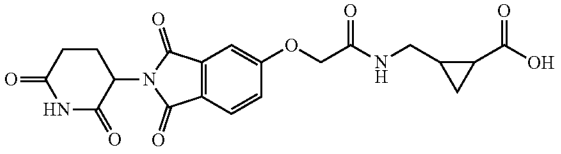

A mixture of C (763.90 mg, 1.00 equiv) in 1,4-dioxane (5.00 mL) and dry HCl in 1,4-dioxane (4M, 5.00 mL) was stirred for 2 h at room temperature. The resulting mixture was concentrated under reduced pressure and the residue was purified by reverse phase flash chromatography under the following conditions: column, C18 silica gel; mobile phase, ACN in water, 10% to 50% gradient over 10 min; detector, UV 254 nm. This resulted in Compound I-23 (338.2 mg) as a yellow solid. $^1$H NMR (400 MHz, DMSO-d6) δ 12.17 (s, 1H), 11.12 (s, 1H), 8.33 (t, 1H), 7.88 (d, 1H), 7.46 (d, 1H), 7.39 (dd, 1H), 5.13 (dd, 1H), 4.74 (s, 2H), 2.96-2.83 (m, 1H), 2.65-2.52 (m, 1H), 2.08 (s, 4H), 1.66 (td, 1H), 1.48 (h, 1H), 1.02 (td, 1H), 0.85 (dt, 1H). LCMS (ESI) m/z: $[M+H]^+$=430.05.

Preparation of methyl 2-[(2-[[2-(2,6-dioxopiperidin-3-yl)-1,3-dioxoisoindol-4-yl]oxy]acetamido)methyl]cyclopropane-1-carboxylic acid (I-24)

I-24

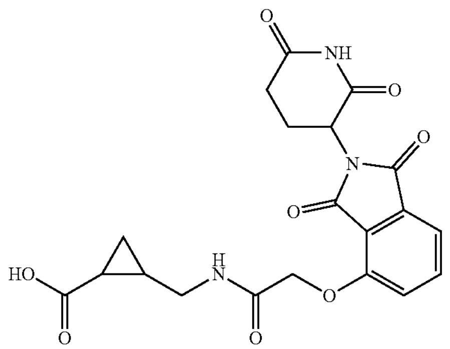

I-24 (423 mg, 35.74%) was prepared as a white solid in a similar manner as described in the preparation of intermediate I-23. $^1$H NMR (300 MHz, DMSO-d6) δ 12.16 (s, 1H), 11.12 (s, 1H), 8.10 (s, 1H), 7.82 (t, 1H), 7.51 (d, 1H), 7.41 (d, 1H), 5.17-5.07 (m, 1H), 4.80 (s, 2H), 2.60 (d, 2H), 2.08 (s, 3H), 1.70-1.60 (m, 1H), 1.47 (d, 1H), 1.03 (d, 1H), 0.84 (d, 1H); LCMS (ESI) m/z: $[M+H]^+$=430.12.

Preparation of N-[2-[(2-aminoethyl)(methyl)amino]ethyl]-2-[[2-(2,6-dioxopiperidin-3-yl)-1,3-dioxoisoindol-5-yl]oxy]acetamide (I-25)

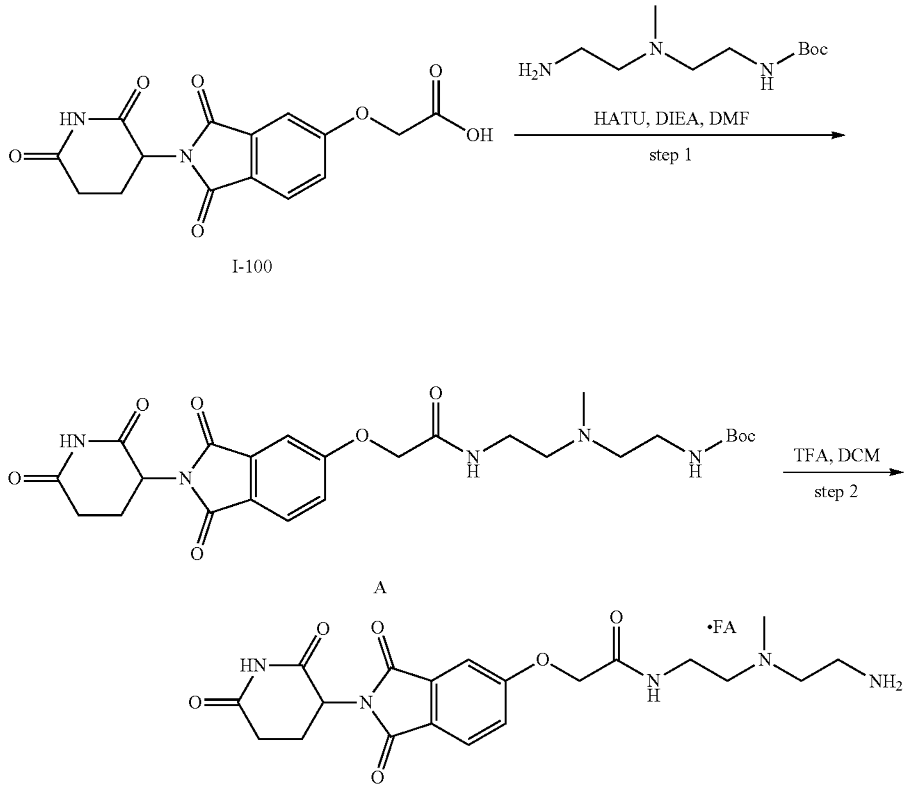

I-100

A

I-25

Step 1: Preparation of tert-butyl N-(2-[[2-(2-[[2-(2,6-dioxopiperidin-3-yl)-1,3-dioxoisoindol-5-yl]oxy]acetamido)ethyl](methyl)amino]ethyl)carbamate (A)

A

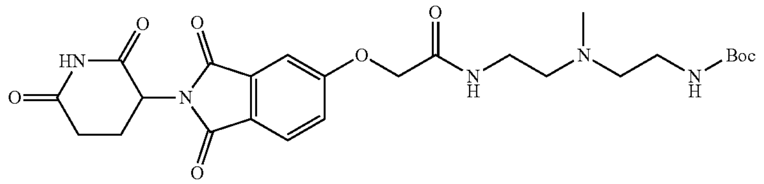

To a stirred solution of I-100 (963.50 mg, 2.900 mmol, 1.00 equiv) and tert-butyl N-[2-[(2-aminoethyl)(methyl)amino]ethyl]carbamate (945.24 mg, 4.350 mmol, 1.50 equiv) in DCM was added HATU (1.65 g, 4.350 mmol, 1.50 equiv), then DIEA (1.12 g, 8.699 mmol, 3.00 equiv) dropwise at 25° C. over 2 h. The residue was purified by silica gel column chromatography, eluting with Petroleum ether/EtOAc (1:1) to afford A (898.6 mg, 58.30%) as a yellow solid. LCMS (ESI) m/z: $[M+H]^+=532$.

Step 2: Preparation of N-[2-[(2-aminoethyl)(methyl)amino]ethyl]-2-[[2-(2,6-dioxopiperidin-3-yl)-1,3-dioxoisoindol-5-yl]oxy]acetamide formate (I-25)

I-25

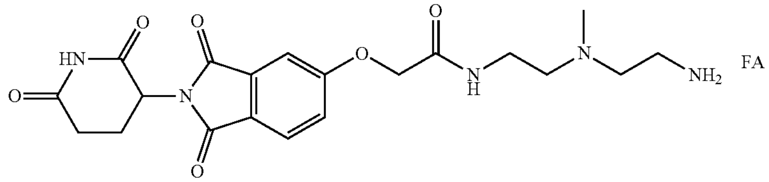

To a stirred mixture of B (309.00 mg, 0.581 mmol, 1.00 equiv) in DCM (4.00 mL, 62.920 mmol, 108.24 equiv) was added TFA (1.00 mL, 13.463 mmol, 23.16 equiv). The solution was stirred at room temperature for 2 h under a nitrogen atmosphere. The resulting mixture was concentrated under reduced pressure, then purified by reverse phase flash chromatography under the following conditions: column, C18 silica gel; mobile phase, ACN in water, 10% to 50% gradient over 35 min; detector, UV 254 nm. This resulted in I-25 (268 mg, 93.71%) as a light yellow solid. $^1$H NMR (300 MHz, methanol-d4) δ 7.88 (d, 1H), 7.53 (d, 1H), 7.46 (dd, 1H), 5.14 (dd, 1H), 4.82 (s, 2H), 3.75 (t, 2H), 3.60 (d, 2H), 3.46 (q, 4H), 3.03 (s, 3H), 2.90-2.64 (m, 3H), 2.22-2.07 (m, 1H). LCMS (ESI) m/z: $[M+H]^+$=432.20.

Preparation of N-[2-[(2-aminoethyl)(methyl)amino]ethyl]-2-[[2-(2,6-dioxopiperidin-3-yl)-1,3-dioxo-2,3-dihydro-1H-isoindol-4-yl]oxy]acetamide (I-26)

I-26

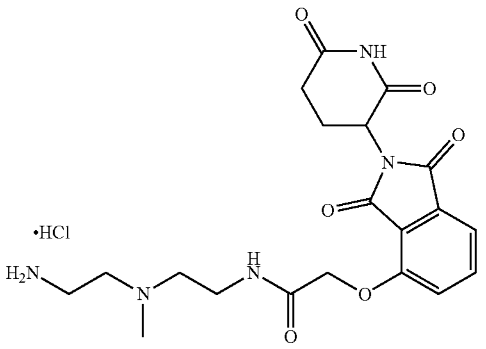

I-26 (200 mg, 41.07%) as a yellow solid was prepared in a similar manner as described in the preparation of I-25. $^1$H NMR (400 MHz, DMSO-d6) δ 11.13 (s, 1H), 11.02 (s, 1H), 8.50-8.42 (m, 4H), 7.85-7.77 (m, 1H), 7.49 (dd, 2H), 5.12 (dd, 1H), 4.90 (s, 2H), 3.65-3.43 (m, 7H), 2.90 (m, 1H), 2.84 (s, 3H), 2.65-2.51 (m, 2H), 2.04 (dtt, 1H), 1.33-1.19 (m, 2H); LCMS (ESI) m/z: $[M+H]^+$=432.18.

Preparation of 4-[[3-(4-aminobutanesulfonyl)propyl]amino]-2-(2,6-dioxopiperidin-3-yl)isoindole-1,3-dione formate (I-27)

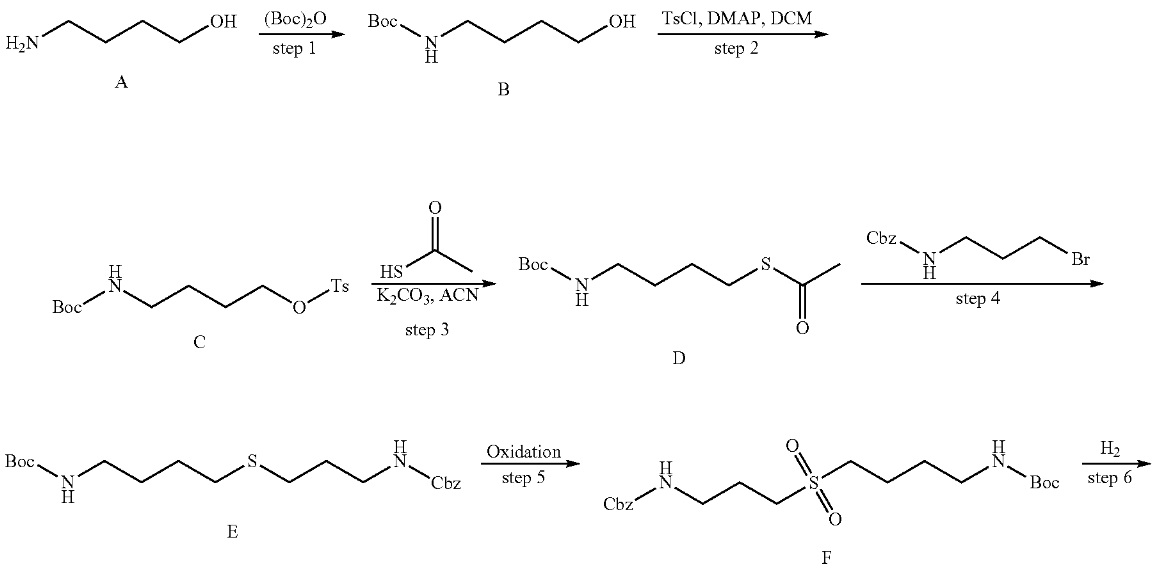

-continued

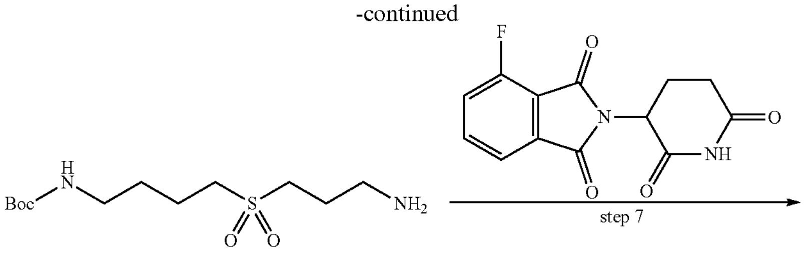

G

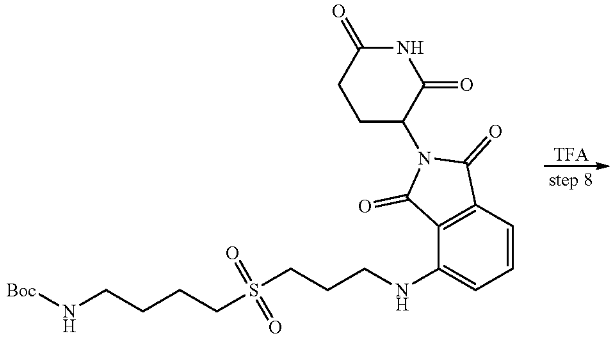

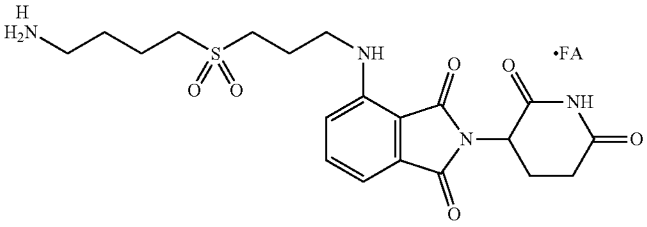

I-27

Step 1: Preparation of tert-butyl N-(4-hydroxybutyl)carbamate (B)

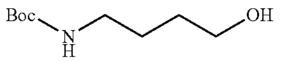

B

Di-tert-butyl dicarbonate (52.89 g, 242.321 mmol, 1.5 equiv) was added to a stirred solution of 4-aminobutan-1-ol (A, 14.40 g, 161.547 mmol, 1.00 equiv) in THE (160.00 mL), and the mixture was stirred at room temperature for 1 h. The solution was concentrated to dryness, and the oily residue was purified by flash column chromatography (40-60% EtOAc-hexane) to give a colorless oil that solidified to a white solid on standing (B, 30.58 g, 100.02%); LCMS (ESI) m/z: $[M+H]^+$=190.

Step 2: Preparation of tert-butyl N-[4-[(4-methylbenzenesulfonyl)oxy]butyl]carbamate (C)

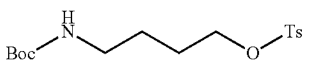

C

To a stirred solution of B (30.58 g, 161.581 mmol, 1.00 equiv) in DCM (400.00 mL) was added DMAP (2.96 g, 24.237 mmol, 0.15 equiv), TEA (40.88 g, 403.952 mmol, 2.5 equiv) and p-toluenesulfonyl chloride (46.21 g, 242.371 mmol, 1.5 equiv) at 0° C. The resulting mixture was stirred for 2 h at 0° C., then warmed to room temperature and stirred for an additional 5 h. The mixture was concentrated and the residue purified by silica gel column chromatography, eluting with Petroleum ether/THF (1:1) to afford C (45.6 g, 82.17%) as a light-yellow oil; LCMS (ESI) m/z: $[M+H]^+$=344.

Step 3: Preparation of tert-butyl N-[4-(acetylsulfany)butyl]carbamate (D)

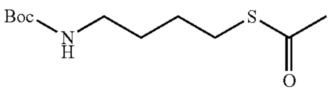

D

To a stirred solution of C (45.60 g, 132.77 mmol, 1.00 equiv) in ACN (300.00 mL) was added Schiff reagent (15.16 g, 199.161 mmol, 1.5 equiv) and $K_2CO_3$ (55.05 g, 398.323 mmol, 3 equiv). The resulting mixture was stirred for 12 h at room temperature, worked up with 1 M HCl, then extracted into DCM and concentrated. The residue was purified by silica gel column chromatography, eluting with Petroleum ether/THF (1:1) to afford D (28.7 g, 87.39%) as a light-yellow oil; LCMS (ESI) m/z: $[M+H]^+$=248.

Step 4: Preparation of benzyl N-[3-([4-[(tert-butoxycarbonyl)amino]butyl]sulfanyl)propyl]carbamate (E)

E

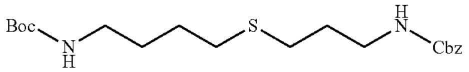

To the solution of D (3.60 g, 14.554 mmol, 1.00 equiv) in MeOH (90.00 mL) was added benzyl N-(3-bromopropyl) carbamate (4.36 g, 16.010 mmol, 1.1 equiv) and NaOMe (3.15 g, 58.217 mmol, 4 equiv). The resulting solution was stirred at room temperature for 3 h. The reaction was quenched with water at room temperature and the resulting mixture extracted with EtOAc (3×100 mL). The combined organic layers were washed with brine (3×100 mL) and dried over anhydrous $Na_2SO_4$. After filtration, the filtrate was concentrated under reduced pressure. The residue was purified by reverse phase flash chromatography under the following conditions: column, C18 silica gel; mobile phase, $NH_4HCO_3$ in water, 0% to 100% gradient over 30 min; detector, UV 254 nm. This resulted in E (4.122 g, 71.42%) as a light-yellow oil; LCMS (ESI) m/z: $[M+H]^+$=397.

Step 5: Preparation of benzyl N-(3-[4-[(tert-butoxycarbonyl)amino]butanesulfonyl]propyl)carbamate (F)

F

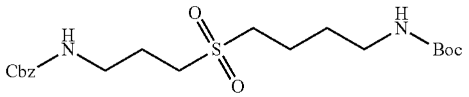

To a solution of E (4.13 g, 10.415 mmol, 1.00 equiv) in MeOH (60.00 mL) was added Oxone® (3.50 g, 20.840 mmol, 2 equiv). The resulting solution was stirred at room temperature for 12 h. Following aqueous workup and DCM extraction, the concentrated residue was purified by reverse phase flash chromatography under the following conditions: column, C18 silica gel; mobile phase, $NH_4HCO_3$ in water, 0% to 100% gradient over 30 min; detector, UV 254 nm. This resulted in F (2 g, 44.81%) as a white solid; LCMS (ESI) m/z: $[M+H]^+$=429.

Step 6: Preparation of tert-butyl N-[4-(3-aminopropanesulfonyl)butyl]carbamate (G)

G

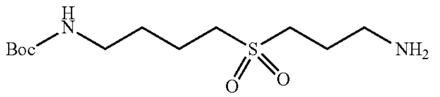

To a solution of F (1.95 g, 4.550 mmol, 1.00 equiv) in EtOH (30.00 mL) was added ammonium formate (573.85 mg, 9.101 mmol, 2 equiv) and $Pd(OH)_2$ on carbon (6.962 mmol, 1.53 equiv). The resulting suspension was stirred at 60° C. for 12 h under 1 atm of hydrogen. The resulting mixture was filtered, and the filter cake was washed with MeOH (3×30 mL). The filtrate was concentrated under reduced pressure to give G (1.12 g, Crude) as a black solid; LCMS (ESI) m/z: $[M+H]^+$=295.

Step 7: Preparation of tert-butyl N-[4-(3-[[2-(2,6-dioxopiperidin-3-yl)-1,3-dioxoisoindol-4-yl]amino]propanesulfonyl)butyl]carbamate (H)

H

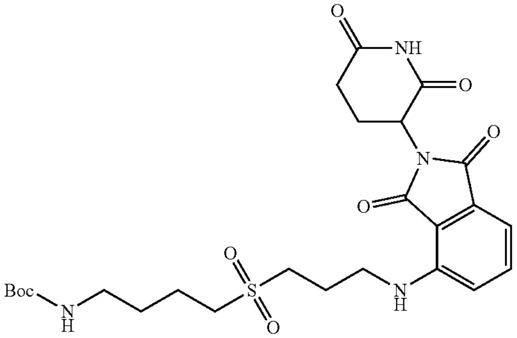

To a solution of G (1.12 g, 3.804 mmol, 1.00 equiv) in NMP (30.00 mL) was added 2-(2,6-dioxopiperidin-3-yl)-4-fluoroisoindole-1,3-dione (1.05 g, 3.804 mmol, 1 equiv) and DIEA (1.48 g, 11.413 mmol, 3 equiv). The resulting solution was stirred at 90° C. for 3 h under a nitrogen atmosphere. The resulting mixture was diluted with water (30 mL) and extracted with EtOAc (3×50 mL). The combined organic layers were washed with brine (3×30 mL) and dried over anhydrous $Na_2SO_4$. After filtration, the filtrate was concentrated under reduced pressure and the residue purified by reverse phase flash chromatography under the following conditions: column, C18 silica gel; mobile phase, ACN/0.1% formic acid in water, 0% to 100% gradient over 45 min; detector, UV 254 nm. This resulted in H (970 mg, 46.31%) as a yellow solid; LCMS (ESI) m/z: $[M+H]^+$=551.

Step 8: Preparation of 4-[[3-(4-aminobutanesulfonyl)propyl]amino]-2-(2,6-dioxopiperidin-3-yl)isoindole-1,3-dione formate (I-27)

I-27

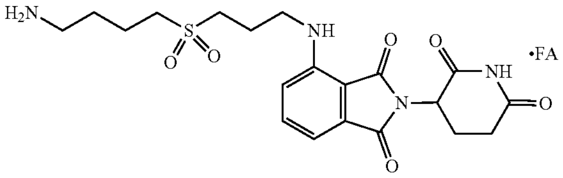

To a solution of H (970.00 mg, 1.762 mmol, 1.00 equiv) in 1,4-dioxane (5 mL) was added dry HCl in 1,4-dioxane (164.559 mmol, 93.41 equiv). The resulting solution was stirred at room temperature for 3 h. After concentration, the residue was purified by reverse phase flash chromatography under the following conditions: column, C18 silica gel; mobile phase, ACN/0.1% formic acid in water, 0% to 100% gradient over 45 min; detector, UV 220 nm. This resulted in I-27 (712 mg, 89.17%) as a yellow solid; $^1H$ NMR (300 MHz, methanol-d4) δ 8.55-8.48 (m, 1H, formic acid), 7.59

(ddd, 1H), 7.12 (ddd, 2H), 5.08 (dd, 1H), 3.56 (t, 2H), 3.33-3.14 (m, 4H), 3.04-2.93 (m, 2H), 2.96-2.63 (m, 3H), 2.24-2.06 (m, 3H), 2.00-1.75 (m, 4H); LCMS (ESI) m/z: $[M+H]^+$=451.16.

Preparation of 4-[[2-(2-aminoethanesulfonyl)ethyl]amino]-2-(2,6-dioxopiperidin-3-yl)isoindole-1,3-dione trifluoroacetate (I-28)

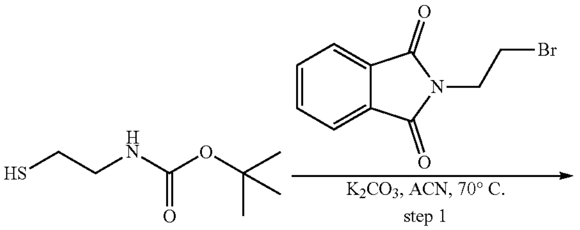

A

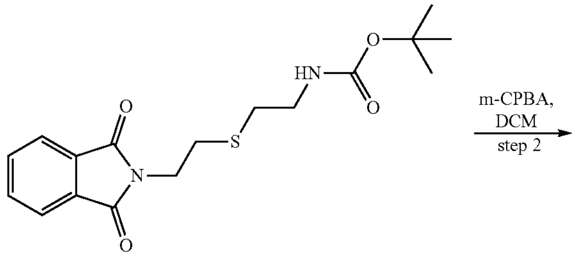

B

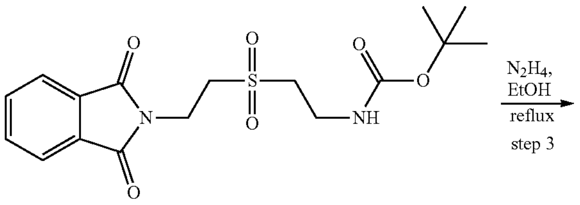

C

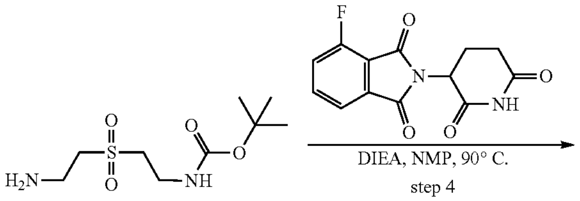

D

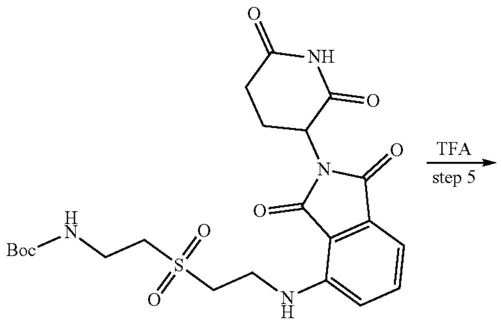

E

-continued

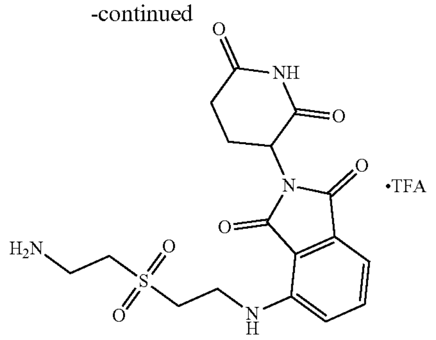

I-28

Step 1: Preparation of tert-butyl N-(2-[[2-(1,3-dioxoisoindol-2-yl)ethyl]sulfanyl]ethyl)carbamate (B)

B

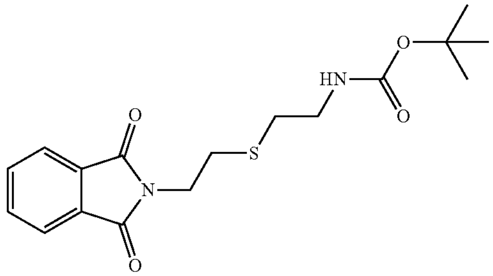

To a stirred mixture of tert-butyl N-(2-sulfanylethyl) carbamate (A, 5.00 g, 28.207 mmol, 1.00 equiv) and N-(2-bromoethyl)phthalimide (7.17 g, 0.028 mmol, 1.00 equiv) in ACN (10.00 mL) was added $K_2CO_3$ (11.70 g, 0.085 mmol, 3.00 equiv) at 70° C. under a nitrogen atmosphere. After 5 h, the resulting mixture was extracted with EtOAc (3×500 mL). The combined organic layers were washed with brine (3×300 mL) and dried over anhydrous $Na_2SO_4$. After filtration, the filtrate was concentrated under reduced pressure and purified by silica gel column chromatography, eluting with Petroleum ether/EtOAc (5:1 to 1:1), and affording B (8.20 g, 82.96%) as a white solid. LCMS (ESI) m/z: $[M+H]^+$= 351.

Step 2: Preparation of tert-butyl N-[2-[2-(1,3-dioxoisoindol-2-yl)ethanesulfonyl]ethyl]carbamate (C)

C

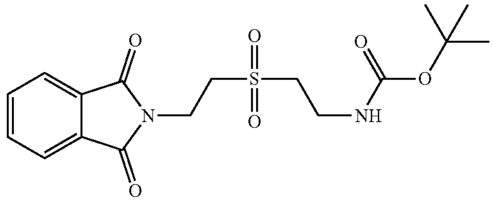

To a stirred mixture of B (8.20 g, 23.400 mmol, 1.00 equiv) in DCM (100 mL) was added m-CPBA (12.11 g, 70.199 mmol, 3.00 equiv) at room temperature under a nitrogen atmosphere. The reaction was quenched with sat.

$Na_2S_2O_3$ (aq) (100 mL) at room temperature. To the mixture was added sat. $NaHCO_3$ (aq.) (100 mL), followed by extraction with EtOAc (3×400 mL) and concentration under reduced pressure. The residue was purified by silica gel column chromatography, eluting with Petroleum ether/EtOAc (5:1 to 1:1) to afford C (8.40 g, 87.30%) as a white solid. LCMS (ESI) m/z: $[M+H]^+$=383.

Step 3: Preparation of tert-butyl N-[2-(2-aminoethanesulfonyl)ethyl]carbamate (D)

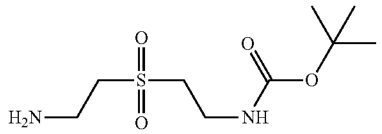 [SMILES: CC(C)(C)OC(=O)NCCS(=O)(=O)CCN]

To a stirred mixture of C (3.40 g, 8.891 mmol, 1.00 equiv) in EtOH (100 mL) was added hydrazine hydrate (0.89 g, 17.781 mmol, 2.00 equiv) at 80° C. The resulting mixture was stirred for 1 h at 80° C. under a nitrogen atmosphere. The suspension was filtered, and the filter cake was washed with EtOH (100 mL). The filtrate was concentrated under reduced pressure which resulted in D (crude, 1.88 g, 77.94%) as a white solid. LCMS (ESI) m/z: $[M+H]^+$=253.

Step 4: Preparation of N-[2-(2-[[2-(2,6-dioxopiperidin-3-yl)-1,3-dioxoisoindol-4-yl]amino]ethanesulfonyl)ethyl]carbamate (E)

E

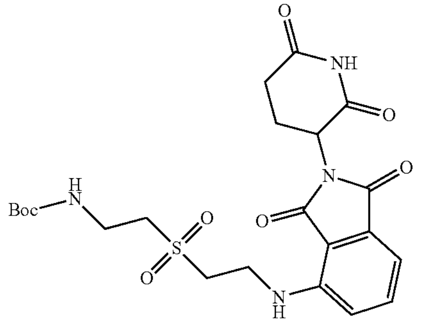

To a mixture of D (1.88 g, 7.451 mmol, 1.00 equiv) and 2-(2,6-dioxopiperidin-3-yl)-4-fluoroisoindole-1,3-dione (2.26 g, 8.196 mmol, 1.10 equiv) in NMP (25.00 mL) was added dropwise DIEA (2.89 g, 22.352 mmol, 3.00 equiv) at 90° C. under a nitrogen atmosphere. The resulting mixture was stirred for 12 h, then extracted with EtOAc (3×300 mL). The combined organic layers were washed with brine (3×100 mL) and dried over anhydrous $Na_2SO_4$. After filtration, the filtrate was concentrated under reduced pressure, and the residue purified by silica gel column chromatography, eluting with Petroleum ether/EtOAc (1:1) to afford E (1.58 g, 40.03%) as a yellow solid. LCMS (ESI) m/z: $[M+H]^+$=509.

Step 5: Preparation of 4-[[2-(2-aminoethanesulfonyl)ethyl]amino]-2-(2,6-dioxopiperidin-3-yl)isoindole-1,3-dione; trifluoroacetate (I-28)

I-28

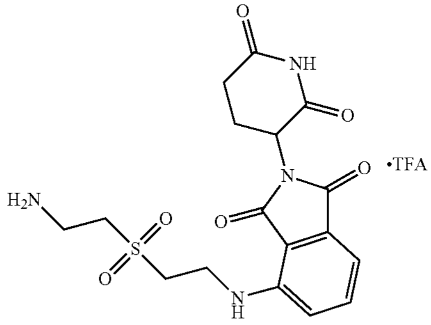

To a stirred mixture of E (1.54 g, 3.028 mmol, 1.00 equiv) in DCM (20 mL) was added trifluoroacetaldehyde (5.0 mL) dropwise at 25° C. under a nitrogen atmosphere. After 1 h, the resulting mixture was concentrated under vacuum. This resulted in I-28 (1.68 g, 122.25%) as a yellow solid. $^1$H NMR (400 MHz, DMSO-d6) δ 11.11 (s, 1H), 7.95 (s, 4H), 7.65 (dd, 1H), 7.18 (d, 1H), 7.12 (d, 1H), 6.84 (t, 1H), 5.07 (dd, 1H), 3.80 (q, 2H), 3.63 (m, 3H), 3.51 (t, 7H), 3.29 (dt, 4H), 2.89 (ddd, 1H), 2.70 (s, 1H), 2.65-2.52 (m, 2H), 2.18 (t, 1H), 2.03 (ddd, 1H), 1.96-1.84 (m, 1H). LCMS (ESI) m/z: $[M+H]^+$=409.11.

Preparation of 4-(2-[2-[(2-aminoethyl)(methyl)amino]ethoxy]ethoxy)-2-(2,6-dioxopiperidin-3-yl)isoindole-1,3-dione formate (I-29)

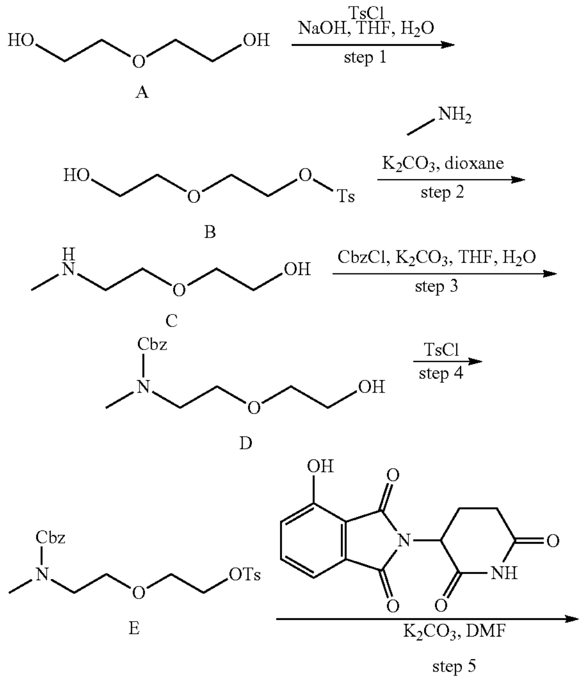

-continued

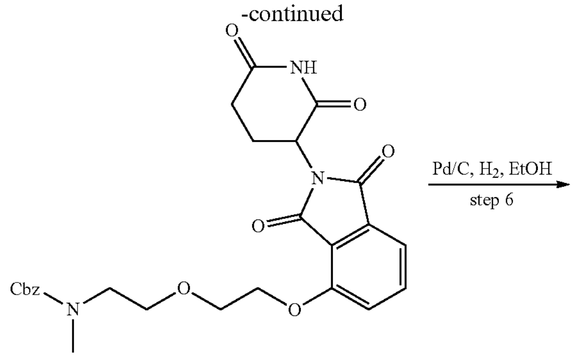

F

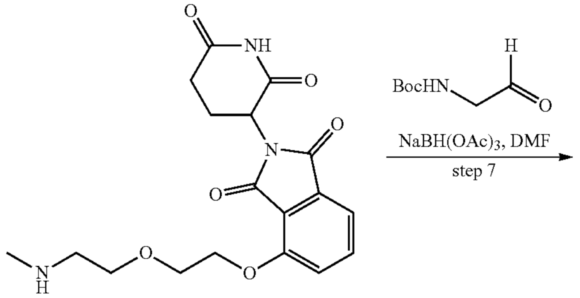

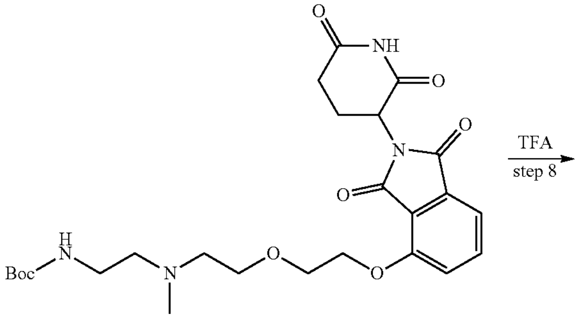

H

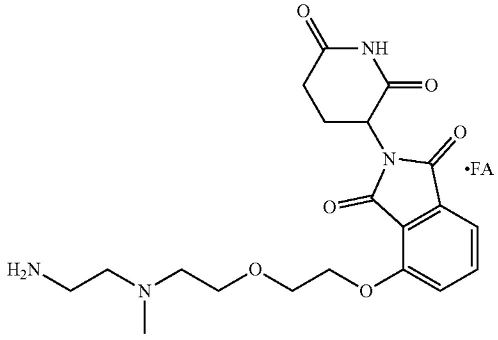

I-29

Step 1: Preparation of 2-[2-[(4-methylbenzenesulfonyl)oxy]ethoxy]ethanol (B)

B

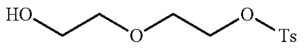

Diethylene glycol (A, 12.72 g, 119.863 mmol, 1.00 equiv) was dissolved in THE (105.00 mL) at 0° C. NaOH (3.60 g, 89.897 mmol, 0.75 equiv) in 45 mL of water was added dropwise to the solution. After stirring for 30 min this solution was added dropwise to a solution of p-toluenesulfonyl chloride (11.43 g, 59.932 mmol, 0.5 equiv) in THF (45.00 mL) at 0° C. After the addition was completed, the aqueous solution was treated with 10% HCl followed by extraction with dichloromethane. The organic layer was washed with distilled water and dried over MgSO4. After the solvent was removed, the residue was purified by column chromatography (Petroleum ether/THF=1:1 v/v). B (12.56 g, 40.26%) was obtained as a colorless oil; LCMS (ESI) m/z: $[M+H]^+=261$.

Step 2: Preparation of 2-[2-(methylamino)ethoxy]ethanol (C)

C

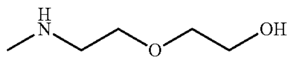

B (12.56 g, 48.252 mmol, 1.00 equiv) was dissolved in 1,4-dioxane (180.00 mL), followed by addition of methylamine hydrochloride (32.58 g, 482.520 mmol, 10 equiv). $K_2CO_3$ (33.34 g, 241.260 mmol, 5 equiv) was added in batches, and the reaction was stirred overnight at 50° C. The solvent was removed under reduced pressure to obtain C (10 g, 73.22%) as a colorless oil; LCMS (ESI) m/z: $[M+H]^+=120$.

Step 3: Preparation of benzyl N-[2-(2-hydroxyethoxy)ethyl]-N-methylcarbamate (D)

D

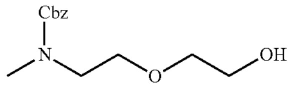

To the solution of C (10.00 g, 83.918 mmol, 1.00 equiv) in THE (30.00 mL) was added benzyl chloroformate (2.29 g, 13.427 mmol, 0.16 equiv), $K_2CO_3$ (3.83 g, 27.693 mmol, 0.33 equiv) and water (30.00 mL). The resulting mixture was stirred at room temperature for 12 h, then extracted with EtOAc (3×60 mL). The combined organic layers were washed with brine (3×60 mL) and dried over anhydrous $Na_2SO_4$. After filtration, the liquid was concentrated under reduced pressure and purified by reverse phase flash chromatography under the following conditions: column, C18 silica gel; mobile phase, $NH_4HCO_3$ in water, 0% to 100% gradient over 30 min; detector, UV 254 nm. This resulted in D (2.14 g, 17.51%) as a colorless oil; LCMS (ESI) m/z: $[M+H]^+=254$.

Step 4: Preparation of benzyl N-methyl-N-(2-[2-[(4-methylbenzenesulfonyl)oxy]ethoxy]ethyl)carbamate (E)

E

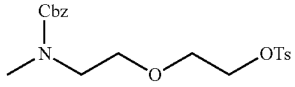

To a stirred solution of D (2.14 g, 8.449 mmol, 1.00 equiv) in DCM (30.00 mL) was added DMAP (0.15 g, 1.267 mmol, 0.15 equiv), TEA (2.14 g, 21.121 mmol, 2.5 equiv) and p-toluenesulfonyl chloride (2.42 g, 12.673 mmol, 1.5 equiv) at 0° C. The resulting mixture was stirred for 2 h at 0° C., then stirred for an additional 5 h at room temperature. The residue was purified by silica gel column chromatography, eluting with Petroleum ether/THF (1:1) to afford E (3.51 g, crude) as a colorless oil; LCMS (ESI) m/z: $[M+H]^+$=408.

Step 5: Preparation of benzyl N-[2-(2-[[2-(2,6-dioxopiperidin-3-yl)-1,3-dioxoisoindol-4-yl]oxy]ethoxy)ethyl]-N-methylcarbamate (F)

F

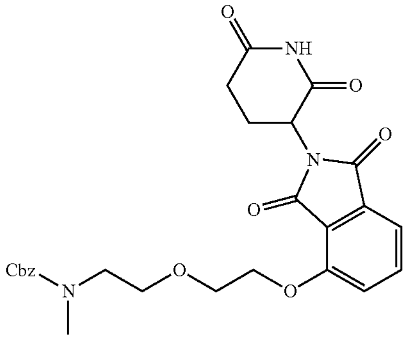

To a solution of E (3.51 g, 8.614 mmol, 1.00 equiv) in DMF (30.00 mL) was added 2-(2,6-dioxopiperidin-3-yl)-4-hydroxyisoindole-1,3-dione (2.36 g, 8.614 mmol, 1 equiv) and $Na_2CO_3$ (1.37 g, 12.921 mmol, 1.5 equiv). The resulting mixture was stirred at 80° C. for 12 h and then concentrated. The residue was purified by reverse phase flash chromatography under the following conditions: column, C18 silica gel; mobile phase, $CH_3CN$ in water, 0% to 100% gradient over 30 min; detector, UV 254 nm. This resulted in F (1.527 g, 34.79%) as a light yellow solid; LCMS (ESI) m/z: $[M+H]^+$=510.

Step 6: Preparation of 2-(2,6-dioxopiperidin-3-yl)-4-[2-[2-(methylamino)ethoxy]ethoxy]isoindole-1,3-dione (G)

G

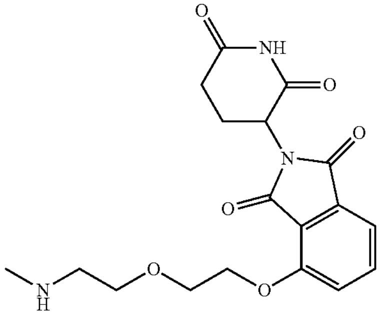

To the solution of F (1.52 g, 2.997 mmol, 1.00 equiv) in EtOH (30.00 mL) was added ammonium formate (377.95 mg, 5.994 mmol, 2 equiv) and $Pd(OH)_2/C$ (5.425 mmol, 1.81 equiv). The resulting suspension was stirred at 60° C. for 12 h under 1 atmosphere of hydrogen, then filtered. The filter cake was washed with MeOH (3×30 mL), and the filtrate concentrated under reduced pressure. This resulted in G (1.062 g, 94.83%) as a light yellow solid; LCMS (ESI) m/z $[M+H]^+$=376.

Step 7: Preparation of tert-butyl N-(2-[[2-(2-[[2-(2,6-dioxopiperidin-3-yl)-1,3-dioxoisoindol-4-yl]oxy]ethoxy)ethyl](methyl)amino]ethyl)carbamate (H)

H

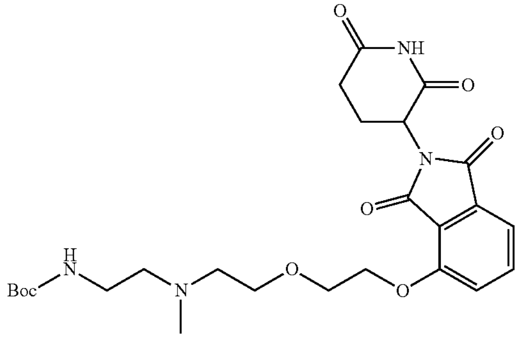

To a solution of G (1.06 g, 2.824 mmol, 1.00 equiv) in DMF (10.00 mL) was added tert-butyl N-(2-oxoethyl)carbamate (539.41 mg, 3.389 mmol, 1.2 equiv) and NaBH$(OAc)_3$ (1.80 g, 8.471 mmol, 3 equiv). The resulting solution was stirred at room temperature for 2 h. Follow aqueous workup, extraction with DCM, and concentration under reduced pressure, the residue was purified by silica gel column chromatography, eluting with DCM/MeOH (10:1) to afford H (386 mg, 26.36%) as a light yellow solid; LCMS (ESI) m/z: $[M+H]^+$=519.

Step 8: Preparation of 4-(2-[2-[(2-aminoethyl)(methyl)amino]ethoxy]ethoxy)-2-(2,6-dioxopiperidin-3-yl)isoindole-1,3-dione formate (I-29)

I-29

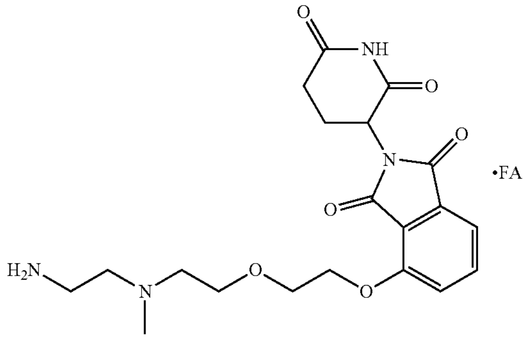

To the solution of H (511.00 mg, 0.985 mmol, 1.00 equiv) in DCM (5.00 mL) was added TFA (5.00 mL, 67.315 mmol, 68.31 equiv). The resulting solution was stirred at room temperature for 3 h. The solution was concentrated, and the residue was purified by reverse phase flash chromatography under the following conditions: column, C18 silica gel; mobile phase, $CH_3CN$ in water, 0% to 100% gradient over 45 min; detector, UV 220 nm. This resulted in I-29 (307 mg, 73.86%) as a brown oil; $^1H$ NMR (300 MHz, DMSO-d6) δ 11.70-10.30 (m, 1H), 8.18 (s, 1H, formic acid), 7.83 (dd, 1H), 7.51 (dd, 2H), 5.09 (dd, 1H), 4.41-4.32 (m, 2H), 3.84-3.75 (m, 2H), 3.63 (d, 2H), 2.99-2.80 (m, 3H), 2.65-2.58 (m, 5H), 2.24 (s, 3H), 2.08 (s, 1H), 1.98-2.06 (m, 1H); LCMS (ESI) m/z: $[M+H]^+$=419.

Preparation of 4-(azetidin-3-ylmethoxy)-2-(2,6-dioxopiperidin-3-yl)isoindole-1,3-dione trifluoroacetate (I-30)

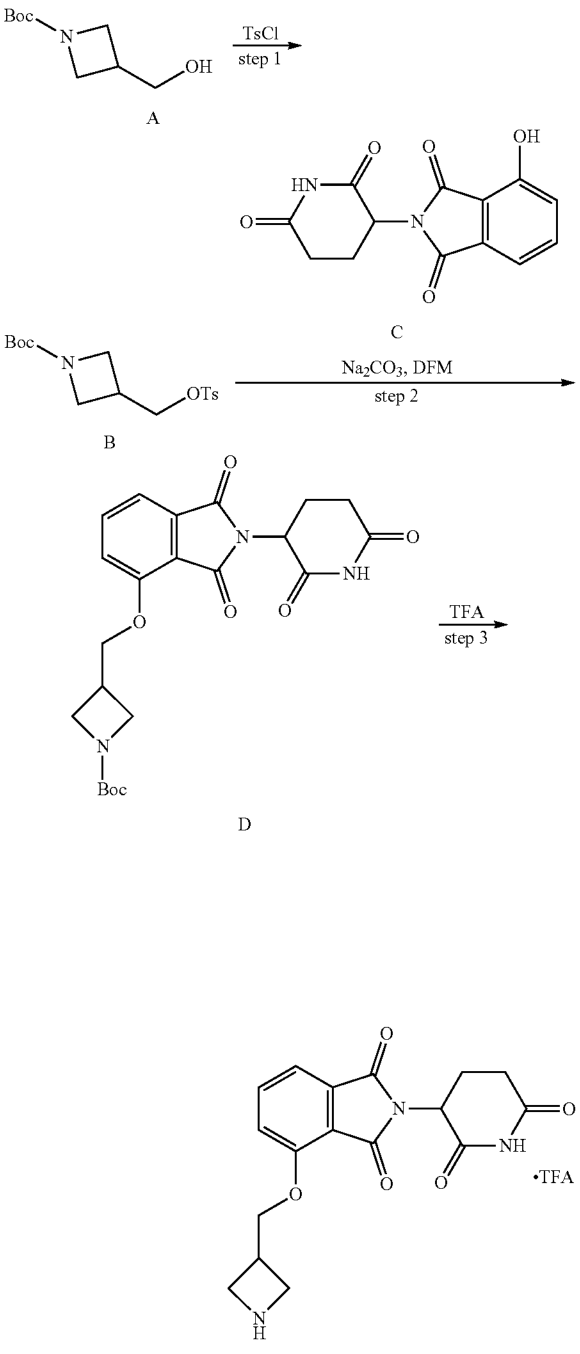

A, B, C, D, I-30

Step 1: Preparation of tert-butyl 3-[[(4-methylbenzenesulfonyl)oxy]methyl]azetidine-1-carboxylate (B)

B

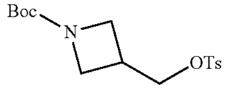

To a stirred solution of tert-butyl 3-(hydroxymethyl) azetidine-1-carboxylate (A, 1.87 g, 9.987 mmol, 1.00 equiv) in DCM (50.00 mL) was added DMAP (0.18 g, 1.498 mmol, 0.15 equiv), TEA (2.53 g, 24.968 mmol, 2.50 equiv) and p-toluenesulfonyl chloride (2.86 g, 14.981 mmol, 1.50 equiv) at 0° C. The resulting mixture was stirred for 2 h at 0° C., then stirred for additional 5 h at room temperature. After aqueous workup and concentration, the residue was purified by silica gel column chromatography, eluting with Petroleum ether/THF (1:1) to afford B (2.65 g, 77.72%) as a colorless oil; LCMS (ESI) m/z: $[M+H]^+$=342.

Step 2: Preparation of tert-butyl 3-([[2-(2,6-dioxopiperidin-3-yl)-1,3-dioxoisoindol-4-yl]oxy] methyl)azetidine-1-carboxylate (D)

D

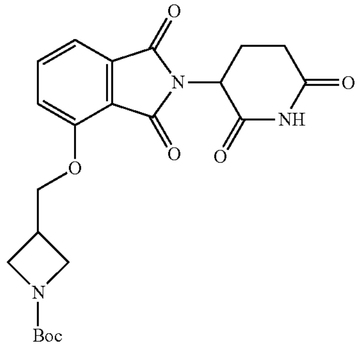

To a solution of C (2.30 g, 8.387 mmol, 1.00 equiv) in DMF (15.00 mL) was added tert-butyl 3-[[(4-methylbenzenesulfonyl)oxy]methyl]azetidine-1-carboxylate (B, 2.86 g, 8.387 mmol, 1 equiv) and $Na_2CO_3$ (1.33 g, 12.581 mmol, 1.5 equiv). The resulting mixture was stirred at 80° C. for 5 h under 1 atmosphere of hydrogen. The reaction was quenched with water at room temperature, and extracted with EtOAc (3×100 mL). The combined organic layers were washed with brine (3×100 mL) and dried over anhydrous $Na_2SO_4$. After filtration, the filtrate was concentrated under reduced pressure. This resulted in D (3.37 g, 90.61%) as a light yellow solid; LCMS (ESI) m/z: $[M+H]^+$=444.

Step 3: Preparation of 4-(azetidin-3-ylmethoxy)-2-(2,6-dioxopiperidin-3-yl)isoindole-1,3-dione trifluoroacetate (I-30)

I-30

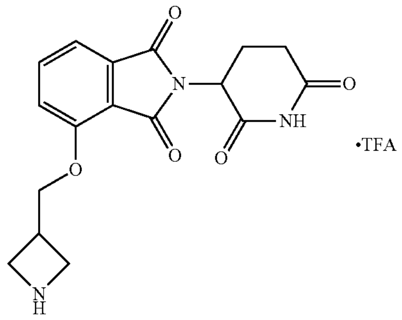

To the solution of D (2.39 g, 5.389 mmol, 1.00 equiv) in DCM (10.00 mL) was added TFA (10.00 mL, 134.630 mmol, 42.34 equiv). The resulting solution was stirred at room temperature for 3 h, the concentrated under reduced pressure. The residue was purified by reverse phase flash chromatography under the following conditions: column, C18 silica gel; mobile phase, ACN in water, 0% to 100% gradient over 45 min; detector, UV 220 nm. This resulted in I-30 (1.712 g, 87.72%) as a light yellow solid; $^{1}$H NMR (300 MHz, DMSO-d6) δ 11.80-10.25 (m, 1H), 9.65-8.35 (m, 1H), 7.87 (dd, 1H), 7.54 (dd, 2H), 5.11 (dd, 1H), 4.39 (d, 2H), 4.09 (dd, 2H), 3.96 (dd, 2H), 3.37-3.24 (m, 1H), 2.99-2.81 (m, 1H), 2.66-2.61 (m, 1H), 2.61-2.53 (m, 1H), 2.11-1.98 (m, 1H); LCMS (ESI) m/z: $[M+H]^+$=344.12.

Preparation of 5-(azetidin-3-ylmethoxy)-2-(2,6-dioxopiperidin-3-yl)isoindole-1,3-dione formate (I-31)

I-31

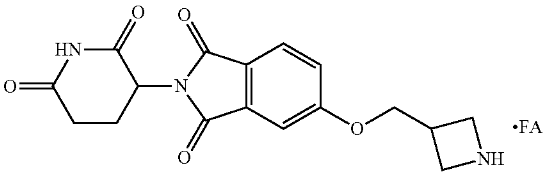

I-31 (906.2 mg, 81.38%) as a white solid was prepared in a similar manner as described in the preparation of I-30. $^{1}$H NMR (300 MHz, DMSO-d6) δ 8.40 (s, 0.4H, formic acid), 7.88 (d, 1H), 7.52 (d, 1H), 7.42 (dd, 1H), 5.13 (dd, 1H), 4.35 (d, 2H), 4.08 (t, 2H), 3.85 (t, 2H), 3.22 (d, 1H), 3.00-2.80 (m, 1H), 2.67-2.61 (m, 1H), 2.60-2.54 (m, 1H), 2.14-1.99 (m, 1H); LCMS (ESI) m/z: $[M+H]^+$=344.12.

Preparation of 4-[2-(azetidin-3-yl)ethoxy]-2-(2,6-dioxopiperidin-3-yl)isoindole-1,3-dione trifluoroacetate (I-32)

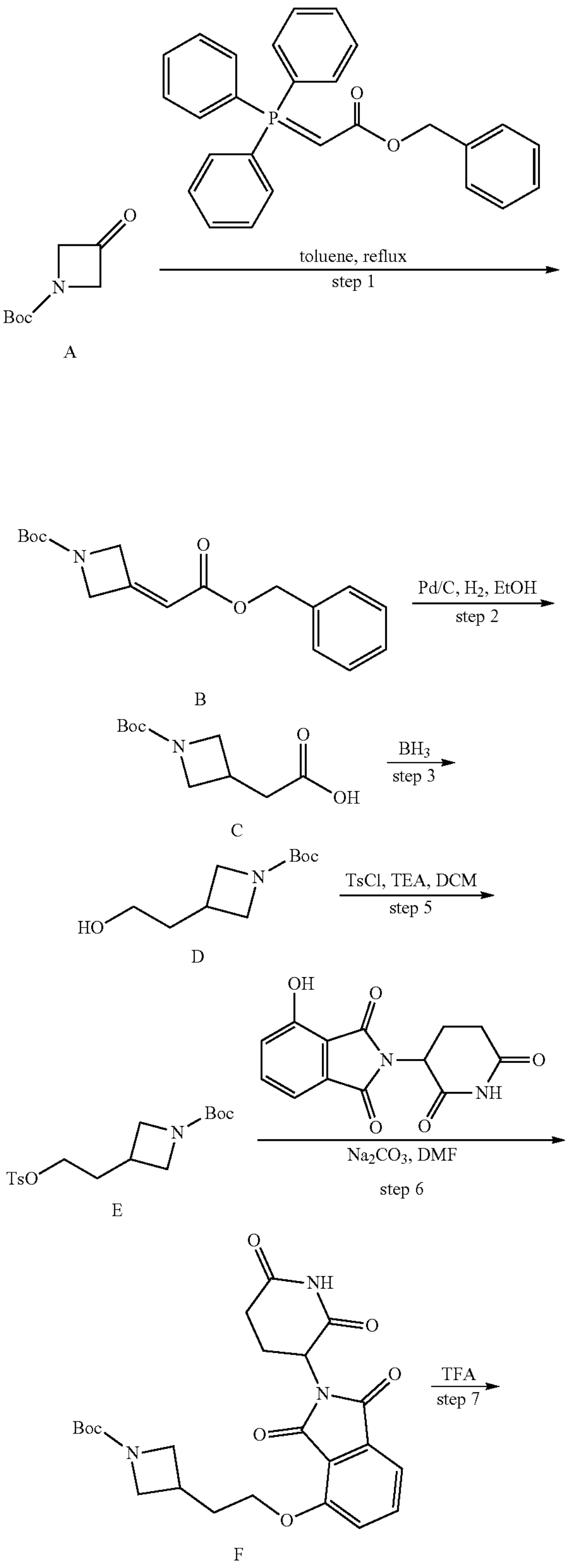

-continued

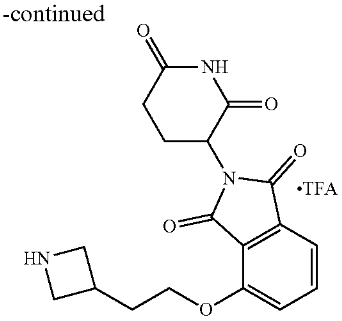

I-32

Step 1: Preparation of tert-butyl 3-(2-ethoxy-2-oxoethylidene)azetidine-1-carboxylate (B)

B

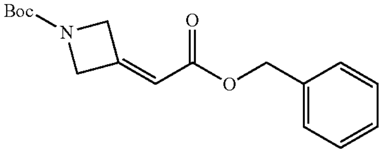

Under nitrogen, a Schlenk flask was charged with tert-butyl 3-oxoazetidine-1-carboxylate (A, 2.50 g, 14.603 mmol, 1.00 equiv) and ethyl 2-(triphenyl-lambda5-phosphanylidene)acetate (5.60 g, 16.063 mmol, 1.10 equiv). Anhydrous toluene (100 mL) was added and the mixture was heated to reflux for 2 h. After cooling down to room temperature, the resulting mixture was concentrated and purified by silica gel column (cyclohexane:EtOAc, 5:1). This resulted in B (3 g, 85.14%) as a colorless oil. LCMS (ESI) m/z $[M+H]^+$=304.

Step 2: Preparation of tert-butyl 3-(2-ethoxy-2-oxoethylidene)azetidine-1-carboxylate (C)

C

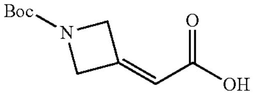

To a stirred solution of B (3.0 g, 9.8 mmol, 1.0 equiv) in EtOH (50 mL) was added 10% Pd/C (500 mg) at room temperature under 1 atmosphere of hydrogen. The reaction was stirred at room temperature for 12 h, then filtered to remove the catalyst. The filtrate was concentrated under vacuum to afford C (2.6 g, 76.16%) as a yellow oil. LCMS (ESI) m/z: $[M+H]^+$=216.

Step 3: Preparation of tert-butyl 3-(2-hydroxyethyl)azetidine-1-carboxylate (D)

D

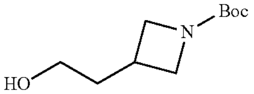

To a stirred solution of C (1.30 g, 5.343 mmol, 1.00 equiv) in THE (15.00 mL) was added LiAlH4 (202.79 mg, 5.343 mmol, 1.00 equiv) in portions at 0° C. under a nitrogen atmosphere. The reaction was quenched by the addition of EtOAc at 0° C. The resulting mixture was filtered, and the filter cake was washed with EtOAc. The filtrate was concentrated under reduced pressure and the residue purified by silica gel column chromatography to afford D (1 g, 92.99%) as a colorless oil, LCMS (ESI) m/z: $[M+H]^+$=202.

Step 4: Preparation of tert-butyl 3-[2-[(4-methylbenzenesulfonyl)oxy]ethyl]azetidine-1-carboxylate (E)

E

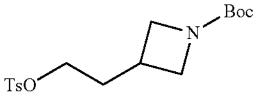

D (950.00 mg, 4.720 mmol, 1.00 equiv) was added to a solution of p-toluenesulfonyl chloride (1079.81 mg, 5.664 mmol, 1.20 equiv) in dry DCM (15 mL) at room temperature, followed by the dropwise addition of TEA (573.15 mg, 5.664 mmol, 1.20 equiv). The mixture was stirred at room temperature for 2 h and then concentrated. The residue was purified by silica gel column chromatography (gradient elution 1:15 to 1:5 EtOAc/Hexanes) to afford E (1.5 g, 90.99%) as a colorless oil, LCMS (ESI) m/z: $[M+H]^+$=356.

Step 5: Preparation of tert-butyl 3-(2-[[2-(2,6-dioxopiperidin-3-yl)-1,3-dioxoisoindol-4-yl]oxy]ethyl)azetidine-1-carboxylate (F)

F

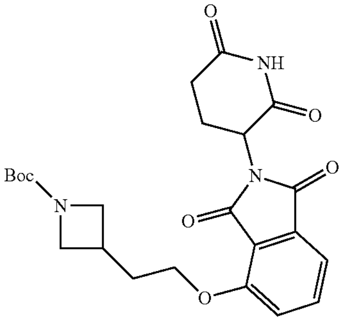

A solution of E (800.00 mg, 2.251 mmol, 1.00 equiv), 2-(2,6-dioxopiperidin-3-yl)-4-hydroxyisoindole-1,3-dione (617.21 mg, 2.251 mmol, 1.00 equiv) and $Na_2CO_3$ (357.82 mg, 3.376 mmol, 1.50 equiv) in DMF (3 mL) was stirred for 2 h at 80° C. The resulting mixture was extracted with EtOAc and the combined organic layers washed with brine and dried over anhydrous Na2SO4. After filtration, the filtrate was concentrated under reduced pressure. The residue was purified by silica gel column chromatography, eluting with EtOAc to afford F (500 mg, 80.12%) as a colorless oil, LCMS (ESI) m/z: $[M+H]^+$=458.

Step 6: Preparation of 4-[2-(azetidin-3-yl)ethoxy]-2-(2,6-dioxopiperidin-3-yl)isoindole-1,3-dione trifluoroacetate (I-32)

I-32

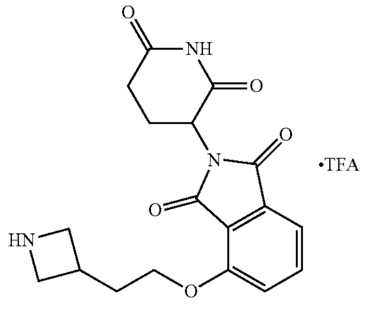

To a stirred solution of F (542.00 mg, 1.185 mmol, 1.00 equiv) in DCM (10 mL) was added TFA (5 mL) dropwise at room temperature. After stirring for 2 h the resulting mixture was concentrated under reduced pressure and the residue was purified by flash column chromatography on silica gel to afford I-32 (503 mg, 95.2%) as a yellow solid. $^1H$ NMR (300 MHz, DMSO-d6) δ 11.11 (s, 1H), 8.58 (d, 2H), 7.84 (dd, 1H), 7.49 (dd, 2H), 5.09 (dd, 1H), 4.24 (t, 2H), 4.10-3.84 (m, 5H), 3.11-2.80 (m, 2H), 2.66-2.53 (m, 1H), 2.16-1.98 (m, 3H). LCMS (ESI) m/z: $[M+H]^+$=358.13.

Preparation of 5-(azetidin-3-yloxy)-2-(2,6-dioxopiperidin-3-yl) isoindole-1,3-dione (I-33)

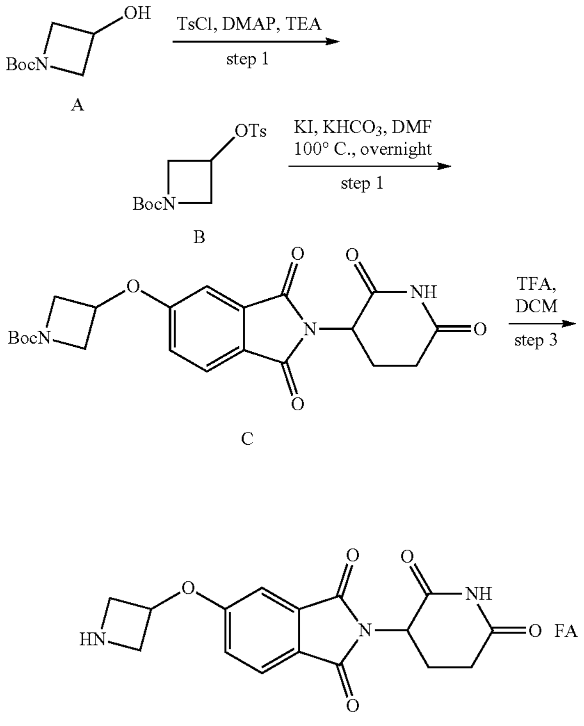

I-33

Step 1: Preparation of t tert-butyl 3-[(4-methylbenzenesulfonyl)oxy]azetidine-1-carboxylate (B)

B

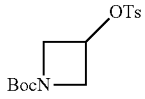

To a stirred solution of tert-butyl 3-hydroxyazetidine-1-carboxylate (A, 2.50 g, 14.433 mmol, 1.00 equiv) and p-toluenesulfonyl chloride (4.13 g, 21.650 mmol, 1.50 equiv) in DCM was added DMAP (264.49 mg, 2.165 mmol, 0.15 equiv) and TEA (4.38 g, 43.300 mmol, 3.00 equiv) in portions at 0° C. The resulting mixture was concentrated under reduced pressure and the residue purified by silica gel column chromatography, eluting with Petroleum ether/EtOAc (1:1) to afford B (4.4 g, 93.11%) as a brown oil. LCMS (ESI) m/z: $[M+H]^+$=328.

Step 2: Preparation of tert-butyl 3-[[2-(2,6-dioxopiperidin-3-yl)-1,3-dioxoisoindol-5-yl] oxy]azetidine-1-carboxylate (C)

C

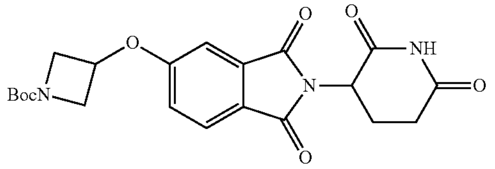

To a stirred solution of B (4.40 g, 13.439 mmol, 1.00 equiv) and KI (0.22 g, 1.344 mmol, 0.10 equiv) in DMF was added KHCO3 (4.04 g, 40.318 mmol, 3.00 equiv) in portions. After stirring for 8 h at 100° C. the resulting mixture was extracted with of EtOAc (3×150 mL) and the organic extracts concentrated under reduced pressure. The residue was purified by reverse phase flash chromatography under the following conditions: column, C18 silica gel; mobile phase, ACN in water, 10% to 50% gradient over 10 min; detector, UV 254 nm. This resulted in C (1.73 g, 29.98%) as an off-white solid. LCMS (ESI) m/z: $[M+H]^+$=430.

Step 3: Preparation of 5-(azetidin-3-yloxy)-2-(2,6-dioxopiperidin-3-yl)isoindole-1,3-dione formate (I-33)

I-33

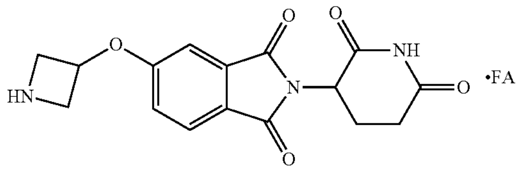

A solution of C (1.53 g, 3.563 mmol, 1.00 equiv) and TFA (5.00 mL, 67.315 mmol, 18.89 equiv) in DCM was stirred for 2 h at room temperature. The resulting mixture was concentrated under reduced pressure and the residue purified by reverse phase flash chromatography under the following conditions: column, C18 silica gel; mobile phase, ACN in water, 10% to 50% gradient over 10 min; detector, UV 254 nm. This resulted in I-33 (1.08 g, 96.43%) as a white solid. $^1$H NMR (300 MHz, DMSO-d6) δ 11.11 (s, 1H), 8.25 (s, formic acid, 1H), 7.88 (d, 1H), 7.32 (d, 2H), 5.30 (p, 1H), 5.13 (dd, 1H), 4.31 (dd, 2H), 3.89 (dd, 2H), 2.99-2.80 (m, 1H), 2.68-2.52 (m, 2H), 2.13-1.97 (m, 1H). LCMS (ESI) m/z: $[M+H]^+$=330.05.

Preparation of 5-[2-(4-aminopiperidin-1-yl)ethoxy]-2-(2,6-dioxopiperidin-3-yl)isoindole-1,3-dione formate (I-34)

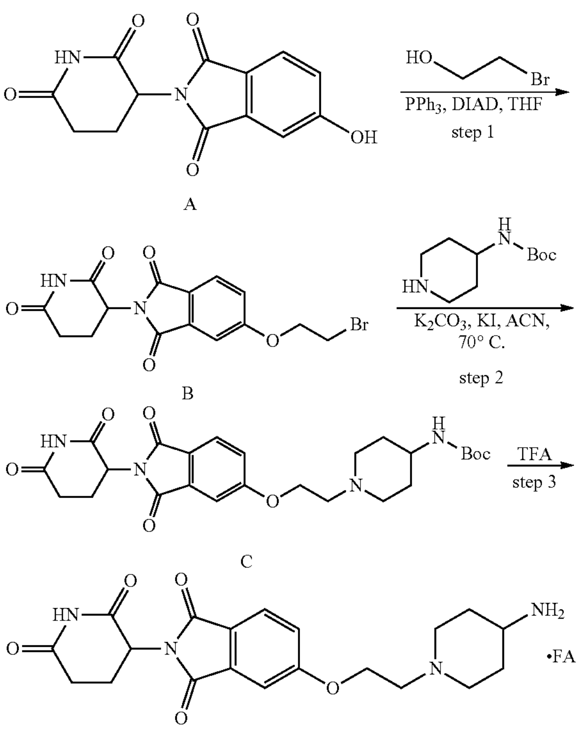

A

B

C

I-34

Step 1: Preparation of 5-(2-bromoethoxy)-2-(2,6-dioxopiperidin-3-yl)isoindole-1,3-dione (B)

B

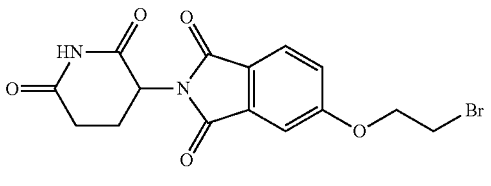

To a solution of 2-(2,6-dioxopiperidin-3-yl)-5-hydroxyisoindole-1,3-dione (A, 1.37 g, 4.996 mmol, 1.00 equiv) in THE (35 mL) was added 2-bromoethanol (0.94 g, 7.494 mmol, 1.5 equiv), $PPh_3$ (1.97 g, 7.494 mmol, 1.5 equiv), and DIAD (1.52 g, 7.494 mmol, 1.5 equiv) at 0° C. The resulting mixture was stirred for 2 h at room temperature. Following aqueous workup and DCM extraction, the residue was purified by reverse phase flash chromatography under the following conditions: column, C18 silica gel; mobile phase, ACN/0.1% formic acid in water, 0% to 100% gradient over 45 min; detector, UV 254 nm. This resulted in B (1.52 g, 79.82%) as a black solid; LCMS (ESI) m/z: $[M+H]^+$=381, 383.

Step 2: Preparation of tert-butyl N-[1-(2-[[2-(2,6-dioxopiperidin-3-yl)-1,3-dioxoisoindol-5-yl]oxy]ethyl)piperidin-4-yl]carbamate (C)

C

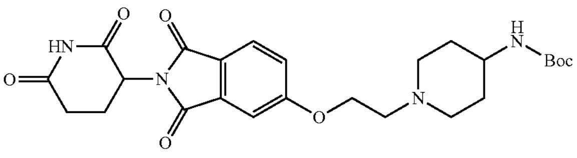

To a solution of B (1.52 g, 3.988 mmol, 1.00 equiv) in ACN (35.00 mL) was added tert-butyl N-(piperidin-4-yl) carbamate (0.80 g, 3.988 mmol, 1.00 equiv), KI (0.66 g, 3.988 mmol, 1.00 equiv), and $K_2CO_3$ (1.65 g, 11.963 mmol, 3.00 equiv). The resulting mixture was stirred at 70° C. for 2 h. Following aqueous workup and DCM extraction the residue was purified by reverse phase flash chromatography under the following conditions: column, C18 silica gel; mobile phase, ACN/0.1% formic acid in water, 0% to 100% gradient over 30 min; detector, UV 254 nm. This resulted in C (1.402 g, 70.24%) as a colorless solid; LCMS (ESI) m/z: $[M+H]^+$=501.

Step 3: Preparation of 5-[2-(4-aminopiperidin-1-yl)ethoxy]-2-(2,6-dioxopiperidin-3-yl)isoindole-1,3-dione formate (I-34)

I-34

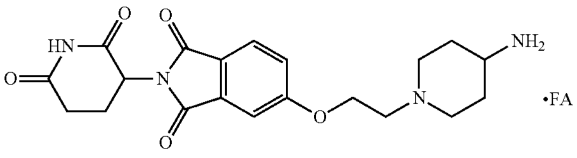

To a solution of C (1.66 g, 3.316 mmol, 1.00 equiv) in DCM (10.00 mL) was added TFA (10.00 mL, 134.630 mmol, 40.60 equiv). The resulting solution was stirred at room temperature for 3 h. Following concentration, the residue was purified by reverse phase flash chromatography under the following conditions: column, C18 silica gel; mobile phase, ACN/0.1% formic acid in water, 0% to 100% gradient over 45 min; detector, UV 220 nm. This resulted in I-34 (840 mg, 62.52%) as a white solid; $^1$H NMR (300 MHz, DMSO-d6) δ 11.13 (s, 1H), 8.52-8.26 (m, 2H), 8.16 (s, 1H, formic acid), 7.88 (d, 1H), 7.51 (d, 1H), 7.40 (dd, 1H), 5.14 (dd, 1H), 4.49 (t, 2H), 3.47 (d, 2H), 3.37-2.28 (m, 2H), 3.29-3.19 (m, 1H), 3.03-2.70 (m, 3H), 2.67-2.62 (m, 1H), 2.61-2.55 (m, 1H), 2.14-1.98 (m, 3H), 1.88-1.68 (m, 2H). LCMS (ESI) m/z: $[M+H]^+$=401.17.

Preparation of 5-[7-azaspiro[3.5]nonan-2-yloxy]-2-(2,6-dioxopiperidin-3-yl)isoindole-1,3-dione formate (I-35)

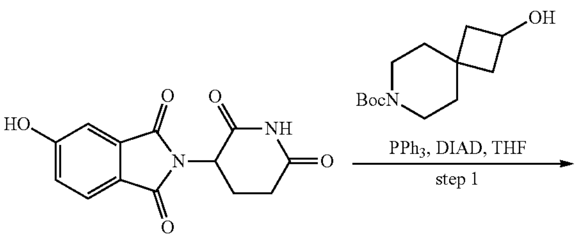

A

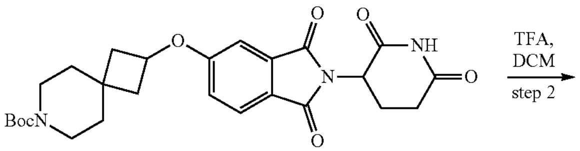

B

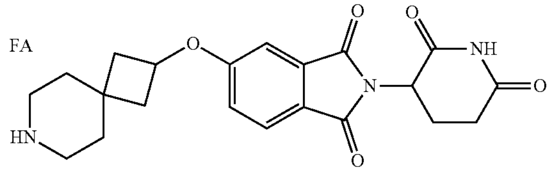

I-35

Step 1: Preparation of tert-butyl 2-[[2-(2,6-dioxopiperidin-3-yl)-1,3-dioxoisoindol-5-yl]oxy]-7-azaspiro[3.5]nonane-7-carboxylate (B)

B

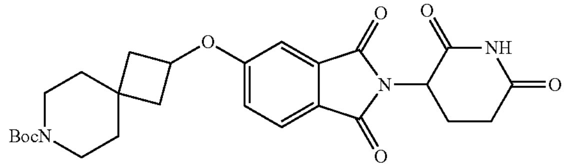

To a solution of 2-(2,6-dioxopiperidin-3-yl)-5-hydroxyisoindole-1,3-dione (A, 1.37 g, 4.99 mmol, 1.00 equiv) and tert-butyl 2-hydroxy-7-azaspiro[3.5]nonane-7-carboxylate (1.81 g, 7.494 mmol, 1.5 equiv) in THE (30.00 mL) was added $PPh_3$ (1.97 g, 7.494 mmol, 1.5 equiv). To this mixture was added DIAD (1.52 g, 7.494 mmol, 1.5 equiv) dropwise over 10 min at 0° C. The reaction was stirred for an additional 5 h at room temperature. The resulting mixture was concentrated under reduced pressure, and the residue purified by reverse phase flash chromatography under the following conditions: column, C18 silica gel; mobile phase, ACN/0.1% formic acid in water, 0% to 100% gradient over 45 min; detector, UV 254 nm. This resulted in B (1.964 g, 79.01%) as a white solid; LCMS (ESI) m/z: $[M+H]^+$=498.

Step 2: Preparation of 5-[7-azaspiro[3.5]nonan-2-yloxy]-2-(2,6-dioxopiperidin-3-yl)isoindole-1,3-dione formate (I-35)

I-35

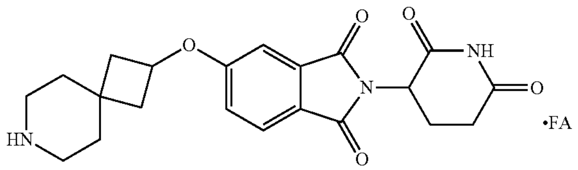

To a solution of B (1.96 g, 3.939 mmol, 1.00 equiv) in DCM (10.00 mL, 157.300 mmol, 39.93 equiv) was added TFA (10.00 mL, 134.630 mmol, 34.18 equiv). The resulting mixture was stirred for 5 h at room temperature, then concentrated and purified by reverse phase flash chromatography under the following conditions: column, C18 silica gel; mobile phase, ACN/0.1% formic acid in water, 0% to 100% gradient over 45 min; detector, UV 254 nm. This resulted in I-35 (1.6318 g, 93.13%) as a light grey solid: $^1H$ NMR (300 MHz, DMSO-d6) δ 8.39 (s, formic acid, 1H), 7.84 (d, 1H), 7.35-7.24 (m, 2H), 5.12 (dd, 1H), 5.00 (p, 1H), 3.00-2.81 (m, 5H), 2.67-2.43 (m, 2H), 2.51-2.43 (m, 3H), 2.16-1.95 (m, 1H), 1.95-1.82 (m, 2H), 1.65-1.78 (m, 4H); LCMS (ESI) m/z: $[M+H]^+$=398.16.

Preparation of 2-(2,6-dioxopiperidin-3-yl)-5-[2-(piperazin-1-yl)ethoxy]isoindole-1,3-dione formate (I-36)

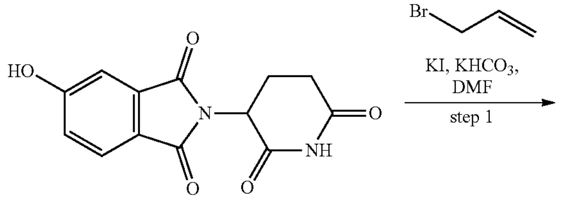

A

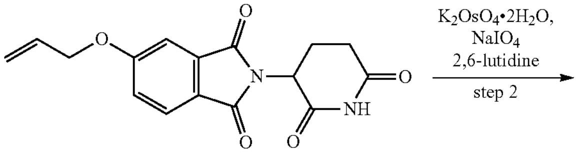

B

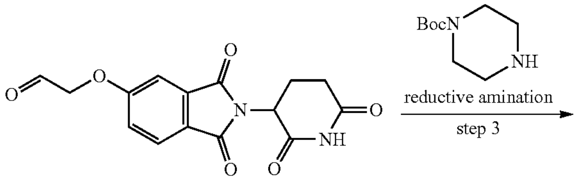

C

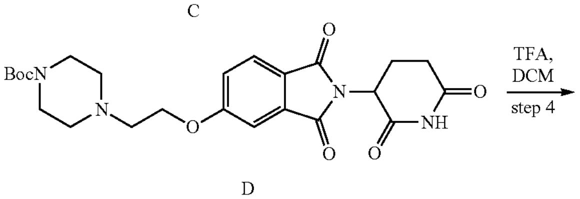

D

-continued

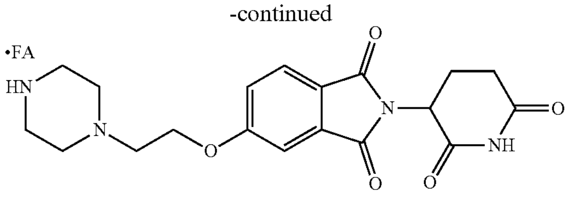

I-36

Step 1: Preparation of 2-(2,6-dioxopiperidin-3-yl)-5-(prop-2-en-1-yloxy)isoindole-1,3-dione (B)

B

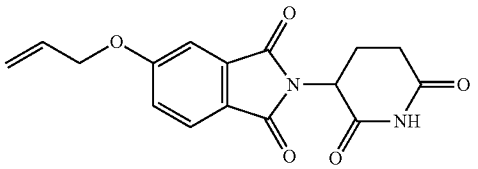

To a solution of 2-(2,6-dioxopiperidin-3-yl)-5-hydroxyisoindole-1,3-dione (A, 5.48 g, 19.983 mmol, 1.00 equiv) and allyl bromide (3.63 g, 29.975 mmol, 1.5 equiv) in DMF (50.00 mL) was added KI (331.72 mg, 1.998 mmol, 0.1 equiv) and $KHCO_3$ (3.00 g, 29.975 mmol, 1.5 equiv). The resulting mixture was stirred for 12 h at 65° C. then diluted with water (100 mL). The resulting mixture was extracted with EtOAc (3×50 mL). The combined organic layers were washed with brine (3×60 mL) and dried over anhydrous Na2SO4. After filtration, the filtrate was concentrated under reduced pressure and purified by silica gel column chromatography, eluting with hexane/EtOAc (1:1) to afford B (6.7 g, crude) as a yellow-green solid; LCMS (ESI) m/z: $[M+H]^+$ =315.

Step 2: Preparation of 2-[[2-(2,6-dioxopiperidin-3-yl)-1,3-dioxoisoindol-5-yl]oxy]acetaldehyde (C)

C

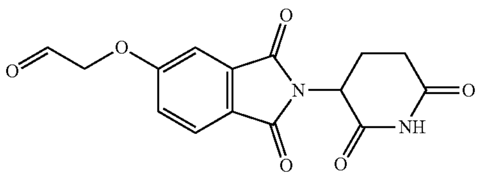

To a solution of B (3.14 g, 9.991 mmol, 1.00 equiv) in 1,4-dioxane (30.00 mL) was added $NaIO_4$ (10.68 g, 49.953 mmol, 5.00 equiv), water (3.00 mL), and 2,6-lutidine (3.21 g, 29.972 mmol, 3 equiv). To the above mixture was added $K_2OsO_4$.dihydrate (0.37 g, 0.999 mmol, 0.1 equiv) at room temperature. The resulting mixture was stirred for an additional 2 h at room temperature, then quenched with water. The resulting mixture was extracted with EtOAc (3×50 mL). The combined organic layers were washed with brine (3×100 mL) and dried over anhydrous $Na_2SO_4$. After filtration, the filtrate was concentrated under reduced pressure. This resulted in C (1.83 g, 57.92%) as a light brown solid; LCMS (ESI) m/z: $[M+H]^+$=317.

Step 3: Preparation of tert-butyl 4-(2-[[2-(2,6-dioxopiperidin-3-yl)-1,3-dioxoisoindol-5-yl]oxy]ethyl)piperazine-1-carboxylate (D)

D

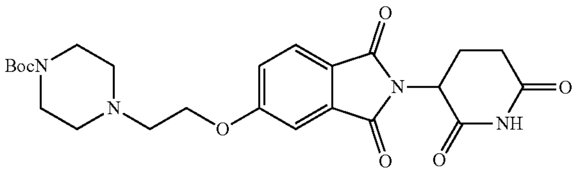

To a solution of C (628.00 mg, 1.986 mmol, 1.00 equiv) and tert-butyl piperazine-1-carboxylate (369.84 mg, 1.986 mmol, 1 equiv) in DMF (10.00 mL) was added $NaBH(OAc)_3$ (1262.52 mg, 5.957 mmol, 3 equiv) at room temperature. The resulting mixture was stirred for 3 h at room temperature then quenched with water, extracted into DCM, and concentrated. The residue was purified by reverse phase flash chromatography under the following conditions: column, C18 silica gel; mobile phase, ACN/0.1% formic acid in water, 0% to 100% gradient over 45 min; detector, UV 254 nm. This resulted in D (812 mg, 84.05%) as an off-white solid; LCMS (ESI) m/z: $[M+H]^+$=487.

Step 4: Preparation of 2-(2,6-dioxopiperidin-3-yl)-5-[2-(piperazin-1-yl)ethoxy]isoindole-1,3-dione formate (I-36)

I-36

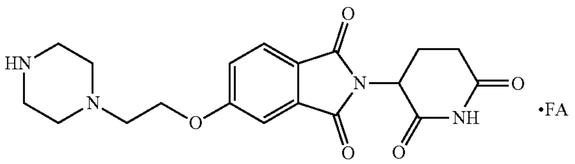

To a solution tert-butyl 4-(2-[[2-(2,6-dioxopiperidin-3-yl)-1,3-dioxoisoindol-5-yl]oxy]ethyl)piperazine-1-carboxylate (D, 2.10 g, 4.316 mmol, 1.00 equiv) in DCM (10.00 mL, 157.300 mmol, 36.44 equiv) was added TFA (10.00 mL, 134.630 mmol, 31.19 equiv). The resulting mixture was stirred for 3 h at room temperature, then concentrated under reduced pressure. The residue was purified by reverse phase flash chromatography under the following conditions: column, C18 silica gel; mobile phase, ACN/0.1% formic acid in water, 0% to 100% gradient over 45 min; detector, UV 254 nm. This resulted in I-36 (1.43 g, 74.24%) as a white solid; $^1H$ NMR (300 MHz, DMSO-d6) δ 11.07 (s, 1H), 8.34 (s, 1H), 7.84 (d, 1H), 7.47 (d, 1H), 7.37 (dd, 1H), 5.12 (dd, 1H), 4.30 (t, 2H), 2.99-2.86 (m, 5H), 2.77 (t, 2H), 2.67-2.55 (m, 5H), 2.13-1.96 (m, 1H); LCMS (ESI) m/z: $[M+H]^+$=387.16.

Preparation of 2-(2,6-dioxopiperidin-3-yl)-5-[3-(piperazin-1-yl)propoxy]isoindole-1,3-dione formate (I-37)

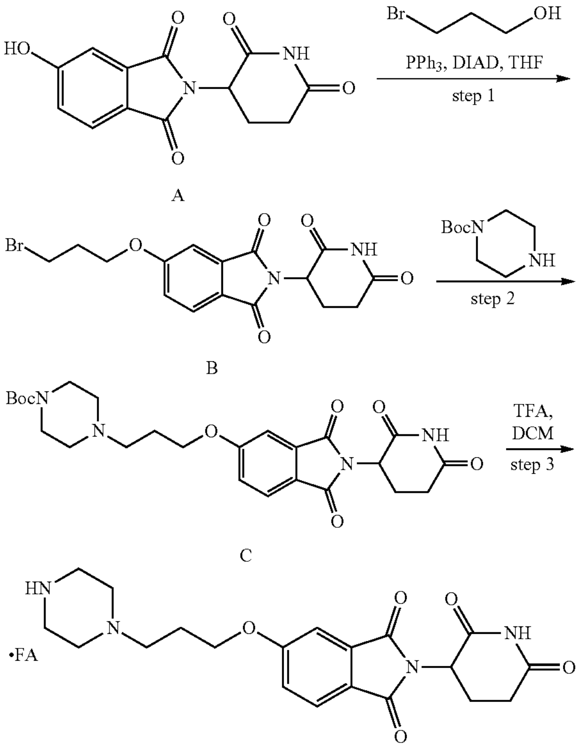

I-37

Step 1: Preparation of 5-(3-bromopropoxy)-2-(2,6-dioxopiperidin-3-yl)isoindole-1,3-dione (B)

B

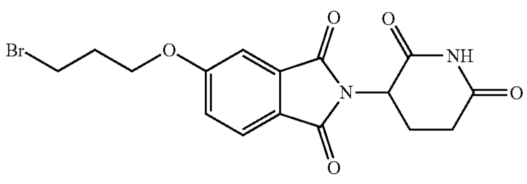

To a solution of 2-(2,6-dioxopiperidin-3-yl)-5-hydroxyisoindole-1,3-dione (A, 1.37 g, 4.996 mmol, 1.00 equiv) and 3-bromopropanol (1.04 g, 7.494 mmol, 1.5 equiv) in THE (20.00 mL) was added $PPh_3$ (1.97 g, 7.494 mmol, 1.5 equiv). To this was added DIAD (1.52 g, 7.494 mmol, 1.5 equiv) dropwise over 10 min at 0° C. The resulting mixture was stirred for an additional 5 h at room temperature. Following aqueous workup and DCM extraction, the organic layer was concentrated under reduced pressure. The residue was purified by reverse phase flash chromatography under the following conditions: column, C18 silica gel; mobile phase, ACN/0.1% formic acid in water, 0% to 100% gradient over 45 min; detector, UV 254 nm. This resulted in B (1.85 g, 93.70%) as a colorless solid; LCMS (ESI) m/z: $[M+H]^+$= 395, 397.

Step 2: Preparation of tert-butyl 4-(3-[[2-(2,6-dioxopiperidin-3-yl)-1,3-dioxoisoindol-5-yl]oxy]propyl)piperazine-1-carboxylate (C)

C

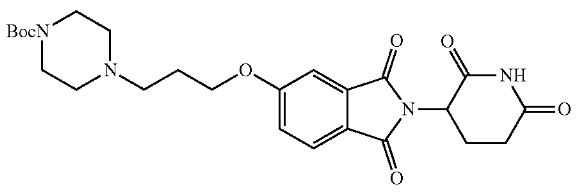

To a solution of B (1.85 g, 4.681 mmol, 1.00 equiv) and tert-butyl piperazine-1-carboxylate (1.05 g, 5.617 mmol, 1.2 equiv) in DMF (30.00 mL) was added DIEA (3.02 g, 23.405 mmol, 5 equiv) and KI (77.71 mg, 0.468 mmol, 0.1 equiv). The resulting mixture was stirred for 5 h at 60° C. Following workup and extraction, the residue was purified by reverse phase flash chromatography under the following conditions: column, C18 silica gel; mobile phase, ACN/0.1% formic acid in water, 0% to 100% gradient over 45 min; detector, UV 254 nm. This resulted in C (975 mg, 41.61%) as an off-white solid; LCMS (ESI) m/z: $[M+H]^+$=501.

Step 3: Preparation of 2-(2,6-dioxopiperidin-3-yl)-5-[3-(piperazin-1-yl)propoxy]isoindole-1,3-dione formate (I-37)

I-37

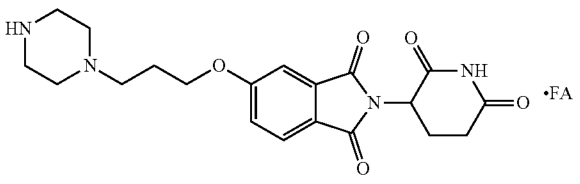

To a solution of C (975.00 mg, 1.948 mmol, 1.00 equiv) in DCM (5.00 mL, 78.650 mmol, 40.38 equiv) was added TFA (5.00 mL, 67.315 mmol, 34.56 equiv). The resulting mixture was stirred for 5 h at room temperature. After concentration, the residue was purified by reverse phase flash chromatography under the following conditions: column, C18 silica gel; mobile phase, ACN/0.1% formic acid in water, 0% to 100% gradient over 45 min; detector, UV 254 nm. This resulted in I-37 (667 mg, 74.17%) as a white solid; $^1H$ NMR (300 MHz, DMSO-d6) δ 11.12 (s, 1H), 8.29 (d, formic acid, 1H), 7.84 (d, 1H), 7.44 (d, 1H), 7.36 (dd, 1H), 5.12 (dd, 1H), 4.23 (t, 2H), 3.17-2.85 (m, 5H), 2.67-2.58 (m, 2H), 2.53-2.57 (m, 4H), 2.50-2.29 (m, 3H), 2.15-2.05 (m, 1H), 2.01-1.82 (m, 2H); LCMS (ESI) m/z: $[M+H]^+$= 401.17.

Preparation of 5-[4-(4-aminopiperidin-1-yl)butoxy]-2-(2,6-dioxopiperidin-3-yl)isoindole-1,3-dione (I-38)

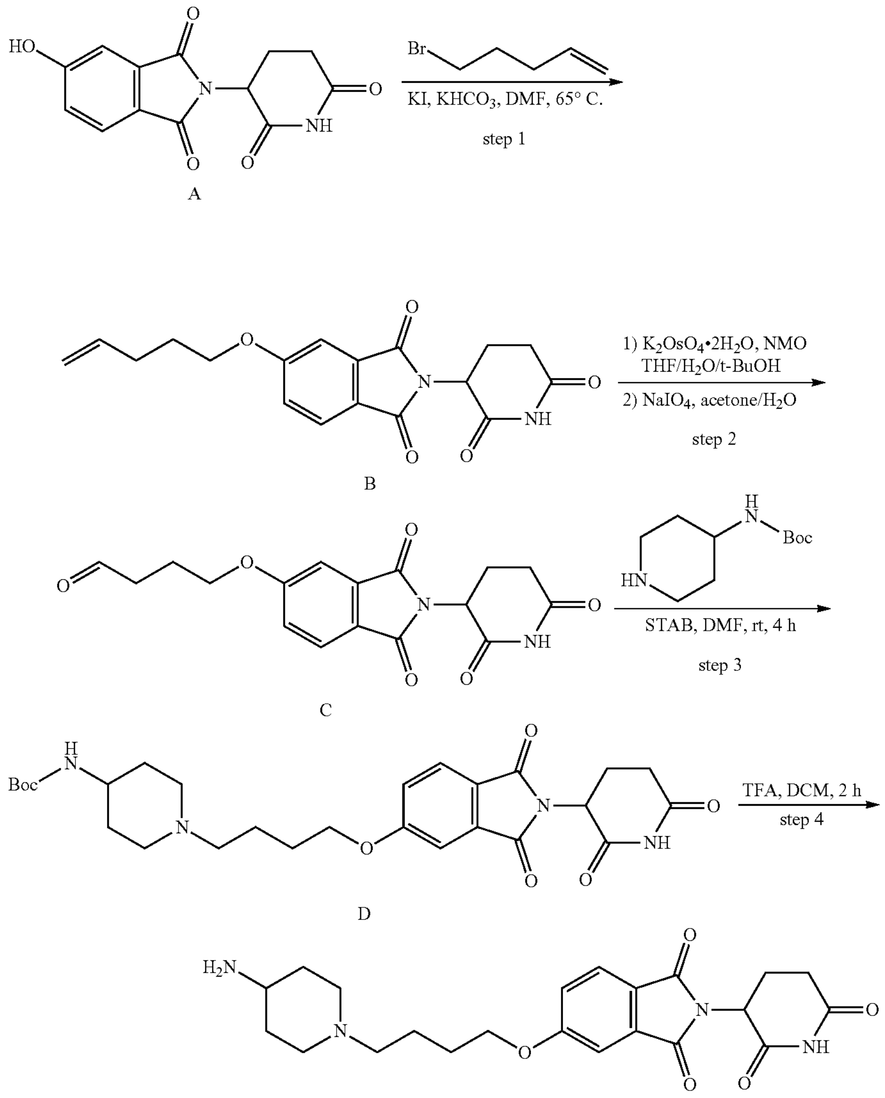

I-38

Step 1: Preparation of 2-(2,6-dioxopiperidin-3-yl)-5-(pent-4-en-1-yloxy)isoindole-1,3-dione (B)

B

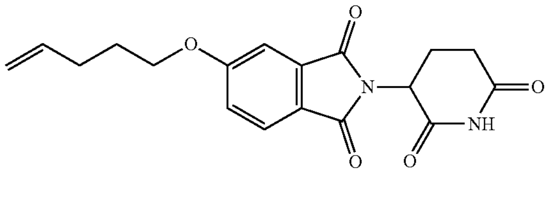

To a stirred mixture of 2-(2,6-dioxopiperidin-3-yl)-5-hydroxyisoindole-1,3-dione (A, 500.00 mg, 1.823 mmol, 1.00 equiv) and $KHCO_3$ (273.81 mg, 2.735 mmol, 1.50 equiv) in DMF (10.00 mL) was added 5-bromo-1-pentene (326.07 mg, 2.188 mmol, 1.20 equiv) and KI (30.27 mg, 0.182 mmol, 0.10 equiv) in portions. The resulting mixture was stirred overnight at 65 degrees C. under nitrogen atmosphere. The mixture was allowed to cool down to room temperature, and the resulting mixture was extracted with EtOAc (2×20 mL). The combined organic layers were washed with water (3×10 mL) and dried over anhydrous $Na_2SO_4$. After filtration, the filtrate was concentrated under reduced pressure and the residue purified by preparative TLC (Petroleum ether/EtOAc 1:1) to afford B (400 mg, 64.08%) as a white solid. LCMS (ESI) m/z: $[M+H]^+$=343.

Step 2: Preparation of 4-[[2-(2,6-dioxopiperidin-3-yl)-1,3-dioxoisoindol-5-yl] oxy]butanal (C)

C

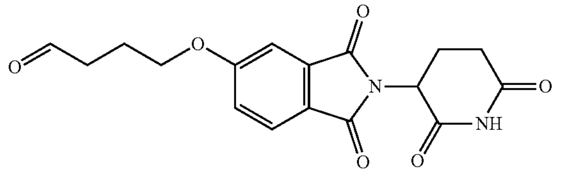

To a stirred solution of 2-(2,6-dioxopiperidin-3-yl)-5-(pent-4-en-1-yloxy)isoindole-1,3-dione (B, 300.00 mg, 0.876 mmol, 1.00 equiv) in THE (1.00 mL), water (5.00 mL), and t-BuOH (5.00 mL) were added NMO (153.98 mg, 1.314 mmol, 1.50 equiv) and $K_2OsO_4$.dihydrate (32.29 mg, 0.088 mmol, 0.10 equiv) in portions at room temperature. The resulting mixture was stirred overnight at room temperature under a nitrogen atmosphere. The resulting mixture was concentrated under reduced pressure. To the above mixture was added $NaIO_4$ (374.86 mg, 1.753 mmol, 2.00 equiv), water (0.50 mL) and acetone (5.00 mL), and. the reaction stirred additional 2 h at room temperature. Following DCM extraction, the resulting solution was concentrated under reduced pressure to afford C (300 mg, 99.43%) as an off-white solid. The crude product was used in the next step directly without further purification. LCMS (ESI) m/z: $[M+H]^+$=345.

Step 3: Preparation of tert-butyl N-[1-(4-[[2-(2,6-dioxopiperidin-3-yl)-1,3-dioxoisoindol-5-yl]oxy] butyl)piperidin-4-yl]carbamate (D)

D

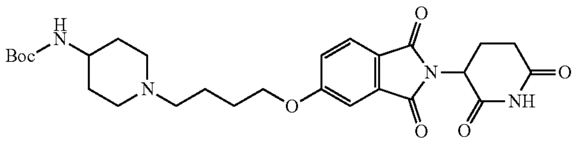

To a stirred solution of 4-[[2-(2,6-dioxopiperidin-3-yl)-1,3-dioxoisoindol-5-yl]oxy]butanal (C, 270.00 mg, 0.784 mmol, 1.00 equiv) in DMF (5.00 mL) was added STAB (249.29 mg, 1.176 mmol, 1.50 equiv) and tert-butyl N-(piperidin-4-yl)carbamate (157.05 mg, 0.784 mmol, 1.00 equiv) in portions at room temperature. The resulting mixture was stirred for overnight at room temperature, then extracted with EtOAc (2×20 mL). The combined organic layers were washed with water (3×10 mL) and dried over anhydrous Na2SO4. After filtration, the filtrate was concentrated under reduced pressure and the residue purified by preparative TLC (DCM/MeOH 10:1) to afford D (130 mg, 31.36%) as an off-white solid. LCMS (ESI) m/z: $[M+H]^+$=529.

Step 4: Preparation of 5-[4-(4-aminopiperidin-1-yl) butoxy]-2-(2,6-dioxopiperidin-3-yl)isoindole-1,3-dione (I-38)

I-38

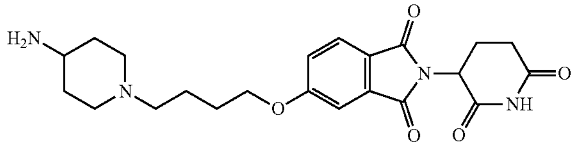

Into an 8 mL vial were added tert-butyl N-[1-(4-[[2-(2,6-dioxopiperidin-3-yl)-1,3-dioxoisoindol-5-yl]oxy]butyl) piperidin-4-yl]carbamate (D, 120.00 mg, 0.227 mmol, 1.00 equiv), TFA (1.00 mL), and DCM (4.00 mL) at room temperature. The resulting mixture was stirred for 2 h at room temperature then concentrated under reduced pressure. This resulted in I-38 (130 mg, 93.55%) as an off-white solid. LCMS (ESI) m/z: $[M+H]^+$=429.

Preparation of 5-[4-(azetidin-3-ylmethyl)piperazin-1-yl]-2-(2,6-dioxopiperidin-3-yl)isoindole-1,3-dione formate (I-40) and of 2-(2,6-dioxopiperidin-3-yl)-5-(piperazin-1-yl)isoindole-1,3-dione formate (I-39)

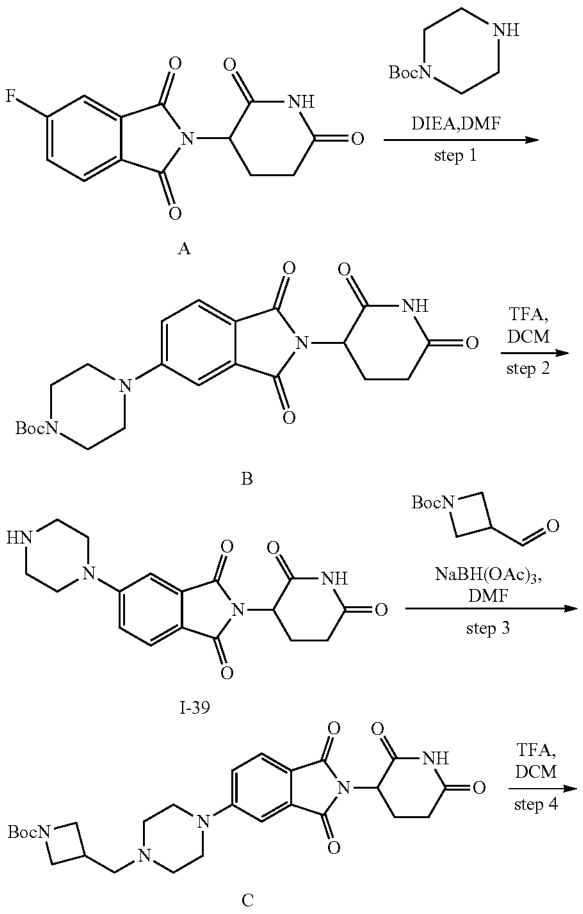

-continued

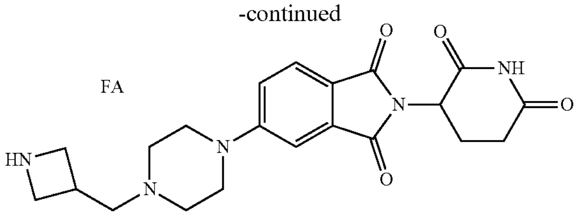

I-40

Step 1: Preparation of tert-butyl 4-[2-(2,6-dioxopiperidin-3-yl)-1,3-dioxoisoindol-5-yl]piperazine-1 carboxylate (B)

B

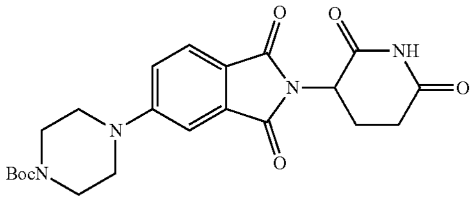

To a solution of 2-(2,6-dioxopiperidin-3-yl)-5-fluoroisoindole-1,3-dione (A, 5.40 g, 19.549 mmol, 1.00 equiv) and tert-butyl piperazine-1-carboxylate (3.64 g, 19.549 mmol, 1 equiv) in DMF (35.00 mL) was added DIEA (7.58 g, 58.648 mmol, 3 equiv). The resulting mixture was stirred for 5 h at 90° C. The reaction was quenched by the addition of water (50 mL) at room temperature. The resulting mixture was extracted with EtOAc (3×50 mL), and the combined organic layers washed with brine (3×100 mL) and dried over anhydrous $Na_2SO_4$. After filtration, the filtrate was concentrated under reduced pressure. This resulted in B (7.32 g, 84.62%) as a light yellow solid; LCMS (ESI) m/z: $[M+H]^+$=443.

Step 2: Preparation of 2-(2,6-dioxopiperidin-3-yl)-5-(piperazin-1-yl)isoindole-1,3-dione formate (I-39)

I-39

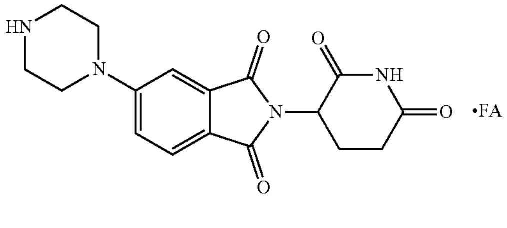

To a solution of B (900.00 mg, 2.034 mmol, 1.00 equiv) in DCM was added TFA (5.00 mL, 67.315 mmol, 33.09 equiv). The resulting mixture was stirred for 3 h at room temperature, then concentrated under vacuum. The residue was purified by reverse phase flash chromatography under the following conditions: column, C18 silica gel; mobile phase, ACN/0.1% formic acid in water, 0% to 100% gradient over 45 min; detector, UV 254 nm. This resulted in I-39 (786.8 mg, 99.41%) as a yellow solid; LCMS (ESI) m/z: $[M+H]^+$=343.

Step 3: Preparation of tert-butyl 3-([4-[2-(2,6-dioxopiperidin-3-yl)-1,3-dioxoisoindol-5-yl]piperazin-1-yl]methyl)azetidine-1-carboxylate (C)

C

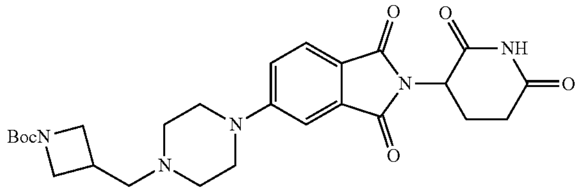

To a solution of I-39 (1.10 g, 3.213 mmol, 1.00 equiv) and tert-butyl 3-formylazetidine-1-carboxylate (595.13 mg, 3.213 mmol, 1 equiv) in DMF (10.00 mL) was added $NaBH(OAc)_3$ (2.04 g, 9.639 mmol, 3 equiv). The resulting mixture was stirred for 3 h at room temperature. After aqueous workup, DCM extraction, and concentration, the residue was purified by reverse phase flash chromatography under the following conditions: column, C18 silica gel; mobile phase, ACN/0.1% formic acid in water, 0% to 100% gradient over 45 min; detector, UV 254 nm. This resulted in C (991 mg, 60.29%) as a light yellow solid; LCMS (ESI) m/z: $[M+H]^+$=512.

Step 4: Preparation of 5-[4-(azetidin-3-ylmethyl)piperazin-1-yl]-2-(2,6-dioxopiperidin-3-yl)isoindole-1,3-dione formate (I-40)

I-40

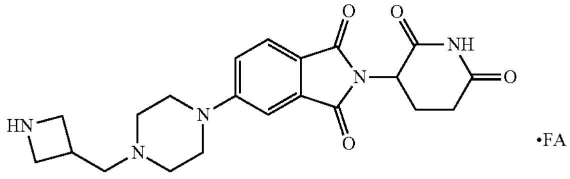

To a solution of C (991.00 mg, 1.937 mmol, 1.00 equiv) in DCM (10.00 mL, 157.300 mmol, 81.20 equiv) was added TFA (10.00 mL, 134.630 mmol, 69.50 equiv). The resulting mixture was stirred for 3 h at room temperature, then concentrated under reduced pressure. The residue was purified by reverse phase flash chromatography under the following conditions: column, C18 silica gel; mobile phase, ACN/0.1% formic acid in water, 0% to 100% gradient over 45 min; detector, UV 254 nm. This resulted in I-40 (702 mg, 85.29%) as a yellow solid; $^1H$ NMR (300 MHz, DMSO-d6) δ 11.07 (s, 1H), 8.25 (s, formic acid, 1H), 7.69 (d, 1H), 7.34 (d, 1H), 7.26 (dd, 1H), 5.08 (dd, 1H), 4.00 (t, 2H), 3.66 (dd, 2H), 3.43 (t, 4H), 3.11-2.96 (m, 1H), 2.95-2.79 (m, 1H), 2.65-2.51 (m, 4H), 2.50-2.44 (m, 4H), 2.09-1.96 (m, 1H); LCMS (ESI) m/z: $[M+H]^+$=412.19.

Preparation of 3-[4-[2-(2,6-dioxopiperidin-3-yl)-1,3-dioxoisoindol-5-yl]piperazin-1-yl]propanoic acid (I-41)

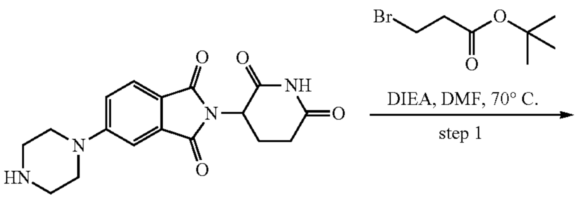

A

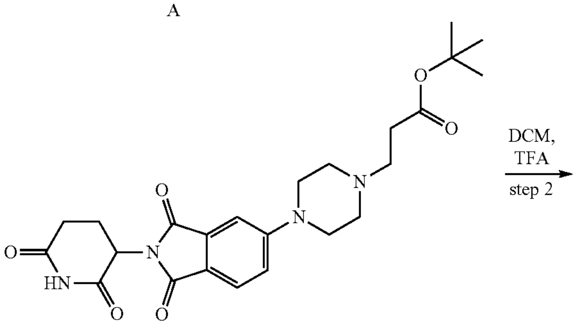

B

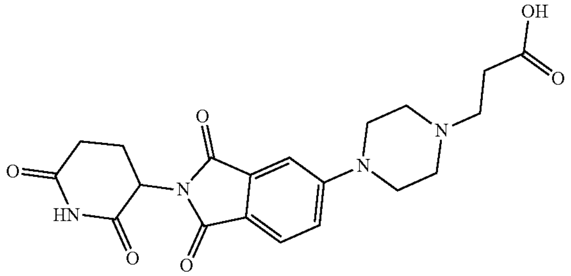

I-41

Step 1: Preparation of tert-butyl 3-[4-[2-(2,6-dioxopiperidin-3-yl)-1,3-dioxoisoindol-5-yl]piperazin-1-yl]propanoate (B)

B

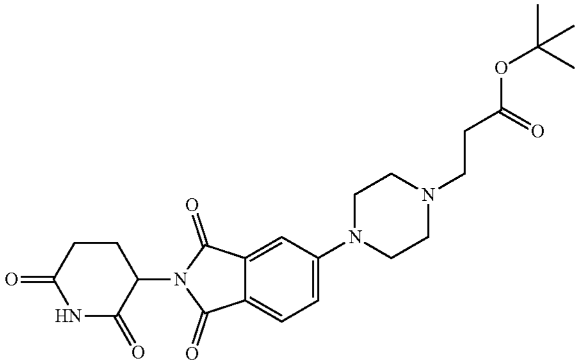

To a solution of 2-(2,6-dioxopiperidin-3-yl)-5-(piperazin-1-yl)isoindole-1,3-dione (A, 5.0 g, 14.6 mmol, 1.0 equiv) and tert-butyl 3-bromopropanoate (3.6 g 17.2 mmol, 1.2 equiv) in DMF (50 mL) was added DIEA (2.8 g, 21.7 mmol, 1.5 equiv) dropwise, and the mixture was stirred at 70° C. for 6 h. The reaction mixture was concentrated, and the residue purified by reverse phase flash chromatography under the following conditions: column, C18 Spherical Column; mobile phase, ACN in water, 10% to 70% gradient over 50 min; detector, UV 254 nm. Tert-butyl 3-[4-[2-(2,6-dioxopiperidin-3-yl)-1,3-dioxoisoindol-5-yl]piperazin-1-yl] propanoate (B) was obtained in (2.1 g, 30.6%) as a yellow solid. LCMS (ESI) m/z $[M+H]^+$=471.

Step 2: Preparation of 3-[4-[2-(2,6-dioxopiperidin-3-yl)-1,3-dioxoisoindol-5-yl] piperazin-1-yl] propanoic acid (I-41)

I-41

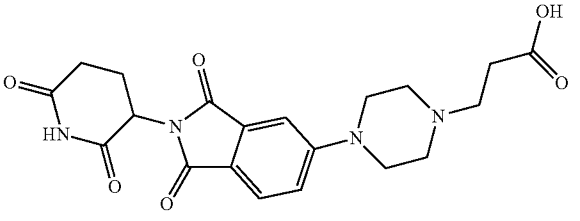

A solution of B (2.1 g, 4.5 mmol) in DCM (20 mL) and TFA (5 mL) was stirred at room temperature for 2 h. The mixture was concentrated under reduced pressure and the residue purified by reverse phase flash chromatography under the following conditions: column, C18 Spherical Column; mobile phase, MeOH in water, 10% to 30% gradient over 50 min; detector, UV 254 nm to afford 3-[4-[2-(2,6-dioxopiperidin-3-yl)-1,3-dioxoisoindol-5-yl] piperazin-1-yl]propanoic acid (I-41) (0.78 g, 42.2%) as yellow solid. $^1$H NMR (300 MHz, DMSO-d6) δ 12.03 (br, 1H), 11.10 (s, 1H), 7.68 (d, J=8.5 Hz, 1H), 7.35 (d, J=1.7 Hz, 1H), 7.27 (dd, J=8.6, 2.0 Hz, 1H), 5.08 (dd, J=12.8, 5.4 Hz, 1H), 3.49-3.40 (m, 4H), 2.96-2.80 (m, 1H), 2.67-2.52 (m, 8H), 2.44 (t, J=6.9 Hz, 2H), 2.07-1.97 (m, 1H). LCMS (ESI) m/z $[M+H]^+$=415.10.

Preparation of 2-(2,6-dioxopiperidin-3-yl)-5-(4-(piperidin-4-ylmethyl)piperazin-1-yl)isoindoline-1,3-dione trifluoroacetate (I-42)

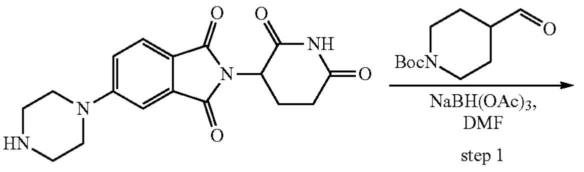

A

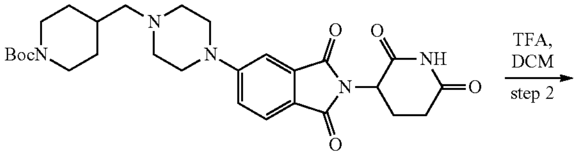

B

-continued

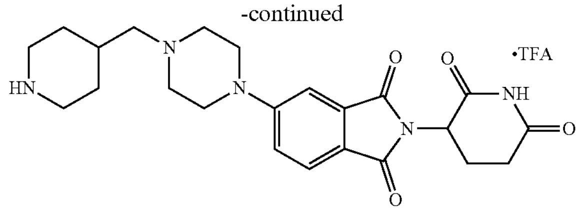

I-42

Step 1: Preparation of tert-butyl 4-((4-(2-(2,6-dioxopiperidin-3-yl)-1,3-dioxoisoindolin-5-yl)piperazin-1-yl)methyl)piperidine-1-carboxylate (B)

B

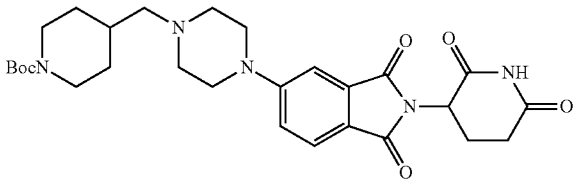

A solution of 2-(2,6-dioxopiperidin-3-yl)-5-(piperazin-1-yl)isoindole-1,3-dione (A, 1.5 g, 4.4 mmol, 1.0 equiv) and tert-butyl 4-formylpiperidine-1-carboxylate (0.93 g, 4.4 mmol, 1.0 equiv) in DMF (20 mL) was stirred at room temperature for 30 minutes. $NaBH(OAc)_3$ (3.7 g, 17.5 mmol, 4.0 equiv) was then added and the resulting mixture stirred at 50° C. for 3.5 h. The mixture was cooled to RT, poured into water (100 mL), extracted with EtOAc (50 mL×3). The combined organic layers were concentrated and the residue was purified by preparative HPLC under the following conditions: C18 Spherical Column, 20-35 um, 330 g; mobile phase, phase A: water (0.16% $NH_4HCO_3$), B: ACN (Gradient B % 0%-70%, run time 40 min); Flow rate: 80 mL/min; Detector, UV detection at 254 nm. B (1.2 g, 50.8%) was obtained from the purification as a yellow solid. LCMS (ESI) m/z: $[M+H]^+$=540.

Step 2: Preparation of 2-(2,6-dioxopiperidin-3-yl)-5-(4-(piperidin-4-ylmethyl)piperazin-1-yl)isoindoline-1,3-dione trifluoroacetate (I-42)

I-42

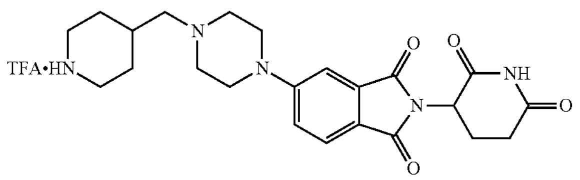

A mixture of tert-butyl 4-([4-[2-(2,6-dioxopiperidin-3-yl)-1,3-dioxoisoindol-5-yl]piperazin-1-yl]methyl)piperidine-1-carboxylate (B, 1.2 g, 2.2 mmol, 1.0 equiv) in DCM (8 mL) and TFA (2.0 mL) was stirred at room temperature for 2 h. The mixture was concentrated and the residue was purified by preparative HPLC under the following conditions: C18 Spherical Column, 20-35 um, 330 g; mobile phase, phase A: water (0.16% $NH_4HCO_3$), B: ACN (Gradient B % 0%-60%, run time 45 min); Flow rate: 80 mL/min; Detector, UV detection at 254 nm. Compound I-42 (0.60 g, 61.3%) was obtained as a yellow solid. $^1H$ NMR (300 MHz, DMSO-d6): δ 10.42 (br, 1H), 9.12 (br, 1H), 7.73-7.60 (m, 1H), 7.35 (s, 1H), 7.26 (d, J=8.7 Hz, 1H), 5.07 (dd, J=12.7, 5.3 Hz, 1H), 4.66 (br, 1H), 3.12-3.33 (m, 5H), 2.93-2.75 (m, 5H), 2.19 (d, J=5.6 Hz, 3H), 2.07-1.98 (m, 2H), 1.85 (d, J=11.7 Hz, 5H), 1.26 (d, J=11.9 Hz, 3H). LCMS (ESI) m/z: $[M+H]^+$=440.35.

Preparation of 5-((2-aminoethyl)amino)-2-(2,6-dioxopiperidin-3-yl)isoindoline-1,3-dione trifluoroacetate (I-43)

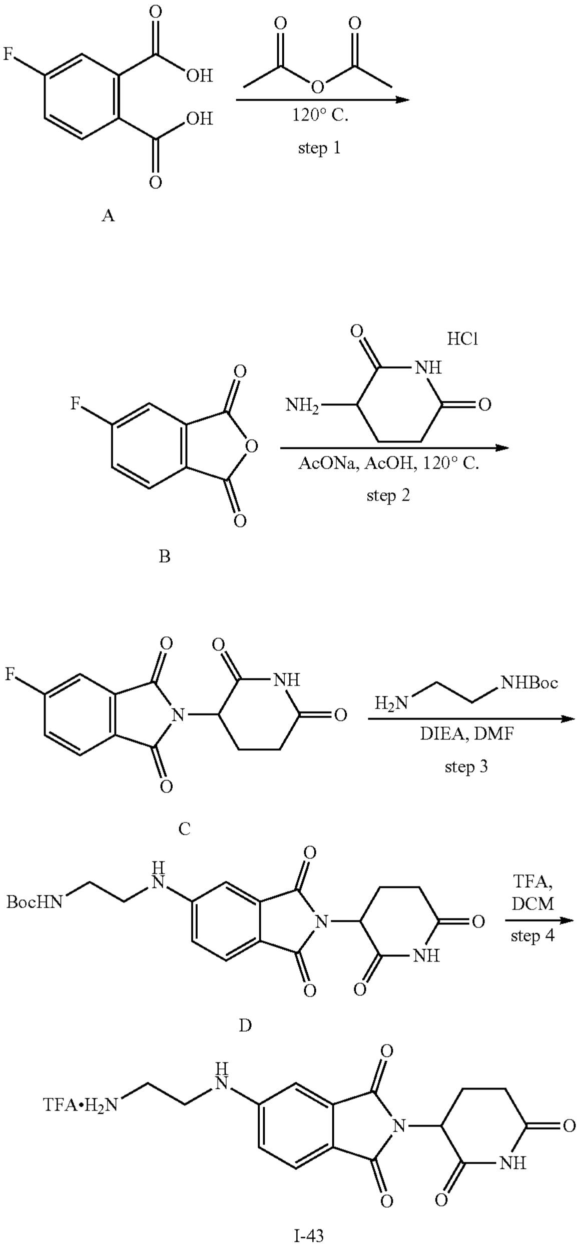

A

B

C

D

I-43

Step 1: Preparation of 5-fluoroisobenzofuran-1,3-dione (B)

B

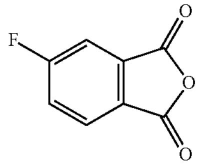

To a solution of 4-fluorobenzene-1,2-dicarboxylic acid (A, 41.4 g, 0.22 mol, 1.00 equiv) was added acetic anhydride (200 mL). The reaction was stirred at 120° C. for 2 h, then cooled to room temperature and concentrated under reduced pressure to afford 5-fluoro-2-benzofuran-1,3-dione (B, 37.2 g, quant.) as a white solid.

Step 2: Preparation of 2-(2,6-dioxopiperidin-3-yl)-5-fluoroisoindoline-1,3-dione (C)

C

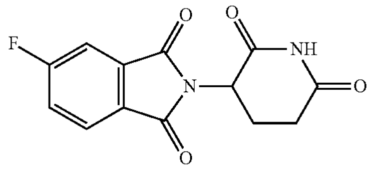

To a stirred solution of 5-fluoro-2-benzofuran-1,3-dione (B, 37.2 g, 0.22 mol, 1.0 equiv) and 3-aminopiperidine-2,6-dione hydrochloride (55.4 g, 0.34 mol, 1.5 equiv) in acetic acid (300 mL) was added sodium NaOAc (55.2 g, 0.67 mol, 3.0 equiv) under a nitrogen atmosphere. The resulting mixture was stirred for 3 h at 120° C., then cooled to room temperature. The suspension was filtered, and the filter cake was washed with water (3×150 mL) to afford 2-(2,6-dioxopiperidin-3-yl)-5-fluoroisoindole-1,3-dione (C, 53.1 g, 87.4%) as a grey solid. LCMS (ESI) m/z: $[M+H]^+$=277.

Step 3: Preparation of tert-butyl (2-((2-(2,6-dioxopiperidin-3-yl)-1,3-dioxoisoindolin-5-yl)amino) ethyl) carbamate (D)

D

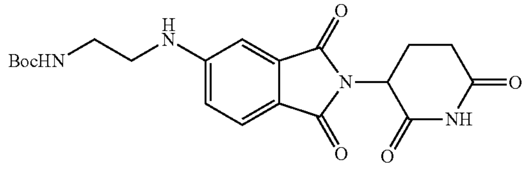

To a solution of tert-butyl N-(2-aminoethyl)carbamate (2.9 g, 18.1 mmol, 1.0 equiv) and 2-(2,6-dioxopiperidin-3-yl)-5-fluoroisoindole-1,3-dione (C, 5.0 g, 18.1 mmol, 1.0 equiv) in DMF (50 mL) was added DIEA (4.7 g, 36.2 mmol, 2.00 equiv). The mixture was stirred at 80° C. for 2 h, then cooled to RT and poured into water (500 mL). The resulting mixture was extracted with EtOAc (500 mL×3). The combined organic layers were concentrated and the residue purified by reverse phase flash chromatography under the following conditions: column, C18 spherical column; mobile phase, ACN in water, 0% to 100% gradient over 50 min; 70 ml/min detector, UV 254 nm to give the desired product tert-butyl N-(2-[[2-(2,6-dioxopiperidin-3-yl)-1,3-dioxoisoindol-5-yl]amino]ethyl)carbamate (D, 1.5 g, 19.5%) as a yellow solid. LCMS (ESI) m/z: $[M+H]^+$=417.

Step 4: Preparation of 5-((2-aminoethyl)amino)-2-(2,6-dioxopiperidin-3-yl)isoindoline-1,3-dione trifluoroacetate (I-43)

I-43

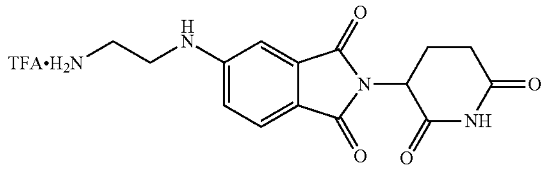

To a stirred solution of tert-butyl N-(2-[[2-(2,6-dioxopiperidin-3-yl)-1,3-dioxoisoindol-5-yl]amino]ethyl) carbamate (D, 1.5 g, 3.6 mmol, 1.0 equiv) in DCM (20 mL) was added TFA (4 mL) dropwise at 0° C. The resulting mixture was warmed to room temperature and stirred for 2 h. The reaction mixture was concentrated under reduced pressure, and the crude product purified by preparative HPLC to afford 5-[(2-aminoethyl)amino]-2-(2,6-dioxopiperidin-3-yl) isoindole-1,3-dione trifluoroacetate (I-43, 0.97 g, 63.1%) as a yellow solid. $^1H$ NMR (300 MHz, DMSO-d6) δ 11.09 (s, 1H), 7.88 (br, 3H), 7.63 (d, J=8.3 Hz, 1H), 7.22 (br, 1H), 7.04 (d, J=1.9 Hz, 1H), 6.92 (dd, J=8.4, 2.1 Hz, 1H), 5.06 (dd, J=12.8, 5.3 Hz, 1H), 3.52-3.39 (m, 2H), 3.08-2.81 (m, 3H), 2.65-2.53 (m, 2H), 2.06-1.96 (m, 1H). LCMS (ESI) m/z: $[M+H]^+$=317.00.

Preparation of 5-(2-aminoethoxy)-2-(2,6-dioxopiperidin-3-yl)isoindoline-1,3-dione trifluoroacetate (I-44)

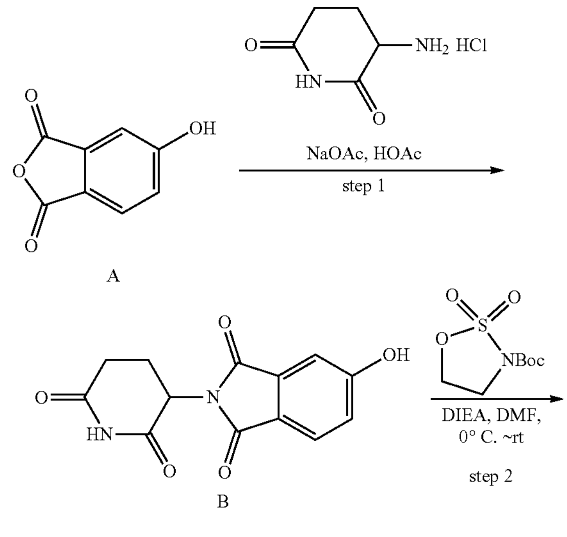

-continued

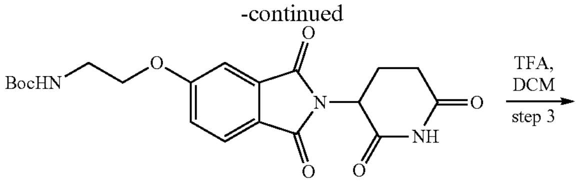

C

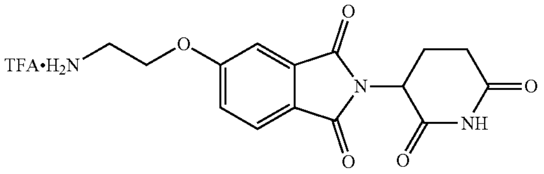

I-44

Step 1: Preparation of 2-(2,6-dioxopiperidin-3-yl)-5-hydroxyisoindoline-1,3-dione (B)

B

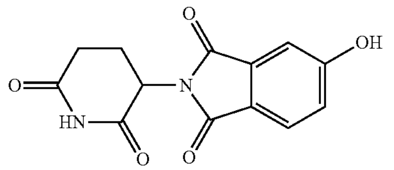

To a stirred solution of 5-hydroxy-2-benzofuran-1,3-dione (A, 2.0 g, 12.2 mmol, 1.0 equiv) and 3-aminopiperidine-2,6-dione hydrochloride (3.0 g, 18.3 mmol, 1.5 equiv) in HOAc (40 mL) was added NaOAc (3.0 g, 36.6 mmol, 3.0 equiv). The reaction mixture was stirred at 120° C. under a nitrogen atmosphere then concentrated to dryness under reduced pressure. The residue was purified by silica gel column chromatography, eluting with Petroleum ether/EtOAc (4:1) to afford B (2.9 g, 86.7%) as a white solid. LCMS (ESI) m/z $[M+H]^+=275$.

Step 2: Preparation of (tert-butyl (2-((2-(2,6-dioxopiperidin-3-yl)-1,3-dioxoisoindolin-5-yl)oxy)ethyl)carbamate (C)

C

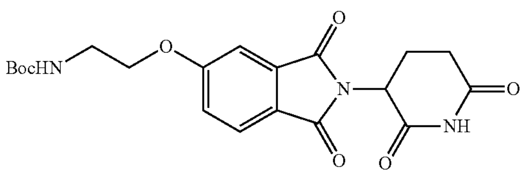

To a stirred solution of B (1.0 g, 3.6 mmol, 1.0 equiv) and tert-butyl 1,2,3-oxathiazolidine-3-carboxylate 2,2-dioxide (0.98 g, 4.4 mmol, 1.2 equiv) in DMF (10 mL) was added DIEA (0.94 g, 7.3 mmol, 2.0 equiv) under a nitrogen atmosphere. After stirring at 80° C. for 2 h, water (100 mL) was added, followed by extraction with EtOAc (3×100 mL). The combined organic layers were washed with water (3×100 mL) and dried over anhydrous $Na_2SO_4$. After filtration, the filtrate was concentrated to dryness under reduced pressure, and the residue purified by reverse phase flash chromatography under the following conditions: column, C18 spherical column; mobile phase, ACN in water, 0% to 100% gradient over 50 min; 70 ml/min detector, UV 254 nm to get C (1.7 g, 94.4%) as a yellow oily material. LCMS (ESI) m/z: $[M+H]^+=418$.

Step 3: Preparation of 5-(2-aminoethoxy)-2-(2,6-dioxopiperidin-3-yl)isoindoline-1,3-dione; trifluoroacetate (I-44)

I-44

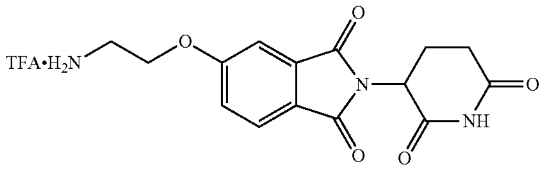

To a stirred solution of C (1.4 g, 3.4 mmol, 1.0 equiv) in DCM (20 mL) was added TFA (5 mL) dropwise. After stirring for 2 h at room temperature, the reaction mixture was concentrated under reduced pressure and the residue purified by flash column chromatography on silica gel to afford I-44 (750 mg, 51.2%) as a yellow solid. $^1H$ NMR (300 MHz, DMSO-d6) δ 11.15 (s, 1H), 8.04 (br, 3H), 7.91 (d, J=8.3 Hz, 1H), 7.50 (d, J=2.2 Hz, 1H), 7.41 (dd, J=8.3, 2.3 Hz, 1H), 5.14 (dd, J=12.9, 5.3 Hz, 1H), 4.38 (t, J=4.9 Hz, 2H), 3.35-3.23 (m, 2H), 2.98-2.81 (m, 1H), 2.66-2.54 (m, 2H), 2.11-2.01 (m, 1H). LCMS (ESI) m/z: $[M+H]^+=418.10$.

Preparation of 3-(4-((2-aminoethyl)amino)-1-oxoisoindolin-2-yl)piperidine-2,6-dione (I-45)

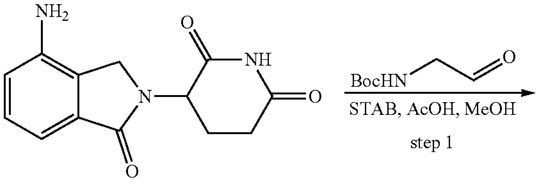

A

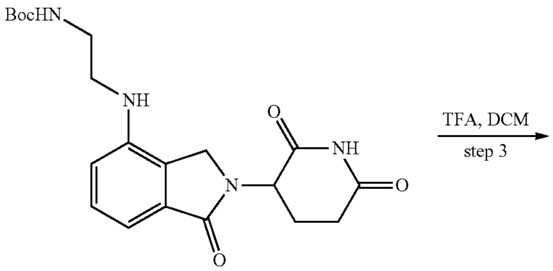

B

-continued

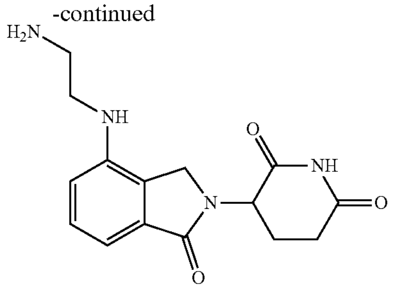

I-45

Step 1: Preparation of tert-butyl (2-((2-(2,6-dioxopiperidin-3-yl)-1-oxoisoindolin-4-l)amino)ethyl) carbamate (B)

B

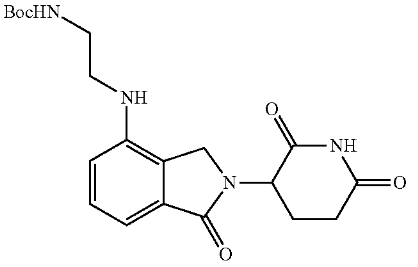

Lenalidomide (A, 442.00 mg, 1.705 mmol, 1.00 equiv), tert-butyl N-(2-oxoethyl)carbamate (229.00 mg, 1.439 mmol, 0.84 equiv) and AcOH (100.00 mg, 1.665 mmol, 0.98 equiv) were suspended in MeOH (20.00 mL). The mixture was stirred at room temperature for 2 h followed by addition of NaBH3CN (145.00 mg, 2.307 mmol, 1.35 equiv). After an additional 1 h the reaction was quenched with saturated aqueous $NaHCO_3$and extracted with DCM (3×40 mL). The combined organic layers were washed with brine (1×100 mL) and dried over anhydrous Na2SO4. After filtration, the filtrate was concentrated under reduced pressure. The residue was purified by silica gel column chromatography, eluting with DCM:MeOH (10:1) to afford B (100 mg, 14.58%) as a yellow solid. LCMS (ESI) m/z: $[M+H]^+$=403.

Step 2: Preparation of 3-(4-((2-aminoethyl)amino)-1-oxoisoindolin-2-yl)piperidine-2,6-dione (I-45)

I-45

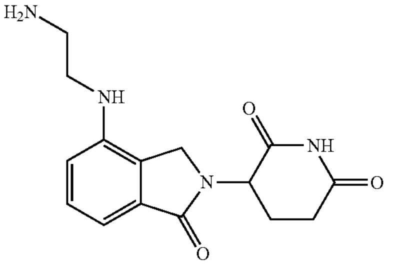

B (100.00 mg, 0.248 mmol, 1.00 equiv) was dissolved in DCM (5.00 mL). TFA (1.00 mL, 13.463 mmol, 54.18 equiv) was added and the resulting solution stirred for 0.5 h at room temperature. Concentration under reduced pressure afforded I-45 as a crude product which was used in the next step without further purification. LCMS (ESI) m/z: $[M+H]^+$= 303.

Preparation of 3-(6-((2-aminoethyl)amino)-1-oxoisoindolin-2-yl)piperidine-2,6-dione (I-46)

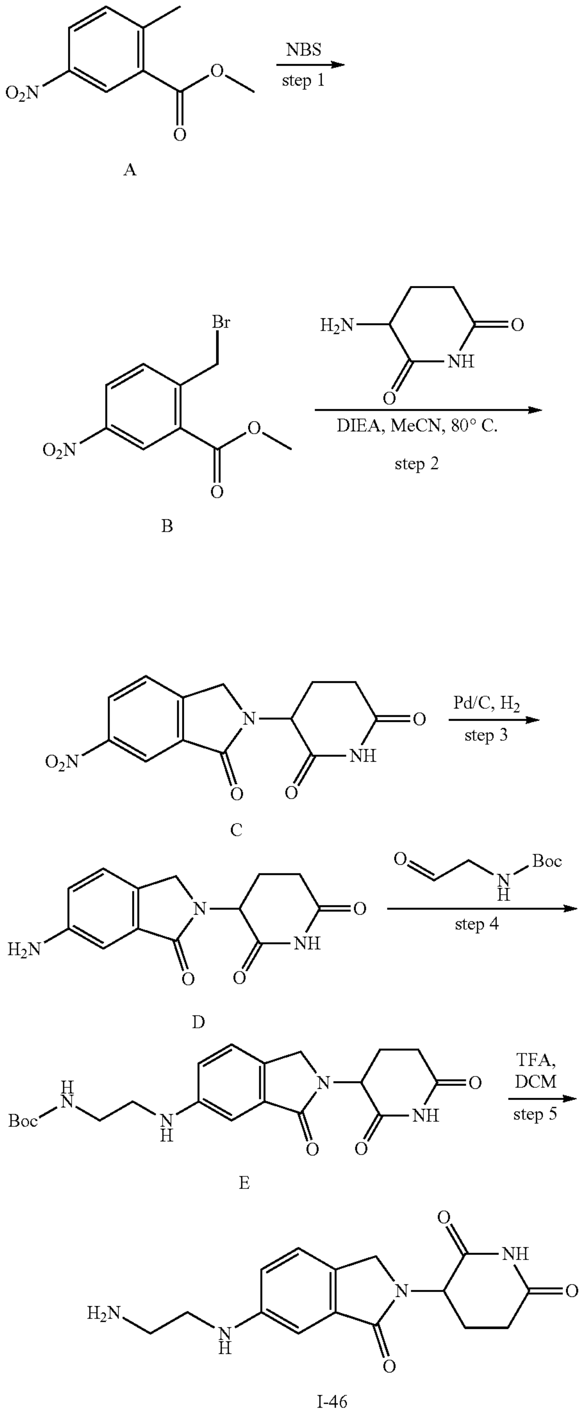

Step 1: Preparation of methyl 2-(bromomethyl)-5-nitrobenzoate (B)

B

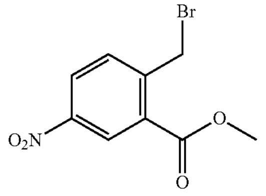

A (2.00 g, 10.247 mmol, 1.00 equiv), NBS (2.40 g, 13.484 mmol, 1.32 equiv) and BPO (80.00 mg, 0.312 mmol, 0.03 equiv) were dissolved in CCl4 (40.00 mL). The solution was heated to reflux and stirred overnight. The resulting mixture was washed with 50 mL of brine, and the residue purified by silica gel column chromatography, eluting with Petroleum ether:EtOAc (5:1) to afford B (1.2 g, 42.73%) as a colorless oil. LCMS (ESI) m/z: $[M+H]^+$=275.

Step 2: Preparation of 3-(6-nitro-1-oxoisoindolin-2-yl)piperidine-2,6-dione (C)

C

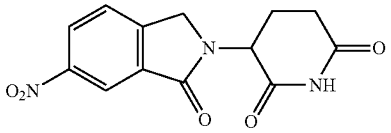

B (510.00 mg, 1.861 mmol, 1.00 equiv), 3-aminopiperidine-2,6-dione (395.00 mg, 3.083 mmol, 1.66 equiv) and DIEA (777.00 mg, 6.012 mmol, 3.23 equiv) were dissolved in ACN (10.00 mL). The mixture was stirred at 80° C. for 2 h. The reaction mixture was concentrated, and the residue purified by silica gel column chromatography, eluting with DCM:ACN (3:1) to afford C (410 mg, 76.17%) as a dark green solid. LCMS (ESI) m/z: $[M+H]^+$=290.

Step 3: Preparation of 3-(6-amino-1-oxoisoindolin-2-yl)piperidine-2,6-dione (D)

D

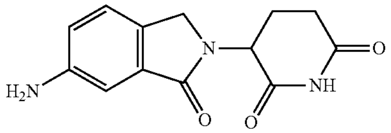

C (410.00 mg, 1.417 mmol, 1.00 equiv) and 10% Pd/C (80.00 mg, 0.752 mmol, 0.53 equiv) were suspended in DMF (15.00 mL). The reaction mixture was stirred overnight at room temperature under 1 atmosphere of hydrogen. The mixture was filtered through Celite, and the filtrate concentrated to afford D (350 mg, 95.24%) as a brown solid. LCMS (ESI) m/z: $[M+H]^+$=260.

Step 4: Preparation of tert-butyl (2-((2-(2,6-dioxopiperidin-3-yl)-3-oxoisoindolin-5-yl)amino)ethyl)carbamate (E)

E

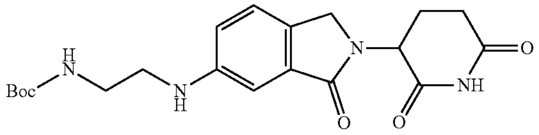

D (350.00 mg, 1.350 mmol, 1.00 equiv), tert-butyl N-(2-oxoethyl)carbamate (257.87 mg, 1.620 mmol, 1.20 equiv) and AcOH (81.07 mg, 1.350 mmol, 1.00 equiv) were suspended in MeOH (15.00 mL). The mixture was stirred for 1 h at room temperature followed by addition of NaBH3CN (101.80 mg, 1.620 mmol, 1.20 equiv). The reaction was stirred for an additional 2 h, then quenched with 5% aqueous Na2HCO3. The resulting mixture was extracted with DCM (40 mL×3) and combined organic layers were dried over Na2SO4 and concentrated to afford E (450 mg, 82.83%) as a white solid. LCMS (ESI) m/z: $[M+H]^+$=403.

Step 5: Preparation of 3-(6-((2-aminoethyl)amino)-1-oxoisoindolin-2-yl)piperidine-2,6-dione (I-46)

I-46

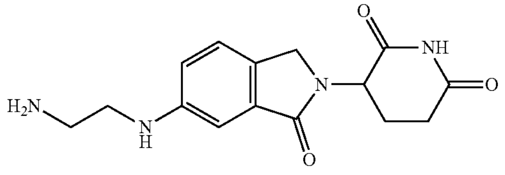

E (50.00 mg, 0.124 mmol, 1.00 equiv) and TFA (0.50 mL, 6.732 mmol, 54.18 equiv) were dissolved in DCM (2.00 mL, 31.460 mmol, 253.22 equiv). The solution was stirred at room temperature for 0.5 h, then concentrated to afford I-46 (50 mg, crude) as a yellow oil which was used without further purification. LCMS (ESI) m/z: $[M+H]^+$=303.

Preparation of 3-(5-((2-aminoethyl)amino)-1-oxoisoindolin-2-yl)piperidine-2,6-dione (I-47)

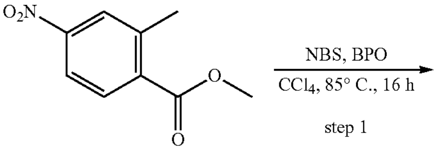

A

-continued

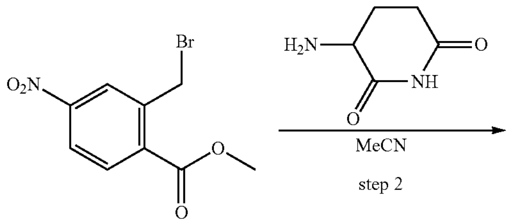

B

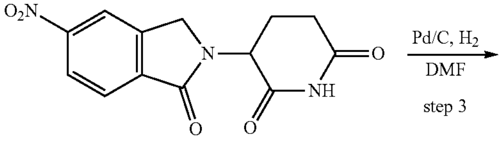

C

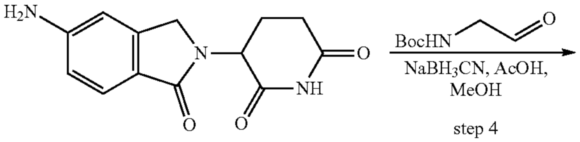

D

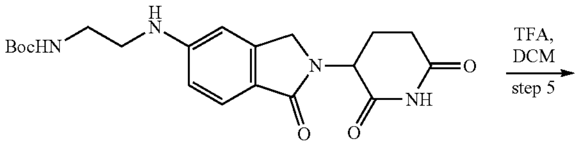

E

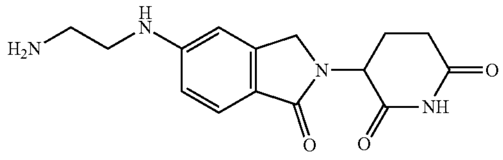

I-47

Step 1: Preparation of methyl 2-(bromomethyl)-4-nitrobenzoate (B)

B

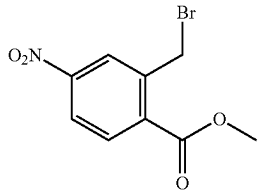

Methyl 2-methyl-4-nitrobenzoate (A, 2.00 g, 1 equiv), NBS (2.40 g) and BPO (88.00 mg) were dissolved in $CCl_4$ (40.00 mL). The solution was heated to reflux and stirred overnight. The resulting mixture was washed with 50 mL of brine, dried over $Na_2SO_4$, and concentrated under reduced pressure. The residue was purified by silica gel column chromatography, eluting with Petroleum ether:EtOAc (5:1) to afford B (2.2 g, 78.33%) as a colorless oil. LCMS (ESI) m/z: $[M+H]^+$=275.

Step 2: Preparation of 3-(5-nitro-1-oxoisoindolin-2-yl)piperidine-2,6-dione (C)

C

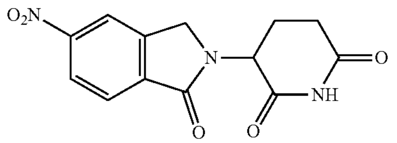

B (508.50 mg, 1.855 mmol, 1.00 equiv), 3-aminopiperidine-2,6-dione (370.70 mg, 2.893 mmol, 1.56 equiv) and DIEA (755.00 mg, 5.842 mmol, 3.15 equiv) were suspended in ACN (10.00 mL). The mixture was stirred at 80° C. for 2 h, then cooled and concentrated under reduced pressure. The residue was purified by silica gel column chromatography, eluting with DCM:ACN (3:1) to afford C (230 mg, 42.86%) as a grey solid. LCMS (ESI) m/z: $[M+H]^+$=290.

Step 3: Preparation of 3-(5-amino-1-oxoisoindolin-2-yl)piperidine-2,6-dione (D)

D

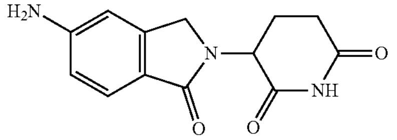

C (190.00 mg, 0.657 mmol, 1.00 equiv) and 10% Pd/C (44 mg) were suspended in DMF (5.00 mL). The mixture was stirred overnight at room temperature under 1 atmosphere of hydrogen. The reaction mixture was filtered through Celite and concentrated to afford D (170 mg, 99.82%) as a yellow solid. LCMS (ESI) m/z: $[M+H]^+$=260.

Step 4: Preparation of tert-butyl (2-((2-(2,6-dioxopiperidin-3-yl)-1-oxoisoindolin-5-yl)amino)ethyl)carbamate (E)

E

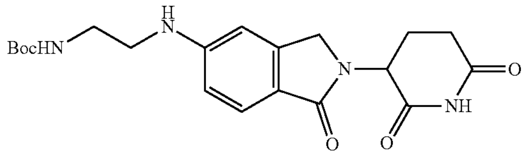

D (250.00 mg, 0.964 mmol, 1.00 equiv), tert-butyl N-(2-oxoethyl)carbamate (153.50 mg, 0.964 mmol, 1.00 equiv) and AcOH (0.10 mL, 1.745 mmol, 1.81 equiv) were suspended in MeOH (10.00 mL). The reaction mixture was stirred at room temperature for 1 h after which time $NaBH_3CN$ (60.60 mg, 0.964 mmol, 1.00 equiv) was added. The mixture was stirred for another 2 h, then diluted with sat. $NaHCO_3$ (20 mL). The aqueous layer was extracted with DCM (3×40 mL) and the combined organic layers were dried over $Na_2SO_4$, filtered, and concentrated. The residue was purified by silica gel column chromatography, eluting with Petroleum ether/EtOAc (1:1) to afford E (100 mg, 25.77%) as a light yellow solid. LCMS (ESI) m/z: $[M+H]^+$=403.

Step 5: Preparation of 3-(5-((2-aminoethyl)amino)-1-oxoisoindolin-2-yl)piperidine-2,6-dione (I-47)

I-47

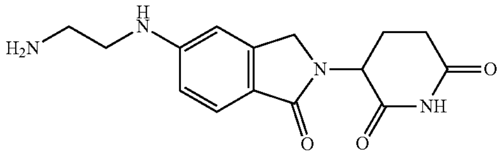

E (100.00 mg, 0.248 mmol, 1.00 equiv) was dissolved in DCM (5.00 mL). TFA (1.00 mL, 13.463 mmol, 54.18 equiv) was added and the resulting solution stirred at room temperature for 0.5 h. The mixture was concentrated to afford I-47 (100 mg, crude) as a yellow oil. LCMS (ESI) m/z: $[M+H]^+$=303

Preparation of 3-(6-((6-aminohexyl) amino)-1-oxoisoindolin-2-yl) piperidine-2,6-dione (I-48 and 3-(5-((6-aminohexyl) amino)-1-oxoisoindolin-2-yl) piperidine-2,6-dione (I-49)

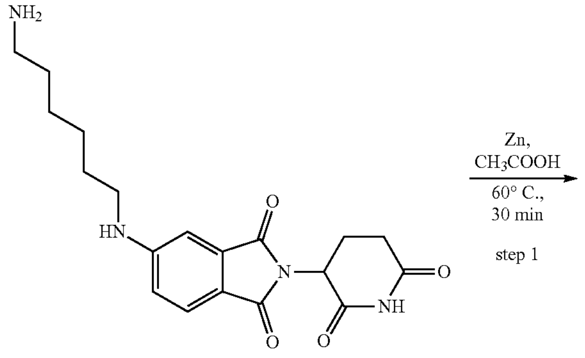

A

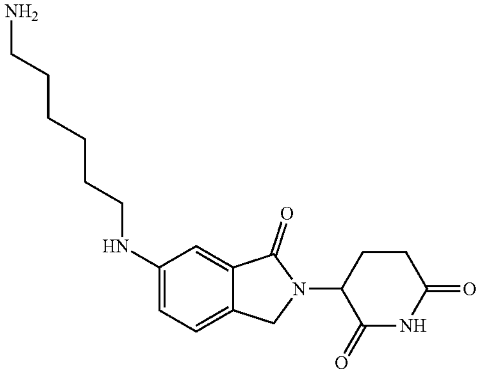

+

I-48

-continued

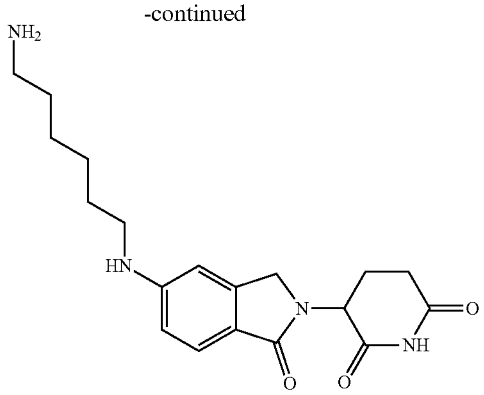

I-49

To a stirred mixture of 5-[(6-aminohexyl)amino]-2-(2,6-dioxopiperidin-3-yl)isoindole-1,3-dione (A, 200.00 mg, 0.537 mmol, 1.00 equiv) in HOAc (10.00 mL) was added Zn powder (351.26 mg, 5.370 mmol, 10.00 equiv) in portions at room temperature. The resulting mixture was stirred for 30 min at 60° C. The resulting mixture was filtered, and the filter cake was washed with EtOAc (4×10 mL). The filtrate was concentrated under reduced pressure and the residue purified by preparative HPLC to afford I-48 (19 mg, 9.87%) as a white solid and I-49 (23 mg, 11.95%) as a white solid. LCMS (ESI) m/z: $[M+H]^+$=359 for each.

Preparation of 7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptanoic acid (I-50)

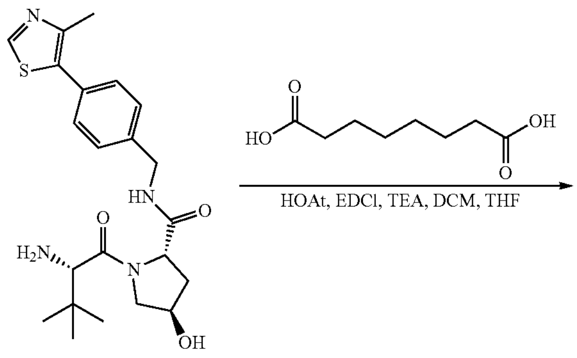

A

-continued

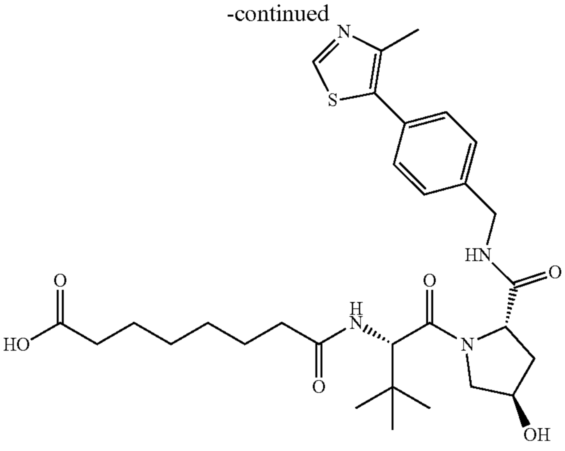

I-50

To a stirred solution of octanedioic acid (2.02 g, 11.596 mmol, 4.99 equiv) in DCM (25.00 mL) and THE (25.00 mL) was added A (1.00 g, 2.323 mmol, 1.00 equiv), TEA (822.55 mg, 8.129 mmol, 3.50 equiv), HOAt (347.73 mg, 2.555 mmol, 1.10 equiv), and EDCI (489.75 mg, 2.555 mmol, 1.10 equiv) at 0° C. The resulting solution was stirred for 2 h at 0° C. The resulting mixture was concentrated under reduced pressure, and the residue purified by reverse phase flash chromatography to afford I-50 (900 mg, 66.04%) as a white solid. LCMS (ESI) m/z: $[M+H]^+$=587.

Preparation of 6-[[(2S)-1-[(2S,4R)-4-hydroxy-2-([[4-(4-methyl-1,3-thiazol-5-yl)phenyl]methyl]-carbamoyl)pyrrolidin-1-yl]-3,3-dimethyl-1-oxobutan-2-yl]carbamoyl]spiro[3.3]heptane-2-carboxylic acid (I-51)

I-51

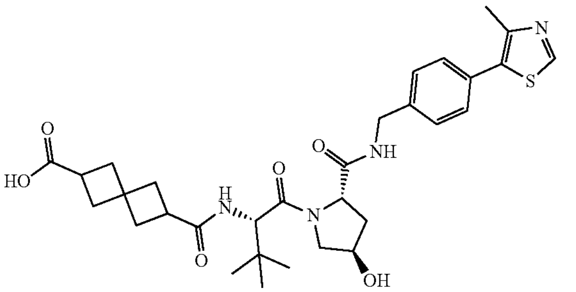

I-51 was prepared in a similar manner as described in the preparation of I-50. LCMS (ESI) m/z: $[M+H]^+$=597.

Preparation of 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoic acid (I-52)

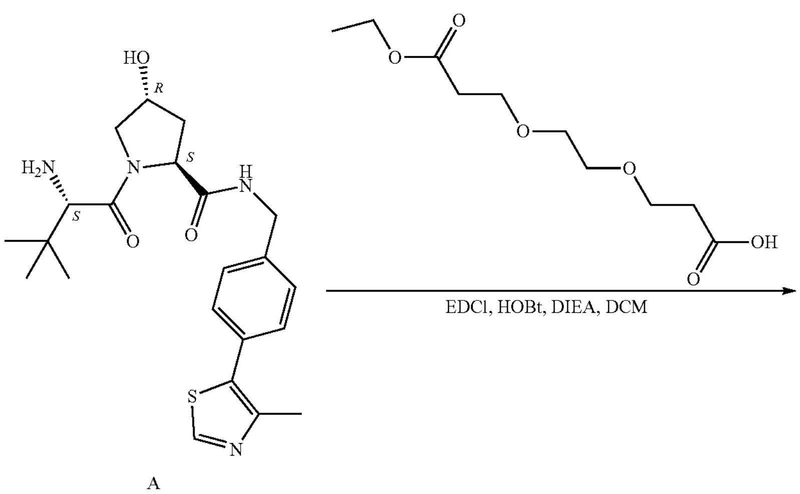

A

-continued
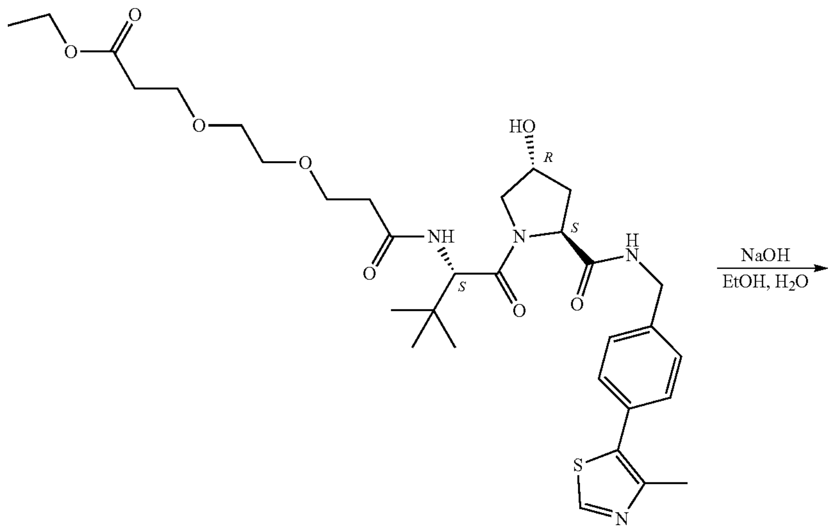
B
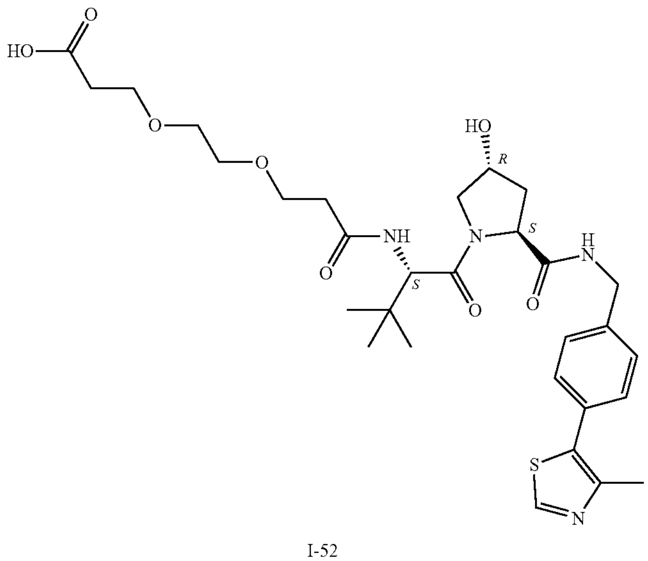
I-52

Step 1: Preparation of Intermediate 20 ethyl 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoate (B)

B

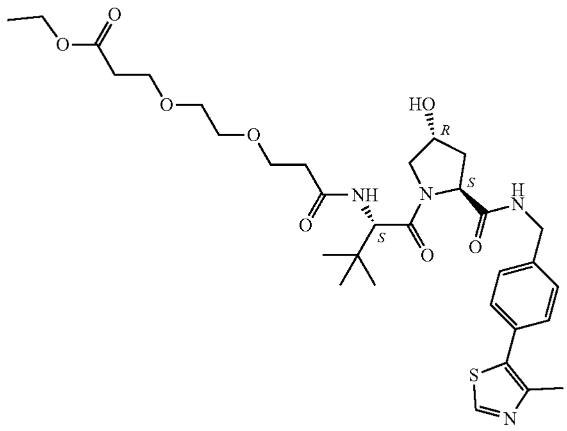

To a solution of A (500 mg, 1.07 mmol, HCl), 3-[2-(3-ethoxy-3-oxo-propoxy)ethoxy]propanoic acid (250.79 mg, 1.07 mmol, 250.79 μL), and DIEA (691.84 mg, 5.35 mmol, 932.40 μL) in DCM (5 mL) was added EDCI (246.29 mg, 1.28 mmol) and HOBt (173.60 mg, 1.28 mmol). The mixture was stirred at 20° C. for 16 h, then concentrated under reduced pressure. The residue was purified by reverse phase flash chromatography (0.1% formic acid in water/ACN) followed by lyophilization to give B (500 mg, 70.00%) as a yellow oil. LCMS (ESI) m/z: $[M+H]^+$=647.6.

Step 2: Preparation of Intermediate 13 3-(2-(3-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoic acid (I-52)

I-52

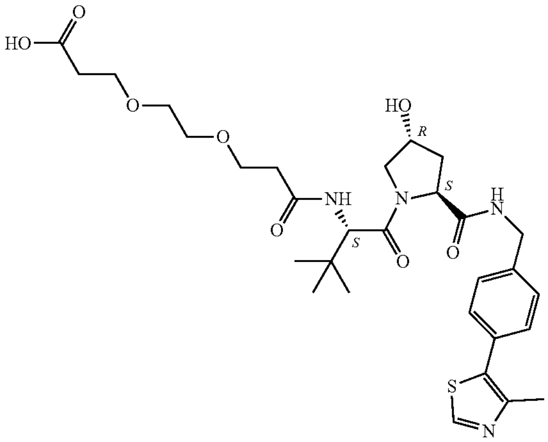

To a solution of B (500 mg, 0.7 mmol) in EtOH (5 mL) was added a solution of NaOH (77.30 mg, 1.93 mmol) in water (1 mL). The mixture was stirred at 20° C. for 1 h then diluted with water (30 mL) and adjusted to pH 6 with 1 N HCl. The mixture was extracted with EtOAc (30 mL×3), and the combined organic layers were dried over with $Na_2SO_4$ and concentrated to give I-52 (470 mg, 95.02%) as a brown solid which was used without further purification. LCMS (ESI) m/z: $[M+Na]^+$=641.2.

TABLE 5

The following intermediates were prepared in a similar manner as described in the preparation of I-52.

| Structures | # | Name | LCMS (ESI) m/z: $[M + H]^+$ |
|---|---|---|---|
| 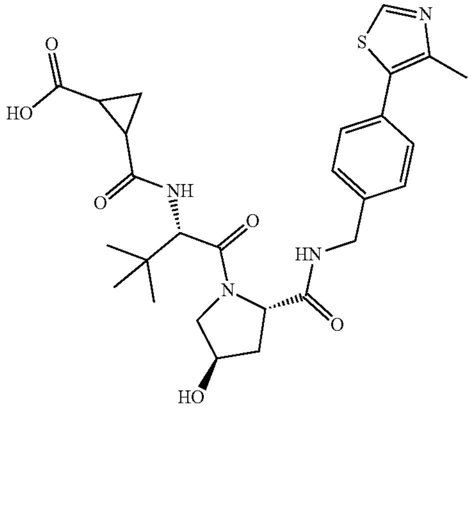 [SMILES: Cc1ncsc1-c1ccc(CNC(=O)[C@@H]2C[C@@H](O)CN2C(=O)[C@@H](NC(=O)C2CC2C(=O)O)C(C)(C)C)cc1] | I-54 | 2-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]cyclopropane-1-carboxylic acid | 543 |

TABLE 5-continued

The following intermediates were prepared in a similar manner as described in the preparation of I-52.

| Structures | # | Name | LCMS (ESI) m/z: [M + H]+ |
|---|---|---|---|
| 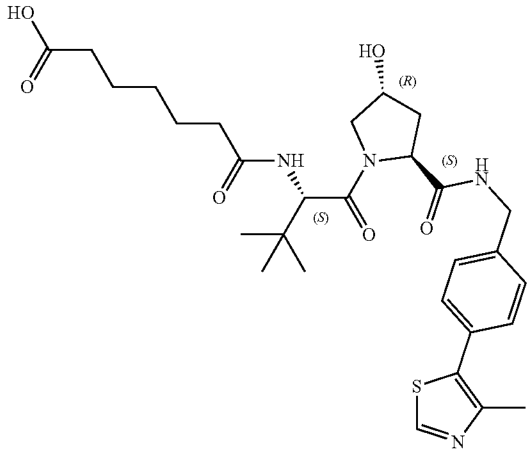 | I-55 | 2 7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid | 573.5 |
| 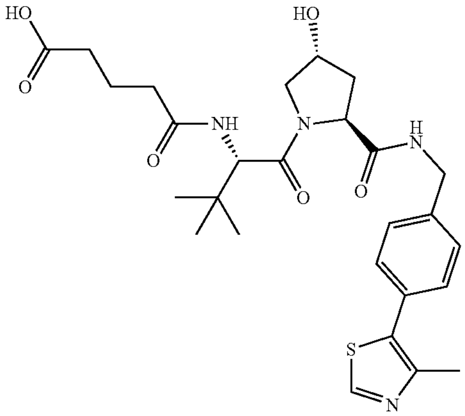 [SMILES: Cc1ncsc1-c1ccc(CNC(=O)[C@@H]2C[C@@H](O)CN2C(=O)[C@@H](NC(=O)CCCC(=O)O)C(C)(C)C)cc1] | I-56 | 5-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-5-oxo-pentanoic acid | 567.4 |
| 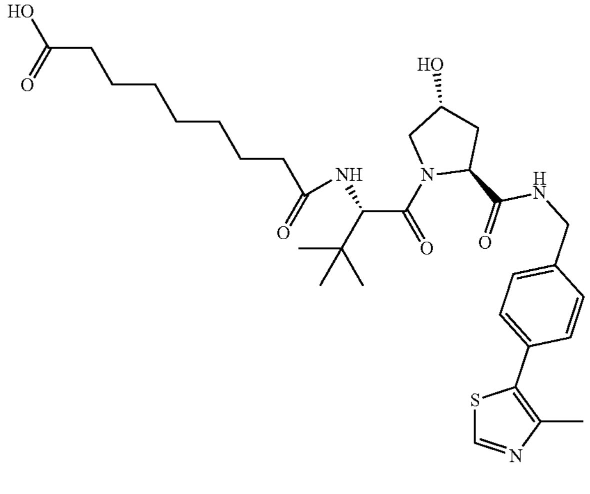 [SMILES: Cc1ncsc1-c1ccc(CNC(=O)[C@@H]2C[C@@H](O)CN2C(=O)[C@@H](NC(=O)CCCCCCCC(=O)O)C(C)(C)C)cc1] | I-57 | 9-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-9-oxononanoic acid | 601.4 |

TABLE 5-continued

The following intermediates were prepared in a similar manner as described in the preparation of I-52.

| Structures | # | Name | LCMS (ESI) m/z: [M + H]$^+$ |
| --- | --- | --- | --- |
| 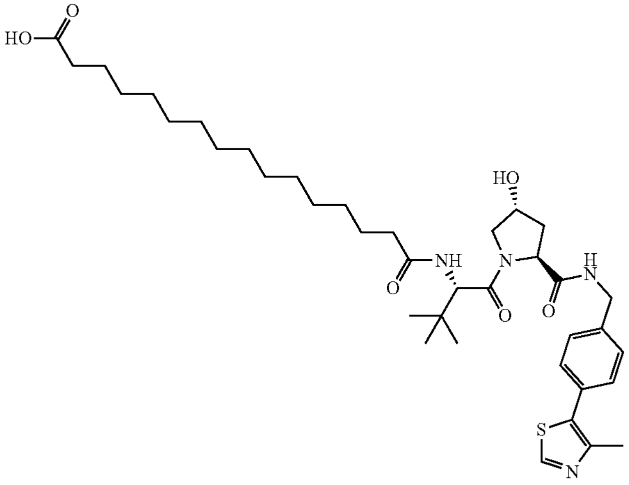 [SMILES: Cc1ncsc1-c1ccc(CNC(=O)[C@@H]2C[C@@H](O)CN2C(=O)[C@@H](NC(=O)CCCCCCCCCCCCCCC(=O)O)C(C)(C)C)cc1] | I-58 | 16-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-16-oxohexadecanoic acid | 699.6 |
| 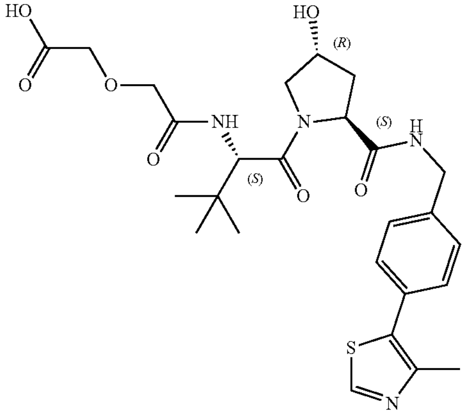 | I-59 | 2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetic acid | 547.4 |
| 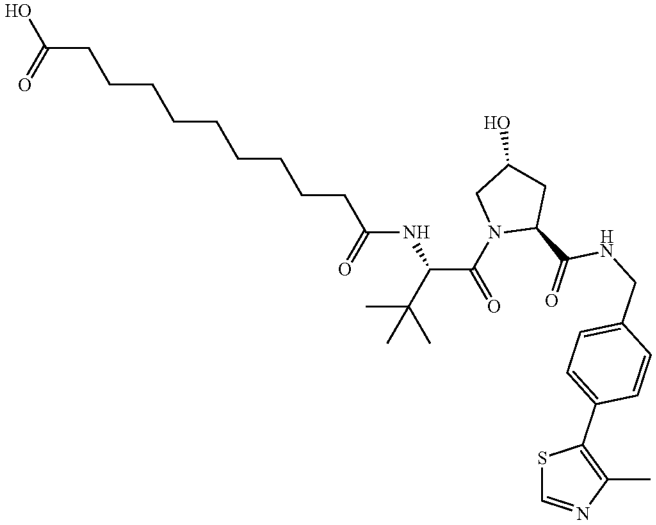 [SMILES: Cc1ncsc1-c1ccc(CNC(=O)[C@@H]2C[C@@H](O)CN2C(=O)[C@@H](NC(=O)CCCCCCCCCC(=O)O)C(C)(C)C)cc1] | I-60 | N-(2-((4-(3-(3-methoxyazetidin-1-yl)phenyl)thiazol-2- yl)amino)-2-oxoethyl)-1-(methylsulfonyl)-1H-pyrrole-3-carboxamide | 651.4 |

TABLE 5-continued

The following intermediates were prepared in a similar manner as described in the preparation of I-52.

| Structures | # | Name | LCMS (ESI) m/z: $[M + H]^+$ |
| --- | --- | --- | --- |
| 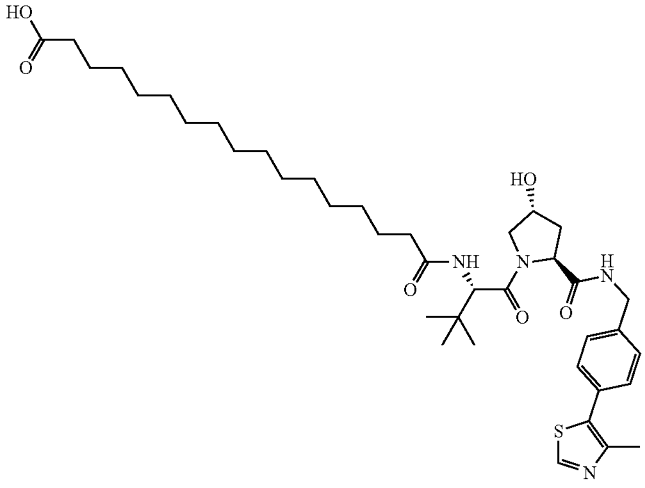 [SMILES: Cc1ncsc1-c1ccc(CNC(=O)[C@@H]2C[C@@H](O)CN2C(=O)[C@@H](NC(=O)CCCCCCCCCCCCCCCC(=O)O)C(C)(C)C)cc1] | I-61 | 17-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-17-oxoheptadecanoic acid | 713.5 |
| 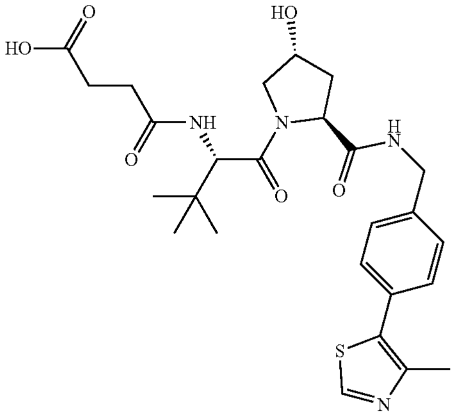 [SMILES: Cc1ncsc1-c1ccc(CNC(=O)[C@@H]2C[C@@H](O)CN2C(=O)[C@@H](NC(=O)CCC(=O)O)C(C)(C)C)cc1] | I-62 | 4-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-4-oxobutanoic acid | 531.2 |
| 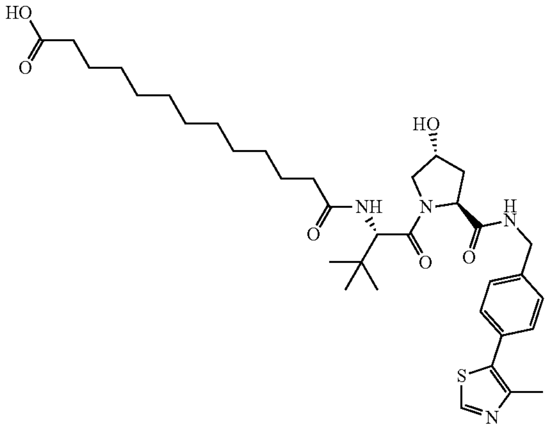 [SMILES: Cc1ncsc1-c1ccc(CNC(=O)[C@@H]2C[C@@H](O)CN2C(=O)[C@@H](NC(=O)CCCCCCCCCCCC(=O)O)C(C)(C)C)cc1] | I-63 | 13-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-13-oxo-tridecanoic acid | 657.3 |

TABLE 5-continued

| The following intermediates were prepared in a similar manner as described in the preparation of I-52. | | | |
|---|---|---|---|
| Structures | # | Name | LCMS (ESI) m/z: [M + H]$^+$ |
| 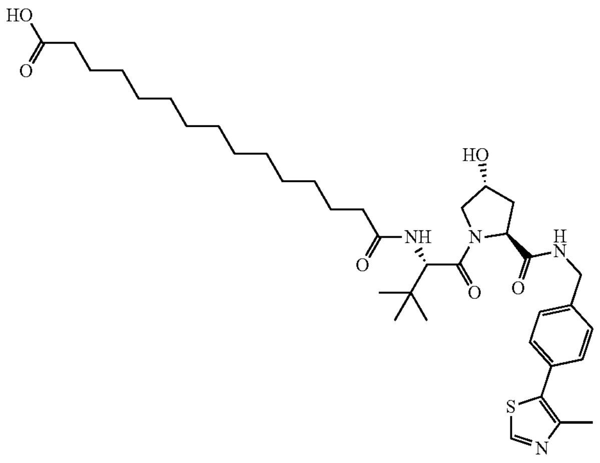 [SMILES: Cc1ncsc1-c1ccc(CNC(=O)[C@@H]2C[C@@H](O)CN2C(=O)[C@@H](NC(=O)CCCCCCCCCCCCCC(=O)O)C(C)(C)C)cc1] | I-64 | 001 15-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-15-oxopentadecanoic acid | 685.4 |
| 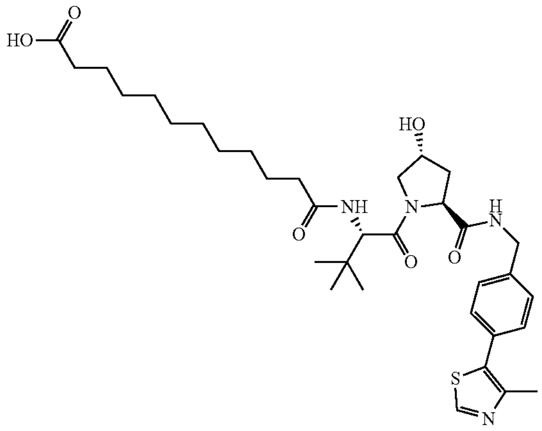 [SMILES: Cc1ncsc1-c1ccc(CNC(=O)[C@@H]2C[C@@H](O)CN2C(=O)[C@@H](NC(=O)CCCCCCCCCCC(=O)O)C(C)(C)C)cc1] | I-65 | 12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoic acid | 643.5 |
| 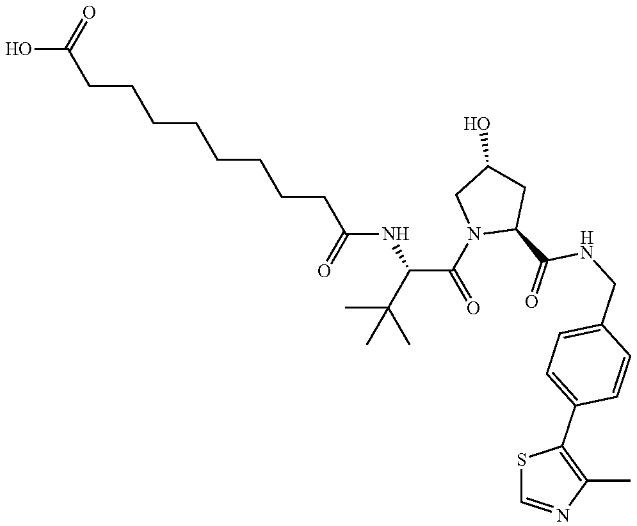 [SMILES: Cc1ncsc1-c1ccc(CNC(=O)[C@@H]2C[C@@H](O)CN2C(=O)[C@@H](NC(=O)CCCCCCCCC(=O)O)C(C)(C)C)cc1] | I-66 | 10-(((S)-1-((2S,4R)-4-hydroxy-2-((4-(4-methylthiazol-5-yl) benzyl)carbamoyl)pyrrolidin-1-yl)-3,3-dimethyl-1-oxobutan-2-yl)amino)-10-oxodecanoic acid | 615.5 |

TABLE 5-continued

| The following intermediates were prepared in a similar manner as described in the preparation of I-52. | | | |
|---|---|---|---|
| Structures | # | Name | LCMS (ESI) m/z: [M + H]$^+$ |
| 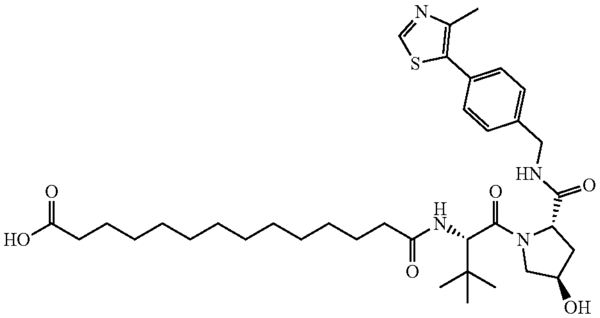 [SMILES: Cc1ncsc1-c1ccc(CNC(=O)[C@@H]2C[C@@H](O)CN2C(=O)[C@@H](NC(=O)CCCCCCCCCCCCC(=O)O)C(C)(C)C)cc1] | I-67 | 14-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-14-oxotetradecanoic acid | 671.4 |
| 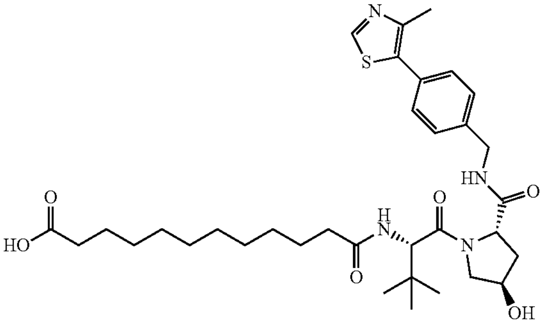 [SMILES: Cc1ncsc1-c1ccc(CNC(=O)[C@@H]2C[C@@H](O)CN2C(=O)[C@@H](NC(=O)CCCCCCCCCCC(=O)O)C(C)(C)C)cc1] | I-68 | 12-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-12-oxododecanoic acid | 643.3 |
| 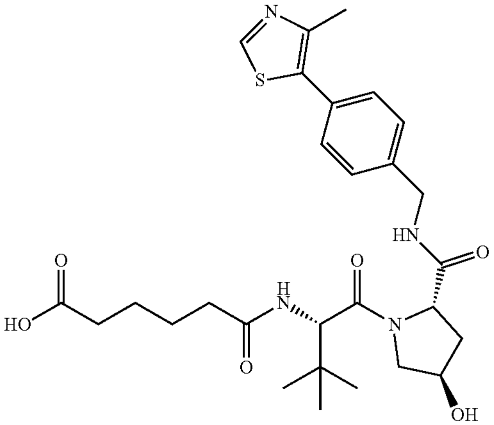 [SMILES: Cc1ncsc1-c1ccc(CNC(=O)[C@@H]2C[C@@H](O)CN2C(=O)[C@@H](NC(=O)CCCCC(=O)O)C(C)(C)C)cc1] | I-69 | 6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid | 559.3 |

Preparation of (2S,4R)-1-[(2S)-2-(2-[2-[2-(2-amino-ethoxy)ethoxy]ethoxy]acetamido)-3,3-dimethylbutanoyl]-4-hydroxy-N-[[4-(4-methyl-1,3-thiazol-5-yl)phenyl]methyl]pyrrolidine-2-carboxamide (I-70)

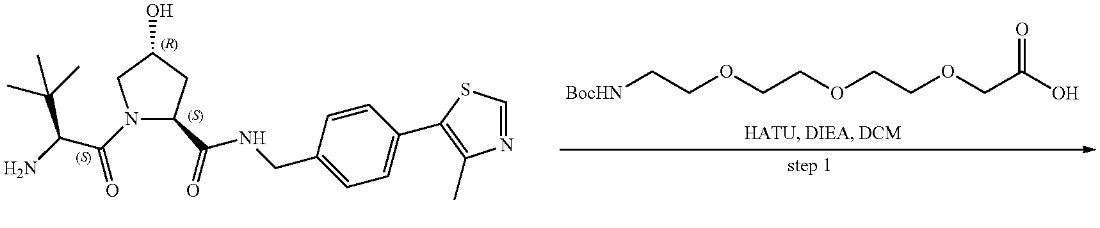

A

-continued
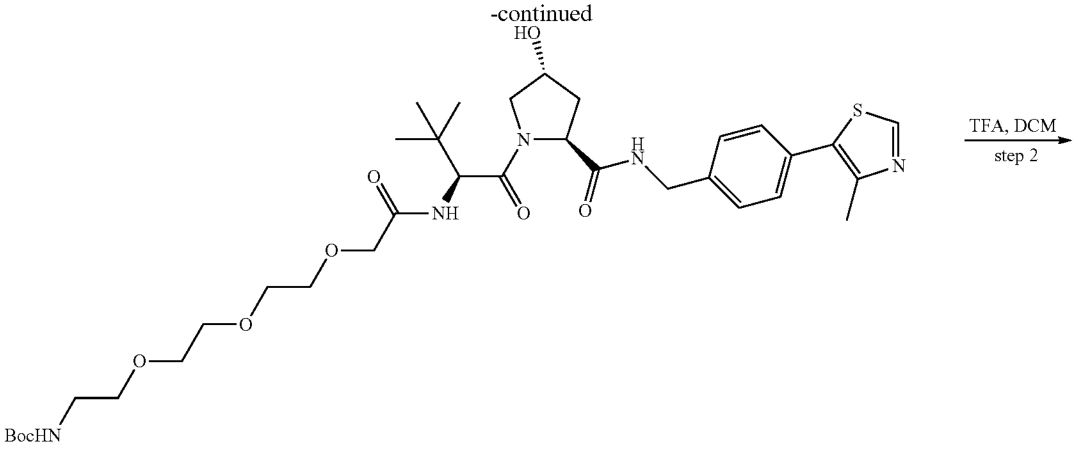
B
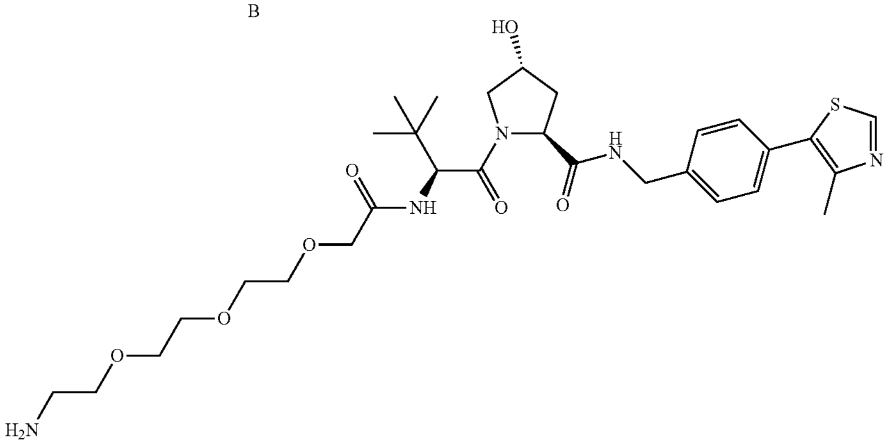
I-70
Step 1: Preparation of tert-butyl N-(2-[2-[2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methoxy)ethoxy]ethoxy]ethyl)carbamate (B)
B
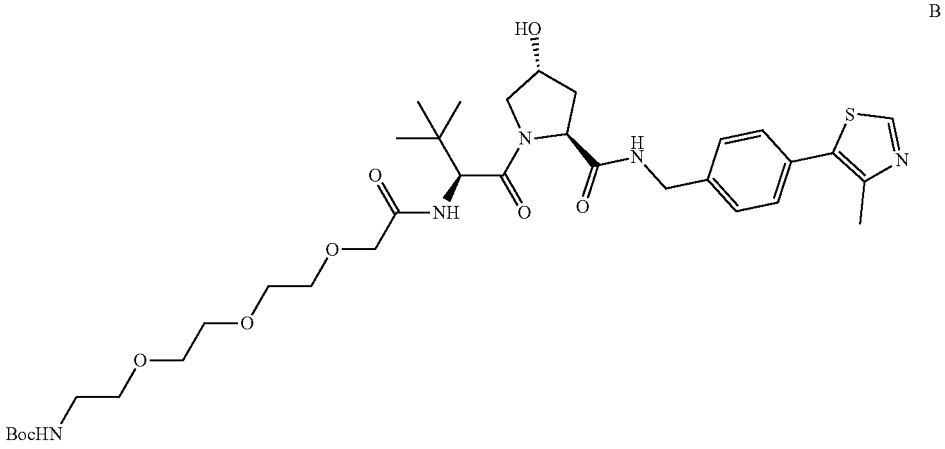 [SMILES: Cc1ncsc1-c1ccc(CNC(=O)[C@@H]2C[C@@H](O)CN2C(=O)[C@@H](NC(=O)COCCOCCOCCNC(=O)OC(C)(C)C)C(C)(C)C)cc1]

To a stirred solution of (2S,4R)-1-[(2S)-2-amino-3,3-dimethylbutanoyl]-4-hydroxy-N-[[4-(4-methyl-1,3-thiazol-5-yl)phenyl] methyl]pyrrolidine-2-carboxamide (A, 1.00 g, 2.323 mmol, 1.00 equiv) and 2-[2-[2-(2-[[(tert-butoxy) carbonyl]amino]ethoxy)ethoxy]ethoxy]acetic acid (785.19 mg, 2.555 mmol, 1.10 equiv) in DCM (10.00 mL) was added HATU (1.32 g, 3.484 mmol, 1.50 equiv) and DIEA (900.50 mg, 6.968 mmol, 3 equiv). The mixture was stirred at 25° C. for 1 h, then diluted with EtOAc (200 mL) and washed with 3×100 mL of water and 1×100 mL saturated brine. The organic layer was dried over $Na_2SO_4$, filtered, and evaporated. The crude product was purified by flash silica chromatography, elution gradient 0 to 50% EtOAc in petroleum ether to afford B (1.4592 g, 87.27%) as an off-white solid. LCMS (ESI) m/z: $[M+H]^+$=720.

Step 2: Preparation of (2S,4R)-1-[(2S)-2-(2-[2-[2-(2-aminoethoxy)ethoxy]ethoxy]acetamido)-3,3-dimethylbutanoyl]-4-hydroxy-N-[[4-(4-methyl-1,3-thiazol-5-yl)phenyl]methyl]pyrrolidine-2-carboxamide (I-70)

I-70

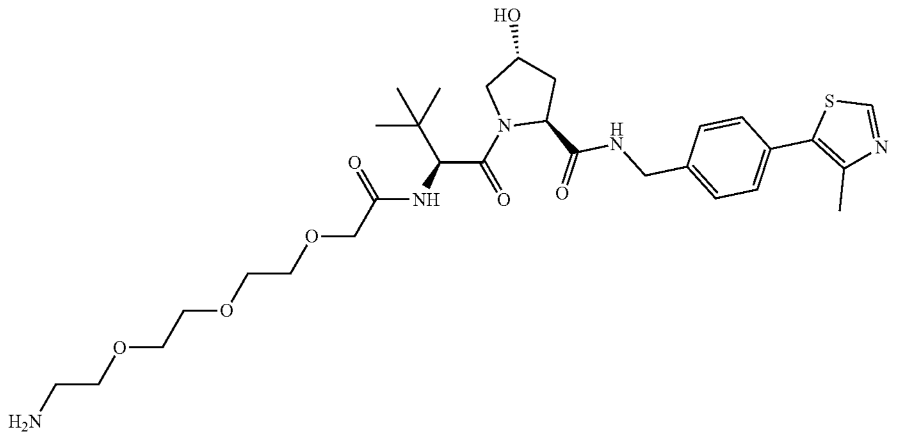

To a solution of B (1.45 g, 2.014 mmol, 1 equiv) in CM (15 mL) was added TEA (3 ml) dropwise After stirring at room temperature for 2 h the mixture was concentrated under reduced pressure and the residue purified by flash column chromatography on silica gel to afford I-70 (1.05 g, 84.11%) as an off-white solid. 1H NMR (400 MHz, Methanol-d4) δ8.90 (s, 1H), 7.51-7.42 (m, 4H), 4.72 (s, 1H), 4.63-4.49 (m, 3H), 4.46-4.35 (m, 1H), 4.16-4.03 (m, 2H), 3.94-3.79 (m, 2H), 3.77-3.62 (m, 8H), 3.59 (t, J=5.2 Hz, 2H), 2.99-2.87 (m, 2H), 2.50 (s, 3H), 2.30-2.21 (m, 1H), 2.19-2.06 (m, 1H), 1.13-0.98 (in, 9H). LCMS (ESI) m/z: $[M+H]^+$=620.30

TABLE 6

Intermediates were prepared in a similar manner as described in the preparation of I-70.

| Structures | # | Name | LCMS (ESI) m/z: $[M + H]^+$ |
|---|---|---|---|
| 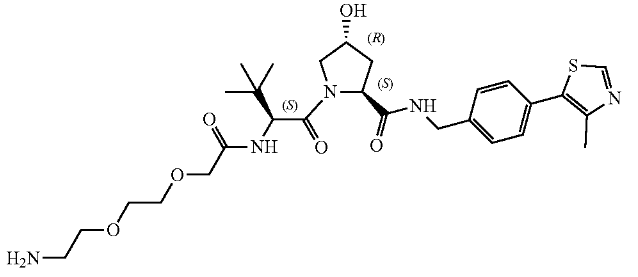 | I-71 | (2S,4R)-1-[(2S)-2-[2-[2-(2-aminoethoxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide | 576.3 |

TABLE 6-continued

Intermediates were prepared in a similar manner as described in the preparation of I-70.

| Structures | # | Name | LCMS (ESI) m/z: $[M + H]^+$ |
|---|---|---|---|
| 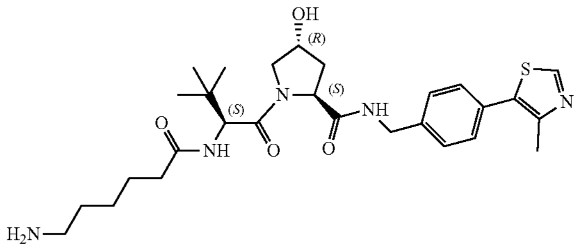 | I-72 | (2S,4R)-1-[(2S)-2-(6-aminohexanamido)-3,3-dimethylbutanoyl]-4-hydroxy-N-[[4-(4-methyl-1,3-thiazol-5-yl)phenyl]methyl]pyrrolidine-2-carboxamide | 544.4 |
| 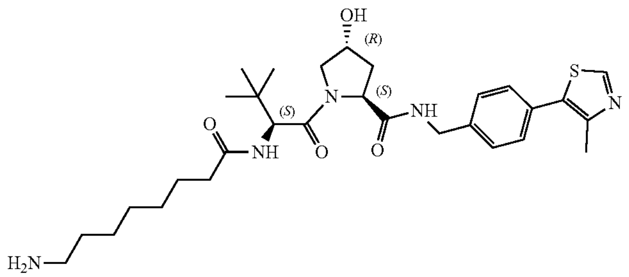 | I-73 | (2S,4R)-1-[(2S)-2-(8-aminooctanamido)-3,3-dimethylbutanoyl]-4-hydroxy-N-[[4-(4-methyl-1,3-thiazol-5-yl)phenyl]methyl]pyrrolidine-2-carboxamide | 572.2 |
| 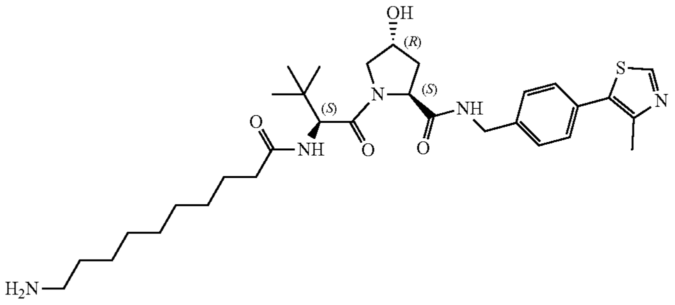 | I-74 | (2S,4R)-1-[(2S)-2-(10-aminodecanamido)-3,3-dimethylbutanoyl]-4-hydroxy-N-[[4-(4-methyl-1,3-thiazol-5-yl)phenyl]methyl]pyrrolidine-2-carboxamide | 600.4 |

Preparation of (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecan-1-oic acid (I-75)
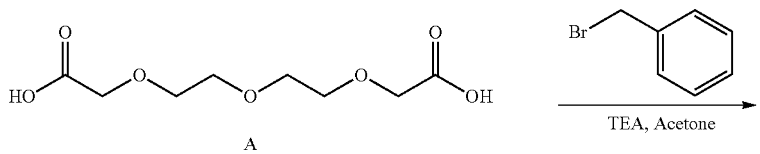
A
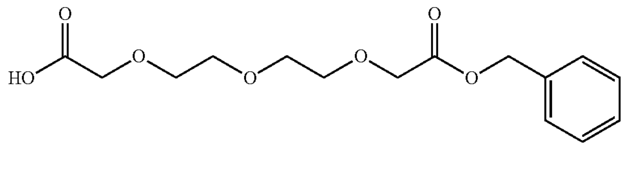
B
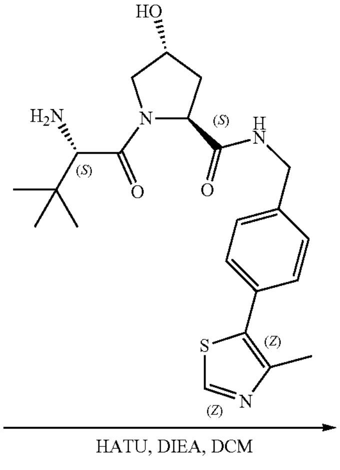

-continued

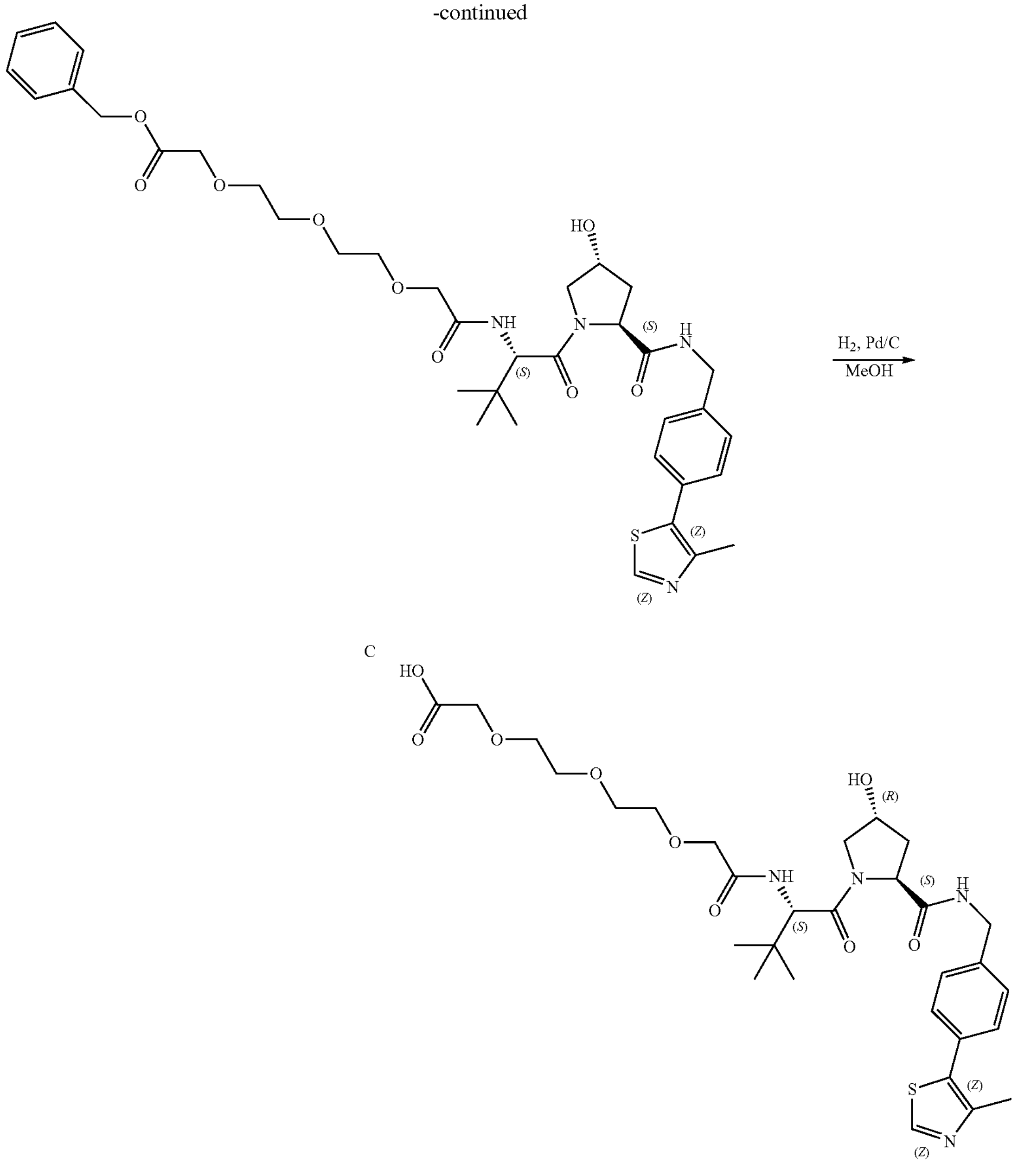

C

I-75

Step 1: Preparation of 2-[2-[2-(2-benzyloxy-2-oxo-ethoxy)ethoxy]ethoxy]acetic acid (B)

B

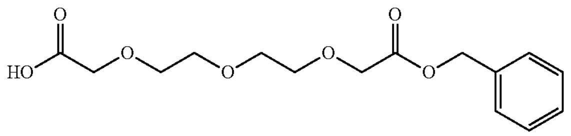

To a mixture of 2-[2-[2-(carboxymethoxy)ethoxy]ethoxy]acetic acid (A, 3 g, 13.50 mmol) and TEA (3.51 g, 34.71 mmol, 4.83 mL) in acetone (20 mL) was added bromomethylbenzene (2.42 g, 14.18 mmol, 1.68 mL) dropwise at 0° C. The mixture was stirred at 20° C. for 16 h during which time a thick precipitate formed. The solids were filtered of and washed with acetone (10 mL). The filtrate was concentrated, and the residue taken up in water (300 mL). The mixture was washed with EtOAc (50 mL×3), and the aqueous layer treated with HCl (2 M) to a final pH 3-5. The mixture was extracted with EtOAc (50 mL×3) and the combined organic layers washed with brine (50 mL), dried over $Na_2SO_4$, and concentrated under vacuum to give B (1.4 g, 4.48 mmol, 33.20% yield) as a yellow oil which was used without further purification. $^1H$ NMR (400 MHz, $CDCl_3$) δ=7.31-7.26 (m, 5H), 5.12 (s, 2H), 4.12 (s, 2H), 4.08 (s, 2H), 3.69-3.61 (m, 8H) ppm.

Step 2: Preparation of (S)-benzyl 13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecan-1-oate (C)
C
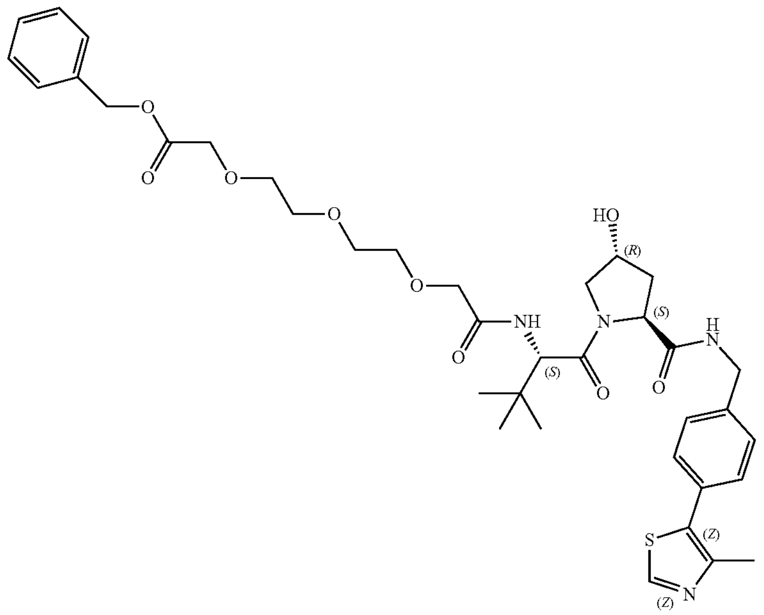

To a solution of B (836.17 mg, 2.68 mmol) in DCM (10 mL) was added HATU (1.32 g, 3.48 mmol) and DIEA (900.50 mg, 6.97 mmol, 1.21 mL). Then (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (1 g, 2.14 mmol, HCl) was added. The mixture was stirred at 30° C. for 2 h. The mixture was concentrated under vacuum to give yellow solid. The residue was purified by reverse phase flash (0.1% formic acid in water/ACN) and the fraction was lyophilized to give C (1.2 g, 1.66 mmol, 71.28% yield) as a yellow oil.

LCMS (ESI) m/z: $[M+H]^+$=725.4. $^1H$ NMR (400 MHz, CHLOROFORM-d) δ=8.69 (s, 1H), 7.42-7.32 (m, 11H), 4.77-4.75 (m, 1H), 4.63-4.47 (m, 3H), 4.37-4.32 (m, 1H), 4.24-4.17 (m, 3H), 4.13 (d, J=11.6 Hz, 1H), 4.09-3.94 (m, 2H), 3.77-3.68 (m, 9H), 3.63-3.59 (m, 1H), 2.64-2.56 (m, 1H), 2.54 (s, 3H), 2.19-2.08 (m, 1H), 1.00-0.92 (m, 9H) ppm.

Step 3: Preparation of (S)-13-((2S,4R)-4-hydroxy-2-((4-(4-methylthiazol-5-yl)benzyl)carbamoyl)pyrrolidine-1-carbonyl)-14,14-dimethyl-11-oxo-3,6,9-trioxa-12-azapentadecan-1-oic acid (I-75)

I-75

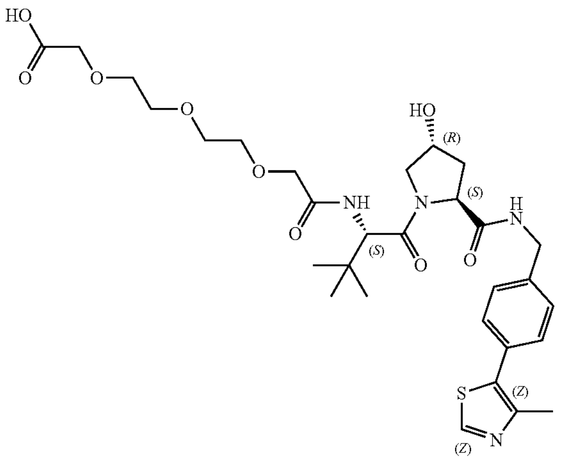

To a mixture of C (1.1 g, 1.52 mmol) in MeOH (20 mL) was added 10% Pd/C (500 mg). The mixture was purged with hydrogen then pressured to 15 psi and stirred at 25° C. for 12 h, then at 40° C. for 8 h. The mixture was filtered, and the filtrate concentrated under vacuum. The residue was purified by reversed phase flash (ammonia/water condition) to give I-75 (560 mg, 882.25 μm, 58.14% yield) as a white solid. LCMS (ESI) m/z: $[M+H]^+$=635.2. $^1H$ NMR (400 MHz, methanol-d4) δ=8.94-8.86 (m, 1H), 7.50-7.43 (m, 4H), 4.62-4.50 (m, 3H), 4.43-4.34 (m, 1H), 4.12 (s, 2H), 4.08 (d, J=5.2 Hz, 2H), 3.93-3.86 (m, 1H), 3.85-3.79 (m, 1H), 3.76-3.70 (m, 8H), 2.51-2.49 (m, 3H), 2.29-2.21 (m, 1H), 2.16-2.07 (m, 1H), 1.06 (s, 9H) ppm.

TABLE 7

The following intermediates were prepared in a similar manner as described in the preparation of I-75.

| Structures | # | Name | LCMS (ESI) m/z: $[M + H]^+$ |
|---|---|---|---|
| 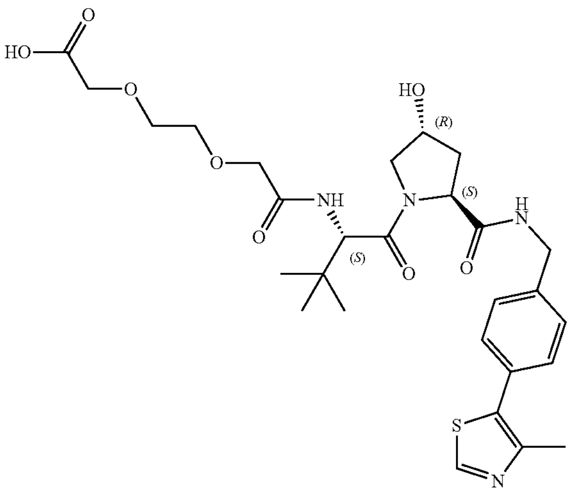 | I-76 | 2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetic acid | 591.5 |

TABLE 7-continued

| The following intermediates were prepared in a similar manner as described in the preparation of I-75. | | | |
|---|---|---|---|
| Structures | # | Name | LCMS (ESI) m/z: [M + H]+ |
| 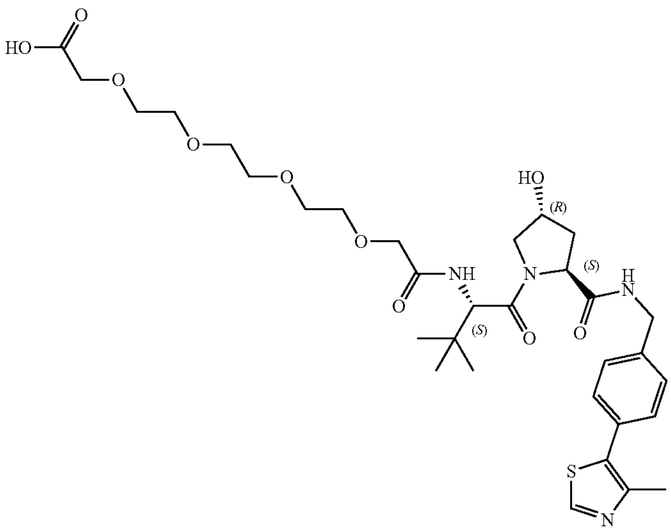 | I-77 | (S)-16-((2S,4R)-4-hydroxy-2-((4-(4-methylthiazol-5-yl)benzyl)carbamoyl)pyrrolidine-1-carbonyl)-17,17-dimethyl-14-oxo-3,6,9,12-tetraoxa-15-azaoctadecan-1-oic acid | 679.2 |

Preparation of 2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-2-azaspiro[3.3]heptane-6-carboxylic acid (I-78)

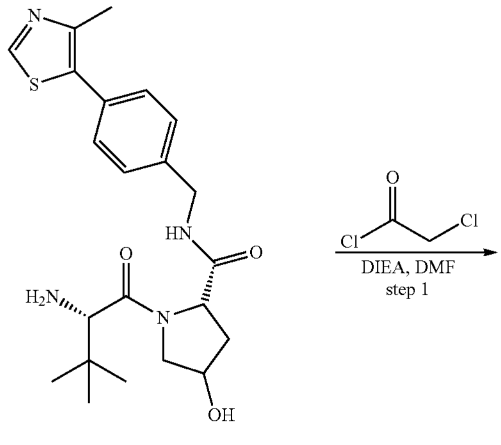

A

-continued

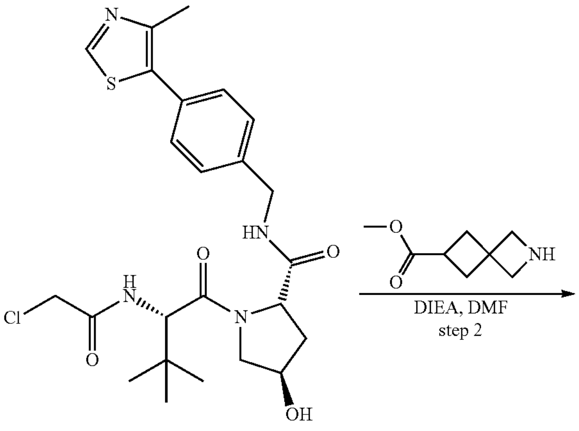

B

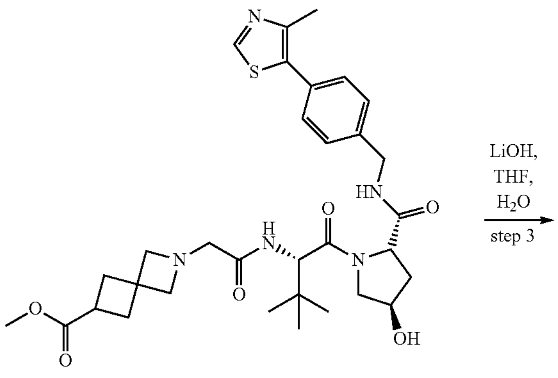

C

-continued

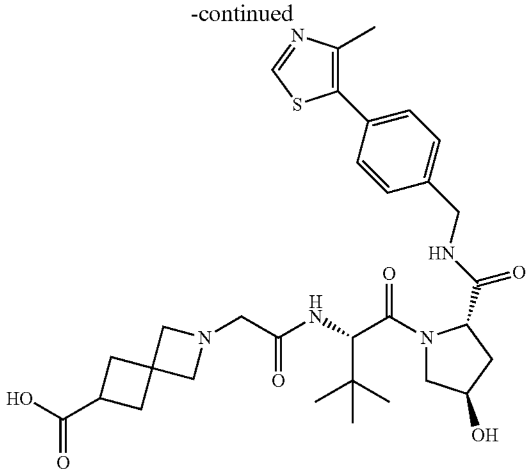

I-78

Step 1: Preparation of (2S,4R)-1-[(2S)-2-(2-chloroacetamido)-3,3-dimethylbutanoyl]-4-hydroxy-N-[[4-(4-methyl-1,3-thiazol-5-yl)phenyl]methyl]pyrrolidine-2-carboxamide (B)

B

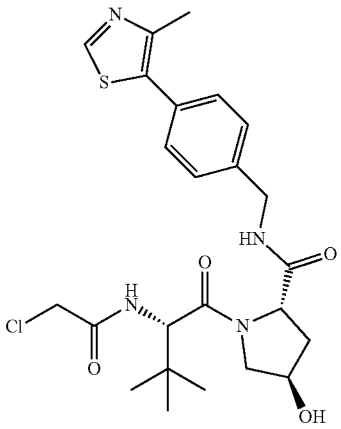

To a solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (A, 500.00 mg, 1.161 mmol, 1.00 equiv) and DIEA (450.25 mg, 3.484 mmol, 3.00 equiv) in DCM (10.00 mL, 0.118 mmol, 0.10 equiv) was added chloroacetyl chloride (137.71 mg, 1.219 mmol, 1.05 equiv) dropwise at 0° C. The solution was stirred at room temperature for 4 h then concentrated under reduced pressure. The residue was purified by silica gel column chromatography, eluting with DCM/MeOH (10:1) to afford B (450 mg, 76.43%) as a yellow oil. LCMS (ESI) m/z: $[M+H]^+$=507.

Step 2: Preparation of methyl 2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-2-azaspiro[3.3]heptane-6-carboxylate (C)

C

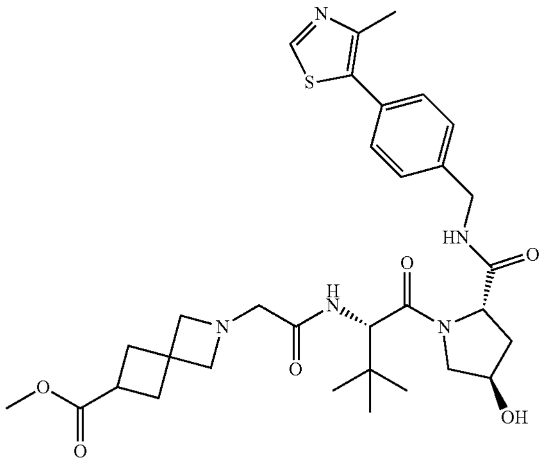

To a suspension of methyl 2-azaspiro[3.3]heptane-6-carboxylate (24.00 mg, 0.155 mmol, 1.00 equiv), and $K_2CO_3$ (64.12 mg, 0.464 mmol, 3.00 equiv) in DMF (3.00 mL) was added B (78.41 mg, 0.155 mmol, 1 equiv). The suspension was stirred at room temperature for 16 h. Following aqueous workup, extraction with DCM, and concentration, the residue was purified by reverse phase flash chromatography under the following conditions: column, C18 silica gel; mobile phase, ACN in water, 5% to 100% gradient over 15 min; detector, UV 254 nm. This resulted in C (30 mg, 31.00%) as a yellow oil. LCMS (ESI) m/z: $[M+H]^+$=626.

Step 3: Preparation of 2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-2-azaspiro[3.3]heptane-6-carboxylic acid (I-78)

I-78

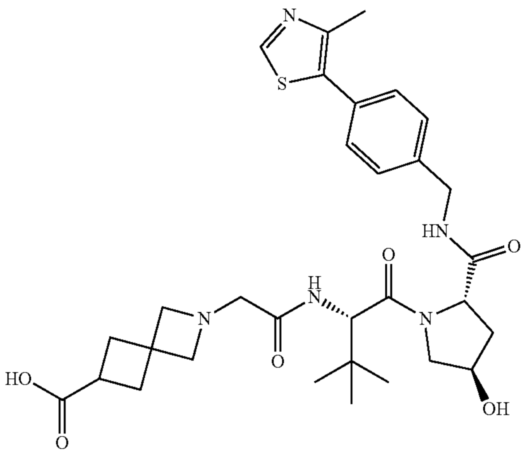

To a solution of C (60.00 mg, 0.096 mmol, 1.00 equiv) in THE (3.00 mL) and water (1.00 mL) was added LiOH (5.74 mg, 0.240 mmol, 3.00 equiv). The solution was stirred at room temperature for 3 h and the mixture was acidified to pH 5 with acetic acid. The mixture was purified directly by reverse phase flash chromatography under the following conditions: column, C18 silica gel; mobile phase, ACN in water, 10% to 100% gradient over 15 min; detector, UV 254 nm. This resulted in I-78 (42 mg, 71.61%) as a white solid. LCMS (ESI) m/z: $[M+H]^+$=612.

Preparation of [6-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-2,6-diazaspiro[3.3]heptan-2-yl]acetic acid (I-79)

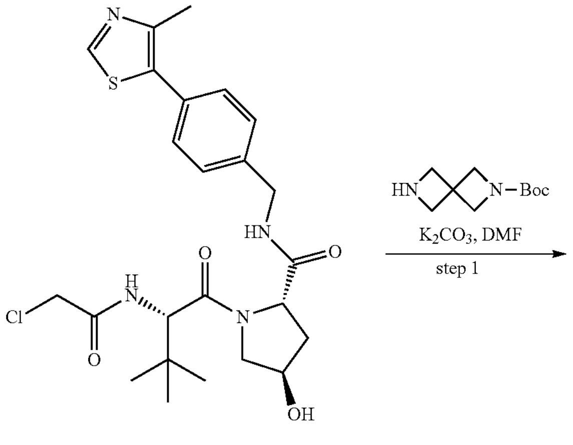

A

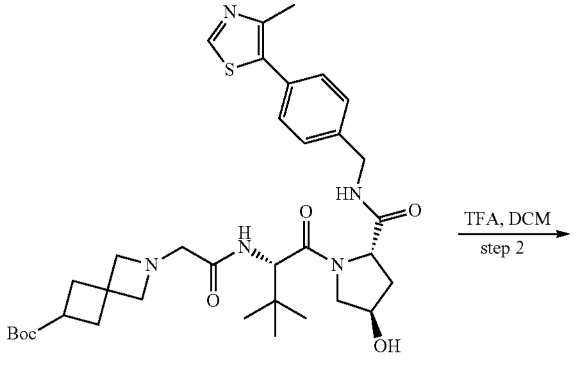

B

-continued

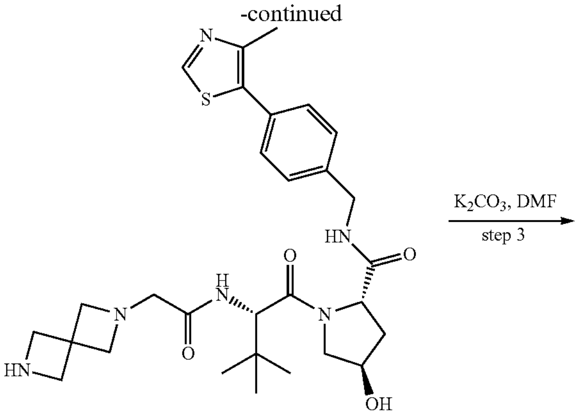

C

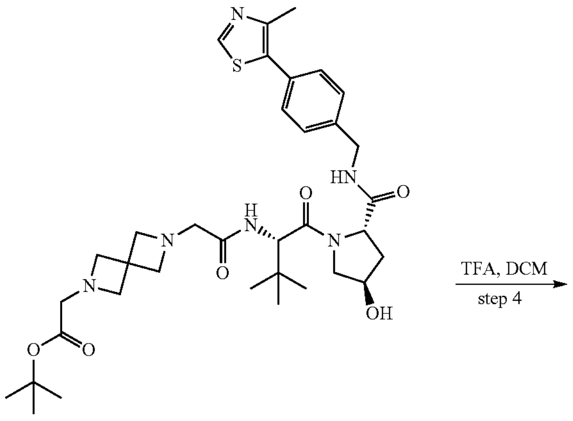

D

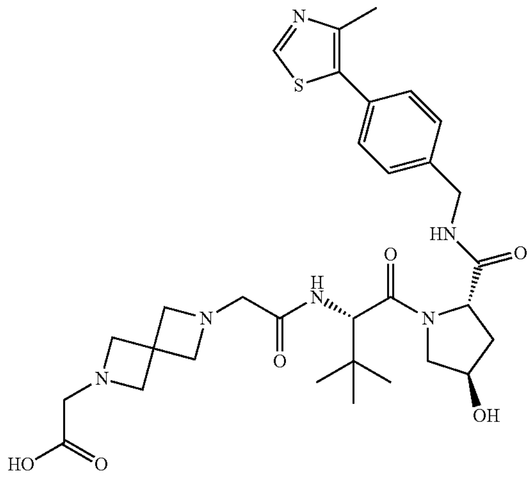

I-79

Step 1: Preparation of tert-butyl 6-([[(2S)-1-[(2S, 4R)-4-hydroxy-2-([[4-(4-methyl-1,3-thiazol-5-yl) phenyl]methyl]carbamoyl)pyrrolidin-1-yl]-3,3-dimethyl-1-oxobutan-2-yl]carbamoyl]methyl)-2,6-diazaspiro[3.3]heptane-2-carboxylate (B)

B

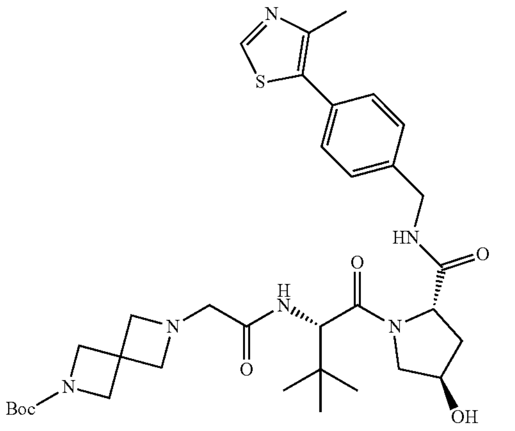

A (200.00 mg, 0.394 mmol, 1.00 equiv), $K_2CO_3$ (136.28 mg, 0.986 mmol, 2.50 equiv), and tert-butyl 2,6-diazaspiro[3.3]heptane-2-carboxylate (156.41 mg, 0.789 mmol, 2.00 equiv) were added to DMF (5.00 mL). The mixture was allowed to react 24 h at room temperature. The resulting mixture was diluted with EtOAc (30 mL), washed with water (20 mL) and brine (20 mL), and dried over $Na_2SO_4$. After removing the organic solvent, the residue was purified by preparative TLC (5% MeOH in EtOAc) to afford B (90 mg, 34.11%) as a white solid. LCMS (ESI) m/z: $[M+H]^+$=669.

Step 2: (2S,4R)-1-[(2S)-2-(2-[2,6-diazaspiro[3.3]heptan-2-yl]acetamido)-3,3-dimethylbutanoyl]-4-hydroxy-N-[[4-(4-methyl-1,3-thiazol-5-yl)phenyl]methyl]pyrrolidine-2-carboxamide (C)

C

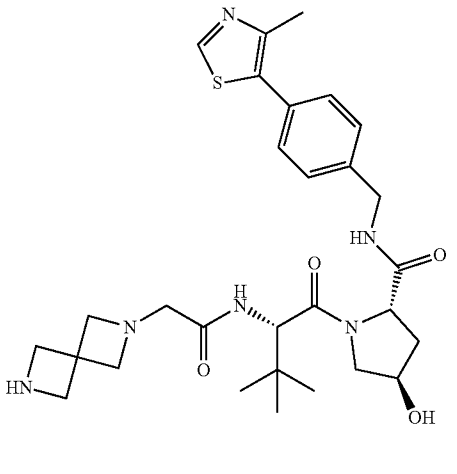

B (60.00 mg, 0.090 mmol, 1.00 equiv) was dissolved in DCM (5.00 mL) followed by addition of TFA (1.00 mL, 13.463 mmol, 150.08 equiv). The mixture was allowed to react for 1 h. After removing the solvent, the crude product C was used without further purification. LCMS (ESI) m/z: $[M+H]^+$=569.

Step 3: Preparation of tert-butyl 2-[6-([[(2S)-1-[(2S, 4R)-4-hydroxy-2-([[4-(4-methyl-1,3-thiazol-5-yl) phenyl]methyl]carbamoyl)pyrrolidin-1-yl]-3,3-dimethyl-1-oxobutan-2-yl]carbamoyl]methyl)-2,6-diazaspiro[3.3]heptan-2-yl]acetate (D)

D

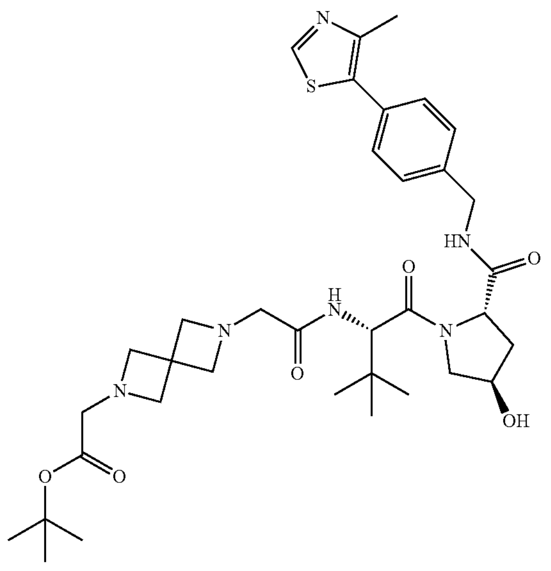

To a suspension of C (41.00 mg, 0.072 mmol, 1.00 equiv) and $K_2CO_3$ (29.89 mg, 0.216 mmol, 3.00 equiv) in DMF (1.50 mL), tert-butyl 2-chloroacetate (10.86 mg, 0.072 mmol, 1.00 equiv) in DMF (0.1 mL) was added dropwise. The mixture was stirred for 4.5 h at room temperature. The reaction mixture was then diluted with 30 mL water followed by extraction with DCM/MeOH (10/1, v/v, 20 mL×3). The combined organic layers were washed with brine (40 mL) and dried by sodium sulfate. After filtration, the filtrate was concentrated under vacuum to afford the crude product D (45 mg, 91.41%) which was used without further purification. LCMS (ESI) m/z: $[M+H]^+$=683.

Step 4: Preparation of [6-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-2,6-diazaspiro[3.3]heptan-2-yl]acetic acid (I-79)

I-79

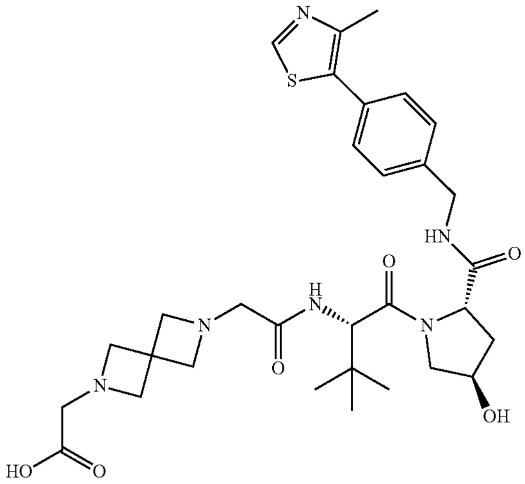

D (25.00 mg, 0.037 mmol, 1.00 equiv) was dissolved in DCM (5.00 mL) followed by addition of TFA (1.25 mL, 10.963 mmol, 459.68 equiv). The mixture was stirred at room temperature for 4 h. After removing the solvent, the crude product I-79 (23 mg, 100.24%) was used without further purification. LCMS (ESI) m/z: $[M+H]^+$=627.

Preparation of 1-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2 yl]carbamoyl]methyl)piperidine-4-carboxylic acid (I-80)

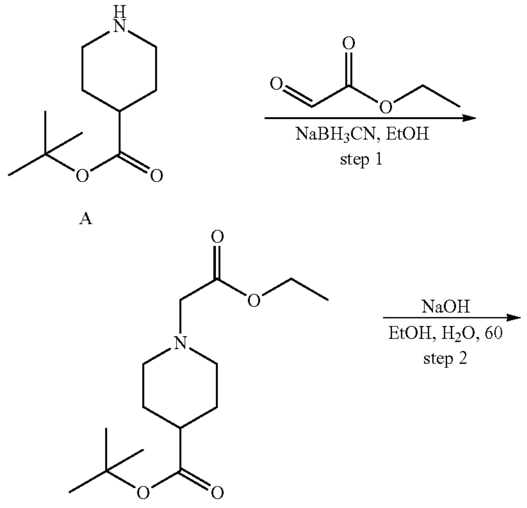

A

B

-continued

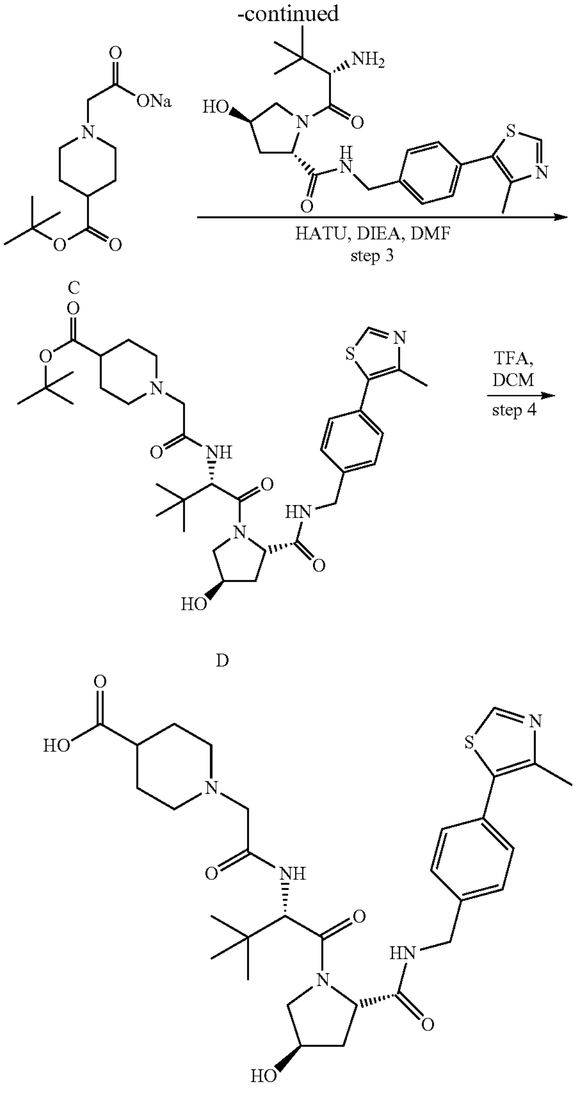

C

D

I-80

Step 1: Preparation of tert-butyl 1-(2-ethoxy-2-oxoethyl)piperidine-4-carboxylate (B)

B

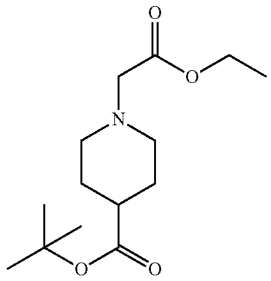

To a solution of ethyl glyoxylate (500.00 mg, 4.898 mmol, 1.00 equiv) and tert-butyl piperidine-4-carboxylate (A, 1088.86 mg, 5.877 mmol, 1.20 equiv) in EtOH (10 mL) was added AcOH (29.41 mg, 0.49 mmol, 0.1 equiv), and the resulting solution stirred for 1 h at room temperature. $NaBH_3CN$ (461.67 mg, 7.347 mmol, 1.50 equiv) was then added, and the resulting solution stirred overnight at room temperature. The reaction was then quenched by the addition of 10 mL of water. The resulting solution was extracted with 3×30 mL of EtOAc and the combined organic extracts concentrated under vacuum. The residue was purified by flash column chromatography on silica gel using EtOAc/petroleum ether (1:3). This resulted in 200 mg (15.05%) of B as yellow oil. $^1H$ NMR (300 MHz, DMSO-d6) δ 4.07 (q, J=7.1 Hz, 2H), 3.19 (s, 2H), 2.77 (d, J=11.7 Hz, 2H), 2.27-2.07 (m, 3H), 1.74 (dd, J=13.1, 3.7 Hz, 2H), 1.60-1.44 (m, 1H), 1.40 (s, 9H), 1.19 (t, J=7.1 Hz, 3H). LCMS (ESI) m/z: $[M+H]^+$=272.

Step 2: Preparation of tert-butyl 1-[2-oxo-2-(sodiooxy)ethyl]piperidine-4-carboxylate (C)

C

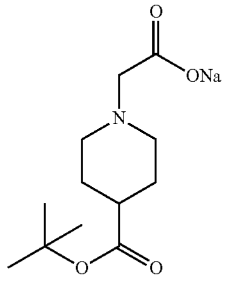

To a solution of B (200.00 mg, 0.737 mmol, 1.00 equiv) in EtOH (5.00 mL) and water (1.00 mL) was added sodium hydroxide (32.43 mg, 0.811 mmol, 1.1 equiv). The resulting solution was overnight at 60° C. The resulting mixture was concentrated under vacuum affording 180 mg (92.06%) of crude C as a yellow solid. LCMS (ESI) m/z: $[M+H]^+$=244.

Step 3: Preparation of tert-butyl 1-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)piperidine-4-carboxylate (D)

D

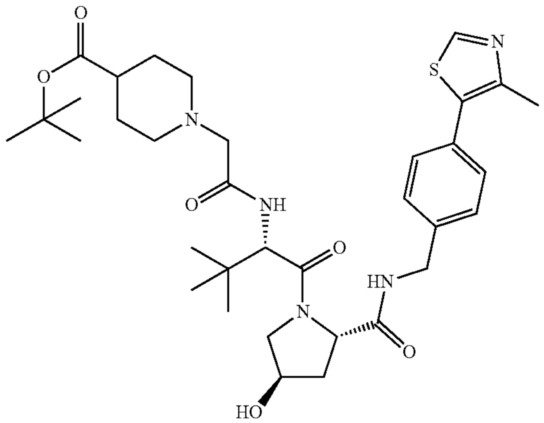

To a solution of C (54.25 mg, 0.223 mmol, 1.20 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (80.00 mg, 0.186 mmol, 1.00 equiv), and DIPEA (72.04 mg, 0.557 mmol, 3.00 equiv) in DMF (3.00 mL) was added HATU (105.97 mg, 0.279 mmol, 1.50 equiv). The resulting solution was stirred overnight at room temperature. The mixture was concentrated, and the residue purified on a C18 column with ACN:water (7:3). This resulted in 40 mg (32.82%) of D as yellow oil. LCMS (ESI) m/z: $[M+H]^+$=656.

Step 4: Preparation of 1-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)piperidine-4-carboxylic acid (I-80)

I-80

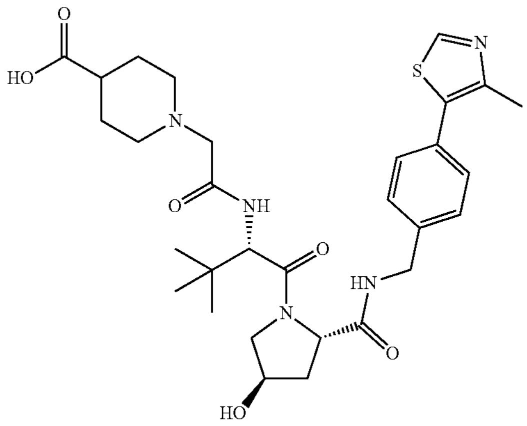

To a solution of D (40.00 mg, 0.061 mmol, 1.00 equiv) in DCM (3 mL) was added TFA (0.30 mL, 4.039 mmol, 66.22 equiv). The mixture was stirred overnight at room temperature, then concentrated under vacuum. This resulted in 120 mg of crude I-80 as a yellow oil. LCMS (ESI) m/z: $[M+H]^+$=600.

Preparation of 4-(5-aminopent-1-yn-1-yl)-2-(2,6-dioxopiperidin-3-yl)isoindole-1,3-dione trifluoroacetate (I-81)

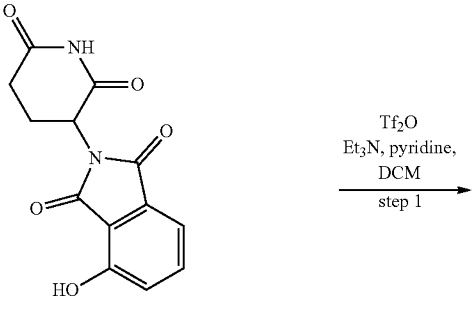

A

-continued

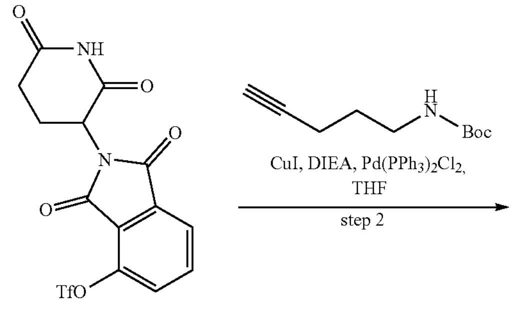

B

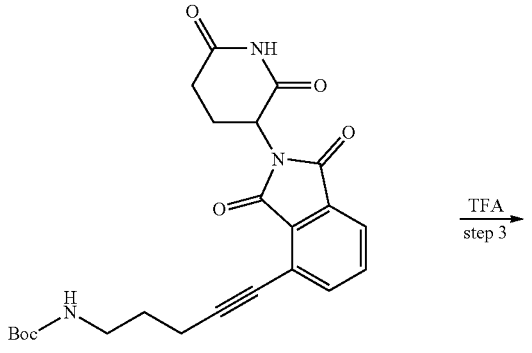

C

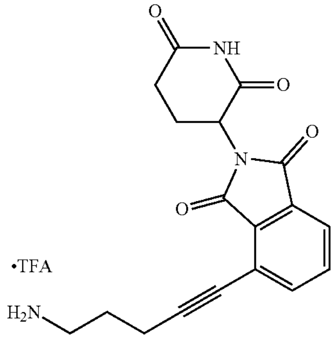

I-81

Step 1: Preparation of 2-(2,6-dioxopiperidin-3-yl)-1,3-dioxoisoindol-4-yl trifluoromethanesulfonate (B)

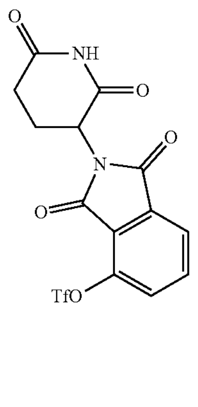

B

To a stirred mixture of 2-(2,6-dioxopiperidin-3-yl)-4-hydroxyisoindole-1,3-dione (A, 2.00 g, 7.293 mmol, 1.00 equiv) in DCM (21.00 mL) was added TEA (2.28 mL, 16.403 mmol, 2.25 equiv) and pyridine (2.28 mL, 28.326 mmol, 3.88 equiv). The reaction was cooled to 0° C., then triflic anhydride (3.09 g, 10.940 mmol, 1.50 equiv) was added dropwise. The mixture was warmed to room temperature and stirred for 2 h. The resulting mixture was diluted with water (100 mL) and extracted with DCM (3×200 mL). The combined organic layers were dried over anhydrous Na2SO4 and concentrated under reduced pressure. The residue was diluted with DCM (50 mL) and stirred for 0.5 h at room temperature. The resulting mixture was filtered, and the filter cake was washed with DCM (10 mL) to give B (1.92 g, 58.32%) as an off-white solid. LCMS (ESI) m/z $[M+H]^+$=407.

Step 2: Preparation of tert-butyl N-[5-[2-(2,6-dioxopiperidin-3-yl)-1,3-dioxoisoindol-4-yl]pent-4-yn-1-yl]carbamate (C)

C

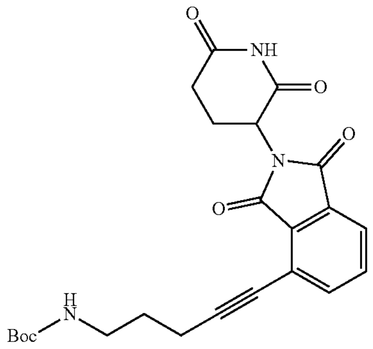

To a stirred solution of B (1.60 g, 3.938 mmol, 1.00 equiv) and tert-butyl N-(pent-4-yn-1-yl)carbamate (2.02 g, 11.027 mmol, 2.80 equiv) in THF (40 mL) was added CuI (75.00 mg, 0.394 mmol, 0.10 equiv), DIEA (6.86 mL, 53.074 mmol, 10.00 equiv), and $Pd(PPh_3)_2Cl_2$ (276.41 mg, 0.394 mmol, 0.10 equiv). The resulting mixture was stirred for 1 h at 70° C. The reaction was filtered, and the filter cake washed with EtOAc (3×10 mL). The filtrate was concentrated under reduced pressure and the residue taken up in water (200 mL) and extracted with EtOAc (2×150 mL). The combined organic layers were washed with brine (200 mL), dried over anhydrous Na2SO4, and concentrated under reduced pressure. The residue was purified by silica gel column chromatography, eluting with Petroleum ether/EtOAc (2:1) to afford C (1.12 g, 64.72%) as an off-white solid. LCMS (ESI) m/z: $[M+H]^+$=440.

Step 3: Preparation of 4-(5-aminopent-1-yn-1-yl)-2-(2,6-dioxopiperidin-3-yl)isoindole-1,3-dione trifluoroacetate (I-81)

I-81

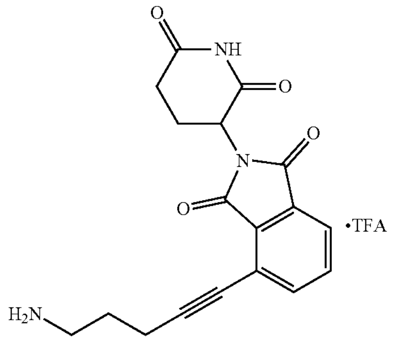

To a stirred solution of C (1.10 g, 2.503 mmol, 1 equiv) in dichloromethane (6 mL) was added TFA (3.00 mL) at room temperature. The resulting mixture was stirred for 1 h at room temperature, followed by concentration under reduced pressure. The residue was purified by flash column chromatography on silica gel to afford I-81 (890 mg, 91.2%) as a white solid. $^1$H NMR (400 MHz, DMSO-d6) δ 11.15 (s, 1H), 7.97-7.73 (m, 6H), 5.14 (dd, 1H), 3.09-2.97 (m, 2H), 2.96-2.84 (m, 1H), 2.67 (t, 3H), 2.62-2.54 (m, 1H), 2.12-2.02 (m, 1H), 1.82-1.94 (m, 2H). LCMS (ESI) m/z: $[M+H]^+$= 340.12.

Preparation of 5-[2-[4-(aminomethyl)piperidin-1-yl]ethoxy]-2-(2,6-dioxopiperidin-3-yl)isoindole-1,3-dione (I-82)

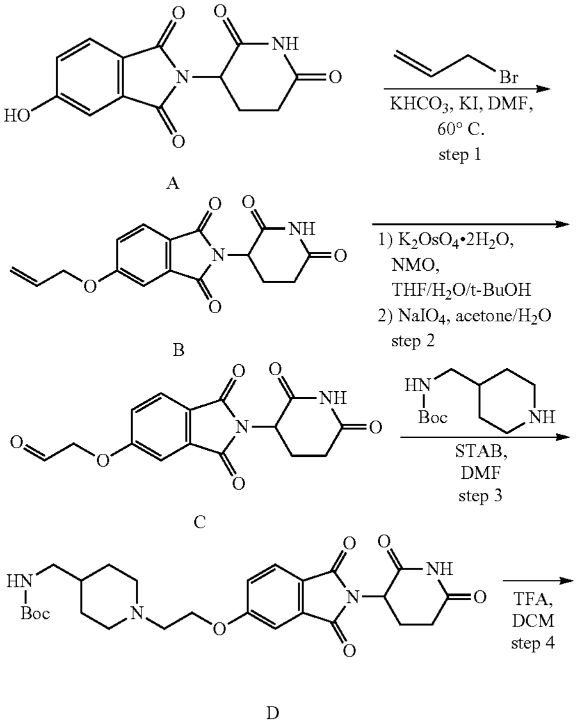

-continued

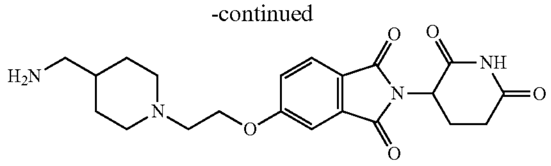

I-82

Step 1: Preparation of 5-(2-bromoethoxy)-2-(2,6-dioxopiperidin-3-yl)isoindole-1,3-dione (B)

B

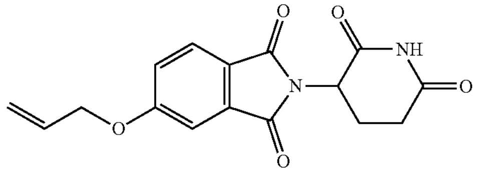

2-(2,6-dioxopiperidin-3-yl)-5-hydroxyisoindole-1,3-dione (A, 300 mg, 1.09 mmol, 1.00 equiv), $KHCO_3$ (164 mg, 1.64 mmol, 1.50 equiv), and allyl bromide (198 mg, 1.64 mmol, 1.50 equiv) were dissolved in DMF (15.00 mL). KI (18 mg, 0.11 mmol, 0.10 equiv) was then added to the mixture. The reaction was allowed to stir at 60° C. for 18 h. After cooling to the room temperature, 20 mL of water was added followed by extraction with EtOAc (3×20 mL). The combined organic layers were washed with water (20 mL) and brine (20 mL) and dried over sodium sulfate. After removing the solvent, the residue was purified by flash column chromatography on silica gel eluting with EtOAc in Petroleum ether (50%, v/v) to afford B (200 mg, 47.9%) as off-white solid. LCMS (ESI) m/z: $[M+H]^+$=315.

Step 2: Preparation of 2-[[2-(2,6-dioxopiperidin-3-yl)-1,3-dioxoisoindol-5-yl]oxy]acetaldehyde (C)

C

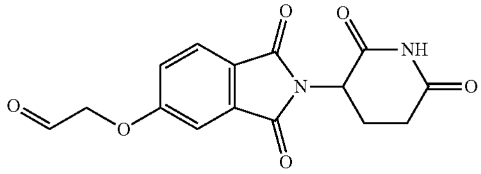

To a mixture of t-BuOH (5.00 mL)/water (5.00 mL)/THF (1.00 mL) was added B (250 mg, 0.80 mmol, 1.00 equiv), NMO (99 mg, 0.80 mmol, 1.5 equiv), and $K_2OsO_4$ dihydrate (15 mg, 0.04 mmol, 0.050 equiv). The resulting suspension was stirred at room temperature for 24 h after which time a clear solution remained. The reaction was quenched with saturated $Na_2S_2O_3$ (20 mL) and extracted with EtOAc (3×20 mL). The combined organic layers were washed with brine and dried over sodium sulfate. After removing the solvent, the residue was dissolved in a water (5.00 mL)/acetone (5.00 mL) mixture together with $NaIO_4$ (255.20 mg, 1.19 mmol, 1.50 equiv). The reaction was stirred at room temperature for 2 h, followed by removal of the solvent under vacuum. The residue was suspended in 20 mL EtOAc. After filtration, the remaining liquid was concentrated under vacuum and the residue purified by preparative TLC (EtOAc/Petroleum ether=1:1, v/v) to afford C (120 mg, 47.7%) as an off-white solid. LCMS (ESI) m/z: $[M-H]^-$=315.

Step 3: Preparation of tert-butyl N-[[1-(2-[[2-(2,6-dioxopiperidin-3-yl)-1,3-dioxoisoindol-5-yl]oxy]-ethyl)piperidin-4-yl]methyl]carbamate (D)

D

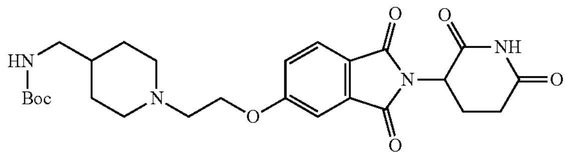

To a solution of C (120 mg, 0.379 mmol, 1.00 equiv) and tert-butyl N-(piperidin-4-ylmethyl)carbamate (81 mg, 0.38 mmol, 1.0 equiv) in DMF (10.00 mL) was added STAB (120 mg, 0.569 mmol, 1.50 equiv) in one portion. The reaction was stirred at room temperature overnight. After concentration, the residue was purified by reverse phase flash chromatography under the following conditions: column, C18 silica gel; mobile phase, water in ACN, 10% to 50% gradient over 10 min; detector, UV 254 nm. This resulted in D (130 mg, 66.7%) as a white solid. LCMS (ESI) m/z: $[M+H]^+$=515.

Step 4: Preparation of 5-[2-[4-(aminomethyl)piperidin-1-yl]ethoxy]-2-(2,6-dioxopiperidin-3-yl)isoindole-1,3-dione (I-82)

I-82

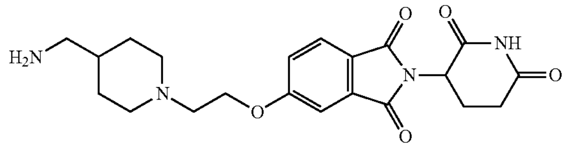

D (130.00 mg, 1.00 equiv) was suspended in DCM (10.00 mL), and TFA (1.00 mL) was added. The clear solution was stirred at room temperature for 2 h. The solvent was then removed under reduced pressure, and the residue I-82 used without further purification. LCMS (ESI) m/z: $[M+H]^+$=415.

Preparation of 1-(2-[[2-(2,6-dioxopiperidin-3-yl)-1,3-dioxoisoindol-5-yl]oxy]ethyl)piperidine-4-carboxylic acid (I-83)

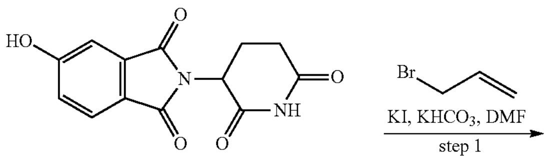

A

-continued

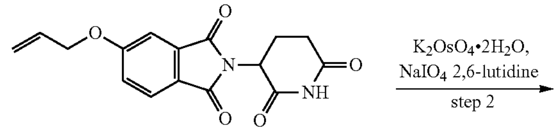

B

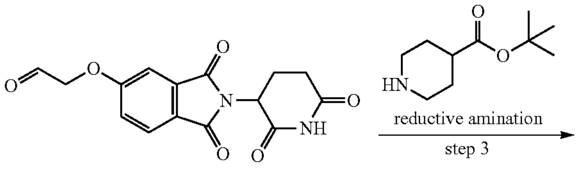

C

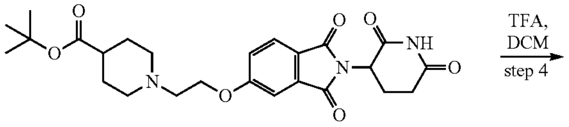

D

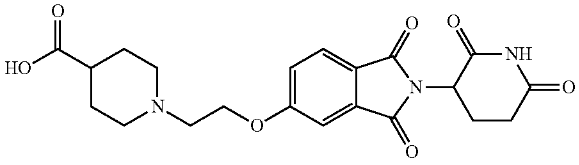

I-83

Step 1: Preparation of 2-(2,6-dioxopiperidin-3-y)-5-(prop-2-en-1-yloxy)isoindole-1,3-dione (B)

B

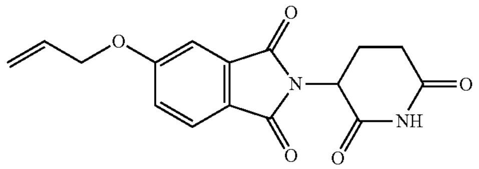

To a solution of 2-(2,6-dioxopiperidin-3-yl)-5-hydroxyisoindole-1,3-dione (A, 5.48 g, 19.983 mmol, 1.00 equiv) and allyl bromide (3.63 g, 29.975 mmol, 1.5 equiv) in DMF (50.00 mL) was added KI (331.72 mg, 1.998 mmol, 0.1 equiv) and $KHCO_3$ (3.00 g, 29.975 mmol, 1.5 equiv). The resulting mixture was stirred for 12 h at 65° C., then diluted with water (100 mL) and extracted with EtOAc (3×50 mL). The combined organic layers were washed with brine (3×60 mL), dried over anhydrous Na2SO4, and concentrated under reduced pressure. The residue was purified by silica gel column chromatography, eluting with hexane/EtOAc (1:1) to afford B (6.7 g, crude) as a yellow green solid; LCMS (ESI) m/z: $[M+H]^+$=315.

Step 2: Preparation of 2-[[2-(2,6-dioxopiperidin-3-yl)-1,3-dioxoisoindol-5-yl]oxy]acetaldehyde (C)

C

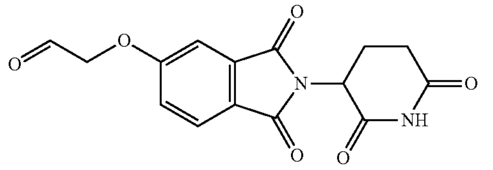

To a solution of B (3.14 g, 9.991 mmol, 1.00 equiv) in 1,4-dioxane (30.00 mL) was added $NaIO_4$ (10.68 g, 49.953 mmol, 5.00 equiv), water (3.00 mL), and 2,6-lutidine (3.21 g, 29.972 mmol, 3 equiv). To this mixture was added $K_2OsO_4$ dihydrate (0.37 g, 0.999 mmol, 0.1 equiv) at room temperature and the reaction stirred for 2 h at room temperature. The reaction was quenched with water and extracted with EtOAc (3×50 mL). The combined organic layers were washed with brine (3×100 mL), dried over anhydrous $Na_2SO_4$, and concentrated under reduced pressure. This resulted in C (1.83 g, 57.92%) as a light brown solid; LCMS (ESI) m/z: $[M+H]^+$=317.

Step 3: Preparation of tert-butyl 1-(2-[[2-(2,6-dioxopiperidin-3-yl)-1,3-dioxoisoindol-5-yl]oxy]ethyl) piperidine-4-carboxylate (D)

D

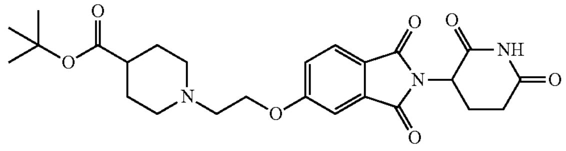

To a solution of C (1.83 g, 5.786 mmol, 1.00 equiv) and tert-butyl piperidine-4-carboxylate (1.07 g, 5.786 mmol, 1.00 equiv) in DMF (35.00 mL) was added $NaBH(OAc)_3$ (3.68 g, 17.359 mmol, 3.00 equiv). The resulting mixture was stirred for 3 h at room temperature. Following aqueous workup, DCM extraction, and concentration under reduced pressure, the residue was purified by reverse phase flash chromatography under the following conditions: column, C18 silica gel; mobile phase, ACN/0.1% formic acid in water, 0% to 100% gradient over 45 min; detector, UV 254 nm. This resulted in D (1.16 g, 41.29%) as an off-white solid; LCMS (ESI) m/z: $[M+H]^+$=401.

Step 4: Preparation of 1-(2-[[2-(2,6-dioxopiperidin-3-yl)-1,3-dioxoisoindol-5-yl]oxy]ethyl)piperidine-4-carboxylic acid (I-83)

I-83

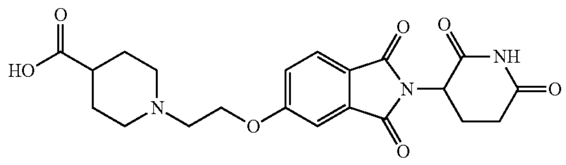

To a solution of D (1.16 g, 2.389 mmol, 1.00 equiv) in DCM (10.00 mL) was added TFA (10.00 mL, 134.630 mmol, 34.18 equiv). The reaction was stirred for 5 h at room temperature, then concentrated under reduced pressure. The residue was purified by reverse phase flash chromatography under the following conditions: column, C18 silica gel; mobile phase, ACN/0.1% formic acid in water, 0% to 100% gradient over 45 min; detector, UV 254 nm. This resulted in I-83 (845 mg, 73.42%) as a white solid; $^1H$ NMR (300 MHz, DMSO-d6) δ 11.11 (s, 1H), 8.15 (d, 1H), 7.84 (d, 1H), 7.47 (d, 1H), 7.37 (dd, 1H), 5.12 (dd, 1H), 4.31 (t, 2H), 3.02-2.85 (m, 3H), 2.79 (t, 2H), 2.66-2.60 (m, 1H), 2.59-2.54 (m, 1H), 2.29-2.12 (m, 3H), 2.15-1.99 (m, 1H), 1.87-1.75 (m, 2H), 1.66-1.47 (m, 2H); LCMS (ESI) m/z: $[M+H]^+$=430.15.

Preparation of 4,5-dimethyl-1-(methylsulfonyl)-N-(2-oxo-2-((4-(3-(pyridin-4-yl)phenyl)thiazol-2-yl) amino)ethyl)-1H-pyrrole-3-carboxamide (I-84)

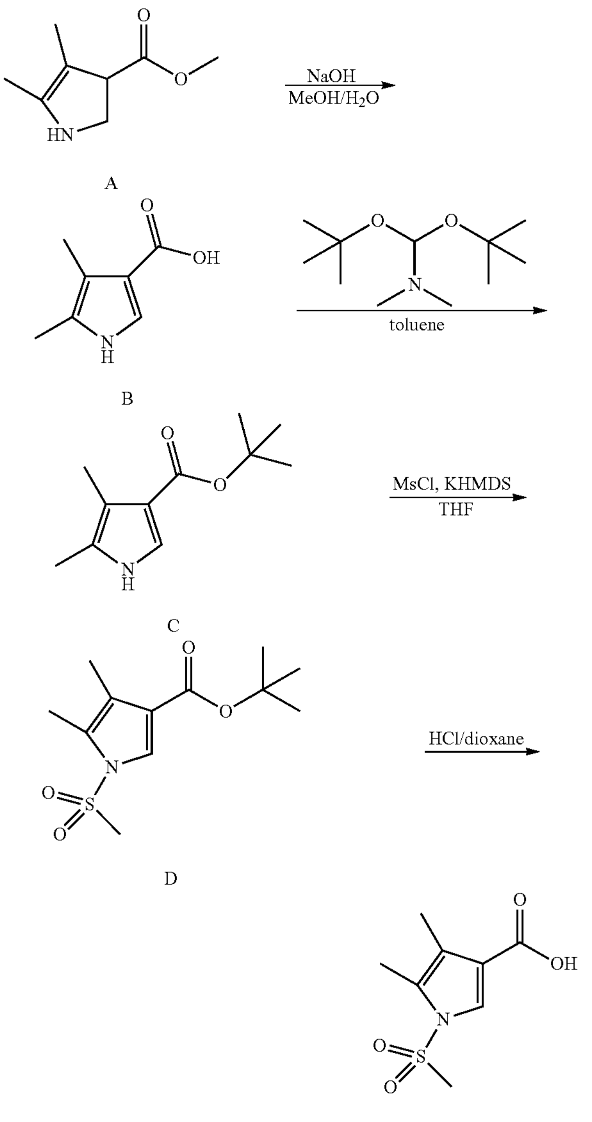

Step 1: Preparation of 4,5-dimethyl-1H-pyrrole-3-carboxylic acid (B)

B

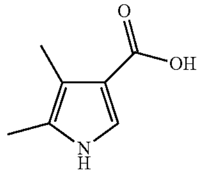

To a solution of methyl 4,5-dimethyl-1H-pyrrole-3-carboxylate (A, 500 mg, 3.26 mmol) in MeOH (4 mL) was added a solution of sodium hydroxide (261.12 mg, 6.53 mmol) in water (1 mL). The mixture was stirred at 25° C. for 36 h. 2M hydrochloric acid (10 mL) and water (10 mL) was added and the reaction mixture extracted with EtOAc (50 mL×2). The combined organic layers were washed with brine (20 mL), dried over $Na_2SO_4$, and concentrated under reduced pressure to give B (400 mg, crude) as a yellow solid, which was used without further purification. LCMS (ESI) m/z: $[M+H]^+$=140.1.

Step 2: Preparation of tert-butyl 4,5-dimethyl-1H-pyrrole-3-carboxylate (C)

C

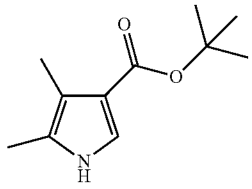

To a solution of B (400 mg, 2.87 mmol) in toluene (10 mL) was added 1,1-ditertbutoxy-N,N-dimethyl-methylamine (2.92 g, 14.37 mmol, 3.45 mL). The mixture was stirred at 80° C. for 2 h. Water (20 mL) was added and the reaction mixture was extracted with EtOAc (50 mL×2). The combined organic layers were washed with brine (20 mL), dried over $Na_2SO_4$, and concentrated under reduced pressure. The residue was purified by flash silica gel chromatography (ISCO; 12 g SepaFlash Silica Flash Column, Eluent of 0-80% EtOAc/Petroleum ether gradient 35 mL/min) and concentrated under vacuum to give C (200 mg, 983.32 μm, 34.21% yield) as red oil. LCMS (ESI) m/z: $[M+H]^+$=196.2.

Step 3: Preparation of tert-butyl 4,5-dimethyl-1-(methylsulfonyl)-1H-pyrrole-3-carboxylate (D)

D

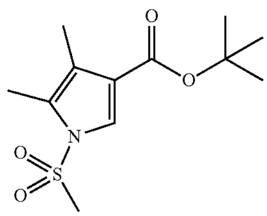

To a solution of C (120 mg, 0.62 mmol) in THE (3 mL) was added KHMDS (1 M, 1.84 mL) at 0° C. under nitrogen. After 0.5 h, methanesulfonyl chloride (140.80 mg, 1.23 mmol, 95.14 μL) was added. The mixture was stirred at 25° C. for 2 h. Water (20 mL) was added and the reaction mixture extracted with EtOAc (50 mL×2). The combined organic layers were washed with brine (20 mL), dried over $Na_2SO_4$, and concentrated under reduced pressure. The residue was purified by flash silica gel chromatography (ISCO; X g SepaFlash Silica Flash Column, Eluent of 0-50% EtOAc/Petroleum ether gradient 60 mL/min) to give D (80 mg, 263.40 μm, 42.86% yield) as a red solid. LCMS (ESI) m/z: $[M+H-56]^+$=218.1.

Step 4: Preparation of 4,5-dimethyl-1-(methylsulfonyl)-1H-pyrrole-3-carboxylic acid (I-84)

I-84

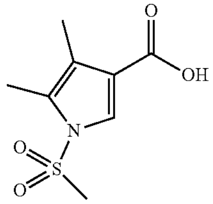

To a solution of D (80 mg, 0.29 mmol) in 1,4-dioxane (2 mL) was added 4 M hydrochloric acid in 1,4-dioxane (2 mL). The mixture was stirred at 25° C. for 12 h, then concentrated under reduced pressure to give I-84 (50 mg, crude) as a purple solid. LCMS (ESI) m/z=$[M+H]^+$=218.2.

Preparation of Preparation of 5-[4-(4-aminopiperidin-1-yl)butoxy]-2-(2,6-dioxopiperidin-3-yl)isoindole-1,3-dione (I-85)

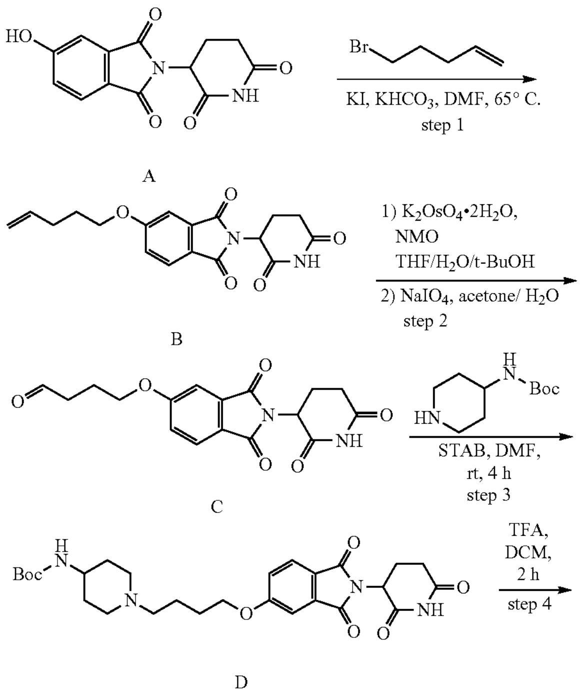

-continued

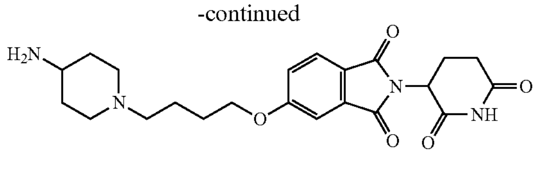

I-85

Step 1: Preparation of 2-(2,6-dioxopiperidin-3-yl)-5-(pent-4-en-1-yloxy)isoindole-1,3-dione (B)

B

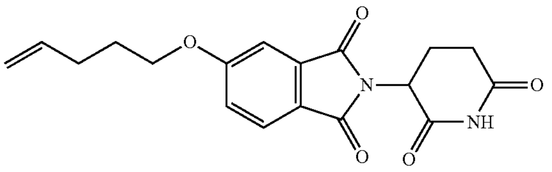

To a stirred mixture of 2-(2,6-dioxopiperidin-3-yl)-5-hydroxyisoindole-1,3-dione (A, 500.00 mg, 1.823 mmol, 1.00 equiv) and $KHCO_3$ (273.81 mg, 2.735 mmol, 1.50 equiv) in DMF (10.00 mL) was added 5-bromo-1-pentene (326.07 mg, 2.188 mmol, 1.20 equiv) and KI (30.27 mg, 0.182 mmol, 0.10 equiv) in portions at room temperature under a nitrogen atmosphere. The resulting mixture was stirred overnight at 65 degrees under nitrogen atmosphere, then cooled and extracted with EtOAc (2×20 mL). The combined organic layers were washed with water (3×10 mL), dried over anhydrous $Na_2SO_4$, and concentrated under reduced pressure. The residue was purified by preparative TLC (Petroleum ether/EtOAc 1:1) to afford B (400 mg, 64.08%) as a white solid. LCMS (ESI) m/z: $[M+H]^+$=343.

Step 2: Preparation of 4-[[2-(2,6-dioxopiperidin-3-yl)-1,3-dioxoisoindol-5-yl] oxy]butanal (C)

C

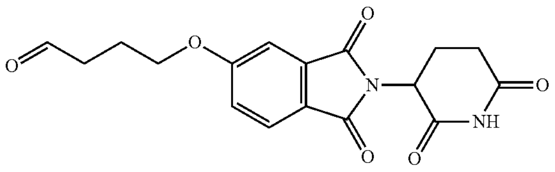

To a stirred solution of 2-(2,6-dioxopiperidin-3-yl)-5-(pent-4-en-1-yloxy)isoindole-1,3-dione (B, 300.00 mg, 0.876 mmol, 1.00 equiv) in THE (1.00 mL)/water (5.00 mL)/t-BuOH (5.00 mL) was added NMO (153.98 mg, 1.314 mmol, 1.50 equiv) and $K_2OsO_4$ dihydrate (32.29 mg, 0.088 mmol, 0.10 equiv) in portions. The resulting mixture was stirred overnight at room temperature under nitrogen atmosphere. The reaction was then concentrated under reduced pressure. $NaIO_4$ (374.86 mg, 1.753 mmol, 2.00 equiv), water (0.50 mL), and acetone (5.00 mL) were then added, and the resulting mixture was stirred for an additional 2 h at room temperature. Following aqueous sodium thiosulfate workup and extraction with DCM, the solution was concentrated under reduced pressure to afford C (300 mg, 99.43%) as an off-white solid. The crude product was used in the next step directly without further purification. LCMS (ESI) m/z: $[M+H]^+$=345.

Step 3: Preparation of tert-butyl N-[1-(4-[[2-(2,6-dioxopiperidin-3-yl)-1,3-dioxoisoindol-5-yl]oxy] butyl)piperidin-4-yl]carbamate (D)

D

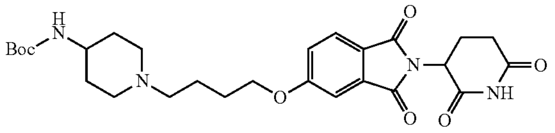

To a stirred solution of 4-[[2-(2,6-dioxopiperidin-3-yl)-1,3-dioxoisoindol-5-yl]oxy]butanal (C, 270.00 mg, 0.784 mmol, 1.00 equiv) in DMF (5.00 mL) was added STAB (249.29 mg, 1.176 mmol, 1.50 equiv) and tert-butyl N-(piperidin-4-yl)carbamate (157.05 mg, 0.784 mmol, 1.00 equiv) in portions. The resulting mixture was stirred for overnight at room temperature, then extracted with EtOAc (2×20 mL). The combined organic layers were washed with water (3×10 mL), dried over anhydrous Na2SO4, and concentrated under reduced pressure. The residue was purified by preparative TLC (DCM/MeOH 10:1) to afford D (130 mg, 31.36%) as an off-white solid. LCMS (ESI) m/z: $[M+H]^+$=529.

Step 4: Preparation of 5-[4-(4-aminopiperidin-1-yl) butoxy]-2-(2,6-dioxopiperidin-3-yl)isoindole-1,3-dione (I-85)

I-85

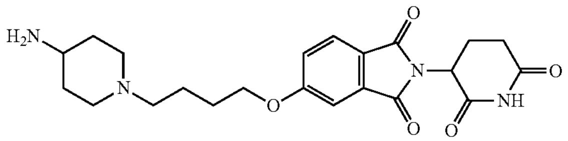

A solution of tert-butyl N-[1-(4-[[2-(2,6-dioxopiperidin-3-yl)-1,3-dioxoisoindol-5-yl]oxy]butyl)piperidin-4-yl]carbamate (D, 120.00 mg, 0.227 mmol, 1.00 equiv) and TFA (1.00 mL) in DCM (4.00 mL) was stirred for 2 h at room temperature. The resulting mixture was concentrated under reduced pressure. This resulted in I-85 (130 mg, 93.55%) as an off-white solid. LCMS (ESI) m/z: $[M+H]^+$=429.

Preparation of tert-butyl 2-[(4-bromo-2-pyridyl)-methyl-amino]acetate (I-86)

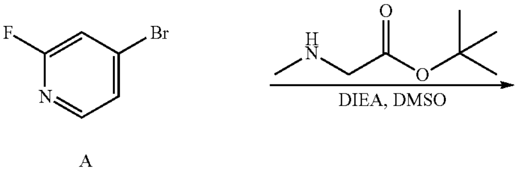

A

-continued

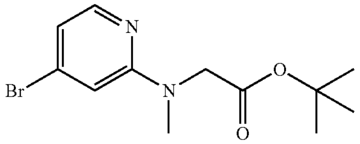

I-86

To a solution of 4-bromo-2-fluoro-pyridine (A, 28 g, 159.10 mmol) and tert-butyl 2-(methylamino)acetate (34.68 g, 190.92 mmol, HCl) in DMSO (200 mL) was added DIEA (41.13 g, 318.21 mmol, 55.43 mL). The mixture was stirred at 120° C. for 12 h. The reaction was diluted with water (2 L) and extracted with EtOAc (500 mL×3). The combined organic phase was washed with brine (500 mL×2), dried over $Na_2SO_4$, filtered, and concentrated. The residue was purified by flash column chromatography (silica gel, Petroleum ether/EtOAc 10:1 to 5:1) to give I-86 (35 g, 104.59 mmol, 65.74%) as a white solid. LCMS (ESI) m/z: $[M+H]^+$= 301.0. $^1H$ NMR (400 MHz, $CDCl_3$) δ=7.86 (d, J=5.2 Hz, 1H), 6.66-6.65 (m, 1H), 6.62 (d, J=1.2 Hz, 1H), 4.12 (s, 2H), 3.00 (s, 3H), 1.35 (s, 9H) ppm.

Preparation of 2-(2,6-dioxo-3-piperidyl)-4-[2-oxo-2-[4-(4-piperidyl)-1-piperidyl]ethoxy]isoindoline-1,3-dione (I-87)

-continued

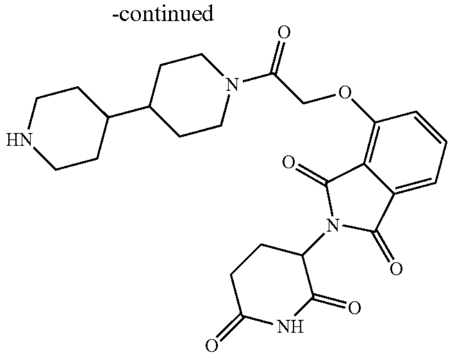

I-87

Step 1: Preparation of tert-butyl 4-[1-[2-[2-(2,6-dioxo-3-piperidyl)-1,3-dioxo-isoindolin-4-yl]oxyacetyl]-4-piperidyl]piperidine-1-carboxylate (B)

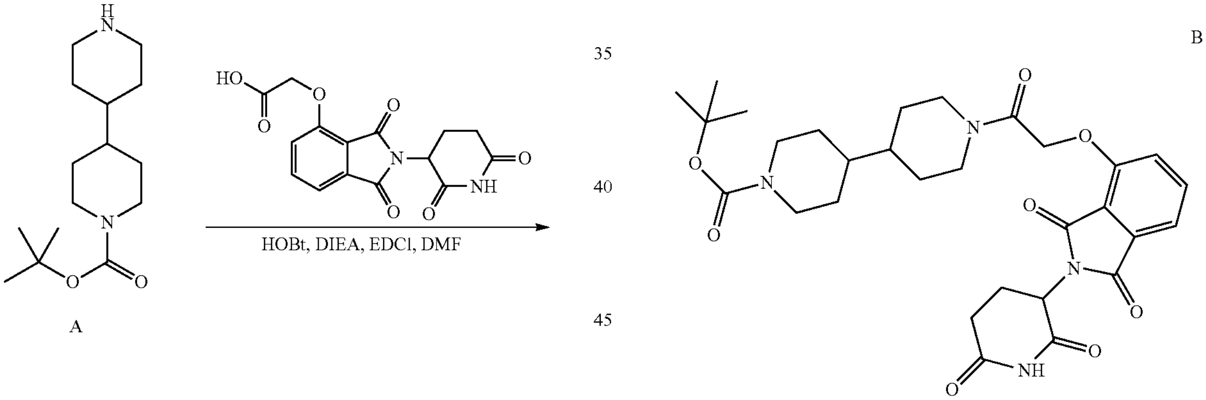

A

B

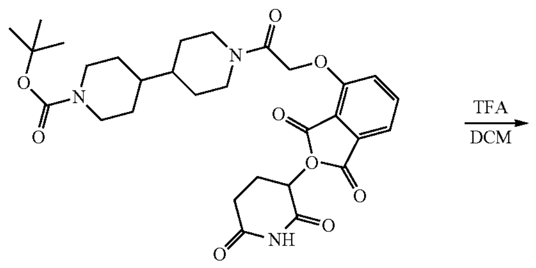

B

To a solution of tert-butyl 4-(4-piperidyl)piperidine-1-carboxylate (A, 730 mg, 2.72 mmol), HOBt (551.28 mg, 4.08 mmol), DIEA (1.76 g, 13.60 mmol, 2.37 mL), and 2-[2-(2,6-dioxo-3-piperidyl)-1,3-dioxo-isoindolin-4-yl]oxyacetic acid (903.72 mg, 2.72 mmol) in DMF (20 mL) was added EDCI (782.11 mg, 4.08 mmol). Then the mixture was stirred at 25° C. for 8 h. Water (30 mL) was added and the mixture was extracted with EtOAc (45 mL×3). The combined organic extracts were dried over anhydrous $Na_2SO_4$ and concentrated under reduced pressure. The residue was purified by reverse phase flash column chromatography (0.1% formic acid in water/ACN). Then the solution was concentrated to remove ACN and the residue was extracted with EtOAc (30 mL×3). The combined organic phase was dried over anhydrous $Na_2SO_4$, filtered, and concentrated under reduced pressure to give B (820 mg, 1.41 mmol, 51.74% yield) as a yellow solid. LCMS (ESI) m/z: $[M-100]^+$=483.2.

Step 2: Preparation of 2-(2,6-dioxo-3-piperidyl)-4-[2-oxo-2-[4-(4-piperidyl)-1-piperidyl]ethoxy]isoindoline-1,3-dione (I-87)

I-87

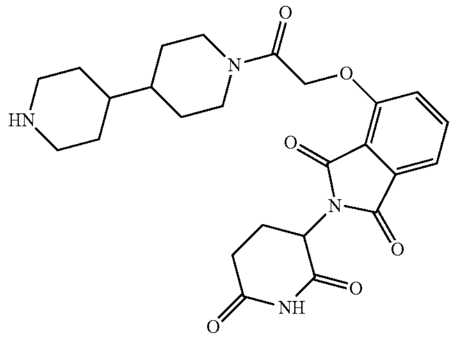

To a solution of B (750 mg, 1.29 mmol) in DCM (10 mL) was added TFA (3.08 g, 27.01 mmol, 2 mL) at 0° C. Then the mixture was stirred at 25° C. for 2 h, then concentrated to give I-87 (700 mg, 1.17 mmol, 91.16% yield, TFA) as a yellow solid. LCMS (ESI) m/z: $[M+H]^+$=783.2. $^1H$ NMR (400 MHz, DMSO-$d_6$) δ=8.37 (s, 1H), 7.82-7.80 (m, 1H), 7.50 (d, J=7.2 Hz, 1H), 7.37 (d, J=8.6 Hz, 1H), 5.19 (s, 2H), 4.44-4.34 (m, 1H), 4.09 (d, J=7.2 Hz, 1H), 3.90-3.79 (m, 2H), 3.03-3.02 (m, 4H), 2.71-2.58 (m, 2H), 2.49-2.48 (m, 2H), 2.14-2.06 (m, 1H), 2.05 (s, 1H), 1.71 (s, 2H), 1.62-1.61 (m, 2H), 1.23-1.22 (m, 4H), 1.10 (d, J=6.0 Hz, 2H) ppm.

TABLE 8

Intermediates were prepared in a similar manner as described in the preparation of I-87.

| Structure | # | Name | LCMS (ESI) m/z: $[M + H]^+$ |
|---|---|---|---|
| 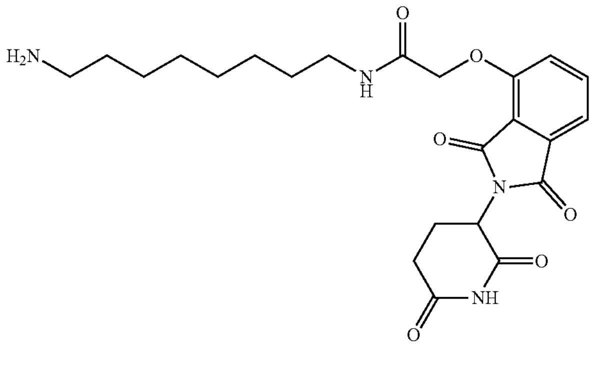 [SMILES: NCCCCCCCCNC(=O)COc1cccc2c1C(=O)N(C1CCC(=O)NC1=O)C2=O] | I-88 | N-(8-aminooctyl)-2-((2-(2,6-dioxopiperidin-3-yl)-1,3-dioxoisoindolin-4-yl)oxy)acetamide | 459.4 |
| 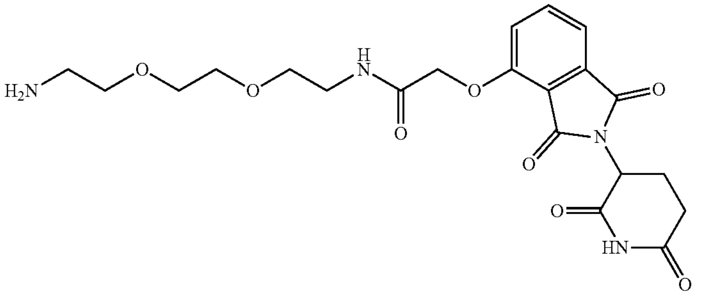 [SMILES: NCCOCCOCCNC(=O)COc1cccc2c1C(=O)N(C1CCC(=O)NC1=O)C2=O] | I-89 | N-(2-(2-(2-aminoethoxy)ethoxy)ethyl)-2-((2-(2,6-dioxopiperidin-3-yl)-1,3-dioxoisoindolin-4-yl)oxy)acetamide | 463.25 |

Preparation of 1-(methylsulfonyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide (I-90) and N-(2-((4-(3-bromophenyl)thiazol-2-yl)amino)-2-oxoethyl)-1-(methylsulfonyl)-1H-pyrrole-3-carboxamide (I-92)

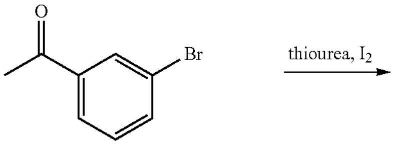

A

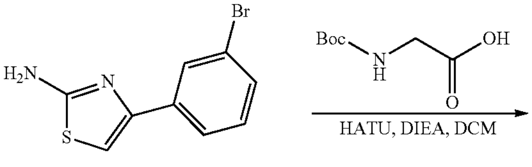

B

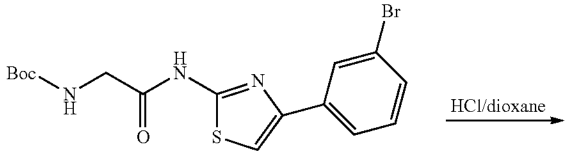

C

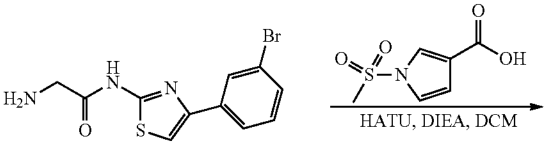

D

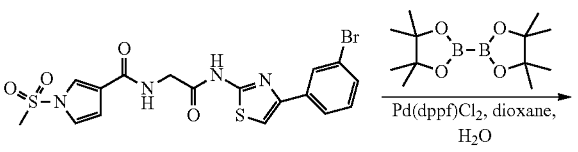

I-92

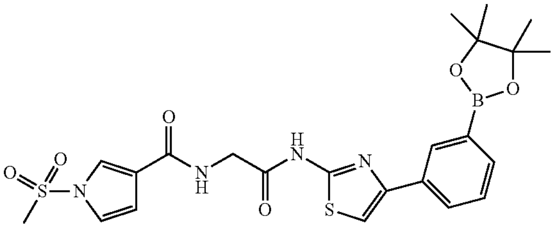

I-90

Step 1: Preparation of 4-(3-bromophenyl)thiazol-2-amine (B)

B

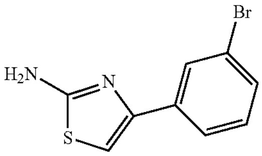

To a mixture of 1-(3-bromophenyl)ethanone (A, 473 g, 2.38 mol, 313.25 mL) and thiourea (361.78 g, 4.75 mol) was added 12 (603.14 g, 2.38 mol, 1 equiv). The mixture was stirred at 110° C. for 16 h. After cooling, the reaction mixture was triturated with MTBE (5 L), and then filtered to remove any unreacted iodine and acetophenone. The filter cake was suspended in ice water (4 L) and treated with 25% aqueous ammonia to pH 9-10. The suspension was stirred at 25° C. for 15 min, then filtered and washed with water (1 L) to give a wet solid. This was dissolved in EtOAc (4 L) and washed with saturated aqueous $NaHCO_3$ (1 L×2) and brine (1 L). The EtOAc layer was dried over $Na_2SO_4$, filtered and concentrated under reduced pressure. The residue was stirred with Petroleum ether/EtOAc 100:1 (4 L) at 25° C. for 3 h, then the suspension was filtered, and the filter cake washed with Petroleum ether (1 L), and dried under vacuum to give B (450 g, 1.69 mol, 71.20% yield, 95.93% purity) as a pink solid. $^1H$ NMR (400 MHz, DMSO-d6) δ=7.98-7.97 (m, 1H), 7.80-7.77 (m, 1H), 7.43-7.42 (m, 1H), 7.34-7.30 (m, 1H), 7.15 (s, 1H), 7.10 (s, 2H). LCMS (ESI) m/z: [$^{79}$Br M+H+]=254.9.

Step 2: Preparation of tert-butyl N-[2-[[4-(3-bromophenyl)thiazol-2-yl]amino]-2-oxo-ethyl]carbamate (C)

C

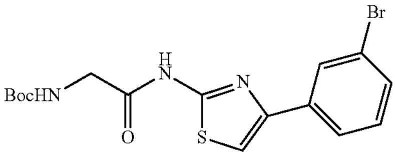

To a solution of 2-(tert-butoxycarbonylamino)acetic acid (82.40 g, 470.34 mmol), HATU (178.84 g, 470.34 mmol), and DIEA (151.97 g, 1.18 mol, 204.81 mL) in DCM (1 L) was added B (100.00 g, 391.95 mmol), and the mixture was stirred at 30° C. for 16 h. The reaction mixture was washed with saturated aqueous citric acid (500 mL×4) and brine (500 mL), dried over $Na_2SO_4$, and concentrated under reduced pressure. The residue was triturated with MeOH (200.0 mL), and the resulting liquid concentrated under reduced pressure to give C (100 g, 241.89 mmol, 61.71% yield) as a white solid. $^1H$ NMR (400 MHz, DMSO-$d_6$) δ=12.29 (s, 1H), 8.09-8.09 (m, 1H), 7.89 (d, J=7.6 Hz, 1H), 7.76 (s, 1H), 7.52-7.49 (m, 1H), 7.41-7.37 (m, 1H), 7.16-7.13 (m, 1H), 3.87-3.81 (m, 2H), 1.39 (s, 9H) ppm. LCMS (ESI) m/z: [$^{81}$BrM+H]$^+$=413.8.

Step 3: Preparation of 2-amino-N-(4-(3-bromophenyl)thiazol-2-yl)acetamide hydrochloride (D)

D

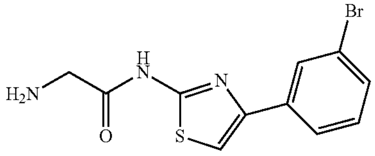

A mixture of C (10 g, 24.25 mmol) and 4 M HCl in 1,4-dioxane (100 mL) was stirred at 30° C. for 2 h. The reaction mixture was concentrated under vacuum to give D (8.4 g, crude, HCl) as a white solid, which was used without further purification. LCMS (ESI) m/z: $[M+H]^+$=313.8

Step 4: Preparation of N-(2-((4-(3-bromophenyl)thiazol-2-yl)amino)-2-oxoethyl)-1-(methylsulfonyl)-1H-pyrrole-3-carboxamide (I-92)

I-92

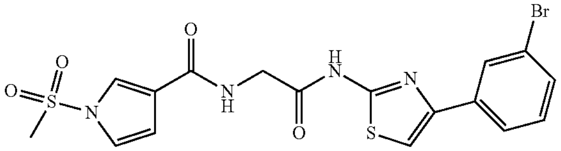

To a solution of D (8.4 g, 24.09 mmol) and 1-methylsulfonylpyrrole-3-carboxylic acid (5.47 g, 28.91 mmol) in DCM (100 mL) was added HATU (10.99 g, 28.91 mmol) and DIEA (18.68 g, 144.56 mmol, 25.18 mL). The mixture was stirred at 20° C. for 16 h. The resulting suspension was filtered and triturated with MTBE (50 mL×2) to give a filter cake, which was dried under vacuum to give I-92 (10 g, 20.58 mmol, 85.43% yield) as a white solid, which was used without further purification. $^1H$ NMR (400 MHz, DMSO-d6) δ=12.40-12.35 (m, 1H), 8.69-8.66 (m, 1H), 8.11-8.10 (m, 1H), 7.92-7.90 (m, 1H), 7.85-7.84 (m, 1H), 7.78 (s, 1H), 7.53-7.51 (m, 1H), 7.42-7.38 (m, 1H), 7.32-7.30 (m, 1H), 6.78-6.77 (m, 1H), 4.14 (d, J=6.0 Hz, 2H), 3.57 (s, 3H). LCMS (ESI) m/z: $[M+H]^+$=484.8

Step 5: Preparation of 1-(methylsulfonyl)-N-(2-oxo-2-((4-(3-(4,4,5,5-tetramethyl-1,3,2-dioxaborolan-2-yl)phenyl)thiazol-2-yl)amino)ethyl)-1H-pyrrole-3-carboxamide (I-90)

I-90

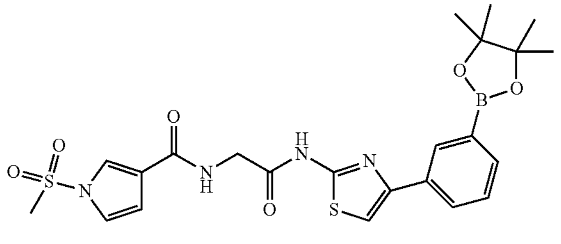

To a solution of I-92 (1.5 g, 3.10 mmol) and 4,4,5,5-tetramethyl-2-(4,4,5,5-tetramethyl-1,3,2-dioxaborolan-2-yl)-1,3,2-dioxaborolane (1.18 g, 4.65 mmol) in 1,4-dioxane (15 mL) was added $Pd(dppf)Cl_2$ (227.07 mg, 0.310 mmol) and KOAc (913.69 mg, 9.31 mmol). The mixture was stirred at 80° C. for 2 h, then poured into water (100 mL) and extracted with EtOAc (100 mL×3). The combined organic layers were washed with brine (50 mL), dried over $Na_2SO_4$ and concentrated under reduced pressure. The residue was suspended in 1:1 Petroleum ether/EtOAc (20 mL), filtered, and the filtrate concentrated under vacuum to give I-90 (6.5 g, 12.00 mmol, 96.71% yield) as a brown solid. $^1H$ NMR (400 MHz, DMSO-d6) δ=12.45 (s, 1H), 8.67 (t, J=6.0 Hz, 1H), 8.29 (s, 1H), 8.01 (br d, J=7.6 Hz, 1H), 7.84 (s, 1H), 7.65 (s, 1H), 7.62 (d, J=7.2 Hz, 1H), 7.44 (t, J=7.6 Hz, 1H), 7.31 (t, J=2.8 Hz, 1H), 6.78 (d, J=1.6 Hz, 1H), 4.14 (d, J=6.0 Hz, 2H), 3.57 (s, 3H), 1.31 (s, 12H). LCMS (ESI) m/z: $[M+H]^+$=531.2

Preparation of tert-butyl 1-(4-(3-(2-(2-(1-(methylsulfonyl)-1H-pyrrole-3-carboxamido)acetamido)thiazol-4-yl)phenyl)pyridin-2-yl)cyclopropanecarboxylate (I-91)

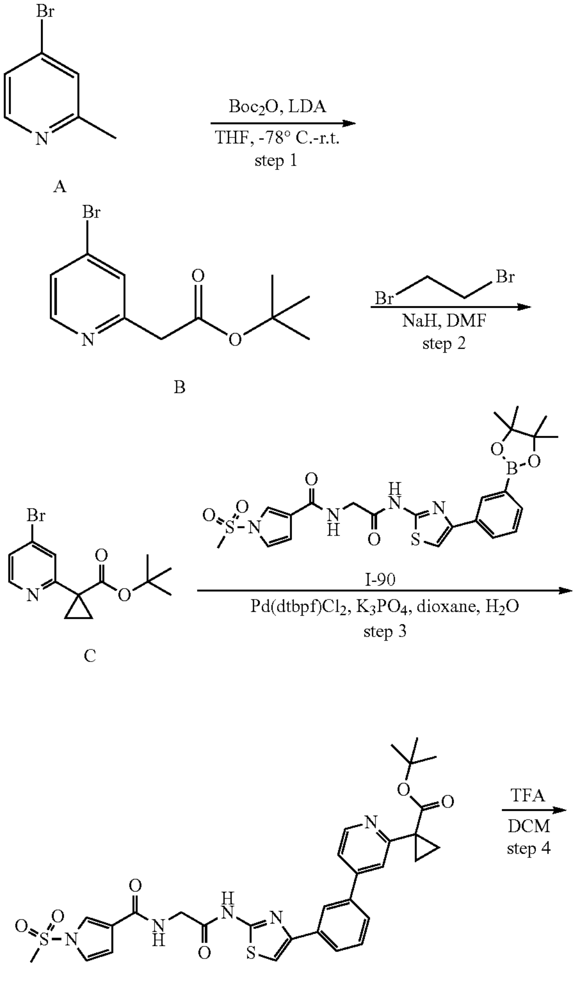

A

B

C

D

-continued

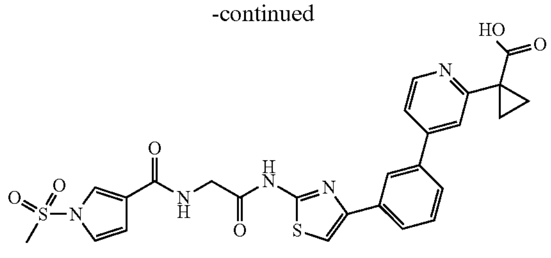

I-91

Step 1: Preparation of tert-butyl 2-(4-bromopyridin-2-yl)acetate (B)

B

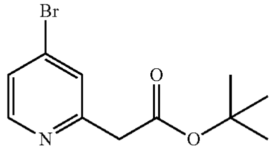

To a solution of 4-bromo-2-methyl-pyridine (A, 10 g, 36.9 mmol) in THE (150 mL) was added LDA (2 M in THF, 100 mL, 200 mmol) dropwise at −78° C. After addition, the mixture was stirred at −78° C. for 1 h. $Boc_2O$ (14.0 g, 64.2 mmol) in THE was then added dropwise at −78° C. The resulting mixture was stirred at 25° C. overnight, then quenched with water (300 mL) and extracted with EtOAc (200 mL×3). The combined organic layers were washed with brine (100 mL×3), dried over $Na_2SO_4$, and concentrated under reduced pressure to give B (17.2 g) as black crude oil. LCMS (ESI) m/z $[M+H]^+$=272.

Step 2: Preparation of tert-butyl 1-(4-bromopyridin-2-yl)cyclopropanecarboxylate (C)

C

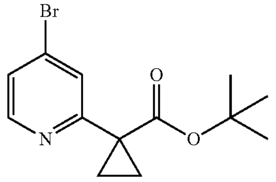

To a solution of B (5.0 g, 18.45 mmol) in DMF (50 mL) was added NaH (1.5 g, 37.5 mmol, 60% in mineral oil) at 0° C. The mixture was stirred at this temperature for 1 h, followed by dropwise addition of 1,2-dibromoethane (6.8 g, 37.5 mmol) at 0° C. The resulting mixture was stirred at 25° C. for 1 h. The reaction mixture was quenched by addition of water (200 mL), followed by extraction with EtOAc (100 mL×3). The combined organic layers were washed with brine (100 mL×3), dried over $Na_2SO_4$, filtered and concentrated under reduced pressure. The residue was purified by silica gel column chromatography, eluting with Petroleum ether/EtOAc (2:1) to give C (3.7 g, 12.4 mmol, 67.5% yield) as yellow oil. LCMS (ESI) m/z $[M+H]^+$=298.

Step 3: Preparation of tert-butyl 1-(4-(3-(2-(2-(1-(methylsulfonyl)-1H-pyrrole-3-carboxamido)acetamido) thiazol-4-yl)phenyl)pyridin-2-yl)cyclopropanecarboxylate (D)

D

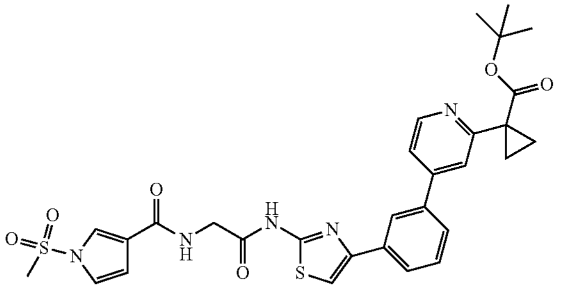

A mixture of C (618.4 mg, 2.07 mmol), I-90 (1.0 g, 1.88 mmol), $K_3PO_4$ (800.4 mg, 3.77 mmol), and di-tert-butyl (cyclopentyl)phosphane dichloropalladium (24.57 mg, 0.03 mmol) in 1,4-dioxane (20 mL)/water (2 mL) was degassed and purged 3 times with nitrogen. The reaction mixture was stirred at 80° C. for 12 h then quenched with water (20 mL), followed by extraction with EtOAc (100 mL×3). The combined organic layers were washed with saturated aqueous NaCl (100 mL×3), dried over $Na_2SO_4$, and concentrated under reduced pressure. The residue was purified by reversed phase chromatography (ACN/0.1% formic acid) and lyophilized to give D (830 mg, 1.33 mmol, 70.81%) as a yellow solid. LCMS (ESI) m/z $[M+H]^+$=622.

Step 4: Preparation of 1-(4-(3-(2-(2-(1-(methylsulfonyl)-1H-pyrrole-3-carboxamido)acetamido) thiazol-4-yl)phenyl)pyridin-2-yl)cyclopropanecarboxylic acid (I-91)

I-91

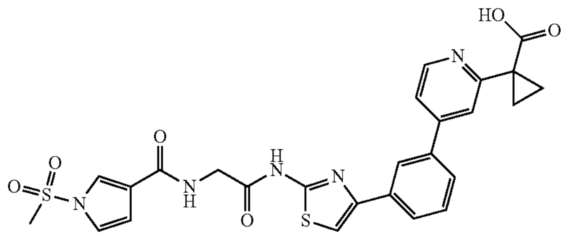

A mixture of D (830 mg, 1.33 mmol) and TFA (2 mL) in DCM (10 mL) was stirred at 25° C. for 1 h. The mixture was concentrated, and the residue used without further purification (I-91, 1.2 g) as a yellow solid. LCMS (ESI) m/z $[M+H]^+$=566.

Compound 11—Preparation of N-[2-[[4-[3-[2-[1-[2-[2-[2-[[2-(2,6-dioxo-3-piperidyl)-1,3-dioxo-isoindolin-4-yl]amino]ethoxy]ethoxy]ethylcarbamoyl]cyclopropyl]-4-pyridyl]phenyl]thiazol-2-yl]amino]-2-oxo-ethyl]-1-methylsulfonylpyrrole-3-carboxamide

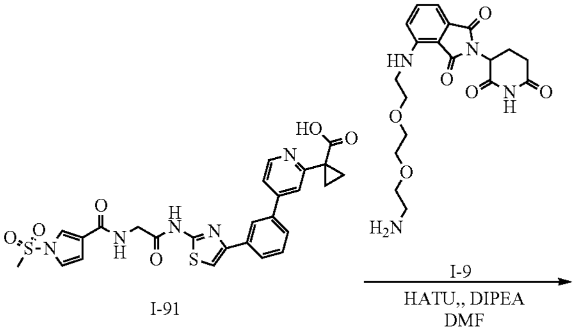

I-91

-continued

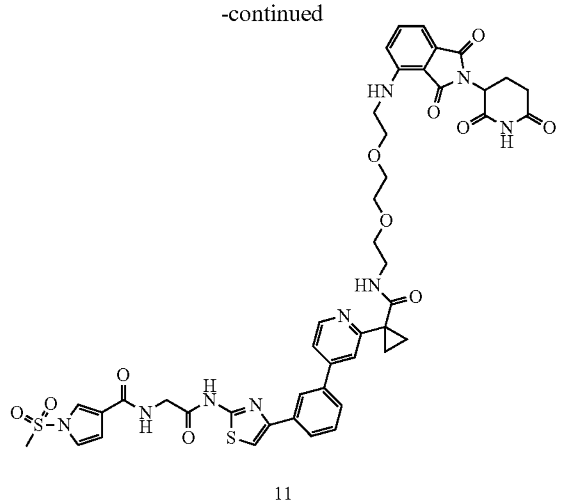

11

A solution of 1-[4-[3-[2-[[2-[(1-methylsulfonylpyrrole-3-carbonyl)amino]acetyl]amino]thiazol-4-yl]phenyl]-2-pyridyl]cyclopropanecarboxylic acid (I-91, 60 mg, 106.08 μm), HATU (121.00 mg, 318.23 μm), and DIEA (68.55 mg, 530.39 μm, 92.38 μL) in DMF (1 mL) was stirred at 30° C. for 1 h. To this mixture was added 4-[2-[2-(2-aminoethoxy)ethoxy]ethylamino]-2-(2,6-dioxo-3-piperidyl)isoindoline-1,3-dione (I-9, 55.00 mg, 0.11 mmol) followed by stirring at 30° C. for 12 h. The mixture was triturated with water (3 mL) and filtered. The filter cake was purified by reversed phase HPLC (column: Phenomenex Synergi C18 150×30 mm×4 μm; mobile phase: [0.225% formic acid in water-ACN]; 30%-60%) to give Compound 11 (21.27 mg, 21.10 μm, 19.89% yield, 98.991%) as a yellow solid. LCMS (ESI) m/z: $[M+H]^+$=952.3. $^1H$ NMR (400 MHz, CHLOROFORM-d) δ=9.36 (d, J=1.6 Hz, 1H), 8.59 (d, J=5.2 Hz, 1H), 8.13 (s, 1H), 7.80-7.75 (m, 2H), 7.61 (s, 2H), 7.58-7.54 (m, 1H), 7.50 (d, J=8.0 Hz, 1H), 7.43-7.35 (m, 2H), 7.19 (s, 1H), 7.13 (m, 1H), 7.08 (d, J=7.2 Hz, 1H), 6.85 (m, 1H), 6.76 (d, J=8.8 Hz, 1H), 6.70 (m, 1H), 6.38 (m, 1H), 4.99-4.95 (m, 1H), 4.39 (m, 2H), 3.61-3.46 (m, 10H), 3.33-3.28 (m, 2H), 3.25-3.25 (m, 1H), 3.23 (s, 2H), 2.89-2.73 (m, 3H), 2.15-2.10 (m, 1H), 1.75-1.70 (m, 2H), 1.35-1.30 (m, 1H), 1.25 (m, 1H) ppm.

TABLE 9

The following compounds were prepared using standard chemical manipulations and procedures similar to those used for the preparation of Compound 11

| Cmpd # | Name | LC-MS (ESI) (m/z) | $^1H$ NMR |
|---|---|---|---|
| 12 | N-(2-((4-(3-(2-(1-((5-((2-(2,6-dioxopiperidin-3-yl)-1,3-dioxoisoindolin-4-yl)amino)pentyl)carbamoyl)cyclopropyl)-pyridin-4-yl)phenyl)thiazol-2-yl)amino)-2-oxoethyl)-1-(methylsulfonyl)-1H-pyrrole-3-carboxamide | 906.4 | $^1H$ NMR (400 MHz, DMSO-$d_6$) δ = 12.42 (br s, 1H), 11.08 (br s, 1H), 8.68 (m, 1H), 8.59 (d, J = 5.2 Hz, 1H), 8.26 (s, 1H), 7.99 (d, J = 7.6 Hz, 1H), 7.93-7.84 (m, 2H), 7.79 (s, 1H), 7.72 (br d, J = 7.6 Hz, 1H), 7.67-7.49 (m, 4H), 7.39-7.29 (m, 1H), 7.06-6.96 (m, 2H), 6.79-6.78 (m, 1H), 6.46-6.45 (m, 1H), 5.05-5.04 (m, 1H), 4.15 (br d, J = 5.6 Hz, 2H), 3.58 (s, 3H), 3.21-3.10 (m, 4H), 2.88 (m, 1H), 2.56-2.54 (m, 2H), 2.06-1.97 (m, 1H), 1.57-1.43 (m, 4H), 1.41-1.24 (m, 6H) ppm. |
| 13 | N-(2-((4-(3-(2-(1-((8-(2-((2-(2,6-dioxopiperidin-3-yl)-1,3-dioxoisoindolin-4-yl)oxy)acetamido)octyl)carbamoyl)-cyclopropyl)pyridin-4-yl)phenyl)thiazol-2-yl)amino)-2-oxoethyl)-1-(methylsulfonyl)-1H-pyrrole-3-carboxamide | 1006.6 | $^1H$ NMR (400 MHz, DMSO-d6) δ = 12.46 (br s, 1H), 11.13 (s, 1H), 8.77-8.56 (m, 2H), 7.78 (s, 6H), 7.74-7.48 (m, 5H), 7.40-7.31 (m, 2H), 6.84-6.70 (m, 1H), 5.12-5.10 (m, 1H), 4.76 (s, 2H), 4.15 (d, J = 5.6 Hz, 2H), 3.58 (s, 3H), 3.10 (d, J = 5.2 Hz, 4H), 2.94-2.84 (m, 1H), 2.63-2.57 (m, 2H), 2.07-1.99 (m, 1H), 1.42-1.28 (m, 8H), 1.25-1.14 (m, 8H) ppm |

TABLE 9-continued

The following compounds were prepared using standard chemical manipulations and procedures similar to those used for the preparation of Compound 11

| Cmpd # | Name | LC-MS (ESI) (m/z) | $^{1}$H NMR |
|---|---|---|---|
| 14 | N-(2-((4-(3-(2-(1-(1'-(2-((2-(2,6-dioxopiperidin-3-yl)-1,3-dioxoisoindolin-4-yl)oxy)acetyl)-[4,4'-bipiperidine]-1-carbonyl)cyclopropyl)pyridin-4-yl)phenyl)thiazol-2-yl)amino)-2-oxoethyl)-1-(methylsulfonyl)-1H-pyrrole-3-carboxamide | 1030.5 | $^{1}$H NMR (400 MHz, DMSO-$d_6$) δ = 12.79-12.12 (m, 1H), 11.39-10.89 (m, 1H), 8.69 (m, 1H), 8.59 (d, J = 5.2 Hz, 1H), 8.24 (s, 1H), 8.00 (s, 1H), 7.85 (s, 1H), 7.82-7.69 (m, 3H), 7.65-7.56 (m, 2H), 7.50-7.40 (m, 2H), 7.36-7.21 (m, 2H), 6.78 (s, 1H), 5.13-5.01 (m, 3H), 4.63-4.51 (m, 1H), 4.26-4.12 (m, 3H), 3.94-3.86 (m, 1H), 3.69-3.64 (m, 1H), 3.58 (s, 3H), 2.90-2.76 (m, 3H), 2.61 (s, 4H), 2.08-1.98 (m, 1H), 1.74-1.57 (m, 2H), 1.50-1.25 (m, 7H), 1.18-1.03 (m, 3H), 0.90-0.71 (m, 2H) ppm. |
| 97 | N-[2-[[4-[3-[2-[1-[2-[2-[[2-(2,6-dioxo-3-piperidyl)-1,3-dioxoisoindolin-4-yl]amino]ethyl-methyl-amino]ethylcarbamoyl]cyclopropyl]-4-pyridyl]phenyl]thiazol-2-yl]amino]-2-oxo-ethyl]-1-methylsulfonyl-pyrrole-3-carboxamide | 921.2 | $^{1}$H NMR (400 MHz, DMSO-d6) δ = 11.07 (br s, 1H), 8.69-8.68 (m, 1H), 8.57 (d, J = 5.2 Hz, 1H), 8.24 (d, J = 5.2 Hz, 2H), 7.98 (d, J = 8.0 Hz, 1H), 7.91-7.66 (m, 5H), 7.61-7.49 (m, 3H), 7.38-7.28 (m, 1H), 7.06-6.92 (m, 2H), 6.78-6.76 (m, 1H), 6.60-6.69 (m, 1H), 5.02-5.01 (m, 1H), 4.15 (d, J = 5.6 Hz, 2H), 3.58 (s, 3H), 3.27-3.22 (m, 4H), 2.93-2.81 (m, 2H), 2.62-2.56 (m, 5H), 2.22 (s, 3H), 2.07-1.95 (m, 1H), 1.49-1.37 (m, 2H), 1.35-1.26 (m, 2H) ppm |
| 98 | N-(2-((4-(3-(2-(1-((10-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-10-oxodecyl)carbamoyl)cyclopropyl)-pyridin-4-yl)phenyl)thiazol-2-yl)amino)-2-oxoethyl)-1-(methylsulfonyl)-1H-pyrrole-3-carboxamide | 1147.5 | $^{1}$H NMR (400 MHz, DMSO-d6) δ = 8.98 (s, 1H), 8.74-8.52 (m, 3H), 8.40 (s, 1H), 8.26 (s, 1H), 8.01 (d, J = 7.6 Hz, 1H), 7.93-7.56 (m, 8H), 7.47-7.29 (m, 5H), 6.79-6.78 (m, 1H), 5.26-4.96 (m, 1H), 4.60-4.13 (m, 7H), 3.66 (d, J = 4.4 Hz, 2H), 3.58 (s, 3H), 3.10-3.08 (m, 2H), 2.44 (s, 3H), 2.29-2.18 (m, 1H), 2.14-2.00 (m, 2H), 1.92 (d, J = 8.4 Hz, 1H), 1.49-1.26 (m, 8H), 1.17 (s, 10H), 0.93 (s, 9H) ppm |
| 99 | N-(2-((4-(3-(2-(1-((8-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-8-oxooctyl)carbamoyl)cyclopropyl)-pyridin-4-yl)phenyl)thiazol-2-yl)amino)-2-oxoethyl)-1-(methylsulfonyl)-1H-pyrrole-3-carboxamide | 1119.4 | $^{1}$H NMR (400 MHz, DMSO-d6) δ = 8.98 (s, 1H), 8.75-8.52 (m, 3H), 8.44 (s, 1H), 8.07-7.57 (m, 9H), 7.47-7.29 (m, 5H), 6.79-6.78 (m, 1H), 5.27-4.96 (m, 1H), 4.60-4.10 (m, 7H), 3.71-3.55 (m, 5H), 3.10-3.08 (m, 2H), 2.44 (s, 3H), 2.26-2.16 (m, 1H), 2.11-1.99 (m, 2H), 1.92-1.90 (m, 1H), 1.51-1.36 (m, 6H), 1.34-1.28 (m, 2H), 1.20 (s, 6H), 1.01-0.86 (m, 9H) ppm |
| 100 | N-(2-((4-(3-(2-(1-((6-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-6-oxohexyl)carbamoyl)cyclopropyl)-pyridin-4-yl)phenyl)thiazol-2-yl)amino)-2-oxoethyl)-1-(methylsulfonyl)-1H-pyrrole-3-carboxamide | 1091.4 | $^{1}$H NMR (400 MHz, DMSO-d6) δ = 9.07-8.97 (m, 1H), 8.77-8.54 (m, 3H), 8.48 (s, 1H), 8.08-7.83 (m, 5H), 7.77-7.59 (m, 4H), 7.47-7.34 (m, 5H), 6.82-6.81 (m, 1H), 5.16 (d, J = 2.0 Hz, 1H), 4.63-4.37 (m, 4H), 4.30-4.14 (m, 3H), 3.73-3.66 (m, 2H), 3.61 (s, 3H), 3.13-3.11 (m, 2H), 2.48 (s, 3H), 2.25-2.23 (m, 1H), 2.15-2.04 (m, 2H), 1.94-1.92 (m, 1H), 1.55-1.40 (m, 6H), 1.36-1.31 (m, 2H), 1.30-1.23 (m, 2H), 0.96 (s, 9H) ppm |
| 101 | N-[2-[[4-[3-[2-[1-[2-[2-[2-[[2-(2,6-dioxo-3-piperidyl)-1,3-dioxo-isoindolin-5-yl]amino]ethoxy]ethoxy]ethylcarbamoyl]-cyclopropyl]-4-pyridyl]phenyl]thiazol-2-yl]amino]-2-oxo-ethyl]-1-methylsulfonylpyrrole-3-carboxamide | 952.1 | $^{1}$H NMR (400 MHz, DMSO-d6) δ = 12.48-12.43 (m, 1H), 11.06 (s, 1H), 8.72-8.69 (m, 1H), 8.59 (d, J = 5.2 Hz, 1H), 8.25 (s, 1H), 8.00-7.98 (m, 2H), 7.85-7.84 (m, 1H), 7.81 (s, 1H), 7.72 (d, J = 7.6 Hz, 1H), 7.64 (s, 1H), 7.61-7.52 (m, 3H), 7.32-7.30 (m, 1H), 7.11-7.10 (m, 1H), 6.96 (s, 1H), 6.84-6.83 (m, 1H), 6.78-6.76 (m, 1H), 5.04-5.00 (m, 1H), 4.15 (d, J = 4.8 Hz, 2H), 3.57 (s, 3H), 3.51-3.43 (m, 8H), 3.28-3.25 (m, 4H), 2.91-2.81 (m, 1H), 2.58-2.57 (m, 2H), 1.99-1.96 (m, 1H), 1.41-1.39 (m, 2H), 1.32-1.29 (m, 2H) ppm |
| 102 | N-[2-[[4-[3-[2-[1-[2-[2-[[2-(2,6-dioxo-3-piperidyl)-1,3-dioxo-isoindolin-4-yl]amino]ethylsulfonyl]ethylcarbamoyl]-cyclopropyl]-4- | 956.1 | $^{1}$H NMR (400 MHz, DMSO-d6) δ = 12.46-12.42 (m, 1H), 11.10 (s, 1H), 8.72-8.89 (m, 1H), 8.59 (d, J = 5.2 Hz, 1H), 8.26-8.25 (m, 1H), 8.08-8.05 (m, 1H), 8.00 (d, J = 8.0 Hz, 1H), 7.84 (d, J = 10.8 Hz, 2H), 7.76 (d, J = 7.6 Hz, 1H), 7.68 (s, |

TABLE 9-continued

The following compounds were prepared using standard chemical manipulations and procedures similar to those used for the preparation of Compound 11

| Cmpd # | Name | LC-MS (ESI) (m/z) | $^1$H NMR |
|---|---|---|---|
| | pyridyl]phenyl]thiazol-2-yl]amino]-2-oxo-ethyl]-1-methylsulfonylpyrrole-3-carboxamide | | 1H), 7.64-7.55 (m, 3H), 7.31 (d, J = 2.8 Hz, 1H), 7.11-7.05 (m, 2H), 6.85-6.77 (m, 2H), 5.07-5.02 (m, 1H), 4.14 (d, J = 3.6 Hz, 2H), 3.75-3.72 (m, 2H), 3.58-3.54 (m, 5H), 3.47-3.44 (m, 2H), 3.38-3.37 (m, 2H), 2.90-2.83 (m, 1H), 2.58-2.57 (m, 2H), 2.02-1.99 (m, 1H), 1.43-1.42 (m, 2H), 1.31-1.30 (m, 2H) ppm |
| 103 | N-(2-((4-(3-(2-(1-((4-((3-((2-(2,6-dioxopiperidin-3-yl)-1,3-dioxoisoindolin-4-yl)amino)propyl)sulfonyl)butyl)carbamoyl)-cyclopropyl)pyridin-4-yl)phenyl)thiazol-2-yl)amino)-2-oxoethyl)-1-(methylsulfonyl)-1H-pyrrole-3-carboxamide | 998.3 | $^1$H NMR (400 MHz, DMSO-d6) δ = 11.07 (s, 1H), 8.69-8.66 (m, 1H), 8.59 (d, J = 5.2 Hz, 1H), 8.25 (s, 1H), 8.00-7.98 (m, 1H), 7.90 7.87 (m, 1H), 7.85-7.84 (m, 1H), 7.80 (s, 1H), 7.73 (d, J = 8.0 Hz, 1H), 7.62-7.56 (m, 4H), 7.31-7.30 (m, 1H), 7.13 (d, J = 8.4 Hz, 1H), 7.03 (d, J = 6.8 Hz, 1H), 6.78-6.76 (m, 1H), 6.74-6.71 (m, 1H), 5.07-5.02 (m, 1H), 4.15 (d, J = 5.6 Hz, 2H), 3.57 (s, 3H), 3.15-3.08 (m, 8H), 2.92-2.83 (m, 2H), 2.05-1.93 (m, 3H), 1.67-1.62 (m, 2H), 1.57-1.52 (m, 2H), 1.40-1.39 (m, 2H), 1.30-1.28 (m, 2H) ppm. |
| 104 | N-[2-[[4-[3-[2-[1-[6-[[2-(2,6-dioxo-3-piperidyl)-1,3-dioxo-isoindolin-5-yl]amino]hexylcarbamoyl]cyclopropyl]-4-pyridyl]phenyl]thiazol-2-yl]amino]-2-oxo-ethyl]-1-methylsulfonyl-pyrrole-3-carboxamide | 920.1 | $^1$H NMR (400 MHz, DMSO-d6) δ = 11.33-10.73 (m, 1H), 8.71 (m, 1H), 8.59 (d, J = 5.2 Hz, 1H), 8.26 (s, 1H), 8.00 (d, J = 8.0 Hz, 1H), 7.90 (m, 1H), 7.86 (m, 1H), 7.80 (s, 1H), 7.71 (d, J = 8.0 Hz, 1H), 7.65-7.51 (m, 4H), 7.35-7.29 (m, 1H), 7.08-7.02 (m, 1H), 6.91 (s, 1H), 6.84-6.77 (m, 2H), 5.02-5.01 (m, 1H), 4.15 (d, J = 5.6 Hz, 2H), 3.58 (s, 3H), 3.15-3.05 (m, 4H), 2.93-2.80 (m, 1H), 2.59 (d, J = 2.4 Hz, 1H), 2.55 (s, 1H), 2.04-1.93 (m, 1H), 1.48-1.46 (m, 4H), 1.41-1.37 (m, 2H), 1.35-1.23 (m, 6H) ppm. |
| 105 | N-[2-[[4-[3-[2-[1-[4-[[2-(2,6-dioxo-3-piperidyl)-1,3-dioxo-isoindolin-5-yl]amino]butylcarbamoyl]cyclopropyl]-4-pyridyl]phenyl]thiazol-2-yl]amino]-2-oxo-ethyl]-1-methylsulfonyl-pyrrole-3-carboxamide | 892.0 | $^1$H NMR (400 MHz, DMSO-$d_6$) δ = 12.61-12.21 (m, 1H), 11.05 (s, 1H), 8.68 (m, 1H), 8.59 (d, J = 5.2 Hz, 1H), 8.26 (s, 1H), 8.00 (d, J = 8.0 Hz, 1H), 7.92 (m, 1H), 7.85 (m, 1H), 7.81 (s, 1H), 7.72 (d, J = 8.0 Hz, 1H), 7.65-7.50 (m, 4H), 7.33-7.31 (m, 1H), 7.08 (m, 1H), 6.92 (d, J = 1.6 Hz, 1H), 6.83-6.76 (m, 2H), 5.04-5.02 (m, 1H), 4.15 (d, J = 5.6 Hz, 2H), 3.58 (s, 3H), 3.16-3.14 (m, 4H), 2.95-2.79 (m, 1H), 2.62-2.56 (m, 2H), 2.04-1.94 (m, 1H), 1.55 (s, 4H), 1.43-1.27 (m, 4H) ppm. |
| 106 | N-(2-((4-(3-(2-(1-((4-((3-((2-(2,6-dioxopiperidin-3-yl)-1,3-dioxoisoindolin-4-yl)amino)propyl)(methyl)amino)butyl)-carbamoyl)cyclopropyl)pyridin-4-yl)phenyl)thiazol-2-yl)amino)-2-oxoethyl)-1-(methylsulfonyl)-1H-pyrrole-3-carboxamide | 963.3 | $^1$H NMR (400MHz, DMSO-d6) δ = 12.50-12.40 (m, 1H), 11.09 (s, 1H), 9.18-9.06 (m, 1H), 8.74-8.62 (m, 2H), 8.34-8.25 (m, 1H), 8.06-8.00 (m, 1H), 7.89-7.82 (m, 3H), 7.80-7.70 (m, 3H), 7.64-7.58 (m, 2H), 7.35-7.31 (m, 1H), 7.16-7.11 (m, 1H), 7.09-7.04 (m, 1H), 6.80-6.77 (m, 1H), 6.75-6.69 (m, 1H), 5.09-5.04 (m, 1H), 4.18-4.14 (m, 2H), 3.58 (s, 3H), 3.40-3.35 (m, 2H), 3.21-3.09 (m, 5H), 2.91-2.86 (m, 1H), 2.74-2.71 (m, 3H), 2.64-2.58 (m, 3H), 2.07-2.00 (m, 1H), 1.98-1.87 (m, 2H), 1.64-1.53 (m, 2H), 1.49-1.41 (m, 4H), 1.37-1.32 (m, 2H) ppm. |
| 107 | N-(2-((4-(3-(2-(1-(3-(((2-(2,6-dioxopiperidin-3-yl)-1,3-dioxoisoindolin-5-yl)oxy)methyl)azetidine-1-carbonyl)cyclopropyl)pyridin-4-yl)phenyl)thiazol-2-yl)amino)-2-oxoethyl)-1-(methylsulfonyl)-1H-pyrrole-3-carboxamide | 891.2 | $^1$H NMR (400 MHz, DMSO-d6) δ = 12.43 (s, 1H), 11.10 (s, 1H), 8.68 (d, J = 6.0 Hz, 1H), 8.61 (d, J = 4.0 Hz, 1H), 8.28 (s, 1H), 8.31-8.25 (m, 1H), 8.02 (d, J = 8.0 Hz, 1H), 7.86 (d, J = 4.0 Hz, 1H), 7.82 (s, 1H), 7.77 (d, J = 8.0 Hz, 1H), 7.72-7.66 (m, 1H), 7.59-7.62 (m, 1H), 7.36 (d, J = 4.0 Hz, 1H), 7.33-7.31 (m, 1H), 7.22-7.19 (m, 1H), 5.22-5.11 (m, 1H), 4.25-4.23 (m, 2H), 4.15 (d, J = 4.0 Hz, 2H), 4.06 (d, J = 4.0 Hz, 2H), 3.83-3.76 (m, 1H), 3.58 (s, 3H), 3.25-3.20 (m, 1H), 2.98-2.85 (m, 2H), 2.64-2.58 (m, 2H), 2.65-2.57 (m, 1H), 2.05-2.10 (m, 1H), 1.41 (s, 4H) ppm. |
| 108 | N-[2-[[4-[3-[2-[1-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethylcarbamoyl]cyclopropyl]-4-pyridyl]phenyl]thiazol-2-yl]amino]-2-oxo-ethyl]-1-methylsulfonyl-pyrrole-3-carboxamide | 1123.3 | $^1$H NMR (400 MHz, DMSO-$d_6$) δ = 9.02-8.94 (m, 1H), 8.68 (m, 1H), 8.63-8.53 (m, 2H), 8.26 (s, 1H), 8.01 (d, J = 7.6 Hz, 2H), 7.88-7.79 (m, 2H), 7.72 (d, J = 8.0 Hz, 1H), 7.66-7.55 (m, 3H), 7.49-7.35 (m, 6H), 7.34-7.29 (m, 1H), 6.78 (d, J = 3.2 Hz, 1H), 5.16 (s, 1H), 4.56 (d, J = 9.6 Hz, 1H), 4.47-4.35 (m, 3H), 4.28 (d, J = 5.6 Hz, 1H), 4.15 (d, J = 5.6 Hz, 2H), 3.91 (s, 2H), 3.64-3.45 (m, 13H), 2.43 (s, 3H), 2.13-1.85 (m, 2H), 1.47-1.24 (m, 4H), 0.92 (s, 9H) ppm. |

TABLE 9-continued

The following compounds were prepared using standard chemical manipulations and procedures similar to those used for the preparation of Compound 11

| Cmpd # | Name | LC-MS (ESI) (m/z) | $^1$H NMR |
|---|---|---|---|
| 109 | N-[4-[3-(2-[1-[3-([[2-(2,6-dioxopiperidin-3-yl)-1,3-dioxoisoindol-4-yl]oxy]methyl)azetidine-1-carbonyl]cyclopropyl]pyridin-4-yl)phenyl]-1,3-thiazol-2-yl]-2-[(1-methanesulfonylpyrrol-3-yl)formamido]acetamide | 891.30 | $^1$H NMR (400 MHz, DMSO-d6) δ 12.40 (s, 1H), 11.12 (s, 1H), 8.72 (s, 1H), 8.58 (s, 1H), 8.23 (s, 1H), 7.98 (s, 1H), 7.83 (d, J = 18.8 Hz, 2H), 7.73 (s, 2H), 7.60 (s, 2H), 7.54 (s, 1H), 7.43 (d, J = 7.3 Hz, 2H), 7.33 (s, 1H), 6.79 (s, 1H), 5.04 (s, 1H), 4.27 (s, 2H), 4.15 (s, 2H), 4.05 (s, 1H), 3.85 (s, 1H), 3.73 (s, 1H), 3.59 (s, 4H), 3.05-2.91 (m, 1H), 2.86 (s, 1H), 2.59 (s, 1H), 2.42 (s, 1H), 1.98 (s, 1H), 1.40 (s, 3H), 1.27 (d, J = 24.6 Hz, 1H). |
| 110 | N-[2-[[4-[3-[2-[1-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethylcarbamoyl]-cyclopropyl]-4-pyridyl]phenyl]thiazol-2-yl]amino]-2-oxo-ethyl]-1-methylsulfonyl-pyrrole-3-carboxamide | 1167.4 | $^1$H NMR (400 MHz, DMSO-$d_6$) δ = 9.02-8.94 (m, 1H), 8.68 (m, 1H), 8.63-8.55 (m, 2H), 8.26 (s, 1H), 8.07-7.95 (m, 2H), 7.88-7.79 (m, 2H), 7.73 (d, J = 7.6 Hz, 1H), 7.68-7.55 (m, 3H), 7.48-7.36 (m, 6H), 7.34-7.29 (m, 1H), 6.78-6.77 (m, 1H), 5.15 (s, 1H), 4.59-4.53 (m, 1H), 4.45-4.34 Hz, 2H), 3.98-3.92 (m, 2H), 3.67-3.61 (m, 2H), 3.58 (s, 3H), 3.55 (d, J = 4.8 Hz, 2H), 3.49-3.41 (m, 8H), 3.27-3.23 (m, 2H), 2.45-2.42 (m, 3H), 2.10-2.03 (m, 1H), 1.93-1.87 (m, 1H), 1.48-1.28 (m, 4H), 0.93 (s, 9H) ppm. |
| 111 | N-[2-[[4-[3-[2-[1-[2-[2-[[2-[2-(2,6-dioxo-3-piperidyl)-1,3-dioxo-isoindolin-5-yl]oxyacetyl]amino]ethyl-methylamino]ethylcarbamoyl]cyclopropyl]-4-pyridyl]phenyl]thiazol-2-yl]amino]-2-oxo-ethyl]-1-methylsulfonyl-pyrrole-3-carboxamide | 979.5 | $^1$H NMR (400 MHz, DMSO-d6) δ = 12.44 (br s, 1H), 11.10 (br s, 1H), 8.71-8.65 ( m, 1H), 8.58 (d, J = 5.6 Hz, 1H), 8.24 (s, 2H), 8.07-8.02 (m, 1H), 8.01-7.96 (m, 1H), 7.88-7.79 (m, 4H), 7.73-7.68 (m, 1H), 7.65 (s, 1H), 7.61-7.54 (m, 2H), 7.38 (d, J = 2.0 Hz, 1H), 7.35-7.30 (m, 2H), 6.79-6.76 (m, 1H), 5.15-5.07 (m, 1H), 4.66 (s, 2H), 4.18-4.12 (m, 2H), 3.57 (s, 3H), 3.23-3.13 (m, 3H), 2.93-2.82 (m, 1H), 2.63-2.57 (m, 2H), 2.44-2.37 (m, 5H), 2.15 (s, 3H), 2.09-1.97 (m, 1H), 1.44-1.37 (m, 2H), 1.33-1.26 (m, 2H) ppm (m, 3H), 4.27 (d, J = 5.6 Hz, 1H), 4.15 (d, J = 5.6 |
| 112 | N-(2-((4-(3-(2-(1-((2-(2-(2-((2-(2,6-dioxopiperidin-3-yl)-1,3-dioxoisoindolin-4-yl)oxy)ethoxy)ethyl)(methyl)amino)-ethyl)carbamoyl)cyclopropyl)-pyridin-4-yl)phenyl)thiazol-2-yl)amino)-2-oxoethyl)-1-(methylsulfonyl)-1H-pyrrole-3-carboxamide | 966.1 | $^1$H NMR (400 MHz, DMSO-d6) δ = 12.42 (s, 1H), 11.09 (s, 1H), 8.68 (d, J = 6.0 Hz, 1H), 8.61-8.59 (d, J = 5.2 Hz, 1H), 8.20 (s, 1H), 8.00-7.99 (d, J = 8.0 Hz, 1H), 7.86-7.85 (d, J = 2.0 Hz, 1H), 7.81 (s, 1H), 7.78 (s, 1H), 7.79-7.68 (m, 4H), 7.65-7.56 (m, 2H), 7.45-7.42 (m, 2H), 7.33-7.31 (d, J = 2.8 Hz, 1H), 6.79-6.78 (m, 1H), 5.09-5.05 (m, 1H), 4.27-4.22 (m, 2H), 4.18-4.15 (m, 2H), 3.68-3.63 (m, 2H), 3.58 (s, 3H), 3.49-3.44 (d, J = 6.0 Hz, 3H), 3.21-3.15 (m, 3H), 2.91-2.81 (m, 1H), 2.47-2.40 (m, 4H), 2.14 (s, 3H), 1.43-1.38 (m, 2H), 1.33-1.25 (m, 2H) ppm. |
| 114 | N-(2-((4-(3-(2-(1-((1-(2-((2-(2,6-dioxopiperidin-3-yl)-1,3-dioxoisoindolin-5-yl)oxy)ethyl)piperidin-4-yl)carbamoyl)cyclopropyl)pyridin-4-yl)phenyl)thiazol-2-yl)amino)-2-oxoethyl)-1-(methylsulfonyl)-1H-pyrrole-3-carboxamide | 948.4 | $^1$H NMR (400 MHz, DMSO-d6) δ = 12.44 (br s, 1H), 11.1 (s, 1H), 8.77-8.64 (d, J = 6.0 Hz, 1H), 8.63-8.56 (d, J = 5.2 Hz, 1H), 8.10-8.08 (d, J = 7.6 Hz, 1H), 8.02-8.00 (d, J = 7.6 Hz, 1H), 7.85-7.81 (m, 3H), 7.81-7.73 (d, J = 8.0 Hz, 2H), 7.62-7.58 (m, 3H), 7.45-7.44 (m, 1H), 7.40-7.24 (m, 2H), 6.82-6.75 (m, 1H), 5.16-5.07 (m, 1H), 4.29-4.23 (d, J = 6.0 Hz, 2H), 4.18-4.13 (m, 2H), 3.71-3.66 (m, 1H), 3.58 (s, 3H), 3.48-3.43 (m, 2H), 2.95-2.79 (m, 4H), 2.73-2.69 (d, J = 6.0 Hz, 2H), 2.22-1.97 (m, 3H), 1.78-1.68 (m, 2H), 1.40-1.36 (m, 2H), 1.36-1.35 (m, 3H) ppm. |
| 128 | N-[2-[[4-[3-[2-[1-[2-[2-[2-[[2-[2-(2,6-dioxo-3-piperidyl)-1,3-dioxo-isoindolin-4-yl]oxyacetyl]amino]ethoxy]-ethoxylethylcarbamoyl]cyclopropyl]-4-pyridyl]phenyl]thiazol-2-yl]amino]-2-oxo-ethyl]-1-methylsulfonyl-pyrrole-3-carboxamide | 1010.4 | $^1$H NMR (400 MHz, DMSO-$d_6$) δ = 12.44 (s, 1H), 11.11 (s, 1H), 8.69 (m, 1H), 8.60 (d, J = 5.2 Hz, 1H), 8.46 (s, 1H), 8.26 (s, 1H), 8.06-7.93 (m, 3H), 7.87-7.71 (m, 4H), 7.68-7.55 (m, 3H), 7.48 (d, J = 7.2 Hz, 1H), 7.38 (d, J = 8.4 Hz, 1H), 7.32 (d, J = 3.2 Hz, 1H), 6.78-6.77(m, 1H), 5.13-5.08 (m, 1H), 4.77 (s, 2H), 4.15 (d, J = 5.6 Hz, 2H), 3.58 (s, 3H), 3.49-3.38 (m, 8H), 3.28-3.24 (m, 4H), 2.96-2.79 (m, 1H), 2.64-2.52 (m, 2H), 2.11-1.95 (m, 1H), 1.42-1.40 (m, 2H), 1.336-1.30 (m, 2H) ppm. |
| 129 | N-[2-[[4-[3-[2-[1-[8-[[2-[2-(1-methyl-2,6-dioxo-3-piperidyl)-1,3-dioxo-isoindolin-4-yl]oxyacetyl]amino]octylcarbamoyl]cyclopropyl]-4-pyridyl]phenyl]thiazol-2- | 1020.5 | 1HNRM (400 MHz, DMSO-$d_6$) δ = 12.41 (s, 1H), 8.68 (m, 1H), 8.59 (d, J = 5.2 Hz, 1H), 8.39 (s, 1H), 8.26 (s, 1H), 8.01 (d, J = 7.6 Hz, 1H), 7.92-7.79 (m, 5H), 7.71 (d, J = 8.0 Hz, 1H), 7.66-7.55 (m, 3H), 7.49 (d, J = 7.2 Hz, 1H), 7.40 (d, J = 8.4 |

TABLE 9-continued

The following compounds were prepared using standard chemical manipulations and procedures similar to those used for the preparation of Compound 11

| Cmpd # | Name | LC-MS (ESI) (m/z) | $^1$H NMR |
|---|---|---|---|
| | yl]amino]-2-oxo-ethyl]-1-methylsulfonyl-pyrrole-3-carboxamide | | Hz, 1H), 7.32 (m, 1H), 6.78 (d, J = 3.2 Hz, 1H), 5.20-5.15 (m, 1H), 4.76 (s, 2H), 4.15 (d, J = 6.0 Hz, 2H), 3.58 (s, 3H), 3.14-3.06 (m, 4H), 3.01 (s, 3H), 2.97-2.90 (m, 1H), 2.79-2.73 (m, 1H), 2.56-2.55 (m, 1H), 2.13-1.99 (m, 1H), 1.45-1.35 (m, 6H), 1.33-1.29 (m, 2H), 1.18-1.17 (m, 8H) ppm. |
| 132 | N-(4-[3-[2-(1-[4-[2-(2,6-dioxopiperidin-3-yl)-1,3-dioxoisoindol-5-yl]piperazine-1-carbonyl]cyclopropyl)pyridin-4-yl]phenyl]-1,3-thiazol-2-yl)-2-[(1-methanesulfonylpyrrol-3-yl)formamido]acetamide | 890.35 | $^1$H NMR (400 MHz, DMSO-d6) δ 12.41 (s, 1H), 11.08 (s, 1H), 8.71 (t, J = 5.9 Hz, 1H), 8.59 (d, J = 5.1 Hz, 1H), 8.21 (d, J = 1.8 Hz, 1H), 7.98 (dt, J = 7.8, 1.4 Hz, 1H), 7.86 (t, J = 2.0 Hz, 1H), 7.75 (s, 1H), 7.73-7.68 (m, 1H), 7.63 (d, J = 8.7 Hz, 1H), 7.60 (dd, J = 5.6, 3.9 Hz, 1H), 7.56 (d, J = 7.7 Hz, 1H), 7.45 (d, J = 1.7 Hz, 1H), 7.33 (dd, J = 3.3, 2.3 Hz, 1H), 7.29 (d, J = 2.3 Hz, 1H), 7.19 (dd, J = 8.6, 2.3 Hz, 1H), 6.79 (dd, J = 3.3, 1.7 Hz, 1H), 5.06 (dd, J = 12.9, 5.4 Hz, 1H), 4.15 (d, J = 5.6 Hz, 2H), 3.73 (s, 2H), 3.59 (s, 3H), 3.55 (s, 4H), 2.92-2.82 (m, 1H), 2.59 (d, J = 3.2 Hz, 1H), 2.57-2.53 (m, 3H), 2.05-1.97 (m, 1H), 1.54 (q, J = 4.1, 3.5 Hz, 2H), 1.44 (q, J = 4.5, 3.9 Hz, 2H) |
| 133 | N-(2-[[2-(2,6-dioxopiperidin-3-yl)-1,3-dioxoisoindol-5-yl]amino]ethyl)-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 864.15 | $^1$H NMR (400 MHz, DMSO-d6) δ 12.45 (s, 1H), 11.07 (s, 1H), 8.70 (t, J = 5.9 Hz, 1H), 8.61 (d, J = 5.3 Hz, 1H), 8.27 (s, 1H), 8.01 (d, J = 7.7 Hz, 1H), 7.92 (s, 1H), 7.88-7.80 (m, 2H), 7.76-7.68 (m, 2H), 7.67 (s, 1H), 7.57 (t, J = 7.8 Hz, 1H), 7.51 (d, J = 8.4 Hz, 1H), 7.32 (dd, J = 3.3, 2.3 Hz, 1H), 7.17 (s, 1H), 6.97 (t, J = 2.8 Hz, 1H), 6.84 (dd, J = 8.4, 2.2 Hz, 1H), 6.78 (dd, J = 3.3, 1.6 Hz, 1H), 5.03 (dd, J = 12.9, 5.4 Hz, 1H), 4.15 (d, J = 5.6 Hz, 2H), 3.58 (s, 3H), 1.45 (d, J = 6.3 Hz, 2H), 1.32 (t, J = 3.4 Hz, 2H). |
| 134 | N-[4-[3-(2-[1-[4-([1-[2-(2,6-dioxopiperidin-3-yl)-1,3-dioxoisoindol-5-yl]piperidin-4-yl]methyl)piperazine-1-carbonyl]cyclopropyl]pyridin-4-yl)phenyl]-1,3-thiazol-2-yl]-2-[(1-methanesulfonylpyrrol-3-yl)formamido]acetamide | 987.55 | $^1$H NMR (300 MHz, DMSO-d6) δ 12.48 (s, 1H), 11.08 (s, 1H), 8.71 (t, J = 5.9 Hz, 1H), 8.58 (d, J = 5.2 Hz, 1H), 8.28 (d, J = 1.8 Hz, 1H), 8.01 (dt, J = 7.7, 1.3 Hz, 1H), 7.85 (t, J = 2.0 Hz, 1H), 7.82-7.72 (m, 2H), 7.67-7.56 (m, 3H), 7.48 (d, J = 1.2 Hz, 1H), 7.35-7.23 (m, 2H), 7.18 (dd, J = 8.7, 2.2 Hz, 1H), 6.76 (dd, J = 3.3, 1.6 Hz, 1H), 5.05 (dd, J = 12.8, 5.4 Hz, 1H), 4.16 (d, J = 5.8 Hz, 2H), 3.97 (d, J = 12.8 Hz, 2H), 3.57 (s, 5H), 2.90 (t, J = 11.8 Hz, 3H), 2.61 (s, 1H), 2.42 (s, 2H), 2.09 (d, J = 8.1 Hz, 5H), 1.98 (t, J = 11.6 Hz, 3H), 1.65 (d, J = 13.4 Hz, 2H), 1.51 (q, J = 4.1, 3.5 Hz, 2H), 1.47-1.32 (m, 2H), 1.03 (d, J = 12.1 Hz, 2H). |
| 135 | N-[4-[3-(2-[1-[4-(3-[[2-(2,6-dioxopiperidin-3-yl)-1,3-dioxoisoindol-5-yl]oxy]propyl)piperazine-1-carbonyl]cyclopropyl]pyridin-4-yl)phenyl]-1,3-thiazol-2-yl]-2-[(1-methanesulfonylpyrrol-3-yl)formamido]acetamide | 948.35 | $^1$H NMR (400 MHz, DMSO-d6) δ 12.46 (s, 1H), 11.12 (s, 1H), 8.70 (t, J = 5.9 Hz, 1H), 8.58 (d, J = 5.1 Hz, 1H), 8.25 (d, J = 2.1 Hz, 1H), 8.01 (d, J = 7.7 Hz, 1H), 7.90-7.84 (m, 1H), 7.84-7.76 (m, 2H), 7.72 (d, J = 7.8 Hz, 1H), 7.66-7.55 (m, 2H), 7.44 (d, J = 1.4 Hz, 1H), 7.38 (d, J = 2.3 Hz, 1H), 7.35-7.26 (m, 2H), 6.78 (dd, J = 3.3, 1.7 Hz, 1H), 5.11 (dd, J = 12.8, 5.4 Hz, 1H), 4.15 (d, J = 6.1 Hz, 4H), 3.58 (s, 3H), 2.93-2.84 (m, 1H), 2.59 (d, J = 17.8 Hz, 2H), 2.54 (s, 4H) 2.41 (s, 3H), 2.17 (s, 2H), 2.07-2.01 (m, 1H), 1.84 (s, 2H), 1.50 (s, 2H), 1.36 (s, 2H). |
| 136 | N-[4-[3-(2-[1-[3-(2-[[2-(2,6-dioxopiperidin-3-yl)-1,3-dioxoisoindol-4-yl]oxy]ethyl)azetidine-1-carbonyl]cyclopropyl]pyridin-4-yl)phenyl]-1,3-thiazol-2-yl]-2-[(1-methanesulfonylpyrrol-3-yl)formamido]acetamide | 905.10 | $^1$H NMR (300 MHz, DMSO-d6) δ 12.46 (s, 1H), 11.12 (s, 1H), 8.71 (t, J = 5.8 Hz, 1H), 8.57 (d, J = 5.1 Hz, 1H), 8.24 (s, 1H), 8.01 (d, J = 7.7 Hz, 1H), 7.89-7.80 (m, 2H), 7.79-7.69 (m, 2H), 7.59 (dd, J = 10.6, 5.5 Hz, 3H), 7.42 (dd, J = 7.9, 5.1 Hz, 2H), 7.32 (t, J = 2.8 Hz, 1H), 6.78 (dd, J = 3.3, 1.6 Hz, 1H), 5.06 (dd, J = 12.8, 5.4 Hz, 1H), 4.15 (d, J = 5.5 Hz, 4H), 4.05 (d, J = 9.1 Hz, 1H), 3.77 (d, J = 8.9 Hz, 2H), 3.59 (s, 3H), 3.54-3.43 (m, 1H), 2.88 (t, J = 15.1 Hz, 1H), 2.76-2.65 (m, 1H), 2.61 (d, J = 3.7 Hz, 1H), 2.54 (s, 1H), 1.99 (t, J = 7.5 Hz, 3H), 1.35 (s, 2H), 1.34 (s, 2H). |
| 139 | N-(8-[[2-(2,6-dioxopiperidin-3-yl)-1,3-dioxoisoindol-5-yl]amino]octyl)-1-[4-[3-(2-[2-[(1-methanesulfonyl-4,5-dimethylpyrrol-3- | 976.30 | $^1$H NMR (400 MHz, DMSO-d6) δ 12.42 (s, 1H), 11.07 (s, 1H), 8.59 (d, J = 5.1 Hz, 1H), 8.51 (t, J = 5.9 Hz, 1H), 8.26 (d, J = 1.9 Hz, 1H), 8.03-7.98 (m, 1H), 7.89 (t, J = 5.8 Hz, 1H), 7.81 (d, J = 1.1 Hz, 2H), 7.74-7.69 (m, 1H), 7.67-7.50 (m, 4H), |

TABLE 9-continued

The following compounds were prepared using standard chemical manipulations and procedures similar to those used for the preparation of Compound 11

| Cmpd # | Name | LC-MS (ESI) (m/z) | $^1$H NMR |
|---|---|---|---|
| | yl)formamido]acetamido]-1,3-thiazol-4-yl)phenyl]pyridin-2-yl]cyclopropane-1-carboxamide | | 7.07 (s, 1H), 6.92 (d, J = 2.0 Hz, 1H), 6.82 (dd, J = 8.4, 2.1 Hz, 1H), 5.03 (dd, J = 12.9, 5.5 Hz, 1H), 4.10 (d, J = 5.5 Hz, 2H), 3.49 (s, 3H), 3.09 (t, J = 6.8 Hz, 4H), 2.94-2.82 (m, 1H), 2.70-2.54 (m, 2H), 2.53 (d, J = 1.9 Hz, 3H), 2.36-2.29 (m, 3H), 2.12 (s, 3H), 2.04-1.95 (m, 1H), 1.50 (t, J = 7.3 Hz, 2H), 1.43-1.24 (m, 9H), 1.21 (s, 2H). |
| 140 | N-[1-(4-[[2-(2,6-dioxopiperidin-3-yl)-1,3-dioxoisoindol-5-yl]oxy]butyl)piperidin-4-yl]-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 976.40 | $^1$H NMR (400 MHz, DMSO-d6) δ 12.47 (s, 1H), 11.13 (s, 1H), 8.71 (t, J = 5.9 Hz, 1H), 8.62-8.56 (m, 1H), 8.26 (t, J = 1.9 Hz, 1H), 8.16 (d, J = 7.6 Hz, 1H), 8.14 (s, 1H), 8.01 (dt, J = 7.7, 1.4 Hz, 1H), 7.88-7.79 (m, 3H), 7.76-7.69 (m, 1H), 7.65-7.56 (m, 3H), 7.43 (d, J = 2.3 Hz, 1H), 7.38-7.29 (m, 2H), 6.78 (dd, J = 3.3, 1.7 Hz, 1H), 5.12 (dd, J = 12.9, 5.4 Hz, 1H), 4.23-4.12 (m, 4H), 3.82 (s, 1H), 3.58 (s, 3H), 3.08 (s, 2H), 2.96-2.82 (m, 2H), 2.68 (p, J = 1.9 Hz, 1H), 2.53 (s, 2H), 2.08-2.01 (m, 2H), 1.89 (d, J = 22.7 Hz, 2H), 1.79-1.50 (m, 7H), 1.45-1.30 (m, 5H). |
| 141 | N-[4-(3-[2-[1-(3-[[2-(2,6-dioxopiperidin-3-yl)-1,3-dioxoisoindol-5-yl]oxy]azetidine-1-carbonyl)cyclopropyl]pyridin-4-yl]phenyl)-1,3-thiazol-2-yl]-2-[(1-methanesulfonylpyrrol-3-yl)formamido]acetamide | 877.25 | $^1$H NMR (300 MHz, DMSO-d6) δ 12.46 (s, 1H), 11.12 (s, 1H), 8.71 (t, J = 5.9 Hz, 1H), 8.66-8.60 (m, 1H), 8.29 (d, J = 1.8 Hz, 1H), 8.04 (d, J = 7.7 Hz, 1H), 7.88-7.82 (m, 2H), 7.79 (dd, J = 8.2, 3.0 Hz, 2H), 7.70 (d, J = 3.1 Hz, 2H), 7.62 (t, J = 7.8 Hz, 1H), 7.36-7.30 (m, 1H), 7.24 (d, J = 2.2 Hz, 1H), 7.20 (dd, J = 8.2, 2.3 Hz, 1H), 6.78 (dd, J = 3.3, 1.6 Hz, 1H), 5.18 (dt, J = 6.2, 2.8 Hz, 1H), 5.10 (dd, J = 12.9, 5.3 Hz, 1H), 4.46 (s, 1H), 4.15 (d, J = 5.6 Hz, 3H), 3.94 (s, 1H), 3.59 (s, 3H), 2.88 (ddd, J = 18.0, 13.9, 5.3 Hz, 1H), 2.76-2.54 (m, 2H), 2.46 (d, J = 12.0 Hz, 1H), 2.11-1.95 (m, 1H), 1.42 (s, 4H). |
| 149 | N-[[1-(2-[[2-(2,6-dioxopiperidin-3-yl)-1,3-dioxoisoindol-5-yl]oxy]ethyl)piperidin-4-yl]methyl]-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 962.15 | $^1$H NMR (400 MHz, DMSO-d6) δ 12.47 (s, 1H), 11.12 (s, 1H), 8.69 (t, J = 5.8 Hz, 1H), 8.59 (d, J = 5.0 Hz, 1H), 8.26 (s, 1H), 8.18 (s, 1H), 8.01 (dd, J = 10.3, 6.5 Hz, 2H), 7.86-7.79 (m, 3H), 7.72 (d, J = 7.9 Hz, 1H), 7.65-7.57 (m, 3H), 7.43 (d, J = 2.3 Hz, 1H), 7.35-7.30 (m, 2H), 6.78 (dd, J = 3.3, 1.7 Hz, 1H), 5.12 (dd, J = 13.0, 5.5 Hz, 1H), 4.22 (t, J = 5.6 Hz, 2H), 4.15 (d, J = 5.5 Hz, 2H), 3.58 (s, 3H), 3.00 (d, J = 6.4 Hz, 2H), 2.85 (d, J = 9.4 Hz, 3H), 2.64 (t, J = 5.8 Hz, 3H), 2.05 (d, J = 10.2 Hz, 1H), 1.92 (t, J = 11.2 Hz, 2H), 1.58 (d, J = 12.1 Hz, 2H), 1.49-1.43 (m, 1H), 1.38 (d, J = 2.8 Hz, 2H), 1.33 (q, J = 4.8, 4.0 Hz, 2H), 1.12 (d, J = 12.8 Hz, 2H). |
| 150 | N-(2-((4-(3-(2-(1-(4-(2-((2-(2,6-dioxopiperidin-3-yl)-1,3-dioxoisoindolin-5-yl)oxy)ethyl)piperazine-1-carbonyl)cyclopropyl)pyridin-4-yl)phenyl)thiazol-2-yl)amino)-2-oxoethyl)-1-(methylsulfonyl)-1H-pyrrole-3-carboxamide | 934.05 | $^1$H NMR (400 MHz, DMSO-d6) δ 12.45 (s, 1H), 11.13 (s, 1H), 8.71 (t, J = 5.8 Hz, 1H), 8.58 (d, J = 5.2 Hz, 1H), 8.23 (d, J = 1.9 Hz, 1H), 7.98 (d, J = 7.7 Hz, 1H), 7.89-7.65 (m, 4H), 7.65-7.51 (m, 2H), 7.49-7.20 (m, 4H), 6.78 (dd, J = 3.3, 1.6 Hz, 1H), 5.11 (dd, J = 12.9, 5.4 Hz, 1H), 4.30-4.02 (m, 4H), 3.58 (s, 5H), 3.45 (m, 3H), 2.98-2.84 (m, 1H), 2.74-2.53 (m, 5H), 2.30 (s, 2H), 2.12-1.98 (m, 1H), 1.58-1.31 (m, 4H). |
| 151 | N-[4-(3-[2-[1-(2-[[2-(2,6-dioxopiperidin-3-yl)-1,3-dioxoisoindol-5-yl]oxy]-7-azaspiro[3.5]nonane-7-carbonyl)cyclopropyl]pyridin-4-yl]phenyl)-1,3-thiazol-2-yl]-2-[(1-methanesulfonylpyrrol-3-yl)formamido]acetamide | 945.15 | $^1$H NMR (300 MHz, DMSO-d6) δ 12.47 (s, 1H), 11.12 (s, 1H), 8.64 (d, J = 38.8 Hz, 2H), 8.22 (s, 1H), 8.01 (d, J = 7.7 Hz, 1H), 7.85 (s, 1H), 7.80 (t, J = 4.1 Hz, 2H), 7.71 (d, J = 7.7 Hz, 1H), 7.59 (d, J = 7.2 Hz, 2H), 7.41 (s, 1H), 7.32 (t, J = 2.7 Hz, 1H), 7.30-7.21 (m, 2H), 6.78 (d, J = 3.2 Hz, 1H), 5.15-4.92 (m, 2H), 4.16 (d, J = 5.3 Hz, 2H), 3.58 (s, 4H), 2.89 (t, J = 13.1 Hz, 1H), 2.62 (s, 1H), 2.40 (s, 2H), 2.08-1.96 (m, 1H), 1.82-1.33 (m, 11H), 1.20 (d, J = 26.5 Hz, 1H). |
| 152 | N-[5-[2-(2,6-dioxopiperidin-3-yl)-1,3-dioxoisoindol-4-yl]pent-4-yn-1-yl]-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 887.05 | $^1$H NMR (400 MHz, DMSO-d6) δ 8.99 (s, 1H), 8.57 (t, J = 6.1 Hz, 1H), 8.36 (t, J = 5.9 Hz, 1H), 8.16 (d, J = 1.9 Hz, 1H), 7.93-7.82 (m, 2H), 7.75 (s, 1H), 7.62-7.49 (m, 4H), 7.41 (dt, J = 15.9, 7.9 Hz, 5H), 5.14 (d, J = 3.5 Hz, 1H), 4.55 (d, J = 9.4 Hz, 1H), 4.47-4.39 (m, 2H), 4.35 (d, J = 5.8 Hz, 3H), 4.22 (dd, J = 15.9, 5.4 Hz, 1H), 3.70-3.61 (m, 4H), 2.71 (t, J = 6.1 Hz, 2H), 2.45 (s, 3H), |

TABLE 9-continued

The following compounds were prepared using standard chemical manipulations and procedures similar to those used for the preparation of Compound 11

| Cmpd # | Name | LC-MS (ESI) (m/z) | $^1$H NMR |
|---|---|---|---|
| | | | 2.27-2.10 (m, 4H), 2.08-2.01 (m, 1H), 1.94-1.87 (m, 1H), 1.56-1.40 (m, 4H), 1.24 (s, 4H), 0.93 (s, 9H). |
| 156 | N-[4-[3-(2-[1-[3-([4-[2-(2,6-dioxopiperidin-3-yl)-1,3-dioxoisoindol-5-yl]piperazin-1-yl]methyl)azetidine-1-carbonyl]cyclopropyl]pyridin-4-yl)phenyl]-1,3-thiazol-2-yl]-2-[(1-methanesulfonylpyrrol-3-yl)formamido]acetamide | 959.45 | $^1$H NMR (300 MHz, DMSO-d6) δ 12.47 (s, 1H), 11.08 (s, 1H), 8.70 (t, J = 5.9 Hz, 1H), 8.60 (d, J = 5.2 Hz, 1H), 8.27 (s, 1H), 8.02 (d, J = 7.8 Hz, 1H), 7.85 (d, J = 3.7 Hz, 2H), 7.76 (d, J = 7.9 Hz, 1H), 7.66-7.54 (m, 4H), 7.36-7.24 (m, 2H), 7.18 (d, J = 8.9 Hz, 1H), 6.79 (d, J = 2.2 Hz, 1H), 5.06 (dd, J = 12.8, 5.4 Hz, 1H), 4.15 (d, J = 5.6 Hz, 2H), 3.99 (d, J = 8.9 Hz, 1H), 3.71 (d, J = 8.3 Hz, 2H), 3.58 (s, 5H), 2.89 (d, J = 5.0 Hz, 1H), 2.61 (s, 1H), 2.45 (s, 2H), 2.38 (s, 4H), 2.01 (d, J = 12.0 Hz, 1H), 1.39 (s, 1H), 1.30 (d, J = 33.2 Hz, 4H). |
| 161 | N-(2-[[2-(2,6-dioxopiperidin-3-yl)-1,3-dioxoisoindol-5-yl]oxylethyl)-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 865.05 | $^1$H NMR (300 MHz, DMSO-d6) δ 12.42 ( s, 1H), 11.13 (s, 1H), 8.71 (t, J = 5.8 Hz, 1H), 8.59 (d, J = 5.2 Hz, 1H), 8.21 (s, 2H), 7.97 (d, J = 7.8 Hz, 1H), 7.86 (t, J = 2.0 Hz, 1H), 7.77 (s, 1H), 7.72-7.57 (m, 4H), 7.51 (t, J = 7.8 Hz, 1H), 7.38-7.29 (m, 2H), 7.21 (dd, J = 8.3, 2.3 Hz, 1H), 6.79 (dd, J = 3.2, 1.6 Hz, 1H), 5.11 (dd, J = 12.9, 5.4 Hz, 1H), 4.25 (t, J = 5.7 Hz, 2H), 4.15 (d, J = 5.4 Hz, 2H), 3.62-3.48 (m, 5H), 2.98-2.80 (m, 1H), 2.65-2.44 (m, 2H), 2.11-2.00 (m, 1H), 1.42 (t, J = 3.2 Hz, 2H), 1.38-1.30 (m, 2H). |
| 162 | N-(2-[[2-(2,6-dioxopiperidin-3-yl)-1,3-dioxoisoindol-5-yl]amino]ethyl)-1-[4-[3-(2-[2-[(1-methanesulfonylpyrrol-3-yl)formamido]acetamido]-1,3-thiazol-4-yl)phenyl]pyridin-2-yl]-N-methylcyclopropane-1-carboxamide | 878.10 | $^1$H NMR (300 MHz, DMSO-d6)δ 10.85 (s, 1H), δ 8.55 (d, J = 5.2 Hz, 1H), 8.40 (s, 1H), 8.18 (t, J = 1.8 Hz, 1H), 7.98 (d, J = 7.5 Hz, 1H), 7.84 (t, J = 2.0 Hz, 1H), 7.71-7.59 (m, 2H), 7.59-7.46 (m, 3H), 7.40 (d, J = 1.6 Hz, 1H), 7.33-7.25 (m, 1H), 6.98 (s, 1H), 6.86-6.75 (m, 2H), 5.00 (dd, J = 12.2, 5.5 Hz, 1H), 4.22-4.14 (m, 2H), 3.59 (d, J = 6.6 Hz, 2H), 3.52 (s, 2H), 3.40 (s, 3H), 2.95 (s, 5H), 2.89-2.87 (m, 2H), 2.68-2.56 (m, 2H), 2.10-1.95 (m, 1H), 1.50 (q, J = 4.0, 3.4 Hz, 2H), 1.38 (q, J = 4.5, 4.0 Hz, 2H) |
| 127 | N-(6-[[2-(2,6-dioxopiperidin-3-yl)-3-oxo-1H-isoindol-5-yl]amino]hexyl)-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 906.40 | $^1$H NMR (400 MHz, DMSO-d6) δ 12.46 (s, 1H), 10.95 (s, 1H), 8.69 (t, J = 5.8 Hz, 1H), 8.59 (d, J = 5.1 Hz, 1H), 8.27 (d, J = 1.9 Hz, 1H), 8.01 (d, J = 7.7 Hz, 1H), 7.91 (t, J = 5.7 Hz, 1H), 7.85 (t, J = 2.0 Hz, 1H), 7.82 (s, 1H), 7.72 (d, J = 7.8 Hz, 1H), 7.67-7.53 (m, 3H), 7.32 (dd, J = 3.2, 2.3 Hz, 1H), 7.24 (d, J = 8.3 Hz, 1H), 6.81 (dd, J = 8.3, 2.2 Hz, 1H), 6.79-6.72 (m, 2H), 5.80 (t, J = 5.4 Hz, 1H), 5.06 (dd, J = 13.3, 5.1 Hz, 1H), 4.31-4.06 (m, 4H), 3.58 (s, 3H), 3.12 (q, J = 6.5 Hz, 2H), 3.02-2.92 (m, 2H), 2.91-2.81 (m, 1H), 2.61 (s, 1H), 2.34 (d, J = 21.8 Hz, 1H), 2.04-1.90 (m, 1H), 1.45 (dq, J = 15.9, 8.9, 8.1 Hz, 4H), 1.38 (t, J = 3.0 Hz, 2H), 1.37-1.23 (m, 6H). |
| 53 | N-(6-[[2-(2,6-dioxopiperidin-3-yl)-1-oxo-3H-isoindol-5-yl]amino]hexyl)-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 906.20 | $^1$H NMR (400 MHz, DMSO-d6) δ 12.47 (s, 1H), 10.93 (s, 1H), 8.70 (t, J = 5.9 Hz, 1H), 8.59 (d, J = 5.2 Hz, 1H), 8.31-8.23 (m, 1H), 8.00 (dt, J = 7.7, 1.3 Hz, 1H), 7.91 (t, J = 5.7 Hz, 1H), 7.85 (t, J = 2.0 Hz, 1H), 7.82 (s, 1H), 7.72 (dt, J = 8.0, 1.3 Hz, 1H), 7.64 (d, J = 1.8 Hz, 1H), 7.63-7.55 (m, 2H), 7.37 (d, J = 8.4 Hz, 1H), 7.32 (dd, J = 3.3, 2.3 Hz, 1H), 6.78 (dd, J = 3.2, 1.7 Hz, 1H), 6.62 (dd, J = 8.4, 2.0 Hz, 1H), 6.58-6.52 (m, 1H), 6.30 (t, J = 5.3 Hz, 1H), 5.01 (dd, J = 13.3, 5.1 Hz, 1H), 4.32-4.01 (m, 4H), 3.58 (s, 3H), 3.12 (q, J = 6.6 Hz, 2H), 2.98 (q, J = 6.5 Hz, 2H), 2.94-2.81 (m, 1H), 2.59 (s, 1H), 2.40-2.27 (m, 1H), 2.01-1.82 (m, 1H), 1.45 (td, J = 16.3, 15.3, 8.3 Hz, 4H), 1.38 (t, J = 3.0 Hz, 2H), 1.36-1.09 (m, 6H). |
| 169 | N-(2-((4-(3-(2-(1-((2-((2-(2,6-dioxopiperidin-3-yl)-1-oxoisoindolin-4-yl)amino)ethyl)carbamoyl)cyclopropyl)pyridin-4-yl)phenyl)thiazol-2-yl)amino)-2-oxoethyl)-1-(methylsulfonyl)-1H-pyrrole-3-carboxamide | 850.30 | $^1$H NMR (300 MHz, DMSO-d6) δ 12.44 (s, 1H), 11.02 (s, 1H), 8.70 (t, J = 5.9 Hz, 1H), 8.59 (d, J = 5.3 Hz, 1H), 8.27 (s, 1H), 8.06-7.90 (m, 2H), 7.88-7.84 (m, 1H), 7.82 (s, 1H), 7.71 (d, J = 7.8 Hz, 1H), 7.69-7.60 (m, 2H), 7.54 (t, J = 7.8 Hz, 1H), 7.32 (dd, J = 3.3, 2.3 Hz, 1H), 7.26 (t, J = 7.7 Hz, 1H), 6.93 (d, J = 7.2 Hz, 1H), 6.84 (d, J = 8.0 Hz, 1H), 6.78 (dd, J = 3.3, 1.6 Hz, 1H), 5.70 (t, J = |

TABLE 9-continued

The following compounds were prepared using standard chemical manipulations and procedures similar to those used for the preparation of Compound 11

| Cmpd # | Name | LC-MS (ESI) (m/z) | $^1$H NMR |
|---|---|---|---|
| | | | 5.5 Hz, 1H), 5.10 (dd, J = 13.2, 5.1 Hz, 1H), 4.30-3.92 (m, 4H), 3.58 (s, 3H), 2.99-2.82 (m, 1H), 2.62 (s, 1H), 2.22 (d, J = 4.4 Hz, 1H), 2.07-1.91 (m, 1H), 1.47-1.38 (m, 2H), 1.31 (d, J = 3.0 Hz, 2H) |
| 168 | N-(2-((4-(3-(2-(1-((2-((2-(2,6-dioxopiperidin-3-yl)-3-oxoisoindolin-5-yl)amino)ethyl)carbamoyl)cyclopropyl)pyridin-4-yl)phenyl)thiazol-2-yl)amino)-2-oxoethyl)-1-(methylsulfonyl)-1H-pyrrole-3-carboxamide | 850.25 | $^1$H NMR (300 MHz, DMSO-d6) δ 8.57 (d, J = 5.2 Hz, 1H), 8.23 (s, 1H), 8.03-7.88 (m, 2H), 7.83 (t, J = 2.0 Hz, 1H), 7.76 (s, 1H), 7.69 (d, J = 7.8 Hz, 1H), 7.65-7.50 (m, 3H), 7.32 (dd, J = 3.3, 2.3 Hz, 1H), 7.20 (d, J = 8.1 Hz, 1H), 6.88-6.73 (m, 3H), 5.02 (dd, J = 13.2, 5.1 Hz, 1H), 4.29-4.08 (m, 4H), 3.31 (d, J = 6.2 Hz, 2H), 3.16 (d, J = 6.6 Hz, 2H), 2.93-2.73 (m, 1H), 2.61 (s, 1H), 2.37-2.22 (m, 1H), 1.97 (s, 1H), 1.49-1.24 (m, 4H) |
| 167 | N-(2-[[2-(2,6-dioxopiperidin-3-yl)-1-oxo-3H-isoindol-5-yl]amino]ethyl)-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 850.20 | $^1$H NMR (300 MHz, DMSO-d6) δ 8.64-8.50 (m, 1H), 8.25 (t, J = 1.8 Hz, 1H), 8.04-7.95 (m, 1H), 7.84 (dd, J = 2.3, 1.7 Hz, 1H), 7.78 (s, 1H), 7.73-7.59 (m, 3H), 7.55 (t, J = 7.8 Hz, 1H), 7.41-7.27 (m, 2H), 6.77 (dd, J = 3.3, 1.7 Hz, 1H), 6.63 (dq, J = 4.4, 2.0 Hz, 2H), 4.97 (dd, J = 13.2, 5.1 Hz, 1H), 4.32-4.01 (m, 4H), 3.31 (t, J = 6.5 Hz, 2H), 3.19 (d, J = 6.4 Hz, 2H), 2.95-2.76 (m, 1H), 2.60 (s, 1H), 2.40-2.23 (m, 1H), 2.04-1.84 (m, 1H), 1.43 (t, J = 3.9 Hz, 2H), 1.30 (q, J = 4.6, 4.0 Hz, 2H) |
| 115 | N-[2-[[4-[3-[2-[1-[8-[[2-(2,6-dioxo-3-piperidyl)-1,3-dioxo-isoindolin-5-yl]amino]octylcarbamoyl]cyclopropyl]-4-pyridyl]phenyl]thiazol-2-yl]amino]-2-oxo-ethyl]-1-methylsulfonyl-pyrrole-3-carboxamide | 948.3 | $^1$H NMR (400 MHz, DMSO-$d_6$) δ = 12.41 (s, 1H), 11.05 (d, J = 1.2 Hz, 1H), 8.68 (m, 1H), 8.59 (d, J = 5.2 Hz, 1H), 8.26 (s, 1H), 8.00 (d, J = 7.6 Hz, 1H), 7.91-7.83 (m, 2H), 7.80 (s, 1H), 7.71 (d, J = 8.0 Hz, 1H), 7.67-7.52 (m, 4H), 7.32 (m, 1H), 7.05 (m, 1H), 6.93 (s, 1H), 6.86-6.74 (m, 2H), 5.05-5.00 (m, 1H), 4.15 (d, J = 5.6 Hz, 2H), 3.58 (s, 3H), 3.10 (d, J = 6.0 Hz, 4H), 2.88 (d, J = 4.8 Hz, 1H), 2.59 (d, J = 1.2 Hz, 2H), 2.08-1.90 (m, 1H), 1.54-1.37 (m, 6H), 1.34-1.17 (m, 10H) ppm. |

Preparation of N-(2-((4-(3'-(aminomethyl)-[1,1'-biphenyl]-3-yl)thiazol-2-yl)amino)-2-oxoethyl)-1-(methylsulfonyl)-1H-pyrrole-3-carboxamide (I-93)

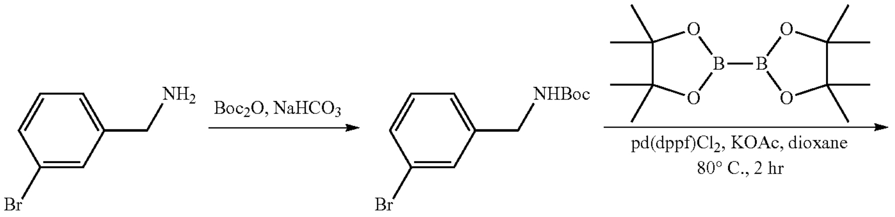

A B

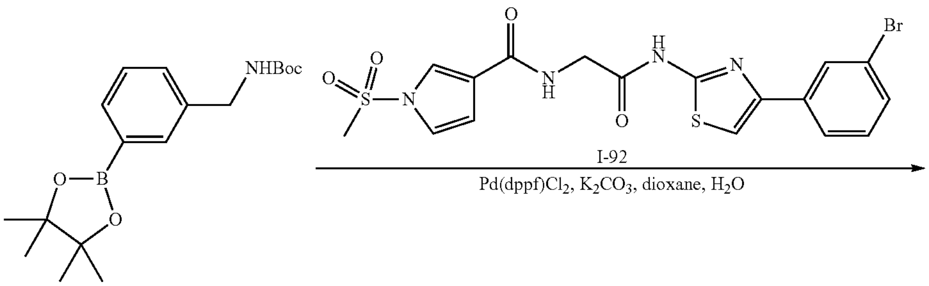

C

-continued

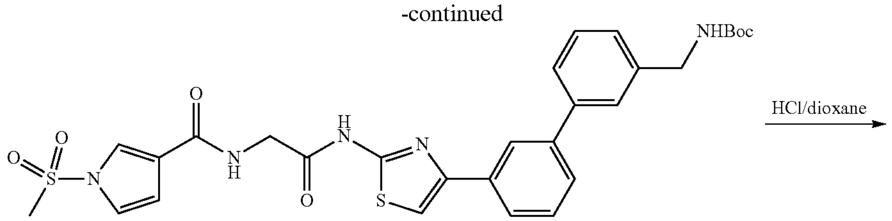

D

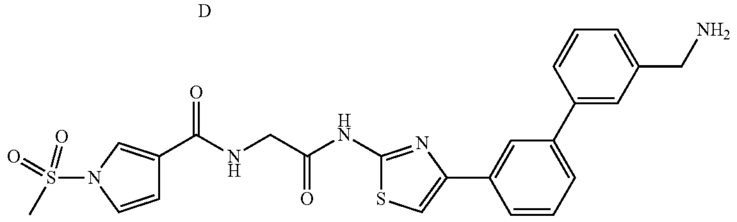

I-93

Step 1: Preparation of tert-butyl 3-bromobenzylcarbamate (B)

B

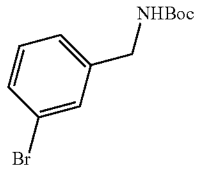

To a solution of (3-bromophenyl)methylamine (A, 3.7 g, 19.89 mmol) in THE (20 mL) was added $NaHCO_3$ (3.34 g, 39.77 mmol, 1.55 mL) and $Boc_2O$ (4.77 g, 21.88 mmol, 5.03 mL). The mixture was stirred at 30° C. for 16 h, filtered, concentrated to give B (5.6 g, 16.67 mmol, 83.85%) as a white solid which was used without further purification. LCMS (ESI) m/z $[M+H-56]^+$=231.9.

Step 2: Preparation of tert-butyl 3-(4,4,5,5-tetramethyl-1,3,2-dioxaborolan-2-yl)benzylcarbamate (C)

C

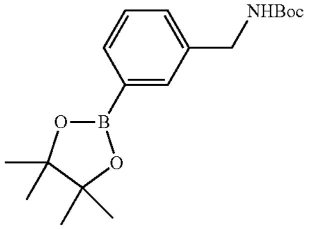

To a solution of B (5.6 g, 16.67 mmol) bis(pinacol) diborane (5.08 g, 20.01 mmol) in 1,4-dioxane (60 mL) was added cyclopentyl(diphenyl)phosphanedichloropalladium (II), DCM adduct (1.36 g, 1.67 mmol) and KOAc (4.91 g, 50.02 mmol). The mixture was stirred at 80° C. for 2 h, then poured into water (100 mL). This mixture was extracted with EtOAc (100 mL×3) and the combined organic layers washed with brine (200 mL), and dried over $Na_2SO_4$, filtered, and concentrated. The residue was purified by column chromatography ($SiO_2$, Petroleum ether/EtOAc 1:0-10:1) to give C (5.5 g, 16.51 mmol, 98.98%) as a white solid. $^1$H NMR (400 MHz, DMSO-d6) δ 7.58 (s, 1H), 7.53 (d, J=6.8 Hz, 1H), 7.35-7.32 (m, 3H), 4.13 (d, J=6.0 Hz, 2H), 1.39 (s, 9H), 1.29 (s, 12H).

Step 3: Preparation of tert-butyl ((3'-(2-(2-(1-(methylsulfonyl)-1H-pyrrole-3-carboxamido)acetamido) thiazol-4-yl)-[1,1'-biphenyl]-3-yl)methyl)carbamate (D)

D

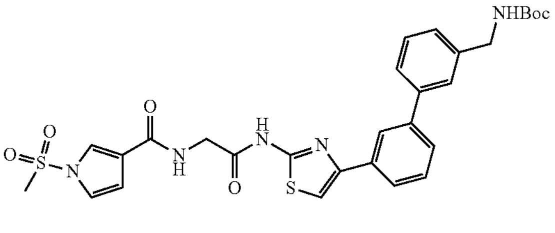

To a solution of N-[2-[[4-(3-bromophenyl)thiazol-2-yl] amino]-2-oxo-ethyl]-1-methylsulfonyl-pyrrole-3-carboxamide (I-92, 500 mg, 1.03 mmol) and C (413.64 mg, 1.24 mmol) in 1,4-dioxane (5 mL)/water (0.5 mL) was added $Pd(dppf)Cl_2$ (75.69 mg, 103.44 μmol) and $K_2CO_3$ (428.89 mg, 3.10 mmol). The mixture was stirred at 80° C. for 2 h, then concentrated, the residue was purified by reverse phase flash HPLC (0.1% formic acid in water/ACN) and lyophilized to give D (600 mg) as a yellow solid. LCMS (ESI) m/z $[M+H]^+$=610.2.

Step 4: Preparation of N-(2-((4-(3'-(aminomethyl)-[1,1'-biphenyl]-3-yl)thiazol-2-yl)amino)-2-oxo-ethyl)-1-(methylsulfonyl)-1H-pyrrole-3-carboxamide (I-93)

I-93

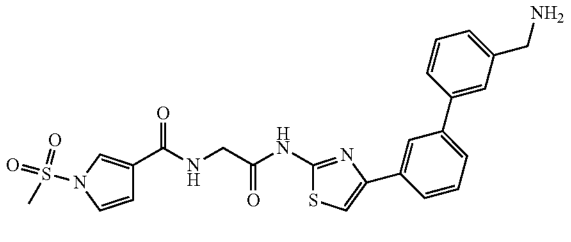

A mixture of D (400 mg, 656.04 μmol) and 4M HCl in 1,4-dioxane (5 mL) was stirred at 30° C. for 2 h. The reaction mixture was concentrated and the residue triturated with MTBE (2 mL), filtered to give a yellow solid, and purified twice by twice preparative HPLC (column: Phenomenex Synergi C18 150×25×10 μm; mobile phase: [water (0.05% HCl)-ACN]; B %: 18%-38%, 10 min) then (column: Shim-pack C18 150×25×10 μm; mobile phase: [0.225% formic acid in water/ACN]; B %:10%-40%, 10 min) to give I-93 (68.49 mg, 134.40 μmol, 56.45%) as a white solid. LCMS (ESI) m/z $[M+H]^+$=510.2. $^1$H NMR (400 MHz, DMSO-d6) δ 8.69-8.67 (m, 1H), 8.33 (s, 1H), 8.20 (s, 1H), 7.90 (d, J=8.0 Hz, 1H), 7.85-7.83 (m, 1H), 7.75 (s, 2H), 7.64-7.60 (m, 2H), 7.55-7.52 (m, 1H), 7.49-7.45 (m, 1H), 7.40-7.38 (m, 1H), 7.32-7.30 (m, 1H), 6.78 (dd, J=1.6, 3.2 Hz, 1H), 4.15 (d, J=5.6 Hz, 2H), 3.92 (s, 2H), 3.57 (s, 3H).

Compound 1—Preparation of N-(2-((4-(3'-((S)-14-((2S,4R)-4-hydroxy-2-((4-(4-methylthiazol-5-yl)benzyl)carbamoyl)pyrrolidine-1-carbonyl)-15,15-dimethyl-3,12-dioxo-6,9-dioxa-2,13-diazahexadecyl)-[1,1'-biphenyl]-3-yl)thiazol-2-yl)amino)-2-oxoethyl)-1-(methylsulfonyl)-1H-pyrrole-3-carboxamide

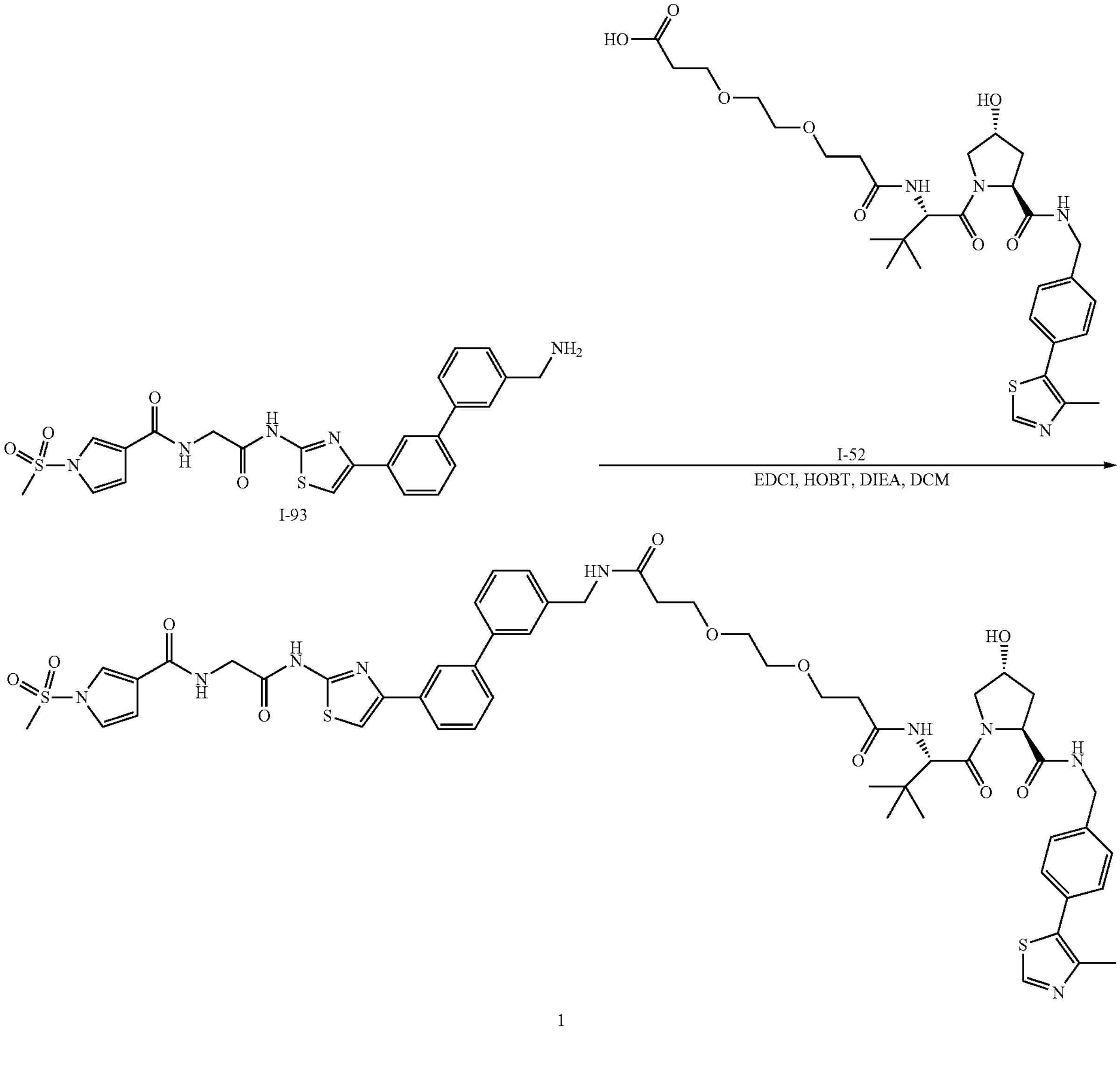

I-93

To a solution of N-[2-[[4-[3-[3-(aminomethyl)phenyl]phenyl]thiazol-2-yl]amino]-2-oxo-ethyl]-1-methylsulfonyl-pyrrole-3-carboxamide (I-93, 50 mg, 0.098 mmol) and 3-[2-[3-[[1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-3-oxo-propoxy]ethoxy]propanoic acid (I-52, 66.78 mg, 0.107 mmol) in DCM (2 mL) was added EDCI (22.57 mg, 117.74 μm), HOBt (15.91 mg, 0.117 mmol) and DIEA (12.68 mg, 0.098 mmol, 17.09 μL). The mixture was stirred at 30° C. for 2 h, then concentrated. The residue was purified by preparative HPLC (column: Phenomenex Synergi C18 150×25×10 μm; mobile phase: [0.225% formic acid in water/ACN]; B %: 33%-63%, 10 min) to give Compound 1 (44.16 mg, 40.54% yield) as a white solid. LCMS (ESI) m/z: $[M+Na]^+$=1132.3. $^1$H NMR (400 MHz, methanol-d4) δ=8.84 (s, 1H), 8.18-8.12 (m, 1H), 7.89-7.81 (m, 2H), 7.60 (s, 1H), 7.55 (br d, J=6.6 Hz, 2H), 7.49-7.34 (m, 7H), 7.32-7.25 (m, 2H), 6.80 (dd, J=1.6, 3.4 Hz, 1H), 4.63 (s, 1H), 4.59-4.44 (m, 6H), 4.35-4.25 (m, 3H), 3.91-3.84 (m, 1H), 3.80-3.70 (m, 3H), 3.62-3.49 (m, 4H), 3.48-3.39 (m, 2H), 3.37 (s, 3H), 2.50-2.48 (m, 2H), 2.46-2.42 (m, 3H), 2.41-2.29 (m, 2H), 2.24-2.14 (m, 1H), 2.10-2.01 (m, 1H), 1.05-0.93 (m, 9H) ppm.

TABLE 10

The following compounds were prepared using standard chemical manipulations and procedures similar to those used for the preparation of Compound 1

| Cmpd # | Name | LC-MS (ESI) (m/z) | $^1$H NMR |
|---|---|---|---|
| 18 | N-[2-[[4-[3-[3-[[[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]acetyl]amino]methyl]-phenyl]phenyl]thiazol-2-yl]amino]-2-oxo-ethyl]-1-methylsulfonyl-pyrrole-3-carboxamide | 1038.4 | $^1$H NMR (400 MHz, DMSO-$d_6$) δ = 0.93 (s, 9H), 1.85-1.94 (m, 1H), 2.00-2.09 (m, 1H), 2.43 (s, 3H), 3.57 (s, 3H), 3.59-3.69 (m, 2H), 4.08 (d, J = 7.2 Hz, 4H), 4.14 (d, J = 5.6 Hz, 2H), 4.23 (m, 1H), 4.34 (s, 1H), 4.37-4.46 (m, 4H), 4.57 (d, J = 9.2 Hz, 1H), 5.15 (d, J = 1.2 Hz, 1H), 6.77 (m, 1H), 7.28-7.34 (m, 2H), 7.36-7.46 (m, 5H), 7.50-7.55 (m, 1H), 7.56-7.63 (m, 3H), 7.75 (s, 1H), 7.79-7.86 (m, 2H), 7.88-7.92 (m, 1H), 8.17 (s, 1H), 8.58 (m, 1H), 8.65-8.71 (m, 2H), 8.97 (s, 1H), 12.27-12.65 (m, 1H) ppm. |
| 19 | N'-[(1S)-1-[(2S,4R)-4-hydroxy-2-[[4-(4-methylthiazol-5-yl)phenyl]methylcarbamoyl]pyrrolidine-1-carbonyl]-2,2-dimethylpropyl]-N-[[3-[3-[2-[[2-[(1-methylsulfonylpyrrole-3-carbonyl)amino]acetyl]amino]thiazol-4-yl]phenyl]phenyl]methyl]decanediamide | 1106.4 | $^1$H NMR (400 MHz, DMSO-$d_6$) δ = 0.93 (s, 9H), 1.21 (s, 8H), 1.39-1.57 (m, 4H), 1.86-1.94 (m, 1H), 1.99-2.16 (m, 4H), 2.20-2.28 (m, 1H), 2.44 (s, 3H), 3.57 (s, 3H), 3.61-3.69 (m, 2H), 4.15 (d, J = 5.6 Hz, 2H), 4.21 (m, 1H), 4.34 (d, J = 5.6 Hz, 3H), 4.39-4.46 (m, 2H), 4.54 (d, J = 9.2 Hz, 1H), 5.07-5.17 (m, 1H), 6.78 (m, 1H), 7.26 (d, J = 7.6 Hz, 1H), 7.31 (m, 1H), 7.36-7.47 (m, 5H), 7.50-7.55 (m, 1H), 7.55-7.60 (m, 3H), 7.75 (s, 1H), 7.80-7.86 (m, 2H), 7.88-7.93 (m, 1H), 8.16 (s, 1H), 8.35 (m, 1H), 8.56 (m, 1H), 8.68 (m, 1H), 8.98 (s, 1H), 12.33-12.54 (m, 1H) ppm. |
| 20 | N-(2-((4-(3'-((9-((2-(2,6-dioxopiperidin-3-yl)-1,3-dioxoisoindolin-4-yl)amino)nonanamido)methyl)-[1,1'-biphenyl]-3-yl)thiazol-2-yl)amino)-2-oxoethyl)-1-(methylsulfonyl)-1H-pyrrole-3-carboxamide | 921.1 | $^1$H NMR (400 MHz, DMSO-$d_6$) δ = 1.23-1.35 (m, 8H), 1.48-1.60 (m, 4H), 1.95-2.04 (m, 1H), 2.16 (m, 2H), 2.59 (s, 2H), 2.82-2.93 (m, 1H), 3.08-3.17 (m, 2H), 3.58 (s, 3H), 4.14 (d, J = 5.6 Hz, 2H), 4.36 (d, J = 5.6 Hz, 2H), 5.03 (m, 1H), 6.78 (m, 1H), 6.83 (m, 1H), 6.94 (s, 1H), 7.04-7.11 (m, 1H), 7.25-7.29 (m, 1H), 7.30-7.34 (m, 1H), 7.42-7.48 (m, 1H), 7.50-7.62 (m, 5H), 7.70-7.76 (m, 1H), 7.85 (d, J = 1.6 Hz, 1H), 7.90 (d, J = 7.6 Hz, 1H), 8.17 (s, 1H), 8.35 (d, J = 6.0 Hz, 1H), 8.58-8.74 (m, 1H), 11.05 (s, 1H), 12.43 (d, J = 1.6 Hz, 1H) ppm. |
| 26 | N-[2-[[4-[3-[3-[[4-[2-(2,6-dioxo-3-piperidyl)-1,3-dioxo-isoindolin-4-yl]oxybutanoylamino]methyl]-phenyl]phenyl]thiazol-2-yl]amino]-2-oxo-ethyl]-1-methylsulfonyl-pyrrole-3-carboxamide | 852.2 | $^1$H NMR (400 MHz, DMSO-$d_6$) δ = 12.43 (s, 1H), 11.10 (s, 1H), 8.67 (s, 1H), 8.47 (s, 1H), 8.17 (s, 1H), 7.85 (s, 1H), 7.78 (s, 1H), 7.59-7.57 (m, 2H), 7.50-7.43 (m, 7H), 7.35-7.31 (m, 2H), 6.78 (s, 1H), 5.10-5.05 (m, 1H), 4.38-4.36 (m, 2H), 4.25-4.22 (m, 2H), 4.15-4.13 (m, 2H), 3.58 (s, 3H), 2.84-2.80 (m, 1H), 2.60-2.56 (m, 2H), 2.42-2.39 (m, 2H), 2.05-2.00 (m, 3H) ppm. |
| 42 | N-(2-((4-(3'-((3-(2-(2-((2-(2,6-dioxopiperidin-3-yl)-1,3-dioxoisoindolin-4-yl)amino)ethoxy)ethoxy)propanamido)-methyl)-[1,1'-biphenyl]-3-yl)thiazol-2-yl)amino)-2-oxoethyl)-1-(methylsulfonyl)-1H-pyrrole-3-carboxamide | 925.2 | $^1$H NMR (400 MHz, DMSO-d6) δ = 11.21-10.95 (m, 1H), 8.69-8.66 (m, 1H), 8.40-8.39 (m, 1H), 8.16 (s, 1H), 7.90-7.88 (m, 1H), 7.85-7.84 (m, 1H), 7.74 (s, 1H), 7.57-7.49 (m, 5H), 7.45-7.41 (m, 1H), 7.32-7.30 (m, 1H), 7.28 (d, J = 7.2 Hz, 1H), 7.09 (d, J = 8.8 Hz, 1H), 7.02 (d, J = 7.2 Hz, 1H), 6.78-6.77 (m, 1H), 6.58-6.55 (m, 1H), 5.06-5.02 (m, 1H), 4.36 (d, J = 6.0 Hz, 2H), 4.14 (d, J = 5.6 Hz, 2H), 3.66-3.63 (m, 2H), 3.57 (s, 3H), 3.55-3.53 (m, 2H), 3.49 (s, 4H), 3.42-3.38 (m, 3H), 2.91-2.81 (m, 1H), 2.59 (d, J = 2.8 Hz, 2H), 2.41-2.37 (m, 2H), 2.02-1.98 (m, 1H) ppm |
| 43 | N-(2-((4-(3'-((7-((2-(2,6-dioxopiperidin-3-yl)-1,3- | 893.9 | $^1$H NMR (400 MHz, methanol-d4) δ = 8.16-8.10 (m, 1H), 7.87-7.79 (m, 2H), 7.70-7.61 |

TABLE 10-continued

The following compounds were prepared using standard chemical manipulations and procedures similar to those used for the preparation of Compound 1

| Cmpd # | Name | LC-MS (ESI) (m/z) | $^1$H NMR |
|---|---|---|---|
| | dioxoisoindolin-4-yl)oxy)heptanamido)methyl)-[1,1'-biphenyl]-3-yl)thiazol-2-yl)amino)-2-oxoethyl)-1-(methylsulfonyl)-1H-pyrrole-3-carboxamide | | (m, 2H), 7.57-7.50 (m, 2H), 7.46-7.34 (m, 4H), 7.31-7.26 (m, 2H), 7.23 (d, J = 8.4 Hz, 1H), 6.82-6.80 (m, 1H), 5.08-5.02 (m, 1H), 4.46 (s, 2H), 4.26 (s, 2H), 4.02-3.98 (m, 2H), 3.38 (s, 3H), 2.88-2.59 (m, 3H), 2.31-2.27 (m, 2H), 2.11-2.03 (m, 1H), 1.74-1.63 (m, 4H), 1.52-1.35 (m, 4H) ppm. |
| 44 | N-(2-((4-(3'-((S)-12-((2S,4R)-4-hydroxy-2-((4-(4-methylthiazol-5-yl)benzyl)carbamoyl)pyrrolidine-1-carbonyl)-13,13-dimethyl-3,10-dioxo-5,8-dioxa-2,11-diazatetradecyl)-[1,1'-biphenyl]-3-yl)thiazol-2-yl)amino)-2-oxoethyl)-1-(methylsulfonyl)-1H-pyrrole-3-carboxamide | 1082.3 | $^1$H NMR (400 MHz, methanol-d4) δ = 8.85-8.83 (m, 1H), 8.15 (s, 1H), 7.86-7.83 (m, 2H), 7.63-7.61 (m, 1H), 7.54 (d, J = 7.6 Hz, 2H), 7.47-7.28 (m, 8H), 7.27-7.26(m, 1H), 6.81-6.80(m, 1H), 4.68 (s, 1H), 4.59-4.55 (m, 1H), 4.53-4.46 (m, 3H), 4.34 (d, J = 0.8 Hz, 2H), 4.26 (s, 2H), 4.14-3.92 (m, 4H), 3.87-3.84 (m, 1H), 3.79-3.67 (m, 5H), 3.37 (s, 3H), 2.44-2.42 (m, 3H), 2.24-2.19 (m, 1H), 2.09-2.03 (m, 1H), 0.97-0.95 (m, 9H) ppm. |
| 45 | N-(2-((4-(3'-((3-(2-(2-((2-(2,6-dioxopiperidin-3-yl)-1,3-dioxoisoindolin-5-yl)amino)ethoxy)ethoxy)propanamido)-methyl)-[1,1'-biphenyl]-3-yl)thiazol-2-yl)amino)-2-oxoethyl)-1-(methylsulfonyl)-1H-pyrrole-3-carboxamide | 925.4 | $^1$H NMR (400 MHz, DMSO-d6) δ = 12.26 (br s, 1H), 11.05 (s, 1H), 8.69-8.66 (m, 1H), 8.42-8.40 (m, 1H), 8.16 (s, 1H), 7.90 (d, J = 7.2 Hz, 1H), 7.85 (s, 1H), 7.74 (s, 1H), 7.62-7.50 (m, 5H), 7.44-7.41 (m, 1H), 7.32-7.31 (m, 1H), 7.28 (d, J = 7.2 Hz, 1H), 7.11-7.08 (m, 1H), 7.00 (d, J = 1.2 Hz, 1H), 6.88-6.85 (m, 1H), 6.78-6.75 (m, 1H), 5.05-5.01 (m, 1H), 4.37 (d, J = 5.6 Hz, 2H), 4.15 (d, J = 6.0 Hz, 2H), 3.66-3.64 (m, 2H), 3.58 (s, 3H), 3.55-3.49 (m, 5H), 2.94-2.79 (m, 1H), 2.60-2.55 (m, 1H), 2.42-2.40 (m, 2H), 2.08-2.07 (m, 1H), 2.04-1.94 (m, 1H) ppm |
| 48 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N6-((3'-(2-(2-(1-(methylsulfonyl)-1H-pyrrole-3-carboxamido)acetamido)thiazol-4-yl)-[1,1'-biphenyl]-3-yl)methyl)adipamide | 1050.0 | $^1$H NMR (400 MHz, methanol-d4) δ = 8.88 (s, 1H), 8.20-8.16 (m, 1H), 7.92-7.82 (m, 3H), 7.63-7.54 (m, 3H), 7.51-7.46 (m, 3H), 7.46-7.33 (m, 5H), 7.33-7.28 (m, 2H), 6.83-6.82 (m, 1H), 4.64-4.60 (m, 1H), 4.60-4.48 (m, 3H), 4.48-4.44 (m, 2H), 4.35 (d, J = 15.6 Hz, 1H), 4.29 (s, 2H), 3.95-3.88 (m, 1H), 3.81-3.77 (m, 1H), 3.40 (s, 3H), 2.47 (s, 3H), 2.38-2.14 (m, 6H), 2.11-2.05 (m, 1H), 1.71-1.64 (m, 4H), 1.03-1.00 (m, 9H) ppm. |
| 49 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N9-((3'-(2-(2-(1-(methylsulfonyl)-1H-pyrrole-3-carboxamido)acetamido)thiazol-4-yl)-[1,1'-biphenyl]-3-yl)methyl)nonanediamide | 1092.5 | $^1$H NMR (400 MHz, methanol-d4) δ = 8.87 (s, 1H), 8.77-8.67 (m, 1H), 8.52-8.49 (m, 1H), 8.16 (s, 1H), 7.94-7.83 (m, 3H), 7.63-7.54 (m, 3H), 7.52-7.38 (m, 8H), 7.33-7.25 (m, 2H), 6.83-6.82 (m, 1H), 4.68 (d, J = 9.2 Hz, 1H), 4.70-4.56 (m, 1H), 4.54-4.44 (m, 3H), 4.40-4.33 (m, 1H), 4.32-4.23 (m, 2H), 3.94 (d, J = 11.4 Hz, 1H), 3.87-3.78 (m, 1H), 3.40 (s, 3H), 2.48-2.44 (m, 3H), 2.32-2.19 (m, 3H), 2.18-2.03 (m, 3H), 1.68-1.61 (m, 2H), 1.54-1.43 (m, 2H), 1.39-1.11 (m, 8H), 1.07 (s, 9H) ppm |
| 50 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N8-((3'-(2-(2-(1-(methylsulfonyl)-1H-pyrrole-3-carboxamido)acetamido)thiazol-4-yl)-[1,1'-biphenyl]-3-yl)methyl)octanediamide | 1078.1 | $^1$H NMR (400 MHz, methanol-d4) δ = 8.87 (s, 1H), 8.16 (d, J = 1.6 Hz, 1H), 7.91-7.84 (m, 2H), 7.80 (d, J = 8.8 Hz, 1H), 7.62-7.54 (m, 3H), 7.51-7.38 (m, 8H), 7.33-7.27 (m, 2H), 6.83-6.82 (m, 1H), 4.66-4.61 (m, 1H), 4.60-4.55 (m, 1H), 4.54-4.48 (m, 2H), 4.46 (s, 2H), 4.35 (d, J = 15.6 Hz, 1H), 4.29 (s, 2H), 3.96-3.89 (m, 1H), 3.82-3.79 (m, 1H), 3.40 (s, 3H), 2.47 (s, 3H), 2.28-2.25 (m, 2H), 2.22-2.17 (m, 3H), 2.12-2.05 (m, 1H), 1.69-1.62 (m, 2H), 1.57-1.49 (m, 2H), 1.36-1.27 (m, 4H), 1.04 (s, 9H) ppm |
| 51 | N-[2-[[4-[3-[3-[[11-[[2-(2,6-dioxo-3-piperidyl)-1,3-dioxo-isoindolin-4-yl]amino]undecanoylamino]methyl]-phenyl]phenyl]thiazol-2-yl]amino]-2-oxo-ethyl]-1-methylsulfonyl-pyrrole-3-carboxamide | 949.2 | $^1$H NMR (400 MHz, DMSO-d6) δ = 12.65-12.10 (m, 1H), 11.11-11.08 (m, 1H), 8.70-8.69 (m, 1H), 8.37-8.35 (m, 1H), 8.16 (s, 1H), 7.92-7.87(m, 1H), 7.85-7.84(m, 1H), 7.75 (s, 1H), 7.61-7.50 (m, 5H), 7.45-7.41 (m, 1H), 7.32-7.30 (m, 1H), 7.26 (d, J = 7.6 Hz, 1H), 7.07 (d, J = 8.8 Hz, 1H), 7.01 (d, J = 6.8 Hz, 1H), 6.78-6.76 (m, 1H), 6.52-6.49 (m, 1H), 5.05-5.02(m, 1H), 4.34 (d, J = 6.0 Hz, 2H), |

TABLE 10-continued

The following compounds were prepared using standard chemical manipulations and procedures similar to those used for the preparation of Compound 1

| Cmpd # | Name | LC-MS (ESI) (m/z) | $^1$H NMR |
|---|---|---|---|
| | | | 4.14 (d, J = 6.0 Hz, 2H), 3.57 (s, 3H), 3.28-3.23 (m, 2H), 2.91-2.82 (m, 1H), 2.62-2.58 (m, 1H), 2.55 (s, 1H), 2.15-2.12 (m, 2H), 2.03-1.99 (m, 1H), 1.54-1.51 (m, 4H), 1.33-1.18 (m, 12H) ppm |
| 52 | N-(2-((4-(3)-((11-((2-(2,6-dioxopiperidin-3-yl)-1,3-dioxoisoindolin-5-yl)amino)undecanamido)methyl)-[1,1'-biphenyl]-3-yl)thiazol-2-yl)amino)-2-oxoethyl)-1-(methylsulfonyl)-1H-pyrrole-3-carboxamide | 949.2 | $^1$H NMR (400 MHz, DMSO-$d_6$) δ = 12.40-12.32 (m, 1H), 11.11-11.03 (m, 1H), 8.69-8.68 (m, 1H), 8.37-8.34 (m, 1H), 8.16 (s, 1H), 7.90 (d, J = 7.6 Hz, 1H), 7.85-7.84(m, 1H), 7.73 (s, 1H), 7.57-7.50 (m, 5H), 7.45-7.42 (m, 1H), 7.31-7.30(m, 1H), 7.26 (d, J = 7.6 Hz, 1H), 7.08-7.06(m, 1H), 6.93 (d, J = 2.0 Hz, 1H), 6.83-6.81 (m, 1H), 6.78-6.76 (m, 1H), 5.04-4.99(m, 1H), 4.35 (d, J = 6.0 Hz, 2H), 4.14 (d, J = 5.6 Hz, 2H), 3.57 (s, 3H), 3.14-3.09 (m, 2H), 2.87-2.85 (m, 1H), 2.67-2.66 (m, 1H), 2.58 (d, J = 2.8 Hz, 1H), 2.16-2.12 (m, 2H), 2.00-1.96 (m, 1H), 1.55-1.52 (m, 4H), 1.22-1.21(m, 12H) ppm. |
| 54 | N-[2-[[4-[3-[3-[[9-[[2-(2,6-dioxo-3-piperidyl)-1,3-dioxo-isoindolin-5-yl]amino]nonanoylamino]methyl]-phenyl]phenyl]thiazol-2-yl]amino]-2-oxo-ethyl]-1-methylsulfonyl-pyrrole-3-carboxamide | 921.2 | $^1$H NMR (400 MHz, methanol-d4) δ = 8.16 (s, 1H), 7.88-7.82 (m, 2H), 7.61 (s, 1H), 7.56 (d, J = 8.8 Hz, 2H), 7.51 (d, J = 8.4 Hz, 1H), 7.48-7.38 (m, 3H), 7.31-7.25 (m, 2H), 6.90 (d, J = 2.0 Hz, 1H), 6.81-6.80 (m, 1H), 6.76-6.73 ( m, 1H), 5.05-5.00 (m, 1H), 4.45 (s, 2H), 4.26 (s, 2H), 3.37 (s, 3H), 3.08-3.04 (m, 2H), 2.90-2.77 (m, 1H), 2.75-2.67 (m, 2H), 2.28-2.24 (m, 2H), 2.13-2.04 (m, 1H), 1.70-1.61 (m, 3H), 1.56-1.47 (m, 2H), 1.41-1.31 (m, 4H), 1.24-1.10 (m, 3H) ppm |
| 55 | N-[2-[[4-[3-[3-[[3-[2-[2-[2-(2,6-dioxo-3-piperidyl)-1,3-dioxo-isoindolin-5-yl]oxyethoxy]ethoxy]propanoylamino]-methyl]phenyl]phenyl]thiazol-2-yl]amino]-2-oxo-ethyl]-1-methylsulfonyl-pyrrole-3-carboxamide | 926.2 | $^1$H NMR (400 MHz, methanol-d4) δ = 8.13 (s, 1H), 7.86-7.84 (m, 2H), 7.68 (d, J = 8.2 Hz, 1H), 7.62 (s, 1H), 7.54-7.46 (m, 2H), 7.50-7.44 (m, 2H), 7.41-7.36 (m, 1H), 7.33-7.28 (m, 2H), 7.23 (d, J = 2.6 Hz, 1H), 7.14 (d, J = 2.42 Hz, 1H), 6.83 (d, J = 3.6 Hz, 1H), 5.09 (d, J = 5.6, 1H), 4.49 (s, 2H), 4.29 (s, 2H), 4.06-3.97 (m, 2H), 3.80-3.78 (m, 2H), 3.69-3.64 (m, 2H), 3.62-3.58 (m, 2H), 3.56-3.53 (m, 2H), 3.41 (s, 3H), 2.92-2.80 (m, 1H), 2.78-2.63 (m, 2H), 2.53 (d, J = 5.6 Hz, 2H), 2.16-2.06 (m, 1H) ppm. |
| 56 | N'-[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]-N-[[3-[3-[2-[[2-[(1-methylsulfonylpyrrole-3-carbonyl)amino]acetyl]amino]thiazol-4-yl]phenyl]phenyl]methyl]pentanediamide | 1036.1 | $^1$H NMR (400 MHz, DMSO-d6) δ = 12.72-12.15 (m, 1H), 9.01-8.95 (m, 1H), 8.99 (s, 1H), 8.74-8.64 (m, 1H), 8.61-8.53 (m, 1H), 8.49-8.44 (m, 1H), 8.41-8.34 (m, 1H), 8.21-8.14 (m, 1H), 7.94-7.87 (m, 2H), 7.87-7.84 (m, 1H), 7.79-7.71 (m, 1H), 7.62-7.57 (m, 3H), 7.56-7.50 (m, 1H), 7.48-7.36 (m, 5H), 7.33-7.30 (m, 1H), 7.30-7.26 (m, 1H), 6.83-6.74 (m, 1H), 5.18-5.10 (m, 1H), 4.54 (d, J = 9.2 Hz, 1H), 4.58-4.51 (m, 1H), 4.48-4.40 (m, 2H), 4.48-4.39 (m, 2H), 4.35 (d, J = 5.6 Hz, 2H), 4.39-4.31 (m, 1H), 4.27-4.19 (m, 1H), 4.26-4.18 (m, 1H), 4.18-4.11 (m, 1H), 4.15 (d, J = 5.6 Hz, 1H), 3.72-3.62 (m, 1H), 3.70-3.62 (m, 1H), 3.69-3.62 (m, 1H), 3.61-3.56 (m, 3H), 2.45 (s, 3H), 2.30-2.14 (m, 4H), 2.09-1.99 (m, 1H), 1.90 (m, 1H), 1.82-1.70 (m, 2H), 0.97-0.89 (m, 9H) ppm. |
| 57 | N-(2-((4-(3'-((5-((2-(2,6-dioxopiperidin-3-yl)-1,3-dioxoisoindolin-4-yl)oxy)pentanamido)methyl)-[1,1'-biphenyl]-3-yl)thiazol-2-yl)amino)-2-oxoethyl)-1-(methylsulfonyl)-1H-pyrrole-3-carboxamide | 866.2 | $^1$H NMR (400 MHz, DMSO-$d_6$) δ = 12.44-12.43 (m, 1H), 11.17-11.04 (m, 1H), 8.74-8.63 (m, 1H), 8.46-8.36 (m, 1H), 8.21-8.10 (m, 1H), 7.92-7.74 (m, 4H), 7.61-7.42 (m, 7H), 7.34-7.25 (m, 2H), 6.78 ( s, 1H), 5.12-4.99 (m, 1H), 4.37-4.36 (m, 2H), 4.21-4.11 (m, 4H), 3.59-3.58 (m, 3H), 2.89-2.84 (m, 2H), 2.68-2.67 (m, 3H), 2.29-2.24 (m, 2H), 2.11-1.94 (m, 2H), 1.82-1.76 (m, 4H) ppm. |
| 59 | N-(2-((4-(3'-((8-((2-(2,6-dioxopiperidin-3-yl)-1,3-dioxoisoindolin-4-yl)oxy)octanamido)methyl)-[1,1'-biphenyl]-3-yl)thiazol-2-yl)amino)-2-oxoethyl)-1- | 908.4 | $^1$H NMR (400 MHz, DMSO-$d_6$) δ = 11.32 (s, 1H), 8.76-8.64 (m, 1H), 8.44-8.32 (m, 1H), 8.17 (s, 1H), 7.93-7.83 (m, 2H), 7.83-7.76 (m, 1H), 7.75 (s, 1H), 7.61-7.49 (m, 4H), 7.49-7.38 (m, 3H), 7.32-7.31 (m, 1H), 7.27-7.26 (m, 1H), 6.82-6.74 (m, 1H), 5.12-5.02 (m, |

TABLE 10-continued

The following compounds were prepared using standard chemical manipulations and procedures similar to those used for the preparation of Compound 1

| Cmpd # | Name | LC-MS (ESI) (m/z) | $^1$H NMR |
|---|---|---|---|
| | (methylsulfonyl)-1H-pyrrole-3-carboxamide | | 1H), 4.43-4.30 (m, 2H), 4.21-4.04 (m, 4H), 3.62-3.54 (m, 3H), 2.94-2.81 (m, 1H), 2.62-2.54 (m, 2H), 2.17-2.16 (m, 2H), 2.07-1.98 (m, 1H), 1.75-1.64 (m, 2H), 1.61-1.50 (m, 2H), 1.45-1.36 (m, 2H), 1.33-1.30 (m, 3H) ppm. |
| 61 | N-[2-[[4-[3-[3-[[[2-[[[2-[2-(2,6-dioxo-3-piperidyl)-1,3-dioxo-isoindolin-5-yl]oxyacetyl]amino]methyl]-cyclopropanecarbonyl]amino]methyl]-phenyl]phenyl]thiazol-2-yl]amino]-2-oxo-ethyl]-1-methylsulfonyl-pyrrole-3-carboxamide | 921.2 | $^1$H NMR (400 MHz, DMSO-d6) δ = 11.38-10.37 (m, 1H), 8.69-8.63 (m, 2H), 8.36 (s, 1H), 8.25-8.21 (m, 1H), 8.16 (s, 1H), 7.90 (d, J = 7.6 Hz, 1H), 7.85-7.83 (m, 2H), 7.74 (s, 1H), 7.60-7.57 (m, 3H), 7.54-7.50 (m, 1H), 7.46-7.43 (m, 2H), 7.37-7.35 (m, 1H), 7.32-7.29 (m, 2H), 6.78-6.77 (m, 1H), 5.14-5.09 (m, 1H), 4.69 (s, 2H), 4.40 (d, J = 5.6 Hz, 2H), 4.15 (d, J = 5.6 Hz, 2H), 3.57 (s, 3H), 3.18-3.14 (m, 1H), 2.95-2.81 (m, 1H), 2.61-2.57 (m, 3H), 2.07-2.02 (m, 1H), 1.78-1.73 (m, 1H), 1.42-1.35 (m, 1H), 0.93-0.88 (m, 2H) ppm. |
| 62 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N7-((3'-(2-(2-(1-(methylsulfonyl)-1H-pyrrole-3-carboxamido)acetamido)thiazol-4-yl)-[1,1'-biphenyl]-3-yl)methyl)heptanediamide | 1064.1 | $^1$H NMR (400 MHz, DMSO-d6) δ = 12.37-12.28 (m, 1H), 8.97 (s, 1H), 8.68-8.65 (m, 1H), 8.56-8.53 (m, 1H), 8.35-8.32 (m, 1H), 8.16 (s, 1H), 7.89 (d, J = 7.6 Hz, 1H), 7.85-7.81 (m, 2H), 7.74 (s, 1H), 7.57-7.50 (m, 4H), 7.46-7.36 (m, 5H), 7.31-7.30 (m, 1H), 7.26 (d, J = 7.6 Hz, 1H), 6.78-6.77 (m, 1H), 5.11 (s, 1H), 4.53 (d, J = 9.6 Hz, 1H), 4.45-4.40 (m, 2H), 4.34 (d, J = 6.0 Hz, 3H), 4.24-4.18 (m, 1H), 4.14 (d, J = 5.6 Hz, 2H), 3.68-3.60(m, 2H), 3.57 (s, 3H), 2.43 (s, 3H), 2.27-2.20 (m, 1H), 2.15-2.00 (m, 4H), 1.93-1.86 (m, 1H), 1.56-1.40(m, 4H), 1.28-1.20 (m, 2H), 0.92-0.88 (m, 9H) ppm. |
| 63 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N4-((3'-(2-(2-(1-(methylsulfonyl)-1H-pyrrole-3-carboxamido)acetamido)thiazol-4-yl)-[1,1'-biphenyl]-3-yl)methyl)succinamide | 1022.3 | $^1$H NMR (400 MHz, methanol-d4) δ = 8.86 (s, 1H), 8.64-8.62 (m, 1H), 8.50-8.47 (m, 1H), 8.17-8.17 (m , 1H), 7.96 (d, J = 8.8 Hz, 1H), 7.87 (d, J = 8.0 Hz, 1H), 7.84-7.83 (m, 1H), 7.61 (s, 1H), 7.59-7.54 (m, 2H), 7.49-7.34 (m, 7H), 7.30-7.27 (m, 2H), 6.81-6.80 (m, 1H), 4.61-4.31 (m, 8H), 4.26 (s, 2H), 3.83 (d, J = 11.2 Hz, 1H), 3.72-3.68 (m, 1H), 3.38 (s, 3H), 2.68-2.53 (m, 4H), 2.45 (s, 3H), 2.21-2.16 (m, 1H), 2.06-1.99 (m, 1H), 0.98 (s, 9H) ppm |
| 64 | N-[2-[[4-[3-[3-[[3-[2-[2-[2-(2,6-dioxo-3-piperidyl)-1,3-dioxo-isoindolin-4-yl]oxyethoxy]ethoxy]propanoylamino]-methyl]phenyl]phenyl]thiazol-2-yl]amino]-2-oxo-ethyl]-1-methylsulfonyl-pyrrole-3-carboxamide | 926.0 | $^1$H NMR (400 MHz, methanol-d4) δ = 8.48-8.46 (m, 1H), 8.11-8.10 (m, 1H), 7.84-7.81 (m, 2H), 7.63-7.59 (m, 2H), 7.53-7.49 (m, 2H), 7.45-7.41 (m, 2H), 7.39-7.33 (m, 2H), 7.27-7.26 (m, 2H), 7.22 (d, J = 8.8 Hz, 1H), 6.81-6.80 (m, 1H), 5.05-5.01 (m, 1H), 4.45 (s, 2H), 4.26 (s, 2H), 4.12-4.10 (m, 2H), 3.79-3.76 (m, 2H), 3.70-3.68 (m, 2H), 3.61-3.56 (m, 4H), 3.38 (s, 3H), 2.85-2.57 (m, 3H), 2.52-2.49 (m, 2H), 2.06-2.02 (m, 1H) ppm. |
| 65 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N11-((3'-(2-(2-(1-(methylsulfonyl)-1H-pyrrole-3-carboxamido)acetamido)thiazol-4-yl)-[1,1'-biphenyl]-3-yl)methyl)undecanediamide | 1120.1 | $^1$H NMR (400 MHz, DMSO-d6) δ = 12.36 (br s, 1H), 9.03-8.94 (m, 1H), 8.71-8.69 (m, 1H), 8.59-8.57 (m, 1H), 8.44-8.34 (m, 1H), 8.17 (s, 1H), 7.93-7.83 (m, 3H), 7.78-7.73 (m, 1H), 7.61-7.50 (m, 4H), 7.47-7.36 (m, 5H), 7.32-7.31 (m, 1H), 7.27 (d, J = 7.6 Hz, 1H), 6.79-6.78 (m, 1H), 5.15 (s, 1H), 4.55-4.53 (m, 1H), 4.49-4.39 (m, 2H), 4.35-4.34 (m, 3H), 4.23-4.21 (m, 1H), 4.15-4.14 (m, 2H), 3.70-3.62 (m, 2H), 3.58 (s, 3H), 2.44 (s, 3H), 2.29-1.98 (m, 6H), 1.91-1.89 (m, 1H), 1.55-1.40 (m, 4H), 1.25-1.14 (m, 10H), 0.93 (s, 8H) ppm |
| 114 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N13-((3'-(2-(2-(1-(methylsulfonyl)-1H-pyrrole-3-carboxamido)acetamido)thiazol-4-yl)-[1,1'-biphenyl]-3- | 1148.7 | $^1$H NMR (400 MHz, DMSO-$d_6$) δ = 12.47 (s, 1H), 8.99 (s, 1H), 8.72-8.69 (d, J = 6.0 Hz, 1H), 8.60-8.57 (d, J = 6.0 Hz, 1H), 8.39-8.36 (d, J = 6.0 Hz, 1H), 8.17 (s, 1H), 7.92-7.85 (m, 3H), 7.76 (s, 1H), 7.59-7.58 (m, 3H), 7.55-7.51 (d, J = 8.0 Hz, 1H), 7.47-7.26 (m, 7H), 6.79-6.78 (m, 1H), 5.15-5.14 (d, J = 4.0 Hz, 1H), 4.56-4.53 (d, J = 9.6 Hz, 1H), 4.47-4.40 |

TABLE 10-continued

| Cmpd # | Name | LC-MS (ESI) (m/z) | $^1$H NMR |
|---|---|---|---|
| | yl)methyl)tridecanediamide | | (m, 2H), 4.36-4.34 (d, J = 6.0 Hz, 3H), 4.24-4.14 (m, 3H), 3.67-3.66 (m, 2H), 3.59 (s, 3H), 2.45 (s, 3H), 2.24-1.87 (m, 7H), 1.54-1.44 (m, 4H), 1.25-1.16 (m, 14H), 0.93 (s, 9H) ppm. |
| 118 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N14-((3'-(2-(2-(1-(methylsulfonyl)-1H-pyrrole-3-carboxamido)acetamido)thiazol-4-yl)-[1,1'-biphenyl]-3-yl)methyl)tetradecanediamide | 1162.8 | $^1$H NMR (400 MHz, methanol-d4) δ = 8.86 (s, 1H), 8.19-8.14 (m, 1H), 7.90-7.86 (m, 1H), 7.85-7.83 (m, 1H), 7.61 (s, 1H), 7.58-7.54 (m, 2H), 7.49-7.43 (m, 4H), 7.42-7.37 (m, 3H), 7.31-7.26 (m, 2H), 6.86-6.77 (m, 1H), 4.64 (s, 1H), 4.61-4.55 (m, 2H), 4.53-4.47 (m, 2H), 4.45 (s, 2H), 4.37-4.30 (m, 1H), 4.28 (d, J = 3.2 Hz, 2H), 3.94-3.88 (m, 1H), 3.84-3.77 (m, 1H), 3.38 (s, 3H), 2.45 (s, 3H), 2.29-2.21 (m, 4H), 2.12-2.02 (m, 1H), 1.69-1.51 (m, 4H), 1.31-1.15 (m, 16H), 1.04 (s, 9H) ppm |
| 119 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N12-((3'-(2-(2-(1-(methylsulfonyl)-1H-pyrrole-3-carboxamido)acetamido)thiazol-4-yl)-[1,1'-biphenyl]-3-yl)methyl)dodecanediamide | 1134.8 | $^1$H NMR (400 MHz, DMSO-d6) δ = 12.42 (s, 1H), 8.98 (s, 1H), 8.68-8.65 (m, 1H), 8.55-8.52 (m, 1H), 8.36-8.33 (m, 1H), 8.17 (s, 1H), 7.91 (d, J = 7.6 Hz, 1H), 7.84-7.83 (m, 1H), 7.82 (d, J = 9.2 Hz, 1H), 7.74 (s, 1H), 7.57 (s, 3H), 7.54 (d, J = 7.6 Hz, 1H), 7.44-7.42 (m, 2H), 7.41-7.39 (m, 3H), 7.33-7.31 (m, 1H), 7.27 (d, J = 7.6 Hz, 1H), 6.78-6.77 (m, 1H), 4.54 (d, J = 9.2 Hz, 1H), 4.44-4.40 (m, 2H), 4.35 (d, J = 5.6 Hz, 3H), 4.23-4.18 (m, 1H), 4.15 (d, J = 6.0 Hz, 2H), 3.65-3.62 (m, 4H), 3.57 (s, 3H), 2.44 (s, 3H), 2.27-2.00 (m, 4H), 1.93-1.88 (m, 1H), 1.52 (d, J = 6.8 Hz, 4H), 1.22-1.18 (m, 12H), 0.93 (s, 9H) ppm |
| 120 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N16-((3'-(2-(2-(1-(methylsulfonyl)-1H-pyrrole-3-carboxamido)acetamido)thiazol-4-yl)-[1,1'-biphenyl]-3-yl)methyl)hexadecanediamide | 1190.5 | $^1$H NMR (400 MHz, DMSO-d6) δ = 12.68-12.05 (m, 1H), 8.97 (s, 1H), 8.68-8.65 (m, 1H), 8.56-8.52 (m, 1H), 8.36-8.33 (m, 1H), 8.16 (s, 1H), 7.90 (d, J = 7.6 Hz, 1H), 7.86-7.78 (m, 2H), 7.74 (s, 1H), 7.61-7.55 (m, 3H), 7.55-7.49 (m, 1H), 7.47-7.35 (m, 5H), 7.33-7.29 (m, 1H), 7.26 (d, J = 7.2 Hz, 1H), 6.78-6.77 (m, 1H), 5.11 (d, J = 2.8 Hz, 1H), 4.54 (d, J = 9.2 Hz, 1H), 4.47-4.38 (m, 2H), 4.34 (d, J = 5.6 Hz, 3H), 4.24-4.18 (m, 1H), 4.14 (d, J = 5.6 Hz, 2H), 3.71-3.60 (m, 2H), 3.57 (s, 3H), 2.44 (s, 3H), 2.29-2.21 (m, 1H), 2.17-1.99 (m, 4H), 1.93-1.86 (m, 1H), 1.57-1.38 (m, 4H), 1.19 (d, J = 4.4 Hz, 20H), 0.93 (s, 9H) ppm. |
| 121 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N14-((3'-(2-(2-(1-(methylsulfonyl)-1H-pyrrole-3-carboxamido)acetamido)thiazol-4-yl)-[1,1'-biphenyl]-3-yl)methyl)-3,6,9,12-tetraoxatetradecane-1,14-diamide | 1170.6 | $^1$H NMR (400 MHz, DMSO-d6) δ = 8.97 (s, 1H), 8.72-8.71 (m, 1H), 8.60-8.59 (m, 1H), 8.31-8.30 (m, 1H), 8.17 (s, 1H), 7.96-7.83 (m, 2H), 7.74 (s, 1H), 7.67-7.26 (m, 13H), 6.79-6.78 (m, 1H), 4.57-4.56 (m, 1H), 4.48-4.34 (m, 5H), 4.26-4.25 (m, 2H), 4.16-4.15 (m, 2H), 3.96-3.95 (m, 4H), 3.62-3.49 (m, 17H), 2.44 (s, 3H), 2.11-2.03 (m, 1H), 1.96-1.86 (m, 1H), 0.94 (s, 9H) ppm. |
| 124 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N17-((3'-(2-(2-(1-(methylsulfonyl)-1H-pyrrole-3-carboxamido)acetamido)thiazol-4-yl)-[1,1'-biphenyl]-3-yl)methyl)heptadecanediamide | 1204.6 | $^1$H NMR (400 MHz, methanol-d4) δ = 8.90-8.84 (m, 1H), 8.68-8.45 (m, 1H), 8.21-8.15 (m, 1H), 7.91-7.79 (m, 3H), 7.64-7.61 (m, 1H), 7.60-7.55 (m, 2H), 7.49-7.41 (m, 6H), 7.33-7.27 (m, 2H), 6.85-6.81 (m, 1H), 4.69-4.64 (m, 1H), 4.63-4.56 (m, 2H), 4.54-4.45 (m, 4H), 4.39-4.32 (m, 1H), 4.31-4.26 (m, 2H), 3.96-3.89 (m, 1H), 3.85-3.78 (m, 1H), 3.41-3.38 (m, 3H), 2.51-2.45 (m, 3H), 2.32-2.20 (m, 5H), 2.15-2.04 (m, 1H), 1.70-1.56 (m, 4H), 1.33-1.18 (m, 23H), 1.07-1.01 (m, 9H) ppm. |
| 126 | N'-[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]-N-[[3-[3-[2-[[2-[(1-methylsulfonylpyrrole-3-carbonyl)amino]acetyl]amino]thiazol-4-yl]phenyl]phenyl]methyl]pentadecanediamide | 1176.5 | $^1$H NMR (400 MHz, DMSO-d6) δ = 12.41 (s, 1H), 8.98 (s, 1H), 8.66-8.72 (m, 1H), 8.55-8.60 (m, 1H), 8.40-8.35 (m, 1H), 8.16 (s, 1H), 7.92-7.83(m, 3H), 7.75 (s, 1H), 7.60-7.55 (m, 3H), 7.54-7.49 (m, 1H), 7.45-7.42 (m, 1H), 7.41-7.36 (m, 3H), 7.33-7.23 (m, 2H), 6.78-6.76 (m, 1H), 5.13 (d, J = 3.6 Hz, 1H), 4.54 (d, J = 9.2 Hz, 1H), 4.47-4.38 (m, 2H), 4.35 (d, J = 5.6 Hz, 3H), 4.23-4.11 (m, 3H), 3.68-3.61 (m, 2H), 3.57 (s, 3H), 2.43 (s, 3H), 2.26 2.15 (m, 1H), |

The following compounds were prepared using standard chemical manipulations and procedures similar to those used for the preparation of Compound 1

TABLE 10-continued

The following compounds were prepared using standard chemical manipulations and procedures similar to those used for the preparation of Compound 1

| Cmpd # | Name | LC-MS (ESI) (m/z) | $^1$H NMR |
|---|---|---|---|
| | | | 2.13-1.97 (m, 5H), 1.91 1.87 (m, 1H), 1.51-1.40 (m, 4H), 1.50 1.20 (m, 18H), 0.92 (s, 9H) ppm. |
| 137 | N2-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N6-[[3'-(2-[2-[(1-methanesulfonylpyrrol-3-yl)formamido]acetamido]-1,3-thiazol-4-yl)-[1,1'-biphenyl]-3-yl]methyl]spiro[3.3]heptane-2,6-dicarboxamide | 1088.20 | $^1$H NMR (300 MHz, DMSO-d6) δ 12.45 (s, 1H), 8.99 (s, 1H), 8.69 (d, J = 5.8 Hz, 1H), 8.58 (s, 1H), 8.25 (s, 1H), 8.17 (s, 1H), 7.91 (d, J = 7.3 Hz, 1H), 7.86 (s, 1H), 7.77 (s, 1H), 7.72-7.66 (m, 1H), 7.55 (d, J = 8.4 Hz, 4H), 7.42 (dd, J = 12.2, 4.1 Hz, 5H), 7.32 (t, J = 2.8 Hz, 1H), 7.25 (d, J = 7.5 Hz, 1H), 6.78 (d, J = 3.2 Hz, 1H), 5.14 (d, J = 3.4 Hz, 1H), 4.52-4.13 (m, 9H), 3.66 (s, 2H), 3.58 (s, 3H), 3.10 (t, J = 8.2 Hz, 1H), 2.93 (t, J = 8.4 Hz, 1H), 2.45 (s, 3H), 2.18 (s, 3H), 2.12-1.84 (m, 7H), 0.92 (s, 9H). |
| 138 | 1-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-N-[[3-(2-[2-[(1-methanesulfonylpyrrol-3-yl)formamido]acetamido]-1,3-thiazol-4-yl)-[1,1-biphenyl]-3-yl]methyl]piperidine-4-carboxamide | 1091.25 | $^1$H NMR (400 MHz, DMSO-d6 + D2O) δ 8.96 (s, 1H), 8.69 (d, J = 9.2 Hz, 1H), 8.14 (d, J = 1.9 Hz, 1H), 7.92-7.86 (m, 1H), 7.83 (t, J = 2.0 Hz, 1H), 7.71 (s, 1H), 7.62-7.49 (m, 4H), 7.48-7.35 (m, 5H), 7.31 (dd, J = 3.3, 2.3 Hz, 1H), 7.26 (d, J = 7.7 Hz, 1H), 6.77 (dd, J = 3.3, 1.7 Hz, 1H), 4.56 (d, J = 9.1 Hz, 1H), 4.46-4.30 (m, 5H), 4.28-4.09 (m, 4H), 4.08-3.84 (m, 2H), 3.62 (d, J = 10.7 Hz, 1H), 3.53 (s, 5H), 3.25 (s, 1H), 3.11-2.93 (m, 2H), 2.76 (s, 1H), 2.43 (s, 3H), 2.04 (s, 1H), 1.93 (dd, J = 9.1, 4.2 Hz, 5H), 0.94 (s, 9H). |
| 159 | N1-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N2-[[3-(2-[2-[(1-methanesulfonylpyrrol-3-yl)formamido]acetamido]-1,3-thiazol-4-yl)-[1,1-biphenyl]-3-yl]methyl]cyclopropane-1,2-dicarboxamide | 1034.50 | $^1$H NMR (400 MHz, DMSO-d6) δ 12.45 (s, 1H), 8.99 (s, 1H), 8.80 (t, J = 5.4 Hz, 1H), 8.70 (t, J = 5.9 Hz, 1H), 8.58 (dt, J = 13.4, 6.0 Hz, 1H), 8.39 (dd, J = 14.9, 9.1 Hz, 1H), 8.18 (d, J = 2.0 Hz, 1H), 7.95-7.89 (m, 1H), 7.89-7.83 (m, 1H), 7.77 (d, J = 3.9 Hz, 1H), 7.62-7.51 (m, 4H), 7.49-7.38 (m, 5H), 7.35-7.26 (m, 2H), 6.78 (dd, J = 3.3, 1.6 Hz, 1H), 5.13 (dd, J = 3.7, 1.8 Hz, 1H), 4.55-4.34 (m, 6H), 4.25-4.13 (m, 4H), 3.58 (s, 5H), 2.45 (d, J = 1.8 Hz, 3H), 2.39 (dt, J = 8.2, 4.1 Hz, 2H), 2.11-1.98 (m, 3H), 1.90 (ddd, J = 12.8, 8.5, 4.9 Hz, 2H), 1.13-1.00 (m, 3H), 0.95 (d, J = 3.2 Hz, 9H). |
| 163 | 2-([[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]methyl)-N-[[3-(2-[2-[(1-methanesulfonylpyrrol-3-yl)formamido]acetamido]-1,3-thiazol-4-yl)-[1,1-biphenyl]-3-yl]methyl]-2-azaspiro[3.3]heptane-6-carboxamide | 1103.20 | $^1$H NMR (400 MHz, DMSO-d6) δ 8.97 (s, 1H), 8.70 (s, 1H), 8.61 (s, 1H), 8.29 (s, 1H), 8.21 (s, 1H), 8.17 (s, 1H), 7.91 (d, J = 7.6 Hz, 1H), 7.85 (t, J = 1.9 Hz, 1H), 7.76 (s, 1H), 7.61-7.51 (m, 5H), 7.40 (s, 5H), 7.33-7.31 (m, 1H), 7.25 (d, J = 7.4 Hz, 1H), 6.79 (s, 1H), 4.50 (d, J = 9.2 Hz, 1H), 4.42 (d, J = 8.4 Hz, 2H), 4.35 (s, 4H), 4.28 (s, 2H), 4.15 (d, J = 5.5 Hz, 3H), 3.58 (s, 5H), 3.21 (s, 2H), 2.44 (s, 3H), 2.35-2.22 (m, 4H), 1.91 (d, J = 7.8 Hz, 2H), 1.76 (s, 1H), 0.93 (s, 9H). |
| 166 | (2S,4R)-4-hydroxy-1-[(2S)-2-(2-[6-[([[3'-(2-[2-[(1-methanesulfonylpyrrol-3-yl)formamido]acetamido]-1,3-thiazol-4-yl)-[1,1'-biphenyl]-3-yl]methyl]carbamoyl)methyl]-2,6-diazaspiro[3.3]heptan-2-yl]acetamido)-3,3-dimethylbutanoyl]-N-[[4-(4-methyl-1,3-thiazol-5-yl)phenyl]methyl]pyrrolidine-2-carboxamide trifluoroacetate | 1118.60 | $^1$H NMR (400 MHz, DMSO-d6) δ 12.44 (s, 1H), 9.00 (d, J = 4.5 Hz, 2H), 8.72 (t, J = 6.0 Hz, 2H), 8.61 (t, J = 6.1 Hz, 1H), 8.17 (d, J = 1.9 Hz, 1H), 7.92 (dt, J = 7.4, 1.6 Hz, 1H), 7.85 (t, J = 2.0 Hz, 1H), 7.77 (s, 1H), 7.65-7.52 (m, 4H), 7.51-7.46 (m, 1H), 7.40 (q, J = 8.3 Hz, 4H), 7.35-7.28 (m, 2H), 6.78 (dd, J = 3.3, 1.7 Hz, 1H), 5.18 (s, 1H), 4.57 (d, J = 9.4 Hz, 1H), 4.49-3.93 (m, 21H), 3.69 (d, J = 6.9 Hz, 1H), 3.58 (s, 3H), 2.45 (s, 3H), 2.07 (d, J = 8.2 Hz, 1H), 1.96-1.87 (m, 1H), 0.95 (s, 9H). |
| 117 | N-(2-((4-(3'-((S)-15-((2S,4R)-4-hydroxy-2-((4-(4-methylthiazol-5-yl)benzyl)carbamoyl)pyrrolidine-1-carbonyl)-16,16-dimethyl-3,13-dioxo-5,8,11-trioxa-2,14-diazaheptadecyl)-[1,1'-biphenyl]-3-yl)thiazol-2-yl)amino)-2-oxoethyl)-1-(methylsulfonyl)-1H-pyrrole-3-carboxamide | 1126.6 | N$^1$H NMR (400 MHz, DMSO-d6) δ = 12.40 (s, 1H), 8.97 (s, 1H), 8.67-8.59 (m, 2H), 8.33-8.30 (m, 1H), 8.17 (s, 1H), 7.90 (d, J = 7.6 Hz, 1H), 7.89-7.84 (m, 1H), 7.76-7.66 (m, 1H), 7.63-7.56 (m, 3H), 7.54-7.52 (m, 1H), 7.46-7.44 (m, 2H), 7.39 (s, 4H), 7.32-7.28 (m, 2H), 6.79-6.77 (m, 1H), 5.18 (d, J = 3.2 Hz, 1H), 4.56 (d, J = 9.6 Hz, 1H), 4.45-4.35 (m, 5H), 4.28-4.22 (m, 1H), 4.12 (d, J = 4.8 Hz, 2H), 3.97-3.89 (m, 4H), 3.68-3.53 (m, 13H), 2.45-2.43 (m, 3H), 2.08-2.03(m, 1H), 1.93-1.86 (m, 1H), 0.92-0.90 (m, 9H) ppm |

Preparation of 2-(methyl(4-(3-(2-(2-(1-(methylsulfonyl)-1H-pyrrole-3-carboxamido)acetamido)thiazol-4-yl)phenyl)pyridin-2-yl)amino)acetic acid (I-94)

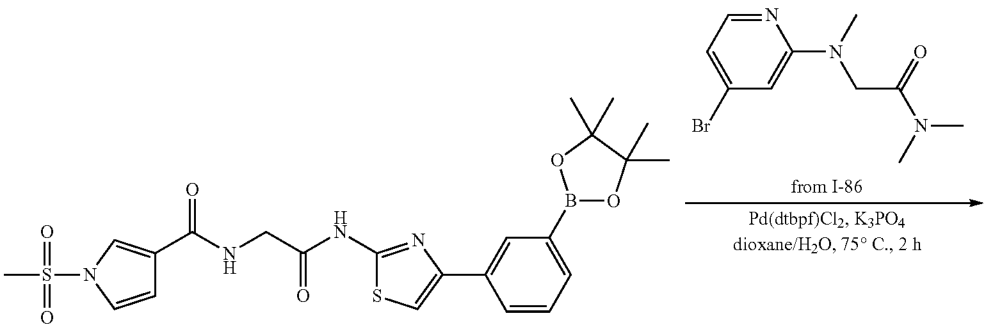

I-90

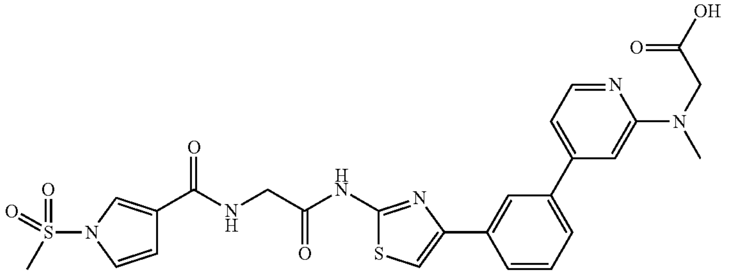

I-94

To a mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (I-90, 100 mg, 0.188 mmol) and 2-[(4-bromo-2-pyridyl)-methyl-amino]-N,N-dimethylacetamide (from I-86, 51.31 mg, 0.188 mmol) in 1,4-dioxane (2 mL)/water (0.5 mL) was added di-tert-butyl (cyclopentyl)phosphane dichloropalladium(II) (12.29 mg, 0.018 mmol) and $K_3PO_4$ (120.06 mg, 0.57 mmol) at 30° C. under nitrogen. The reaction mixture stirred at 75° C. for 2 h, then concentrated under reduced pressure. The residue was purified by reverse phase HPLC (0.1% formic acid in water/ACN) (column: Phenomenex Synergi C18 150×25×10 μm) to afford I-94 (10 mg, 8.63%) as a white solid. LCMS (ESI) m/z: $[M+H]^+$=569.3. $^1$H NMR (400 MHz, DMSO-d6) δ=12.40 (br s, 1H), 8.69-8.66 (m, 1H), 8.21 (s, 1H), 8.14 (d, J=5.2 Hz, 1H), 7.97 (d, J=7.6 Hz, 1H), 7.87-7.78 (m, 2H), 7.69 (d, J=7.6 Hz, 1H), 7.61-7.52 (m, 1H), 7.32-7.30 (m, 1H), 6.96-6.85 (m, 2H), 6.77 (br s, 1H), 4.31 (s, 2H), 4.15 (d, J=5.6 Hz, 2H), 3.56 (s, 3H), 3.13 (s, 3H) ppm.

Compound 9—Preparation of N-(2-((4-(3-(2-((2-((2-(2-(2-((2-(2,6-dioxopiperidin-3-yl)-1,3-dioxoisoindolin-4-yl)amino)ethoxy)ethoxy)ethyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide

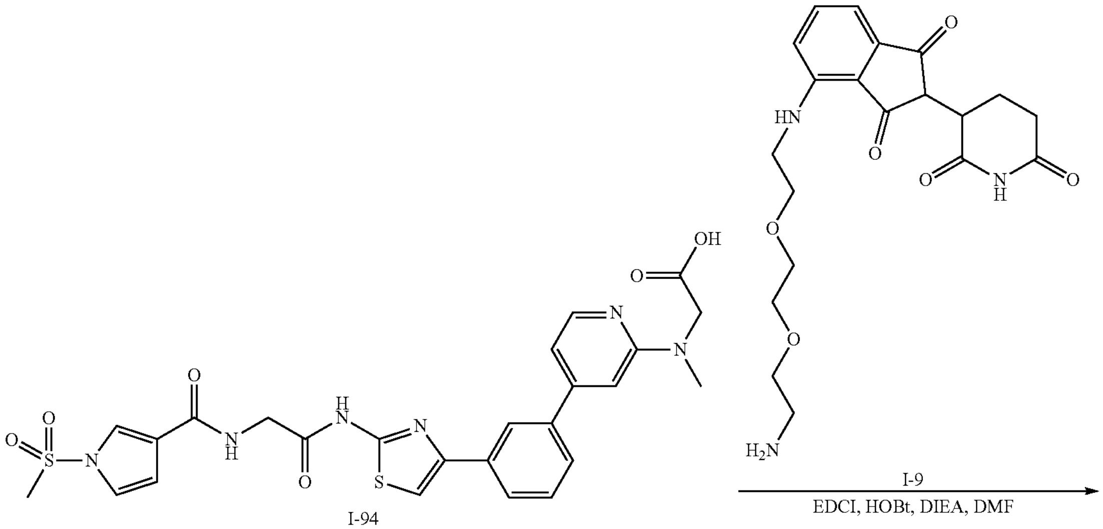

I-94

-continued

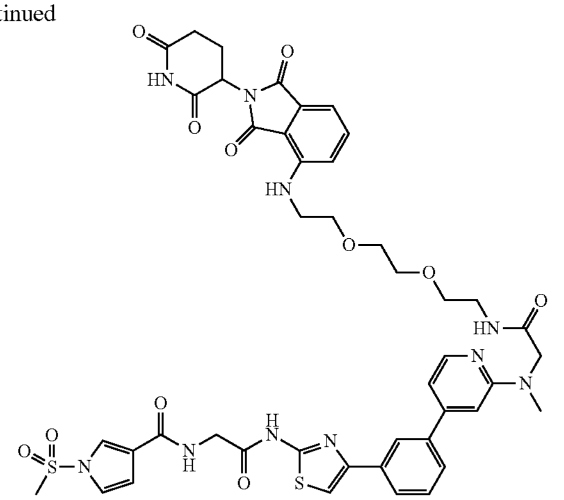

9

To a solution of 2-[methyl-[4-[3-[2-[[2-[(1-methylsulfonylpyrrole-3-carbonyl)amino]acetyl]amino]thiazol-4-yl] phenyl]-2-pyridyl]amino]acetic acid (I-94, 50 mg, 0.082 mmol), DIEA (42.72 mg, 0.33 mmol, 57.57 μL), EDCI (15.84 mg, 0.082 mmol), and HOBt (11.16 mg, 0.082 mmol) in DMF (1 mL) was added 4-[2-[2-(2-aminoethoxy)ethoxy] ethylamino]-2-(2,6-dioxo-3-piperidyl)isoindoline-1,3-dione (I-9, 42.84 mg, 0.082 mmol). The mixture was stirred at 25° C. for 2 h, then poured into water (40 mL), filtered, triturated with water (10 mL×2), and dried under vacuum to give Compound 9 (27.03 mg, 32.88%) as a yellow solid. LCMS (ESI) m/z: $[M+H]^+$=955.3. $^1$H NMR (400 MHz, DMSO-$d_6$) δ=12.40 (s, 1H), 11.08 (s, 1H), 8.69-8.66 (m, 1H), 8.20-8.13 (m, 2H), 7.97 (d, J=8.0 Hz, 1H), 7.87-7.84 (m, 2H), 7.78 (s, 1H), 7.67 (d, J=8.0 Hz, 1H), 7.59-7.53 (m, 2H), 7.32-7.31 (m, 1H), 7.11 (d, J=8.8 Hz, 1H), 7.03 (d, J=6.8 Hz, 1H), 6.92 (d, J=5.2 Hz, 1H), 6.86 (s, 1H), 6.78-6.77 (m, 1H), 6.60-6.57 (m, 1H), 5.07-5.02 (m, 1H), 4.21-4.14 (m, 4H), 3.60-3.58 (m, 5H), 3.51-3.50 (m, 4H), 3.45-3.40 (m, 4H), 3.25-3.22 (m, 2H), 3.12 (s, 3H), 2.88-2.86 (m, 1H), 2.59 (s, 2H), 2.06-1.98 (m, 1H) ppm.

TABLE 11

The following compounds were prepared using standard chemical manipulations and procedures similar to those used for the preparation of Compound 9

| Cmpd # | Name | LC-MS (ESI) (m/z) | $^1$H NMR |
|---|---|---|---|
| 15 | N-(2-((4-(3-(2-((2-((8-(2-((2-(2,6-dioxopiperidin-3-yl)-1,3-dioxoisoindolin-4-yl)oxy)acetamido)octyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 1009.4 | $^1$H NMR (400 MHz, DMSO-$d_6$) δ = 12.47-12.37 (m, 1H), 11.11 (s, 1H), 8.68-8.65 (m, 1H), 8.20-8.13 (m, 2H), 7.96 (d, J = 7.2 Hz, 1H), 7.90-7.88 (m, 1H), 7.84-7.78 (m, 4H), 7.66 (d, J = 7.2 Hz, 1H), 7.57-7.53 (m, 1H), 7.58 (d, J = 7.2 Hz, 1H), 7.38 (d, J = 8.4 Hz, 1H), 7.31-7.30 (m, 1H), 6.92-6.76 (m, 3H), 5.13-5.08(m, 1H), 4.75 (s, 2H), 4.17-4.13 (m, 4H), 3.57 (s, 3H), 3.14-3.11 (m, 4H), 3.08-3.06 (m, 1H), 2.89-2.84 (m, 3H), 2.04-2.01 (m, 1H), 1.39-1.37 (m, 5H), 1.20-1.19 (m, 9H) ppm. |
| 16 | N-(2-((4-(3-(2-((2-((5-((2-(2,6-dioxopiperidin-3-yl)-1,3-dioxoisoindolin-4-yl)amino)pentyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 909.8 | $^1$H NMR (400 MHz, DMSO-$d_6$) δ = 12.40 (s, 1H), 11.07 (s, 1H), 8.68-8.65 (m, 1H), 8.20-8.13 (m, 2H), 7.95 (d, J = 8.0 Hz, 1H), 7.85-7.77 (m, 3H), 7.66 (d, J = 8.0 Hz, 1H), 7.56-7.52 (m, 2H), 7.31-7.30 (m, 1H), 7.03-6.99 (m, 2H), 6.92-6.84 (m, 2H), 6.78-6.76 (m, 1H), 6.48-6.45 (m, 1H), 5.06-5.01 (m, 1H), 4.18-4.13 (m, 4H), 3.57 (s, 3H), 3.23-3.18 (m, 2H), 3.12 (s, 3H), 3.10-3.05 (m, 2H), 2.91-2.84 (m, 3H), 2.03-1.99 (m, 1H), 1.54-1.51 (m, 2H), 1.45-1.41 (m, 2H), 1.31-1.27 (m, 2H) ppm. |
| 17 | N-(2-((4-(3-(2-((2-(1'-(2-((2-(2,6-dioxopiperidin-3-yl)-1,3-dioxoisoindolin-4-yl)oxy)acetyl)-[4,4'-bipiperidin]-1-yl)-2-oxoethyl)(methyl)amino)pyridin-4-yl)phenyl)thiazol-2-yl)amino)-2-oxoethyl)-1-(methylsulfonyl)-1H-pyrrole-3-carboxamide | 1033.4 | $^1$H NMR (400 MHz, DMSO-d6) δ = 12.41 (s, 1H), 11.09 (s, 1H), 8.68-8.65 (m, 1H), 8.21-8.11 (m, 2H), 7.96 (d, J = 7.2 Hz, 1H), 7.84-7.83 (m, 1H), 7.80-7.74 (m, 2H), 7.66 (d, J = 7.6 Hz, 1H), 7.57-7.53 (m, 1H), 7.4d (d, J = 7.6 Hz, 1H), 7.32-7.30 (m, 2H), 6.88 (d, J = 5.2 Hz, 1H), 6.82 (s, 1H), 6.77-6.76 (m, 1H), 5.17-5.07 (m, 3H), 4.52-4.51 (m, 2H), 4.36-4.31 (m, 2H), 4.15-4.13 (m, 2H), 3.97-3.93 (m, 1H), 3.83-3.79 (m, 1H), 3.56 |

TABLE 11-continued

The following compounds were prepared using standard chemical manipulations and procedures similar to those used for the preparation of Compound 9

| Cmpd # | Name | LC-MS (ESI) (m/z) | $^1$H NMR |
|---|---|---|---|
| | | | (s, 3H), 3.09 (s, 3H), 3.02-2.95 (m, 2H), 2.88-2.82 (m, 2H), 2.08-1.99 (m, 1H), 1.75-1.65 (m, 4H), 1.38-1.28 (m, 2H), 1.26-1.19 (m, 2H), 1.07-0.92 (m, 2H) ppm |
| 21 | N-(2-((4-(3-(2-((2-((2-((2-((2-(2,6-dioxopiperidin-3-yl)-1,3-dioxoisoindolin-4-yl)amino)ethyl)(methyl)amino)ethyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 924.2 | $^1$H NMR (400 MHz, DMSO-d6) δ = 11.06 (br s, 1H), 8.62 (s, 1H), 8.18 (s, 1H), 8.12 (d, J = 5.2 Hz, 1H), 7.94 (d, J = 7.2 Hz, 1H), 7.84 (s, 1H), 7.71-7.70 (m, 2H), 7.63 (d, J = 7.8 Hz, 1H), 7.59-7.47 (m, 2H), 7.31-7.30 (m, 1H), 7.04-7.02 (m, 2H), 6.90(d, J = 5.6 Hz, 1H), 6.83 (s, 1H), 6.79-6.74 (m, 1H), 6.68 (s, 1H), 5.05-5.01 (m, 1H), 4.19 (d, J = 4.4 Hz, 2H), 4.11 (s, 2H), 3.57 (s, 3H), 3.26 (s, 2H), 3.21 (d, J = 6.4 Hz, 2H), 3.10 (s, 3H), 2.66 (d, J = 1.6 Hz, 2H), 2.61-2.59 (m, 4H), 2.32 (s, 2H), 2.20 (s, 3H), 1.99 (d, J = 6.0 Hz, 1H) ppm. |
| 27 | N-(2-((4-(3-(2-((2-(3-(((2-(2,6-dioxopiperidin-3-yl)-1,3-dioxoisoindolin-4-oxoethyl)(methyl)amino)pyridin-4-yl)phenyl)thiazol-2-yl)amino)-2-oxoethyl)-1-(methylsulfonyl)-1H-pyrrole-3-carboxamide | 894.2 | $^1$H NMR (400 MHz, DMSO-d6) δ = 12.62-12.14 (m, 1H), 11.09 (s, 1H), 8.66 (s, 1H), 8.20 (s, 1H), 8.13 (d, J = 5.2 Hz, 1H), 7.96 (d, J = 7.2 Hz, 1H), 1H), 7.13-7.10 (m, 1H), 6.99 (d, J = 1.6 Hz, 1H), 6.92-6.90 (m, 1H), 6.89-6.85 (m, 2H), 6.78-6.76 (m, 1H), 5.04-4.99 (m, 1H), 4.21 (s, 2H), 4.15 (d, J = 5.6 Hz, 2H), 3.57-3.54 (m, 5H), 3.50 (s, 4H), 3.42-3.39 (m, 2H), 3.29-3.27 (m, 2H), 3.24-3.20 (m, 2H), 3.11 (s, 3H), 2.94-2.81 (m, 1H), 2.58-2.52 (m, 2H), 2.01-1.95 (m, 1H) ppm. |
| 94 | N-(2-((4-(3-(2-(((S)-13-((2S,4R)-4-hydroxy-2-((4-(4-methylthiazol-5-yl)benzyl)carbamoyl)pyrrolidine-1-carbonyl)-14,14-dimethyl-2,11-dioxo-6,9-dioxa-3,12-diazapentadecyl)(methyl)amino)-pyridin-4-yl)phenyl)thiazol-2-yl)amino)-2-oxoethyl)-1-(methylsulfonyl)-1H-pyrrole-3-carboxamide | 1126.5 | $^1$H NMR (400 MHz, DMSO-$d_6$) δ = 12.43-12.37 (m, 1H), 8.97-8.96 (m, 1H), 8.64 (d, J = 4.0 Hz, 1H), 8.58-8.55 (m, 1H), 8.19 (s, 1H), 8.13 (d, J = 5.2 Hz, 1H), 7.96 (d, J = 7.6 Hz, 1H), 7.91-7.88 (m, 1H), 7.84-7.83 (m, 1H), 7.75 (s, 1H), 7.66 (d, J = 7.6 Hz, 1H), 7.56-7.52 (m, 1H), 7.43-7.35 (m, 5H), 7.31-7.30 (m, 1H), 6.92-6.90 (m, 1H), 6.85 (s, 1H), 6.78-6.77 (m, 1H), 5.16 (d, J = 3.2 Hz, 1H), 4.58 (d, J = 9.6 Hz, 1H), 4.47-4.43 (m, 1H), 4.37-4.32 (m, 2H), 4.28-4.22 (m, 3H), 4.13 (d, J = 5.2 Hz, 2H), 3.95 (s, 2H), 3.69-3.65 (m, 1H), 3.62-3.57 (m, 3H), 3.56 (s, 3H), 3.53-3.52 (m, 2H), 3.45-3.42 (m, 2H), 3.26-3.21 (m, 2H), 3.09 (s, 3H), 2.43 (s, 3H), 2.09-2.03 (m, 1H), 1.93-1.86 (m, 1H), 0.94 (s, 9H) ppm. |
| 46 | N-[2-[[4-[3-[2-[[2-[6-[[2-(2,6-dioxo-3-piperidyl)-1,3-dioxo-isoindolin-5-yl]amino]hexylamino]-2-oxo-ethyl]-methyl-amino]-4-pyridyl]phenyl]thiazol-2-yl]amino]-2-oxo-ethyl]-1-methylsulfonyl-pyrrole-3-carboxamide | 923.0 | $^1$H NMR (400 MHz, DMSO-d6) δ = 12.60-12.14 (m, 1H), 11.27-10.90 (m, 1H), 8.71-8.61 (m, 1H), 8.20 (s, 1H), 8.14 (d, J = 5.2 Hz, 1H), 8.01-7.93 (m, 1H), 7.88-7.80 (m, 2H), 7.78 (s, 1H), 7.71-7.63 (m, 1H), 7.61-7.50 (m, 2H), 7.37-7.28 (m, 1H), 7.11-7.02 (m, 1H), 6.97-6.89 (m, 2H), 6.87-6.75 (m, 3H), 5.13-4.88 (m, 1H), 4.19 (s, 2H), 4.15 (d, J = 6.0 Hz, 2H), 3.58 (s, 3H), 3.13 (s, 3H), 3.12-3.07 (m, 4H), 2.90-2.86 (m, 3H), 2.06-1.91 (m, 1H), 1.57-1.47 (m, 2H), 1.46-1.38 (m, 2H), 1.36-1.24 (m, 4H) ppm |
| 26 | N-(2-((4-(3-(2-((2-((1-(2-((2-(2,6-dioxopiperidin-3-yl)-1,3-dioxoisoindolin-5-yl)oxy)ethyl)piperidin-4-yl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 951.2 | $^1$H NMR (400 MHz, methanol-d4) δ = 8.20 (s, 1H), 8.13 (d, J = 5.2 Hz, 1H), 7.94 (d, J = 7.6 Hz, 1H), 7.84-7.83 (m, 1H), 7.79(d, J = 8.4 Hz, 1H), 7.62 (d, J = 8.0 Hz, 1H), 7.54-7.47 (m, 2H), 7.41 (d, J = 2.0 Hz, 1H), 7.33-7.25 (m, 2H), 6.97 (d, J = 5.6 Hz, 1H), 6.88 (s, 1H), 6.81-6.80 (m, 1H), 5.12-5.07 (m, 1H), 4.62 (s, 1H), 4.30-4.21 (m, 6H), 3.76 (d, J = 4.0 Hz, 1H), 3.38 (s, 3H), 3.21 (s, 3H), 3.15-3.12 (m, 1H), 2.98-2.89 (m, 2H), 2.88-2.80 (m, 3H), 2.78-2.75 (m, 1H), 2.74-2.68 (m, 1H), 2.34-2.23 (m, 2H), 2.18-2.07 (m, 1H), 1.86 (d, J = 10.4 Hz, 2H), 1.66-1.52 (m, 2H) ppm. |
| 58 | N-(2-((4-(3-(2-((2-((2-((2-((2-(2,6-dioxopiperidin-3-yl)-1,3-dioxoisoindolin-4-yl)amino)ethyl)sulfonyl)ethyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 959.3 | $^1$H NMR (400 MHz, DMSO-$d_6$) δ = 12.41-12.40 (m, 1H), 11.08 (s, 1H), 8.70-8.65 (m, 1H), 8.72-8.65 (m, 1H), 8.20 (s, 1H), 8.13 (d, J = 5.2 Hz, 1H), 7.97-7.96 (m, 1H), 7.85 (s, 1H), 7.78 (s, 1H), 7.68-7.67 (m, 1H), 7.58-7.55 (m, 2H), 7.31-7.30 (m, 1H), 7.14 (d, J = 9.2 Hz, 1H), 7.07 (d, J = 6.8 Hz, 1H), 6.93 (d, J = 5.2 Hz, 1H), 6.88 (s, 1H), 6.85-6.76 (m, 2H), 5.08-5.02 (m, 1H), 4.21 |

TABLE 11-continued

| The following compounds were prepared using standard chemical manipulations and procedures similar to those used for the preparation of Compound 9 | | | |
|---|---|---|---|
| Cmpd # | Name | LC-MS (ESI) (m/z) | $^1$H NMR |
| | | | (s, 2H), 4.14 (s, 2H), 3.75-3.74 (m, 4H), 3.57 (s, 3H), 3.51 (s, 4H), 3.11 (s, 3H), 2.89-2.85 (m, 3H), 2.02-2.01 (m, 1H) ppm. |
| 28 | N-(2-((4-(3-(2-((2-((4-((3-((2-(2,6-dioxopiperidin-3-yl)-1,3-dioxoisoindolin-4-yl)amino)propyl)(methyl)amino)-butyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 966.3 | $^1$H NMR (400 MHz, DMSO-d6) δ = 12.36 (s, 1H), 11.07 (s, 1H), 8.65 (s, 1H), 8.19 (s, 1H), 8.13 (d, J = 5.2 Hz, 1H), 7.96 (d, J = 8.0 Hz, 1H), 7.87-7.78 (m, 2H), 7.75 (s, 1H), 7.65 (d, J = 7.2 Hz, 1H), 7.59-7.51 (m, 2H), 7.31 (s, 1H), 7.06 (d, J = 8.8 Hz, 1H), 6.99 (d, J = 7.6 Hz, 1H), 6.91 (d, J = 5.2 Hz, 1H), 6.84 (s, 1H), 6.80-6.71 (m, 2H), 5.06-5.01 (m, 1H), 4.18 (s, 2H), 4.13 (d, J = 5.6 Hz, 2H), 3.57 (s, 3H), 3.12 (s, 3H), 3.05 (s, 4H), 2.35-2.29 (m, 4H), 2.23 (s, 3H), 2.09 (s, 3H), 2.02(s, 1H), 1.68-1.65 (m, 2H), 1.38 (s, 4H) ppm. |
| 25 | N-(2-((4-(3-(2-((2-(3-(((2-(2,6-dioxopiperidin-3-yl)-1,3-dioxoisoindolin-5-yl)oxy)methyl)azetidin-1-yl)-2-oxoethyl)(methyl)amino)pyridin-4-yl)phenyl)thiazol-2-yl)amino)-2-oxoethyl)-1-(methylsulfonyl)-1H-pyrrole-3-carboxamide | 894.2 | $^1$H NMR (400 MHz, methanol-d4) δ = 8.22 (br s, 1H), 8.13 (d, J = 5.2 Hz, 1H), 7.93 (d, J = 8.0 Hz, 1H), 7.84 (d, J = 2.0 Hz, 1H), 7.76 (d, J = 8.2 Hz, 1H), 7.62 (d, J = 6.0 Hz, 1H), 7.54-7.48 (m, 2H), 7.37 (s, 1H), 7.32-7.23 (m, 2H), 6.95 (d, J = 4.8 Hz, 1H), 6.88 (s, 1H), 6.81 (d, J = 1.6 Hz, 1H), 5.17-5.06 (m, 1H), 4.49 (s, 1H), 4.27 (d, J = 8.0 Hz, 5H), 4.39-4.15 (m, 1H), 3.96 (s, 1H), 3.39 (s, 3H), 3.22 (s, 3H), 3.13 (s, 1H), 2.93-2.69 (m, 2H), 2.68-2.64 (m, 1H), 2.13 (s, 1H) ppm. |
| 24 | N-(2-((4-(3-(2-((2-((2-((2-(2-((2-(2,6-dioxopiperidin-3-yl)-1,3-dioxoisoindolin-5-yl)oxy)acetamido)ethyl)(methyl)-amino)ethyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 982.2 | $^1$H NMR (400 MHz, DMSO-$d_6$) δ = 12.41 (br s, 1H), 11.10 (s, 1H), 8.62 (s, 1H), 8.17 (s, 1H), 8.11 (d, J = 5.2 Hz, 2H), 7.93(d, J = 7.6 Hz, 1H), 7.84-7.79 (m, 2H), 7.75-7.73 (m, 1H), 7.62 (d, J = 7.6 Hz, 1H), 7.55-7.48 (m, 1H), 7.39 (d, J = 2.0 Hz, 1H), 7.33-7.30 (m, 1H), 7.29-7.28 (m, 1H), 6.89-6.88 (m, 1H), 6.82 (s, 1H), 6.76-6.75 (m, 1H), 5.11-5.06 (m, 1H), 4.69 (s, 2H), 4.18 (s, 2H), 4.09 (s, 2H), 3.56 (s, 3H), 3.30 (s, 3H), 3.21-3.11 (m, 4H), 3.09 (s, 3H), 2.92-2.79 (m, 1H), 2.37-2.35 (m, 4H), 2.13 (s, 3H), 2.05-1.97 (m, 1H) ppm. |
| 23 | N-(2-((4-(3-(2-((2-((2-((2-(2-((2-(2,6-dioxopiperidin-3-yl)-1,3-dioxoisoindolin-4-yl)oxy)acetamido)ethyl)(methyl)-amino)ethyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 982.3 | $^1$H NMR (400 MHz, DMSO-$d_6$) δ = 12.44 (br s, 1H), 11.28-10.91 (m, 1H), 8.68 (s, 1H), 8.18 (s, 1H), 8.12 (d, J = 5.2 Hz, 1H), 7.95 (d, J = 7.6 Hz, 1H), 7.91-7.90 (m, 1H), 7.84-7.83 (m, 1H), 7.80-7.69 (m, 3H), 7.64 (d, J = 7.6 Hz, 1H), 7.53-7.51 (m, 1H), 7.46 (d, J = 7.2 Hz, 1H), 7.36 (d, J = 8.4 Hz, 1H), 7.33-7.28 (m, 1H), 6.90 (d, J = 5.2 Hz, 1H), 6.84 (s, 1H), 6.77-6.66 (m, 1H), 5.12-5.08 (m, 1H), 4.76 (s, 2H), 4.18 (s, 2H), 4.12 (s, 2H), 3.57 (s, 3H), 3.31 (s, 3H), 3.22-3.12 (m, 5H), 3.10 (s, 3H), 2.94-2.81 (m, 1H), 2.68-2.67 (m, 4H), 2.66-2.65 (m, 1H), 2.39-2.36 (m, 4H), 2.35-2.34 (m, 3H), 2.33-2.30 (m, 1H), 2.15 (s, 3H), 2.05-1.95 (m, 1H) ppm. |
| 22 | N-(2-((4-(3-(2-((2-((2-((2-(2-((2-(2,6-dioxopiperidin-3-yl)-1,3-dioxoisoindolin-4-yl)oxy)ethoxy)ethyl)(methyl)-amino)ethyl)amino)-2-oxoethyl)(methyl)amino)pyridin-4-yl)phenyl)thiazol-2-yl)amino)-2-oxoethyl)-1-(methylsulfonyl)-1H-pyrrole-3-carboxamide | 969.3 | $^1$H NMR (400 MHz, DMSO-d6) δ = 11.06 (br s, 1H), 8.63 (s, 1H), 8.19 (s, 1H), 8.13 (d, J = 5.6 Hz, 1H), 7.94 (d, J = 7.2 Hz, 1H), 7.85-7.82 (m, 1H), 7.79-7.72 (m, 2H), 7.65 (d, J = 5.2 Hz, 2H), 7.53-7.52 (m, 1H), 7.48 (d, J = 8.4 Hz, 1H), 7.42 (d, J = 7.2 Hz, 1H), 7.32-7.27 (m, 1H), 6.91 (d, J = 5.2 Hz, 1H), 6.85 (s, 1H), 6.77-6.76(m, 1H), 5.08-5.05 (m, 1H), 4.33-4.24 (m, 2H), 4.17 (s, 2H), 4.11 (s, 2H), 3.74-3.68 (m, 2H), 3.56 (s, 3H), 3.52-3.51 (m, 3H), 3.28 (s, 3H), 3.12 (d, J = 6.0 Hz, 2H), 3.10 (s, 3H), 2.68-2.64 (m, 2H), 2.39-2.35 (m, 2H), 2.34-2.30 (m, 2H), 2.14 (s, 3H), 2.03-1.96 (m, 1H) ppm. |

Compound 123—N-[2-[[4-[3-[2-[[2-[4-[1-[2-[2-(2,6-dioxo-3-piperidyl)-1,3-dioxo-isoindolin-4-yl]oxy-acetyl]-4-piperidyl]-1-piperidyl]-2-oxo-ethyl]-methyl-amino]-4-pyridyl]phenyl]thiazol-2-yl]amino]-2-oxo-ethyl]-4,5-dimethyl-1-methylsulfonyl-pyrrole-3-carboxamide
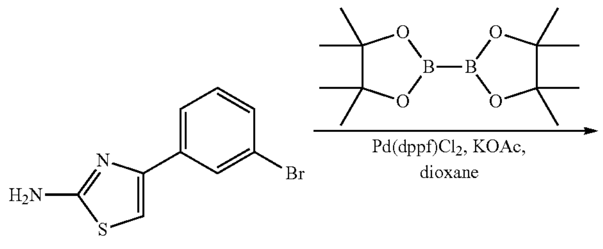
A
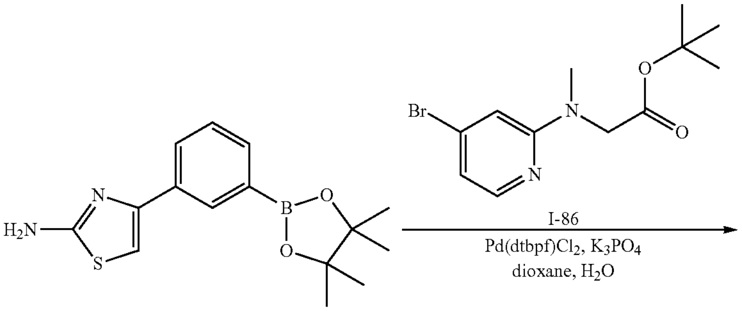
B
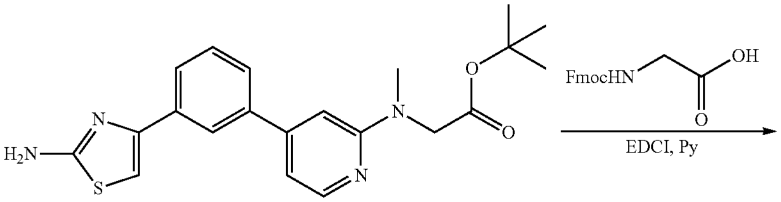
C
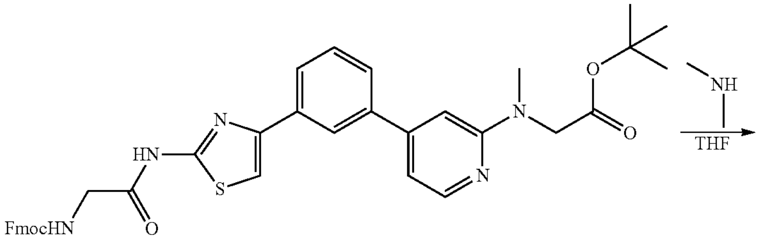
D
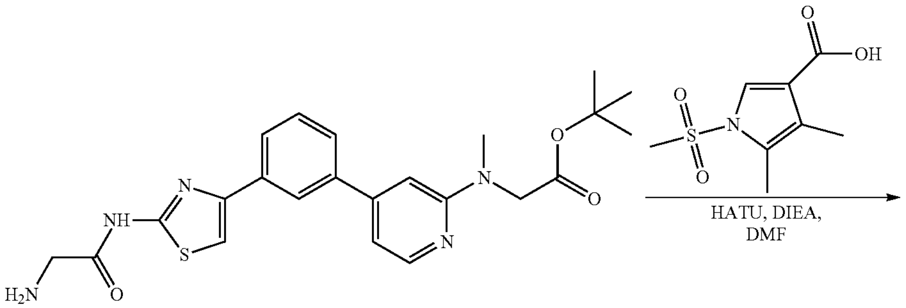
E -continued
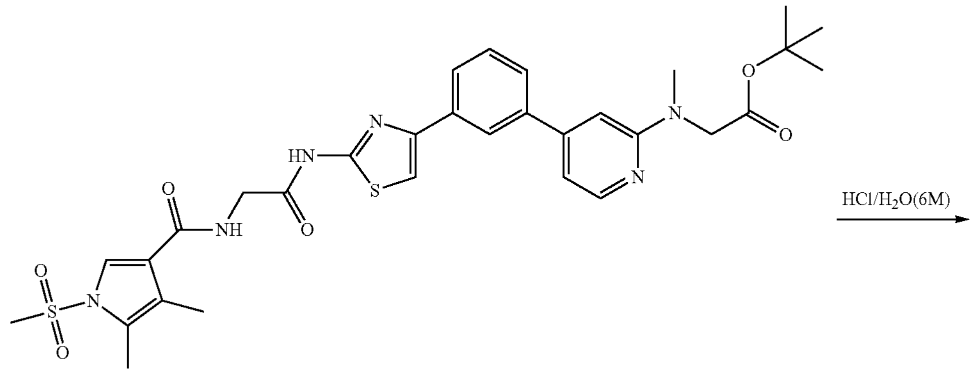
F
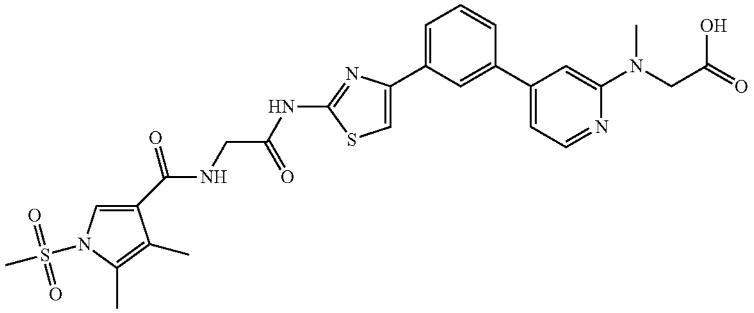
I-95
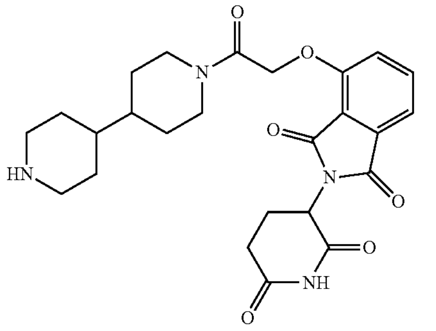
I-87
EDCI, HOBT, DIEA, DMF
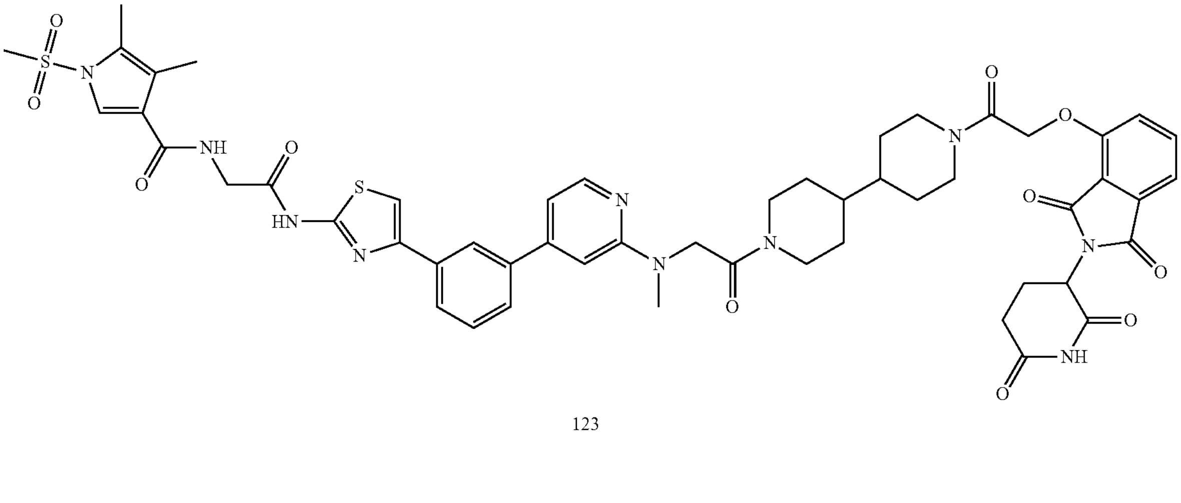
123

Step 1: Preparation of 4-[3-(4,4,5,5-tetramethyl-1,3,2-dioxaborolan-2-yl)phenyl]thiazol-2-amine (B)

B

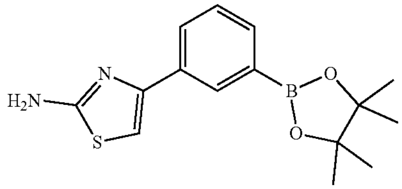

To a solution of 4-(3-bromophenyl)thiazol-2-amine (A, 20 g, 78.39 mmol) and bis(pinacol)diborane (29.86 g, 117.59 mmol) in 1,4-dioxane (200 mL) was added Pd(dppf)$Cl_2$ (5.74 g, 7.84 mmol) and KOAc (23.08 g, 235.17 mmol). The mixture was stirred at 70° C. for 2 h, then diluted with water (2 L), extracted with EtOAc (500 mL×3), combined the organic layer, dried over $Na_2SO$, and concentrated. The residue was purified by column chromatography ($SiO_2$, Petroleum ether/EtOAc 10:1 to 5:1) to give B (21 g, 78.98%) as a brown solid. LCMS (ESI) m/z: $[M+H]^+$=303.1. $^1H$ NMR (400 MHz, $CDCl_3$) δ=8.20 (s, 1H), 7.87 (d, J=7.6 Hz, 1H), 7.73 (d, J=7.2 Hz, 1H), 7.40 (d, J=7.6 Hz, 1H), 6.76 (s, 1H), 5.64 (s, 2H), 1.38 (s, 12H) ppm.

Step 2: Preparation of Intermediate 5 tert-butyl 2-[[4-[3-(2-aminothiazol-4-yl)phenyl]-2-pyridyl]-methyl-amino]acetate (C)

C

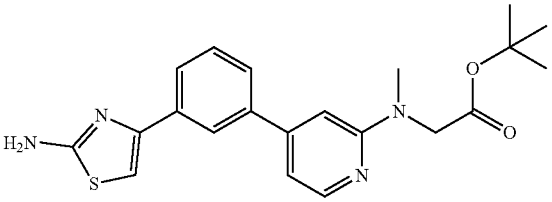

A mixture of B (13.2 g, 43.83 mmol), I-86 (14.57 g, 48.21 mmol), $K_3PO_4$ (27.91 g, 131.48 mmol), and di-tert-butyl (cyclopentyl)phosphane dichloropalladium(II) (2.86 g, 4.38 mmol) in 1,4-dioxane (150 mL)/water (40 mL) was degassed and purged 3 times with nitrogen. The mixture was stirred at 80° C. for 2 h then diluted with water (1 L) and extracted with EtOAc (300 mL×3). The combined organic phase was dried over $Na_2SO_4$, filtered, and concentrated. The residue was purified by column chromatography ($SiO_2$, Petroleum ether/EtOAc 10:1 to 1:1). This solid material was subsequently triturated with MeOH (200 mL) to give C (15 g, 35.94 mmol, 63.13% 1) as a brown solid. LCMS (ESI) m/z: $[M+H]^+$=397.2. $^1H$ NMR (400 MHz, DMSO-$d_6$) δ=8.15-8.08 (m, 2H), 7.86 (d, J=7.6 Hz, 1H), 7.61 (d, J=8.0 Hz, 1H), 7.50-7.46 (m, 1H), 7.17 (s, 1H), 7.09 (s, 2H), 6.92-6.90 (m, 1H), 6.86 (s, 1H), 4.28 (s, 2H), 3.12 (s, 3H), 1.37 (s, 9H) ppm.

Step 3: Preparation of tert-butyl 2-((4-(3-(2-(2-((((9H-fluoren-9-yl)methoxy)carbonyl)amino)acetamido)thiazol-4-yl)phenyl)pyridin-2-yl)(methyl)amino)acetate (D)

D

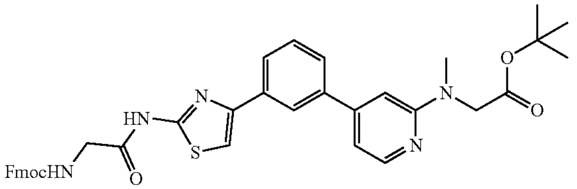

To a solution of C (12.00 g, 40.35 mmol) in pyridine (60 mL) was added EDCI (9.67 g, 50.44 mmol). The mixture was stirred at 25° C. for 0.5 h. Tert-butyl 2-[[4-[3-(2-aminothiazol-4-yl)phenyl]-2-pyridyl]-methyl-amino]acetate (4 g, 10.09 mmol) was then added and the reaction stirred at 25° C. for an additional 12 h. The reaction was slowly poured into water (600 mL) slowly and filtered. The filter cake was purified by column chromatography ($SiO_2$, DCM/EtOAc 1:0 to 5:1), to give D (5.2 g, 72.46% yield) as a yellow solid. LCMS (ESI) m/z: $[M+H]^+$=676.2. $^1H$ NMR (400 MHz, DMSO-$d_6$) δ=12.37 (s, 1H), 8.22 (s, 1H), 8.15 (d, J=4.8 Hz, 1H), 7.98 (d, J=7.2 Hz, 1H), 7.91 (d, J=7.6 Hz, 2H), 7.81 (s, 1H), 7.77-7.68 (m, 4H), 7.60-7.54 (m, 1H), 7.43 (d, J=7.6 Hz, 2H), 7.38-7.33 (m, 2H), 6.95-6.90 (m, 1H), 6.91 (s, 1H), 4.36-4.32 (m, 2H), 4.30 (s, 2H), 4.27 (d, J=6.8 Hz, 1H), 3.97 (d, J=6.0 Hz, 2H), 3.14 (s, 3H), 1.39 (s, 9H) ppm.

Step 4: Preparation of tert-butyl 2-[[4-[3-[2-[(2-aminoacetyl)amino]thiazol-4-yl]phenyl]-2-pyridyl]-methyl-amino]acetate (E)

E

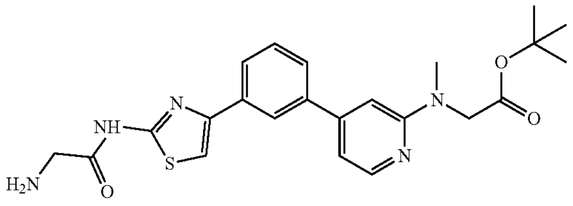

A mixture of D (5.1 g, 7.55 mmol) and dimethylamine in THE (2.0 M, 120 mL) was stirred at 25° C. for 1 h. The reaction mixture was concentrated, and the residue triturated with Petroleum ether (50 mL) to give E (3.2 g, 7.06 mmol, 93.49% yield) as a white solid. LCMS (ESI) m/z: $[M+H]^+$=454.2. $^1H$ NMR (400 MHz, DMSO-$d_6$) δ=8.22 (s, 1H), 8.15 (d, J=5.2 Hz, 1H), 7.98 (d, J=7.6 Hz, 1H), 7.79 (s, 1H), 7.69 (d, J=7.6 Hz, 1H), 7.57-7.54 (m, 1H), 6.96 (d, J=5.2 Hz, 1H), 6.91 (s, 1H), 5.64-5.54 (m, 2H), 4.30 (s, 2H), 3.44 (s, 2H), 3.14 (s, 3H), 1.38 (s, 9H) ppm.

Step 5: Preparation of tert-butyl 2-[[4-[3-[2-[[2-[(4,5-dimethyl-1-methylsulfonyl-pyrrole-3-carbonyl)amino]acetyl]amino]thiazol-4-yl]phenyl]-2-pyridyl]-methyl-amino]acetate (F)

F

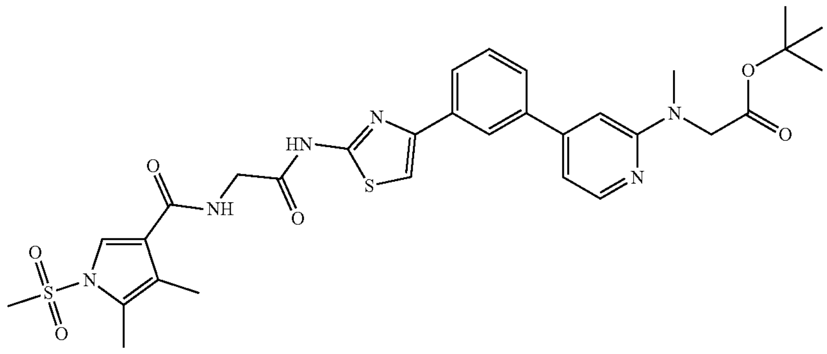

A mixture of 4,5-dimethyl-1-methylsulfonyl-pyrrole-3-carboxylic acid (E, 263.44 mg, 1.21 mmol), HATU (628.75 mg, 1.65 mmol), and DIEA (427.43 mg, 3.31 mmol, 576.05 μL) in DMF (10 mL) was stirred at 30° C. for 0.5 h. Then I-84 (500 mg, 1.10 mmol) was added and the mixture was stirred for an additional 2 h. The reaction mixture was poured into water (100 mL), filtered, and purified by column chromatography ($SiO_2$, Petroleum ether/EtOAc 5:1 to 1:1) to give F (430 mg, 54.91% yield, 91.9% purity) as a white solid. LCMS (ESI) m/z: $[M+H]^+$=653.2. $^1H$ NMR (400 MHz, DMSO-$d_6$) δ=12.38 (s, 1H), 8.48-8.47 (m, 1H), 8.22 (s, 1H), 8.16 (d, J=5.2 Hz, 1H), 7.98 (d, J=7.6 Hz, 1H), 7.80 (s, 2H), 7.70 (d, J=8.0 Hz, 1H), 7.59-7.57 (m, 1H), 6.96-6.94 (m, 1H), 6.91 (s, 1H), 4.30 (s, 2H), 4.11 (d, J=5.6 Hz, 2H), 3.48 (s, 3H), 3.14 (s, 3H), 2.32 (s, 3H), 2.12 (s, 3H), 1.39 (s, 9H) ppm.

Step 6: Preparation of Intermediate 12 2-[[4-[3-[2-[[2-[(4,5-dimethyl-1-methylsulfonyl-pyrrole-3-carbonyl)amino]acetyl]amino]thiazol-4-yl]phenyl]-2-pyridyl]-methyl-amino]acetic acid (I-95)

I-95

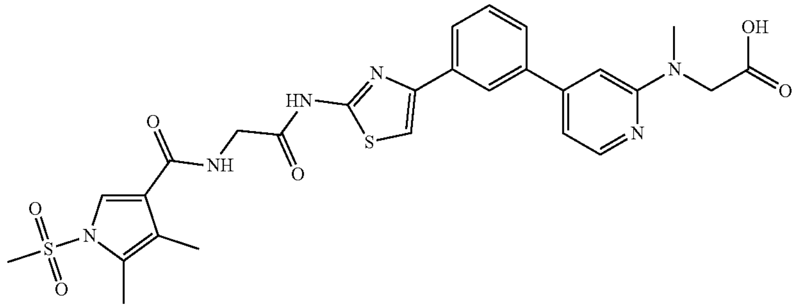

A mixture of F (430 mg, 0.66 mmol) in HCl (6 M, 20 mL) was stirred at 30° C. for 15 h. The reaction was filtered, and the filter cake was triturated with Petroleum ether/EtOAc (10:1) to give I-95 (260 mg, 57.35% yield) as a gray solid. LCMS (ESI) m/z: $[M+H]^+$=597.2. $^1H$ NMR (400 MHz, DMSO-$d_6$) δ=12.44 (br s, 1H), 8.54-8.51 (m, 1H), 8.34 (s, 1H), 8.16 (d, J=6.4 Hz, 1H), 8.11 (d, J=7.6 Hz, 1H), 7.88-7.87 (m, 2H), 7.81 (s, 1H), 7.67-7.63 (m, 1H), 7.51 (s, 1H), 7.39 (d, J=6.4 Hz, 1H), 4.70 (s, 2H), 4.11 (d, J=5.6 Hz, 2H), 3.49 (s, 3H), 2.32 (s, 3H), 2.12 (s, 3H) ppm.

Step 7: Preparation of N-[2-[[4-[3-[2-[[2-[4-[1-[2-[2-(2,6-dioxo-3-piperidyl)-1,3-dioxo-isoindolin-4-yl]oxyacetyl]-4-piperidyl]-1-piperidyl]-2-oxo-ethyl]-methyl-amino]-4-pyridyl]phenyl]thiazol-2-yl]amino]-2-oxo-ethyl]-4,5-dimethyl-1-methylsulfonyl-pyrrole-3-carboxamide (Compound 123)

123

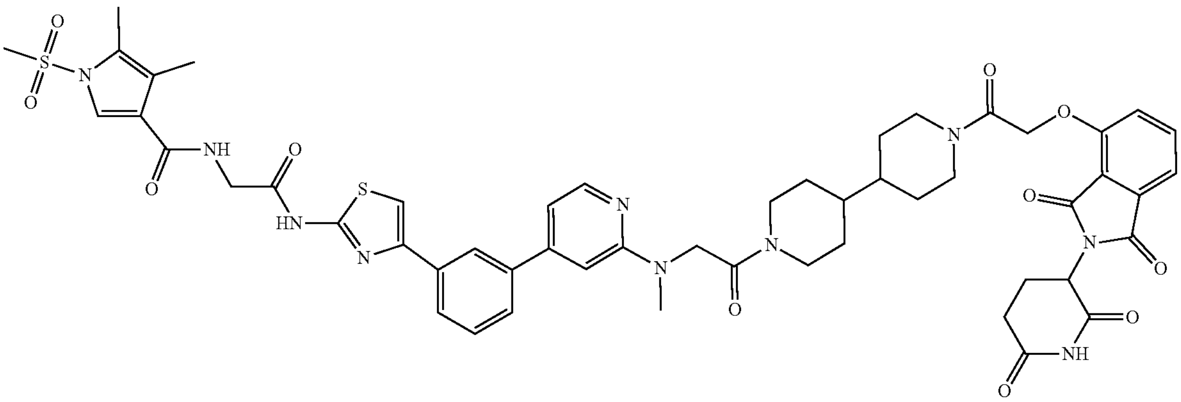

To a mixture of I-95 (50 mg, 0.079 mmol), I-87 (49.99 mg, 0.083 mmol) and DIEA (43.32 mg, 0.335 mmol, 58.38 μL) in DMF (1 mL) was added EDCI (20.88 mg, 0.11 mmol), and HOBt (14.72 mg, 0.11 mmol) and the mixture was stirred at 30° C. for 2 h. The reaction mixture was added to water (8 mL) and the precipitate was collected by filtration. The solid was purified by preparative HPLC (column: Waters Xbridge 150×25 mm×5 μm; mobile phase: [10 mM aqueous $NH_4HCO_3$/ACN]; B %: 27%-60%, 11 min) to give Compound 123 (10.42 mg, 8.91 μm, 11.28% yield) as an orange solid. LCMS (ESI) m/z: $[M+H]^+$=1061.5. $^1H$ NMR (400 MHz, DMSO-$d_6$) δ=12.51-12.30 (m, 1H), 11.12 (s, 1H), 8.50 (m, 1H), 8.21 (s, 1H), 8.12 (d, J=5.3 Hz, 1H), 7.97 (d, J=7.6 Hz, 1H), 7.82-7.74 (m, 3H), 7.67 (d, J=7.6 Hz, 1H), 7.58-7.52 (m, 1H), 7.45 (d, J=7.1 Hz, 1H), 7.31 (d, J=8.6 Hz, 1H), 6.89 (d, J=5.3 Hz, 1H), 6.82 (s, 1H), 5.28-5.01 (m, 3H), 4.61-4.44 (m, 2H), 4.40-4.28 (m, 2H), 4.13-4.05 (m, 2H), 3.99-3.89 (m, 1H), 3.86-3.76 (m, 1H), 3.48 (s, 3H), 3.09 (s, 3H), 3.03-2.93 (m, 2H), 2.92-2.83 (m, 1H), 2.64-2.54 (m, 3H), 2.46-2.44 (m, 1H), 2.31 (s, 3H), 2.11 (s, 3H), 2.08-1.97 (m, 1H), 1.79-1.61 (m, 4H), 1.40-1.12 (m, 4H), 1.08-0.89 (m, 2H) ppm.

TABLE 12

The following compounds were prepared using standard chemical manipulations and procedures similar to those used for the preparation of Compound 123.

| Cmpd # | Name | LC-MS (ESI) (m/z) | $^1H$ NMR |
|---|---|---|---|
| 41 | N-[2-[[4-[3-[2-[[2-[8-[[2-[2-(2,6-dioxo-3-piperidyl)-1,3-dioxo-isoindolin-4-yl]oxyacetyl]amino]octylamino]-2-oxo-ethyl]-methyl-amino]-4-pyridyl]phenyl]thiazol-2-yl]amino]-2-oxo-ethyl]-4,5-dimethyl-1-methylsulfonyl-pyrrole-3-carboxamide | 1037.6 | $^1H$ NMR (400 MHz, DMSO-$d_6$) δ = 12.37 (s, 1H), 11.10 (s, 1H), 8.47-8.46 (m, 1H), 8.20-8.14 (m, 2H), 7.96-7.78 (m, 6H), 7.55-7.74 (m, 1H), 7.50-7.40 (m, 3H), 6.93-6.85 (m, 2H), 5.13-5.09 (m, 1H), 4.76 (s, 2H), 4.18-4.09 (m, 4H), 3.48 (s, 3H), 3.13-3.04 (m, 7H), 2.93-2.84 (m, 2H), 2.32 (s, 4H), 2.12-2.10 (m, 4H), 1.39-1.35 (m, 3H), 1.24-1.19 (m, 9H) ppm. |
| 96 | N-[2-[[4-[3-[2-[[2-[5-[[2-(2,6-dioxo-3-piperidyl)-1,3-dioxo-isoindolin-4- | 937.2 | $^1H$ NMR (400 MHz, DMSO-d6) δ = 12.37 (s, 1H), 11.04 (s, 1H), 8.49-8.46 (m, 1H), 8.20 (s, 1H), 8.14 (d, J = 5.2 Hz, 1H), 7.96 (d, J = 7.6 Hz, 1H), |

TABLE 12-continued

The following compounds were prepared using standard chemical manipulations and procedures similar to those used for the preparation of Compound 123.

| Cmpd # | Name | LC-MS (ESI) (m/z) | $^1$H NMR |
|---|---|---|---|
| | yl]amino]pentylamino]-2-oxo-ethyl]-methyl-amino]-4-pyridyl]phenyl]thiazol-2-yl]amino]-2-oxo-ethyl]-4,5-dimethyl-1-methylsulfonyl-pyrrole-3-carboxamide | | 7.85-7.82 (m, 1H), 7.78 (d, J = 8.4 Hz, 2H), 7.66 (d, J = 8.0 Hz, 1H), 7.58-7.52 (m, 2H), 7.05-7.03 (m, 1H), 6.91-6.90 (m, 2H), 6.85 (s, 1H), 6.81-6.78 (m, 1H), 5.04-5.00 (m, 1H), 4.19 (s, 2H), 4.09 (d, J = 5.2 Hz, 2H), 3.47 (s, 3H), 3.13 (s, 3H), 3.09-3.07 (m, 2H), 2.91-2.81 (m, 2H), 2.31 (s, 3H), 2.11 (s, 3H), 2.02-1.95 (m, 2H), 1.55-1.29 (m, 8H) ppm. |
| 66 | N-(2-((4-(3-(2-((2-((2-(2-(2-((2-(2,6-dioxopiperidin-3-yl)-1,3-dioxoisoindolin-4-yl)amino)ethoxy)ethoxy)ethyl)amino)-2-oxoethyl)(methyl)amino)pyridin-4-yl)phenyl)thiazol-2-yl)amino)- | 983.4 | $^1$H NMR (400 MHz, methanol-d4) δ = 8.17 (s, 1H), 8.13 (d, J = 5.4 Hz, 1H), 7.90 (d, J = 7.6 Hz, 1H), 7.74 (s, 1H), 7.59 (d, J = 7.8 Hz, 1H), 7.49-7.40 (m, 3H), 6.96 (d, J = 6.8 Hz, 2H), 6.92-6.87 (m, 2H), 5.00-4.98 (m, 1H), 4.27-4.19 (m, 4H), 3.58-3.50 (m, 8H), 3.42-3.38 (m, 2H), 3.35-3.32 (m, |

Compound 91—N-[2-[[4-[3-[2-[[2-[5-[[2-(2,6-dioxo-3-piperidyl)-1,3-dioxo-isoindolin-4-yl]amino]pentylamino]-2-oxo-ethyl]-methyl-amino]-4-pyridyl]phenyl]thiazol-2-yl]amino]-2-oxo-ethyl]-1-isopropylsulfonyl-4,5-dimethyl-pyrrole-3-carboxamide

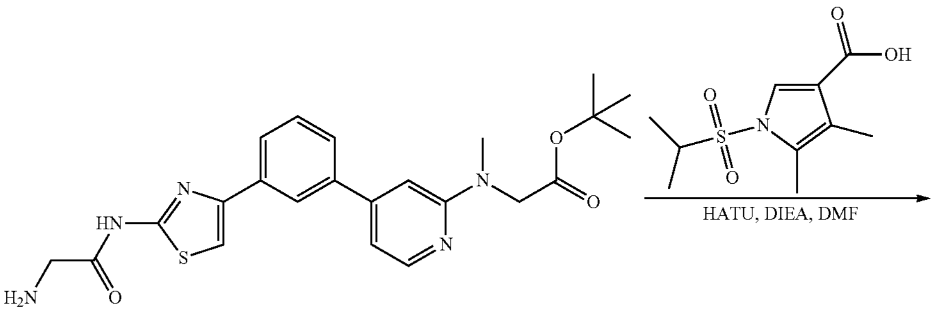

A

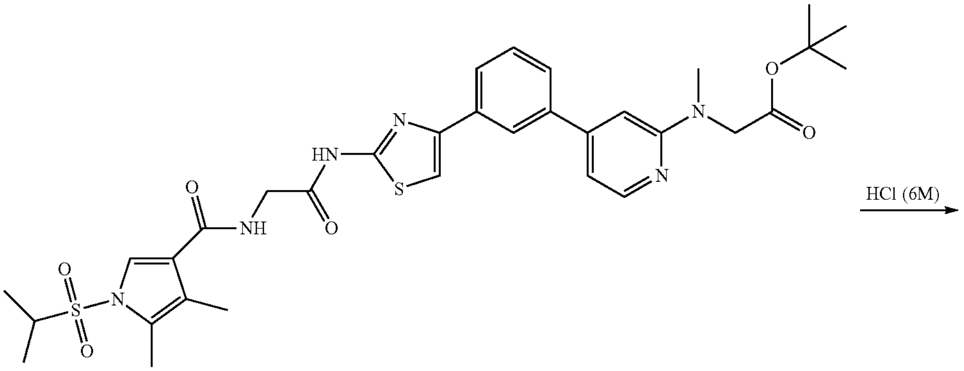

B

-continued
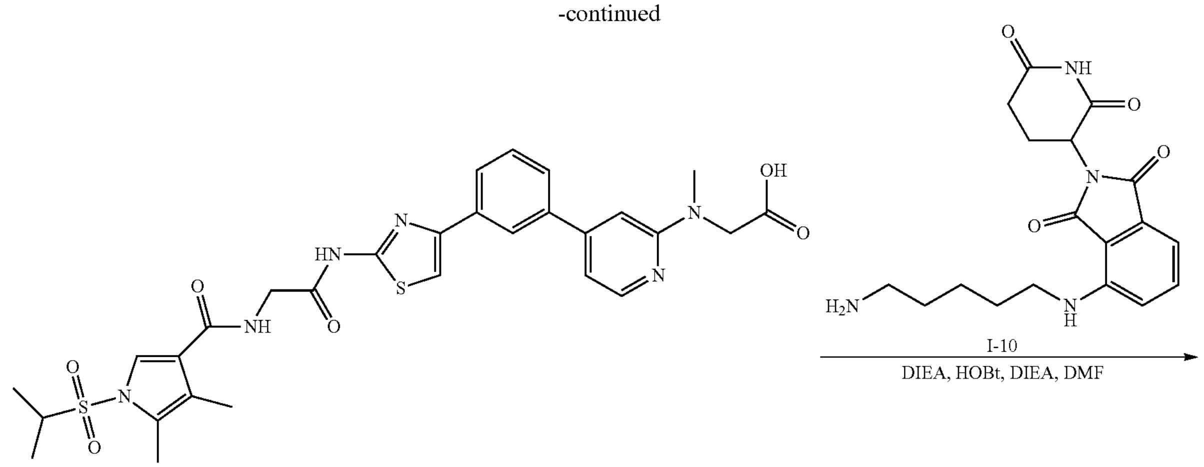
C
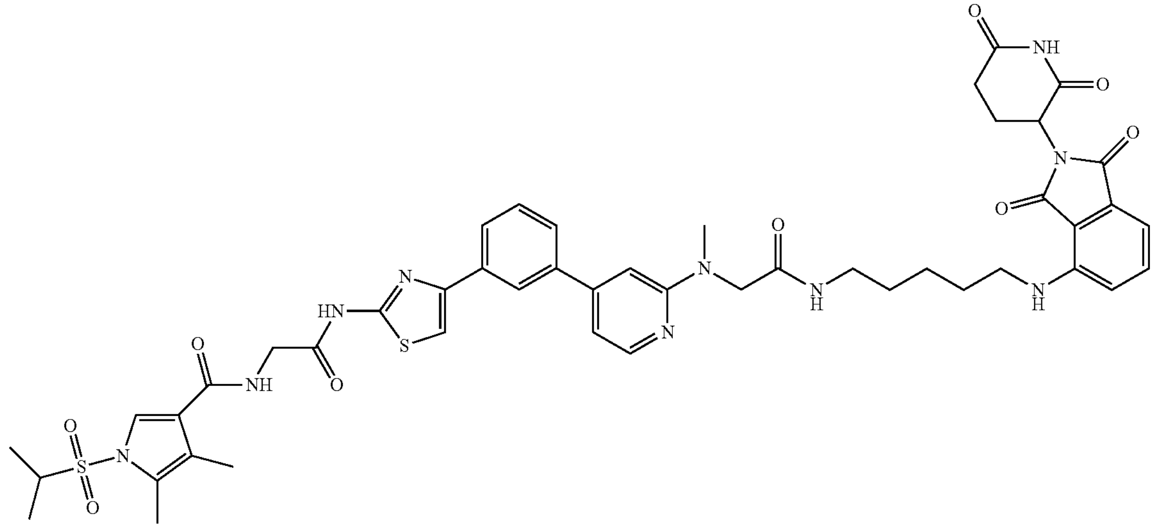
91
Step 1: Preparation of tert-butyl 2-[[4-[3-[2-[[2-[(1-isopropylsulfonyl-4,5-dimethyl-pyrrole-3-carbonyl)amino]acetyl]amino]thiazol-4-yl]phenyl]-2-pyridyl]-methyl-amino]acetate (B)
B
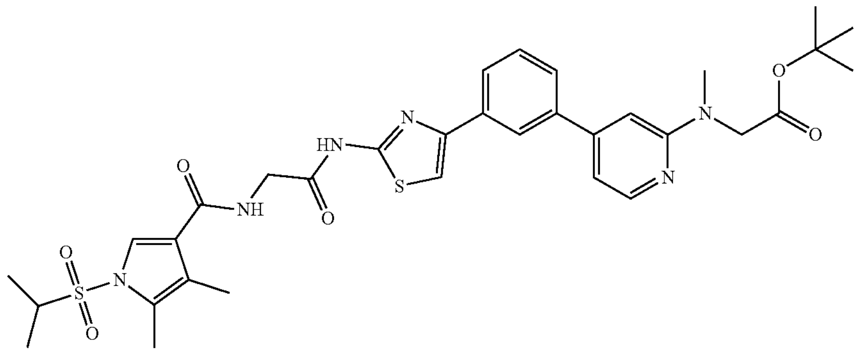

To a solution of 1-isopropylsulfonyl-4,5-dimethyl-pyrrole-3-carboxylic acid (A, 416.44 mg, 1.70 mmol) in DMF (15 mL) was added HATU (880.25 mg, 2.32 mmol) and DIPEA (997.34 mg, 7.72 mmol, 1.34 mL). The mixture was stirred at 30° C. for 0.5 h after which time tert-butyl 2-[[4-[3-[2-[(2-aminoacetyl)amino]thiazol-4-yl]phenyl]-2-pyridyl]-methylamino]acetate (prepared according to the method for I-84, 700 mg, 1.54 mmol) was added. The reaction was stirred at 30° C. for 2.5 h, then poured into water (150 mL), and filtered. The filter cake was purified by column chromatography ($SiO_2$, Petroleum ether/EtOAc 5:1 to 1:1) to give B (630 mg, 54.36% yield) as a yellow solid. LCMS (ESI) m/z: $[M+H]^+$=681.2. $^1H$ NMR (400 MHz, DMSO-$d_6$) δ=12.41 (s, 1H), 8.54-8.21 (m, 1H), 8.22-8.21 (m, 1H), 8.15 (d, J=5.2 Hz, 1H), 7.98-7.96 (m, 1H), 7.81 (s, 1H), 7.77 (s, 1H), 7.70-7.68 (m, 1H), 7.58-7.54 (m, 1H), 6.95-6.94 (m, 1H), 6.90 (s, 1H), 4.29 (s, 2H), 4.09 (d, J=5.6 Hz, 2H), 3.76-3.73 (m, 1H), 3.13 (s, 3H), 2.29 (s, 3H), 2.11 (s, 3H), 1.38 (s, 9H), 1.23 (s, 3H), 1.22 (s, 3H) ppm.

Step 2: Preparation of 2-[[4-[3-[2-[[2-[(1-isopropylsulfonyl-4,5-dimethyl-pyrrole-3-carbonyl)amino]acetyl]amino]thiazol-4-yl]phenyl]-2-pyridyl]-methyl-amino]acetic acid (C)

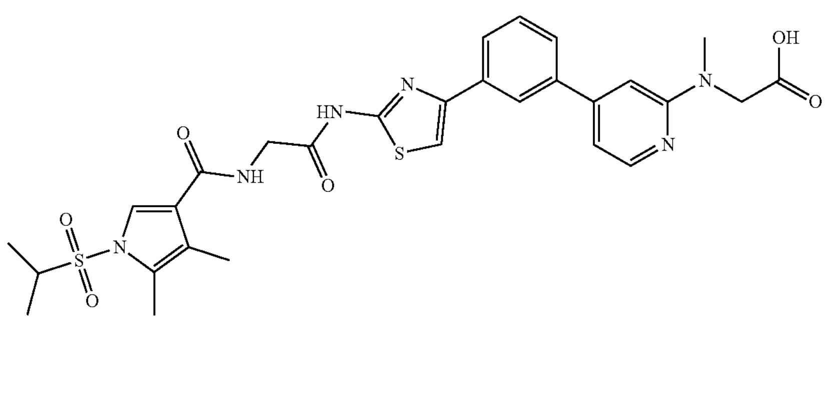

C

A mixture of B (620 mg, 0.91 mmol) in HCl (6 M, 20 mL) was stirred at 30° C. for 15 h. The mixture was filtered, then triturated with Petroleum Ether/EtOAc (10:1) to give C (320 mg, 47.83% yield) as a pink solid. LCMS (ESI) m/z: $[M+H]^+$=625.2. $^1$H NMR (400 MHz, DMSO-$d_6$) δ=12.44 (br s, 1H), 8.55 (d, J=5.6 Hz, 1H), 8.33 (s, 1H), 8.15 (d, J=6.8 Hz, 1H), 8.09 (d, J=7.6 Hz, 1H), 7.89-7.86 (m, 2H), 7.77 (s, 1H), 7.65 (d, J=7.6 Hz, 1H), 7.49 (s, 1H), 7.38 (d, J=6.4 Hz, 1H), 4.68 (s, 2H), 4.10 (sd, J=5.2 Hz, 2H), 3.77-3.71 (m, 1H), 3.32 (s, 3H), 2.29 (s, 3H), 2.11 (s, 3H), 1.23 (s, 3H), 1.22 (s, 3H) ppm.

Step 3: Preparation of N-[2-[[4-[3-[2-[[2-[5-[[2-(2,6-dioxo-3-piperidyl)-1,3-dioxo-isoindolin-4-yl]amino]pentylamino]-2-oxo-ethyl]-methyl-amino]-4-pyridyl]phenyl]thiazol-2-yl]amino]-2-oxo-ethyl]-1-isopropylsulfonyl-4,5-dimethyl-pyrrole-3-carboxamide (Compound 91)

91

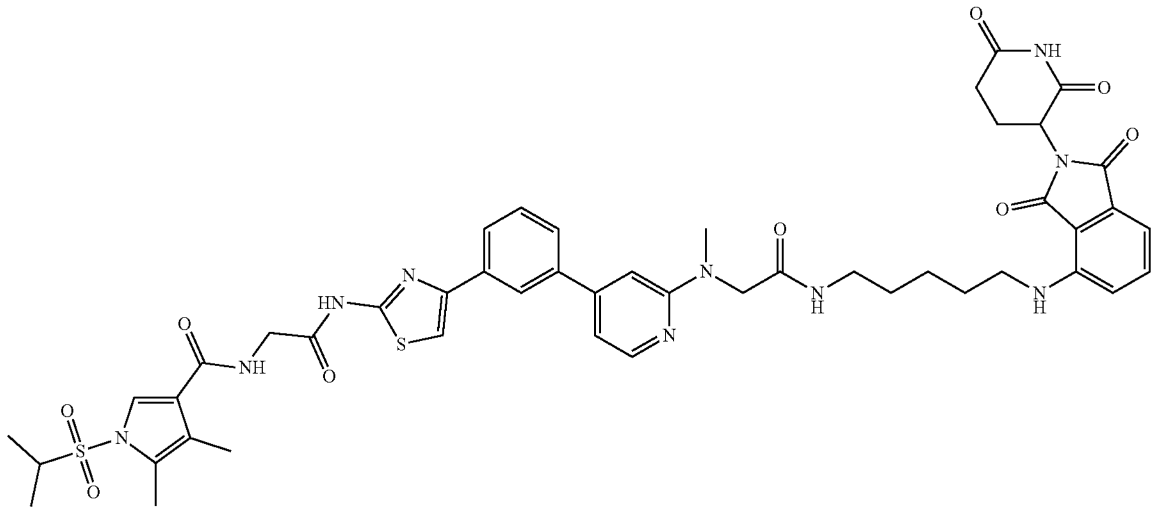

To a solution of C (25 mg, 0.040 mmol), 4-(5-aminopentylamino)-2-(2,6-dioxo-3-piperidyl)isoindoline-1,3-dione (I-10, 18.90 mg, 0.041 mmol), and DIEA (25.86 mg, 0.220 mmol, 34.85 μL) in DMF (0.5 mL) was added HOBt (6.49 mg, 0.048 mmol) and EDCI (9.21 mg, 0.048 mmol), and the stirred at 30° C. for 2 h. The reaction mixture was concentrated, and the residue purified by reverse phase flash chromatography (water/ACN) to give Compound 91 (16.77 mg, 41.44% yield) as a yellow solid. LCMS (ESI) m/z: $[M+H]^+$=965.7. $^1$H NMR (400 MHz, DMSO-$d_6$) δ=12.81-12.02 (m, 1H), 11.08-11.07 (m, 1H), 8.52-8.49 (m, 1H), 8.22-8.20 (m, 1H), 8.14 (d, J=5.2 Hz, 1H), 7.96 (d, J=8.0 Hz, 1H), 7.86-7.81 (m, 1H), 7.78-7.76 (m, 2H), 7.67 (d, J=7.6 Hz, 1H), 7.59-7.52 (m, 2H), 7.06-6.99 (m, 2H), 6.92-6.89 (m, 1H), 6.84 (s, 1H), 6.48-6.45 (m, 1H), 5.10-4.98 (m, 1H), 4.18 (s, 2H), 4.09 (d, J=6.0 Hz, 2H), 3.77-3.71 (m, 1H), 3.23-3.18 (m, 2H), 3.14-3.12 (m, 3H), 3.10-3.05 (m, 2H), 2.59-2.54 (m, 2H), 2.29 (s, 3H), 2.11 (s, 3H), 2.04-1.98 (m, 1H), 1.56-1.49 (m, 2H), 1.46-1.40 (m, 3H), 1.33-1.26 (m, 2H), 1.23 (d, J=6.8 Hz, 6H) ppm.

TABLE 13

The following compounds were prepared using standard chemical manipulations and procedures similar to those used for the preparation of Compound 91.

| Cmpd # | Name | LC-MS (ESI) (m/z) | $^1$H NMR |
|---|---|---|---|
| 90 | N-[2-[[4-[3-[2-[[2-[2-[2-[2-[[2-(2,6-dioxo-3-piperidyl)-1,3-dioxo-isoindolin-4-yl]amino]ethoxy]ethoxy]ethylamino]-2-oxo-ethyl]-methyl-amino]-4-pyridyl]phenyl]thiazol-2-yl]amino]-2-oxo-ethyl]-1-isopropylsulfonyl-4,5-dimethyl- | 1011.6 | $^1$H NMR (400 MHz, DMSO-d6) δ = 12.30 (s, 1H), 11.08 (br s, 1H), 8.50-8.48 (m, 1H), 8.19 (s, 1H), 8.13 (d, J = 5.2 Hz, 1H), 7.96 (d, J = 8.0 Hz, 1H), 7.86-7.82 (m, 1H), 7.77-7.76 (m, 2H), 7.66 (d, J = 8.0 Hz, 1H), 7.58-7.52 (m, 2H), 7.10 (d, J = 8.4 Hz, 1H), 7.02 (d, J = 7.2 Hz, 1H), 6.91 (d, J = 5.6 Hz, 1H), 6.85 (s, 1H), 6.60-6.56 (m, 1H), 5.06-5.01 (m, 1H), 4.20 (s, 2H), 4.08 (d, J = 5.6 Hz, |

TABLE 13-continued

The following compounds were prepared using standard chemical manipulations and procedures similar to those used for the preparation of Compound 91.

| Cmpd # | Name | LC-MS (ESI) (m/z) | $^1$H NMR |
|---|---|---|---|
| | pyrrole-3-carboxamide | | 2H), 3.79-3.69 (m, 1H), 3.59-3.56 (m, 2H), 3.50 (d, J = 4.0 Hz, 4H), 3.45-3.39 (m, 4H), 3.25-3.19 (m, 2H), 3.11 (s, 3H), 2.89-2.81 (m, 1H), 2.59-2.54 (m, 2H), 2.29 (s, 3H), 2.11 (s, 3H), 2.02-1.97 (m, 1H), 1.23 (d, J = 6.4 Hz, 6H) ppm |
| 116 | N-(2-((4-(3-(2-((2-(1'-(2-((2-(2,6-dioxopiperidin-3-yl)-1,3-dioxoisoindolin-4-yl)oxy)acetyl)-[4,4'-bipiperidin]-1-yl)-2-oxoethyl)(methyl)amino)pyridin-4-yl)phenyl)thiazol-2-yl)amino)-2-oxoethyl)-1-(isopropylsulfonyl)-4,5-dimethyl-1H-pyrrole-3-carboxamide | 1089.9 | $^1$H NMR (400 MHz, DMSO-$d_6$) δ = 8.53-8.47 (m, 1H), 8.25-8.19 (m, 1H), 8.16-8.10 (m, 1H), 8.01-7.94 (m, 1H), 7.86-7.74 (m, 3H), 7.71-7.51 (m, 2H), 7.49-7.42 (m, 1H), 7.37-7.22 (m, 1H), 6.92-6.86 (m, 1H), 6.84-6.80 (m, 1H), 5.26-5.02 (m, 3H), 4.60-4.46 (m, 2H), 4.41-4.28 (m, 2H), 4.12-4.08 (m, 2H), 4.02-3.79 (m, 2H), 3.75-3.74 (m, 1H), 3.31-3.29 (m, 3H), 3.11-3.09 (m, 2H), 3.05-2.80 (m, 3H), 2.64-2.57 (m, 3H), 2.32-2.28 (m, 3H), 2.14-2.11 (m, 3H), 2.07-1.99 (m, 1H), 1.75-1.61 (m, 3H), 1.42-1.29 (m, 2H), 1.24 (d, J = 6.8 Hz, 6H), 1.12-0.87 (m, 2H) ppm. |
| 95 | N-[2-[[4-[3-[2-[[2-[8-[[2-[2-(2,6-dioxo-3-piperidyl)-1,3-dioxo-isoindolin-4-yl]oxyacetyl]amino]octylamino]-2-oxo-ethyl]-methyl-amino]-4-pyridyl]phenyl]thiazol-2-yl]amino]-2-oxo-ethyl]-1-isopropylsulfonyl-4,5-dimethyl-pyrrole-3-carboxamide | 1065.2 | $^1$H NMR (400 MHz, DMSO-d6) δ = 12.27 (s, 1H), 12.46-12.21 (m, 1H), 12.53-12.15 (m, 1H), 11.37-10.94 (m, 1H), 8.50-8.52 (m, 1H), 8.21 (s, 1H), 8.15 (d, J = 5.2 Hz, 1H), 7.97 (d, J = 8.0 Hz, 1H), 7.92-7.90 (m, 1H), 7.84-7.76 (m, 4H), 7.67 (d, J = 8.0 Hz, 1H), 7.59-7.53 (m, 1H), 7.49 (d, J = 7.2 Hz, 1H), 7.39 (d, J = 8.4 Hz, 1H), 6.94-6.93 (m, 1H), 6.88-6.81 (m, 1H), 5.14-5.10 (m, 1H), 4.76 (s, 2H), 4.19 (s, 2H), 4.10 (d, J = 5.6 Hz, 2H), 3.76-3.73 (m, 1H), 3.16-3.09 (m, 5H), 3.09-3.02 (m, 2H), 2.90-2.86 (m, 1H), 2.61 (d, J = 2.4 Hz, 2H), 2.30 (s, 3H), 2.12 (s, 3H), 2.08-2.00 (m, 1H), 1.44-1.35 (m, 4H), 1.26-1.18 (m, 14H) ppm |

Preparation of 2-[methyl-[4-[3-[2-[[2-[(5-methyl-1-methylsulfonyl-pyrrole-3-carbonyl)amino]acetyl]amino]thiazol-4-yl]phenyl]-2-pyridyl]amino]acetic acid (I-102)

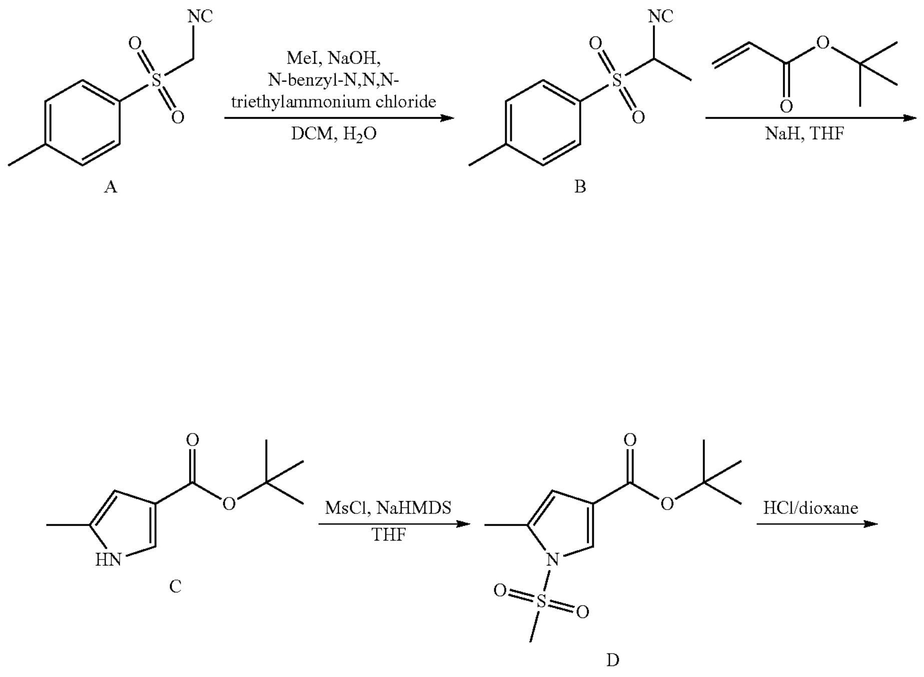

-continued
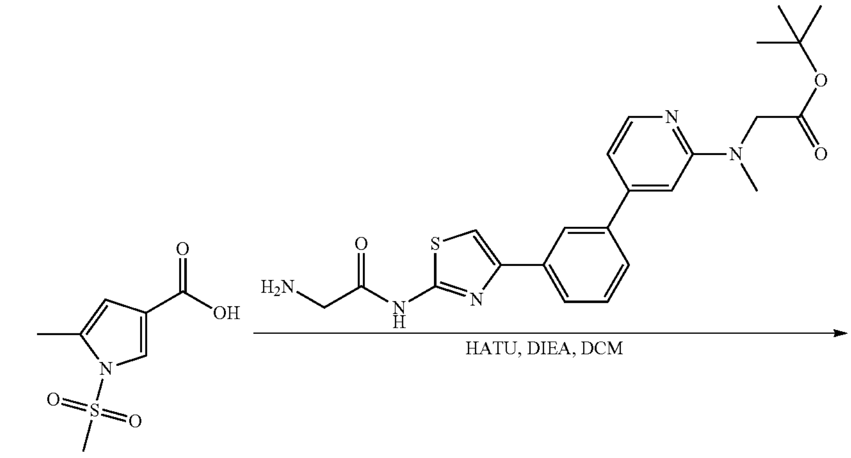
E
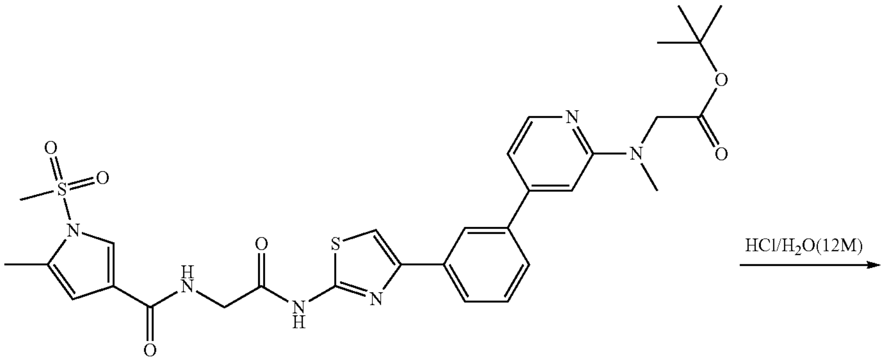
F
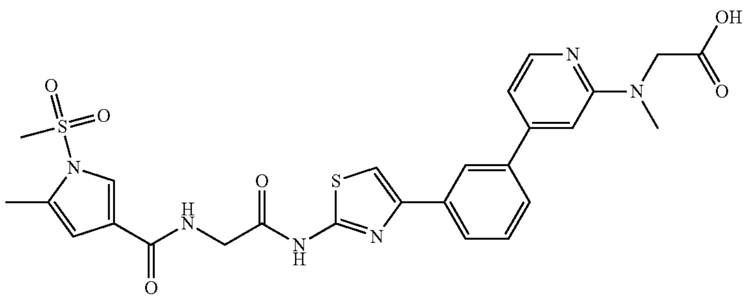
I-102

Step 1: Preparation of 1-(1-isocyanoethylsulfonyl)-4-methyl-benzene (B)

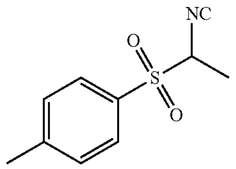

B

To a solution of 1-(isocyanomethylsulfonyl)-4-methyl-benzene (A, 30 g, 153.66 mmol) in DCM (300 mL) was added benzyl(triethyl)ammonium chloride (7.00 g, 30.73 mmol) and MeI (43.62 g, 307.32 mmol, 19.13 mL) at 0° C. NaOH (307.29 g, 2.30 mol, 30% in water) was added slowly and the reaction mixture stirred at 0° C. for 4 h. The reaction mixture was diluted with water (300 mL) and extracted with DCM (300 mL×3). The combined organic layers were washed with water (300 mL×3), dried over anhydrous $Na_2SO_4$, and under reduced pressure to give B (31 gl, 81.36% yield, 84.396% purity) as a brown oil. $^1$H NMR (400 MHz, CHLOROFORM-d) δ=7.89 (d, J=8.0 Hz, 2H), 7.45 (d, J=7.6 Hz, 2H), 4.63-4.57 (m, 1H), 2.51 (s, 3H), 1.76 (d, J=6.8 Hz, 3H) ppm.

Step 2: Preparation of tert-butyl 5-methyl-1H-pyrrole-3-carboxylate (C)

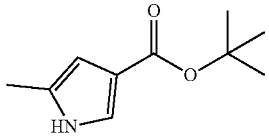

C

To a solution of tert-butylprop-2-enoate (18.99 g, 148.14 mmol, 21.50 mL) and B (31 g, 148.14 mmol) in THE (400 mL) was added NaH (7.11 g, 177.77 mmol, 60% in mineral oil) slowly at 40° C. The reaction mixture was heated to 70° C. and stirred for 1 h. The reaction mixture was poured into a saturated aqueous $NH_4Cl$ (500 mL) and extracted with EtOAc (300 mL×3). The combined organic phase was washed with brine (300 mL), dried over anhydrous $Na_2SO_4$, and concentrated under reduced pressure. The residue was purified by silica gel column chromatography (Petroleum ether/EtOAc 1:0-10:1) to give C (5.1 g, 20.09 mmol, 13.56% yield, 71.40% purity) as a yellow oil. LCMS (ESI) m/z: $[M-56+H]^+$=126.1. $^1$H NMR (400 MHz, CHLOROFORM-d) δ=8.08 (s, 1H), 7.23-7.21 (m, 1H), 6.26 (s, 1H), 2.25 (s, 3H), 1.54 (s, 9H) ppm.

Step 3: Preparation of tert-butyl 5-methyl-1-methylsulfonyl-pyrrole-3-carboxylate (D)

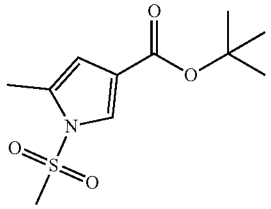

D

To a mixture of C (4.6 g, 25.38 mmol) in THE (80 mL) was slowly added NaHMDS (1 M, 50.76 mL) at 0° C. The reaction mixture was stirred for 30 min followed by drop-wise addition of methanesulfonyl chloride (4.36 g, 38.07 mmol, 2.95 mL) at 0° C. The reaction mixture was stirred at 15° C. for an additional 16 h, then slowly poured into a saturated aqueous $NH_4Cl$ solution (150 mL) and extracted with EtOAc (100 mL×3). The combined organic layers were washed with brine (60 mL), dried over anhydrous $Na_2SO_4$, and concentrated under reduced pressure. The residue was purified by reverse phase column chromatography (0.1% aqueous ammonia) to give D (3.1 g, 47.10%) as a white solid. $^1$H NMR (400 MHz, chloroform-d) δ=7.63 (d, J=2.0 Hz, 1H), 6.40-6.39 (m, 1H), 3.19 (s, 3H), 2.44 (d, J=0.8 Hz, 3H), 1.54 (s, 9H) ppm.

Step 4: Preparation of 5-methyl-1-methylsulfonyl-pyrrole-3-carboxylic acid (E)

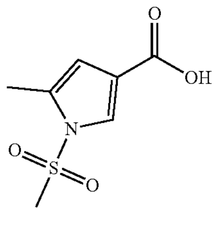

E

A mixture of D (3.1 g, 11.95 mmol) in HCl/1,4-dioxane (4 M, 50 mL) was stirred at 15° C. for 48 h. The reaction mixture was concentrated under reduced pressure, and the residue was triturated with MTBE (15 mL) and Petroleum ether (15 mL) at 15° C. for 10 min. The mixture was filtered to give E (2.35 g, 96.74% yield) as a yellow solid. LCMS (ESI) m/z: $[M+H]^+$=204.1. $^1$H NMR (400 MHz, methanol-d4) δ=7.69 (d, J=1.6 Hz, 1H), 6.41 (s, 1H), 3.35 (s, 3H), 2.44 (d, J=0.8 Hz, 3H) ppm.

Step 5: Preparation of tert-butyl 2-[methyl-[4-[3-[2-[[2-[(5-methyl-1-methylsulfonyl-pyrrole-3-carbonyl)amino]acetyl]amino]thiazol-4-yl]phenyl]-2-pyridyl]amino]acetate (F)

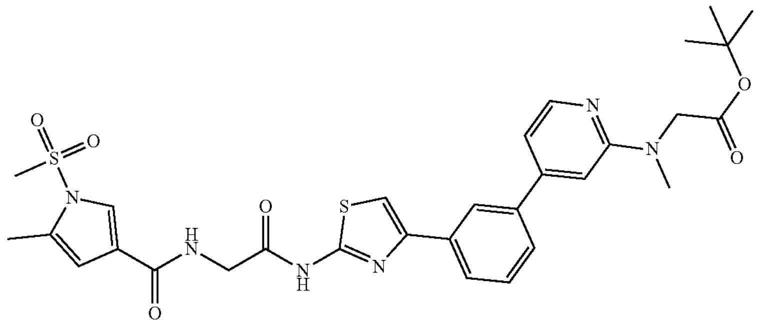

F

To a mixture of E (224.02 mg, 1.10 mmol) in DCM (5 mL) was added DIEA (427.43 mg, 3.31 mmol, 576.05 μL), HATU (628.75 mg, 1.65 mmol) and tert-butyl 2-[[4-[3-[2-[(2-aminoacetyl)amino]thiazol-4-yl]phenyl]-2-pyridyl]-methyl-amino]acetate (500 mg, 1.10 mmol) at 30° C. The reaction mixture was stirred for 16 h, then washed with water (10 mL×3). The organic layers were concentrated under reduced pressure and the residue triturated with EtOAc (10 mL) to give F (550 mg, 76.58% yield) as a yellow solid. LCMS (ESI) m/z: $[M+H]^+$=639.3. $^1H$ NMR (400 MHz, DMSO-$d_6$) δ=12.40 (s, 1H), 8.62-8.58 (m, 1H), 8.26 (s, 1H), 8.15 (d, J=6.0 Hz, 1H), 8.03 (d, J=7.6 Hz, 1H), 7.81 (s, 1H), 7.77 (d, J=7.2 Hz, 1H), 7.74 (d, J=2.0 Hz, 1H), 7.63-7.59 (m, 1H), 7.16 (s, 2H), 6.48 (s, 1H), 4.45 (s, 2H), 4.12 (d, J=6.0 Hz, 2H), 3.53 (s, 3H), 3.21 (s, 3H), 2.41 (s, 3H), 1.40 (s, 9H) ppm.

Step 6: Preparation of 2-[methyl-[4-[3-[2-[[2-[(5-methyl-1-methylsulfonyl-pyrrole-3-carbonyl)amino]acetyl]amino]thiazol-4-yl]phenyl]-2-pyridyl]amino]acetic acid (I-102)

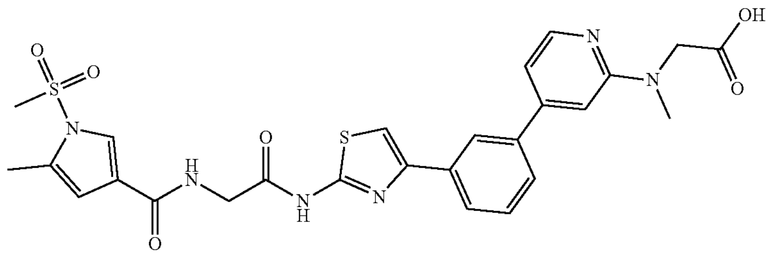

I-102

A mixture of F (510 mg, 798.43 μm) in HCl (12 M, 5 mL) was stirred at 25° C. for 20 min. The reaction mixture filtered to give I-102 (340 mg, 68.78%) as a yellow solid. LCMS (ESI) m/z: $[M+H]^+$=583.0. $^1H$ NMR (400 MHz, DMSO-$d_6$) δ=12.42 (s, 1H), 8.63-8.60 (m, 1H), 8.31 (s, 1H), 8.14 (d, J=6.4 Hz, 1H), 8.08 (d, J=7.6 Hz, 1H), 7.89-7.82 (m, 2H), 7.74 (d, J=2.0 Hz, 1H), 7.67-7.62 (m, 1H), 7.44 (s, 1H), 7.33 (d, J=5.6 Hz, 1H), 6.48 (s, 1H), 4.61 (s, 2H), 4.12 (d, J=5.6 Hz, 2H), 3.53 (s, 3H), 3.29 (s, 3H), 2.41 (s, 3H) ppm.

Compound 122—Preparation of N-(2-((4-(3-(2-((2-((2-(2-(2-((2-(2,6-dioxopiperidin-3-yl)-1,3-dioxoisoindolin-4-yl)amino)ethoxy)ethoxy)ethyl)amino)-2-oxoethyl)(methyl)amino)pyridin-4-yl)phenyl)thiazol-2-yl)amino)-2-oxoethyl)-5-methyl-1-(methylsulfonyl)-1H-pyrrole-3-carboxamide

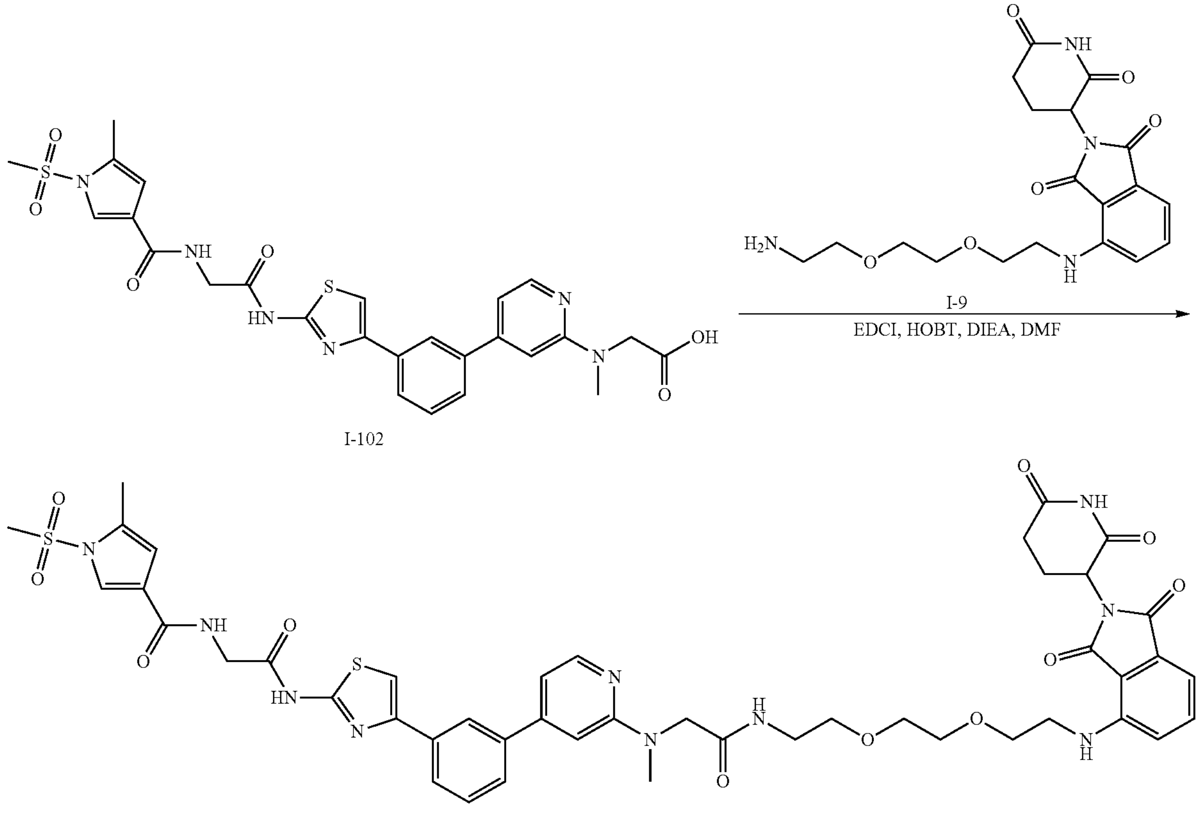

I-102

122

To a mixture of 2-[methyl-[4-[3-[2-[[2-[(5-methyl-1-methylsulfonyl-pyrrole-3-carbonyl)amino]acetyl]amino]thiazol-4-yl]phenyl]-2-pyridyl]amino]acetic acid (I-102, 40 mg, 0.064 mmol) and 4-[2-[2-(2-aminoethoxy)ethoxy]ethylamino]-2-(2,6-dioxo-3-piperidyl)isoindoline-1,3-dione (I-9, 26.13 mg, 0.064 mmol) in DMF (1 mL) was added DIEA (41.75 mg, 0.32 mmol, 56.27 μL). The mixture was stirred at 30° C. for 15 min, then EDCI (18.58 mg, 0.096 mmol) and HOBt (13.10 mg, 0.096 mmol) were added. After stirring for an additional 16 h, the mixture was poured into water (10 mL) and extracted with EtOAc (10 mL×3). The combined organic extracts were washed with brine (20 mL), dried over $Na_2SO_4$ and concentrated. The residue was purified by preparative HPLC (column: Waters Xbridge 150×25 mm×5 μm; mobile phase: [water (10 Mm $NH_4HCO_3$)-ACN]; B %: 26%-56%, 10 min) to give Compound 122 (9.9 mg, 14.48%) as a yellow solid. LCMS (ESI) m/z: $[M+H]^+$=969.5. $^1H$ NMR (400 MHz, DMSO-$d_6$) δ=12.44-12.36 (m, 1H), 11.11 (d, J=4.4 Hz, 1H), 8.63-8.60 (m, 1H), 8.19 (s, 1H), 8.13 (d, J=5.2 Hz, 1H), 7.96 (d, J=8.0 Hz, 1H), 7.90-7.87 (m, 1H), 7.78 (s, 1H), 7.74 (d, J=2.0 Hz, 1H), 7.67 (d, J=7.6 Hz, 1H), 7.58-7.52 (m, 2H), 7.11 (d, J=8.8 Hz, 1H), 7.03 (d, J=7.2 Hz, 1H), 6.92-6.90 (m, 1H), 6.85 (s, 1H), 6.60-6.57 (m, 1H), 6.48 (s, 1H), 5.06-5.02 (m, 1H), 4.20 (s, 2H), 4.11 (d, J=5.6 Hz, 2H), 3.58-3.56 (m, 2H), 3.53 (s, 3H), 3.50-3.48 (m, 4H), 3.45-3.38 (m, 4H), 3.23-3.19 (m, 2H), 3.16 (d, J=5.2 Hz, 1H), 3.11 (s, 3H), 2.90-2.81 (m, 1H), 2.58 (d, J=2.4 Hz, 1H), 2.40 (s, 3H), 2.07-1.96 (m, 1H) ppm.

TABLE 14

The following compounds were prepared using standard chemical manipulations and procedures similar to those used for the preparation of Compound 122.

| Cmpd # | Name | LC-MS (ESI) (m/z) | $^1$H NMR |
|---|---|---|---|
| 125 | N-(2-((4-(3-(2-((2-((5-((2-(2,6-dioxopiperidin-3-yl)-1,3-dioxoisoindolin-4-yl)amino)pentyl)amino)-2-oxoethyl)(methyl)amino)pyridin-4-yl)phenyl)thiazol-2-yl)amino)-2-oxoethyl)-5-methyl-1-(methylsulfonyl)-1H-pyrrole-3-carboxamide | 923.3 | $^1$H NMR (400 MHz, DMSO-d6) δ = 12.42 (br s, 1H), 11.10 (s, 1H), 8.64-8.62 (m, 1H), 8.20 (s, 1H), 8.15 (d, J = 5.2 Hz, 1H), 7.97 (d, J = 7.6 Hz, 1H), 7.88-7.85 (m, 1H), 7.78 (s, 1H), 7.75 (d, J = 1.6 Hz, 1H), 7.68-7.66 (m, 1H), 7.57-7.53 (m, 2H), 7.04-7.00 (m, 2H), 6.92-6.91 (m, 1H), 6.85 (s, 1H), 6.49 (s, 2H), 5.07-5.04 (m, 1H), 4.19 (s, 2H), 4.12 (d, J = 5.6 Hz, 2H), 3.54 (s, 3H), 3.21 (d, J = 6.0 Hz, 2H), 3.12 (s, 3H), 3.10-3.07 (m, 2H), 2.91-2.83 (m, 1H), 2.56 (s, 2H), 2.41 (s, 3H), 2.04-2.00 (m, 1H), 1.54-1.51 (m, 2H), 1.45-1.41 (m, 2H), 1.31-1.29 (m, 2H) ppm. |
| 130 | N-[2-[[4-[3-[2-[[2-[4-[1-[2-[2-(2,6-dioxo-3-piperidyl)-1,3-dioxo-isoindolin-4-yl]oxyacetyl]-4-piperidyl]-1-piperidyl]-2-oxo-ethyl]-methyl-amino]-4-pyridyl]phenyl]thiazol-2-yl]amino]-2-oxo-ethyl]-5-methyl-1-methylsulfonyl-pyrrole-3-carboxamide | 1047.5 | $^1$H NMR (400 MHz, DMSO-d6) δ = 12.45-12.41 (m, 1H), 11.12 (s, 1H), 8.62-8.61 (m, 1H), 8.21-8.20 (m, 1H), 8.12-8.11 (m, 1H), 7.97 (d, J = 8.0 Hz, 1H), 7.80-7.74 (m, 3H), 7.67 (d, J = 7.6 Hz, 1H), 7.57-7.53 (m, 1H), 7.45 (d, J = 7.2 Hz, 1H), 7.34-7.30 (m, 1H), 6.89-6.88 (m, 1H), 6.82 (s, 1H), 6.48 (s, 1H), 5.18-5.12 (m, 2H), 4.53-4.52 (m, 2H), 4.34-4.33 (m, 2H), 4.12 (d, J = 6.0 Hz, 2H), 3.97-3.92 (m, 1H), 3.83-3.78 (m, 1H), 3.54 (s, 3H), 3.09 (s, 3H), 3.02-2.85 (m, 4H), 2.62-2.56 (m, 4H), 2.40 (s, 3H), 2.08-2.01 (m, 1H), 1.74-1.65 (m, 4H), 1.34-1.22 (m, 4H), 1.00-0.93 (m, 2H) ppm |
| 131 | N-(2-((4-(3-(2-((2-((8-(2-((2-(2,6-dioxopiperidin-3-yl)-1,3-dioxoisoindolin-4-yl)oxy)acetamido)octyl)amino)-2-oxoethyl)(methyl)amino)pyridin-4-yl)phenyl)thiazol-2-yl)amino)-2-oxoethyl)-5-methyl-1-(methylsulfonyl)-1H-pyrrole-3-carboxamide | 1023.4 | $^1$H NMR (400 MHz, DMSO-$d_6$) δ = 12.44-12.39 (m, 1H), 11.13-11.11 (m, 1H), 8.63-8.59 (m, 1H), 8.44 (s, 1H), 8.20 (s, 1H), 8.14 (d, J = 5.2 Hz, 1H), 7.97-7.95 (m, 1H), 7.93-7.90 (m, 1H), 7.82 (d, J = 5.2 Hz, 1H), 7.78 (d, J = 1.6 Hz, 1H), 7.73 (d, J = 2.0 Hz, 1H), 7.67 (d, J = 8.4 Hz, 1H), 7.56-7.53 (m, 1H), 7.49-7.47 (m, 1H), 7.38-7.36 (m, 1H), 6.92-6.91 (m, 1H), 6.84 (s, 1H), 6.48 (s, 1H), 5.13-5.09 (m, 1H), 4.75 (s, 2H), 4.17 (s, 2H), 4.12-4.08 (m, 2H), 3.53 (s, 3H), 3.12-3.10 (m, 4H), 3.06-3.01 (m, 2H), 2.61-2.55 (m, 2H), 2.40 (s, 3H), 2.04-2.00 (m, 1H), 1.40-1.34 (m, 4H), 1.25-1.17 (m, 8H) ppm. |

Preparation of N-[2-[[4-[3-[2-(2-aminoethoxy)-4-pyridyl]phenyl]thiazol-2-yl]amino]-2-oxo-ethyl]-1-methylsulfonyl-pyrrole-3-carboxamide (I-96)

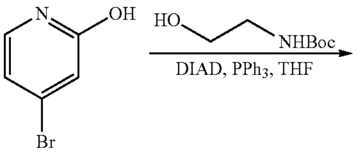

A

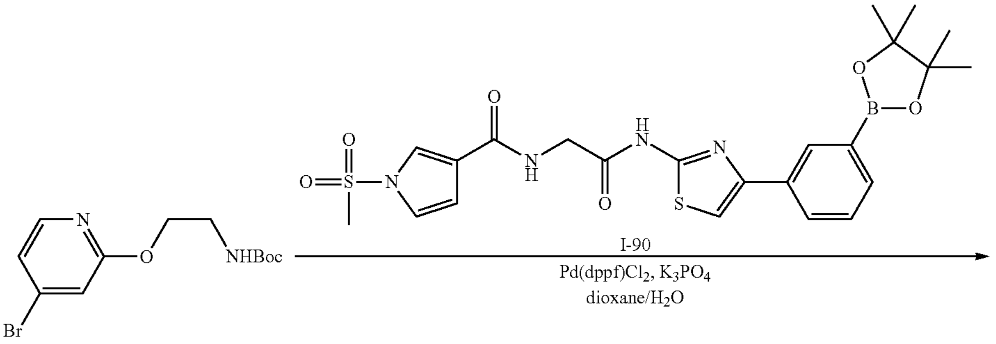

B

-continued

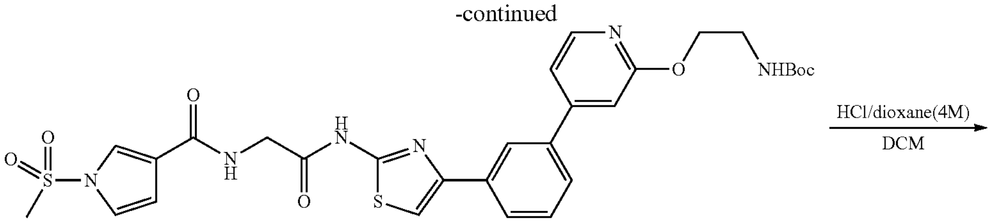

C

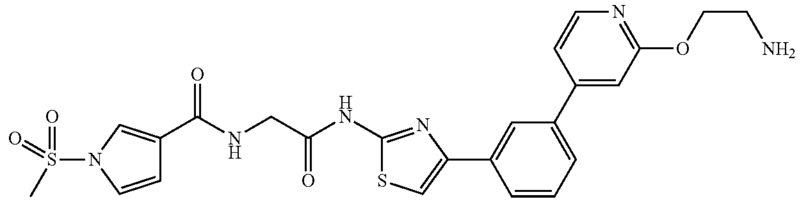

I-96

Step 1: Preparation of tert-butyl N-[2-[(4-bromo-2-pyridyl)oxy]ethyl]carbamate (B)

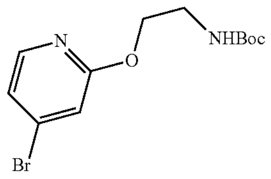

B

To a solution of 4-bromopyridin-2-ol (A, 0.5 g, 2.87 mmol) in THE (5 mL) was added $PPh_3$ (1.13 g, 4.31 mmol) and tert-butyl N-(2-hydroxyethyl)carbamate (555.87 mg, 3.45 mmol, 534.49 μL) at 0° C. DIAD (871.62 mg, 4.31 mmol, 838.10 μL) was added dropwise and the mixture was stirred at 20° C. for 2 h. The reaction mixture was quenched with water (10 mL) and extracted with DCM (20 mL). The combined organic layers were washed with water (10 mL), dried over $Na_2SO_4$, and concentrated under reduced pressure. The residue was purified by column chromatography ($SiO_2$, Petroleum ether/EtOAc 3:1) to afford B (0.6 g, 1.89 mmol, 65.83%) as a white solid. LCMS (ESI) m/z: [$^{81}$BrM+H]$^+$=318.9. $^1$H NMR (400 MHz, chloroform-d) δ=1.46 (s, 9H), 3.54-3.52 (m, 2H), 4.38-4.36 (m, 2H), 4.95 (s, 1H), 6.96 (d, J=1.6 Hz, 1H), 7.06-7.04 (m, 1H), 7.97 (d, J=5.6 Hz, 1H) ppm.

Step 2: Preparation of tertbutyl N-[2-[[4-[3-[2-[[2-[(1-methylsulfonylpyrrole-3-carbonyl)amino]acetyl]amino]thiazol-4-yl]phenyl]-2-pyridyl]oxy]ethyl]carbamate (C)

C

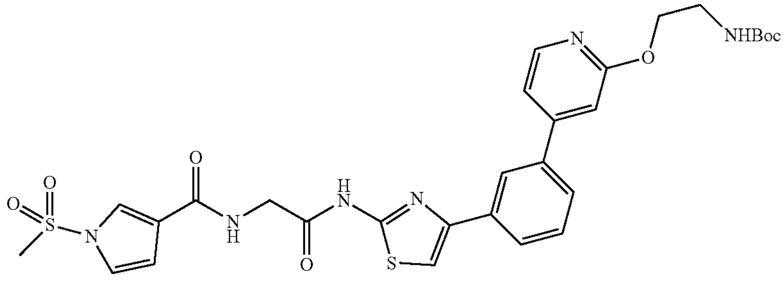

A mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (I-90, 530 mg, 1.0 mmol), B (380.31 mg, 1.20 mmol), $K_3PO_4$ (636.30 mg, 3.00 mmol), and $Pd(dppf)Cl_2$ (73.11 mg, 0.1 mmol) in 1,4-dioxane (6 mL)/water (2 mL) was degassed and purged three times with nitrogen. The mixture was stirred at 80° C. for 2 h then concentrated under reduced pressure. The residue was purified by column chromatography ($SiO_2$, Petroleum ether/EtOAc 1:1) to give C (0.4 g, 62.48%) as a yellow solid. LCMS (ESI) m/z: $[M+H]^+$=641.2.

$^1$H NMR (400 MHz, DMSO-$d_6$) δ=1.39 (s, 9H), 3.58 (s, 3H), 4.16-4.14 (m, 2H), 4.33-4.31 (m, 2H), 6.79-6.77 (m, 1H), 7.01 (s, 1H), 7.16 (s, 1H), 7.34-7.30 (m, 1H), 7.38-7.36 (m, 1H), 7.59-7.57 (m, 1H), 7.75-7.73 (m, 1H), 7.85 (s, 2H), 8.01 (d, J=7.6 Hz, 1H), 8.25 (d, J=5.2 Hz, 1H), 8.30 (s, 1H), 8.70-8.68 (m, 1H), 12.44 (s, 1H) ppm.

Step 3: Preparation of N-[2-[[4-[3-[2-(2-aminoethoxy)-4-pyridyl]phenyl]thiazol-2-yl]amino]-2-oxo-ethyl]-1-methylsulfonyl-pyrrole-3-carboxamide (I-96)

I-96

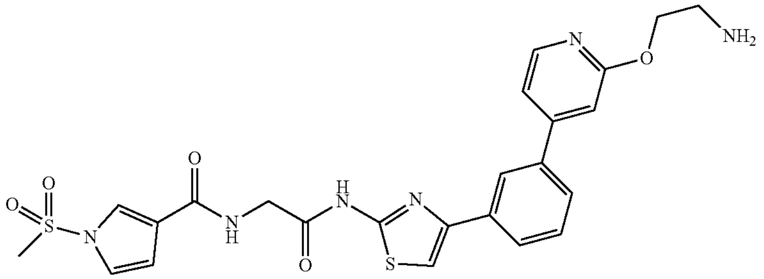

To a solution of C (300 mg, 0.468 mmol) in DCM (0.5 mL) was added HCl/1,4-dioxane (4 M, 2.34 mL). The mixture was stirred at 20° C. for 2 h, then concentrated under reduced pressure. The residue was suspended in MTBE (10 mL), filtered, and triturated with TBME (3 mL) to give the crude I-96 (0.25 g, 92.53% yield) as a yellow solid. LCMS (ESI) m/z: $[M+H]^+$=541.1. $^1$H NMR (400 MHz, DMSO-$d_6$) δ=12.44 (s, 1H), 8.71 (s, 1H), 8.33-8.26 (m, 2H), 8.03 (d, J=7.8 Hz, 3H), 7.85 (d, J=6.0 Hz, 2H), 7.73 (d, J=8.4 Hz, 1H), 7.64-7.57 (m, 1H), 7.45 (d, J=5.2 Hz, 1H), 7.35-7.30 (m, 1H), 7.19 (s, 1H), 6.78 (s, 1H), 4.57-4.47 (m, 2H), 4.16-4.14 (m, 2H), 3.58 (s, 3H), 3.29-3.25 (m, 2H) ppm.

Compound 36—Preparation of N-[2-[[4-[3-[2-[2-[4-[2-(2,6-dioxo-3-piperidyl)-1,3-dioxo-isoindolin-4-yl]oxybutanoylamino]ethoxy]-4-pyridyl]phenyl]thiazol-2-yl]amino]-2-oxo-ethyl]-1-methylsulfonyl-pyrrole-3-carboxamide

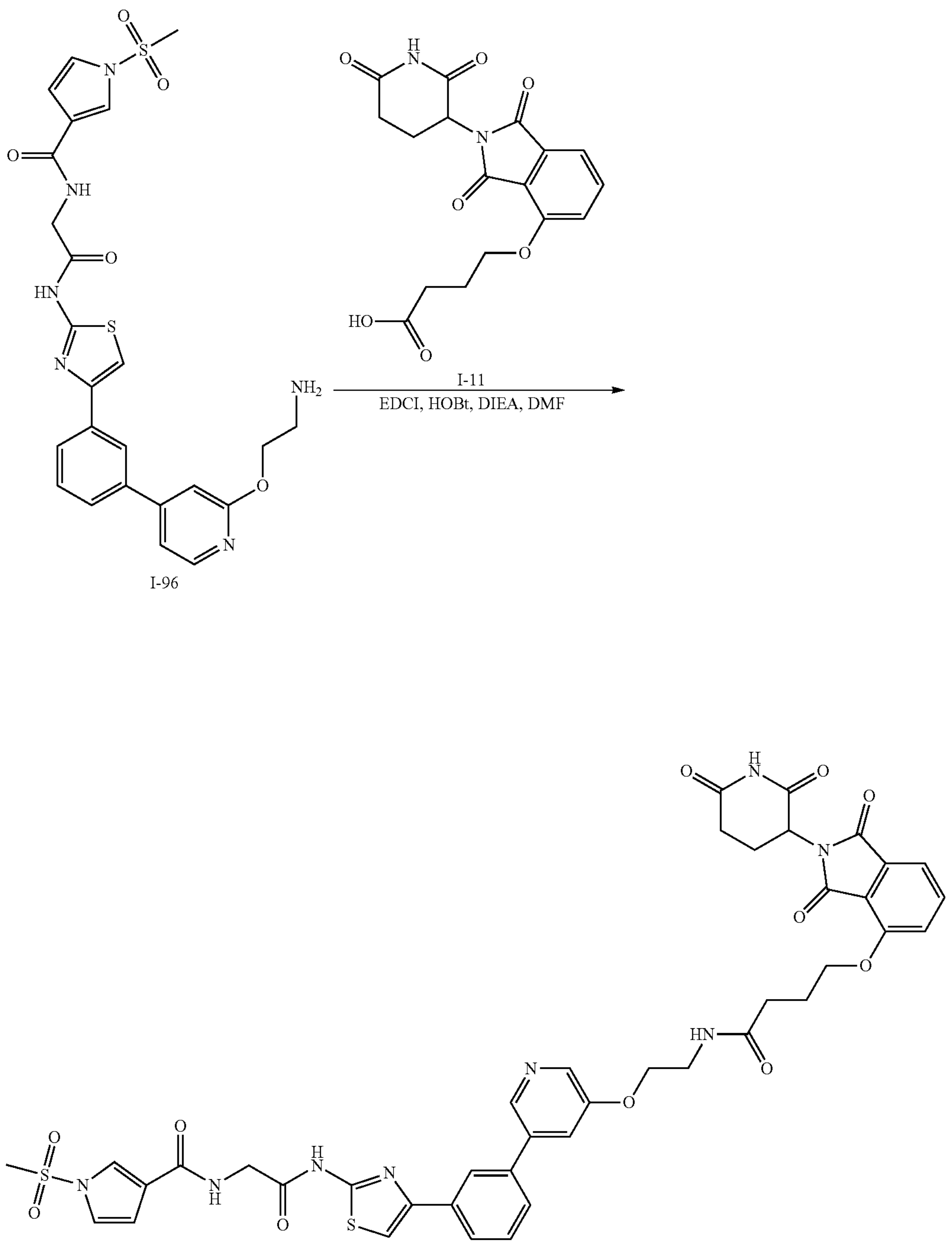

I-96

36

To a solution of N-[2-[[4-[3-[2-(2-aminoethoxy)-4-pyridyl]phenyl]thiazol-2-yl]amino]-2-oxo-ethyl]-1-methylsulfonyl-pyrrole-3-carboxamide (I-96, 30 mg, 0.052 mmol), 4-[2-(2,6-dioxo-3-piperidyl)-1,3-dioxo-isoindolin-4-yl]oxybutanoic acid (I-11, 22.48 mg, 0.06 mmol), EDCI (19.93 mg, 0.103 mmol), and HOBt (14.05 mg, 0.103 mmol) in DMF (1 mL) was added DIEA (33.59 mg, 0.259 mmol, 45.28 μL). The mixture was stirred at 25° C. for 16 h. The reaction mixture was filtered and the filtrate was purified directly by preparative HPLC (column: Phenomenex Synergi C18 150×25×10 μm; mobile phase: [0.225% formic acid in water/ACN: 38%-68%, 9 min) to give Compound 36 (14.03 mg, 28.94% yield) as a white solid. LCMS (ESI) m/z: $[M+H]^+$=883.2. $^1$H NMR (400 MHz, DMSO-$d_6$) δ=8.76-8.74 (m, 1H), 8.32-8.22 (m, 2H), 8.16-8.14 (m, 1H), 8.00 (d, J=7.6 Hz, 1H), 7.89-7.69 (m, 4H), 7.60-7.30 (m, 5H), 7.14 (s, 1H), 6.79-6.78 (m, 1H), 5.09-5.06 (m, 1H), 4.40-4.13 (m, 6H), 3.59 (s, 3H), 3.51-3.47 (m, 2H), 2.94-2.81 (m, 1H), 2.62-2.53 (m, 2H), 2.34-2.32 (m, 2H), 2.06-1.94 (m, 3H) ppm.

TABLE 15

The following were prepared using standard chemical manipulations and procedures similar to those used for the preparation of Compound 36.

| Cmpd # | Name | LC-MS (ESI) (m/z) | $^1$H NMR |
|---|---|---|---|
| 37 | N-[2-[[4-[3-[2-[2-[[2-[[[2-[2-(2,6-dioxo-3-piperidyl)-1,3-dioxoisoindolin-4-yl]oxyacetyl]amino]methyl]cyclopropanecarbonyl]amino]ethoxy]-4-pyridyl]phenyl]thiazol-2-yl]amino]-2-oxoethyl]-1-methylsulfonyl-pyrrole-3-carboxamide | 952.2 | $^1$H NMR (400 MHz, DMSO-d6) δ = 8.74-8.73 (m, 1H), 8.38-8.19 (m, 3H), 8.03-7.70 (m, 6H), 7.59-7.29 (m, 5H), 7.13 (s, 1H), 6.79-6.78 (m, 1H), 5.14-5.11 (m, 1H), 4.76 (s, 2H), 4.33-4.31 (m, 2H), 4.15 (d, J = 5.6 Hz, 2H), 3.59 (s, 3H), 3.52-3.47 (m, 2H), 3.35-3.31 (m, 2H), 2.97-2.83 (m, 1H), 2.64-2.53 (m, 2H), 2.07-1.98 (m, 1H), 1.77-1.67 (m, 1H), 1.42-1.30 (m, 1H), 0.96-0.80 (m, 2H) ppm |
| 38 | N-(2-((4-(3-(2-(2-(3-(2-(2-((2-(2,6-dioxopiperidin-3-yl)-1,3-dioxoisoindolin-5-yl)oxy)ethoxy)ethoxy)propanamido)ethoxy)pyridin-4-yl)phenyl)thiazol-2-yl)amino)-2-oxoethyl)-1-(methylsulfonyl)-1H-pyrrole-3-carboxamide | 957.3 | $^1$H NMR (400 MHz, DMSO-d6) δ = 8.74-8.73 (m, 1H), 8.32-8.22 (m, 2H), 8.12-8.11 (m, 1H), 8.00 (d, J = 7.6 Hz, 1H), 7.89-7.71 (m, 4H), 7.57-7.55 (m, 1H), 7.43-7.29 (m, 4H), 7.15 (s, 1H), 6.79 (d, J = 1.6 Hz, 1H), 5.13-5.10 (m, 1H), 4.33-4.31 (m, 2H), 4.28-4.22 (m, 2H), 4.15 (d, J = 5.6 Hz, 2H), 3.81-3.70 (m, 2H), 3.63-3.54 (m, 7H), 3.52-3.46 (m, 4H), 2.94-2.82 (m, 1H), 2.64-2.53 (m, 2H), 2.35-2.33 (m, 2H), 2.10-1.99 (m, 1H) ppm |
| 68 | N-[2-[[4-[3-[2-[2-[3-[2-[2-[2-(2,6-dioxo-3-piperidyl)-1,3-dioxoisoindolin-4-yl]oxyethoxy]ethoxy]propanoylamino]ethoxy]-4-pyridyl]phenyl]thiazol-2-yl]amino]-2-oxo-ethyl]-1-methylsulfonyl-pyrrole-3-carboxamide | 957.3 | $^1$H NMR (400 MHz, DMSO-d6) δ = 8.75-8.73 (m, 1H), 8.32-8.21 (m, 2H), 8.12-8.10 (m, 1H), 8.00 (d, J = 7.6 Hz, 1H), 7.89-7.70 (m, 4H), 7.59-7.31 (m, 5H), 7.15 (s, 1H), 6.80-6.79 (m, 1H), 5.10-5.07 (m, 1H), 4.37-4.26 (m, 4H), 4.15 (d, J = 5.6 Hz, 2H), 3.81-3.73 (m, 2H), 3.64-3.58 (m, 7H), 3.52-3.46 (m, 4H), 2.95-2.82 (m, 1H), 2.63-2.52 (m, 2H), 2.36-2.34 (m, 2H), 2.06-1.96 (m, 1H) ppm |
| 69 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N10-(2-((4-(3-(2-(2-(1-(methylsulfonyl)-1H-pyrrole-3-carboxamido)acetamido)thiazol-4-yl)phenyl)pyridin-2-yl)oxy)ethyl)decanediamide | 1137.1 | $^1$H NMR (400 MHZ, methanol-d4) δ = 8.89-8.84 (m, 1H), 8.28-8.22 (m, 1H), 8.22-8.16 (m, 1H), 8.02-7.97 (m, 1H), 7.87-7.84 (m, 1H), 7.69-7.63 (m, 1H), 7.58-7.52 (m, 2H), 7.49-7.44 (m, 2H), 7.43-7.38 (m, 2H), 7.34-7.27 (m, 2H), 7.14-7.11 (m, 1H), 6.84-6.81 (m, 1H), 4.67-4.48 (m, 4H), 4.46-4.32 (m, 3H), 4.30-4.27 (m, 2H), 3.95-3.88 (m, 1H), 3.84-3.78 (m, 1H), 3.65-3.57 (m, 2H), 3.42-3.38 (m, 3H), 2.50-2.44 (m, 3H), 2.24-2.03 (m, 6H), 1.62-1.47 (m, 4H), 1.32-1.20 (m, 8H), 1.05 (s, 9H) ppm |
| 71 | N-(2-((4-(3-(2-(((S)-13-((2S,4R)-4-hydroxy-2-((4-(4-methylthiazol-5-yl)benzyl)carbamoyl)pyrrolidine-1-carbonyl)-14,14-dimethyl-4,11-dioxo-6,9-dioxa-3,12-diazapentadecyl)oxy)pyridin-4-yl)phenyl)thiazol-2-yl)amino)-2-oxoethyl)-1-(methylsulfonyl)-1H-pyrrole-3-carboxamide | 1113.0 | $^1$H NMR (400 MHz, DMSO-d6) δ = 8.98-8.96 (m, 1H), 8.69-8.66 (m, 1H), 8.60-8.66 (m, 1H), 8.49 (s, 1H), 8.29 (s, 1H), 8.25 (d, J = 5.2 Hz, 1H), 8.02-7.93 (m, 2H), 7.86-7.82 (m, 2H), 7.72 (d, J = 7.6 Hz, 1H), 7.59-7.48 (m, 2H), 7.38-7.36 (m, 4H), 7.33-7.31 (m, 1H), 7.15 (s, 1H), 6.79-6.77 (m, 1H), 5.19-5.16 (m, 1H), 4.58 (d, J = 9.6 Hz, 1H), 4.48-4.43 (m, 1H), 4.39-4.29 (m, 4H), 4.15 (d, J = 6.0 Hz, 2H), 4.00 (d, J = 5.2 Hz, 1H), 3.95 (s, 2H), 3.66-3.54 (m, 12H), 2.43 (s, 3H), 2.10-2.04 (m, 1H), 1.94-1.90 (m, 1H), 0.94-0.91 (m, 9H) ppm |
| 76 | N'-[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]-N-[2-[[4-[3-[2-[[2-[(1-methylsulfonylpyrrole-3-carbonyl)amino]acetyl]amino]thi- | 1053.3 | $^1$H NMR (400 MHz, DMSO-$d_6$) δ = 8.98 (s, 1H), 8.70-8.65 (m, 1H), 8.55 (m, 1H), 8.30 (s, 1H), 8.26 (d, J = 5.6 Hz, 1H), 8.07 (m, 1H), 8.01 (d, J = 7.6 Hz, 1H), 7.90 (d, J = 9.6 Hz, 1H), 7.87-7.83 (m, 2H), 7.74 (d, J = 8.0 Hz, 1H), 7.58 (m, 1H), 7.44-7.37 (m, 5H), 7.32 (d, J = 5.2 Hz, 1H), 7.17 (s, 1H), 6.78 (d, J = 3.2 Hz, 1H), 5.11 (d, J = 3.2 |

TABLE 15-continued

The following were prepared using standard chemical manipulations and procedures similar to those used for the preparation of Compound 36.

| Cmpd # | Name | LC-MS (ESI) (m/z) | $^1H$ NMR |
|---|---|---|---|
| | azol-4-yl]phenyl]-2-pyridyl]oxy]ethyl]butanediamide | | Hz, 1H), 4.56-4.39 (m, 3H), 4.36-4.31 (m, 3H), 4.27-4.13 (m, 3H), 3.70-3.60 (m, 2H), 3.58 (S, 3H), 3.51-3.42 (m, 2H), 2.45 (s, 3H), 2.42-2.33 (m, 4H), 2.07-1.85 (m, 2H), 0.93 (s, 9H) ppm. |
| 77 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N5-(2-((4-(3-(2-(2-(1-(methylsulfonyl)-1H-pyrrole-3-carboxamido)acetamido)thiazol-4-yl)phenyl)pyridin-2-yl)oxy)ethyl)glutaramide | 1067.1 | $^1H$ NMR (400 MHZ, methanol-d4) δ = 8.88-8.80 (s, 1H), 8.23 (m, 1H), 8.19-8.11 (m, 1H), 7.98-7.91 (m, 1H), 7.90-7.80 (m, 1H), 7.67-7.54 (m, 1H), 7.53-7.47 (m, 2H), 7.46-7.39 (m, 2H), 7.38-7.31 (m, 2H), 7.31-7.22 (m, 2H), 7.10 (d, J = 0.8 Hz, 1H), 6.81 (m, 1H), 4.64-4.56 (m, 2H), 4.54 (m, 2H), 4.44-4.36 (m, 2H), 4.30 (s, 1H), 4.29-4.23 (m, 2H), 3.96-3.74(m, 2H), 3.66-3.55 (m, 2H), 3.38 (s, 3H), 2.47-2.37 (s, 3H), 2.31-2.30 (m, 2H), 2.27 (s, 2H), 2.21-1.99 (m, 2H), 1.98-1.83(m, 2H), 1.09-0.92 (s, 9H) ppm. |
| 78 | N-[2-[[4-[3-[2-[2-[[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]acetyl]amino]ethoxy]-4-pyridyl]phenyl]thiazol-2-yl]amino]-2-oxo-ethyl]-1-methylsulfonyl-pyrrole-3-carboxamide | 1069.3 | $^1H$ NMR (400 MHz, DMSO-$d_6$) δ = 8.97 (s, 1H), 8.68 (s, 1H), 8.58 (m 1H), 8.33-8.22 (m, 3H), 8.01 (d, J = 7.6 Hz, 1H), 7.88-7.83 (m, 2H), 7.81 (d, J = 9.6 Hz, 1H), 7.74 (d, J = 8.0 Hz, 1H), 7.57 (m, 1H), 7.40 (s, 4H), 7.39-7.36 (m, 1H), 7.34-7.30 (m, 1H), 7.16 (s, 1H), 6.79 (d, J = 4.8 Hz, 1H), 5.14 (d, J = 2.8 Hz, 1H), 4.57 (d, J = 9.6 Hz, 1H), 4.46-4.37 (m, 4H), 4.26 (d, J = 5.2 Hz, 1H), 4.15 (d, J = 5.6 Hz, 2H), 4.08 (s, 2H), 4.02 (s, 2H), 3.63 (d, J = 6.0 Hz, 1H), 3.58 (s, 3H), 3.55-3.54 (m, 1H), 2.44 (s, 3H), 2.11-2.01 (m, 1H), 1.97-1.84 (m, 1H), 0.93 (s, 9H) ppm. |
| 80 | N-[2-[[4-[3-[2-[2-[[2-[[[2-[2-(2,6-dioxo-3-piperidyl)-1,3-dioxoisoindolin-5-yl]oxyacetyl]amino]methyl]cyclopropanecarbonyl]amino]ethoxy]-4-pyridyl]phenyl]thiazol-2-yl]amino]-2-oxoethyl]-1-methylsulfonyl-pyrrole-3-carboxamide | 952.2 | $^1H$ NMR (400 MHz, DMSO-$d_6$) δ = 11.12 (br s, 1H), 8.72-8.70 (m, 1H), 8.41-8.18 (m, 4H), 8.04-7.54 (m, 6H), 7.46-7.29 (m, 4H), 7.17-7.12 (m, 1H), 6.80-6.79 (m, 1H), 5.12-5.10 (m, 1H), 4.76-4.63 (m, 2H), 4.36-4.35 (m, 2H), 4.16 (d, J = 5.6 Hz, 2H), 3.58 (s, 3H), 3.53-3.47 (m, 3H), 3.34-3.30 (m, 2H), 2.96-2.82 (m, 1H), 2.64-2.56 (m, 1H), 2.11-1.98 (m, 1H), 1.76-1.67 (m, 1H), 1.45-1.32 (m, 1H), 0.90-0.86 (m, 2H) ppm. |
| 81 | N-[2-[[4-[3-[2-[2-[3-[2-[2-[[2-(2,6-dioxo-3-piperidyl)-1,3-dioxoisoindolin-4-yl]amino]ethoxy]ethoxy]propanoylamino]ethoxy]-4-pyridyl]phenyl]thiazol-2-yl]amino]-2-oxo-ethyl]-1-methylsulfonyl-pyrrole-3-carboxamide | 956.3 | $^1H$ NMR (400 MHz, DMSO-d6) δ = 11.09 (br s, 1H), 8.72-8.71 (m, 1H), 8.33-8.21 (m, 2H), 8.13-7.53 (m, 7H), 7.42-6.95 (m, 5H), 6.79-6.78 (m, 1H), 6.57-6.56 (m, 1H), 5.07-5.04 (m, 1H), 4.42-4.09 (m, 4H), 3.64-3.56 (m, 7H), 3.54-3.44 (m, 8H), 2.92-2.82 (m, 1H), 2.63-2.55 (m, 2H), 2.36-2.33 (m, 2H), 2.08-1.93 (m, 1H) ppm |
| 82 | N-[2-[[4-[3-[2-[2-[11-[[2-(2,6-dioxo-3-piperidyl)-1,3-dioxo-isoindolin-4-yl]amino]undecanoylamino]ethoxy]-4-pyridyl]phenyl]thiazol-2-yl]amino]-2-oxo-ethyl]-1-methylsulfonylpyrrole-3-carboxamide | 980.3 | $^1H$ NMR (400 MHz, DMSO-d6) δ = 8.69-8.68 (m, 1H), 8.36-8.22 (m, 2H), 8.07-7.28 (m, 10H), 7.14 (s, 1H), 7.04-7.02 (m, 2H), 6.84-6.74 (m, 1H), 6.49-6.47 (m, 1H), 5.06-5.04 (m, 1H), 4.34-4.33 (m, 2H), 4.15 (d, J = 5.6 Hz, 2H), 3.58 (s, 3H), 3.46-3.45 (m, 2H), 3.28-3.21 (m, 2H), 2.94-2.84 (m, 2H), 2.61 (d, J = 2.4 Hz, 2H), 2.12-2.01 (m, 3H), 1.54-1.44 (m, 4H), 1.20 (s, 10H) ppm |
| 83 | N-[2-[[4-[3-[2-[2-[3-[2-[2-[[2-(2,6-dioxo-3-piperidyl)-1,3-dioxoisoindolin-5-yl]amino]ethoxy]ethoxy]propanoylamino]ethoxy]-4-pyridyl]phenyl]thiazol-2-yl]amino]-2-oxo-ethyl]-1-methylsulfonyl-pyrrole-3-carboxamide | 956.3 | $^1H$ NMR (400 MHz, DMSO-d6) δ = 8.72-8.70 (m, 1H), 8.33-7.70 (m, 7H), 7.59-7.11 (m, 6H), 7.00 (s, 1H), 6.89-6.87 (m, 1H), 6.79 (d, J = 1.2 Hz, 1H), 5.04-5.03 (m, 1H), 4.38-4.14 (m, 4H), 3.66-3.47 (m, 15H), 2.91-2.82 (m, 1H), 2.59 (s, 2H), 2.35-2.33 (m, 2H), 2.03-1.94 (m, 1H) ppm |

TABLE 15-continued

The following were prepared using standard chemical manipulations and procedures similar to those used for the preparation of Compound 36.

| Cmpd # | Name | LC-MS (ESI) (m/z) | $^1$H NMR |
|---|---|---|---|
| 85 | N1-((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)-N7-(2-((4-(3-(2-(2-(1-(methylsulfonyl)-1H-pyrrole-3-carboxamido)acetamido)thiazol-4-yl)phenyl)pyridin-2-yl)oxy)ethyl)heptanediamide | 1095.1 | $^1$H NMR (400 MHz, DMSO-d6) δ = 12.44 (br s, 1H), 8.98 (s, 1H), 8.70-8.68 (m, 1H), 8.56-8.54 (m, 1H), 8.25 (d, J = 5.6 Hz, 1H), 8.01 (d, J = 6.4 Hz, 2H), 7.86-7.81 (m, 3H), 7.74 (d, J = 7.6 Hz, 1H), 7.59-7.57 (m, 1H), 7.46-7.35 (m, 6H), 7.34-7.30 (m, 1H), 7.16 (s, 1H), 6.80-6.78 (m, 1H), 5.14 (s, 1H), 4.54 (d, J = 9.2 Hz, 1H), 4.46-4.41 (m, 2H), 4.36-4.31 (m, 3H), 4.25-4.15 (m, 3H), 3.66 (s, 2H), 3.58 (s, 4H), 2.44 (s, 3H), 2.29-2.20 (m, 1H), 2.15-2.00 (m, 5H), 1.94-1.87 (m, 1H), 1.54-1.46 (m, 4H), 1.26-1.20 (m, 2H), 0.93 (s, 9H) ppm |

Preparation of 1-methylsulfonyl-N-[2-oxo-2-[[4-[3-(2-piperazin-1-yl-4-pyridyl)phenyl]thiazol-2-yl]amino]ethyl]pyrrole-3-carboxamide (I-97)

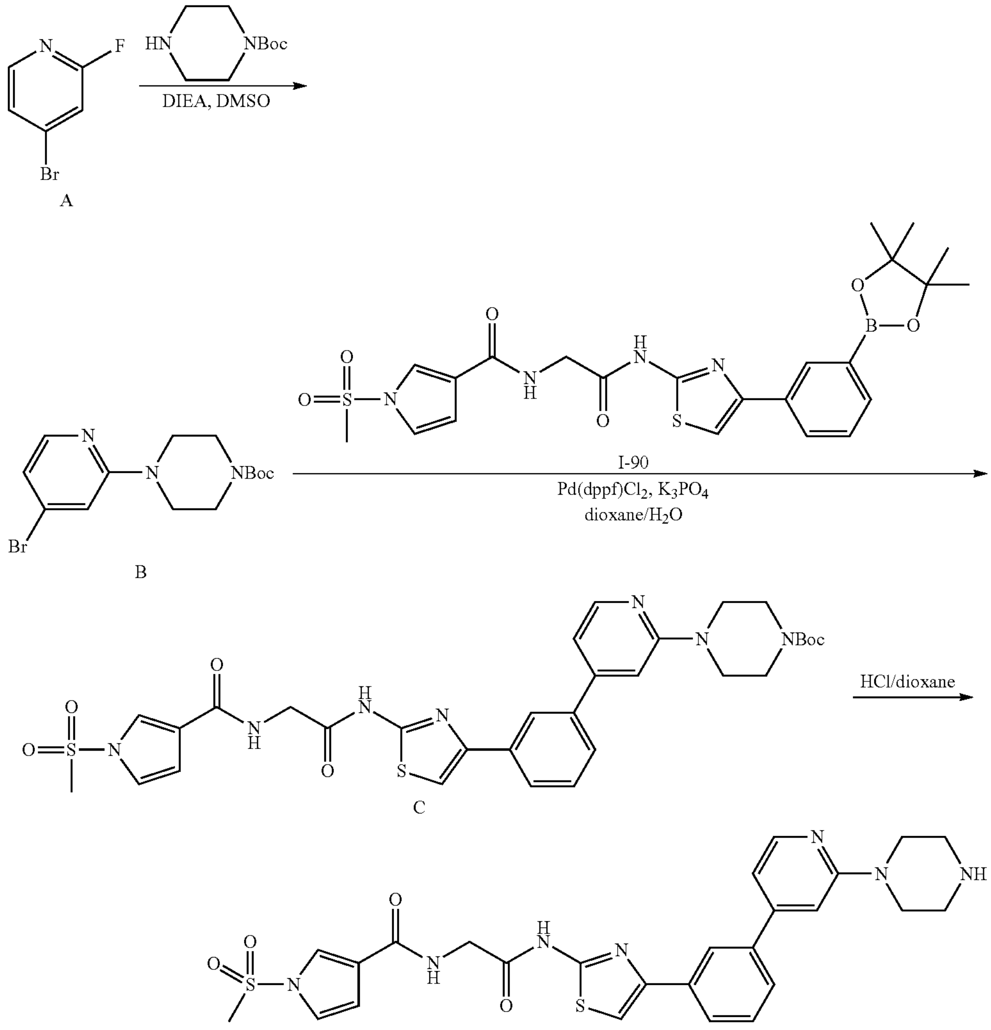

I-97

Step 1: Preparation of tert-butyl 4-(4-bromo-2-pyridyl)piperazine-1-carboxylate (B)

B

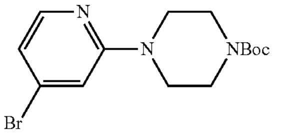

To a solution of 4-bromo-2-fluoro-pyridine (A, 2 g, 11.36 mmol) and tert-butyl piperazine-1-carboxylate (4.23 g, 22.73 mmol) in DMSO (20 mL) was added DIPEA (7.34 g, 56.82 mmol, 9.90 mL). The mixture was stirred at 120° C. for 16 h, then poured into water (50 mL) and extracted with EtOAc (50 mL×3). The combined organic extracts were washed with brine (100 mL), dried over $Na_2SO_4$, and concentrated to give B (3.5 g, 85.86%) as a brown solid which was used without further purification. LCMS (ESI) m/z: $[^{81}BrM+H]^+$=343.9. $^1H$ NMR (400 MHz, DMSO-$d_6$) δ=7.99 (d, J=5.2 Hz, 1H), 7.06 (s, 1H), 6.85-6.83 (m, 1H), 3.54-3.48 (m, 4H), 3.41-3.39 (m, 4H), 1.42 (s, 9H) ppm.

Step 2: Preparation of tert-butyl 4-[4-[3-[2-[[2-[(1-methylsulfonylpyrrole-3-carbonyl)amino]acetyl]amino]thiazol-4-yl]phenyl]-2-pyridyl]piperazine-1-carboxylate (C)

C

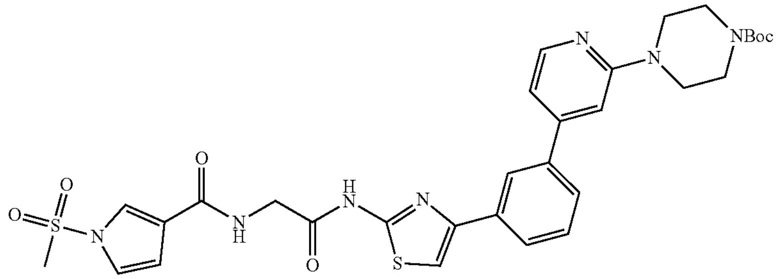

To a solution of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (I-90, 800 mg, 1.51 mmol) and B (774.24 mg, 2.26 mmol) in 1,4-dioxane (8 mL)/water (0.8 mL) was added $Pd(dppf)Cl_2$ (110.36 mg, 0.150 mmol) and $K_3PO_4$ (960.44 mg, 4.52 mmol) under an atmosphere of nitrogen. The mixture was stirred at 100° C. for 4 h, then diluted with water (15 mL), and extracted with EtOAc (20 mL×3). The combined organic extracts were washed with brine (20 mL×2), dried over anhydrous $Na_2SO_4$, and concentrated under reduced pressure. The residue was purified by column chromatography ($SiO_2$, Petroleum ether/EtOAc 5:1 to 1:2) to give C (650 mg, 57.96%, 89.533% purity) as a yellow solid. LCMS (ESI) m/z: $[M+H]^+$=666.1.

Step 3: Preparation of 1-methylsulfonyl-N-[2-oxo-2-[[4-[3-(2-piperazin-1-yl-4-pyridyl)phenyl]thiazol-2-yl]amino]ethyl]pyrrole-3-carboxamide (I-97)

I-97

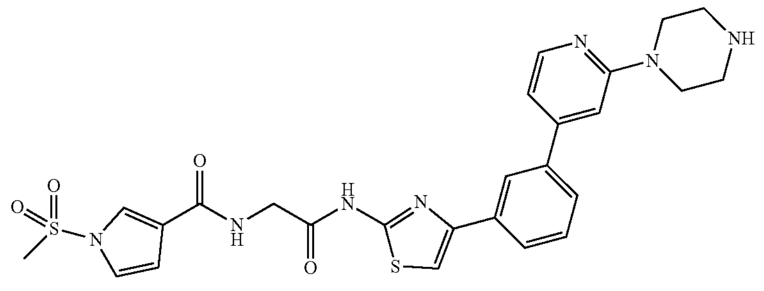

A solution of C (400 mg, 0.660 mmol) in 4 M HCl/1,4-dioxane (4 mL) was stirred at 20° C. for 1 h. The reaction mixture was concentrated under reduce pressure and the residue was stirred with MTBE (5 mL) for 5 min. The solid was filtered and triturated with MTBE (3 mL×3) to give I-97 (120 mg, 23.92%, 72.112% purity) as a brown solid which was used without further purification. LCMS (ESI) m/z: $[M+H]^+$=566.1. $^1H$ NMR (400 MHz, methanol-d4) δ=8.36 (s, 1H), 8.15-8.09 (m, 2H), 7.86-7.82 (m, 2H), 7.71 (s, 1H), 7.65 (s, 1H), 7.63-7.59 (m, 1H), 7.51 (d, J=6.4 Hz, 1H), 7.29-7.28 (m, 1H), 6.83-6.82 (m, 1H), 4.28 (s, 2H), 4.14-4.11 (m, 4H), 3.55-3.51 (m, 4H), 3.39 (s, 3H) ppm.

Compound 31—Preparation of N-[2-[[4-[3-[2-[4-[3-[2-[2-[[2-(2,6-dioxo-3-piperidyl)-1,3-dioxo-isoindolin-4-yl]amino]ethoxy]ethoxy]propanoyl]piperazin-1-yl]-4-pyridyl]phenyl]thiazol-2-yl]amino]-2-oxo-ethyl]-1-methylsulfonyl-pyrrole-3-carboxamide

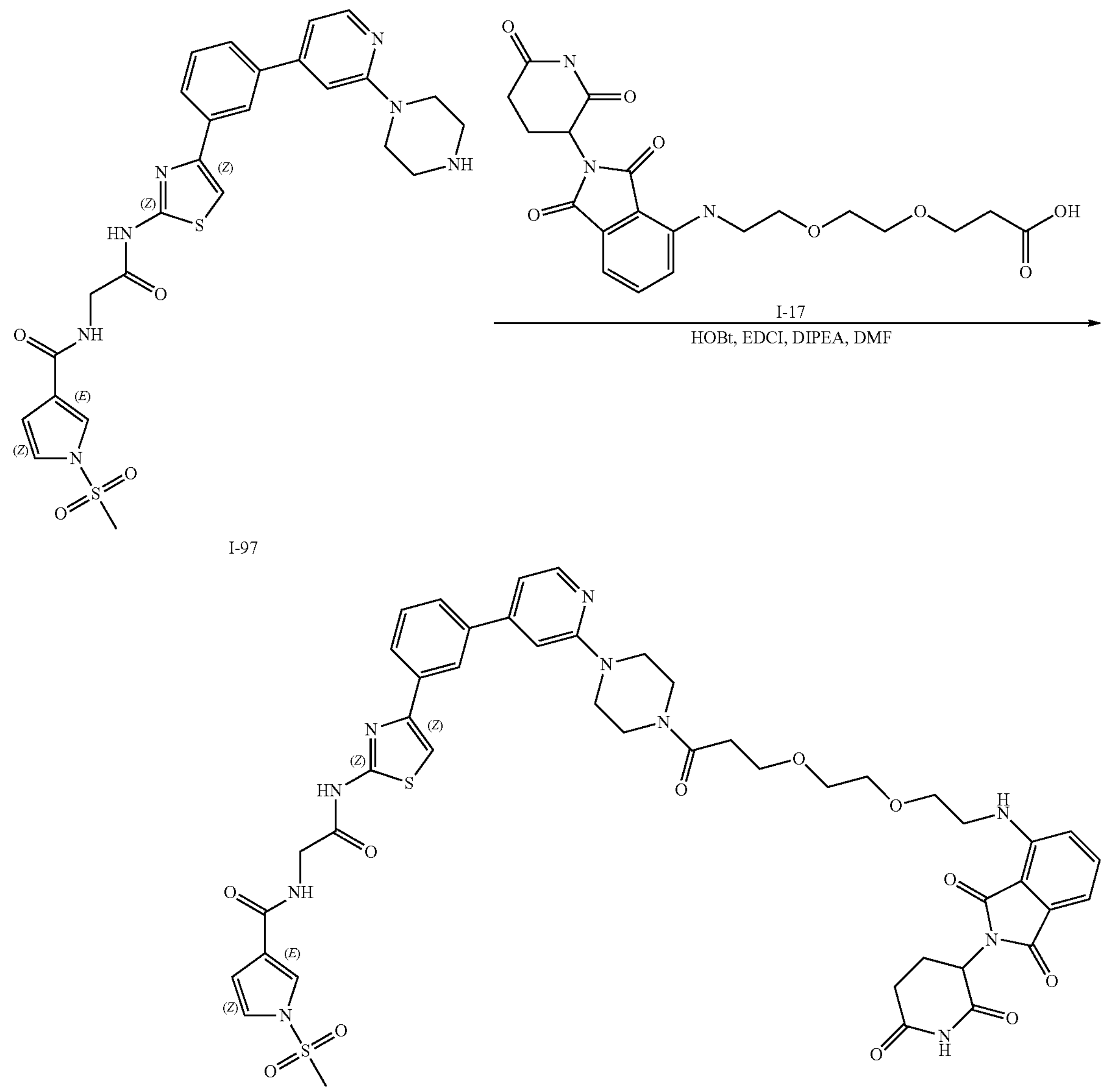

I-97

31

To a solution of 3-[2-[2-[[2-(2,6-dioxo-3-piperidyl)-1,3-dioxo-isoindolin-4-yl]amino]ethoxy]ethoxy]propanoic acid (I-17, 17.99 mg, 0.041 mmol) in DMF (0.4 mL) was added EDCI (11.94 mg, 0.062 mmol) and HOBt (8.42 mg, 0.062 mmol) at 10° C. 1-Methylsulfonyl-N-[2-oxo-2-[[4-[3-(2-piperazin-1-yl-4-pyridyl)phenyl]thiazol-2-yl]amino]ethyl] pyrrole-3-carboxamide (I-97, 25 mg, 0.041 mmol) and DIPEA (16.10 mg, 0.124 mmol, 21.70 μL) were added and the mixture stirred at 25° C. for 2.5 h. reaction was purified directly by preparative HPLC (column: Waters Xbridge 150×25 mm×5 μm; mobile phase: [10 mM aqueous NH4HCO3/ACN] 26%-56%, 10 min) to give Compound 31 (15.33 mg, 37.64%) as a yellow solid. LCMS (ESI) m/z: $[M+H]^+$=981.3. $^1$H NMR (400 MHz, DMSO-$d_6$) δ=12.44-12.31 (m, 1H), 11.12-11.05 (m, 1H), 8.66-8.64 (m, 1H), 8.21-8.20 (m, 2H), 7.98-7.76 (m, 1H), 7.85-7.84 (m, 1H), 7.79 (m, 1H), 7.70-7.68 (m, 1H), 7.57-7.53 (m, 2H), 7.32-7.30 (m, 1H), 7.12-7.10 (m, 2H), 7.02-6.99 (m, 2H), 6.78-6.76 (m, 1H), 6.60-6.57 (m, 1H), 5.06-5.02 (m, 1H), 4.14-4.13 (d, J=6.0 Hz, 2H), 3.67-3.52 (m, 19H), 3.46-3.42 (m, 3H), 2.90-2.82 (m, 2H), 2.62-2.59 (m, 4H), 2.05-1.98 (m, 2H) ppm.

TABLE 16

The following compounds were prepared using standard chemical manipulations and procedures similar to those used for the preparation of Compound 31.

| Cmpd # | Name | LC-MS ESI (m/z) | $^1$H NMR |
|---|---|---|---|
| 32 | N-[2-[[4-[3-[2-[4-[2-[[[2-[2-(2,6-dioxo-3-piperidyl)-1,3-dioxo-isoindolin-4-yl]oxyacetyl]amino]methyl]cyclopropanecarbonyl]piperazin-1-yl]-4-pyridyl]phenyl]thiazol-2-yl]amino]-2-oxo-ethyl]-1-methylsulfonyl-pyrrole-3-carboxamide | 977.3 | $^1$H NMR (400 MHz, DMSO-d6) δ = 12.42-12.31 (m, 1H), 11.14-11.08 (m, 1H), 8.69-8.66 (m, 1H), 8.22-8.15 (m, 2H), 7.98-7.96 (d, J = 7.6 Hz, 1H), 7.92-7.87 (m, 1H), 7.85-7.84 (m, 2H), 7.79 (s, 1H), 7.75-7.71 (m, 1H), 7.67-7.65 (m, 1H), 7.56-7.52 (m, 1H), 7.42-7.40 (m, 1H), 7.37-7.35 (m, 1H), 7.32-7.30 (m, 1H), 7.04 (s, 1H), 6.97-6.96 (m, 1H), 6.78-6.77 (m, 1H), 5.12-5.07 (m, 1H), 4.79-4.68 (m, 2H), 4.15-4.13 (m, 2H), 3.77-3.52 (m, 13H), 3.16-3.13 (m, 2H), 2.91-2.79 (m, 2H), 2.13-1.98 (m, 2H), 1.58-1.48 (m, 1H), 1.00-0.96 (m, 1H), 0.92-0.88 (m, 1H) ppm |
| 33 | N-[2-[[4-[3-[2-[4-[4-[2-(2,6-dioxo-3-piperidyl)-1,3-dioxo-isoindolin-4-yl]oxybutanoyl]piperazin-1-yl]-4-pyridyl]phenyl]thiazol-2-yl]amino]-2-oxo-ethyl]-1-methylsulfonyl-pyrrole-3-carboxamide | 908.2 | $^1$H NMR (400 MHz, methanol-d4) δ = 8.23 (s, 1H), 8.19 (d, J = 5.6 Hz, 1H), 7.97 (d, J = 7.6 Hz, 1H), 7.86 (m, 1H), 7.82-7.75 (m, 1H), 7.64 (d, J = 7.2 Hz, 1H), 7.57-7.51 (m, 2H), 7.48-7.44 (m, 2H), 7.30-7.29 (m, 1H), 7.10 (s, 1H), 7.05-7.03 (m, 1H), 6.83 -6.82(m, 1H), 5.11-5.06 (m, 1H), 4.33-4.30 (m, 1H), 4.29 (s, 2H), 3.84-3.74 (m, 4H), 3.73-3.53 (m, 5H), 3.40 (s, 3H), 2.88-2.69 (m, 5H), 2.26-2.19 (m, 2H), 2.16-2.08 (m, 1H) ppm. |
| 34 | N-(2-((4-(3-(2-(4-(3-(2-(2-((2-(2,6-dioxopiperidin-3-yl)-1,3-dioxoisoindolin-4-yl)oxy)ethoxy)ethoxy)propanoyl)piperazin-1-yl)pyridin-4-yl)phenyl)thiazol-2-yl)amino)-2-oxoethyl)-1-(methylsulfonyl)-1H-pyrrole-3-carboxamide | 982.3 | $^1$H NMR (400 MHz, DMSO-d6) δ = 12.54-12.22 (m, 1H), 11.16-11.02 (m, 1H), 8.68-8.65 (m, 1H), 8.21-8.19 (m, 2H), 7.92 (d, J = 8.0 Hz, 1H), 7.85-7.84 (m, 1H), 7.79-7.75 (m, 2H), 7.70-7.68 (m, 1H), 7.56-7.53 (m, 1H), 7.50-7.48 (m, 1H), 7.43-7.41 (m, 1H), 7.32-7.30 (m, 1H), 7.10 (s, 1H), 7.00-6.99 (m, 1H), 6.78-6.76 (m, 1H), 5.09-5.05 (m, 1H), 4.32-4.30 (m, 2H), 4.14-4.13 (m, 2H), 3.80-3.77 (m, 2H), 3.67-3.63 (m, 7H), 3.57-3.52 (m, 12H), 2.91-2.82 (m, 1H), 2.63-2.59 (m, 4H), 2.04-1.98 (m, 1H) ppm. |
| 35 | N-[2-[[4-[3-[2-[4-[11-[[2-(2,6-dioxo-3-piperidyl)-1,3-dioxo-isoindolin-5-yl]amino]undecanoyl]piperazin-1-yl]-4-pyridyl]phenyl]thiazol-2-yl]amino]-2-oxo-ethyl]-1-methylsulfonyl-pyrrole-3-carboxamide | 1005.4 | $^1$H NMR (400 MHz, DMSO-$d_6$) δ = 8.69 (m, 1H), 8.26-8.18 (m, 2H), 7.98 (d, J = 7.6 Hz, 1H), 7.85 (m, 1H), 7.81 (s, 1H), 7.72 (d, J = 8.4 Hz, 1H), 7.62-7.52 (m, 2H), 7.35-7.28 (m, 1H), 7.13 (s, 1H), 7.09 (m, 1H), 7.02 (d, J = 5.6 Hz, 1H), 6.94 (d, J = 1.6 Hz, 1H), 6.85-6.82 (m, 1H), 6.79-6.77 (m, 1H), 5.05-5.00 (m, 1H), 4.15 (d, J = 5.6 Hz, 2H), 3.64 (s, 2H), 3.58 (s, 8H), 3.17-3.12 (m, 2H), 2.94-2.82 (m, 1H), 2.40-2.31 (m, 3H), 2.05-1.94 (m, 1H), 1.62-1.48 (m, 4H), 1.44-1.32 (m, 4H), 1.31-1.21 (m, 10H) ppm. |
| 39 | N-[2-[[4-[3-[2-[4-[2-[[[2-[2-(2,6-dioxo-3-piperidyl)-1,3-dioxo-isoindolin-5-yl]oxyacetyl]amino]methyl]cyclopropanecarbonyl]piperazin-1-yl]-4-pyridyl]phenyl]thiazol-2-yl]amino]-2-oxo-ethyl]-1-methylsulfonyl-pyrrole-3-carboxamide | 976.9 | $^1$H NMR (400 MHz, DMSO-d6) δ = 8.71-8.68 (m, 1H), 8.32-8.29 (m, 1H), 8.20-8.17 (m, 2H), 7.97 (d, J = 7.6 Hz, 1H), 7.86-7.84 (m, 1H), 7.79 (s, 1H), 7.75 (d, J = 8.4 Hz, 1H), 7.67 (d, J = 7.6 Hz, 1H), 7.58-7.52 (m, 1H), 7.39 (d, J = 2.0 Hz, 1H), 7.33-7.30 (m, 2H), 7.07 (s, 1H), 6.97 (d, J = 5.2 Hz, 1H), 6.79-6.77 (m, 1H), 5.12-5.08 (m, 1H), 4.72-4.66 (m, 2H), 4.14 (d, J = 6.0 Hz, 2H), 3.77-3.71 (m, 4H), 3.59-3.52 (m, 7H), 3.19-3.06 (m, 2H), 2.98-2.82 (m, 3H), 2.11-2.06 (m, 1H), 2.05-2.00 (m, 1H), 1.58-1.55 (m, 1H), 1.00-0.98 (m, 1H), 0.90-0.86 (m, 1H) ppm. |

TABLE 16-continued

The following compounds were prepared using standard chemical manipulations and procedures similar to those used for the preparation of Compound 31.

| Cmpd # | Name | LC-MS ESI (m/z) | $^1$H NMR |
|---|---|---|---|
| 40 | N-(2-((4-(3-(2-(4-(3-(2-(2-((2-(2,6-dioxopiperidin-3-yl)-1,3-dioxoisoindolin-5-yl)amino)ethoxy)ethoxy)propanoyl)piperazin-1-yl)pyridin-4-yl)phenyl)thiazol-2-yl)amino)-2-oxoethyl)-1-(methylsulfonyl)-1H-pyrrole-3-carboxamide | 981.0 | $^1$H NMR (400 MHz, DMSO-d6) δ = 12.44 (s, 1H), 11.08 (s, 1H), 8.72-8.28 (m, 1H), 8.23-8.21 (m, 2H), 7.98 (d, J = 7.6 Hz, 1H), 7.86-7.84 (m, 1H), 7.81 (s, 1H), 7.71 (d, J = 8.0 Hz, 1H), 7.59-7.53 (m, 2H), 7.34-7.31 (m, 1H), 7.18-7.15 (m, 1H), 7.13 (s, 1H), 7.03-7.00 (m, 2H), 6.91-6.87 (m, 1H), 6.79-6.77 (m, 1H), 5.06-5.00 (m, 1H), 4.15 (d, J = 5.6 Hz, 2H), 3.67-3.64 (m, 4H), 3.59-3.54 (m, 14H), 2.91-2.82 (m, 1H), 2.74 (s, 1H), 2.65-2.62 (m, 2H), 2.57-2.54 (m, 2H), 2.54-2.52 (m, 2H), 2.01-1.97 (m, 1H) ppm. |
| 70 | | 1162.2 | $^1$H NMR (400 MHZ, methanol-d4) δ = 8.88-8.85 (m, 1H), 8.47-8.41 (m, 1H), 8.27-8.24 (m, 1H), 8.22-8.18 (m, 1H), 8.01-7.95 (m, 1H), 7.88-7.83 (m, 1H), 7.83-7.77 (m, 1H), 7.68-7.63 (m, 1H), 7.56-7.38 (m, 7H), 7.31-7.28 (m, 1H), 7.13- 7.11 (m, 1H), 7.07-7.03 (m, 1H), 6.85-6.82 (m, 1H), 4.66-4.49 (m, 4H), 4.41-4.33 (m, 1H), 4.30-4.25 (m, 2H), 3.95-3.59 (m, 10H), 3.40 (s, 3H), 2.51-2.45 (m, 5H), 2.35-2.22 (m, 3H), 2.16-2.04 (m, 1H), 1.67-1.58 (m, 4H), 1.39-1.33 (m,8H), 1.05 (s, 9H) ppm. |
| 72 | N-[2-[[4-[3-[2-[4-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy]acetyl]piperazin-1-yl]-4-pyridyl]phenyl]thiazol-2-yl]amino]-2-oxo-ethyl]-1-methylsulfonyl-pyrrole-3-carboxamide | 1094.4 | $^1$H NMR (400 MHz, DMSO-$d_6$) δ = 8.98 (s, 1H), 8.69 (m, 1H), 8.58 (m, 1H), 8.26-8.20 (m, 2H), 7.99 (d, J = 7.8 Hz, 1H), 7.86 (m, 1H), 7.83-7.76 (m, 2H), 7.72 (d, J = 7.6 Hz, 1H), 7.57 (m, 1H), 7.40 (s, 5H), 7.32 (d, J = 3.2 Hz, 1H), 7.13 (s, 1H), 7.06-6.98 (m, 1H), 6.79 (d, J = 4.8 Hz, 1H), 5.15 (d, J = 3.2 Hz, 1H), 4.58 (d, J = 9.6 Hz, 1H), 4.49-4.26 (m, 7H), 4.16 (d, J = 6.0 Hz, 2H), 4.05 (s, 2H), 3.72-3.61 (m, 7H), 3.58 (s, 3H), 3.51 (d, J = 2.4 Hz, 2H), 2.45 (s, 3H), 2.12-2.01 (m, 1H), 1.94-1.90 (m, 1H), 0.97 (s, 9H) ppm. |
| 73 | N-[2-[[4-[3-[2-[4-[3-[2-[2-[2-(2,6-dioxo-3-piperidyl)-1,3-dioxo-isoindolin-5-yl]oxyethoxy]ethoxy]propanoyl]piperazin-1-yl]-4-pyridyl]phenyl]thiazol-2-yl]amino]-2-oxo-ethyl]-1-methylsulfonyl-pyrrole-3-carboxamide | 982.0 | $^1$H NMR (400 MHz, DMSO-$d_6$) δ = 12.43-12.39 (m, 1H), 11.10 (s, 1H), 8.70-8.66 (m, 1H), 8.23-8.21 (m, 2H), 7.98 (d, J = 7.6 Hz, 1H), 7.86-7.85 (m, 1H), 7.82-7.79 (m, 2H), 7.71 (d, J = 8.4 Hz, 1H), 7.58-7.54 (m, 1H), 7.44 (d, J = 2.4 Hz, 1H), 7.37-7.31 (m, 2H), 7.12 (s, 1H), 7.02-6.99 (m, 1H), 6.80-6.77 (m, 1H), 5.14-5.10 (m, 1H), 4.30-4.28 (m, 2H), 4.15 (d, J = 6.0 Hz, 2H), 3.80-3.77 (m, 2H), 3.70-3.54 (m, 18H), 2.94-2.84 (m, 1H), 2.66-2.60 (m, 3H), 2.06-2.04 (m, 1H) ppm. |
| 74 | N-[2-[[4-[3-[2-[4-[4-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-4-oxo-butanoyl]piperazin-1-yl]-4-pyridyl]phenyl]thiazol-2-yl]amino]-2-oxo-ethyl]-1-methylsulfonyl-pyrrole-3-carboxamide | 1078.3 | $^1$H NMR (400 MHz, DMSO-$d_6$) δ = 8.99 (s, 1H), 8.68 (m, 1H), 8.56 (m, 1H), 8.26-8.19 (m, 2H), 8.02 -7.90 (m, 2H), 7.85 (m, 1H), 7.81 (s, 1H), 7.72 (d, J = 8.0 Hz, 1H), 7.60-7.53 (m, 1H), 7.46-7.37 (m, 5H), 7.32 (d, J = 2.4 Hz, 1H), 7.13 (s, 1H), 7.02 (d, J = 5.6 Hz, 1H), 6.78 (d, J = 3.2 Hz, 1H), 5.12 (d, J = 3.2 Hz, 1H), 4.54 (d, J = 9.6 Hz, 1H), 4.49-4.32 (m, 4H), 4.30-4.11 (m, 4H), 3.70-3.64 (m, 4H), 3.59 (s, 4H), 3.58 (s, 3H), 2.65-2.57 (m, 4H), 2.45 (s, 4H), 2.07-1.87 (m, 2H), 0.95 (s, 9H) ppm. |
| 75 | N-(2-((4-(3-(2-(4-(2-(2-(2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetyl)piperazin-1-yl)pyridin-4-yl)phenyl)thiazol-2-yl)amino)-2-oxoethyl)-1-(methylsulfonyl)-1H-pyrrole-3-carboxamide | 1138.1 | $^1$H NMR (400 MHz, DMSO-d6) δ = 12.40-12.32 (m, 1H), 8.97 (s, 1H), 8.59-8.57 (m, 2H), 8.23-8.21 (m, 2H), 7.98 (d, J = 8.0 Hz, 1H), 7.86-87.84 (m, 1H), 7.77-7.69 (m, 2H), 7.58-7.53 (m, 1H), 7.48 (d, J = 9.6 Hz, 1H), 7.38 (s, 3H), 7.33-7.30 (m, 1H), 7.12 (s, 1H), 7.02 (d, J = 4.8 Hz, 1H), 6.79- 6.78 (m, 1H), 5.16 (d, J = 3.6 Hz, 1H), 4.58 (d, J = 9.6 Hz, 1H), 4.48- 4.43 (m, 1H), 4.40-4.28 (s, 5H), 4.14 (d, J = 5.6 Hz, 2H), 3.97-3.95 (m, 2H), 3.67-3.58 (m, 16H), 2.43 (s, 3H), 2.06-2.03 (m, 1H), 1.95-1.89 (m, 1H), 0.95-0.92 (m, 9H) ppm |
| 79 | N-(2-((4-(3-(2-(4-(5-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-5-oxopentanoyl)piperazin-1- | 1092.2 | $^1$H NMR (400 MHZ, methanol-d4) δ = 8.85 (s, 1H), 8.25 (s, 1H), 8.25-8.21 (m, 1H), 8.17-8.14 (m, 1H), 7.98-7.94 (m, 1H), 7.86-7.82 (m, 1H), 7.64-7.60 (m, 1H), 7.54-7.47 (m, 2H), 7.44-7.38 (m, 2H), 7.38-7.33 (m, 2H), 7.31-7.25 (m, 1H), 7.08(s, 1H), 7.03-7.01 (m, 1H), 6.82-6.81 (m, 1H), 4.71-4.58 (m, 2H), 4.57-4.53 (m, 1H), 4.53- |

TABLE 16-continued

The following compounds were prepared using standard chemical manipulations and procedures similar to those used for the preparation of Compound 31.

| Cmpd # | Name | LC-MS ESI (m/z) | $^1$H NMR |
|---|---|---|---|
| | yl)pyridin-4-yl)phenyl)thiazol-2-yl)amino)-2-oxoethyl)-1-(methylsulfonyl)-1H-pyrrole-3-carboxamide | | 4.43 (m, 2H), 4.37-4.30 (m, 1H), 4.29 -4.24 (m, 2H), 3.98-3.78 (m, 2H), 3.76-3.57 (m, 7H), 3.38 (s, 3H), 2.51-2.45 (m, 2H), 2.44 (s, 3H), 2.40-2.33 (m, 2H), 2.27 -2.04 (m, 2H), 1.98-1.88 (m, 2H), 1.10-0.97 (s, 9H) ppm. |
| 86 | N-(2-((4-(3-(2-(4-(7-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-7-oxoheptanoyl)piperazin-1-yl)pyridin-4-yl)phenyl)thiazol-2-yl)amino)-2-oxoethyl)-1-(methylsulfonyl)-1H-pyrrole-3-carboxamide | 1120.1 | $^1$H NMR (400 MHz, DMSO-d6) δ = 12.43 (s, 1H), 8.98 (s, 1H), 8.71-8.67 (m, 1H), 8.57-8.54 (m, 1H), 8.25-8.21 (m, 2H), 7.99 (d, J = 7.6 Hz, 1H), 7.86-7.80 (m, 3H), 7.72 (d, J = 7.6 Hz, 1H), 7.60-7.54 (m, 1H), 7.43-7.32 (m, 5H), 7.14 (s, 1H), 7.03 (d, J = 5.2 Hz, 1H), 6.79 (d, J = 1.6 Hz, 1H), 5.13 (d, J = 2.0 Hz, 1H), 4.55 (d, J = 9.2 Hz, 1H), 4.46-4.35 (m, 3H), 4.25-4.15 (m, 3H), 3.70-3.54 (m, 15H), 2.44 (s, 3H), 2.38-2.33 (m, 2H), 2.27-2.12 (m, 2H), 2.07-1.90 (m, 2H), 1.56-1.47 (m, 4H), 1.32-1.25 (m, 2H), 0.94 (s, 9H) ppm |

Preparation of 2-methyl-2-[3-[3-[2-[[2-[(1-methylsulfonylpyrrole-3-carbonyl)amino]acetyl]amino]thiazol-4-yl]phenyl]pyrazol-1-yl]propanoic acid (I-98)

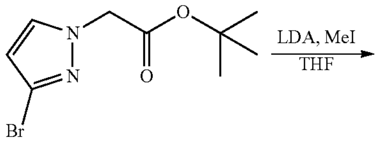

A

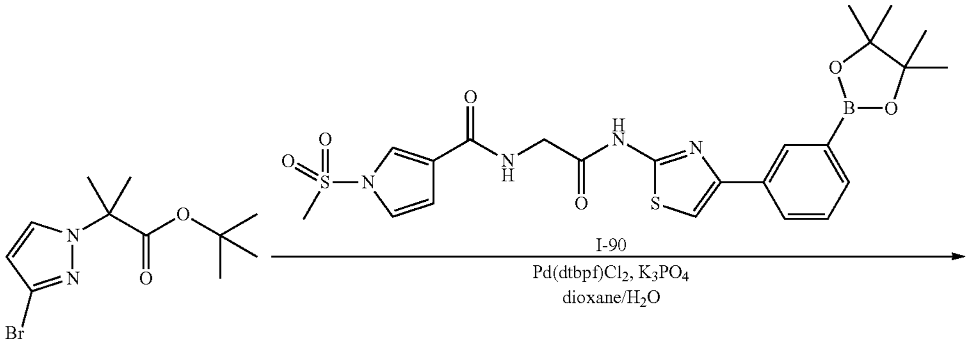

B

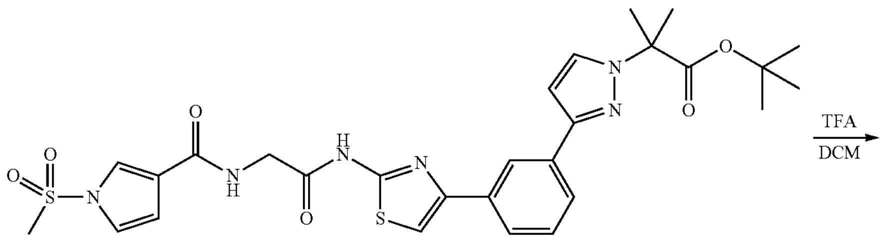

C

-continued

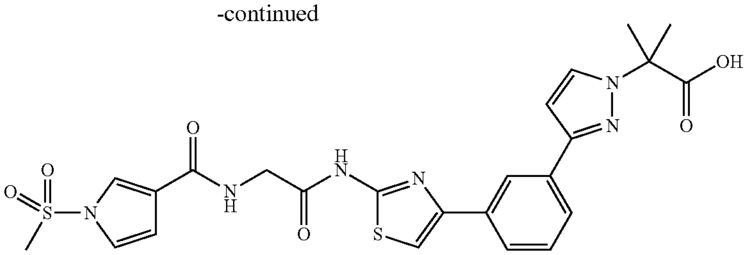

I-98

Step 1: Preparation of tert-butyl 2-(3-bromopyrazol-1-yl)-2-methyl-propanoate (B)

B

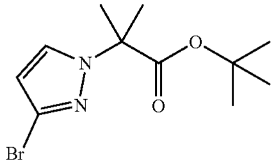

To a solution of tert-butyl 2-(3-bromopyrazol-1-yl)acetate (A, 550 mg, 2.11 mmol) in THE (5 mL) was added LDA (2 M in THF, 2.63 mL) at −60° C. The mixture was stirred for 30 min followed by addition of a solution of MeI (747.43 mg, 5.27 mmol, 327.82 μL) in THE (0.5 mL). The reaction mixture was allowed to warm to 25° C. and stirred for 1 h, then quenched with saturated aqueous $NH_4Cl$ (5 mL) and extracted with EtOAc (5 mL×3). The combined organic extracts were washed with brine (5 mL×3) and concentrated under reduced pressure. The residue was purified by flash silica gel chromatography (ISCO®; 24 g SepaFlash® Silica Flash Column, Eluent of 0-50% EtOAc/Petroleum ether gradient at 35 mL/min) to afford B (350 mg, 55.16%) as a colorless oil. LCMS (ESI) m/z: $[^{79}Br\ M-56+H]^+=233.1$. $^1H$ NMR (400 MHz, DMSO-$d_6$) δ=7.91 (d, J=2.4 Hz, 1H), 6.42 (d, J=2.4 Hz, 1H), 1.71 (s, 6H), 1.34 (s, 9H) ppm.

Step 2: Preparation of tert-butyl 2-methyl-2-[3-[3-[2-[[2-[(1-methylsulfonylpyrrole-3-carbonyl)amino]acetyl]amino]thiazol-4-yl]phenyl]pyrazol-1-yl]propanoate (C)

C

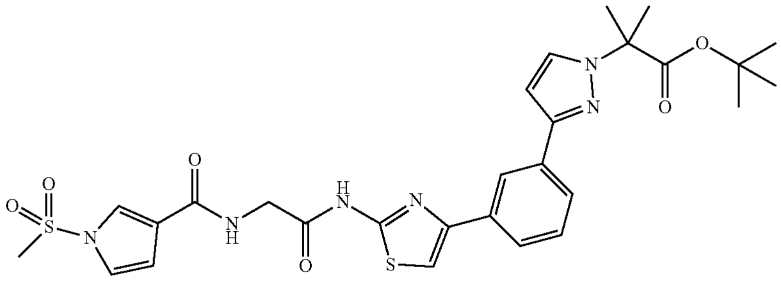

A mixture of 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (I-90, 580 mg, 1.09 mmol), B (350 mg, 1.16 mmol), di-tert-butyl(cyclopentyl)phosphane dichloropalladium(II) (142.53 mg, 0.21 mmol), and $K_3PO_4$ (696.32 mg, 3.28 mmol) in 1,4-dioxane (5 mL)/water (1 mL) was degassed and purged 3 times with nitrogen. The mixture was stirred at 80° C. for 2 h then diluted with water (10 mL) and extracted with EtOAc (10 mL×3). The combined organic layers were washed with brine (10 mL). The organic phase was concentrated under reduced pressure and the residue was triturated with EtOAc (20 mL) and petroleum ether (5 mL) for 10 min and filtered. The filter cake was dried under reduced pressure to afford C (500 mg, 68.66%) as a white solid. LCMS (ESI) m/z: $[M+H]^+$=613.5. $^1H$ NMR (400 MHz, DMSO-$d_6$) δ=12.43 (br s, 1H), 8.70-8.68 (m, 1H), 8.33 (s, 1H), 7.95 (d, J=2.4 Hz, 1H), 7.87-7.80 (m, 2H), 7.75 (d, J=7.6 Hz, 1H), 7.69 (s, 1H), 7.47-7.45 (m, 1H), 7.33-7.31 (m, 1H), 6.83-6.75 (m, 2H), 4.16 (d, J=5.6 Hz, 2H), 3.58 (s, 3H), 1.79 (s, 6H), 1.35 (s, 9H) ppm.

Step 3: Preparation of 2-methyl-2-[3-[3-[2-[[2-[(1-methylsulfonylpyrrole-3-carbonyl)amino]acetyl]amino]thiazol-4-yl]phenyl]pyrazol-1 yl]propanoic acid (I-98)

I-98

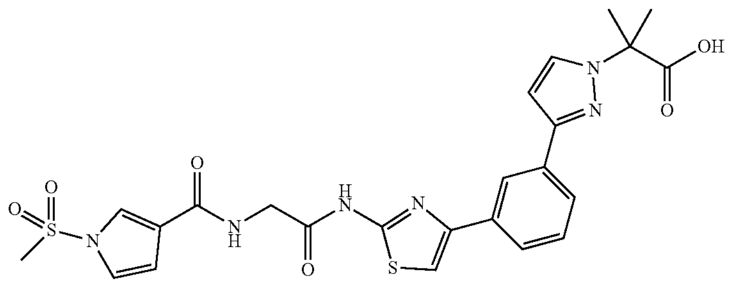

To a solution of C (500 mg, 0.816 mmol) in DCM (10 mL) was added TFA (3.85 g, 33.77 mmol, 2.5 mL) at 25° C. The mixture was stirred at 25° C. for 16 h, then concentrated under reduced pressure. The residue was triturated with EtOAc (20 mL) and filtered to afford I-98 (460 mg, 99.05% yield) as a white solid. LCMS (ESI) m/z: $[M+H]^+$=557.3. $^1H$ NMR (400 MHz, DMSO-$d_6$) δ=12.48 (s, 1H), 8.71-8.69 (m, 1H), 8.36 (s, 1H), 7.97 (d, J=2.4 Hz, 1H), 7.88-7.79 (m, 2H), 7.75-7.73 (m, 1H), 7.70 (s, 1H), 7.47-7.45 (m, 1H), 7.33-7.31 (m, 1H), 6.79 (d, J=2.4 Hz, 2H), 4.16-4.14 (m, 2H), 3.58 (s, 3H), 1.81 (s, 6H) ppm.

Compound 6—Preparation of N-(2-((4-(3-(1-(1-((2-(2-(2-((2-(2,6-dioxopiperidin-3-yl)-1,3-dioxoisoindolin-4-yl)amino)ethoxy)ethoxy)ethyl)amino)-2-methyl-1-oxopropan-2-yl)-1H-pyrazol-3-yl)phenyl)thiazol-2-yl)amino)-2-oxoethyl)-1-(methylsulfonyl)-1H-pyrrole-3-carboxamide

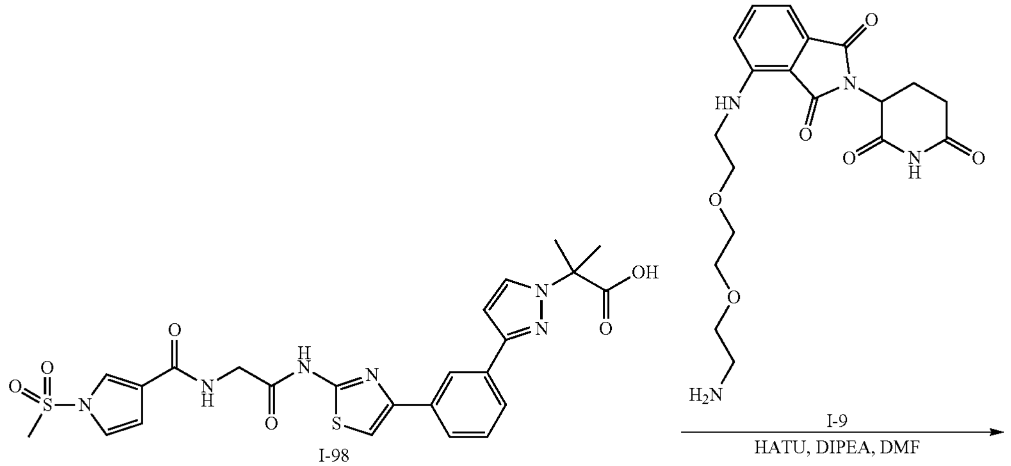

I-98

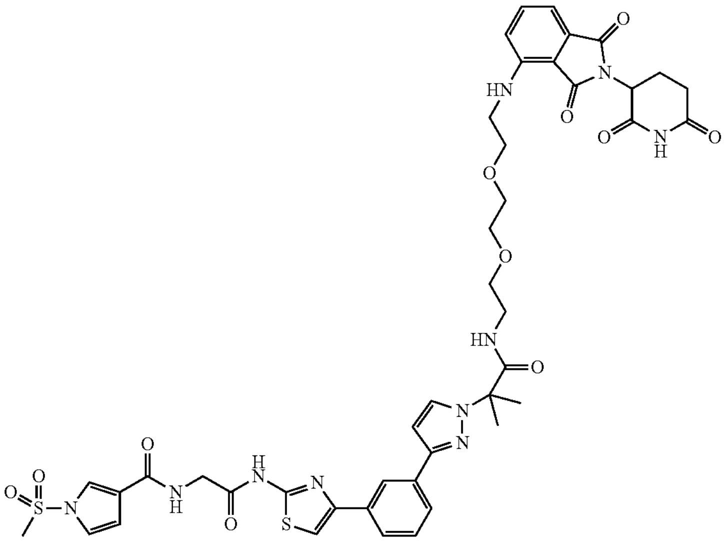

6

A mixture of 2-methyl-2-[3-[3-[2-[[2-[(1-methylsulfonylpyrrole-3-carbonyl)amino]acetyl]amino]thiazol-4-yl]phenyl]pyrazol-1-yl]propanoic acid (I-98, 40 mg, 0.059 mmol), HATU (41 mg, 0.107 mmol), and DIPEA (27.88 mg, 0.215 mmol, 37.57 μL) in DMF (0.8 mL) was stirred at 30° C. for 10 min. Following this, 4-[2-[2-(2-aminoethoxy)ethoxy]ethylamino]-2-(2,6-dioxo-3-piperidyl)isoindoline-1,3-dione (I-9, 24 mg, 0.046 mmol) was added and the resulting mixture was stirred at 30° C. for 12 h under an atmosphere of nitrogen. The reaction mixture was quenched with water (10 mL) and extracted with EtOAc (5 mL×3). The organic phase was dried over anhydrous $Na_2SO_4$ and concentrated under reduced pressure. The residue was purified by reversed phase column chromatography (0.1% formic acid in water/ACN) to give Compound 6 (13.84 mg, 22.62%) as a yellow solid. LCMS (ESI) m/z: $[M+H]^+$ =943.3. $^1H$ NMR (400 MHz, $CDCl_3$) δ=11.07-10.96 (m, 1H), 9.27 (d, J=4.4 Hz, 1H), 8.30 (s, 1H), 7.76-7.73 (m, 2H), 7.71-7.65 (m, 2H), 7.43-7.31 (m, 3H), 7.17 (s, 1H), 7.07-7.05 (m, 1H), 7.02 (d, J=6.8 Hz, 1H), 6.82 (m, 1H), 6.73-6.65 (m, 3H), 6.30-6.28 (m, 1H), 4.97-4.96 (m, 1H), 4.36 (d, J=5.6 Hz, 2H), 3.45-3.31 (m, 1-OH), 3.22-3.14 (m, 5H), 2.91-2.71 (m, 3H), 2.09 (d, J=7.2 Hz, 1H), 1.91 (s, 6H) ppm.

TABLE 17

The following compounds were prepared using standard chemical manipulations and procedures similar to those used for the preparation of Compound 6.

| Cmpd # | Name | LC-MS (ESI) (m/z) | $^1H$ NMR |
|---|---|---|---|
| 7 | N-[2-[[4-[3-[1- [2-[5-[[2-(2,6-dioxo-3-piperidyl)-1,3-dioxo-isoindolin-4-yl]amino]pentylamino]-1,1-dimethyl-2-oxo-ethyl]pyrazol-3-yl]phenyl]thiazol-2-yl]amino]-2-oxo-ethyl]-1-methylsulfonyl-pyrrole-3-carboxamide | 897.3 | $^1H$ NMR (400 MHz, DMSO-$d_6$) δ = 13.12-11.75 (m, 1H), 11.09 (br s, 1H), 8.72-8.70 (m, 1H), 8.36 (s, 1H), 7.90 (d, J = 2.4 Hz, 1H), 7.85 (s, 1H), 7.77-7.76 (m, 2H), 7.64 (s, 1H), 7.50-7.49 (m, 1H), 7.43-7.43 (m, 1H), 7.34-7.29 (m, 2H), 6.98 (d, J = 7.0 Hz, 1H), 6.89 (d, J = 8.4 Hz, 1H), 6.82-6.76 (m, 2H), 6.36-6.34 (m, 1H), 5.03-5.02 (m, 1H), 4.15 (d, J = 5.4 Hz, 2H), 3.57 (s, 3H), 3.13-3.02 (m, 4H), 2.92-2.80 (m, 1H), 2.60 (d, J = 2.4 Hz, 1H), 2.57-2.53 (m, 1H), 2.06-1.97 (m, 1H), 1.74 (s, 6H), 1.50-1.37 (m, 4H), 1.26-1.19 (m, 2H) ppm. |
| 8 | N-(2-((4-(3-(1-(1-((8-(2-((2-(2,6-dioxopiperidin-3-yl)-1,3-dioxoisoindolin-4-yl)oxy)acetamido)octyl)amino)-2-methyl-1-oxopropan-2-yl)-1H-pyrazol-3-yl)phenyl)thiazol-2-yl)amino)-2-oxoethyl)-1-(methylsulfonyl)-1H-pyrrole-3-carboxamide | 997.4 | $^1H$ NMR (400 MHz, DMSO-$d_6$) δ = 12.84-12.05 (m, 1H), 11.33-10.88 (m, 1H), 8.69 (d, J = 5.6 Hz, 1H), 8.36 (d, J = 3.2 Hz, 1H), 7.91-7.74 (m, 6H), 7.67 (d, J = 6.4 Hz, 1H), 7.48-7.47 (m, 2H), 7.38-7.31 (m, 1H), 7.31 (d, J = 2.8 Hz, 1H), 7.26 (d, J = 5.6 Hz, 1H), 6.82-6.75 (m, 2H), 5.17-5.06 (m, 1H), 4.75 (d, J = 5.6 Hz, 2H), 4.15 (br s, 2H), 3.57 (d, J = 6.0 Hz, 3H), 3.07-3.01 (m, 4H), 2.91-2.85 (m, 1H), 2.68-2.57 (m, 2H), 2.03 (d, J = 6.0 Hz, 1H), 1.78-1.71 (m, 6H), 1.33 (d, J = 4.8 Hz, 4H), 1.12 (br s, 8H) ppm. |
| 10 | N-[2-[[4-[3-[1-[2-[4-[1-[2-[2-(2,6-dioxo-3-piperidyl)-1,3-dioxo-isoindolin-4-yl]oxyacetyl]-4-piperidyl]-1-piperidyl]-1,1-dimethyl-2-oxo-ethyl]pyrazol-3-yl]phenyl]thiazol-2-yl]amino]-2-oxo-ethyl]-1-methylsulfonylpyrrole-3-carboxamide | 1021.5 | $^1H$ NMR (400 MHz, DMSO-$d_6$) δ = 12.68-12.28 (m, 1H), 11.25-10.90 (m, 1H), 8.66 (s, 1H), 8.38 (s, 1H), 7.97 (s, 1H), 7.88-7.79 (m, 2H), 7.74 (d, J = 7.6 Hz, 2H), 7.66 (s, 1H), 7.48-7.40 (m, 2H), 7.31 (s, 1H), 7.23-7.13 (m, 1H), 6.88 (s, 1H), 6.77 (s, 1H), 5.21-4.91 (m, 4H), 4.15 (s, 4H), 3.57 (s, 3H), 2.94-2.83 (m, 3H), 2.74-2.66 (m, 4H), 2.31-2.19 (m, 1H), 2.11-1.96 (m, 1H), 1.73 (s, 6H), 1.51-1.33 (m, 3H), 1.24-0.96 (m, 5H), 0.91-0.68 (m, 2H) ppm. |

Compound 143—Preparation of N-{4-[1-(11-{[2-(2,6-dioxopiperidin-3-yl)-1,3-dioxo-2,3-dihydro-1H-isoindol-5-yl]amino}undecanoyl)piperidin-3-yl]-1,3-thiazol-2-yl}-2-[(1-methanesulfonyl-1H-pyrrol-3-yl)formamido]acetamide)

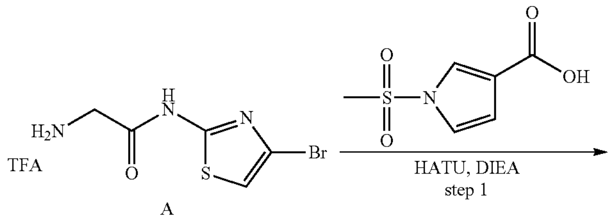

A

-continued

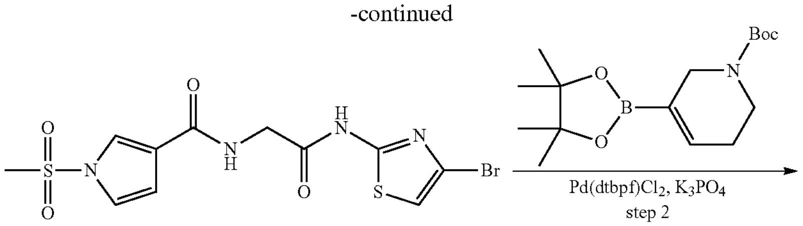

B

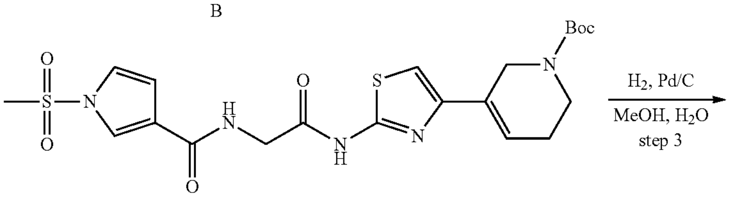

C

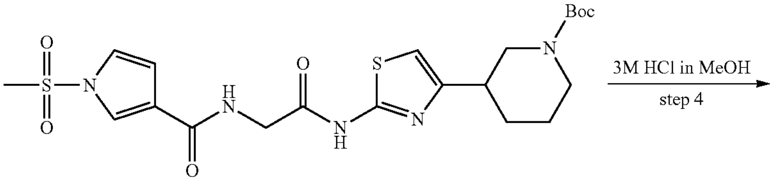

D

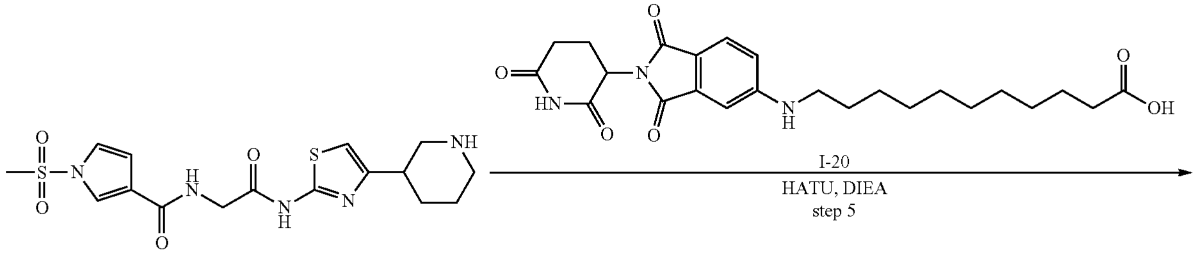

E

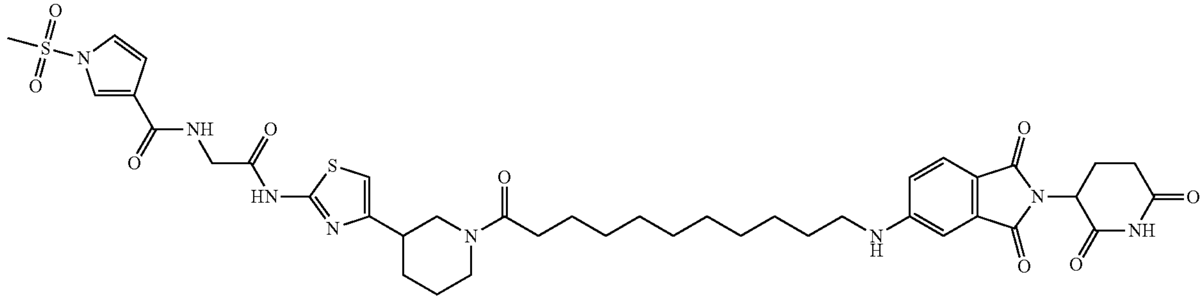

143

Step 1: Preparation of N-(4-bromo-1,3-thiazol-2-yl)-2-[(1-methanesulfonyl-1H-pyrrol-3-yl)formamido]acetamide (B)

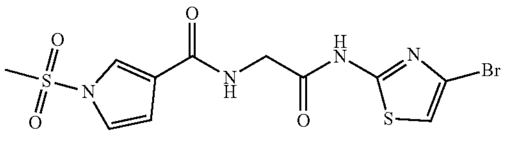

B 2-amino-N-(4-bromo-1,3-thiazol-2-yl)acetamide trifluoroacetate (A, 1 g, 2.99 mmol) 1-methanesulfonyl-1H-pyrrole-3-carboxylic acid (620 mg, 3.28 mmol), 1-[(dimethylamino)(dimethyliminiumyl)methyl]-3-oxo-1H,2H,3H-3λ$^6$-[1,2,3]triazolo[5,4-b]pyridin-3-ylium-2-ide; hexafluoro-λ$^6$-phosphanuide (2.27 g, 5.98 mmol), and bis(propan-2-yl) amine (1.50 g, 14.9 mmol) were dissolved in DMF (5 mL) and stirred at room temperature for 1 h. Water was added and the mixture extracted with EtOAc (20 mL). The organic layer was separated and concentrated under reduced pressure. The residue was purified by column chromatography (silica gel, 0-20% MeOH in DCM) to give B (960 mg, 79% yield) as white solid. LCMS (ESI) m/z: $[M+H]^+$=407.

Step 2: Preparation of tert-butyl 5-(2-{2-[(1-methanesulfonyl-1H-pyrrol-3-yl)formamido]acetamido}-1,3-thiazol-4-yl)-1,2,3,6-tetrahydropyridine-1-carboxylate (C)

C

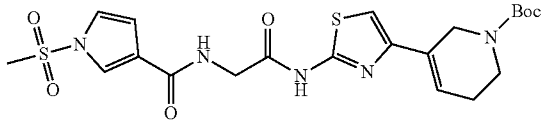

To a mixture of tert-butyl 5-(4,4,5,5-tetramethyl-1,3,2-dioxaborolan-2-yl)-1,2,3,6-tetrahydropyridine-1-carboxylate (151 mg, 0.49 mmol), B (100 mg, 0.245 mmol), palladium(II) bis(2-(di-tert-butylphosphanyl)cyclopenta-2,4-dien-1-yl) iron dichloride (15.9 mg, 0.245 mmol), and tripotassium phosphate (156 mg, 0.735 mmol) was added 1,4-dioxane (0.8 mL) and water (0.2 mL) under a nitrogen atmosphere. The mixture was microwaved at 75° C. for 1 h, then poured into water (40 mL) and stirred for 5 min. The aqueous phase was extracted with EtOAc (30 mL×3), washed with brine (10 mL), and concentrated under vacuum. The crude C was used without further purification. LCMS (ESI) m/z: $[M+H]^{+}=510$.

Step 3: Preparation of tert-butyl 3-(2-{2-[(1-methanesulfonyl-1H-pyrrol-3-yl)formamido]acetamido}-1,3-thiazol-4-yl)piperidine-1-carboxylate (D)

D

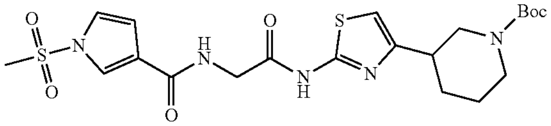

To a solution of C (700 mg, 1.37 mmol) in MeOH (200 mL) was added 10% palladium/C (500 mg) under nitrogen. The gas was exchanged for 1 atmosphere of hydrogen and the reaction stirred at room temperature for 18 h. The mixture was filtered through Celite and concentrated. The residue was purified by column chromatography (silica gel 12 g, 0-20% MeOH in DCM) to give D (700 mg, 99% yield) as yellow oil. LCMS (ESI) m/z: $[M+H]^{+}=512$.

Step 4: Preparation of 2-[(1-methanesulfonyl-1H-pyrrol-3-yl)formamido]-N-[4-(piperidin-3-yl)-1,3-thiazol-2-yl]acetamide (E)

E

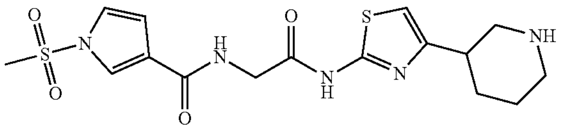

D (900 mg, 1.75 mmol) was added to 3M HCl in MeOH (15 mL, 0.416 mmol) and stirred at room temperature for 1.5 h. The mixture was concentrated to give crude E as yellow oil, which was used without further purification. LCMS (ESI) m/z: $[M+H]^{+}=412$.

Step 5: Preparation of N-{4-[1-(11-{[2-(2,6-dioxopiperidin-3-yl)-1,3-dioxo-2,3-dihydro-1H-isoindol-5-yl]amino}undecanoyl)piperidin-3-yl]-1,3-thiazol-2-yl}-2-[(1-methanesulfonyl-1H-pyrrol-3-yl)formamido]acetamide (Compound 143)

143

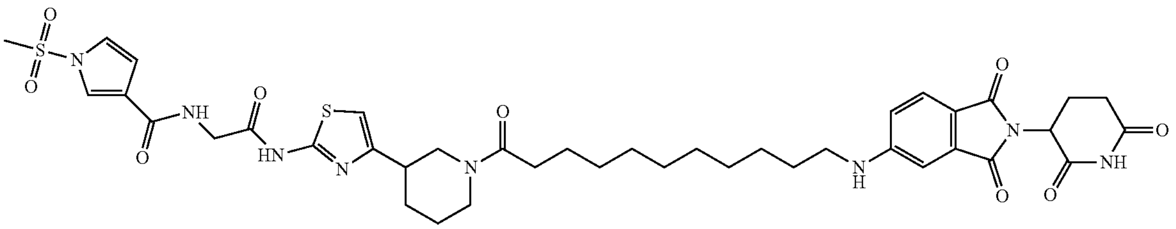

A mixture of E (8 mg, 0.19 mmol), 11-{[2-(2,6-dioxopiperidin-3-yl)-1,3-dioxo-2,3-dihydro-1H-isoindol-5-yl]amino}undecanoic acid (I-20, 9.74 mg, 0.21 mmol), bis(propan-2-yl)amine (5.87 mg, 0.58 mmol), and 1-[(dimethylamino)(dimethyliminiumyl)methyl]-3-oxo-1H,2H,3H-3$\lambda^5$-[1,2,3]triazolo[5,4-b]pyridin-3-ylium-2-ide; hexafluoro-$\lambda^5$-phosphanuide (14.7 mg, 0.39 mmol) in DMF (1 mL) was stirred at room temperature for 1 h. The mixture was purified by MDAP to give Compound 143 (6.00 mg, 36%) as a yellow solid. LCMS (ESI) m/z: $[M+H]^+$=851.5. $^1$H NMR (400 MHz, DMSO-$d_6$) δ 12.20 (d, J=6.2 Hz, 1H), 11.01 (s, 1H), 8.60 (t, J=5.8 Hz, 1H), 7.81 (t, J=2.0 Hz, 1H), 7.53 (d, J=8.3 Hz, 1H), 7.31-7.25 (m, 1H), 7.05 (s, 1H), 6.92 (s, 1H), 6.88-6.78 (m, 2H), 6.74 (dd, J=3.3, 1.7 Hz, 1H), 5.00 (dd, J=12.9, 5.4 Hz, 1H), 4.57 (d, J=7.9 Hz, 1H), 4.32 (d, J=13.1 Hz, 1H), 4.06 (d, J=5.7 Hz, 2H), 4.00 (d, J=13.9 Hz, 1H), 3.81 (d, J=13.9 Hz, 1H), 3.54 (s, 3H), 3.15 (s, 1H), 3.13 (s, 2H), 3.06-2.51 (m, 5H), 2.28 (t, J=7.4 Hz, 2H), 2.06-1.89 (m, 2H), 1.76-1.18 (m, 16H).

TABLE 18

The following compounds were prepared using standard chemical manipulations and procedures similar to those used for the preparation of Compound 143.

| Cmpd # | Name | LC-MS (ESI) (m/z) | $^1$H NMR |
|---|---|---|---|
| 144 | N-[4-(1-{3-[2-(2-{[2-(2,6-dioxopiperidin-3-yl)-1,3-dioxo-2,3-dihydro-1H-isoindol-5-yl]oxy}ethoxy)ethoxy]propanoyl}piperidin-3-yl)-1,3-thiazol-2-yl]-2-[(1-methanesulfonyl-1H-pyrrol-3-yl) formamido]acetamide | 828.3 | $^1$H NMR (400 MHz, DMSO-$d_6$) δ 12.21 (d, J = 4.5 Hz, 1H), 11.07 (s, 1H), 8.79-8.50 (m, 1H), 8.04-7.64 (m, 2H), 7.42 (d, J = 2.1 Hz, 1H), 7.34 (dt, J = 8.4, 2.9 Hz, 1H), 7.31-7.25 (m, 1H), 6.83 (d, J = 16.3 Hz, 1H), 6.74 (t, J = 2.5 Hz, 1H), 5.09 (dd, J = 12.9, 5.4 Hz, 1H), 4.57 (d, J = 8.8 Hz, 1H), 4.28 (q, J = 5.2 Hz, 3H), 4.06 (d, J = 5.8 Hz, 2H), 3.83 (d, J = 13.4 Hz, 1H), 3.76 (q, J = 5.2 Hz, 2H), 3.62 (t, J = 6.7 Hz, 2H), 3.59-3.49 (m, 8H), 3.08-2.69 (m, 2H), 2.56 (dq, J = 13.9, 4.5 Hz, 5H), 2.07-1.99 (m, 2H), 1.73-1.33 (m, 2H). |
| 146 | N-{4-[1-(3-{4-[2-(2,6-dioxopiperidin-3-yl)-1,3-dioxo-2,3-dihydro-1H-isoindol-5-yl]piperazin-1-yl}propanoyl)piperidin-3-yl]-1,3-thiazol-2-yl}-2-[(1-methanesulfonyl-1H-pyrrol-3-yl)formamido]acetamide formate | 808.4 | $^1$H NMR (400 MHz, DMSO-$d_6$) δ 12.21 (s, 1H), 11.04 (s, 1H), 8.61 (t, J = 5.9 Hz, 1H), 8.12 (s, 1H), 7.81 (t, J = 2.0 Hz, 1H), 7.66 (dd, J = 8.5, 3.0 Hz, 1H), 7.35-7.22 (m, 3H), 6.87 (d, J = 18.6 Hz, 1H), 6.74 (dd, J = 3.2, 1.6 Hz, 1H), 6.48 (s, 1H), 5.05 (dd, J = 12.8, 5.4 Hz, 1H), 4.58 (d, J = 8.0 Hz, 0.5H), 4.31 (d, J = 12.4 Hz, 0.5H), 4.06 (d, J = 5.6 Hz, 2.5H), 3.88 (d, J = 13.1 Hz, 0.5H), 3.54 (s, 3H), 3.41 (d, J = 5.0 Hz, 5H), 3.15-2.76 (m, 4H), 2.58 (dt, J = 25.6, 7.9 Hz, 12H), 2.03 (d, J = 14.7 Hz, 2H), 1.81-1.61 (m, 2H). |
| 145 | N-(4-{1-[1-(2-{[2-(2,6-dioxopiperidin-3-yl)-1,3-dioxo-2,3-dihydro-1H-isoindol-5-yl]oxy}ethyl)piperidine-4-carbonyl]piperidin-3-yl}-1,3-thiazol-2-yl)-2-[(1-methanesulfonyl-1H-pyrrol-3-yl)formamido]acetamide formate | 823.4 | $^1$H NMR (400 MHz, DMSO-$d_6$) δ 12.19 (s, 1H), 11.07 (s, 1H), 8.61 (t, J = 5.9 Hz, 1H), 8.12 (s, 1H), 7.81 (dt, J = 4.0, 2.2 Hz, 2H), 7.44 (d, J = 2.3 Hz, 1H), 7.38-7.25 (m, 2H), 6.87 (d, J = 27.6 Hz, 1H), 6.74 (dd, J = 3.3, 1.6 Hz, 1H), 6.49 (s, 1H), 5.09 (dd, J = 13.0, 5.3 Hz, 1H), 4.54 (d, J = 9.8 Hz, 0.5H), 4.27 (t, J = 5.8 Hz, 2.5H), 4.06 (d, J = 5.7 Hz, 2.5H), 3.88 (d, J = 13.0 Hz, 0.5H), 3.54 (s, 3H), 3.10-2.52 (m, 13H), 2.26-1.93 (m, 4H), 1.59 (t, J = 45.1 Hz, 7H). |
| 148 | N-{4-[1-(8-{[2-(2,6-dioxopiperidin-3-yl)-1,3-dioxo-2,3-dihydro-1H-isoindol-4-yl]oxy}octanoyl)piperidin-3-yl]-1,3-thiazol-2-yl}-2-[(1-methanesulfonyl-1H-pyrrol-3-yl)formamido]acetamide | 810.4 | $^1$H NMR (400 MHz, DMSO-$d_6$) δ 12.20 (d, J = 7.3 Hz, 1H), 11.06 (s, 1H), 8.60 (t, J = 5.9 Hz, 1H), 7.83-7.74 (m, 2H), 7.49 (dd, J = 8.7, 3.9 Hz, 1H), 7.42 (d, J = 7.2 Hz, 1H), 7.28 (t, J = 2.8 Hz, 1H), 6.85 (d, J = 15.4 Hz, 1H), 6.78-6.67 (m, 1H), 5.05 (dd, J = 12.9, 5.4 Hz, 1H), 4.57 (d, J = 8.0 Hz, 0.5H), 4.32 (d, J = 13.4 Hz, 0.5H), 4.19 (t, J = 6.6 Hz, 2H), 4.06 (d, J = 5.8 Hz, 2H), 4.00 (d, J = 13.1 Hz, 0.5H), 3.82 (d, J = 13.6 Hz, 0.5H), 3.54 (s, 3H), 3.12-2.50 (m, 5H), 2.27 (dt, J = 21.2, 7.4 Hz, 2H), 2.07-1.98 (m, 2H), 1.81-1.25 (m, 17H). |
| 147 | N-{4-[1-(5-{[2-(2,6-dioxopiperidin-3-yl)-1,3-dioxo-2,3-dihydro-1H-isoindol-4-yl]oxy}pentanoyl)piperidin-3-yl]-1,3-thiazol-2-yl}-2-[(1-methanesulfonyl-1H-pyrrol-3-yl)formamido]acetamide | 768.4 | $^1$H NMR (400 MHz, DMSO-$d_6$) δ 12.20 (d, J = 14.2 Hz, 1H), 11.06 (s, 1H), 8.60 (t, J = 5.9 Hz, 1H), 7.83-7.74 (m, 2H), 7.49 (t, J = 7.7 Hz, 1H), 7.42 (t, J = 6.5 Hz, 1H), 7.28 (t, J = 2.8 Hz, 1H), 6.83 (d, J = 6.3 Hz, 1H), 6.74 (dd, J = 3.4, 1.6 Hz, 1H), 5.05 (dt, J = 11.8, 5.7 Hz, 1H), 4.59 (d, J = 9.0 Hz, 0.5H), 4.34 (d, J = 12.9 Hz, 0.5H), 4.21 (q, J = 6.2 Hz, 2H), 4.06 (d, J = 5.8 Hz, 2.5H), 3.86 (d, J = 13.6 Hz, 0.5H), 3.54 (s, 3H), 3.10-2.69 (m, 2H), 2.62-2.51 (m, 2H), 2.43 (t, J = 6.3 Hz, 2H), 2.04-1.95 (m, 3H), 1.72 (ddd, J = 34.2, 17.0, 10.2 Hz, 8H). |

Preparation of 2-[3-[3-[2-[[2-[(1-methylsulfonylpyrrole-3-carbonyl)amino]acetyl]amino]thiazol-4-yl]phenyl]pyrazol-1-yl]acetic acid (I-99)
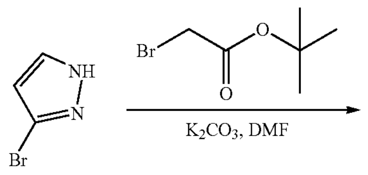
A
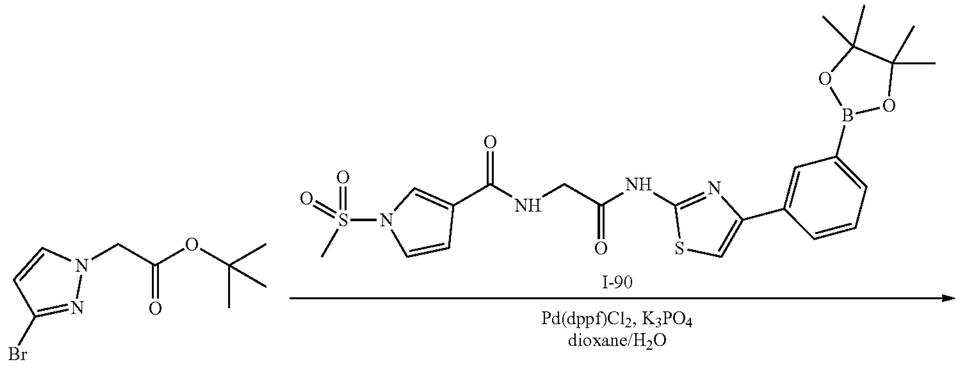
B
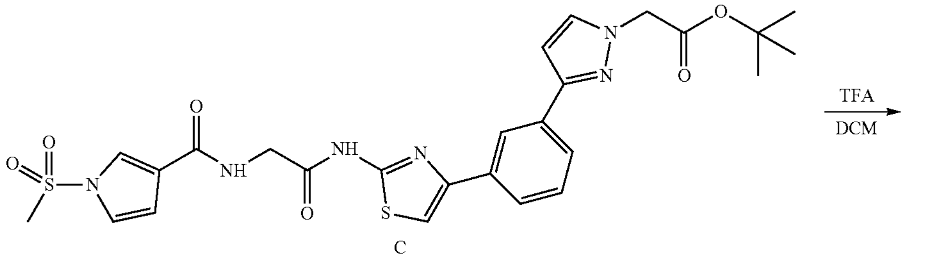
C
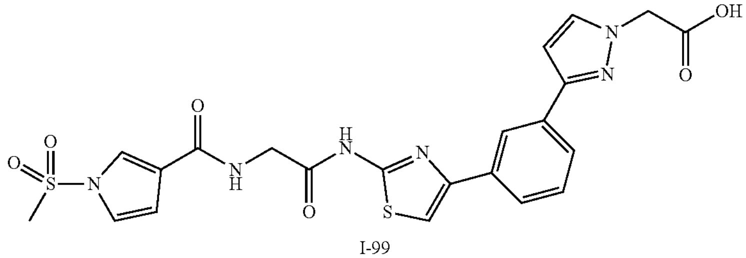
I-99

Step 1: Preparation of tert-butyl 2-(3-bromopyrazol-1-yl)acetate (B)

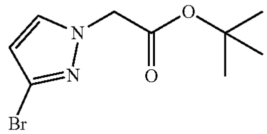

B

To a solution of 3-bromo-1H-pyrazole (A, 1 g, 6.80 mmol) in DMF (10 mL) was added tert-butyl 2-bromoacetate (1.99 g, 10.21 mmol, 1.51 mL), and $K_2CO_3$ (2.82 g, 20.41 mmol) at 25° C. The reaction was stirred at 50° C. for 3 h, then was diluted with saturated aqueous $NH_4Cl$ (10 mL), followed by extraction with EtOAc (10 mL×3). The combined organic layers were washed with aqueous brine (10 mL×3), dried over $Na_2SO_4$, and concentrated under reduced pressure. The residue was purified by flash silica gel chromatography (ISCO®; 40 g SepaFlash® Silica Flash Column, Eluent of 0-30% EtOAc/Petroleum ether gradient at 40 mL/min) to afford B (1.5 g, 5.74 mmol, 84.43% yield, 100% purity) as a colorless oil. LCMS (ESI) m/z: $[^{79}BrM-56+H]^+=205.0$. $^1H$ NMR (400 MHz, DMSO-$d_6$) δ=7.75 (d, J=2.4 Hz, 1H), 6.41 (d, J=2.4 Hz, 1H), 4.95 (s, 2H), 1.43 (s, 9H) ppm.

Step 2: Preparation of tert-butyl 2-[3-[3-[2-[[2-[(1-methylsulfonylpyrrole-3-carbonyl)amino]acetyl]amino]thiazol-4-yl]phenyl]pyrazol-1-yl]acetate (C)

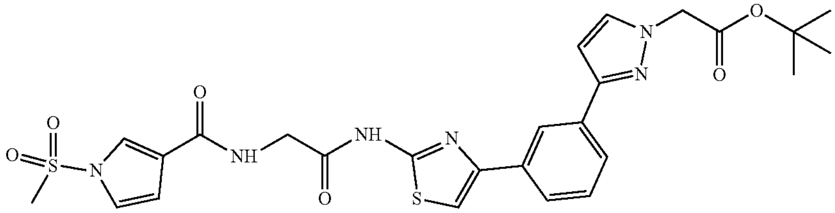

C

A mixture of B (708.88 mg, 2.71 mmol), 1-methylsulfonyl-N-[2-oxo-2-[[4-[3-(4,4,5,5-tetramethyl-1,3,2-dioxaborolan-2-yl)phenyl]thiazol-2-yl]amino]ethyl]pyrrole-3-carboxamide (I-90, 1.2 g, 2.26 mmol), Pd(dppf)$Cl_2$ (331.08 mg, 0.452 mmol), and $K_3PO_4$ (1.44 g, 6.79 mmol) in 1,4-dioxane (10 mL)/water (2 mL) was degassed and purged 3 times with nitrogen. The mixture was stirred at 70° C. for 1.5 h, then diluted with saturated aqueous $NH_4Cl$ (10 mL) and extracted with EtOAc (10 mL×3). The combined organic layers were washed with brine (10 mL×3), dried over $Na_2SO_4$, and concentrated under reduced pressure. The residue was purified by flash silica gel chromatography (ISCO®; 40 g SepaFlash® Silica Flash Column, Eluent of 0-100% EtOAc/Petroleum ether gradient at 40 mL/min) to afford C (1 g, 73.33%) as a white solid. LCMS (ESI) m/z: $[M+H]^+$=585.3. $^1$H NMR (400 MHz, DMSO-$d_6$) δ=12.48 (s, 1H), 8.69-8.67 (m, 1H), 8.40 (s, 1H), 7.87-7.78 (m, 3H), 7.76-7.72 (m, 1H), 7.48-7.46 (m, 1H), 7.35-7.26 (m, 1H), 6.82-6.74 (m, 2H), 5.02 (s, 2H), 4.15 (d, J=5.6 Hz, 2H), 3.58 (s, 3H), 1.46 (s, 9H) ppm.

Step 3: Preparation of 2-[3-[3-[2-[[2-[(1-methylsulfonylpyrrole-3-carbonyl)amino]acetyl]amino]thiazol-4-yl]phenyl]pyrazol-1-yl]acetic acid (I-99)

I-99

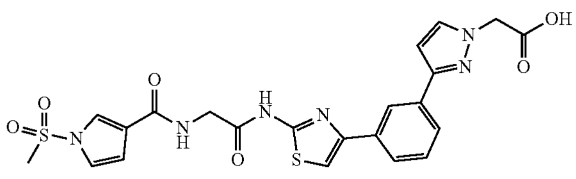

To a solution of C (900 mg, 1.54 mmol) in DCM (20 mL) was added TFA (7.70 g, 67.53 mmol, 5 mL). The mixture was stirred at 25° C. for 12 h, then concentrated under reduced pressure. The residue was purified by reverse phase flash chromatography (0.1% formic acid in water/ACN) to afford I-99 (600 mg, 67.84%) as a gray solid. LCMS (ESI) m/z: $[M+H]^+$=529.3. $^1$H NMR (400 MHz, DMSO-$d_6$) δ=12.54 (s, 1H), 8.76-8.69 (m, 1H), 8.51-8.40 (m, 1H), 7.93-7.85 (m, 3H), 7.82-7.78 (m, 1H), 7.77-7.76 (m, 1H), 7.55-7.49 (m, 1H), 7.38 (m, 1H), 6.92-6.73 (m, 1H), 5.08 (s, 2H), 4.29-4.16 (m, 2H), 3.64 (s, 4H), 3.27-3.19 (m, 1H) ppm Compound 2—Preparation of N-[2-[[4-[3-[1-[2-[5-[[2-(2,6-dioxo-3-piperidyl)-1,3-dioxoisoindolin-4-yl]amino]pentylamino]-2-oxo-ethyl]pyrazol-3-yl]phenyl]thiazol-2-yl]amino]-2-oxo-ethyl]-1-methylsulfonylpyrrole-3-carboxamide

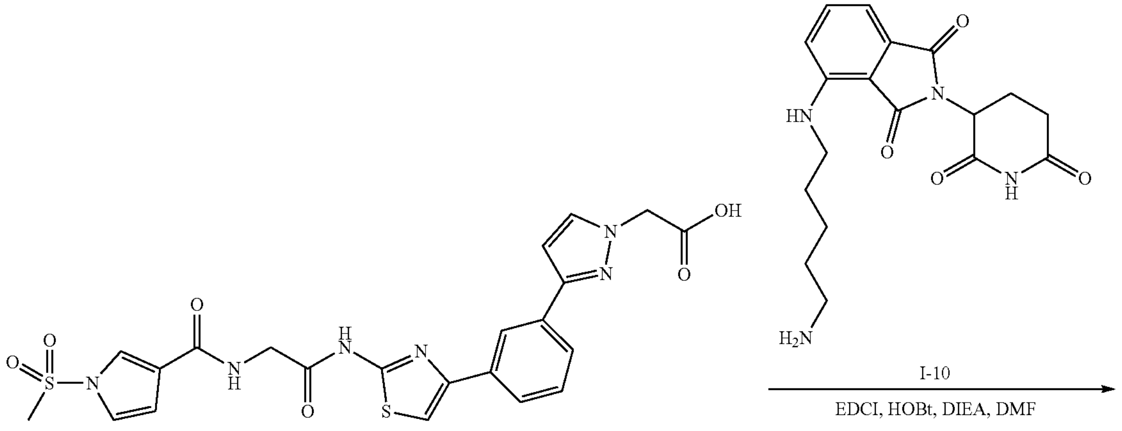

I-99

-continued

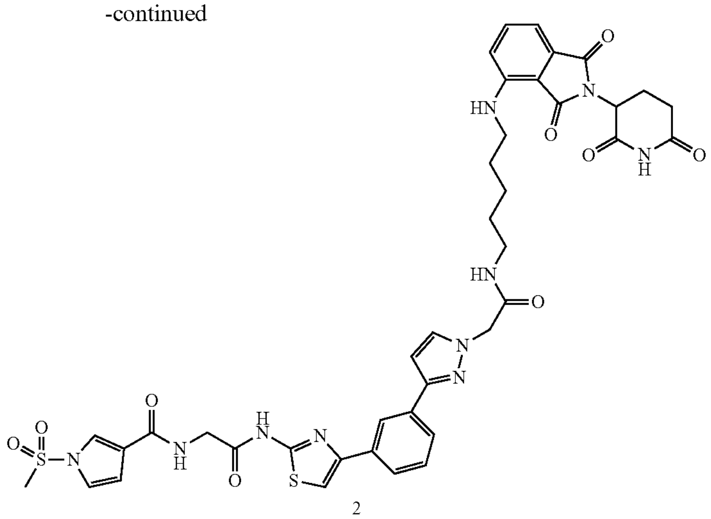

2

To a solution of 4-(5-aminopentylamino)-2-(2,6-dioxo-3-piperidyl)isoindoline-1,3-dione (I-10, 50 mg, 0.139 mmol) and 2-[3-[3-[2-[[2-[(1-methylsulfonylpyrrole-3-carbonyl)amino]acetyl]amino]thiazol-4-yl]phenyl]pyrazol-1-yl]acetic acid (I-99, 88.49 mg, 0.167 mmol) in DMF (1 mL) was added EDCI (40.12 mg, 0.209 mmol), HOBt (28.28 mg, 0.209 mmol), and DIEA (90.16 mg, 0.697 mmol, 121.50 μL). The reaction was stirred at 25° C. for 16 h. The reaction mixture was added to water (10 mL). The mixture was filtered and concentrated to give yellow solid which was purified by preparative HPLC (column: Shim-pack C18 150×25×10 μm; mobile phase: [0.225% formic acid in water/ACN]; B %: 33%-63%, 10 min) to give Compound 2 (42.31 mg, 40.18%) as a yellow solid. LCMS (ESI) m/z: $[M+H]^+$=869.3. $^1$H NMR (400 MHz, DMSO-$d_6$) δ=12.85-12.13 (m, 1H), 11.30-10.84 (m, 1H), 8.69-8.67 (m, 1H), 8.39 (s, 1H), 8.15-8.13 (m, 1H), 7.89-7.76 (m, 3H), 7.74-7.66 (m, 2H), 7.58-7.56 (m, 1H), 7.46-7.44 (m, 1H), 7.33-7.31 (m, 1H), 7.11-6.96 (m, 2H), 6.85-6.71 (m, 2H), 6.53-6.51 (m, 1H), 5.06-5.04 (m, 1H), 4.84 (s, 2H), 4.15 (d, J=5.6 Hz, 2H), 3.58 (s, 3H), 3.28 (d, J=6.4 Hz, 2H), 3.17-3.08 (m, 2H), 2.94-2.82 (m, 1H), 2.63-2.53 (m, 2H), 2.07-1.97 (m, 1H), 1.60-1.58 (m, 2H), 1.51-1.49 (m, 2H), 1.42-1.32 (m, 2H) ppm.

TABLE 19

The following compounds were prepared using standard chemical manipulations and procedures similar to those used for the preparation of Compound 2.

| Cmpd # | Name | LC-MS (ESI) (m/z) | $^1$H NMR |
|---|---|---|---|
| 3 | N-[2-[[4-[3-[1-[2-[2-[2-[2-[[2-(2,6-dioxo-3-piperidyl)-1,3-dioxoisoindolin-4-yl]amino]ethoxy]ethoxy]ethyl-amino]-2-oxo-ethyl]pyrazol-3-yl]phenyl]thiazol-2-yl]amino]-2-oxo-ethyl]-1-methylsulfonyl-pyrrole-3-carboxamide | 915.3 | $^1$H NMR (400 MHz, DMSO-$d_6$) δ = 12.49 (s, 1H), 11.08 (s, 1H), 8.68-8.66 (m, 1H), 8.39 (s, 1H), 8.17-8.15 (m, 1H), 7.91-7.77 (m, 3H), 7.75-7.68 (m, 2H), 7.58-7.56 (m, 1H), 7.46-7.44 (m, 1H), 7.33-7.31 (m, 1H), 6.82-6.72 (m, 2H), 6.64-6.55 (m, 1H), 5.06-5.04 (m, 1H), 4.87 (s, 2H), 4.15 (d, J = 5.2 Hz, 2H), 3.65-3.50 (m, 9H), 3.50-3.41 (m, 4H), 3.34 (d, J = 4.0 Hz, 3H), 3.31-3.25 (m, 2H), 2.97-2.79 (m, 1H), 2.58 (d, J = 17.2 Hz, 1H), 2.03 (s, 1H) ppm. |
| 4 | N-[2-[[4-[3-[1-[2-[4-[1-[2-[2-(2,6-dioxo-3-piperidyl)-1,3-dioxoisoindolin-4-yl]oxyacetyl]-4-piperidyl]-1-piperidyl]-2-oxo-ethyl]pyrazol-3-yl]phenyl]thiazol-2-yl]amino]-2-oxo-ethyl]-1-methylsulfonyl-pyrrole-3-carboxamide | 993.5 | $^1$H NMR (400 MHz, DMSO-$d_6$) δ = 12.48 (s, 1H), 11.10 (s, 1H), 8.69-8.67 (m, 1H), 8.40 (s, 1H), 7.88-7.66 (m, 6H), 7.52-7.42 (m, 2H), 7.36-7.27 (m, 2H), 6.83-6.72 (m, 2H), 5.35-5.00 (m, 5H), 4.47-4.26 (m, 2H), 4.16-4.14 (m, 2H), 3.98-3.96 (m, 1H), 3.82 (d, J = 12.4 Hz, 1H), 3.73-3.66 (m, 4H), 3.09-2.82 (m, 3H), 2.64-2.56 (m, 2H), 2.07-1.99 (m, 1H), 1.82-1.59 (m, 4H), 1.44-0.97 (m, 6H) ppm. |
| 5 | N-[2-[[4-[3-[1-[2-[8-[[2-[2-(2,6-dioxo-3-piperidyl)-1,3-dioxoisoindolin-4-yl]oxyacetyl]amino]octylamino]-2-oxo-ethyl]pyrazol-3-yl]phenyl]thiazol-2-yl]amino]-2-oxo-ethyl]-1-methylsulfonyl-pyrrole-3-carboxamide | 969.4 | $^1$H NMR (400 MHz, DMSO-$d_6$) δ = 12.49 (s, 1H), 11.11 (s, 1H), 8.68-8.66 (m, 1H), 8.39 (s, 1H), 8.11-8.09 (m, 1H), 7.92-7.90 (m, 1H), 7.86-7.77 (m, 4H), 7.74-7.67 (m, 2H), 7.52-7.37 (m, 3H), 7.33-7.31 (m, 1H), 6.81-6.73 (m, 2H), 5.13-5.11 (m, 1H), 4.90-4.70 (m, 4H), 4.15 (d, J = 5.6 Hz, 2H), 3.67-3.60 (m, 3H), 3.12-3.10 (m, 4H), 2.97-2.82 (m, 1H), 2.63-2.55 (m, 2H), 2.11-2.01 (m, 1H), 1.42 (s, 4H), 1.25 (s, 8H) ppm. |

Compound 142—Preparation of N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N-([4-[3-(2-[2-[(1-methanesulfonylpyrrol-3-yl)formamido]acetamido]-1,3-thiazol-4-yl)phenyl]pyridin-2-yl]methyl)octanediamide
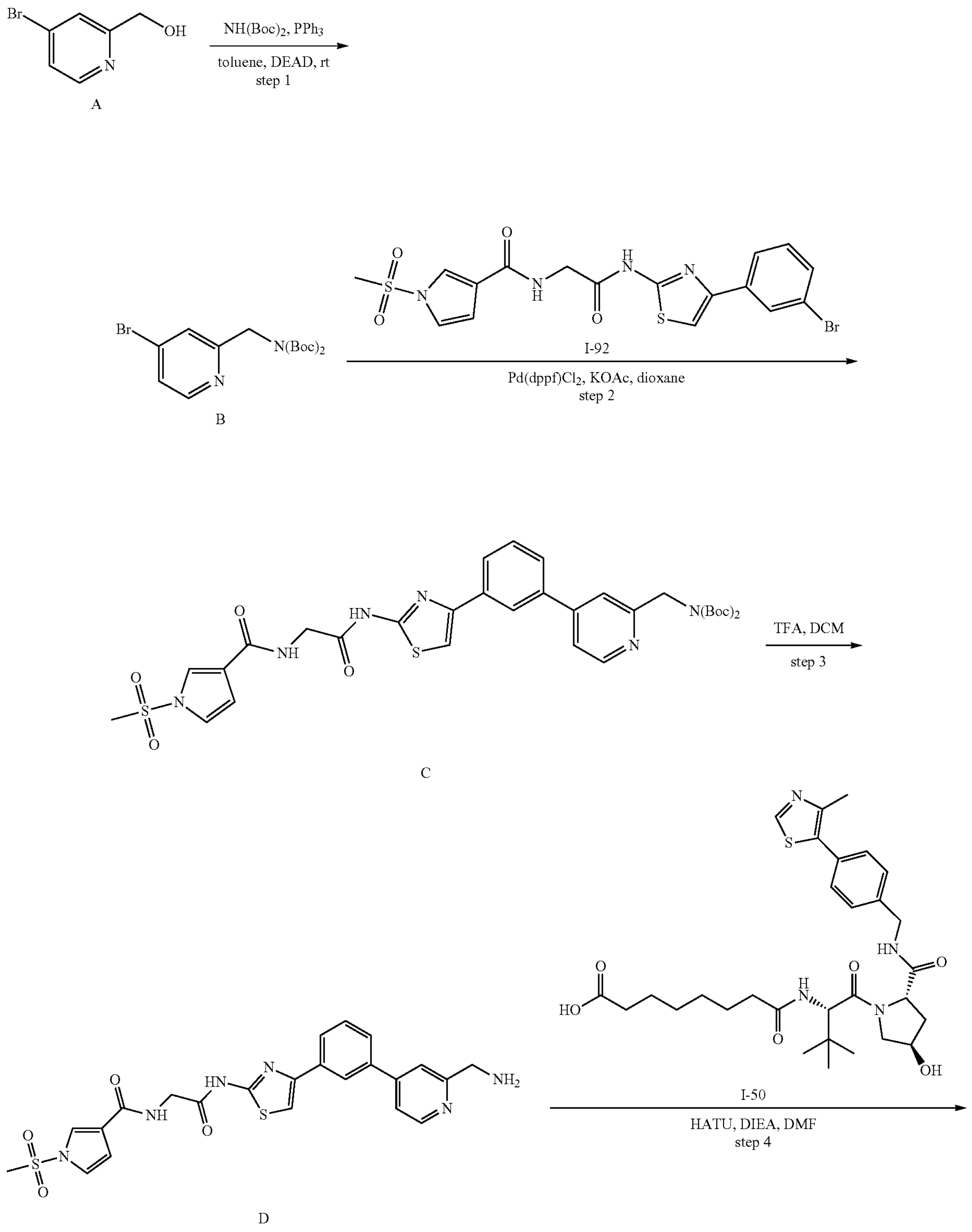

-continued

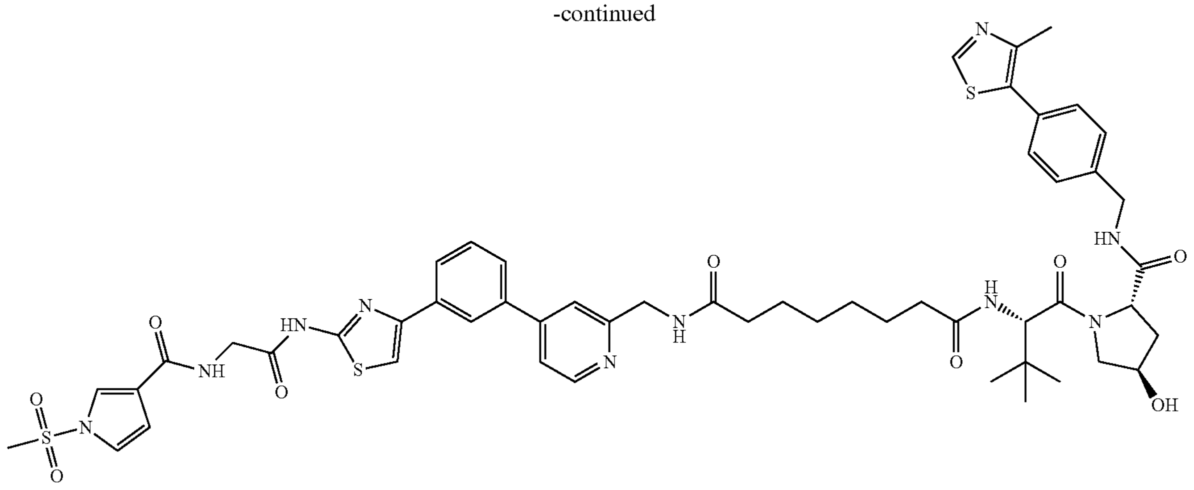

142

Step 1: Preparation of tert-butyl N-[(4-bromopyridin-2-yl)methyl]-N-(tert-butoxycarbonyl)carbamate (B)

B

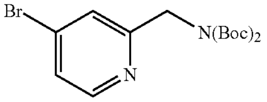

To a stirred solution of (4-bromopyridin-2-yl)methanol (A, 100.00 mg, 0.532 mmol, 1.00 equiv), tert-butyl N-(tert-butoxycarbonyl)carbamate (173.33 mg, 0.798 mmol, 1.50 equiv), and $PPh_3$ (195.29 mg, 0.745 mmol, 1.40 equiv) in toluene (2.00 mL) was added DEAD (138.94 mg, 0.798 mmol, 1.50 equiv) dropwise at 0° C. under an argon atmosphere. The resulting mixture was stirred overnight at room temperature and the resulting mixture was concentrated under vacuum. The residue was purified by silica gel column chromatography, eluting with Petroleum ether/EtOAc (3:1) to afford B (110 mg, 53.41%) as a light yellow solid. LCMS (ESI) m/z: $[M+H]^+$=387.

Step 2: Preparation of tert-butyl N-(tert-butoxycarbonyl)-N-([4-[3-(2-[2-[(1-methane sulfonylpyrrol-3-yl) formamido]acetamido]-1,3-thiazol-4-yl)phenyl] pyridin-2-yl]methyl)carbamate (C)

C

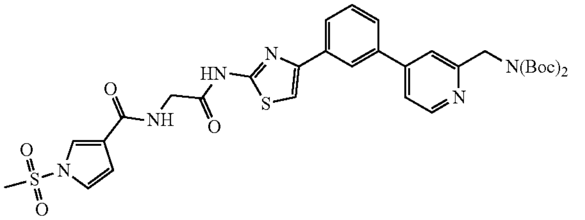

A solution of B (100.00 mg, 0.258 mmol, 2.74 equiv), 2-[(1-methanesulfonylpyrrol-3-yl)formamido]-N-[4-[3-(4,4,5,5-tetramethyl-1,3,2-dioxaborolan-2-yl)phenyl]-1,3-thiazol-2-yl]acetamide (I-92, 50.00 mg, 0.094 mmol, 1.00 equiv), KOAc (18.50 mg, 0.189 mmol, 2.00 equiv), and $Pd(dppfCl_2$ (6.90 mg, 0.009 mmol, 0.10 equiv) in 1,4-dioxane (1.00 mL) was stirred for overnight at 90° C. under a nitrogen atmosphere. After aqueous workup and DCM extraction, the residue was purified by preparative TLC (Petroleum ether/EtOAc 1:2) to afford C (39 mg, 58.20%) as a yellow solid. LCMS (ESI) m/z: $[M+H]^+$=711.

Step 3: Preparation of N-(4-[3-[2-(aminomethyl) pyridin-4-yl]phenyl]-1,3-thiazol-2-yl)-2-[(1-methanesulfonylpyrrol-3-yl)formamido]acetamide (D)

D

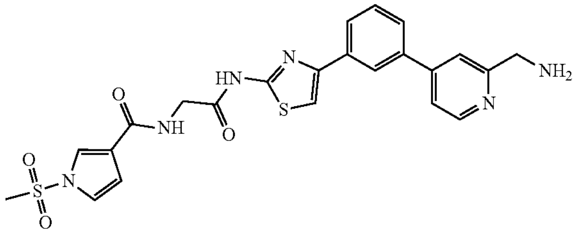

A solution of C (39.00 mg, 0.055 mmol, 1.00 equiv) and TFA (0.30 mL) in DCM (0.90 mL) was stirred for 2 h at room temperature. The resulting mixture was concentrated under vacuum to give D (25 mg, 89.24%) as a yellow solid that was used without further purification. LCMS (ESI) m/z: $[M+H]^+$=511.

Step 4: Preparation of N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N-([4-[3-(2-[2-[(1-methanesulfonylpyrrol-3-yl)formamido]acetamido]-1,3-thiazol-4-yl)phenyl]pyridin-2-yl]methyl) octanediamide (Compound 142)

142

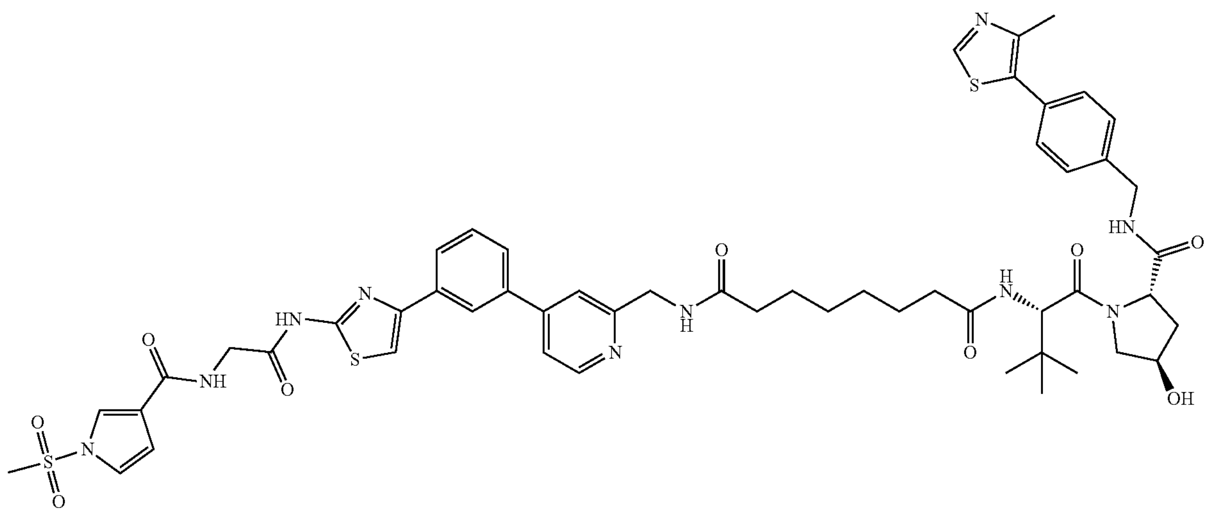

A solution of I-50 (20.00 mg, 0.039 mmol, 1.00 equiv), 7-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]heptanoic acid (D, 22.98 mg, 0.039 mmol, 1.00 equiv), HATU (29.79 mg, 0.078 mmol, 2.00 equiv), and DIEA (25.31 mg, 0.196 mmol, 5.00 equiv) in DMF (0.50 mL) was stirred overnight at room temperature. Following aqueous workup and DCM extraction the residue was purified by reverse phase flash chromatography under the following conditions: column, C18 silica gel; mobile phase, ACN in water, 0% to 100% gradient over 30 min; detector, UV 254 nm to give Compound 142 (4.5 mg, 10.64%) as an off-white solid. LCMS (ESI) m/z: $[M+H]^+$=1079.20. $^1H$ NMR (300 MHz, DMSO-d6) δ 12.48 (s, 1H), 8.99 (s, 1H), 8.71 (t, J=5.8 Hz, 1H), 8.59 (t, J=7.0 Hz, 2H), 8.44 (t, J=6.0 Hz, 1H), 8.26 (s, 1H), 8.01 (d, J=7.6 Hz, 1H), 7.90-7.78 (m, 2H), 7.67 (s, 1H), 7.64 (s, 1H), 7.63 (s, 1H), 7.62-7.56 (m, 2H), 7.47-7.35 (m, 4H), 7.32 (dd, J=3.3, 2.3 Hz, 1H), 6.78 (dd, J=3.3, 1.6 Hz, 1H), 5.15 (d, J=3.5 Hz, 1H), 4.54 (d, J=9.3 Hz, 1H), 4.44 (d, J=6.6 Hz, 4H), 4.40 (s, 1H), 4.35 (s, 1H), 4.23 (s, 1H), 4.15 (d, J=5.8 Hz, 2H), 3.66 (s, 2H), 3.58 (s, 3H), 2.44 (s, 3H), 2.22 (dt, J=23.2, 6.7 Hz, 3H), 2.10 (d, J=8.4 Hz, 1H), 1.98-1.91 (m, 1H), 1.90 (s, 1H), 1.55-1.36 (m, 4H), 1.24 (s, 4H), 0.93 (s, 9H).

Compound 153—Preparation of N-[(2S)-1-[(2S,4R)-4-hydroxy-2-([[4-(4-methyl-1,3-thiazol-5-yl)phenyl] methyl]carbamoyl)pyrrolidin-1-yl]-3,3-dimethyl-1-oxobutan-2-yl]-N'-([4-[3-(2-[2-[(1-methanesulfonylpyrrol-3-yl)formamido]acetamido]-1,3-thiazol-4-yl)phenyl]pyridin-2-yl]methyl)-N'-methyloctanediamide

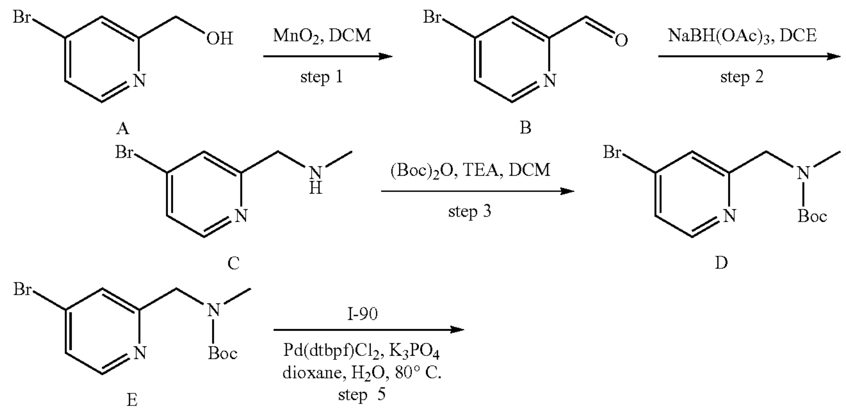

-continued

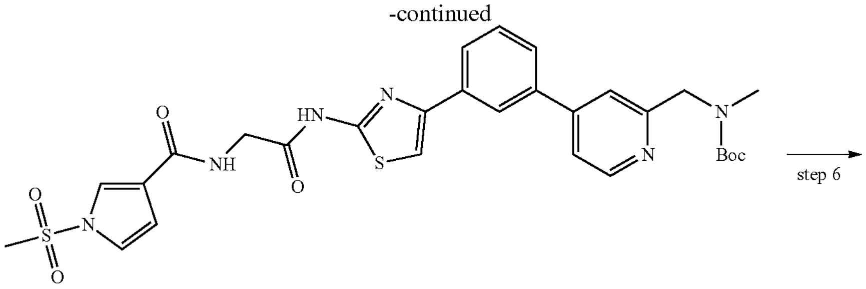

F

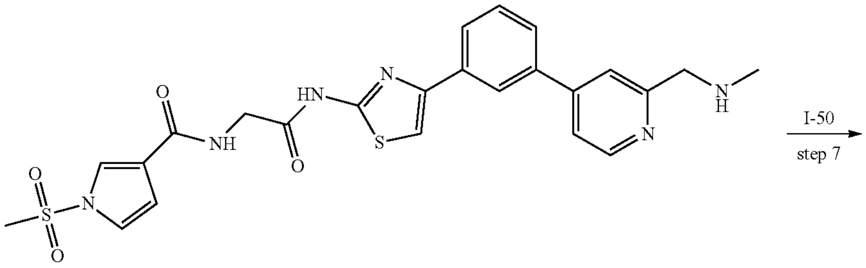

G

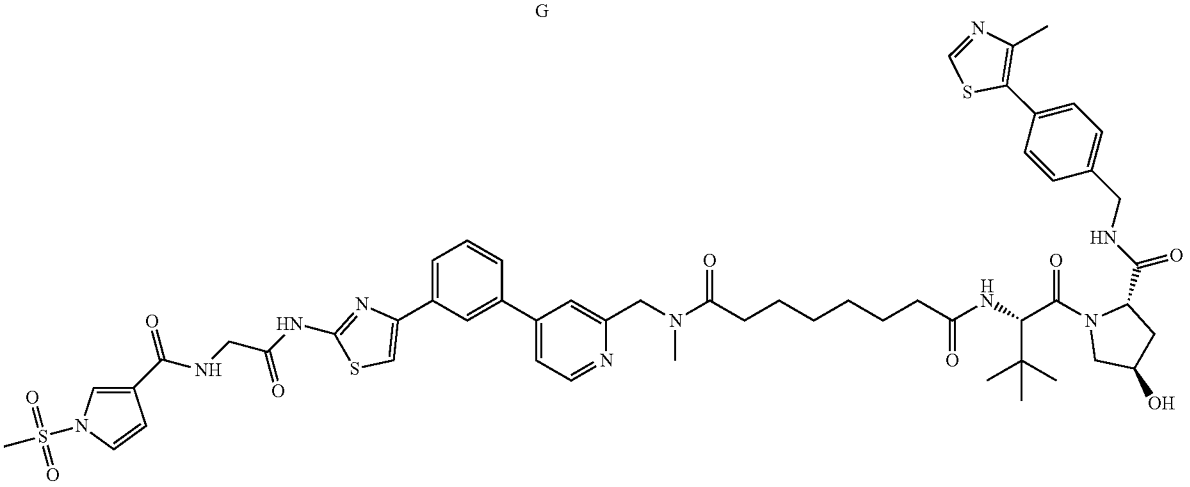

153

Step 1: Preparation of 4-bromopyridine-2-carbaldehyde (B)

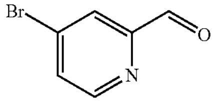

B

Into a 25-mL round-bottom flask, was placed 4-bromopyridin-2-yl)methanol (A, 500.00 mg, 2.659 mmol, 1.00 equiv), $CHCl_3$ (2.00 mL), and $MnO_2$ (2.77 g, 31.862 mmol, 11.98 equiv). The resulting suspension was stirred for 1 h at 60° C. The solids were removed by filtration, and the filtrate concentrated under reduced pressure. The residue was purified by flash column chromatography on silica gel with Petroleum ether/EtOAc (4:1) to afford B (470 mg, 94%) as yellow oil. LCMS (ESI) m/z: $[M+H]^+$=186.

Step 2: Preparation of [(4-bromopyridin-2-yl)methyl](methyl)amine (C)

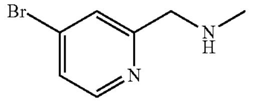

C

Into a 25-mL round-bottom flask, was placed B (230.00 mg, 1.237 mmol, 1.00 equiv), DCE (2.00 mL), $CH_3NH_2$ (96.01 mg, 3.091 mmol, 2.50 equiv), HOAc (0.07 mL, 1.180 mmol, 1.00 equiv), and $NaBH_3(OAC)_3$ (393.10 mg, 1.855 mmol, 1.50 equiv). The resulting solution was stirred for 12 h at room temperature. The resulting solution was extracted with dichloromethane and concentrated to afford C (138 mg, 52.73%) as brown oil. LCMS (ESI) m/z: $[M+H]^+$=201

Step 3: Preparation of tert-butyl N-[(4-bromopyridin-2-yl)methyl]-N-methylcarbamate (D)

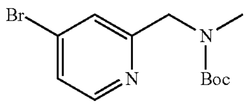

D

Into an 8-mL sealed tube, was placed C (138.00 mg, 0.686 mmol, 1.00 equiv), $(Boc)_2O$ (224.69 mg, 1.030 mmol, 1.50 equiv), TEA (208.35 mg, 2.059 mmol, 3.00 equiv), and DCM (2.00 mL). The resulting solution was stirred for 1 h at room temperature. Following concentration, the residue was purified by flash column chromatography on silica gel with EtOAc/hexane (1:4) to afford D (120 mg 58.05%) as yellow oil. LCMS (ESI) m/z: $[M+H]^+$=301.

Step 4: Preparation of tert-butyl N-([4-[3-(2-[2-[(1-methanesulfonylpyrrol-3-yl)formamido] acetamido]-1,3-thiazol-4-yl)phenyl]pyridin-2-yl]methyl)-N-methylcarbamate (E)

E

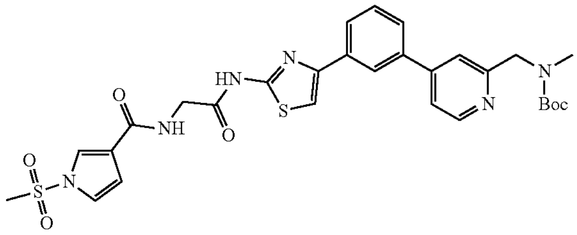

Into a 10-mL pressure reactor purged and maintained with an inert atmosphere of nitrogen, was placed I-90 (40.00 mg, 0.075 mmol, 1.00 equiv), D (33.39 mg, 0.111 mmol, 1.47 equiv), $K_3PO_4$ (53.30 mg, 0.251 mmol, 3.33 equiv), 1,4-dioxane (2.00 mL), water (0.50 mL), and $Pd(dtbpf)Cl_2$ (6.88 mg, 0.011 mmol, 0.14 equiv). The resulting solution was stirred for 2 h at 80° C., then extracted from water with EtOAc. After concentration, the residue purified by flash column chromatography on silica gel with Petroleum ether/EtOAc (1:1) to give E (35 mg, 74.29%) as a brown solid. LCMS (ESI) m/z: $[M+H]^+$=625.

Step 5: Preparation of 2-[(1-methanesulfonylpyrrol-3-yl)formamido]-N-[4-(3-[2-[(methylamino)methyl] pyridin-4-yl]phenyl)-1,3-thiazol-2-yl]acetamide (F)

F

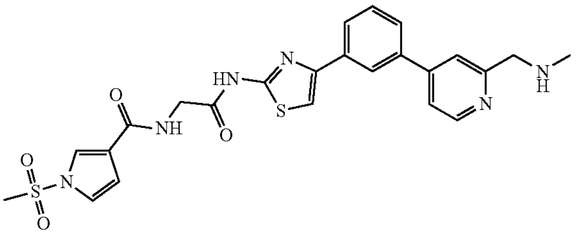

To a stirred solution of E (30.00 mg, 1.00 equiv) in DCM (2.50 mL) was added 4 M HCl in 1,4-dioxane (2.00 mL) dropwise, and the resulting solution was stirred at room temperature for 1 h. The mixture was concentrated under reduced pressure to give F that was used in the next step without further purification. LCMS (ESI) m/z:$[M+H]^+$=525.

Step 6: Preparation of N-[(2S)-1-[(2S,4R)-4-hydroxy-2-([[4-(4-methyl-1,3-thiazol-5-yl)phenyl] methyl]carbamoyl)pyrrolidin-1-yl]-3,3-dimethyl-1-oxobutan-2-yl]-N'-([4-[3-(2-[2-[(1-methanesulfonylpyrrol-3-yl)formamido]acetamido]-1,3-thiazol-4-yl)phenyl]pyridin-2-yl]methyl)-N'-methyloctanediamide (Compound 153)

153

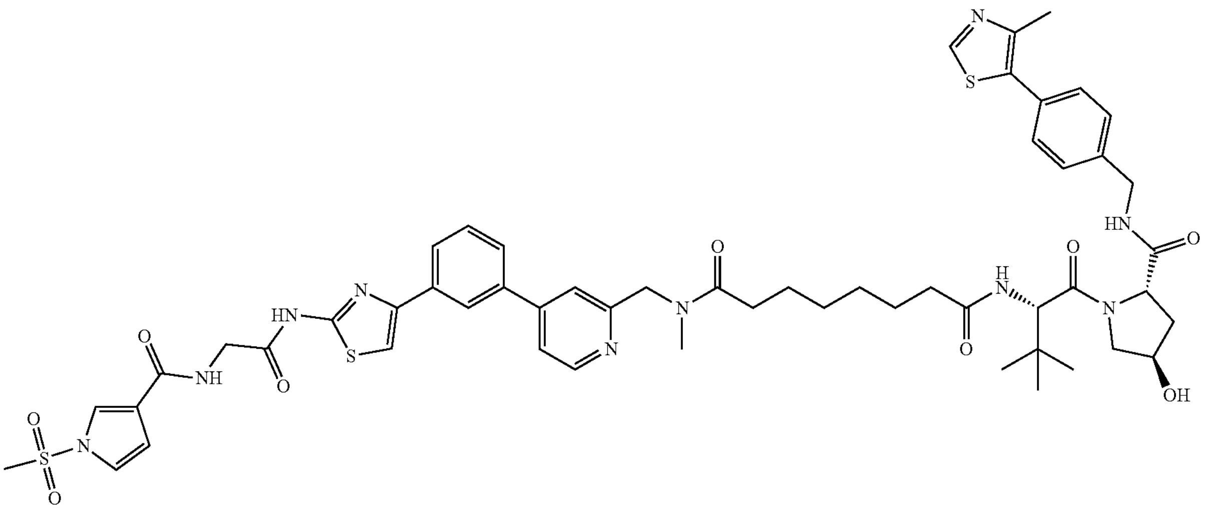

To a stirred solution of 7-[[(2S)-1-[(2S,4R)-4-hydroxy-2-([[4-(4-methyl-1,3-thiazol-5-yl)phen yl]methyl]carbamoyl) pyrrolidin-1-yl]-3,3-dimethyl-1-oxobutan-2-yl]carbamoyl] heptanoic acid (F, 67.11 mg, 0.114 mmol, 1.20 equiv) in DMF (3 mL) was added HATU (54.36 mg, 0.143 mmol, 1.50 equiv), DIEA (36.95 mg, 0.286 mmol, 3.00 equiv), and I-50 (50.00 mg, 0.095 mmol, 1.00 equiv) at room temperature. After 2 h the solution was extracted with 3×40 mL of EtOAc, and the combined organic combined, washed with aqueous sodium carbonate and brine, dried and concentrated under vacuum. The crude product (20 mg) was purified by preparative HPLC under the following conditions (Column: Xselect CSH F-Phenyl OBD column, 19×250, 5 μm; Mobile Phase A:Water (0.05% formic acid), Mobile Phase B:ACN; Flow rate:25 mL/min; Gradient:35 B to 55 B in 12 min; 254/220 nm) to afford Compound 153 (7.2 mg, 6.86%) as a white solid. LCMS $[M+H]^+$=1093.35. $^1H$ NMR (400 MHz, DMSO-d6) δ 12.48 (s, 1H), 8.99 (s, 1H), 8.75-8.53 (m, 3H), 8.27 (d, J=11.9 Hz, 1H), 8.01 (d, J=7.6 Hz, 1H), 7.89-7.80 (m, 3H), 7.76-7.48 (m, 4H), 7.40 (q, J=8.1 Hz, 4H), 7.32 (t, J=2.8 Hz, 1H), 6.78 (dd, J=3.3, 1.6 Hz, 1H), 5.14 (s, 1H), 4.70 (d, J=22.4 Hz, 2H), 4.54 (dd, J=9.5, 5.4 Hz, 1H), 4.48-4.38 (m, 2H), 4.35 (s, 1H), 4.20 (dd, J=32.9, 5.3 Hz, 3H), 3.65 (s, 2H), 3.58 (s, 3H), 3.08 (s, 2H), 2.88 (s, 1H), 2.44 (s, 3H), 2.40 (td, J=7.4, 4.0 Hz, 2H), 2.23 (q, J=10.7, 8.0 Hz, 1H), 2.14-2.01 (m, 2H), 1.94-1.85 (m, 1H), 1.55-1.40 (m, 4H), 1.23 (d, J=8.2 Hz, 4H), 0.92 (s, 9H).

Compound 164—Preparation of (2S,4R)-4-hydroxy-1-[(2S)-2-([[3'-(2-[2-[(1-methanesulfonylpyrrol-3-yl)formamido]acetamido]-1,3-thiazol-4-yl)-[1,1'-biphenyl]-3-yl]methyl]amino)-3,3-dimethylbutanoyl]-N-[[4-(4-methyl-1,3-thiazol-5-yl)phenyl]methyl]pyrrolidine-2-carboxamide

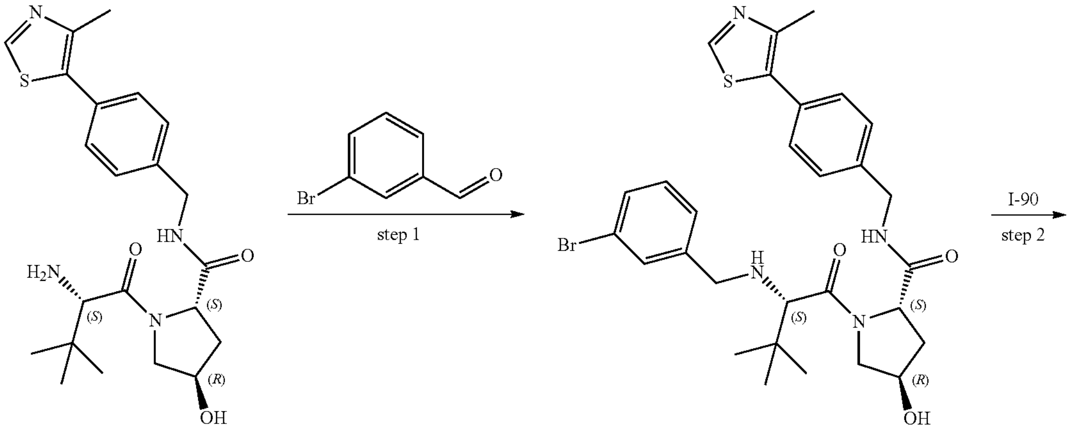

A B

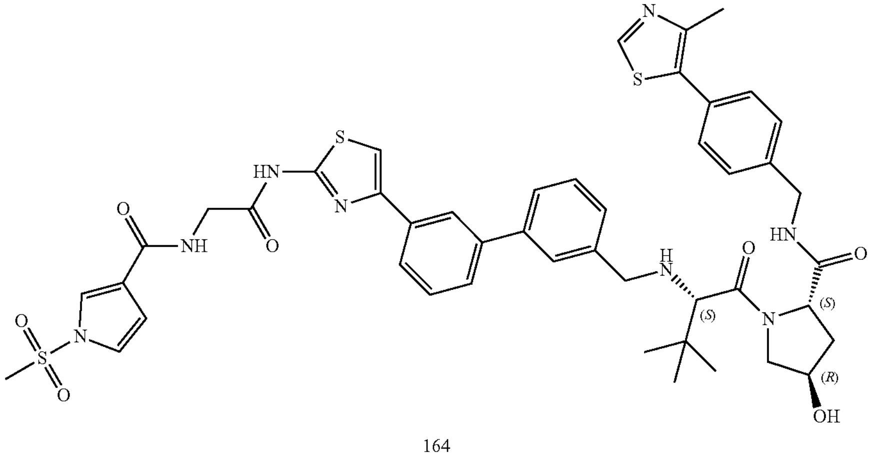

164

Step 1: Preparation of (2S,4R)-1-[(2S)-2-[[(3-bromophenyl)methyl]amino]-3,3-dimethylbutanoyl]-4-hydroxy-N-[[4-(4-methyl-1,3-thiazol-5-yl)phenyl]methyl]pyrrolidine-2-carboxamide (B)

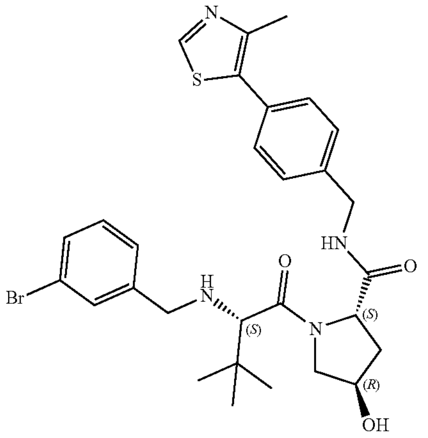

B

To a stirred solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (A, 100.00 mg, 0.232 mmol, 1.00 equiv) and 3-bromobenzaldehyde (42.98 mg, 0.232 mmol, 1.00 equiv) in DCM (3.00 mL) was added AcOH dropwise at room temperature and stirred for 1 h. $NaBH(AcO)_3$ (73.84 mg, 0.348 mmol, 1.5 equiv) was added and the reaction stirred for 4 h at room temperature. The reaction mixture was partitioned between DCM and water. The aqueous layer was extracted again with DCM. The combined organic layer was dried over anhydrous sodium sulfate and concentrated under vacuum. The residue was purified by preparative TLC (EtOAc/Petroleum ether 1:1) to afford B (80 mg, 57.45%). LCMS (ESI) m/z: $[M+H]^+=599$.

Step 2: Preparation of (2S,4R)-4-hydroxy-1-[(2S)-2-([[3'-(2-[2-[(1-methanesulfonylpyrrol-3-yl)formamido]acetamido]-1,3-thiazol-4-yl)-[1,1'-biphenyl]-3-yl]methyl]amino)-3,3-dimethylbutanoyl]-N-[[4-(4-methyl-1,3-thiazol-5-yl)phenyl]methyl]pyrrolidine-2-carboxamide (Compound 164)

164

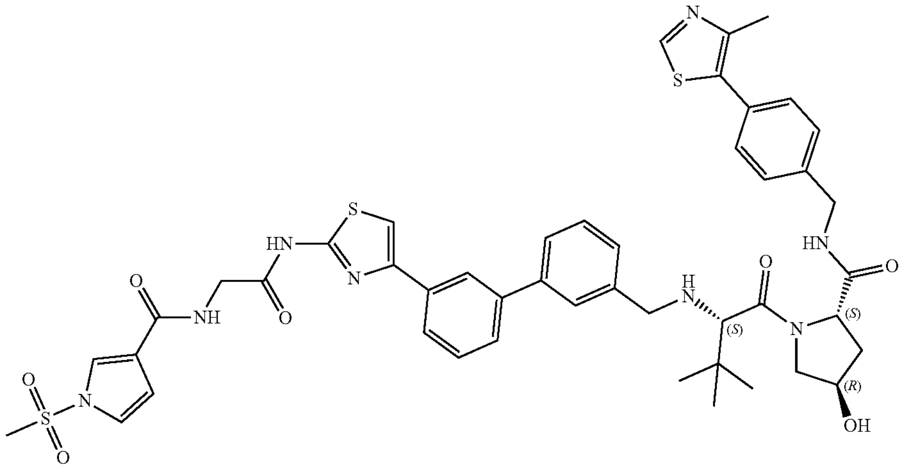

To a solution of B (80.00 mg, 0.133 mmol, 1.00 equiv) in 1,4-dioxane (4.00 mL)/water (1.00 mL) was added 2-[(1-methanesulfonylpyrrol-3-yl)formamido]-N-[4-[3-(4,4,5,5-tetramethyl-1,3,2-dioxaborolan-2-yl)phenyl]-1,3-thiazol-2-yl] acetamide (I-90, 132.70 mg, 0.250 mmol, 1.50 equiv), $Na_2CO_3$ (53.03 mg, 0.500 mmol, 3.00 equiv), and XPhos Pd $G_3$ (14.12 mg, 0.017 mmol, 0.10 equiv) in portions at 50° C. The reaction was stirred for 5 h under $N_2$ atmosphere and the crude product (60 mg) was purified by preparative HPLC to afford Compound 164 (14.0 mg, 8.92%) as a white solid. LCMS $[M+H]^+$=923.30. $^1H$ NMR (400 MHz, DMSO-d6) δ 12.43 (s, 1H), 9.30 (brs, 1H), 9.00 (s, 1H), 8.77-8.69 (m, 2H), 8.24-8.19 (m, 1H), 8.01 (s, 1H), 7.94 (d, J=7.7 Hz, 1H), 7.87-7.80 (m, 2H), 7.76 (s, 1H), 7.68 (d, J=7.8 Hz, 1H), 7.61-7.51 (m, 3H), 7.41 (s, 4H), 7.36-7.29 (m, 1H), 6.78 (dd, J=3.3, 1.6 Hz, 1H), 5.37 (brs, 1H), 4.61 (t, J=8.0 Hz, 1H), 4.51-4.41 (m, 1H), 4.37 (s, 1H), 4.29-4.22 (m, 2H), 4.15 (d, J=5.6 Hz, 2H), 4.05-3.98 (m, 1H), 3.80-3.77 (m, 1H), 3.59-3.58 (m, 3H), 3.43-3.35 (m, 2H), 2.45 (s, 3H), 2.17-2.07 (m, 1H), 1.99-1.89 (m, 1H), 1.06 (s, 9H).

Compound 165—Preparation of N-[4-[3-(2-[4-[2-(2,6-dioxopiperidin-3-yl)-1,3-dioxoisoindol-5-yl]piperazin-1-yl]pyridin-4-yl)phenyl]-1,3-thiazol-2-yl]-2-[(1-methanesulfonylpyrrol-3-yl)formamido]acetamide trifluoroacetate

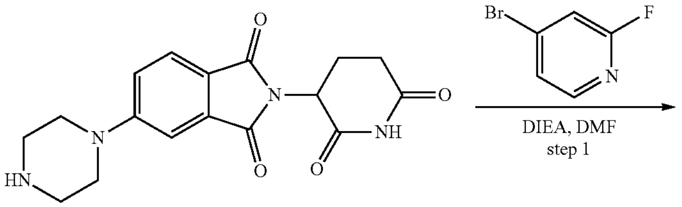

I-39

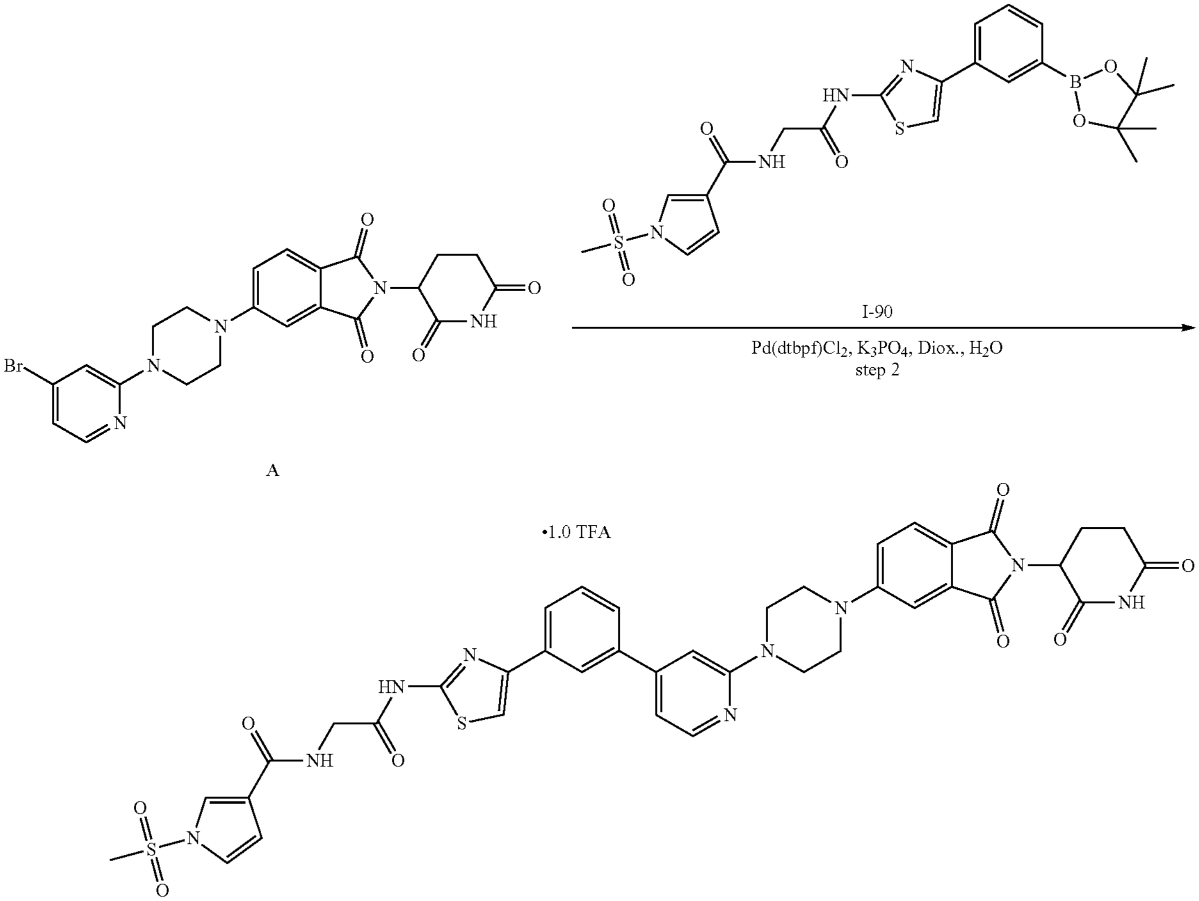

A

165

Step 1: Preparation of tert-butyl 5-[4-(4-bromopyridin-2-yl)piperazin-1-yl]-2-(2,6-dioxopiperidin-3-yl)isoindole-1,3-dione (A)

A

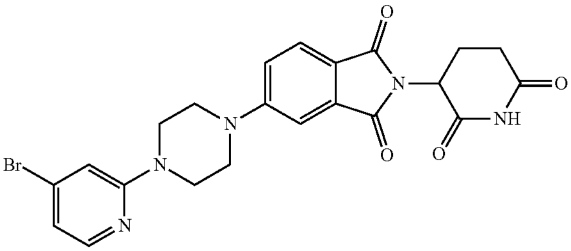

To a solution of 2-(2,6-dioxopiperidin-3-yl)-5-(piperazin-1-yl)isoindole-1,3-dione (I-39, 100.00 mg, 0.292 mmol, 1.00 equiv), and DIEA (226.51 mg, 1.753 mmol, 6.00 equiv) in DMF (4.00 mL) was added 4-bromo-2-fluoropyridine (51.41 mg, 0.292 mmol, 1 equiv). The solution was stirred overnight at 80° C. Following aqueous workup and DCM extraction, the residue was purified by reverse phase flash chromatography under the following conditions: column, C18 silica gel; mobile phase, ACN in water, 0% to 100% gradient over 20 min; detector, UV 254 nm, providing A (54 mg, 37.10%) as a yellow solid. LCMS (ESI) m/z: $[M+H]^+$ =498.07.

Step 2: Preparation of N-[4-[3-(2-[4-[2-(2,6-dioxopiperidin-3-yl)-1,3-dioxoisoindol-5-yl]piperazin-1-yl]pyridin-4-yl)phenyl]-1,3-thiazol-2-yl]-2-[(1-methanesulfonylpyrrol-3-yl)formamido]acetamide trifluoroacetate (Compound 165)

165

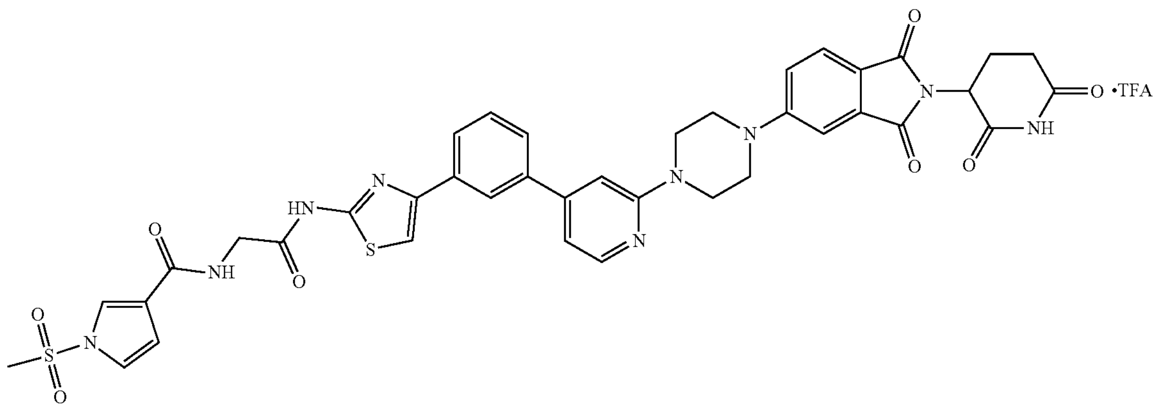

To a suspension of 2-[(1-methanesulfonylpyrrol-3-yl)formamido]-N-[4-[3-(4,4,5,5-tetramethyl-1,3,2-dioxaborolan-2-yl)phenyl]-1,3-thiazol-2-yl]acetamide (I-90, 42.58 mg, 0.080 mmol, 1.00 equiv), A (40.00 mg, 0.080 mmol, 1.00 equiv), and $K_3PO_4$ (34.08 mg, 0.161 mmol, 2.00 equiv) in 1,4-dioxane (3.00 mL)/water (0.30 mL) was added Pd(dtbpf)$Cl_2$ (5.23 mg, 0.008 mmol, 0.10 equiv). The suspension was stirred at 80° C. for 5 h. The resulting mixture was filtered, and the filter cake was washed with EtOAc (3×30 mL). The filtrate was concentrated under reduced pressure. The crude product (40 mg) was purified by preparative HPLC with the following conditions (Column: XSelect CSH Prep C18 OBD Column, 5 um, 19×150 mm; Mobile Phase A:Water (0.05% TFA), Mobile Phase B:ACN; Flow rate:25 mL/min; Gradient:12 B to 39 B in 10 min; 254/220 nm; RT 1:9.52 to afford Compound 165 (8.3 mg, 10.72%) as a yellow solid. LCMS (ESI) m/z: $[M+H]^+$=822.10. $^1$H NMR (400 MHz, DMSO-d6) δ: 12.46 (s, 1H), 11.10 (s, 1H), 8.71 (t, J=5.9 Hz, 1H), 8.32-8.19 (m, 2H), 8.03 (d, J=7.8 Hz, 1H), 7.89-7.70 (m, 4H), 7.61 (t, J=7.8 Hz, 1H), 7.42 (d, J=2.2 Hz, 1H), 7.36-7.29 (m, 3H), 7.15 (d, J=5.8 Hz, 1H), 6.78 (dd, J=3.3, 1.7 Hz, 1H), 5.09 (dd, J=12.9, 5.4 Hz, 1H), 4.15 (d, J=5.7 Hz, 2H), 3.93-3.82 (m, 4H), 3.70 (t, J=5.2 Hz, 4H), 3.58 (s, 3H), 2.90 (ddd, J=17.3, 13.9, 5.5 Hz, 1H), 2.71-2.55 (m, 2H), 2.04 (ddd, J=12.2, 6.7, 2.7 Hz, 1H). $^{19}$F NMR (377 MHz, DMSO-$d_6$) δ: −74.11.

Compound 160—Preparation of N1-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N3-[[3-(2-[2-[(1-methanesulfonylpyrrol-3-yl)formamido]acetamido]-1,3-thiazol-4-yl)-[1,1-biphenyl]-3-yl]methyl]azetidine-1,3-dicarboxamide

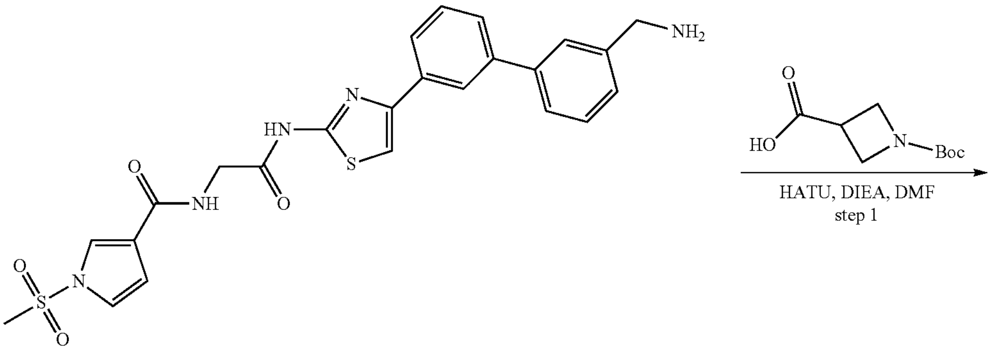

I-93

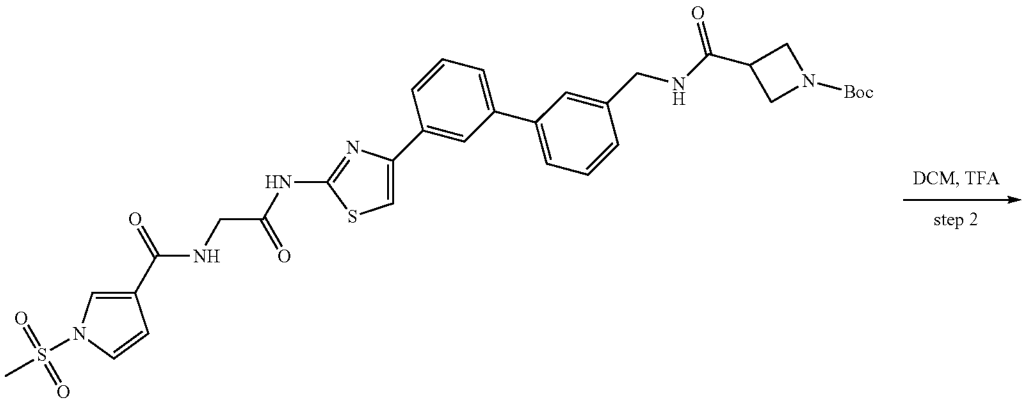

A

-continued
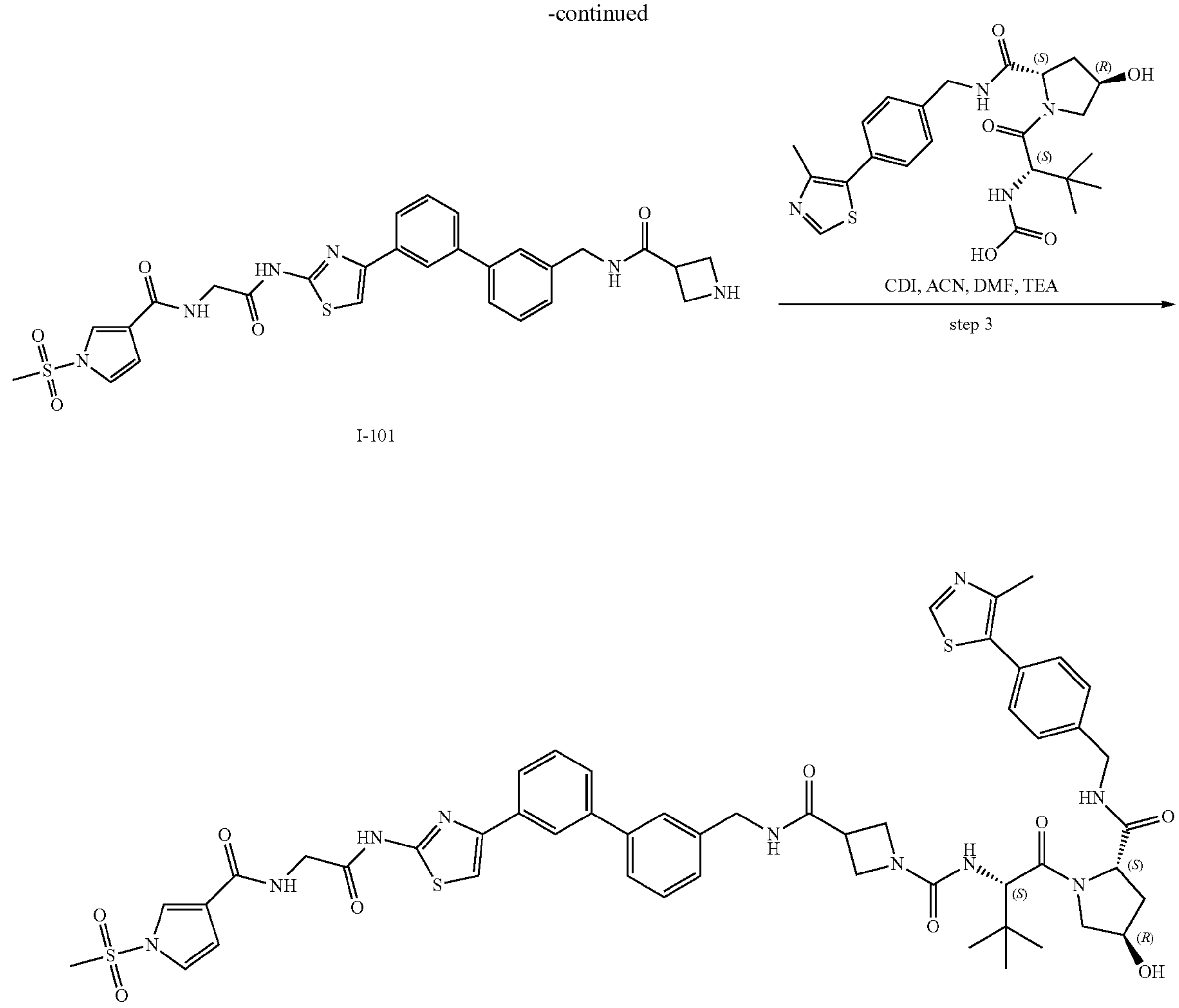
I-101
160
Step 1: Preparation of tert-butyl 3-([[3-(2-[2-[(1-methanesulfonylpyrrol-3-yl)formamido]acetamido]-1,3-thiazol-4-yl)-[1,1-biphenyl]-3-yl]methyl]carbamoyl)azetidine-1-carboxylate (A)
A
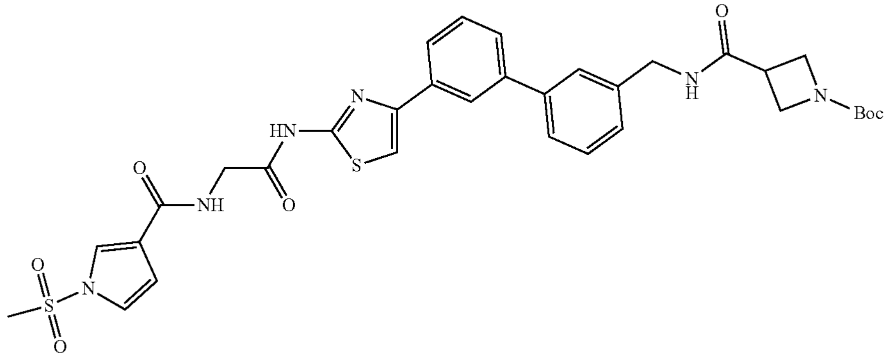

To a stirred solution of 1-(tert-butoxycarbonyl)azetidine-3-carboxylic acid (23.69 mg, 0.118 mmol, 1.20 equiv), HATU (44.77 mg, 0.118 mmol, 1.20 equiv), and DIEA (38.04 mg, 0.294 mmol, 3.00 equiv) in DMF (2.00 mL) was added N-[4-[3-(aminomethyl)-[1,1-biphenyl]-3-yl]-1,3-thiazol-2-yl]-2-[(1-methanesulfonylpyrrol-3-yl)formamido]acetamide (I-93, 50.00 mg, 0.098 mmol, 1.00 equiv) in portions at room temperature. The resulting mixture was stirred for 2 h at room temperature. The mixture was diluted with water (5 mL) and extracted with EtOAc (3×5 mL). The organic layers were combined and dried over anhydrous sodium sulfate, filtered and concentrated to afford A (30 mg, 44.12%) as a reddish-brown oil. LCMS (ESI) m/z: $[M+H]^+$ =693.

Step 2: Preparation of N-[[3-(2-[2-[(1-methanesulfonylpyrrol-3-yl)formamido]acetamido]-1,3-thiazol-4-yl)[1,1-biphenyl]-3-yl]methyl]azetidine-3-carboxamide (I-101)

I-101

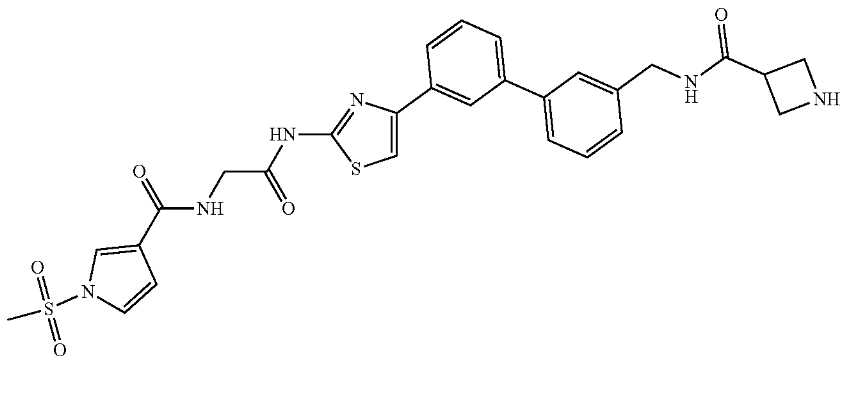

To a stirred solution of A (30.00 mg) in DCM (0.80 mL) was added TFA (0.20 mL) dropwise at room temperature. The resulting mixture was stirred for 2 h at room temperature. The resulting mixture was concentrated under vacuum to afford I-101 (30 mg, crude) as a colorless oil. LCMS (ESI) m/z: $[M+H]^+$=593.

Step 3: Preparation of N1-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N3-[[3-(2-[2-[(1-methanesulfonylpyrrol-3-yl)formamido]acetamido]-1,3-thiazol-4-yl)-[1,1-biphenyl]-3-yl]methyl]azetidine-1,3-dicarboxamide (Compound 160)

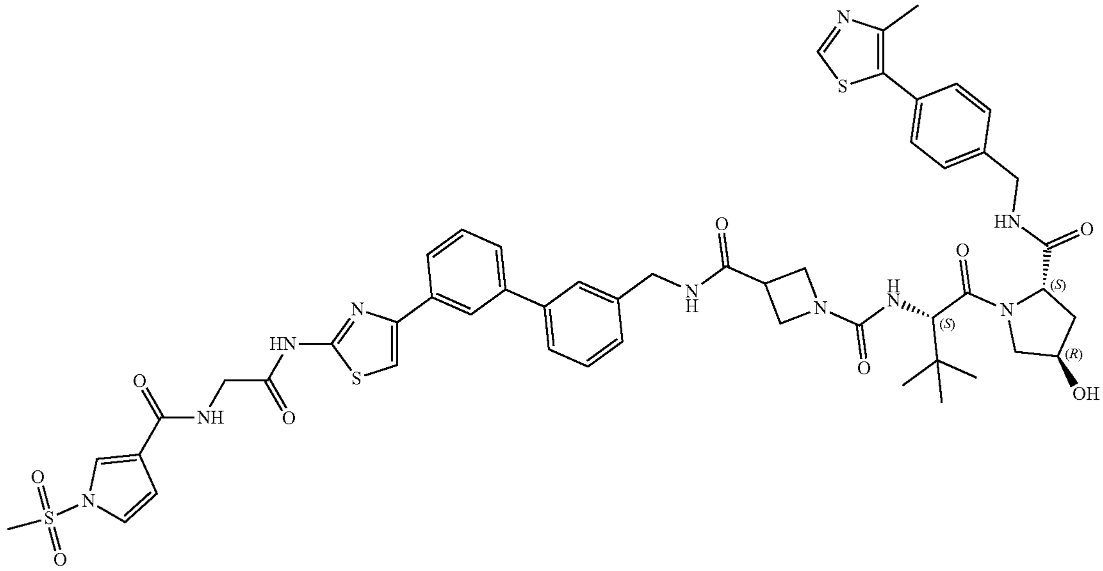

160

To a stirred solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (21.79 mg, 0.051 mmol, 1.00 equiv) and CDI (8.21 mg, 0.051 mmol, 1.00 equiv) in ACN (1.80 mL)/DMF (0.60 mL) was added triethylamine (20.49 mg, 0.202 mmol, 4.00 equiv) in portions at 0° C. The resulting mixture was stirred for 1 h at 0° C. To the above mixture was added I-101 (30.00 mg, 0.051 mmol, 1.00 equiv) in portions at room temperature. The resulting mixture was stirred for 16 h at room temperature. The crude product (30 mg) was purified by preparative HPLC to afford Compound 160 (6.5 mg, 12.24%) as a white solid. LCMS (ESI) m/z: $[M+H]^+$=1049.20. $^1H$ NMR (300 MHz, DMSO-$d_6$) δ 8.98 (s, 1H), 8.16 (d, J=1.9 Hz, 1H), 7.95-7.81 (m, 2H), 7.76 (s, 1H), 7.65-7.42 (m, 5H), 7.47-7.35 (m, 4H), 7.35-7.23 (m, 2H), 6.78 (dd, J=3.3, 1.7 Hz, 1H), 4.45 (d, J=8.1 Hz, 1H), 4.36 (d, J=12.6 Hz, 5H), 4.22 (d, J=15.9 Hz, 1H), 4.15 (s, 2H), 4.02 (t, J=8.3 Hz, 1H), 3.90 (dd, J=20.5, 7.5 Hz, 3H), 3.66 (s, 2H), 3.57 (s, 3H), 2.44 (s, 3H), 2.10-1.98 (m, 1H), 1.97-1.82 (m, 1H), 1.23 (s, 1H), 0.93 (s, 9H).

Compound 158—Preparation of (2S,4R)-4-hydroxy-1-[(2S)-2-[({[3-(2-[2-[(1-methanesulfonylpyrrol-3-yl)formamido]acetamido]-1,3-thiazol-4-yl)-[1,1-biphenyl]-3-yl]methyl]carbamoyl)amino]-3,3-dimethylbutanoyl]-N-[[4-(4-methyl-1,3-thiazol-5-yl)phenyl]methyl]pyrrolidine-2-carboxamide

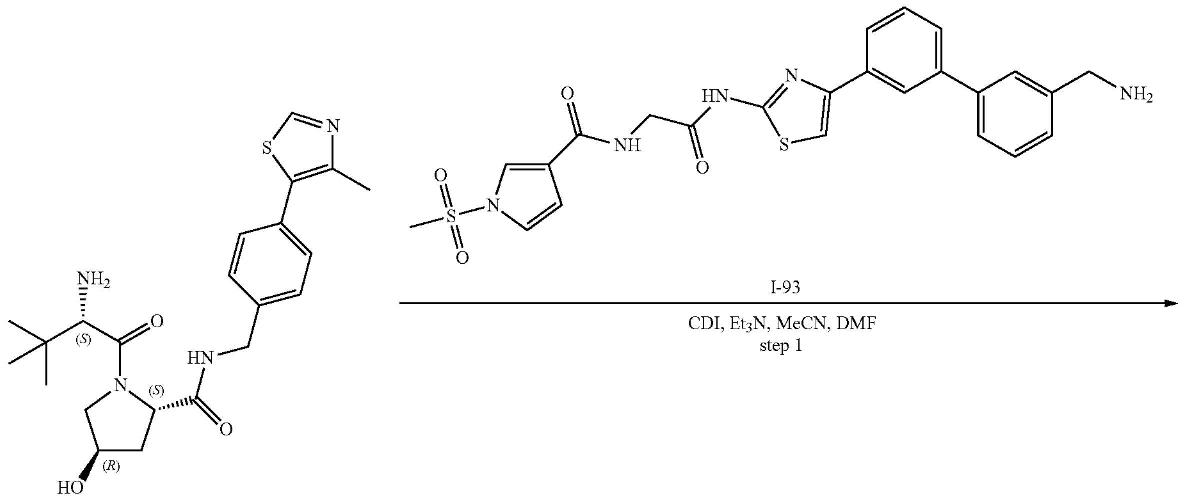

A

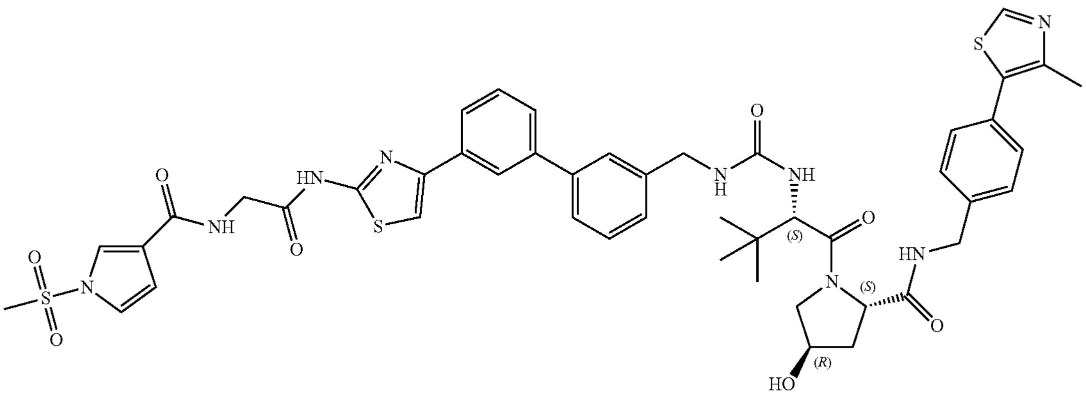

158

To a stirred solution of (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (A, 84.49 mg, 0.196 mmol, 1.00 equiv) in ACN (3.00 mL)/DMF (1.00 mL) were added CDI (31.82 mg, 0.196 mmol, 1.00 equiv), and $Et_3N$ (19.86 mg, 0.196 mmol, 1.00 equiv) in portions at room temperature under a nitrogen atmosphere. The resulting mixture was stirred for 20 min at room temperature. To the above mixture was added N-[4-[3-(aminomethyl)-[1,1-biphenyl]-3-yl]-1,3-thiazol-2-yl]-2-[(1-methanesulfonylpyrrol-3-yl)formamido]acetamide (I-93, 100.00 mg, 0.196 mmol, 1.00 equiv) in portions at room temperature. The resulting mixture was stirred for overnight at room temperature. The resulting mixture was extracted with EtOAc (3×10 mL). The combined organic layers were washed with water (3×10 mL), dried over anhydrous $Na_2SO_4$. After filtration, the filtrate was concentrated under reduced pressure. The residue was purified by preparative TLC (CHCl3/MeOH 10:1) to afford the crude product. The crude product was purified by preparative HPLC to afford Compound 158 (9.5 mg, 24.88%) as a white solid. LCMS (ESI) m/z: $[M+H]^+$ =966.15 $^1H$ NMR (300 MHz, DMSO-d6) δ 12.43 (s, 1H), 8.98 (s, 1H), 8.69 (t, J=5.8 Hz, 1H), 8.57 (t, J=6.1 Hz, 1H), 8.18 (d, J=1.8 Hz, 1H), 7.95-7.82 (m, 2H), 7.76 (s, 1H), 7.63-7.47 (m, 4H), 7.47-7.34 (m, 5H), 7.34-7.25 (m, 2H), 6.78 (dd, J=3.3, 1.6 Hz, 1H), 6.66 (t, J=5.9 Hz, 1H), 6.32 (d, J=9.6 Hz, 1H), 5.15 (d, J=3.5 Hz, 1H), 4.50-4.30 (m, 5H), 4.30-4.11 (m, 4H), 3.68 (d, J=3.0 Hz, 2H), 3.58 (s, 3H), 2.44 (s, 3H), 2.05 (s, 1H), 1.99-1.84 (m, 1H), 0.93 (s, 9H).

Compound 154—Preparation of (2S,4R)-4-hydroxy-1-[(2S)-2-[3-[3-([[3-(2-[2-[(1-methanesulfonylpyrrol-3-yl)formamido]acetamido]-1,3-thiazol-4-yl)-[1,1-biphenyl]-3-yl]methyl]carbamoyl)azetidin-1-yl]propanamido]-3,3-dimethylbutanoyl]-N-[[4-(4-methyl-1,3-thiazol-5-yl)phenyl]methyl]pyrrolidine-2-carboxamide formate

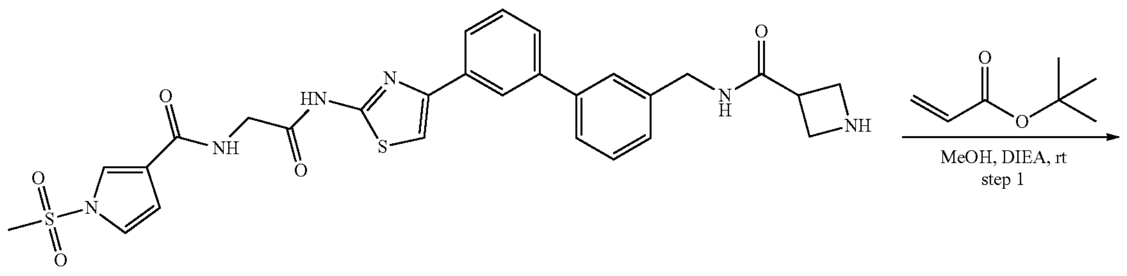

I-101

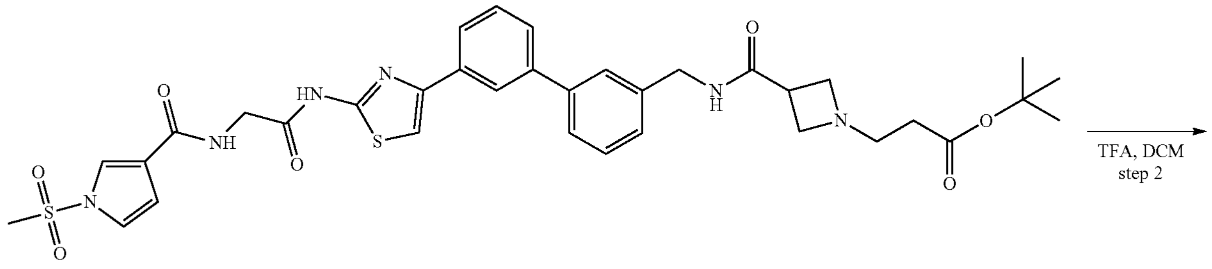

A

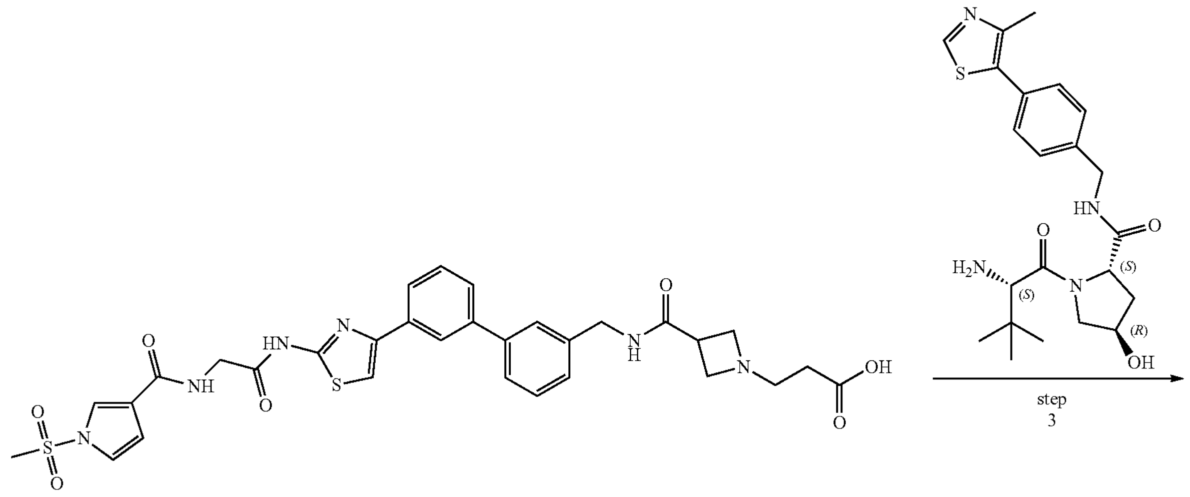

B

-continued
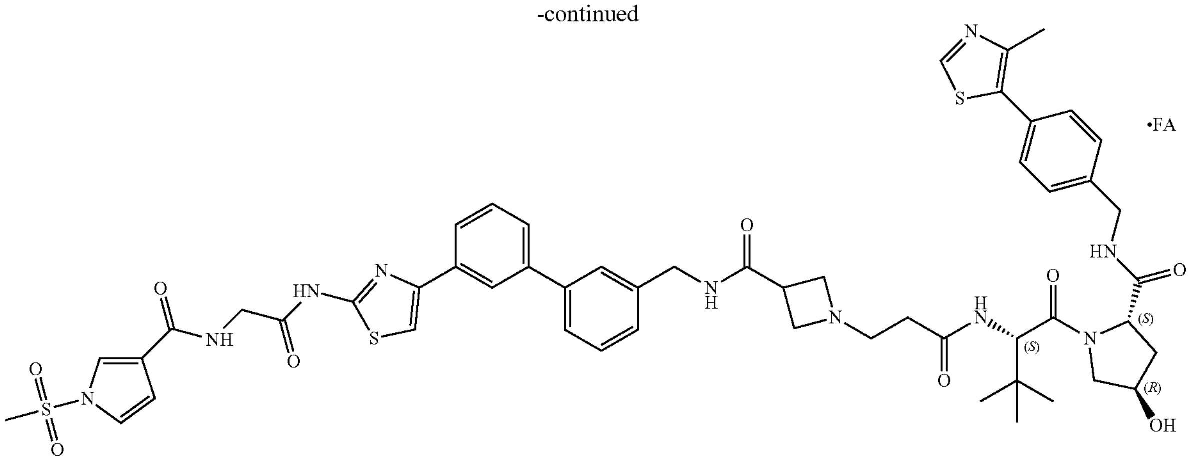
154
Step 1: Preparation of tert-butyl 3-[3-([[3-(2-[2-[(1-methanesulfonylpyrrol-3-yl)formamido]acetamido]-1,3-thiazol-4-yl)-[1,1-biphenyl]-3-yl]methyl]carbamoyl)azetidin-1-yl]propanoate (A)
A
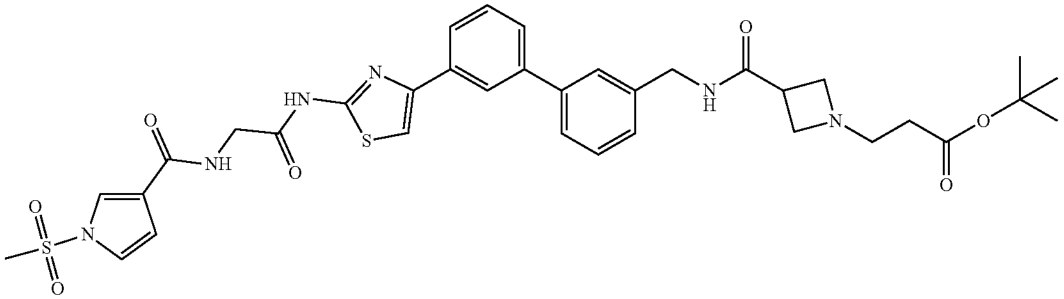

A solution of I-101 (30.00 mg, 0.051 mmol, 1.00 equiv), tert-butyl prop-2-enoate (9.73 mg, 0.076 mmol, 1.50 equiv), and DIEA (52.33 mg, 0.405 mmol, 8.00 equiv) in MeOH (0.50 mL) was stirred overnight at room temperature under a nitrogen atmosphere. The resulting mixture was concentrated under reduced pressure. This resulted in A (25 mg, 68.52%) as an off-white solid. LCMS (ESI) m/z: $[M+H]^+$ =721.

Step 2: Preparation of 3-[3-([[3-(2-[2-[(1-methanesulfonylpyrrol-3-yl)formamido]acetamido]-1,3-thiazol-4-yl)-[1,1-biphenyl]-3-yl]methyl]carbamoyl)azetidin-1-yl]propanoic acid (B)

B

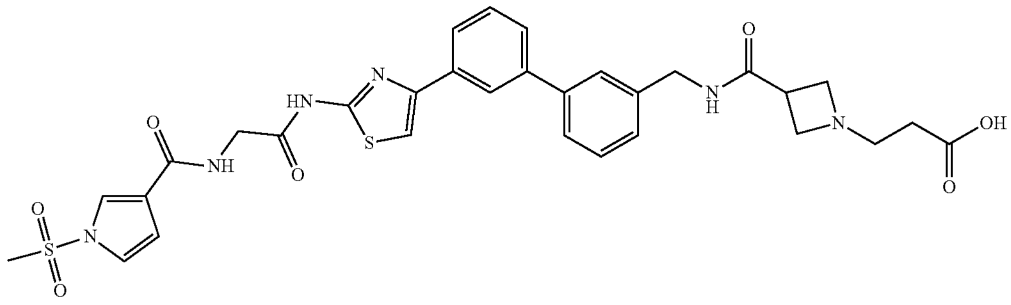

A solution of A (25.00 mg, 0.035 mmol, 1.00 equiv) and TFA (0.20 mL) in DCM (0.60 mL) was stirred for 2 h at room temperature under a nitrogen atmosphere. The resulting mixture was concentrated under reduced pressure to afford B (20 mg, 86.75%) as a yellow oil that was used for next step without further purification. LCMS (ESI) m/z: $[M+H]^+$=665.

Step 3: Preparation of (2S,4R)-4-hydroxy-1-[(2S)-2-[3-[3-([[3-(2-[2-[(1-methanesulfonylpyrrol-3-yl)formamido]acetamido]-1,3-thiazol-4-yl)-[1,1-biphenyl]-3-yl]methyl]carbamoyl)azetidin-1-yl]propanamido]-3,3-dimethylbutanoyl]-N-[[4-(4-methyl-1,3-thiazol-5-yl)phenyl]methyl]pyrrolidine-2-carboxamide formate (Compound 154)

154

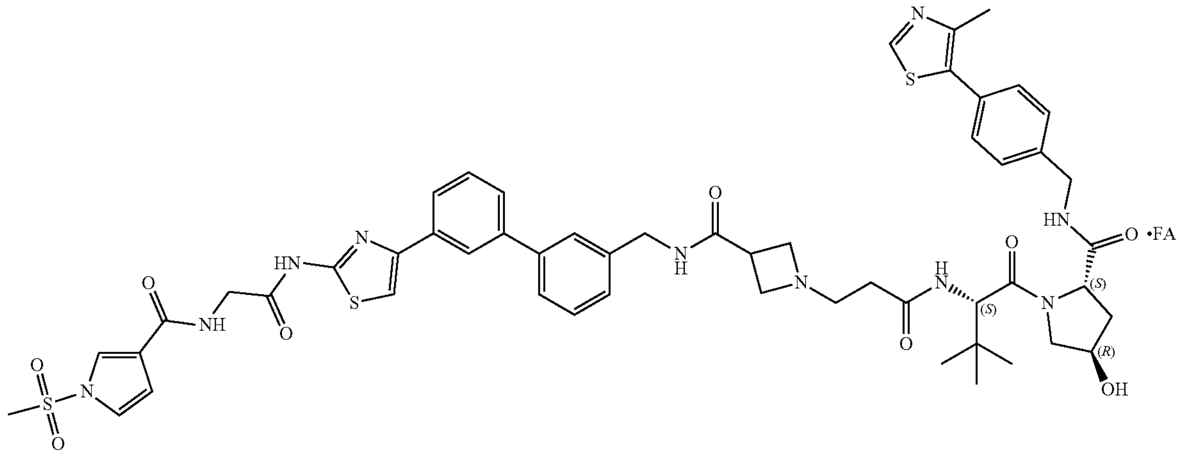

A solution of B (15.00 mg, 0.023 mmol, 1.00 equiv), HATU (17.16 mg, 0.045 mmol, 2.00 equiv), DIEA (11.67 mg, 0.090 mmol, 4.00 equiv), and (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (10.69 mg, 0.025 mmol, 1.10 equiv) in DMF (0.50 mL) was stirred for 2 h at room temperature under a nitrogen atmosphere. The crude product was purified directly by preparative HPLC to afford Compound 154 (4.6 mg, 18.15%) as an off-white solid. LCMS (ESI) m/z: $[M+H]^+$=1077.25. $^1H$ NMR (400 MHz, DMSO-d6) δ 12.46 (s, 1H), 8.98 (s, 1H), 8.71 (s, 1H), 8.58 (s, 1H), 8.51-8.23 (m, 2H), 8.18 (s, 2H), 7.91 (d, J=7.6 Hz, 1H), 7.85 (s, 1H), 7.77 (m, 2H), 7.62-7.49

(m, 4H), 7.50-7.34 (m, 5H), 7.32-7.26 (m, 2H), 6.79 (s, 1H), 4.51 (d, J=9.0 Hz, 1H), 4.46-4.27 (m, 5H), 4.29-4.20 (m, 1H), 4.15 (d, J=5.6 Hz, 2H), 3.61 (d, J=26.1 Hz, 4H), 3.16 (s, 2H), 2.44 (s, 3H), 2.34-1.74 (m, 4H), 1.23 (t, J=6.9 Hz, 1H), 0.94 (s, 9H).

Compound 157—Preparation of (2S,4R)-4-hydroxy-1-[(2S)-2-[2-[3-([[3-(2-[2-[(1-methan-esulfonyl-pyrrol-3-yl)formamido]acetamido]-1,3-thiazol-4-yl)-[1,1-biphenyl]-3-yl]methyl]carbamoyl) azetidin-1-yl]acetamido]-3,3-dimethylbutanoyl]-N-[[4-(4-methyl-1,3-thiazol-5-yl)phenyl]methyl]pyrroledine-2-carboxamide

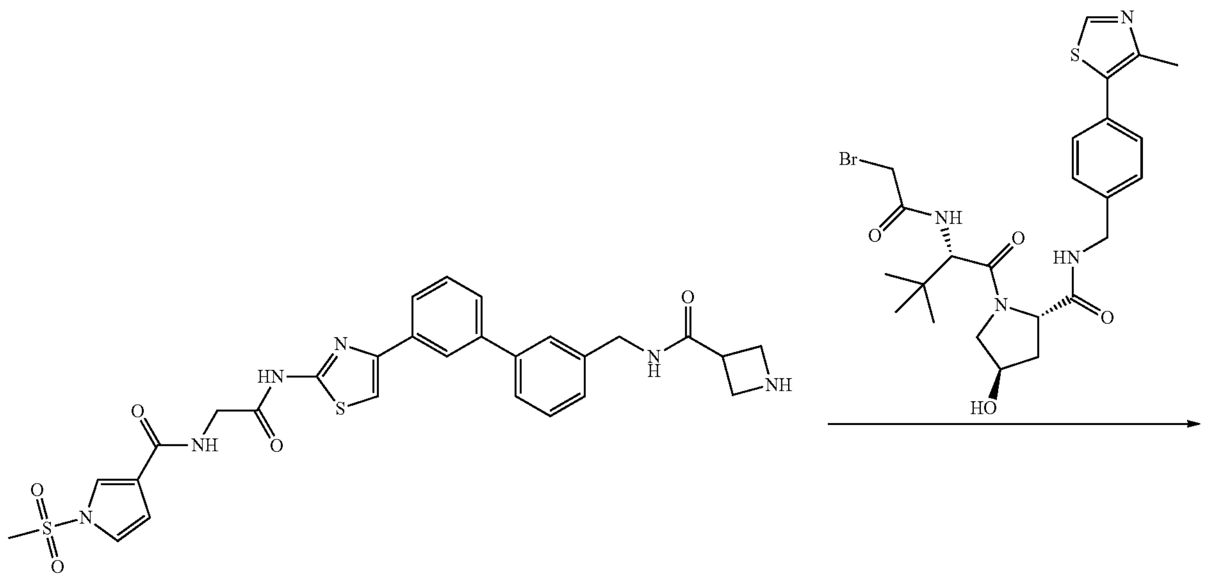

I-101

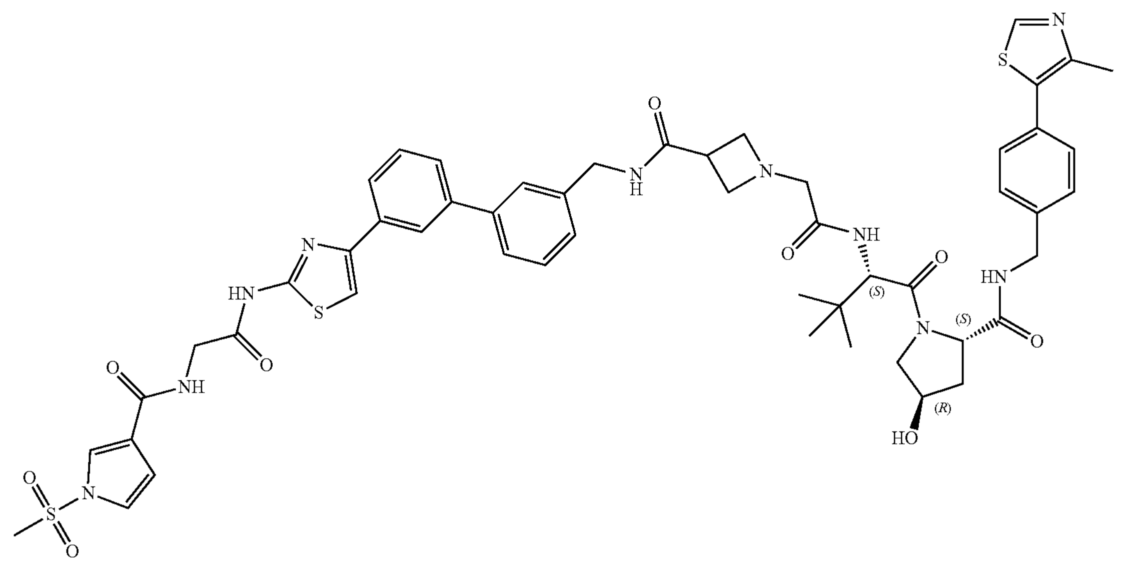

157

A solution of I-101 (50.00 mg, 0.084 mmol, 1.00 equiv), (2S,4R)-1-[(2S)-2-(2-bromoacetamido)-3,3-dimethylbutanoyl]-4-hydroxy-N-[[4-(4-methyl-1,3-thiazol-5-yl)phenyl]methyl]pyrolid-ine-2-carboxamide (According to the method for I-78, 93.05 mg, 0.169 mmol, 2.00 equiv), and $K_2CO_3$ (58.30 mg, 0.422 mmol, 5.00 equiv) in DMF (3.00 mL) was stirred for overnight at room temperature. The resulting mixture was extracted with EtOAc (3×20 mL). The combined organic layers were washed with brine and dried over anhydrous $Na_2SO_4$. After filtration, the filtrate was concentrated under reduced pressure. The crude product was purified by preparative HPLC to afford Compound 157 (9.5 mg, 10.59%) as an off-white solid. LCMS (ESI) m/z: $[M+H]^+$=1063.45. $^1$H NMR (400 MHz, DMSO-d6) δ 8.89 (s, 1H), 8.11 (s, 1H), 7.94-7.76 (m, 2H), 7.66 (s, 1H), 7.54 (m, 4H), 7.47-7.33 (m, 5H), 7.33-7.18 (m, 2H), 6.77 (d, J=2.6 Hz, 1H), 4.52-4.28 (m, 6H), 4.22 (d, J=16.0 Hz, 1H), 4.13 (s, 2H), 3.75-3.39 (m, 9H), 3.39-3.20 (m, 3H), 2.40 (s, 3H), 2.07 (dd, J=12.4, 7.6 Hz, 1H), 1.90 (d, J=8.8 Hz, 1H), 0.88 (s, 9H).

Compound 155—Preparation of 1-(2-[[(2S)-1-[(2S, 4R)-4-hydroxy-2-([[4-(4-methyl-1,3-thiazol-5-yl) phenyl]methyl]carbamoyl)pyrrolidin-1-yl]-3,3-dimethyl-1-oxobutan-2-yl]carbamoyl]ethyl)-N-[[3-(2-[2-[(1-methanesulfonylpyrrol-3-yl)formamido] acetamido]-1,3-thiazol-4-yl)-[1,1-biphenyl]-3-yl] methyl]piperidine-4-carboxamide formate

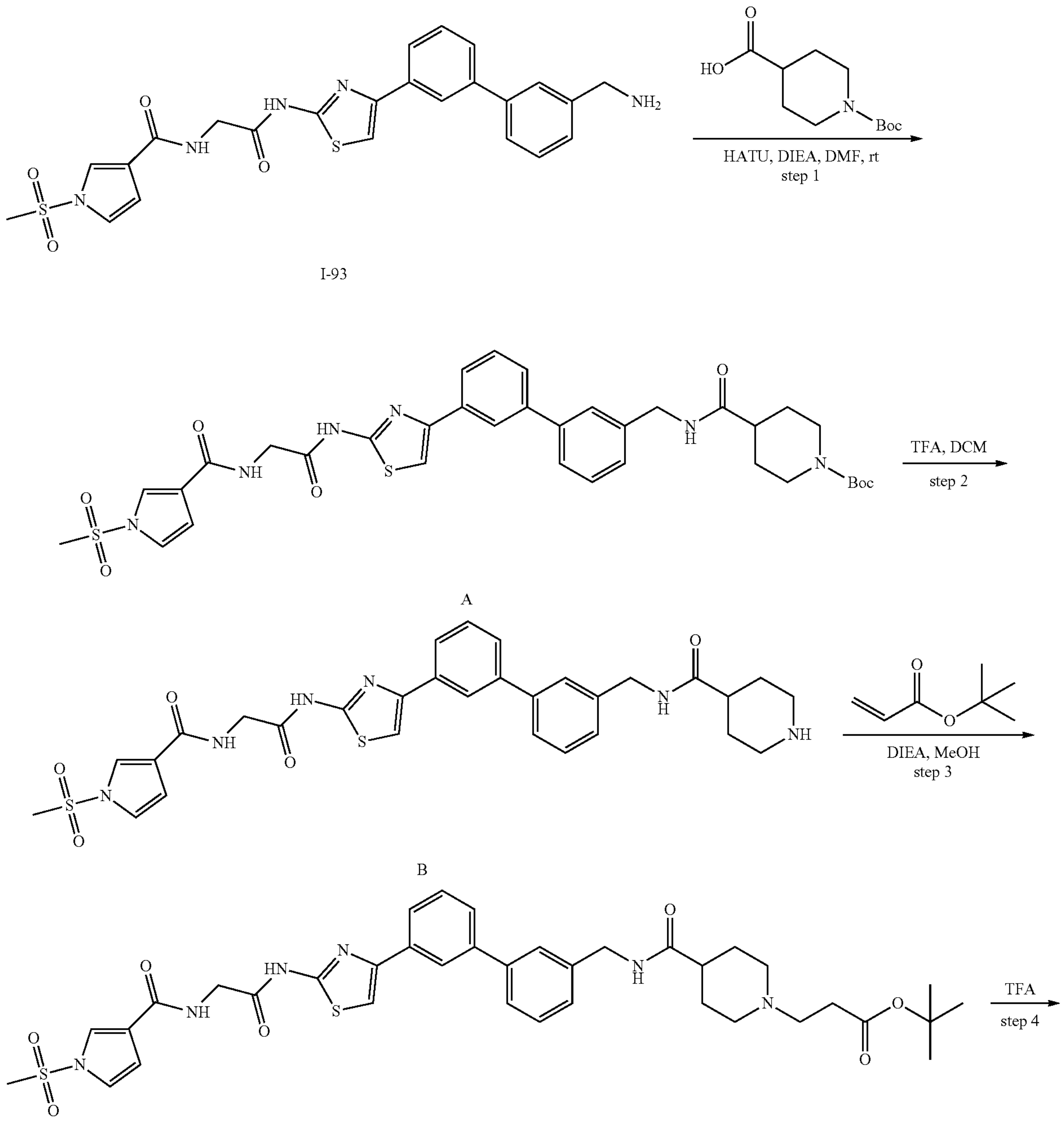

I-93

A

B

C

-continued
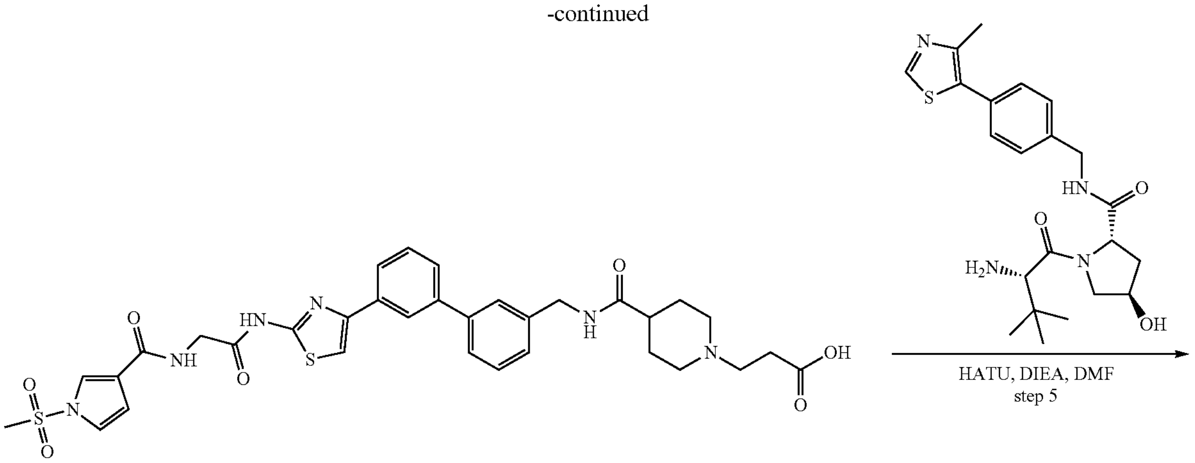
D
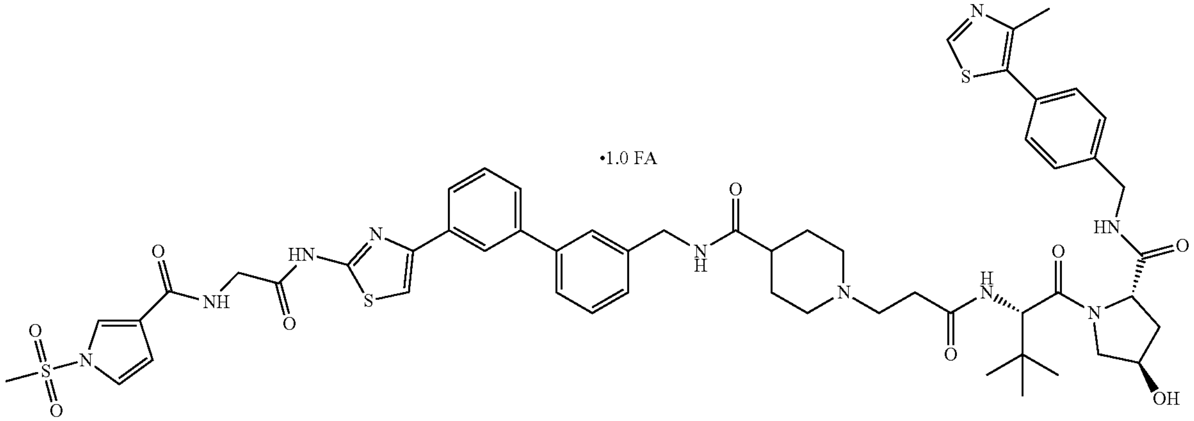
155
Step 1: Preparation of tert-butyl 4-([[3'-(2-[2-[(1-methanesulfonylpyrrol-3-yl)formamido]acetamido]-1,3-thiazol-4-yl)-[1,1'-biphenyl]-3-yl]methyl]carbamoyl)piperidine-1-carboxylate (A)
A
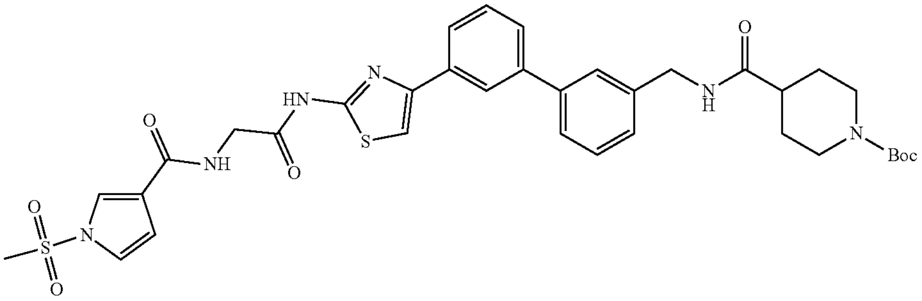

To a solution of 1-(tert-butoxycarbonyl)piperidine-4-carboxylic acid (25.00 mg, 0.109 mmol, 1.00 equiv), and DIEA (42.28 mg, 0.327 mmol, 3 equiv) in DMF (1 mL) was added HATU (62.19 mg, 0.164 mmol, 1.50 equiv), and the resulting solution was stirred for 40 min at room temperature. Then I-93 (55.57 mg, 0.109 mmol, 1.00 equiv) was added. The resulting solution was stirred overnight at room temperature. The residue was purified by reverse phase flash chromatography under the following conditions: column, C18 silica gel; mobile phase, ACN in water, 0% to 100% gradient over 15 min; detector, UV 254 nm. This resulted in 70 mg (89.06%) of A as a yellow solid. LCMS (ESI) m/z: $[M+H]^+$=721.

Step 2: Preparation of N-[[3'-(2-[2-[(1-methanesulfonylpyrrol-3-yl)formamido]acetamido]-1,3-thiazol-4-yl)-[1,1'-biphenyl]-3-yl]methyl]piperidine-4-carboxamide (B)

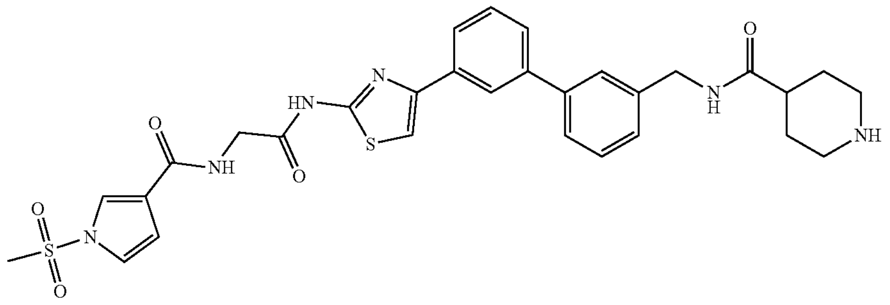

B

To a solution of A (95.00 mg, 0.132 mmol, 1.00 equiv) in DCM (4.00 mL) was added TFA (0.80 mL, 10.770 mmol, 81.73 equiv). The resulting solution was stirred for 2 h at room temperature. The resulting mixture was concentrated under vacuum. This resulted in 150 mg of B as a yellow crude solid. LCMS (ESI) m/z: $[M+H]^+$=621.

Step 3: Preparation of tert-butyl 3-[4-([[3-(2-[2-[(1-methanesulfonylpyrrol-3-yl)formamido]acetamido]-1,3-thiazol-4-yl)-[1,1-biphenyl]-3-yl]methyl]carbamoyl)piperidin-1-yl]propanoate (C)

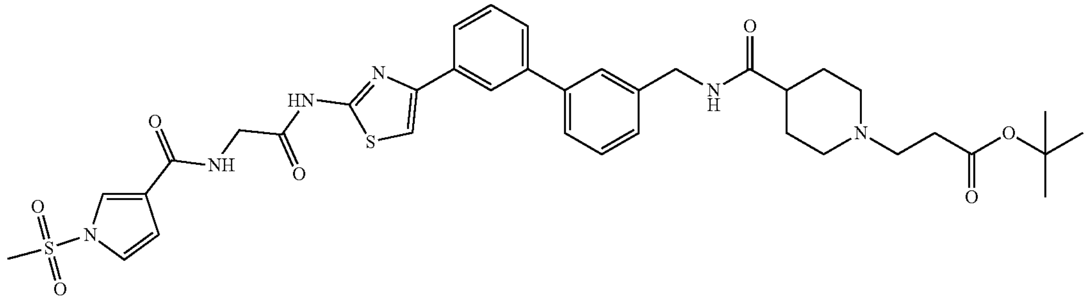

C

To a solution of B (77.00 mg, 0.124 mmol, 1.00 equiv), and DIEA (80.16 mg, 0.620 mmol, 5 equiv) in MeOH (5.00 mL, 0.156 mmol, 1.26 equiv) was added tert-butyl prop-2-enoate (23.85 mg, 0.186 mmol, 1.5 equiv). The resulting solution was stirred overnight at room temperature. The resulting mixture was concentrated under vacuum. The residue was purified by reverse phase flash chromatography under the following conditions: column, C18 silica gel; mobile phase, ACN in water, 10% to 100% gradient over 15 min; detector, UV 254 nm. This resulted in C (60 mg, 64.59%) as a yellow solid. LCMS (ESI) m/z: $[M+H]^+$=749.

Step 4: Preparation of 3-[4-([[3-(2-[2-[(1-methanesulfonylpyrrol-3-yl)formamido]acetamido]-1,3-thiazol-4-yl)-[1,1-biphenyl]-3-yl]methyl]carbamoyl) piperidin-1-yl]propanoic acid (D)

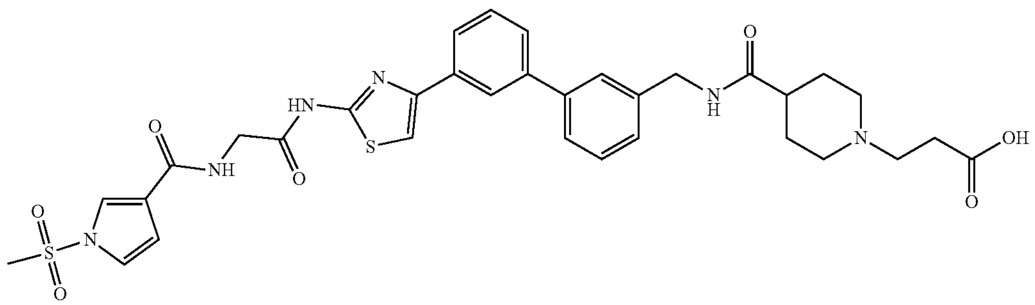

D

To a solution of C (60.00 mg, 0.080 mmol, 1.00 equiv) in DCM (2.00 mL) was added TFA (0.40 mL, 5.385 mmol, 67.22 equiv). The resulting solution was stirred for 4 h at room temperature. The resulting mixture was concentrated under reduced pressure to afford D (110 mg, 198.18%) as a yellow crude oil. LCMS (ESI) m/z: $[M+H]^+$=693.

Step 5: Preparation of 1-(2-[[(2S)-1-[(2S,4R)-4-hydroxy-2-([[4-(4-methyl-1,3-thiazol-5-yl)phenyl] methyl]carbamoyl)pyrrolidin-1-yl]-3,3-dimethyl-1-oxobutan-2-yl]carbamoyl]ethyl)-N-[[3-(2-[2-[(1-methanesulfonylpyrrol-3-yl)formamido]acetamido]-1,3-thiazol-4-yl)-[1,1-biphenyl]-3-yl]methyl] piperidine-4-carboxamide formate (Compound 155)

155

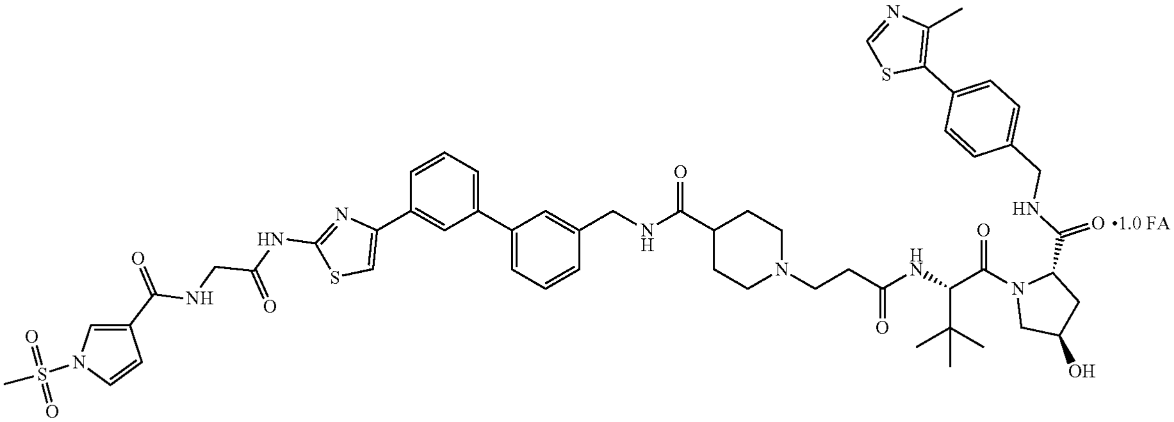

To a solution of D (50.00 mg, 0.072 mmol, 1.00 equiv), and DIEA (74.62 mg, 0.577 mmol, 8.00 equiv) in DMF (3.00 mL) at 0° C. was added EDCI (20.75 mg, 0.108 mmol, 1.50 equiv). The solution was stirred at 0° C. for 30 min. Then (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (31.07 mg, 0.072 mmol, 1.00 equiv) and HOBt (14.63 mg, 0.108 mmol, 1.50 equiv) were added. The solution was stirred at room temperature for 16 h. The aqueous layer was extracted with EtOAc (3×30 mL). The crude product (60 mg) was purified by preparative HPLC under the following conditions (Column: XSelect CSH Prep C18 OBD Column, 5 um, 19×150 mm; Mobile Phase A:Water (0.05% formic acid), Mobile Phase B:ACN; Flow rate:25 mL/min; Gradient:8 B to 40 B in 12 min; 254/220 nm) to afford Compound 155 (22.8 mg, 26.83%) as a white solid. LCMS (ESI) m/z: $[M+H]^+$=1105.15. $^1$H NMR (300 MHz, DMSO-$d_6$+$D_2O$) δ 8.95 (s, 1H), 8.18 (d, J=13.1 Hz, 2H), 7.94-7.81 (m, 2H), 7.75 (s, 1H), 7.56 (q, J=7.2, 6.3 Hz, 4H), 7.48-7.35 (m, 5H), 7.32 (t, J=2.8 Hz, 1H), 7.24 (d, J=7.5 Hz, 1H), 6.78 (dd, J=3.3, 1.6 Hz, 1H), 4.52 (s, 1H), 4.48-4.17 (m, 6H), 4.15 (s, 2H), 3.66 (d, J=5.2 Hz, 2H), 3.57 (s, 3H), 2.94 (s, 2H), 2.43 (s, 6H), 2.35-2.13 (m, 2H), 2.09-1.81 (m, 4H), 1.73 (d, J=16.8 Hz, 4H), 0.94 (s, 9H).

Preparation of 5-[3-(2-aminoethoxy)azetidin-1-yl]-2-(2,6-dioxopiperidin-3-yl)isoindole-1,3-dione

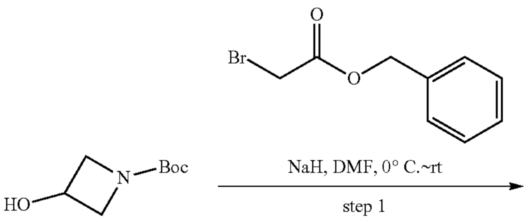

1

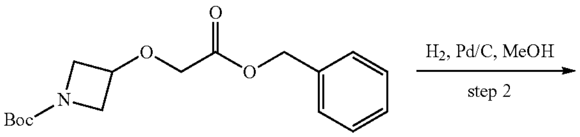

2

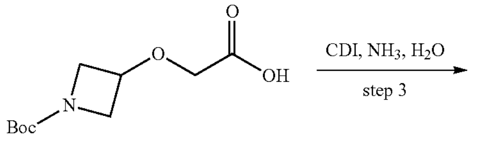

3

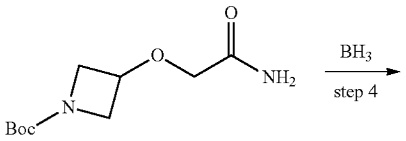

4

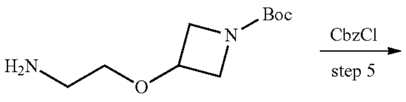

5

-continued

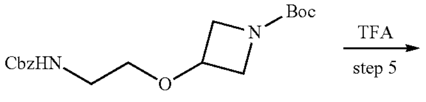

6

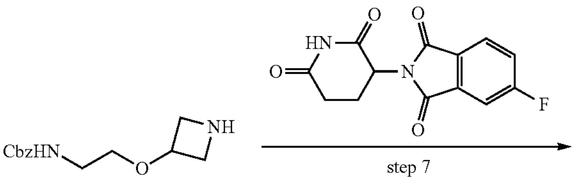

7

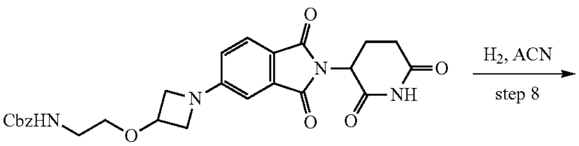

8

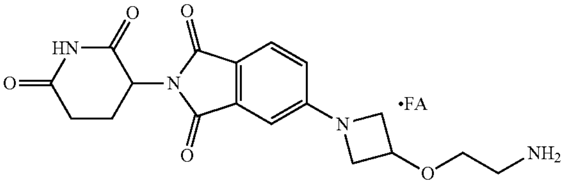

Step 1: Preparation of tert-butyl 3-[2-(benzyloxy)-2-oxoethoxy]azetidine-1-carboxylate (Intermediate 2)

2

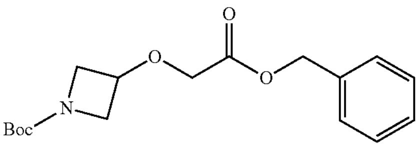

To the solution of tert-butyl 3-hydroxyazetidine-1-carboxylate (10.00 g, 57.733 mmol, 1.00 equiv) in DMF (150.00 mL) was added benzyl 2-bromoacetate (15.87 g, 69.279 mmol, 1.2 equiv) and NaH (1.66 g, 69.279 mmol, 1.2 equiv). The resulting solution was stirred at 0° C. for 3 hours. The resulting mixture was diluted with water (200 mL) and extracted with EtOAc (3×50 mL). The combined organic layers were washed with brine (3×70 mL), dried over anhydrous $Na_2SO4$, and concentrated under reduced pressure. The residue was purified by silica gel column chromatography, eluted with hexane/EtOAc (6:1) to afford intermediate 2 (16 g, 86.24%) as a light yellow oil; LCMS (ESI) m/z: $[M+H]^+$=322.

Step 2: Preparation of [[1-(tert-butoxycarbonyl) azetidin-3-yl]oxy]acetic acid (Intermediate 3)

3

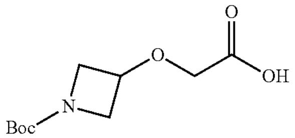

To the stirred solution of intermediate 2 (16.00 g, 49.786 mmol, 1.00 equiv) in MeOH (60.00 mL) were added 10% Pd/C (8.00 g, 75.174 mmol, 1.51 equiv). The resulting mixture was stirred for 3 h at room temperature under a hydrogen atmosphere. The resulting mixture was filtered, the filter cake washed with MeOH (3×100 mL), and the filtrate concentrated under reduced pressure. This resulted in intermediate 3 (12 g) as a light yellow solid; LCMS (ESI) m/z: $[M+H]^+$=232.

Step 3: Preparation of tert-butyl 3-(carbamoylmethoxy)azetidine-1-carboxylate (Intermediate 4)

4

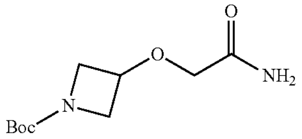

To a heated solution (60° C.) of intermediate 3 (12.00 g, 51.892 mmol, 1.00 equiv) in THE (100.00 mL) was added carbonyldiimidazole (18.51 g, 114.163 mmol, 2.2 equiv). The reaction was then stirred for 1 hour at 60° C. The resulting solution was poured into $NH_4OH$ (100.00 mL, 2568.068 mmol, 49.49 equiv) at room temperature and was stirred for an additional 1 hour. The contents were diluted with water (100 mL) and the resulting mixture was extracted with ethyl acetate (3×100 mL). The organic layers were combined, washed with saturated aqueous sodium chloride (100 ml), dried over anhydrous sodium sulfate, filtered, and then concentrated under vacuum to afford intermediate 4 (11.23 g, 93.98%) as white solid; LCMS (ESI) m/z: $[M+H]^+$= 231.

Step 4: Preparation of tert-butyl 3-(2-aminoethoxy)azetidine-1-carboxylate (Intermediate 5)

5

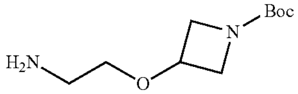

A solution of intermediate 4 (8.23 g, 35.742 mmol, 1.00 equiv) in $BH_3$-THF (150.00 mL, 1567.354 mmol, 43.85 equiv) was stirred for 10 minutes at 700° C. The solution was quenched by the addition of aqueous hydrogen chloride (2 mL of a 1 M solution), diluted with water (150 ml), and extracted with ethyl acetate (3×150 ml). The aqueous layer was adjusted to pH 8 with saturated aqueous sodium bicarbonate and extracted further with dichloromethane (3×200 ml). The organic layers were combined and concentrated under vacuum to afford intermediate 5 (10.23 g) as light yellow oil; LCMS (ESI) m/z: $[M+H]^+$=217.

Step 5: Preparation of tert-butyl 3-(2-[[(benzyloxy) carbonyl]amino]ethoxy)azetidine-1-carboxylate (Intermediate 6)

6

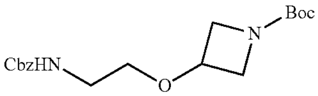

To a solution of intermediate 5 (10.23 g, 47.300 mmol, 1.00 equiv) in THE (50.00 mL) was added benzyl chloroformate (8.07 g, 47.300 mmol, 1 equiv), water (50.00 mL) and $K_2CO_3$ (19.61 g, 141.899 mmol, 3.00 equiv). The resulting solution was stirred at room temperature for 3 hours, then extracted with EtOAc (3×100 mL). The combined organic layers were washed with brine (3×100 mL), dried over anhydrous $Na_2SO_4$, and concentrated under reduced pressure. The residue was purified by silica gel column chromatography, eluted with hexane/EtOAc (5:1) to afford intermediate 6 (4.231 g, 25.53%) as a colorless oil; LCMS (ESI) m/z: $[M+H]^+$=351.

Step 6: Preparation of benzyl N-[2-(azetidin-3-yloxy)ethyl]carbamate (Intermediate 7)

7

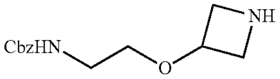

To a stirred solution of intermediate 6 (4.23 g, 12.071 mmol, 1.00 equiv) in DCM (10.00 mL, 157.300 mmol, 13.03 equiv) was added TFA (10.00 mL, 134.630 mmol, 11.15 equiv). The resulting mixture was stirred for 2 h at room temperature, then concentrated under vacuum. The residue was purified by reverse phase flash chromatography with the following conditions: column, C18 silica gel; mobile phase, $NH_4HCO_3$ in water, 0% to 100% gradient in 40 min; detector, UV 254 nm. This provided intermediate 7 (4.56 g) as a colorless oil; LCMS (ESI) m/z $[M+H]^+$=251.

Step 7: Preparation of benzyl N-[2-([1-[2-(2,6-dioxopiperidin-3-yl)-1,3-dioxoisoindol-5-yl]azetidin-3-yl]oxy)ethyl]carbamate (Intermediate 8)

8

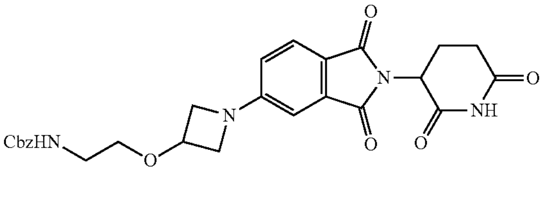

To a stirred solution of intermediate 7 (3.30 g, 11.947 mmol, 1.00 equiv) in DMF (45.00 mL) was added benzyl N-[2-(azetidin-3-yloxy)ethyl]carbamate (2.99 g, 11.947 mmol, 1 equiv) and DIEA (4.63 g, 35.841 mmol, 3 equiv). The resulting mixture was stirred for 2 h at 90° C. The reaction was quenched with water at room temperature and the resulting mixture was extracted with EtOAc (3×100 ml). The combined organic layers were washed with brine (3×100 mL), dried over anhydrous Na2SO4, and concentrated under reduced pressure. This provided intermediate 8 (3.41 g) as a light yellow solid; LCMS (ESI) m/z: $[M+H]^+$=507.

Step 8: Preparation of 5-[3-(2-aminoethoxy)azetidin-1-yl]-2-(2,6-dioxopiperidin-3-yl)isoindole-1,3-dione

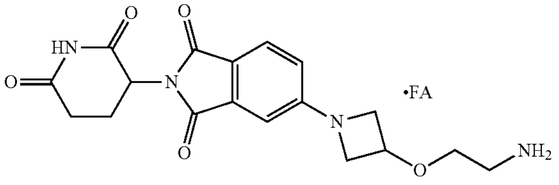

To a stirred solution of intermediate 8 (3.10 g, 6.120 mmol, 1.00 equiv) in ACN (45.00 mL, 774.609 mmol, 126.56 equiv) was added 10% Pd/C (1.55 g, 14.565 mmol, 2.38 equiv). The resulting mixture was stirred for 2 h at room temperature under a hydrogen atmosphere. After catalyst filtration, the resulting mixture was concentrated under vacuum. The residue was purified by reverse phase flash chromatography with the following conditions: column, C18 silica gel; mobile phase, 0.1% FA in water, 0% to 100% gradient in 45 min; detector, UV 254 nm. This provided the title product (391.3 mg, 17.17%) as a light yellow solid; 1H NMR (300 MHz, DMSO) δ 8.45-8.25 (d, 1H), 7.71-7.51 (m, 1H), 7.44-7.25 (m, 1H), 6.83 (d, 1H), 6.69 (dd, 1H), 5.12-4.99 (m, 1H), 4.61-4.50 (m, 1H), 4.27 (dd, 2H), 3.90 (dd, 2H), 3.61-3.43 (m, 2H), 2.98-2.69 (m, 3H), 2.66-2.51 (m, 1H), 2.10-1.95 (m, 1H); LCMS (ESI) m/z: $[M+H]^+$=373.14.

Preparation of 5-([2-[3-(2-aminoethoxy)phenoxy]ethyl]amino)-2-(2,6-dioxopiperidin-3-yl)isoindole-1,3-dione

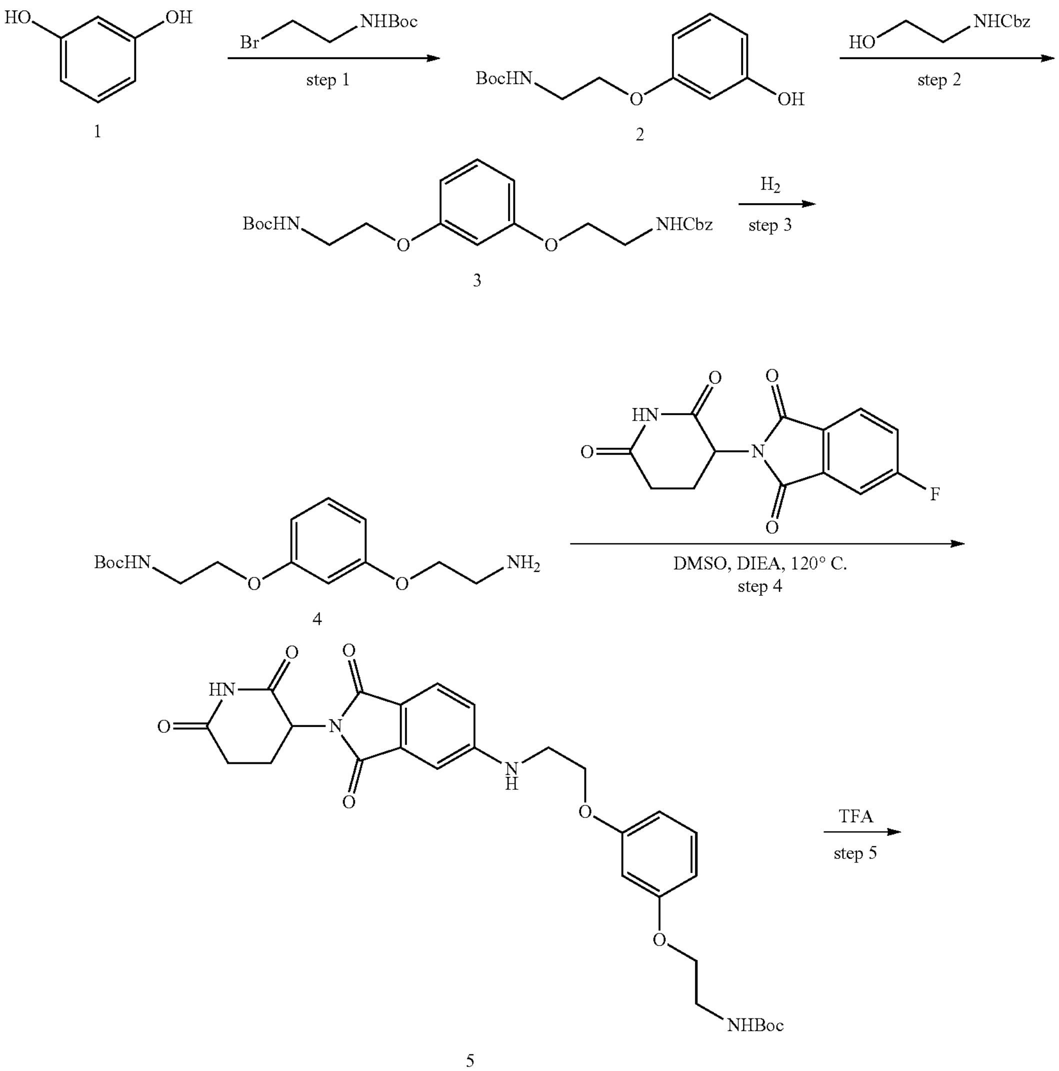

1
2
3
4
5

-continued

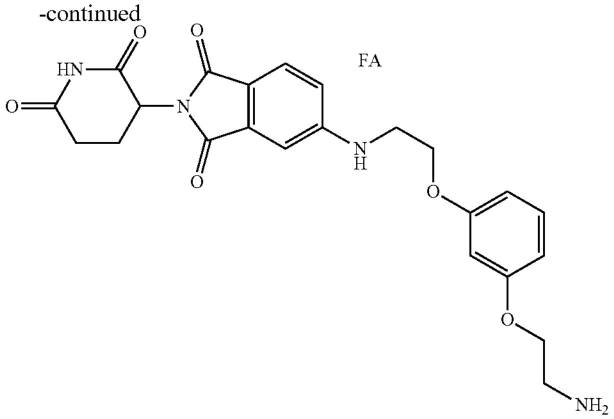

FA

Step 1: Preparation of tert-butyl N-[2-(3-hydroxyphenoxy)ethy]carbamate (Intermediate 2)

2

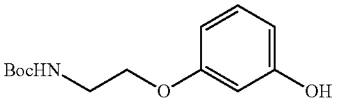

To a stirred solution of resorcinol (10.00 g, 90.817 mmol, 1.00 equiv) and tert-butyl N-(2-bromoethyl)carbamate (20.35 g, 90.817 mmol, 1.00 equiv) in DMF (250.00 mL) was added $Cs_2CO_3$ (88.77 g, 272.450 mmol, 3.00 equiv) in several portions at 40 degrees C. The resulting mixture stirred for 2 h, and the solids washed with 3×300 mL of EtOAc. The resulting mixture was concentrated under reduced pressure, and the residue was purified by reverse phase flash chromatography with the following conditions: column, C18 silica gel; mobile phase, MeOH in water, 10% to 50% gradient in 10 min; detector, UV 254 nm, to afford intermediate 2 (4.45 g, 19.34%) as a yellow oil. LCMS (ESI) m/z: $[M+H]^+$=254.

Step 2: Preparation of benzyl N-[2-(3-[2-[(tert-butoxycarbonyl)amino]ethoxy]phenoxy)ethyl] carbamate (Intermediate 3)

3

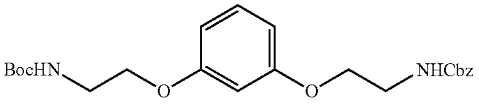

To a stirred solution of intermediate 2 (4.30 g, 16.976 mmol, 1.00 equiv) and benzyl N-(2-hydroxyethyl)carbamate (3.31 g, 16.976 mmol, 1.00 equiv) in THE (25.00 mL) were added $PPh_3$ (6.68 g, 25.464 mmol, 1.50 equiv) and DIAD (5.15 g, 25.464 mmol, 1.50 equiv) in portions at room temperature. The resulting mixture was stirred for 2 hours, then concentrated under reduced pressure. The residue was purified by reverse phase flash chromatography with the following conditions: column, C18 silica gel; mobile phase, MeOH in water, 10% to 50% gradient in 10 min; detector, UV 254 nm. This provided intermediate 3 (5 g, 68.42%) as a yellow oil. LCMS (ESI) m/z: $[M+H]^+$=431.

Step 3: Preparation of benzyl N-[2-[3-(2-aminoethoxy)phenoxy]ethyl]carbamate (Intermediate 4)

4

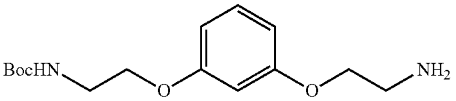

A suspension of intermediate 3 (2.85 g, 6.62 mmol, 1.00 equiv) and 10% Pd/C (1.43 g, 13.437 mmol, 2.03 equiv) in MeOH (15.00 mL) was stirred overnight at 50 degrees C. under a hydrogen atmosphere. The resulting mixture was filtered, and the filter cake was washed with MeOH (3×100 mL). The filtrate was concentrated under reduced pressure, and the crude product was used in the next step directly without further purification. This resulted in intermediate 4 (2.07 g, 86.87%) as an off-white oil. LCMS (ESI) m/z: $[M+H]^+$=297.

Step 4: Preparation of tert-butyl N-[2-[3-(2-[[2-(2,6-dimethylidenepiperidin-3-yl)-1,3-dioxoisoindol-5-yl]amino]ethoxy)phenoxy]ethyl]carbamate (Intermediate 5)

5

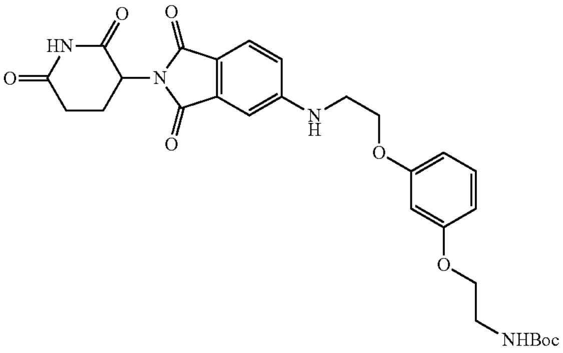

To a stirred solution of intermediate 4 (1.85 g, 6.242 mmol, 1.00 equiv) and 2-(2,6-dioxopiperidin-3-yl)-5-fluoroisoindole-1,3-dione (1.72 g, 6.242 mmol, 1.00 equiv) in NMP (10.00 mL) was added DIEA (2.42 g, 18.727 mmol, 3.00 equiv) in portions at 90 degrees C. The reaction was stirred for 3 h, then cooled and concentrated. The residue was purified by reverse phase flash chromatography with the following conditions: column, C18 silica gel; mobile phase, MeOH in water, 10% to 50% gradient in 10 min; detector, UV 254 nm. to afford intermediate 5 (324.5 mg, 9.48%) as a yellow green oil. LCMS (ESI) m/z: $[M+H]^+$=553.

Step 5: Preparation of 5-([2-[3-(2-aminoethoxy)phenoxy]ethyl]amino)-2-(2,6-dioxopiperidin-3-yl)isoindole-1,3-dione

FA

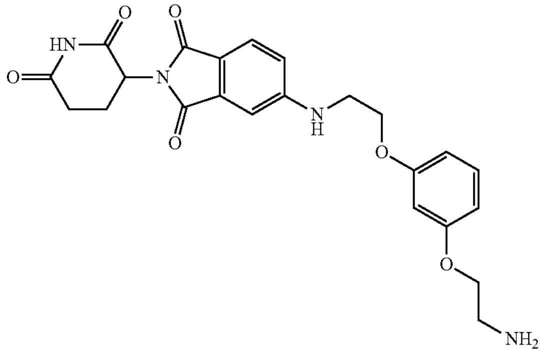

A solution of intermediate 5 (301.40 mg, 0.545 mmol, 1.00 equiv) and TFA (2.00 mL, 26.926 mmol, 49.37 equiv) in DCM (6.00 mL) was stirred for 2 h at room temperature. The resulting mixture was concentrated under reduced pressure. The residue was purified by reverse phase flash chromatography with the following conditions: column, C18 silica gel; mobile phase, ACN in water with 0.1% FA, 0% to 100% gradient in 40 min; detector, UV 254 nm. This provided the title compound (126 mg, 51.06%) as a yellow solid. $^1$H NMR (400 MHz, DMSO) δ 8.32 (s, 1H), 7.62 (dd, 1H), 7.43-7.28 (m, 1H), 7.27-7.11 (m, 1H), 7.09 (t, 1H), 7.03-6.98 (m, 1H), 6.65-6.45 (m, 3H), 5.14-5.96 (m, 1H), 4.17 (t, 2H), 4.07 (t, 2H), 3.67 (q, 2H), 3.08 (t, 2H), 2.96-2.82 (m, 1H), 2.63-2.52 (m, 1H), 2.10-1.98 (m, 1H). LCMS (ESI) m/z: $[M+H]^+$=453.17.

Preparation of 4-([2-[3-(2-aminoethoxy)phenoxy]ethyl]amino)-2-(2,6-dioxopiperidin-3-yl)isoindole-1,3-dione

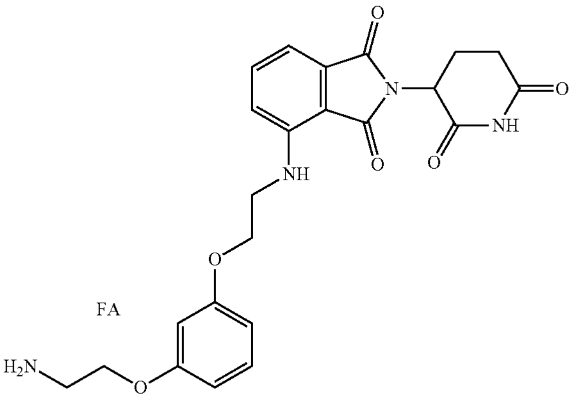 [SMILES: NCCOc1cccc(OCCNc2cccc3c2C(=O)N(C2CCC(=O)NC2=O)C3=O)c1 ; "FA"]

FA

The title compound (710 mg, 34.68%, yellow solid) was prepared in a similar manner as described in the preparation of 5-([2-[3-(2-aminoethoxy)phenoxy]ethyl]amino)-2-(2,6-dioxopiperidin-3-yl)isoindole-1,3-dione. $^1$H NMR (400 MHz, DMSO) δ 9.10-7.71 (m, 2H), 7.62 (dd, 1H), 7.28-7.17 (m, 2H), 7.08 (d, 1H), 6.77 (t, 1H), 6.63-6.49 (m, 3H), 5.11-5.02 (m, 1H), 4.17 (t, 2H), 4.11 (t, 2H), 3.73 (q, 2H), 3.17 (t, 2H), 2.96-2.82 (m, 1H), 2.65-2.51 (m, 1H), 2.10-1.98 (m, 1H). LCMS (ESI) m/z: $[M+H]^+$=453.10.

Preparation of 5-[2-([3-[(2-aminoethoxy)methyl]phenyl]methoxy)ethoxy]-2-(2,6-dioxopiperidin-3-yl)isoindole-1,3-dione

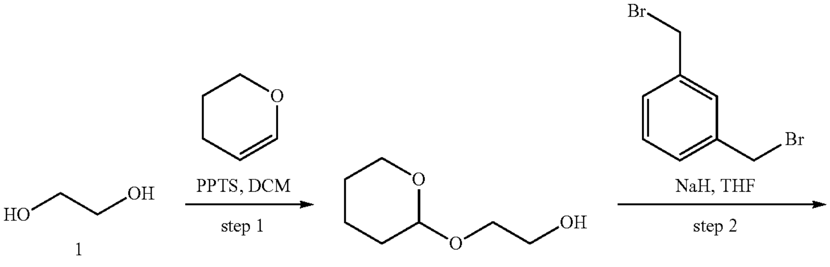

1

2

-continued
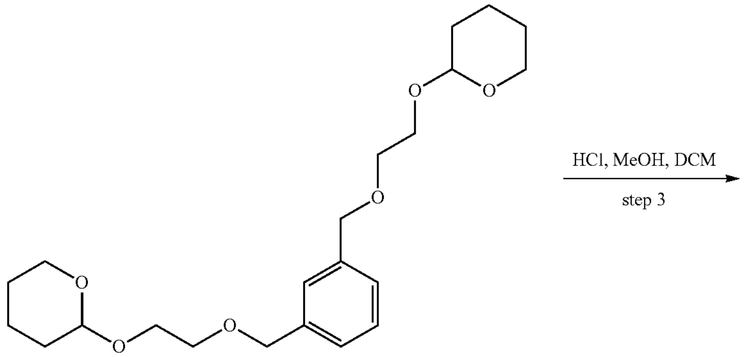
3
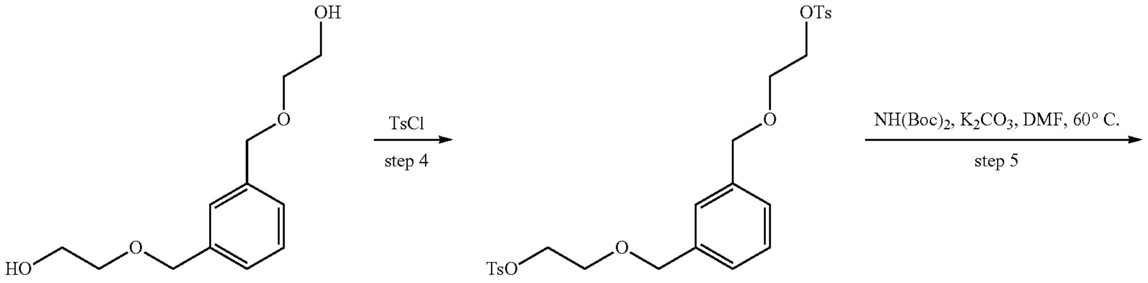
4
5
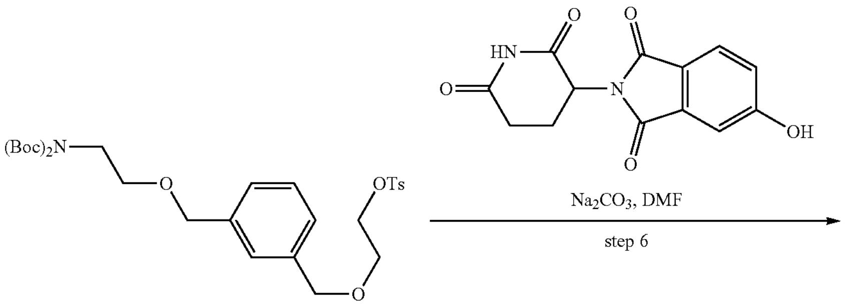
8
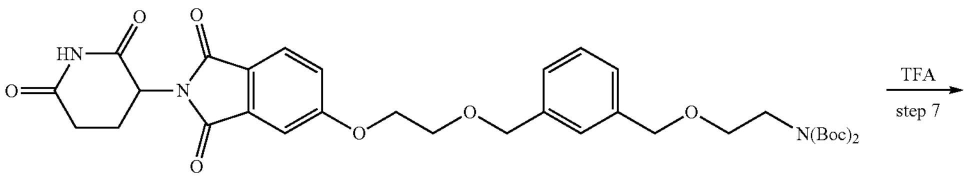
7
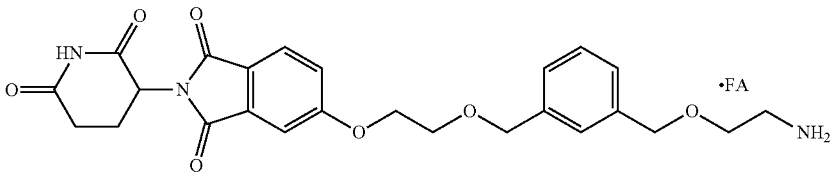

Step 1: Preparation of 2-(oxan-2-yloxy)ethanol (Intermediate 2)

2

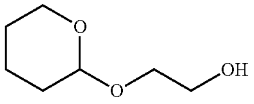

Dihydropyran (32.4 mL, 1.00 equiv) in $CH_2Cl_2$ (150 mL) was added dropwise to a solution of ethylene glycol (30 mL, 1.5 equiv) and PPTS (1.35 g, 0.15 equiv) in DCM (750 mL) over 1 h. After the reaction mixture was stirred overnight and the solvent was removed under reduced pressure, the crude product was purified by flash column chromatography ($Al_2O_3$, hexanes/THF 3:1 and 1:1). Removal of the solvents and drying under high vacuum gave intermediate 2 (10.6 g, 18.83%); LCMS (ESI) m/z: $[M+H]^+$=147.

Step 2: Preparation of 2-[2-[(3-[[2-(oxan-2-yloxy) ethoxy]methyl]phenyl)methoxy]ethoxy]oxane (Intermediate 3)

3

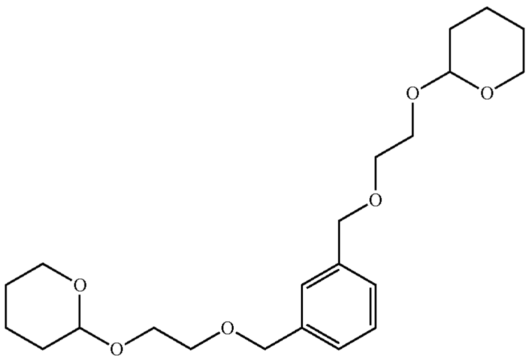

To an anhydrous THE (75.00 mL) of intermediate 2 (9.50 g, 64.986 mmol, 1.00 equiv) was added NaH (2.34 g, 97.479 mmol, 1.50 equiv). The reaction mixture was stirred for 70° C. THE solvent was evaporated. The crude material was dissolved in ethyl acetate, washed with water, and then saturated sodium chloride solution, dried over $Na_2SO_4$ and evaporated. The residue was purified by column chromatography to give the compound intermediate 3 (13.9 g, 54.22%); LCMS (ESI) m/z: $[M+H]^+$=395.

Step 3: Preparation of 2-([3-[(2-hydroxyethoxy) methyl]phenyl]methoxy)ethanol (Intermediate 4)

4

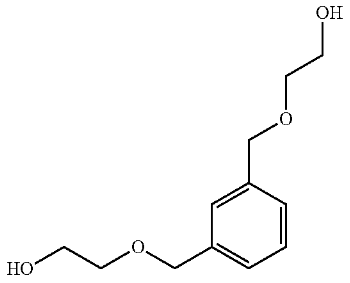

To a stirred solution of intermediate 3 (13.90 g, 35.234 mmol, 1.00 equiv) in MeOH (15.00 mL) was added DCM (15.00 mL) and HCl (30.00 mL, 987.356 mmol, 28.02 equiv) at room temperature. The contents were stirred overnight at rt. The residue was purified by reverse phase flash chromatography with the following conditions: column, C18 silica gel; mobile phase, FA in water, 0% to 100% gradient in 45 min; detector, UV 220 nm. This resulted in intermediate 4 (5.2 g, 65.22%) as a colorless oil; LCMS (ESI) m/z: $[M+H]^+$=227.

Step 4: Preparation of 2-[[3-([2-[(4-methylbenzenesulfonyl)oxy]ethoxy]methyl)phenyl]methoxy]ethyl 4-methylbenzenesulfonate (Intermediate 5)

5

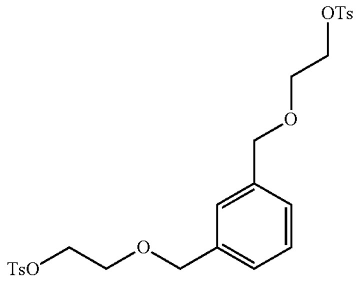

To a stirred solution of intermediate 4 (5.20 g, 22.981 mmol, 1.00 equiv) in DCM (80.00 mL) was added DMAP (421.13 mg, 3.447 mmol, 0.15 equiv), TEA (9.30 g, 91.925 mmol, 4 equiv) and P-toluenesulfonyl chloride (13.14 g, 68.944 mmol, 3 equiv) at 0° C. The resulting mixture was stirred for 2 h at 0° C. The resulting mixture was stirred for additional 5 h at room temperature. The residue was purified by silica gel column chromatography, eluted with PE/THF (1:1) to afford intermediate 5 (10.25 g, 83.42%) as a light yellow oil; LCMS (ESI) m/z: $[M+H]^+$=535.

Step 5: Preparation of tert-butyl N-(tert-butoxycarbonyl)-N-(2-[[3-([2-[(4-methylbenzenesulfonyl)oxy]ethoxy]methyl)phenyl]methoxy]ethyl)carbamate (Intermediate 6)

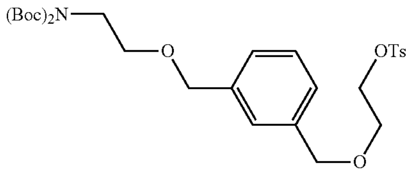

6

Intermediate 5 (10.25 g, 19.172 mmol, 1.00 equiv) was dissolved in DMF (80.00 mL) followed by addition of tert-butyl N-(tert-butoxycarbonyl)carbamate (4.58 g, 21.089 mmol, 1.10 equiv) and $K_2CO_3$ (3.97 g, 28.758 mmol, 1.50 equiv). The reaction mixture was stirred at 60° C. for 9 hours. The reaction mixture was then cooled to room temperature and poured into 50 mL EtOAc. The EtOAc layer was then washed with 3×25 mL 1 N HCl and 1×40 mL brine. The EtOAc layer was dried over $MgSO_4$, filtered, and the solvent was removed by rotary evaporation to give a light brown oil. The crude product was purified by flash chromatography over silica gel (40% EtOAc/60% Hexanes) to give compound. This resulted in intermediate 6 (1.689 g, 15.20%) as a colorless oil; LCMS (ESI) m/z: $[M+H]^+$=580.

Step 6: Preparation of tert-butyl N-(tert-butoxycarbonyl)-N-[2-([3-[(2-[[2-(2,6-dioxopiperidin-3-yl)-1,3-dioxoisoindol-5-yl]oxy]ethoxy)methyl]phenyl]methoxy)ethyl]carbamate (Intermediate 7)

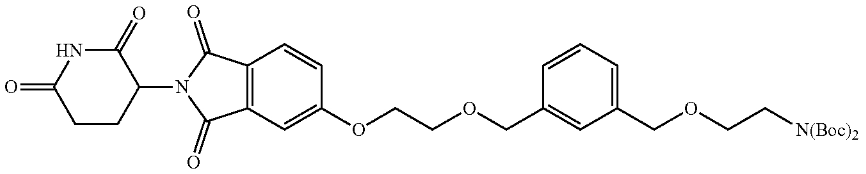

7

To a solution of intermediate 6 (800.00 mg, 1.380 mmol, 1.00 equiv) and 2-(2,6-dioxopiperidin-3-yl)-5-hydroxyisoindole-1,3-dione (798.51 mg, 2.912 mmol, 2.11 equiv) in DMF (20.00 mL) was added $Na_2CO_3$ (438.79 mg, 4.140 mmol, 3.00 equiv). The resulting mixture was stirred for 5 h at 80° C. The residue was purified by reverse phase flash chromatography with the following conditions: column, C18 silica gel; mobile phase, MeOH in water, 0% to 100% gradient in 45 min; detector, UV 220 nm. This resulted in intermediate 7 (920 mg, 97.79%) as a colorless solid; LCMS (ESI) m/z $[M+H]^+$=682.

Step 7: Preparation of 5-[2-([3-[(2-aminoethoxy)methyl]phenyl]methoxy)ethoxy]-2-(2,6-dioxopiperidin-3-yl)isoindole-1,3-dione

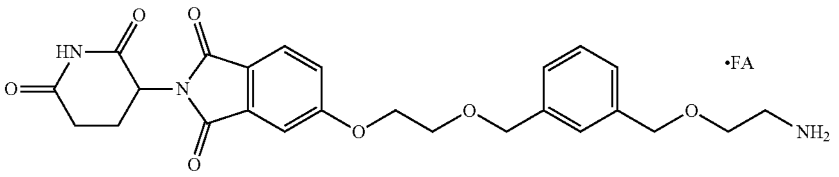

•FA

To a solution of intermediate 7 (920.00 mg) in DCM was added TFA (5.00 mL). The resulting mixture was stirred for 3 h at room temperature. The resulting mixture was concentrated under reduced pressure. The residue was purified by reverse phase flash chromatography with the following conditions: column, C18 silica gel; mobile phase, 0.1% FA in water/ACN, 0% to 100% gradient in 30 min; detector, UV 254 nm. This provided the title compound (510 mg) as a light yellow solid; $^{1}$H NMR (300 MHz, DMSO) δ 8.40 (s, 1H), 7.85 (d, 1H), 7.48 (d, 1H), 7.42-7.24 (m, 5H), 5.13 (dd, 1H), 4.58 (s, 2H), 4.50 (s, 2H), 4.43-4.34 (m, 2H), 3.83 (t, 2H), 3.54 (t, 2H), 2.96-2.82 (m, 3H), 2.66-2.46 (m, 2H), 2.12-1.98 (m, 1H); LCMS (ESI) m/z: $[M+H]^+$=482.18.

Preparation of 2-(2,6-dioxopiperidin-3-yl)-5-(5-(piperazin-1-yl)pent-1-yn-1-yl)isoindoline-1,3-dione trifluoroacetic acid

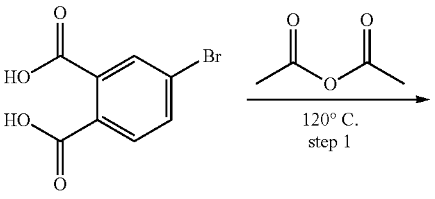

1

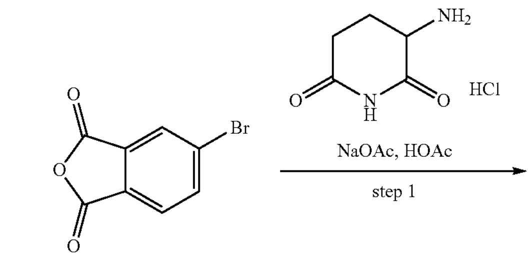

2

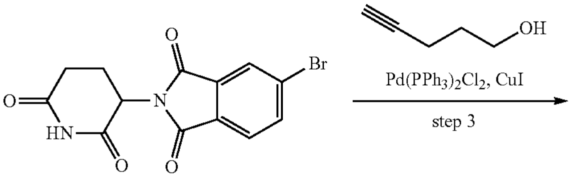

3

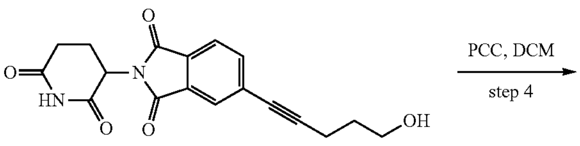

4

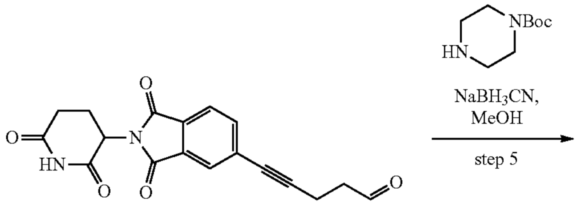

5

-continued

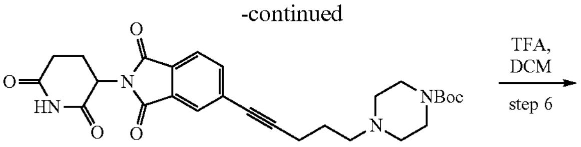

6

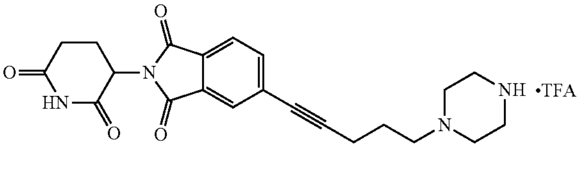

Step 1: Preparation of 5-bromoisobenzofuran-1,3-dione (Intermediate 2)

2

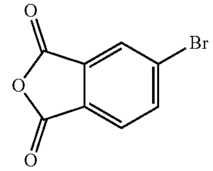

Acetic anhydride (25 mL) was added to 4-bromobenzene-1,2-dicarboxylic acid (5.0 g, 20.4 mmol, 1.0 equiv) at room temperature. The resulting mixture was stirred at 120 degrees C. for 3 h. The resulting mixture was concentrated under vacuum to give intermediate 2 (4.6 g, quant.) as off-white solid, which was used in the next step directly without further purification.

Step 2: Preparation of 5-bromo-2-(2,6-dioxopiperidin-3-yl)isoindoline-1,3-dione (Intermediate 3)

3

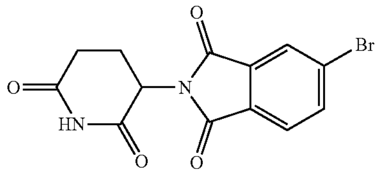

To a stirred solution of Intermediate 2 (4.6 g, 20.4 mmol, 1.0 equiv), 3-aminopiperidine-2,6-dione, and hydrogen chloride (4.0 g, 24.5 mmol, 1.2 equiv) in acetic acid (50 mL) was added NaOAc (5.0 g, 61.2 mmol, 3.0 equiv) at room temperature. The resulting mixture was stirred for 3 h at 120° C., then cooled to room temperature. The precipitated solids were collected by filtration and washed with water (3×200 mL). The resulting solid was dried under vacuum to give intermediate 3 (5.1 g, 74.2%) as off-white solid. $[M+H]^+$=337/339.

Step 3: Preparation of 2-(2,6-dioxopiperidin-3-yl)-5-(5-hydroxypent-1-yn-1-yl)isoindoline-1,3-dione (Intermediate 4)

4

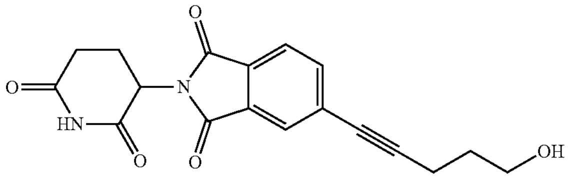

To a stirred solution of Intermediate 3 (5.0 g, 14.8 mmol, 1.0 equiv), $Pd(PPh_3)_2Cl_2$ (2.1 g, 3.0 mmol, 0.2 equiv), and copper(I) iodide (0.56 g, 3.0 mmol, 0.2 equiv) in tetrahydrofuran (40 mL) were added DIEA (19.2 g, 148.3 mmol, 10.0 equiv) and pent-4-yn-1-ol (3.7 g, 44.5 mmol, 3.0 equiv) dropwise at room temperature. The resulting mixture was stirred for 4 h at 50° C. The resulting mixture was filtered, the filter cake was washed with THE (3×50 mL). The filtrate was concentrated under reduced pressure and concentrated. The residue was purified by silica gel column chromatography, eluted with PE/EtOAc (1:1) to afford Intermediate 4 (1.9 g, 37.6%) as a yellow solid. LCMS (ESI) m/z: $[M+H]^+$=341.

Step 4: Preparation of 5-(2-(2,6-dioxopiperidin-3-yl)-1,3-dioxoisoindolin-5-yl)pent-4-ynal (Intermediate 5)

5

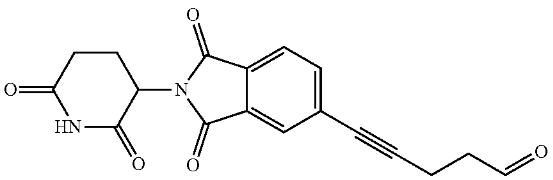

To a stirred solution of Intermediate 4 (4.0 g, 11.7 mmol, 1.0 equiv) in DCM (40 mL) was added DCC (5.1 g, 23.5 mmol, 2.0 equiv) in portions at room temperature. The resulting mixture was stirred for 8 h at room temperature. The mixture was filtered and the filter cake was washed with DCM (150 mL×3). The filtrate was concentrated under reduced pressure to afford Intermediate 5 (3.6 g, 89.8%) as a yellow solid, which was used in the next step directly without further purification. LCMS (ESI) m/z: $[M+H]^+$=339.

Step 5: Preparation of tert-butyl 4-(5-(2-(2,6-dioxopiperidin-3-yl)-1,3-dioxoisoindolin-5-yl)pent-4-yn-1-yl)piperazine-1-carboxylate (Intermediate 6)

6

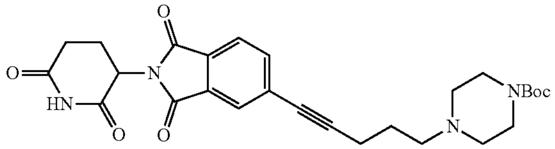

To a stirred mixture of Intermediate 5 (3.6 g, 10.6 mmol, 1.0 equiv) and tert-butyl piperazine-1-carboxylate (1.98 g, 10.6 mmol, 1.0 equiv) in MeOH (35.00 mL) was added $NaBH_3CN$ (2.7 g, 42.6 mmol, 4 equiv) in portions at room temperature. The mixture was stirred for 3 h at room temperature. The resulting mixture was added to aqueous $NH_4Cl$ solution (150 mL) and extracted with EtOAc (3×150 mL). The combined organic layers were washed with water (2×50 mL), dried over anhydrous $Na_2SO_4$, and concentrated under reduced pressure. The residue was purified by silica gel column chromatography, eluted with DCM/MeOH (20:1) to afford Intermediate 6 (2.1 g, 38.9%) as a yellow semi-solid. LCMS (ESI) m/z: $[M+H]^+$=509.

Step 6: Preparation of 2-(2,6-dioxopiperidin-3-yl)-5-(5-(piperazin-1-yl)pent-1-yn-1-yl)isoindoline-1,3-dione trifluoroacetic acid

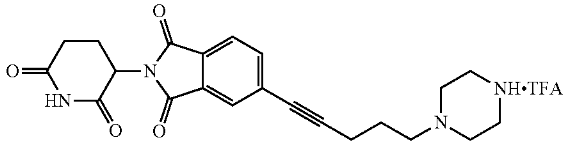

To a stirred solution of Intermediate 6 (1.2 g, 2.4 mmol, 1.0 equiv) in DCM (20 mL) was added TFA (5 mL) dropwise at room temperature. The resulting mixture was stirred for 3 h at room temperature, then concentrated under vacuum. The residue was purified by reverse phase flash chromatography with the following conditions: column, C18 spherical column; mobile phase, phase A: $H_2O$ (0.05% TFA), B: acetonitrile (Gradient B % 0%~70%, run time 50 min); detector, UV 254 nm. This resulted in the title compound as trifluoroacetic acid salt (0.80 g, 66.7%) as a light yellow solid. $^1H$ NMR (400 MHz, DMSO-d6) δ 11.16 (s, 1H), 9.01 (br, 2H), 7.96-7.85 (m, 3H), 5.17 (dd, J=12.8, 5.4 Hz, 1H), 4.49 (br, 3H), 3.08 (br, 3H), 2.90 (ddd, J=16.9, 13.9, 5.3 Hz, 1H), 2.66-2.57 (m, 4H), 2.56-2.53 (m, 4H), 2.12-2.03 (m, 1H), 1.98-1.85 (m, 1H). LCMS (ESI) m/z: $[M+H]^+$=409.40.

Preparation of 5-(5-aminopent-1-yn-1-yl)-2-(2,6-dioxopiperidin-3-yl)isoindole-1,3-dione

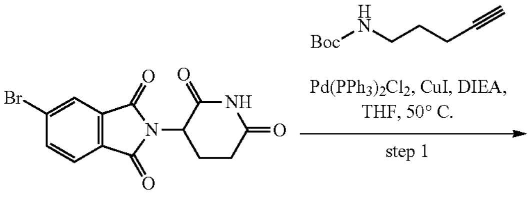

1

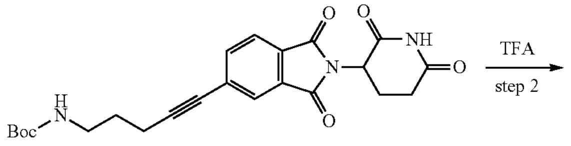

2

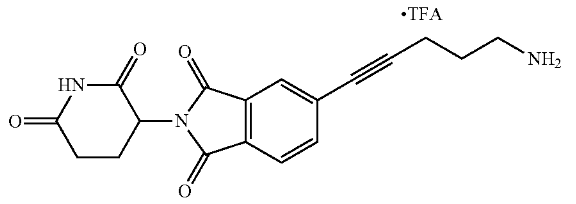

Step 1: Preparation of tert-butyl N-[5-[2-(2,6-dioxopiperidin-3-yl)-1,3-dioxoisoindol-5-yl]pent-4-yn-1-yl]carbamate (Intermediate 2)

2

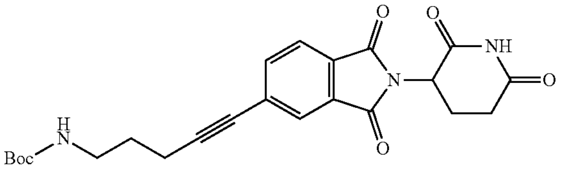

To a stirred solution of 5-bromo-2-(2,6-dioxopiperidin-3-yl)isoindole-1,3-dione (1.00 g, 2.966 mmol, 1.00 equiv) and tert-butyl N-(pent-4-yn-1-yl)carbamate (1304.55 mg, 7.119 mmol, 2.40 equiv) in THF (12 mL) were added CuI (56.49 mg, 0.297 mmol, 0.10 equiv), $Pd(PPh_3)_2Cl_2$ (208.20 mg, 0.297 mmol, 0.10 equiv) and DIEA (3.83 g, 29.662 mmol, 10.00 equiv) at room temperature. The resulting mixture was stirred for 2 h at 70° C. under nitrogen atmosphere. Following aqueous workup, the residue was purified by silica gel column chromatography, eluted with PE/EtOAc (5:1) to afford intermediate 2 (970 mg) as a red solid. LCMS (ESI) m/z $[M+H]^+$=440.

Step 2: Preparation of 5-(5-aminopent-1-yn-1-yl)-2-(2,6-dioxopiperidin-3-yl)isoindole-1,3-dione

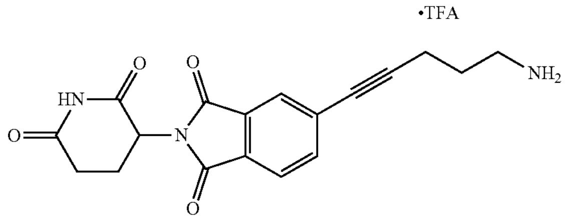 [SMILES: NCCCC#Cc1ccc2c(c1)C(=O)N(C1CCC(=O)NC1=O)C2=O]

To a solution of intermediate 2 (970.00 mg, 2.207 mmol, 1.00 equiv) in dichloromethane was added TFA (2.00 mL, 26.926 mmol, 12.20 equiv) at room temperature. The resulting mixture was stirred for 2 h at room temperature. The resulting mixture was concentrated under reduced pressure. The residue was purified by reverse phase flash chromatography with the following conditions: column, C18 spherical column; mobile phase, phase A: $H_2O$ (0.05% TFA), B: acetonitrile (Gradient B % 0%~70%, run time 50 min); detector, UV 254 nm. to afford the title compound (870 mg, 89.2%) as a white solid. $^1H$ NMR (300 MHz, DMSO) δ 11.15 (s, 1H), 7.97-7.84 (m, 3H), 7.78-7.84 (m, 2H), 5.17 (dd, 1H), 3.03-2.94 (m, 2H), 2.93-2.83 (m, 1H), 2.69-2.51 (m, 4H), 2.14-1.99 (m, 1H), 1.94-1.78 (m, 2H). LCMS (ESI) m/z: $[M+H]^+$=340.12.

Preparation of 2-(2,6-dioxopiperidin-3-yl)-5-[3-(piperazin-1-ylmethyl)azetidin-1-yl]isoindole-1,3-dione trifluoroacetic acid

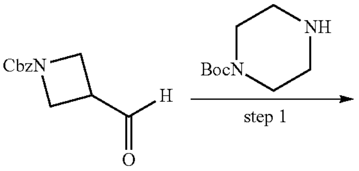

1

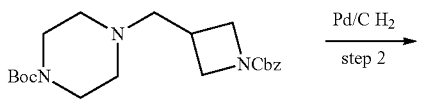

2

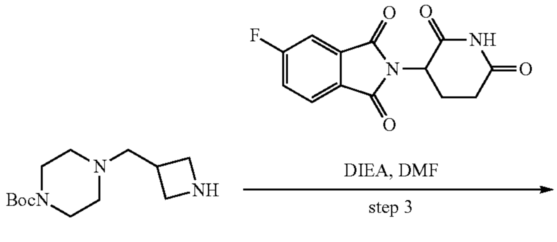

3

-continued

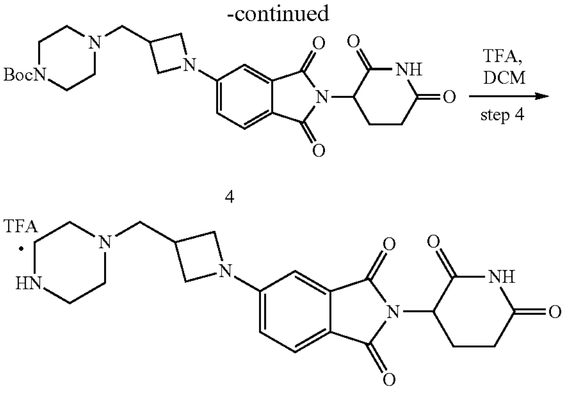

4

Step 1: Preparation of tert-butyl 4-([1-[(benzyloxy) carbonyl]azetidin-3-yl]methyl)piperazine-1-carboxylate (Intermediate 2)

2

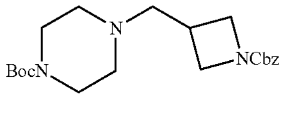

To a stirred solution of benzyl 3-formylazetidine-1-carboxylate (2.0 g, 9.1 mmol, 1.0 equiv) and tert-butyl piperazine-1-carboxylate (1.9 g, 10.2 mmol, 1.1 equiv) in DMF (20 mL) was added $NaBH(OAc)_3$ (7.6 g, 35.8 mmol, 4.0 equiv) in portions. The mixture was stirred at 50° C. overnight, and then added into aqueous $NH_4Cl$ (100 mL), extracted with EA (3×100 mL), and the combined organic phase was concentrated to dryness under reduced pressure. The residue was purified by reverse phase flash chromatography with the following conditions: column, C18 Spherical Column; mobile phase, acetonitrile in water, 0% to 80% gradient in 50 min; detector, UV 254 nm. to afford Intermediate 2 (2.8 g, 79.1%) as a colorless oil. LCMS (ESI) m/z $[M+H]^+$=390.

Step 2: Preparation of tert-butyl 4-(azetidin-3-ylmethyl)piperazine-1-carboxylate (Intermediate 3)

3

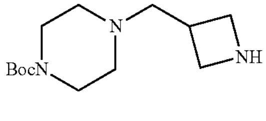

A solution of Intermediate 2 (2.8 g, 7.2 mmol) and 10% Pd/C (0.28 g) in methanol (30 mL) was stirred under an atmosphere of hydrogen at room temperature for 2 hours. The resulting mixture was filtered and the filter cake was washed with MeOH. The filtrate was concentrated under reduced pressure. The crude product (1.8 g, quant.) was used in the next step directly without further purification. LCMS (ESI) m/z $[M+H]^+$=256.

Step 3: Preparation of Synthesis of tert-butyl 4-([1-[2-(2,6-dioxopiperidin-3-yl)-1,3-dioxoisoindol-5-yl]azetidin-3-yl]methyl)piperazine-1-carboxylate (Intermediate 4)

4

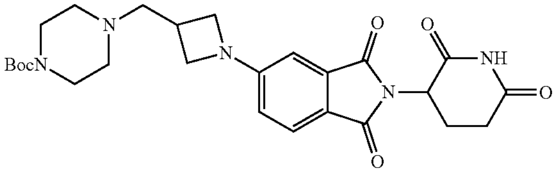

To a stirred mixture of intermediate 3 (1.8 g, 7.2 mmol, 1.1 equiv) and 2-(2,6-dioxopiperidin-3-yl)-5-fluoroisoindole-1,3-dione (1.8 g, 6.6 mmol, 1.0 equiv) in dimethylformamide (15 mL) was added DIEA (1.8 g, 14.4 mmol, 1.0 equiv), and the mixture was stirred at 80° C. for 3 hours. After standard workup, the crude material was purified by reverse phase flash chromatography with the following conditions: column, C18 Spherical Column; mobile phase, acetonitrile in water, 0% to 70% gradient in 50 min; detector, UV 254 nm. to afford tert-butyl 4-([1-[2-(2,6-dioxopiperidin-3-yl)-1,3-dioxoisoindol-5-yl]azetidin-3-yl]methyl)piperazine-1-carboxylate (1.8 g, 48.9%) as a yellow solid. LCMS (ESI) m/z $[M+H]^+$=512.

Step 4: Preparation of 2-(2,6-dioxopiperidin-3-yl)-5-[3-(piperazin-1-ylmethyl)azetidin-1-yl]isoindole-1,3-dione trifluoroacetic acid

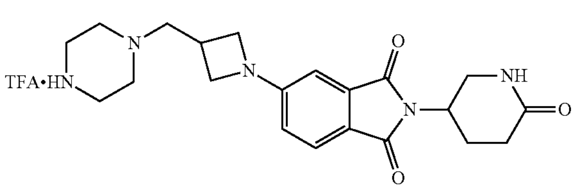

To a solution of tert-butyl 4-([1-[2-(2,6-dioxopiperidin-3-yl)-1,3-dioxoisoindol-5-yl]azetidin-3-yl]methyl)piperazine-1-carboxylate (1.8 g, 3.5 mmol, 1.0 equiv) in DCM (15 mL) was added TFA (5 mL). After stirring at rt for 2 hours, the mixture was concentrated under reduced pressure to afford the title compound (1.8 g, quant.) as a yellow solid. $^1H$ NMR (400 MHz, DMSO-d6) δ 11.09 (s, 1H), 8.94 (br, 2H), 7.67 (d, J=8.3 Hz, 1H), 6.80 (d, J=1.6 Hz, 1H), 6.66 (dd, J=8.3, 1.9 Hz, 1H), 5.06 (dd, J=12.9, 5.3 Hz, 1H), 4.23-4.11 (m, 2H), 3.80-3.74 (m, 2H), 3.38-2.80 (m, 12H), 2.63-2.52 (m, 2H), 2.05-1.98 (m, 1H). LCMS (ESI) m/z $[M+H]^+$=412.15.

Preparation of 2-(2,6-dioxopiperidin-3-yl)-5-[4-[4-(piperidin-4-yl)butyl]piperazin-1-yl]isoindole-1,3-dione
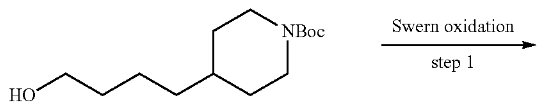
1
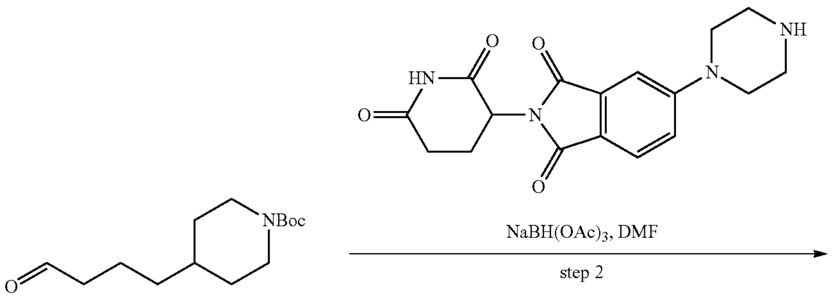
2
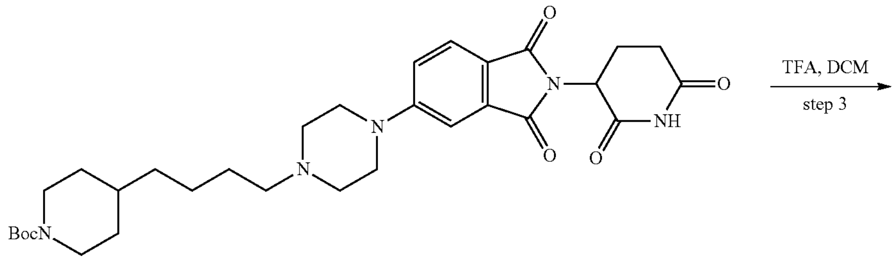
3
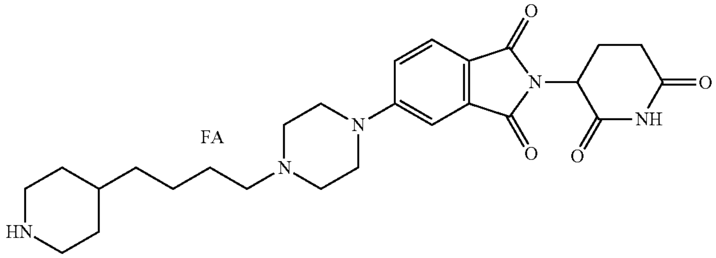

Step 1: Preparation of tert-butyl 4-(4-oxobutyl)piperidine-1-carboxylate (Intermediate 2)

2

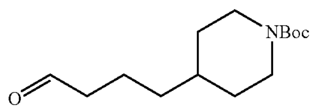

To a solution of oxalyl chloride (757.49 mg, 5.968 mmol, 1.2 equiv) in DCM (7.5 mL) was added DMSO (408.01 mg, 5.222 mmol, 1.05 equiv) in DCM (8.00 mL) dropwise at −78° C. under nitrogen atmosphere. The resulting mixture was stirred for 5 min at −78° C. followed by addition of tert-butyl 4-(4-hydroxybutyl)piperidine-1-carboxylate (1.28 g, 4.973 mmol, 1.00 equiv) in DCM (6.5 mL). The resulting mixture was stirred for additional 15 min at −78° C., followed by the addition of TEA (2.52 g, 24.867 mmol, 5 equiv) at −78° C. The resulting mixture was stirred for additional 10 min at −78° C., warmed to room temperature, and stirred for an additional 2 hours. The mixture was extracted with $CH_2Cl_2$ (3×20 mL). The combined organic layers were washed with brine (3×30 mL), dried over anhydrous $Na_2SO_4$. After filtration, the filtrate was concentrated under reduced pressure. This provided Intermediate 2 (1.427 g) as a light yellow oil; LCMS (ESI) m/z: $[M+H]^+$=256.

Step 2: Preparation of tert-butyl 4-(4-[4-[2-(2,6-dioxopiperidin-3-yl)-1,3-dioxoisoindol-5-yl]piperazin-1-yl]butyl)piperidine-1-carboxylate (Intermediate 3)

3

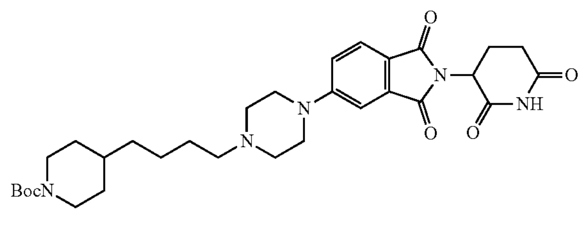

To a solution of Intermediate 2 (1.60 g, 4.674 mmol, 1.00 equiv) and tert-butyl 4-(4-oxobutyl)piperidine-1-carboxylate (1.43 g, 5.608 mmol, 1.2 equiv) in DMF (35.00 mL) was added $NaBH(OAc)_3$ (2.97 g, 14.021 mmol, 3 equiv) at room temperature. The resulting mixture was stirred for 5 h then quenched with water at room temperature. The resulting mixture was extracted with EtOAc (3×50 mL). The combined organic layers were washed with brine (3×50 mL), dried over anhydrous $Na_2SO_4$, and concentrated under reduced pressure. This resulted in Intermediate 3 (2.036 g, 74.89%) as a light yellow solid; LCMS (ESI) m/z: $[M+H]^+$=582.

Step 3: Preparation of 2-(2,6-dioxopiperidin-3-yl)-5-[4-[4-(piperidin-4-yl)butyl]piperazin-1-yl]isoindole-1,3-dione

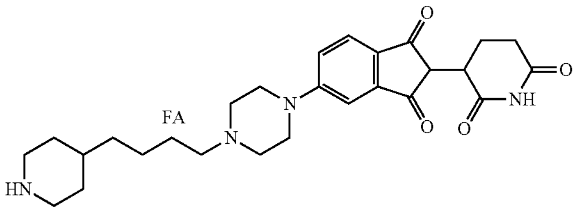

To a solution of Intermediate 3 (2.03 g, 3.490 mmol, 1.00 equiv) in DCM (5.00 mL) was added TFA (5.00 mL, 67.315 mmol, 19.29 equiv) at room temperature. The resulting mixture was stirred for 5 h at room temperature, then concentrated under vacuum. The residue was purified by reverse phase flash chromatography with the following conditions: column, C18 silica gel; mobile phase, 0.1% FA in water/ACN, 0% to 100% gradient in 45 min; detector, UV 220 nm. This provided the title compound (1.3 g, 77.35%) as a yellow green solid; $^1H$ NMR (300 MHz, DMSO) δ 11.08 (s, 1H), 9.10-9.32 (m, 1H), 8.17 (d, 1H), 7.69 (d, 1H), 7.34 (d, 1H), 7.26 (dd, 1H), 5.31-4.88 (m, 1H), 3.52-3.41 (m, 4H), 3.30-3.20 (dt, 3H), 2.96-2.75 (m, 4H), 2.66-2.55 (m, 1H), 2.39-2.29 (m, 2H), 2.09-1.96 (m, 1H), 1.79 (d, 3H), 1.62-1.41 (m, 4H), 1.36-1.17 (m, 8H); LCMS (ESI) m/z: $[M+H]^+$=482.27.

Preparation of 5-((3-(2,7-diazaspiro[3.5]nonan-7-yl)propyl)amino)-2-(2,6-dioxopiperidin-3-yl)isoindoline-1,3-dione di-trifluoroacetic acid

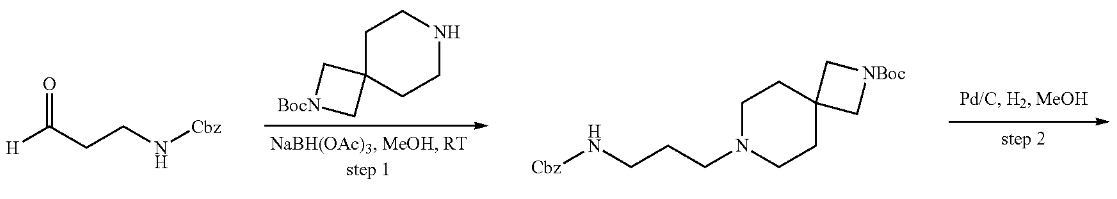

1

2

-continued

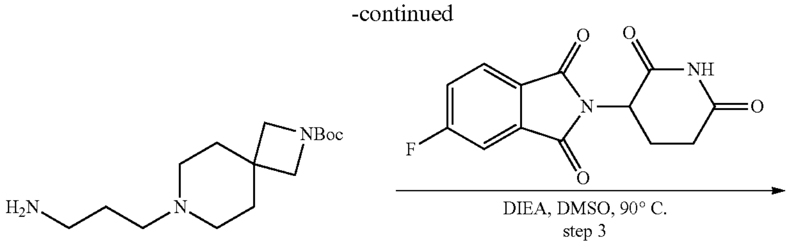

3

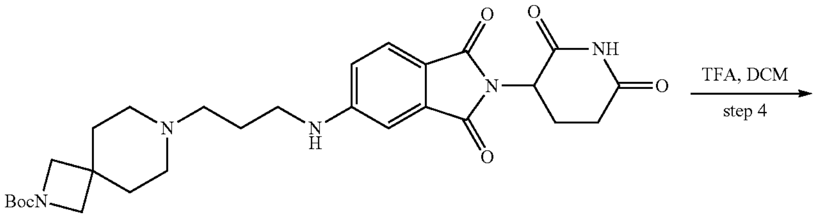

4

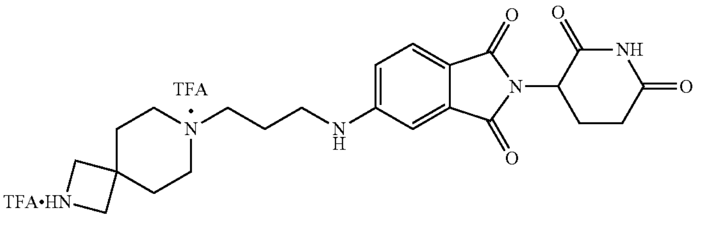

Step 1: Preparation of tert-butyl 7-(3-(((benzyloxy)carbonyl)amino)propyl)-2,7-diazaspiro[3.5]nonane-2-carboxylate (Intermediate 2)

2

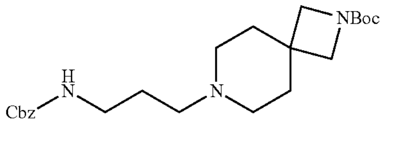

A solution of benzyl N-(3-oxopropyl)carbamate (7.7 g, 36.9 mmol, 1.0 equiv) and tert-butyl 2,7-diazaspiro[3.5]nonane-2-carboxylate (8.4 g, 36.9 mmol, 1.0 equiv) in MeOH (50 mL) was stirred at RT for 30 minutes. NaBH$(OAc)_3$ (31.3 g, 147.7 mmol, 4 equiv) was then added and the resulting mixture was stirred at RT for 3 hours. The mixture was filtered and the filtrate was concentrated. The residue was purified by silica gel column chromatography eluted with DCM to DCM/MeOH=50:1 to afford intermediate 2 (6.4 g, 41.5% yield) as light yellow oil. LCMS (ESI) m/z: $[M+H]^+$=418.

Step 2: Preparation of tert-butyl 7-(3-aminopropyl)-2,7-diazaspiro[3.5]nonane-2-carboxylate (Intermediate 3)

3

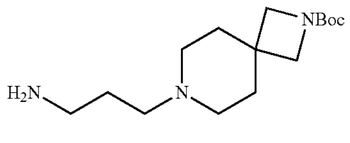

To a solution of tert-butyl 7-(3-[[(benzyloxy)carbonyl]amino]propyl)-2,7-diazaspiro[3.5]nonane-2-carboxylate (3.8 g, 9.1 mmol, 1.0 equiv) in MeOH (40 mL) was added 10% Pd/C (0.38 g, 3.5 mmol, 0.39 equiv) at RT under $N_2$. The resulting mixture was stirred at RT under $H_2$ for 1.5 hours. The mixture was filtered, concentrated, and the residue was purified by silica gel column chromatography eluted with DCM to DCM/MeOH=5:1 to give intermediate 3 (1.0 g, 38.7% yield) as colorless oil. LCMS (ESI) m/z: $[M+H]^+$=284.

Step 3: Preparation of tert-butyl 7-(3-((2-(2,6-dioxopiperidin-3-yl)-1,3-dioxoisoindolin-5-yl)amino)propyl)-2,7-diazaspiro[3.5]nonane-2-carboxylate (Intermediate 4)

4

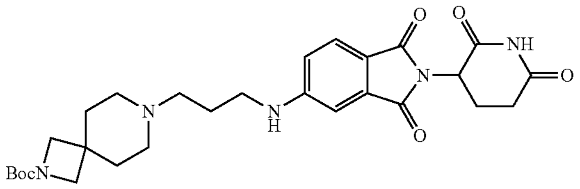

To a mixture of 2-(2,6-dioxopiperidin-3-yl)-5-fluoroisoindole-1,3-dione (0.97 g, 3.5 mmol, 1.0 equiv) and DIEA (0.92 g, 7.0 mmol, 2.0 equiv) in DMSO (100 mL) at 90° C. was added a solution of tert-butyl 7-(3-aminopropyl)-2,7-diazaspiro[3.5]nonane-2-carboxylate (1.0 g, 3.5 mmol, 1.0 equiv) in DMSO (20 mL) drop wise. After the addition, the mixture was stirred at 90° C. for 17 hours. The mixture was cooled to RT, purified by prep-HPLC with the following conditions: C18 Spherical Column, 20-35 um, 80 g; mobile phase, phase A: $H_2O$ (0.16% $NH_4HCO_3$), B: acetonitrile (Gradient B % 0%~55%, run time 60 min); Flow rate: 60 ml/min; Detector, UV detection at 254 nm. Intermediate 4 (0.37 g, 19.4%) was obtained from the purification as a yellow solid. LCMS (ESI) m/z: $[M+H]^+$=540.

Step 4: Preparation of 5-((3-(2,7-diazaspiro[3.5]nonan-7-yl)propyl)amino)-2-(2,6-dioxopiperidin-3-yl)isoindoline-1,3-dione di-trifluoroacetic acid

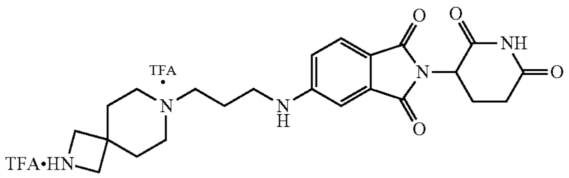

To a solution of tert-butyl 7-(3-[[2-(2,6-dioxopiperidin-3-yl)-1,3-dioxoisoindol-5-yl]amino]propyl)-2,7-diazaspiro[3.5]nonane-2-carboxylate (0.37 g, 0.69 mmol, 1.0 equiv) in DCM (8 mL) was added drop wise a solution of TFA (1 mL) in DCM (2 mL) at 0° C. After the addition, the mixture was warmed to RT and stirred for 20 hours. The mixture was concentrated to remove DCM and the residue was purified by prep-HPLC with the following conditions: C18 Spherical Column, 20-35 um, 80 g; mobile phase, phase A: $H_2O$ (0.1% TFA), B: acetonitrile (Gradient B % 0%~30%, run time 30 min); Flow rate: 50 ml/min; Detector, UV detection at 254 nm. The title compound (0.3 g, 99.5%) was obtained from the purification as a yellow solid. $^1H$ NMR (400 MHz, DMSO-d6) δ 11.08 (br, 1H), 9.76 (br, 1H), 8.93 (br, 2H), 7.60 (d, J=8.3 Hz, 1H), 7.21-7.32 (m, 1H), 6.99 (d, J=1.7 Hz, 1H), 6.89 (dd, J=8.4, 2.0 Hz, 1H), 5.04 (dd, J=12.9, 5.3 Hz, 1H), 3.84-3.72 (m, 5H), 3.31-3.25 (m, 3H), 3.15-3.00 (m, 2H), 2.95-2.82 (m, 3H), 2.63-2.55 (m, 2H), 2.17 (d, J=13.8 Hz, 2H), 2.04-1.77 (m, 5H). LCMS (ESI) m/z: $[M+H]^+$=440.20.

Preparation of 2-(2,6-dioxopiperidin-3-yl)-5-[[5-(piperazin-1-yl) pentyl]oxy]isoindole-1,3-dione

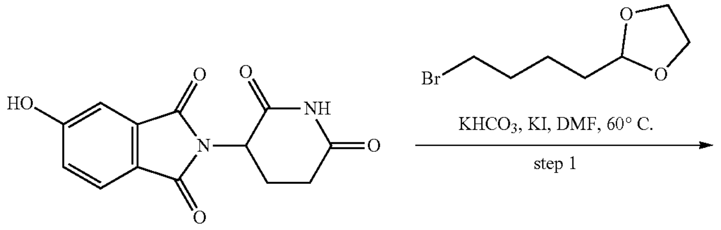

1

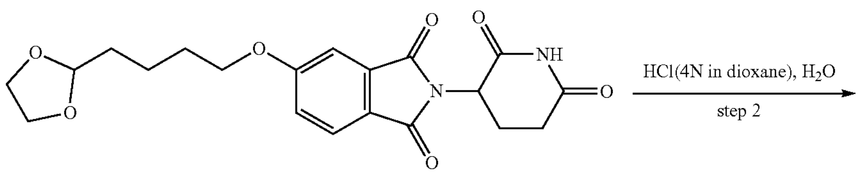

2

-continued

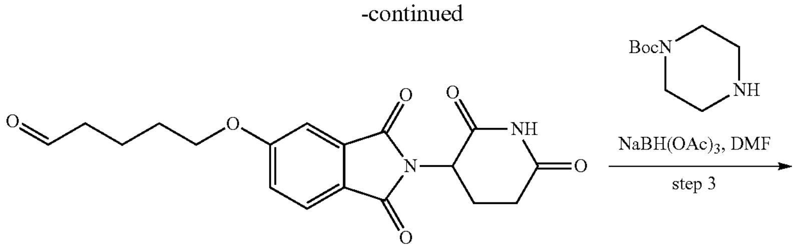

3

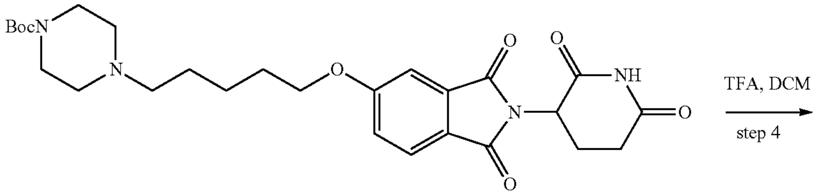

4

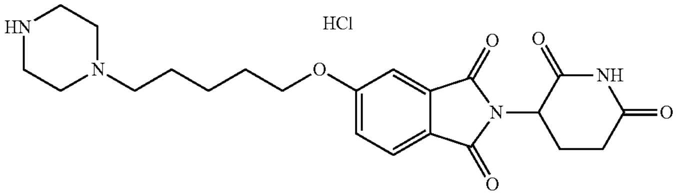

Step 1: Preparation oft 5-[4-(1,3-dioxolan-2-yl)butoxy]-2-(2,6-dioxopiperidin-3-yl)isoindole-1,3-dione (Intermediate 2)

2

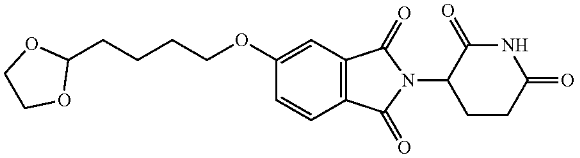

To a stirred solution of 2-(2,6-dioxopiperidin-3-yl)-5-hydroxyisoindole-1,3-dione (3.00 g, 10.940 mmol, 1.00 equiv) and 2-(4-bromobutyl)-1,3-dioxolane (2.74 g, 13.128 mmol, 1.20 equiv) in DMF (25.00 mL) were added $KHCO_3$ (2.19 g, 21.879 mmol, 2.00 equiv) and KI (272.40 mg, 1.641 mmol, 0.15 equiv) in portions at 60 degrees C. After stirring for 5 h and standard workup, the residue was purified by reverse phase flash chromatography with the following conditions: column, C18 silica gel; mobile phase, MeCN in water, 0% to 100% gradient in 40 min; detector, UV 254 nm. This provided intermediate 2 (2.4 g, 54.52%) as an off-white solid. LCMS (ESI) m/z: $[M+H]^+$=403.

Step 2: Preparation of 5-[[2-(2,6-dioxopiperidin-3-yl)-1,3-dioxoisoindol-5-yl]oxy]pentanal (Intermediate 3)

3

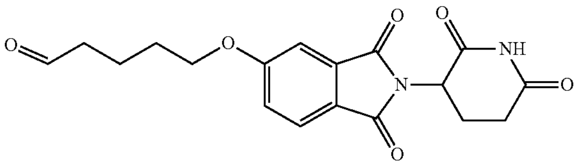

A solution of intermediate 2 (2.40 g, 5.964 mmol, 1.00 equiv) and dry HCl in 1,4-dioxane (12.00 mL, 394.943 mmol, 66.22 equiv) in 1,4-dioxane (12.00 mL) was stirred for 2 h at room temperature. The resulting mixture was concentrated under reduced pressure. The crude product was used in the next step directly without further purification (1.92 g, 89.83%) as an off-white solid. LCMS (ESI) m/z: $[M+H]^+$=359.

Step 3: Preparation of tert-butyl 4-(5-[[2-(2,6-dioxopiperidin-3-yl)-1,3-dioxoisoindol-5-yl]oxy]pentyl)piperazine-1-carboxylate (Intermediate 4)

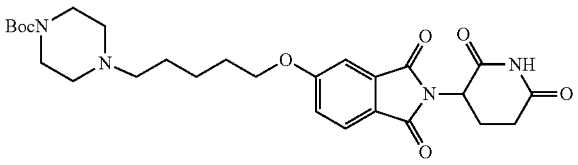 [SMILES: CC(C)(C)OC(=O)N1CCN(CCCCCOc2ccc3c(c2)C(=O)N(C2CCC(=O)NC2=O)C3=O)CC1]

To a stirred solution of intermediate 3 (1.89 g, 5.274 mmol, 1.00 equiv) and tert-butyl piperazine-1-carboxylate (0.98 g, 5.274 mmol, 1.00 equiv) in DMF (20.00 mL) was added $NaBH(AcO)_3$ (2.24 g, 10.548 mmol, 2.00 equiv) in portions at room temperature. After standard workup, the residue was purified by reverse phase flash chromatography with the following conditions: column, C18 silica gel; mobile phase, MeCN in water, 0% to 100% gradient in 30 min; detector, UV 254 nm. This provided intermediate 4 (1.46 g, 52.37%) as an off-white solid. LCMS (ESI) m/z: $[M+H]^+$=529.

Step 4: Preparation of 2-(2,6-dioxopiperidin-3-yl)-5-[[5-(piperazin-1-yl)pentyl]oxy] isoindole-1,3-dione

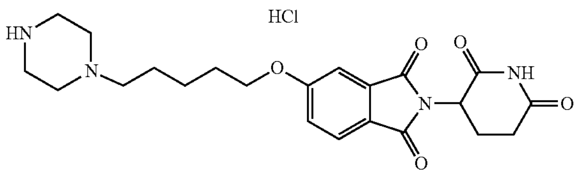 [SMILES: O=C1CCC(N2C(=O)c3ccc(OCCCCCN4CCNCC4)cc3C2=O)C(=O)N1 ; Cl]

A solution of intermediate 4 (1.40 g, 2.648 mmol, 1.00 equiv) and TFA (5.00 mL, 67.315 mmol, 25.42 equiv) in DCM was stirred for 2 h at room temperature. The resulting mixture was concentrated under reduced pressure. The residue was purified by reverse phase flash chromatography with the following conditions: column, C18 silica gel; mobile phase, MeCN in water, 0% to 100% gradient in 30 min; detector, UV 254 nm. This provided the title compound (723.6 mg, 63.76%) as a white solid. $^1H$ NMR (300 MHz, DMSO) δ 11.81 (s, 1H), 11.12 (s, 1H), 9.75 (s, 2H), 7.85 (d, 1H), 7.46-7.32 (m, 2H), 5.12 (dd, 1H), 4.20 (t, 2H), 3.66 (s, 1H), 3.48 (s, 2H), 3.40-3.30 (m, 1H), 3.15 (d, 2H), 2.99-2.81 (m, 1H), 2.67-2.52 (m, 1H), 2.13-1.98 (m, 1H), 1.88-1.71 (m, 4H), 1.56-1.40 (m, 2H). LCMS (ESI) m/z: $[M+H]^+$= 429.15.

Preparation of 5-(4-(2-aminoethyl)piperidin-1-yl)-2-(2,6-dioxopiperidin-3-yl)isoindoline-1,3-dione trifluoroacetic acid

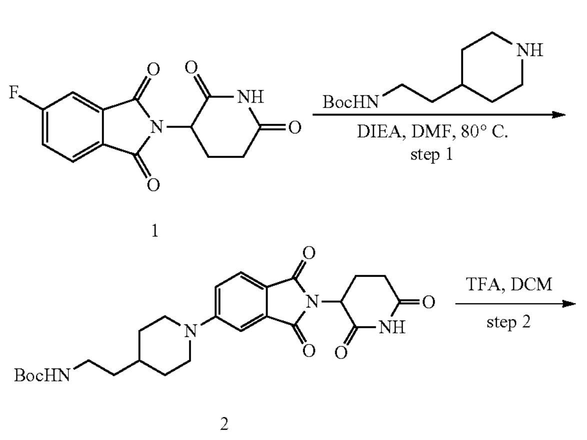

-continued

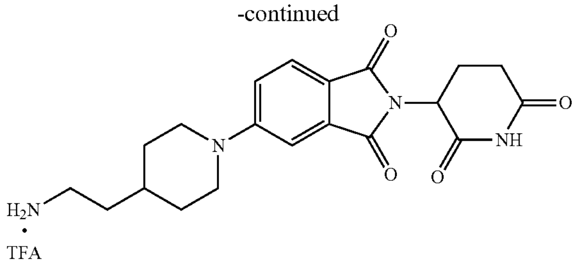

Step 1: Preparation of tert-butyl (2-(1-(2-(2,6-dioxopiperidin-3-yl)-1,3-dioxoisoindolin-5-yl)piperidin-4-yl)ethyl)carbamate (Intermediate 2)

2

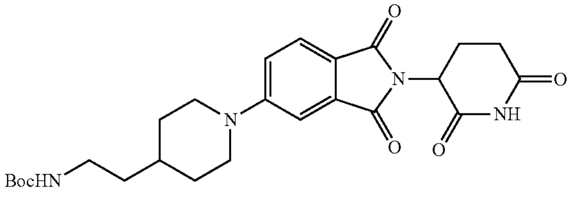

2 To a solution of 2-(2,6-dioxopiperidin-3-yl)-5-fluoroisoindole-1,3-dione (2.0 g, 7.2 mmol, 1.0 equiv) and tert-butyl N-[2-(piperidin-4-yl)ethyl]carbamate (2.0 g, 8.7 mmol, 1.2 equiv) in DMF (20 mL) was added DIEA (1.9 g, 14.5 mmol, 2 equiv) at RT. After the addition, the mixture was stirred at 80° C. for 2.5 hours. The mixture was cooled to RT and poured into $H_2O$ (100 mL). The resulting mixture was stirred at RT for 4 hours and then filtered. The cake was washed with $H_2O$ (15 mL×2), triturated with MTBE (30 mL), and this cake was dried to give Intermediate 2 (3.2 g, 90.0% yield) as a yellow solid. LCMS (ESI) m/z: $[M+H]^+$= 485.

Step 2: Preparation of 5-(4-(2-aminoethyl)piperidin-1-yl)-2-(2,6-dioxopiperidin-3-yl)isoindoline-1,3-dione trifluoroacetic acid

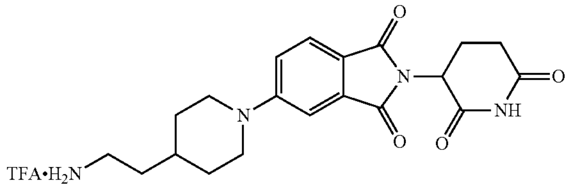

A mixture of tert-butyl N-(2-[1-[2-(2,6-dioxopiperidin-3-yl)-1,3-dioxoisoindol-5-yl]piperidin-4-yl]ethyl)carbamate (3.1 g, 6.3 mmol, 1.0 equiv) in DCM (20 mL) and TFA (5 mL) was stirred at 50° C. for 2.5 hours. The mixture was cooled to RT and concentrated. The residue was purified by prep-HPLC with the following conditions: C18 Spherical Column, 20-35 um, 330 g; mobile phase, phase A: $H_2O$ (0.05% TFA), B: acetonitrile (Gradient B % 0%~50%, run time 20 min); Flow rate: 80 ml/min; Detector, UV detection at 254 nm. The title compound (1.6 g, 64.7%) was obtained from the purification as a yellow solid. $^1$H NMR (400 MHz, DMSO-d6) δ 11.08 (s, 1H), 7.75 (br, 3H), 7.66 (d, J=8.6 Hz, 1H), 7.32 (d, J=2.1 Hz, 1H), 7.25 (dd, J=8.7, 2.3 Hz, 1H), 5.07 (dd, J=12.9, 5.4 Hz, 1H), 4.06 (d, J=13.2 Hz, 2H), 3.01-2.79 (m, 5H), 2.64-2.52 (m, 2H), 2.07-1.96 (m, 1H), 1.75 (d, J=11.6 Hz, 2H), 1.69-1.60 (m, 1H), 1.50 (q, J=7.1 Hz, 2H), 1.26-1.11 (m, 2H). LCMS (ESI) m/z: $[M+H]^+$= 385.20.

Preparation of 3-(6-(2-(2,6-dioxopiperidin-3-yl)-1,3-dioxoisoindolin-5-yl)-2,6-diazaspiro[3.3] heptan-2-yl)propanoic acid formic acid

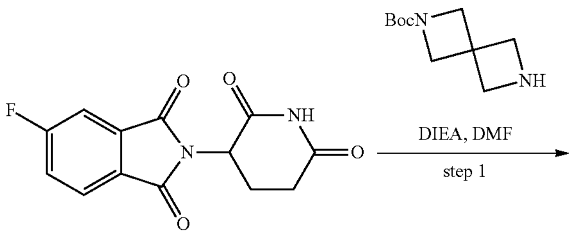

1

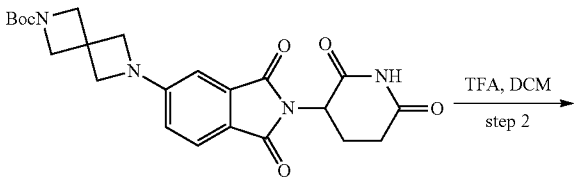

2

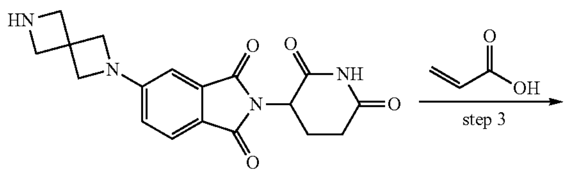

3

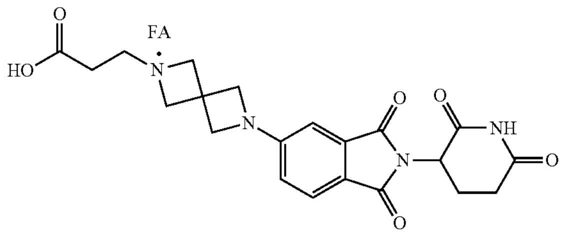

Step 1: Preparation of tert-butyl 6-(2-(2,6-dioxopiperidin-3-yl)-1,3-dioxoisoindolin-5-yl)-2,6-diazaspiro[3.3]heptane-2-carboxylate (Intermediate 2)

2

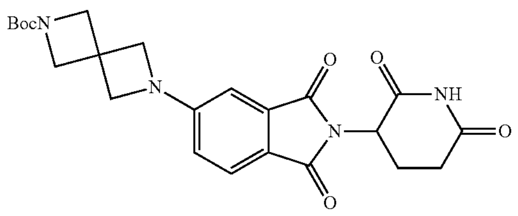

To a stirred solution of 2-(2,6-dioxopiperidin-3-yl)-5-fluoroisoindole-1,3-dione (12.0 g, 43.5 mmol, 1.0 equiv) and DIEA (16.8 g, 130.3 mmol, 3.0 equiv) in DMF (120 mL) was added tert-butyl 2,6-diazaspiro[3.3]heptane-2-carboxylate (8.6 g, 43.4 mmol, 1.0 equiv) at room temperature. The resulting mixture was stirred for 2 h at 80° C. The resulting mixture was cooled to the temperature, concentrated, and purified by reverse phase flash chromatography with the following conditions: column, C18 spherical column; mobile phase, $CH_3CN$ in water, 10% to 50% gradient in 50 min; detector, UV 254 nm to afford Intermediate 2 (4.2 g, 21.3%). LCMS (ESI) m/z $[M+H]^+$=455.

Step 2: Preparation of 2-(2,6-dioxopiperidin-3-yl)-5-(2,6-diazaspiro[3.3]heptan-2-yl)isoindoline-1,3-dione (Intermediate 3)

3

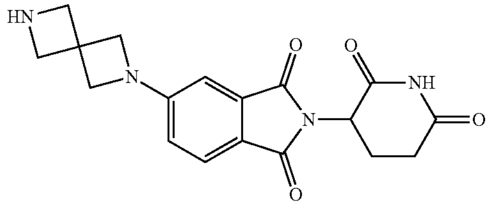

To a stirred mixture of Intermediate 2 (4.0 g, 8.8 mmol, 1.0 equiv) and DCM (40 mL) was added TFA (8 mL) dropwise. After stirring at rt for 2 h, the mixture was concentrated under vacuum to afford the crude product Intermediate 3 (3.1 g, quant.). LCMS (ESI) m/z $[M+H]^+$= 355.

Step 3: Preparation of 3-(6-(2-(2,6-dioxopiperidin-3-yl)-1,3-dioxoisoindolin-5-yl)-2,6-diazaspiro[3.3]heptan-2-yl)propanoic acid formic acid

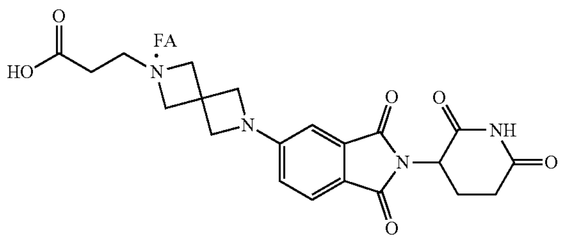

To a stirred solution of 5-[2,6-diazaspiro[3.3]heptan-2-yl]-2-(2,6-dioxopiperidin-3-yl)isoindole-1,3-dione (12.0 g, 33.9 mmol, 1.0 equiv) and acrylic acid (4.9 g, 68.1 mmol, 2 equiv) was added DIEA (8.8 g, 68.2 mmol, 2 equiv) drop-wise at room temperature. The resulting mixture was stirred for 2 hrs at room temperature. The reaction mixture was concentrated and the residue was purified by reverse phase flash chromatography with the following conditions: column, C18 spherical column; mobile phase, phase A: $H_2O$ (0.05% FA), B: acetonitrile (Gradient B % 0%~50%, run time 50 min), detector, UV 254 nm to afford the title compound (1.8 g, 12.5%) as a yellow solid. $^1H$ NMR (400 MHz, DMSO-d6) δ 11.12 (br, 1H), 8.28 (s, 1H), 7.64 (d, J=8.3 Hz, 1H), 6.79 (d, J=2.1 Hz, 1H), 6.64 (dd, J=8.3, 2.1 Hz, 1H), 5.06 (dd, J=12.9, 5.4 Hz, 1H), 4.10 (s, 4H), 4.10 (s, 5H), 2.95-2.81 (m, 1H), 2.61-2.59 (m, 2H), 2.57-2.54 (m, 1H), 2.19 (t, J=6.8 Hz, 2H), 2.05-1.96 (m, 1H). LCMS (ESI) m/z: $[M+H]^+$=427.15.

Preparation of (2S)-6-amino-2-[(1-methanesulfonylpyrrol-3-yl)formamido]-N-(4-phenyl-1,3-thiazol-2-yl)hexanamide

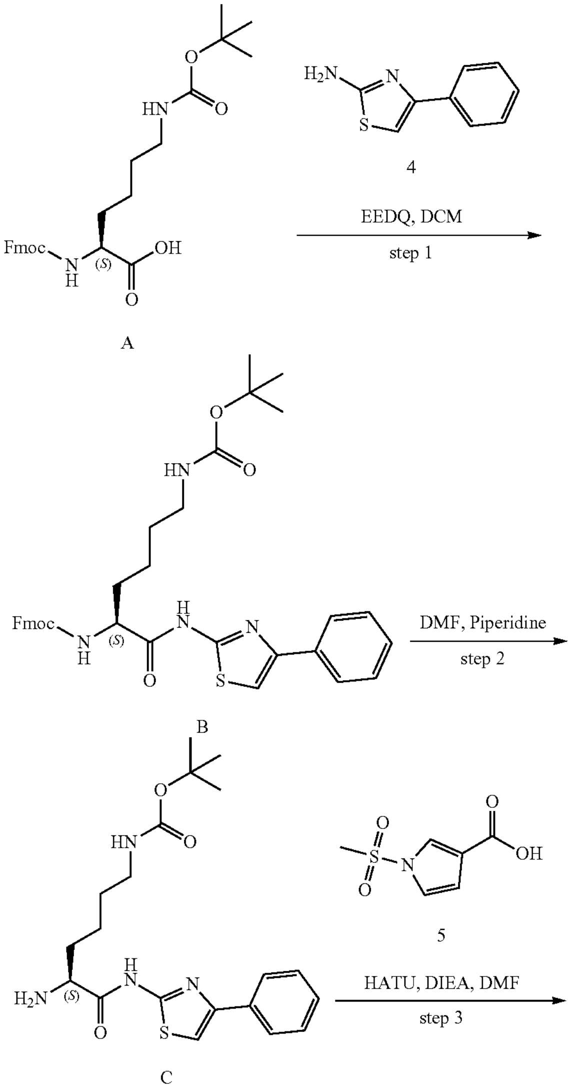

-continued

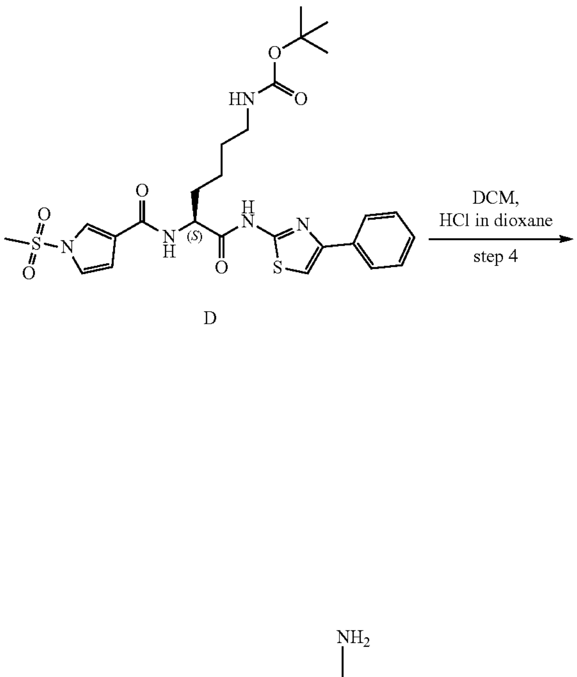

Step 1: Preparation of tert-butyl N-[(5S)-5-[[(9H-fluoren-9-ylmethoxy)carbonyl]amino]-5-[(4-phenyl-1,3-thiazol-2-yl)carbamoyl]pentyl]carbamate (Intermediate B)

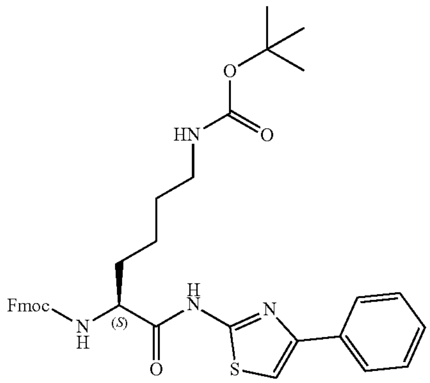

B

Into a 100-mL 3-necked round-bottom flask, was placed (2S)-6-[(tert-butoxycarbonyl)amino]-2-[[(9H-fluoren-9-yl-methoxy)carbonyl]amino]hexanoic acid (A, 500.48 mg, 1.068 mmol, 1.50 equiv), phenthiazamine (125.50 mg, 0.712 mmol, 1.00 equiv), DCM (20.00 mL), ethyl 2-ethoxy-1,2-dihydroquinoline-1-carboxylate (264.14 mg, 1.068 mmol, 1.50 equiv). The resulting solution was stirred for 2 h at room temperature. The resulting solution was extracted with 3×10 mL of ethyl acetate. The residue obtained after concentration of the combined organic extracts was purified by silica gel column with ethyl acetate/hexane (4:1). This resulted in 400 mg (89.62%) of intermediate B as a yellow green solid. LCMS (ESI) m/z: $[M+H]^+$=627.

Step 2: Preparation of tert-butyl N-[(5S)-5-amino-5-[(4-phenyl-1,3-thiazol-2-yl)carbamoyl]pentyl]carbamate (Intermediate C)

C

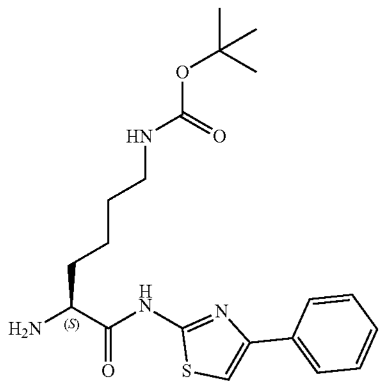

Into a 50-mL round-bottom flask, was placed intermediate B (200.00 mg), DMF (10.00 mL), and piperidine (2.00 mL). The resulting solution was stirred for 2 h at room temperature, followed by extraction with 3×30 mL of dichloromethane and concentration of the combined organic layers. This provided intermediate C (60 mg, 46.48%) as a solid. LCMS (ESI) m/z: $[M+H]^+$=405.

Step 3: Preparation of tert-butyl N-[(5S)-5-[(1-methanesulfonylpyrrol-3-yl)formamido]-5-[(4-phenyl-1,3-thiazol-2-yl)carbamoyl]pentyl]carbamate (Intermediate D)

D

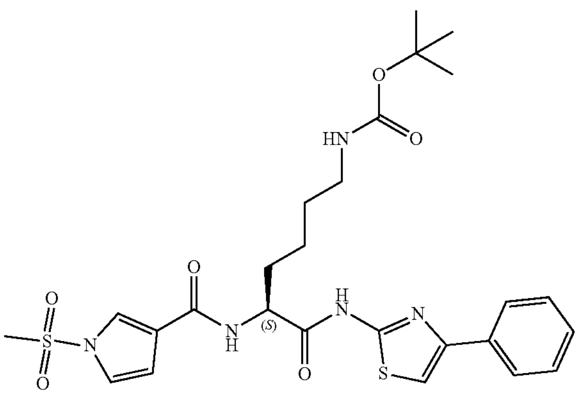

Into a 25-mL round-bottom flask, was placed 1-methanesulfonylpyrrole-3-carboxamide (33.50 mg, 0.178 mmol, 1.20 equiv), DMF (5.00 mL), DIEA (76.68 mg, 0.593 mmol, 4.00 equiv), HATU (67.67 mg, 0.178 mmol, 1.20 equiv), and intermediate C (60.00 mg, 0.148 mmol, 1.00 equiv). The resulting solution was stirred for 1 h at room temperature, followed by extracted with 3×10 mL of ethyl acetate. The crude product (30 mg) was purified by Prep-HPLC to provide 3.5 mg (4.02%) of intermediate D as a white solid. $^1$H NMR (400 MHz, DMSO-d6) δ 12.43 (s, 1H), 8.40 (d, J=7.2 Hz, 1H), 8.01-7.95 (m, 1H), 7.95-7.86 (m, 2H), 7.63 (s, 1H), 7.44 (t, J=7.7 Hz, 2H), 7.38-7.21 (m, 2H), 6.88-6.73 (m, 2H), 4.60 (q, J=7.2 Hz, 1H), 3.57 (s, 3H), 2.92 (d, J=6.4 Hz, 2H), 1.78 (s, 2H), 1.42 (s, 3H), 1.35 (s, 9H), 1.24-1.12 (m, 1H). LCMS (ESI) m/z: $[M+H]^+$=576.20.

Step 4: Preparation of (2S)-6-amino-2-[(1-methanesulfonylpyrrol-3-yl)formamido]-N-(4-phenyl-1,3-thiazol-2-yl)hexanamide

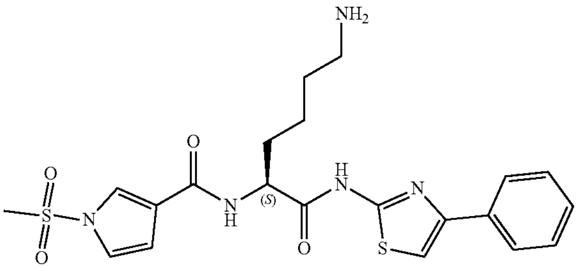

Into a 25-mL round-bottom flask, was placed tert-butyl N-[(5S)-5-[(1-methanesulfonylpyrrol-3-yl)formamido]-5-[(4-phenyl-1,3-thiazol-2-yl)carbamoyl]pentyl]carbamate (50.00 mg, 0.087 mmol, 1.00 equiv), DCM (3.00 mL, 15.730 mmol), and dry HCl in 1,4-dioxane (3.00 mL, 32.912 mmol). The resulting solution was stirred for 1 hr at room temperature. The resulting mixture was concentrated, providing 50 mg (crude) of the title compound as an oil. LCMS (ESI) m/z: $[M+H]^+$=476.

Compound 264—Preparation of N-[(2S)-1-[(2S, 4R)-4-hydroxy-2-([[4-(4-methyl-1,3-thiazol-5-yl) phenyl]methyl]carbamoyl)pyrrolidin-1-yl]-3,3-dimethyl-1-oxobutan-2-yl]-N-[(5S)-5-[(1-methanesulfonylpyrrol-3-yl)formamido]-5-[(4-phenyl-1,3-thiazol-2-yl)carbamoyl]pentyl] hexanediamide
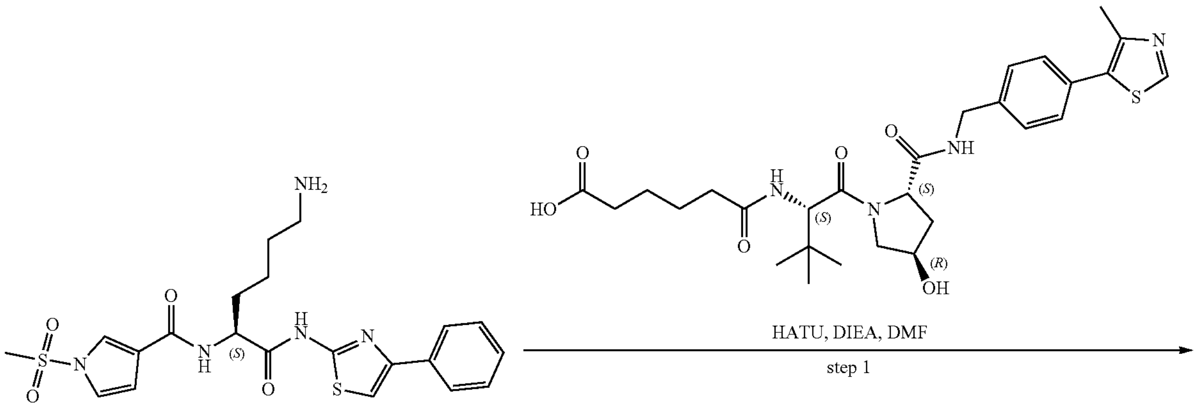
1
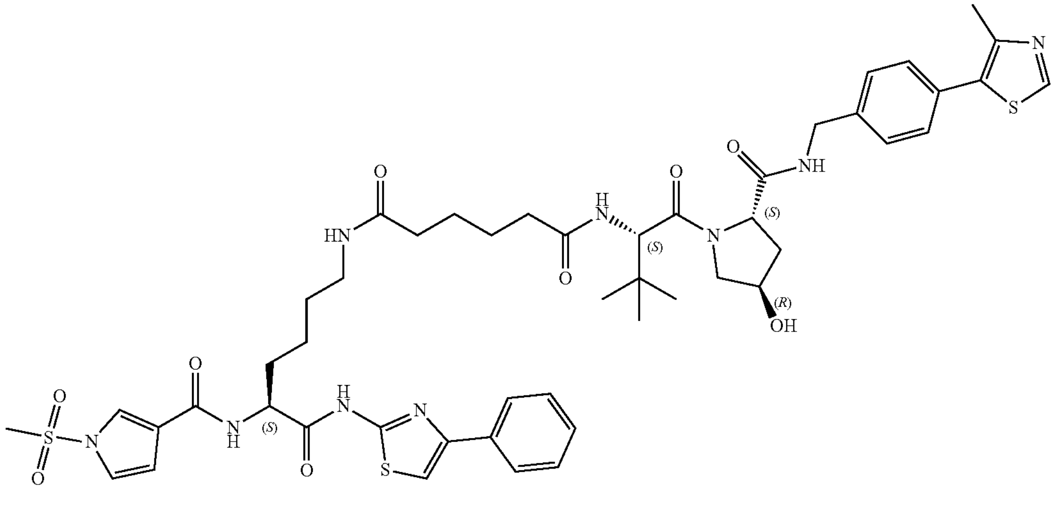
264

Step 1: Preparation of N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N-[(5S)-5-[(1-methanesulfonylpyrrol-3-yl)formamido]-5-[(4-phenyl-1,3-thiazol-2-yl)carbamoyl]pentyl]hexanediamide (Compound 264)

264

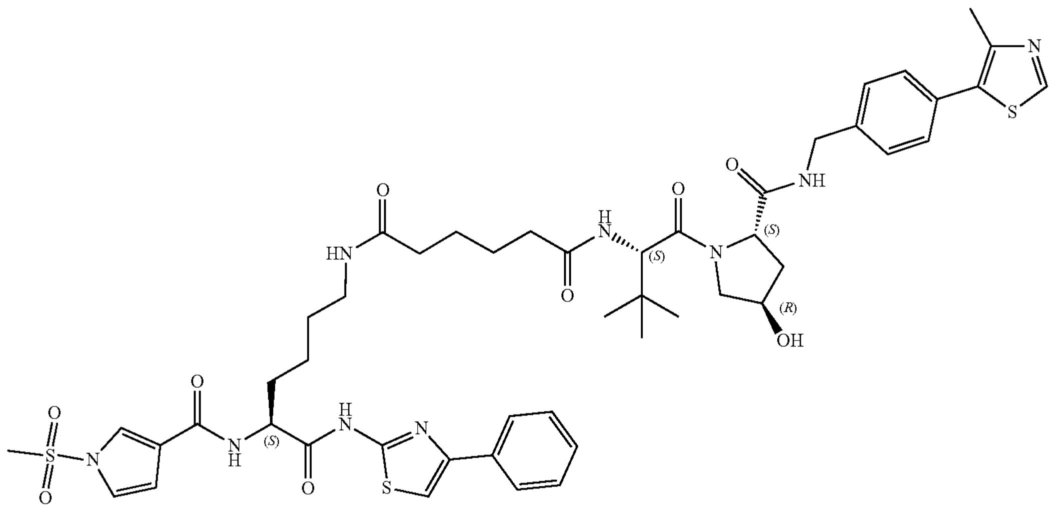

To a stirred solution of 5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentanoic acid (10.00 mg, 0.018 mmol, 1.00 equiv), HATU (6.81 mg, 0.018 mmol, 1.00 equiv) and DIEA (6.94 mg, 0.054 mmol, 3.00 equiv) in DMF (1.00 mL) was added (2S)-6-amino-2-[(1-methanesulfonylpyrrol-3-yl)formamido]-N-(4-phenyl-1,3-thiazol-2-yl)hexanamide (8.51 mg, 0.018 mmol, 1.00 equiv) dropwise. The resulting mixture was stirred for 2 h at room temperature, followed by extraction with EtOAc (3x3 mL). The combined organic layers were washed with water, dried over anhydrous $Na_2SO_4$, and concentrated under reduced pressure. The crude product (10 mg) was purified by Prep-HPLC to afford Compound 264 (5 mg, 27.49%) as a white solid. $^1$H NMR (400 MHz, DMSO-$d_6$) δ 12.42 (s, 1H), 8.98 (s, 1H), 8.56 (t, J=6.1 Hz, 1H), 8.39 (d, J=7.1 Hz, 1H), 7.99-7.93 (m, 1H), 7.93-7.87 (m, 2H), 7.83 (d, J=9.3 Hz, 1H), 7.79-7.72 (m, 1H), 7.62 (s, 1H), 7.47-7.36 (m, 6H), 7.36-7.27 (m, 2H), 6.82-6.76 (m, 1H), 5.15-5.10 (m, 1H), 4.65-4.56 (m, 1H), 4.53 (d, J=9.3 Hz, 1H), 4.49-4.38 (m, 2H), 4.34 (s, 1H), 4.30-4.17 (m, 1H), 3.71-3.60 (m, 2H), 3.56 (s, 3H), 3.05-3.01 (m, 2H), 2.44 (s, 3H), 2.30-2.20 (m, 1H), 2.15-2.06 (m, 1H), 2.06-1.98 (m, 3H), 1.95-1.84 (m, 1H), 1.83-1.73 (m, 2H), 1.50-1.37 (m, 7H), 1.32-1.25 (m, 1H), 0.92 (s, 9H). LCMS (ESI) m/z: $[M+H]^+$=1016.20.

TABLE 20

The following compounds were prepared using standard chemical manipulations and procedures similar to those used for the preparation of Compound 264

| Cmpd # | Name | LC-MS (ESI) (m/z) | $^1$H NMR |
|---|---|---|---|
| 297 | N-((2S)-6-(3-(4-(2-(2,6-dioxopiperidin-3-yl)-1,3-dioxoisoindolin-5-yl)piperazin-1-yl)propanamido)-1-oxo-1-((4-phenylthiazol-2-yl)amino)hexan-2-yl)-1-(methylsulfonyl)-1H-pyrrole-3-carboxamide | 872.15 | $^1$H NMR (400 MHz, DMSO-d6) δ 12.43 (s, 1H), 11.08 (s, 1H), 8.38 (d, J = 7.1 Hz, 1H), 7.98 (t, J = 1.9 Hz, 1H), 7.96-7.84 (m, 3H), 7.69-7.63 (m, 1H), 7.62 (s, 1H), 7.43 (t, J = 7.6 Hz, 2H), 7.38-7.27 (m, 3H), 7.25-7.18 (m, 1H), 6.79 (dd, J = 3.3, 1.6 Hz, 1H), 5.07 (dd, J = 12.9, 5.4 Hz, 1H), 4.67-4.55 (m, 1H), 3.57 (s, 3H), 3.43-3.36 (m, 4H), 3.12-3.02 (m, 2H), 2.94-2.83 (m, 1H), 2.63-2.55 (m, 2H), 2.55-2.52 (m, 2H), 2.48-2.42 (m, 4H), 2.25 (t, J = 7.1 Hz, 2H), 2.06-1.98 (m, 1H), 1.85-1.74 (m, 2H), 1.53-1.38 (m, 3H), 1.38-1.30 (m, 1H). |
| 265 | (2S)-6-([1,12-dihydroxy-12-[(1-hydroxy-1-[4-hydroxy-2-[hydroxy([[4-(4-methyl-1,3-thiazolidin-5-yl)cyclohexyl]methyl]amino)methyl]pyrrolidin-1-yl]-3,3- | 1100.25 | $^1$H NMR (400 MHz, DMSO-$d_6$) δ 12.72-12.08 (m, 1H), 8.98 (s, 1H), 8.59-8.52 (m, 1H), 8.41-8.35 (m, 1H), 7.99-7.88 (m, 3H), 7.85-7.70 (m, 2H), 7.62 (s, 1H), 7.47-7.37 (m, 6H), 7.35-7.26 (m, 2H), 6.82-6.76 (m, 1H), 5.12 (s, 1H), 4.63-4.57 (m, 1H), 4.56-4.51 (m, 1H), 4.47-4.38 (m, 2H), |

TABLE 20-continued

The following compounds were prepared using standard chemical manipulations and procedures similar to those used for the preparation of Compound 264

| Cmpd # | Name | LC-MS (ESI) (m/z) | $^1$H NMR |
|---|---|---|---|
| | dimethylbutan-2-yl)amino]dodecyl]amino)-2-[(1-methanesulfonylpyrrol-3-yl)formamido]-N-(4-phenyl-1,3-thiazol-2-yl)hexanamide | | 4.35 (s, 1H), 4.25-4.17 (m, 1H), 3.71-3.59 (m, 2H), 3.56 (s, 3H), 3.08-2.99 (m, 2H), 2.44 (s, 3H), 2.31-2.19 (m, 1H), 2.15-2.03 (m, 1H), 2.07-1.97 (m, 3H), 1.95-1.84 (m, 1H), 1.83-1.75 (m, 2H), 1.49-1.33 (m, 8H), 1.19 (s, 12H), 0.93 (s, 9H). |
| 266 | N'-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N-[(5S)-5-[(1-methanesulfonylpyrrol-3-yl)formamido]-5-[(4-phenyl-1,3-thiazol-2-yl)carbamoyl]pentyl]octane-diamide | 1044.35 | $^1$H NMR (300 MHz, DMSO-$d_6$) δ 12.43 (s, 1H), 8.99 (s, 1H), 8.57 (t, J = 6.1 Hz, 1H), 8.39 (d, J = 7.0 Hz, 1H), 7.98 (t, J = 2.0 Hz, 1H), 7.94-7.87 (m, 2H), 7.84 (d, J = 9.3 Hz, 1H), 7.75 (t, J = 5.6 Hz, 1H), 7.63 (s, 1H), 7.42 (m, 6H), 7.34-7.21 (m, 2H), 6.80 (m, 1H), 5.13 (d, J = 3.5 Hz, 1H), 4.58 (m, 2H), 4.51-4.31 (m, 3H), 4.22 (m, 5.4 Hz, 1H), 3.66 (s, 2H), 3.57 (s, 3H), 3.04 (m, 2H), 2.45 (s, 3H), 2.30-1.98 (m, 5H), 1.92 (m, 1H), 1.79 (s, 2H), 1.43 (s, 8H), 1.22 (m, 4H), 0.93 (s, 9H). |
| 267 | N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N-[(5S)-5-[(1-methanesulf-onylpyrrol-3-yl)formamido]-5-[(4-phenyl-1,3-thiazol-2-yl)carbamoyl]pentyl]tetradecanediamide | 1128.35 | $^1$H NMR (300 MHz, DMSO-d6) δ 12.42 (s, 1H), 8.98 (s, 1H), 8.56 (t, J = 6.2 Hz, 1H), 8.38 (d, J = 7.0 Hz, 1H), 7.97 (t, J = 2.0 Hz, 1H), 7.90 (dd, J = 7.2, 1.8 Hz, 2H), 7.83 (d, J = 9.3 Hz, 1H), 7.74 (t, J = 5.7 Hz, 1H), 7.62 (s, 1H), 7.48-7.26 (m, 8H), 6.79 (dd, J = 3.3, 1.6 Hz, 1H), 5.12 (s, 1H), 4.70-4.49 (m, 2H), 4.49-4.18 (m, 4H), 3.68-3.62 (m, 2H), 3.56 (s, 3H), 3.03 (d, J = 4.8 Hz, 2H), 2.44 (s, 3H), 2.33-2.17 (m, 1H), 2.16-2.04 (m, 1H), 2.05-1.96 (m, 3H), 1.95-1.84 (m, 1H), 1.79 (d, J = 7.4 Hz, 2H), 1.51-1.35 (m, 7H), 1.23-1.17 (m, 17H), 0.93 (s, 9H). |
| 268 | N-[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]-N-[(5S)-5-[(1-methane-sulfonylpyrrol-3-yl)formamido]-5-[(4-phenyl-1,3-thiazol-2-yl)carbamoyl]pentyl]decanediamide | 1072.30 | $^1$H NMR (300 MHz, DMSO-d6) δ 12.43 (s, 1H), 8.99 (s, 1H), 8.57 (t, J = 6.0 Hz, 1H), 8.39 (d, J = 7.1 Hz, 1H), 7.98 (t, J = 2.0 Hz, 1H), 7.95-7.87 (m, 2H), 7.84 (d, J = 9.3 Hz, 1H), 7.75 (t, J = 5.7 Hz, 1H), 7.63 (s, 1H), 7.47-7.22 (m, 8H), 6.80 (dd, J = 3.3, 1.6 Hz, 1H), 5.13 (s, 1H), 4.67-4.49 (m, 2H), 4.50-4.30 (m, 3H), 4.31-4.16 (m, 1H), 3.66 (d, J = 4.1 Hz, 2H), 3.57 (s, 3H), 3.04 (d, J = 6.1 Hz, 2H), 2.45 (s, 3H), 2.30-2.18 (m, 1H), 2.17-1.97 (m, 4H), 1.96-1.84 (m, 1H), 1.83-1.75 (m, 2H), 1.47-1.41 (m, 8H), 1.26-1.11 (m, 8H), 0.93 (s, 9H). |
| 269 | (2S)-6-[[1-(2-[[2-(2,6-dioxopiperidin-3-yl)-1,3-dioxoisoindol-5-yl]oxylethyl)piperidin-4-yl]formamido]-2-[(1-methanesulfonylpyrrol-3-yl)formamido]-N-(4-phenyl-1,3-thiazol-2-yl)hexanamide | 887.45 | $^1$H NMR (400 MHz, DMSO-d6) δ 12.43 (s, 1H), 11.11 (s, 1H), 8.38 (d, J = 7.1 Hz, 1H), 7.97 (t, J = 2.0 Hz, 1H), 7.94-7.87 (m, 2H), 7.83 (d, J = 8.3 Hz, 1H), 7.70 (t, J = 5.7 Hz, 1H), 7.62 (s, 1H), 7.47-7.39 (m, 3H), 7.38-7.28 (m, 3H), 6.79 (dd, J = 3.3, 1.6 Hz, 1H), 5.12 (dd, J = 13.0, 5.3 Hz, 1H), 4.60 (q, J = 7.2 Hz, 1H), 4.23 (t, J = 5.8 Hz, 2H), 3.56 (s, 3H), 3.04 (q, J = 6.2 Hz, 2H), 2.93-2.84 (m, 3H), 2.67 (t, J = 5.8 Hz, 2H), 2.64-2.51 (m, 2H), 2.09-1.92 (m, 4H), 1.78 (d, J = 7.2 Hz, 2H), 1.65-1.49 (m, 4H), 1.43 (d, J = 6.3 Hz, 3H), 1.32 (d, J = 7.4 Hz, 1H). |
| 284 | (2S)-6-([2-[(2-[[2-(2,6-dioxopiperidin-3-yl)-1,3-dioxoisoindol-4-yl]oxy]acetamido)methyl]cyclopropyl]formamido)-2-[(1-methanesulfonylpyrrol-3-yl)formamido]-N-(4-phenyl-1,3-thiazol-2-yl)hexanamide | 887.10 | $^1$H NMR (300 MHz, DMSO-d6) δ 12.41 (brs, 1H), 11.27-10.96 (m, 1H), 8.40 (d, J = 7.2 Hz, 1H), 8.09-8.00 (m, 1H), 8.00-7.85 (m, 4H), 7.84-7.975(m, 1H), 7.63 (s, 1H), 7.52-7.37 (m, 4H), 7.37-7.27 (m, 2H), 6.79 (dd, J = 3.3, 1.7 Hz, 1H), 5.12 (dd, J = 12.8, 5.3 Hz, 1H), 4.77 (s, 2H), 4.66-4.54 (m, 1H), 3.57 (s, 3H), 3.27-3.22 (m, 2H), 3.18-2.93 (m, 3H), 2.92-2.80 (m, 1H), 2.67-2.55 (m, 1H), 2.07-1.98 (m, 1H), 1.86-1.70 (m, 2H), 1.70-1.58 (m, 1H), 1.54-1.37 (m, 3H), 1.37-1.22 (m, 2H), 0.92-0.75 (m, 2H). |
| 288 | (2S)-6-[3-[2-(2-[[2-(2,6-dioxopiperidin-3-yl)-1,3-dioxoisoindol-4-yl]oxy]ethoxy)ethoxy]propanamido]-2-[(1-methanesulfonylpyrrol-3-yl)formamido]-N-(4-phenyl-1,3-thiazol-2-yl)hexanamide | 892.25 | $^1$H NMR (300 MHz, DMSO-d6) δ 12.42 (s, 1H), 11.10 (s, 1H), 8.38 (d, J = 7.1 Hz, 1H), 7.98 (t, J = 2.0 Hz, 1H), 7.95-7.87 (m, 2H), 7.86-7.76 (m, 2H), 7.63 (s, 1H), 7.52 (d, J = 8.5 Hz, 1H), 7.49-7.39 (m, 3H), 7.37-7.27 (m, 2H), 6.82-6.76 (m, 1H), 5.13-5.04 (m, 1H), 4.64-4.53 (m, 1H), 4.33 (dd, J = 5.5, 3.7 Hz, 2H), 3.88-3.72 (m, 2H), 3.68-3.53 (m, 7H), 3.48 (dd, J = 5.9, 3.6 Hz, 2H), 3.05 (d, J = 5.8 Hz, 2H), 2.89-2.79 (m, 1H), 2.67-2.55 (m, 2H), 2.28 (t, J = 6.5 Hz, 2H), 2.13-1.96 (m, 1H), 1.79 (d, J = 7.6 Hz, 2H), 1.38 (d, J = 31.2 Hz, 4H). |

TABLE 20-continued

The following compounds were prepared using standard chemical manipulations and procedures similar to those used for the preparation of Compound 264

| Cmpd # | Name | LC-MS (ESI) (m/z) | $^1$H NMR |
|---|---|---|---|
| 289 | 8-[[2-(2,6-dioxopiperidin-3-yl)-1,3-dioxoisoindol-4-yl]oxy]-N-[(5S)-5-[(1-methanesulfonylpyrrol-3-yl)formamido]-5-[(4-phenyl-1,3-thiazol-2-yl)carbamoyl]pentyl]octanamide | 874.25 | $^1$H NMR (400 MHz, DMSO-d6) δ 12.43 (s, 1H), 11.10 (s, 1H), 8.38 (d, J = 7.1 Hz, 1H), 7.97 (t, J = 2.0 Hz, 1H), 7.94-7.86 (m, 2H), 7.83-7.77 (m, 1H), 7.75 (t, J = 5.7 Hz, 1H), 7.62 (s, 1H), 7.49 (d, J = 8.5 Hz, 1H), 7.43 (td, J = 6.8, 6.0, 2.0 Hz, 3H), 7.36-7.31 (m, 1H), 7.30 (dd, J = 3.3, 2.2 Hz, 1H), 6.79 (dd, J = 3.2, 1.6 Hz, 1H), 5.08 (dd, J = 12.8, 5.4 Hz, 1H), 4.60 (q, J = 7.2 Hz, 1H), 4.17 (t, J = 6.5 Hz, 2H), 3.56 (s, 3H), 3.04 (q, J = 6.2 Hz, 2H), 2.95-2.81 (m, 1H), 2.63-2.51 (m, 2H), 2.02 (qd, J = 5.7, 5.2, 2.8 Hz, 3H), 1.75 (dq, J = 28.6, 7.0, 6.6 Hz, 4H), 1.44 (tq, J = 15.2, 7.6 Hz, 7H), 1.33-1.19 (m, 5H). |
| 290 | 7-[[2-(2,6-dioxopiperidin-3-yl)-1,3-dioxoisoindol-4-yl]oxy]-N-[(5S)-5-[(1-methanesulfonylpyrrol-3-yl)formamido]-5-[(4-phenyl-1,3-thiazol-2-yl)carbamoyl]pentyl]heptanamide. | 860.45 | $^1$H NMR (300 MHz, DMSO-$d_6$) δ 12.42 (s, 1H), 11.10 (s, 1H), 8.38 (d, J = 7.1 Hz, 1H), 8.02-7.95 (m, 1H), 7.95-7.86 (m, 2H), 7.85-7.79 (m, 1H), 7.79-7.70 (m, 1H), 7.63 (s, 1H), 7.49 (d, J = 8.5 Hz, 1H), 7.44 (ddd, J = 7.8, 5.1, 3.0 Hz, 3H), 7.38-7.32 (m, 1H), 7.30 (dd, J = 3.3, 2.2 Hz, 1H), 6.80 (dd, J = 3.2, 1.6 Hz, 1H), 5.08 (dd, J = 12.8, 5.4 Hz, 1H), 4.61 (q, J = 7.2 Hz, 1H), 4.17 (t, J = 6.4 Hz, 2H), 3.57 (s, 3H), 3.05 (d, J = 5.9 Hz, 2H), 2.96-2.79 (m, 1H), 2.58 (d, J = 19.6 Hz, 2H), 2.11-1.95 (m, 3H), 1.88-1.63 (m, 4H), 1.57-1.35 (m, 7H), 1.30 (t, J = 7.1 Hz, 3H). |
| 291 | (2S)-6-[3-[2-(2-[[2-(2,6-dioxopiperidin-3-yl)-1,3-dioxoisoindol-5-yl]oxy]ethoxy)ethoxy]propanamido]-2-[(1-methanesulfonylpyrrol-3-yl)formamido]-N-(4-phenyl-1,3-thiazol-2-yl)hexanamide | 892.15 | $^1$H NMR (300 MHz, DMSO-d6) δ 12.44 (s, 1H), 11.12 (s, 1H), 8.39 (d, J = 7.0 Hz, 1H), 7.98 (t, J = 1.9 Hz, 1H), 7.93-7.88 (m, 2H), 7.86-7.77 (m, 2H), 7.63 (s, 1H), 7.45-7.29 (m, 6H), 6.79 (dd, J = 3.3, 1.6 Hz, 1H), 5.12 (dd, J = 12.9, 5.3 Hz, 1H), 4.68-4.52 (m, 1H), 4.33-4.22 (m, 2H), 3.82-3.70 (m, 2H), 3.61-3.48 (m, 10H), 3.12-2.97 (m, 2H), 2.95-2.79 (m, 1H), 2.77-2.58 (m, 1H), 2.29 (t, J = 6.4 Hz, 2H), 2.15-1.97 (m, 1H), 1.89-1.68 (m, 2H), 1.53-1.36 (m, 4H). |
| 292 | (2S)-6-[3-[2-(2-[[2-(2,6-dioxopiperidin-3-yl)-1,3-dioxoisoindol-5-yl]amino]ethoxy)ethoxy]propanamido]-2-[(1-methanesulfonylpyrrol-3-yl)formamido]-N-(4-phenyl-1,3-thiazol-2-yl)hexanamide | 891.15 | $^1$H NMR (400 MHz, DMSO-d6) δ 12.44 (s, 1H), 11.10 (s, 1H), 8.39 (d, J = 7.1 Hz, 1H), 7.98 (t, J = 2.0 Hz, 1H), 7.95-7.87 (m, 2H), 7.82 (t, J = 5.6 Hz, 1H), 7.67-7.52 (m, 2H), 7.44 (dd, J = 8.3, 6.7 Hz, 2H), 7.38-7.26 (m, 2H), 7.13 (d, J = 8.6 Hz, 1H), 7.03 (d, J = 7.0 Hz, 1H), 6.80 (dd, J = 3.3, 1.6 Hz, 1H), 6.63-6.57 (m, 1H), 5.06 (dd, J = 12.8, 5.4 Hz, 1H), 4.61 (d, J = 7.2 Hz, 1H), 3.73-3.50 (m, 10H), 3.50-3.43 (m, 4H), 3.09-3.01 (m, 2H), 2.91-2.79 (m, 1H), 2.64-2.58 (m, 1H), 2.28 (t, J = 6.4 Hz, 2H), 2.07-1.97 (m, 1H), 1.82-1.76 (m, 2H), 1.46-1.40 (m, 3H), 1.38-1.32 (m, 1H). |
| 293 | N-(2-[[2-(2,6-dioxopiperidin-3-yl)-1-oxo-3H-isoindol-5-yl]amino]ethyl)-1-[4-[3-(2-[2-[(1-methanesulfonylpyrrol-3-yl)formamido]acetamido]-1,3-thiazol-4-yl)phenyl]pyridin-2-yl]cyclopropane-1-carboxamide | 818.20 | $^1$H NMR (400 MHz, DMSO-d6) δ 12.43 (s, 1H), 11.10 (s, 1H), 8.39 (d, J = 7.1 Hz, 1H), 7.97 (t, J = 2.0 Hz, 1H), 7.94-7.83 (m, 3H), 7.80 (dd, J = 8.5, 7.2 Hz, 1H), 7.62 (s, 1H), 7.49 (d, J = 8.5 Hz, 1H), 7.43 (dd, J = 8.6, 6.9 Hz, 3H), 7.36-7.31 (m, 1H), 7.29 (dd, J = 3.3, 2.3 Hz, 1H), 6.79 (dd, J = 3.3, 1.7 Hz, 1H), 5.08 (dd, J = 12.7, 5.4 Hz, 1H), 4.61 (q, J = 7.2 Hz, 1H), 4.18 (t, J = 6.4 Hz, 2H), 3.56 (s, 3H), 3.06 (q, J = 6.4 Hz, 2H), 2.88 (ddd, J = 16.6, 13.6, 5.3 Hz, 1H), 2.64-2.55 (m, 1H), 2.27 (t, J = 7.4 Hz, 2H), 2.07-1.88 (m, 3H), 1.87-1.69 (m, 2H), 1.44 (d, J = 5.5 Hz, 3H), 1.34 (t, J = 9.4 Hz, 1H). |
| 294 | (2S)-6-(3-[6-[2-(2,6-dioxopiperidin-3-yl)-1,3-dioxoisoindol-5-yl]-2,6-diazaspiro[3.3]heptan-2-yl]propanamido)-2-[(1-methanesulfonylpyrrol-3-yl)formamido]-N-(4-phenyl-1,3-thiazol-2-yl)hexanamide | 884.30 | $^1$H NMR (300 MHz, DMSO-d6) δ 12.46 (s, 1H), 11.08 (s, 1H), 8.41 (d, J = 7.1 Hz, 1H), 7.98 (t, J = 2.0 Hz, 1H), 7.90 (d, J = 7.3 Hz, 3H), 7.69-7.58 (m, 2H), 7.43 (t, J = 7.6 Hz, 2H), 7.38-7.27 (m, 2H), 6.85-6.74 (m, 2H), 6.62-6.58 (m, 1H), 5.06-5.00 (m, 1H), 4.62 (d, J = 7.2 Hz, 1H), 4.06 (s, 4H), 3.60 (s, 1H), 3.06 (s, 2H), 2.92-2.82 (m, 1H), 2.61 (s, 1H), 2.05 (t, J = 7.1 Hz, 3H), 1.80 (s, 2H), 1.44 (s, 4H). |
| 295 | (2S)-6-(5-[[2-(2,6-dioxopiperidin-3-yl)-1,3-dioxoisoindol-4-yl]oxy]pentanemido)-2-[(1-methanesulfonylpyrrol-3- | 832.20 | $^1$H NMR (300 MHz, DMSO-d6) δ 12.43 (s, 1H), 11.10 (s, 1H), 8.39 (d, J = 7.1 Hz, 1H), 7.98 (t, J = 2.0 Hz, 1H), 7.94-7.85 (m, 2H), 7.85-7.75 (m, 2H), 7.63 (s, 1H), 7.52-7.38 (m, 4H), 7.38-7.26 (m, 2H), 6.80 (dd, J = 3.3, 1.6 Hz, 1H), 5.08 (dd, J = 12.8, 5.4 |

TABLE 20-continued

| Cmpd # | Name | LC-MS (ESI) (m/z) | $^1$H NMR |
|---|---|---|---|
| | yl)formamido]-N-(4-phenyl-1,3-thiazol-2-yl)hexanamide | | Hz, 1H), 4.61 (q, J = 7.2 Hz, 1H), 4.23-4.13 (m, 2H), 3.57 (s, 3H), 3.06 (d, J = 6.0 Hz, 2H), 2.88 (m, 1H), 2.65-2.52 (m, 2H), 2.19-1.98 (m, 3H), 1.83-1.65 (m, 6H), 1.44 (s, 4H). |
| 296 | 11-[[2-(2,6-dioxopiperidin-3-yl)-1,3-dioxoisoindol-4-yl]amino]-N-[(5S)-5-[(1-methanesulfonylpyrrol-3-yl)formamido]-5-[(4-phenyl-1,3-thiazol-2-yl)carbamoyl]pentyl] undecanamide | 915.20 | $^1$H NMR (400 MHz, DMSO-d6) δ 12.42 (s, 1H), 11.09 (s, 1H), 8.37 (d, J = 7.0 Hz, 1H), 7.97 (t, J = 2.0 Hz, 1H), 7.93-7.86 (m, 2H), 7.74 (t, J = 5.7 Hz, 1H), 7.62 (s, 1H), 7.60-7.53 (m, 1H), 7.47-7.38 (m, 2H), 7.36-7.26 (m, 2H), 7.07 (d, J = 8.6 Hz, 1H), 7.01 (d, J = 7.0 Hz, 1H), 6.79 (dd, J = 3.3, 1.7 Hz, 1H), 6.55-6.49 (m, 1H), 5.05 (dd, J = 12.8, 5.4 Hz, 1H), 4.65-4.55 (m, 1H), 3.56 (s, 3H), 3.30-3.22 (m, 2H), 3.07-3.01 (m, 2H), 2.95-2.81 (m, 1H), 2.63-2.50 (m, 1H), 2.07-1.96 (m, 3H), 1.82-1.75 (m, 2H), 1.59-1.51 (m, 2H), 1.45-1.41 (m, 5H), 1.26-1.18 (m, 14H). |

The following compounds were prepared using standard chemical manipulations and procedures similar to those used for the preparation of Compound 264

Compound 218—Preparation of (2S,4R)-4-hydroxy-1-[(2S)-2-(8-[4-[(3S)-3-[(1-methanesulfonylpyrrol-3-yl)formamido]-3-[(4-phenyl-1,3-thiazol-2-yl)carbamoyl]propoxy]butanamido]octanamido)-3,3-dimethylbutanoyl]-N-[[4-(4-methyl-1,3-thiazol-5-yl)phenyl]methyl]pyrrolidine-2-carboxamide

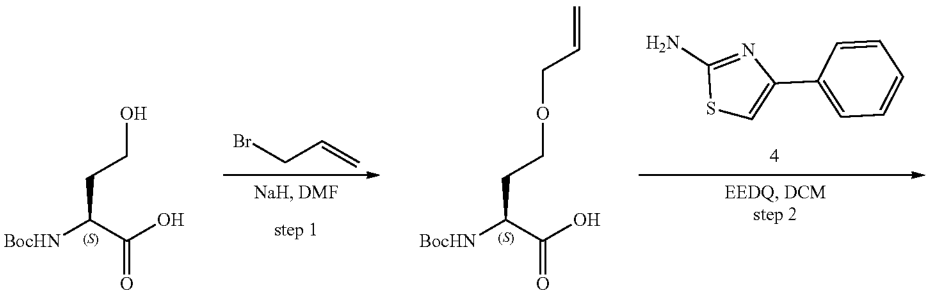

A B

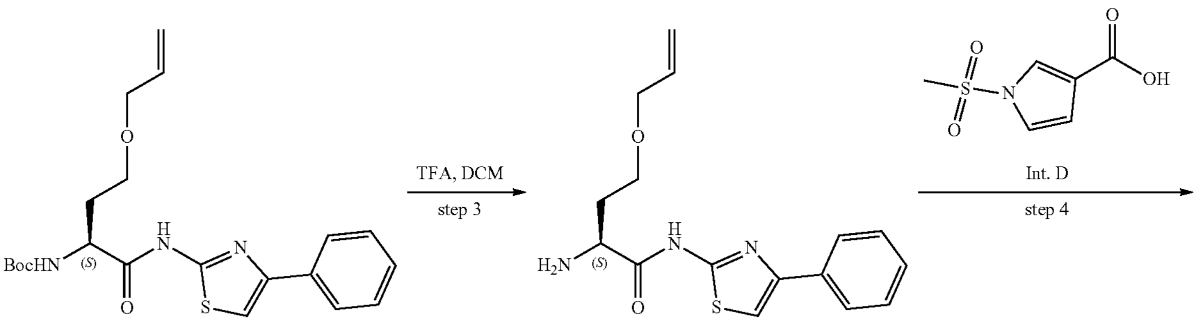

C D

-continued
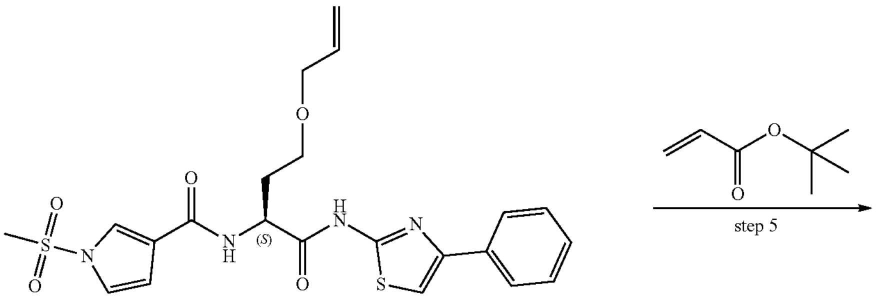
E
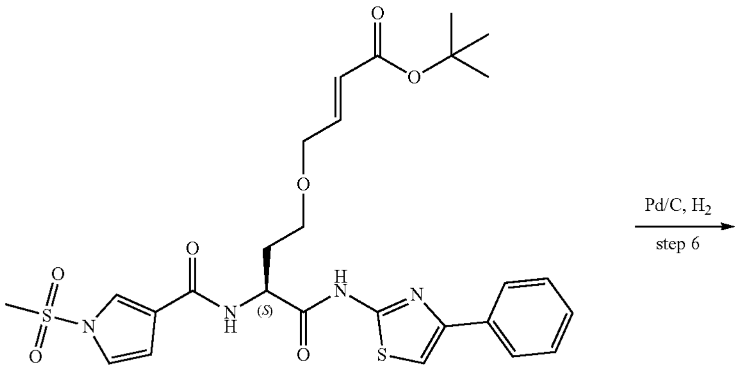
F
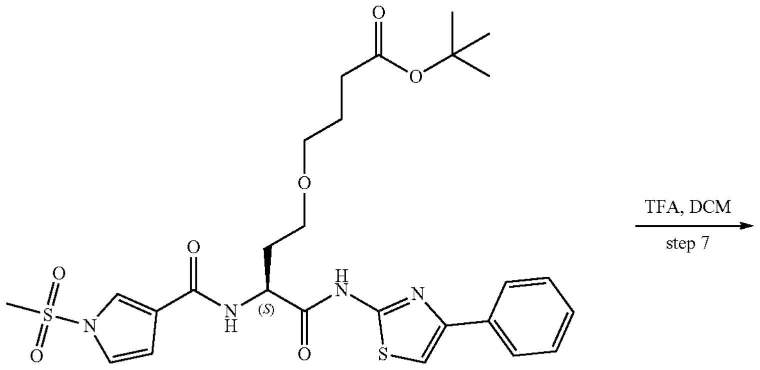
G
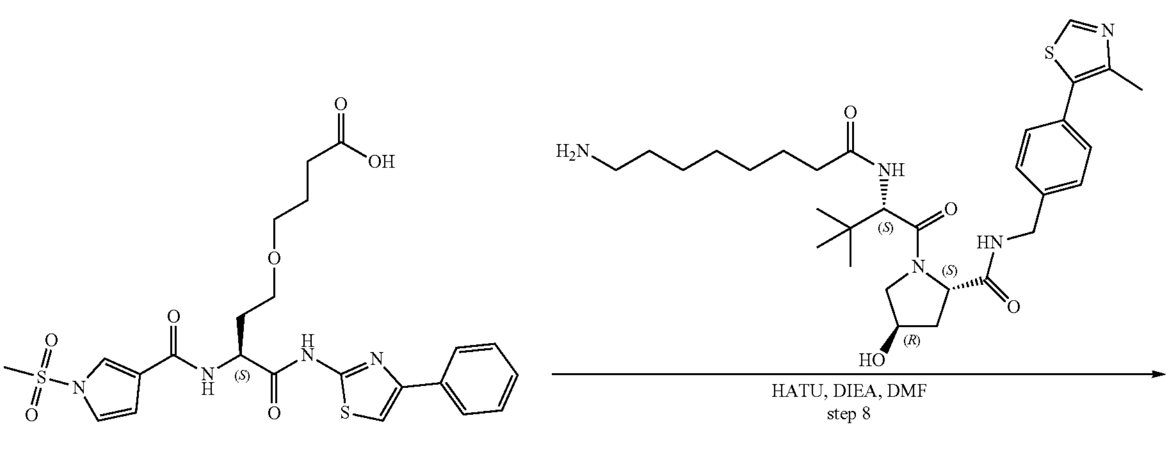
H

-continued

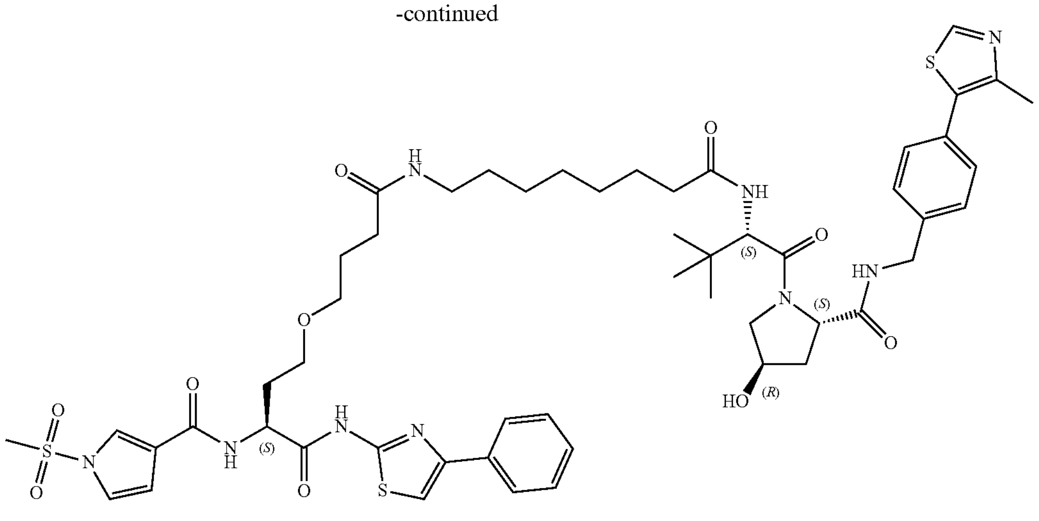

218

Step 1: Preparation of (2S)-2-[(tert-butoxycarbonyl)amino]-4-(prop-2-en-1-yloxy)butanoic acid (Intermediate B)

B

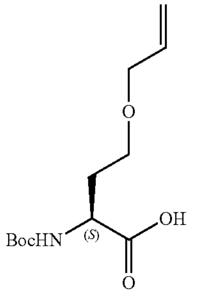

To a stirred solution of (2S)-2-[(tert-butoxycarbonyl)amino]-4-hydroxybutanoic acid (3.00 g, 13.684 mmol, 1.00 equiv) in DMF (2.00 mL) was added NaH (0.66 g, 0.027 mmol, 2.00 equiv) dropwise at 0 degrees C. To the above mixture was added allyl bromide (1.99 g, 0.016 mmol, 1.20 equiv) dropwise over 1 h at 0 degrees C. The resulting mixture was stirred for additional 2 h at 0 degrees. The reaction was quenched by 40 mL water at 0 degrees C. The aqueous layer was washed by EtOAc (30 mL×3) and then acidified to PH ~3 at 0 degrees C. The aqueous fraction was then extracted by EtOAc (30 mL×3). The combined organic layer was dried by sodium sulfate. After removing the organic solvent, the residue was purified by silica gel column chromatography, eluted with DCM/MeOH/AcOH (20/1/0.2) to afford intermediate 3 (3.1 g, 87.37%) as yellow oil. LCMS (ESI) m/z: $[M+H]^+$=260.

Step 2: Preparation of tert-butyl N-[(1S)-1-[(4-phenyl-1,3-thiazol-2-yl)carbamoyl]-3-(prop-2-en-1-yloxy)propyl]carbamate (Intermediate C)

C

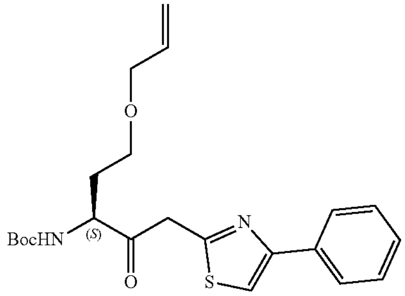

To a stirred solution of intermediate B (1103.48 mg, 4.256 mmol, 1.50 equiv) and ethyl 2-ethoxy-1,2-dihydroquinoline-1-carboxylate (841.89 mg, 3.404 mmol, 1.20 equiv) in DCM (70.00 mL) was added phenthiazamine (500.00 mg, 2.837 mmol, 1.00 equiv). The resulting mixture was stirred overnight at room temperature then concentrated under reduced pressure. The residue was dissolved in EtOAc (50 mL) and washed with 3×20 mL of water. The combined organic layers were dried over anhydrous $Na_2SO_4$ and concentrated under reduced pressure. The residue was purified by silica gel column chromatography, eluted with PE/EtOAc (1:1) to afford intermediate C (800 mg, 67.54%) as a yellow oil. LCMS (ESI) m/z: $[M+H]^+$=418.

Step 3: Preparation of (2S)-2-amino-N-(4-phenyl-1,3-thiazol-2-yl)-4-(prop-2-en-1-yloxy)butanamide (Intermediate D)

D

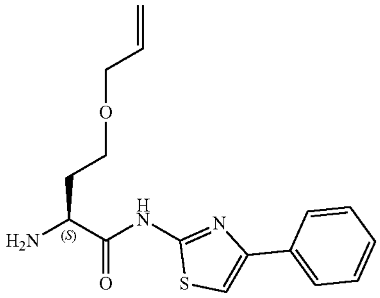

To a stirred solution of intermediate C (400.00 mg, 0.958 mmol, 1.00 equiv) in DCM (5.00 mL) was added TFA (1.00 mL). The resulting mixture was stirred for 2 h at room temperature then concentrated under vacuum to afford intermediate D (400 mg, crude) as a yellow oil. LCMS (ESI) m/z: $[M+H]^+$=318.

Step 4: Preparation of (2S)-2-[(1-methanesulfonylpyrrol-3-yl)formamido]-N-(4-phenyl-1,3-thiazol-2-yl)-4-(prop-2-en-1-yloxy)butanamide (Intermediate E)

E

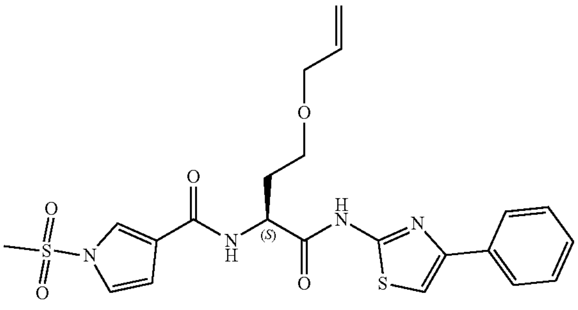

To a stirred solution of 1-(1-methanesulfonylpyrrol-3-yl)ethanone (141.55 mg, 0.756 mmol, 1.20 equiv), HATU (287.50 mg, 0.756 mmol, 1.20 equiv) and DIEA (244.31 mg, 1.890 mmol, 3.00 equiv) in DMF (10.00 mL) was added intermediate D (200.00 mg, 0.630 mmol, 1.00 equiv) dropwise at 0 degrees C. The resulting mixture was stirred for 2 h at room temperature followed by extraction with EtOAc (3x5 mL). The combined organic layers were washed with brine (2x4 mL), dried over anhydrous $Na_2SO_4$, and concentrated under reduced pressure. The residue was purified by silica gel column chromatography, eluted with PE/EtOAc (1:1) to afford intermediate E (100 mg, 35.73%) as a yellow oil. LCMS (ESI) m/z: $[M+H]^+$=489.

Step 5: Preparation of 4-[(3S)-3-[(1-methanesulfonylpyrrol-3-yl)formamido]-3-[(4-phenyl-1,3-thiazol-2-yl)carbamoyl]propoxy]but-2-enoate (Intermediate F)

F

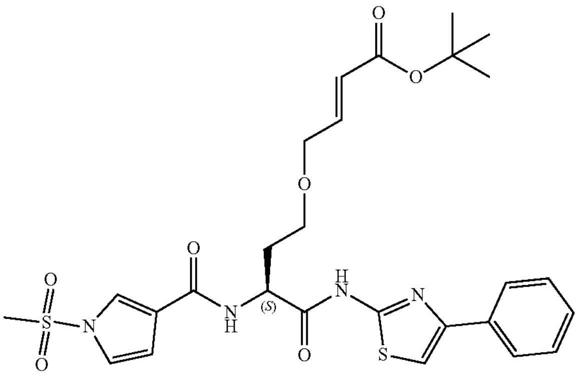

To a stirred solution of intermediate E (110.00 mg, 0.225 mmol, 1.00 equiv) and tert-butyl prop-2-enoate (288.57 mg, 2.251 mmol, 10.00 equiv) in DCM (30.00 mL) was added [1,3-bis(2,4,6-trimethylphenyl)imidazolidin-2-ylidene]dichloro[[2-(propan-2-yloxy)phenyl]methylidene]ruthenium (14.11 mg, 0.023 mmol, 0.10 equiv). The resulting mixture was stirred for overnight at 40 degrees C. under a nitrogen atmosphere, then concentrated under vacuum. The residue was purified by silica gel column chromatography, eluted with PE/EtOAc (1:1) to afford intermediate F (80 mg, 60.36%). LCMS (ESI) m/z: $[M+H]^+$=589.

Step 6: Preparation of tert-butyl 4-[(3S)-3-[(1-methanesulfonylpyrrol-3-yl)formamido]-3-[(4-phenyl-1,3-thiazol-2-yl)carbamoyl]propoxy]butanoate (Intermediate G)

G

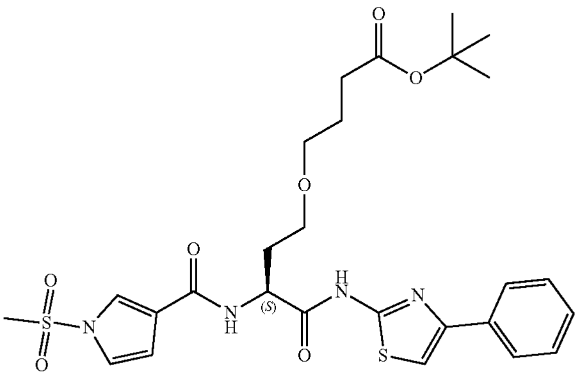

To a stirred solution of intermediate F (80.00 mg, 0.136 mmol, 1.00 equiv) in MeOH (6.00 mL) was added 10% Pd/C (43.39 mg, 0.408 mmol, 3.00 equiv). The resulting mixture was stirred for 2 h at room temperature under a hydrogen atmosphere. The mixture was filtered, and concentrated under vacuum to afford intermediate G (70 mg, 87.20%) as a brown oil. LCMS (ESI) m/z: $[M+H]^+$=591.

Step 7: Preparation of 4-[(3S)-3-[(1-methanesulfonylpyrrol-3-yl)formamido]-3-[(4-phenyl-1,3-thiazol-2-yl)carbamoyl]propoxy]butanoic acid (Intermediate H)

H

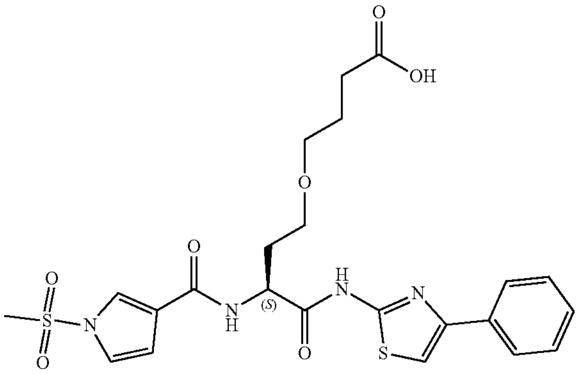

To a stirred solution of intermediate G (70.00 mg, 0.119 mmol, 1.00 equiv) in DCM (1.20 mL) was added TFA (0.40 mL) dropwise. The resulting mixture was stirred for 1 h then concentrated under vacuum to afford intermediate H (50 mg, 78.93%) as a black oil. LCMS (ESI) m/z: $[M+H]^+=535$.

Step 8: Preparation of (2S,4R)-4-hydroxy-1-[(2S)-2-(8-[4-[(3S)-3-[(1-methanesulfonylpyrrol-3-yl)formamido]-3-[(4-phenyl-1,3-thiazol-2-yl)carbamoyl]propoxy]butanamido]octanamido)-3,3-dimethylbutanoyl]-N-[[4-(4-methyl-1,3-thiazol-5-yl)phenyl]methyl]pyrrolidine-2-carboxamide (Compound 218)

218

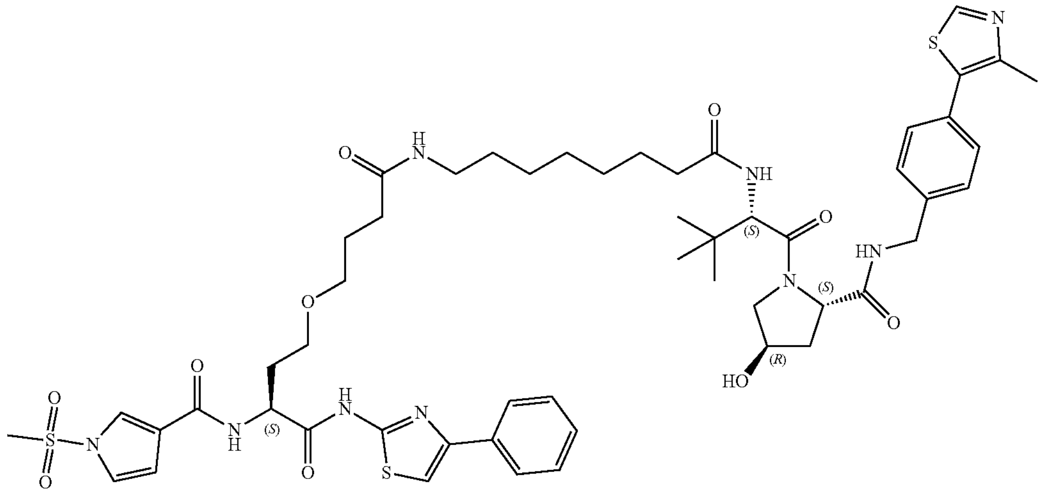

To a stirred solution of intermediate H (9.00 mg, 0.017 mmol, 1.00 equiv) and HATU (6.40 mg, 0.017 mmol, 1.00 equiv) in DMF (1.50 mL) was added DIEA (6.53 mg, 0.051 mmol, 3.00 equiv) and (2S,4R)-1-[(2S)-2-(8-aminooctanamido)-3,3-dimethylbutanoyl]-4-hydroxy-N-[[4-(4-methyl-1,3-thiazol-5-yl)phenyl]methyl]pyrrolidine-2-carboxamide (9.63 mg, 0.017 mmol, 1.00 equiv). After stirring at rt for 2 h, the reaction mixture was purified directly by HPLC to afford Compound 218 (1.8 mg) as a white solid. $^1$H NMR (400 MHz, DMSO-d6) δ 12.41 (s, 1H), 8.98 (s, 1H), 8.56 (t, J=6.0 Hz, 1H), 8.44 (d, J=7.1 Hz, 1H), 7.98-7.93 (m, 1H), 7.93-7.87 (m, 2H), 7.85-7.79 (m, 1H), 7.68 (t, J=5.5 Hz, 1H), 7.62 (s, 1H), 7.46-7.36 (m, 6H), 7.35-7.28 (m, 2H), 6.7-6.75 (m, 1H), 5.12 (d, J=3.5 Hz, 1H), 4.74-4.64 (m, 1H), 4.54 (d, J=9.3 Hz, 1H), 4.47-4.38 (m, 2H), 4.37-4.31 (m, 1H), 4.27-4.17 (m, 1H), 3.70-3.60 (m, 2H), 3.57 (s, 3H), 3.53-3.41 (m, 3H), 2.99 (q, J=6.6 Hz, 2H), 2.44 (s, 3H), 2.28-2.18 (m, 1H), 2.13-1.95 (m, 6H), 1.94-1.85 (m, 1H), 1.72-1.63 (m, 2H), 1.52-1.38 (m, 2H), 1.38-1.28 (m, 2H), 1.26-1.12 (m, 7H), 0.93 (s, 9H). LCMS [M+H]$^+$=1088.15.

TABLE 21

The following compounds were prepared using standard chemical manipulations and procedures similar to those used for the preparation of Compound 218

| Cmpd # | Name | LC-MS (ESI) (m/z) | $^1$H NMR |
|---|---|---|---|
| 219 | (2S)-4-[4-[4-(2-[[2-(2,6-dioxopiperidin-3-yl)-1,3-dioxoisoindol-5-yl]oxy]ethyl)piperazin-1-yl]-4-oxobutoxy]-2-[(1-methanesulfonylpyrrol-3-yl)formamido]-N-(4-phenyl-1,3-thiazol-2-yl)butanamide. | 903.45 | $^1$H NMR (300 MHz, DMSO-$d_6$) δ 12.42 (s, 1H), 11.13 (s, 1H), 8.45 (d, J = 7.2 Hz, 1H), 8.00-7.85 (m, 4H), 7.63 (s, 1H), 7.53-7.27 (m, 6H), 6.78 (dd, J = 3.3, 1.6 Hz, 1H), 5.13 (dd, J = 12.9, 5.4 Hz, 1H), 4.76-4.68 (m, 1H),4.61-4.00 (m, 3H), 3.54 (s, 3H), 3.46-3.38 (m, 3H),3.40-3.37 (m, 6H), 2.93-2.85 (m, 2H), 2.62-2.54 (m, 3H), 2.35 (s, 3H), 2.16-1.92 (m, 4H), 1.70 (d, J = 6.9 Hz, 2H). |
| 220 | N-((2S)-4-(4-(4-((4-(2-(2,6-dioxopiperidin-3-yl)-1,3-dioxoisoindolin-5-yl)piperazin-1-yl)methyl)piperidin-1-yl)-4-oxobutoxy)-1-oxo-1-((4-phenylthiazol-2-yl)amino)butan-2-yl)-1-(methylsulfonyl)-1H-pyrrole-3-carboxamide formate | 956.15 | $^1$H NMR (400 MHz, DMSO-d6) δ 12.41 (s, 1H), 11.08 (s, 1H), 8.43 (d, J = 7.2 Hz, 1H), 7.97-7.86 (m, 3H), 7.63 (s, 2H), 7.51-7.21 (m, 6H), 6.78 (dd, J = 3.3, 1.6 Hz, 1H), 5.08 (d, J = 12.8 Hz, 1H), 4.72 (d, J = 7.3 Hz, 1H), 4.36 (s, 1H), 4.20 (s, 1H), 3.78 (s, 1H), 3.57 (s, 4H), 3.50 (t, J = 6.2 Hz, 2H), 3.40 (s, 4H), 3.10 (d, J = 31.6 Hz, 1H), 2.89 (td, J = 16.0, 14.4, 5.7 Hz, 2H), 2.70-2.54 (m, 3H), 2.47-2.539 (m, 3H), 2.35-2.23 (m, 2H), 2.19-1.92 (m, 5H), 1.68 (d, J = 7.8 Hz, 5H), 0.98 (s, 2H). |
| 221 | (2S)-4-[4-[3-([4-[2-(2,6-dioxopiperidin-3-yl)-1,3-dioxoisoindol-5-yl]piperazin-1-yl]methyl)azetidin-1-yl]-4-oxobutoxy]-2-[(1-methanesulfonylpyrrol-3-yl)formamido]-N-(4-phenyl-1,3-thiazol-2-yl)butanamide | 928.25 | $^1$H NMR (300 MHz, DMSO-$d_6$) δ 12.43 (s, 1H), 11.10 (s, 1H), 10.56 (s, 1H), 8.46 (d, J = 7.2 Hz, 1H), 8.02-7.85 (m, 3H), 7.76 (d, J = 8.5 Hz, 1H), 7.64 (s, 1H), 7.54-7.39 (m, 3H), 7.38-7.26 (m, 3H), 6.79 (dd, J = 3.3, 1.6 Hz, 1H), 5.10 (dd, J = 12.8, 5.3 Hz, 1H), 4.71 (m, 1H), 4.20 (m, 3H), 3.93 (m, 2H), 3.74-3.63 (m, 1H), 3.58 (s, 3H), 3.55-3.46 (m, 4H), 3.31 (s, 4H), 3.12 (m, 4H), 2.98-2.81 (m, 1H), 2.77-2.55 (m, 2H), 2.32-2.24 (m, 1H), 2.05 (m, 5H), 1.67 (t, J = 6.9 Hz, 2H). |
| 249 | (2S,4R)-4-hydroxy-1-[(2S)-2-[2-[2-(2-[4-[(3S)-3-[(1-methanesulfonylpyrrol-3-yl)formamido]-3-[(4-phenyl-1,3-thiazol-2-yl)carbamoyl]propoxy]butanamido]ethoxy)ethoxy]acetamido]-3,3-dimethylbutanoyl]-N-[[4-(4-methyl-1,3-thiazol-5-yl)phenyl]methyl]pyrrolidine-2-carboxamide | 1092.50 | $^1$H NMR (400 MHz, DMSO-d6) δ 12.40 (s, 1H), 8.97 (s, 1H), 8.57 (t, J = 6.0 Hz, 1H), 8.43 (d, J = 7.9 Hz, 1H), 7.95 (t, J = 2.0 Hz, 1H), 7.93-7.86 (m, 2H), 7.81 (t, J = 6.0 Hz, 1H), 7.61 (s, 1H), 7.46-7.39 (m, 3H), 7.38 (s, 3H), 7.32 (d, J = 7.9 Hz, 1H), 7.30 (t, J = 2.0 Hz, 1H), 6.77 (dd, J = 3.3, 2.0 Hz, 1H), 5.16 (s, 1H), 4.73-4.62 (m, 1H), 4.58 (d, J = 9.6 Hz, 1H), 4.44 (t, J = 8.1 Hz, 1H), 4.41-4.33 (m, 2H), 4.31-4.22 (m, 1H), 3.96 (s, 2H), 3.70-3.55 (m, 8H), 3.55-3.50 (m, 2H), 3.47 (t, J = 6.7 Hz, 2H), 3.40 (t, J = 6.7 Hz, 2H), 3.37-3.35 (m, 1H), 3.28-3.25 (m, 1H), 3.24-3.17 (m, 2H), 2.43 (s, 3H), 2.15-2.07 (m, 4H), 2.04-1.94 (m, 1H), 1.94-1.86 (m, 1H), 1.73-1.64 (m, 2H), 0.94 (s, 9H). |
| 250 | (2R,4R)-4-hydroxy-1-[(2S)-2-(2-[2-[2-(2-[4-[(3S)-3-[(1-methanesulfonylpyrrol-3-yl)formamido]-3-[(4-phenyl-1,3-thiazol-2-yl)carbamoyl]propoxy]butanamido]ethoxy)ethoxy]ethoxy]acetamido)-3,3-dimethylbutanoyl]-N-[[4-(4-methyl-1,3-thiazol-5-yl)phenyl]methyl]pyrrolidine-2-carboxamide | 1136.15 | $^1$H NMR (400 MHz, DMSO-d6) δ 8.97 (brs, 1H), 8.59 (t, J = 6.0 Hz, 1H), 8.44 (d, J = 7.1 Hz, 1H), 7.97-7.93 (m, 1H), 7.92-7.87 (m, 2H), 7.79 (t, J = 5.6 Hz, 1H), 7.62 (s, 1H), 7.47-7.36 (m, 6H), 7.35-7.27 (m, 2H), 6.7-6.76 (m, 1H), 5.15 (s, 1H), 4.73-4.63 (m, 1H), 4.56 (d, J = 9.6 Hz, 1H), 4.46-4.39 (m, 3H), 4.38-4.32 (m, 2H), 4.30-4.19 (m, 1H), 3.96 (s, 2H), 3.69-3.45 (m, 17H), 3.19-3.10 (m, 2H), 2.44 (s, 3H), 2.14-2.04 (m, 4H), 2.03-1.96 (m, 1H), 1.93-1.85 (m, 1H), 1.72-1.63 (m, 2H), 0.94 (s, 9H). |
| 251 | (2S,4R)-4-hydroxy-1-[(2S)-2-(6-[4-[(3S)-3-[(1-methanesulfonylpyrrol-3-yl)formamido]-3-[(4-phenyl-1,3-thiazol-2-yl)carbamoyl]propoxy]bu- | 1060.55 | $^1$H NMR (300 MHz, DMSO-$d_6$) δ 12.42 (s, 1H), 8.99 (s, 1H), 8.57 (t, J = 6.1 Hz, 1H), 8.45 (d, J = 7.1 Hz, 1H), 8.00-7.79 (m, 4H), 7.74 (t, 1H) 7.61 (s, 1H), 7.49-7.26 (m, 8H), 6.78 (dd, J = 3.3, 1.6 Hz, 1H), 5.13 (d, J = 3.4 Hz, 1H), 4.70 (q, J = 7.5, 6.6 Hz, 1H), 4.54 (d, 1H), 4.47-4.39 (m, 2H), 4.36 (s, 1H), 4.21 |

TABLE 21-continued

The following compounds were prepared using standard chemical manipulations and procedures similar to those used for the preparation of Compound 218

| Cmpd # | Name | LC-MS (ESI) (m/z) | $^1$H NMR |
|---|---|---|---|
| | tanamido]hexanamido)-3,3-dimethylbutanoyl]-N-[[4-(4-methyl-1,3-thiazol-5-yl)phenyl]methyl]pyrrolidine-2-carboxamide. | | (dd, 1H), 3.66 (d, J = 3.7 Hz, 2H), 3.58 (s, 3H), 3.49 (t, J = 6.6 Hz, 2H), 3.44-3.36 (m, 2H), 2.99 (q, J = 6.6 Hz, 2H), 2.45 (s, 3H), 2.26-2.18 (m, 1H), 2.12-2.04 (m, 6H), 1.94-1.86 (m, 1H), 1.69 (q, J = 6.9 Hz, 2H), 1.49-1.41 (m, 2H), 1.37-1.29 (m, 2H), 1.24-1.16 (m, 2H), 0.92 (s, 9H). |
| 252 | (2S)-4-[3-[(2-[[2-(2-[[2-(2,6-dioxopiperidin-3-yl)-1,3-dioxoisoindol-4-yl]oxy]acetamido)ethyl](methyl)amino]ethyl)carbamoyl]propoxy]-2-[(1-methanesulfonylpyrrol-3-yl)formamido]-N-(4-phenyl-1,3-thiazol-2-yl)butanamide; formic acid | 948.10 | $^1$H NMR (300 MHz, DMSO-d6) δ 12.42 (s, 1H), 11.12 (s, 1H), 8.45 (d, J = 7.1 Hz, 1H), 7.96 (t, J = 2.0 Hz, 1H), 7.94-7.87 (m, 3H), 7.80 (dd, J = 8.5, 7.3 Hz, 1H), 7.62 (d, J = 5.2 Hz, 2H), 7.52-7.36 (m, 4H), 7.36-7.28 (m, 2H), 6.78 (dd, J = 3.3, 1.6 Hz, 1H), 5.13 (dd, J = 12.8, 5.4 Hz, 1H), 4.78 (s, 2H), 4.69 (q, J = 7.0, 5.3 Hz, 1H), 3.57 (s, 4H), 3.21 (t, J = 6.1 Hz, 3H), 3.12 (q, J = 6.4 Hz, 3H), 2.99-2.90 (m, 2H), 2.66-2.54 (m, 2H), 2.48-2.30 (m, 4H), 2.17 (s, 3H), 2.06 (q, J = 9.3, 8.4 Hz, 5H), 1.67 (p, J = 6.8 Hz, 2H). |
| 253 | (2S)-4-(3-[[2-(2-[[2-(2,6-dioxopiperidin-3-yl)-1,3-dioxoisoindol-4-yl]amino]ethanesulfonyl)ethyl]carbamoyl]propoxy)-2-[(1-methanesulfonylpyrrol-3-yl)formamido]-N-(4-phenyl-1,3-thiazol-2-yl)butanamide | 925.10 | $^1$H NMR (400 MHz, DMSO-$d_6$) δ 12.40 (s, 1H), 11.09 (s, 1H), 8.43 (d, J = 7.2 Hz, 1H), 8.07-7.99 (m, 1H), 7.98-7.93 (m, 1H), 7.93-7.86 (m, 2H), 7.66-7.57 (m, 2H), 7.47-7.38 (m, 2H), 7.36-7.25 (m, 2H), 7.18-7.12 (m, 1H), 7.11-7.05 (m, 1H), 6.87-6.80 (m, 1H), 6.80-6.75 (m, 1H), 5.10-5.01 (m, 1H), 4.74-4.64 (m, 1H), 3.81-3.71 (m, 2H), 3.57 (s, 3H), 3.53-3.40 (m, 6H), 3.40-3.33 (m, 2H), 3.33-3.27 (m, 2H), 2.95-2.81 (m, 1H), 2.64-2.50 (m, 2H), 2.16-1.86 (m, 5H), 1.74-1.62 (m, 2H). |
| 254 | (2S)-4-[4-[4-(5-[[2-(2,6-dioxopiperidin-3-yl)-1,3-dioxoisoindol-5-yl]oxy]pentyl)piperazin-1-yl]-4-oxobutoxy]-2-[(1-methanesulfonylpyrrol-3-yl)formamido]-N-(4-phenyl-1,3-thiazol-2-yl)butanamide | 945.25 | $^1$H NMR (300 MHz, DMSO-$d_6$) δ 12.42 (s, 1H), 11.12 (s, 1H), 8.45 (d, J = 7.2 Hz, 1H), 7.99-7.80 (m, 4H), 7.64 (s, 1H), 7.48-7.39 (m, 3H), 7.38-7.28 (m, 3H), 6.78 (m, 1H), 5.12 (dd, J = 12.9, 5.3 Hz, 1H), 4.73 (q, J = 7.2, 6.2 Hz, 1H), 4.18 (t, J = 6.4 Hz, 2H), 3.58 (s, 3H), 3.54-3.47 (m, 3H), 3.43 (m, 4H), 3.02-2.80 (m, 3H), 2.78-2.54 (m, 4H), 2.42-2.21 (m, 3H), 2.17-1.91 (m, 4H), 1.84-1.52 (m, 6H), 1.44 (s, 2H), 1.26 (d, J = 7.7 Hz, 1H). |
| 255 | (2S)-4-[4-[4-(3-[[2-(2,6-dioxopiperidin-3-yl)-1,3-dioxoisoindol-5-yl]oxy]propyl) piperazin-1-yl]-4-oxobutoxy]-2-[(1-methanesulfonylpyrrol-3-yl)formamido]-N-(4-phenyl-1,3-thiazol-2-yl)butanamide | 917.45 | 1H NMR (400 MHz, DMSO-d6) δ 12.41 (s, 1H), 11.11 (s, 1H), 8.43 (d, J = 7.2 Hz, 1H), 7.95 (t, J = 2.1 Hz, 1H), 7.93-7.87 (m, 2H), 7.83 (d, J = 8.3 Hz, 1H), 7.62 (s, 1H), 7.48-7.38 (m, 3H), 7.37-7.28 (m, 3H), 6.77 (dd, J = 3.4, 1.6 Hz, 1H), 5.12 (dd, J = 12.9, 5.4 Hz, 1H), 4.74-4.68 (m, 1H), 4.20 (t, J = 6.3 Hz, 2H), 3.57 (s, 3H), 3.50 (d, J = 6.1 Hz, 3H), 3.25-3.17 (m, 4H), 2.87 (d, J = 13.8 Hz, 2H), 2.64-2.53 (m, 2H), 2.40 (t, J = 7.0 Hz, 2H), 2.29 (q, J = 7.3, 5.6 Hz, 6H), 2.12-1.97 (m, 3H), 1.91-1.85 (m, 2H), 1.71-1.63 (m, 2H). |
| 256 | (2S)-4-[4-(3-[[2-(2,6-dioxopiperidin-3-yl)-1,3-dioxoisoindol-5-yl]oxy]azetidin-1-yl)-4-oxobutoxy]-2-[(1-methanesulfonylpyrrol-3-yl)formamido]-N-(4-phenyl-1,3-thiazol-2-yl)butanamide | 846.30 | $^1$H NMR (400 MHz, DMSO-$d_6$) δ 12.41 (s, 1H), 11.12 (s, 1H), 8.43 (d, J = 7.1 Hz, 1H), 7.99-7.93 (m, 1H), 7.92-7.87 (m, 2H), 7.87-7.82 (m, 1H), 7.62 (s, 1H), 7.46-7.38 (m, 2H), 7.35-7.25 (m, 4H), 6.82-6.72 (m, 1H), 5.26-5.09 (m, 2H), 4.76-4.66 (m, 1H), 4.62-4.51 (m, 1H), 4.37-4.26 (m, 1H), 4.14-4.06 (m, 1H), 3.84-3.75 (m, 1H), 3.61-3.55 (m, 3H), 3.53-3.46 (m, 2H), 3.44-3.37 (m, 2H), 2.96-2.82 (m, 1H), 2.69-2.54 (m, 2H), 2.14-1.94 (m, 5H), 1.73-1.60 (m, 2H). |
| 257 | ((2S)-4-[4-[4-(4-[4-[2-(2,6-dioxopiperidin-3-yl)-1,3-dioxoisoindol-5-yl]piperazin-1-yl]butyl)piperidin-1-yl]-4-oxobutoxy]-2-[(1-methanesulfonylpyrrol-3-yl)formamido]-N-(4-phenyl-1,3-thiazol-2-yl)butanamide; formic acid | 998.20 | $^1$H NMR (300 MHz, DMSO-$d_6$) δ 12.41 (s, 1H), 11.09 (s, 1H), 8.43 (d, J = 7.1 Hz, 1H), 8.14 (s, 1H), 7.98-7.94 (m, 1H), 7.94-7.88 (m, 2H), 7.70 (d, J = 8.4 Hz, 1H), 7.63 (s, 1H), 7.49-7.40 (m, 2H), 7.40-7.24 (m, 4H), 6.82-6.74 (m, 1H), 5.16-5.02 (m, 1H), 4.79-4.66 (m, 1H), 4.45-4.29 (m, 1H), 3.84-3.71 (m, 1H), 3.58 (s, 3H), 3.55-3.45 (m, 4H), 3.44-3.38 (m, 2H), 2.98-2.81 (m, 2H), 2.75-2.59 (m, 3H), 2.59-2.54 (m, 1H), 2.42 (d, J = 13.2 Hz, 2H), 2.34-2.23 (m, 3H), 2.15-1.92 (m, 4H), 1.74-1.34 (m, 8H), 1.34-1.12 (m, 5H), 1.05-0.77 (m, 3H). |
| 258 | (2S)-4-(3-[[2-(2-[2-[2-(2-[[2-(2,6-dioxopiperidin-3-yl)-1,3-dioxoisoindol-4-yl]oxy] acetamido)ethoxy]ethoxy]ethoxy)ethyl]carbamoyl]propoxy)-2-[(1- | 1023.50 | $^1$H NMR (400 MHz, DMSO-d6) δ 12.40 (s, 1H), 11.11 (s, 1H), 8.43 (d, J = 7.1 Hz, 1H), 8.00 (t, J = 5.6 Hz, 1H), 7.95 (t, J = 2.0 Hz, 1H), 7.92-7.87 (m, 2H), 7.84-7.75 (m, 2H), 7.62 (s, 1H), 7.49 (d, J = 7.2 Hz, 1H), 7.46-7.37 (m, 3H), 7.36-7.28 (m, 2H), 6.77 (dd, J = 3.3, 1.7 Hz, 1H), 5.11 (dd, J = 12.9, 5.4 Hz, |

TABLE 21-continued

The following compounds were prepared using standard chemical manipulations and procedures similar to those used for the preparation of Compound 218

| Cmpd # | Name | LC-MS (ESI) (m/z) | $^1$H NMR |
|---|---|---|---|
| | methanesulfonylpyrrol-3-yl)formamido]-N-(4-phenyl-1,3-thiazol-2-yl)butanamide | | 1H), 4.78 (s, 2H), 4.72-4.66 (m, 1H), 3.57 (s, 3H), 3.53-3.42 (m, 12H),3.40-3.38 (m, 1H), 3.38-3.34 (m, 2H), 3.32-3.31 (m, 3H), 3.16 (d, J = 5.8 Hz, 2H), 2.93-2.86 (m, 1H), 2.69-2.53 (m, 2H), 2.13-1.95 (m, 5H), 1.68 (p, J = 6.9 Hz, 2H). |
| 259 | (2S)-4-[4-[3-([[2-(2,6-dioxopiperidin-3-yl)-1,3-dioxoisoindol-4-yl]oxy]methyl)azetidin-1-yl]-4-oxobutoxy]-2-[(1-methanesulfonylpyrrol-3-yl)formamido]-N-(4-phenyl-1,3-thiazol-2-yl)butanamide. | 860.40 | $^1$H NMR (300 MHz, DMSO-$d_6$) δ 12.42 (s, 1H), 11.12 (s, 1H), 8.43 (d, J = 7.1 Hz, 1H), 7.97-7.89 (m, 3H), 7.86-7.78 (m, 1H), 7.62 (s, 1H), 7.49-7.41 (m, 4H), 7.34-7.27 (m, 2H), 6.76 (d, J = 3.0 Hz, 1H), 5.18 (dd, J = 12.9, 5.4 Hz, 1H), 4.71 (q, J = 7.2, 6.7 Hz, 1H), 4.32 (d, J = 6.6 Hz, 2H), 4.19 (q, J = 8.1 Hz, 1H), 3.91 (dd, J = 12.3, 7.1 Hz, 2H), 3.68 (d, J = 10.2 Hz, 1H), 3.57 (s, 3H), 3.54-3.46 (m, 2H), 3.44-3.36 (m, 2H), 3.03 (s, 1H), 2.86-2.78 (m, 1H), 2.59 (d, J = 19.9 Hz, 2H), 2.04 (d, J = 9.1 Hz, 5H), 1.67-1.59 (m, 2H). |
| 260 | (2S)-4-[4-[3-([[2-(2,6-dioxopiperidin-3-yl)-1,3-dioxoisoindol-5-yl]oxy]methyl)azetidin-1-yl]-4-oxobutoxy]-2-[(1-methanesulfonylpyrrol-3-yl)formamido]-N-(4-phenyl-1,3-thiazol-2-yl)butanamide. | 860.40 | $^1$H NMR (300 MHz, DMSO-$d_6$) δ 12.42 (s, 1H), 11.12 (s, 1H), 8.43 (d, J = 7.1 Hz, 1H), 8.02-7.76 (m, 4H), 7.62 (s, 1H), 7.48-7.40 (m, 3H), 7.36-7.28 (m, 3H), 6.77 (d, J = 3.0 Hz, 1H), 5.12 (dd, J = 12.9, 5.4 Hz, 1H), 4.71 (q, J = 7.2, 6.7 Hz, 1H), 4.31 (d, J = 6.6 Hz, 2H), 4.19 (q, J = 8.1 Hz, 1H), 3.91 (dd, J = 12.3, 7.1 Hz, 2H), 3.65 (d, J = 10.2 Hz, 1H), 3.57 (s, 3H), 3.54-3.46 (m, 2H), 3.44-3.36 (m, 2H), 3.01-2.93 (s, 1H), 2.89-2.81 (m, 1H), 2.59 (d, J = 19.9 Hz, 2H), 2.06 (d, J = 9.1 Hz, 5H), 1.73-1.60 (m, 2H). |
| 261 | (2S)-4-(3-[[2-([3-[(2-[[2-(2,6-dioxopiperidin-3-yl)-1,3-dioxoisoindol-5-yl]oxy]ethoxy)meth-yl]phenyl]methoxy)ethyl]car-bamoyl]propoxy)-2-[(1-methanesulfonylpyrrol-3-yl)formamido]-N-(4-phenyl-1,3-thiazol-2-yl)butanamide | 998.15 | $^1$H NMR (300 MHz, DMSO-d6) δ 12.42 (s, 1H), 11.12 (s, 1H), 8.44 (d, J = 7.1 Hz, 1H), 7.96 (t, J = 2.2, Hz, 1H), 7.93-7.80 (m, 4H), 7.62 (s, 1H), 7.49-7.26 (m, 8H), 7.23 (d, J = 7.0 Hz, 2H), 6.78 (dd, J = 3.3, 1.6 Hz, 1H), 5.12 (dd, J = 12.9, 5.4 Hz, 1H), 4.69 (q, J = 7.1, 5.8 Hz, 1H), 4.55 (s, 2H), 4.45 (s, 2H), 4.36 (t, J = 4.4 Hz, 2H), 3.81 (t, J = 4.4 Hz, 2H), 3.57 (s, 3H), 3.48 (t, J = 6.4 Hz, 2H), 3.40 (d, J = 5.8 Hz, 2H), 3.33-3.30 (m, 1H), 3.28-3.24 (m, 1H), 3.23 (d, J = 5.7 Hz, 2H), 2.97-2.82 (m, 1H), 2.60 (d, J = 19.2 Hz, 2H), 2.13-2.90 (m, 5H), 1.68 (p, J = 6.9 Hz, 2H). |
| 262 | (2S)-4-[4-(2-[[2-(2,6-dioxopiperidin-3-yl)-1,3-dioxoisoindol-5-yl]oxy]-7-azaspiro[3.5]nonan-7-yl)-4-oxobutoxy]-2-[(1-methanesulfonylpyrrol-3-yl)formamido]-N-(4-phenyl-1,3-thiazol-2-yl)butanamide | 914.15 | $^1$H NMR (300 MHz, DMSO-d6) δ 12.42 (s, 1H), 11.12 (s, 1H), 8.44 (d, J = 7.0 Hz, 1H), 7.96 (q, J = 2.1 Hz, 1H), 7.94-7.87 (m, 2H), 7.83 (d, J = 8.2 Hz, 1H), 7.63 (d, J = 3.1 Hz, 1H), 7.46-7.39 (m, 2H), 7.37-7.23 (m, 4H), 6.78 (t, J = 3.1, Hz, 1H), 5.13 (dd, J = 12.8, 5.4 Hz, 1H), 4.97 (t, J = 12.2 Hz, 1H), 4.72 (s, 1H), 3.58 (d, J = 1.5 Hz, 3H), 3.51 (s, 2H), 3.40 (s, 3H), 3.31 (s, 2H), 3.22-3.18 (m, 1H), 2.97-2.81 (m, 1H), 2.69-2.58 (m, 2H), 2.45 (d, J = 5.2 Hz, 2H), 2.29 (q, J = 7.7 Hz, 2H), 2.05 (d, J = 15.1 Hz, 3H), 1.91-1.76 (m, 2H), 1.67 (s, 2H), 1.60-1.38 (m, 4H). |
| 263 | (2S)-4-[4-(4-[5-[2-(2,6-dioxopiperidin-3-yl)-1,3-dioxoisoindol-5-yl]pent-4-yn-1-yl]piperazin-1-yl)-4-oxobutoxy]-2-[(1-methanesulfonylpyrrol-3-yl)formamido]-N-(4-phenyl-1,3-thiazol-2-yl)butanamide; formic acid | 925.15 | $^1$H NMR (400 MHz, DMSO-$d_6$) δ 12.41 (s, 1H), 11.13 (s, 1H), 8.43 (d, J = 7.2 Hz, 1H), 7.98-7.93 (m, 1H), 7.93-7.81 (m, 5H), 7.62 (s, 1H), 7.47-7.38 (m, 2H), 7.36-7.27 (m, 2H), 6.80-6.75 (m, 1H), 5.20-5.11 (m, 1H), 4.76-4.66 (m, 1H), 3.57 (s, 3H), 3.54-3.46 (m, 2H), 3.44-3.34 (m, 6H), 2.96-2.82 (m, 1H), 2.72-2.53 (m, 2H), 2.51 (s, 1H), 2.39 (t, J = 7.0 Hz, 2H), 2.34-2.24 (m, 6H), 2.16-1.88 (m, 4H), 1.77-1.61 (m, 4H) |
| 270 | (2S)-4-[3-([2-[3-(2-[[2-(2,6-dioxopiperidin-3-yl)-1,3-dioxoisoindol-4-yl]amino]ethoxy)phenoxy]eth-yl]carbamoyl)propoxy]-2-[(1-methanesulfonylpyrrol-3-yl)formamido]-N-(4-phenyl-1,3-thiazol-2-yl)butanamide. | 969.30 | $^1$H NMR (300 MHz, DMSO-$d_6$) δ 12.39 (s, 1H), 11.10 (s, 1H), 8.45 (d, J = 7.1 Hz, 1H), 8.05-7.94 (m, 2H), 7.94-7.85 (m, 2H), 7.62 (s, 1H), 7.60 (dd, J = 8.6, 7.1 Hz, 1H), 7.43 (t, J = 7.6 Hz, 2H), 7.38-7.27 (m, 2H), 7.23 (d, J = 8.6 Hz, 1H), 7.16 (dd, J = 8.9, 7.5 Hz, 1H), 7.06 (d, J = 7.0 Hz, 1H), 6.82-6.71 (m, 2H), 6.52 (d, J = 8.7 Hz, 3H), 5.06 (dd, J = 12.8, 5.4 Hz, 1H), 4.69 (td, J = 8.1, 7.3, 5.1 Hz, 1H), 4.15 (t, J = 5.4 Hz, 2H), 3.94 (t, J = 5.7 Hz, 2H), 3.70 (q, J = 5.7 Hz, 2H), 3.54-3.40 (m, 8H), 2.88 (ddd, J = 17.2, 13.9, 5.3 Hz, 1H), 2.64-2.52 (m, 2H), 2.14-1.94 (m, 6H), 1.70 (p, J = 6.8 Hz, 2H). |
| 271 | (2S)-4-[3-([5-[2-(2,6-dioxopiperidin-3-yl)-1,3-dioxoisoindol-5-yl]pent-4-yn-1-yl]carbamoyl)propoxy]-2-[(1-methanesulfonylpyrrol-3- | 856.40 | $^1$H NMR (400 MHz, DMSO-d6) δ 12.41 (s, 1H), 11.13 (s, 1H), 8.43 (d, J = 7.3 Hz, 1H), 7.95 (t, J = 2.0 Hz, 1H), 7.93-7.86 (m, 3H), 7.84 (d, J = 7.2 Hz, 3H), 7.62 (s, 1H), 7.42 (dd, J = 8.4, 6.9 Hz, 2H), 7.35-7.27 (m, 2H), 6.78 (dd, J = 3.3, 1.6 Hz, 1H), 5.15 (dd, |

TABLE 21-continued

The following compounds were prepared using standard chemical manipulations and procedures similar to those used for the preparation of Compound 218

| Cmpd # | Name | LC-MS (ESI) (m/z) | $^1$H NMR |
|---|---|---|---|
| | yl)formamido]-N-(4-phenyl-1,3-thiazol-2-yl)butanamide | | J = 12.7, 5.4 Hz, 1H), 4.69 (q, J = 7.2, 6.1 Hz, 1H), 3.57 (s, 3H), 3.49 (t, J = 6.5 Hz, 2H), 3.37 (s, 1H), 3.30 (s, 2H), 3.18 (q, J = 6.5 Hz, 2H), 2.92-2.88(m, 1H), 2.60 (d, J = 19.1 Hz, 2H), 2.54 (s, 1H), 2.15-1.95 (m, 5H), 1.75-1.63 (m, 4H). |
| 272 | (2S)-4-[3-([5-[2-(2,6-dioxopiperidin-3-yl)-1,3-dioxoisoindol-4-yl]pent-4-yn-1-yl]carbamoyl)propoxy]-2-[(1-methanesulfonylpyrrol-3-yl)formamido]-N-(4-phenyl-1,3-thiazol-2-yl)butanamide | 856.05 | $^1$H NMR (400 MHz, DMSO-d6) δ 12.40 (s, 1H), 11.12 (s, 1H), 8.43 (d, J = 7.1 Hz, 1H), 7.95 (t, J = 2.0 Hz, 1H), 7.92-7.87 (m, 2H), 7.85 (td, J = 5.7, 2.3 Hz, 2H), 7.82-7.79 (m, 2H), 7.62 (s, 1H), 7.42 (t, J = 7.7 Hz, 2H), 7.36-7.27 (m, 2H), 6.78 (dd, J = 3.3, 1.6 Hz, 1H), 5.14 (dd, J = 12.8, 5.4 Hz, 1H), 4.74-4.64 (m, 1H), 3.57 (s, 3H), 3.49 (t, J = 6.6 Hz, 2H), 3.38 (d, J = 9.3 Hz, 2H), 3.33-3.27 (m, 2H), 3.30 (d, J = 3.3 Hz, 0H), 3.21 (q, J = 6.5 Hz, 2H), 2.95-2.82 (m, 1H), 2.61 (d, J = 3.5 Hz, 1H), 2.57 (s, 1H), 2.54 (d, J = 6.5 Hz, 1H), 2.14-1.94 (m, 5H), 1.76-1.65 (m, 4H). |
| 273 | (2S)-4-(3-[[2-(2-[2-[2-(2-[[2-(2,6-dioxopiperidin-3-yl)-1,3-dioxoisoindol-5-yl]oxy]acetamido)ethoxy]ethoxy]ethoxy)ethyl]carbamoyl]propoxy)-2-[(1-methanesulfonylpyrrol-3-yl)formamido]-N-(4-phenyl-1,3-thiazol-2-yl)butanamide | 1023.55 | $^1$H NMR (400 MHz, DMSO-d6) δ 12.41 (s, 1H), 11.11 (s, 1H), 8.43 (d, J = 7.1 Hz, 1H), 8.24 (t, J = 5.6 Hz, 1H), 7.95 (t, J = 1.9 Hz, 1H), 7.92-7.83 (m, 3H), 7.78 (t, J = 5.7 Hz, 1H), 7.62 (s, 1H), 7.48-7.39 (m, 3H), 7.37 (dd, J = 8.3, 2.3 Hz, 1H), 7.35-7.28 (m, 2H), 6.77 (dd, J = 3.3, 1.6 Hz, 1H), 5.12 (dd, J = 12.9, 5.3 Hz, 1H), 4.73 (s, 3H), 3.57 (s, 3H), 3.53-3.38 (m, 12H), 3.36-3.31 (m, 3H), 3.29-3.27 (m, 3H), 3.17 (q, J = 5.9 Hz, 2H), 2.93-2.83 (m, 1H), 2.69-2.54 (m, 2H), 2.21-1.89 (m, 6H), 1.68 (p, J = 6.8 Hz, 2H). |
| 274 | (2S)-4-[3-[(2-[2-[2-(2-[[2-(2,6-dioxopiperidin-3-yl)-1,3-dioxoisoindol-5-yl]oxy]acetamido)ethoxy]ethoxy]ethyl)carbamoyl]propoxy]-2-[(1-methanesulfonylpyrrol-3-yl)formamido]-N-(4-phenyl-1,3-thiazol-2-yl)butanamide | 979.10 | $^1$H NMR (400 MHz, DMSO-d6) δ 11.15 (s, 1H), 8.44 (d, J = 7.2 Hz, 1H), 8.25 (t, J = 5.8 Hz, 1H), δ 7.95 (t, J = 2.0 Hz, 1H), 7.92-7.87 (m, 2H), 7.84 (s, 1H), 7.82 (d, J = 5.7 Hz, 1H), 7.60 (s, 1H), 7.48-7.40 (m, 3H), 7.38 (dd, J = 8.3, 2.3 Hz, 1H), 7.36-7.32 (m, 1H), 7.31 (dd, J = 3.3, 2.2 Hz, 1H), 6.79 (dd, J = 3.3, 1.7 Hz, 1H), 5.11 (dd, J = 12.8, 5.4 Hz, 1H), 4.70 (d, J = 14.5 Hz, 3H), 3.55 (s, 3H), 3.50-3.46 (m, 6H), 3.46-3.38 (m, 2H), 3.38-3.31 (m, 3H), 3.29 (d, J = 6.0 Hz, 3H), 3.18 (q, J = 5.7 Hz, 2H), 2.95-2.81 (m, 1H), 2.66-2.57 (m, 2H), 2.12 (d, J = 7.4 Hz, 2H), 2.09-1.90 (m, 3H), 1.68 (p, J = 6.8 Hz, 2H). |
| 275 | (2S)-4-(3-[[4-(3-[[2-(2,6-dioxopiperidin-3-yl)-1,3-dioxoisoindol-4-yl]amino]propanesulfonyl)butyl]carbamoyl]propoxy)-2-[(1-methanesulfonylpyrrol-3-yl)formamido]-N-(4-phenyl-1,3-thiazol-2-yl)butanamide | 967.45 | $^1$H NMR (300 MHz, DMSO-d6) δ 12.41 (s, 1H), 11.10 (s, 1H), 8.44 (d, J = 7.1 Hz, 1H), 7.96 (t, J = 2.0 Hz, 1H), 7.93-7.86 (m, 2H), 7.78 (t, J = 5.6 Hz, 1H), 7.67-7.55 (m, 2H), 7.43 (dd, J = 8.2, 6.7 Hz, 2H), 7.38-7.27 (m, 2H), 7.15 (d, J = 8.6 Hz, 1H), 7.04 (d, J = 7.0 Hz, 1H), 6.83-6.70 (m, 2H), 5.06 (dd, J = 12.8, 5.4 Hz, 1H), 4.79-4.61 (m, 1H), 3.58 (s, 3H), 3.54-3.41 (m, 5H), 3.22-3.01 (m, 6H), 2.99-2.89 (m, 1H), 2.65-2.52 (m, 3H), 2.15-1.90 (m, 7H), 1.79-1.55 (m, 4H), 1.49 (q, J = 7.1 Hz, 2H). |
| 276 | (2S)-4-[3-([2-[(2-[[2-(2,6-dioxopiperidin-3-yl)-1,3-dioxoisoindol-4-yl]amino]ethyl)(methyl)amino]ethyl]carbamoyl)propoxy]-2-[(1-methanesulfonylpyrrol-3-yl)formamido]-N-(4-phenyl-1,3-thiazol-2-yl)butanamide; formic acid | 890.45 | $^1$H NMR (300 MHz, DMSO-d6) δ 12.41 (s, 1H), 11.09 (s, 1H), 8.44 (d, J = 7.1 Hz, 1H), 7.96 (t, J = 2.0 Hz, 1H), 7.94-7.87 (m, 2H), 7.66-7.53 (m, 3H), 7.43 (dd, J = 8.3, 6.8 Hz, 2H), 7.38-7.28 (m, 2H), 7.05 (dd, J = 11.6, 7.8 Hz, 2H), 6.78 (dd, J = 3.3, 1.6 Hz, 1H), 6.72 (d, J = 5.0 Hz, 1H), 5.05 (dd, J = 12.8, 5.4 Hz, 1H), 4.67 (d, J = 12.6 Hz, 1H), 3.57 (s, 3H), 3.47 (t, J = 6.5 Hz, 2H), 3.34-3.25 (m, 4H),3.17 (q, J = 6.6 Hz, 2H), 2.95-2.80 (m, 1H), 2.58 (dd, J = 11.7, 5.8 Hz, 4H), 2.43 (t, J = 6.9 Hz, 2H), 2.22 (s, 3H), 2.04 (dq, J = 16.5, 6.0, 4.7 Hz, 5H), 1.75-1.58 (m, 2H). |
| 277 | (2S)-4-[3-[(2-[1-[2-(2,6-dioxopiperidin-3-yl)-1,3-dioxoisoindol-5-yl]piperidin-4-yl]ethyl)carbamoyl]propoxy]-2-[(1-methanesulfonylpyrrol-3-yl)formamido]-N-(4-phenyl-1,3-thiazol-2-yl)butanamide. | 901.40 | $^1$H NMR (300 MHz, DMSO-$d_6$) δ 12.43 (s, 1H), 11.08 (s, 1H), 8.45 (d, J = 7.1 Hz, 1H), 7.96 (t, J = 1.9 Hz, 1H), 7.94-7.86 (m, 2H), 7.73 (t, J = 5.6 Hz, 1H), 7.68-7.59 (m, 2H), 7.43 (dd, J = 8.2, 6.7 Hz, 2H), 7.32 (tdd, J = 8.0, 3.5, 1.8 Hz, 3H), 7.19 (dd, J = 8.6, 2.3 Hz, 1H), 6.78 (dd, J = 3.3, 1.6 Hz, 1H), 5.07 (dd, J = 12.7, 5.4 Hz, 1H), 4.70 (q, J = 7.2, 6.3 Hz, 1H), 4.00 (d, J = 12.9 Hz, 2H), 3.58 (s, 3H), 3.49 (t, J = 6.7 Hz, 2H), 3.41(t, 2H),3.08 (q, J = 6.6 Hz, 2H), 2.89 (t, J = 12.4 Hz, 3H), 2.65-2.53 (m, 2H), 2.20-1.92 (m, 5H), 1.71 (q, J = 6.4 Hz, 4H), 1.54 (s, 1H), 1.32 (d, J = 7.2 Hz, 2H), 1.23-1.03 (m, 2H). |
| 278 | (2S)-4-(3-[[2-([1-[2-(2,6-dioxopiperidin-3-yl)-1,3- | 889.10 | $^1$H NMR (300 MHz, DMSO-d6) δ 12.42 (s, 1H), 11.08 (s, 1H), 8.44 (d, J = 7.2 Hz, 1H), 8.05-7.80 (m, 4H), |

TABLE 21-continued

The following compounds were prepared using standard chemical manipulations and procedures similar to those used for the preparation of Compound 218

| Cmpd # | Name | LC-MS (ESI) (m/z) | $^1$H NMR |
|---|---|---|---|
| | dioxoisoindol-5-yl]azetidin-3-yl]oxy) ethyl]carbamoyl]propoxy)-2-[(1-methanesulfonylpyrrol-3-yl)formamido]-N-(4-phenyl-1,3-thiazol-2-yl)-butanemide | | 7.68-7.60 (m, 2H), 7.46-7.28 (m, 4H), 6.79 (s, 2H), 6.64 (d, J = 8.4 Hz, 1H), 5.16-4.92 (m, 1H), 4.70 (s, 1H), 4.46 (s, 1H), 4.24 (t, J = 9.0 Hz, 2H), 3.89-3.80 (m, 2H), 3.57 (s, 3H), 3.53-3.44 (m, 2H), 3.45-3.37 (m, 2H), 3.35-3.25 (m, 2H), 3.27-3.16 (m, 2H), 3.02-2.73 (m, 1H), 2.72-2.56 (m, 1H), 2.30-1.81 (m, 6H), 1.88-1.54 (m, 2H). |
| 280 | (2S)-4-[3-[(2-[[2-(2,6-dioxopiperidin-3-yl)-1,3-dioxoisoindol-5-yl]oxy]ethyl)carbamoyl]propoxy]-2-[(1-methanesulfonylpyrrol-3-yl)formamido]-N-(4-phenyl-1,3-thiazol-2-yl)butanamide | 834.00 | $^1$H NMR (400 MHz, DMSO-$d_6$) δ 12.41 (s, 1H), 11.11 (s, 1H), 8.43 (d, J = 7.1 Hz, 1H), 8.04 (t, J = 5.6 Hz, 1H), 7.98-7.93 (m, 1H), 7.93-7.86 (m, 2H), 7.82 (d, J = 8.3 Hz, 1H), 7.62 (s, 1H), 7.46-7.38 (m, 3H), 7.37-7.27 (m, 3H), 6.80-6.74 (m, 1H), 5.16-5.07 (m, 1H), 4.74-4.64 (m, 1H), 4.21-4.14 (m, 2H), 3.57 (s, 3H), 3.52-3.42 (m, 4H), 3.45-3.34 (m, 2H), 2.95-2.82 (m, 1H), 2.64-2.52 (m, 2H), 2.18-2.10 (m, 2H), 2.09-1.90 (m, 3H), 1.75-1.64 (m, 2H). |
| 281 | (2S)-4-[3-[(8-[[2-(2,6-dioxopiperidin-3-yl)-1,3-dioxoisoindol-4-yl]amino]octyl)carbamoyl]propoxy]-2-[(1-methanesulfonylpyrrol-3-yl)formamido]-N-(4-phenyl-1,3-thiazol-2-yl)butanamide | 917.10 | $^1$H NMR (400 MHz, DMSO-d6) δ 12.41 (s, 1H), 11.09 (s, 1H), 8.43 (d, J = 7.2 Hz, 1H), 7.95 (t, J = 2.0 Hz, 1H), 7.93-7.86 (m, 2H), 7.68 (t, J = 5.6 Hz, 1H), 7.62 (s, 1H), 7.60-7.53 (m, 1H), 7.46-7.38 (m, 2H), 7.36-7.27 (m, 2H), 7.07 (d, J = 8.6 Hz, 1H), 7.01 (d, J = 7.0 Hz, 1H), 6.80-6.75 (m, 1H), 6.50 (t, J = 6.0 Hz, 1H), 5.09-5.00 (m, 1H), 4.75-4.65 (m, 1H), 3.57 (s, 3H), 3.48 (t, J = 6.6 Hz, 2H), 3.40-3.35 (m, 1H), 3.32-3.21 (m, 3H), 3.04-2.95 (m, 2H), 2.95-2.81 (m, 1H), 2.63-2.54 (m, 1H), 2.16-1.91 (m, 5H), 1.74-1.62 (m, 2H), 1.58-1.50 (m, 2H), 1.41-1.13 (m, 11H). |
| 282 | (2S)-4-[3-[(4-[[2-(2,6-dioxopiperidin-3-yl)-1,3-dioxoisoindol-5-yl]amino]butyl)carbamoyl]propoxy]-2-[(1-methanesulfonylpyrrol-3-yl)formamido]-N-(4-phenyl-1,3-thiazol-2-yl)butanamide | 861.15 | $^1$H NMR (400 MHz, DMSO-$d_6$) δ 12.41 (s, 1H), 11.05 (s, 1H), 8.43 (d, J = 7.2 Hz, 1H), 7.97-7.93 (m, 1H), 7.92-7.87 (m, 2H), 7.79-7.72 (m, 1H), 7.62 (s, 1H), 7.55 (d, J = 8.4 Hz, 1H), 7.47-7.38 (m, 2H), 7.35-7.27 (m, 2H), 7.12-7.06 (m, 1H), 6.95-6.90 (m, 1H), 6.86-6.80 (m, 1H), 6.80-6.75 (m, 1H), 5.09-4.95 (m, 1H), 4.74-4.65 (m, 1H), 3.57 (s, 3H), 3.51-3.44 (m, 2H), 3.41-3.34 (m, 1H), 3.31-3.25 (m, 1H), 3.18-3.10 (m, 2H), 3.10-3.02 (m, 2H), 2.95-2.80 (m, 1H), 2.61-2.52 (m, 2H), 2.14-1.91 (m, 5H), 1.75-1.64 (m, 2H), 1.59-1.42 (m, 4H). |
| 283 | (2S)-4-[3-[(6-[[2-(2,6-dioxopiperidin-3-yl)-1,3-dioxoisoindol-5-yl]amino]hexyl)carbamoyl]propoxy]-2-[(1-methanesulfonylpyrrol-3-yl)formamido]-N-(4-phenyl-1,3-thiazol-2-yl)butanamide | 889.10 | $^1$H NMR (300 MHz, DMSO-$d_6$) δ 12.42 (s, 1H), 11.06 (s, 1H), 8.44 (d, J = 7.2 Hz, 1H), 7.99-7.95 (m, 1H), 7.93-7.87 (m, 2H), 7.70 (t, J = 5.6 Hz, 1H), 7.63 (s, 1H), 7.56 (d, J = 8.4 Hz, 1H), 7.46-7.39 (m, 2H), 7.36-7.28 (m, 2H), 7.08 (s, 1H), 6.96-6.91 (m, 1H), 6.86-6.76 (m, 2H), 5.07-4.99 (m, 1H), 4.76-4.65 (m, 1H), 3.58 (s, 3H), 3.49 (t, J = 6.6 Hz, 2H), 3.39 (s, 2H), 3.18-3.07 (m, 2H), 3.06-2.97 (m, 2H), 2.95-2.79 (m, 1H), 2.57 (d, J = 17.5 Hz, 1H), 2.13-1.94 (m, 6H), 1.74-1.63 (m, 2H), 1.60-1.48 (m, 2H), 1.42-1.21 (m, 6H). |
| 285 | (2S)-4-[3-([2-[3-(2-[[2-(2,6-dioxopiperidin-3-yl)-1,3-dioxoisoindol-5-yl]amino]ethoxy)phenoxy]ethyl]carbamoyl)propoxy]-2-[(1-methanesulfonylpyrrol-3-yl)formamido]-N-(4-phenyl-1,3-thiazol-2-yl)butanamide | 969.45 | $^1$H NMR (300 MHz, DMSO-d6) δ 12.42 (s, 1H), 11.07 (s, 1H), 8.44 (d, J = 7.1 Hz, 1H), 8.04-7.94 (m, 2H), 7.94-7.87 (m, 2H), 7.66-7.54 (m, 2H), 7.48-7.39 (m, 2H), 7.37-7.27 (m, 3H), 7.16 (dd, J = 9.0, 7.8 Hz, 1H), 7.06 (d, J = 2.1 Hz, 1H), 6.95 (dd, J = 8.5, 2.1 Hz, 1H), 6.78 (dd, J = 3.3, 1.6 Hz, 1H), 6.58-6.47 (m, 3H), 5.04 (dd, J = 12.7, 5.4 Hz, 1H), 4.69 (q, J = 7.6, 7.0 Hz, 1H), 4.13 (t, J = 5.0 Hz, 2H), 3.94 (t, J = 5.7 Hz, 2H), 3.57 (s, 5H), 3.48 (t, J = 6.4 Hz, 2H), 3.40 (s, 3H), 3.31 (s, 1H), 2.98-2.76 (m, 1H), 2.58 (d, J = 17.7 Hz, 2H), 2.14 (t, J = 7.4 Hz, 2H), 2.04 (dd, J = 21.5, 6.0 Hz, 3H), 1.70 (p, J = 6.8 Hz, 2H). |
| 286 | (2S)-4-[3-[(2-[[2-(2,6-dioxopiperidin-3-yl)-1,3-dioxoisoindol-5-yl]amino]ethyl)carbamoyl]propoxy]-2-[(1-methanesulfonylpyrrol-3-yl)formamido]-N-(4-phenyl-1,3-thiazol-2-yl)butanamide | 833.10 | $^1$H NMR (400 MHz, DMSO-$d_6$) δ 12.41 (s, 1H), 11.05 (s, 1H), 8.43 (d, J = 7.1 Hz, 1H), 7.97-7.85 (m, 4H), 7.62 (s, 1H), 7.56 (d, J = 8.3 Hz, 1H), 7.42 (t, J = 7.6 Hz, 2H), 7.36-7.27 (m, 2H), 7.14 (s, 1H), 6.97 (s, 1H), 6.90-6.83 (m, 1H), 6.80-6.75 (m, 1H), 5.03 (dd, J = 12.9, 5.4 Hz, 1H), 4.74-4.64 (m, 1H), 3.57 (s, 3H), 3.48 (t, J = 6.5 Hz, 2H), 3.42-3.35 (m, 2H), 3.22 (s, 4H), 2.94-2.80 (m, 1H), 2.70-2.54 (m, 2H), 2.16-2.01 (m, 3H), 2.02-1.92 (m, 2H), 1.75-1.66 (m, 2H). |

TABLE 21-continued

The following compounds were prepared using standard chemical manipulations and procedures similar to those used for the preparation of Compound 218

| Cmpd # | Name | LC-MS (ESI) (m/z) | $^1$H NMR |
| --- | --- | --- | --- |
| 287 | (2S)-4-[3-[(5-[[2-(2,6-dioxopiperidin-3-yl)-1,3-dioxoisoindol-5-yl]amino]pentyl)carbamoyl]propoxy]-2-[(1-methanesulfonylpyrrol-3-yl)formamido]-N-(4-phenyl-1,3-thiazol-2-yl)butanamide | 875.10 | $^1$H NMR (300 MHz, DMSO-d6) δ 12.41 (s, 1H), 11.06 (s, 1H), 8.45 (d, J = 7.2 Hz, 1H), 7.96 (t, J = 2.0 Hz, 1H), 7.94-7.86 (m, 2H), 7.72 (t, J = 5.6 Hz, 1H), 7.63 (s, 1H), 7.56 (d, J = 8.4 Hz, 1H), 7.49-7.38 (m, 2H), 7.38-7.27 (m, 2H), 7.14-7.03 (m, 1H), 6.98-6.91 (m, 1H), 6.88-6.81 (m, 1H), 6.79-6.74 (m, 1H), 5.12-4.94 (m, 1H), 4.77-4.62 (m, 1H), 3.58 (s, 3H), 3.54-3.43 (m, 2H), 3.43-3.35 (m, 2H), 3.19-3.06 (m, 2H), 3.08-2.96 (m, 2H), 2.96-2.80 (m, 1H), 2.65-2.53 (m, 2H), 2.14-2.05 (m, 3H), 2.05-1.93 (m, 2H), 1.78-1.63 (m, 2H), 1.63-1.48 (m, 2H), 1.48-1.26 (m, 4H). |
| 183 | (2S)-4-[4-[4-([1-[2-(2,6-dioxopiperidin-3-yl)-1,3-dioxoisoindol-5-yl]azetidin-3-yl]methyl)piperazin-1-yl]-4-oxobutoxy]-2-[(1-methanesulfonylpyrrol-3-yl)formamido]-N-(4-phenyl-1,3-thiazol-2-yl)butanamide; formic acid | 928.15 | $^1$H NMR (400 MHz, DMSO-d6) δ 12.41 (s, 1H), 11.07 (s, 1H), 8.45 (d, J = 7.2 Hz, 1H), 8.22 (s, 1H), 8.00-7.83 (m, 3H), 7.63 (t, J = 4.2 Hz, 2H), 7.42 (dd, J = 8.3, 6.9 Hz, 2H), 7.36-7.23 (m, 2H), 6.84-6.70 (m, 2H), 6.62 (dd, J = 8.4, 2.1 Hz, 1H), 5.03 (dd, J = 12.8, 5.5 Hz, 1H), 4.71 (dd, J = 8.8, 5.4 Hz, 1H), 4.09 (t, J = 8.2 Hz, 2H), 3.64 (dd, J = 8.5, 5.5 Hz, 2H), 3.53 (d, J = 5.9 Hz, 6H), 3.45-3.29 (m, 6H), 2.99-2.88 (m, 2H), 2.67-2.58 (m, 2H), 2.56 (s, 1H), 2.34-2.28 (m, 6H), 2.16-1.99 (m, 3H), 1.69 (q, J = 6.8 Hz, 2H). |
| 222 | (2S)-4-[4-[7-(3-[[2-(2,6-dioxopiperidin-3-yl)-1,3-dioxoisoindol-5-yl]amino]propyl)-2,7-diazaspiro[3.5]nonan-2-yl]-4-oxobutoxy]-2-[(1-methanesulfonylpyrrol-3-yl)formamido]-N-(4-phenyl-1,3-thiazol-2-yl)butanamide; formic acid | 956.15 | $^1$H NMR (400 MHz, DMSO-d6) δ 12.41 (s, 1H), 11.06 (s, 1H), 8.43 (d, J = 7.2 Hz, 1H), 7.95 (t, J = 2.0 Hz, 1H), 7.93-7.87 (m, 2H), 7.68 (s, 1H), 7.65-7.56 (m, 1H), 7.43 (t, J = 7.7 Hz, 2H), 7.36-7.28 (m, 2H), 7.18 (t, J = 5.7 Hz, 1H), 6.97 (d, J = 2.1 Hz, 1H), 6.87 (dd, J = 8.5, 2.1 Hz, 1H), 6.77 (dd, J = 3.3, 1.6 Hz, 1H), 5.04 (dd, J = 12.9, 5.4 Hz, 1H), 4.75-4.65 (m, 1H), 3.78 (s, 2H), 3.61 (s, 1H), 3.57 (s, 5H), 3.49 (t, J = 6.5 Hz, 2H),3.45-3.39 (m, 2H), 3.27-3.21 (m, 2H), 3.2 (s, 1H), 2.88 (ddd, J = 17.4, 14.0, 5.5 Hz, 5H), 2.58 (d, J = 16.8 Hz, 2H), 2.03 (qt, J = 13.4, 7.1 Hz, 6H), 1.86 (s, 5H), 1.67 (q, J = 6.9 Hz, 2H), 1.25 (q, J = 7.5, 6.3 Hz, 4H). |
| 223 | (2S)-4-[3-[(2-[2-[2-(2-[[2-(2,6-dioxopiperidin-3-yl)-1,3-dioxoisoindol-4-yl]oxy]acetamido)ethoxy]ethoxy]ethyl)carbamoyl]propoxy]-2-[(1-methanesulfonylpyrrol-3-yl)formamido]-N-(4-phenyl-1,3-thiazol-2-yl)butanamide | 979.05 | $^1$H NMR (400 MHz, DMSO-d6) δ 12.41 (s, 1H), 11.11 (s, 1H), 8.43 (d, J = 7.1 Hz, 1H), 8.00 (t, J = 5.7 Hz, 1H), 7.95 (t, J = 2.0 Hz, 1H), 7.93-7.86 (m, 2H), 7.84-7.74 (m, 2H), 7.62 (s, 1H), 7.49 (d, J = 7.3 Hz, 1H), 7.46-7.36 (m, 3H), 7.36-7.27 (m, 2H), 6.77 (dd, J = 3.3, 1.6 Hz, 1H), 5.11 (dd, J = 13.0, 5.3 Hz, 1H), 4.78 (s, 3H), 3.57 (s, 3H), 3.51-3.41 (m, 6H), 3.37 (d, J = 5.8 Hz, 3H), 3.17 (q, J = 5.8 Hz, 4H), 2.89 (ddd, J = 17.2, 14.1, 5.4 Hz, 2H), 2.59 (d, J = 17.5 Hz, 1H), 2.51 (dt, J = 16.0, 7.3 Hz, 2H), 2.01 (s, 6H), 1.67 (p, J = 6.9 Hz, 2H). |
| 224 | (2S)-4-[4-[3-(2-[[2-(2,6-dioxopiperidin-3-yl)-1,3-dioxoisoindol-4-yl]oxy]ethyl)azetidin-1-yl]-4-oxobutoxy]-2-[(1-methanesulfonylpyrrol-3-yl)formamido]-N-(4-phenyl-1,3-thiazol-2-yl)butanamide | 874.05 | $^1$H NMR (400 MHz, DMSO-$d_6$) δ 12.41 (s, 1H), 11.10 (s, 1H), 8.43 (d, J = 7.1 Hz, 1H), 7.98-7.93 (m, 1H), 7.93-7.86 (m, 2H), 7.84-7.76 (m, 1H), 7.62 (s, 1H), 7.50-7.38 (m, 4H), 7.35-7.27 (m, 2H), 6.80-6.74 (m, 1H), 5.13-5.04 (m, 1H), 4.75-4.65 (m, 1H), 4.22-4.09 (m, 3H), 3.96-3.86 (m, 1H), 3.86-3.77 (m, 1H), 3.65-3.58 (m, 1H), 3.57 (s, 3H), 3.53-3.45 (m, 2H), 3.42-3.35 (m, 2H), 2.95-2.81 (m, 1H), 2.77-2.66 (m, 1H), 2.66-2.54 (m, 2H), 2.15-1.93 (m, 7H), 1.71-1.59 (m, 2H). |
| 279 | (2S)-4-(3-[[1-(2-[[2-(2,6-dioxopiperidin-3-yl)-1,3-dioxoisoindol-5-yl]oxylethyl)piperidin-4-yl]carbamoyl]propoxy)-2-[(1-methanesulfonylpyrrol-3-yl)formamido]-N-(4-phenyl-1,3-thiazol-2-yl)butanamide; formic acid | 917.1 | $^1$H NMR (400 MHz, DMSO-d6) δ 12.41 (s, 1H), 11.11 (s, 1H), 8.43 (d, J = 7.2 Hz, 1H), 7.95 (t, J = 2.0 Hz, 1H), 7.93-7.86 (m, 2H), 7.83 (d, J = 8.3 Hz, 1H), 7.67 (d, J = 7.7 Hz, 1H), 7.62 (s, 1H), 7.47-7.38 (m, 3H), 7.38-7.27 (m, 3H), 6.80-6.75 (m, 1H), 5.16-5.07 (m, 1H), 4.74-4.64 (m, 1H), 4.26 (t, J = 5.6 Hz, 2H), 3.57 (s, 3H), 3.54-3.45 (m, 3H), 3.41-3.38 (m, 1H), 3.37-3.34 (m, 1H), 3.31-3.30 (m, 1H), 2.96-2.84 (m, 3H), 2.73 (s, 2H), 2.64-2.60 (m, 1H), 2.60-2.52 (m, 1H), 2.22-2.03 (m, 5H), 2.03-1.88 (m, 1H), 1.74-1.62 (m, 4H), 1.43-1.30 (m, 2H). |

Preparation of 4-[(2S)-2-[(1-methanesulfonylpyrrol-3-yl)formamido]-2-[(4-phenyl-1,3-thiazol-2-yl)carbamoyl]ethoxy]butanoic acid
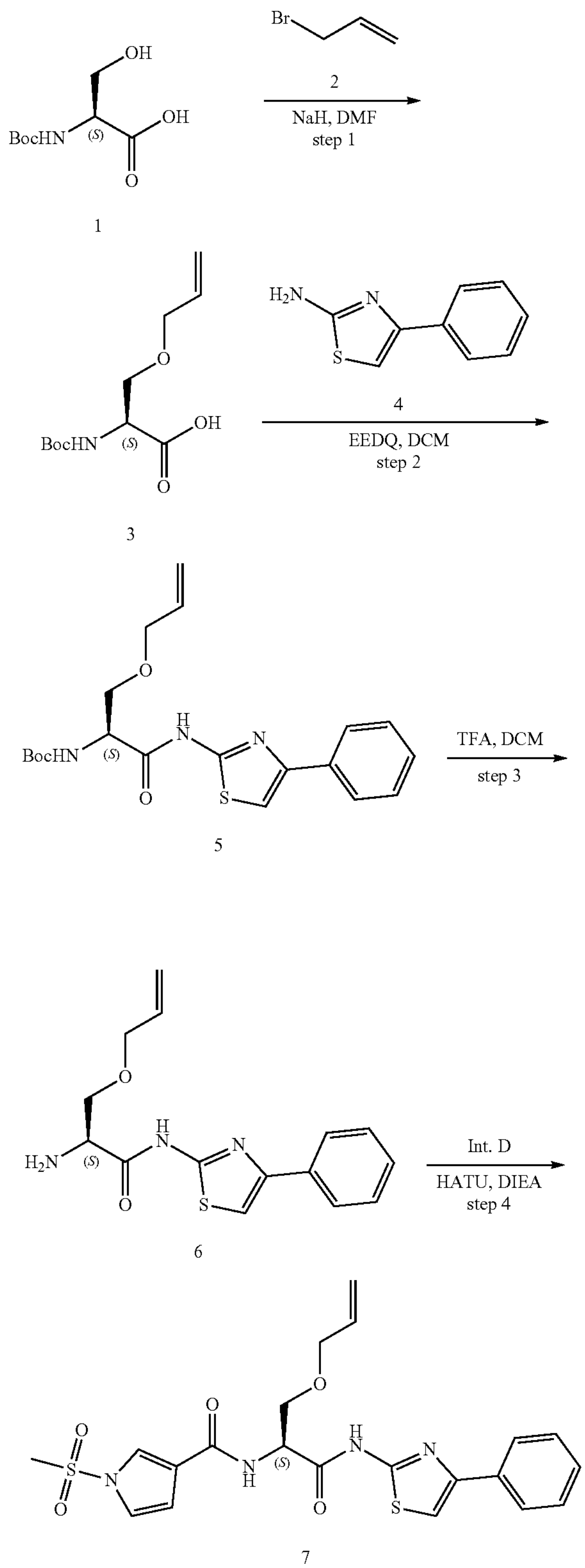
-continued
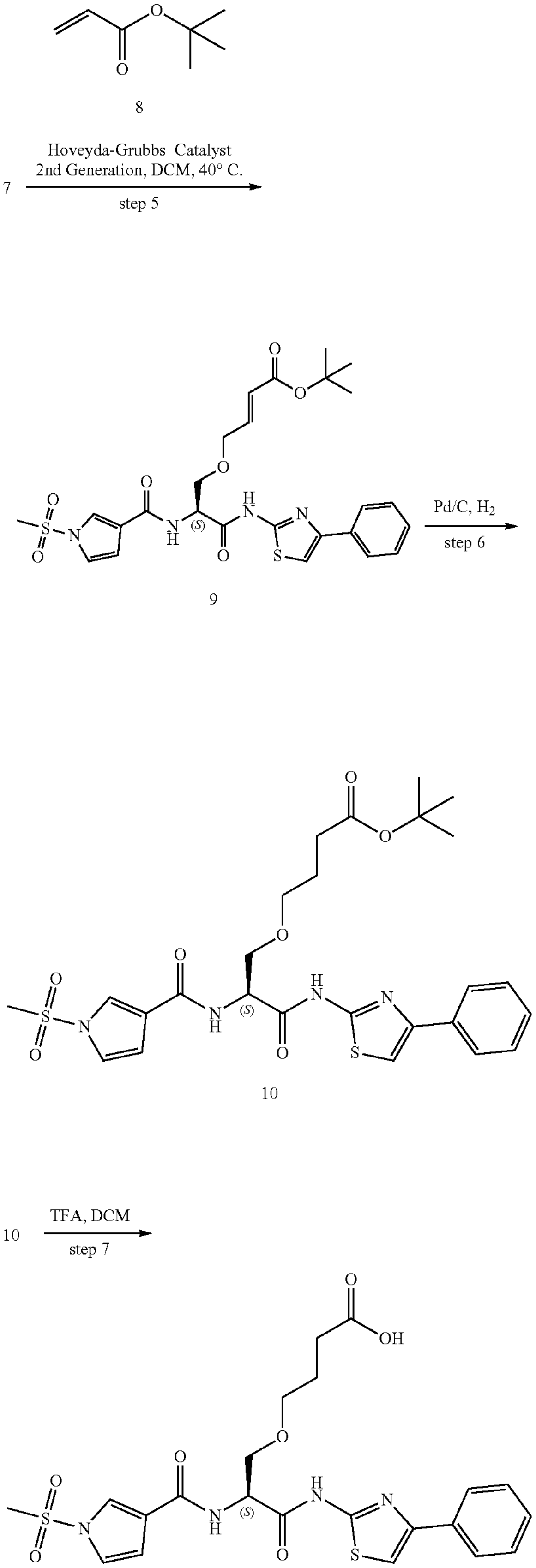

Step 1: Preparation of (2S)-2-[(tert-butoxycarbonyl)amino]-3-(prop-2-en-1-yloxy)propanoic acid (Intermediate 3)

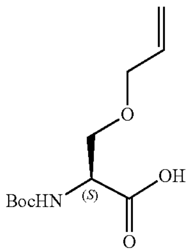

3

To a solution of (2S)-2-[(tert-butoxycarbonyl)amino]-3-hydroxypropanoic acid (3.0 g, 14.619 mmol, 1.00 equiv) in DMF (60.00 mL) at 0 degrees C. was added NaH (60%) (1.17 g, 29.238 mmol, 2.00 equiv). The suspension was stirred at 0 degrees C. for 1 h followed by addition of allyl bromide (1.86 g, 15.350 mmol, 1.05 equiv). The solution was stirred for 2 h then quenched with 100 mL water at 0 degrees C. The aqueous layer was washed by EtOAc (60 mL×3) and then acidified to PH ~3 at 0 degrees C. The organic fraction was set aside, and the aqueous layer was then extracted by EtOAc (60 mL×3). The combined organic layer was dried by sodium sulfate and concentrated. The residue was purified by silica gel column chromatography, eluted with DCM/MeOH/HOAc (20/1/0.2) to afford intermediate 3 (3.4 g, 94.82%) as a yellow oil. LCMS (ESI) m/z: $[M+H]^+$=246.

Step 2: Preparation of tert-butyl N-[(1S)-1-[(4-phenyl-1,3-thiazol-2-yl)carbamoyl]-2-(prop-2-en-1-yloxy)ethyl]carbamate (Intermediate 5)

5

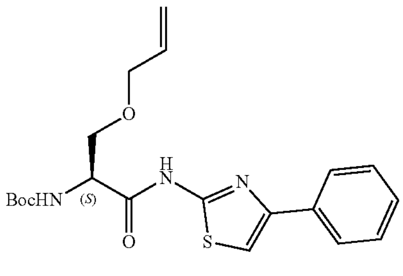

To a solution of phenthiazamine (240.00 mg, 1.362 mmol, 1.00 equiv) and intermediate 3 (501.02 mg, 2.043 mmol, 1.50 equiv) in DCM (50.00 mL) was added ethyl 2-ethoxy-1,2-dihydroquinoline-1-carboxylate (336.75 mg, 1.362 mmol, 1.00 equiv). The solution was stirred at room temperature for 16 h. The aqueous layer was extracted with $CH_2Cl_2$ (3×30 mL) and these combined extracts concentrated under vacuum. The residue was purified by silica gel column chromatography, eluted with PE/EtOAc (5:1) to afford intermediate 5 (440 mg, 80.08%) as an off-white oil. LCMS (ESI) m/z: $[M+H]^+$=404.

Step 3: Preparation of (2S)-2-amino-N-(4-phenyl-1,3-thiazol-2-yl)-3-(prop-2-en-1-yloxy)propanamide (Intermediate 6)

6

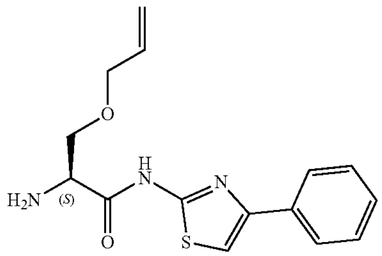

To a solution of intermediate 5 (440.00 mg, 1.090 mmol, 1.00 equiv) in DCM (2.00 mL) was added TFA (0.80 mL). The solution was stirred at room temperature for 1 h. The resulting mixture was concentrated under vacuum providing intermediate 6 (330 mg, 99.75%) as a yellow oil. LCMS (ESI) m/z: $[M+H]^+$=304.

Step 4: Preparation of (2S)-2-[(1-methanesulfonylpyrrol-3-yl)formamido]-N-(4-phenyl-1,3-thiazol-2-yl)-3-(prop-2-en-1-yloxy)propanamide (Intermediate 7)

7

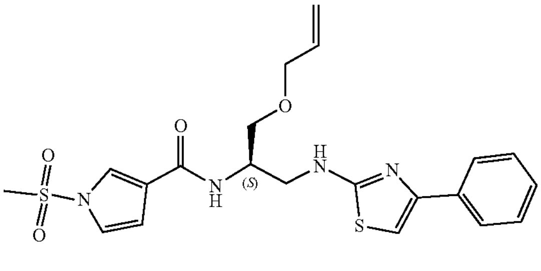

To a solution of 1-methanesulfonylpyrrole-3-carboxylic acid (205.79 mg, 1.088 mmol, 1 equiv), intermediate 6 (330.00 mg, 1.088 mmol, 1.00 equiv), and DIEA (421.75 mg, 3.263 mmol, 3 equiv) in DMF (6.00 mL) was added HATU (496.31 mg, 1.305 mmol, 1.2 equiv). The solution was stirred at 25 degrees C. for 16 h, then concentrated, and the residue purified by silica gel column chromatography, eluted with PE/EtOAc (5:1) to afford intermediate 7 (370 mg, 71.68%) as a yellow oil. LCMS (ESI) m/z: $[M+H]^+$=475.

Step 5: Preparation of tert-butyl (2E)-4-[(2S)-2-[(1-methanesulfonylpyrrol-3-yl)formamido]-2-[(4-phenyl-1,3-thiazol-2-yl)carbamoyl]ethoxy]but-2-enoate (Intermediate 9)

9

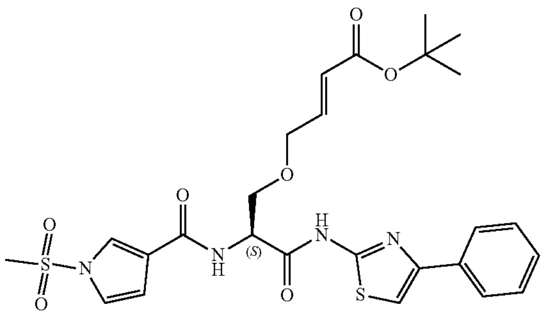

To a solution of tert-butyl prop-2-enoate (1080.36 mg, 8.429 mmol, 20.00 equiv) and intermediate 7 (200.00 mg, 0.421 mmol, 1.00 equiv) in DCM (20.00 mL) was added Hoveyda-Grubbs Catalyst (26.41 mg, 0.042 mmol, 0.10 equiv). The solution was stirred at 40 degrees C. for 16 h. Following concentration, the residue was purified by silica gel column chromatography, eluted with PE/EtOAc (1:1) to afford intermediate 9 (230 mg, 94.96%) as a yellow solid. LCMS (ESI) m/z: $[M+H]^+$=575.

Step 6: Preparation of tert-butyl 4-[(2S)-2-[(1-methanesulfonylpyrrol-3-yl)formamido]-2-[(4-phenyl-1,3-thiazol-2-yl)carbamoyl]ethoxy]butanoate (Intermediate 10)

10

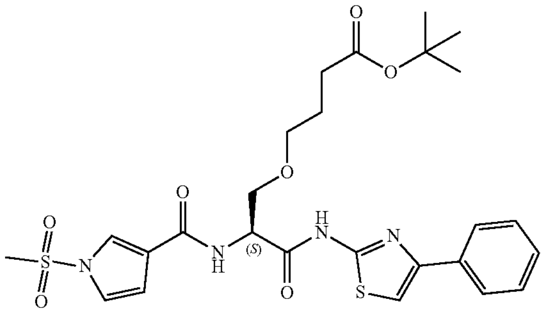

To a solution of intermediate 9 (230.00 mg, 0.400 mmol, 1.00 equiv) in MeOH (5.00 mL) was added 10% Pd/C (110.00 mg). The solution was stirred at 25 degrees C. for 1 h under an atmosphere of hydrogen. The resulting mixture was concentrated under vacuum to provide intermediate 10 (200 mg, 86.65%) as a yellow oil. LCMS (ESI) m/z: $[M+H]^+$=577.

Step 7: Preparation of 4-[(2S)-2-[(1-methanesulfonylpyrrol-3-yl)formamido]-2-[(4-phenyl-1,3-thiazol-2-yl)carbamoyl]ethoxy]butanoic acid

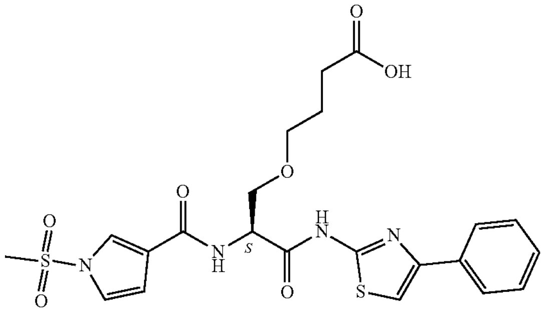

To a solution of intermediate 10 (218.00 mg, 0.378 mmol, 1.00 equiv) in DCM (2.00 mL) was added TEA (0.60 mL). The solution was stirred at 25 degrees C. for 1 h. The resulting mixture was concentrated under vacuum to provide the title compound (160 mg, 81.30%) as a yellow oil. LCMS (ESI) m/z: $[M+H]^+$=521.

Compound 229—Preparation of N-(4-[[2-(2,6-dioxopiperidin-3-yl)-1,3-dioxoisoindol-5-yl]amino]butyl)-4-[(2S)-2-[(1-methanesulfonylpyrrol-3-yl)formamido]-2-[(4-phenyl-1,3-thiazol-2-yl)carbamoyl]ethoxy]butanamide

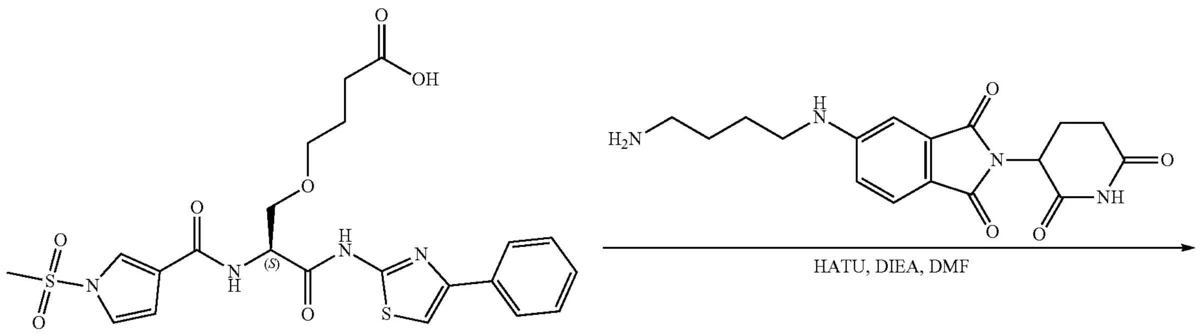

-continued

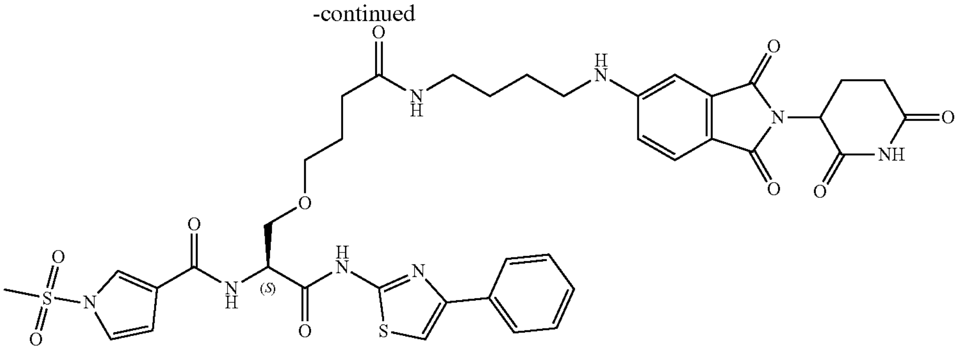

229

To a mixture of intermediate 2 (15 mg, 1 equiv), HATU (10.6 mg) and DIEA (0.04 mL) was added 5-[(4-aminobutyl)amino]-2-(2,6-dioxopiperidin-3-yl)isoindole-1,3-dione (10 mg, 1.00 equiv). The mixture was stirred at room temperature for 1 h then purified directly by Prep-HPLC afford Compound 229 (7.6 mg, 30.90%) as a yellow solid. $^1$H NMR (400 MHz, DMSO-d6) δ 12.50 (s, 1H), 11.05 (s, 1H), 8.50 (d, J=7.0 Hz, 1H), 7.98 (t, J=2.1 Hz, 1H), 7.94-7.86 (m, 2H), 7.74 (t, J=5.6 Hz, 1H), 7.63 (s, 1H), 7.55 (d, J=8.4 Hz, 1H), 7.43 (dd, J=8.4, 7.0 Hz, 2H), 7.36-7.31 (m, 1H), 7.30 (dd, J=3.3, 2.1 Hz, 1H), 7.09 (t, J=5.6 Hz, 1H), 6.93 (d, J=2.1 Hz, 1H), 6.86-6.81 (m, 1H), 6.80 (dd, J=3.3, 2.1 Hz, 1H), 5.03 (dd, J=12.9, 5.4 Hz, 1H), 4.90 (q, J=6.6 Hz, 1H), 3.80-3.68 (m, 2H), 3.56 (s, 3H), 3.51-3.42 (m, 2H), 3.17-3.11 (m, 2H), 3.10-3.03 (m, 2H), 2.93-2.84 (m, 1H), 2.64-2.52 (m, 2H), 2.09 (t, J=7.4 Hz, 2H), 2.02-1.95 (m, 1H), 1.76-1.68 (m, 2H), 1.58-1.39 (m, 4H). LCMS (ESI) m/z: [M+H]$^+$=847.40.

TABLE 22

The following compounds were prepared using standard chemical manipulations and procedures similar to those used for the preparation of Compound 1

| Cmpd # | Name | LC-MS (ESI) (m/z) | $^1$H NMR |
|---|---|---|---|
| 186 | N-(8-[[2-(2,6-dioxopiperidin-3-yl)-1,3-dioxoisoindol-4-yl]amino]octyl)-4-[(2S)-2-[(1-methanesulfonylpyrrol-3-yl)formamido]-2-[(4-phenyl-1,3-thiazol-2-yl)carbamoyl]ethoxy]butanamide | 903.45 | $^1$H NMR (400 MHz, DMSO-d$_6$) δ12.49 (s, 1H), 11.09 (s, 1H), 8.50 (d, J = 7.2 Hz, 1H), 8.00-7.96 (m, 1H), 7.93-7.87 (m, 2H), 7.69-7.61 (m, 2H), 7.61-7.52 (m, 1H), 7.47-7.38 (m, 2H), 7.36-7.26 (m, 2H), 7.07 (d, J = 8.6 Hz, 1H), 7.01 (d, J = 7.0 Hz, 1H), 6.81-6.77 (m, 1H), 6.57-6.45 (m, 1H), 5.10-5.00 (m, 1H), 4.95-4.87 (m, 1H), 3.79-3.71 (m, 2H), 3.56 (s, 3H), 3.49-3.42 (m, 2H), 3.30-3.23 (m, 2H), 3.03-2.95 (m, 2H), 2.94-2.81 (m, 1H), 2.63-2.55 (m, 2H), 2.12-1.97 (m, 3H), 1.78-1.65 (m, 2H), 1.62-1.49 (m, 2H), 1.39-1.16 (m, 10H). |
| 225 | (2S,4R)-4-hydroxy-1-[(2S)-2-(2-[2-[2-(2-[4-[(2S)-2-[(1-methanesulfonylpyrrol-3-yl)formamido]-2-[(4-phenyl-1,3-thiazol-2-yl)carbamoyl]ethoxy]-butanamido]ethoxy)ethoxy]-ethoxy]acetamido)-3,3-dimethylbutanoyl]-N-[[4-(4-methyl-1,3-thiazol-5-yl)phenyl]methyl]pyrrolidine-2-carboxamide | 1122.35 | $^1$H NMR (300 MHz, DMSO-d6) δ 12.86 (s, 1H), 8.98 (s, 1H), 8.60 (t, J = 6.0 Hz, 1H), 8.49 (s, 1H), 7.98 (s, 1H), 7.90 (d, J = 7.7 Hz, 2H), 7.82 (s, 1H), 7.61 (s, 1H), 7.40 (s, 7H), 7.30 (dd, J = 5.9, 2.8 Hz, 2H), 6.80 (dd, J = 3.3, 1.6 Hz, 1H), 5.16 (s, 1H), 4.88 (s, 1H), 4.57 (d, J = 9.6 Hz, 1H), 4.50-4.40 (m, 2H), 4.37 (d, J = 6.3 Hz, 2H), 4.28 (d, J = 5.4 Hz, 1H), 4.23 (d, J = 5.5 Hz, 1H), 3.96 (s, 3H), 3.75 (d, J = 6.2 Hz, 3H), 3.68-3.47 (m, 14H), 2.44 (s, 4H), 2.10 (t, J = 7.5 Hz, 3H), 1.70 (t, J = 7.1 Hz, 2H), 1.24 (s, 1H), 0.94 (s, 9H). |
| 226 | (2S,4R)-4-hydroxy-1-[(2S)-2-(6-[4-[(2S)-2-[(1-methanesulfonylpyrrol-3-yl)formamido]-2-[(4-phenyl-1,3-thiazol-2-yl)carbamoyl]ethoxy]-butanamido]hexanamido)-3,3-dimethylbutanoyl]-N-[[4-(4-methyl-1,3-thiazol-5-yl)phenyl]methyl]pyrrolidine-2-carboxamide | 1046.25 | $^1$H NMR (400 MHz, DMSO-d6) δ 12.50 (s, 1H), 8.98 (s, 1H), 8.60-8.45 (m, 2H), 7.98 (t, J = 2.0 Hz, 1H), 7.94-7.87 (m, 2H), 7.83 (d, J = 9.4 Hz, 1H), 7.66 (d, J = 16.3 Hz, 2H), 7.41 (p, J = 8.2 Hz, 6H), 7.35-7.27 (m, 2H), 6.80 (dd, J = 3.3, 1.7 Hz, 1H), 5.12 (d, J = 3.5 Hz, 1H), 4.90 (q, J = 6.5 Hz, 1H), 4.53 (d, J = 9.4 Hz, 1H), 4.47-4.39 (m, 2H), 4.35 (s, 1H), 4.22 (dd, J = 15.9, 5.4 Hz, 1H), 3.74 (d, J = 6.6 Hz, 2H), 3.70-3.61 (m, 2H), 3.56 (s, 3H), 3.45 (td, J = 6.5, 3.7 Hz, 2H), 3.03-2.92 (m, 2H), 2.44 (s, 3H), 2.27-2.18 (m, 1H), 2.06 (h, J = 8.4, 7.8 Hz, 4H), 1.94-1.86 (m, 1H), 1.70 (p, J = 6.8 Hz, 2H), 1.46 (dp, J = 15.1, 7.1 Hz, 2H), 1.34 (p, J = 7.3 Hz, 2H), 1.23-1.16 (m, 2H), 0.93 (s, 9H). |
| 227 | (2S,4R)-4-hydroxy-1-[(2S)-2-(8-[4-[(2S)-2-[(1-methanesulfonylpyrrol-3- | 1074.20 | $^1$H NMR (400 MHz, DMSO-d6) δ 12.50 (s, 1H), 8.98 (s, 1H), 8.59-8.46 (m, 2H), 7.98 (t, J = 2.0 Hz, 1H), 7.93-7.87 (m, 2H), 7.82 (d, J = 9.4 Hz, 1H), 7.65 (d, J = 13.9 Hz, |

TABLE 22-continued

The following compounds were prepared using standard chemical manipulations and procedures similar to those used for the preparation of Compound 1

| Cmpd # | Name | LC-MS (ESI) (m/z) | $^1$H NMR |
|---|---|---|---|
| | yl)formamido]-2-[(4-phenyl-1,3-thiazol-2-yl)carbamoyl]ethoxy]-butanamido]octanamido)-3,3-dimethylbutanoyl]-N-[[4-(4-methyl-1,3-thiazol-5-yl)phenyl]methyl]pyrrolidine-2-carboxamide | | 2H), 7.41 (dt, J = 15.7, 8.1 Hz, 6H), 7.35-7.28 (m, 2H), 6.80 (dd, J = 3.3, 1.7 Hz, 1H), 5.12 (d, J = 3.5 Hz, 1H), 4.90 (q, J = 6.6 Hz, 1H), 4.54 (d, J = 9.4 Hz, 1H), 4.47-4.39 (m, 2H), 4.34 (s, 1H), 4.21 (dd, J = 15.9, 5.5 Hz, 1H), 3.78-3.70 (m, 2H), 3.65 (d, J = 5.4 Hz, 2H), 3.56 (s, 3H), 3.45 (d, J = 4.7 Hz, 2H), 2.98 (q, J = 6.7 Hz, 2H), 2.44 (s, 3H), 2.26-2.19 (m, 1H), 2.14-2.02 (m, 4H), 1.93-1.86 (m, 1H), 1.71 (q, J = 7.0 Hz, 2H), 1.45 (s, 2H), 1.32 (s, 2H), 1.17 (d, J = 21.0 Hz, 6H), 0.93 (s, 9H). |
| 185 | N-((2S)-3-(4-((2-((2-(2,6-dioxopiperidin-3-yl)-1,3-dioxoisoindolin-5-yl)amino)ethyl)amino)-4-oxobutoxy)-1-oxo-1-((4-phenylthiazol-2-yl)amino)propan-2-yl)-1-(methylsulfonyl)-1H-pyrrole-3-carboxamide | 819.00 | $^1$H NMR (400 MHz, DMSO-d6) δ 12.50 (s, 1H), 11.06 (s, 1H), 8.50 (d, J = 7.2 Hz, 1H), 7.98 (t, J = 2.0 Hz, 1H), 7.94-7.86 (m, 3H), 7.63 (s, 1H), 7.55 (d, J = 8.3 Hz, 1H), 7.43 (t, J = 7.7 Hz, 2H), 7.36-7.27 (m, 2H), 7.13 (s, 1H), 6.97 (d, J = 2.2 Hz, 1H), 6.86 (dd, J = 8.4, 2.2 Hz, 1H), 6.80 (dd, J = 3.2, 1.6 Hz, 1H), 5.03 (dd, J = 13.0, 5.4 Hz, 1H), 4.91 (q, J = 6.5 Hz, 1H), 3.75 (d, J = 6.5 Hz, 2H), 3.56 (s, 3H), 3.52-3.41 (m, 2H), 3.21 (s, 4H), 2.93-2.80 (m, 1H), 2.69-2.54 (m, 2H), 2.10 (q, J = 8.9, 8.2 Hz, 2H), 2.03-1.94 (m, 1H), 1.79-1.66 (m, 2H). |
| 230 | N-(6-[[2-(2,6-dioxopiperidin-3-yl)-1,3-dioxoisoindol-5-yl]amino]hexyl)-4-[(2S)-2-[(1-methanesulfonylpyrrol-3-yl)formamido]-2-[(4-phenyl-1,3-thiazol-2-yl)carbamoyl]ethoxy]-butanamide | 875.40 | $^1$H NMR (300 MHz, DMSO-d6) δ 12.51 (s, 1H), 11.06 (s, 1H), 8.50 (d, J = 7.2 Hz, 1H), 7.99 (t, J = 2.0 Hz, 1H), 7.92 (d, J = 1.5 Hz, 1H), 7.90 (t, J = 1.3 Hz, 1H), 7.70 (t, J = 5.6 Hz, 1H), 7.64 (s, 1H), 7.56 (d, J = 8.4 Hz, 1H), 7.48-7.40 (m, 2H), 7.37-7.28 (m, 2H), 7.08 (t, J = 5.3 Hz, 1H), 6.93 (d, J = 2.0 Hz, 1H), 6.86-6.79 (m, 2H), 5.03 (dd, J = 12.7, 5.4 Hz, 1H), 4.91 (q, J = 6.5 Hz, 1H), 3.75 (d, J = 6.5 Hz, 2H), 3.57 (s, 3H), 3.49-3.39 (m, 2H), 3.12 (q, J = 6.5 Hz, 2H), 3.01 (q, J = 6.5 Hz, 2H), 2.92-2.81 (m, 1H), 2.64-2.53 (m, 2H), 2.09 (t, J = 7.4 Hz, 2H), 2.05-1.94 (m, 1H), 1.71 (p, J = 6.8 Hz, 2H), 1.53 (q, J = 7.1 Hz, 2H), 1.46-1.20 (m, 6H). |
| 172 | N-(4-[[2-(2,6-dioxopiperidin-3-yl)-1,3-dioxoisoindol-5-yl]amino]butyl)-4-[(2S)-2-[(1-methanesulfonylpyrrol-3-yl)formamido]-2-[(4-phenyl-1,3-thiazol-2-yl)carbamoyl]ethoxy]-butanamide | 953 | $^1$H NMR (300 MHz, DMSO-d6) δ 12.50 (s, 1H), 11.10 (s, 1H), 8.50 (d, J = 7.2 Hz, 1H), 7.99 (t, J = 2.0 Hz, 1H), 7.94-7.87 (m, 2H), 7.78 (t, J = 6.3 Hz, 1H), 7.64 (s, 1H), 7.59 (dd, J = 8.6, 7.1 Hz, 1H), 7.44 (dd, J = 8.6, 7.1 Hz, 2H), 7.37-7.32 (m, 1H), 7.30 (dd, J = 3.3, 2.2 Hz, 1H), 7.15 (d, J = 8.6 Hz, 1H), 7.04 (d, J = 7.1 Hz, 1H), 6.81 (dd, J = 3.3, 1.6 Hz, 1H), 6.75 (t, J = 6.3 Hz, 1H), 5.06 (dd, J = 12.8, 5.4 Hz, 1H), 4.91 (q, J = 6.6 Hz, 1H), 3.75 (d, J = 6.4 Hz, 2H), 3.57 (s, 3H), 3.49-3.43 (m, 4H), 3.17-3.01 (m, 6H), 2.96-2.81 (m, 1H), 2.64-2.59 (m, 2H), 2.14-1.92 (m, 5H), 1.77-1.58 (m, 4H), 1.55-1.41 (m, 2H). |
| 173 | (2S,4R)-4-hydroxy-1-[(2S)-2-[2-[2-(2-[4-[(2S)-2-[(1-methanesulfonylpyrrol-3-yl)formamido]-2-[(4-phenyl-1,3-thiazol-2-yl)carbamoyl]ethoxy]-butanamido]ethoxy)ethoxy]-acetamido]-3,3-dimethylbutanoyl]-N-[[4-(4-methyl-1,3-thiazol-5-yl)phenyl]methyl]pyrrolidine-2-carboxamide | 1078.55 | $^1$H NMR (300 MHz, DMSO-$d_6$) δ 12.50 (s, 1H), 8.98 (s, 1H), 8.75-8.50 (m, 2H), 8.02-7.72 (m, 4H), 7.64 (s, 1H), 7.52-7.37 (m, 6H), 7.36-7.28 (m, 3H), 6.80 (dd, J = 3.3, 1.6 Hz, 1H), 5.17 (d, J = 3.5 Hz, 1H), 4.91 (q, J = 6.5 Hz, 1H), 4.58 (d, J = 9.6 Hz, 1H), 4.50-4.20 (m, 4H), 3.96 (s, 2H), 3.78-3.62 (m, 3H), 3.61-3.50 (m, 7H), 3.49-3.38 (m, 4H), 3.26-3.14 (m, 2H), 2.44 (s, 3H), 2.09 (q, J = 11.8, 9.6 Hz, 3H), 1.98-1.83 (m, 1H), 1.71 (q, J = 6.9 Hz, 2H), 1.27-1.16 (m, 1H), 0.94 (s, 9H). |
| 187 | N-(5-[[2-(2,6-dioxopiperidin-3-yl)-1,3-dioxoisoindol-5-yl]amino]pentyl)-4-[(2S)-2-[(1-methanesulfonylpyrrol-3-yl)formamido]-2-[(4-phenyl-1,3-thiazol-2-yl)carbamoyl]ethoxy]-butanamide | 861.1 | $^1$H NMR (400 MHz, DMSO-d6) δ 12.50 (s, 1H), 11.05 (s, 1H), 8.50 (d, J = 7.2 Hz, 1H), 7.98 (t, J = 2.0 Hz, 1H), 7.94-7.87 (m, 2H), 7.71 (t, J = 5.6 Hz, 1H), 7.63 (s, 1H), 7.55 (d, J = 8.3 Hz, 1H), 7.43 (dd, J = 8.4, 6.9 Hz, 2H), 7.37-7.27 (m, 2H), 7.07 (t, J = 5.3 Hz, 1H), 6.93 (d, J = 2.2 Hz, 1H), 6.86-6.77 (m, 2H), 5.02 (dd, J = 12.9, 5.4 Hz, 1H), 4.90 (q, J = 6.4 Hz, 1H), 3.78-3.70 (m, 2H), 3.46 (tt, J = 6.4, 3.6 Hz, 3H), 3.32 (s, 2H), 3.14-3.07 (m, 2H), 3.02 (q, J = 6.5 Hz, 2H), 2.87 (ddd, J = 17.5, 14.0, 5.5 Hz, 1H), 2.62-2.53 (m, 2H), 2.09 (t, J = 7.5 Hz, 2H), 1.99 (ddd, J = 12.7, 6.4, 4.1 Hz, 1H), 1.71 (p, J = 6.8 Hz, 2H), 1.54 (p, J = 7.2 Hz, 2H), 1.40-1.32 (m, 4H). |

TABLE 22-continued

The following compounds were prepared using standard chemical manipulations and procedures similar to those used for the preparation of Compound 1

| Cmpd # | Name | LC-MS (ESI) (m/z) | $^1$H NMR |
|---|---|---|---|
| 228 | N-(2-[[2-(2,6-dioxopiperidin-3-yl)-1,3-dioxoisoindol-5-yl]oxylethyl)-4-[(2S)-2-[(1-methanesulfonylpyrrol-3-yl)formamido]-2-[(4-phenyl-1,3-thiazol-2-yl)carbamoyl]ethoxy]-butanamide | 820 | 1H NMR (400 MHz, DMSO-d6) δ 12.49 (s, 1H), 11.11 (s, 1H), 8.49 (d, J = 7.2 Hz, 1H), 8.05 (t, J = 5.6 Hz, 1H), 7.98 (t, J = 2.0 Hz, 1H), 7.93-7.86 (m, 2H), 7.81 (d, J = 8.3 Hz, 1H), 7.63 (s, 1H), 7.47-7.38 (m, 3H), 7.37-7.26 (m, 3H), 6.82-6.77 (m, 1H), 5.16-5.07 (m, 1H), 4.95-4.86 (m, 1H), 4.17 (t, J = 5.6 Hz, 2H), 3.74 (d, J = 6.4 Hz, 2H), 3.56 (s, 3H), 3.53-3.40 (m, 4H), 2.96-2.82 (m, 1H), 2.64-2.51 (m, 2H), 2.14 (t, J = 7.4 Hz, 2H), 2.10-2.00 (m, 1H), 1.78-1.67 (m, 2H). |

Preparation of tert-butyl 4-[[(2S)-2-[(1-methanesulfonylpyrrol-3-yl)formamido]-2-[(4-phenyl-1,3-thiazol-2-yl)carbamoyl]ethoxy]methyl]benzoate

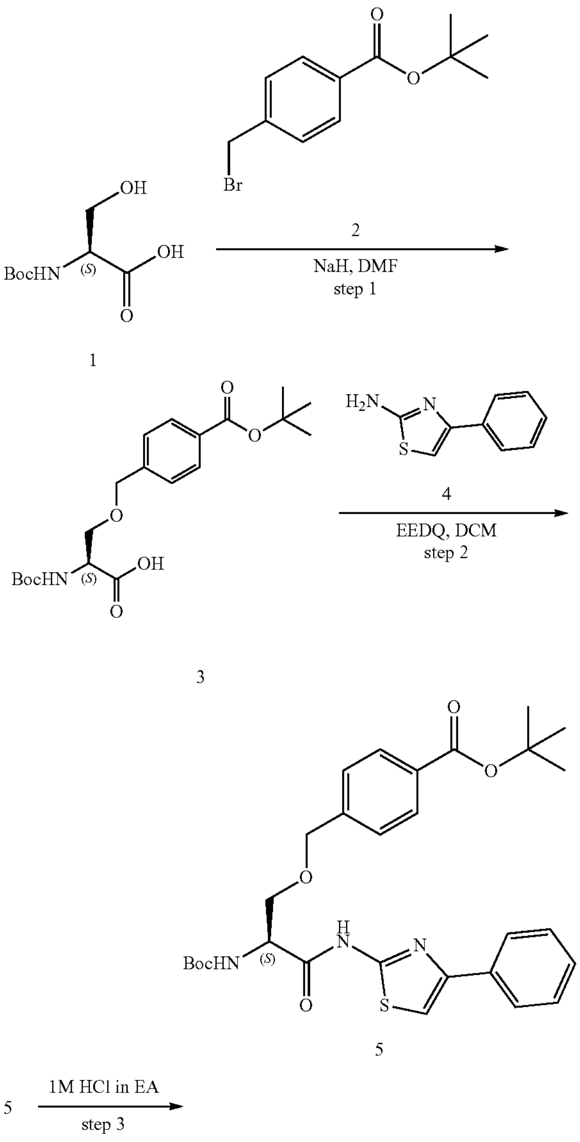

-continued

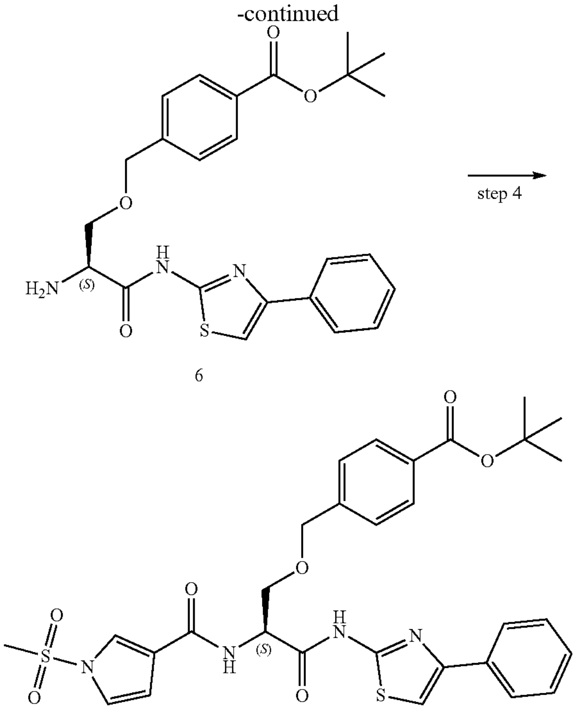

Step 1: Preparation of (2S)-2-[(tert-butoxycarbonyl)amino]-3-[[4-(tert-butoxycarbonyl)phenyl]methoxy]propanoic acid (Intermediate 3)

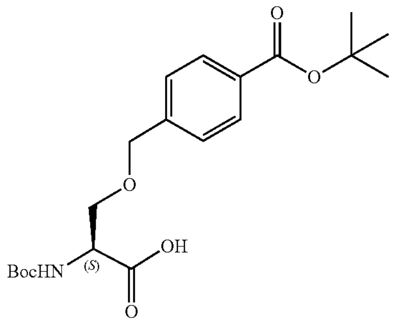

3

To a solution of (2S)-2-[(tert-butoxycarbonyl)amino]-3-hydroxypropanoic acid (1.00 g, 4.873 mmol, 1.00 equiv) in DMF (40.00 mL) was added NaH (233.88 mg, 9.746 mmol, 2.00 equiv). The solution was stirred at room temperature for 1 h. Then tert-butyl 4-(bromomethyl)benzoate (1321.35 mg, 4.873 mmol, 1.00 equiv) was added and the solution was stirred for 16 h at room temperature. The reaction was quenched with 40 mL water at 0 degrees C. The aqueous layer was washed by EtOAc (30 mL×3) and then acidified to PH ~3 at 0 degrees C. The aqueous phase was then extracted into EtOAc (30 mL×3). The combined organic layers were dried by sodium sulfate. After removing the organic solvent, the residue was purified by reverse phase flash chromatography with the following conditions: column, C18 silica gel; mobile phase, ACN in water, 10% to 100% gradient in 10 min; detector, UV 210 nm. This resulted in intermediate 3 (1.2 g, 62.27%) as a white solid. LCMS (ESI) m/z: $[M+H]^+$=396.

Step 2: Preparation of tert-butyl 4-[[(2S)-2-[(tert-butoxycarbonyl)amino]-2-[(4-phenyl-1,3-thiazol-2-yl)carbamoyl]ethoxy]methyl]benzoate (Intermediate 5)

5

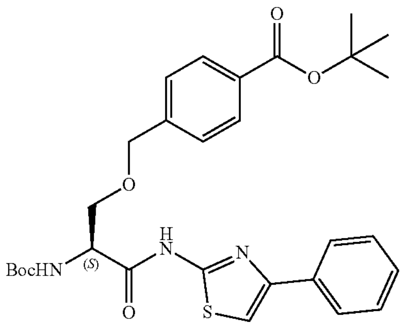

To a solution of phenthiazamine (445.67 mg, 2.529 mmol, 1.00 equiv) and intermediate 3 (1000.00 mg, 2.529 mmol, 1.00 equiv) in DCM (100.00 mL) was added ethyl 2-ethoxy-1,2-dihydroquinoline-1-carboxylate (687.87 mg, 2.782 mmol, 1.10 equiv). The solution was stirred at room temperature for 16 h. The resulting mixture was concentrated under reduced pressure and the residue was purified by silica gel column chromatography, eluted with PE/EtOAc (5:1) to afford intermediate 5 (1200 mg, 85.71%) as a yellow oil. LCMS (ESI) m/z: $[M+H]^+$=554.

Step 3: Preparation of tert-butyl 4-[[(2S)-2-amino-2-[(4-phenyl-1,3-thiazol-2-yl)carbamoyl]ethoxy]methyl]benzoate (Intermediate 6)

6

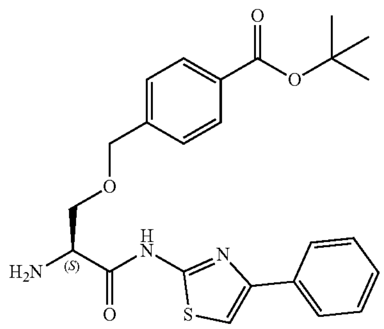

A solution of intermediate 5 (240.00 mg, 0.433 mmol, 1.00 equiv) in HCl (1 M in EA) (6.00 mL) was stirred at room temperature for 5 h. The precipitated solids were collected by filtration and washed with EtOAc (3×3 mL). This provided intermediate 6 (72 mg, 36.62%) as a white solid. LCMS (ESI) m/z: $[M+H]^+$=454.

Step 4: Preparation of (tert-butyl 4-[[(2S)-2-[(1-methanesulfonylpyrrol-3-yl)formamido]-2-[(4-phenyl-1,3-thiazol-2-yl)carbamoyl]ethoxy]methyl]benzoate

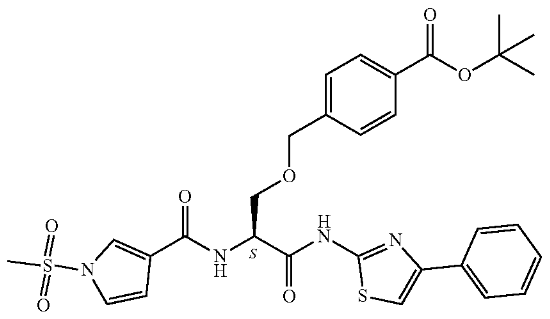

To a solution of 1-methanesulfonylpyrrole-3-carboxylic acid (68.00 mg, 0.359 mmol, 1.00 equiv), intermediate 6 (163.02 mg, 0.359 mmol, 1.00 equiv), and DIEA (139.36 mg, 1.078 mmol, 3.00 equiv) in DMF (2 mL) was added HATU (136.66 mg, 0.359 mmol, 1.00 equiv). The solution was stirred at room temperature for 2 h. The resulting mixture was extracted into EtOAc (3×30 mL), dried over anhydrous $MgSO_4$. After filtration, the filtrate was concentrated under reduced pressure and the residue was purified by reverse phase flash chromatography with the following conditions: column, C18 silica gel; mobile phase, ACN in water, 0% to 100% gradient in 15 min; detector, UV 254 nm. This provided in the title compound (9.9 mg, 4.37%) as a white solid. $^1$H NMR (400 MHz, DMSO-$d_6$) δ 12.52 (s, 1H), 8.54 (d, J=7.2 Hz, 1H), 8.01-7.95 (m, 1H), 7.94-7.87 (m, 2H), 7.84-7.77 (m, 2H), 7.65 (s, 1H), 7.48-7.38 (m, 4H), 7.37-7.26 (m, 2H), 6.85-6.76 (m, 1H), 4.99 (q, J=6.4 Hz, 1H), 4.65 (s, 2H), 3.83 (d, J=6.4 Hz, 2H), 3.57 (s, 3H), 1.50 (s, 9H). LCMS (ESI) m/z: $[M+H]^+$=625.35.

Compound 171—Preparation of (4-[[(2S)-2-[(1-tert-butylpyrrol-3-yl)formamido]-2-[(4-phenyl-1,3-thiazol-2-yl)carbamoyl]ethoxy]methyl]-N-[2-([1-[2-(2,6-dioxopiperidin-3-yl)-1,3-dioxoisoindol-5-yl]azetidin-3-yl]oxy)ethyl]benzamide
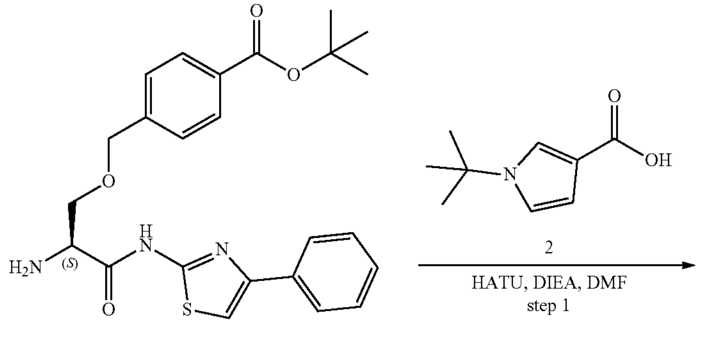
1
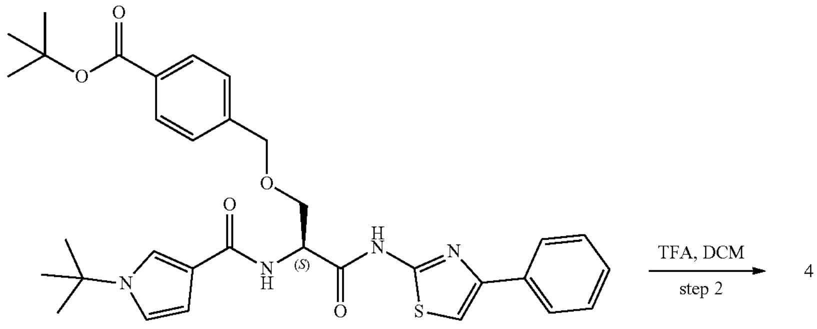
3
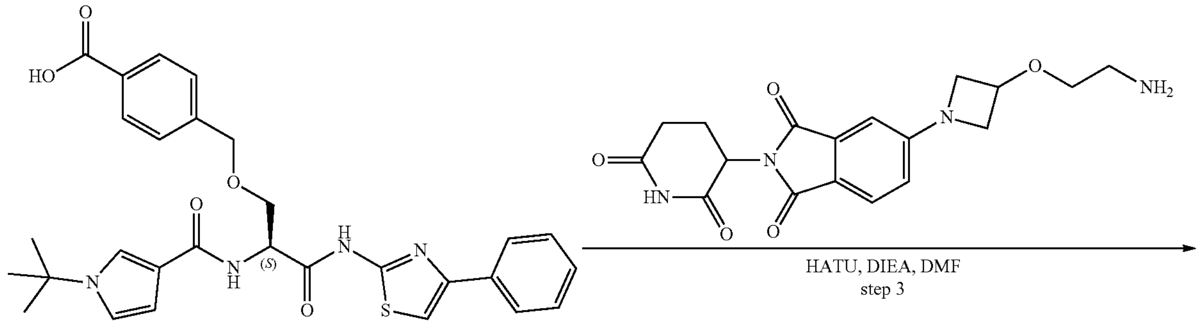
4
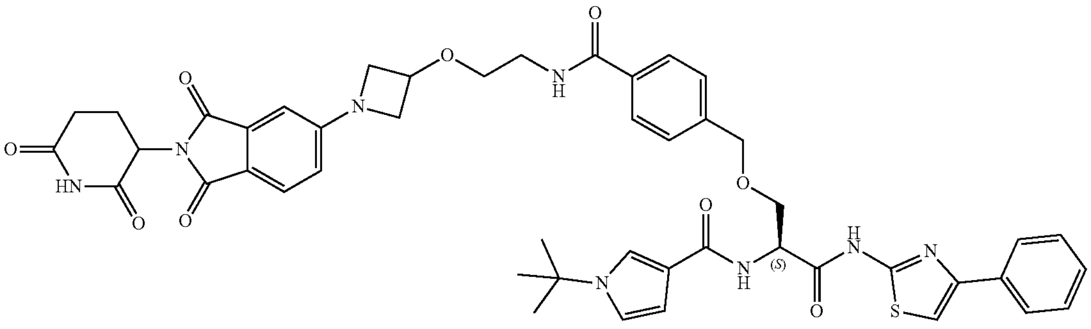
171

Step 1: Preparation of (prop-2-en-1-yl (2S)-2-[(tert-butoxycarbonyl)amino]-4-(4-hydroxyphenyl)butanoate (Intermediate 3)

3

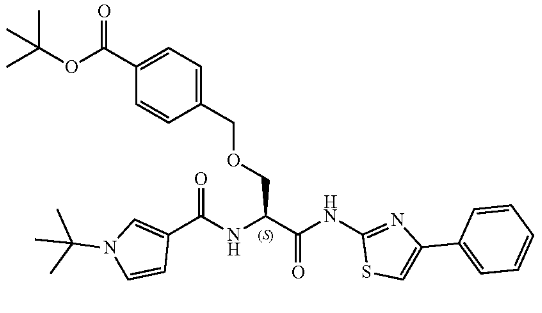

To a solution of 1-tert-butylpyrrole-3-carboxylic acid (40.00 mg, 0.239 mmol, 1.00 equiv), tert-butyl 4-[[(2S)-2-amino-2-[(4-phenyl-1,3-thiazol-2-yl)carbamoyl]ethoxy]methyl]benzoate (108.50 mg, 0.239 mmol, 1.00 equiv), and DIEA (92.75 mg, 0.718 mmol, 3.00 equiv) in DMF (0.50 mL) was added HATU (109.15 mg, 0.287 mmol, 1.20 equiv). The solution was stirred at room temperature for 1 h. The reaction was purified directly by reverse phase flash chromatography with the following conditions: column, C18 silica gel; mobile phase, ACN in water, 10% to 100% gradient in 20 min; detector, UV 254 nm. This provided intermediate 3 (120 mg, 83.22%) as a white solid. LCMS (ESI) m/z: $[M+H]^+$=603.

Step 2: Preparation of prop-2-en-1-yl (2S)-4-[4-[2-(tert-butoxy)-2-oxoethoxy]phenyl]-2-[(tert-butoxycarbonyl)amino]butanoate (Intermediate 4)

4

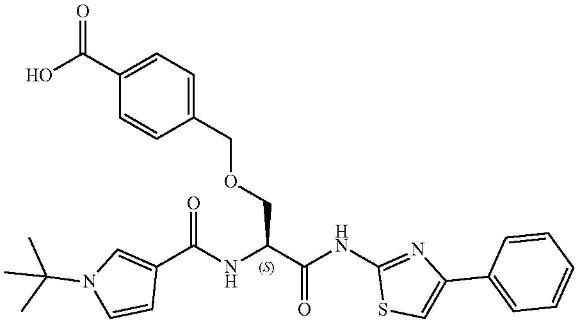

To a solution of intermediate 3 (190.00 mg) in DCM (2.00 mL) was added TFA (0.50 mL). The solution was stirred at room temperature for 1 h. The resulting mixture was concentrated under reduced pressure, providing intermediate 4 (150 mg) as a yellow solid. LCMS (ESI) m/z: $[M+H]^+$=547.

Step 3: Preparation of (4-[[(2S)-2-[(1-tert-butylpyrrol-3-yl)formamido]-2-[(4-phenyl-1,3-thiazol-2-yl)carbamoyl]ethoxy]methyl]-N-[2-([1-[2-(2,6-dioxopiperidin-3-yl)-1,3-dioxoisoindol-5-yl]azetidin-3-yl]oxy)ethyl]benzamide (Compound 171)

171

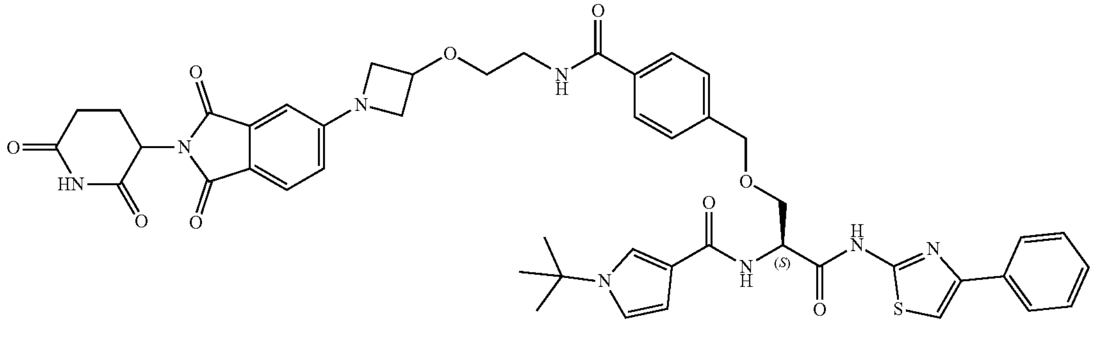

To a solution of 3-[6-[3-(2-aminoethoxy)azetidin-1-yl]-1-oxo-3H-isoindol-2-yl]piperidine-2,6-dione (6.56 mg, 0.018 mmol, 1.00 equiv), intermediate 4 (10.00 mg, 0.018 mmol, 1.00 equiv), and DIEA (11.82 mg, 0.091 mmol, 5.00 equiv) in DMF (1.00 mL) was added HATU (8.35 mg, 0.022 mmol, 1.20 equiv). The solution was stirred at room temperature for 1 h. The crude reaction mixture was purified by Prep-HPLC to afford Compound 171 (3.8 mg, 22.78%) as a yellow solid. $^1$H NMR (300 MHz, DMSO-d6) δ 12.42 (s, 1H), 11.14 (s, 1H), 8.65-8.57 (m, 1H), 8.05 (d, J=7.5 Hz, 1H), 8.01-7.93 (m, 2H), 7.91-7.79 (m, 2H), 7.76-7.63 (m, 3H), 7.57-7.35 (m, 5H), 7.07-7.00 (m, 1H), 6.91-6.83 (m, 1H), 6.73 (dd, J=8.3, 2.1 Hz, 1H), 6.60-6.55 (m, 1H), 5.20-5.01 (m, 2H), 4.74-4.65 (m, 2H), 4.63-4.51 (m, 1H), 4.38-4.27 (m, 2H), 3.98-3.85 (m, 4H), 3.68-3.58 (m, 2H), 3.53-3.45 (m, 2H), 3.08-2.89 (m, 1H), 2.72-2.60 (m, 2H), 2.12-1.99 (m, 1H), 1.56 (s, 9H). LCMS (ESI) m/z: [M+H]$^+$=901.10.

Compound 170—Preparation of 4-[[(2S)-2-[(1-tert-butylpyrrol-3-yl)formamido]-2-[(4-phenyl-1,3-thiazol-2-yl)carbamoyl]ethoxy]methyl]-N-[1-(2-[[2-(2,6-dioxopiperidin-3-yl)-1,3-dioxoisoindol-5-yl]oxy]ethyl)piperidin-4-yl]benzamide

170

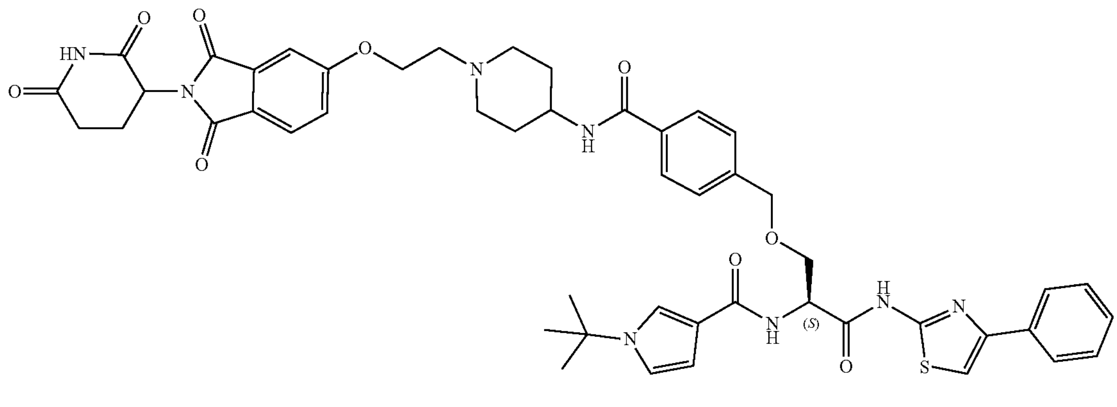

Compound 170 (5.6 mg, 23.00%, white solid) was prepared in a similar manner as described in the preparation of Compound 171. $^1$H NMR (300 MHz, DMSO-d$_6$) δ 12.47 (s, 1H), 11.13 (s, 1H), 8.27 (s, 1H), 7.99 (d, J=7.4 Hz, 1H), 7.95-7.84 (m, 3H), 7.78 (d, J=8.0 Hz, 2H), 7.66 (s, 1H), 7.61 (t, J=2.1 Hz, 1H), 7.53 (s, 1H), 7.49-7.36 (m, 5H), 7.35-7.29 (m, 1H), 6.97 (t, J=2.7 Hz, 1H), 6.54-6.48 (m, 1H), 5.14 (dd, J=12.9, 5.4 Hz, 1H), 4.99 (q, J=6.5 Hz, 1H), 4.63 (d, J=2.7 Hz, 2H), 4.44 (s, 2H), 3.82 (d, J=6.3 Hz, 3H), 3.25-3.02 (m, 4H), 3.00-2.81 (m, 2H), 2.64-2.57 (m, 2H), 2.13-2.00 (m, 2H), 1.98-1.80 (m, 2H), 1.79-1.60 (m, 2H), 1.50 (s, 9H). LCMS (ESI) m/z: [M+H]$^+$=929.50.

Compound 191—Preparation of (2S)-3-([4-[4-(2-[[2-(2,6-dioxopiperidin-3-yl)-1,3-dioxoisoindol-5-yl]oxy]ethyl)piperazine-1-carbonyl]phenyl]methoxy)-2-[(1-methanesulfonylpyrrol-3-yl)formamido]-N-(4-phenyl-1,3-thiazol-2-yl)propanamide; formic acid

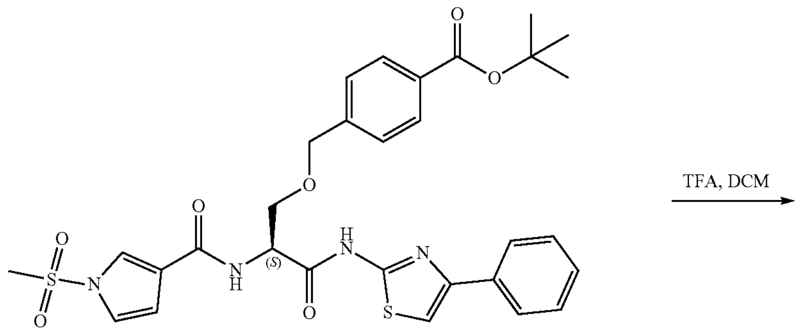

1

-continued
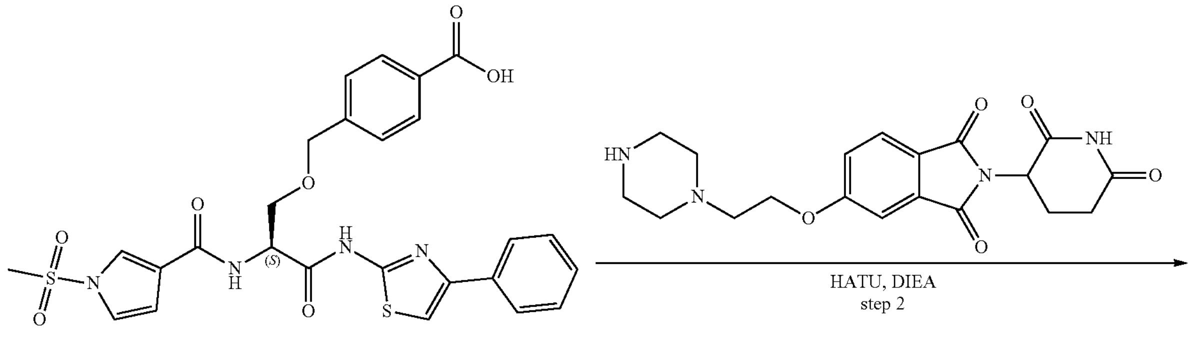
2
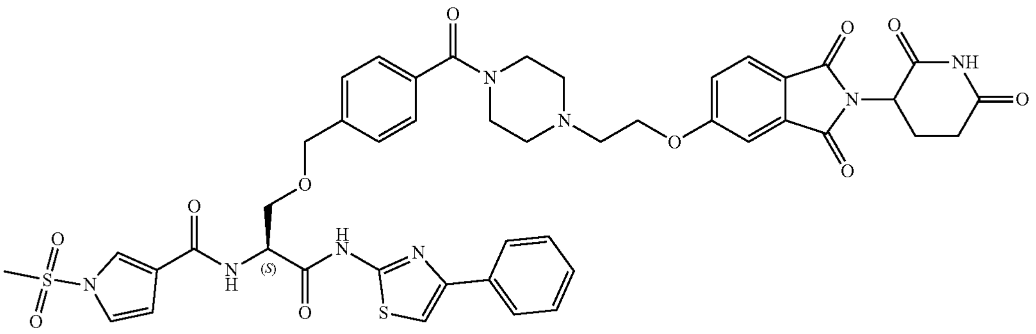
191

Step 1: Preparation of 4-[[(2S)-2-[(1-methanesulfonylpyrrol-3-yl)formamido]-2-[(4-phenyl-1,3-thiazol-2-yl)carbamoyl]ethoxy]methyl]benzoic acid (Intermediate 2)

2

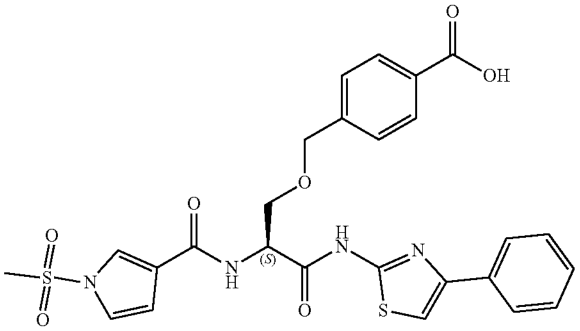

To a stirred mixture of tert-butyl 4-[[(2S)-2-[(1-methanesulfonylpyrrol-3-yl)formamido]-2-[(4-phenyl-1,3-thiazol-2-yl)carbamoyl]ethoxy]methyl]benzoate (14.00 mg, 0.023 mmol, 1.00 equiv) in DCM (0.50 mL) was added TFA (0.10 mL) dropwise at room temperature. The resulting mixture was stirred for 1 h then was concentrated under reduced pressure to afford intermediate 2 (13 mg, crude) as a light yellow oil.

Step 2: Preparation of (2S)-3-([4-[4-(2-[[2-(2,6-dioxopiperidin-3-yl)-1,3-dioxoisoindol-5-yl]oxy]ethyl)piperazine-1-carbonyl]phenyl]methoxy)-2-[(1-methanesulfonylpyrrol-3-yl)formamido]-N-(4-phenyl-1,3-thiazol-2-yl)propanamide; formic acid (Compound 191)

191

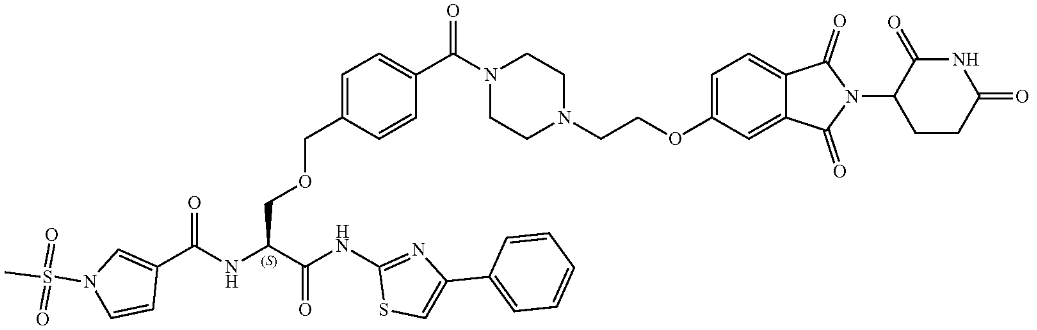

FA

To a stirred solution of 4-[[(2S)-2-[(1-methanesulfonylpyrrol-3-yl)formamido]-2-[(4-phenyl-1,3-thiazol-2-yl)carbamoyl]ethoxy]methyl]benzoic acid (13.00 mg, 0.023 mmol, 1.00 equiv) and HATU (9.56 mg, 0.025 mmol, 1.10 equiv) in DMF (2.00 mL) were added DIEA (8.86 mg, 0.069 mmol, 3.00 equiv) and 2-(2,6-dioxo piperidin-3-yl)-5-[2-(piperazin-1-yl)ethoxy]isoindole-1,3-dione (9.72 mg, 0.025 mmol, 1.10 equiv) dropwise. The crude product was purified by Prep-HPL C to afford Compound 191 (3.4 mg, 14.93%) as a white solid.

$^1$H NMR (400 MHz, DMSO-d6) δ 12.55 (s, 1H), 11.11 (s, 1H), 8.55 (d, J=7.2 Hz, 1H), 8.13 (s, 1H), 8.00-7.96 (m, 1H), 7.94-7.88 (m, 2H), 7.83 (d, J=8.3 Hz, 1H), 7.65 (s, 1H), 7.48-7.46 (m, 1H), 7.46-7.40 (m, 2H), 7.40-7.26 (m, 7H), 6.82-6.77 (m, 1H), 5.16-5.07 (m, 1H), 5.03-4.95 (m, 1H), 4.61 (d, J=1.8 Hz, 2H), 4.36-4.24 (m, 2H), 3.84 (d, J=6.4 Hz, 2H), 3.69-3.48 (m, 5H), 3.40-3.33 (m, 3H), 2.95-2.83 (m, 1H), 2.80-2.71 (m, 2H), 2.65-2.53 (m, 3H), 2.10-2.00 (m, 1H). LCMS [M+H]$^+$=937.0.

TABLE 23

The following compounds were prepared using standard chemical manipulations and procedures similar to those used for the preparation of Compound 191

| Cmpd # | Name | LC-MS (ESI) (m/z) | $^1$H NMR |
|---|---|---|---|
| 190 | N-[2-(2-[[2-(2,6-dioxopiperidin-3-yl)-1,3-dioxoisoindol-4-yl]amino]ethanesulfonyl)-ethyl]-4-[[(2S)-2-[(1-methanesulfonylpyrrol-3-yl)formamido]-2-[(4-phenyl-1,3-thiazol-2-yl)carbamoyl]ethoxy]-methyl]benzamide. | 959.40 | $^1$H NMR (300 MHz, DMSO-d$_6$) δ 12.56 (s, 1H), 11.10 (s, 1H), 8.68 (t, J = 5.5 Hz, 1H), 8.57 (d, J = 7.2 Hz, 1H), 7.98 (t, J = 2.0 Hz, 1H), 7.95-7.87 (m, 2H), 7.77 (d, J = 8.3 Hz, 2H), 7.66 (s, 1H), 7.59 (dd, J = 8.5, 7.1 Hz, 1H), 7.50-7.27 (m, 6H), 7.15 (d, J = 8.6 Hz, 1H), 7.08 (d, J = 7.0 Hz, 1H), 6.90-6.76 (m, 2H), 5.12-4.94 (m, 2H), 4.63 (d, J = 2.1 Hz, 2H), 3.81 (dd, J = 17.1, 6.4 Hz, 4H), 3.66 (t, J = 6.3 Hz, 2H), 3.57(s, 3H), 3.49-3.41 (m, 4H), 2.91-2.79 (m, 1H), 2.61 (s, 2H), 2.11-1.97 (m, 1H). |
| 192 | (2S)-3-([4-[4-([4-[2-(2,6-dioxopiperidin-3-yl)-1,3-dioxoisoindol-5-yl]piperazin-1-yl]methyl)-piperidine-1-carbonyl]phenyl]methoxy)-2-[(1-methanesulfonylpyrrol-3-yl)formamido]-N-(4-phenyl-1,3-thiazol-2-yl)propanamide; formic acid | 990.45 | $^1$H NMR (400 MHz, DMSO-d6) δ 12.54 (s, 1H), 11.08 (s, 1H), 8.55 (d, J = 7.2 Hz, 1H), 8.19 (s, 1H), 8.01-7.96 (m, 1H), 7.91 (d, J = 7.6 Hz, 2H), 7.72-7.63 (m, 2H), 7.50-7.21 (m, 10H), 6.82-6.77 (m, 1H), 5.12-5.04 (m, 1H), 5.03-4.95 (m, 1H), 4.61 (s, 2H), 4.51-4.34 (brs, 1H), 3.85 (d, J = 6.3 Hz, 2H), 3.57 (s, 3H), 3.02-2.83 (m, 1H), 2.81-2.71 (m, 1H), 2.64-2.56 (m, 1H), 2.45-2.40 (m, 2H), 2.22-2.13 (m, 2H), 2.06-1.97 (m, 1H), 1.86-1.73 (m, 2H), 1.66-1.55 (m, 1H), 1.08-0.95 (m, 2H). |
| 193 | (2S)-3-([4-[3-([4-[2-(2,6-dioxopiperidin-3-yl)-1,3-dioxoisoindol-5-yl]piperazin-1-yl]methyl)azetidine-1-carbonyl]phenyl]methoxy)-2-[(1-methanesulfonylpyrrol-3-yl)formamido]-N-(4-phenyl-1,3-thiazol-2-yl)propanamide; formic acid | 962.35 | $^1$H NMR (400 MHz, DMSO-d6) δ 12.54 (s, 1H), 11.08 (s, 1H), 8.55 (d, J = 7.2 Hz, 1H), 8.13 (s, 1H), 8.00-7.96 (m, 1H), 7.93-7.88 (m, 2H), 7.74-7.67 (m, 1H), 7.66 (s, 1H), 7.58-7.52 (m, 2H), 7.48-7.21 (m, 8H), 6.82-6.77 (m, 1H), 5.12-5.04 (m, 1H), 5.03-4.96 (m, 1H), 4.62 (s, 2H), 4.41-4.25 (m, 1H), 4.22-4.02 (m, 2H), 4.00-3.79 (m, 4H), 3.77-3.66 (m, 1H), 3.57 (s, 3H), 3.49-3.35 (m, 7H), 2.95-2.77 (m, 2H), 2.65-2.53 (m, 3H), 2.06-1.98 (m, 1H). |
| 194 | N-((2S)-3-((4-(3-((2-(2,6-dioxopiperidin-3-yl)-1,3-dioxoisoindolin-5-yl)oxy)azetidine-1-carbonyl)benzyl)oxy)-1-oxo-1-((4-phenylthiazol-2-yl)amino)propan-2-yl)-1-(methylsulfonyl)-1H-pyrrole-3-carboxamide | 880.00 | $^1$H NMR (400 MHz, DMSO-d6) δ 12.54 (s, 1H), 11.12 (s, 1H), 8.55 (d, J = 7.3 Hz, 1H), 7.98 (t, J = 2.0 Hz, 1H), 7.94-7.88 (m, 2H), 7.87 (d, J = 8.1 Hz, 1H), 7.65 (s, 1H), 7.59 (d, J = 7.9 Hz, 2H), 7.47-7.36 (m, 4H), 7.34-7.27 (m, 4H), 6.79 (dd, J = 3.3, 1.7 Hz, 1H), 5.27 (s, 1H), 5.13 (dd, J = 12.8, 5.4 Hz, 1H), 4.99 (q, J = 6.6 Hz, 1H), 4.72 (s, 1H), 4.63 (s, 2H), 4.56 (s, 1H), 4.32 (s, 1H), 4.02 (s, 1H), 3.84 (d, J = 6.3 Hz, 2H), 3.56 (s, 3H), 2.97-2.83 (m, 1H), 2.71-2.54 (m, 2H), 2.05 (dd, J = 11.9, 5.8 Hz, 1H). |
| 195 | N-((2S)-3-((4-(4-(4-(4-(2-(2,6-dioxopiperidin-3-yl)-1,3-dioxoisoindolin-5-yl)piperazin-1-yl)butyl)piperidine-1-carbonyl)benzyl)oxy)-1-oxo-1-((4-phenylthiazol-2-yl)amino)propan-2-yl)-1-(methylsulfonyl)-1H-pyrrole-3-carboxamide formate | 1032.20 | $^1$H NMR (400 MHz, DMSO-d6) δ 12.53 (s, 1H), 11.08 (s, 1H), 8.54 (d, J = 7.2 Hz, 1H), 8.15 (s, 1H), 7.98 (t, J = 2.0 Hz, 1H), 7.94-7.86 (m, 2H), 7.71-7.62 (m, 2H), 7.47-7.40 (m, 2H), 7.38-7.32 (m, 4H), 7.32-7.29 (m, 1H), 7.29-7.22 (m, 3H), 6.80 (dd, J = 3.3, 1.6 Hz, 1H), 5.07 (dd, J = 12.9, 5.4 Hz, 1H), 4.99 (q, J = 6.4 Hz, 1H), 4.61 (s, 2H), 3.84 (d, J = 6.3 Hz, 2H), 3.56 (s, 3H), 3.43 (t, J = 5.0 Hz, 4H), 2.88 (td, J = 17.1, 15.2, 5.5 Hz, 3H), 2.75-2.55 (m, 2H), 2.52 (d, J = 2.7 Hz, 2H), 2.36-2.26 (m, 2H), 2.04-1.96 (m, 1H), 1.79-1.38 (m, 6H), 1.34-1.11 (m, 6H), 0.99 (s, 3H). |
| 199 | (2S)-3-[[4-(2-[[2-(2,6-dioxopiperidin-3-yl)-1,3-dioxoisoindol-5-yl]oxy]-7-azaspiro[3.5]nonane-7-carbonyl)phenyl]methoxy]-2-[(1-methanesulfonylpyrrol-3-yl)formamido]-N-(4-phenyl-1,3-thiazol-2-yl)propanamide | 948.35 | $^1$H NMR (400 MHz, DMSO-d$_6$) δ 12.51 (s, 1H), 11.11 (s, 1H), 8.54 (d, J = 7.2 Hz, 1H), 8.02-7.96 (m, 1H), 7.95-7.88 (m, 2H), 7.83 (d, J = 8.3 Hz, 1H), 7.65 (s, 1H), 7.48-7.40 (m, 2H), 7.39-7.23 (m, 8H), 6.84-6.75 (m, 1H), 5.12 (dd, J = 12.9, 5.4 Hz, 1H), 5.06-4.91 (m, 2H), 4.61 (s, 2H), 3.84 (d, J = 6.3 Hz, 2H), 3.64-3.52 (m, 4H), 3.52-3.41 (m, 1H), 3.17-3.03 (m, 2H), 2.95-2.82 (m, 1H), 2.69-2.57 (m, 2H), 2.56-2.51 (m, 2H), 2.10-2.00 (m, 1H), 1.92-1.77 (m, 2H), 1.73-1.36 (m, 4H). |

TABLE 23-continued

The following compounds were prepared using standard chemical manipulations and procedures similar to those used for the preparation of Compound 191

| Cmpd # | Name | LC-MS (ESI) (m/z) | $^1$H NMR |
|---|---|---|---|
| 202 | (2S)-3-[(4-[[2-(2-[2-[2-(2-[[2-(2,6-dioxopiperidin-3-yl)-1,3-dioxoisoindol-5-yl]oxy]acetamido)ethoxy]-ethoxy]ethoxy)ethyl]carbamoyl]-phenyl)methoxy]-2-[(1-methanesulfonylpyrrol-3-yl)formamido]-N-(4-phenyl-1,3-thiazol-2-yl)propanamide. | 1057.45 | $^1$H NMR (300 MHz, DMSO-d$_6$) δ 12.56 (s, 1H), 11.12 (s, 1H), 8.56 (d, J = 7.2 Hz, 1H), 8.45 (t, J = 5.5 Hz, 1H), 8.25 (t, J = 5.7 Hz, 1H), 7.98-7.78 (m, 6H), 7.65 (s, 1H), 7.49-7.27 (m, 8H), 6.80 (dd, J = 3.3, 1.7 Hz, 1H), 5.13 (dd, J = 12.8, 5.3 Hz, 1H), 5.07-4.96 (m, 1H), 4.73 (s , 2H), 4.64 (s, 2H), 3.84 (d, J = 6.4 Hz, 2H), 3.56 (s, 3H), 3.50-3.48 (m, 5H), 3.47-3.46 (m, 4H), 3.45-3.41 (m, 4H), 3.39 (s, 1H), 3.28 (s, 1H), 2.94-2.90 (m, 1H), 2.61 (s, 3H), 2.05 (d, J = 11.8 Hz, 1H). |
| 203 | (2S)-3-([4-[(2-[2-[2-(2-[[2-(2,6-dioxopiperidin-3-yl)-1,3-dioxoisoindol-5-yl]oxy]acetamido)-ethoxy]ethoxy]ethyl)-carbamoyl]phenyl]methoxy)-2-[(1-methanesulfonylpyrrol-3-yl)formamido]-N-(4-phenyl-1,3-thiazol-2-yl)propanamide | 1113.10 | .$^1$H NMR (300 MHz, DMSO-d6) δ 12.54 (s, 1H), 11.15 (s, 1H), 8.57 (d, J = 7.2 Hz, 1H), 8.46 (t, J = 5.1 Hz, 1H), 8.26 (t, J = 5.8 Hz, 1H), 7.98 (s, 1H), 7.95-7.82 (m, 3H), 7.82-7.74 (m, 2H), 7.65 (s, 1H), 7.48-7.34 (m, 6H), 7.35-7.26 (m, 2H), 6.80 (d, J = 3.3, 1.6 Hz, 1H), 5.19-5.07 (m, 1H), 5.07-4.94 (m, 1H), 4.73 (s, 2H), 4.63 (s, 2H), 3.84 (d, J = 6.3 Hz, 2H), 3.57 (s, 3H), 3.54-3.47 (m, 6H), 3.48-3.36 (m, 5H), 3.28-3.23 (m, 1H), 2.97-2.80 (m, 1H), 2.71-2.54 (m, 2H), 2.11-2.00 (m, 1H). |
| 204 | N-[5-[2-(2,6-dioxopiperidin-3-yl)-1,3-dioxoisoindol-5-yl]pent-4-yn-1-yl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 890.00 | $^1$H NMR (300 MHz, DMSO-d6) δ 12.54 (s, 1H), 11.15 (s, 1H), 8.61-8.48 (m, 2H), 7.99 (s, 1H), 7.96-7.75 (m, 7H), 7.66 (s, 1H), 7.49-7.27 (m, 6H), 6.80 (s, 1H), 5.22-5.10 (m, 1H), 5.01 (d, J = 6.9 Hz, 1H), 4.63 (s, 2H), 3.84 (d, J = 6.4 Hz, 2H), 3.57 (s, 3H), 3.45-3.36 (m, 2H), 2.99-2.81 (m, 1H), 2.67-2.51 (m, 4H), 2.11-2.05 (m, 1H), 1.89-1.78 (m, 2H). |
| 205 | N-[5-[2-(2,6-dioxopiperidin-3-yl)-1,3-dioxoisoindol-4-yl]pent-4-yn-1-yl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 888.00 | $^1$H NMR (300 MHz, DMSO-d$_6$) δ 12.56 (s, 1H), 11.13 (s, 1H), 8.57 (d, J = 7.2 Hz, 1H), 8.50 (t, J = 5.6 Hz, 1H), 8.01-7.97 (m, 1H), 7.95-7.88 (m, 2H), 7.85 (m, 1H), 7.80 (m, 4H), 7.66 (s, 1H), 7.48-7.28 (m, 6H), 6.80 (dd, J = 3.3, 1.7 Hz, 1H), 5.15 (m, 1H), 5.01 (q, J = 6.6 Hz, 1H), 4.63 (s, 2H), 3.84 (d, J = 6.4 Hz, 2H), 3.57 (s, 3H), 3.43 (q, J = 6.5 Hz, 2H), 3.31 (s, 3H), 2.97-2.81 (m, 1H), 2.58 (m, 4H), 2.08 (s, 1H), 1.87 (m, 2H). |
| 206 | N-[2-[3-(2-[[2-(2,6-dioxopiperidin-3-yl)-1,3-dioxoisoindol-4-yl]amino]ethoxy)phenoxy] ethyl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 1003.25 | $^1$H NMR (300 MHz, DMSO-d$_6$) δ 12.56 (s, 1H), 11.10 (s, 1H), 8.64 (t, J = 5.5 Hz, 1H), 8.57 (d, J = 7.2 Hz, 1H), 7.98 (t, J = 2.0 Hz, 1H), 7.95-7.87 (m, 2H), 7.85-7.77 (m, 2H), 7.68-7.57 (m, 2H), 7.42 (m, 4H), 7.37-7.28 (m, 2H), 7.19 (m, 2H), 7.06 (d, J = 7.0 Hz, 1H), 6.83-6.70 (m, 2H), 6.60-6.49 (m, 3H), 5.03 (m, 2H), 4.64 (m, 2H), 4.11 (m, 4H), 3.84 (d, J = 6.4 Hz, 2H), 3.70 (m, , 2H), 3.57 (m, 5H), 2.97-2.80 (m, 1H), 2.58 (m, 2H), 2.02 (m, 1H). |
| 207 | N-[2-[3-(2-[[2-(2,6-dioxopiperidin-3-yl)-1,3-dioxoisoindol-5-yl]amino]ethoxy)phenoxy]-ethyl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 1003.25 | $^1$H NMR (300 MHz, DMSO-d$_6$) δ 12.56 (s, 1H), 11.07 (s, 1H), 8.64 (t, J = 5.5 Hz, 1H), 8.57 (d, J = 7.2 Hz, 1H), 7.98 (m, 1H), 7.95-7.87 (m, 2H), 7.81 (d, J = 8.1 Hz, 2H), 7.65 (s, 1H), 7.59 (d, J = 8.3 Hz, 1H), 7.42 (m, 4H), 7.37-7.26 (m, 3H), 7.17 (t, J = 8.6 Hz, 1H), 7.07 (m, 1H), 6.95 (m, 1H), 6.80 (dd, J = 3.3, 1.6 Hz, 1H), 6.63-6.49 (m, 3H), 5.02 (m, 2H), 4.64 (s, 2H), 4.20-4.02 (m, 4H), 3.84 (d, 2H), 3.57 (m, 7H), 2.88 (m, 1H), 2.60 (s, 2H), 2.06-1.94 (m, 1H). |
| 233 | (2S)-3-([4-[4-(5-[[2-(2,6-dioxopiperidin-3-yl)-1,3-dioxoisoindol-5-yl]oxy]pentyl)piperazine-1-carbonyl]phenyl]methoxy)-2-[(1-methanesulfonylpyrrol-3-yl)formamido]-N-(4-phenyl-1,3-thiazol-2-yl)propanamide | 979.15 | $^1$H NMR (400 MHz, DMSO-d6) δ 12.54 (s, 1H), 11.11 (s, 1H), 8.55 (d, J = 7.2 Hz, 1H), 7.98 (t, J = 2.0 Hz, 1H), 7.94-7.88 (m, 2H), 7.83 (d, J = 8.3 Hz, 1H), 7.65 (s, 1H), 7.46-7.40 (m, 3H), 7.39-7.26 (m, 7H), 6.80 (dd, J = 3.3, 1.6 Hz, 1H), 5.12 (dd, J = 12.9, 5.4 Hz, 1H), 4.99 (q, J = 6.6 Hz, 1H), 4.66-4.57 (m, 2H), 4.17 (t, J = 6.5 Hz, 2H), 3.84 (d, J = 6.4 Hz, 2H), 3.56 (s, 4H), 3.27-3.21 (m, 3H), 2.92-2.85 (m, 1H), 2.60 (d, J = 17.6 Hz, 2H), 2.29 (s, 6H), 2.08-2.01 (m, 1H), 1.77 (t, J = 7.0 Hz, 2H), 1.44 (d, J = 15.3 Hz, 4H). |
| 234 | (2S)-3-([4-[7-(3-[[2-(2,6-dioxopiperidin-3-yl)-1,3-dioxoisoindol-5-yl]amino]propyl)-2,7-diazaspiro[3.5]nonane-2- | 990.15 | $^1$H NMR (400 MHz, DMSO-d6) δ 12.47 (s, 1H), 10.99 (s, 1H), 8.48 (d, J = 7.2 Hz, 1H), 7.91 (t, J = 2.0 Hz, 1H), 7.87-7.80 (m, 2H), 7.58 (s, 1H), 7.49 (d, J = 8.2 Hz, 3H), 7.37 (t, J = 7.6 Hz, 2H), 7.33-7.21 (m, 4H), 7.07 (t, J = 5.6 Hz, 1H), 6.88 (d, J = 2.1 Hz, 1H), 6.78 (dd, J = 8.4, 2.1 Hz, 1H), |

TABLE 23-continued

The following compounds were prepared using standard chemical manipulations and procedures similar to those used for the preparation of Compound 191

| Cmpd # | Name | LC-MS (ESI) (m/z) | $^1$H NMR |
|---|---|---|---|
| | carbonyl]phenyl]methoxy)-2-[(1-methanesulfonylpyrrol-3-yl)formamido]-N-(4-phenyl-1,3-thiazol-2-yl)propanamide | | 6.73 (dd, J = 3.3, 1.7 Hz, 1H), 4.98-4.89 (m, 2H), 4.55 (d, J = 2.3 Hz, 2H), 3.84 (s, 2H), 3.77 (d, J = 6.3 Hz, 2H), 3.62 (s, 2H), 3.50 (s, 3H), 3.12 (d, J = 6.0 Hz, 2H), 2.87-2.73 (m, 2H), 2.54-2.48 (m, 1H), 2.24 (d, J = 7.1 Hz, 6H), 1.96-1.89 (m, 1H), 1.62 (d, J = 6.7 Hz, 6H). |
| 235 | (2S)-3-([4-[4-(3-[[2-(2,6-dioxopiperidin-3-yl)-1,3-dioxoisoindol-5-yl]oxy]propyl) piperazine-1-carbonyl]phenyl]methoxy)-2-[(1-methanesulfonylpyrrol-3-yl)formamido]-N-(4-phenyl-1,3-thiazol-2-yl)propanamide | 951.20 | $^1$H NMR (400 MHz, DMSO-d6) δ 12.55 (s, 1H), 11.11 (s, 1H), 8.55 (d, J = 7.2 Hz, 1H), 7.98 (t, J = 2.0 Hz, 1H), 7.94-7.88 (m, 2H), 7.84 (d, J = 8.3 Hz, 1H), 7.65 (s, 1H), 7.43 (t, J = 7.6 Hz, 3H), 7.40-7.23 (m, 7H), 6.80 (dd, J = 3.3, 1.6 Hz, 1H), 5.12 (dd, J = 12.9, 5.4 Hz, 1H), 4.99 (t, J = 6.7 Hz, 1H), 4.62 (s, 2H), 4.23 (s, 2H), 3.85 (d, J = 6.3 Hz, 2H), 3.57 (s, 4H), 3.29-3.17 (m, 4H), 2.93-2.87 (m, 1H), 2.64-2.53 (m, 2H), 2.49-2.37 (m, 4H), 2.34 (s, 1H), 2.08-1.92 (m, 3H). |
| 236 | N-((2S)-3-((4-((1-((2-(2,6-dioxopiperidin-3-yl)-1,3-dioxoisoindolin-4-yl)oxy)-2-oxo-6,9,12-trioxa-3-azatetradecan-14-yl)carbamoyl)benzyl)oxy)-1-oxo-1-((4-phenylthiazol-2-yl)amino)propan-2-yl)-1-(methylsulfonyl)-1H-pyrrole-3-carboxamide | 1057.15 | $^1$H NMR (400 MHz, DMSO-d6) δ 12.54 (s, 1H), 11.10 (s, 1H), 8.54 (d, J = 7.2 Hz, 1H), 8.43 (t, J = 5.6 Hz, 1H), 8.02-7.94 (m, 2H), 7.92-7.86 (m, 2H), 7.82-7.73 (m, 3H), 7.64 (s, 1H), 7.48 (d, J = 7.3 Hz, 1H), 7.45-7.34 (m, 5H), 7.34-7.27 (m, 2H), 6.78 (dd, J = 3.3, 1.7 Hz, 1H), 5.10 (dd, J = 12.9, 5.4 Hz, 1H), 4.99 (q, J = 6.6 Hz, 1H), 4.77 (s, 2H), 4.68-4.54 (m, 2H), 3.82 (d, J = 6.3 Hz, 2H), 3.55 (s, 3H), 3.49 (d, J = 3.9 Hz, 10H), 3.43 (t, J = 5.7 Hz, 2H), 3.36 (q, J = 8.0, 6.8 Hz, 4H), 2.93-2.83 (m, 1H), 2.69-2.53 (m, 2H), 2.06-1.97 (m, 1H). |
| 237 | N-[2-([3-[(2-[[2-(2,6-dioxopiperidin-3-yl)-1,3-dioxoisoindol-5-yl]oxy]ethoxy)methyl]phenyl]-methoxy)ethyl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 1032.35 | $^1$H NMR (400 MHz, DMSO-$d_6$) δ 12.54 (s, 1H), 11.11 (s, 1H), 8.61-8.46 (m, 2H), 7.99-7.96 (m, 1H), 7.92-7.88 (m, 2H), 7.84-7.75 (m, 3H), 7.64 (s, 1H), 7.47-7.31 (m, 7H), 7.31-7.26 (m, 3H), 7.25-7.20 (m, 2H), 6.83-6.76 (m, 1H), 5.12 (dd, J = 13.0, 5.4 Hz, 1H), 4.99 (q, J = 6.6 Hz, 1H), 4.69-4.57 (m, 2H), 4.51 (s, 2H), 4.48 (s, 2H), 4.39-4.28 (m, 2H), 3.87-3.73 (m, 4H), 3.58-3.49 (m, 5H), 3.47-3.40 (m, 2H), 2.96-2.82 (m, 1H), 2.64-2.53 (m, 2H), 2.07-2.00 (m, 1H). |
| 238 | (2S)-3-([4-[3-(2-[[2-(2,6-dioxopiperidin-3-yl)-1,3-dioxoisoindol-4-yl]oxy]ethyl)azetidine-1-carbonyl]phenyl]methoxy)-2-[(1-methanesulfonylpyrrol-3-yl)formamido]-N-(4-phenyl-1,3-thiazol-2-yl)propanamide | 908.10 | $^1$H NMR (400 MHz, DMSO-$d_6$) δ 12.53 (s, 1H), 11.11 (s, 1H), 8.54 (d, J = 7.3 Hz, 1H), 7.99-7.96 (m, 1H), 7.90 (d, J = 7.6 Hz, 2H), 7.84-7.78 (m, 1H), 7.65 (s, 1H), 7.58-7.53 (m, 2H), 7.51-7.47 (m, 1H), 7.47-7.40 (m, 3H), 7.38-7.33 (m, 2H), 7.33-7.28 (m, 2H), 6.81-6.78 (m, 1H), 5.12-5.06 (m, 1H), 5.02-4.96 (m, 1H), 4.61 (s, 2H), 4.33 (s, 1H), 4.25-4.19 (m, 2H), 4.17-4.07 (m, 2H), 3.87-3.80 (m, 3H), 3.56 (s, 3H), 2.96-2.82 (m, 1H), 2.82-2.72 (m, 1H), 2.69-2.56 (m, 2H), 2.12-1.96 (m, 3H). |
| 239 | (2S)-3-[[4-(4-[5-[2-(2,6-dioxopiperidin-3-yl)-1,3-dioxoisoindol-5-yl]pent-4-yn-1-yl]piperazine-1-carbonyl)phenyl]methoxy]-2-[(1-methanesulfonylpyrrol-3-yl)formamido]-N-(4-phenyl-1,3-thiazol-2-yl)propanamide; formic acid | 959.10 | $^1$H NMR (400 MHz, DMSO-$d_6$) δ 12.54 (s, 1H), 11.14 (s, 1H), 8.58-8.52 (m, 1H), 8.01-7.95 (m, 1H), 7.94-7.82 (m, 5H), 7.65 (s, 1H), 7.47-7.40 (m, 2H), 7.40-7.33 (m, 3H), 7.33-7.26 (m, 3H), 6.83-6.77 (m, 1H), 5.20-5.11 (m, 1H), 5.04-4.94 (m, 1H), 4.67-4.55 (m, 2H), 3.87-3.81 (m, 2H), 3.63-3.44 (m, 5H), 3.25-3.18 (m, 2H), 2.96-2.82 (m, 1H), 2.66-2.59 (m, 1H), 2.59-2.50 (m, 2H), 2.45-2.32 (m, 4H), 2.35-2.17 (m, 2H), 2.11-2.00 (m, 1H), 1.79-1.67 (m, 2H), 1.11-1.07 (m, 1H). |
| 240 | N-(2-[[2-(2,6-dioxopiperidin-3-yl)-1,3-dioxoisoindol-5-yl]amino]ethyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 867.00 | $^1$H NMR (400 MHz, DMSO-$d_6$) δ 12.54-12.49 (m, 1H), 11.06 (s, 1H), 8.62-8.53 (m, 2H), 8.01-7.95 (m, 1H), 7.94-7.87 (m, 2H), 7.83-7.76 (m, 2H), 7.64 (s, 1H), 7.57 (d, J = 8.4 Hz, 1H), 7.47-7.37 (m, 4H), 7.35-7.23 (m, 3H), 7.06-7.01 (m, 1H), 6.94-6.87 (m, 1H), 6.83-6.77 (m, 1H), 5.08-4.95 (m, 2H), 4.69-4.57 (m, 2H), 3.84 (d, J = 6.3 Hz, 2H), 3.57 (s, 3H), 3.45-3.38 (m, 2H), 3.37-3.34 (m, 2H), 2.95-2.81 (m, 1H), 2.63-2.51 (m, 2H), 2.04-1.95 (m, 1H). |
| 241 | N-(5-[[2-(2,6-dioxopiperidin-3-yl)-1,3-dioxoisoindol-5-yl]amino]pentyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 951.1 | $^1$H NMR (400 MHz, DMSO-d6) δ 11.09 (s, 1H), 8.55 (d, J = 7.3 Hz, 1H), 8.36 (t, J = 6.0 Hz, 1H), 7.98 (t, J = 2.0 Hz, 1H), 7.93-7.86 (m, 2H), 7.77 (d, J = 8.2 Hz, 2H), 7.64 (s, 1H), 7.57 (dd, J = 8.2, 7.6 Hz, 1H), 7.43 (t, J = 7.6 Hz, 2H), 7.38 (d, J = 8.0 Hz, 2H), 7.33 (d, J = 7.3 Hz, 1H), 7.30 (dd, J = 3.3, 2.0 Hz, 1H), 7.08 (d, J = 8.6 Hz, 1H), 7.01 (d, J = 7.3 Hz, 1H), 6.80 (dd, J = 3.3, 2.0 Hz, 1H), 6.52 (t, J = 6.0 Hz, 1H), 5.09-4.95 (m, 2H), 4.67-4.57 (m, 2H), 3.83 (d, J = 6.4 Hz, 2H), 3.56 (s, 3H), 3.28-3.16 (m, 4H), 2.96-2.79 (m, 1H), 2.63-2.52 (m, 2H), 2.06-1.96 (m, 1H), 1.59-1.53 (m, 2H), 1.53-1.46 (m, 2H), 1.30 (s, 9H). |

TABLE 23-continued

The following compounds were prepared using standard chemical manipulations and procedures similar to those used for the preparation of Compound 191

| Cmpd # | Name | LC-MS (ESI) (m/z) | $^1$H NMR |
|---|---|---|---|
| 242 | N-(5-[[2-(2,6-dioxopiperidin-3-yl)-1,3-dioxoisoindol-5-yl]amino]pentyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 895.1 | $^1$H NMR (400 MHz, DMSO-d6) δ 12.54 (s, 1H), 11.05 (s, 1H), 8.55 (d, J = 7.2 Hz, 1H), 8.42 (t, J = 5.7 Hz, 1H), 7.98 (t, J = 2.0 Hz, 1H), 7.94-7.87 (m, 2H), 7.82-7.74 (m, 2H), 7.65 (s, 1H), 7.55 (d, J = 8.4 Hz, 1H), 7.43 (dd, J = 8.4, 7.2 Hz, 2H), 7.38 (d, J = 8.4 Hz, 2H), 7.36-7.28 (m, 2H), 7.12 (t, J = 5.7 Hz, 1H), 6.95 (d, J = 2.0 Hz, 1H), 6.84 (dd, J = 8.4, 2.0 Hz, 1H), 6.80 (dd, J = 3.3, 1.6 Hz, 1H), 5.09-4.94 (m, 2H), 4.69-4.55 (m, 2H), 3.83 (d, J = 6.4 Hz, 2H), 3.57 (s, 3H), 3.29-3.25 (m, 2H), 3.23-3.16 (m, 2H), 2.94-2.78 (m, 1H), 2.70-2.52 (m, 2H), 2.05-1.92 (m, 1H), 1.70-1.50 (m, 4H). |
| 243 | N-(5-[[2-(2,6-dioxopiperidin-3-yl)-1,3-dioxoisoindol-5-yl]amino]pentyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 909.40 | $^1$H NMR (400 MHz, DMSO-d6) δ 12.54 (s, 1H), 11.05 (s, 1H), 8.55 (d, J = 7.2 Hz, 1H), 8.40 (t, J = 5.6 Hz, 1H), 7.98 (t, J = 2.0 Hz, 1H), 7.94-7.87 (m, 2H), 7.77 (d, J = 8.1 Hz, 2H), 7.65 (s, 1H), 7.55 (d, J = 8.1 Hz, 1H), 7.43 (t, J = 7.6 Hz, 2H), 7.38 (d, J = 8.1 Hz, 2H), 7.34 (dd, J = 7.6, 2.0 Hz, 1H), 7.30 (dd, J = 3.3, 2.2 Hz, 1H), 7.10 (t, J = 5.6 Hz, 1H), 6.94 (d, J = 2.2 Hz, 1H), 6.84 (dd, J = 8.1, 2.2 Hz, 1H), 6.80 (dd, J = 3.3, 2.2 Hz, 1H), 4.97-5.08 (m, 2H), 4.69-4.57 (m, 2H), 3.83 (d, J = 6.4 Hz, 2H), 3.56 (s, 3H), 3.28-3.20 (m, 2H), 3.12-3.18 (m, 2H), 2.94-2.80 (m, 1H), 2.51-2.62 (m, 2H), 2.04-1.92 (m, 1H), 1.51-1.62 (m, 4H), 1.34-1.43 (m, 2H). |
| 244 | (N-[2-[(2-[[2-(2,6-dioxopiperidin-3-yl)-1,3-dioxoisoindol-4-yl]amino]ethyl)(methyl)amino]-ethyl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 924.10 | $^1$H NMR (400 MHz, DMSO-d6) 612.55 (s, 1H), 11.08 (s, 1H), 8.56 (d, J = 7.2 Hz, 1H), 8.29 (d, J = 10.1 Hz, 2H), 7.98 (t, J = 2.0 Hz, 1H), 7.90 (d, J = 7.7 Hz, 2H), 7.73 (d, J = 8.1 Hz, 2H), 7.64 (s, 1H), 7.56 (t, J = 7.8 Hz, 1H), 7.43 (t, J = 7.6 Hz, 2H), 7.32 (dd, J = 13.8, 5.5 Hz, 4H), 7.07 (d, J = 8.5 Hz, 1H), 7.01 (d, J = 7.1 Hz, 1H), 6.80 (dd, J = 3.4, 1.6 Hz, 1H), 6.70 (s, 1H), 5.07-4.96 (m, 2H), 4.66-4.54 (m, 2H), 3.83 (d, J = 6.3 Hz, 2H), 3.56 (s, 3H), 3.40-3.29 (m, 1H), 2.88-2.80 (m, 1H), 2.68-2.58 (m, 2H), 2.56 (s, 2H), 2.29 (s, 3H), 2.03-1.95 (m, 1H), 1.24 (s, 1H). |
| 245 | N-(2-[1-[2-(2,6-dioxopiperidin-3-yl)-1,3-dioxoisoindol-5-yl]piperidin-4-yl]ethyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 935.15 | $^1$H NMR (400 MHz, DMSO-d6) δ 12.55 (s, 1H), 11.07 (s, 1H), 8.56 (d, J = 7.2 Hz, 1H), 8.54 (s, 1H), 7.98 (t, J = 2.0 Hz, 1H), 7.94-7.87 (m, 2H), 7.78 (d, J = 8.1 Hz, 2H), 7.68-7.61 (m, 2H), 7.45-7.43 (m, 2H), 7.41-7.39 (m, 2H), 7.39-7.37 (m, 1H), 7.34-7.30 (m, 2H), 7.25 (s, 1H), 6.80 (dd, J = 3.2, 1.6 Hz, 1H), 5.11-4.97 (m, 2H), 4.69-4.57 (m, 2H), 4.04 (d, J = 12.9 Hz, 2H), 3.83 (d, J = 6.5 Hz, 2H), 3.56 (s, 3H), 2.91 (q, J = 17.9, 15.2 Hz, 4H), 2.63-2.52 (m, 2H), 2.02 (s, 1H), 1.79 (d, J = 12.8 Hz, 2H), 1.60 (s, 1H), 1.47 (t, J = 7.1 Hz, 2H), 1.24 (s, 1H), 1.18 (d, J = 12.6 Hz, 2H). |
| 246 | N-[2-([1-[2-(2,6-dioxopiperidin-3-yl)-1,3-dioxoisoindol-5-yl]azetidin-3-yl]oxy)ethyl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 923.40 | $^1$H NMR (300 MHz, DMSO-d6) δ 12.55 (s, 1H), 11.08 (s, 1H), 8.60-8.50 (m, 2H), 7.98 (t, J = 2.0 Hz, 1H), 7.95-7.88 (m, 2H), 7.80 (d, J = 8.2 Hz, 2H), 7.68-7.61 (m, 2H), 7.49-7.27 (m, 6H), 6.80 (dd, J = 3.2, 1.7 Hz, 2H), 6.66 (dd, J = 8.4, 2.1 Hz, 1H), 5.16-4.94 (m, 2H), 4.63 (s, 2H), 4.52 (s, 1H), 4.30-4.19 (m, 2H), 3.95-3.78 (m, 4H), 3.57 (d, J = 4.1 Hz, 5H), 3.48-3.39 (m, 2H) 2.92-2.81 (m, 1H), 2.58 (d, J = 16.9 Hz, 2H), 2.03 (s, 1H). |
| 247 | N-[1-(2-[[2-(2,6-dioxopiperidin-3-yl)-1,3-dioxoisoindol-5-yl]oxy]ethyl)piperidin-4-yl]-4-[[(2S)-2-[(1-methanesulfonylpyrrol-3-yl)formamido]-2-[(4-phenyl-1,3-thiazol-2-yl)carbamoyl]ethoxy]methyl]-benzamide | 951.45 | $^1$H NMR (300 MHz, DMSO-d6) δ 12.55 (s, 1H), 11.12 (s, 1H), 8.56 (d, J = 7.2 Hz, 1H), 8.18 (d, J = 7.2 Hz, 1H), 7.98 (t, J = 2.0 Hz, 1H), 7.95-7.88 (m, 2H), 7.84 (d, J = 8.3 Hz, 1H), 7.78 (d, J = 8.2 Hz, 2H), 7.66 (s, 1H), 7.50-7.28 (m, 8H), 6.80 (dd, J = 3.3, 1.6 Hz, 1H), 5.13 (dd, J = 12.8, 5.4 Hz, 1H), 5.07-4.96 (m, 1H), 4.63 (s, 2H), 4.30 (t, J = 5.7 Hz, 2H), 3.83 (d, J = 6.4 Hz, 2H), 3.75 (d, J = 7.2 Hz, 1H), 3.57 (s, 3H), 3.01-2.83 (m, 3H), 2.75 (s, 2H), 2.63 (s, 1H), 2.55 (s, 1H), 2.12 (q, J = 11.5 Hz, 3H), 1.74 (s, 2H), 1.57 (t, J = 11.2 Hz, 2H). |
| 248 | N-[4-(3-[[2-(2,6-dioxopiperidin-3-yl)-1,3-dioxoisoindol-4-yl]amino]propanesulfonyl)-butyl]-4-[[(2S)-2-[(1-methanesulfonylpyrrol-3-yl)formamido]-2-[(4- | 1001.45 | $^1$H NMR (300 MHz, DMSO-d6) δ 12.56 (s, 1H), 11.10 (s, 1H), 8.56 (d, J = 7.2 Hz, 1H), 8.46 (t, J = 5.7 Hz, 1H), 7.98 (t, J = 2.0 Hz, 1H), 7.96-7.87 (m, 2H), 7.78 (d, J = 8.2 Hz, 2H), 7.65 (s, 1H), 7.59 (dd, J = 8.5, 7.1 Hz, 1H), 7.49-7.28 (m, 6H), 7.15 (d, J = 8.6 Hz, 1H), 7.04 (d, J = 7.0 Hz, 1H), 6.80 (dd, J = 3.3, 1.6 Hz, 1H), 6.76 (t, J = 6.3 Hz, 1H), 5.12-4.95 (m, 2H), 4.63 (d, J = 2.1 Hz, 2H), 3.84 (d, J = 6.3 Hz, |

TABLE 23-continued

| Cmpd # | Name | LC-MS (ESI) (m/z) | $^1$H NMR |
|---|---|---|---|
| The following compounds were prepared using standard chemical manipulations and procedures similar to those used for the preparation of Compound 191 | | | |
| | phenyl-1,3-thiazol-2-yl)carbamoyl]ethoxy]methyl]-benzamide | | 2H), 3.57 (s, 3H), 3.45 (d, J = 6.7 Hz, 2H), 3.26 (d, J = 6.0 Hz, 2H), 3.15 (t, J = 7.7 Hz, 4H), 2.97-2.82 (m, 1H), 2.66-2.55 (m, 2H), 2.06-1.91 (m, 3H), 1.76-1.55 (m, 4H). |
| | (2S,4R)-4-hydroxy-1-[(2S)-2-[8-[(4-[[(2S)-2-[(1-methanesulfonylpyrrol-3-yl)formamido]-2-[(4-phenyl-1,3-thiazol-2-yl)carbamoyl]ethoxy]methyl]-phenyl)formamido]octanamido]-3,3-dimethylbutanoyl]-N-[[4-(4-methyl-1,3-thiazol-5-yl)phenyl]methyl]pyrrolidine-2-carboxamide | 1122.55 | $^1$H NMR (300 MHz, DMSO-$d_6$) δ 12.56 (s, 1H), 8.99 (s, 1H), 8.57 (dd, J = 6.7, 4.7 Hz, 2H), 7.98 (t, J = 2.0 Hz, 1H), 8.38 (t, J = 5.6 Hz, 1H), 7.97-7.71 (m, 5H), 7.65 (s, 1H), 7.52-7.32 (m, 9H), 7.31 (dd, J = 3.3, 2.3 Hz, 1H), 6.80 (dd, J = 3.3, 1.6 Hz, 1H), 5.12 (d, J = 3.5 Hz, 1H), 4.99 ( q, J = 6.4 Hz, 1H), 4.65-4.53 (m, 3H), 4.47-4.36 (m, 3H), 4.22 (dd, J = 15.9, 5.4 Hz, 1H), 3.84 (d, J = 6.4 Hz, 2H), 3.66 (d, J = 3.9 Hz, 2H), 3.57 (s, 3H), 3.21 (q, J = 6.7 Hz, 2H), 2.45 (s, 3H), 2.29-2.19 (m, 1H), 2.16-2.08 (m, 1H), 2.06-1.98 (m, 1H), 1.90 (ddd, J = 12.9, 8.7, 4.6 Hz, 1H), 1.48 (s, 4H), 1.25 (d, J = 7.3 Hz, 6H), 0.93 (s, 9H). |
| 175 | (2S)-3-(14-[(2-[[2-(2-[[2-(2,6-dioxopiperidin-3-yl)-1,3-dioxoisoindol-4-yl]oxy]acetamido)ethyl]-(methyl)amino]ethyl)carbamoyl]-phenyl]methoxy)-2-[(1-methanesulfonylpyrrol-3-yl)formamido]-N-(4-phenyl-1,3-thiazol-2-yl)propanamide | 982.4 | $^1$H NMR (300 MHz, DMSO-$d_6$) δ 12.56 (s, 1H), 11.12 (s, 1H), 8.57 (d, J = 7.2 Hz, 1H), 8.24 (d, J = 2.6 Hz, 1H), 7.98 (t, J = 2.0 Hz, 1H), 7.97-7.85 (m, 3H), 7.83-7.69 (m, 3H), 7.65 (s, 1H), 7.44 (q, J = 7.4 Hz, 3H), 7.43-7.27 (m, 5H), 6.80 (dd, J = 3.3, 1.6 Hz, 1H), 5.12 (dd, J = 5.3 Hz, 1H), 5.00 (q, J = 6.5 Hz, 1H), 4.73 (s, 2H), 4.59 (s, 2H), 3.83 (d, J = 6.4 Hz, 2H), 3.57 (s, 3H), 3.32 (t, J = 6.3 Hz, 2H), 3.24 (t, J = 6.2 Hz, 2H), 2.89 (ddd, J = 18.3, 13.8, 5.3 Hz, 1H), 2.61-2.55 (m, 5H), 2.46 (d, J = 6.6 Hz, 1H), 2.23 (s, 3H), 2.09-1.98 (m, 1H). |
| 188 | (2S,4R)-4-hydroxy-1-[(2S)-2-[2-(2-[2-[(4-[[(2S)-2-[(1-methanesulfonylpyrrol-3-yl)formamido]-2-[(4-phenyl-1,3-thiazol-2-yl)carbamoyl]ethoxy]methyl]-phenyl)formamido]ethoxy]-ethoxy)acetamido]-3,3-dimethylbutanoyl]-N-[[4-(4-methyl-1,3-thiazol-5-yl)phenyl]methyl]pyrrolidine-2-carboxamide | 1126.6 | $^1$H NMR (400 MHz, DMSO-d6) δ 12.47 (s, 1H), 8.89 (s, 1H), 8.54-8.46 (m, 2H), 8.39 (t, J = 5.6 Hz, 1H), 7.91 (t, J = 2.0 Hz, 1H), 7.86-7.80 (m, 2H), 7.70 (d, J = 8.0 Hz, 2H), 7.57 (s, 1H), 7.39-7.33 (m, 3H), 7.31-7.29 (m, 6H), 7.27-7.25 (m, 1H), 7.24-7.21 (m, 1H), 6.73 (dd, J = 3.3, 1.6 Hz, 1H), 5.10 (d, J = 3.5 Hz, 1H), 4.93 (q, J = 6.5 Hz, 1H), 4.55 (d, J = 3.0 Hz, 2H), 4.49 (d, J = 9.6 Hz, 1H), 4.37 (t, J = 8.2 Hz, 1H), 4.32-4.25 (m, 2H), 4.21-4.15 (m, 1H), 3.89 (s, 2H), 3.76 (d, J = 6.3 Hz, 2H), 3.62-3.58 (m, 1H), 3.56-3.44 (m, 10H), 3.39-3.34 (m, 2H), 2.36 (s, 3H), 2.01-1.97 (m, 1H), 1.86-1.79 (m, 1H), 0.86 (s, 9H). |
| 189 | (2S,4R)-4-hydroxy-1-[(2S)-2-[2-[2-(2-[2-[(4-[[(2S)-2-[(1-methanesulfonylpyrrol-3-yl)formamido]-2-[(4-phenyl-1,3-thiazol-2-yl)carbamoyl]ethoxy]methyl]-phenyl)formamido]ethoxy]-ethoxy)ethoxy]acetamido]-3,3-dimethylbutanoyl]-N-[[4-(4-methyl-1,3-thiazol-5-yl)phenyl]methyl]pyrrolidine-2-carboxamide | 1070.65 | $^1$H NMR (400 MHz, DMSO-d6) δ 12.48 (s, 1H), 8.90 (s, 1H), 8.56-8.46 (m, 2H), 8.38 (t, J = 5.7 Hz, 1H), 7.91 (t, J = 1.9 Hz, 1H), 7.86-7.80 (m, 2H), 7.71 (d, J = 8.1 Hz, 2H), 7.58 (s, 1H), 7.40-7.29 (m, 9H), 7.28-7.21 (m, 2H), 6.73-6.72 (m, 1H), 5.09 (d, J = 3.5 Hz, 1H), 4.93 (q, J = 6.5 Hz, 1H), 4.56 (d, J = 3.4 Hz, 2H), 4.49 (d, J = 9.6 Hz, 1H), 4.41-4.26 (m, 3H), 4.18-4.14 (m, 1H), 3.88 (s, 2H), 3.76 (d, J = 6.4 Hz, 2H), 3.62-3.55 (m, 2H), 3.52-3.48 (m, 8H), 3.46-3.44 (m, 3H), 3.42-3.39 (m, 4H), 2.37 (s, 3H), 2.01-1.96 (m, 1H), 1.86-1.80 (m, 1H), 0.86 (s, 9H). |
| 196 | (2S)-3-(14-[(2-[2-[2-(2-[[2-(2,6-dioxopiperidin-3-yl)-1,3-dioxoisoindol-4-yl]oxy]acetamido)ethoxy]-ethoxy]ethyl)carbamoyl]-phenyl]methoxy)-2-[(1-methanesulfonylpyrrol-3-yl)formamido]-N-(4-phenyl-1,3-thiazol-2-yl)propanamide | 1013.4 | $^1$H NMR (400 MHz, DMSO-d6) δ 12.55 (s, 1H), 11.11 (s, 1H), 8.55 (d, J = 7.2 Hz, 1H), 8.44 (t, J = 5.6 Hz, 1H), 8.03-7.93 (m, 2H), 7.93-7.87 (m, 2H), 7.84-7.74 (m, 3H), 7.65 (s, 1H), 7.48 (d, J = 7.2 Hz, 1H), 7.47-7.39 (m, 2H), 7.38 (d, J = 8.2 Hz, 3H), 7.36-7.32 (m, 1H), 7.32-7.28 (m, 1H), 6.82-6.77 (m, 1H), 5.16-5.07 (m, 1H), 5.05-4.95 (m, 1H), 4.78 (s, 2H), 4.68-4.57 (m, 2H), 3.83 (d, J = 6.4 Hz, 2H), 3.56 (s, 3H), 3.55-3.47 (m, 6H), 3.47-3.42 (m, 2H), 3.41-3.36 (m, 2H), 3.32-3.26 (m, 2H), 2.96-2.82 (m, 1H), 2.69-2.52 (m, 2H), 2.06-2.00 (m, 1H). |
| 197 | (2S)-3-([4-[3-([[2-(2,6-dioxopiperidin-3-yl)-1,3-dioxoisoindol-4-yl]oxy]methyl)azetidine-1-carbonyl]phenyl]methoxy)-2-[(1-methanesulfonylpyrrol-3-yl)formamido]-N-(4-phenyl-1,3-thiazol-2-yl)propanamide | 894.3 | $^1$H NMR (400 MHz, DMSO-d6) δ 12.53 (s, 1H), 11.10 (s, 1H), 8.55 (d, J = 7.2 Hz, 1H), 7.98 (t, J = 2.0 Hz, 1H), 7.90 (d, J = 7.7 Hz, 2H), 7.83 (t, J = 7.9 Hz, 1H), 7.64 (d, J = 2.3 Hz, 1H), 7.60-7.50 (m, 3H), 7.48 (d, J = 7.3 Hz, 1H), 7.42 (t, J = 7.5 Hz, 2H), 7.37 (d, J = 7.9 Hz, 2H), 7.35-7.27 (m, 2H), 6.87-6.71 (m, 1H), 5.14-4.97 (m, 2H), 4.62 (s, 2H), 4.45-4.28 (m, 3H), 4.13 (t, J = 9.2 Hz, 2H), 3.95-3.80 (m, 3H), 3.56 (s, 3H), 3.07 (s, 1H), 2.91-2.80 (m, 1H), 2.70-2.52 (m, 2H), 2.04-1.95 (m, 1H). |
| 198 | (2S)-3-([4-[3-([[2-(2,6-dioxopiperidin-3-yl)-1,3-dioxoisoindol-5-yl]oxy]methyl)azetidine-1-carbonyl]phenyl]methoxy)- | 894.1 | $^1$H NMR (400 MHz, DMSO-d6) δ 12.54 (s, 1H), 11.11 (s, 1H), 8.55 (d, J = 7.2 Hz, 1H), 7.98 (t, J = 2.0 Hz, 1H), 7.95-7.88 (m, 2H), 7.84 (d, J = 8.3 Hz, 1H), 7.65 (s, 1H), 7.60-7.53 (m, 2H), 7.47-7.42 (m, 2H), 7.42-7.36 (m, 3H), 7.37-7.31 (m, 2H), 7.31-7.28 (m, 1H), 6.81-6.78 (m, |

TABLE 23-continued

The following compounds were prepared using standard chemical manipulations and procedures similar to those used for the preparation of Compound 191

| Cmpd # | Name | LC-MS (ESI) (m/z) | $^1$H NMR |
|---|---|---|---|
| | 2-[(1-methanesulfonylpyrrol-3-yl)formamido]-N-(4-phenyl-1,3-thiazol-2-yl)propanamide | | 1H), 5.16-5.09 (m, 1H), 5.02-4.96 (m, 1H), 4.63 (s, 2H), 4.41-4.31 (m, 3H), 4.18-4.07 (m, 2H), 3.91-3.81 (m, 3H), 3.57 (s, 3H), 3.11-3.04 (m, 1H), 2.93-2.85 (m, 1H), 2.65-2.57 (m, 1H), 2.57-2.53 (m, 1H), 2.08-2.02 (m, 1H). |
| 200 | N-(2-[[2-(2,6-dioxopiperidin-3-yl)-1,3-dioxoisoindol-5-yl]oxy]ethyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 868.3 | $^1$H NMR (400 MHz, DMSO-$d_6$) δ 12.55 (s, 1H), 11.11 (s, 1H), 8.70-8.63 (m, 1H), 8.56 (d, J = 7.2 Hz, 1H), 8.00-7.94 (m, 1H), 7.94-7.87 (m, 2H), 7.86-7.77 (m, 3H), 7.65 (s, 1H), 7.49-7.27 (m, 8H), 6.82-6.77 (m, 1H), 5.16-5.07 (m, 1H), 5.05-4.95 (m, 1H), 4.69-4.57 (m, 2H), 4.35-4.28 (m, 2H), 3.87-3.80 (m, 2H), 3.70-3.61 (m, 2H), 3.56 (s, 3H), 2.96-2.82 (m, 1H), 2.68-2.53 (m, 2H), 2.06-1.97 (m, 1H). |
| 201 | N-(6-[[2-(2,6-dioxopiperidin-3-yl)-1,3-dioxoisoindol-5-yl]amino]hexyl)-4-[[(2S)-2-[(1-methanesulfonylpyrrol-3-yl)formamido]-2-[(4-phenyl-1,3-thiazol-2-yl)carbamoyl]ethoxy]methyl]-benzamide | 923.1 | $^1$H NMR (400 MHz, DMSO-d6) δ 12.55 (s, 1H), 11.05 (s, 1H), 8.55 (d, J = 7.2 Hz, 1H), 8.38 (t, J = 5.6 Hz, 1H), 7.98 (t, J = 2.0 Hz, 1H), 7.94-7.87 (m, 2H), 7.80-7.74 (m, 2H), 7.65 (s, 1H), 7.55 (d, J = 8.3 Hz, 1H), 7.43 (t, J = 7.6 Hz, 2H), 7.42-7.37 (m, 2H), 7.37-7.27 (m, 2H), 7.09 (t, J = 5.4 Hz, 1H), 6.94 (d, J = 2.1 Hz, 1H), 6.87 (s, 1H), 6.77 (s, 1H), 5.01 (ddd, J = 13.4, 10.7, 5.9 Hz, 2H), 4.68-4.57 (m, 2H), 3.83 (d, J = 6.4 Hz, 2H), 3.56 (s, 3H), 3.24-3.19 (m, 2H), 3.18 (dt, J = 32.3, 6.5 Hz, 2H), 2.87 (ddd, J = 17.3, 14.1, 5.5 Hz, 1H), 2.57 (d, J = 16.7 Hz, 2H), 2.05-1.94 (m, 1H), 1.57 (t, J = 6.9 Hz, 2H), 1.37-1.31 (m, 4H)1.36 (td, J = 10.3, 6.8 Hz, 1H). |
| 231 | (2S)-3-([4-[4-([1-[2-(2,6-dioxopiperidin-3-yl)-1,3-dioxoisoindol-5-yl]azetidin-3-yl]methyl)piperazine-1-carbonyl]phenyl]methoxy)-2-[(1-methanesulfonylpyrrol-3-yl)formamido]-N-(4-phenyl-1,3-thiazol-2-yl)propanamide; formic acid | 962.45 | $^1$H NMR (400 MHz, DMSO-d6) δ 12.53 (s, 1H), 11.07 (s, 1H), 8.55 (d, J = 7.3 Hz, 1H), 8.01-7.96 (m, 1H), 7.91 (d, J = 7.7 Hz, 2H), 7.68-7.60 (m, 2H), 7.43 (t, J = 7.7 Hz, 2H), 7.36 (t, J = 8.5 Hz, 2H), 7.33-7.27 (m, 3H), 6.80-6.77 (m, 2H), 6.64 (dd, J = 8.3, 2.2 Hz, 1H), 5.04-4.98 (m, 2H), 4.61 (s, 2H), 4.11 (t, J = 8.2 Hz, 2H), 3.84 (d, J = 6.3 Hz, 2H), 3.68-3.66 (m, 2H), 3.57-3.51 (m, 6H), 3.03-2.81 (m, 2H), 2.64-2.55 (m, 3H), 2.33-2.32 (m, 2H), 2.30-2.25 (m, 1H), 2.05-1.94 (m, 1H), 1.34 (s, 1H), 1.24-1.19 (m, 2H), 1.16-1.48 (m, 1H). |
| 232 | (2S,4R)-4-hydroxy-1-[(2S)-2-[6-[(4-[[(2S)-2-[(1-methanesulfonylpyrrol-3-yl)formamido]-2-[(4-phenyl-1,3-thiazol-2-yl)carbamoyl]ethoxy]methyl]-phenyl)formamido]hexanamido]-3,3-dimethylbutanoyl]-N-[[4-(4-methyl-1,3-thiazol-5-yl)phenyl]methyl]pyrrolidine-2-carboxamide | 1094.55 | $^1$H NMR (400 MHz, DMSO-d6) δ 12.54 (s, 1H), 8.99 (s, 1H), 8.56 (dd, J = 6.7, 3.9 Hz, 2H), 8.37 (t, J = 5.7 Hz, 1H), 7.98 (t, J = 2.0 Hz, 1H), 7.94-7.88 (m, 2H), 7.84 (d, J = 9.4 Hz, 1H), 7.80-7.74 (m, 2H), 7.65 (s, 1H), 7.47-7.33 (m, 9H), 7.31-7.30 (m, 1H), 6.80 (dd, J = 3.3, 1.7 Hz, 1H), 5.13 (d, J = 3.6 Hz, 1H), 5.00 (q, J = 6.5 Hz, 1H), 4.69-4.59 (m, 2H), 4.54 (d, J = 9.4 Hz, 1H), 4.49-4.39 (m, 2H), 4.35 (s, 1H), 4.25-4.19 (m, 1H), 3.84 (d, J = 6.4 Hz, 2H), 3.71-3.61 (m, 2H), 3.57 (s, 3H), 3.21-3.19 (m, 1H), 2.45 (s, 3H), 2.30-2.21 (m, 1H), 2.18-1.99 (m, 2H), 1.94-1.87 (m, 1H), 1.53-1.42 (m, 4H), 1.31-1.24 (m, 3H), 0.93 (s, 9H). |

Preparation of (2S)-3-[[4-(aminomethyl)phenyl]methoxy]-2-[(1-methanesulfonylpyrrol-3-yl)formamido]-N-(4-phenyl-1,3-thiazol-2-yl)propanamide

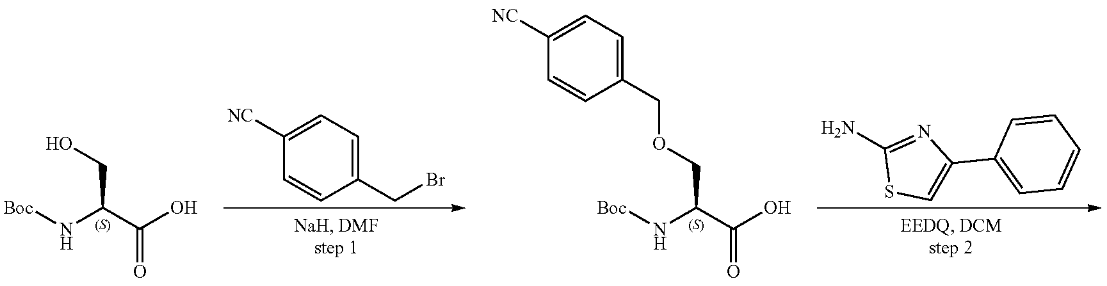

1

2

-continued
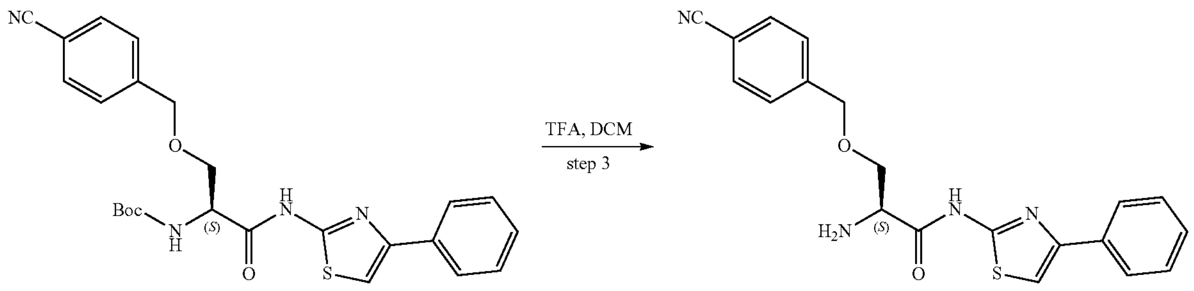
3 4
4
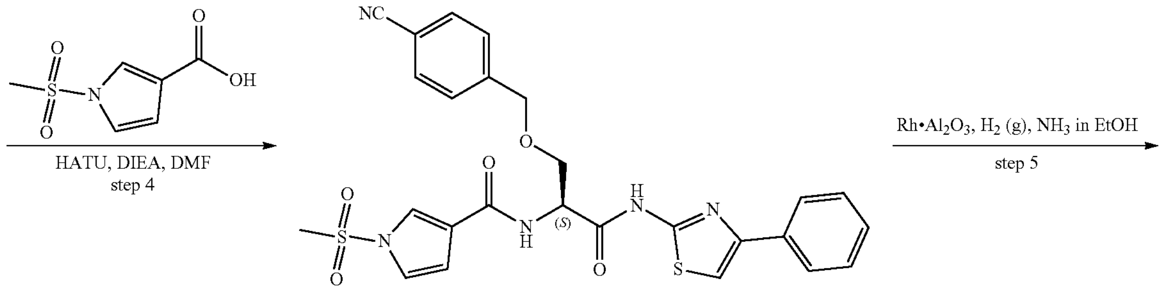
5
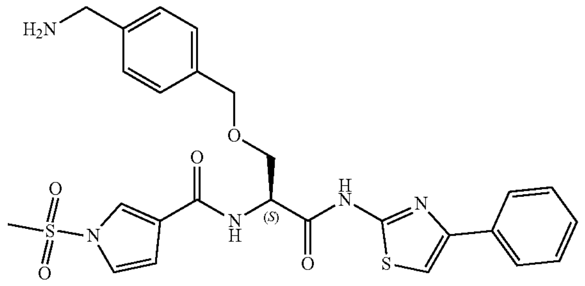

Step 1: Preparation of (2S)-2-[(tert-butoxycarbonyl)amino]-3-[(4-cyanophenyl)methoxy]propanoic acid (Intermediate 2)

2

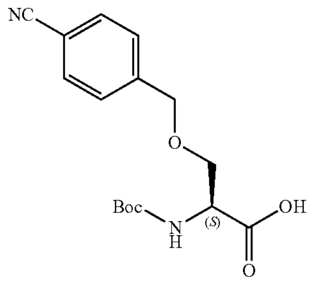

To a stirred solution of (2S)-2-[(tert-butoxycarbonyl)amino]-3-hydroxypropanoic acid (10.00 g, 48.731 mmol, 1.00 equiv) in DMF (50.00 mL) was added NaH (60%) (4.29 g, 107.208 mmol, 2.20 equiv) portion-wise at 0 degrees C. The resulting mixture was stirred for 0.5 h at 0 degrees C., followed by addition of 4-(bromomethyl)benzonitrile (9.55 g, 48.731 mmol, 1.00 equiv). The resulting mixture was stirred for an additional 2 h at room temperature, then quenched with water at 0 degrees C. The resulting mixture was extracted with EtOAc (3×15 mL). The combined organic layers were dried over anhydrous $Na_2SO_4$ and concentrated under reduced pressure. The residue was purified by silica gel column chromatography to afford intermediate 2 (12 g, 76.87%) as a light yellow oil. LCMS (ESI) m/z: $[M+H]^+$=321.

Step 2: Preparation of tert-butyl N-[(1S)-2-[(4-cyanophenyl)methoxy]-1-[(4-phenyl-1,3-thiazol-2-yl)carbamoyl]ethyl]carbamate (Intermediate 3)

3

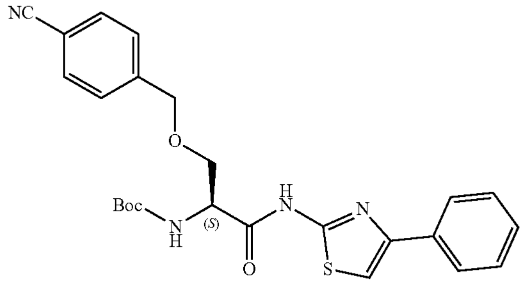

To a stirred solution of intermediate 2 (3.27 g, 10.213 mmol, 1.20 equiv) and phenthiazamine (1.50 g, 8.511 mmol, 1.00 equiv) in DCM (30.00 mL) was added ethyl 2-ethoxy-1,2-dihydroquinoline-1-carboxylate (2.53 g, 10.213 mmol, 1.20 equiv) at room temperature. The resulting mixture was stirred overnight followed by concentration under reduced pressure. The crude product was purified by reverse phase flash to afford intermediate 3 (4 g, 98.20%) as a white solid. LCMS (ESI) m/z: $[M+H]^+$=479.

Step 3: Preparation of (2S)-2-amino-3-[(4-cyanophenyl)methoxy]-N-(4-phenyl-1,3-thiazol-2-yl)propanamide (Intermediate 4)

4

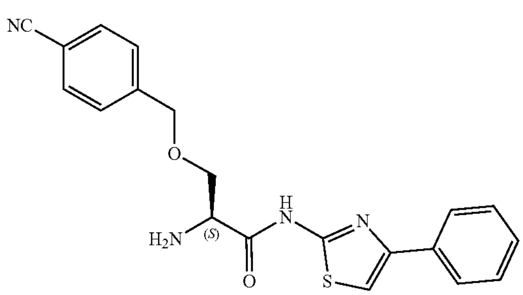

A solution of intermediate 3 (1.10 g, 2.299 mmol, 1.00 equiv) and TFA (3.00 mL) in DCM (15.00 mL) was stirred for 2 h at room temperature. The resulting mixture was concentrated under reduced pressure to afford intermediate 4 (1.3 g, crude) as a brown oil. The crude product was used in the next step directly without further purification. LCMS (ESI) m/z: $[M+H]^+$=379.

Step 4: Preparation of (2S)-3-[(4-cyanophenyl)methoxy]-2-[(1-methanesulfonylpyrrol-3-yl)formamido]-N-(4-phenyl-1,3-thiazol-2-yl)propanamide (Intermediate 5)

5

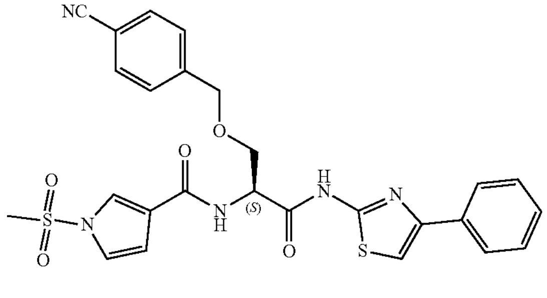

A solution of 1-methanesulfonylpyrrole-3-carboxylic acid (0.78 g, 4.122 mmol, 1.20 equiv), DIEA (1.33 g, 10.305 mmol, 3.00 equiv) and HATU (1.57 g, 4.122 mmol, 1.20 equiv) in DMF (15.00 mL) was stirred for 30 min at room temperature. To the above mixture was added intermediate 4 (1.30 g, 3.435 mmol, 1.00 equiv) and stirring continued for an additional 2 h at room temperature. The crude product was purified by reverse phase flash to afford intermediate 5 (1.4 g, 74.15%) as a white solid. LCMS (ESI) m/z: $[M+H]^+$=550.

Step 5: Preparation of (2S)-3-[[4-(aminomethyl) phenyl]methoxy]-2-[(1-methanesulfonylpyrrol-3-yl) formamido]-N-(4-phenyl-1,3-thiazol-2-y)propanamide

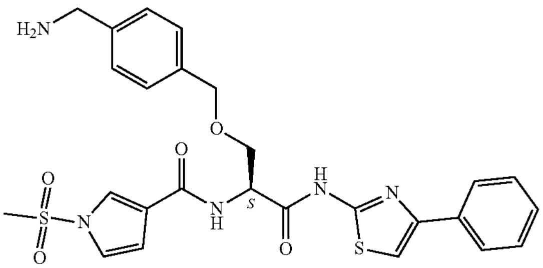

A suspension of Rh·$Al_2O_3$ (1.95 g, 18.949 mmol, 20.83 equiv) and intermediate 5 (500.00 mg, 0.910 mmol, 1.00 equiv) in ethanolic ammonia (10.00 mL) was stirred at 50 degrees C. under 20 atm of hydrogen overnight. After filtration and concentration the residue was purified by reverse phase flash chromatography to afford the title compound (100 mg, 19.85%) as an off-white solid. LCMS (ESI) m/z: $[M+H]^+$=554.

Compound 208—Preparation of N-[(2S)-1-[(2S, 4R)-4-hydroxy-2-([[4-(4-methyl-1,3-thiazol-5-yl) phenyl]methyl]carbamoyl)pyrrolidin-1-yl]-3,3-dimethyl-1-oxobutan-2-yl]-N'-[(4-[[(2S)-2-[(1-methanesulfonylpyrrol-3-yl)formamido]-2-[(4-phenyl-1,3-thiazol-2-yl)carbamoyl]ethoxy]methyl] phenyl)methyl]hexanediamide

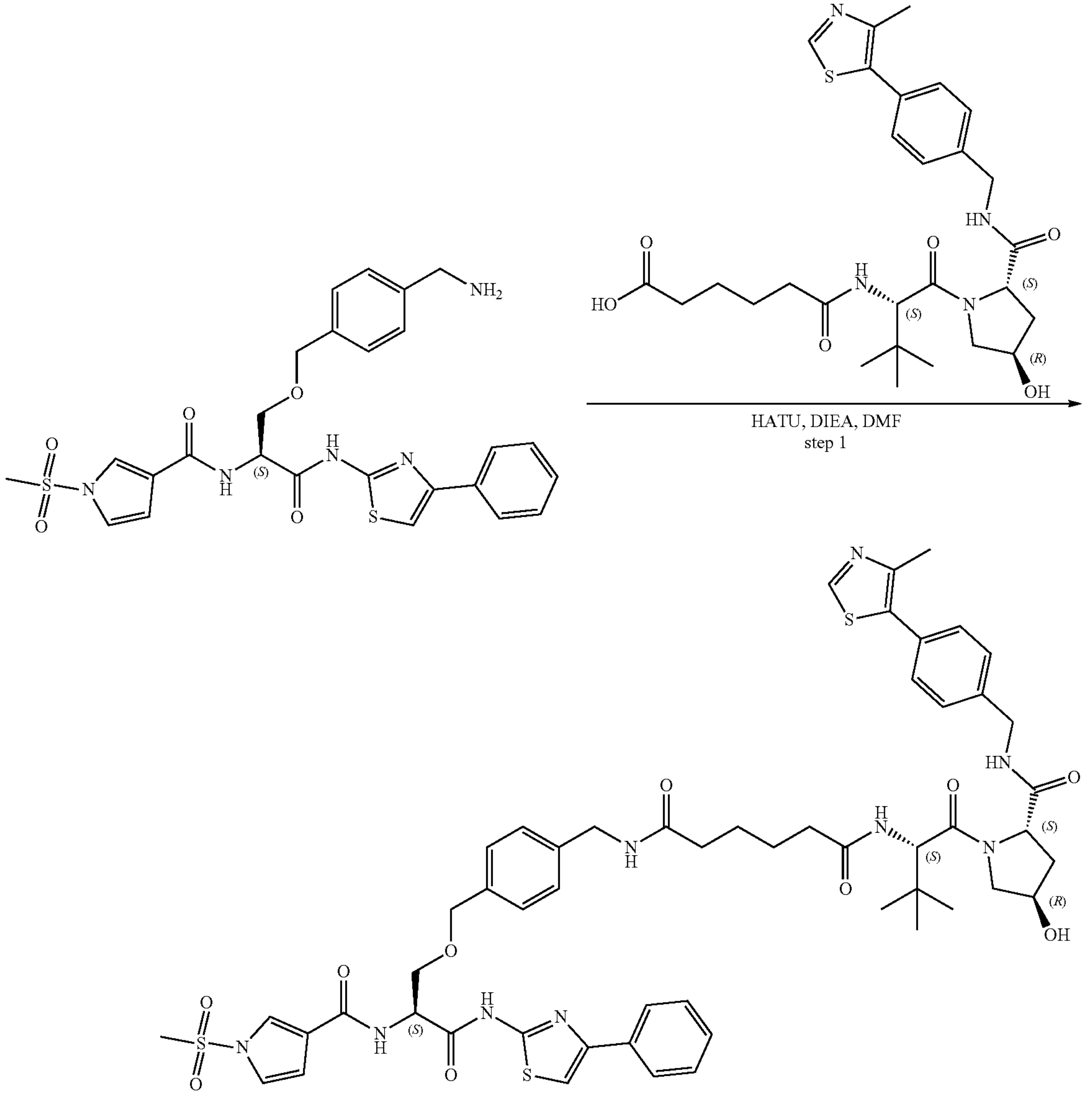

208

To a stirred mixture of (2S)-3-[[4-(aminomethyl)phenyl]methoxy]-2-[(1-methanesulfonylpyrrol-3-yl)formamido]-N-(4-phenyl-1,3-thiazol-2-yl)propanamide (13.00 mg, 0.023 mmol, 1.00 equiv) and 5-[[(2S)-1-[(2S,4R)-4-hydroxy-2-([[4-(4-methyl-1,3-thiazol-5-yl)phenyl]methyl]carbamoyl)pyrrolidin-1-yl]-3,3-dimethyl-1-oxobutan-2-yl]carbamoyl]pentanoic acid (13.12 mg, 0.023 mmol, 1.00 equiv) in DMF (1 mL) were added HATU (10.71 mg, 0.028 mmol, 1.20 equiv) and DIEA (0.20 mL, 1.148 mmol, 48.90 equiv) in portions at room temperature under nitrogen atmosphere. The resulting mixture was stirred for 1 h at room temperature under nitrogen atmosphere, then concentrated under reduced pressure. The crude product was purified by Prep-HPLC to afford Compound 208 (3.0 mg, 11.68%) as a white solid. LCMS (ESI) m/z: $[M+H]^+$=1094.55 $^1$H NMR (300 MHz, DMSO-$d_6$) δ 12.53 (s, 1H), 8.99 (s, 1H), 8.61-8.49 (m, 2H), 8.24 (t, J=5.9 Hz, 1H), 7.98 (t, J=1.9 Hz, 1H), 7.93-7.80 (m, 3H), 7.65 (s, 1H), 7.50-7.36 (m, 7H), 7.33-7.27 (m, 1H), 7.26-7.21 (m, 2H), 7.17 (d, J=7.9 Hz, 2H), 6.79 (dd, J=3.3, 1.6 Hz, 1H), 5.14 (d, J=3.6 Hz, 1H), 4.98 (t, J=6.5 Hz, 1H), 4.54 (s, 3H), 4.52-4.38 (m, 2H), 4.35 (s, 1H), 4.29-4.17 (m, 3H), 3.79 (d, J=6.4 Hz, 2H), 3.66 (s, 2H), 3.57 (s, 3H), 2.45 (s, 3H), 2.11 (s, 5H), 2.06-1.83 (m, 1H), 1.48 (s, 4H), 0.94 (s, 9H).

TABLE 24

The following compounds were prepared using standard chemical manipulations and procedures similar to those used for the preparation of Compound 208

| Cmpd # | Name | LC-MS (ESI) (m/z) | $^1$H NMR |
|---|---|---|---|
| 209 | N-[(2S)-1-[(2S,4R)-4-hydroxy-2-([[4-(4-methyl-1,3-thiazol-5-yl)phenyl]methyl]-carbamoyl)pyrrolidin-1-yl]-3,3-dimethyl-1-oxobutan-2-yl]-N'-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]dodecanediamide | 1178.65 | $^1$H NMR (400 MHz, DMSO-d6) δ 12.51 (s, 1H), 8.98 (s, 1H), 8.59-8.49 (m, 2H), 8.22 (t, J = 5.9 Hz, 1H), 7.97 (t, J = 2.0 Hz, 1H), 7.93-7.88 (m, 2H), 7.83 (d, J = 9.3 Hz, 1H), 7.64 (s, 1H), 7.48-7.36 (m, 6H), 7.36-7.28 (m, 2H), 7.25 (d, J = 7.9 Hz, 2H), 7.16 (d, J = 7.9 Hz, 2H), 6.79 (dd, J = 3.3, 1.6 Hz, 1H), 5.12 (d, J = 3.6 Hz, 1H), 4.97 (q, J = 6.6 Hz, 1H), 4.59-4.49 (m, 3H), 4.47-4.40 (m, 2H), 4.35 (s, 1H), 4.22 (dd, J = 12.5, 5.7 Hz, 3H), 3.78 (d, J = 6.4 Hz, 2H), 3.69-3.62 (m, 2H), 3.56 (s, 3H), 2.44 (s, 3H), 2.28-2.22 (m, 1H), 2.13-2.06 (m, 3H), 2.04-1.99 (m, 1H), 1.94-1.88 (m, 1H), 1.53-1.41 (m, 4H), 1.21 (s, 12H), 0.93 (s, 9H). |
| 210 | N-[(2S)-1-[(2S,4R)-4-hydroxy-2-([[4-(4-methyl-1,3-thiazol-5-yl)phenyl]methyl] carbamoyl)pyrrolidin-1-yl]-3,3-dimethyl-1-oxobutan-2-yl]-N'-[(4-[[(2S)-2-[(1-methanesulfonylpyrrol-3-yl)formamido]-2-[(4-phenyl-1,3-thiazol-2-yl)carbamoyl]ethoxy]methyl] phenyl)methyl]octanediamide | 1122.30 | $^1$H NMR (400 MHz, DMSO-d6) δ 12.52 (s, 1H), 8.98 (s, 1H), 8.59-8.48 (m, 2H), 8.22 (t, J = 5.9 Hz, 1H), 7.97 (t, J = 2.0 Hz, 1H), 7.94-7.87 (m, 2H), 7.83 (d, J = 9.3 Hz, 1H), 7.64 (s, 1H), 7.48-7.36 (m, 6H), 7.35-7.28 (m, 2H), 7.25 (d, J = 7.8 Hz, 2H), 7.16 (d, J = 7.9 Hz, 2H), 6.79 (dd, J = 3.3, 1.6 Hz, 1H), 5.12 (d, J = 3.5 Hz, 1H), 4.97 (q, J = 6.7 Hz, 1H), 4.58-4.49 (m, 3H), 4.47-4.39 (m, 2H), 4.38-4.32 (m, 1H), 4.22 (dd, J = 12.7, 5.6 Hz, 3H), 3.78 (d, J = 6.4 Hz, 2H), 3.66 (d, J = 4.4 Hz, 2H), 3.56 (s, 3H), 2.44 (s, 3H), 2.24 (dt, J = 14.7, 7.7 Hz, 1H), 2.11-2.03 (m, 3H), 2.04-1.97 (m, 1H), 1.94-1.86 (m, 1H), 1.47 (s, 4H), 1.23 (d, J = 6.2 Hz, 4H), 0.93 (s, 9H). |
| 212 | 5-[[2-(2,6-dioxopiperidin-3-yl)-1,3-dioxoisoindol-4-yl]oxy]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]pentanamide | 910.40 | $^1$H NMR (400 MHz, DMSO-$d_6$) 012.52 (s, 1H), 11.10 (s, 1H), 8.52 (d, J = 7.2 Hz, 1H), 8.28 (t, J = 5.9 Hz, 1H), 7.97 (t, J = 2.0 Hz, 1H), 7.94-7.88 (m, 2H), 7.84-7.77 (m, 1H), 7.64 (s, 1H), 7.49 (d, J = 8.6 Hz, 1H), 7.46-7.40 (m, 3H), 7.36-7.28 (m, 2H), 7.27-7.23 (m, 2H), 7.20-7.15 (m, 2H), 6.79 (dd, J = 3.3, 1.6 Hz, 1H), 5.07 (dd, J = 12.8, 5.4 Hz, 1H), 4.97 (q, J = 6.5 Hz, 1H), 4.57-4.49 (m, 2H), 4.27-4.13 (m, 4H), 3.78 (d, J = 6.4 Hz, 2H), 3.56 (s, 3H), 2.94-2.82 (m, 1H), 2.62-2.52 (m, 2H), 2.24-2.15 (m, 2H), 2.07-1.97 (m, 1H), 1.80-1.65 (m, 4H). |
| 214 | 11-[[2-(2,6-dioxopiperidin-3-yl)-1,3-dioxoisoindol-4-yl]amino]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]undecanamide | 993.45 | $^1$H NMR (400 MHz, DMSO-d6) δ 12.49 (s, 1H), 11.09 (s, 1H), 8.52 (d, J = 7.2 Hz, 1H), 8.23 (t, J = 6.0 Hz, 1H), 7.97 (t, J = 2.0 Hz, 1H), 7.94-7.87 (m, 2H), 7.64 (s, 1H), 7.57 (dd, J = 8.4, 7.0 Hz, 1H), 7.43 (dd, J = 8.4, 7.0 Hz, 2H), 7.36-7.30 (m, 1H), 7.29 (dd, J = 3.3, 2.0 Hz, 1H), 7.25 (d, J = 8.0 Hz, 2H), 7.16 (d, J = 8.0 Hz, 2H), 7.08 (d, J = 8.4 Hz, 1H), 7.01 (d, J = 7.0 Hz, 1H), 6.79 (dd, J = 3.3, 2.0 Hz, 1H), 6.51 (t, J = 6.0 Hz, 1H), 5.05 (dd, J = 13.0, 5.3 Hz, 1H), 4.97 (q, J = 6.6 Hz, 1H), 4.61-4.46 (m, 2H), 4.20 (d, J = 5.9 Hz, 2H), 3.78 (d, J = 6.4 Hz, 2H), 3.56 (s, 3H), 3.28-3.24 (m, 2H), 2.95-2.80 (m, 1H), 2.65-2.52 (m, 2H), 2.08 (t, J = 7.4 Hz, 2H), 2.05-1.96 (m, 1H), 1.60-1.53 (m, 2H), 1.53-1.45 (m, 2H), 1.36-1.28 (m, 4H), 1.28-1.20 (m, 8H). |
| 216 | 1-(2-[[2-(2,6-dioxopiperidin-3-yl)-1,3-dioxoisoindol-5-yl]oxy]ethyl)-N-[(4-[[(2S)-2-[(1-methanesulfonylpyrrol-3-yl)formamido]-2-[(4-phenyl-1,3-thiazol-2- | 965.45 | $^1$H NMR (300 MHz, DMSO-d6) δ 12.53 (s, 1H), 11.12 (s, 1H), 8.53 (d, J = 7.2 Hz, 1H), 8.26 (t, J = 5.9 Hz, 1H), 7.98 (t, J = 2.0 Hz, 1H), 7.96-7.88 (m, 2H), 7.84 (d, J = 8.3 Hz, 1H), 7.65 (s, 1H), 7.50-7.40 (m, 3H), 7.40-7.23 (m, 5H), 7.16 (d, J = 8.1 Hz, 2H), 6.80 (dd, J = 3.3, 1.6 Hz, 1H), 5.13 (dd, J = 12.8, 5.3 Hz, 1H), 4.97 (q, J = 6.5 Hz, |

TABLE 24-continued

The following compounds were prepared using standard chemical manipulations and procedures similar to those used for the preparation of Compound 208

| Cmpd # | Name | LC-MS (ESI) (m/z) | $^1$H NMR |
|---|---|---|---|
| | yl)carbamoyl]ethoxy]methyl]-phenyl)methyl]piperidine-4-carboxamide; formic acid | | 1H), 4.61-4.47 (m, 2H), 4.31 (s, 2H), 4.22 (d, J = 5.8 Hz, 2H), 3.79 (d, J = 6.4 Hz, 2H), 3.57 (s, 3H), 3.00 (d, J = 11.3 Hz, 3H), 2.82 (d, J = 21.8 Hz, 3H), 2.63 (d, J = 3.1 Hz, 1H), 2.22-1.98 (m, 4H), 1.65-1.51 (m, 4H). |
| 217 | 3-[2-(2-[[2-(2,6-dioxopiperidin-3-yl)-1,3-dioxoisoindol-5-yl]oxy]ethoxy)ethoxy]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]propanamide | 970.45 | $^1$H NMR (300 MHz, DMSO-d6) δ 12.53 (s, 1H), 11.12 (s, 1H), 8.53 (d, J = 7.2 Hz, 1H), 8.31 (t, J = 5.9 Hz, 1H), 7.98 (t, J = 2.0 Hz, 1H), 7.94-7.88 (m, 2H), 7.82 (d, J = 8.3 Hz, 1H), 7.65 (s, 1H), 7.48-7.40 (m, 3H), 7.37-7.22 (m, 5H), 7.18 (d, J = 8.2 Hz, 2H), 6.79 (dd, J = 3.3, 1.6 Hz, 1H), 5.12 (dd, J = 12.8, 5.3 Hz, 1H), 4.97 (q, J = 6.6 Hz, 1H), 4.53 (d, J = 2.6 Hz, 2H), 4.35-4.17 (m, 4H), 3.78 (t, J = 5.8 Hz, 4H), 3.63 (t, J = 6.3 Hz, 2H), 3.56 (d, J = 3.0 Hz, 5H), 3.51 (dd, J = 6.1, 3.4 Hz, 2H), 2.96-2.81 (m, 1H), 2.59 (d, J = 19.3 Hz, 2H), 2.36 (t, J = 6.3 Hz, 2H), 2.13-1.99 (m, 1H). |
| 176 | (2S)-3-([4-[(3-[6-[2-(2,6-dioxopiperidin-3-yl)-1,3-dioxoisoindol-5-yl]-2,6-diazaspiro[3.3]heptan-2-yl]propanamido)methyl]phenyl]-methoxy)-2-[(1-methanesulfonylpyrrol-3-yl)formamido]-N-(4-phenyl-1,3-thiazol-2-yl)propanamide | 962.45 | $^1$H NMR (300 MHz, DMSO-d6) δ 12.55 (s, 1H), 11.08 (s, 1H), 8.54 (d, J = 7.1 Hz, 1H), 8.34 (s, 1H), 7.98 (d, J = 2.1 Hz, 1H), 7.91 (d, J = 7.5 Hz, 2H), 7.64 (t, J = 4.1 Hz, 2H), 7.44 (t, J = 7.5 Hz, 2H), 7.37-7.24 (m, 4H), 7.20 (d, J = 7.9 Hz, 2H), 6.78 (d, J = 3.0 Hz, 2H), 6.63 (d, J = 8.3 Hz, 1H), 5.11-4.95 (m, 2H), 4.55 (d, J = 2.7 Hz, 2H), 4.23 (d, J = 5.6 Hz, 2H), 4.07 (s, 4H), 3.80 (d, J = 6.3 Hz, 2H), 3.57 (s, 3H), 3.29 (s, 4H), 2.86 (d, J = 14.1 Hz, 2H), 2.58 (t, J = 7.9 Hz, 3H), 2.14 (d, J = 7.3 Hz, 2H), 2.01 (d, J = 11.5 Hz, 1H) |
| 177 | N-[(2S)-1-[(2S,4R)-4-hydroxy-2-([[4-(4-methyl-1,3-thiazol-5-yl)phenyl]methyl]carbamoyl)-pyrrolidin-1-yl]-3,3-dimethyl-1-oxobutan-2-yl]-N'-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]decanediamide | 1150.6 | $^1$H NMR (300 MHz, DMSO-d6) δ 12.51 (s, 1H), 8.98 (s, 1H), 8.60-8.47 (m, 2H), 8.23 (t, J = 5.8 Hz, 1H), 7.97 (t, J = 2.0 Hz, 1H), 7.93-7.87 (m, 2H), 7.83 (d, J = 9.3 Hz, 1H), 7.64 (s, 1H), 7.48-7.37 (m, 5H), 7.37-7.28 (m, 3H), 7.25 (d, J = 8.1 Hz, 2H), 7.16 (d, J = 7.9 Hz, 2H), 6.79 (dd, J = 3.2, 1.6 Hz, 1H), 5.12 (d, J = 3.5 Hz, 1H), 4.97 (q, J = 6.6 Hz, 1H), 4.58-4.53 (m, 2H), 4.48-4.38 (m, 2H), 4.35-4.33 (m, 1H), 4.25-4.19 (m, 3H), 3.78 (d, J = 6.3 Hz, 2H), 3.66-3.64 (m, 2H), 3.56 (s, 3H), 2.54 (s, 1H), 2.44 (s, 3H), 2.54-2.20 (m, 1H), 2.14-2.03 (m, 4H), 1.94-1.87 (m, 1H), 1.51-1.45 (m, 4H), 1.25-1.17 (m, 8H), 0.93 (s, 9H). |
| 178 | 4-[[2-(2,6-dioxopiperidin-3-yl)-1,3-dioxoisoindol-4-yl]oxy]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]butanamide | 896.3 | $^1$H NMR (400 MHz, DMSO-$d_6$) 512.51(s, 1H), 11.11 (s, 1H), 8.58-8.50 (m, 1H), 8.39-8.30 (m, 1H), 8.00-7.97 (m, 1H), 7.95-7.88 (m, 2H), 7.86-7.76 (m, 1H), 7.68-7.64 (m, 1H), 7.53-7.40 (m, 4H), 7.37-7.28 (m, 2H), 7.28-7.22 (m, 2H), 7.21-7.15 (m, 2H), 6.83-6.77 (m, 1H), 5.12-5.04 (m, 1H), 5.02-4.93 (m, 1H), 4.54 (s, 2H), 4.29-4.12 (m, 4H), 3.79 (d, J = 6.4 Hz, 2H), 3.57 (s, 3H), 2.87 (d, J = 13.2 Hz, 1H), 2.66-2.53 (m, 2H), 2.35 (t, J = 7.4 Hz, 2H), 2.13-1.87 (m, 3H). |
| 179 | 7-[[2-(2,6-dioxopiperidin-3-yl)-1,3-dioxoisoindol-4-yl]oxy]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]heptanamide | 938.1 | $^1$H NMR (400 MHz, DMSO-d6) δ 12.52 (s, 1H), 11.10 (s, 1H), 8.52 (d, J = 7.2 Hz, 1H), 8.27-8.20 (m, 1H), 8.00-7.94 (m, 1H), 7.94-7.87 (m, 2H), 7.84-7.76 (m, 1H), 7.64 (s, 1H), 7.53-7.47 (m, 1H), 7.47-7.39 (m, 3H), 7.37-7.27 (m, 2H), 7.27-7.22 (m, 2H), 7.20-7.13 (m, 2H), 6.82-6.76 (m, 1H), 5.12-5.03 (m, 1H), 5.01-4.92 (m, 1H), 4.59-4.47 (m, 2H), 4.24-4.14 (m, 4H), 3.81-3.75 (m, 2H), 3.56 (s, 3H), 2.94-2.80 (m, 1H), 2.66-2.51 (m, 2H), 2.16-2.05 (m, 2H), 2.05-1.98 (m, 1H), 1.77-1.68 (m, 2H), 1.59-1.47 (m, 2H), 1.50-1.38 (m, 2H), 1.37-1.28 (m, 2H). |
| 180 | 11-[[2-(2,6-dioxopiperidin-3-yl)-1,3-dioxoisoindol-4-yl]amino]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]undecanamide | 993.45 | $^1$H NMR (400 MHz, DMSO-d6) δ 12.49 (s, 1H), 11.09 (s, 1H), 8.52 (d, J = 7.2 Hz, 1H), 8.23 (t, J = 6.0 Hz, 1H), 7.97 (t, J = 2.0 Hz, 1H), 7.94-7.87 (m, 2H), 7.64 (s, 1H), 7.57 (dd, J = 8.4, 7.0 Hz, 1H), 7.43 (dd, J = 8.4, 7.0 Hz, 2H), 7.36-7.30 (m, 1H), 7.29 (dd, J = 3.3, 2.0 Hz, 1H), 7.25 (d, J = 8.0 Hz, 2H), 7.16 (d, J = 8.0 Hz, 2H), 7.08 (d, J = 8.4 Hz, 1H), 7.01 (d, J = 7.0 Hz, 1H), 6.79 (dd, J = 3.3, 2.0 Hz, 1H), 6.51 (t, J = 6.0 Hz, 1H), 5.05 (dd, J = 13.0, 5.3 Hz, 1H), 4.97 (q, J = 6.6 Hz, 1H), 4.61-4.46 (m, 2H), 4.20 (d, J = 5.9 Hz, 2H), 3.78 (d, J = 6.4 Hz, 2H), 3.56 (s, 3H), 3.28-3.24 (m, 2H), 2.95-2.80 (m, 1H), 2.65-2.52 (m, 2H), 2.08 (t, J = 7.4 Hz, 2H), 2.05-1.96 (m, 1H), 1.60-1.53 (m, 2H), 1.53-1.45 (m, 2H), 1.36-1.28 (m, 4H), 1.28-1.20 (m, 8H). |
| 181 | (3-[2-(2-[[2-(2,6-dioxopiperidin-3-yl)-1,3- | 969.4 | $^1$H NMR (400 MHz, DMSO-d6) δ 12.51 (s, 1H), 11.09 (s, 1H), 8.52 (d, J = 7.2 Hz, 1H), 8.27 (t, J = 6.0 Hz, 1H), 7.97 |

TABLE 24-continued

The following compounds were prepared using standard chemical manipulations and procedures similar to those used for the preparation of Compound 208

| Cmpd # | Name | LC-MS (ESI) (m/z) | $^1$H NMR |
|---|---|---|---|
| | dioxoisoindol-4-yl]amino]ethoxy)ethoxy]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]propanamide | | (t, J = 2.0 Hz, 1H), 7.94-7.87 (m, 2H), 7.64 (s, 1H), 7.57 (dd, J = 8.6, 7.1 Hz, 1H), 7.43 (t, J = 7.6 Hz, 2H), 7.36-7.27 (m, 2H), 7.24 (d, J = 7.9 Hz, 2H), 7.17 (d, J = 7.9 Hz, 2H), 7.12 (d, J = 8.6 Hz, 1H), 7.03 (d, J = 7.0 Hz, 1H), 6.79 (dd, J = 3.3, 1.6 Hz, 1H), 6.59 (t, J = 5.9 Hz, 1H), 5.05-4.97 (m, 2H), 4.58-4.47 (m, 2H), 4.22 (d, J = 5.9 Hz, 2H), 3.78 (d, J = 6.4 Hz, 4H), 3.65-3.58 (m, 3H), 3.49 (dd, J = 6.1, 3.5 Hz, 2H), 3.43 (q, J = 5.6 Hz, 2H), 2.87 (ddd, J = 17.4, 14.0, 5.4 Hz, 1H), 2.63-2.51 (m, 2H), 2.35 (t, J = 6.4 Hz, 2H), 2.10-1.97 (m, 1H). |
| 182 | 3-[2-(2-[[2-(2,6-dioxopiperidin-3-yl)-1,3-dioxoisoindol-4-yl]oxy]ethoxy)ethoxy]-N-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]propanamide | 970 | $^1$H NMR (400 MHz, DMSO-d6) δ 12.52 (s, 1H), 11.10 (s, 1H), 8.52 (d, J = 7.2 Hz, 1H), 8.28 (t, J = 6.1 Hz, 1H), 7.97 (t, J = 2.0 Hz, 1H), 7.94-7.85 (m, 2H), 7.79 (dd, J = 8.5, 7.3 Hz, 1H), 7.64 (s, 1H), 7.50 (d, J = 8.5 Hz, 1H), 7.47-7.39 (m, 3H), 7.36-7.31 (m, 1H), 7.31-7.28 (m, 1H), 7.24 (d, J = 8.0 Hz, 2H), 7.17 (d, J = 7.9 Hz, 2H), 6.79 (dd, J = 3.3, 1.6 Hz, 1H), 5.10-5.05-5.01 (m, 1H), 4.97 (q, J = 6.6 Hz, 1H), 4.52 (d, J = 4.3 Hz, 2H), 4.31 (t, J = 4.6 Hz, 2H), 4.22 (d, J = 5.9 Hz, 2H), 3.79-3.76 (m, 4H), 3.66-3.58 (m, 4H), 3.56 (s, 3H), 3.51-3.48 (m, 2H), 2.93-2.84 (m, 1H), 2.61-2.55 (m, 2H), 2.39-2.28 (m, 2H), 2.05-1.96 (m, 1H). |
| 211 | N-[(2S)-1-[(2S,4R)-4-hydroxy-2-([[4-(4-methyl-1,3-thiazol-5-yl)phenyl]methyl]carbamoyl)-pyrrolidin-1-yl]-3,3-dimethyl-1-oxobutan-2-yl]-N'-[(4-[[(2S)-2-[(1-methanesulfonylpyrrol-3-yl)formamido]-2-[(4-phenyl-1,3-thiazol-2-yl)carbamoyl]ethoxy]methyl]-phenyl)methyl]tetradecanediamide | 1206.3 | $^1$H NMR (400 MHz, DMSO-d6) δ 12.50 (s, 1H), 8.98 (s, 1H), 8.64-8.43 (m, 2H), 8.33-8.13 (m, 1H), 7.97 (s, 1H), 7.91 (d, J = 7.7 Hz, 2H), 7.83 (d, J = 9.3 Hz, 1H), 7.64 (s, 1H), 7.52-7.34 (m, 6H), 7.35-7.28 (m, 2H), 7.28-7.20 (m, 2H), 7.22-7.10 (m, 2H), 6.79 (s, 1H), 5.12 (s, 1H), 5.03-4.86 (m, 1H), 4.62-4.47 (m, 3H), 4.49-4.30 (m, 3H), 4.30-4.11 (m, 3H), 3.90-3.74 (m, 2H), 3.71-3.60 (m, 2H), 3.56 (s, 3H), 2.44 (s, 3H), 2.31-2.17 (m, 1H), 2.16-2.05 (m, 3H), 2.06-1.97 (m, 1H), 1.91 (s, 1H), 1.60-1.36 (m, 4H), 1.22 (s, 16H), 0.93 (s, 9H). |
| 213 | 8-[[2-(2,6-dioxopiperidin-3-yl)-1,3-dioxoisoindol-4-yl]oxy]-N-[(4-[[(2S)-2-[(1-methanesulfonylpyrrol-3-yl)formamido]-2-[(4-phenyl-1,3-thiazol-2-yl)carbamoyl]ethoxy]-methyl]phenyl)methyl]octanamide | 952.4 | $^1$H NMR (400 MHz, DMSO-$d_6$) δ 12.52 (s, 1H), 11.10 (s, 1H), 8.52 (d, J = 7.2 Hz, 1H), 8.27-8.19 (m, 1H), 8.00-7.94 (m, 1H), 7.94-7.86 (m, 2H), 7.84-7.76 (m, 1H), 7.64 (s, 1H), 7.50 (d, J = 8.6 Hz, 1H), 7.47-7.39 (m, 3H), 7.37-7.27 (m, 2H), 7.27-7.22 (m, 2H), 7.20-7.13 (m, 2H), 6.81-6.76 (m, 1H), 5.12-5.03 (m, 1H), 5.01-4.92 (m, 1H), 4.59-4.47 (m, 2H), 4.24-4.14 (m, 4H), 3.81-3.75 (m, 2H), 3.56 (s, 3H), 2.94-2.80 (m, 1H), 2.63-2.55 (m, 1H), 2.55-2.51 (m, 1H), 2.13-2.09 (m, 2H), 2.05-1.97 (m, 1H), 1.79-1.67 (m, 2H), 1.57-1.44 (m, 2H), 1.47-1.34 (m, 2H), 1.33-1.22 (m, 4H). |
| 215 | (2S)-3-([4-[(3-[4-[2-(2,6-dioxopiperidin-3-yl)-1,3-dioxoisoindol-5-yl]piperazin-1-yl]propanamido)methyl]-phenyl]methoxy)-2-[(1-methanesulfonylpyrrol-3-yl)formamido]-N-(4-phenyl-1,3-thiazol-2-yl)propanamide; formic acid | 950.45 | $^1$H NMR (400 MHz, DMSO-d6) δ 7.97 (t, J = 2.0 Hz, 1H), 7.94-7.86 (m, 2H), 7.70 (d, J = 8.5 Hz, 1H), 7.62 (s, 1H), 7.45 (t, J = 7.7 Hz, 2H), 7.39-7.28 (m, 3H), 7.23 (q, J = 8.2 Hz, 5H), 6.80 (dd, J = 3.3, 1.7 Hz, 1H), 5.07 (dd, J = 12.7, 5.4 Hz, 1H), 4.94 (t, J = 6.3 Hz, 1H), 4.52 (d, J = 4.2 Hz, 2H), 4.25 (s, 2H), 3.79 (d, J = 6.4 Hz, 2H), 3.54 (s, 4H), 3.45 (s, 4H), 2.94-2.71 (m, 4H), 2.70-2.55 (m, 3H), 2.51-2.45 (m, 1H), 2.45-2.32 (m, 2H), 2.04 (dd, J = 13.1, 6.3 Hz, 1H). |

Preparation of methyl 3-(2-amino-1,3-thiazol-4-yl) piperidine-1-carboxylate

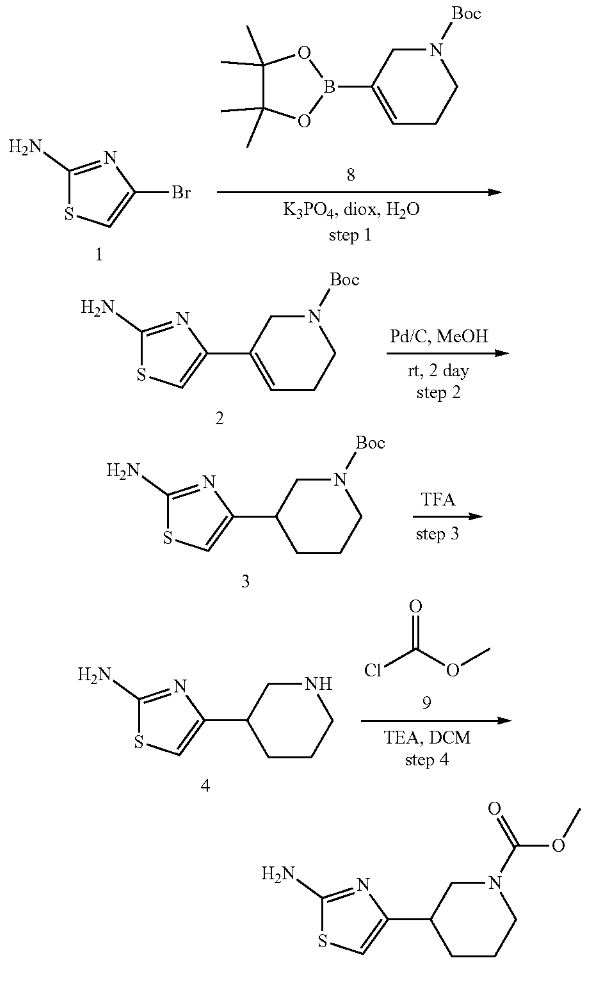

Step 1: Preparation of tert-butyl 3-(2-amino-1,3-thiazol-4-yl)-5,6-dihydro-2H-pyridine-1-carboxylate (Intermediate 2)

2

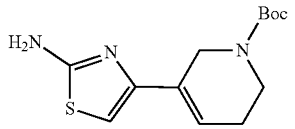

A solution of 4-bromo-1,3-thiazol-2-amine (900.00 mg, 5.027 mmol, 1.00 equiv), tert-butyl 3-(4,4,5,5-tetramethyl-1,3,2-dioxaborolan-2-yl)-5,6-dihydro-2H-pyridine-1-carboxylate (1554.34 mg, 5.027 mmol, 1.00 equiv), $K_3PO_4$ (2134.04 mg, 10.054 mmol, 2.00 equiv), $Pd(dtbpf)Cl_2$ (655.24 mg, 1.005 mmol, 0.20 equiv), and $H_2O$ (9.00 mL) in dioxane (45.00 mL) was stirred overnight at 80 degrees C. under a nitrogen atmosphere. The resulting mixture was extracted with EtOAc (3×50 mL). The combined organic layers were washed with brine (100 mL), dried over anhydrous $Na_2SO_4$ and concentrated under reduced pressure. The residue was purified by silica gel column chromatography, eluted with PE/EtOAc (1:1) to afford intermediate 2 (1.1 g, 77.77%) as a yellow solid. LCMS (ESI) m/z: $[M+H]^+$=282.

Step 2: Preparation of tert-butyl 3-(2-amino-1,3-thiazol-4-yl)piperidine-1-carboxylate (Intermediate 3)

3

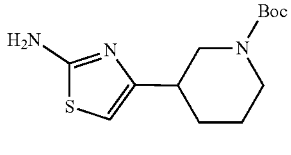

A solution of intermediate 2 (300.00 mg, 1.066 mmol, 1.00 equiv) and 10% Pd/C (120.00 mg, 1.128 mmol, 1.06 equiv) in MeOH (15.00 mL) was stirred for 2 days at 30 degrees C. under an atmosphere of hydrogen. The resulting mixture was filtered, the filter cake was washed with MeOH. The filtrate was concentrated under reduced pressure and the residue was purified by reverse phase flash chromatography to afford intermediate 3 (100 mg, 33.10%) as a light yellow solid. LCMS (ESI) m/z: $[M+H]^+$=284.

Step 3: Preparation of 4-(piperidin-3-yl)-1,3-thiazol-2-amine (Intermediate 4)

4

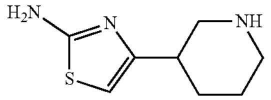

A solution of intermediate 3 (100.00 mg, 0.353 mmol, 1.00 equiv) and TFA (0.50 mL) in DCM (2.00 mL) was stirred for 2 h at room temperature. The resulting mixture was concentrated under reduced pressure to provide intermediate 4 (60 mg, 92.78%) as a light yellow oil. LCMS (ESI) m/z: $[M+H]^+$=184.

Step 4: Preparation of methyl 3-(2-amino-1,3-thiazol-4-yl)piperidine-1-carboxylate

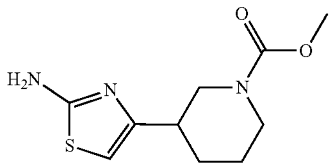 [SMILES: COC(=O)N1CCCC(c2csc(N)n2)C1]

To a stirred solution of intermediate 4 (60.00 mg, 0.327 mmol, 1.00 equiv) and TEA (198.77 mg, 1.964 mmol, 6.00 equiv) in DCM (4.00 mL) was added methyl chloroformate (27.84 mg, 0.295 mmol, 0.90 equiv) in DCM (1.00 mL) dropwise at 0 degrees C. The resulting mixture was stirred for 1 h at 0 degrees C. then concentrated under reduced pressure. The residue was purified by Prep-TLC (PE/EtOAc 1:2) to afford the title compound (55 mg, 69.62%) as a light yellow solid. LCMS (ESI) m/z: $[M+H]^+$=242.

Preparation of methyl 3-[2-[(2S)-6-[(tert-butoxycarbonyl)amino]-2-[[(9H-fluoren-9-ylmethoxy) carbonyl]amino]hexanamido]-1,3-thiazol-4-yl]piperidine-1-carboxylate

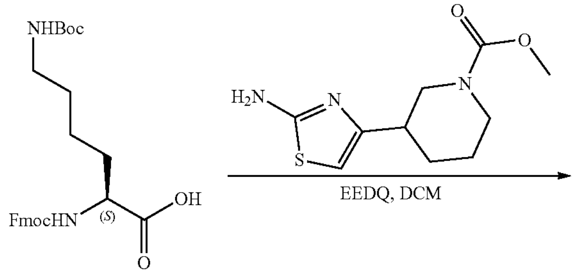

1

-continued

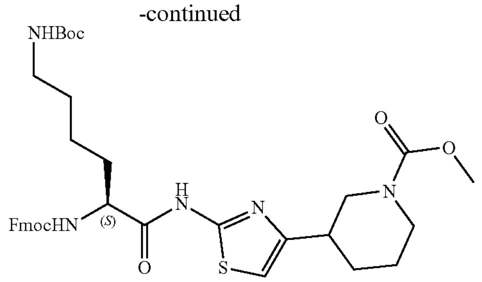

A solution of (2S)-6-[(tert-butoxycarbonyl)amino]-2-[[(9H-fluoren-9-ylmethoxy)carbonyl]amino]-hexanoic acid (300.00 mg, 0.640 mmol, 1.00 equiv), methyl 3-(2-amino-1,3-thiazol-4-yl)piperidine-1-carboxylate (154.50 mg, 0.640 mmol, 1.00 equiv), and ethyl 2-ethoxy-2H-quinoline-1-carboxylate (158.34 mg, 0.640 mmol, 1.00 equiv) in DCM (15.00 mL) was stirred overnight at room temperature. The resulting mixture was concentrated under reduced pressure. The residue was purified by silica gel column chromatography, eluted with PE/EtOAc (1:1) to afford the title compound (400 mg, 90.30%) as an off-white solid. LCMS (ESI) m/z: $[M+H]^+$=692.

Compound 184—Preparation of methyl 3-[2-[(2S)-2-[(1-tert-butylpyrrol-3-yl)formamido]-6-(11-[[2-(2,6-dioxopiperidin-3-yl)-1,3-dioxoisoindol-4-yl]amino]undecanamido)hexanamido]-1,3-thiazol-4-yl]piperidine-1-carboxylate

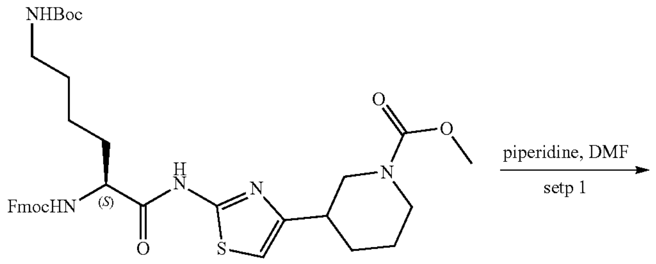

1

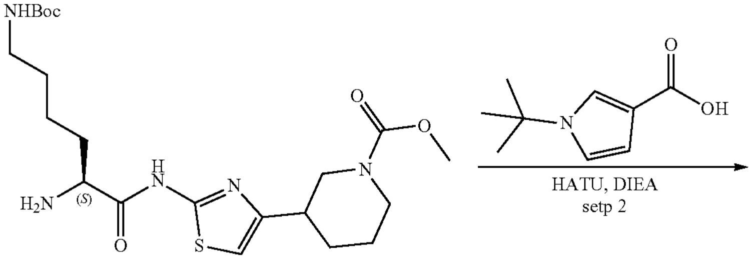

2

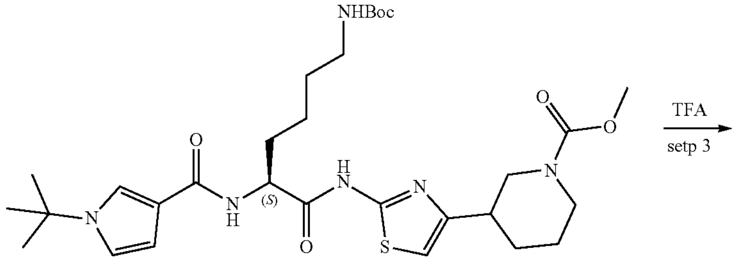

4

3

-continued

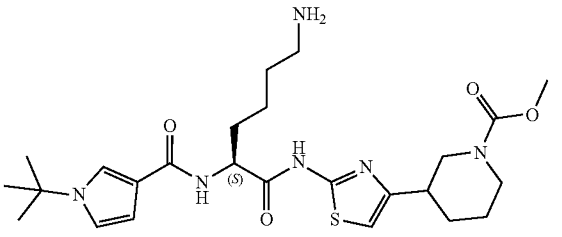

4

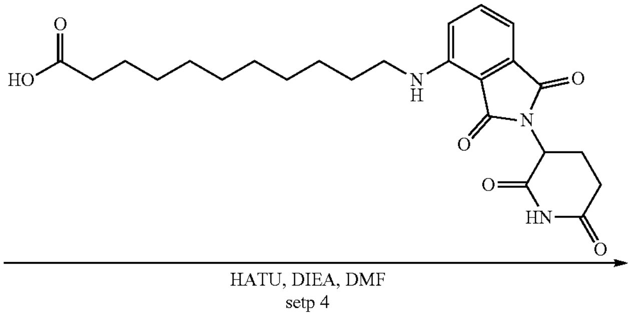

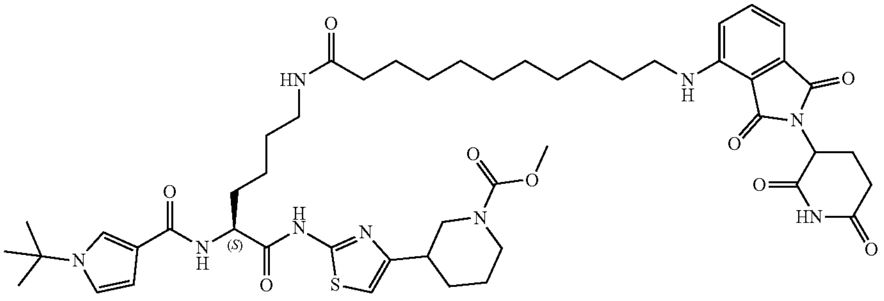

184

Step 1: Preparation of methyl 3-[2-[(2S)-2-amino-6-[(tert-butoxycarbonyl)amino]hexanamido]-1,3-thiazol-4-yl]piperidine-1-carboxylate (Intermediate 2)

2

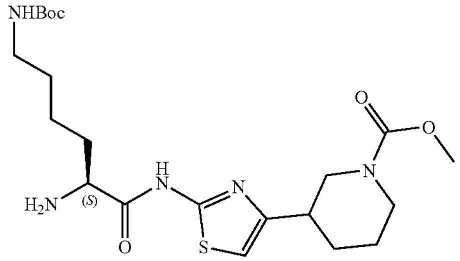

To a stirred solution of methyl 3-[2-[(2S)-6-[(tert-butoxycarbonyl)amino]-2-[[(9H-fluoren-9-ylmethoxy)carbonyl]amino]hexanamido]-1,3-thiazol-4-yl]piperidine-1-carboxylate (100.00 mg, 0.145 mmol, 1.00 equiv) in DMF (2.00 mL) was added piperidine (0.40 mL). The resulting mixture was stirred for 2 h at room temperature. The reaction was purified directly by reverse phase flash chromatography to afford intermediate 2 (50 mg, 73.66%) as an off-white solid. LCMS (ESI) m/z: $[M+H]^+$=470.

Step 2: Preparation of methyl 3-[2-[(2S)-6-[(tert-butoxycarbonyl)amino]-2-[(1-tert-butylpyrrol-3-yl)formamido]hexanamido]-1,3-thiazol-4-yl]piperidine-1-carboxylate (Intermediate 3)

3

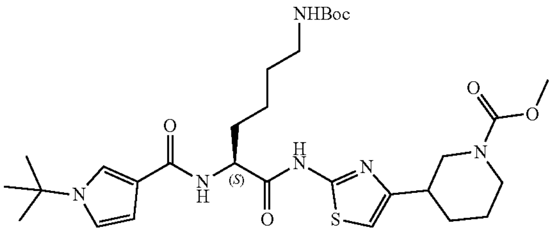

To a stirred solution of 1-tert-butylpyrrole-3-carboxylic acid (17.80 mg, 0.106 mmol, 1.00 equiv), HATU (48.58 mg, 0.128 mmol, 1.20 equiv), and DIEA (41.28 mg, 0.319 mmol, 3.00 equiv) in DMF (2.00 mL) was added intermediate 2 (50.00 mg, 0.106 mmol, 1.00 equiv). The resulting mixture was stirred for 2 h at room temperature. The resulting mixture was extracted with EtOAc (3×10 mL). The combined organic layers were washed with brine (2×10 mL), dried over anhydrous Na2SO4, and concentrated under reduced pressure. The residue was purified by Prep-TLC (PE/EtOAc 1:2) to afford intermediate 3 (60 mg, 91.07%) as an off-white solid. LCMS (ESI) m/z: $[M+H]^+$=619.

Step 3: Preparation of methyl 3-[2-[(2S)-6-amino-2-[(1-tert-butylpyrrol-3-yl)formamido]hexanamido]-1,3-thiazol-4-yl]piperidine-1-carboxylate (Intermediate 4)

4

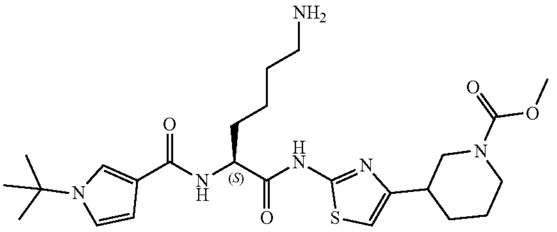

To a stirred solution of intermediate 3 (14.00 mg, 0.023 mmol, 1.00 equiv) in DCM (0.30 mL) was added TFA (0.10 mL) at room temperature. The resulting mixture was stirred for 1 h at room temperature, then concentrated under vacuum to afford intermediate 4 (11.4 mg, 97.15%) as a yellow oil. LCMS (ESI) m/z: $[M+H]^+=519$.

Step 4: Preparation of methyl 3-[2-[(2S)-2-[(1-tert-butylpyrrol-3-yl)formamido]-6-(11-[[2-(2,6-dioxopiperidin-3-yl)-1,3-dioxoisoindol-4-yl]amino]undecanamido)hexanamido]-1,3-thiazol-4-yl]piperidine-1-carboxylate (Compound 184)

184

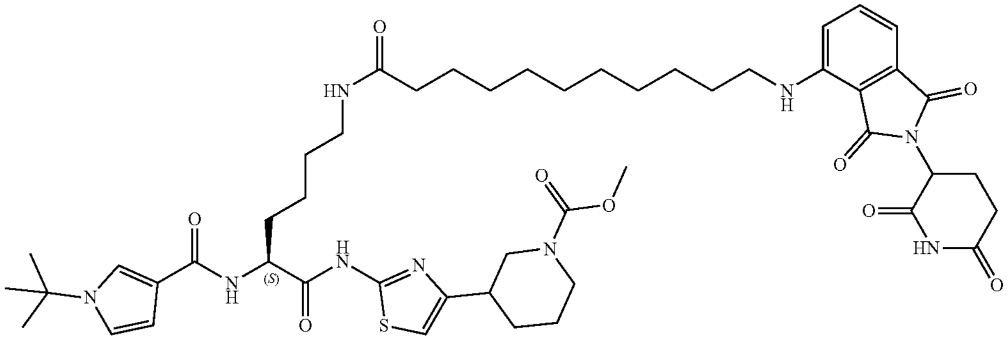

To a stirred solution of 11-[[2-(2,6-dioxopiperidin-3-yl)-1,3-dioxoisoindol-4-yl]amino]undecanoic acid (10.00 mg, 0.022 mmol, 1.00 equiv), HATU (9.97 mg, 0.026 mmol, 1.20 equiv), and DIEA (8.47 mg, 0.066 mmol, 3.00 equiv) in DMF (0.50 mL) was added intermediate 4 (11.34 mg, 0.022 mmol, 1.00 equiv) at room temperature. The resulting mixture was stirred for 2 h at room temperature. and the crude product was purified by Prep-HPLC to afford Compound 184 (5.6 mg, 26.74%) as a yellow green solid. $^1H$ NMR (300 MHz, DMSO-d6) δ 12.19 (s, 1H), 11.10 (s, 1H), 7.81 (d, J=7.3 Hz, 1H), 7.73 (t, J=5.6 Hz, 1H), 7.63-7.52 (m, 2H), 7.09 (d, J=8.6 Hz, 1H), 7.02 (d, J=7.0 Hz, 1H), 6.95 (t, J=2.7 Hz, 1H), 6.85 (s, 1H), 6.57-6.46 (m, 2H), 5.11-4.99 (m, 1H), 4.53 (q, J=7.1 Hz, 1H), 4.24-4.15 (m, 1H), 3.99-3.93 (m, 1H), 3.60 (s, 3H), 3.32-3.24 (m, 2H), 3.03 (d, J=5.9 Hz, 2H), 2.97-2.58 (m, 4H), 2.58-2.52 (m, 1H), 2.07-1.96 (m, 4H), 1.91-1.63 (m, 4H), 1.63-1.51 (m, 3H), 1.49 (s, 9H), 1.46-1.37 (m, 5H), 1.36-1.27 (m, 5H), 1.25-1.19 (m, 9H). LCMS (ESI) m/z: $[M+H]^+=958.60$.

Example 2. Degradation of BRM and BRG1 by Compounds of the Invention

This example demonstrates the ability of the compounds of the disclosure to degrade a HiBit-BRM or HiBit-BRG1 fusion protein in a cell-based degradation assay.

Procedure: A stable HeLa cell line expressing HiBiT-BRM was generated. On day 0, 5000 cells were seeded in 40 μL of media into each well of 384-well cell culture plates. On day 1, cells were treated with 120 nL DMSO or 120 nL of 3-fold serially DMSO-diluted compounds (10 points in duplicate with 30 μM as final top dose). Subsequently plates were incubated for 24 h in a standard tissue culture incubator and equilibrated at room temperature for 15 minutes. Nano-Glo HiBiT Lytic Detection System (Promega N3050) reagent was freshly prepared and 20 ul was added to each well. Upon addition of this LgBit-containing reagent, the HiBiT and LgBiT proteins associate to form the luminescent NanoBiT luciferase. The plates were shaken for 10 minutes at room temperature and the bioluminescence read using an EnVision plate reader (PerkinElmer).

For measurement of BRG1 degradation, a stable HeLa cell line expressing HiBit-BRG1 and LgBit was generated. The same protocol as above was then followed.

The degradation % was calculated using the following formula: % degradation=100%−100%×($Lum_{Sample}$−$Lum_{LC}$)/($Lum_{HC}$−$Lum_{LC}$). DMSO treated cells are employed as High Control (HC) and 2 μM of a known BRM/BRG1 degrader standard treated cells are employed as Low Control (LC). The data was fit to a four parameter, non-linear curve fit to calculate $IC_{50}$ (μM) values as shown in Table 19.

Results: As shown in Table 25 below, the compounds of the invention degraded both BRM and BRG1. As shown by the results in Table 25, a number of compounds of the present disclosure exhibit an $IC_{50}$ value of <1 μM for the degradation of BRM, indicating their use as compounds for reducing the levels and/or activity of BRM and their potential for treating BRM-related disorders.

TABLE 25

| Compound No. | BRM HiBit Degradation $IC_{50}$ (μM) | BRM HiBit Degradation Maximum measured | BRG1 HiBit Degradation $IC_{50}$ (μM) | BRG1 HiBit Degradation Maximum measured |
|---|---|---|---|---|
| 1 | +++ | A | +++ | A |
| 2 | + | C | + | C |
| 3 | + | C | + | C |
| 4 | + | C | + | C |
| 5 | + | C | + | C |
| 6 | + | C | + | C |
| 7 | + | C | + | C |
| 8 | +++ | B | +++ | B |
| 9 | + | C | + | C |
| 10 | + | C | + | C |
| 11 | + | C | ++ | B |
| 12 | + | C | +++ | A |
| 13 | + | C | +++ | B |
| 14 | + | C | + | C |
| 15 | + | C | + | C |
| 16 | + | C | + | C |
| 17 | + | C | + | C |
| 18 | + | C | + | C |
| 19 | ++++ | A | +++ | A |
| 20 | + | C | + | B |
| 21 | + | C | + | C |
| 27 | + | C | + | C |
| 29 | + | C | + | C |
| 30 | + | C | + | C |
| 31 | +++ | A | +++ | A |
| 32 | + | C | + | C |
| 33 | + | C | + | C |
| 34 | +++ | B | +++ | B |
| 35 | +++ | A | ++++ | A |
| 36 | + | C | + | C |
| 37 | + | C | + | C |
| 38 | + | C | +++ | A |
| 39 | + | C | + | C |
| 40 | ++++ | A | ++++ | A |
| 41 | + | C | + | C |
| 42 | + | C | +++ | B |
| 43 | + | C | +++ | B |
| 44 | ++ | B | ++ | A |
| 45 | + | C | + | C |
| 47 | ++++ | B | ++++ | B |
| 48 | + | C | ++ | B |
| 49 | ++++ | A | ++++ | A |
| 50 | +++ | A | +++ | A |
| 51 | + | C | +++ | B |
| 52 | + | C | +++ | B |
| 53 | ++++ | A | ++++ | A |
| 54 | + | C | + | C |
| 55 | +++ | B | +++ | B |
| 56 | + | C | + | C |
| 57 | + | C | + | C |
| 59 | + | C | + | C |

TABLE 25-continued

| Compound No. | BRM HiBit Degradation $IC_{50}$ (μM) | BRM HiBit Degradation Maximum measured | BRG1 HiBit Degradation $IC_{50}$ (μM) | BRG1 HiBit Degradation Maximum measured |
|---|---|---|---|---|
| 60 | + | C | + | C |
| 61 | ++ | B | +++ | B |
| 62 | +++ | A | +++ | A |
| 63 | + | C | + | C |
| 64 | + | C | + | C |
| 65 | ++++ | A | ++++ | A |
| 67 | + | C | + | C |
| 68 | +++ | B | +++ | B |
| 69 | ++++ | A | +++ | A |
| 70 | ++++ | A | ++++ | A |
| 71 | + | C | + | C |
| 72 | + | C | + | C |
| 73 | +++ | A | +++ | A |
| 74 | + | C | + | C |
| 75 | +++ | B | +++ | A |
| 76 | + | C | + | C |
| 77 | + | C | + | C |
| 78 | + | C | + | C |
| 79 | + | C | + | C |
| 80 | + | C | + | C |
| 81 | + | C | +++ | B |
| 82 | + | C | + | C |
| 83 | + | C | + | C |
| 84 | + | C | + | C |
| 85 | +++ | A | +++ | A |
| 86 | +++ | B | +++ | B |
| 87 | + | C | + | C |
| 88 | ++++ | B | ++++ | B |
| 89 | + | C | + | C |
| 90 | + | C | + | C |
| 91 | + | C | + | C |
| 92 | + | C | + | C |
| 93 | + | C | + | C |
| 94 | + | C | + | C |
| 97 | + | C | + | C |
| 98 | ++++ | A | ++++ | A |
| 99 | ++++ | A | ++++ | A |
| 100 | +++ | A | ++++ | A |
| 101 | + | C | + | C |
| 102 | + | C | +++ | B |
| 103 | +++ | B | +++ | A |
| 104 | ++++ | A | ++++ | A |
| 105 | ++++ | A | ++++ | A |
| 106 | + | C | + | C |
| 107 | + | C | + | C |
| 108 | +++ | A | +++ | A |
| 109 | + | C | + | C |
| 110 | +++ | B | +++ | A |
| 111 | + | C | + | C |
| 112 | + | C | + | C |
| 113 | ++++ | A | ++++ | A |
| 114 | +++ | A | +++ | A |
| 116 | + | C | + | C |
| 118 | +++ | B | +++ | B |
| 119 | +++ | A | +++ | A |
| 120 | + | C | + | C |
| 121 | ++ | B | ++ | B |
| 122 | + | C | + | C |
| 123 | + | C | + | C |
| 124 | + | C | + | C |
| 125 | + | C | + | C |
| 126 | +++ | B | +++ | B |
| 171 | ++++ | A | ++++ | A |
| 128 | + | C | + | C |
| 129 | + | C | + | C |
| 130 | + | C | + | C |
| 131 | + | C | + | C |
| 132 | + | C | + | C |
| 133 | +++ | B | ++++ | A |
| 134 | +++ | A | ++++ | A |
| 135 | +++ | B | +++ | A |
| 136 | + | C | + | C |
| 137 | + | C | + | C |
| 138 | ++ | B | ++ | B |
| 139 | + | C | +++ | B |

TABLE 25-continued

| Compound No. | BRM HiBit Degradation $IC_{50}$ (μM) | BRM HiBit Degradation Maximum measured | BRG1 HiBit Degradation $IC_{50}$ (μM) | BRG1 HiBit Degradation Maximum measured |
|---|---|---|---|---|
| 140 | +++ | A | +++ | A |
| 141 | +++ | B | + | C |
| 142 | + | C | + | C |
| 143 | + | C | + | C |
| 144 | + | C | + | C |
| 145 | + | C | + | C |
| 146 | + | C | + | C |
| 147 | + | C | + | C |
| 148 | + | C | + | C |
| 149 | +++ | A | +++ | A |
| 150 | +++ | B | +++ | A |
| 151 | + | C | ++++ | B |
| 152 | + | C | + | C |
| 153 | +++ | B | +++ | A |
| 154 | + | C | + | C |
| 155 | + | C | + | C |
| 156 | +++ | A | +++ | A |
| 157 | + | C | + | C |
| 158 | + | C | + | C |
| 159 | + | C | + | C |
| 160 | + | C | + | C |
| 161 | +++ | B | +++ | A |
| 162 | + | C | + | C |
| 163 | +++ | B | + | C |
| 164 | + | C | + | C |
| 165 | + | C | + | C |
| 166 | +++ | B | + | C |
| 167 | ++++ | A | ++++ | A |
| 168 | ++++ | A | ++++ | A |
| 169 | + | C | + | C |
| 170 | +++ | A | +++ | A |
| 171 | ++++ | B | ++++ | B |
| 172 | + | C | + | C |
| 173 | + | C | + | C |
| 174 | +++ | B | +++ | B |
| 175 | + | C | + | C |
| 176 | +++ | B | +++ | B |
| 177 | + | C | +++ | B |
| 178 | + | C | + | C |
| 179 | + | C | + | C |
| 180 | +++ | B | +++ | B |
| 181 | +++ | B | +++ | B |
| 182 | + | C | + | C |
| 183 | + | C | + | C |
| 184 | + | C | + | C |
| 185 | + | C | + | C |
| 186 | + | C | + | C |
| 187 | + | C | + | C |
| 188 | + | C | ++ | B |
| 189 | + | C | + | C |
| 190 | + | C | + | C |
| 191 | + | C | + | C |
| 192 | + | C | + | C |
| 193 | +++ | B | +++ | A |
| 194 | + | C | + | C |
| 195 | + | C | + | C |
| 196 | + | C | + | C |
| 197 | + | C | + | C |
| 198 | + | C | + | C |
| 199 | + | C | + | C |
| 200 | + | C | + | C |
| 201 | +++ | A | ++++ | A |
| 202 | + | C | + | C |
| 203 | + | C | + | C |
| 204 | + | C | +++ | B |
| 205 | + | C | + | C |
| 206 | + | C | + | C |
| 207 | +++ | B | +++ | B |
| 208 | + | C | + | C |
| 209 | + | C | + | C |
| 210 | + | C | + | C |
| 211 | + | C | + | C |
| 212 | + | C | + | C |
| 213 | +++ | B | +++ | B |
| 214 | +++ | B | +++ | B |

TABLE 25-continued

| Compound No. | BRM HiBit Degradation $IC_{50}$ (μM) | BRM HiBit Degradation Maximum measured | BRG1 HiBit Degradation $IC_{50}$ (μM) | BRG1 HiBit Degradation Maximum measured |
|---|---|---|---|---|
| 215 | +++ | B | +++ | A |
| 216 | +++ | A | +++ | A |
| 217 | +++ | B | +++ | B |
| 218 | + | C | + | C |
| 219 | + | C | + | C |
| 220 | + | C | + | C |
| 221 | + | C | + | C |
| 222 | + | C | + | C |
| 223 | + | C | + | C |
| 224 | + | C | + | C |
| 225 | + | C | + | C |
| 226 | + | C | + | C |
| 227 | + | C | + | C |
| 228 | + | C | + | C |
| 229 | + | C | + | C |
| 230 | + | C | + | C |
| 231 | + | C | + | C |
| 232 | + | C | + | C |
| 233 | + | C | +++ | B |
| 234 | +++ | B | +++ | B |
| 235 | + | C | + | C |
| 236 | + | C | + | C |
| 237 | +++ | B | +++ | B |
| 238 | + | C | + | C |
| 239 | + | C | + | C |
| 240 | + | C | + | C |
| 241 | +++ | A | +++ | A |
| 242 | +++ | B | +++ | B |
| 243 | +++ | B | +++ | A |
| 244 | + | C | + | C |
| 245 | ++++ | A | ++++ | A |
| 246 | +++ | B | +++ | A |
| 247 | +++ | A | +++ | A |
| 248 | ++ | B | +++ | B |
| 249 | + | C | + | C |
| 250 | + | C | + | C |
| 251 | + | C | + | C |
| 252 | + | C | + | C |
| 253 | + | C | + | C |
| 254 | + | C | + | C |
| 255 | + | C | + | C |
| 256 | + | C | + | C |
| 257 | + | C | + | C |
| 258 | + | C | + | C |
| 259 | + | C | + | C |
| 260 | + | C | + | C |
| 261 | + | C | + | C |
| 262 | + | C | + | C |
| 263 | + | C | + | C |
| 264 | + | C | + | C |
| 265 | + | C | + | C |
| 266 | + | C | + | C |
| 267 | + | C | + | C |
| 268 | + | C | + | C |
| 269 | + | C | + | C |
| 270 | + | C | + | C |
| 271 | + | C | + | C |
| 272 | + | C | + | C |
| 273 | + | C | + | C |
| 274 | + | C | + | C |
| 275 | + | C | + | C |
| 276 | + | C | + | C |
| 277 | + | C | + | C |
| 278 | + | C | + | C |
| 279 | + | C | + | C |
| 280 | + | C | + | C |
| 281 | + | C | + | C |
| 282 | + | C | + | C |
| 283 | + | C | + | C |
| 284 | + | C | + | C |
| 285 | + | C | + | C |
| 286 | + | C | + | C |
| 287 | + | C | + | C |
| 288 | + | C | + | C |
| 289 | + | C | + | C |

TABLE 25-continued

| Compound No. | BRM HiBit Degradation $IC_{50}$ (μM) | BRM HiBit Degradation Maximum measured | BRG1 HiBit Degradation $IC_{50}$ (μM) | BRG1 HiBit Degradation Maximum measured |
|---|---|---|---|---|
| 290 | + | C | + | C |
| 291 | + | C | + | C |
| 292 | + | C | + | C |
| 293 | + | C | + | C |
| 294 | + | C | + | C |
| 295 | + | C | + | C |
| 296 | + | C | + | C |
| 297 | + | C | + | C |

'++++' = <0.1 μM;
'+++' = ≥0.1 μM to <1 μM;
'++' = ≥1 μM to <10 μM;
'+' = >10 μM
'A' = Maximum degradation >75%;
'B' = Maximum degradation ≥50% and ≤75%;
'C' = Maximum degradation <50%

The invention claimed is:

1. A compound having the structure of Formula I:

A-L-B Formula I, wherein

L is a linker of the formula:

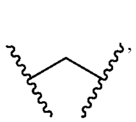
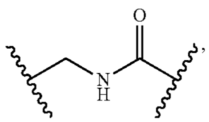
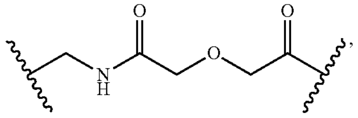
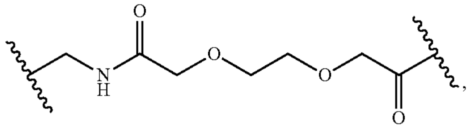
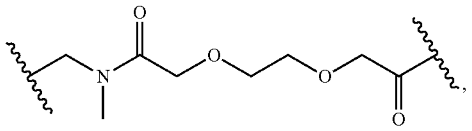
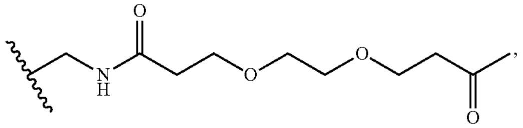
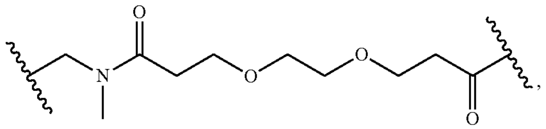
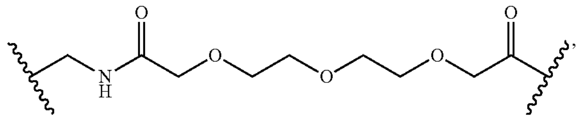
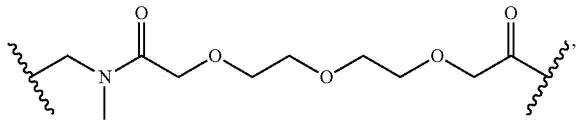

-continued

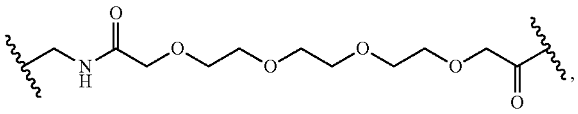
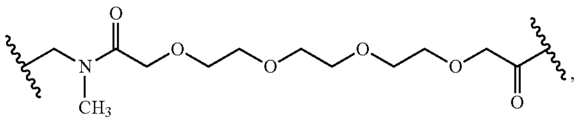
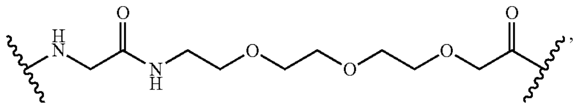
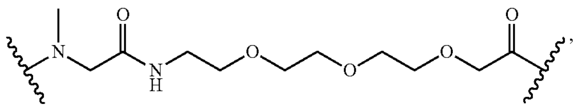
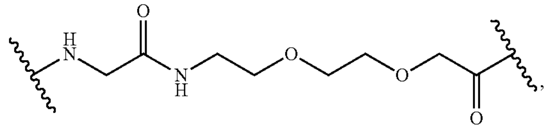
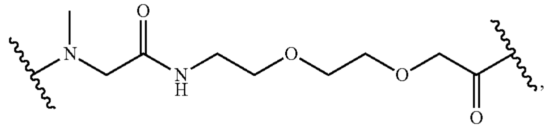
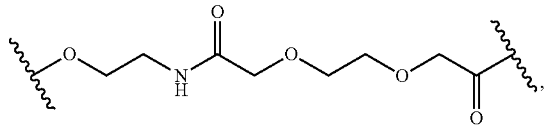
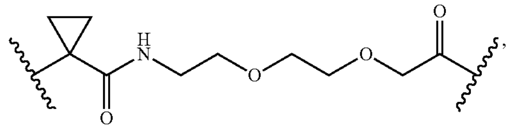
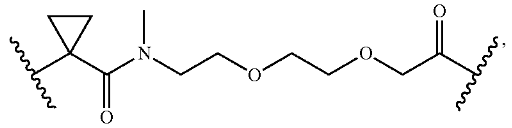
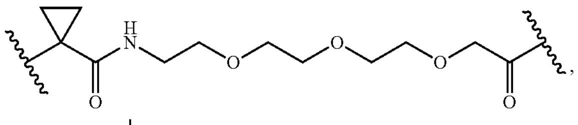
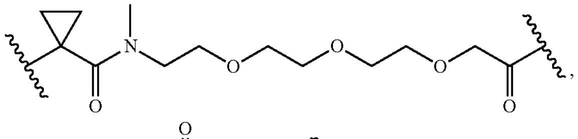
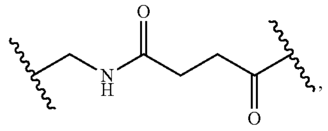
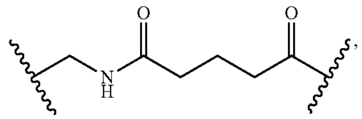
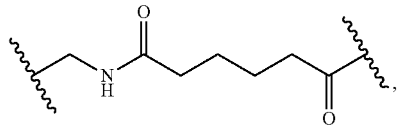

-continued
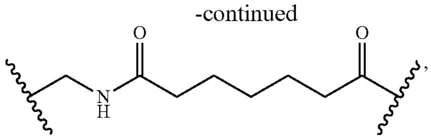,
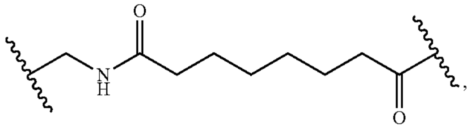,
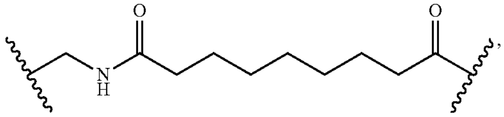,
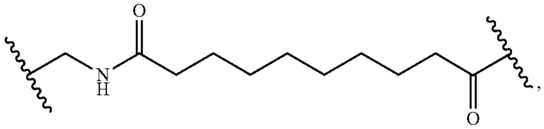,
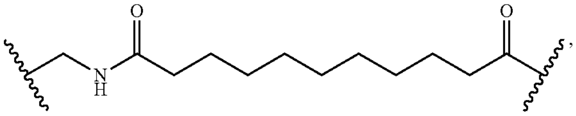,
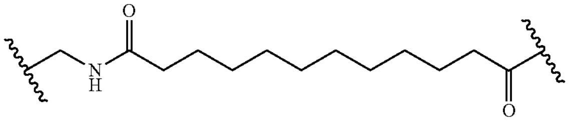,
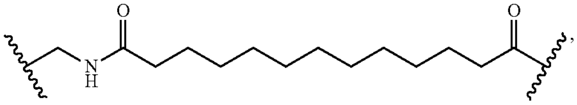,
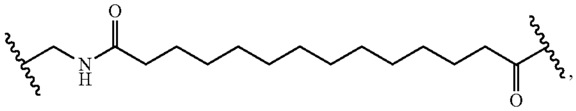,
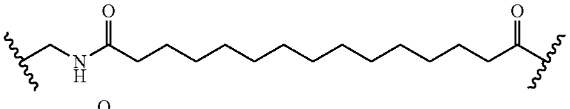,
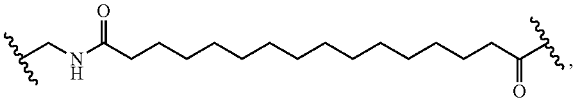,
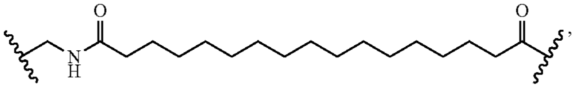,
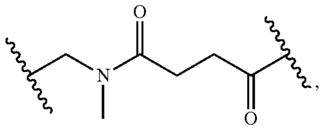,
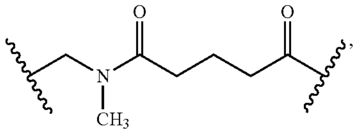,
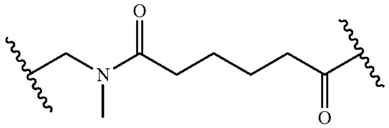,
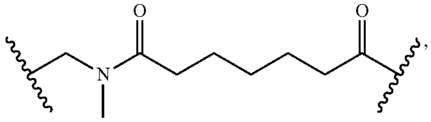,
-continued
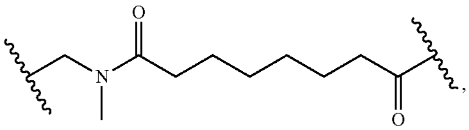,
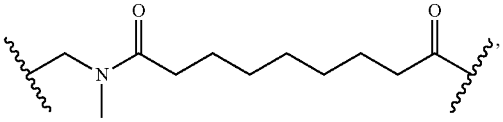,
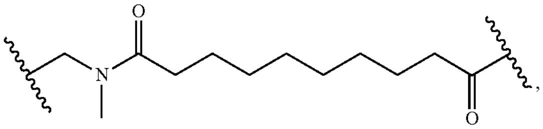,
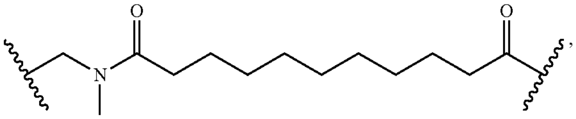,
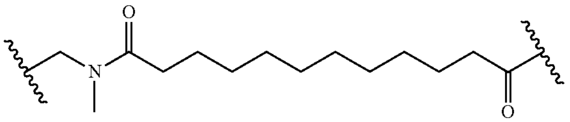,
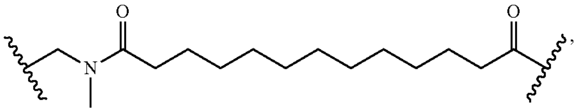,
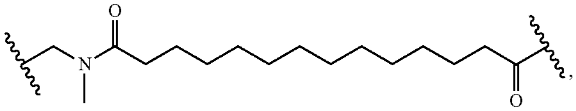,
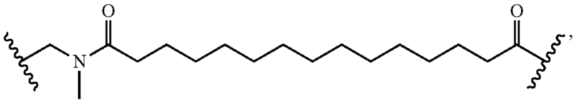,
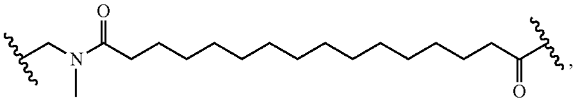,
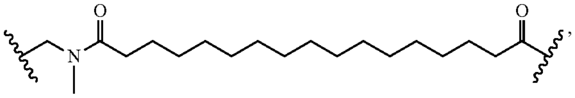,
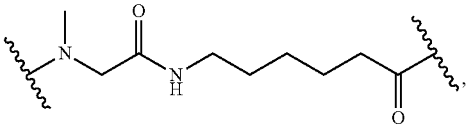,
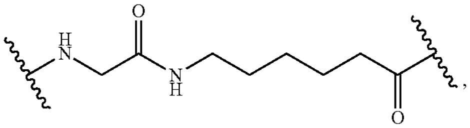,
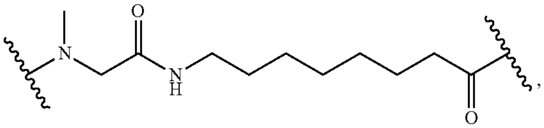,
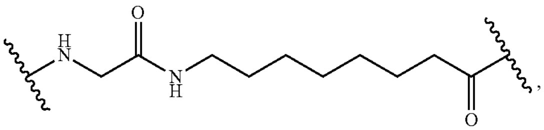, -continued
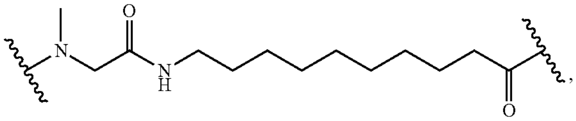,
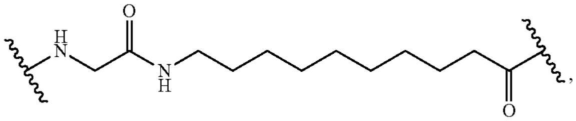,
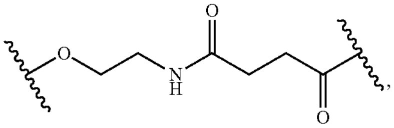,
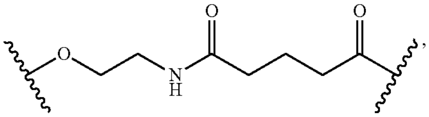,
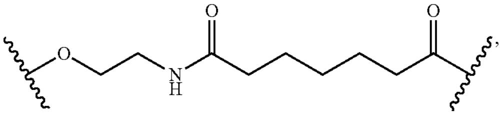,
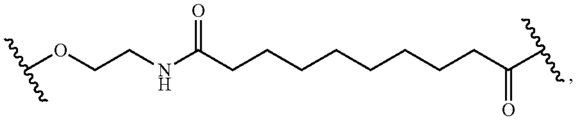,
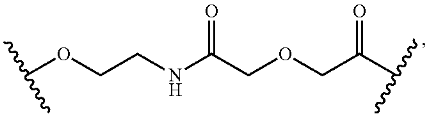,
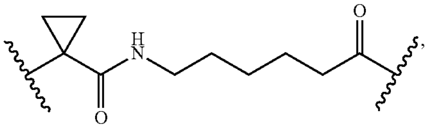,
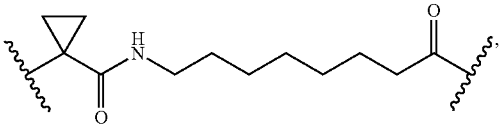,
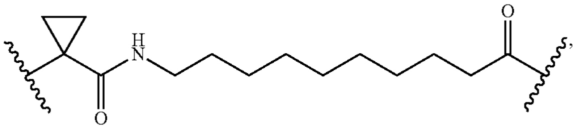,
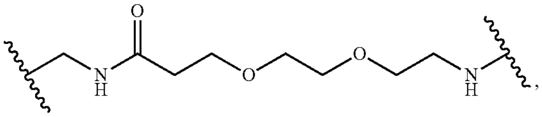,
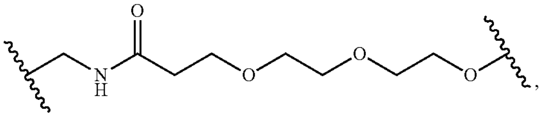,
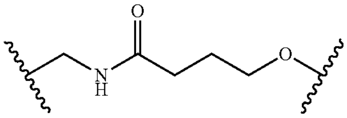,
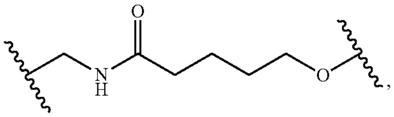,
-continued
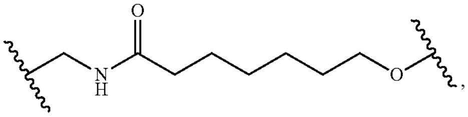,
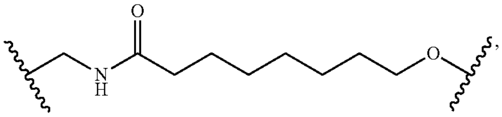,
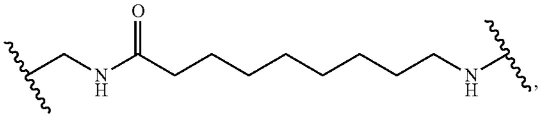,
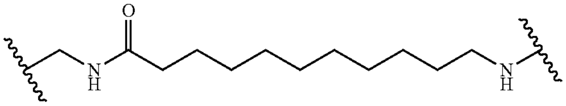,
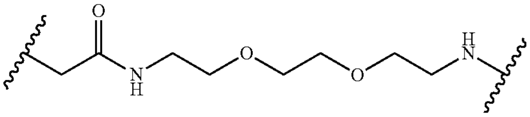,
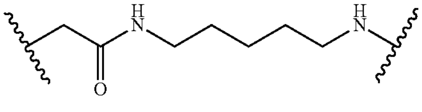,
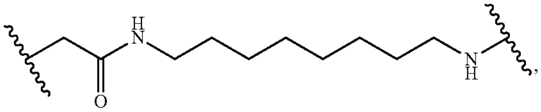,
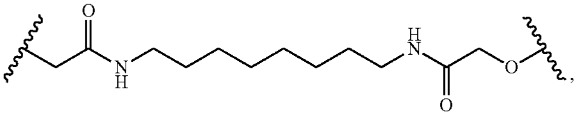,
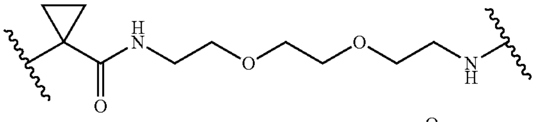,
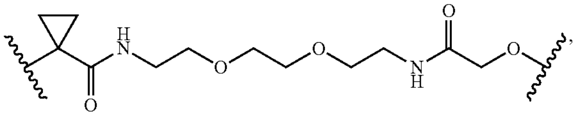,
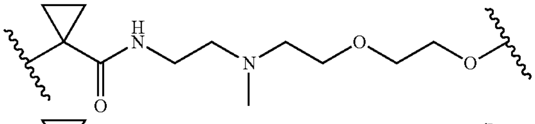,
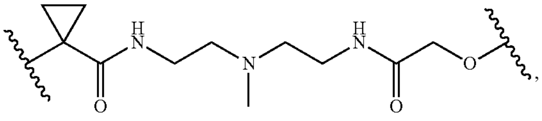,
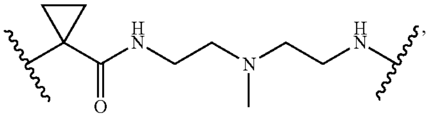,
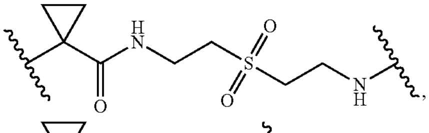,
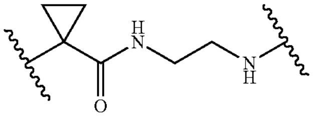

-continued
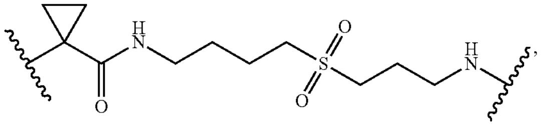
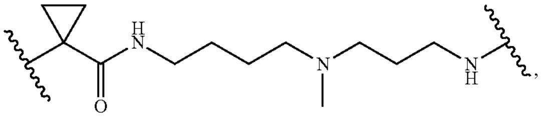
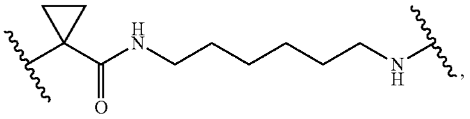
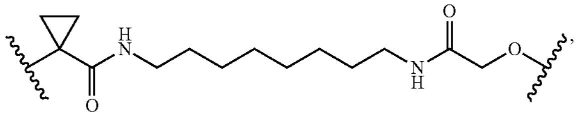
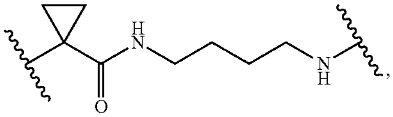
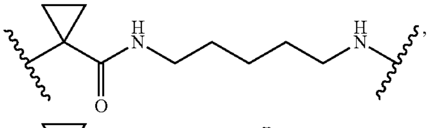
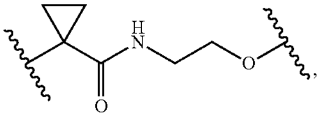
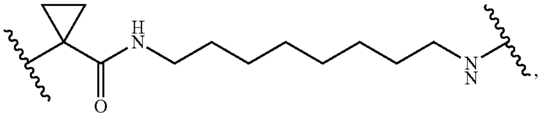
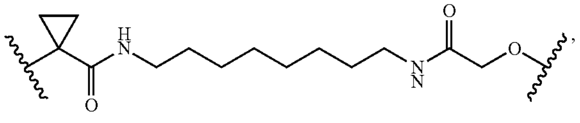
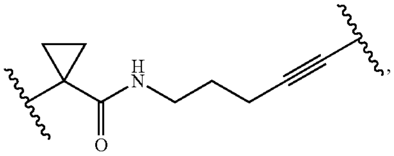
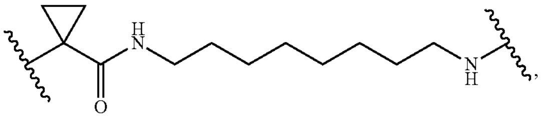
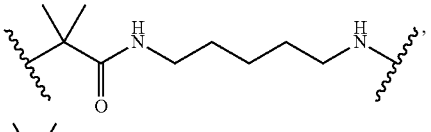
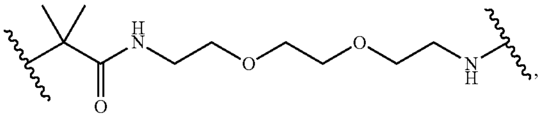
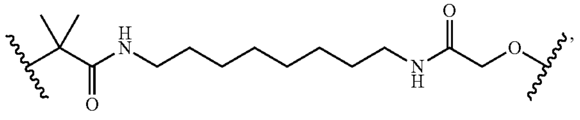
-continued
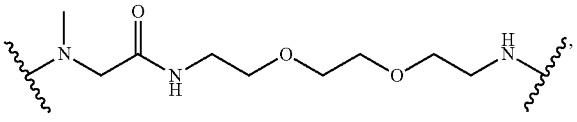
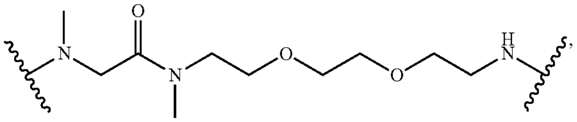
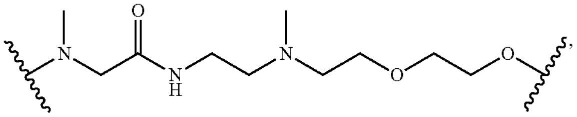
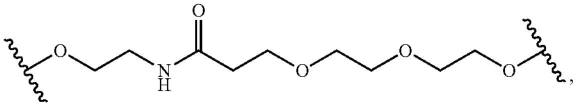
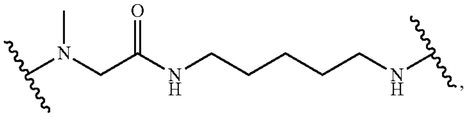
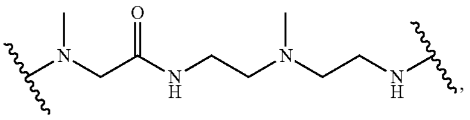
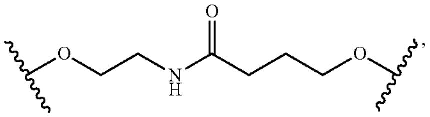
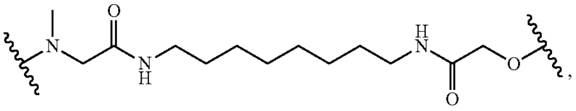
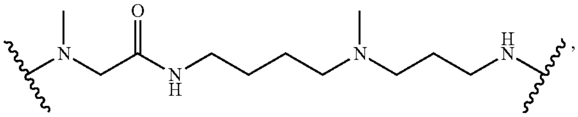
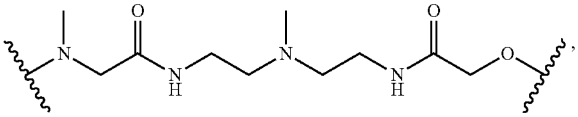
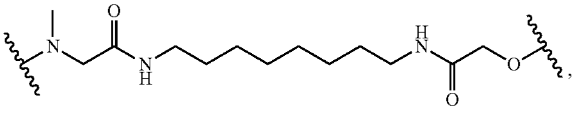
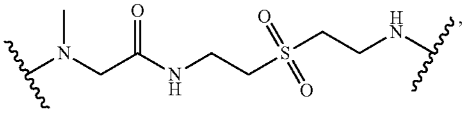
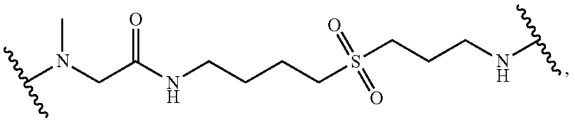
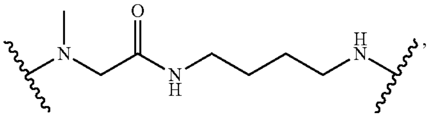

-continued

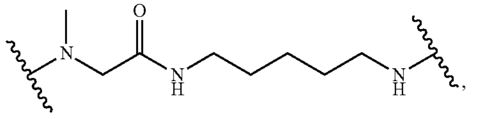

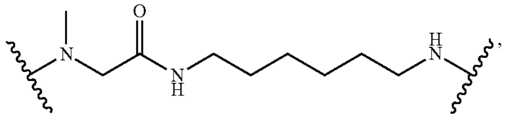

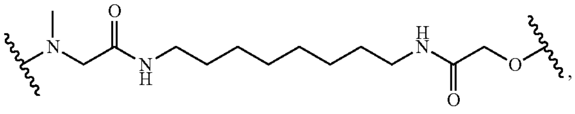

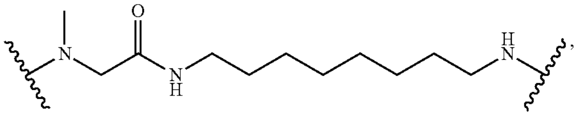

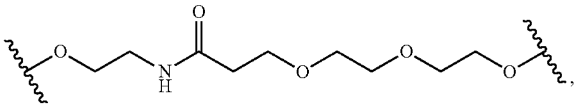

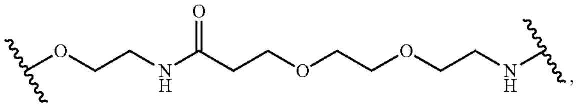

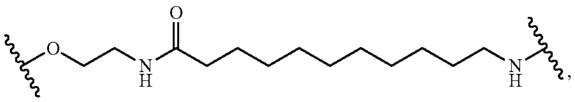

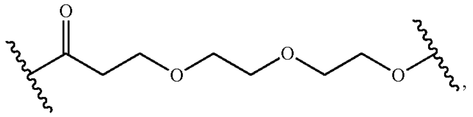

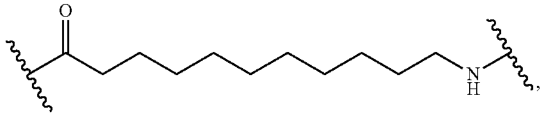

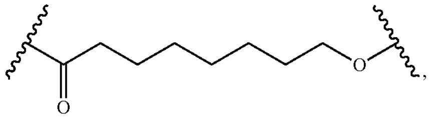

or

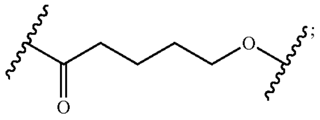

B is a degradation moiety of Formula A:

Formula A

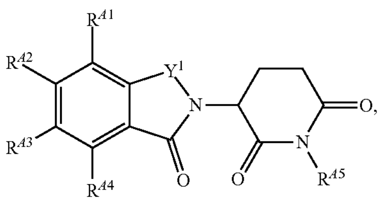

wherein $Y^1$ is

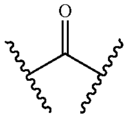 [SMILES: *C(*)=O]

$R^{A5}$ is H or $C_1$-$C_6$ alkyl;

one of $R^{A1}$, $R^{A2}$, $R^{A3}$, and $R^{A4}$ is a bond between B and the linker and the others are H;

and

A has the structure of Formula II:

Formula II

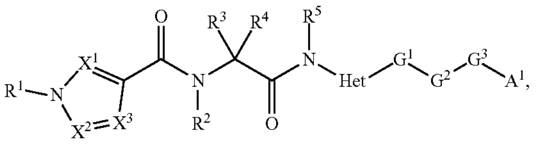

wherein $X^1$ is CH;

$X^2$, and $X^3$ are, independently, CH, or $C(CH_3)$;

$R^1$ is $—SO_2R^6$;

$R^2$ and $R^5$ are each;

$R^3$ is H or a bond between A and the linker;

$R^4$ is H;

$R^6$ is $C_1$-$C_6$ alkyl;

Het is

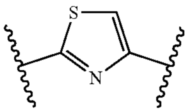 [SMILES: *c1csc(*)n1]

$G^1$ is

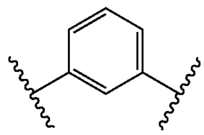

or

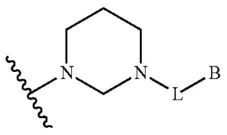

$G^2$ is absent,

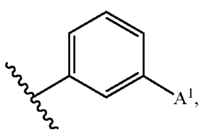

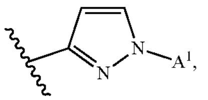

or

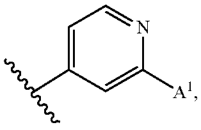

and
$A^1$ is H or a bond between A and the linker,
provided that only one of $R^3$ and $A^1$ is a bond between A and the linker and the other is H,
or a pharmaceutically acceptable salt thereof.
2. The compound of claim 1, wherein each of $X^1$, $X^2$, and $X^3$ is CH.
3. The compound of claim 1, wherein $R^1$ is
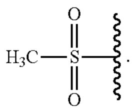
4. A compound that has the structure of any one of the following compounds

| # | Structure |
| --- | --- |
| 2 | 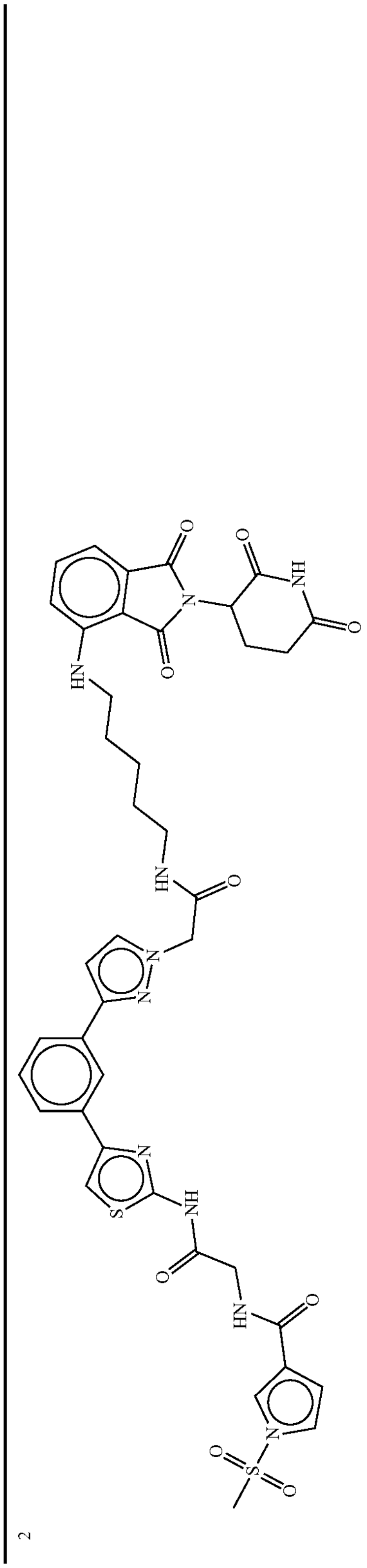 |
| 3 | 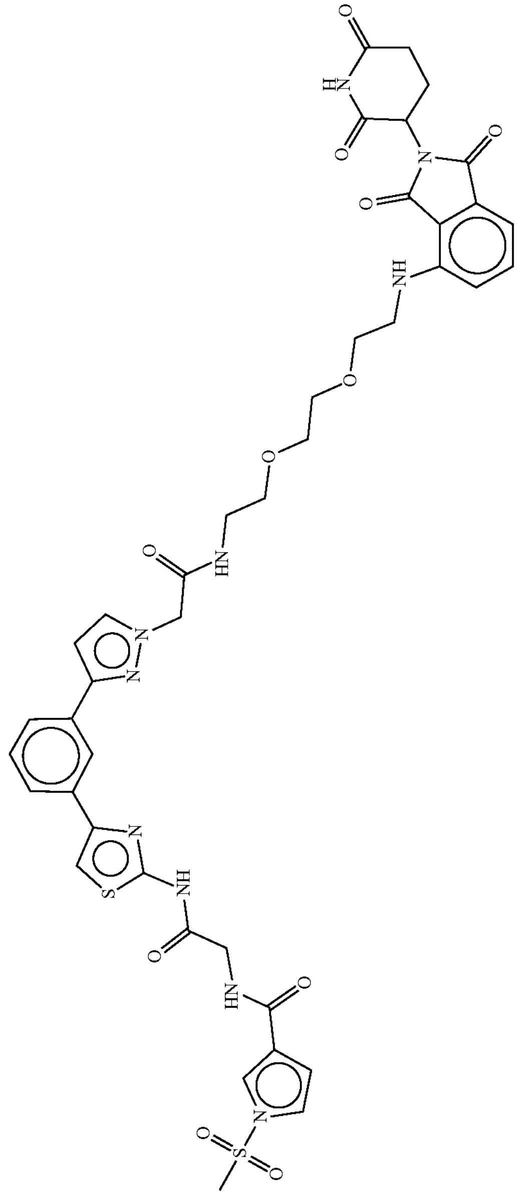 |

-continued
| # | Structure |
|---|---|
| 5 | 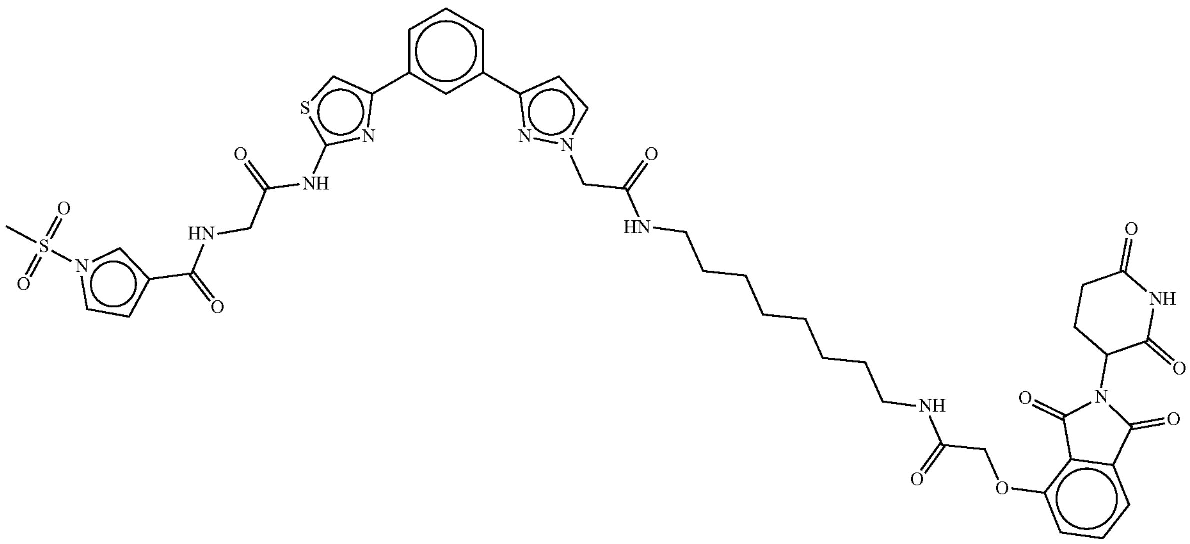 |
| 6 | 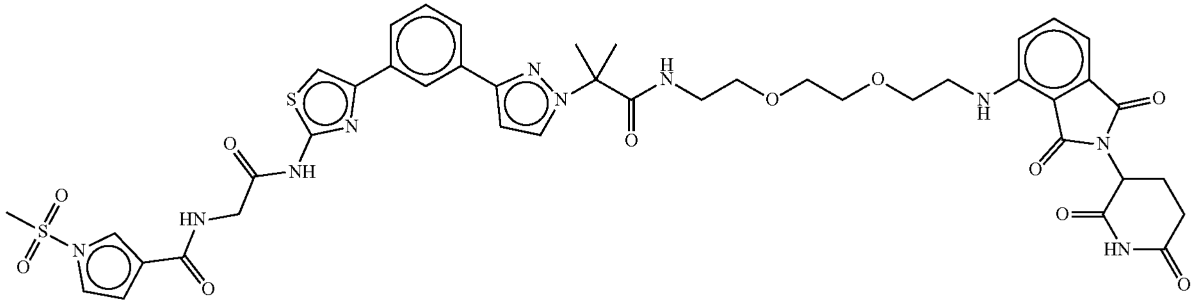 |

-continued
| # | Structure |
|---|---|
| 7 | 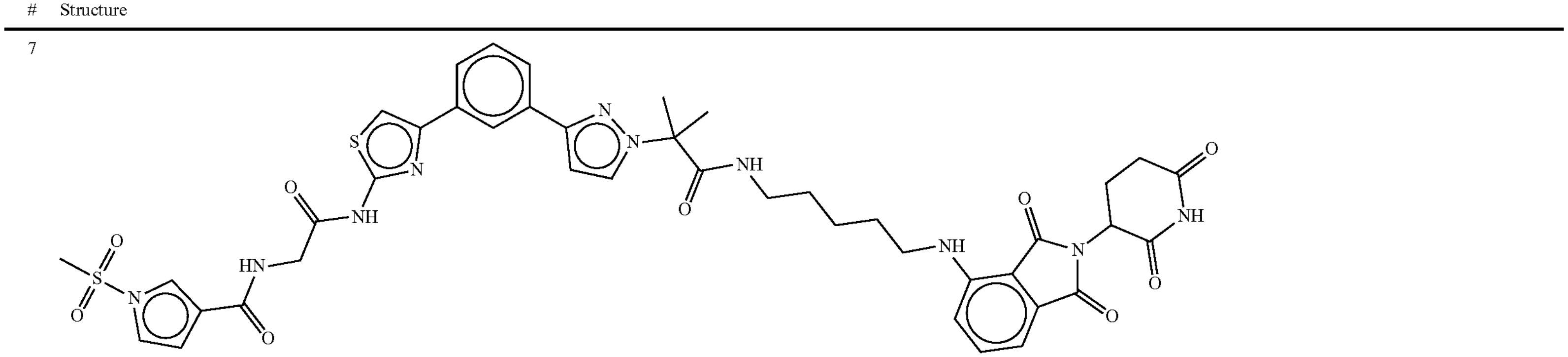 |
| 8 | 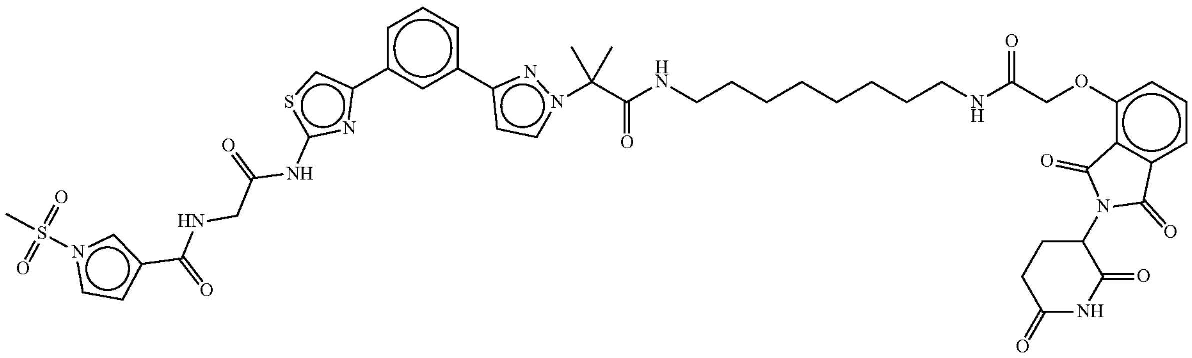 |
| 9 | 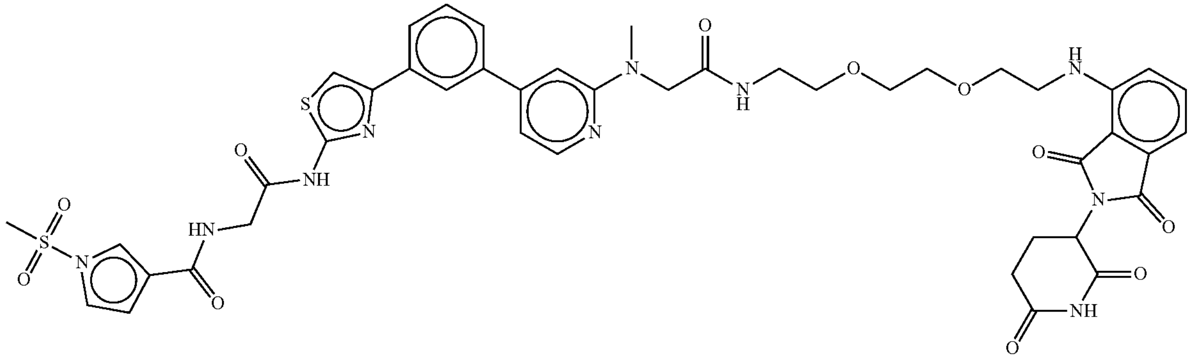 |

-continued
| # | Structure |
| --- | --- |
| 11 | 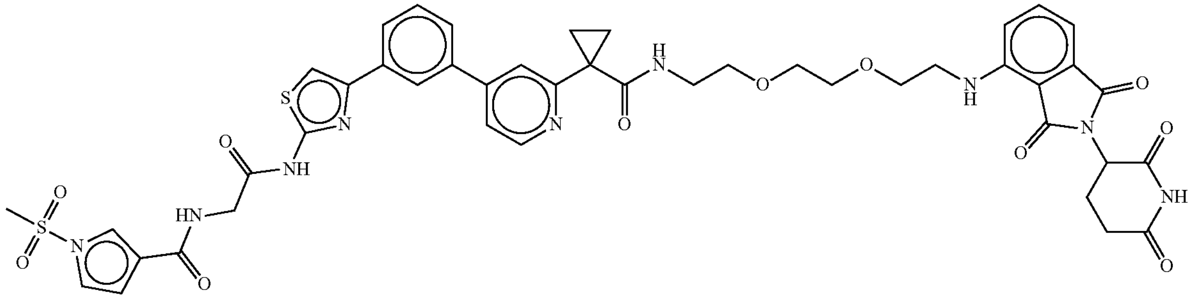 |
| 12 | 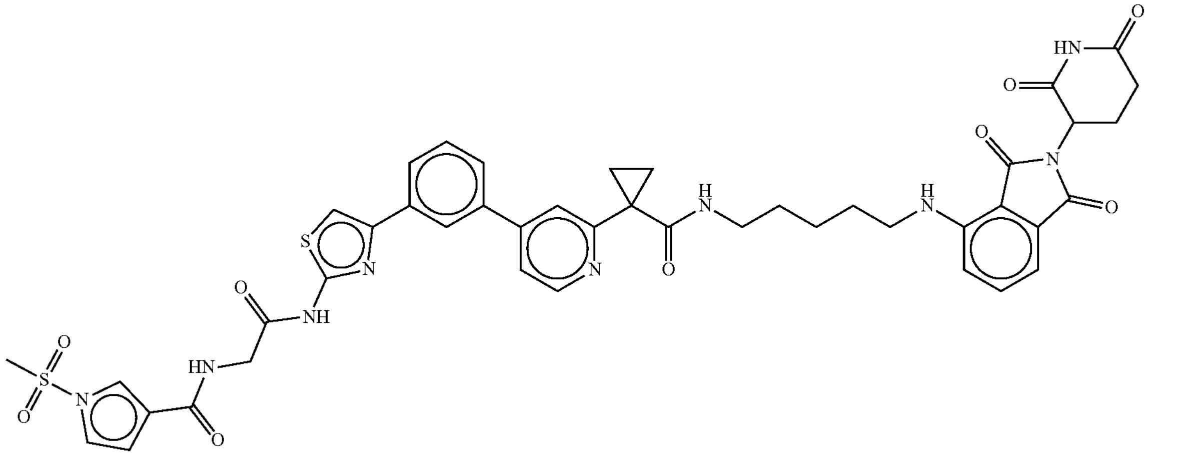 |

-continued
| # | Structure |
|---|---|
| 13 | 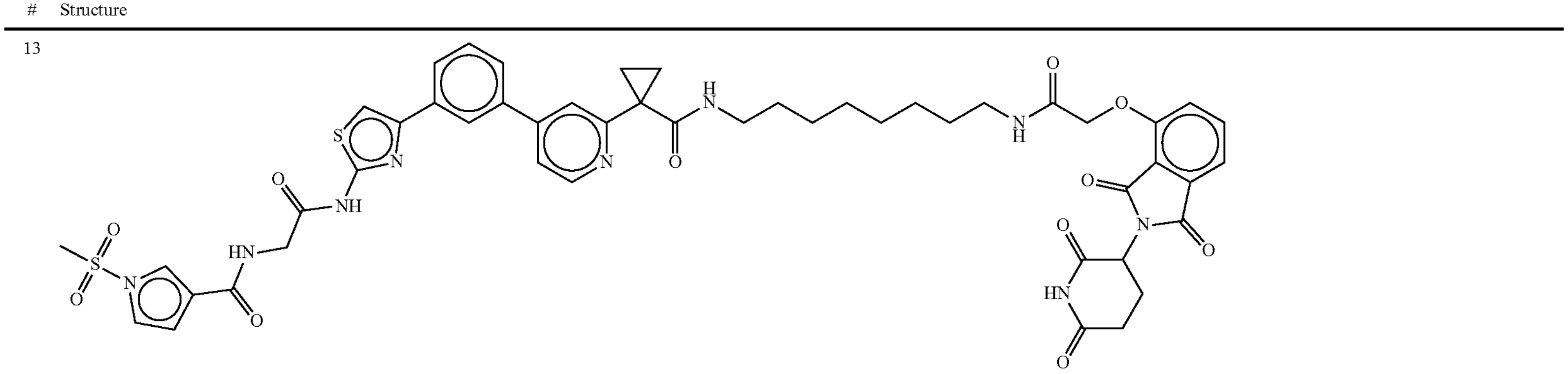 |
| 15 | 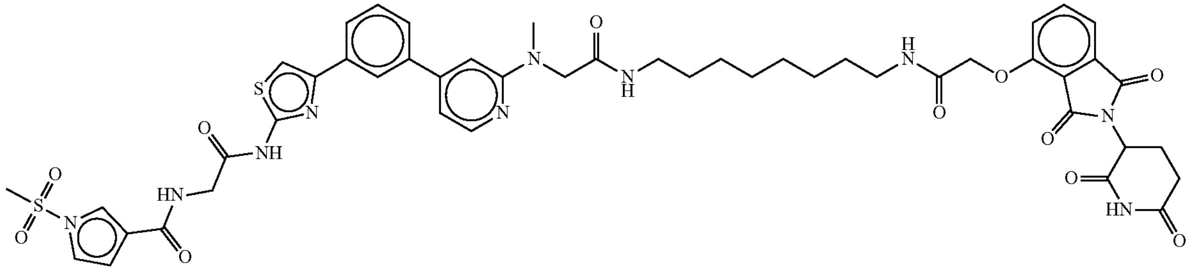 |
| 16 | 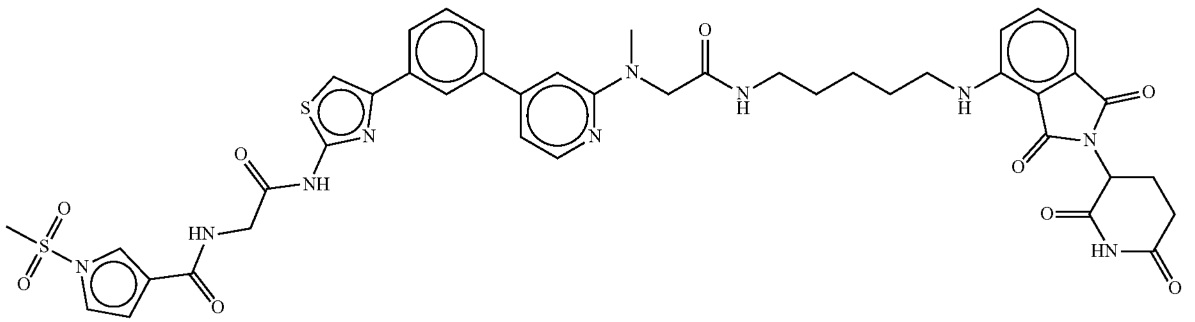 |

-continued
| # | Structure |
|---|---|
| 20 | 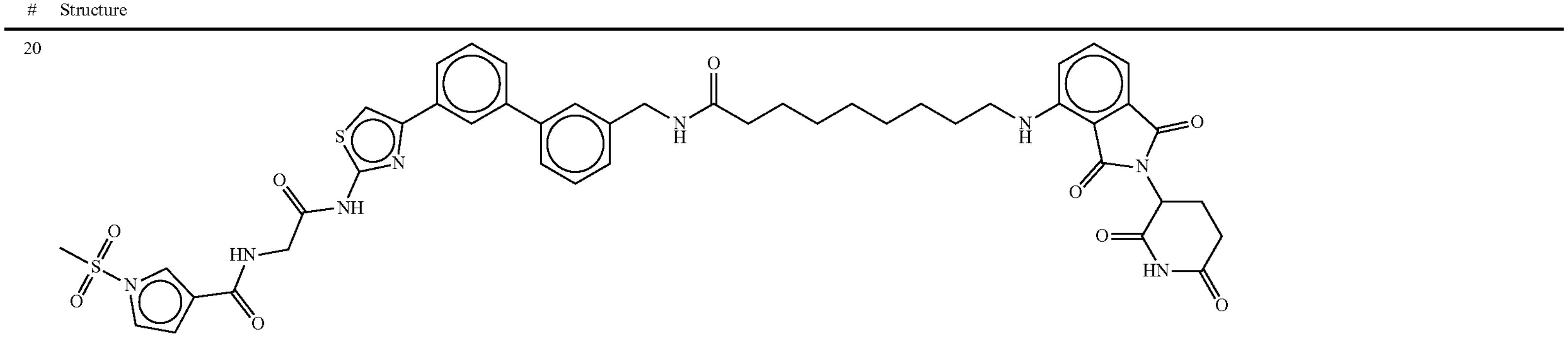 |
| 21 | 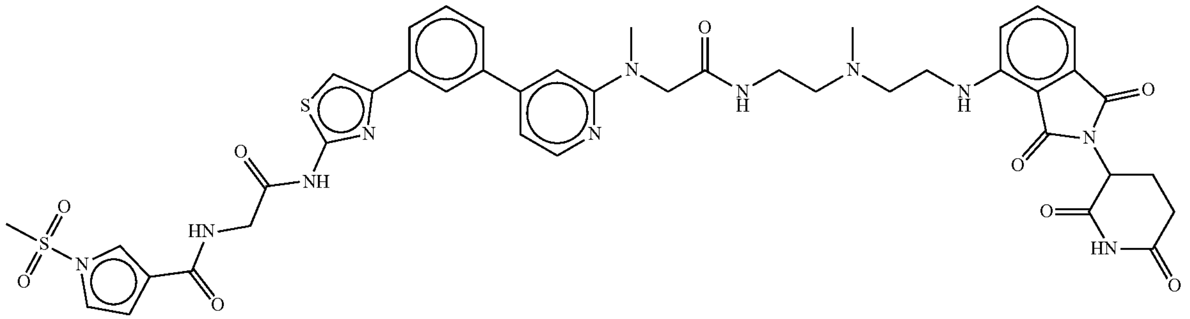 |
| 22 | 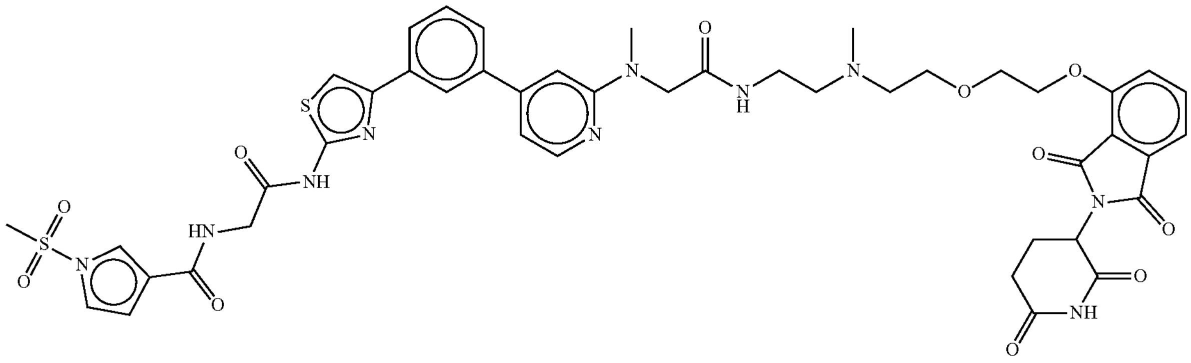 |

-continued
| # | Structure |
|---|---|
| 23 | 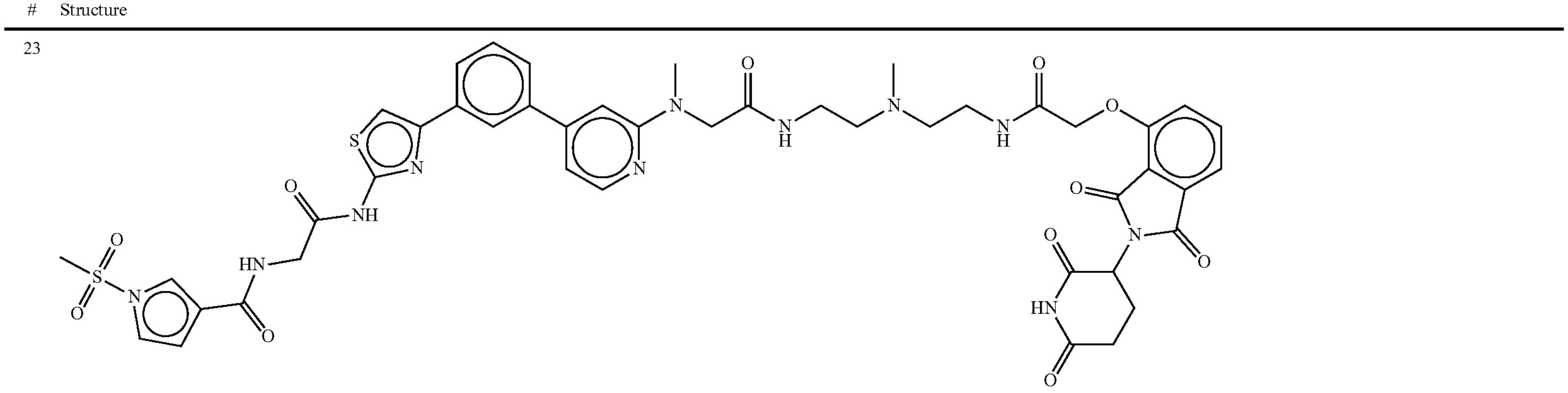 |
| 24 | 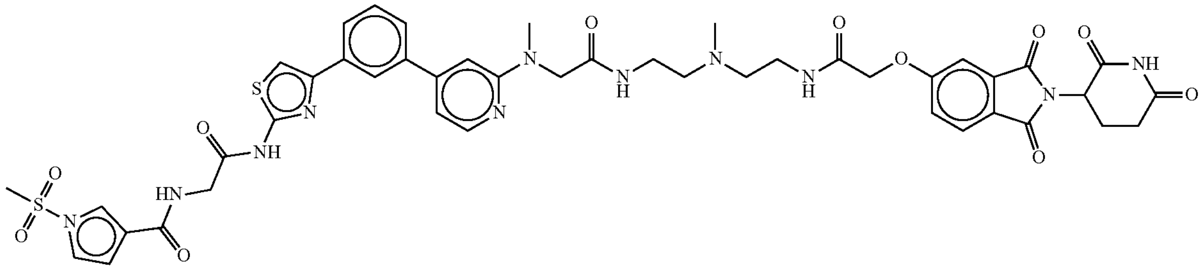 |
| 28 | 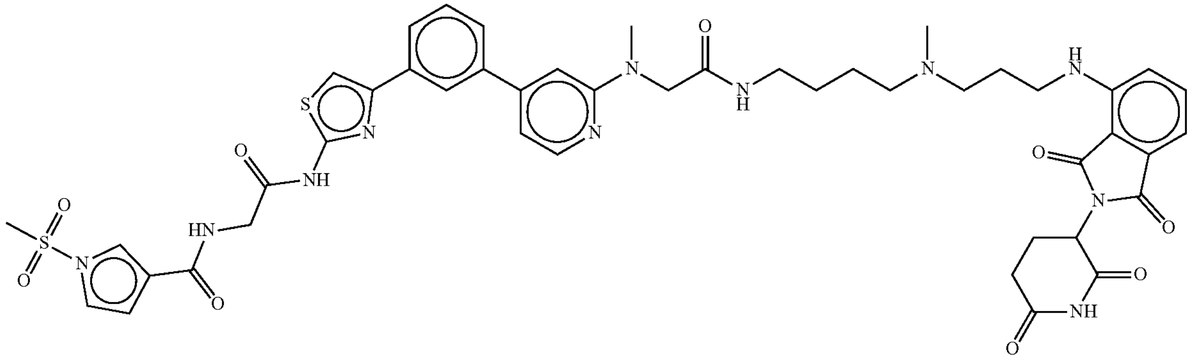 |

-continued
| # | Structure |
|---|---|
| 29 | 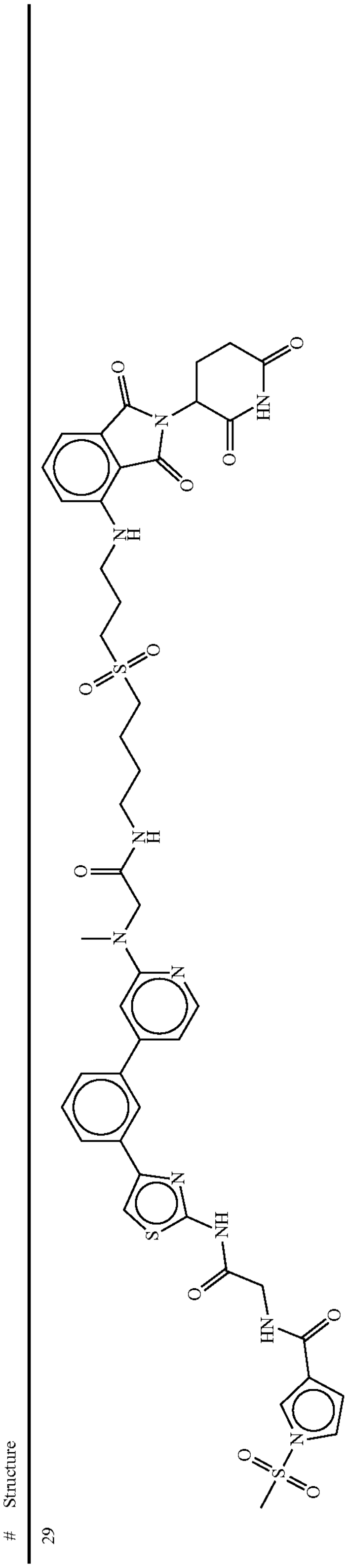 |
| 30 | 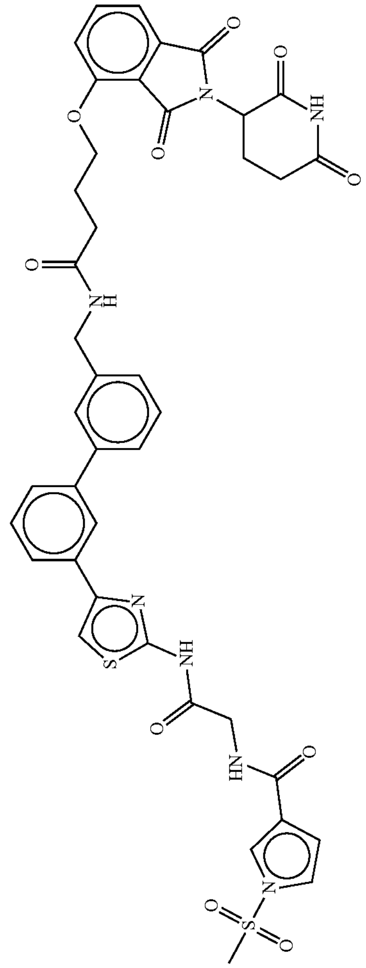 |
| 36 | 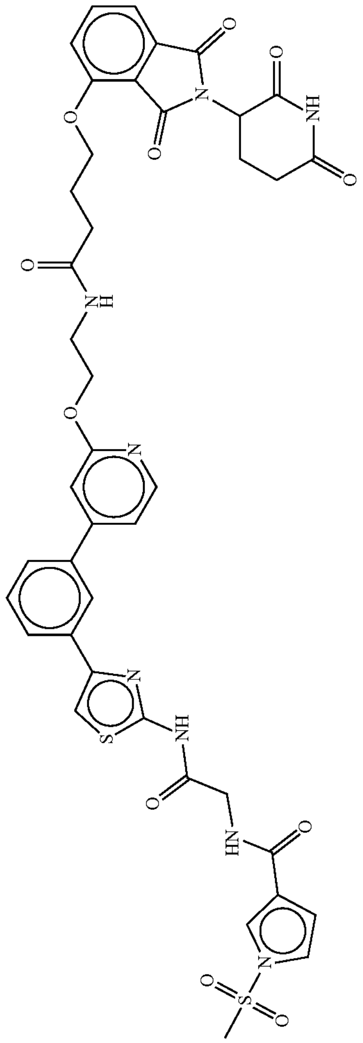 |

-continued
| # | Structure |
|---|---|
| 38 | 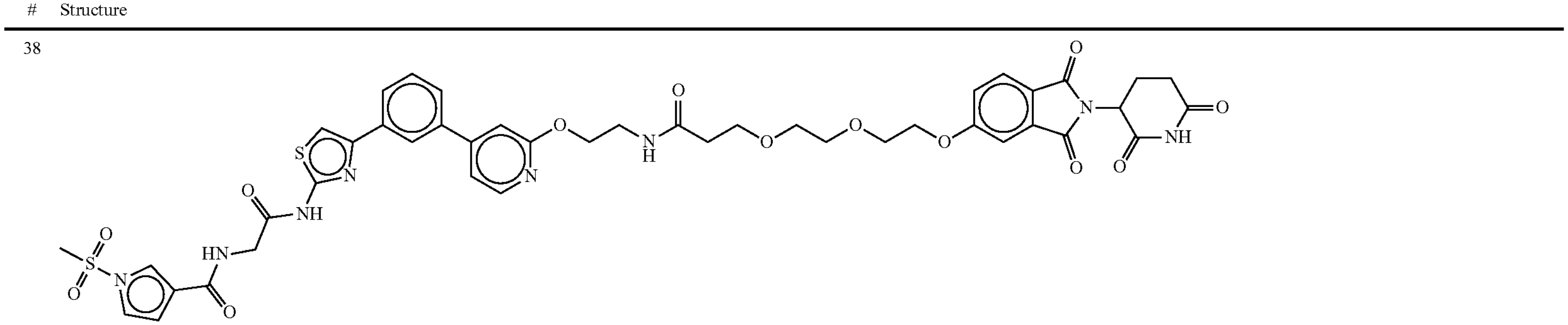 |
| 41 | 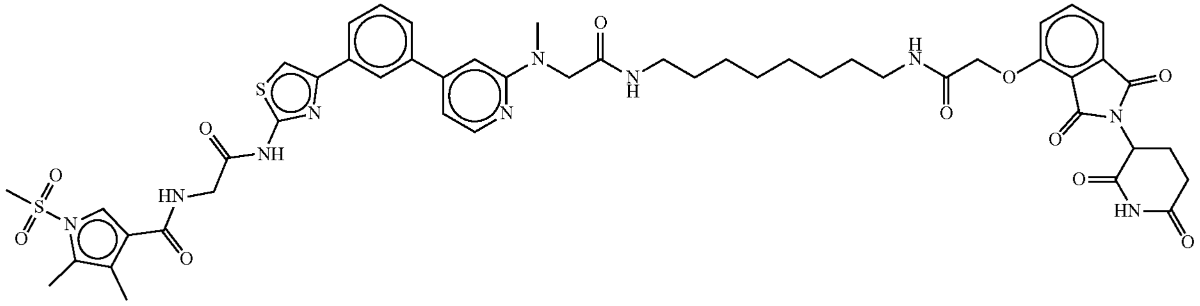 |
| 42 | 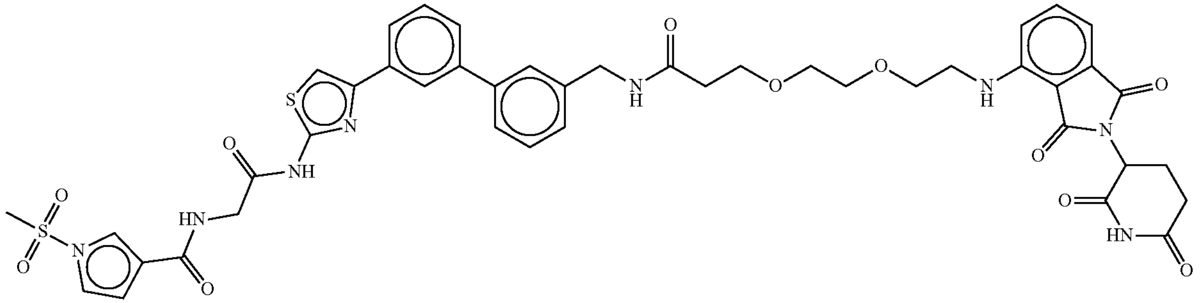 |

-continued
| # | Structure |
|---|---|
| 43 | 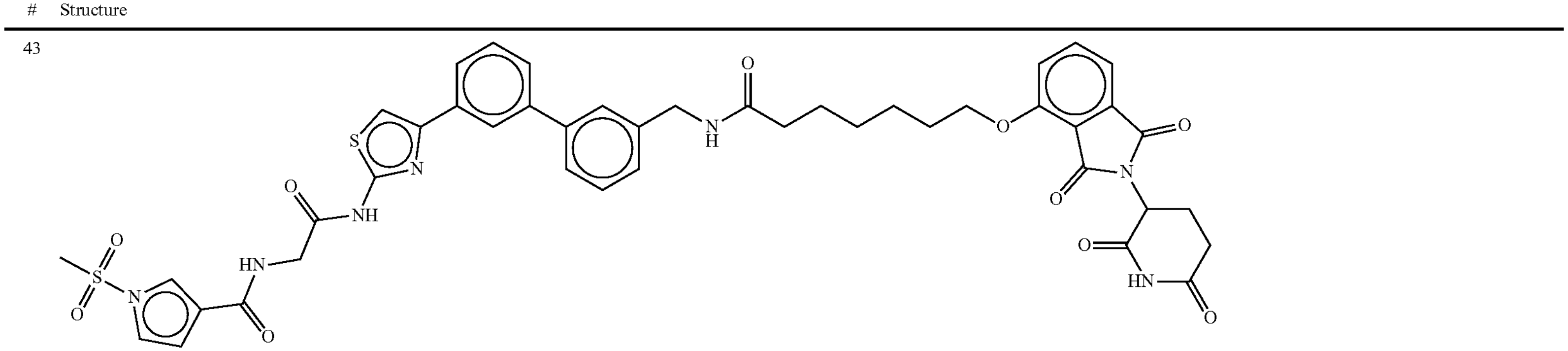 |
| 45 | 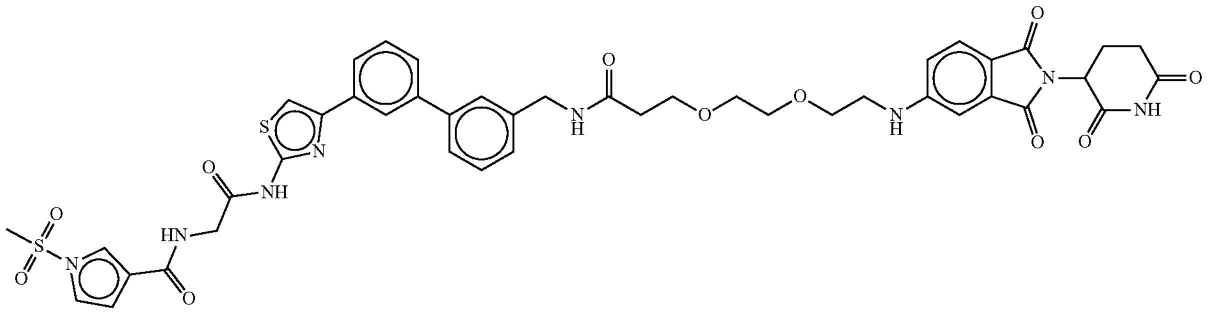 |
| 46 | 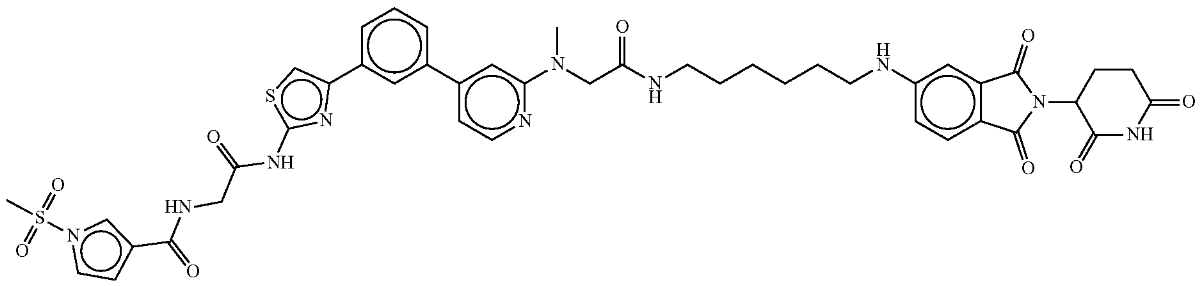 |

-continued
| # | Structure |
| --- | --- |
| 51 | 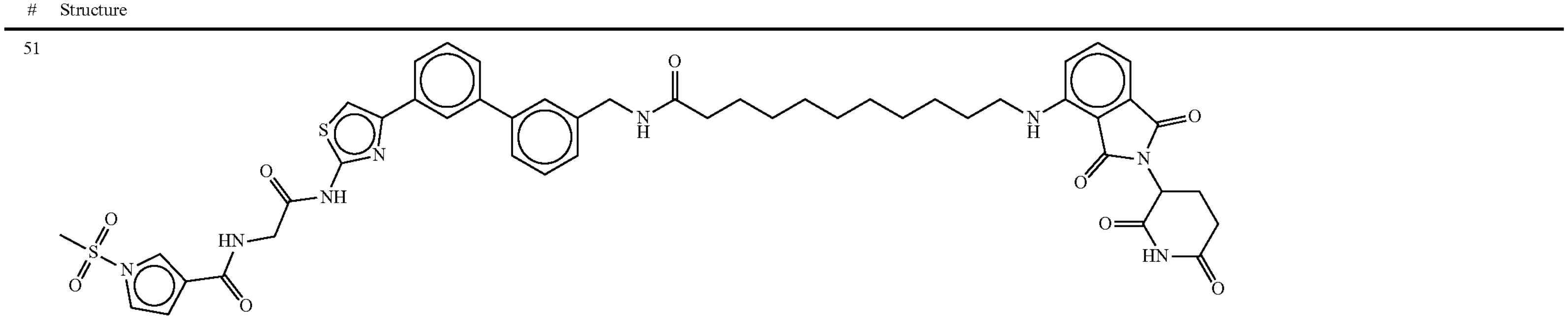 |
| 52 | 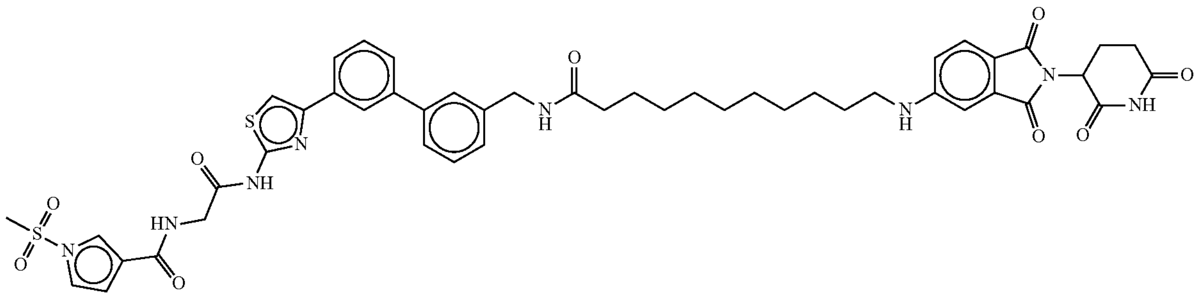 |
| 53 | 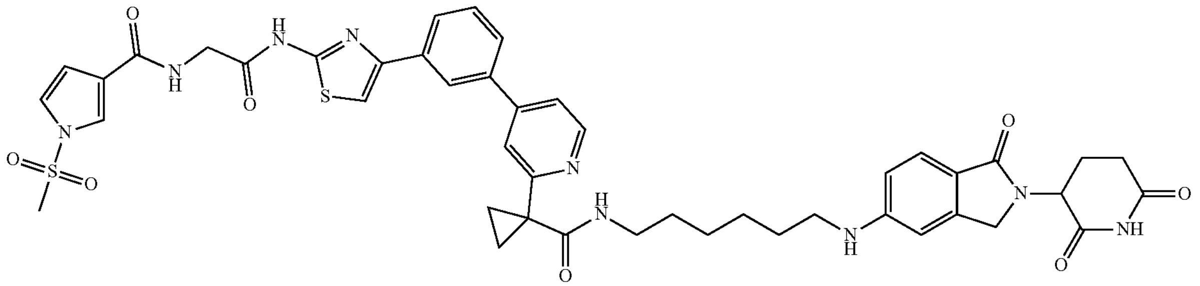 [SMILES: CS(=O)(=O)n1ccc(C(=O)NCC(=O)Nc2nc(-c3cccc(-c4ccnc(C5(C(=O)NCCCCCCNc6ccc7c(c6)CN(C6CCC(=O)NC6=O)C7=O)CC5)c4)c3)cs2)c1] |

-continued
| # | Structure |
| --- | --- |
| 54 | 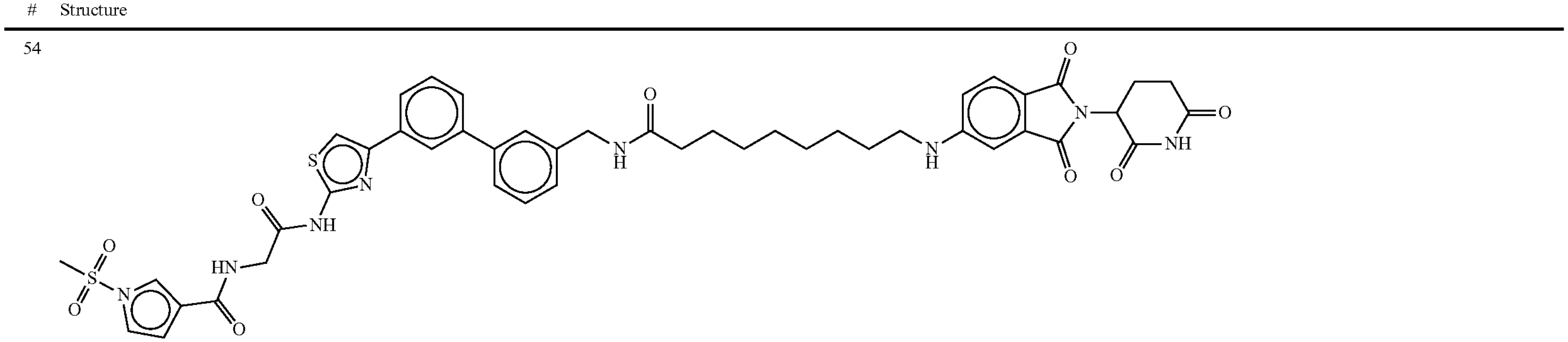 |
| 55 | 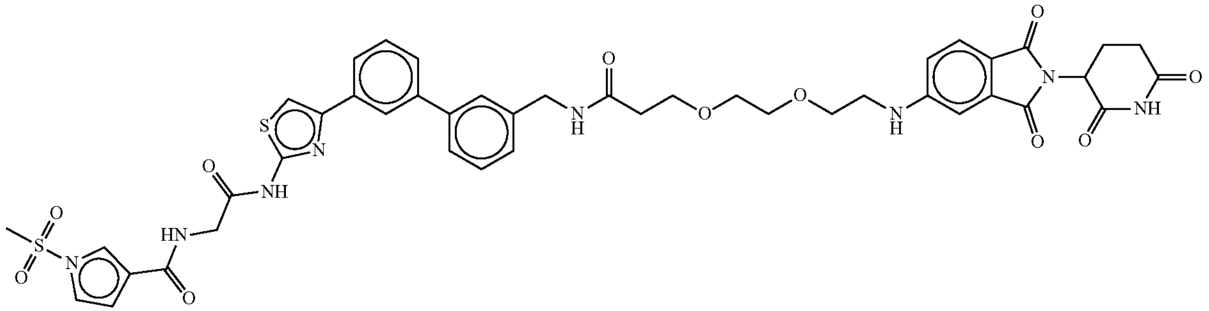 |
| 57 | 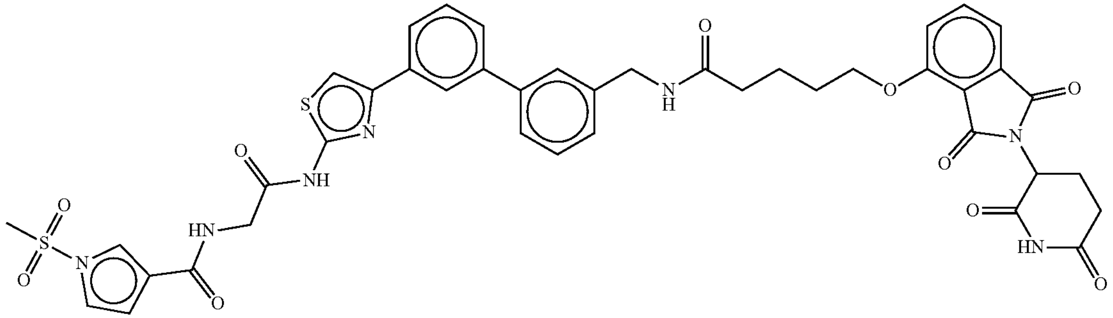 |

-continued
| # | Structure |
| --- | --- |
| 58 | 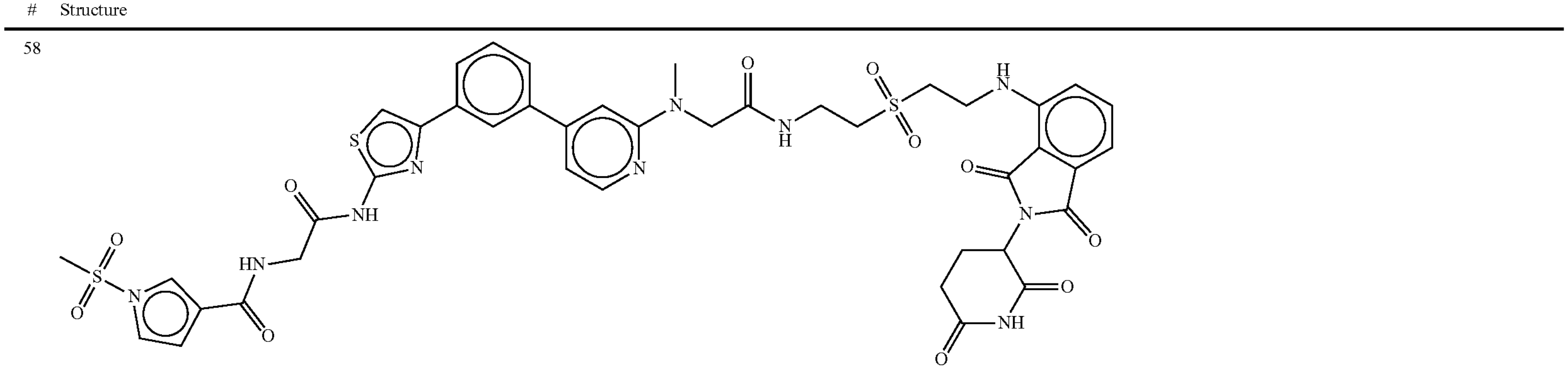 |
| 59 | 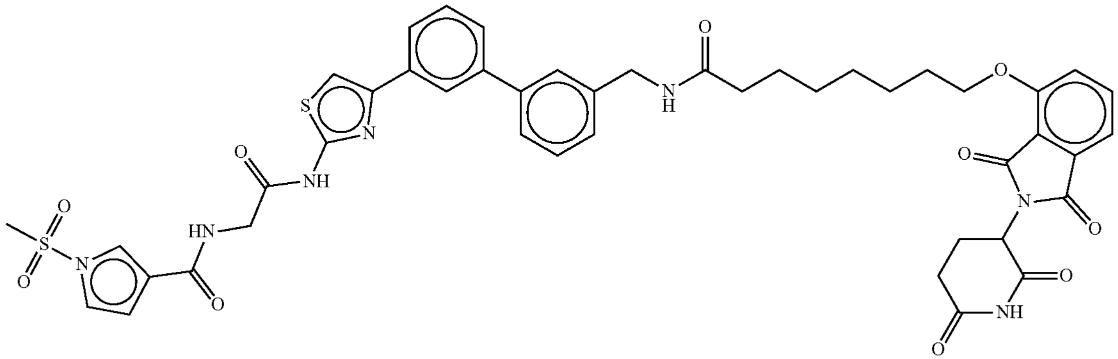 |
| 60 | 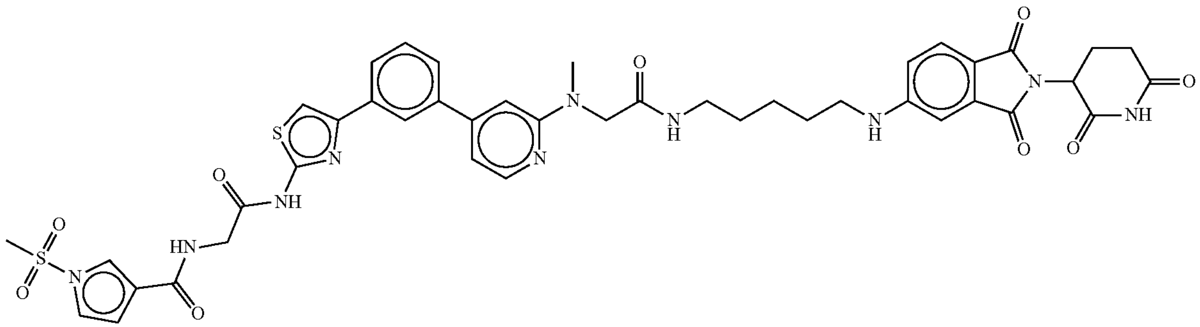 |

-continued
| # | Structure |
| --- | --- |
| 64 | 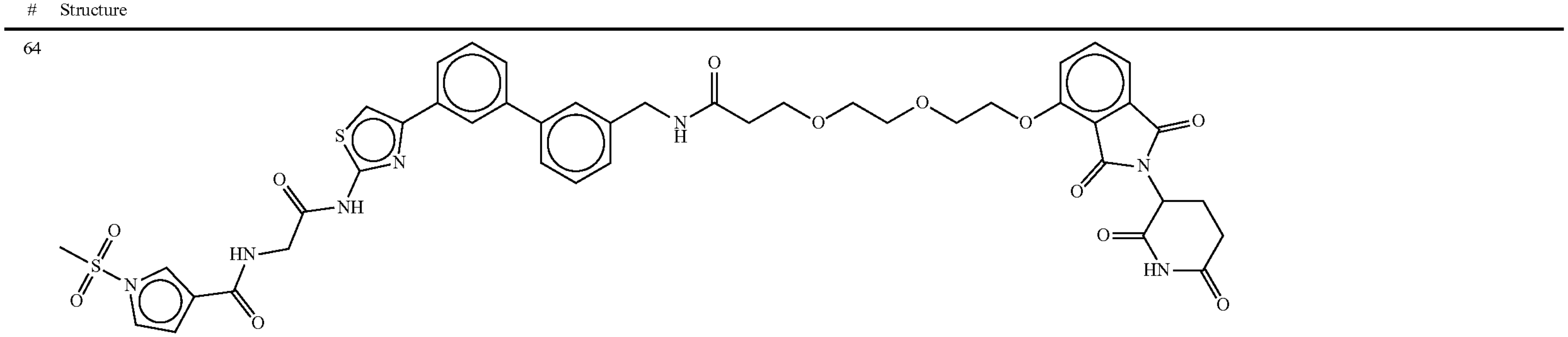 |
| 66 | 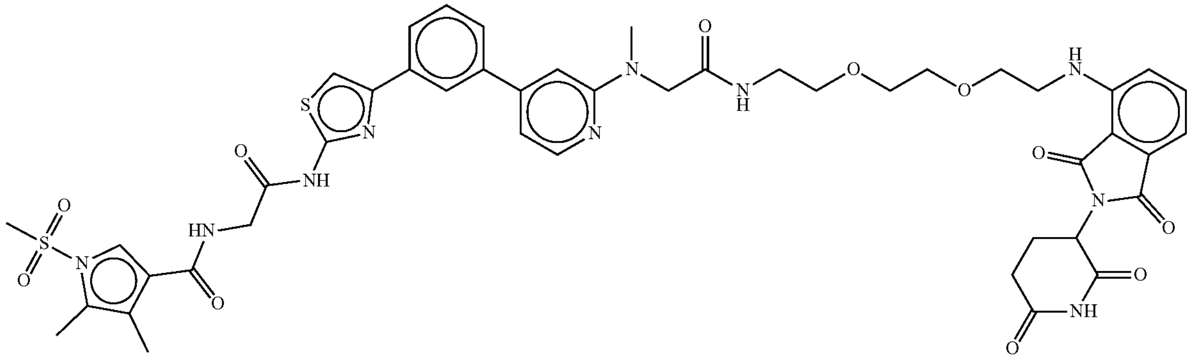 |
| 67 | 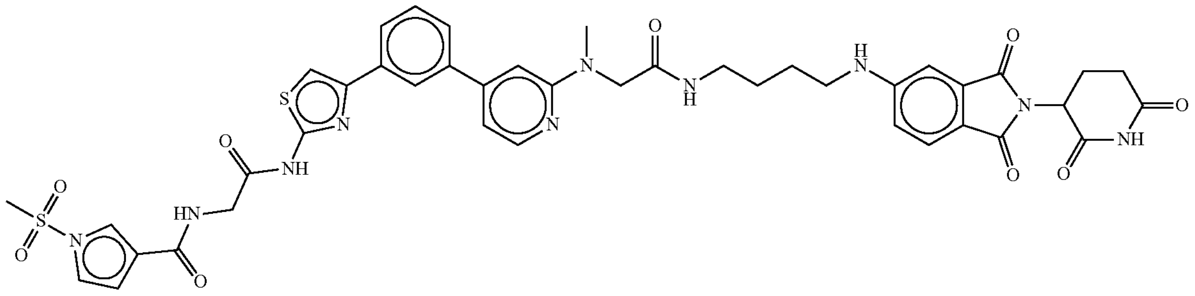 |

-continued
| # | Structure |
| --- | --- |
| 68 | 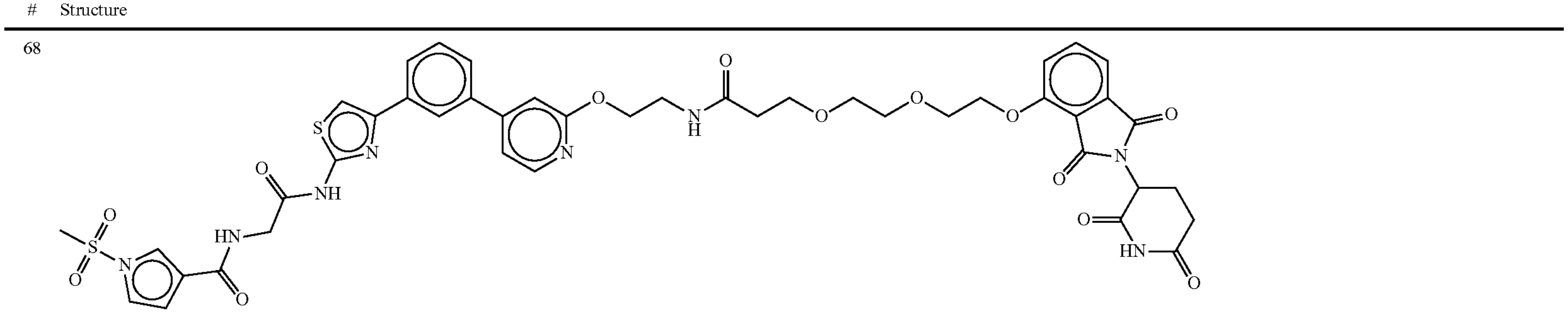 |
| 73 | 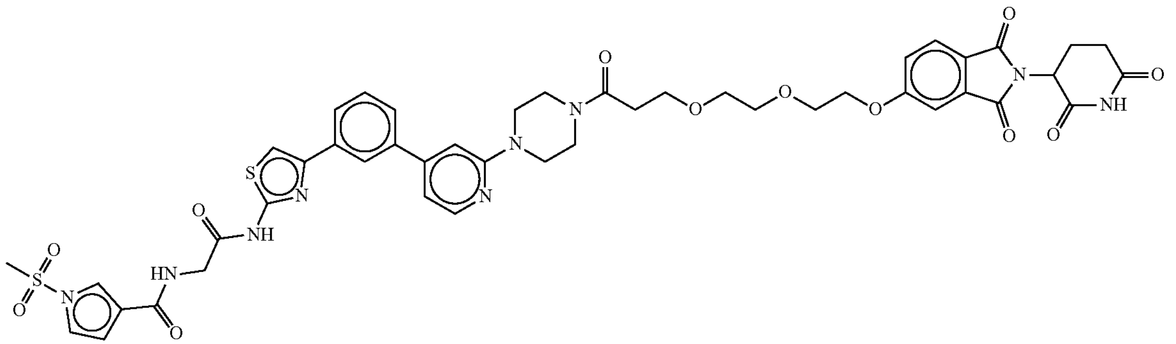 |
| 81 | 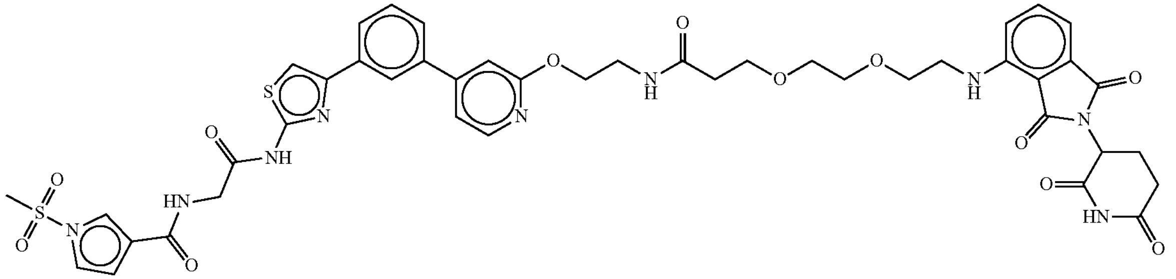 |

-continued
| # | Structure |
| --- | --- |
| 82 | 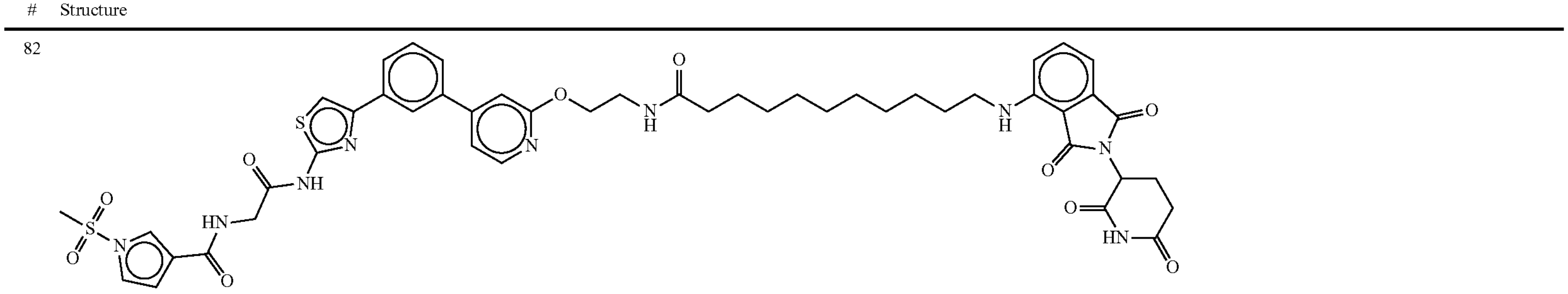 |
| 83 | 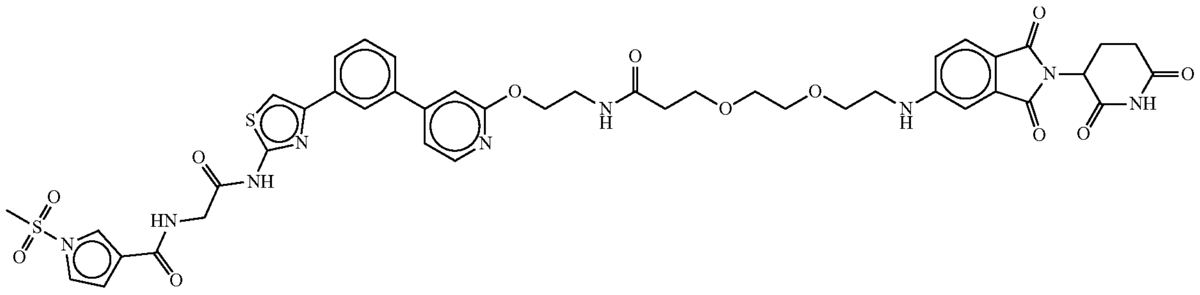 |
| 84 | 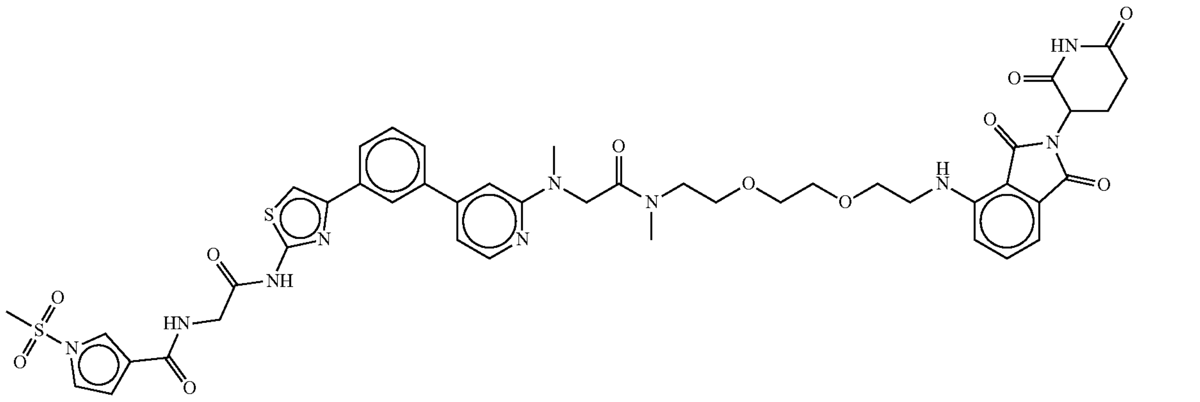 |

-continued
| # | Structure |
| --- | --- |
| 90 | 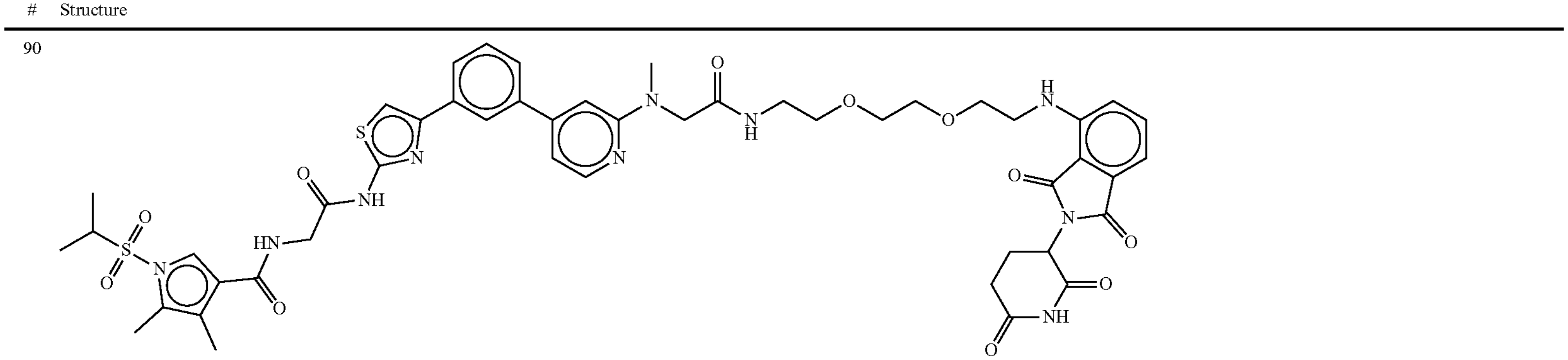 |
| 91 | 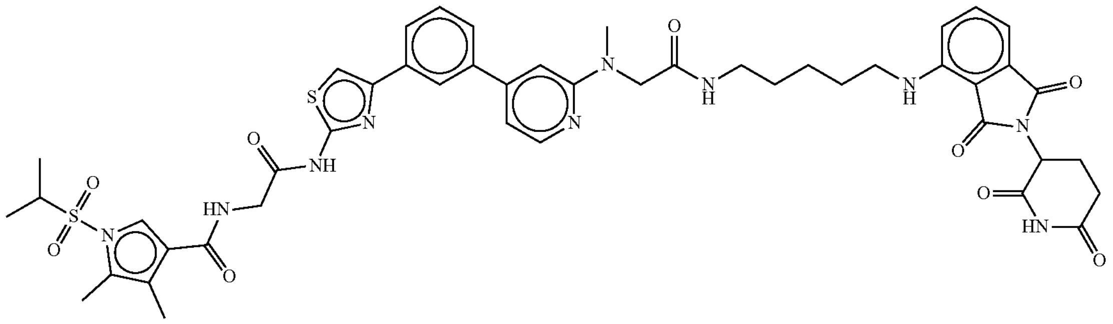 |
| 92 | 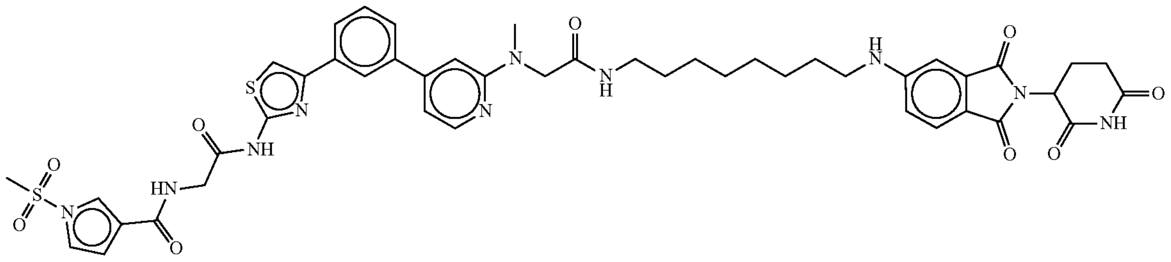 |

-continued
| # | Structure |
| --- | --- |
| 93 | 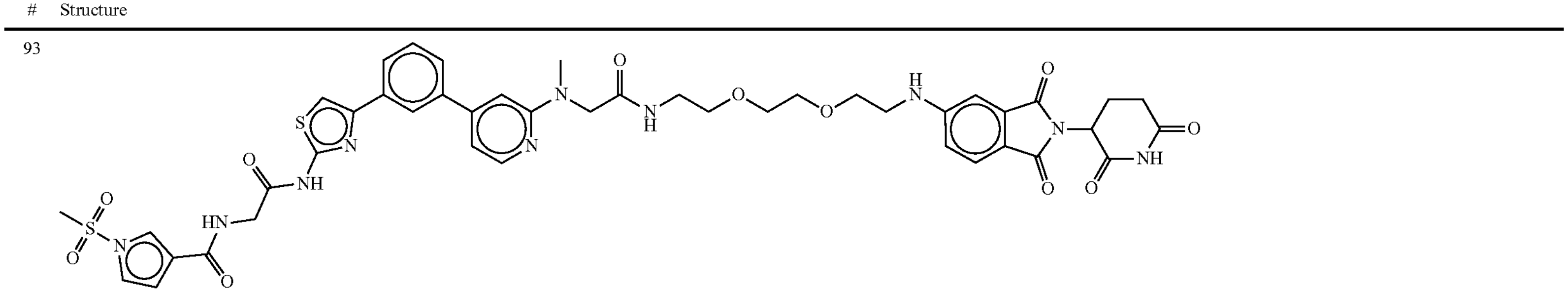 |
| 95 | 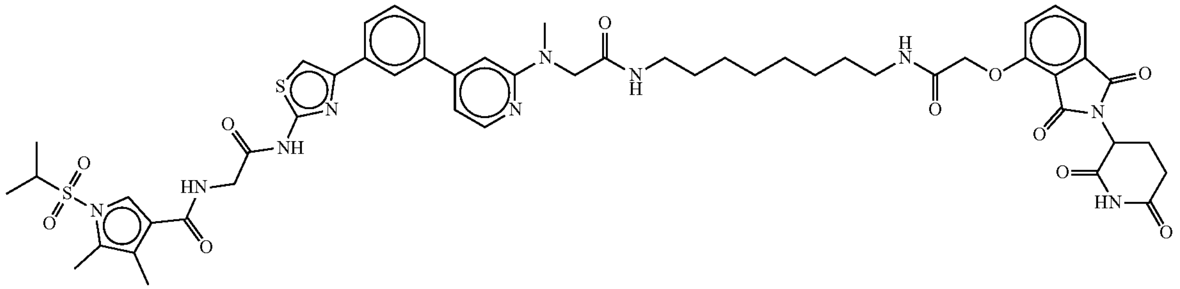 |
| 96 | 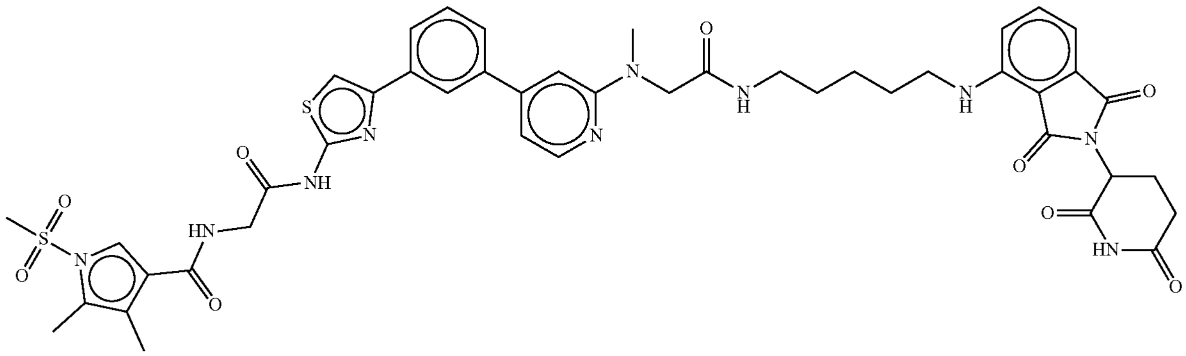 |

-continued
| # | Structure |
| --- | --- |
| 97 | 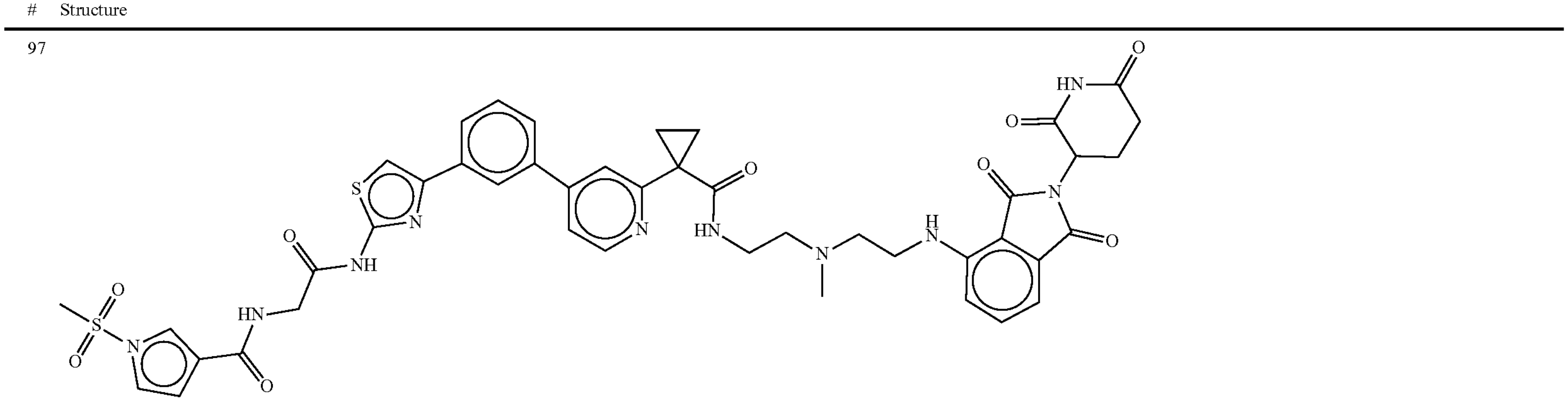 |
| 101 | 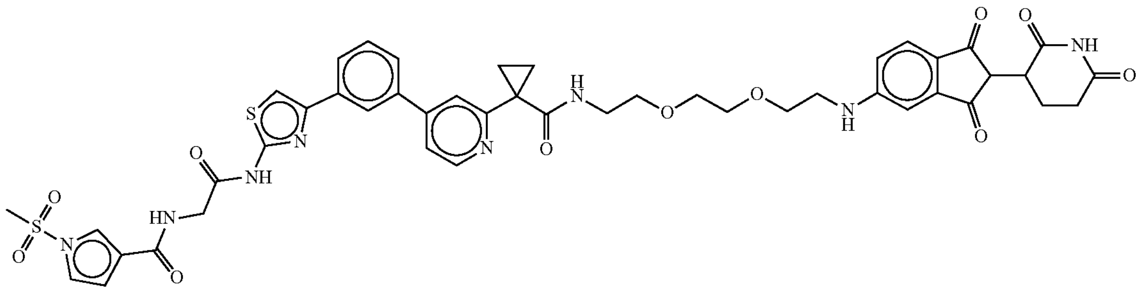 |
| 102 | 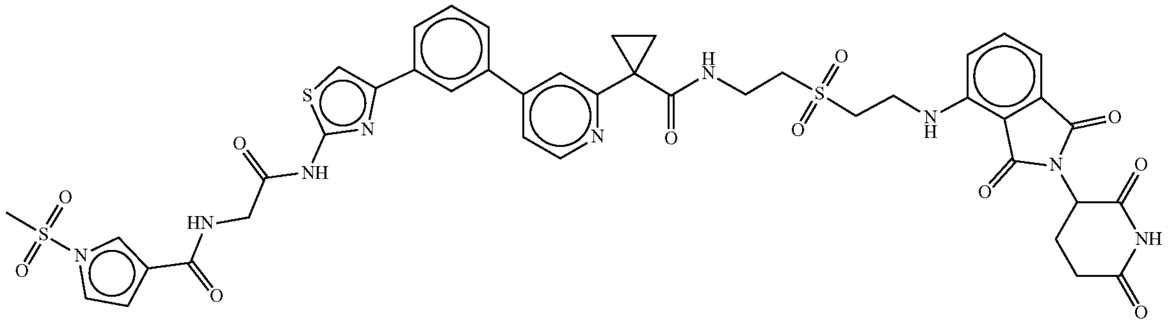 |

-continued
| # | Structure |
| --- | --- |
| 103 | 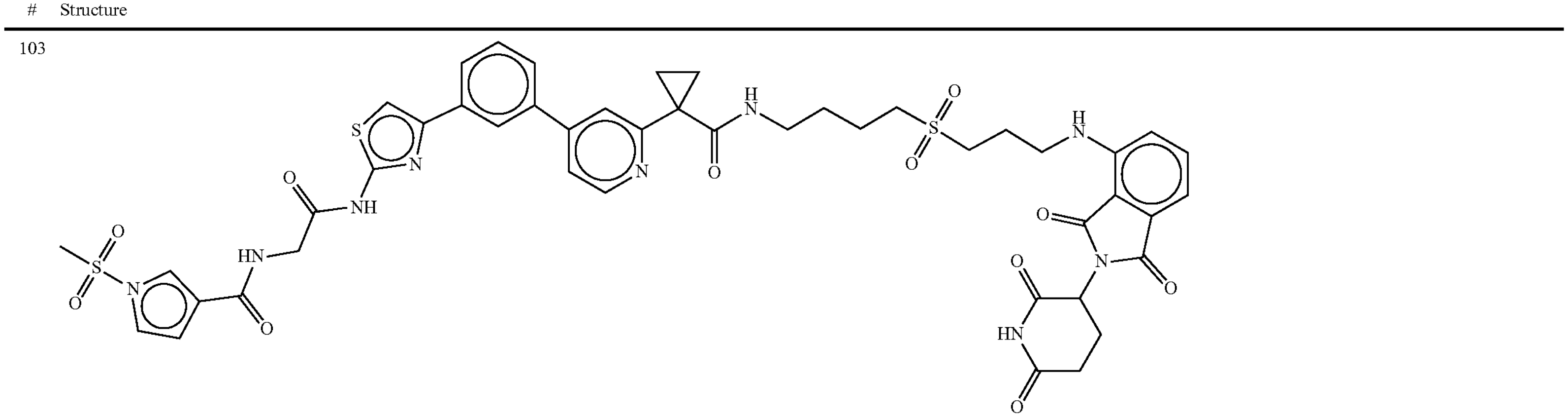 |
| 104 | 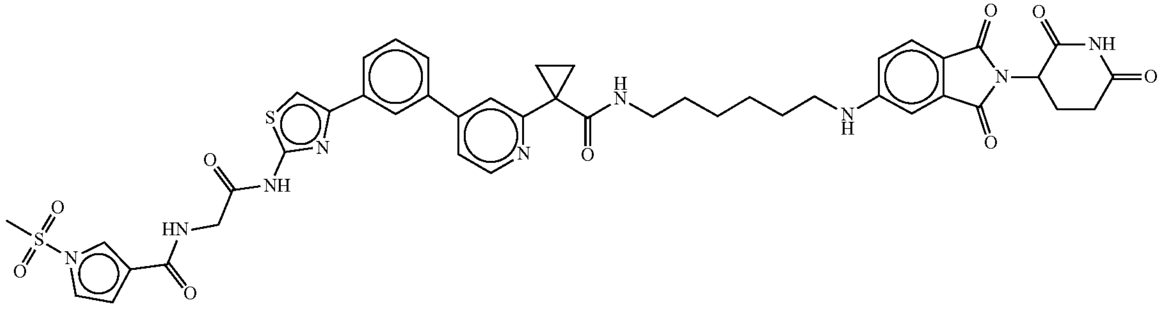 |
| 105 | 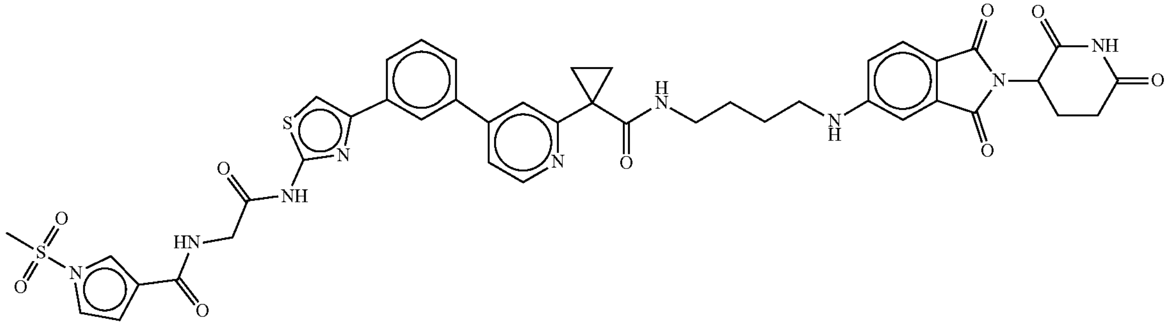 |

-continued
| # | Structure |
| --- | --- |
| 106 | 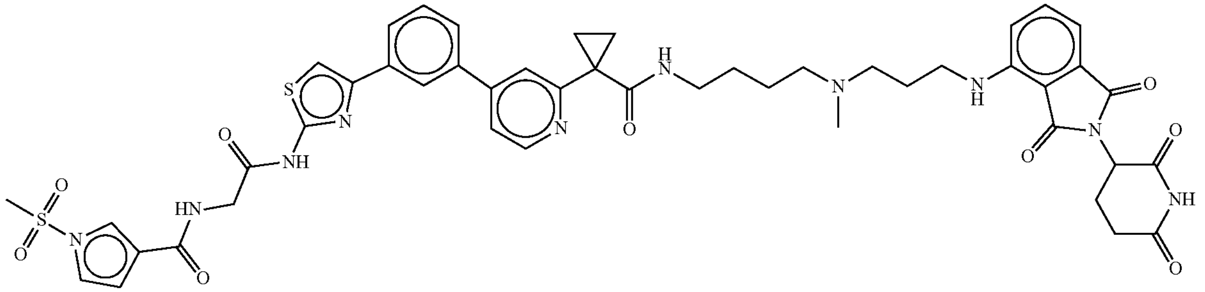 |
| 111 | 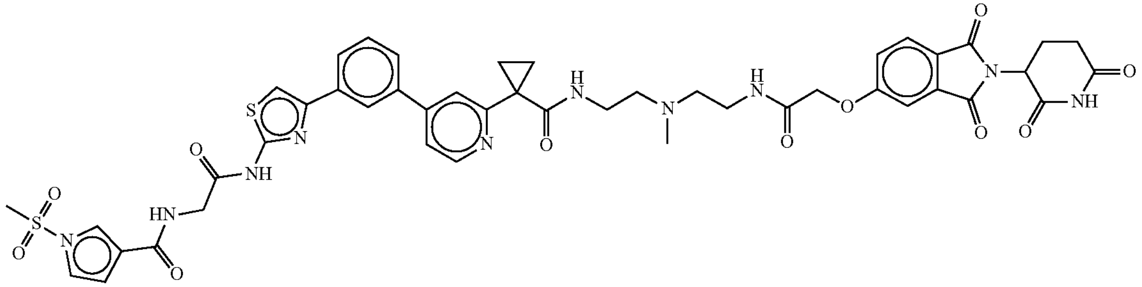 |
| 112 | 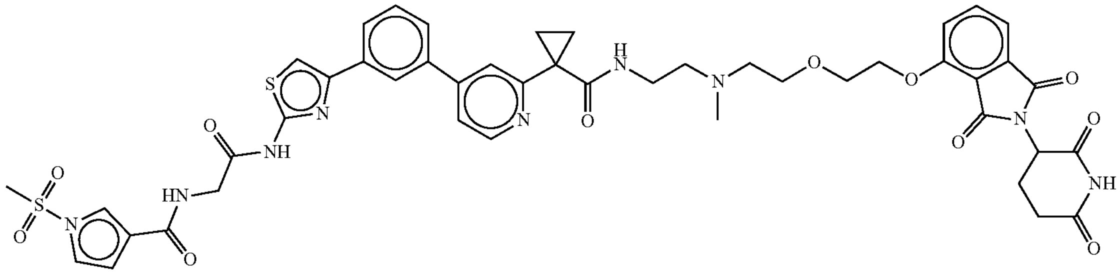 |

-continued
| # | Structure |
| --- | --- |
| 115 | 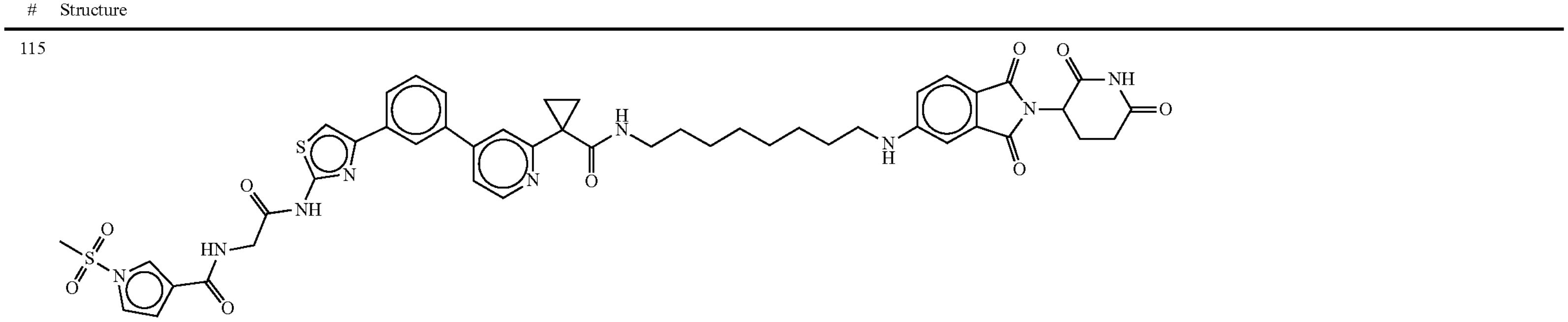 |
| 122 | 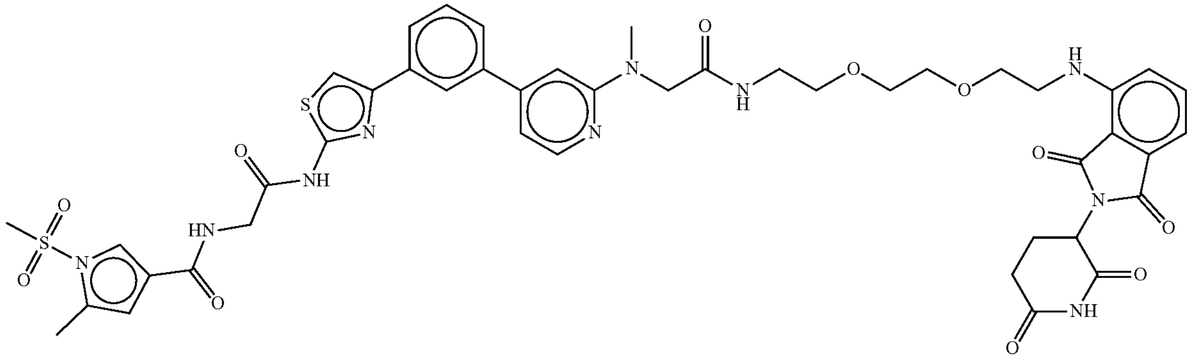 |
| 125 | 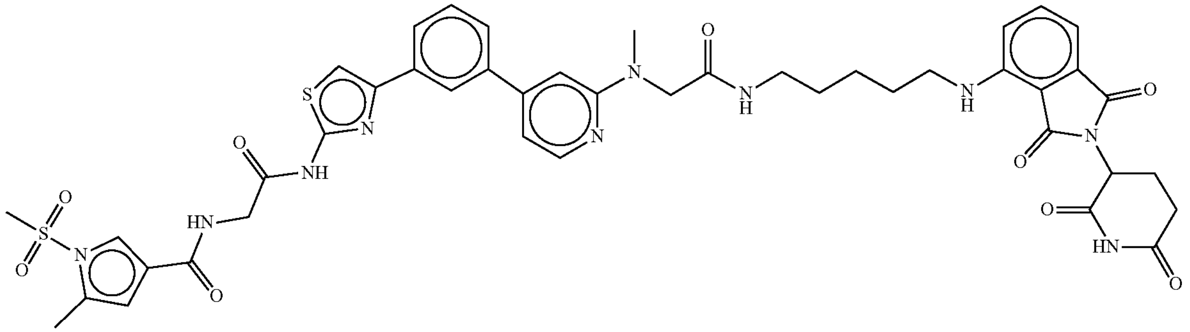 |

-continued
| # | Structure |
|---|---|
| 127 | 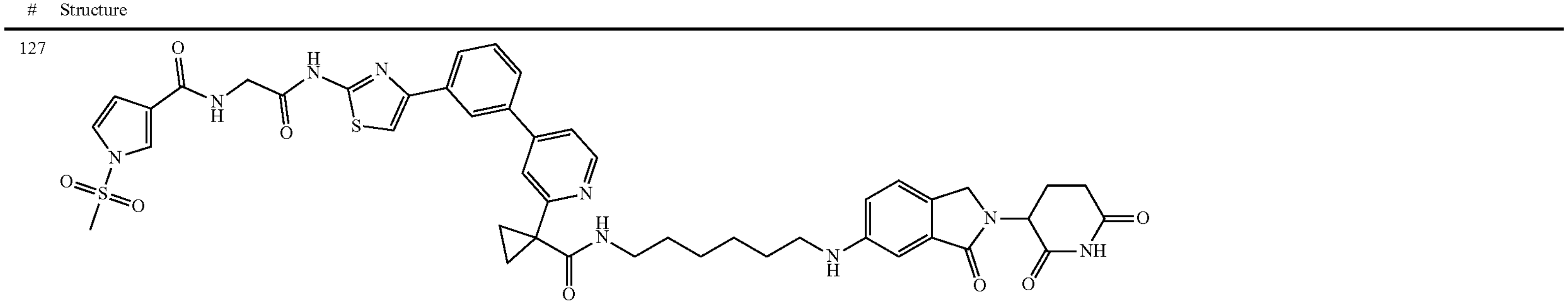 |
| 128 | 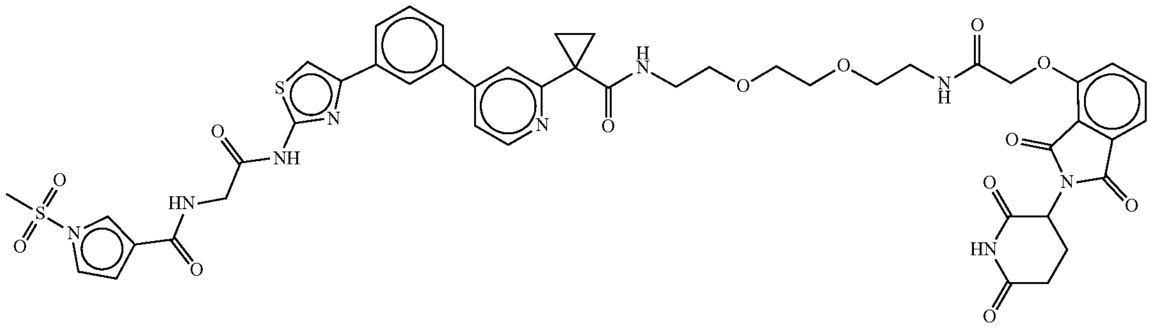 |
| 129 | 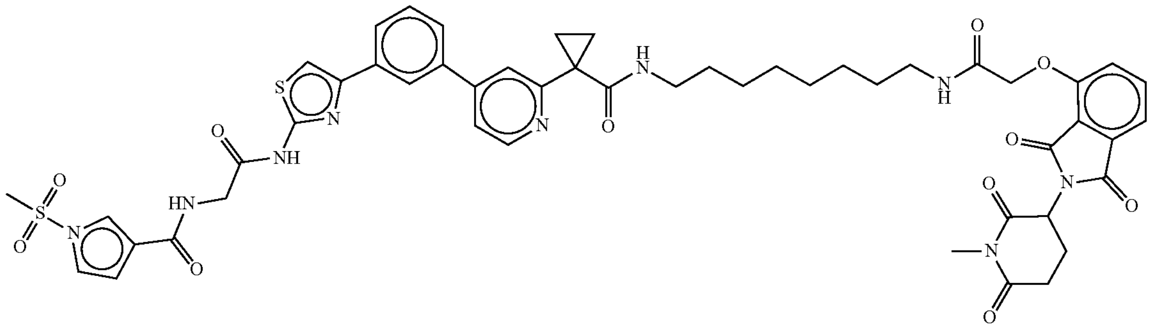 |

-continued
| # | Structure |
|---|---|
| 131 | 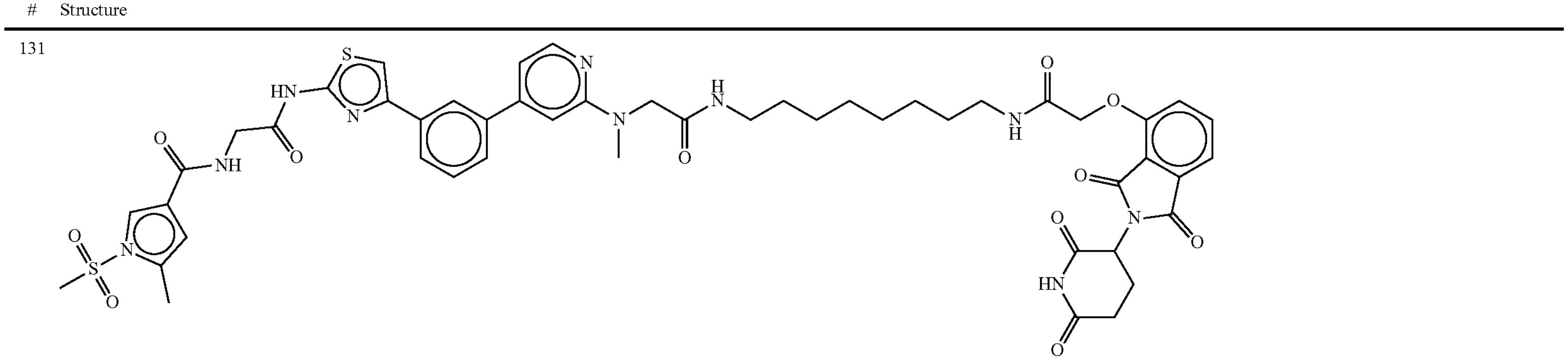 |
| 133 | 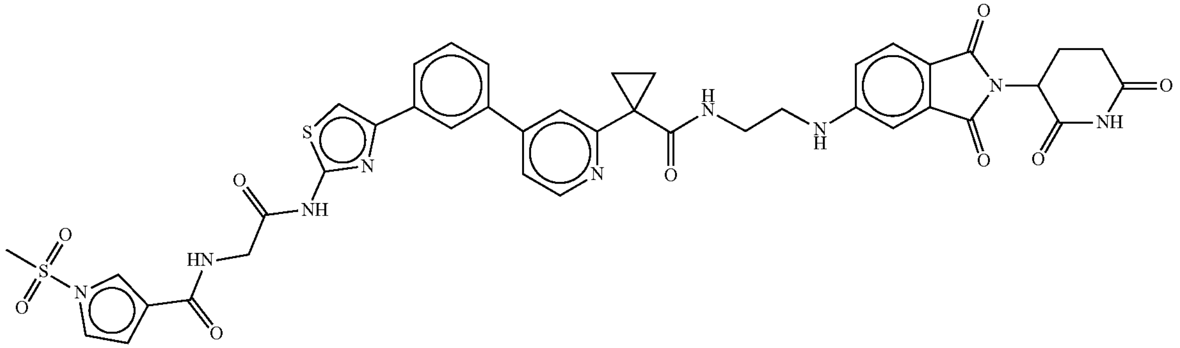 |
| 139 | 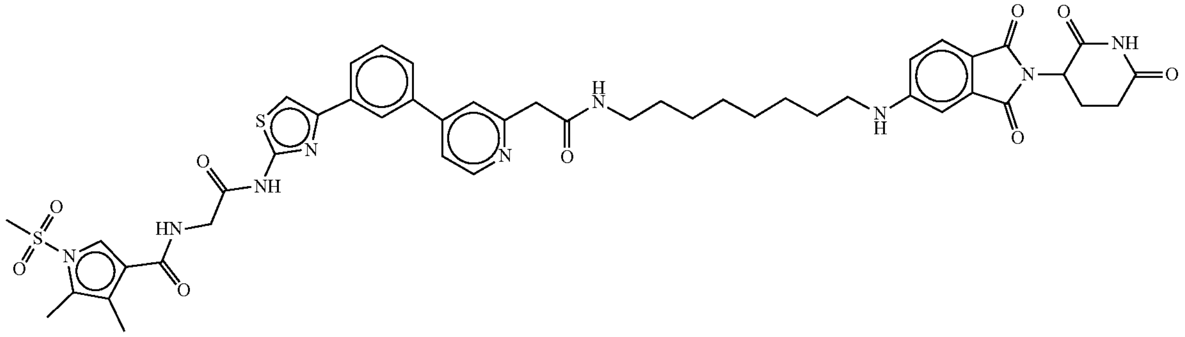 |

-continued
| # | Structure |
|---|---|
| 143 | 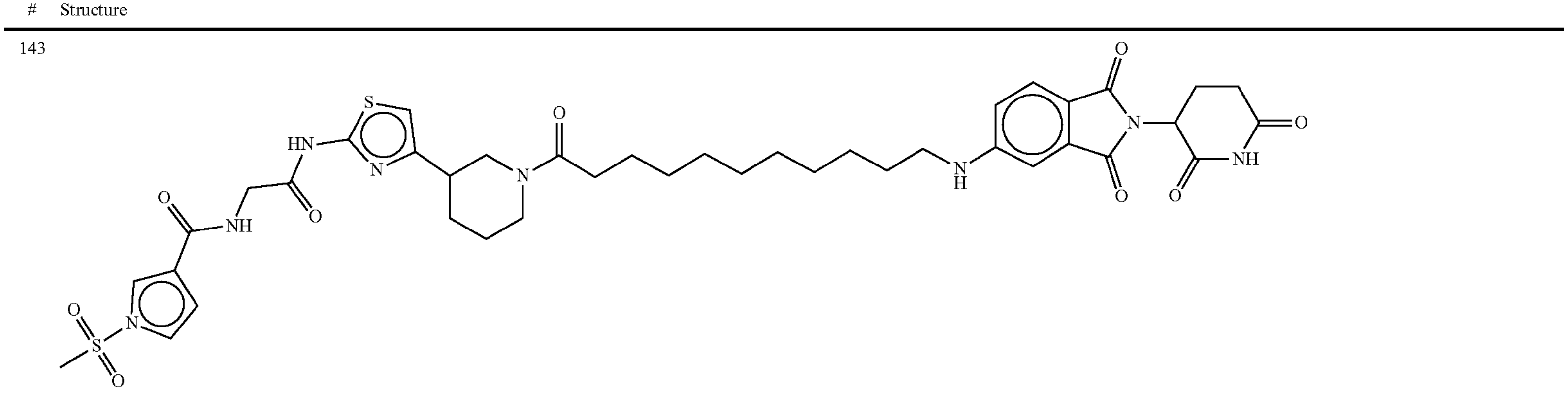 |
| 144 | 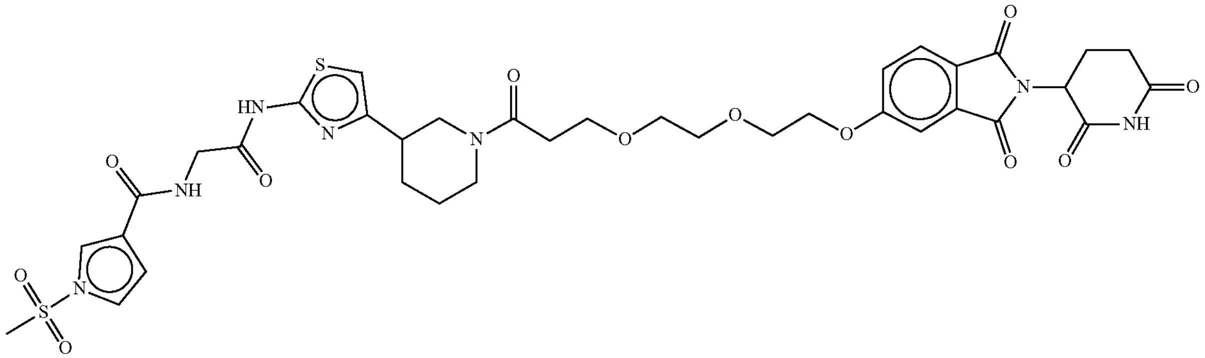 |

-continued
| # | Structure |
|---|---|
| 147 | 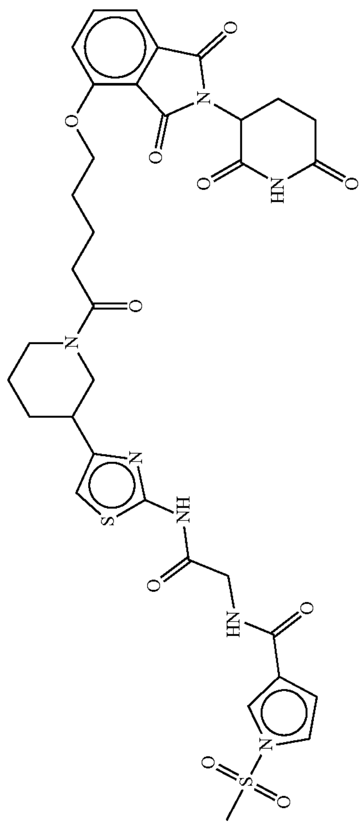 |
| 148 | 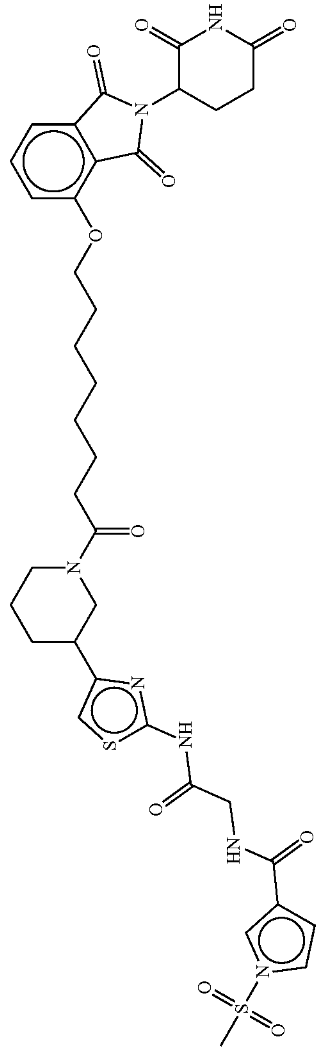 |
| 149 | 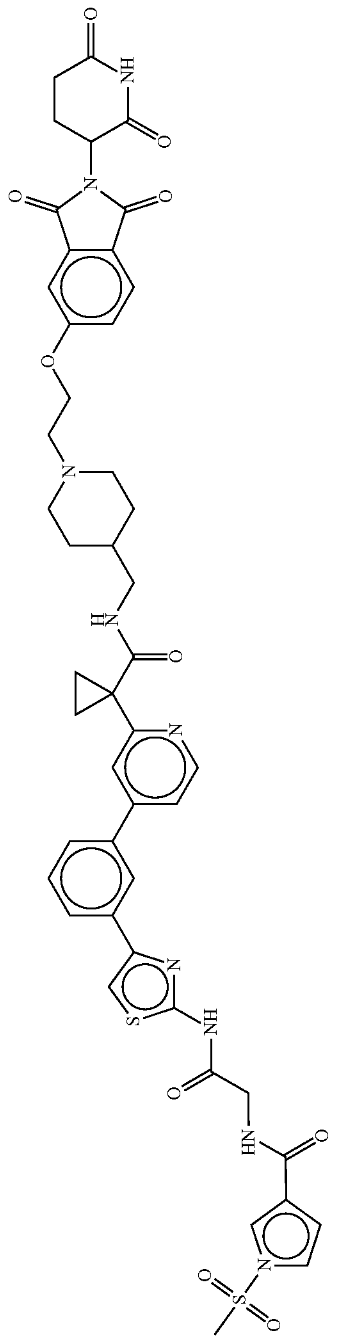 |

-continued
| # | Structure |
|---|---|
| 152 | 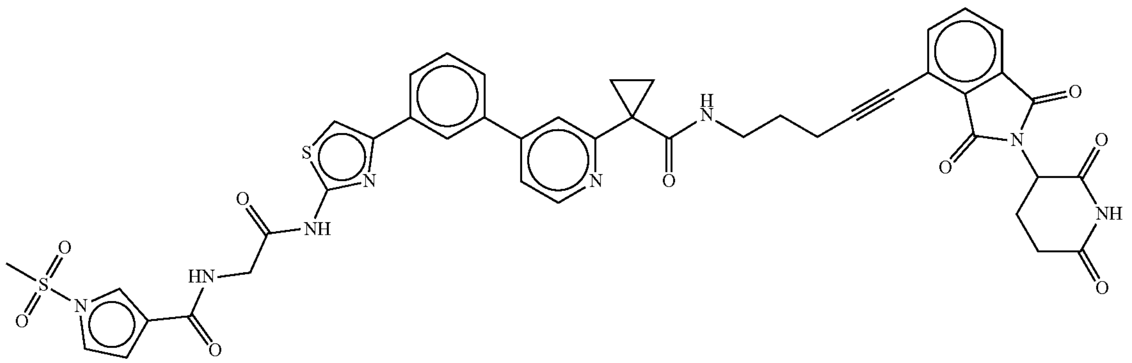 |
| 161 | 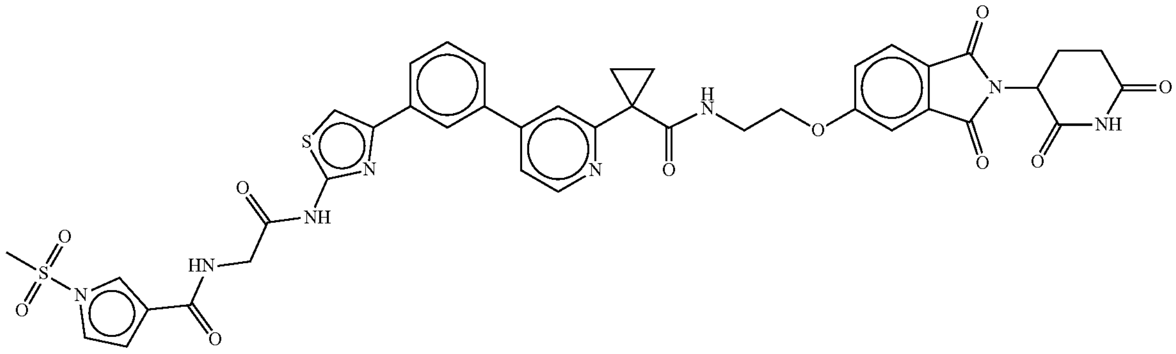 |

-continued
| # | Structure |
| --- | --- |
| 162 | 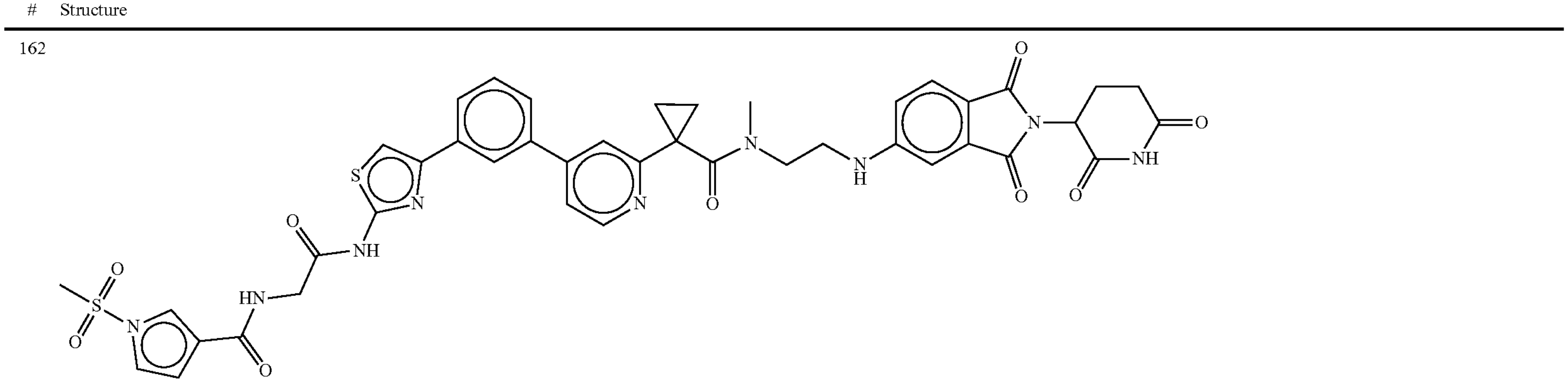 |
| 167 | 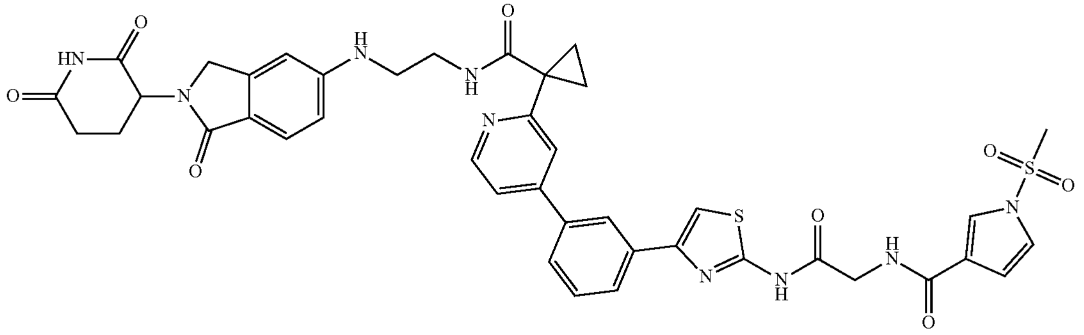 [SMILES: CS(=O)(=O)n1ccc(C(=O)NCC(=O)Nc2nc(-c3cccc(-c4ccnc(C5(C(=O)NCCNc6ccc7c(c6)CN(C6CCC(=O)NC6=O)C7=O)CC5)c4)c3)cs2)c1] |
| 168 | 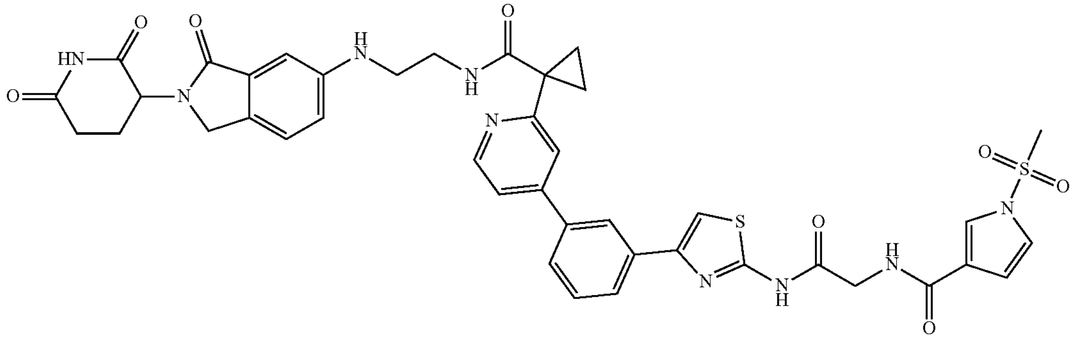 [SMILES: CS(=O)(=O)n1ccc(C(=O)NCC(=O)Nc2nc(-c3cccc(-c4ccnc(C5(C(=O)NCCNc6ccc7c(c6)C(=O)N(C6CCC(=O)NC6=O)C7)CC5)c4)c3)cs2)c1] |

-continued
| # | Structure |
| --- | --- |
| 169 | 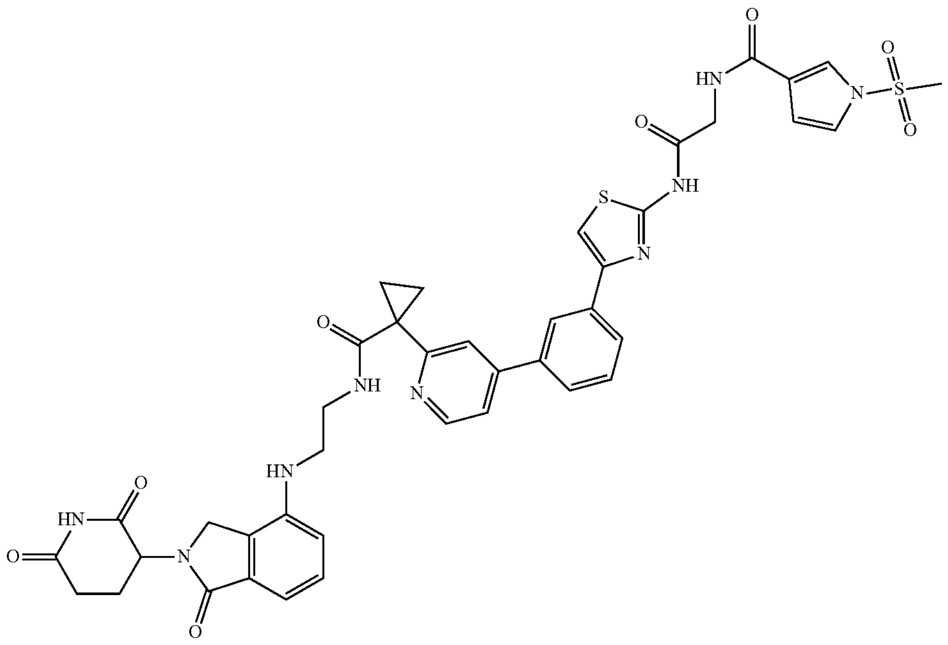 [SMILES: CS(=O)(=O)n1ccc(C(=O)NCC(=O)Nc2nc(-c3cccc(-c4ccnc(C5(C(=O)NCCNc6cccc7c6CN(C6CCC(=O)NC6=O)C7=O)CC5)c4)c3)cs2)c1] |

-continued
| # | Structure |
|---|---|
| 172 | 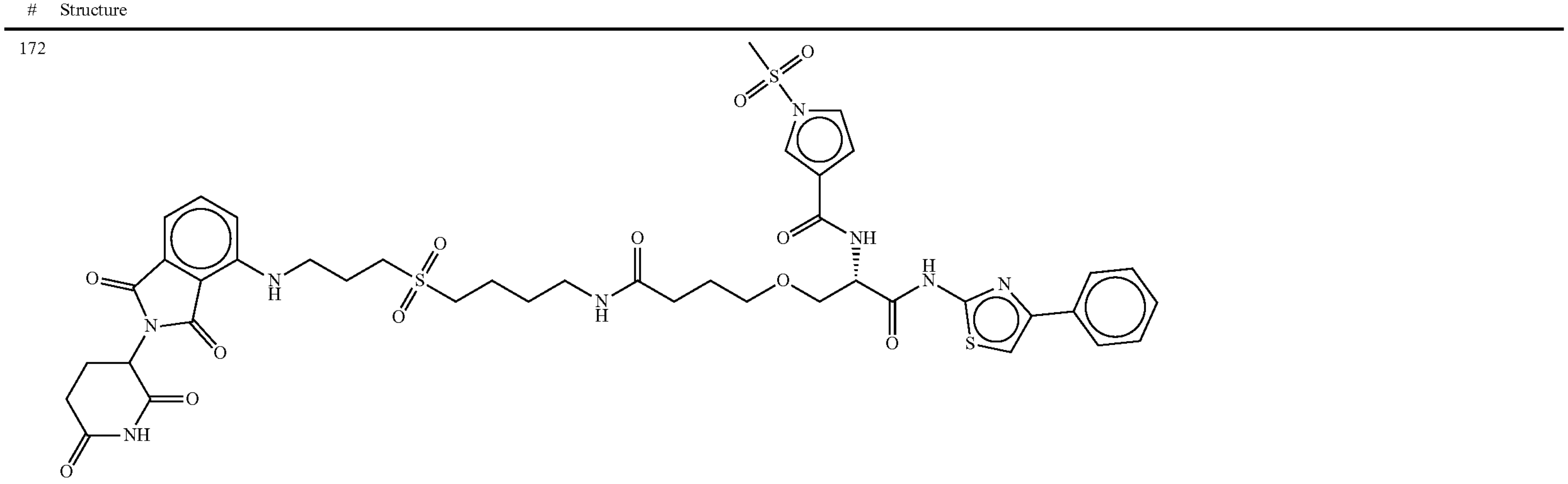 |
| 184 | 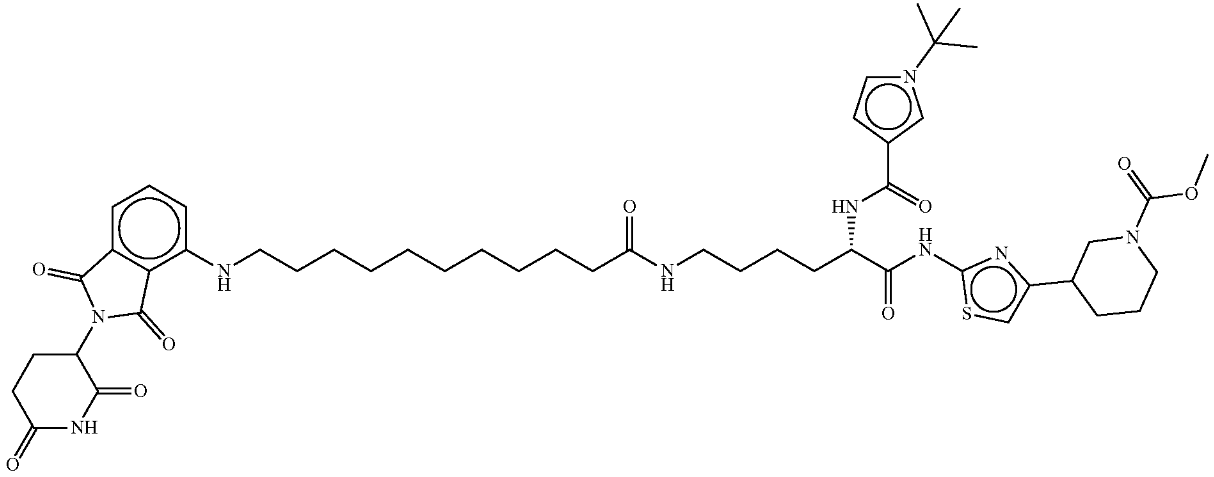 |

-continued
| # | Structure |
| --- | --- |
| 185 | 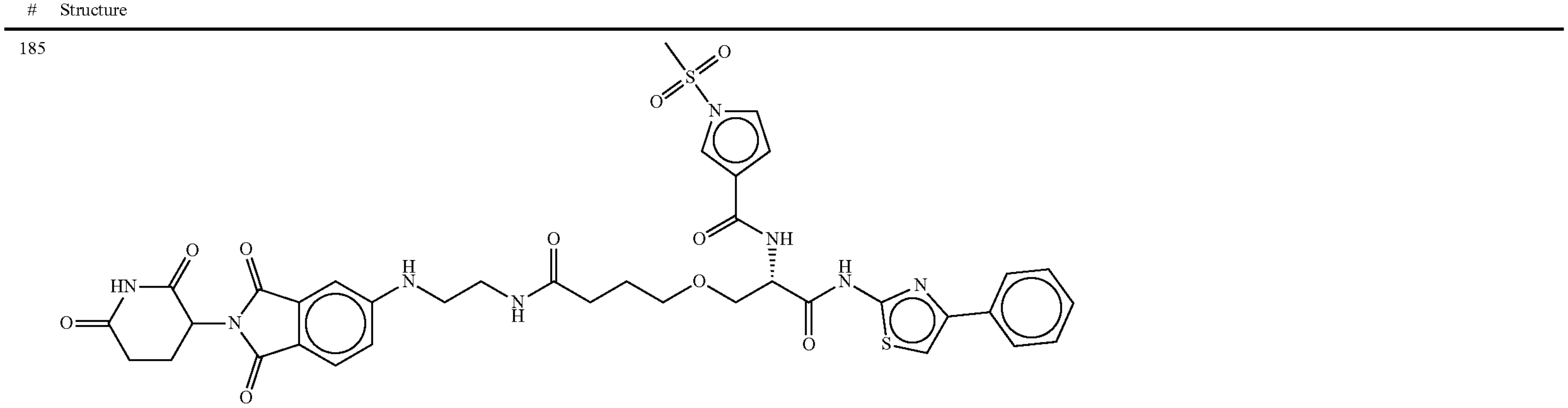 |
| 186 | 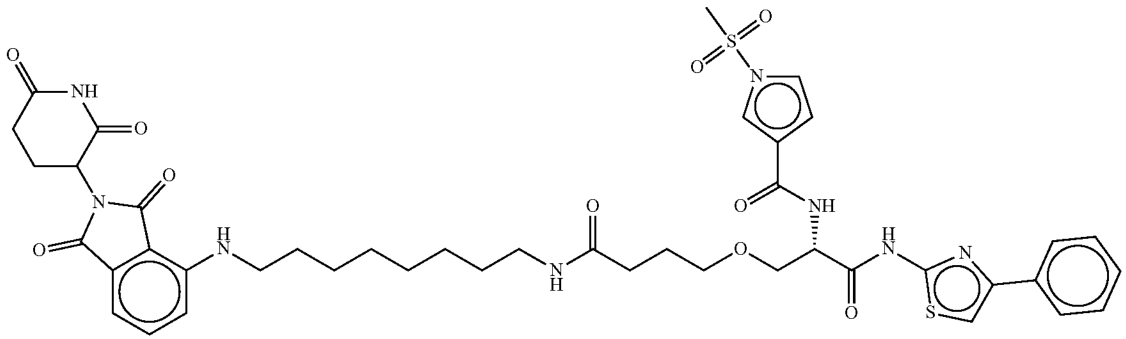 |
| 187 | 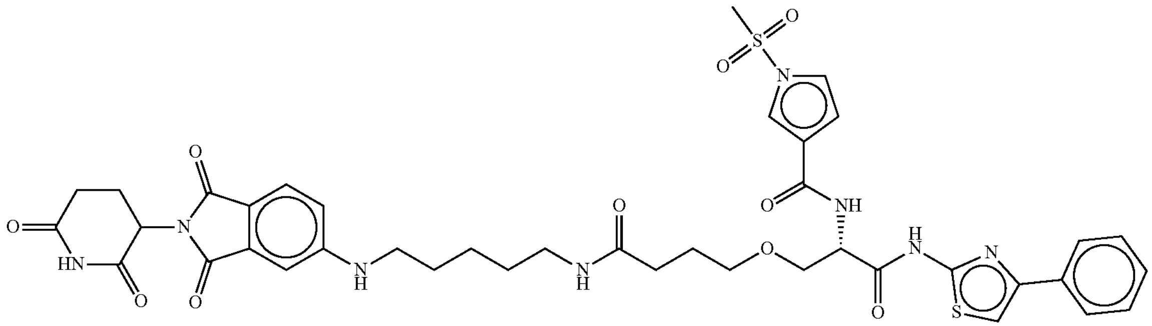 |

-continued
| # | Structure |
|---|---|
| 223 | 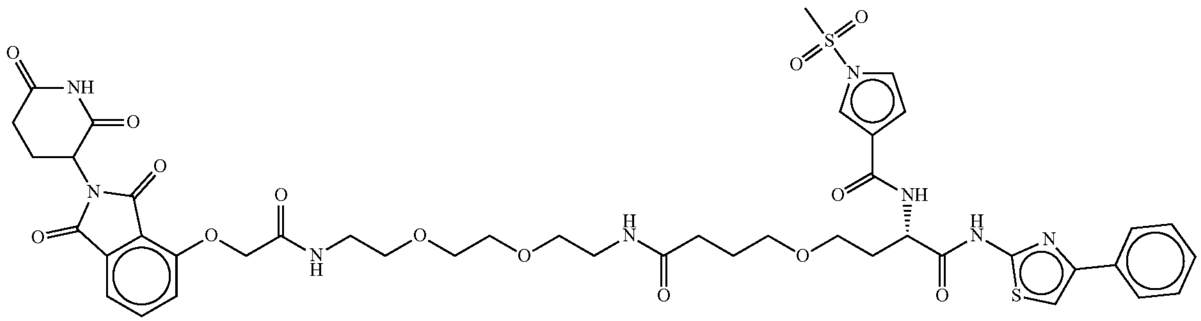 |
| 228 | 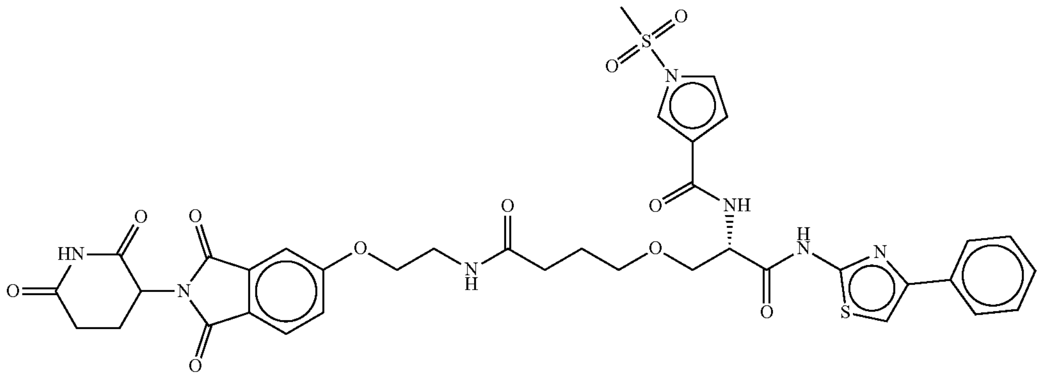 |

-continued
| # | Structure |
| --- | --- |
| 229 | 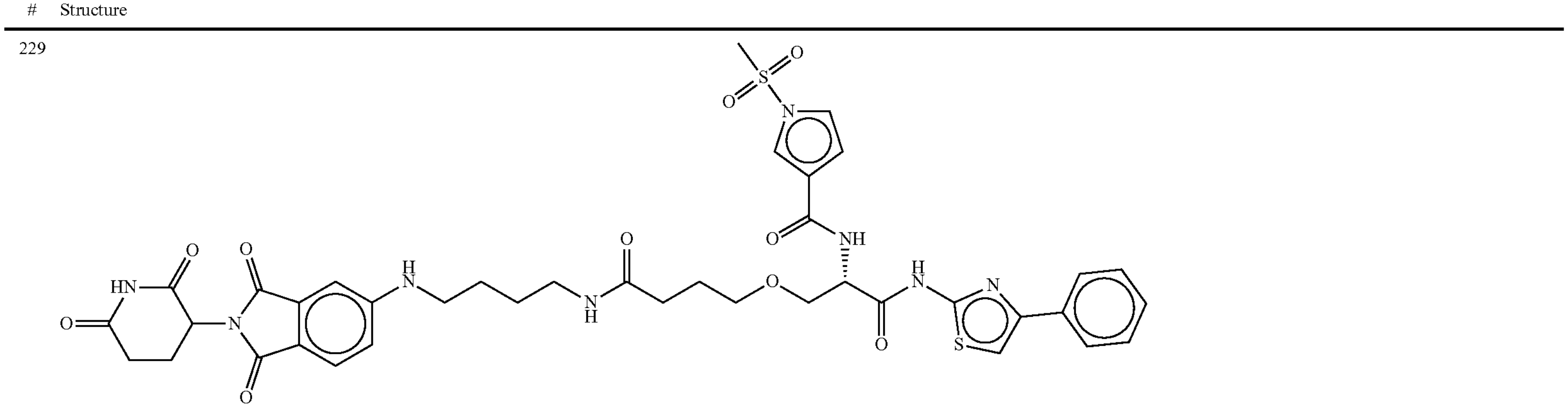 |
| 230 | 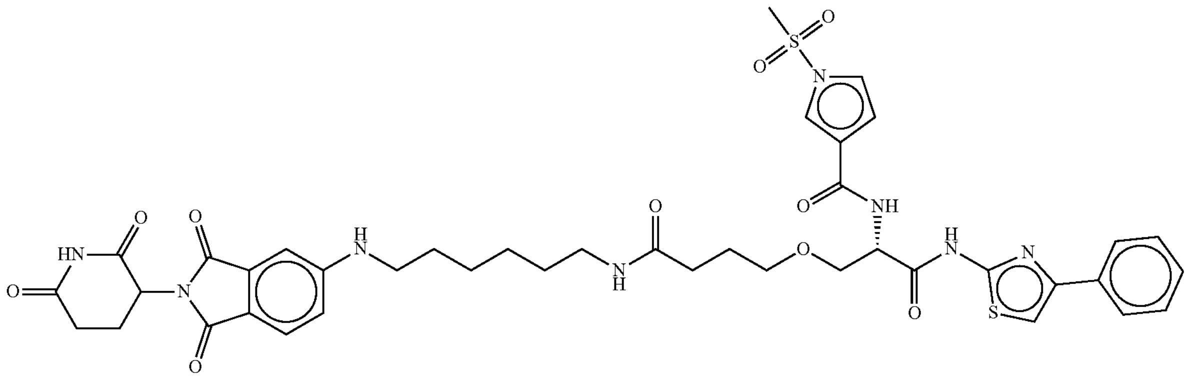 |

-continued
| # | Structure |
| --- | --- |
| 252 | 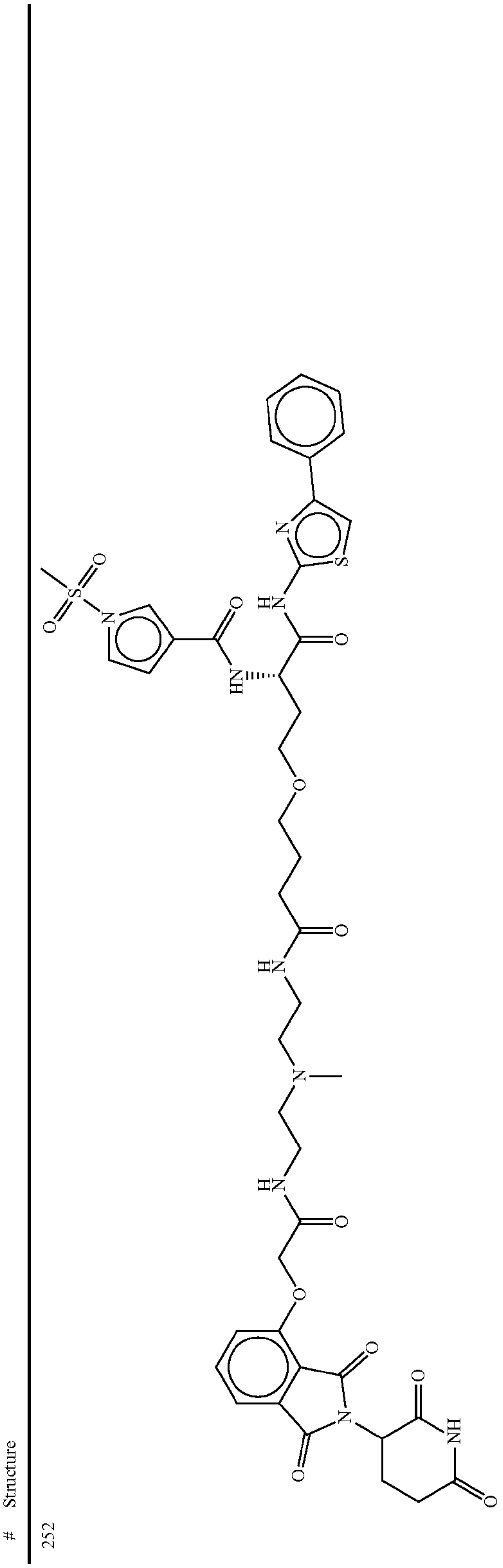 |
| 253 | 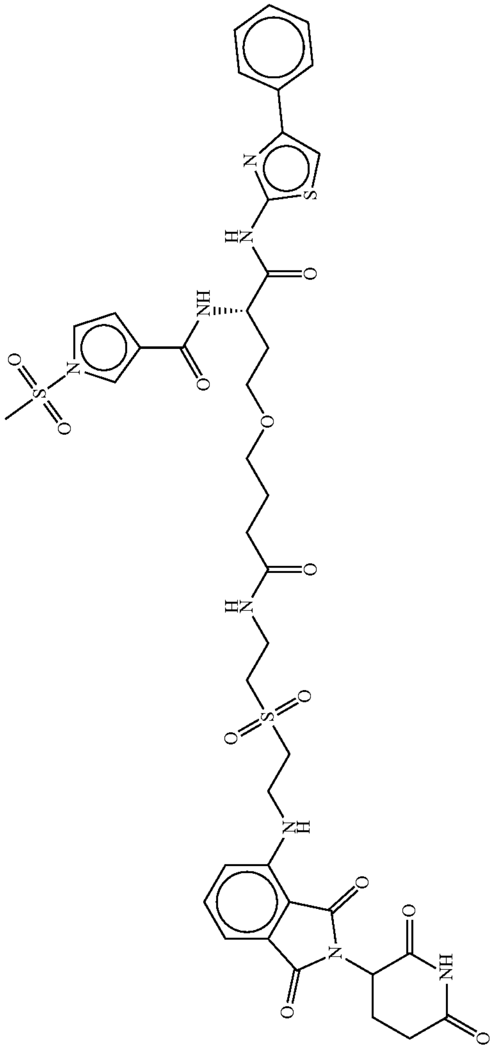 |

-continued
| # | Structure |
|---|---|
| 258 | 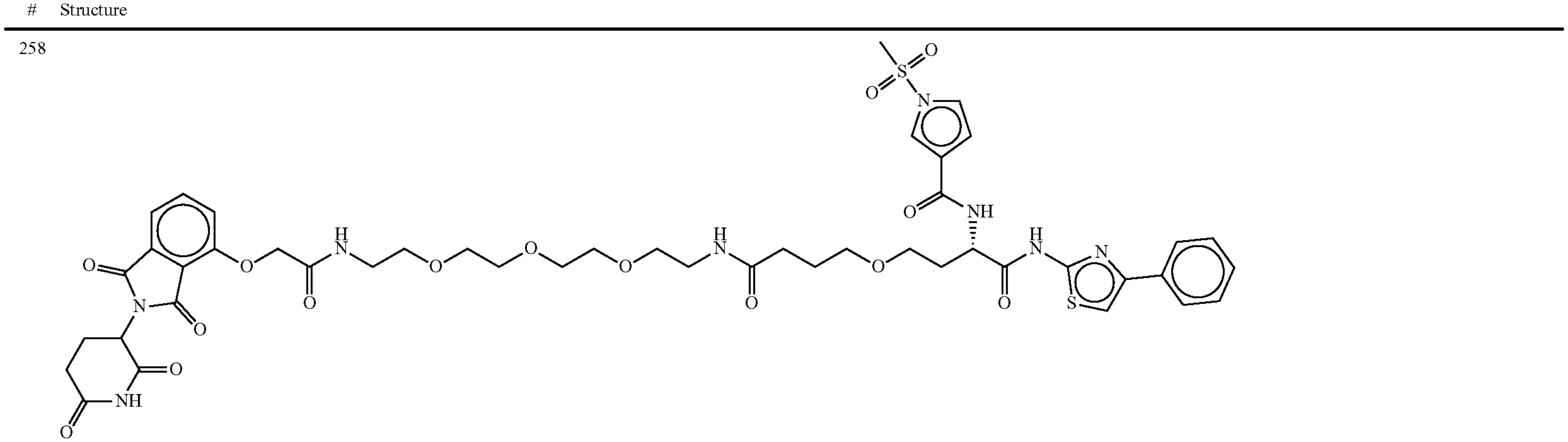 |
| 271 | 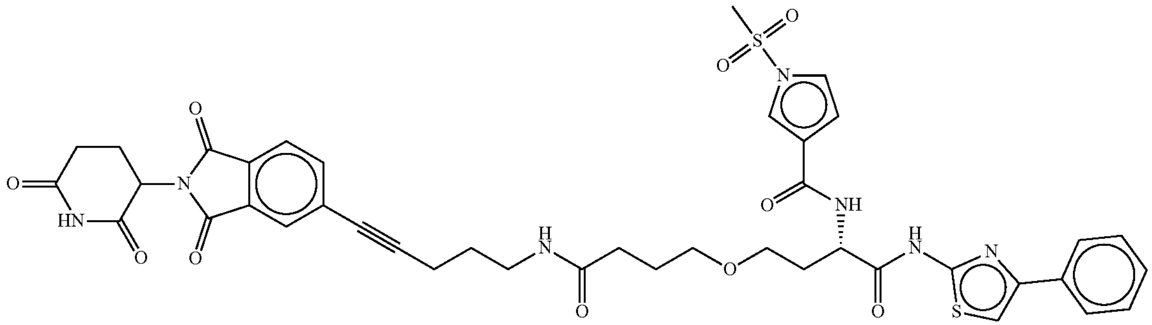 |

-continued
| # | Structure |
|---|---|
| 272 | 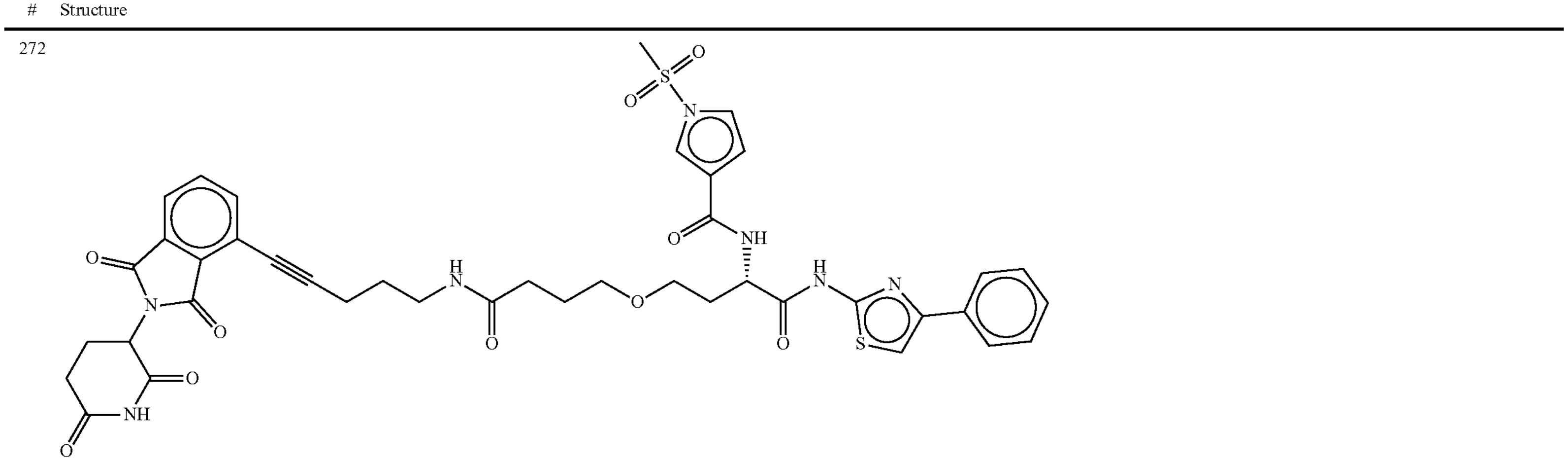 |
| 273 | 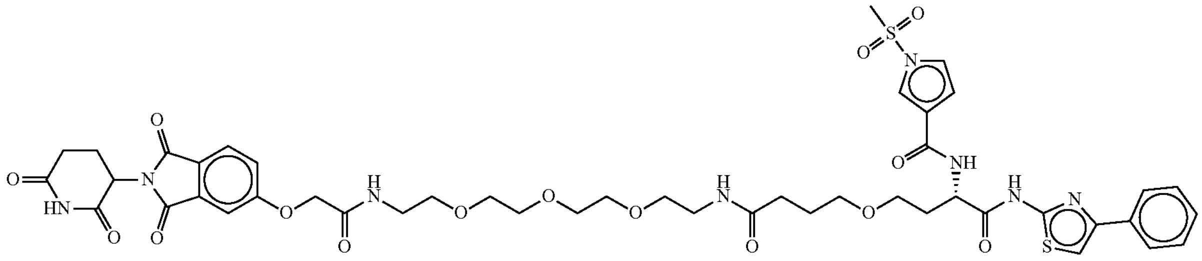 |
| 274 | 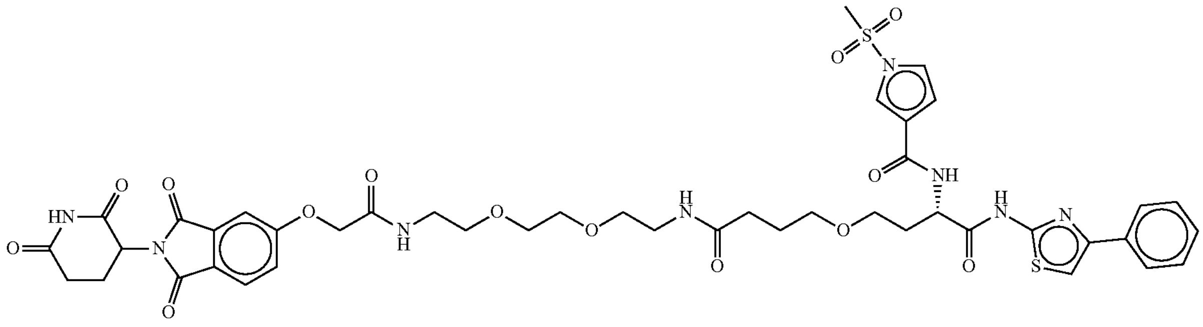 |

-continued
| # | Structure |
| --- | --- |
| 275 | 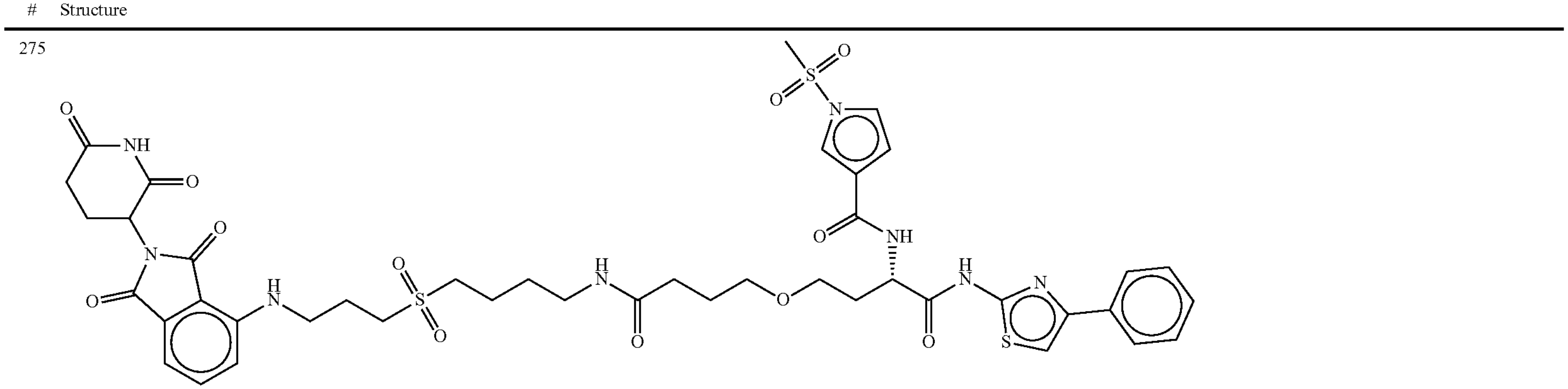 |
| 276 | 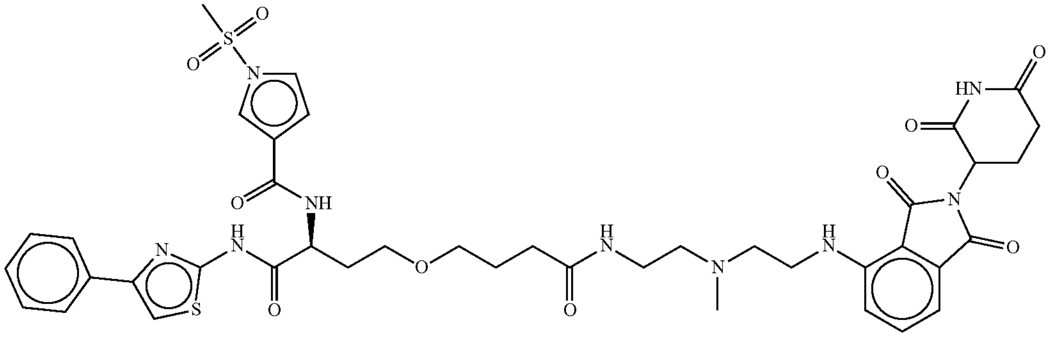 |

-continued
| # | Structure |
| --- | --- |
| 277 | 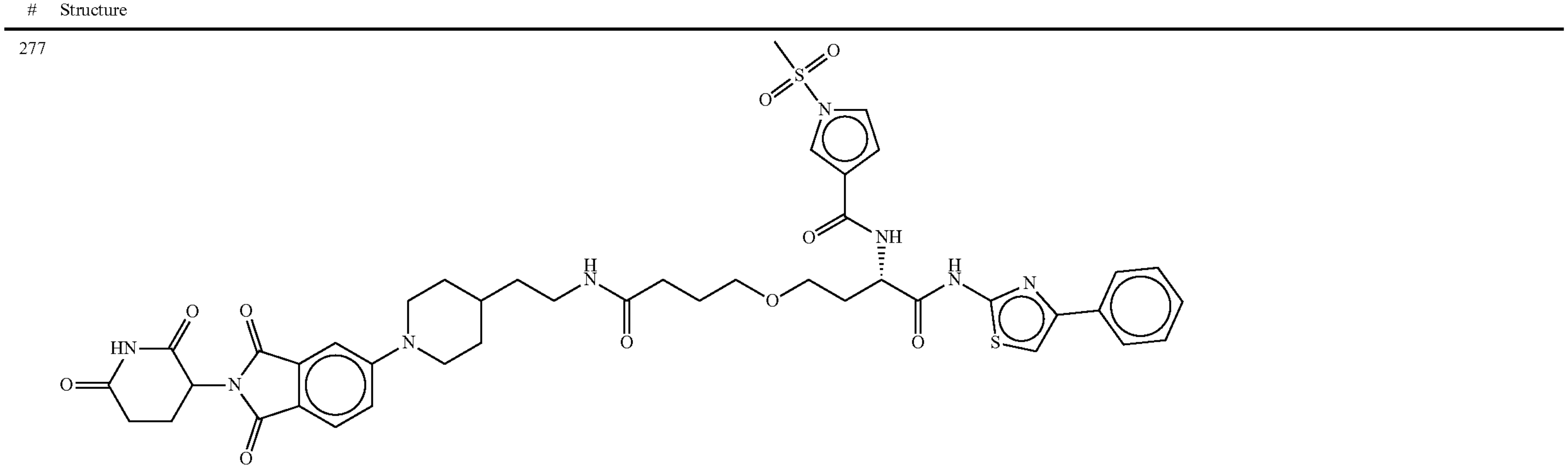 |
| 278 | 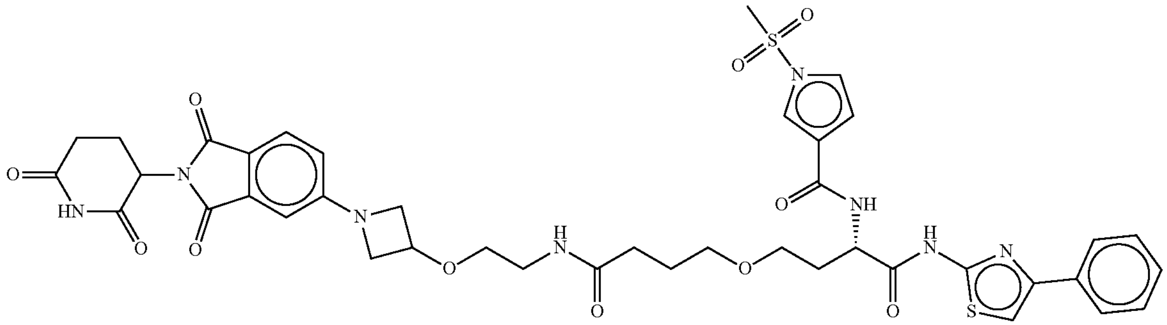 |

-continued
| # | Structure |
|---|---|
| 280 | 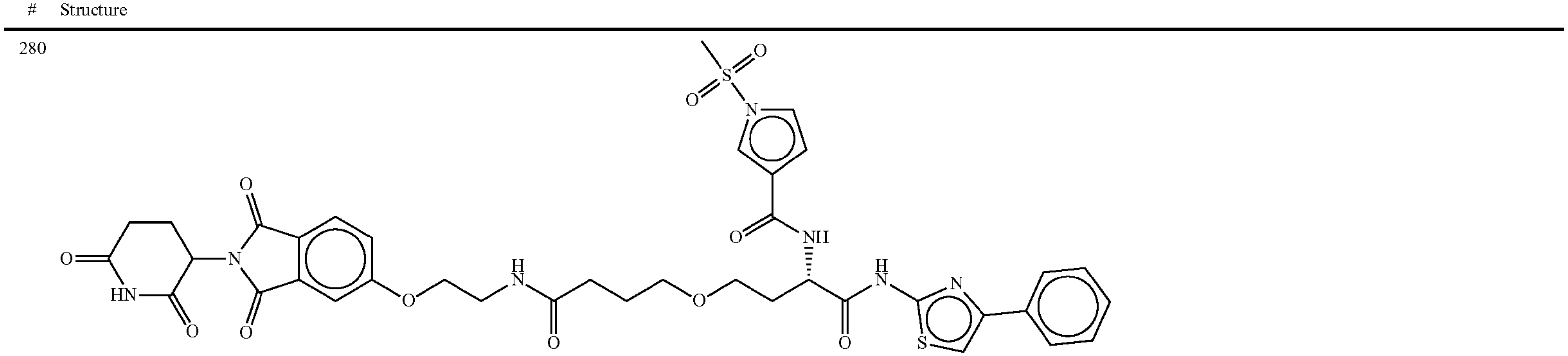 |
| 281 | 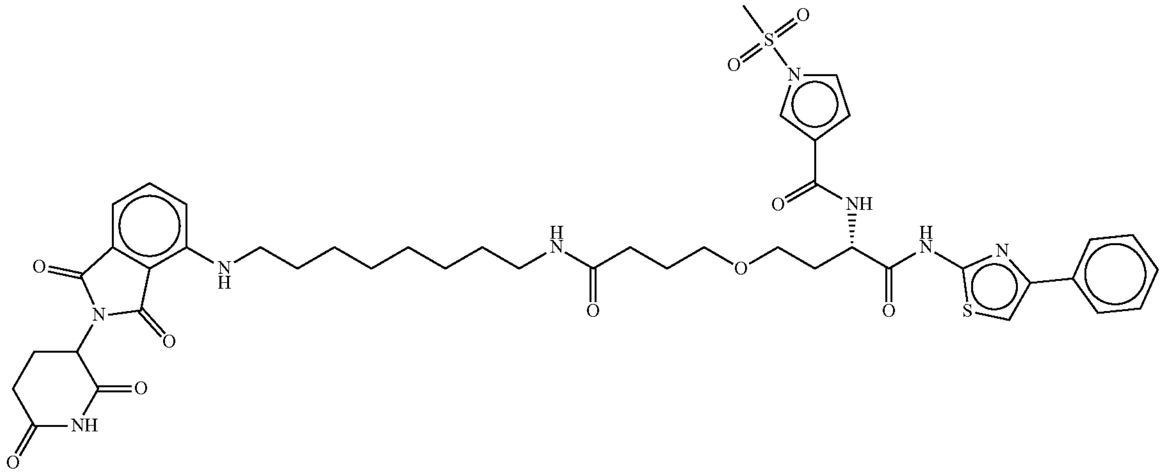 |

-continued
| # | Structure |
|---|---|
| 282 | 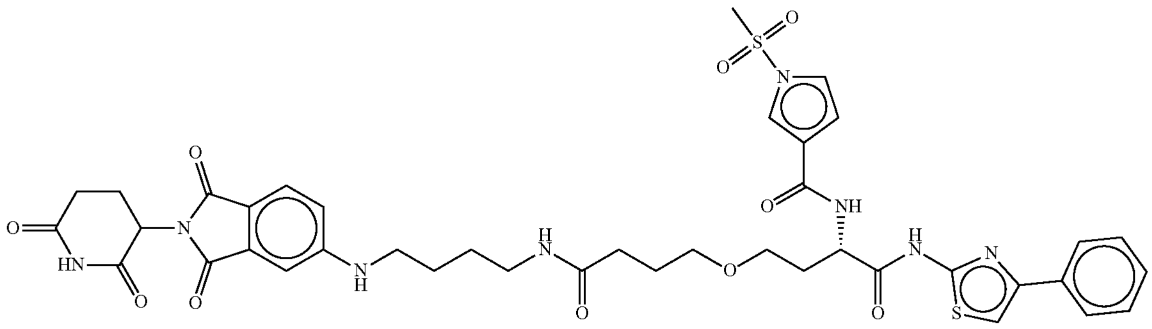 |
| 283 | 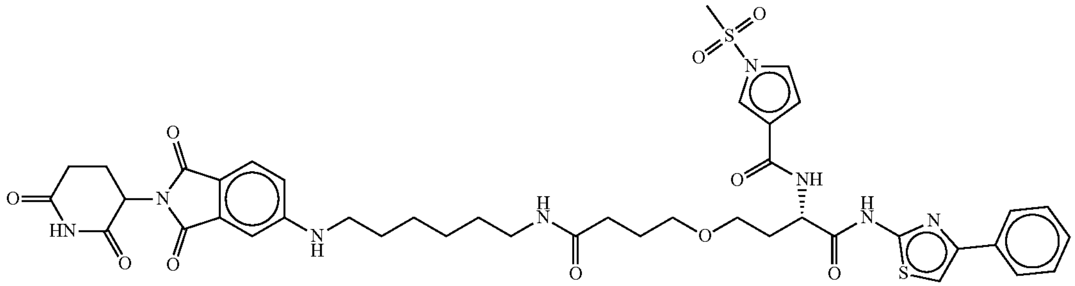 |
| 286 | 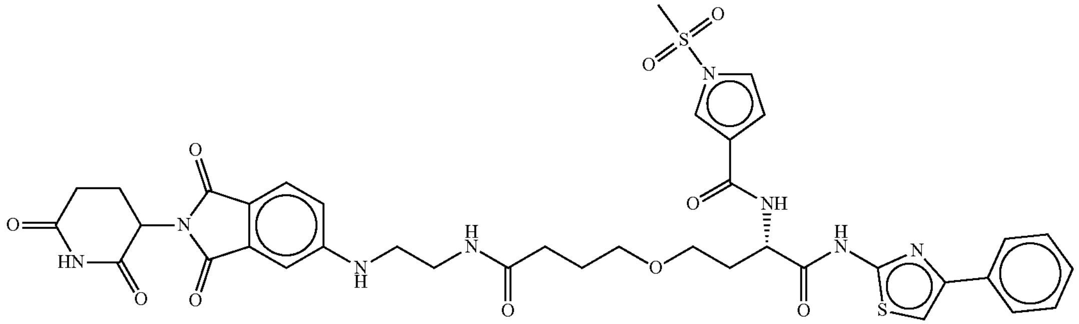 |

-continued
| # | Structure |
|---|---|
| 287 | 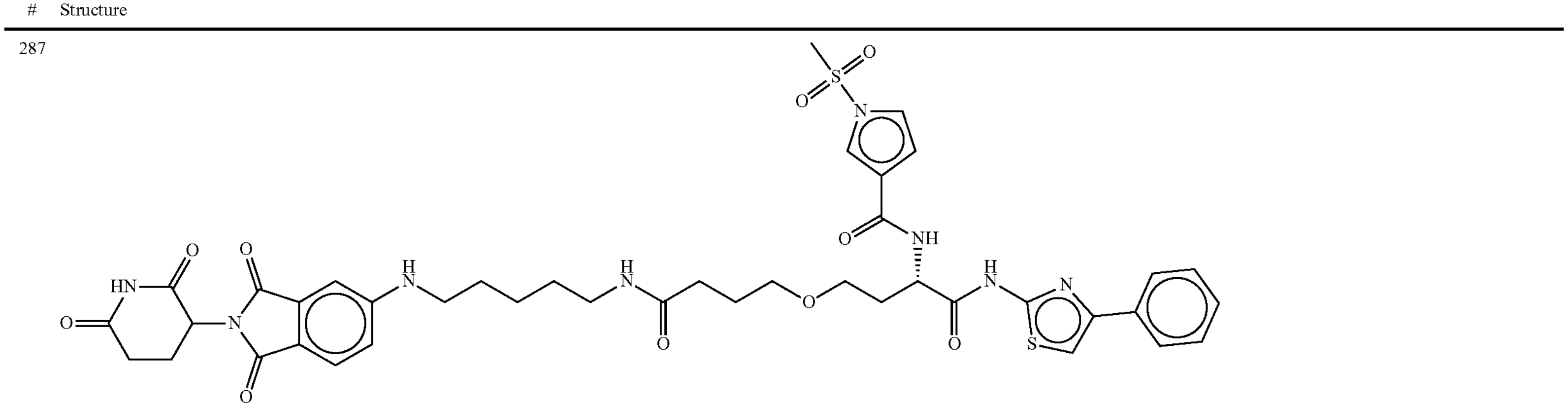 |
| 288 | 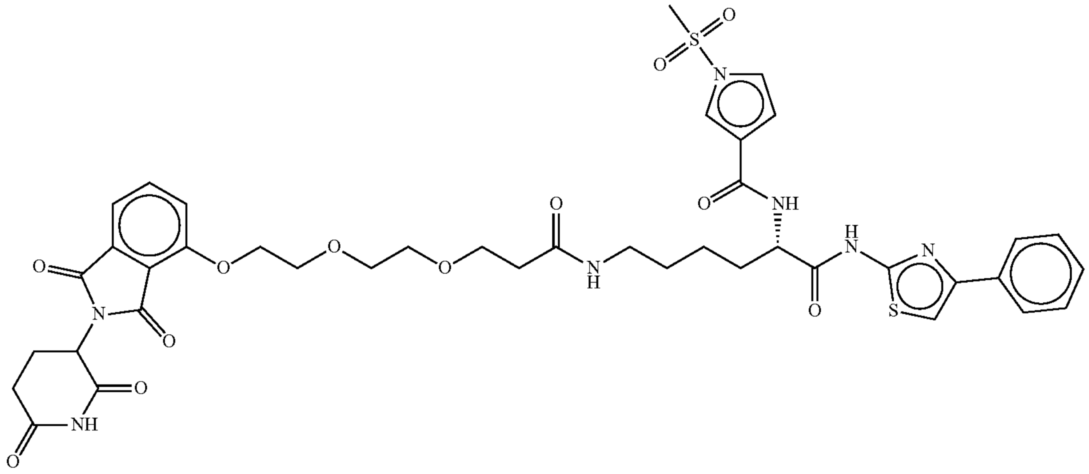 |

-continued
| # | Structure |
|---|---|
| 289 | 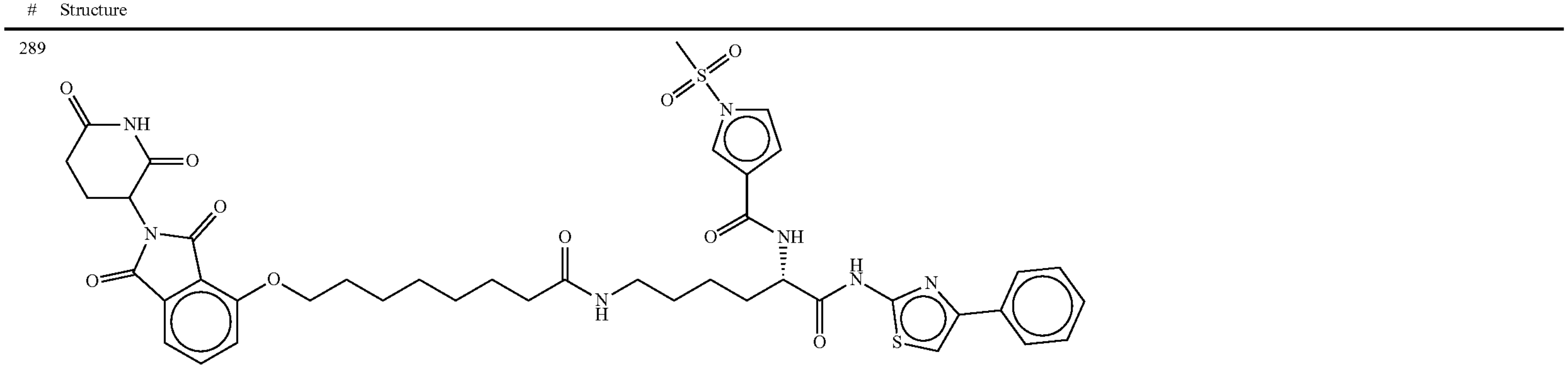 |
| 290 | 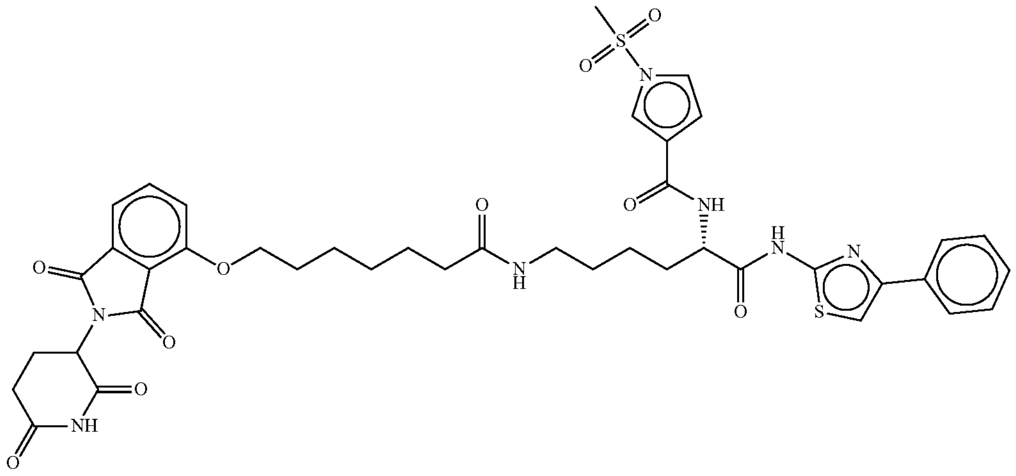 |

-continued
| # | Structure |
|---|---|
| 291 | 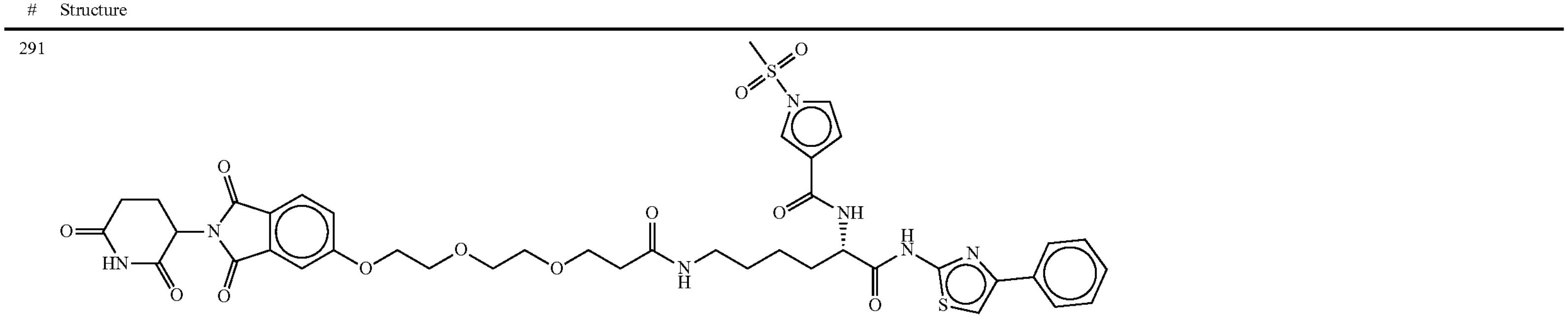 |
| 292 | 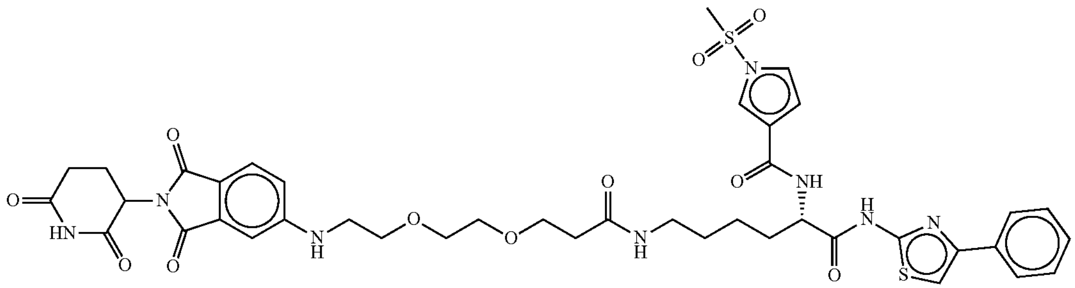 |
| 293 | 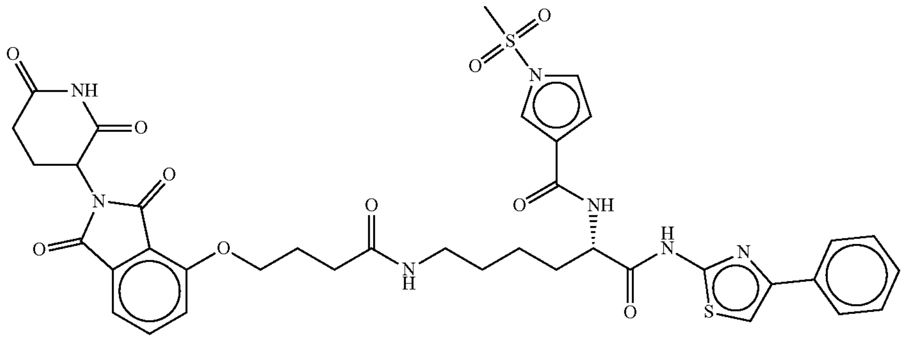 |

-continued
| # | Structure |
| --- | --- |
| 295 | 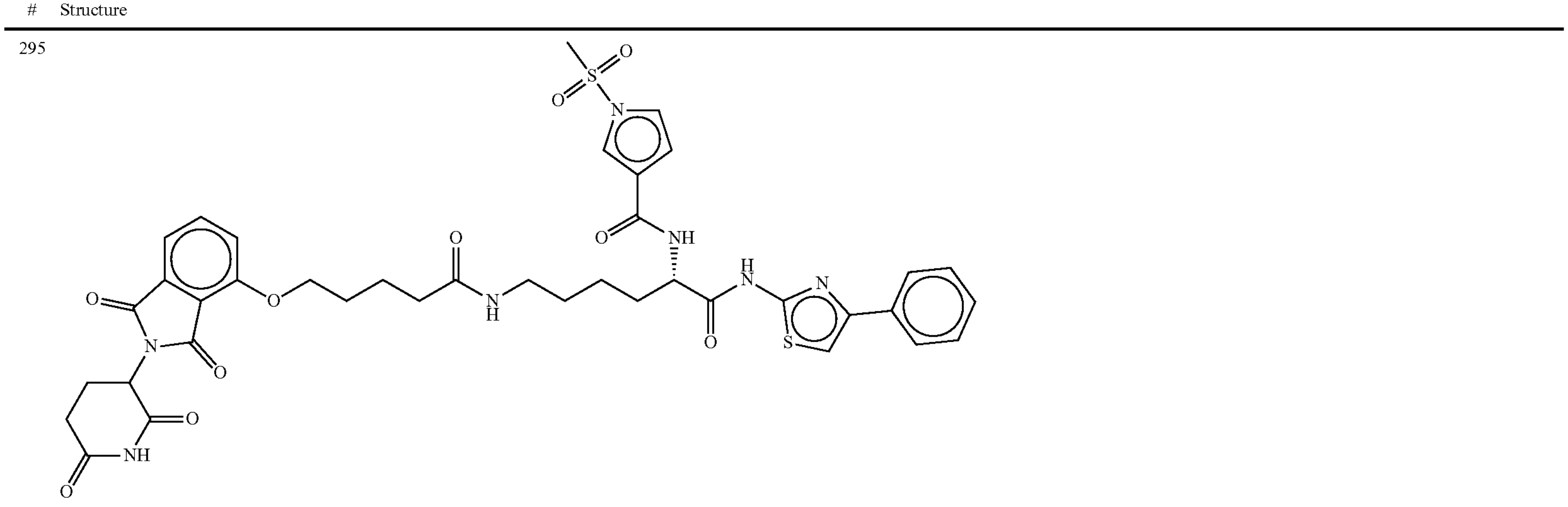 |
| 296 | 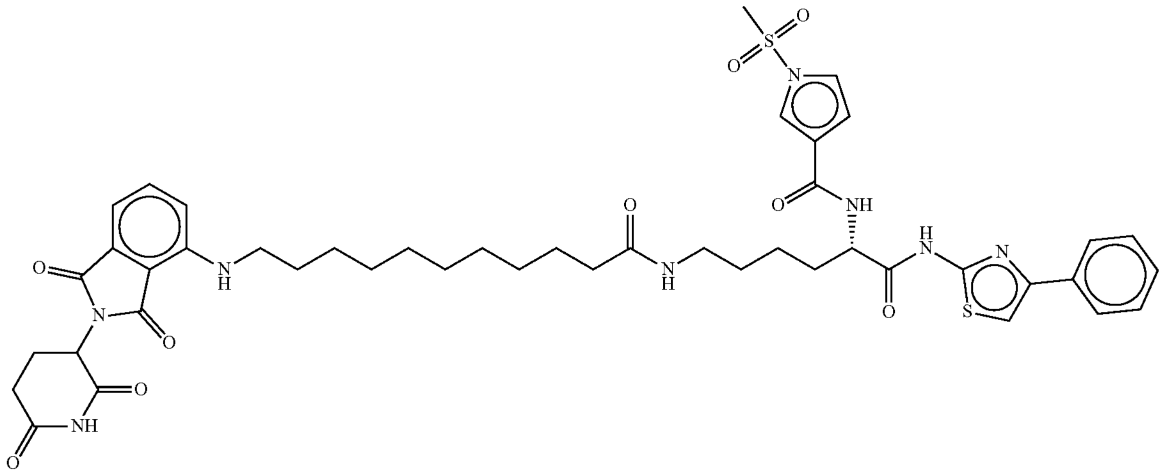 |

or a pharmaceutically acceptable salt thereof.

5. A pharmaceutical composition comprising a compound of claim 1 and a pharmaceutically acceptable excipient.

* * * * *